US012129250B2

(12) United States Patent
Wan et al.

(10) Patent No.: US 12,129,250 B2
(45) Date of Patent: Oct. 29, 2024

(54) TYK2 INHIBITORS AND COMPOSITIONS AND METHODS THEREOF

(71) Applicant: LYNK PHARMACEUTICALS CO. LTD., Zhejiang (CN)

(72) Inventors: Zhaokui Wan, Hangzhou (CN); Michael Lawrence Vazquez, Creve Coeur, MO (US); Gurmit Grewal, Lexington, MA (US); Xiaodong Li, Hangzhou (CN); Lin Su, Hangzhou (CN); Jingyu Wu, Hangzhou (CN)

(73) Assignee: LYNK PHARMACEUTICALS CO. LTD., Hangzhou (CN)

( * ) Notice: Subject to any disclaimer, the term of this patent is extended or adjusted under 35 U.S.C. 154(b) by 0 days.

(21) Appl. No.: 18/372,417

(22) Filed: Sep. 25, 2023

(65) Prior Publication Data

US 2024/0124448 A1 Apr. 18, 2024

Related U.S. Application Data

(63) Continuation of application No. PCT/CN2022/139649, filed on Dec. 16, 2022, which is a continuation-in-part of application No. PCT/CN2022/106876, filed on Jul. 20, 2022, and a continuation-in-part of application No. PCT/CN2021/138744, filed on Dec. 16, 2021.

(51) Int. Cl.
| | | |
|---|---|---|
| C07D 471/04 | (2006.01) | |
| C07D 401/12 | (2006.01) | |
| C07D 401/14 | (2006.01) | |
| C07D 403/12 | (2006.01) | |
| C07D 403/14 | (2006.01) | |
| C07D 405/12 | (2006.01) | |
| C07D 471/18 | (2006.01) | |
| C07D 487/04 | (2006.01) | |
| C07D 487/08 | (2006.01) | |
| C07D 491/04 | (2006.01) | |
| C07D 495/04 | (2006.01) | |
| C07D 498/08 | (2006.01) | |
| C07D 498/18 | (2006.01) | |

(52) U.S. Cl.
CPC ......... *C07D 471/04* (2013.01); *C07D 401/12* (2013.01); *C07D 401/14* (2013.01); *C07D 403/12* (2013.01); *C07D 403/14* (2013.01); *C07D 405/12* (2013.01); *C07D 471/18* (2013.01); *C07D 487/04* (2013.01); *C07D 487/08* (2013.01); *C07D 491/04* (2013.01); *C07D 495/04* (2013.01); *C07D 498/08* (2013.01); *C07D 498/18* (2013.01)

(58) Field of Classification Search
None
See application file for complete search history.

(56) References Cited

U.S. PATENT DOCUMENTS

| | | |
|---|---|---|
| 9,315,494 B2 | 4/2016 | Moslin et al. |
| 9,505,748 B2 | 11/2016 | Moslin et al. |
| 9,663,467 B2 | 5/2017 | Moslin et al. |
| 9,987,266 B2 | 6/2018 | Moslin et al. |
| 10,000,480 B2 | 6/2018 | Moslin et al. |
| 10,526,321 B2 | 1/2020 | Wrobleski et al. |
| 11,021,462 B2 | 6/2021 | Liu et al. |
| 11,021,475 B2 | 6/2021 | Moslin et al. |
| 2022/0002267 A1 | 1/2022 | Zhuang et al. |

FOREIGN PATENT DOCUMENTS

| | | |
|---|---|---|
| CN | 1625400 A | 6/2005 |
| CN | 101506177 A | 8/2009 |
| CN | 102066339 A | 5/2011 |
| CN | 102066340 A | 5/2011 |
| CN | 103492370 A | 1/2014 |
| CN | 104470363 A | 3/2015 |
| CN | 104781252 A | 7/2015 |
| CN | 104884454 A | 9/2015 |
| CN | 106660960 A | 5/2017 |
| CN | 111484480 A | 8/2020 |
| CN | 111936486 A | 11/2020 |
| CN | 113490664 A | 10/2021 |
| CN | 113563309 A | 10/2021 |
| CN | 113968846 A | 1/2022 |
| CN | 115197196 A | 10/2022 |
| CN | 115466257 A | 12/2022 |
| JP | 2014198693 A | 10/2014 |
| WO | 2007027238 A2 | 3/2007 |
| WO | 2013104573 A1 | 7/2013 |
| WO | 2013171690 A1 | 11/2013 |
| WO | 2014074660 A1 | 5/2014 |
| WO | 2014074661 A1 | 5/2014 |
| WO | 2015069310 A1 | 5/2015 |
| WO | 2019076716 A1 | 4/2019 |
| WO | 2020086616 A1 | 4/2020 |
| WO | 2020092196 A1 | 5/2020 |
| WO | 2020156311 A1 | 8/2020 |
| WO | 2021180072 A1 | 9/2021 |
| WO | 2021202652 A1 | 10/2021 |

(Continued)

OTHER PUBLICATIONS

Vera, et al. "DiscoveryofDiaminopyrimidineCarboxamideHPK1Inhibitorsas PreclinicalImmunotherapyToolCompounds" ACS Med. Chem. Lett. 2021, 12, 653-661 (Mar. 19, 2021).

(Continued)

*Primary Examiner* — Samantha L Shterengarts

(74) *Attorney, Agent, or Firm* — Milstein Zhang & Wu LLC

(57) ABSTRACT

The invention provides a novel class of therapeutic agents that are safe and effective TYK2 inhibitors and pharmaceutical compositions of these compounds and methods of preparation and use thereof against various TYK2-mediated diseases and disorders.

22 Claims, No Drawings

(56) References Cited

FOREIGN PATENT DOCUMENTS

| WO | 2021211741 A1 | 10/2021 |
| WO | 2022213980 A1 | 10/2022 |
| WO | 2022219380 A1 | 10/2022 |

OTHER PUBLICATIONS

PCT/CN2021/138744, Int'l Search Report and Written Opinion of ISA, Sep. 8, 2022.
PCT/CN2022/106876, Int'l Search Report and Written Opinion of ISA, Oct. 20, 2022.
PCT/CN2022/139649, Int'l Search Report and Written Opinion of ISA, Mar. 9, 2023.

TYK2 INHIBITORS AND COMPOSITIONS AND METHODS THEREOF

PRIORITY CLAIMS AND RELATED PATENT APPLICATIONS

This application claims the benefit of priority to PCT International application Nos. PCT/CN2022/139649, filed Dec. 16, 2022; PCT/CN2022/106876, filed Jul. 20, 2022 and PCT/CN2021/138744, filed on Dec. 16, 2021, the entire content of each of which is incorporated herein by reference for all purposes.

TECHNICAL FIELDS OF THE INVENTION

The invention generally relates to novel compounds and methods for their therapeutic use. More particularly, the invention provides a novel class of tyrosine kinase 2 inhibitors as well as pharmaceutical compositions of these compounds and methods of preparation and use thereof against various diseases and conditions.

BACKGROUND OF THE INVENTION

Janus kinase (JAK) is a family of intracellular, nonreceptor tyrosine kinases that transduce cytokine-mediated signals via the Janus kinase-Signal Transduction Activators of Transcription (JAK-STAT) pathway. There are four members in the JAK family of enzymes in humans, i.e., JAK1, JAK2, JAK3 and tyrosine kinase 2 (TYK2). The family is defined by the presence of two adjacent kinase domains, JH1 and JH2, of which JH1 performs the phosphorylation involved in pathway activation whereas JH2 regulates JH1 function. (Thomas, et al., 2015 *British Journal of Cancer* 113, 365-371.)

These cytoplasmic tyrosine kinases are associated with membrane cytokine receptors such as common gamma-chain receptors and the glycoprotein 130 (gp130) transmembrane proteins. (Murray, et al. 2007 *Immunol*. 178(5):2623-2629.) About 40 cytokine receptors signal through combinations of these four JAKs and their 7 downstream substrates: the STAT family members. (Ghoreschi et al. 2009 *Immunol Rev.* 228(1):273-287.)

TYK2 is a key component of the JAK-STAT signaling pathway. TYK2 regulates INFα, IL12 and IL23. (Ihle, et al. 1995 *Annu Rev Immunol.* 13:369-398; Leonard, et al. 1998 *Annu Rev Immunol.* 16:293-322; Liu, et al. 1998 *Curr Opin Immunol.* 10:271-278.) Cytokines implicated in TYK2 activation include interferons (e.g., IFN-a, IFN-b, IFN-k, IFN-d, IFN-e, IFN-t, IFN-w, and IFN-z, and interleukins (e.g., IL-4, IL-6, IL-10, IL-11, IL-12, IL-13, L-22, IL-23, IL-27, IL-31, oncostatin M, ciliary neurotrophic factor, cardiotrophin 1, cardiotrophin-like cytokine, and LIF). The activated TYK2 goes on to phosphorylate further signaling proteins such as members of the STAT family, including STAT1, STAT2, STAT4, and STAT6. Selective inhibition of TYK2 can be utilized to treat a variety of autoimmune inflammatory diseases, such as psoriasis, systemic lupus erythematosus (SLE), inflammatory bowel disease (IBD), rheumatoid arthritis (RA), as well as cancer and diabetes.

The selectivity against other JAK family subtypes is regarded as crucial in order to increase the intended pharmacological effects and to reduce side effects. Identifying kinase inhibitors with a high degree of TYK2 selectivity has posed a significant challenge partly due to the high sequence homology of the active site among the JAK family kinases. TYK2 specificity is critical for clinical application of TYK2 kinase inhibitors, because Tyk2 knockout mice are viable with normal blood cell counts, whereas deficiency of JAK3 results in severe combined immunodeficiency in mice, and JAK1 or JAK2 knockout mice show perinatal lethality. (Ghoreschi, et al. 2009 *Immunol Rev.* 228:273-287; Karaghiosoff, et al. 2000 *Immunity.* 13:549-560; Shimoda, et al. 2000 *Immunity.* 13:561-571.) Genetic evidence suggests that pharmacological inhibition of TYK2 should not result in acute toxicity in human patients, but careful monitoring for viral or mycobacterial infections would be warranted in patients treated for prolonged periods. (Akahane, et al. 2017 *Br J Haematol.* 177(2): 271-282.)

An urgent need exists and challenges remain across broad therapeutic areas for selective TYK2 inhibitors with improved potency and minimal side effects.

SUMMARY OF THE INVENTION

The invention provides novel, selective and potent compounds that are orally available. These therapeutic agents are safe and effective TYK2 inhibitors and exhibit fewer and/or lesser side effects than currently available drugs. The invention also provides pharmaceutical compositions of these compounds and methods of their preparation and use.

In one aspect, the invention generally relates to a compound having the structural formula (I):

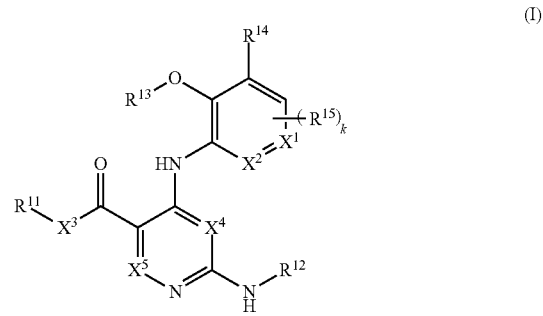

or a pharmaceutically acceptable form or an isotope derivative thereof,
wherein
each of $X^1$ and $X^2$ is independently selected from CH and N;
each of $X^4$ and $X^5$ is independently selected from CH, CF and N;
$X^3$ is NR, O, $CH_2$ or $CF_2$;
$R^{11}$ is a H, F, $C_1$-$C_3$ alkyl or $CD_3$, provided that $R^{11}$ is not F when $X^3$ is NR or O;
$R^{12}$ is C(=O)$R^{12'}$ or $R^{12'}$, wherein $R^{12'}$ is a $C_1$-$C_6$ alkyl, $C_3$-$C_6$ cycloalkyl or heterocycloalkyl, aryl or heteroaryl, each substituted with 0-2 $R^{12a}$, wherein $R^{12a}$ is selected from the group consisting of halogen, $CF_3$, CN, OR, amino, alkyl, cycloalkyl, heterocyclic, aryl and heteroaryl;
$R^{13}$ is a $C_1$-$C_3$ alkyl, $CD_3$ or $CF_3$;
$R^{14}$ is H, $C_1$-$C_6$ alkyl or heteroalkyl or a $C_3$-$C_6$ cycloalkyl or heterocycloalkyl, or a 5- or 6-membered heteroaryl group comprising 1, 2 or 3 hetero atoms selected from N, O and S, or $R^{14}$ is $OR^{14'}$, wherein $R^{14'}$ is $C_1$-$C_6$ alkyl or heteroalkyl or a $C_3$-$C_6$ cycloalkyl or heterocycloalkyl, each substituted with 0-2 $R^{14a}$, wherein $R^{14a}$ is selected from the group consisting of halogen, R, OR, amino, $CF_3$ and CN;

$R^{15}$ at each occurrence is independently selected from F, Cl, CN, OR, NRR', and a $C_1$-$C_3$ alkyl;

R at each occurrence is independently H or a $C_1$-$C_6$ alkyl; and k is 0, 1, 2 or 3.

In another aspect, the invention generally relates to a compound having the structural formula (II):

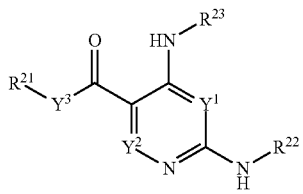
(II)

or a pharmaceutically acceptable form or an isotope derivative thereof,
wherein
$Y^1$ is CH, CF or N;
$Y^2$ is CH or N;
$Y^3$ is NR, O, $CH_2$ or $CF_2$;
$R^{21}$ is a H, F, $C_1$-$C_3$ alkyl and $CD_3$, provided that $R^{21}$ is not F when $Y^3$ is N or O;
$R^{22}$ is
  $R^{22'}$, wherein $R^{22'}$ is a $C_1$-$C_6$ alkyl, $C_3$-$C_6$ cycloalkyl or heterocycloalkyl, aryl or heteroaryl, each substituted with 0-2 $R^{22a}$, wherein $R^{22a}$ is selected from the group consisting of halogen, CN, OR, amino, alkyl, cycloalkyl, heterocyclic;
  an aryl or heteroaryl group, each substituted with 0-2 $R^{22a}$; or (C=O)$R^{27}$;
$R^{23}$ is

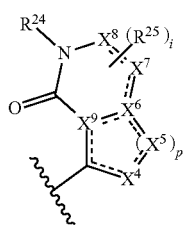

wherein
each of $X^4$, $X^5$, $X^6$, $X^7$, $X^8$ and $X^9$ is independently selected from O, C, CH, S, N and $NR^{26}$;
$R^{24}$ is H and $C_{1-6}$ alkyl, substituted with 0-3 $R^{24a}$, or $C_{3-10}$ cycloalkyl or heterocycloalkyl, $C_{5-10}$ aryl or heteroaryl, or a 4- to 10-membered heterocycle having 1-4 heteroatoms selected from N, O and S, each group is substituted with 0-4 $R^{24b}$;
$R^{24a}$ at each occurrence is independently H, D, halo, OH, OR, $CH_3$, $CF_3$, $CH_2CF_3$ or CN, NRR', $(CH_2)_n$NRR' or a 4- to 6-membered heterocycle having 1-4 heteroatoms selected from N, O and S;
$R^{24b}$ at each occurrence is independently H, halo, CN, OR, NRR', $OCF_3$, $CF_3$, $C_{1-6}$ alkyl, $C_{3-10}$ cycloalkyl, heterocycloalkyl, aryl, or heteroaryl, each substituted with 0-3 $R^{24a}$, $C_{1-6}$ haloalkyl, $C_{2-6}$ alkenyl substituted with 0-3 $R^{24a}$, $C_{2-6}$ alkynyl substituted with 0-3 $R^{24a}$;
$R^{25}$ is F, Cl, CN, $CD_3$, $CH_2CF_3$, $CF_3$, OR, NRR', $C_1$-$C_3$ alkyl, $C_3$-$C_5$ cycloalkyl, substituted with 0-2 $R^{24b}$;

$R^{26}$ is H, a $C_1$-$C_6$ alkyl, $CD_3$, or $C_3$-$C_6$ cycloalkyl, substituted with 0-3 $R^{24a}$;
$R^{27}$ is a $C_{1-6}$ alkyl or $C_{3-6}$ cycloalkyl, aryl or heteroaryl, each substituted with 0-2 $R^{24b}$;
each of R and R' is independently H or a $C_1$-$C_6$ alkyl, or R and R', together with the nitrogen atom to which they are bound, form a 4- to 7-membered ring comprising 0-2 heteroatoms selected from O, NR, S and $SO_2$;
n is 0, 1, 2, 3 or 4;
i is 0, 1 or 2; and
p is 1 or 2.

In yet another aspect, the invention generally relates to a compound having the structural formula (III):

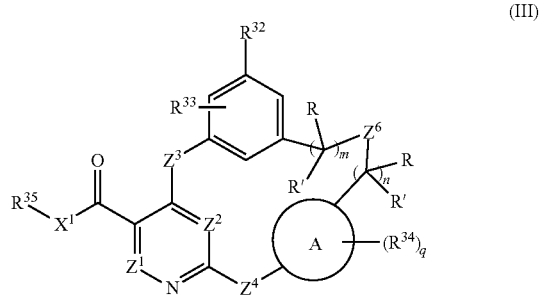
(III)

or a pharmaceutically acceptable form or an isotope derivative thereof,
wherein
Ring A is a 5- or 6-membered aryl or heteroaryl;
$X^1$ is selected from NR, O, $CH_2$ and $CF_2$;
$Z^1$ is CH or N;
$Z^2$ is CH, CF or N;
each of $Z^3$ and $Z^4$ is independently selected from NR, $CH_2$ and $CF_2$;
$Z^6$ is $NR^{36}$, $CH_2$, O, S, SO or $SO_2$;
$R^{32}$ is $R^{32'}$ or $OR^{32'}$, wherein $R^{32'}$ is a $C_{1-12}$ alkyl, 3- to 6-membered cycloalkyl or heterocycloalkyl comprising 1, 2 or 3 heteroatoms selected from N, O and S, or a 5- or 6-membered aryl or heteroaryl group, each substituted with 0-3 $R^{32a}$;
$R^{32a}$ is independently at each occurrence, H, $OCF_3$, CN, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, $(CH_2)_rNR^gR^g$, —$(CH_2)_rC(O)NR^gR^g$, —$(CH_2)_rNR^bC(O)R^c$, —$(CH_2)_rNR^bC(O)OR^c$, —$NR^bC(O)NR^gR^g$, —$S(O)_vNR^gR^g$, —$NR^b$ $S(O)_vR^c$, —$S(O)_vR^c$, $C_{1-6}$ alkyl substituted with 0-3 $R^a$, $C_{1-6}$ haloalkyl, $C_{2-6}$ alkenyl substituted with 0-3 $R^a$, 3- to 6-membered cycloalkyl substituted with 0-3 $R^a$, or 3- to 6-membered heterocycloalkyl comprising 1-3 heteroatoms selected from N, O and S substituted with 0-3 $R^a$;
each of $R^{33}$ and $R^{34}$ is independently selected from H, F, Cl, CN, $OR^g$, $CH_3$, $CD_3$, $CF_3$, $OCD_3$, $OCF_3$ and —$(CH_2)_p$-Q;
$R^{35}$ is H, F, a $C_1$-$C_3$ alkyl and $CD_3$, provided that $R^{35}$ is not F when $X^1$ is O or N;
$R^{36}$ is R substituted with 0-3 $R^d$;
$R^a$ at each occurrence is independently H, F, Cl, Br, $OCF_3$, $CF_3$, $CHF_2$, CN, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^gR^g$, —$(CH_2)_rC(O)$ $NR^gR^g$, —$(CH_2)_rNR^bC(O)R^c$, —$(CH_2)_rNR^bC(O)$ $OR^c$, —$NR^bC(O)NR^gR^g$, —$S(O)_vNR^gR^g$, —$NR^bS$ (O)$_v$R$^c$, —S(O)R$^c$, —S(O)$_2$R$^c$, C$_{1-6}$ alkyl substituted with 0-3 R$^f$, C$_{1-6}$ haloalkyl, 3- to 6-membered cycloalkyl substituted with 0-3 R$^f$, or 3- to 6-membered heterocycloalkyl comprising 1-3 heteroatoms selected from N, O and S substituted with 0-3 R$^f$;

R$^b$ is H, C$_{1-6}$ alkyl substituted with 0-3 R$^d$, C$_{1-6}$ haloalkyl, C$_{3-6}$ cycloalkyl substituted with 0-2 R$^d$, or 5- to 7-membered heterocycloalkyl comprising 1-3 heteroatoms selected from N, O and S substituted with 0-3 R$^f$ or (CH$_2$)$_r$-phenyl substituted with 0-3 R$^f$;

R$^c$ is C$_{1-6}$ alkyl substituted with 0-3 R$^f$, (CH$_2$), —C$_3$-C$_6$ cycloalkyl substituted with 0-3 R$^f$ or (CH$_2$)$_r$-phenyl substituted with 0-3 R$^f$;

R$^d$ is independently at each occurrence, hydrogen, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, C$_{1-6}$ alkyl or (CH$_2$)$_r$-phenyl substituted with 0-3 R$^f$;

R$^e$ is independently at each occurrence, hydrogen, C$_{1-6}$ alkyl, C$_{3-6}$ cycloalkyl or (CH$_2$)$_r$-phenyl substituted with 0-3 R$^f$;

R$^f$ is independently at each occurrence, hydrogen, halo, CN, NH$_2$, OH, C$_{3-6}$ cycloalkyl, CF$_3$, O(C$_{1-6}$ alkyl) or a 5- to 7-membered heterocycloalkyl comprising 1-3 heteroatoms selected from N, O and S;

R$^g$ at each occurrence is independently H, C$_{1-4}$ alkyl substituted with 0-3 R$^f$, CF$_3$, C$_{3-10}$ cycloalkyl substituted with 0-1 R$^f$, (CH) r-phenyl substituted with 0-3 R$^d$ or 5- to 7-membered heterocycloalkyl comprising 1-3 heteroatoms selected from N, O and S substituted with 0-3 R$^d$;

Q is a water solubilizing group, optionally selected from OH, OR, NRR', heterocyclic and heteroaryl groups, wherein R and R', together with the nitrogen atom to which they are bound, form a 4- to 7-membered ring comprising 0-2 heteroatoms selected from O, NR, S and SO$_2$;

R is H or a C$_1$-C$_6$ alkyl substituted with 0-3 R$^d$;

R' is H or a C$_1$-C$_6$ alkyl substituted with 0-3 R$^d$;

m is 0, 1, 2 and 3;
n is 0, 1, 2 and 3;
p is 0, 1, 2, 3 or 4;
q is 0, 1, 2, 3 or 4;
v is 0, 1, or 2; and
r is 0, 1, 2, 3, 4 or 5.

In yet another aspect, the invention generally relates to a compound having the structural formula (IV):

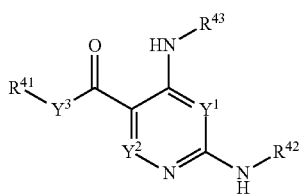

(IV)

or a pharmaceutically acceptable form or an isotope derivative thereof,
wherein
Y$^1$ is CH, CF or N;
Y$^2$ is CH or N;
Y$^3$ is NR, O, CH$_2$ or CF$_2$;
R$^{41}$ is a H, F, C$_1$-C$_3$ alkyl and CD$_3$, provided that R$^{41}$ is not F when Y$^3$ is NR or O;

R$^{42}$ is
R$^{42'}$, wherein R$^{42'}$ is a C$_1$-C$_6$ alkyl, C$_3$-C$_6$ cycloalkyl or heterocycloalkyl, aryl or heteroaryl, each substituted with 0-2 of halogen, CN, OR, amino, alkyl, cycloalkyl, heterocyclic, aryl and heteroaryl;

an aryl or heteroaryl group substituted with 0-2 R$^{42a}$; or (C=O)R$^{42b}$;

R$^{43}$ is

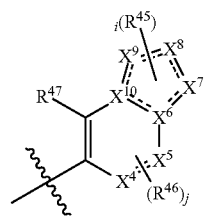

wherein each of X$^4$, X$^5$, X$^6$, X$^7$, X$^8$, X$^9$ and X$^{10}$ is independently selected from C, CH, O, N and NH;

R$^{42a}$ at each occurrence is independently H, D, halo, OH, OR, CH$_3$, CF$_3$, CH$_2$CF$_3$, CN, C(O)NR, NRR', (CH$_2$)$_n$NRR' or a 4- to 6-membered heterocycle having 1-4 heteroatoms selected from N, O and S;

R$^{42b}$ is a C$_{1-6}$ alkyl or C$_{3-6}$ cycloalkyl, aryl or heteroaryl, each substituted with 0-2 R$^{42c}$;

R$^{42c}$ at each occurrence is independently H, halo, CN, OR, NRR', OCF$_3$, CF$_3$, C$_{1-6}$ alkyl substituted with 0-3 R$^{42a}$, C$_{1-6}$ haloalkyl, C$_{2-6}$ alkenyl substituted with 0-3 R$^{42a}$, C$_{2-6}$ alkynyl substituted with 0-3 R$^{42a}$;

R$^{45}$ each occurrence is independently H, halo, CN, OR, NRR', OCF$_3$, CF$_3$, C$_{1-6}$ alkyl, substituted with 0-3 R$^{42a}$, or C$_{3-10}$ cycloalkyl or heterocycloalkyl, C$_{5-10}$ aryl or heteroaryl, or a 4- to 10-membered heterocycle having 1-4 heteroatoms selected from N, O and S, each group is substituted with 0-4 R$^{42c}$, optionally two R$^{45}$s, along with the C or N atoms that they are attached to, form a 4- to 6-membered ring;

R$^{46}$ each occurrence is independently F, Cl, CN, OR, C$_1$-C$_3$ alkyl, C$_3$-C$_5$ cycloalkyl, CD$_3$, CH$_2$CF$_3$ or CF$_3$;

R$^{47}$ is H, OCF$_3$, C$_1$-C$_3$ alkyl, C$_1$-C$_3$ alkoxy or OCD$_3$;

each of R and R' is independently H or a C$_1$-C$_6$ alkyl, or R and R', together with the nitrogen atom to which they are bound, form a 4- to 7-membered ring comprising 0-2 heteroatoms selected from O, NR, S and SO$_2$;

n is 0, 1, 2, 3 or 4;
i is 0, 1 or 2; and
j is 0, 1 or 2.

In yet another aspect, the invention generally relates to a compound having the structural formula (V):

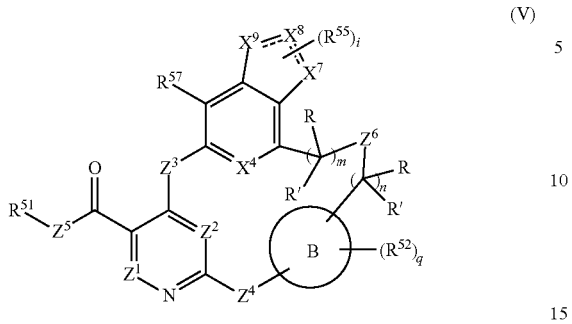

(V)

or a pharmaceutically acceptable form or an isotope derivative thereof,
wherein
Ring B is a 5- or 6-membered aryl or heteroaryl;
$Z^1$ is CH or N;
$Z^2$ is CH, CF or N;
each of $Z^3$ and $Z^4$ is independently selected from NR, $CH_2$ and $CF_2$;
$Z^5$ is selected from NR, O, $CH_2$ and $CF_2$;
$Z^6$ is $NR^{56}$, $CH_2$, O, S, SO or $SO_2$;
each of $X^4$, $X^7$, $X^8$ and $X^9$ is independently selected from CH, N and NH;
$R^{51}$ is a H, F, $C_1$-$C_3$ alkyl and $CD_3$, provided that $R^{51}$ is not F when $Z^5$ is N or O;
$R^{52}$ is independently selected from H, F, Cl, CN, $OR^g$, $CH_3$, $CF_3$, $OCF_3$ and —$(CH_2)_p$-Q;
$R^{52a}$ at each occurrence is independently H, D, halo, OH, OR, $CH_3$, $CF_3$, $CH_2CF_3$ or CN, NRR', $(CH_2)_n$NRR' or a 4- to 6-membered heterocycle having 1-4 heteroatoms selected from N, O and S;
$R^{52c}$ at each occurrence is independently H, halo, CN, OR, NRR', $OCF_3$, $CF_3$, $C_{1-6}$ alkyl substituted with 0-3 $R^{52a}$, $C_{1-6}$ haloalkyl, $C_{2-6}$ alkenyl substituted with 0-3 $R^{52a}$, $C_{2-6}$ alkynyl substituted with 0-3 $R^{52a}$;
$R^{55}$ each occurrence is independently H, $C_{1-6}$ alkyl, substituted with 0-3 $R^{52a}$, or $C_{3-10}$ cycloalkyl or heterocycloalkyl, $C_{5-10}$ aryl or heteroaryl, or a 4- to 10-membered heterocycle having 1-4 heteroatoms selected from N, O and S, each group is substituted with 0-4 $R^{52c}$;
$R^{56}$ is R substituted with 0-3 $R^d$;
$R^{57}$ is H, $C_1$-$C_3$ alkyl, $C_1$-$C_3$ alkoxy, $OCD_3$ or $OCF_3$;
$R^c$ is $C_{1-6}$ alkyl substituted with 0-3 $R^f$, $(CH_2)_r$—$C_{3-6}$ cycloalkyl substituted with 0-3 $R^f$ or $(CH_2)_r$-phenyl substituted with 0-3 $R^f$;
$R^d$ is independently at each occurrence, hydrogen, F, Cl, Br, $OCF_3$, $CF_3$, CN, $NO_2$, —$OR^e$, —$(CH_2)_rC(O)$ $R^c$, —$NR^eR^e$, —$NR^eC(O)OR^c$, $C_{1-6}$ alkyl or $(CH_2)_r$-phenyl substituted with 0-3 $R^f$;
$R^e$ is independently at each occurrence, hydrogen, $C_{1-6}$ alkyl, $C_{3-6}$ cycloalkyl or $(CH_2)_r$-phenyl substituted with 0-3 $R^f$;
$R^f$ is independently at each occurrence, hydrogen, halo, CN, $NH_2$, OH, $C_{3-6}$ cycloalkyl, $CF_3$, $O(C_{1-6}$ alkyl) or a 5- to 7-membered heterocycloalkyl comprising 1-3 heteroatoms selected from N, O and S;
$R^g$ at each occurrence is independently H, $C_{1-4}$ alkyl substituted with 0-3 $R^f$, $CF_3$, $C_{3-10}$ cycloalkyl substituted with 0-1 $R^f$, $(CH)_r$-phenyl substituted with 0-3 $R^d$ or 5- to 7-membered heterocycloalkyl comprising 1-3 heteroatoms selected from N, O and S substituted with 0-3 $R^d$;
Q is a water solubilizing group, optionally selected from OH, OR, NRR', heterocyclic and heteroaryl groups, wherein R and R', together with the nitrogen atom to which they are bound, form a 4- to 7-membered ring comprising 0-2 heteroatoms selected from O, NR, S and $SO_2$;
R is H or a $C_1$-$C_6$ alkyl substituted with 0-3 $R^d$;
R' is H or a $C_1$-$C_6$ alkyl substituted with 0-3 $R^d$;
i is 0, 1, 2 and 3;
m is 0, 1, 2 and 3;
n is 0, 1, 2 and 3;
p is 0, 1, 2, 3 or 4; and
q is 0, 1, 2, 3 or 4.

In yet another aspect, the invention generally relates to a pharmaceutical composition comprising a compound disclosed herein, effective to treat or reduce one or more diseases or disorders, in a mammal, including a human, and a pharmaceutically acceptable excipient, carrier, or diluent.

In yet another aspect, the invention generally relates to a pharmaceutical composition comprising an amount of a compound having the structural formula of (I):

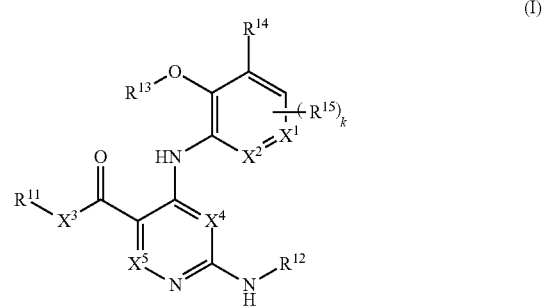

(I)

or a pharmaceutically acceptable form or an isotope derivative thereof,
wherein
each of $X^1$ and $X^2$ is independently selected from CH and N;
each of $X^4$ and $X^5$ is independently selected from CH, CF and N;
$X^3$ is NR, O, $CH_2$ or $CF_2$;
$R^{11}$ is a H, F, $C_1$-$C_3$ alkyl or $CD_3$, provided that $R^{11}$ is not F when $X^3$ is NR or O;
$R^{12}$ is C(=O)$R^{12'}$ or $R^{12'}$, wherein $R^{12'}$ is a $C_1$-$C_6$ alkyl, $C_3$-$C_6$ cycloalkyl or heterocycloalkyl, aryl or heteroaryl, each substituted with 0-2 $R^{12a}$, wherein $R^{12a}$ is selected from the group consisting of halogen, $CF_3$, CN, OR, amino, alkyl, cycloalkyl, heterocyclic, aryl and heteroaryl;
$R^{13}$ is a $C_1$-$C_3$ alkyl, $CD_3$ or $CF_3$;
$R^{14}$ is H, $C_1$-$C_6$ alkyl or heteroalkyl or a $C_3$-$C_6$ cycloalkyl or heterocycloalkyl, or a 5- or 6-membered heteroaryl group comprising 1, 2 or 3 hetero atoms selected from N, O and S, or $R^{14}$ is $OR^{14'}$, wherein $R^{14'}$ is $C_1$-$C_6$ alkyl or heteroalkyl or a $C_3$-$C_6$ cycloalkyl or heterocycloalkyl, each substituted with 0-2 $R^{14a}$, wherein $R^{14a}$ is selected from the group consisting of halogen, R, OR, amino, $CF_3$ and CN;
$R^{15}$ at each occurrence is independently selected from F, Cl, CN, OR, NRR', and a $C_1$-$C_3$ alkyl;

R at each occurrence is independently H or a $C_1$-$C_6$ alkyl; and k is 0, 1, 2 or 3, or a pharmaceutically acceptable form or an isotope derivative thereof, effective to treat, or reduce one or more diseases or disorders, in a mammal, including a human, and a pharmaceutically acceptable excipient, carrier, or diluent.

In yet another aspect, the invention generally relates to a pharmaceutical composition comprising an amount of a compound having the structural formula of (II):

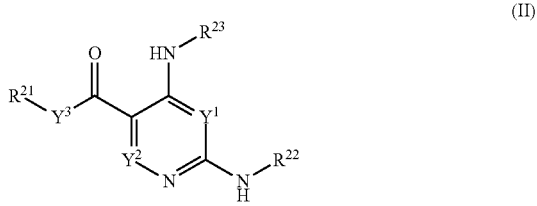

(II)

or a pharmaceutically acceptable form or an isotope derivative thereof, wherein $Y^1$ is CH, CF or N;

$Y^2$ is CH or N;

$Y^3$ is NR, O, $CH_2$ or $CF_2$;

$R^{21}$ is a H, F, $C_1$-$C_3$ alkyl and $CD_3$, provided that $R^{21}$ is not F when $Y^3$ is N or O;

$R^{22}$ is $R^{22'}$, wherein $R^{22'}$ is a $C_1$-$C_6$ alkyl, $C_3$-$C_6$ cycloalkyl or heterocycloalkyl, aryl or heteroaryl, each substituted with 0-2 $R^{22a}$, wherein $R^{22a}$ is selected from the group consisting of halogen, CN, OR, amino, alkyl, cycloalkyl, heterocyclic;

an aryl or heteroaryl group, each substituted with 0-2 $R^{22a}$; or (C=O)$R^{27}$;

$R^{23}$ is

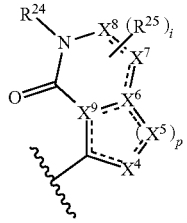

wherein each of $X^4$, $X^5$, $X^6$, $X^7$, $X^8$ and $X^9$ is independently selected from O, C, CH, S, N and $NR^{26}$;

$R^{24}$ is H and $C_{1-6}$ alkyl, substituted with 0-3 $R^{24a}$, or $C_{3-10}$ cycloalkyl or heterocycloalkyl, $C_{5-10}$ aryl or heteroaryl, or a 4- to 10-membered heterocycle having 1-4 heteroatoms selected from N, O and S, each group is substituted with 0-4 $R^{24b}$;

$R^{24a}$ at each occurrence is independently H, D, halo, OH, OR, $CH_3$, $CF_3$, $CH_2CF_3$ or CN, NRR', $(CH_2)_n$NRR' or a 4- to 6-membered heterocycle having 1-4 heteroatoms selected from N, O and S;

$R^{24b}$ at each occurrence is independently H, halo, CN, OR, NRR', $OCF_3$, $CF_3$, $C_{1-6}$ alkyl, $C_{3-10}$ cycloalkyl, heterocycloalkyl, aryl, or heteroaryl, each substituted with 0-3 $R^{24a}$, $C_{1-6}$ haloalkyl, $C_{2-6}$ alkenyl substituted with 0-3 $R^{24a}$, $C_{2-6}$ alkynyl substituted with 0-3 $R^{24a}$;

$R^{25}$ is F, Cl, CN, $CD_3$, $CH_2CF_3$, $CF_3$, OR, NRR', $C_1$-$C_3$ alkyl, $C_3$-$C_5$ cycloalkyl, substituted with 0-2 $R^{24b}$;

$R^{26}$ is H, a $C_1$-$C_6$ alkyl, $CD_3$, or $C_3$-$C_6$ cycloalkyl, substituted with 0-3 $R^{24a}$;

$R^{27}$ is a $C_{1-6}$ alkyl or $C_{3-6}$ cycloalkyl, aryl or heteroaryl, each substituted with 0-2 $R^{24b}$;

each of R and R' is independently H or a $C_1$-$C_6$ alkyl, or R and R', together with the nitrogen atom to which they are bound, form a 4- to 7-membered ring comprising 0-2 heteroatoms selected from O, NR, S and $SO_2$;

n is 0, 1, 2, 3 or 4;

i is 0, 1 or 2; and p is 1 or 2, effective to treat, or reduce one or more diseases or disorders, in a mammal, including a human, and a pharmaceutically acceptable excipient, carrier, or diluent.

In yet another aspect, the invention generally relates to a pharmaceutical composition comprising an amount of a compound having the structural formula (III):

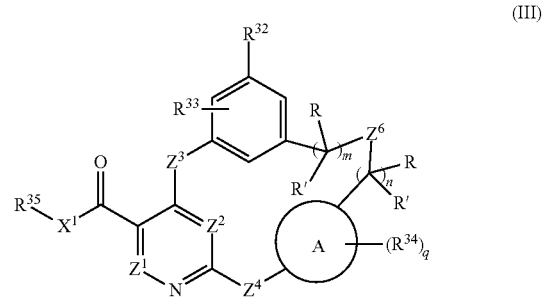

(III)

or a pharmaceutically acceptable form or an isotope derivative thereof, wherein

Ring A is a 5- or 6-membered aryl or heteroaryl;

$X^1$ is selected from NR, O, $CH_2$ and $CF_2$;

$Z^1$ is CH or N;

$Z^2$ is CH, CF or N;

each of $Z^3$ and $Z^4$ is independently selected from NR, $CH_2$ and $CF_2$;

$Z^6$ is $NR^{36}$, $CH_2$, O, S, SO or $SO_2$;

$R^{32}$ is $R^{32'}$ or $OR^{32'}$, wherein $R^{32'}$ is a $C_{1-12}$ alkyl, 3- to 6-membered cycloalkyl or heterocycloalkyl comprising 1, 2 or 3 heteroatoms selected from N, O and S, or a 5- or 6-membered aryl or heteroaryl group, each substituted with 0-3 $R^{32a}$;

$R^{32a}$ is independently at each occurrence, H, $OCF_3$, CN, $-(CH_2)_rOR^b$, $-(CH_2)_rSR^b$, $-(CH_2)_rC(O)R^b$, $-(CH_2)_rC(O)OR^b$, $-(CH_2)_rOC(O)R^b$, $(CH_2)_rNR^gR^g$, $-(CH_2)_rC(O)NR^gR^g$, $-(CH_2)_rNR^bC(O)R^c$, $-(CH_2)_rNR^bC(O)OR^c$, $-NR^bC(O)NR^gR^g$, $-S(O)_vNR^gR^g$, $-NR^bS(O)_vR^c$, $-S(O)_vR^c$, $C_{1-6}$ alkyl substituted with 0-3 $R^a$, $C_{1-6}$ haloalkyl, $C_{2-6}$ alkenyl substituted with 0-3 $R^a$, 3- to 6-membered cycloalkyl substituted with 0-3 $R^a$, or 3- to 6-membered heterocycloalkyl comprising 1-3 heteroatoms selected from N, O and S substituted with 0-3 $R^a$;

each of $R^{33}$ and $R^{34}$ is independently selected from H, F, Cl, CN, $OR^g$, $CH_3$, $CD_3$, $CF_3$, $OCD_3$, $OCF_3$ and $-(CH_2)_p$-Q;

$R^{35}$ is H, F, a $C_1$-$C_3$ alkyl and $CD_3$, provided that $R^{35}$ is not F when $X^1$ is O or N;

11

$R^{36}$ is R substituted with 0-3 $R^d$;

$R^a$ at each occurrence is independently H, F, Cl, Br, $OCF_3$, $CF_3$, $CHF_2$, CN, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^gR^g$, —$(CH_2)_rC(O)NR^gR^g$, —$(CH_2)_rNR^bC(O)R^c$, —$(CH_2)_rNR^bC(O)OR^c$, —$NR^bC(O)NR^gR^g$, —$S(O)_vNR^gR^g$, —$NR^bS(O)_vR^c$, —$S(O)R^c$, —$S(O)_2R^c$, $C_{1-6}$ alkyl substituted with 0-3 $R^f$, $C_{1-6}$ haloalkyl, 3- to 6-membered cycloalkyl substituted with 0-3 $R^f$, or 3- to 6-membered heterocycloalkyl comprising 1-3 heteroatoms selected from N, O and S substituted with 0-3 $R^f$;

$R^b$ is H, $C_{1-6}$ alkyl substituted with 0-3 $R^d$, $C_{1-6}$ haloalkyl, $C_{3-6}$ cycloalkyl substituted with 0-2 $R^d$, or 5- to 7-membered heterocycloalkyl comprising 1-3 heteroatoms selected from N, O and S substituted with 0-3 $R^f$ or $(CH_2)_r$-phenyl substituted with 0-3 $R^d$;

$R^c$ is $C_{1-6}$ alkyl substituted with 0-3 $R^f$, $(CH_2)_r$—$C_{3-6}$ cycloalkyl substituted with 0-3 $R^f$ or $(CH_2)_r$-phenyl substituted with 0-3 $R^f$;

$R^d$ is independently at each occurrence, hydrogen, F, Cl, Br, $OCF_3$, $CF_3$, CN, $NO_2$, —$OR^e$, —$(CH_2)_rC(O)R^c$, —$NR^eR^e$, —$NR^eC(O)OR^e$, $C_{1-6}$ alkyl or $(CH_2)_r$-phenyl substituted with 0-3 $R^f$;

$R^e$ is independently at each occurrence, hydrogen, $C_{1-6}$ alkyl, $C_{3-6}$ cycloalkyl or $(CH_2)_r$-phenyl substituted with 0-3 $R^f$;

$R^f$ is independently at each occurrence, hydrogen, halo, CN, $NH_2$, OH, $C_{3-6}$ cycloalkyl, $CF_3$, $O(C_{1-6}$ alkyl) or a 5- to 7-membered heterocycloalkyl comprising 1-3 heteroatoms selected from N, O and S;

$R^g$ at each occurrence is independently H, $C_{1-4}$ alkyl substituted with 0-3 $R^f$, $CF_3$, $C_{3-10}$ cycloalkyl substituted with 0-1 $R^f$, $(CH_2)_r$-phenyl substituted with 0-3 $R^d$ or 5- to 7-membered heterocycloalkyl comprising 1-3 heteroatoms selected from N, O and S substituted with 0-3 $R^d$;

Q is a water solubilizing group, optionally selected from OH, OR, NRR', heterocyclic and heteroaryl groups, wherein R and R', together with the nitrogen atom to which they are bound, form a 4- to 7-membered ring comprising 0-2 heteroatoms selected from O, NR, S and $SO_2$;

R is H or a $C_1$-$C_6$ alkyl substituted with 0-3 $R^d$;
R' is H or a $C_1$-$C_6$ alkyl substituted with 0-3 $R^d$;
m is 0, 1, 2 and 3;
n is 0, 1, 2 and 3;
p is 0, 1, 2, 3 or 4;
q is 0, 1, 2, 3 or 4;
v is 0, 1, or 2; and
r is 0, 1, 2, 3, 4 or 5, effective to treat, or reduce one or more diseases or disorders, in a mammal, including a human, and a pharmaceutically acceptable excipient, carrier, or diluent.

In yet another aspect, the invention generally relates to a pharmaceutical composition comprising an amount of a compound having the structural formula of (IV):

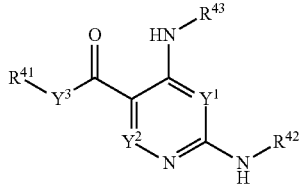

(IV)

or a pharmaceutically acceptable form or an isotope derivative thereof, wherein
$Y^1$ is CH, CF or N;
$Y^2$ is CH or N;
$Y^3$ is NR, O, $CH_2$ or $CF_2$;
$R^{41}$ is a H, F, $C_1$-$C_3$ alkyl and $CD_3$, provided that $R^{41}$ is not F when $Y^3$ is NR or O;
$R^{42}$ is
  $R^{42'}$, wherein $R^{42'}$ is a $C_1$-$C_6$ alkyl, $C_3$-$C_6$ cycloalkyl or heterocycloalkyl, aryl or heteroaryl, each substituted with 0-2 of halogen, CN, OR, amino, alkyl, cycloalkyl, heterocyclic, aryl and heteroaryl;
  an aryl or heteroaryl group substituted with 0-2 $R^{42a}$; or
  $(C=O)R^{42b}$;
$R^{43}$ is

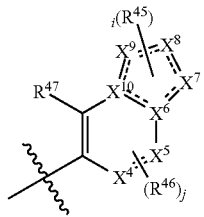

wherein
each of $X^4$, $X^5$, $X^6$, $X^7$, $X^8$, $X^9$ and $X^{10}$ is independently selected from C, CH, O, N and NH;
$R^{42a}$ at each occurrence is independently H, D, halo, OH, OR, $CH_3$, $CF_3$, $CH_2CF_3$, CN, C(O)NR, NRR', $(CH_2)_nNRR'$ or a 4- to 6-membered heterocycle having 1-4 heteroatoms selected from N, O and S;
$R^{42b}$ is a $C_{1-6}$ alkyl or $C_{3-6}$ cycloalkyl, aryl or heteroaryl, each substituted with 0-2 $R^{42c}$;
$R^{42c}$ at each occurrence is independently H, halo, CN, OR, NRR', $OCF_3$, $CF_3$, $C_{1-6}$ alkyl substituted with 0-3 $R^{42a}$, $C_{1-6}$ haloalkyl, $C_{2-6}$ alkenyl substituted with 0-3 $R^{42a}$, $C_{2-6}$ alkynyl substituted with 0-3 $R^{42a}$;
$R^{45}$ each occurrence is independently H, halo, CN, OR, NRR', $OCF_3$, $CF_3$, $C_{1-6}$ alkyl, substituted with 0-3 $R^{42a}$, or $C_{3-10}$ cycloalkyl or heterocycloalkyl, $C_{5-10}$ aryl or heteroaryl, or a 4- to 10-membered heterocycle having 1-4 heteroatoms selected from N, O and S, each group is substituted with 0-4 $R^{42c}$, optionally two $R^{45s}$, along with the C or N atoms that they are attached to, form a 4- to 6-membered ring;
$R^{46}$ each occurrence is independently F, Cl, CN, OR, $C_1$-$C_3$ alkyl, $C_3$-$C_5$ cycloalkyl, $CD_3$, $CH_2CF_3$ or $CF_3$;
$R^{47}$ is H, $OCF_3$, $C_1$-$C_3$ alkyl, $C_1$-$C_3$ alkoxy or $OCD_3$;
each of R and R' is independently H or a $C_1$-$C_6$ alkyl, or R and R', together with the nitrogen atom to which they are bound, form a 4- to 7-membered ring comprising 0-2 heteroatoms selected from O, NR, S and $SO_2$;
n is 0, 1, 2, 3 or 4;
i is 0, 1 or 2; and
j is 0, 1 or 2, effective to treat, or reduce one or more diseases or disorders, in a mammal, including a human, and a pharmaceutically acceptable excipient, carrier, or diluent.

In yet another aspect, the invention generally relates to a pharmaceutical composition comprising an amount of a compound having the structural formula of (V):

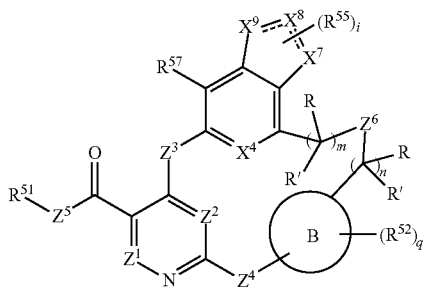

(V)

or a pharmaceutically acceptable form or an isotope derivative thereof,
wherein
Ring B is a 5- or 6-membered aryl or heteroaryl;
$Z^1$ is CH or N;
$Z^2$ is CH, CF or N;
each of $Z^3$ and $Z^4$ is independently selected from NR, $CH_2$ and $CF_2$;
$Z^5$ is selected from NR, O, $CH_2$ and $CF_2$;
$Z^6$ is $NR^{56}$, $CH_2$, O, S, SO or $SO_2$;
each of $X^4$, $X^7$, $X^8$ and $X^9$ is independently selected from CH, N and NH;
$R^{51}$ is a H, F, $C_1$-$C_3$ alkyl and $CD_3$, provided that $R^{51}$ is not F when $Z^5$ is N or O;
$R^{52}$ is independently selected from H, F, Cl, CN, $OR^g$, $CH_3$, $CF_3$, $OCF_3$ and $-(CH_2)_p$-Q;
$R^{52a}$ at each occurrence is independently H, D, halo, OH, OR, $CH_3$, $CF_3$, $CH_2CF_3$ or CN, NRR', $(CH_2)_n$NRR' or a 4- to 6-membered heterocycle having 1-4 heteroatoms selected from N, O and S;
$R^{52c}$ at each occurrence is independently H, halo, CN, OR, NRR', $OCF_3$, $CF_3$, $C_{1-6}$ alkyl substituted with 0-3 $R^{52a}$, $C_{1-6}$ haloalkyl, $C_{2-6}$ alkenyl substituted with 0-3 $R^{52a}$, $C_{2-6}$ alkynyl substituted with 0-3 $R^{52a}$;
$R^{55}$ each occurrence is independently H, $C_{1-6}$ alkyl, substituted with 0-3 $R^{52a}$, or $C_{3-10}$ cycloalkyl or heterocycloalkyl, $C_{5-10}$ aryl or heteroaryl, or a 4- to 10-membered heterocycle having 1-4 heteroatoms selected from N, O and S, each group is substituted with 0-4 $R^{52c}$;
$R^{56}$ is R substituted with 0-3 $R^d$;
$R^{57}$ is H, $C_1$-$C_3$ alkyl, $C_1$-$C_3$ alkoxy, $OCD_3$ or $OCF_3$;
$R^c$ is $C_{1-6}$ alkyl substituted with 0-3 $R^f$, $(CH_2)_r$—$C_{3-6}$ cycloalkyl substituted with 0-3 $R^f$ or $(CH_2)_r$-phenyl substituted with 0-3 $R^f$;
$R^d$ is independently at each occurrence, hydrogen, F, Cl, Br, $OCF_3$, $CF_3$, CN, $NO_2$, $-OR^e$, $-(CH_2)_rC(O)R^c$, $-NR^eR^e$, $-NR^eC(O)OR^c$, $C_{1-6}$ alkyl or $(CH_2)_r$-phenyl substituted with 0-3 $R^f$;
$R^e$ is independently at each occurrence, hydrogen, $C_{1-6}$ alkyl, $C_{3-6}$ cycloalkyl or $(CH_2)_r$-phenyl substituted with 0-3 $R^f$;
$R^f$ is independently at each occurrence, hydrogen, halo, CN, $NH_2$, OH, $C_{3-6}$ cycloalkyl, $CF_3$, $O(C_{1-6}$ alkyl) or a 5- to 7-membered heterocycloalkyl comprising 1-3 heteroatoms selected from N, O and S;
$R^g$ at each occurrence is independently H, $C_{1-4}$ alkyl substituted with 0-3 $R^f$, $CF_3$, $C_{3-10}$ cycloalkyl substituted with 0-1 $R^f$, $(CH)_r$-phenyl substituted with 0-3 $R^d$ or 5- to 7-membered heterocycloalkyl comprising 1-3 heteroatoms selected from N, O and S substituted with 0-3 $R^d$;
Q is a water solubilizing group, optionally selected from OH, OR, NRR', heterocyclic and heteroaryl groups, wherein R and R', together with the nitrogen atom to which they are bound, form a 4- to 7-membered ring comprising 0-2 heteroatoms selected from O, NR, S and $SO_2$;
R is H or a $C_1$-$C_6$ alkyl substituted with 0-3 $R^d$;
R' is H or a $C_1$-$C_6$ alkyl substituted with 0-3 $R^d$;
i is 0, 1, 2 and 3;
m is 0, 1, 2 and 3;
n is 0, 1, 2 and 3;
p is 0, 1, 2, 3 or 4; and
q is 0, 1, 2, 3 or 4,
effective to treat, or reduce one or more diseases or disorders, in a mammal, including a human, and a pharmaceutically acceptable excipient, carrier, or diluent.

In yet another aspect, the invention generally relates to a unit dosage form comprising a pharmaceutical composition disclosed herein.

In yet another aspect, the invention generally relates to a method for treating, reducing or preventing a disease or disorder, comprising administering to a subject in need thereof a therapeutically effective amount of a compound having the structural formula (I):

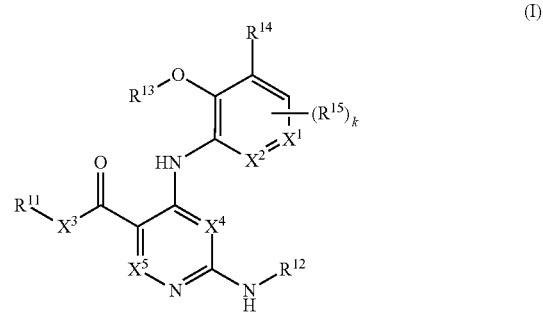

(I)

or a pharmaceutically acceptable form or an isotope derivative thereof,
wherein
each of $X^1$ and $X^2$ is independently selected from CH and N;
each of $X^4$ and $X^5$ is independently selected from CH, CF and N;
$X^3$ is NR, O, $CH_2$ or $CF_2$;
$R^{11}$ is a H, F, $C_1$-$C_3$ alkyl or $CD_3$, provided that $R^{11}$ is not F when $X^3$ is NR or O;
$R^{12}$ is $C(=O)R^{12'}$ or $R^{12'}$, wherein $R^{12'}$ is a $C_1$-$C_6$ alkyl, $C_3$-$C_6$ cycloalkyl or heterocycloalkyl, aryl or heteroaryl, each substituted with 0-2 $R^{12a}$, wherein $R^{12a}$ is selected from the group consisting of halogen, $CF_3$, CN, OR, amino, alkyl, cycloalkyl, heterocyclic, aryl and heteroaryl;
$R^{13}$ is a $C_1$-$C_3$ alkyl, $CD_3$ or $CF_3$;
$R^{14}$ is H, $C_1$-$C_6$ alkyl or heteroalkyl or a $C_3$-$C_6$ cycloalkyl or heterocycloalkyl, or a 5- or 6-membered heteroaryl group comprising 1, 2 or 3 hetero atoms selected from N, O and S, or $R^{14}$ is $OR^{14'}$, wherein $R^{14'}$ is $C_1$-$C_6$ alkyl or heteroalkyl or a $C_3$-$C_6$ cycloalkyl or heterocycloalkyl, each substituted with 0-2 $R^{14a}$, wherein $R^{14a}$ is selected from the group consisting of halogen, R, OR, amino, $CF_3$ and CN;

$R^{15}$ at each occurrence is independently selected from F, Cl, CN, OR, NRR', and a $C_1$-$C_3$ alkyl;

R at each occurrence is independently H or a $C_1$-$C_6$ alkyl; and k is 0, 1, 2 or 3, wherein the disease or disorder is selected from inflammatory diseases, immune-mediated diseases, cancer, or a related disease or disorder thereof, in a mammal, including a human.

In yet another aspect, the invention generally relates to a method for treating, reducing or preventing a disease or disorder, comprising administering to a subject in need thereof a therapeutically effective amount of a compound having the structural formula (II):

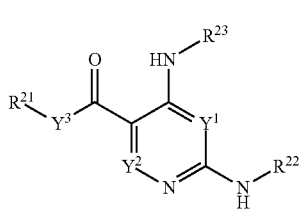

(II)

or a pharmaceutically acceptable form or an isotope derivative thereof, wherein $Y^1$ is CH, CF or N;

$Y^2$ is CH or N;

$Y^3$ is NR, O, $CH_2$ or $CF_2$;

$R^{21}$ is a H, F, $C_1$-$C_3$ alkyl and $CD_3$, provided that $R^{21}$ is not F when $Y^3$ is N or O;

$R^{22}$ is $R^{22'}$, wherein $R^{22'}$ is a $C_1$-$C_6$ alkyl, $C_3$-$C_6$ cycloalkyl or heterocycloalkyl, aryl or heteroaryl, each substituted with 0-2 $R^{22a}$, wherein $R^{22a}$ is selected from the group consisting of halogen, CN, OR, amino, alkyl, cycloalkyl, heterocyclic;

an aryl or heteroaryl group, each substituted with 0-2 $R^{22a}$; or (C=O)$R^{27}$;

$R^{23}$ is

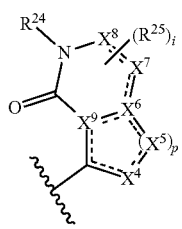

wherein each of $X^4$, $X^5$, $X^6$, $X^7$, $X^8$ and $X^9$ is independently selected from O, C, CH, S, N and $NR^{26}$;

$R^{24}$ is H and $C_{1-6}$ alkyl, substituted with 0-3 $R^{24a}$, or $C_{3-10}$ cycloalkyl or heterocycloalkyl, $C_{5-10}$ aryl or heteroaryl, or a 4- to 10-membered heterocycle having 1-4 heteroatoms selected from N, O and S, each group is substituted with 0-4 $R^{24b}$;

$R^{24a}$ at each occurrence is independently H, D, halo, OH, OR, $CH_3$, $CF_3$, $CH_2CF_3$ or CN, NRR', $(CH_2)_n$NRR' or a 4- to 6-membered heterocycle having 1-4 heteroatoms selected from N, O and S;

$R^{24b}$ at each occurrence is independently H, halo, CN, OR, NRR', $OCF_3$, $CF_3$, $C_{1-6}$ alkyl, $C_{3-10}$ cycloalkyl, heterocycloalkyl, aryl, or heteroaryl, each substituted with 0-3 $R^{24a}$, $C_{1-6}$ haloalkyl, $C_{2-6}$ alkenyl substituted with 0-3 $R^{24a}$, $C_{2-6}$ alkynyl substituted with 0-3 $R^{24a}$;

$R^{25}$ is F, Cl, CN, $CD_3$, $CH_2CF_3$, $CF_3$, OR, NRR', $C_1$-$C_3$ alkyl, $C_3$-$C_5$ cycloalkyl, substituted with 0-2 $R^{24b}$;

$R^{26}$ is H, a $C_1$-$C_6$ alkyl, $CD_3$, or $C_3$-$C_6$ cycloalkyl, substituted with 0-3 $R^{24a}$;

$R^{27}$ is a $C_{1-6}$ alkyl or $C_{3-6}$ cycloalkyl, aryl or heteroaryl, each substituted with 0-2 $R^{24b}$;

each of R and R' is independently H or a $C_1$-$C_6$ alkyl, or R and R', together with the nitrogen atom to which they are bound, form a 4- to 7-membered ring comprising 0-2 heteroatoms selected from O, NR, S and $SO_2$;

n is 0, 1, 2, 3 or 4;

i is 0, 1 or 2; and p is 1 or 2, wherein the disease or disorder is selected from inflammatory diseases, immune-mediated diseases, cancer, or a related disease or disorder thereof, in a mammal, including a human.

In yet another aspect, the invention generally relates to a method for treating, reducing or preventing a disease or disorder, comprising administering to a subject in need thereof a therapeutically effective amount of a compound having the structural formula (III):

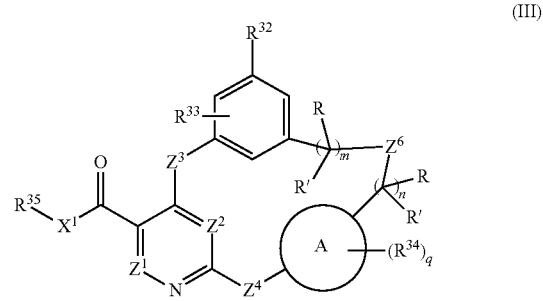

(III)

or a pharmaceutically acceptable form or an isotope derivative thereof, wherein

Ring A is a 5- or 6-membered aryl or heteroaryl;

$X^1$ is selected from NR, O, $CH_2$ and $CF_2$;

$Z^1$ is CH or N;

$Z^2$ is CH, CF or N;

each of $Z^3$ and $Z^4$ is independently selected from NR, $CH_2$ and $CF_2$;

$Z^6$ is $NR^{36}$, $CH_2$, O, S, SO or $SO_2$;

$R^{32}$ is $R^{32'}$ or $OR^{32'}$, wherein $R^{32'}$ is a $C_{1-12}$ alkyl, 3- to 6-membered cycloalkyl or heterocycloalkyl comprising 1, 2 or 3 heteroatoms selected from N, O and S, or a 5- or 6-membered aryl or heteroaryl group, each substituted with 0-3 $R^{32a}$;

$R^{32a}$ is independently at each occurrence, H, $OCF_3$, CN, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, $(CH_2)_rNR^gR^g$, —$(CH_2)_r$ C(O)$NR^gR^g$, —$(CH_2)_rNR^bC(O)R^c$, —$(CH_2)_rNR^bC(O)OR^c$, —$NR^bC(O)NR^gR^g$, —S(O)$_rNR^gR^g$, —$NR^bS(O)_rR^c$, —S(O)$_rR^c$, $C_{1-6}$ alkyl substituted with 0-3 $R^a$, $C_{1-6}$ haloalkyl, $C_{2-6}$ alkenyl substituted with 0-3 $R^a$, 3- to 6-membered cycloalkyl substituted with 0-3 $R^a$, or 3- to 6-membered heterocycloalkyl comprising 1-3 heteroatoms selected from N, O and S substituted with 0-3 $R^a$;

each of $R^{33}$ and $R^{34}$ is independently selected from H, F, Cl, CN, $OR^e$, $CH_3$, $CD_3$, $CF_3$, $OCD_3$, $OCF_3$ and —$(CH_2)_p$-Q;

$R^{35}$ is H, F, a $C_1$-$C_3$ alkyl and $CD_3$, provided that $R^{35}$ is not F when $X^1$ is O or N;

$R^{36}$ is R substituted with 0-3 $R^d$;

$R^a$ at each occurrence is independently H, F, Cl, Br, $OCF_3$, $CF_3$, $CHF_2$, CN, —$(CH_2)_r$ $OR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^gR^g$, —$(CH_2)_rC(O)NR^gR^g$, —$(CH_2)_rNR^bC(O)R^c$, —$(CH_2)_rNR^bC(O)OR^c$, —$NR^bC(O)NR^gR^g$, —$S(O)_vNR^gR^g$, —$NR^bS(O)_vR^c$, —$S(O)R^c$, —$S(O)_2R^c$, $C_{1-6}$ alkyl substituted with 0-3 $R^f$, $C_{1-6}$ haloalkyl, 3- to 6-membered cycloalkyl substituted with 0-3 $R^f$, or 3- to 6-membered heterocycloalkyl comprising 1-3 heteroatoms selected from N, O and S substituted with 0-3 $R^f$;

$R^b$ is H, $C_{1-6}$ alkyl substituted with 0-3 $R^d$, $C_{1-6}$ haloalkyl, $C_{3-6}$ cycloalkyl substituted with 0-2 $R^d$, or 5- to 7-membered heterocycloalkyl comprising 1-3 heteroatoms selected from N, O and S substituted with 0-3 $R^f$ or $(CH_2)_r$-phenyl substituted with 0-3 $R^d$;

$R^c$ is $C_{1-6}$ alkyl substituted with 0-3 $R^f$, $(CH_2)_r$—$C_{3-6}$ cycloalkyl substituted with 0-3 $R^f$ or $(CH_2)_r$-phenyl substituted with 0-3 $R^f$;

$R^d$ is independently at each occurrence, hydrogen, F, Cl, Br, $OCF_3$, $CF_3$, CN, $NO_2$, —$OR^e$, —$(CH_2)_rC(O)R^c$, —$NR^eR^e$, —$NR^eC(O)OR^c$, $C_{1-6}$ alkyl or $(CH_2)_r$-phenyl substituted with 0-3 $R^f$;

$R^e$ is independently at each occurrence, hydrogen, $C_{1-6}$ alkyl, $C_{3-6}$ cycloalkyl or $(CH_2)_r$-phenyl substituted with 0-3 $R^f$;

$R^f$ is independently at each occurrence, hydrogen, halo, CN, $NH_2$, OH, $C_{3-6}$ cycloalkyl, $CF_3$, $O(C_{1-6}$ alkyl) or a 5- to 7-membered heterocycloalkyl comprising 1-3 heteroatoms selected from N, O and S;

$R^g$ at each occurrence is independently H, $C_{1-4}$ alkyl substituted with 0-3 $R^f$, $CF_3$, $C_{3-10}$ cycloalkyl substituted with 0-1 $R^f$, $(CH)_r$-phenyl substituted with 0-3 $R^d$ or 5- to 7-membered heterocycloalkyl comprising 1-3 heteroatoms selected from N, O and S substituted with 0-3 $R^d$;

Q is a water solubilizing group, optionally selected from OH, OR, NRR', heterocyclic and heteroaryl groups, wherein R and R', together with the nitrogen atom to which they are bound, form a 4- to 7-membered ring comprising 0-2 heteroatoms selected from O, NR, S and $SO_2$;

R is H or a $C_1$-$C_6$ alkyl substituted with 0-3 $R^d$;
R' is H or a $C_1$-$C_6$ alkyl substituted with 0-3 $R^d$;
m is 0, 1, 2 and 3;
n is 0, 1, 2 and 3;
p is 0, 1, 2, 3 or 4;
q is 0, 1, 2, 3 or 4;
v is 0, 1, or 2; and
r is 0, 1, 2, 3, 4 or 5, wherein the disease or disorder is selected from inflammatory diseases, immune-mediated diseases, cancer, or a related disease or disorder thereof, in a mammal, including a human.

In yet another aspect, the invention generally relates to a method for treating, reducing or preventing a disease or disorder, comprising administering to a subject in need thereof a therapeutically effective amount of a compound having the structural formula (IV):

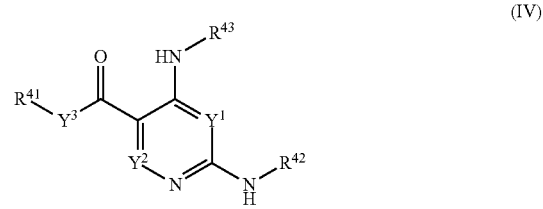

(IV)

or a pharmaceutically acceptable form or an isotope derivative thereof,
wherein
  $Y^1$ is CH, CF or N;
  $Y^2$ is CH or N;
  $Y^3$ is NR, O, $CH_2$ or $CF_2$;
  $R^{41}$ is a H, F, $C_1$-$C_3$ alkyl and $CD_3$, provided that $R^{41}$ is not F when $Y^3$ is NR or O;
  $R^{42}$ is
    $R^{42'}$, wherein $R^{42'}$ is a $C_1$-$C_6$ alkyl, $C_3$-$C_6$ cycloalkyl or heterocycloalkyl, aryl or heteroaryl, each substituted with 0-2 of halogen, CN, OR, amino, alkyl, cycloalkyl, heterocyclic, aryl and heteroaryl;
    an aryl or heteroaryl group substituted with 0-2 $R^{42a}$; or
    (C=O)$R^{42b}$;
  $R^{43}$ is

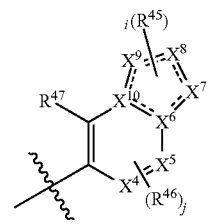

wherein
  each of $X^4$, $X^5$, $X^6$, $X^7$, $X^8$, $X^9$ and $X^{10}$ is independently selected from C, CH, O, N and NH;
  $R^{42a}$ at each occurrence is independently H, D, halo, OH, OR, $CH_3$, $CF_3$, $CH_2CF_3$, CN, C(O)NR, NRR', $(CH_2)_n$NRR' or a 4- to 6-membered heterocycle having 1-4 heteroatoms selected from N, O and S;
  $R^{42b}$ is a $C_{1-6}$ alkyl or $C_{3-6}$ cycloalkyl, aryl or heteroaryl, each substituted with 0-2 $R^{42c}$;
  $R^{42c}$ at each occurrence is independently H, halo, CN, OR, NRR', $OCF_3$, $CF_3$, $C_{1-6}$ alkyl substituted with 0-3 $R^{42a}$, $C_{1-6}$ haloalkyl, $C_{2-6}$ alkenyl substituted with 0-3 $R^{42a}$, $C_{2-6}$ alkynyl substituted with 0-3 $R^{42a}$;
  $R^{45}$ each occurrence is independently H, halo, CN, OR, NRR', $OCF_3$, $CF_3$, $C_{1-6}$ alkyl, substituted with 0-3 $R^{42a}$, or $C_{3-10}$ cycloalkyl or heterocycloalkyl, $C_{5-10}$ aryl or heteroaryl, or a 4- to 10-membered heterocycle having 1-4 heteroatoms selected from N, O and S, each group is substituted with 0-4 $R^{42c}$, optionally two $R^{45}$s, along with the C or N atoms that they are attached to, form a 4- to 6-membered ring;

$R^{46}$ each occurrence is independently F, Cl, CN, OR, $C_1$-$C_3$ alkyl, $C_3$-$C_5$ cycloalkyl, $CD_3$, $CH_2CF_3$ or $CF_3$;

$R^{47}$ is H, $OCF_3$, $C_1$-$C_3$ alkyl, $C_1$-$C_3$ alkoxy or $OCD_3$;

each of R and R' is independently H or a $C_1$-$C_6$ alkyl, or R and R', together with the nitrogen atom to which they are bound, form a 4- to 7-membered ring comprising 0-2 heteroatoms selected from O, NR, S and $SO_2$;

n is 0, 1, 2, 3 or 4;

i is 0, 1 or 2; and j is 0, 1 or 2, wherein the disease or disorder is selected from inflammatory diseases, immune-mediated diseases, cancer, or a related disease or disorder thereof, in a mammal, including a human.

In yet another aspect, the invention generally relates to a method for treating, reducing or preventing a disease or disorder, comprising administering to a subject in need thereof a therapeutically effective amount of a compound having the structural formula (V):

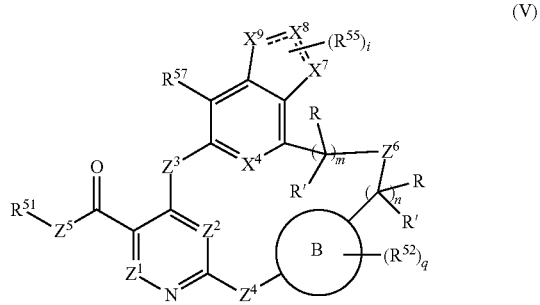

(V)

or a pharmaceutically acceptable form or an isotope derivative thereof, wherein

Ring B is a 5- or 6-membered aryl or heteroaryl;

$Z^1$ is CH or N;

$Z^2$ is CH, CF or N;

each of $Z^3$ and $Z^4$ is independently selected from NR, $CH_2$ and $CF_2$;

$Z^5$ is selected from NR, O, $CH_2$ and $CF_2$;

$Z^6$ is $NR^{56}$, $CH_2$, O, S, SO or $SO_2$;

each of $X^4$, $X^7$, $X^8$ and $X^9$ is independently selected from CH, N and NH;

$R^{51}$ is a H, F, $C_1$-$C_3$ alkyl and $CD_3$, provided that $R^{5'}$ is not F when $Z^5$ is N or O;

$R^{52}$ is independently selected from H, F, Cl, CN, $OR^e$, $CH_3$, $CF_3$, $OCF_3$ and —$(CH_2)_p$-Q;

$R^{52a}$ at each occurrence is independently H, D, halo, OH, OR, $CH_3$, $CF_3$, $CH_2CF_3$ or CN, NRR', $(CH_2)_n$NRR' or a 4- to 6-membered heterocycle having 1-4 heteroatoms selected from N, O and S;

$R^{52c}$ at each occurrence is independently H, halo, CN, OR, NRR', $OCF_3$, $CF_3$, $C_{1-6}$ alkyl substituted with 0-3 $R^{52a}$, $C_{1-6}$ haloalkyl, $C_{2-6}$ alkenyl substituted with 0-3 $R^{52a}$, $C_{2-6}$ alkynyl substituted with 0-3 $R^{52a}$;

$R^{55}$ each occurrence is independently H, $C_{1-6}$ alkyl, substituted with 0-3 $R^{52a}$, or $C_{3-10}$ cycloalkyl or heterocycloalkyl, $C_{5-10}$ aryl or heteroaryl, or a 4- to 10-membered heterocycle having 1-4 heteroatoms selected from N, O and S, each group is substituted with 0-4 $R^{52c}$;

$R^{56}$ is R substituted with 0-3 $R^d$;

$R^{57}$ is H, $C_1$-$C_3$ alkyl, $C_1$-$C_3$ alkoxy, $OCD_3$ or $OCF_3$;

$R^c$ is $C_{1-6}$ alkyl substituted with 0-3 $R^f$, $(CH_2)_r$—$C_{3-6}$ cycloalkyl substituted with 0-3 $R^f$ or $(CH_2)_r$-phenyl substituted with 0-3 $R^f$;

$R^d$ is independently at each occurrence, hydrogen, F, Cl, Br, $OCF_3$, $CF_3$, CN, $NO_2$, —$OR^c$, —$(CH_2)_rC(O)R^c$, —$NR^eR^c$, —$NR^cC(O)OR^c$, $C_{1-6}$ alkyl or $(CH_2)_r$-phenyl substituted with 0-3 $R^f$;

$R^e$ is independently at each occurrence, hydrogen, $C_{1-6}$ alkyl, $C_{3-6}$ cycloalkyl or $(CH_2)_r$-phenyl substituted with 0-3 $R^f$;

$R^f$ is independently at each occurrence, hydrogen, halo, CN, $NH_2$, OH, $C_{3-6}$ cycloalkyl, $CF_3$, $O(C_{1-6}$ alkyl) or a 5- to 7-membered heterocycloalkyl comprising 1-3 heteroatoms selected from N, O and S;

$R^g$ at each occurrence is independently H, $C_{1-4}$ alkyl substituted with 0-3 $R^f$, $CF_3$, $C_{3-10}$ cycloalkyl substituted with 0-1 $R^f$, $(CH)_r$-phenyl substituted with 0-3 $R^d$ or 5- to 7-membered heterocycloalkyl comprising 1-3 heteroatoms selected from N, O and S substituted with 0-3 $R^d$;

Q is a water solubilizing group, optionally selected from OH, OR, NRR', heterocyclic and heteroaryl groups, wherein R and R', together with the nitrogen atom to which they are bound, form a 4- to 7-membered ring comprising 0-2 heteroatoms selected from O, NR, S and $SO_2$;

R is H or a $C_1$-$C_6$ alkyl substituted with 0-3 $R^d$;

R' is H or a $C_1$-$C_6$ alkyl substituted with 0-3 $R^d$;

i is 0, 1, 2 and 3;

m is 0, 1, 2 and 3;

n is 0, 1, 2 and 3;

p is 0, 1, 2, 3 or 4; and q is 0, 1, 2, 3 or 4, wherein the disease or disorder is selected from inflammatory diseases, immune-mediated diseases, cancer, or a related disease or disorder thereof, in a mammal, including a human.

In yet another aspect, the invention generally relates to use of a compound disclosed herein, and a pharmaceutically acceptable excipient, carrier, or diluent, in preparation of a medicament for treating a disease or disorder.

Definitions

Unless defined otherwise, all technical and scientific terms used herein have the same meaning as commonly understood by one of ordinary skill in the art to which this invention belongs. General principles of organic chemistry, as well as specific functional moieties and reactivity, are described in "Organic Chemistry", Thomas Sorrell, University Science Books, Sausalito: 2006.

The following terms, unless indicated otherwise according to the context wherein the terms are found, are intended to have the following meanings.

Ranges provided herein are understood to be shorthand for all of the values within the range. For example, a range of 1 to 16 is understood to include any number, combination of numbers, or sub-range from the group consisting 1, 2, 3, 4, 5, 6, 7, 8, 9, 10, 11, 12, 13, 14, 15 or 16.

As used herein, "at least" a specific value is understood to be that value and all values greater than that value.

As used herein, "more than one" is understood as 2, 3, 4, 5, 6, 7, 8, 9, 10, 11, 12, 13, 14, 15, 16, 17, 18, 19, 20, 25, 30, 40, 50, 100, etc., or any value therebetween.

In this specification and the appended claims, the singular forms "a," "an," and "the" include plural reference, unless the context clearly dictates otherwise.

Unless specifically stated or obvious from context, asysed herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

Unless specifically stated or obvious from context, as used herein, the term "or" is understood to be inclusive.

Any compositions or methods disclosed herein can be combined with one or more of any of the other compositions and methods provided herein.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

The term "comprising", when used to define compositions and methods, is intended to mean that the compositions and methods include the recited elements, but do not exclude other elements. The term "consisting essentially of", when used to define compositions and methods, shall mean that the compositions and methods include the recited elements and exclude other elements of any essential significance to the compositions and methods. For example, "consisting essentially of" refers to administration of the pharmacologically active agents expressly recited and excludes pharmacologically active agents not expressly recited. The term consisting essentially of does not exclude pharmacologically inactive or inert agents, e.g., pharmaceutically acceptable excipients, carriers or diluents. The term "consisting of", when used to define compositions and methods, shall mean excluding trace elements of other ingredients and substantial method steps. Embodiments defined by each of these transition terms are within the scope of this invention.

Certain compounds of the present invention may exist in particular geometric or stereoisomeric forms. The present invention contemplates all such compounds, including cis- and trans-isomers, atropisomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess of either the R- or S-configuration. For optically active compounds, it is often preferred to use one enantiomer to the substantial exclusion of the other enantiomer.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

A mixture of isomers can be separated on the basis of the physicochemical differences of the constituents, into the pure or substantially pure geometric or optical isomers, diastereomers, racemates, for example, by chromatography and/or fractional crystallization.

Definitions of specific functional groups and chemical terms are described in more detail below. When a range of values is listed, it is intended to encompass each value and sub-range within the range. For example, "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

Where substituent groups are specified by their conventional chemical formulae, written from left to right, they equally encompass the chemically identical substituents that would result from writing the structure from right to left, e.g., —C(=O)—O— is equivalent to —O—C(=O)—.

Structures of compounds of the invention are limited by principles of chemical bonding known to those skilled in the art. Accordingly, where a group may be substituted by one or more of a number of substituents, such substitutions are selected so as to comply with principles of chemical bonding and to give compounds that are not inherently unstable and/or would be known to one of ordinary skill in the art as likely to be unstable under ambient conditions (e.g., aqueous, neutral, and several known physiological conditions).

Solvates and polymorphs of the compounds of the invention are also contemplated herein. Solvates of the compounds of the present invention include, for example, hydrates.

As used herein, the term "alkyl" refers to a straight or branched hydrocarbon chain radical consisting solely of carbon and hydrogen atoms, containing no unsaturation, having from one to ten carbon atoms (e.g., $C_{1-10}$ alkyl). Whenever it appears herein, a numerical range such as "1 to 10" refers to each integer in the given range; e.g., "1 to 10 carbon atoms" means that the alkyl group can consist of 1 carbon atom, 2 carbon atoms, 3 carbon atoms, etc., up to and including 10 carbon atoms, although the present definition also covers the occurrence of the term "alkyl" where no numerical range is designated. In some embodiments, "alkyl" can be a $C_{1-6}$ alkyl group. In some embodiments, alkyl groups have 1 to 10, 1 to 8, 1 to 6, or 1 to 3 carbon atoms. Representative saturated straight chain alkyls include, but are not limited to, -methyl, -ethyl, -n-propyl, -n-butyl, -n-pentyl, and -n-hexyl; while saturated branched alkyls include, but are not limited to, -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like. The alkyl is attached to the parent molecule by a single bond. Unless stated otherwise in the specification, an alkyl group is optionally substituted by one or more of substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$N(R$^a$)$_2$ (where t is 1 or 2), —P(=O)(R$^a$)(R$^a$), or —O—P(=O)(OR$^a$)$_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. In a non-limiting embodiment, a substituted alkyl can be selected from fluoromethyl, difluoromethyl, trifluoromethyl, 2-fluoroethyl, 3-fluoropropyl, hydroxymethyl, 2-hydroxyethyl, 3-hydroxypropyl, benzyl, and phenethyl.

As used herein, the term "alkoxy" refers to the group —O-alkyl, including from 1 to 10 carbon atoms ($C_{1-10}$) of a straight, branched, saturated cyclic configuration and combinations thereof, attached to the parent molecular structure through an oxygen. Unless stated otherwise in the specification, the term is intended to include both substituted and unsubstituted alkoxy groups. Examples include methoxy, ethoxy, propoxy, isopropoxy, butoxy, t-butoxy, pentoxy, cyclopropyloxy, cyclohexyloxy and the like. "Lower alkoxy" refers to alkoxy groups containing one to six carbons. In some embodiments, $C_{1-3}$ alkoxy is an alkoxy group that encompasses both straight and branched chain alkyls of from 1 to 3 carbon atoms. Unless stated otherwise in the specification, an alkoxy group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$N(R$^a$)$_2$ (where t is 1 or 2), —P(=O)(R$^a$)(R$^a$), or —O—P(=O)(OR$^a$)$_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, the terms "aromatic" or "aryl" refer to a radical with 6 to 14 ring atoms (e.g., $C_{6-14}$ aromatic or $C_{6-14}$ aryl) that has at least one ring having a conjugated pi electron system which is carbocyclic (e.g., phenyl, fluorenyl, and naphthyl). Unless stated otherwise in the specification, the term is intended to include both substituted and unsubstituted aryl groups. In some embodiments, the aryl is a $C_{6-10}$ aryl group. For example, bivalent radicals formed from substituted benzene derivatives and having the free valences at ring atoms are named as substituted phenylene radicals. In other embodiments, bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 14 aryl" refers to each integer in the given range; e.g., "6 to 14 ring atoms" means that the aryl group can consist of 6 ring atoms, 7 ring atoms, etc., up to and including 14 ring atoms. The term includes monocyclic or fused-ring polycyclic (i.e., rings which share adjacent pairs of ring atoms) groups. Polycyclic aryl groups include bicycles, tricycles, tetracycles, and the like. In a multi-ring group, only one ring is required to be aromatic, so groups such as indanyl are encompassed by the aryl definition. Non-limiting examples of aryl groups include phenyl, phenalenyl, naphthalenyl, tetrahydronaphthyl, phenanthrenyl, anthracenyl, fluorenyl, indolyl, indanyl, and the like. Unless stated otherwise in the specification, an aryl moiety can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$N(R$^a$)$_2$ (where t is 1 or 2), —P(=O)(R$^a$)(R$^a$), or —O—P(=O)(OR$^a$)$_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, the terms "cycloalkyl" and "carbocyclyl" each refers to a monocyclic or polycyclic radical that contains only carbon and hydrogen, and can be saturated or partially unsaturated. Partially unsaturated cycloalkyl groups can be termed "cycloalkenyl" if the carbocycle contains at least one double bond, or "cycloalkynyl" if the carbocycle contains at least one triple bond. Cycloalkyl groups include groups having from 3 to 13 ring atoms (i.e., $C_{3-13}$ cycloalkyl). Unless stated otherwise in the specification, the term is intended to include both substituted and unsubstituted cycloalkyl groups. Whenever it appears herein, a numerical range such as "3 to 10" refers to each integer in the given range; e.g., "3 to 13 carbon atoms" means that the cycloalkyl group can consist of 3 carbon atoms, 4 carbon atoms, 5 carbon atoms, etc., up to and including 13 carbon atoms. The term "cycloalkyl" also includes bridged and spiro-fused cyclic structures containing no heteroatoms. The term also includes monocyclic or fused-ring polycyclic (i.e., rings which share adjacent pairs of ring atoms) groups. Polycyclic aryl groups include bicycles, tricycles, tetracycles, and the like. In some embodiments, "cycloalkyl" can be a $C_{3-8}$ cycloalkyl radical. In some embodiments, "cycloalkyl" can be a $C_{3-5}$ cycloalkyl radical. Illustrative examples of cycloalkyl groups include, but are not limited to the following moieties: $C_{3-6}$ carbocyclyl groups include, without limitation, cyclopropyl ($C_3$), cyclobutyl ($C_4$), cyclopentyl ($C_5$), cyclopentenyl ($C_5$), cyclohexyl ($C_6$), cyclohexenyl ($C_6$), cyclohexadienyl ($C_6$) and the like. Examples of $C_{3-7}$ carbocyclyl groups include norbornyl ($C_7$). Examples of $C_{3-8}$ carbocyclyl groups include the aforementioned $C_{3-7}$ carbocyclyl groups as well as cycloheptyl ($C_7$), cycloheptadienyl ($C_7$), cycloheptatrienyl ($C_7$), cyclooctyl ($C_8$), bicyclo[2.2.1]heptanyl, bicyclo[2.2.2]octanyl, and the like. Examples of $C_{3-13}$ carbocyclyl groups include the aforementioned $C_{3-8}$ carbocyclyl groups as well as octahydro-1H indenyl, decahydronaphthalenyl, spiro[4.5]decanyl and the like. Unless stated otherwise in the specification, a cycloalkyl group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. The terms "cycloalkenyl" and "cycloalkynyl" mirror the above description of "cycloalkyl" wherein the prefix "alk" is replaced with "alken" or "alkyn" respectively, and the parent "alkenyl" or "alkynyl" terms are as described herein. For example, a cycloalkenyl group can have 3 to 13 ring atoms, such as 5 to 8 ring atoms. In some embodiments, a cycloalkynyl group can have 5 to 13 ring atoms.

As used herein, the term "halogen" refers to fluorine (F), chlorine (Cl), bromine (Br), or iodine (I). As used herein, the term "halide" or "halo", means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine, such as, but not limited to, trifluoromethyl, difluoromethyl, 2,2,2-trifluoroethyl, 1-fluoromethyl-2-fluoroethyl, and the like. Each of the alkyl, alkenyl, alkynyl and alkoxy groups are as defined herein and can be optionally further substituted as defined herein.

As used herein, the term "heteroatom" refers to oxygen (O), nitrogen (N), sulfur (S), and phosphorus ($I^a$).

As used herein, the term "heteroalkyl" refers to an alkyl radical, which have one or more skeletal chain atoms selected from an atom other than carbon, e.g., oxygen, nitrogen, sulfur, phosphorus or combinations thereof. Unless stated otherwise in the specification, the term is intended to include both substituted and unsubstituted heteroalkyl groups. A numerical range can be given, e.g., $C_{1-4}$ heteroalkyl, which refers to the chain length in total, which in this example is 4 atoms long. For example, a —CH$_2$OCH$_2$CH$_3$ radical is referred to as a "$C_4$" heteroalkyl, which includes the heteroatom center in the atom chain length description. Connection to the parent molecular structure can be through either a heteroatom or a carbon in the heteroalkyl chain. For example, an N-containing heteroalkyl moiety refers to a group in which at least one of the skeletal atoms is a nitrogen atom. One or more heteroatom(s) in the heteroalkyl radical can be optionally oxidized. One or more nitrogen atoms, if present, can also be optionally quaternized. For example, heteroalkyl also includes skeletal chains substituted with one or more nitrogen oxide (—O—) substituents. Exemplary heteroalkyl groups include, without limitation, ethers such as methoxyethanyl (—CH$_2$CH$_2$OCH$_3$), ethoxymethanyl (—CH$_2$OCH$_2$CH$_3$), (methoxymethoxy)ethanyl (—CH$_2$CH$_2$OCH$_2$OCH$_3$), (methoxymethoxy) methanyl (—CH$_2$OCH$_2$OCH$_3$) and (methoxyethoxy)methanyl (—CH$_2$OCH$_2$CH$_2$OCH$_3$) and the like; amines such as (—CH$_2$CH$_2$NHCH$_3$, —CH$_2$CH$_2$N(CH$_3$)$_2$, —CH$_2$NHCH$_2$CH$_3$, —CH$_2$N(CH$_2$CH$_3$)(CH$_3$)) and the like.

As used herein, the term "heterocycloalkyl" refers to a cycloalkyl radical, which have one or more skeletal chain atoms selected from an atom other than carbon, e.g., oxygen, nitrogen, sulfur, phosphorus or combinations thereof. Unless stated otherwise in the specification, the term is intended to include both substituted and unsubstituted heterocycloalkyl groups. Illustrative examples of heterocycloalkyl include 2-hydroxy-aziridin-1-yl, 3-oxo-1-oxacyclobutan-2-yl, 2,2-dimethyl-tetrahydrofuran-3-yl, 3-carboxy-morpholin-4-yl, 1-cyclopropyl-4-methyl-piperazin-2-yl. 2-pyrrolinyl, 3-pyrrolinyl, dihydro-2H-pyranyl, 1,2,3,4-tetrahydropyridine, 3,4-dihydro-2H-[1,4]oxazine, etc.

As used herein, the term "heteroaryl" or, alternatively, "heteroaromatic" refers to a radical of a 5-18 membered monocyclic or polycyclic (e.g., bicyclic, tricyclic, tetracyclic and the like) aromatic ring system (e.g., having 6, 10 or 14 π electrons shared in a cyclic array) having ring carbon atoms and 1-6 ring heteroatoms provided in the aromatic ring system, wherein each heteroatom is independently selected from nitrogen, oxygen, phosphorous and sulfur ("5-18 membered heteroaryl"). Unless stated otherwise in the specification, the term is intended to include both substituted and unsubstituted heteroaryl groups. Heteroaryl polycyclic ring systems can include one or more heteroatoms in one or both rings. Whenever it appears herein, a numerical range such as "5 to 18" refers to each integer in the given range; e.g., "5 to 18 ring atoms" means that the heteroaryl group can consist of 5 ring atoms, 6 ring atoms, etc., up to and including 18 ring atoms. In some instances, a heteroaryl can have 5 to 14 ring atoms. In some embodiments, the heteroaryl has, for example, bivalent radicals derived from univalent heteroaryl radicals whose names end in "-yl" by removal of one hydrogen atom from the atom with the free valence are named by adding "-ene" to the name of the corresponding univalent radical, e.g., a pyridyl group with two points of attachment is a pyridylene.

For example, an N-containing "heteroaromatic" or "heteroaryl" moiety refers to an aromatic group in which at least one of the skeletal atoms of the ring is a nitrogen atom. One or more heteroatom(s) in the heteroaryl radical can be optionally oxidized. One or more nitrogen atoms, if present, can also be optionally quaternized. Heteroaryl also includes ring systems substituted with one or more nitrogen oxide (—O—) substituents, such as pyridinyl N-oxides. The heteroaryl is attached to the parent molecular structure through any atom of the ring(s).

"Heteroaryl" also includes ring systems wherein the heteroaryl ring, as defined above, is fused with one or more aryl groups wherein the point of attachment to the parent molecular structure is either on the aryl or on the heteroaryl ring, or wherein the heteroaryl ring, as defined above, is fused with one or more cycloalkyl or heterocycyl groups wherein the point of attachment to the parent molecular structure is on the heteroaryl ring. For polycyclic heteroaryl groups wherein one ring does not contain a heteroatom (e.g., indolyl, quinolinyl, carbazolyl and the like), the point of attachment to the parent molecular structure can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, phosphorous, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, phosphorous, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, phosphorous, and sulfur ("5-6 membered heteroaryl"). In some embodiments, the 5-6 membered heteroaryl has 1-3 ring heteroatoms selected from nitrogen, oxygen, phosphorous, and sulfur. In some embodiments, the 5-6 membered heteroaryl has 1-2 ring heteroatoms selected from nitrogen, oxygen, phosphorous, and sulfur. In some embodiments, the 5-6 membered heteroaryl has 1 ring heteroatom selected from nitrogen, oxygen, phosphorous, and sulfur.

Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzopyranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno [2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e., thienyl). Unless stated otherwise in the specification, a heteroaryl moiety can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$N(R$^a$)$_2$ (where t is 1 or 2), —P(=O)(R$^a$)(R$^a$), or —O—P(=O)(OR$^a$)$_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, the term "administering" refers to oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Suitable routes of administration for a particular patient will depend on the nature and severity of the disease or condition being treated or the nature of the therapy being used and on the nature of the active compound.

Administration may be by any suitable route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

By "co-administer" it is meant that a composition described herein is administered at the same time, just prior to, or just after the administration of one or more additional therapies.

The compound of the invention can be administered alone or can be co-administered to the patient. Co-administration is meant to include simultaneous or sequential administration of the compound individually or in combination (more than one compound or agent). Thus, the preparations can also be combined, when desired, with other active substances (e.g., to reduce metabolic degradation).

The compositions of the present invention can be delivered transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, gels, for example, water or water/propylene glycol solutions.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, 1995 *J Biomater Sci. Polym.* Ed. 7:623-645; as biodegradable and injectable gel formulations (see, e.g., Gao 1995 *Pharm. Res.* 12:857-863); or, as microspheres for oral administration (see, e.g., Eyles 1997 *J. Pharm. Pharmacol.* 49:669-674).

As used herein, the terms "disease," "condition," and "disorder" are used interchangeably herein and refer to a state of being or health status of a patient or subject capable of being treated with a compound, pharmaceutical composition, or method provided herein.

As used herein, the term "effective amount" of an active agent refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the patient.

As used herein, the terms "inhibition," "inhibit" and "inhibiting" and the like in reference to a biological target (e.g., TYK2) inhibitor interaction refers to negatively affecting (e.g., decreasing) the activity or function of the protein relative to the activity or function of the protein in the absence of the inhibitor. In embodiments, inhibition means negatively affecting (e.g., decreasing) the concentration or levels of the protein relative to the concentration or level of the protein in the absence of the inhibitor. In embodiments, inhibition refers to reduction of a disease or symptoms of disease. In embodiments, inhibition refers to a reduction in the activity of a particular protein target. Inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g., an inhibitor binds to the target protein). In embodiments, inhibition refers to a reduction of activity of a target protein from an indirect interaction (e.g., an inhibitor binds to a protein that activates the target protein, thereby preventing target protein activation).

As used herein, the terms "isolated" or "purified" refer to a material that is substantially or essentially free from components that normally accompany it in its native state. Purity and homogeneity are typically determined using analytical chemistry techniques such as polyacrylamide gel electrophoresis or high-performance liquid chromatography.

As used herein, the term "modulate" refers to the production, either directly or indirectly, of an increase or a decrease, a stimulation, inhibition, interference, or blockage in a measured activity when compared to a suitable control. A "modulator" of a polypeptide or polynucleotide refers to a substance that affects, for example, increases, decreases, stimulates, inhibits, interferes with, or blocks a measured activity of the polypeptide or polynucleotide, when compared to a suitable control. For example, a "modulator" may bind to and/or activate or inhibit the target with measurable affinity, or directly or indirectly affect the normal regulation of a receptor activity.

As used herein, a "pharmaceutically acceptable form" of a disclosed compound includes, but is not limited to, pharmaceutically acceptable salts, esters, hydrates, solvates, isomers, prodrugs, and isotopically labeled derivatives thereof. In one embodiment, a "pharmaceutically acceptable form" includes, but is not limited to, pharmaceutically acceptable salts, esters, prodrugs and isotopically labeled derivatives thereof. In some embodiments, a "pharmaceutically acceptable form" includes, but is not limited to, pharmaceutically acceptable isomers and stereoisomers, prodrugs and isotopically labeled derivatives thereof.

In certain embodiments, the pharmaceutically acceptable form is a pharmaceutically acceptable salt. As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in *J. Pharmaceutical Sciences* (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchlorate acid or with organic acids such as acetic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, p-toluenesulfonate, undecanoate, valerate salts, and the like. In some embodiments, organic acids from which salts can be derived include, for example, acetic acid, propionic acid, glycolic acid, pyruvic acid, lactic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The salts can be prepared in situ during the isolation and purification of the disclosed compounds, or separately, such as by reacting the free base or free acid of a parent compound with a suitable base or acid, respectively. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Organic bases from which salts can be derived include, for example, primary, secondary, and tertiary amines, substituted amines, including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt can be chosen from ammonium, potassium, sodium, calcium, and magnesium salts.

In certain embodiments, the pharmaceutically acceptable form is a "solvate" (e.g., a hydrate). As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate." Pharmaceutically acceptable solvates and hydrates are complexes that, for example, can include 1 to about 100, or 1 to about 10, or 1 to about 2, about 3 or about 4, solvent or water molecules. It will be understood that the term "compound" as used herein encompasses the compound and solvates of the compound, as well as mixtures thereof.

In certain embodiments, the pharmaceutically acceptable form is a prodrug. As used herein, the term "prodrug" (or "pro-drug") refers to compounds that are transformed in vivo to yield a disclosed compound or a pharmaceutically acceptable form of the compound. A prodrug can be inactive when administered to a subject, but is converted in vivo to an active compound, for example, by hydrolysis (e.g., hydrolysis in blood). In certain cases, a prodrug has improved physical and/or delivery properties over the parent compound. Prodrugs can increase the bioavailability of the compound when administered to a subject (e.g., by permitting enhanced absorption into the blood following oral administration) or which enhance delivery to a biological compartment of interest (e.g., the brain or lymphatic system) relative to the parent compound. Exemplary prodrugs include derivatives of a disclosed compound with enhanced aqueous solubility or active transport through the gut membrane, relative to the parent compound.

The prodrug compound often offers advantages of solubility, tissue compatibility or delayed release in a mammalian organism (see, e.g., Bundgard, H., *Design of Prodrugs* (1985), pp. 7-9, 21-24 (Elsevier, Amsterdam). A discussion of prodrugs is provided in Higuchi, T., et al., "Pro-drugs as Novel Delivery Systems," *A.C.S. Symposium Series*, Vol. 14, and in *Bioreversible Carriers in Drug Design*, ed. Edward B. Roche, American Pharmaceutical Association and Pergamon Press, 1987, both of which are incorporated in full by reference herein.

Prodrug forms often offer advantages of solubility, tissue compatibility, or delayed release in the mammalian organism. (See, Bundgard, Design of Prodrugs, pp. 7-9, 21-24, Elsevier, Amsterdam 1985 and Silverman, The Organic Chemistry of Drug Design and Drug Action, pp. 352-401, Academic Press, San Diego, Calif., 1992.) Prodrugs commonly known in the art include well-known acid derivatives, such as, for example, esters prepared by reaction of the parent acids with a suitable alcohol, amides prepared by reaction of the parent acid compound with an amine, basic groups reacted to form an acylated base derivative, etc. Other prodrug derivatives may be combined with other features disclosed herein to enhance bioavailability. As such, those of skill in the art will appreciate that certain of the presently disclosed compounds having free amino, amido, hydroxy or carboxylic groups can be converted into prodrugs. Prodrugs include compounds having a carbonate, carbamate, amide or alkyl ester moiety covalently bonded to any of the above substituents disclosed herein.

Exemplary advantages of a prodrug can include, but are not limited to, its physical properties, such as enhanced water solubility for parenteral administration at physiological pH compared to the parent compound, or it can enhance absorption from the digestive tract, or it can enhance drug stability for long-term storage.

As used herein, the term "pharmaceutically acceptable" excipient, carrier, or diluent refers to a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

As used herein, the term "subject" refers to any animal (e.g., a mammal), including, but not limited to humans, non-human primates, rodents, and the like, which is to be the recipient of a particular treatment. A subject to which administration is contemplated includes, but is not limited to, humans (e.g., a male or female of any age group, e.g., a pediatric subject (e.g., infant, child, adolescent) or adult subject (e.g., young adult, middle-aged adult or senior adult)) and/or other non-human animals, for example, non-human mammals (e.g., primates (e.g., cynomolgus monkeys, rhesus monkeys); commercially relevant mammals such as cattle, pigs, horses, sheep, goats, cats, and/or dogs), rodents (e.g., rats and/or mice), etc. In certain embodiments, the non-human animal is a mammal. The non-human animal may be a male or female at any stage of development. A non-human animal may be a transgenic animal. Typically, the terms "subject" and "patient" are used interchangeably herein in reference to a human subject.

As used herein, the terms "treatment" or "treating" a disease or disorder refers to a method of reducing, delaying or ameliorating such a condition before or after it has occurred. Treatment may be directed at one or more effects or symptoms of a disease and/or the underlying pathology. The treatment can be any reduction and can be, but is not limited to, the complete ablation of the disease or the symptoms of the disease. Treating or treatment thus refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters, for example, the results of a physical examination, neuropsychiatric exams, and/or a psychiatric evaluation. As compared with an equivalent untreated control, such reduction or degree of amelioration may be at least 5%, 10%, 20%, 40%, 50%, 60%, 80%, 90%, 95%, or 100% as measured by any standard technique.

Treatment methods include administering to a subject a therapeutically effective amount of a compound described herein. The administering step may be a single administration or may include a series of administrations. The length of the treatment period depends on a variety of factors, such as the severity of the condition, the patient's age, the concentration of the compound, the activity of the compositions used in the treatment, or a combination thereof. It will also be appreciated that the effective dosage of an agent used for the treatment may increase or decrease over the course of a particular treatment regime. Changes in dosage may result and become apparent by standard diagnostic assays known in the art. In some instances, chronic administration may be required. For example, the compositions are administered to the subject in an amount and for a duration sufficient to treat the patient.

DETAILED DESCRIPTION OF THE INVENTION

The invention is based on an unexpected discovery of novel, selective and potent compounds that are TYK2 inhibitors. The invention also provides pharmaceutical compositions of these compounds and methods of their preparation and use. The compounds are orally available and exhibit fewer and/or lesser side effects than currently available drugs.

The new class of TYK2 inhibitors disclosed herein exhibit exceptional potency profiles and are useful in treating one or more TYK2-mediated diseases and conditions, such as allergic, autoimmune, inflammatory, metabolic, neurological and proliferative diseases and conditions. Without wishing to be bound by the theory, compounds of the invention are modulators of interleukins (e.g., IL-12, IL-23) and interferons (e.g., IFN-α) by inhibiting TYK2-mediated signal transduction.

These compounds are designed to show good potency against TYK2 with good oral absorption and good in vivo stability. The invention also provides pharmaceutical compositions of these compounds and methods of preparation and use thereof. The TYK2 inhibitors disclosed herein exhibit favorable pharmacokinetic profiles and drug properties that are suitable for the target indications.

In one aspect, the invention generally relates to a compound having the structural formula (I):

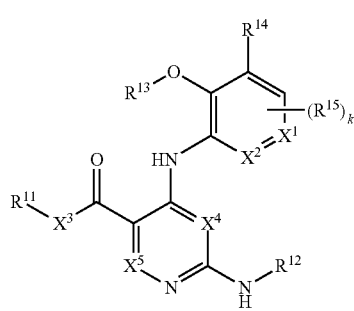

(I)

or a pharmaceutically acceptable form or an isotope derivative thereof, wherein
each of $X^1$ and $X^2$ is independently selected from CH and N;
each of $X^4$ and $X^5$ is independently selected from CH, CF and N;
$X^3$ is NR, O, $CH_2$ or $CF_2$;
$R^{11}$ is a H, F, $C_1$-$C_3$ alkyl or $CD_3$, provided that $R^{11}$ is not F when $X^3$ is NR or O;
$R^{12}$, is C(=O)$R^{12'}$ or $R^{12'}$, wherein $R^{12'}$ is a $C_1$-$C_6$ alkyl, $C_3$-$C_6$ cycloalkyl or heterocycloalkyl, aryl or heteroaryl, each substituted with 0-2 $R^{12a}$ wherein $R^{12a}$ is selected from the group consisting of halogen, $CF_3$, CN, OR, amino, alkyl, cycloalkyl, heterocyclic, aryl and heteroaryl;
$R^{13}$ is a $C_1$-$C_3$ alkyl, $CD_3$ or $CF_3$;
$R^{14}$ is H, $C_1$-$C_6$ alkyl or heteroalkyl or a $C_3$-$C_6$ cycloalkyl or heterocycloalkyl, or a 5- or 6-membered heteroaryl group comprising 1, 2 or 3 hetero atoms selected from N, O and S, or $R^{14}$ is $OR^{14'}$, wherein $R^{14'}$ is $C_1$-$C_6$ alkyl or heteroalkyl or a $C_3$-$C_6$ cycloalkyl or heterocycloalkyl, each substituted with 0-2 $R^{14a}$, wherein $R^{14a}$ is selected from the group consisting of halogen, R, OR, amino, $CF_3$ and CN;
$R^{15}$ at each occurrence is independently selected from F, Cl, CN, OR, NRR', and a $C_1$-$C_3$ alkyl;
R at each occurrence is independently H or a $C_1$-$C_6$ alkyl; and
k is 0, 1, 2 or 3.

In certain embodiments of formula (I), $R^{12}$ is C(=O)$R^{12'}$.
In certain embodiments of formula (I), $R^{12}$ is $R^{12'}$.
In certain embodiments of formula (I), $R^{12}$ is an aryl.
In certain embodiments of formula (I), $R^{12}$ is a heteroaryl.
In certain embodiments of formula (I), $R^{12}$ is unsubstituted or substituted phenyl, pyridinyl, pyrazolyl or pymidinyl group.
In certain embodiments of formula (I), each of $X^1$ and $X^2$ is CH.
In certain embodiments of formula (I), each of $X^4$ and $X^5$ is CH.
In certain embodiments of formula (I), $X^4$ is CF.
In certain embodiments of formula (I), $X^4$ is CH and $X^5$ is N.
In certain embodiments of formula (I), each of $X^1$ and $X^2$ is CH.
In certain embodiments of formula (I), each of $X^4$ and $X^5$ is CH.
In certain embodiments of formula (I), $X^4$ is CH and $X^5$ is N.
In certain embodiments of formula (I), $X^4$ is N and $X^5$ is CH, and the compound has the structural formula:

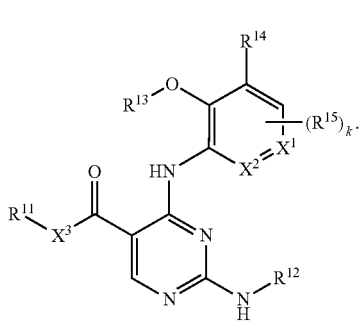

(Iª)

In certain embodiments of formulae (I)-(I$^a$), X$^3$ is NR. In certain embodiments, X$^3$ is NH.

In certain embodiments of formulae (I)-(I$^a$), X$^3$ is O.

In certain embodiments of formulae (I)-(I$^a$), R$^{12}$ is R$^{12'}$ and R$^{12'}$ is an aryl group (e.g., an unsubstituted or substituted phenyl).

In certain embodiments of formulae (I)-(I$^a$), R$^{12}$ is R$^{12'}$ and R$^{12'}$ is a heteroaryl group (e.g., an unsubstituted or substituted pyrazolyl, pyridinyl or pyrimidyl group).

In certain embodiments of formulae (I)-(I$^a$), R$^{12}$ is C(=O)R$^{12'}$ and R$^{12'}$ is an unsubstituted or substituted C$_3$-C$_6$ cycloalkyl. In certain embodiments, R$^{12'}$ is cyclopropyl. In certain embodiments, R$^{12'}$ is cyclobutyl.

In certain embodiments of formulae (I)-(I$^a$), R$^{12'}$ is a C$_1$-C$_6$ alkyl substituted with an amino or morpholino group.

In certain embodiments of formulae (I)-(I$^a$), R$^{13}$ is CH$_3$.

In certain embodiments of formulae (I)-(I$^a$), R$^{13}$ is CD$_3$.

In certain embodiments of formulae (I)-(I$^a$), R$^{13}$ is CF$_3$.

In certain embodiments of formulae (I)-(I$^a$), R$^{14}$ is 5-membered heteroaryl group (e.g., 1, 2, 4-triazole).

In certain embodiments of formulae (I)-(I$^a$), R$^{14}$ is OR$^{14'}$. In certain embodiments, R$^{14'}$ is a heterocycloalkyl (e.g., tetrahydropyran).

In certain embodiments of formulae (I)-(I$^a$), R$^{14}$ is H.

In certain embodiments of formulae (I)-(I$^a$), k is 0 (i.e., R$^{15}$ is absent).

In certain embodiments of formulae (I)-(I$^a$), k is 1.

In certain embodiments of formulae (I)-(I$^a$), k is 2.

In certain embodiments of formulae (I)-(I$^a$), the compound has the structural formula:

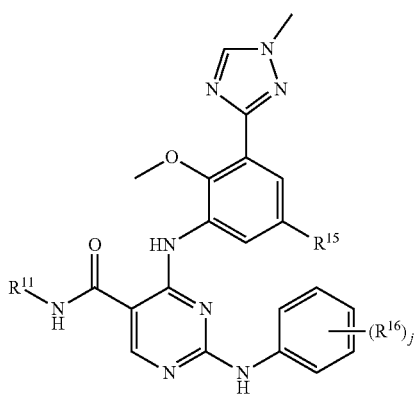

(I$^b$)

wherein each R$^{16}$ is independently selected from CN, Cl, F, a C$_1$-C$_3$ alkyl, a C$_{3-6}$ heterocyclic, and OR, and j is 0, 1, 2, 3, 4 or 5.

In certain embodiments of formulae (I)-(I$^b$), j is 0 (i.e., R$^{16}$ is absent).

In certain embodiments of formulae (I)-(I$^b$), j is 1.

In certain embodiments of formulae (I)-(I$^b$), j is 2.

In certain embodiments of formula (I$^b$), j is 1 and R$^{16}$ is at the meta position:

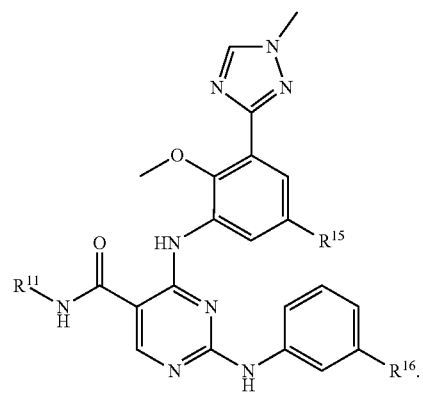

(I$^c$)

In certain embodiments of formula (I$^b$), the compound has the structural formula:

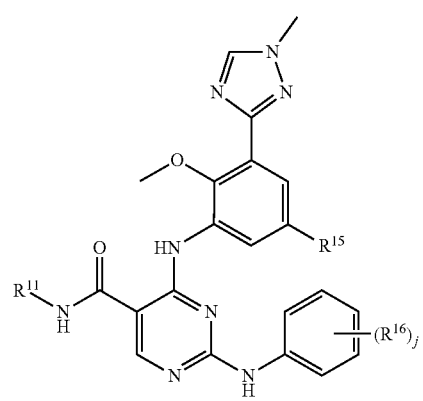

(I$^d$)

wherein
each R$^{16}$ is independently selected from CN, Cl, F, a C$_1$-C$_3$ alkyl and OR, and j is 0, 1, 2, 3, 4 or 5.

In certain embodiments of formulae (I)-(I$^d$), R$^{11}$ is CH$_3$.

In certain embodiments of formulae (I)-(I$^d$), R$^{11}$ is CD$_3$.

In certain embodiments of formulae (I)-(I$^d$), R$^{15}$ is F.

In certain embodiments of formula (I d), j is 1.

In certain embodiments of formula (I$^d$), j is 2.

In certain embodiments of formulae (I)-(I$^d$), each R$^{16}$ is independently selected from F, Cl, CN and CF$_3$.

In certain embodiments of formulae (I)-(I$^d$), a substituted or unsubstituted morpholino group In another aspect, the invention generally relates to a compound having the structural formula (II):

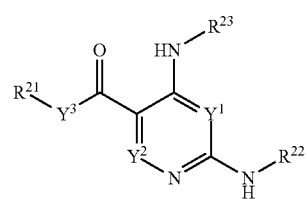

(II)

or a pharmaceutically acceptable form or an isotope derivative thereof, wherein

Y$^1$ is CH, CF or N;

Y$^2$ is CH or N;

Y$^3$ is NR, O, CH$_2$ or CF$_2$;

R$^{21}$ is a H, F, C$_1$-C$_3$ alkyl and CD$_3$, provided that R$^{21}$ is not F when Y$^3$ is N or O;

R$^{22}$ is

R$^{22'}$, wherein R$^{22'}$ is a C$_1$-C$_6$ alkyl, C$_3$-C$_6$ cycloalkyl or heterocycloalkyl, aryl or heteroaryl, each substituted with 0-2 R$^{22a}$, wherein R$^{22a}$ is selected from the group consisting of halogen, CN, OR, amino, alkyl, cycloalkyl, heterocyclic;

an aryl or heteroaryl group, each substituted with 0-2 R$^{22a}$; or (C=O)R$^{27}$;

R$^{23}$ is

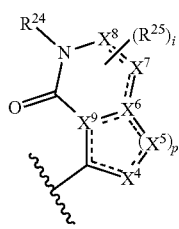

wherein each of X$^4$, X$^5$, X$^6$, X$^7$, X$^8$ and X$^9$ is independently selected from O, C, CH, S, N and NR$^{26}$;

R$^{24}$ is H and C$_{1-6}$ alkyl, substituted with 0-3 R$^{24a}$, or C$_{3-10}$ cycloalkyl or heterocycloalkyl, C$_{5-10}$ aryl or heteroaryl, or a 4- to 10-membered heterocycle having 1-4 heteroatoms selected from N, O and S, each group is substituted with 0-4 R$^{24b}$;

R$^{24a}$ at each occurrence is independently H, D, halo, OH, OR, CH$_3$, CF$_3$, CH$_2$CF$_3$ or CN, NRR', (CH$_2$)$_n$NRR' or a 4- to 6-membered heterocycle having 1-4 heteroatoms selected from N, O and S;

R$^{24b}$ at each occurrence is independently H, halo, CN, OR, NRR', OCF$_3$, CF$_3$, C$_{1-6}$ alkyl, C$_{3-10}$ cycloalkyl, heterocycloalkyl, aryl, or heteroaryl, each substituted with 0-3 R$^{24a}$, C$_{1-6}$ haloalkyl, C$_{2-6}$ alkenyl substituted with 0-3 R$^{24a}$, C$_{2-6}$ alkynyl substituted with 0-3 R$^{24a}$;

R$^{25}$ is F, Cl, CN, CD$_3$, CH$_2$CF$_3$, CF$_3$, OR, NRR', C$_1$-C$_3$ alkyl, C$_3$-C$_5$ cycloalkyl, substituted with 0-2 R$^{24b}$;

R$^{26}$ is H, a C$_1$-C$_6$ alkyl, CD$_3$, or C$_3$-C$_6$ cycloalkyl, substituted with 0-3 R$^{24a}$;

R$^{27}$ is a C$_{1-6}$ alkyl or C$_3$-C$_6$ cycloalkyl, aryl or heteroaryl, each substituted with 0-2 R$^{24b}$;

each of R and R' is independently H or a C$_1$-C$_6$ alkyl, or R and R', together with the nitrogen atom to which they are bound, form a 4- to 7-membered ring comprising 0-2 heteroatoms selected from O, NR, S and SO$_2$;

n is 0, 1, 2, 3 or 4;

i is 0, 1 or 2; and p is 1 or 2.

In certain embodiments of formula (II), p is 1 and R$^{23}$ is

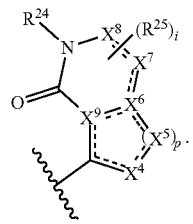

In certain embodiments of formula (II), p is 2.

In certain embodiments of formula (II), Y$^1$ is CH and Y$^2$ is CH, and the compound has the structural formula:

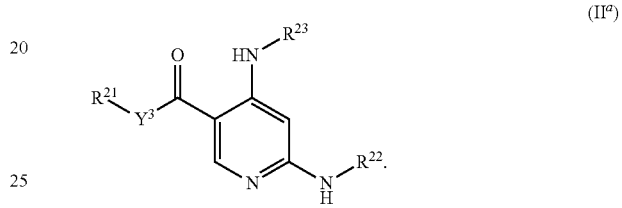

(II$^a$)

In certain embodiments of formula (II), Y$^1$ is CH and Y$^2$ is N, and the compound has the structural formula:

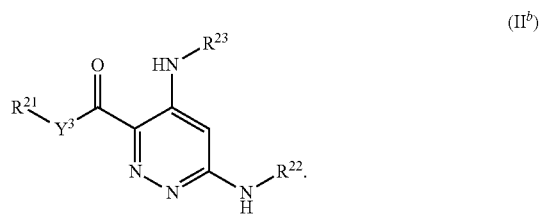

(II$^b$)

In certain embodiments of formula (II), Y$^1$ is N and Y$^2$ is CH, and the compound has the structural formula:

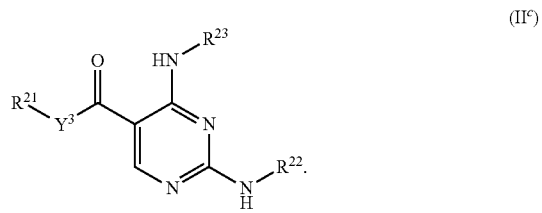

(II$^c$)

In certain embodiments of formula (II), Y$^1$ is N and Y$^2$ is N, and the compound has the structural formula:

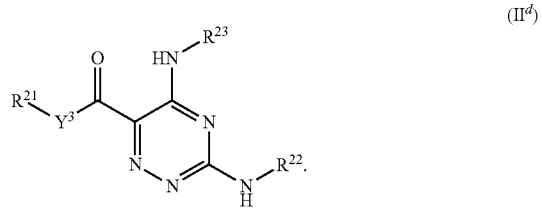

(II$^d$)

In certain embodiments of formulae (II)-(II$^d$), Y$^1$ is CF.

In certain embodiments of formulae (II)-(II$^d$), Y$^3$ is NR. In certain embodiments, Y$^3$ is NH.

In certain embodiments of formulae (II)-(II$^d$), Y$^3$ is CH$_2$.

In certain embodiments of formulae (II)-(II$^d$), Y$^3$ is CF$_2$.

In certain embodiments of formulae (II)-(II$^d$), R$^{23}$ is a group selected from:

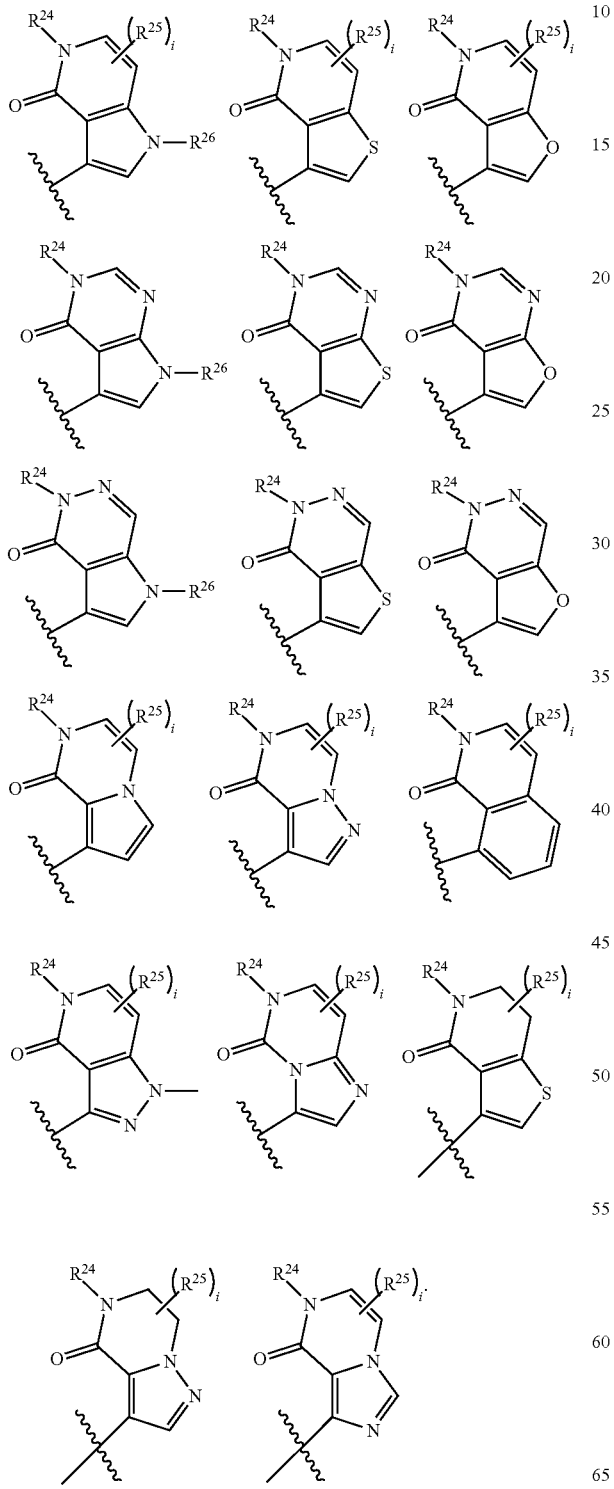

In certain embodiments, R$^{23}$ is:

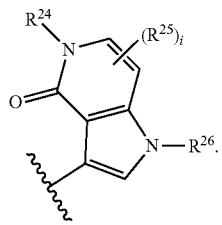

In certain embodiments, R$^{23}$ is:

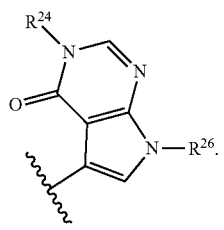

In certain embodiments, R$^{26}$ is C$_{1-3}$ alkyl, optionally substituted with OCH$_3$.

In certain embodiments, R$^{26}$ is methyl.

In certain embodiments, R$^{23}$ is:

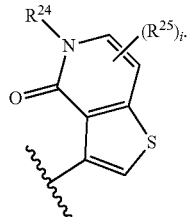

In certain embodiments, R$^{23}$ is:

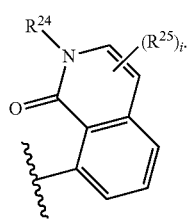

In certain embodiments of formulae (II)-(II$^d$), R$^{21}$ is F.
In certain embodiments of formulae (II)-(II$^d$), R$^{21}$ is CH$_3$.
In certain embodiments of formulae (II)-(II$^d$), R$^{21}$ is CD$_3$.
In certain embodiments of formulae (II)-(II$^d$), R$^{22}$ is an aryl (e.g., phenyl), optionally substituted with 1 or 2 halogen (e.g., F, Cl) atoms.
In certain embodiments of formulae (II)-(II$^d$), R$^{22}$ is a heteroaryl group (e.g., pyridinyl), optionally substituted with 1 or 2 halogen (e.g., F, Cl) atoms.
In certain embodiments of formulae (II)-(II$^d$), R$^{22}$ is (C=O)R$^{27}$, wherein R$^{27}$ is selected from C$_1$-C$_6$ alkyl, cyclopropyl or cyclobutyl, substituted with 0-2 R$^{24b}$.
In certain embodiments of formulae (II)-(II$^d$), R$^{22}$ is pyridine substituted with 0-2 R$^{24b}$.

In certain embodiments, the compound has the structural formula:

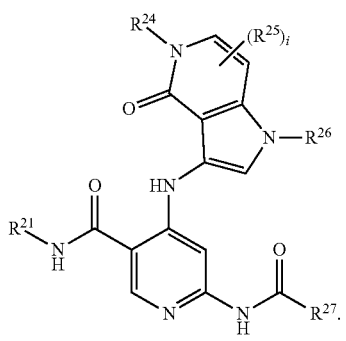

(II$^e$)

In certain embodiments, the compound has the structural formula:

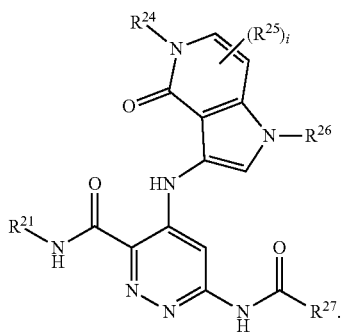

(II$^f$)

In certain embodiments, the compound has the structural formula:

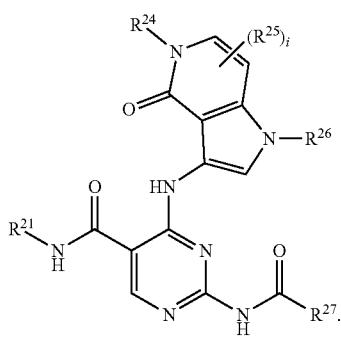

(II$^g$)

In certain embodiments, the compound has the structural formula:

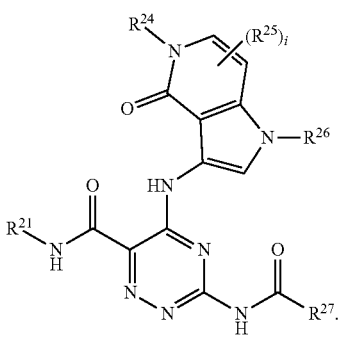

(II$^h$)

In certain embodiments, the compound has the structural formula:

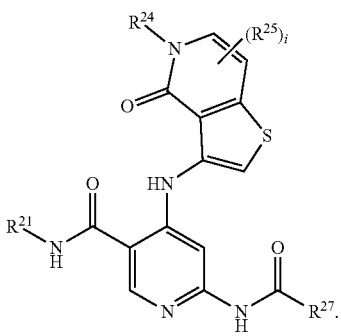

(II$^i$)

In certain embodiments, the compound has the structural formula:

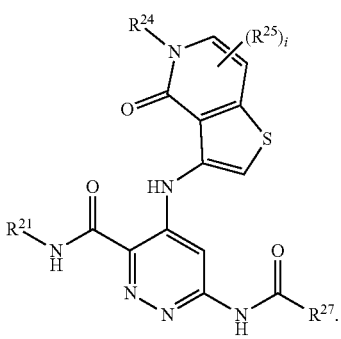

(II$^j$)

In certain embodiments, the compound has the structural formula:

(II$^k$)

In certain embodiments, the compound has the structural formula:

(II$^l$)

In certain embodiments of formulae (II)-(II$^l$), R$^{27}$ is cyclopropyl.

In certain embodiments of formulae (II)-(II$^l$), R$^{27}$ is cyclobutyl.

In certain embodiments of formulae (II)-(II$^l$), R$^{24}$ is a C$_1$-C$_{12}$ alkyl, cycloalkyl, heterocycloalkyl, aryl or heteroaryl, optionally substituted with one or more of F, Cl, CN, OR, CH$_3$, CF$_3$ and OCF$_3$.

In certain embodiments of formulae (II)-(II$^l$), R$^{24}$ is a C$_1$-C$_{12}$ alkyl, optionally substituted with one or more of F, Cl, CN, OR, NRR', CH$_3$, CF$_3$ and OCF$_3$. In certain embodiments, R$^{24}$ is CH$_3$. In certain embodiments, R$^{24}$ is ethyl.

In certain embodiments of formulae (II)-(II$^l$), R$^{24}$ is a C$_3$-C$_{12}$ cycloakyl or heterocycloalkyl, optionally substituted with one or more of F, Cl, CN, OR, NRR', CH$_3$, CF$_3$ and OCF$_3$.

In certain embodiments of formulae (II)-(II$^l$), R$^{24}$ is a C$_4$-C$_{12}$ aryl, optionally substituted with one or more of F, Cl, CN, OR, NRR', CH$_3$, CF$_3$ and OCF$_3$.

In certain embodiments of formulae (II)-(II$^l$), R$^{24}$ is a C$_3$-C$_{12}$ heteroaryl, optionally substituted with one or more of F, Cl, CN, OR, NRR', CH$_3$, CF$_3$ and OCF$_3$.

In certain embodiments of formulae (II)-(II$^l$), R$^{25}$ is H.

In certain embodiments of formulae (II)-(II$^l$), R$^{25}$ is F or C$_1$.

In certain embodiments of formulae (II)-(II$^l$), R$^{25}$ is CH$_3$, CHF$_2$ or CF$_3$.

In certain embodiments of formulae (II)-(II$^l$), R$^{25}$ is CN.

In certain embodiments of formulae (II)-(II$^l$), R$^{25}$ is OR.

In certain embodiments of formulae (II)-(II$^l$), i is 0 (i.e., R$^{25}$ is absent).

In certain embodiments of formulae (II)-(II$^l$), i is 1.

In certain embodiments of formulae (II)-(II$^l$), i is 2.

In yet another aspect, the invention generally relates to a compound having the structural formula (III):

(III)

or a pharmaceutically acceptable form or an isotope derivative thereof,
wherein
Ring A is a 5- or 6-membered aryl or heteroaryl;
X$^1$ is selected from NR, O, CH$_2$ and CF$_2$;
Z$^1$ is CH or N;
Z$^2$ is CH, CF or N;
each of Z$^3$ and Z$^4$ is independently selected from NR, CH$_2$ and CF$_2$;
Z$^6$ is NR$^{36}$, CH$_2$, O, S, SO or SO$_2$;
R$^{32}$ is R$^{32'}$ or OR$^{32'}$, wherein R$^{32'}$ is a C$_{1-12}$ alkyl, 3- to 6-membered cycloalkyl or heterocycloalkyl comprising 1, 2 or 3 heteroatoms selected from N, O and S, or a 5- or 6-membered aryl or heteroaryl group, each substituted with 0-3 R$^{32a}$;
R$^{32a}$ is independently at each occurrence, H, OCF$_3$, CN, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, (CH$_2$)$_r$NR$^g$R$^g$, —(CH$_2$)$_r$C(O)NR$^g$R$^g$, —(CH$_2$)$_r$NR$^b$C(O)R$^c$, —(CH$_2$)$_r$NR$^b$C(O)OR$^c$, —NR$^b$C(O)NR$^g$R$^g$, —S(O)$_v$NR$^g$R$^g$, —NR$^b$S(O)$_v$R$^c$, —S(O)$_v$R$^c$, C$_{1-6}$ alkyl substituted with 0-3 R$^a$, C$_{1-6}$ haloalkyl, C$_{2-6}$ alkenyl substituted with 0-3 R$^a$, 3- to 6-membered cycloalkyl substituted with 0-3 R$^a$, or 3- to 6-membered heterocycloalkyl comprising 1-3 heteroatoms selected from N, O and S substituted with 0-3 R$^a$;
each of R$^{33}$ and R$^{34}$ is independently selected from H, F, Cl, CN, OR$^g$, CH$_3$, CD$_3$, CF$_3$, OCD$_3$, OCF$_3$ and —(CH$_2$)$_p$-Q;
R$^{35}$ is H, F, a C$_1$-C$_3$ alkyl and CD$_3$, provided that R$^{35}$ is not F when X$^1$ is O or N;
R$^{36}$ is R substituted with 0-3 R$^d$;
R$^a$ at each occurrence is independently H, F, Cl, Br, OCF$_3$, CF$_3$, CHF$_2$, CN, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^g$R$^g$, —(CH$_2$)$_r$C(O)NR$^g$R$^g$, —(CH$_2$)$_r$NR$^b$C(O)R$^c$, —(CH$_2$)$_r$NR$^b$C(O)OR$^c$, —NR$^b$C(O)NR$^g$R$^g$, —S(O)$_v$NR$^g$R$^g$, —NR$^b$S(O)$_v$R$^c$, —S(O)R$^c$, —S(O)$_2$R$^c$, C$_{1-6}$ alkyl substituted with 0-3 R$^f$, C$_{1-6}$ haloalkyl, 3- to 6-membered cycloalkyl substituted with 0-3 R$^f$, or 3- to 6-membered heterocycloalkyl comprising 1-3 heteroatoms selected from N, O and S substituted with 0-3 R$^f$;
R$^b$ is H, C$_{1-6}$ alkyl substituted with 0-3 R$^d$, C$_{1-6}$ haloalkyl, C$_{3-6}$ cycloalkyl substituted with 0-2 R$^d$, or 5- to 7-membered heterocycloalkyl comprising 1-3 heteroatoms selected from N, O and S substituted with 0-3 $R^f$ or $(CH_2)_r$-phenyl substituted with 0-3 $R^d$;

$R^c$ is $C_{1-6}$ alkyl substituted with 0-3 $R^f$, $(CH_2)_r$—$C_{3-6}$ cycloalkyl substituted with 0-3 $R^f$ or $(CH_2)_r$-phenyl substituted with 0-3 $R^f$;

$R^d$ is independently at each occurrence, hydrogen, F, Cl, Br, $OCF_3$, $CF_3$, CN, $NO_2$, —OR', —$(CH_2)_rC(O)$ $R^e$, —$NR^eR^e$, —$NR^eC(O)OR^e$, $C_{1-6}$ alkyl or $(CH_2)_r$-phenyl substituted with 0-3 $R^f$;

$R^e$ is independently at each occurrence, hydrogen, $C_{1-6}$ alkyl, $C_{3-6}$ cycloalkyl or $(CH_2)_r$-phenyl substituted with 0-3 $R^f$;

$R^f$ is independently at each occurrence, hydrogen, halo, CN, $NH_2$, OH, $C_{3-6}$ cycloalkyl, $CF_3$, $O(C_{1-6}$ alkyl) or a 5- to 7-membered heterocycloalkyl comprising 1-3 heteroatoms selected from N, O and S;

$R^g$ at each occurrence is independently H, $C_{1-4}$ alkyl substituted with 0-3 $R^f$, $CF_3$, $C_{3-10}$ cycloalkyl substituted with 0-1 $R^f$, $(CH)_r$-phenyl substituted with 0-3 $R^d$ or 5- to 7-membered heterocycloalkyl comprising 1-3 heteroatoms selected from N, O and S substituted with 0-3 $R^d$;

Q is a water solubilizing group, optionally selected from OH, OR, NRR', heterocyclic and heteroaryl groups, wherein R and R', together with the nitrogen atom to which they are bound, form a 4- to 7-membered ring comprising 0-2 heteroatoms selected from O, NR, S and $SO_2$;

R is H or a $C_1$-$C_6$ alkyl substituted with 0-3 $R^d$;

R' is H or a $C_1$-$C_6$ alkyl substituted with 0-3 $R^d$;

m is 0, 1, 2 and 3;

n is 0, 1, 2 and 3;

p is 0, 1, 2, 3 or 4;

q is 0, 1, 2, 3 or 4;

v is 0, 1, or 2; and r is 0, 1, 2, 3, 4 or 5.

In certain embodiments of formula (III), $X^1$ is NH, having the structural formula (III$_1$):

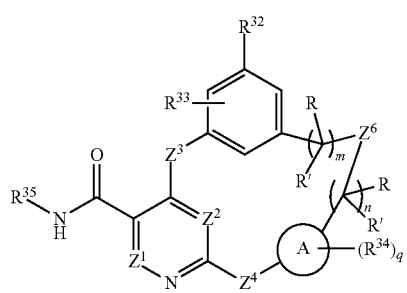

(III$_1$)

In certain embodiments of formulae (III)-(III$_1$), Ring A is a 6-membered aryl.

In certain embodiments of formulae (III)-(III$_1$), Ring A is a 6-membered heteroaryl.

In certain embodiments of formulae (III)-(III$_1$), the compound has the structural formula (III$_2$):

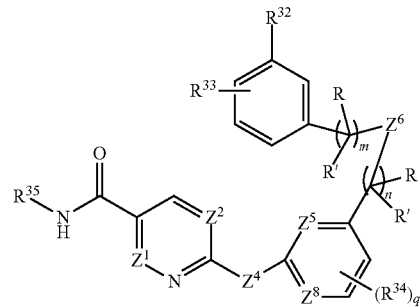

(III$_2$)

wherein each of $Z^5$ and $Z^8$ is CH or N.

In certain embodiments of formula (III$_2$), wherein $Z^8$ is CH and the compound has the structural formula (III$_3$):

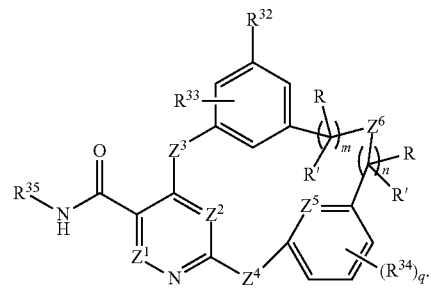

(III$_3$)

In certain embodiments of formula (III$_3$), $Z^2$ and $Z^5$ are not both CH.

In certain embodiments of formulae (III) or (III$_3$), $Z^7$ is NR. In certain embodiments, R is H and $Z^7$ is NH.

In certain embodiments of formulae (III) or (III$_3$), $Z^7$ is $CH_2$.

In certain embodiments of formulae (III) or (III$_3$), $Z^7$ is $CF_2$.

In certain embodiments of formulae (III) or (III$_3$), each of $Z^3$ and $Z^4$ is NH.

In certain embodiments of formula (III$_3$), $Z^1$ is CH, $Z^2$ is CH, each of $Z^3$ and $Z^4$ is NH, and $Z^5$ is N.

In certain embodiments of formula (III$_3$), $(CRR')_m$ is $(CH_2)_m$ and $(CRR')_n$ is $(CH_2)_n$.

In certain embodiments of formula (III$_3$), the compound has the structural formula:

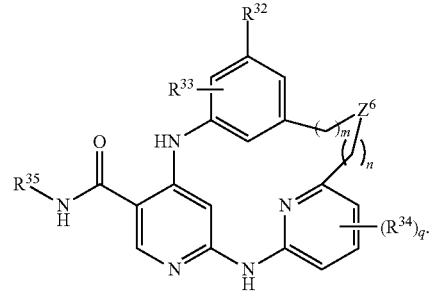

(III$_3^a$)

In certain embodiments of formula (III$_3$), $Z^1$ is N, $Z^2$ is CH, and $Z^5$ is N.

In certain embodiments of formula (III₃), the compound has the structural formula:

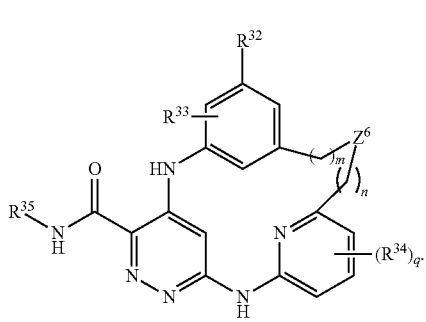

(III₃ᵇ)

In certain embodiments of formula (III₃), $Z^1$ is CH, $Z^2$ is N, and $Z^5$ is N.

In certain embodiments of formula (III₃), the compound has the structural formula:

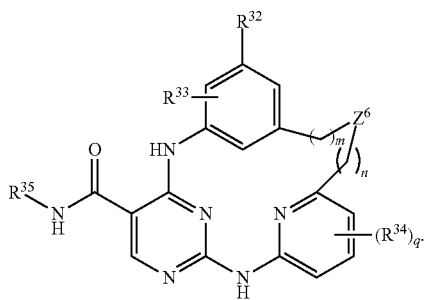

(III₃ᶜ)

In certain embodiments of formula (III₃), $Z^1$ is CH, $Z^2$ is N, and $Z^5$ is CH.

In certain embodiments of formula (III₃), the compound has the structural formula:

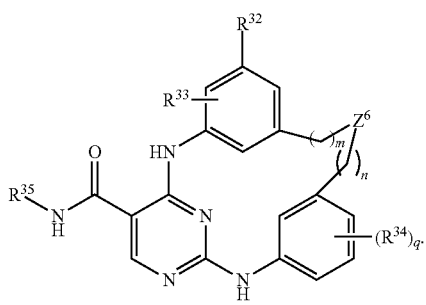

(III₃ᵈ)

In certain embodiments of formula (III₃), $Z^1$ is N, $Z^2$ is N, and $Z^5$ is N.

In certain embodiments of formula (III₃), the compound has the structural formula:

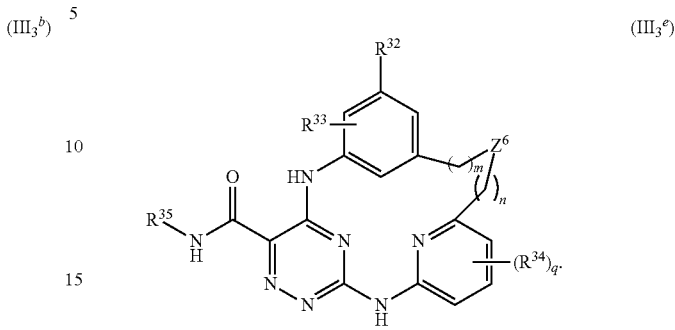

(III₃ᵉ)

In certain embodiments of formulae (III₃)-(III₃ᵉ), $R^{32}$ is a 6-membered aryl or heteroaryl group comprising 0, 1 or 2 nitrogen atoms and 0 or 1 oxygen atom.

In certain embodiments of formulae (III₃)-(III₃ᵉ), $R^{32}$ is selected from:

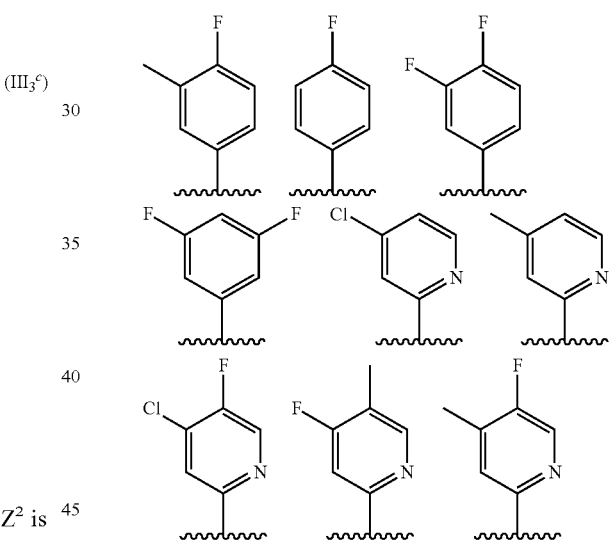

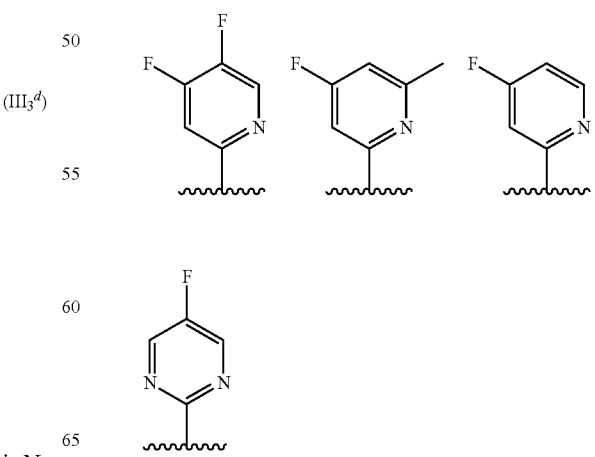

In certain embodiments of formulae (III₃)-(III₃ᵉ), R³² is a 3- to 6-membered cycloalkyl or heterocycloalkyl comprising 1, 2 or 3 heteroatoms wherein the heteroatoms are selected from N, O and S, substituted with 0-3 R³²ᵃ.

In certain embodiments of formulae (III₃)-(III₃ᵉ), R³² is a 3-membered cycloalkyl substituted with 0-3 R³²ᵃ.

In certain embodiments of formulae (III₃)-(III₃ᵉ), R³² is cyclopropyl substituted with 0-3 R³²ᵃ.

In certain embodiments of formulae (III₃)-(III₃ᵉ), R³² is a 5-membered heteroaryl group comprising 1, 2 or 3 nitrogen atoms and 0 or 1 oxygen atom.

In certain embodiments of formulae (III₃)-(III₃ᵉ), R³² is a triazole, oxadiazole, thiazole, oxazole or pyrazole substituted with 0-3 R³²ᵃ.

In certain embodiments of formulae (III₃)-(III₃ᵉ), R³² is selected from:

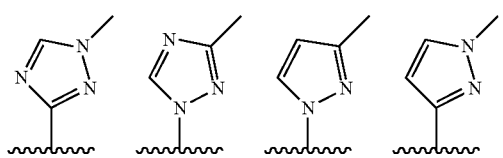

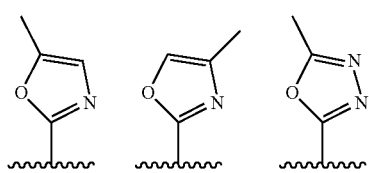

In certain embodiments, R³² is a N-methyl-1, 2, 4-triazole.

In certain embodiments of formulae (III₃)-(III₃ᵉ), q is 0 (i.e., R³⁴ is absent).

In certain embodiments of formulae (III₃)-(III₃ᵉ), q is 1.

In certain embodiments of formulae (III₃)-(III₃ᵉ), q is 2.

In certain embodiments of formulae (III₃), the compound has the structural formula:

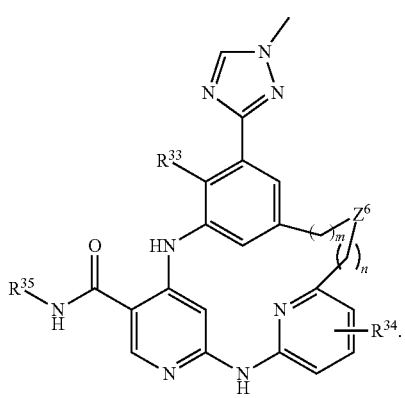

(III₃ᶠ)

In certain embodiments of formulae (III₂), the compound has the structural formula:

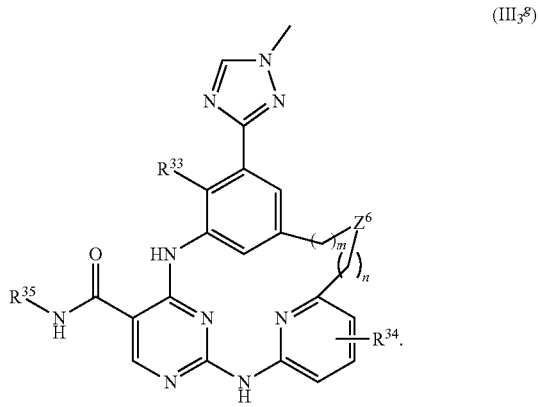

(III₃ᵍ)

In certain embodiments of formulae (III₂), the compound has the structural formula:

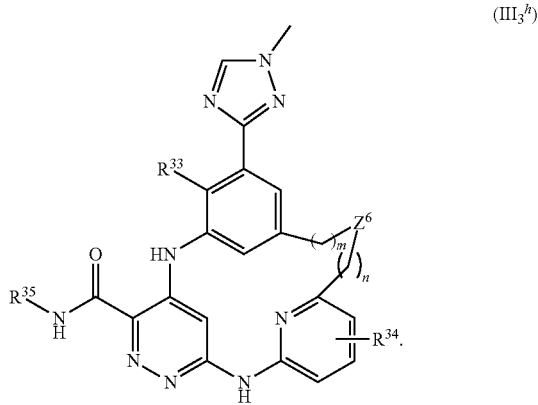

(III₃ʰ)

In certain embodiments of formulae (III₂), the compound has the structural formula:

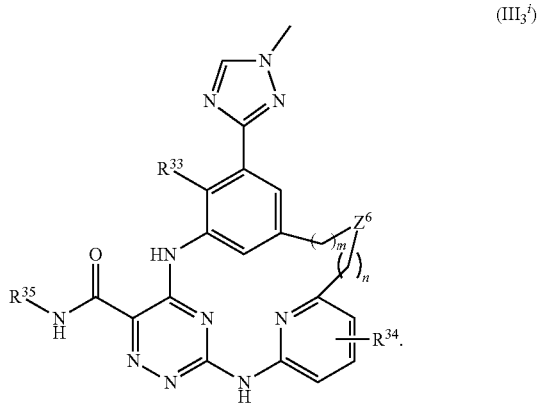

(III₃ⁱ)

In certain embodiments of formulae (III₃)-(III₃ⁱ), Z⁶ is NR³⁶. In certain embodiments, R³⁶ is CH₃.

In certain embodiments of formulae (III₃)-(III₃ⁱ), Z⁶ is O.

In certain embodiments of formulae (III₃)-(III₃ⁱ), Z⁶ is S.

In certain embodiments of formulae (III₃)-(III₃ⁱ), Z⁶ is CH₂.

In certain embodiments of formulae (III₃)-(III₃ⁱ), m=1.
In certain embodiments of formulae (III₃)-(III₃ⁱ), m=2.
In certain embodiments of formulae (III₃)-(III₃ⁱ), n=1.
In certain embodiments of formulae (III₃)-(III₃ⁱ), n=2.
In certain embodiments of formulae (III₃)-(III₃ⁱ), m=n=1.
In certain embodiments of formulae (III₃)-(III₃ⁱ), m=n=2.

In certain embodiments of formulae (III₃), the compound has the structural formula:

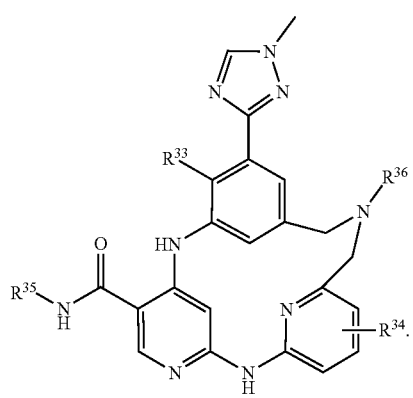

(III₃ʲ)

In certain embodiments of formulae (III₃), the compound has the structural formula:

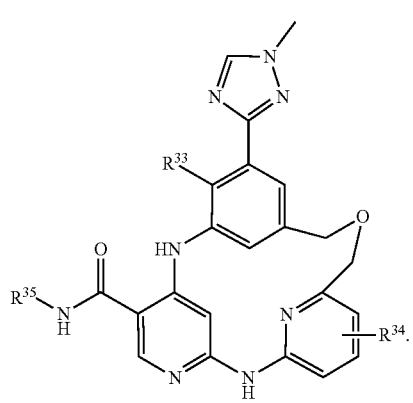

(III₃ᵏ)

In certain embodiments of formulae (III₃), the compound has the structural formula:

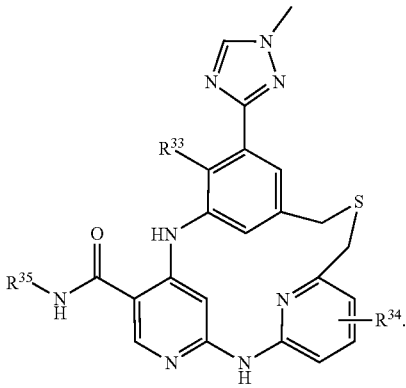

(III₃ˡ)

In certain embodiments of formulae (III₃), the compound has the structural formula:

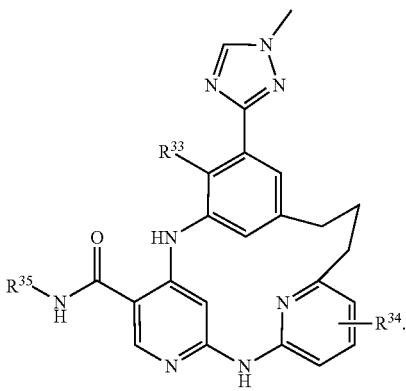

(III₃ᵐ)

In certain embodiments of formulae (III₃), the compound has the structural formula:

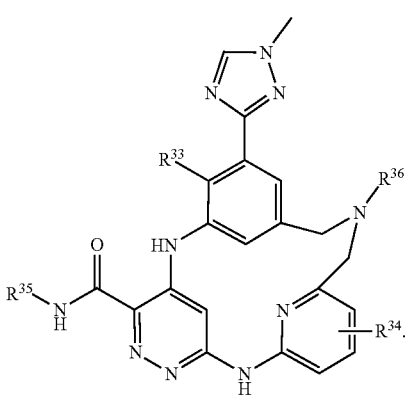

(III₃ⁿ)

In certain embodiments of formulae (III₃), the compound has the structural formula:

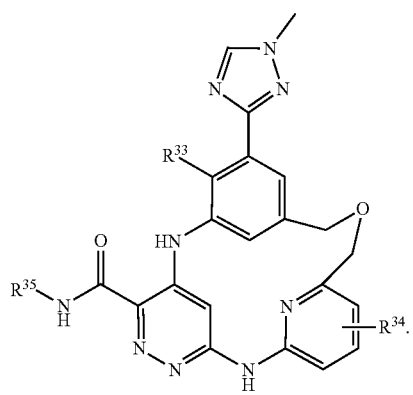

(III₃ᵒ)

In certain embodiments of formulae (III₃), the compound has the structural formula:

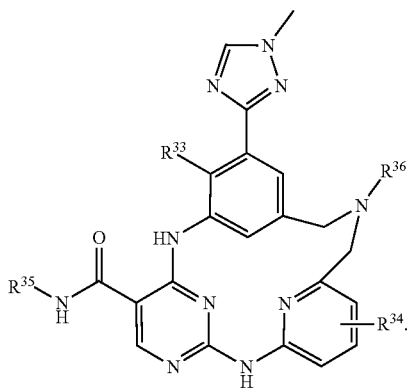

(III₃ʳ)

In certain embodiments of formulae (III₃), the compound has the structural formula:

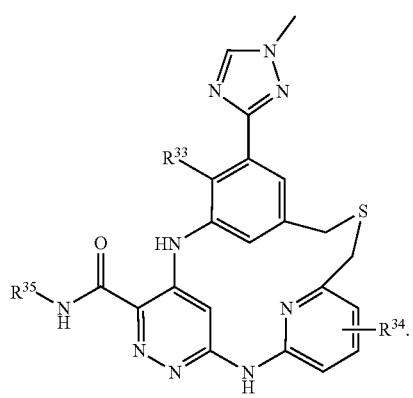

(III₃ᵖ)

In certain embodiments of formulae (III₃), the compound has the structural formula:

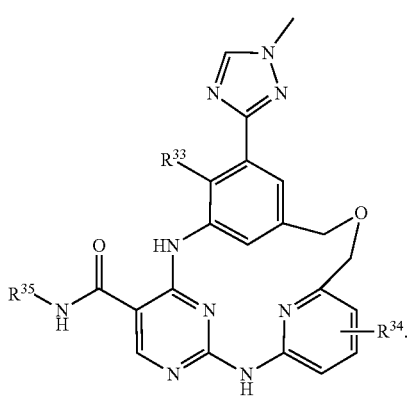

(III₃ˢ)

In certain embodiments of formulae (III₃), the compound has the structural formula:

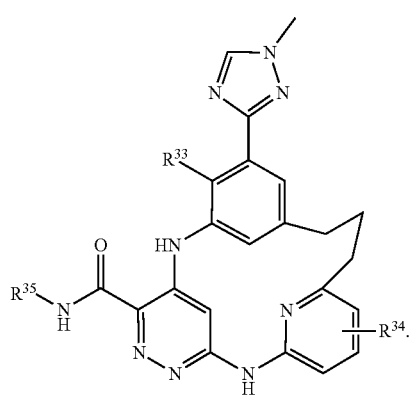

(III₃ᑫ)

In certain embodiments of formulae (III₃), the compound has the structural formula:

(III₃ᵗ)

In certain embodiments of formulae (III₃), the compound has the structural formula:

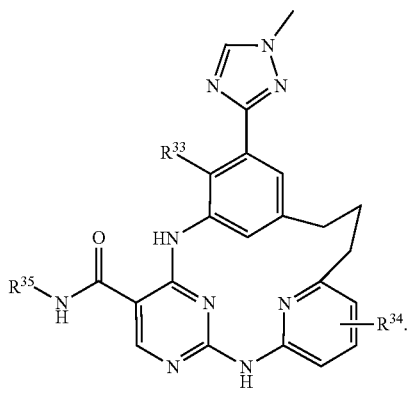

(III₃ᵘ)

In certain embodiments of formulae (III₃), the compound has the structural formula:

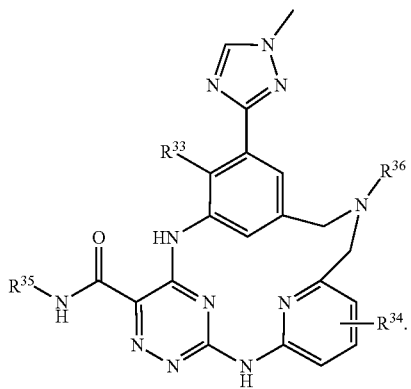

(III₃ᵛ)

In certain embodiments of formulae (III₃), the compound has the structural formula:

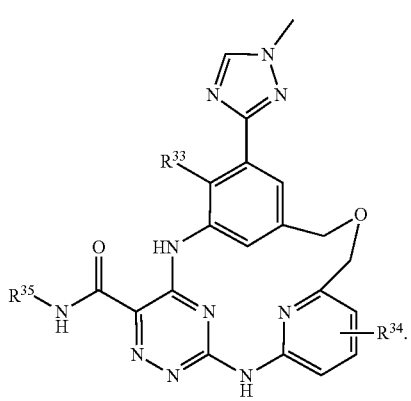

(III₃ʷ)

In certain embodiments of formulae (III₃), the compound has the structural formula:

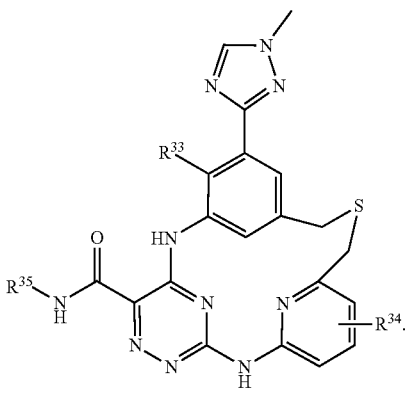

(III₃ˣ)

In certain embodiments of formulae (III₃), the compound has the structural formula:

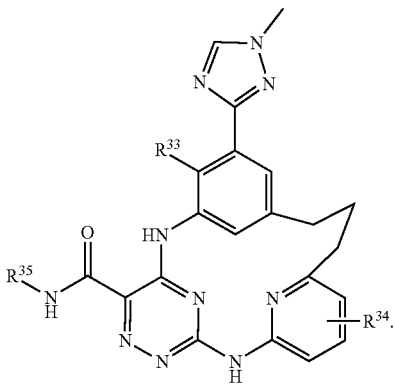

(III₃ʸ)

In certain embodiments of formula (III₁), $Z^5$ is N and $Z^8$ is N.

In certain embodiments of formula (III₁), the compound has the structural formula (III₄):

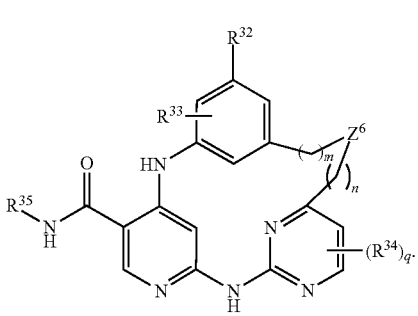

(III₄)

In certain embodiments of formula (III₄), the compound has the structural formula (III₄ᵃ):

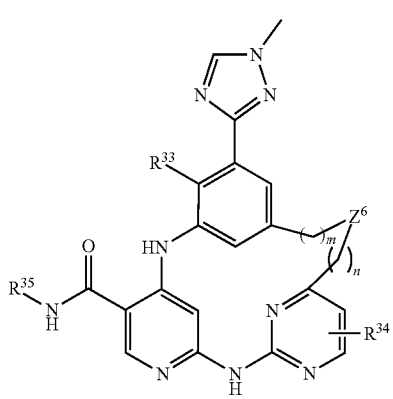

(III₄ᵃ)

In certain embodiments of formula (III₄), the compound has the structural formula (III₄ᵇ):

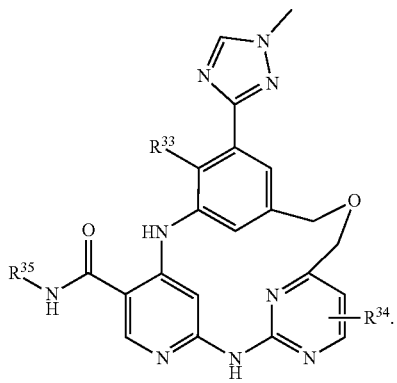

(III₄ᵇ)

In certain embodiments of formula (III₄), the compound has the structural formula (III₄ᶜ):

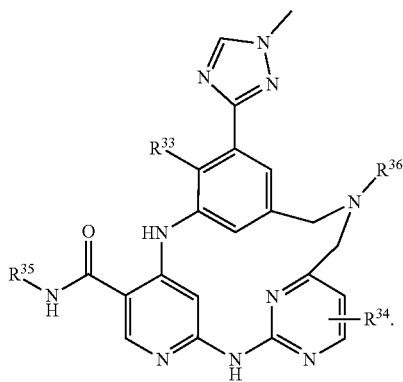

(III₄ᶜ)

In certain embodiments of formula (III₄), the compound has the structural formula (III₄ᵈ):

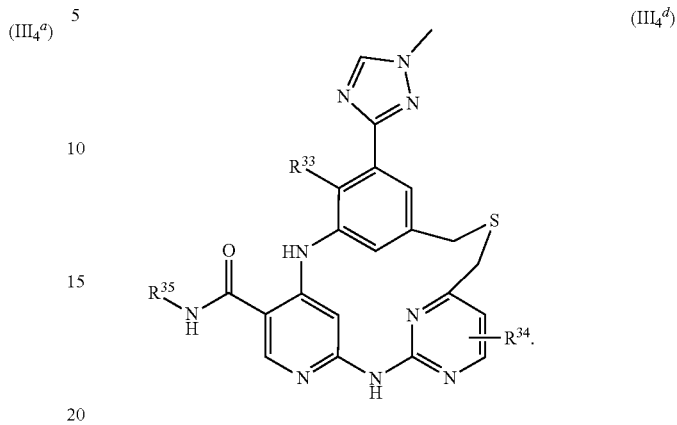

(III₄ᵈ)

In certain embodiments of formula (III₄), the compound has the structural formula (III₄ᵉ):

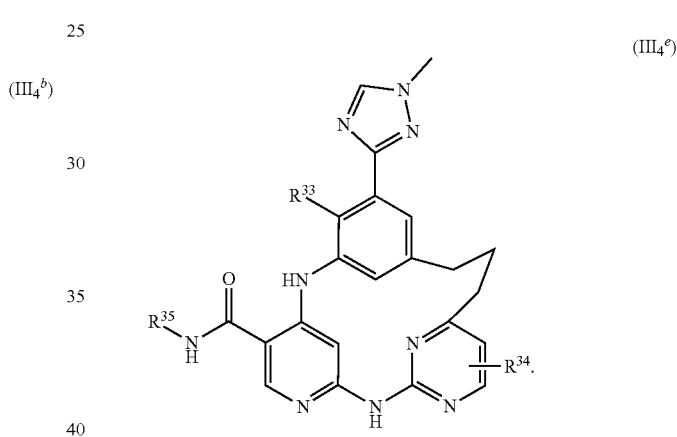

(III₄ᵉ)

In certain embodiments of formulae (III)-(III₄ᵉ) $R^{33}$ is OR. In certain embodiments, R is $CH_3$ and $R^{33}$ is $OCH_3$. In certain embodiments, R is $CD_3$ and $R^{33}$ is $OCD_3$.

In certain embodiments of formulae (III)-(III₄ᵉ), $R^{34}$ is H.

In certain embodiments of formulae (III)-(III₄ᵉ), $R^{34}$ is selected from F or Cl.

In certain embodiments of formulae (III)-(III₄ᵉ), $R^{34}$ is selected from CN.

In certain embodiments of formulae (III)-(III₄ᵉ), $R^{34}$ is selected from $CH_3$ and $CF_3$.

In certain embodiments of formulae (III)-(III₄ᵉ), $R^{34}$ is selected from $OCF_3$.

In certain embodiments of formulae (III)-(III₄ᵉ), $R^{34}$ is —$(CH_2)_p$-Q. In certain embodiments, p is 1 or 2 and Q is OH, OR or NRR' (e.g., $N(CH_3)_2$). In certain embodiments, Q is a heterocyclic (e.g., morpholine) or heteroaryl group.

In certain embodiments of formulae (III)-(III₄ᵉ), $R^{34}$ is —$(CH_2)_p$-Q and Q is an amino or morpholino group.

In certain embodiments of formulae (III)-(III₄ᶜ), $R^{35}$ is $CH_3$.

In certain embodiments of formulae (III)-(III₄ᵉ), $R^{35}$ is $CD_3$.

In certain embodiments of formulae (III)-(III₁), Ring A is a 5-membered aryl.

In certain embodiments of formulae (III)-(III₁), Ring A is a 5-membered heteroaryl.

In certain embodiments of formulae (III)-(III$_1$), the compound has the structural formula (III$_5$):

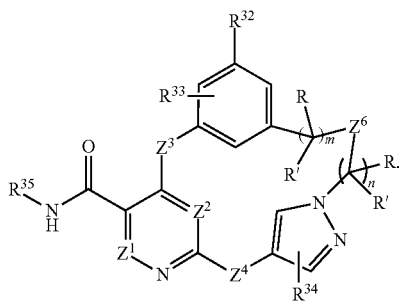
(III$_5$)

In certain embodiments of formula (III$_5$), (CRR')$_m$, is (CH$_2$)$_m$ and (CRR')$_n$ is (CH$_2$)$_n$.

In certain embodiments of formula (III$_5$), the compound has the structural formula:

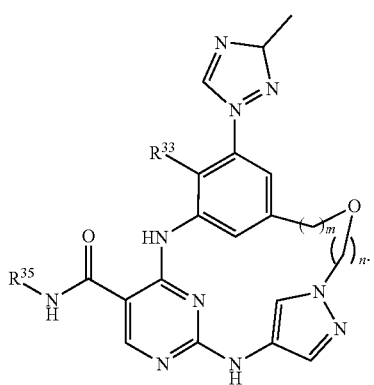
(III$_5{}^a$)

In certain embodiments of formula (III$_1$), the compound has the structural formula:

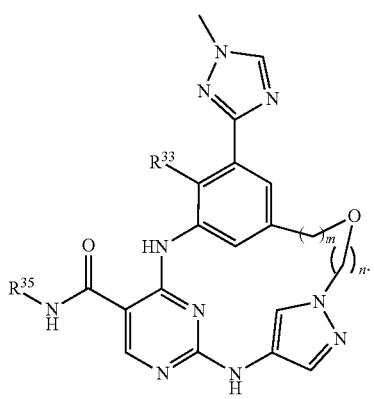
(III$_5{}^b$)

In certain embodiments of formulae (III$_5$) or (III$_5{}^b$), R$^{35}$ is CH$_3$.

In certain embodiments of formulae (III$_5$) or (III$_5{}^b$), R$^{35}$ is CD$_3$.

In certain embodiments of formulae (III$_5$) or (III$_5{}^b$), wherein R$^{33}$ is OCH$_3$.

In certain embodiments of formulae (III$_5$) or (III$_5{}^b$), m is 1 and n is 2.

In yet another aspect, the invention generally relates to a compound having the structural formula (IV):

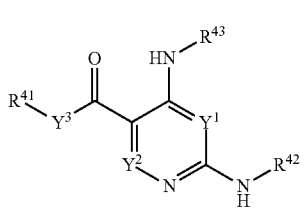
(IV)

or a pharmaceutically acceptable form or an isotope derivative thereof,
wherein
Y$^1$ is CH, CF or N;
Y$^2$ is CH or N;
Y$^3$ is NR, O, CH$_2$ or CF$_2$;
R$^{41}$ is a H, F, C$_1$-C$_3$ alkyl and CD$_3$, provided that R$^{41}$ is not F when Y$^3$ is NR or O;
R$^{42}$ is
  R$^{42'}$, wherein R$^{42'}$ is a C$_1$-C$_6$ alkyl, C$_3$-C$_6$ cycloalkyl or heterocycloalkyl, aryl or heteroaryl, each substituted with 0-2 of halogen, CN, OR, amino, alkyl, cycloalkyl, heterocyclic, aryl and heteroaryl;
  an aryl or heteroaryl group substituted with 0-2 R$^{42a}$; or
  (C=O)R$^{42b}$;
R$^{43}$ is

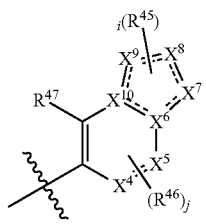

wherein
each of X$^4$, X$^5$, X$^6$, X$^7$, X$^8$, X$^9$ and X$^{10}$ is independently selected from C, CH, O, N and NH;
R$^{42a}$ at each occurrence is independently H, D, halo, OH, OR, CH$_3$, CF$_3$, CH$_2$CF$_3$, CN, C(O)NR, NRR', (CH$_2$)$_n$NRR' or a 4- to 6-membered heterocycle having 1-4 heteroatoms selected from N, O and S;
R$^{42b}$ is a C$_{1-6}$ alkyl or C$_{3-6}$ cycloalkyl, aryl or heteroaryl, each substituted with 0-2 R$^{42c}$;
R$^{42c}$ at each occurrence is independently H, halo, CN, OR, NRR', OCF$_3$, CF$_3$, C$_{1-6}$ alkyl substituted with 0-3 R$^{42a}$, C$_{1-6}$ haloalkyl, C$_{2-6}$ alkenyl substituted with 0-3 R$^{42a}$, C$_{2-6}$ alkynyl substituted with 0-3 R$^{42a}$;
R$^{45}$ each occurrence is independently H, halo, CN, OR, NRR', OCF$_3$, CF$_3$, C$_{1-6}$ alkyl, substituted with 0-3 R$^{42a}$, or C$_{3-10}$ cycloalkyl or heterocycloalkyl, C$_{5-10}$ aryl or heteroaryl, or a 4- to 10-membered heterocycle having 1-4 heteroatoms selected from N, O and S, each group is substituted with 0-4 R$^{42c}$, optionally two R$^{45s}$, along with the C or N atoms that they are attached to, form a 4- to 6-membered ring;

$R^{46}$ each occurrence is independently F, Cl, CN, OR, $C_1$-$C_3$ alkyl, $C_3$-$C_5$ cycloalkyl, $CD_3$, $CH_2CF_3$ or $CF_3$;

$R^{47}$ is H, $OCF_3$, $C_1$-$C_3$ alkyl, $C_1$-$C_3$ alkoxy or $OCD_3$;

each of R and R' is independently H or a $C_1$-$C_6$ alkyl, or R and R', together with the nitrogen atom to which they are bound, form a 4- to 7-membered ring comprising 0-2 heteroatoms selected from O, NR, S and $SO_2$;

n is 0, 1, 2, 3 or 4;

i is 0, 1 or 2; and j is 0, 1 or 2.

In certain embodiments of formula (IV), $R^{43}$ is selected from:

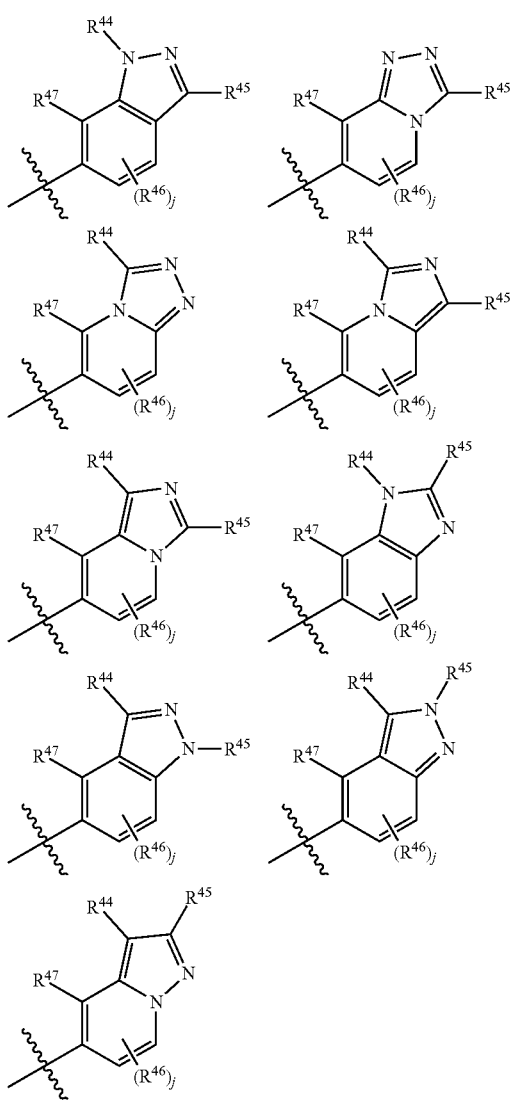

wherein $R^{44}$ or $R^{45}$, when bond to N, is H, a $C_{1-6}$ alkyl, $CD_3$, $C_{3-8}$ cycloalkyl, 3- to 7-membered heterocycloalkyl, or $C_5$-$C_6$ aryl or heteroaryl, substituted with 0-3 $R^{52a}$; and $R^{44}$ or $R^{45}$, when bond to C, is H, F, Cl, CN, $C_{1-6}$ alkyl, $CD_3$, or $C_{1-6}$ alkoxy, $C_{3-8}$ cycloalkyl, 3- to 7-membered heterocycloalkyl, or $C_5$-$C_6$ aryl or heteroaryl substituted with 0-3 $R^{42a}$.

In certain embodiments of formula (IV), $R^{43}$ is selected from:

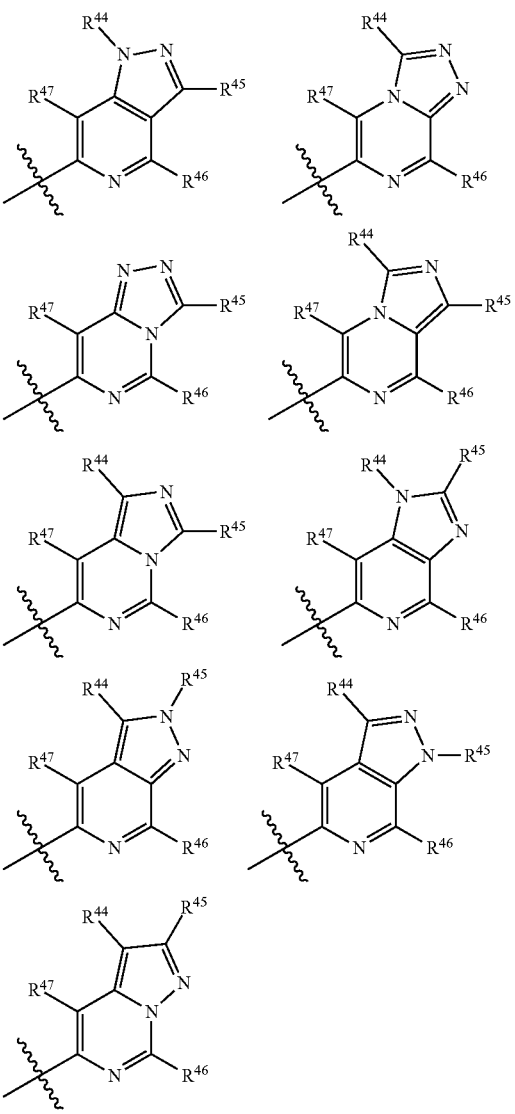

wherein $R^{44}$ or $R^{45}$, when bond to N, is H, a $C_{1-6}$ alkyl, $CD_3$, $C_{3-8}$ cycloalkyl, 3- to 7-membered heterocycloalkyl, or $C_5$-$C_6$ aryl or heteroaryl, substituted with 0-3 $R^{52a}$; and $R^{44}$ or $R^{45}$, when bond to C, is H, F, Cl, CN, $C_{1-6}$ alkyl, $CD_3$, or $C_{1-6}$ alkoxy, $C_{3-8}$ cycloalkyl, 3- to 7-membered heterocycloalkyl, or $C_5$-$C_6$ aryl or heteroaryl substituted with 0-3 $R^{42a}$.

In certain embodiments, $R^{47}$ is $C_1$-$C_3$ alkoxy.

In certain embodiments, $R^{47}$ is $OCH_3$.

In certain embodiments, $R^{47}$ is $OCD_3$.

In certain embodiments, j is 0.

In certain embodiments, j is 1.

In certain embodiments, $R^{46}$ is F.

In certain embodiments, $R^{46}$ is Cl.

In certain embodiments of formula (IV), $Y^1$ is CH and $Y^2$ is CH:

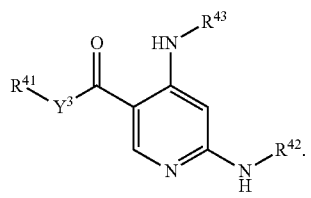
(IV$^a$)

In certain embodiments of formula (IV), $Y^1$ is CH and $Y^2$ is N:

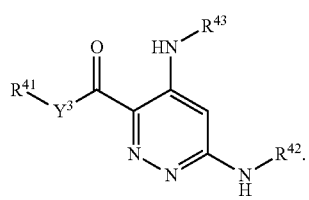
(IV$^b$)

In certain embodiments of formula (IV), $Y^1$ is N and $Y^2$ is CH:

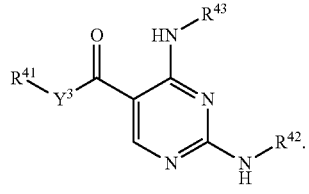
(IV$^c$)

In certain embodiments of formula (IV), $Y^1$ is N and $Y^2$ is N:

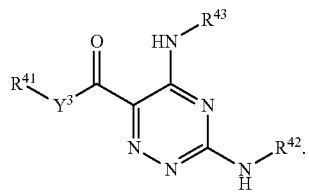
(IV$^d$)

In certain embodiments of formula (IV), $Y^1$ is CF.
In certain embodiments of formulae (IV)-(IV$^d$), $Y^3$ is NR.
In certain embodiments of formulae (IV)-(IV$^d$), $Y^3$ is NH.

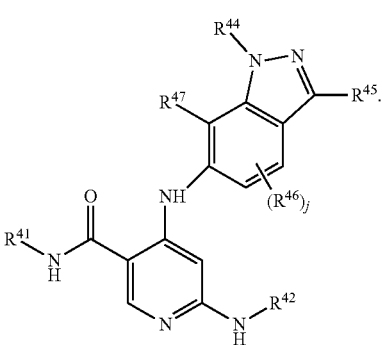
(IV$^e$)

In certain embodiments of formula (IV), the compound has the structural formula:

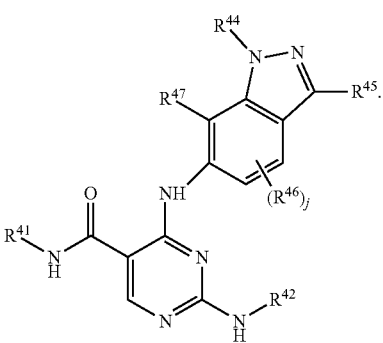
(IV$^f$)

In certain embodiments of formula (IV), the compound has the structural formula:

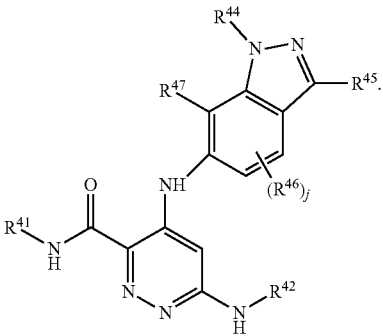
(IV$^g$)

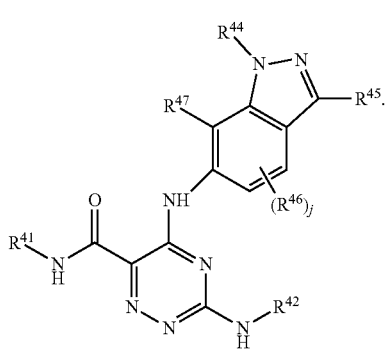
(IV$^h$)
In certain embodiments of formula (IV), the compound has the structural formula:
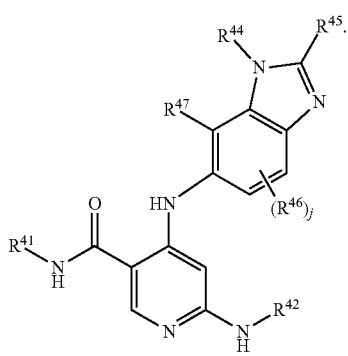
(IV$^i$)
In certain embodiments of formula (IV), the compound has the structural formula:
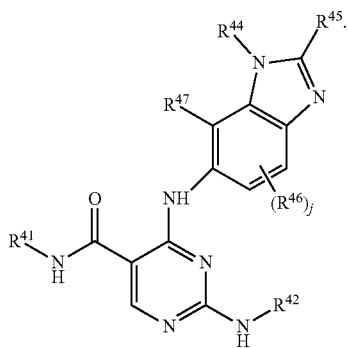
(IV$^j$)
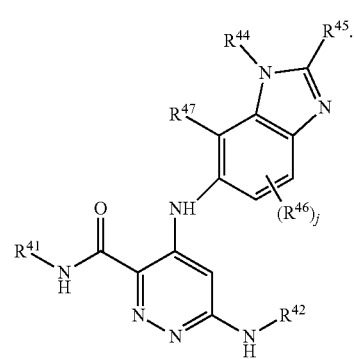
(IV$^k$)
In certain embodiments of formula (IV), the compound has the structural formula:
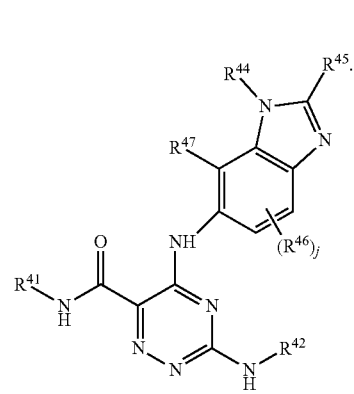
(IV$^l$)
In certain embodiments of formula (IV), the compound has the structural formula:
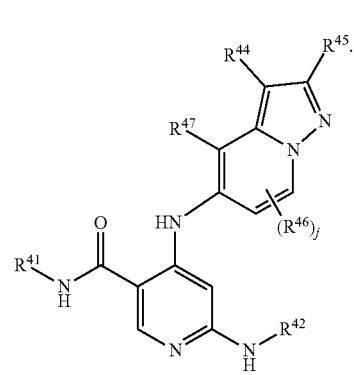
(IV$^m$)

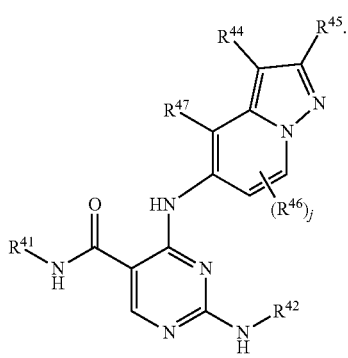

(IV<sup>n</sup>)

In certain embodiments of formula (IV), the compound has the structural formula:

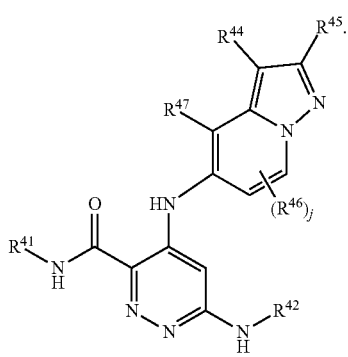

(IV<sup>o</sup>)

In certain embodiments of formula (IV), the compound has the structural formula:

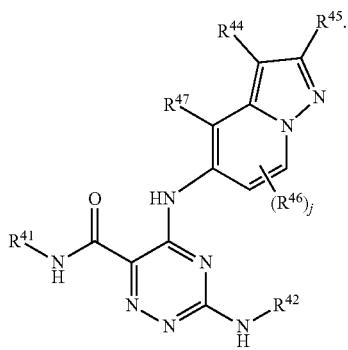

(IV<sup>p</sup>)

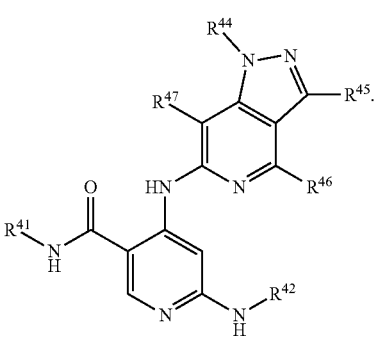

(IV<sup>q</sup>)

In certain embodiments of formula (IV), the compound has the structural formula:

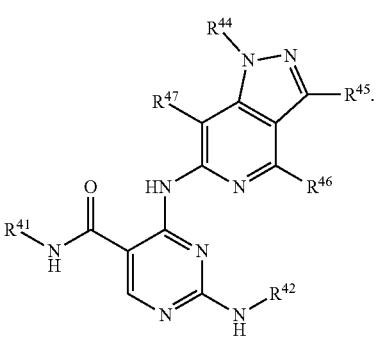

(IV<sup>r</sup>)

In certain embodiments of formula (IV), the compound has the structural formula:

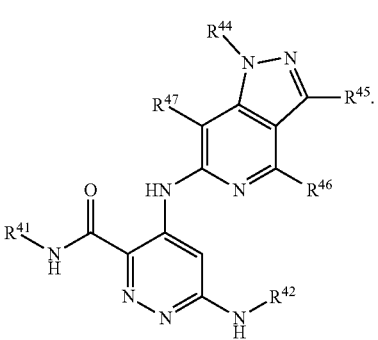

(IV<sup>s</sup>)

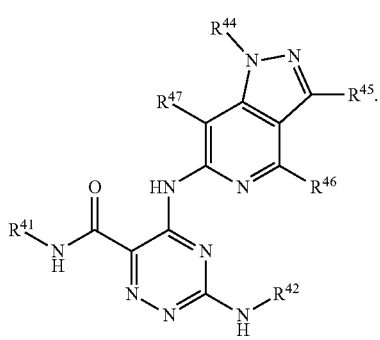 (IV^t)

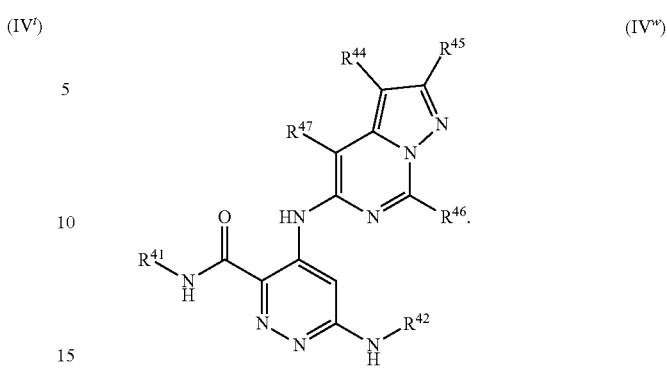 (IV^w)

In certain embodiments of formula (IV), the compound has the structural formula:

In certain embodiments of formula (IV), the compound has the structural formula:

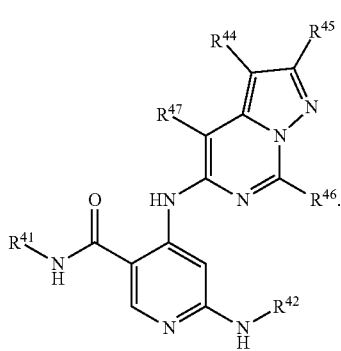 (IV^u)

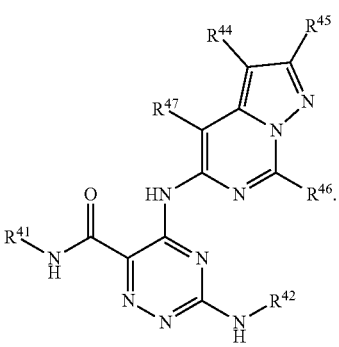 (IV^x)

In certain embodiments of formula (IV), the compound has the structural formula:

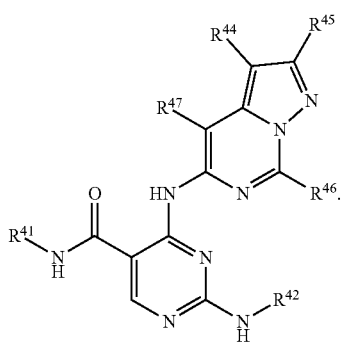 (IV^v)

In certain embodiments of formulae (IV)-(IV^x), wherein $R^{41}$ is $CH_3$.

In certain embodiments of formulae (IV)-(IV^x), wherein $R^{41}$ is $CD_3$.

In certain embodiments of formulae (IV)-(IV^x), wherein $R^{42}$ is $(C=O)R^{42b}$, wherein $R^{42b}$ is selected from $C_1$-$C_6$ alkyl, cyclopropyl or cyclobutyl, substituted with 0-2 $R^{42c}$.

In certain embodiments, $R^{42}$ is $(C=O)R^{42b}$, wherein $R^{42b}$ is cyclopropyl optionally substituted with one or more of F, Cl, $CH_3$, $CF_3$ and CN.

In certain embodiments, $R^{42}$ is $(C=O)R^{42b}$, wherein $R^{42b}$ is cyclobutyl, optionally substituted with one or more of F, Cl, $CH_3$, $CF_3$ and CN.

In certain embodiments, $R^{42}$ is $(C=O)R^{42b}$, wherein $R^{42b}$ is $C_1$-$C_6$ alkyl, optionally substituted with one or more of F, Cl, $CH_3$, $CF_3$, CN, NRR' and OR.

In certain embodiments, $R^{42}$ is pyridine substituted with 0-2 $R^{42c}$.

In certain embodiments, $R^{42}$ is phenyl substituted with 0-2 $R^{42c}$.

In certain embodiments, $R^{42}$ is pyrazolyl substituted with 0-2 $R^{42c}$.

In certain embodiments, $R^{42}$ is pyrimidyl substituted with 0-2 $R^{42c}$.

In certain embodiments, $R^{42c}$ is $CH_3$.

In certain embodiments of formula (IV), the compound has the structural formula:

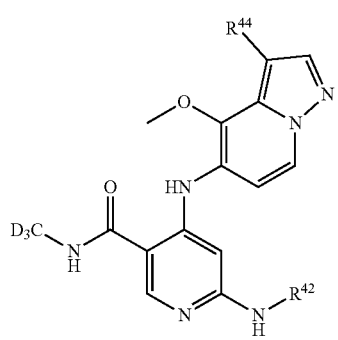

(IV$^y$)

wherein
  $R^{44}$ is halo, CN, $CD_3$, $OC_{1-3}$ alkyl, $C_{1-3}$ alkyl or cyclopropyl, optionally substituted with 0-3 halo, OH, NRR' or CN; and
  $R^{42}$ is phenyl, pyridinyl, pyrazole or pyrimidyl, each substituted with 0-2 $R^{42c}$.

In certain embodiments of formula (IV), the compound has the structural formula:

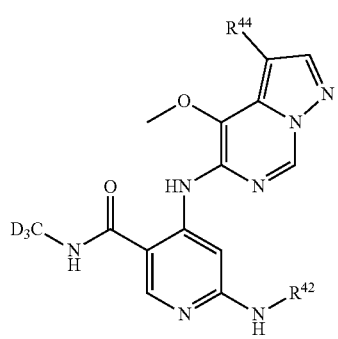

(IV$^z$)

wherein
  $R^{44}$ is halo, CN, $CD_3$, $OC_{1-3}$ alkyl, or $C_{1-3}$ alkyl or cyclopropyl, optionally substituted with 0-3 halo, OH, NRR' or CN; and
  $R^{42}$ is phenyl, pyridinyl, pyrazole or pyrimidyl, each substituted with 0-2 $R^{42c}$.

In certain embodiments of formula (IV), the compound has the structural formula:

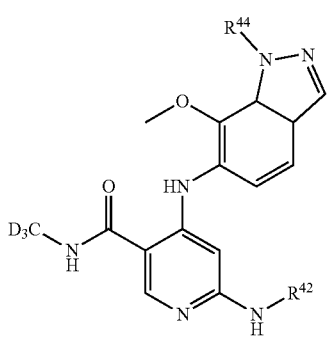

(IV$^{a1}$)

wherein
  $R^{44}$ is $CD_3$, $CD_2CD_3$, or $C_{1-3}$ alkyl or cyclopropyl, optionally substituted with 0-3 halo, OH, NRR' or CN; and
  $R^{42}$ is phenyl, pyridinyl, pyrazole or pyrimidyl, each substituted with 0-2 $R^{42c}$.

In certain embodiments of formula (IV), the compound has the structural formula:

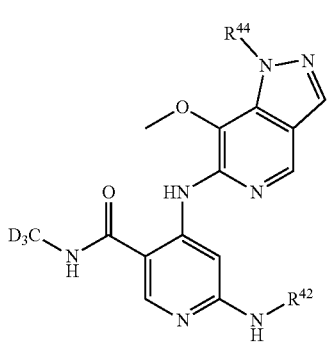

(IV$^{b1}$)

wherein
  $R^{44}$ is $CD_3$, $CD_2CD_3$, or $C_{1-3}$ alkyl or cyclopropyl, optionally substituted with 0-3 halo, OH, NRR' or CN; and
  $R^{42}$ is phenyl, pyridinyl, pyrazole or pyrimidyl, each substituted with 0-2 $R^{42c}$.

In certain embodiments of formula (IV), the compound has the structural formula:

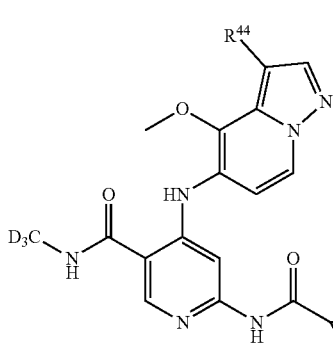

(IV$^{c1}$)

wherein
  $R^{44}$ is halo, CN, $CD_3$, $OC_{1-3}$ alkyl, or $C_{1-3}$ alkyl or cyclopropyl, optionally substituted with 0-3 halo, OH, NRR' or CN; and
  $R^{42c}$ is H, F or $CF_3$.

In certain embodiments of formula (IV), the compound has the structural formula:

(IV$^{d1}$)

wherein
  $R^{44}$ is halo, CN, $CD_3$, $OC_{1-3}$ alkyl, or $C_{1-3}$ alkyl or cyclopropyl, optionally substituted with 0-3 halo, OH, NRR' or CN; and
  $R^{42c}$ is H, F or $CF_3$.

In certain embodiments of formula (IV), the compound has the structural formula:

(IV$^{e1}$)

wherein
  $R^{44}$ is $CD_3$, or $C_{1-3}$ alkyl or cyclopropyl, optionally substituted with 0-3 halo, OH, NRR' or CN; and
  $R^{42c}$ is H, F or $CF_3$.

In certain embodiments of formula (IV), the compound has the structural formula:

(IV$^{f1}$)

wherein
  $R^{44}$ is $CD_3$, $CD_2CD_3$, $C_{1-3}$ alkyl or cyclopropyl, optionally substituted with 0-3 halo, OH, NRR' or CN; and
  $R^{42c}$ is H, F or $CF_3$.

In certain embodiments of formulas (IV$^{c1}$)-(IV$^{f1}$), $R^{42c}$ is H.

In certain embodiments of formulas (IV$^{c1}$)-(IV$^{f1}$), $R^{42c}$ is F.

In certain embodiments where $R^{44}$ is boned to N, $R^{44}$ is $CD_3$, methyl or ethyl, optionally substituted with F, Cl or CN.

In certain embodiments where $R^{44}$ is boned to C, $R^{44}$ is Cl, CN, $CD_3$, methyl or ethyl, optionally substituted with F, Cl or CN.

In yet another aspect, the invention generally relates to a compound having the structural formula (V):

(V)

or a pharmaceutically acceptable form or an isotope derivative thereof,
wherein
  Ring B is a 5- or 6-membered aryl or heteroaryl;
  $Z^1$ is CH or N;
  $Z^2$ is CH, CF or N;
  each of $Z^3$ and $Z^4$ is independently selected from NR, $CH_2$ and $CF_2$;
  $Z^5$ is selected from NR, O, $CH_2$ and $CF_2$;
  $Z^6$ is $NR^{56}$, $CH_2$, O, S, SO or $SO_2$;
  each of $X^4$, $X^7$, $X^8$ and $X^9$ is independently selected from CH, N and NH;
  $R^{51}$ is a H, F, $C_1$-$C_3$ alkyl and $CD_3$, provided that $R^{51}$ is not F when $Z^5$ is N or O;
  $R^{52}$ is independently selected from H, F, Cl, CN, OR$^g$, $CH_3$, $CF_3$, $OCF_3$ and —$(CH_2)_p$-Q;

- $R^{52a}$ at each occurrence is independently H, D, halo, OH, OR, CH$_3$, CF$_3$, CH$_2$CF$_3$ or CN, NRR', (CH$_2$)$_n$NRR' or a 4- to 6-membered heterocycle having 1-4 heteroatoms selected from N, O and S;
- $R^{52c}$ at each occurrence is independently H, halo, CN, OR, NRR', OCF$_3$, CF$_3$, C$_{1-6}$ alkyl substituted with 0-3 R$^{52a}$, C$_{1-6}$ haloalkyl, C$_{2-6}$ alkenyl substituted with 0-3 R$^{52a}$, C$_{2-6}$ alkynyl substituted with 0-3 R$^{52a}$;
- $R^{55}$ each occurrence is independently H, C$_{1-6}$ alkyl, substituted with 0-3 R$^{52a}$, or C$_{3-10}$ cycloalkyl or heterocycloalkyl, C$_{5-10}$ aryl or heteroaryl, or a 4- to 10-membered heterocycle having 1-4 heteroatoms selected from N, O and S, each group is substituted with 0-4 R$^{52c}$;
- $R^{56}$ is R substituted with 0-3 R$^d$;
- $R^{57}$ is H, C$_1$-C$_3$ alkyl, C$_1$-C$_3$ alkoxy, OCD$_3$ or OCF$_3$;
- $R^c$ is C$_{1-6}$ alkyl substituted with 0-3 R$^f$, (CH$_2$)$_r$—C$_{3-6}$ cycloalkyl substituted with 0-3 R$^f$ or (CH$_2$)$_r$-phenyl substituted with 0-3 R$^f$;
- $R^d$ is independently at each occurrence, hydrogen, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, C$_{1-6}$ alkyl or (CH$_2$)$_r$-phenyl substituted with 0-3 R$^f$;
- $R^e$ is independently at each occurrence, hydrogen, C$_{1-6}$ alkyl, C$_{3-6}$ cycloalkyl or (CH$_2$)$_r$-phenyl substituted with 0-3 R$^f$;
- $R^f$ is independently at each occurrence, hydrogen, halo, CN, NH$_2$, OH, C$_{3-6}$ cycloalkyl, CF$_3$, O(C$_{1-6}$ alkyl) or a 5- to 7-membered heterocycloalkyl comprising 1-3 heteroatoms selected from N, O and S;
- $R^g$ at each occurrence is independently H, C$_{1-4}$ alkyl substituted with 0-3 R$^f$, CF$_3$, C$_{3-10}$ cycloalkyl substituted with 0-1 R$^f$, (CH)$_r$-phenyl substituted with 0-3 R$^d$ or 5- to 7-membered heterocycloalkyl comprising 1-3 heteroatoms selected from N, O and S substituted with 0-3 R$^d$;
- Q is a water solubilizing group, optionally selected from OH, OR, NRR', heterocyclic and heteroaryl groups, wherein R and R', together with the nitrogen atom to which they are bound, form a 4- to 7-membered ring comprising 0-2 heteroatoms selected from O, NR, S and SO$_2$;
- R is H or a C$_1$-C$_6$ alkyl substituted with 0-3 R$^d$;
- R' is H or a C$_1$-C$_6$ alkyl substituted with 0-3 R$^d$;
- i is 0, 1, 2 and 3;
- m is 0, 1, 2 and 3;
- n is 0, 1, 2 and 3;
- p is 0, 1, 2, 3 or 4; and
- q is 0, 1, 2, 3 or 4.

In certain embodiments of formula (V), each of $Z^3$, $Z^4$ and $Z^5$ is NH, having the structural formula (V$_1$):

(V$_1$)

In certain embodiments of formulae (V)-(V$_1$), wherein Ring B is a 6-membered aryl.

In certain embodiments of formulae (V)-(V$_1$), wherein Ring B is a 6-membered heteroaryl.

In certain embodiments of formulae (V)-(V$_1$), the compound has the structural formula (V$_2$):

(V$_2$)

wherein each of $Z^7$ and $Z^8$ is independently CH or N.

In certain embodiments of formula (V$_2$), the compound has the structural formula (V$_3$):

(V$_3$)

wherein
$R^{54}$ is H, a C$_1$-C$_6$ alkyl or C$_{1-6}$ alkoxy, CD$_3$, or C$_3$-C$_5$ cycloalkyl, substituted with 0-3 R$^{52a}$; and
$R^{55}$ is H or C$_{1-6}$ alkyl or C$_{1-6}$ alkoxy, substituted with 0-3 R$^{52a}$.

In certain embodiments of formula (V$_2$), the compound has the structural formula (V$_4$):

(V$_4$)

wherein

R$^{54}$ is H, a C$_1$-C$_6$ alkyl or C$_{1-6}$ alkoxy, CD$_3$, or C$_3$-C$_5$ cycloalkyl, substituted with 0-3 R$^{52a}$; and R$^{55}$ is H or C$_{1-6}$ alkyl or C$_{1-6}$ alkoxy, substituted with 0-3 R$^{52a}$.

In certain embodiments of formulae (V)-(V$_4$), Z$^6$ is O or S.

In certain embodiments of formulae (V)-(V$_4$), Z$^6$ is NR.

In certain embodiments of formulae (V)-(V$_4$), each of m and n is 1.

In certain embodiments of formulae (V)-(V$_4$), R$^{51}$ is CH$_3$.

In certain embodiments of formulae (V)-(V$_4$), R$^{51}$ is CD$_3$.

In certain embodiments of formulae (V)-(V$_4$), R$^{57}$ is C$_1$-C$_3$ alkoxy.

In certain embodiments of formulae (V)-(V$_4$), R$^{57}$ is OCH$_3$.

In certain embodiments of formulae (V)-(V$_4$), R$^{57}$ is OCD$_3$.

In certain embodiments of formulae (V)-(V$_4$), R$^{57}$ is OCF$_3$.

In certain embodiments of formulae (V)-(V$_4$), q is 1 and R$^{52}$ is F, Cl, CN, CH$_3$, CF$_3$, OCF$_3$ or morpholino.

Non-limiting examples of compounds of the invention include:

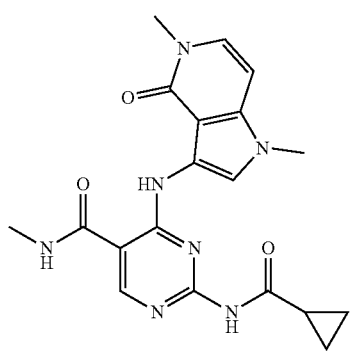 [SMILES: CNC(=O)c1cnc(NC(=O)C2CC2)nc1Nc1cn(C)c2ccn(C)c(=O)c12]

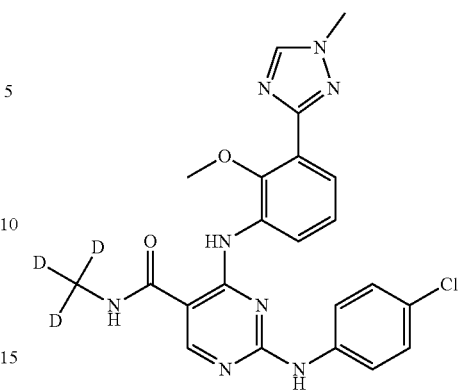

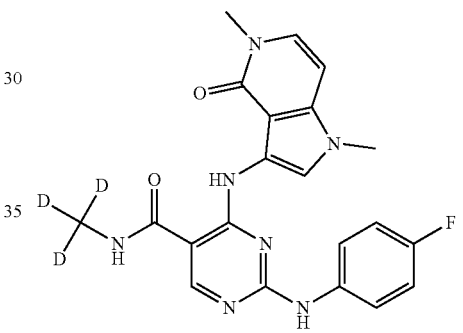

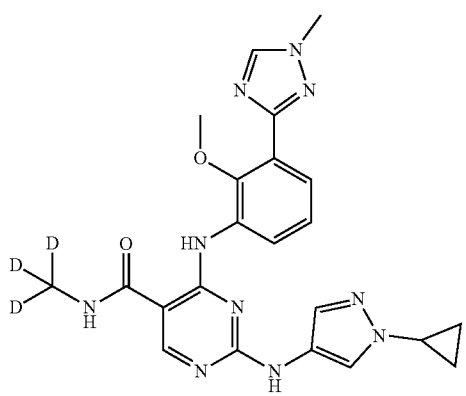 [SMILES: [2H]C([2H])([2H])NC(=O)c1cnc(Nc2cnn(C3CC3)c2)nc1Nc1cccc(-c2ncn(C)n2)c1OC]

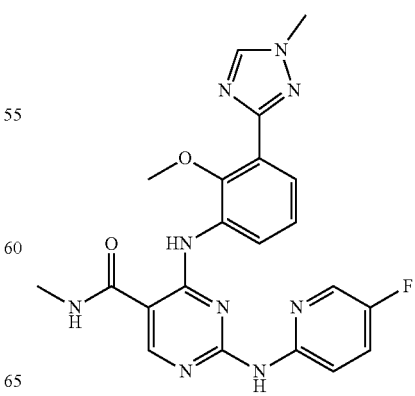

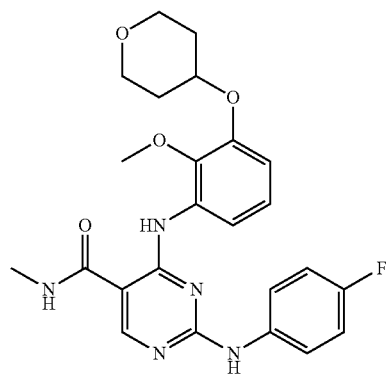 [SMILES: CNC(=O)c1cnc(Nc2ccc(F)cc2)nc1Nc1cccc(OC2CCOCC2)c1OC]
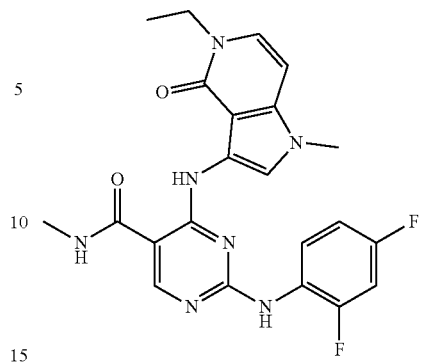
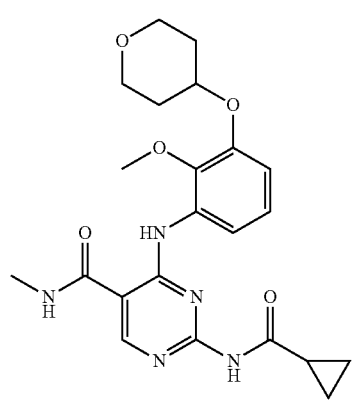 [SMILES: CNC(=O)c1cnc(NC(=O)C2CC2)nc1Nc1cccc(OC2CCOCC2)c1OC]
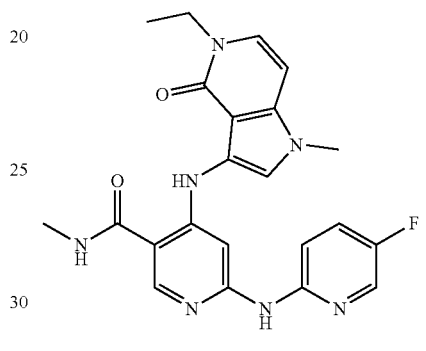
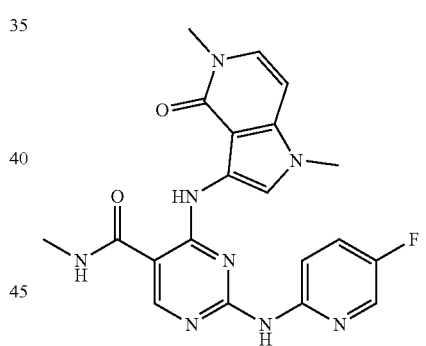
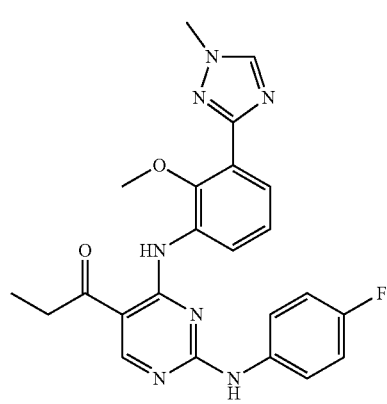 [SMILES: CCC(=O)c1cnc(Nc2ccc(F)cc2)nc1Nc1cccc(-c2ncn(C)n2)c1OC]
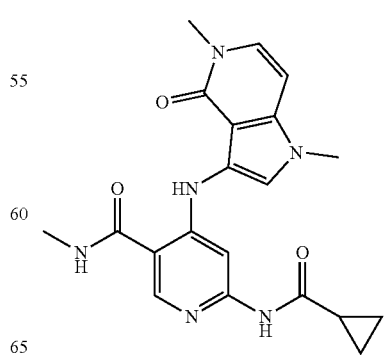

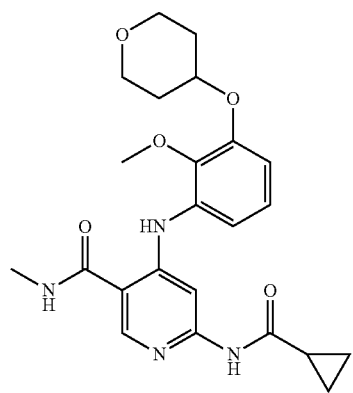 [SMILES: CNC(=O)c1cnc(NC(=O)C2CC2)cc1Nc1cccc(OC2CCOCC2)c1OC]
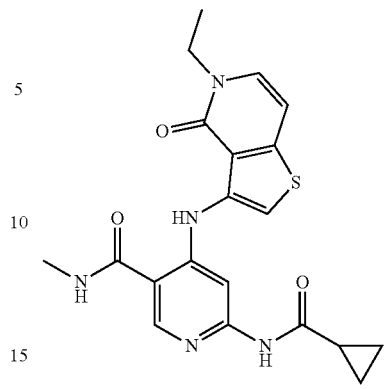
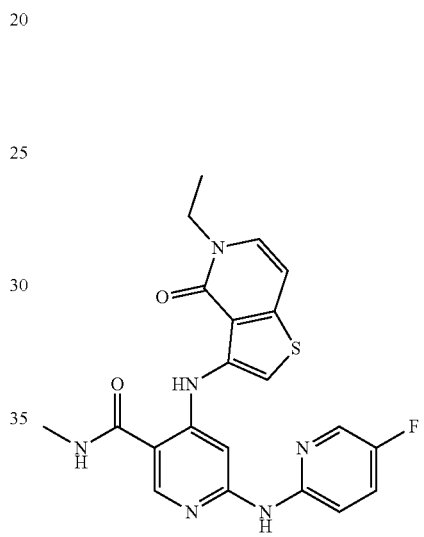
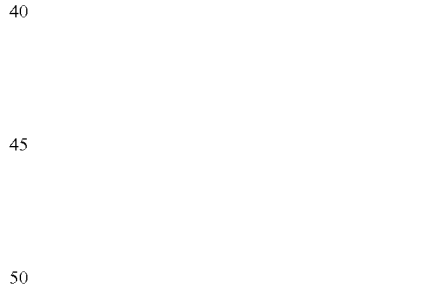
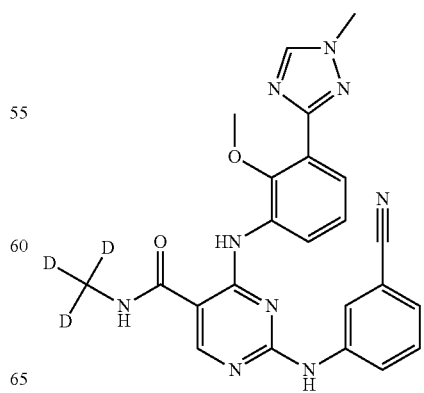

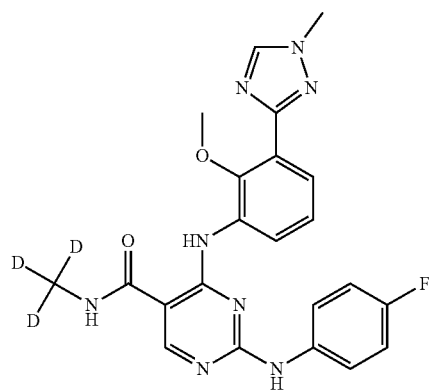 [SMILES: [2H]C([2H])([2H])NC(=O)c1cnc(Nc2ccc(F)cc2)nc1Nc1cccc(-c2ncn(C)n2)c1OC]
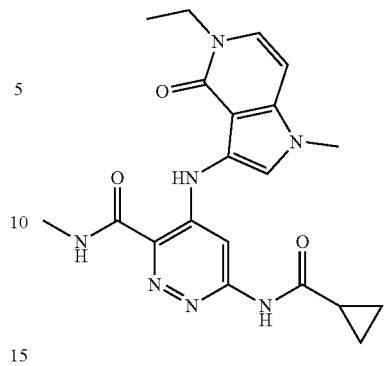
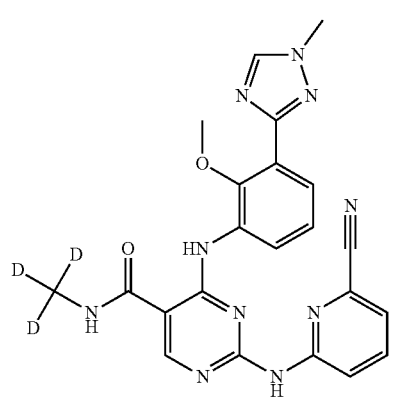 [SMILES: [2H]C([2H])([2H])NC(=O)c1cnc(Nc2cccc(C#N)n2)nc1Nc1cccc(-c2ncn(C)n2)c1OC]
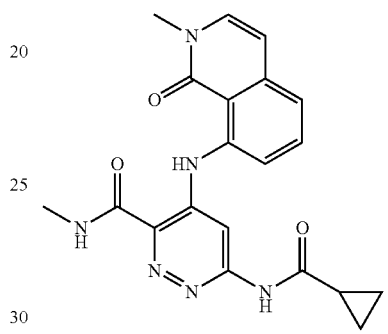
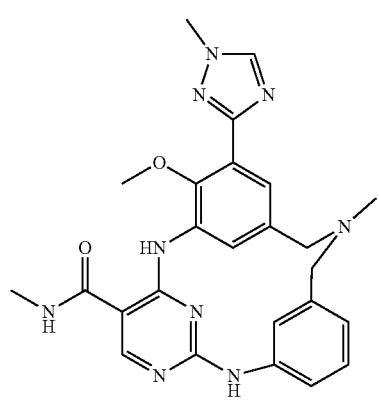
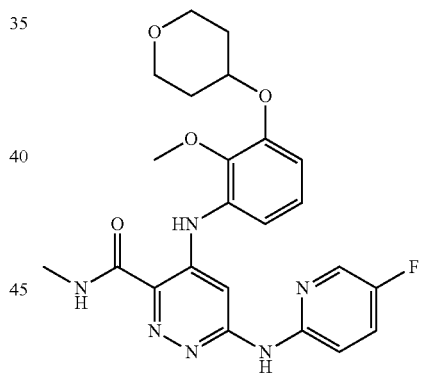
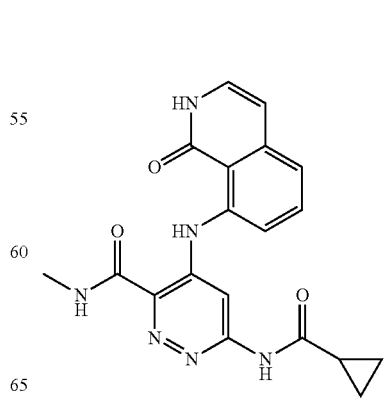

85
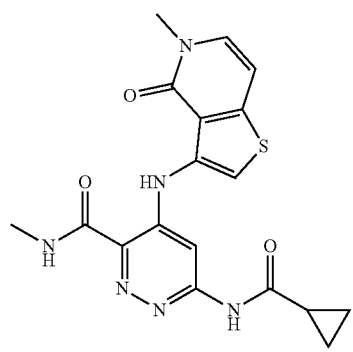
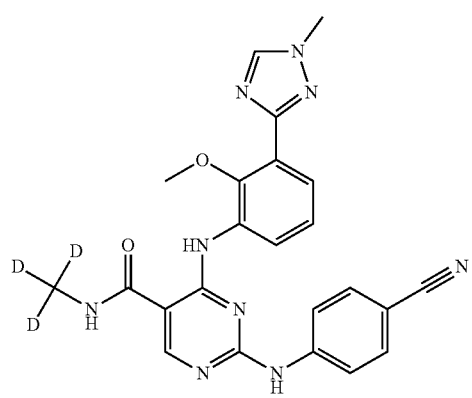 [SMILES: [2H]C([2H])([2H])NC(=O)c1cnc(Nc2ccc(C#N)cc2)nc1Nc1cccc(-c2ncn(C)n2)c1OC]
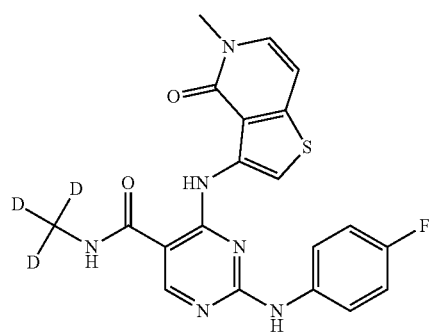 [SMILES: [2H]C([2H])([2H])NC(=O)c1cnc(Nc2ccc(F)cc2)nc1Nc1csc2ccn(C)c(=O)c12]
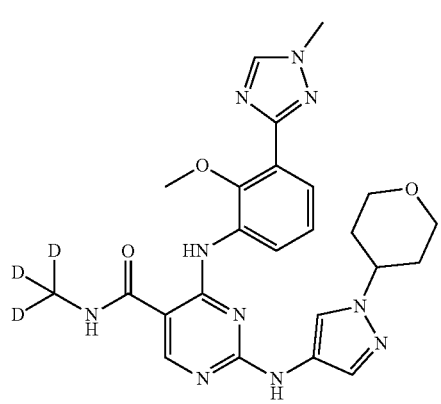 [SMILES: [2H]C([2H])([2H])NC(=O)c1cnc(Nc2cnn(C3CCOCC3)c2)nc1Nc1cccc(-c2ncn(C)n2)c1OC]
86
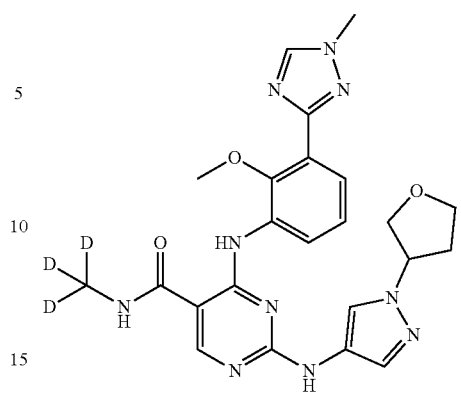
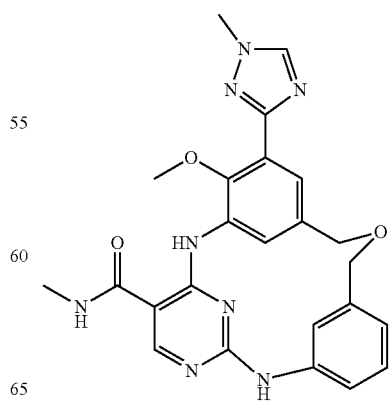

87
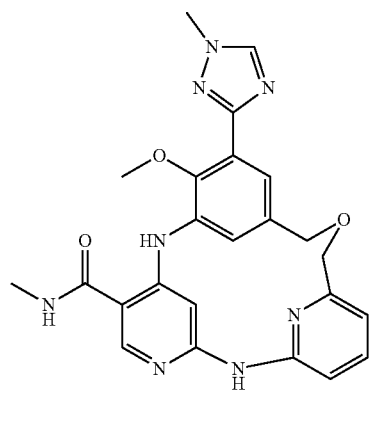 [SMILES: CNC(=O)c1cnc2cc1Nc1cc(cc(-c3ncn(C)n3)c1OC)COCc1cccc(n1)N2]
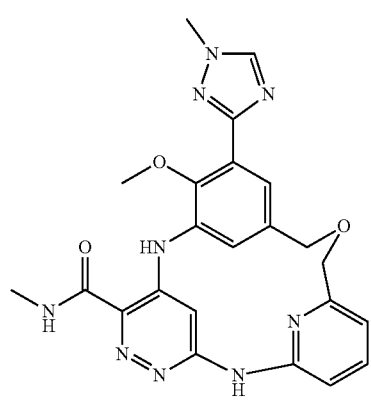 [SMILES: CNC(=O)c1nnc2cc1Nc1cc(cc(-c3ncn(C)n3)c1OC)COCc1cccc(n1)N2]
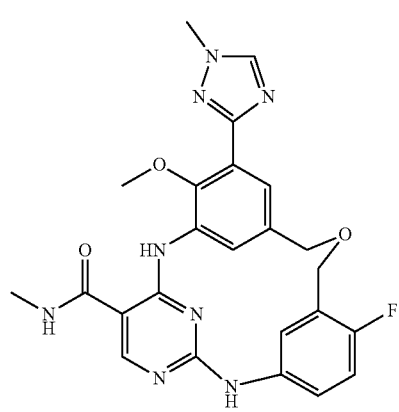 [SMILES: CNC(=O)c1cnc2nc1Nc1cc(cc(-c3ncn(C)n3)c1OC)COCc1cc(ccc1F)N2]
88
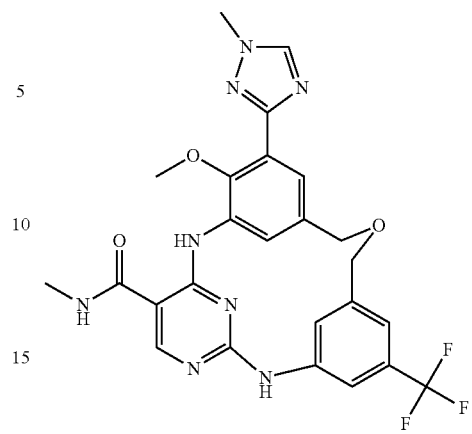
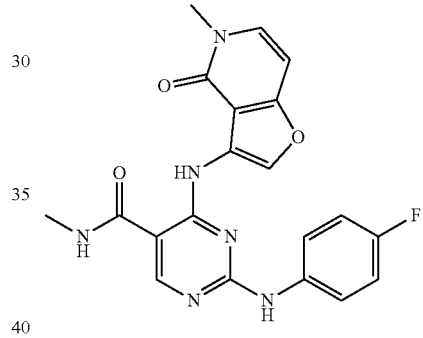
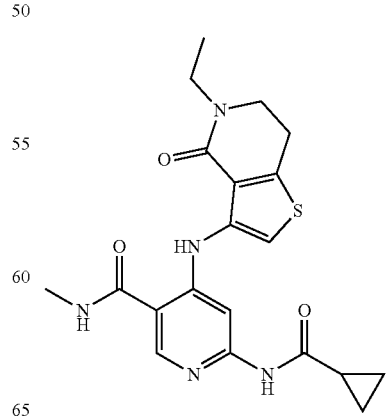

| 89 | 90 |
|---|---|
| 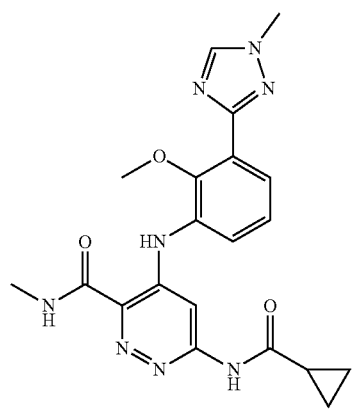 [SMILES: CNC(=O)c1nnc(NC(=O)C2CC2)cc1Nc1cccc(-c2ncn(C)n2)c1OC] | 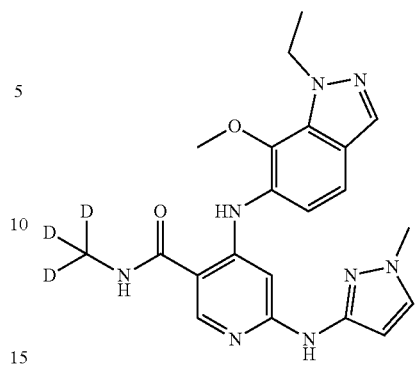 |
| 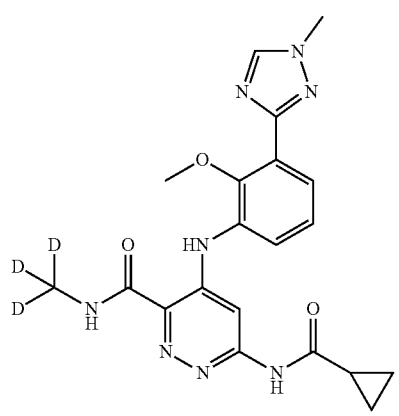 [SMILES: [2H]C([2H])([2H])NC(=O)c1nnc(NC(=O)C2CC2)cc1Nc1cccc(-c2ncn(C)n2)c1OC] | 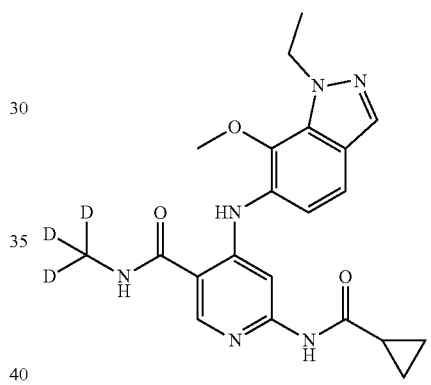 |
| 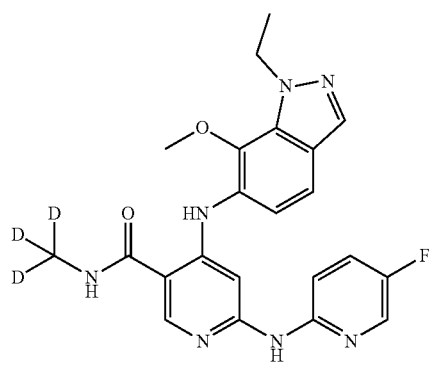 | 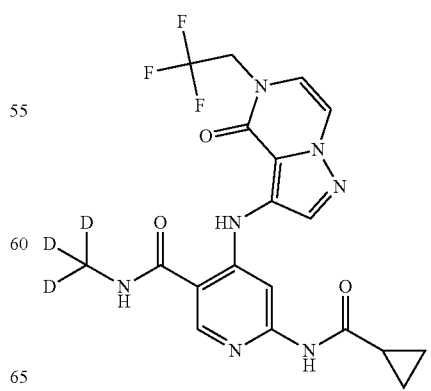 |

91
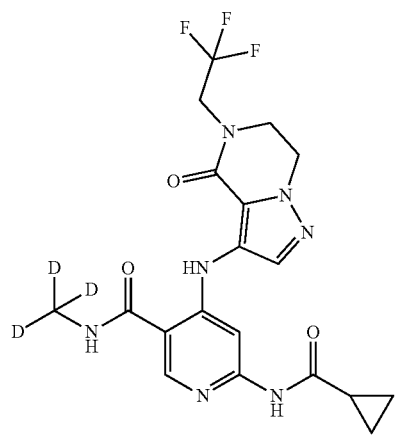 [SMILES: [2H]C([2H])([2H])NC(=O)c1cnc(NC(=O)C2CC2)cc1Nc1cnn2c1C(=O)N(CC(F)(F)F)CC2]
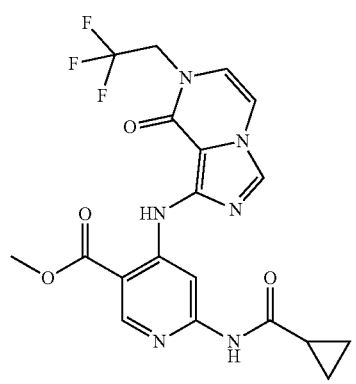 [SMILES: COC(=O)c1cnc(NC(=O)C2CC2)cc1Nc1ncn2ccn(CC(F)(F)F)c(=O)c12]
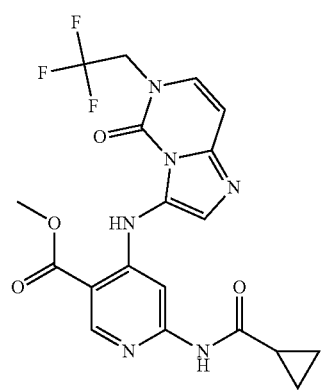 [SMILES: COC(=O)c1cnc(NC(=O)C2CC2)cc1Nc1cnc2ccn(CC(F)(F)F)c(=O)n12]
92
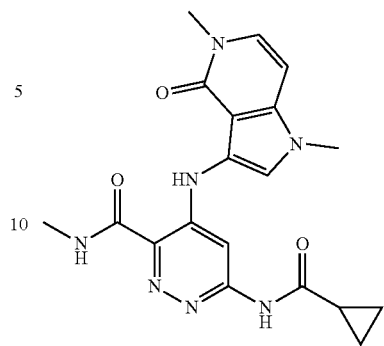
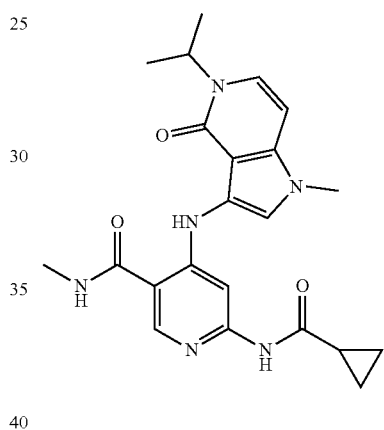
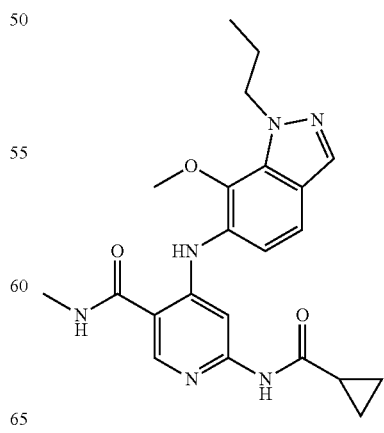

93
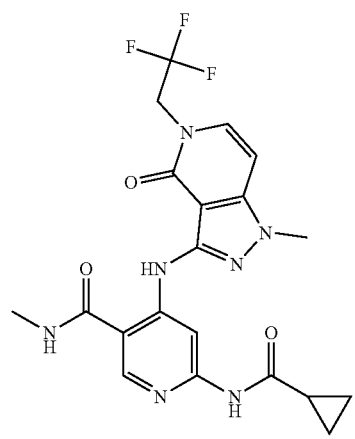 [SMILES: CNC(=O)c1cnc(NC(=O)C2CC2)cc1Nc1nn(C)c2ccn(CC(F)(F)F)c(=O)c12]
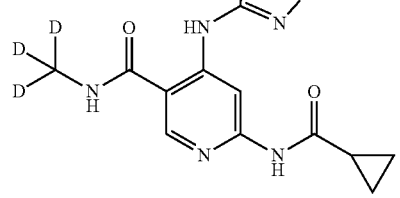
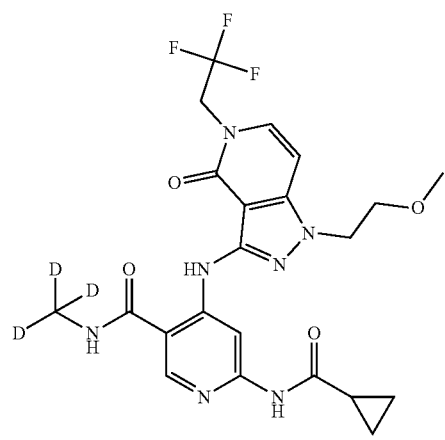 [SMILES: [2H]C([2H])([2H])NC(=O)c1cnc(NC(=O)C2CC2)cc1Nc1nn(CCOC)c2ccn(CC(F)(F)F)c(=O)c12]
94
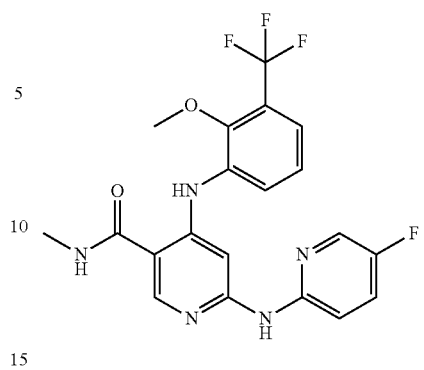
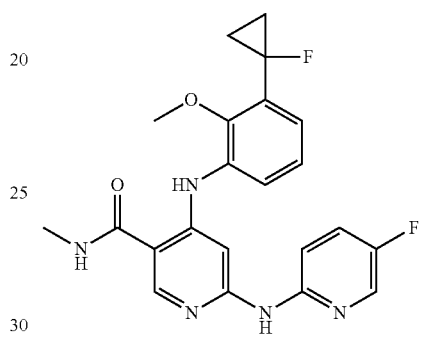
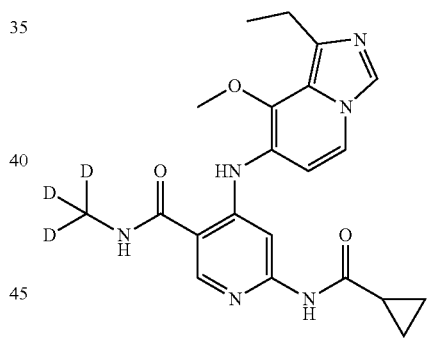
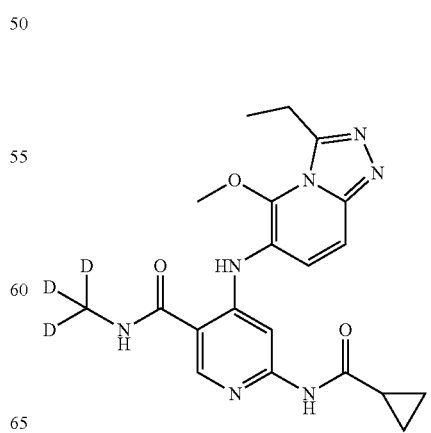

95
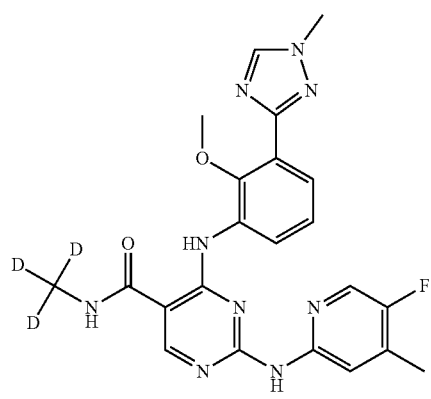 [SMILES: [2H]C([2H])([2H])NC(=O)c1cnc(Nc2cc(C)c(F)cn2)nc1Nc1cccc(-c2ncn(C)n2)c1OC]
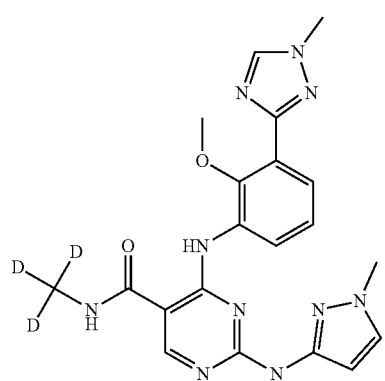
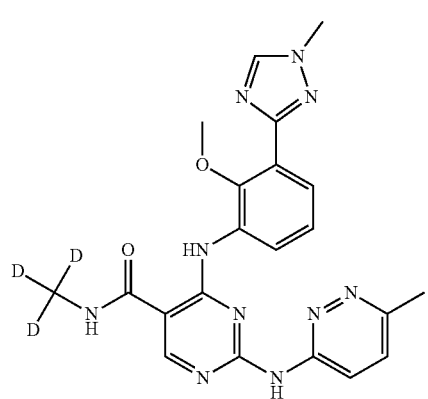 [SMILES: [2H]C([2H])([2H])NC(=O)c1cnc(Nc2ccc(C)nn2)nc1Nc1cccc(-c2ncn(C)n2)c1OC]
96
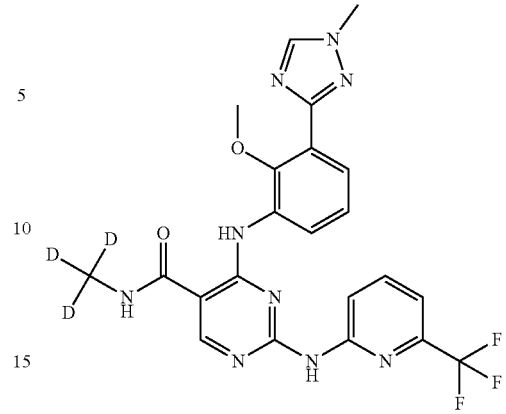
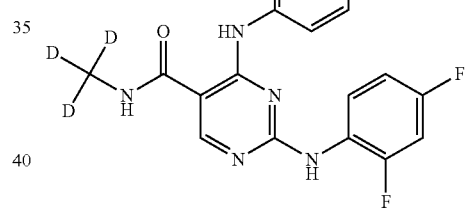
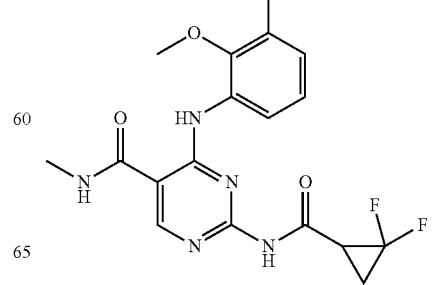

97
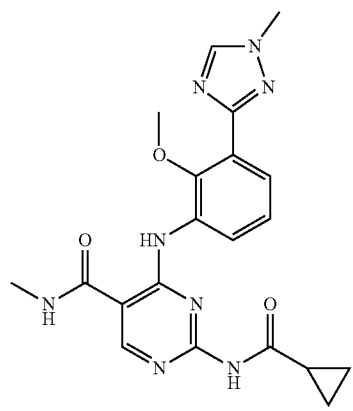 [SMILES: CNC(=O)c1cnc(NC(=O)C2CC2)nc1Nc1cccc(-c2ncn(C)n2)c1OC]
98
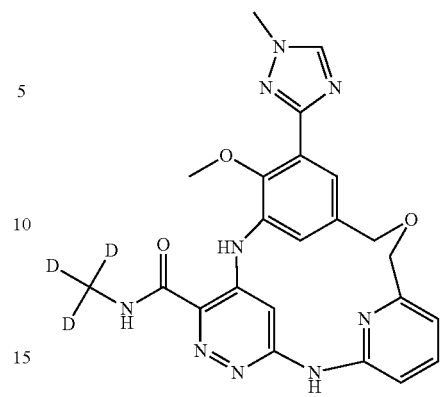
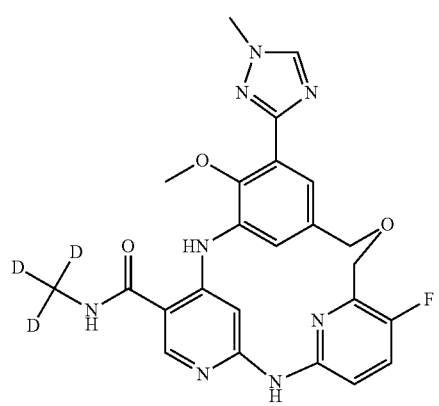 [SMILES: [2H]C([2H])([2H])NC(=O)c1cnc2cc1Nc1cc(cc(-c3ncn(C)n3)c1OC)COCc1nc(ccc1F)N2]
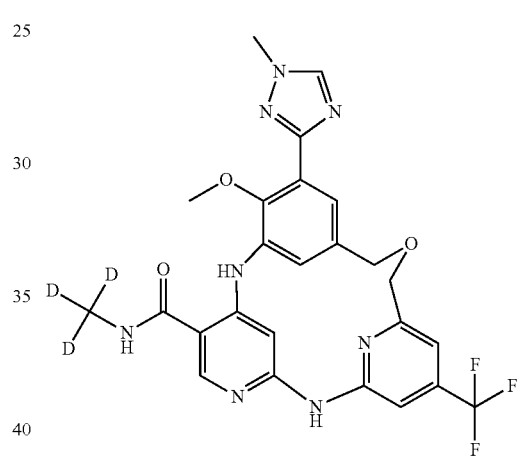
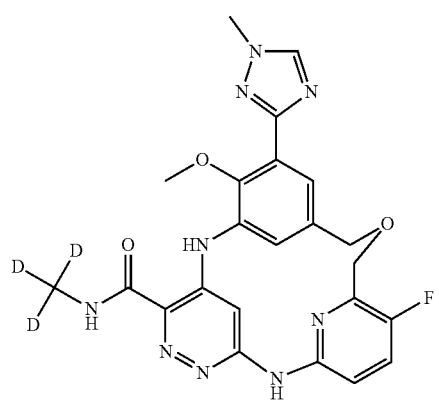 [SMILES: [2H]C([2H])([2H])NC(=O)c1nnc2cc1Nc1cc(cc(-c3ncn(C)n3)c1OC)COCc1nc(ccc1F)N2]
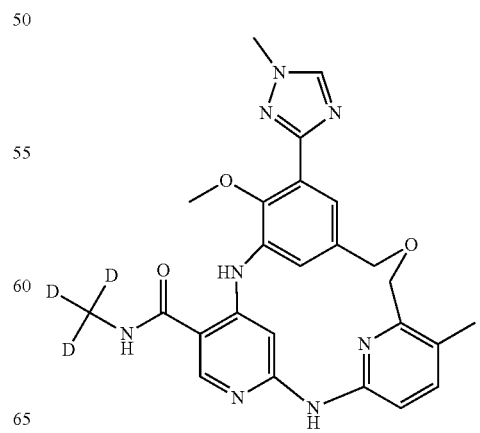

99
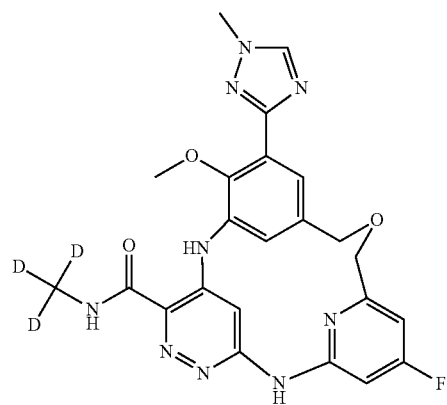 [SMILES: [2H]C([2H])([2H])NC(=O)c1nnc2cc1Nc1cc(cc(-c3ncn(C)n3)c1OC)COCc1cc(F)cc(n1)N2]
100
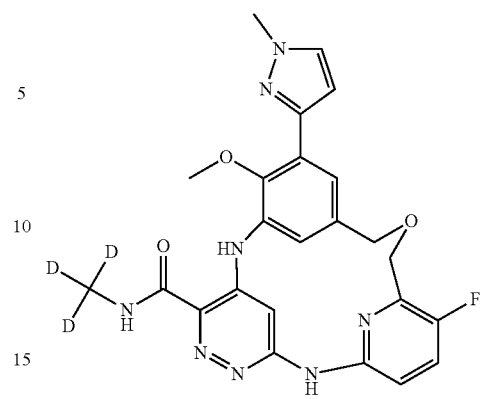
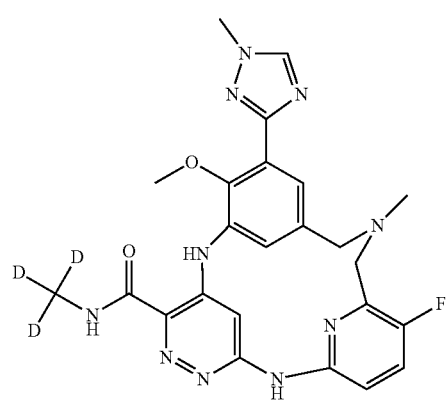 [SMILES: [2H]C([2H])([2H])NC(=O)c1nnc2cc1Nc1cc(cc(-c3ncn(C)n3)c1OC)CN(C)Cc1nc(ccc1F)N2]
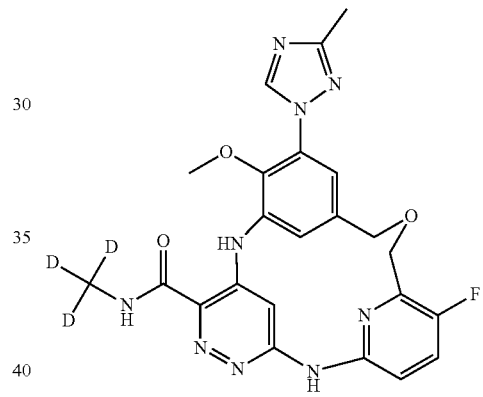
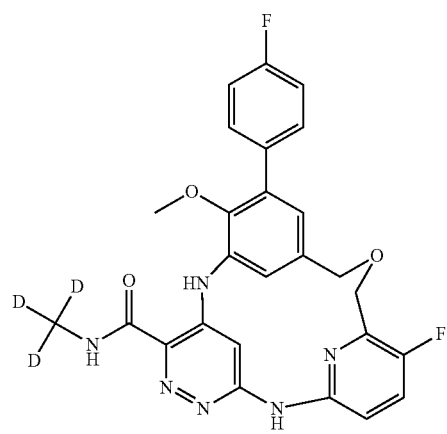 [SMILES: [2H]C([2H])([2H])NC(=O)c1nnc2cc1Nc1cc(cc(-c3ccc(F)cc3)c1OC)COCc1nc(ccc1F)N2]
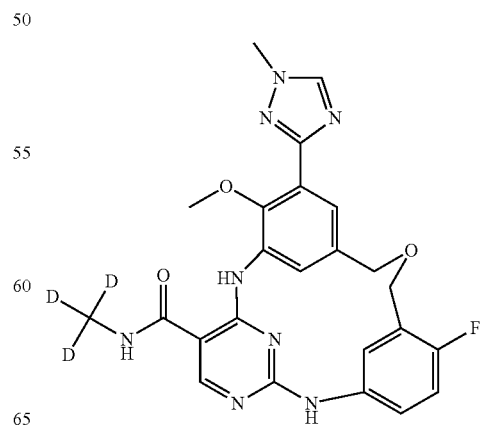

101
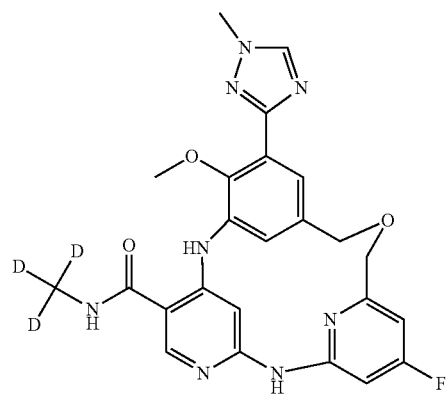 [SMILES: [2H]C([2H])([2H])NC(=O)c1cnc2cc1Nc1cc(cc(-c3ncn(C)n3)c1OC)COCc1cc(F)cc(n1)N2]
102
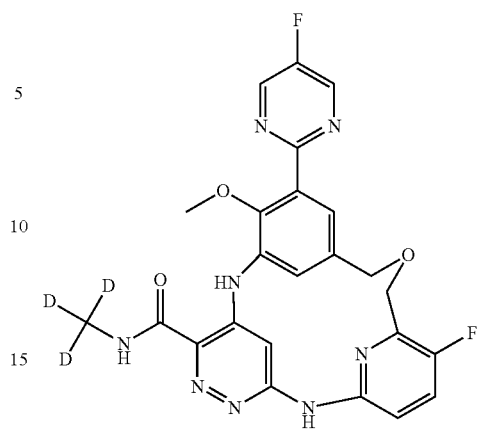
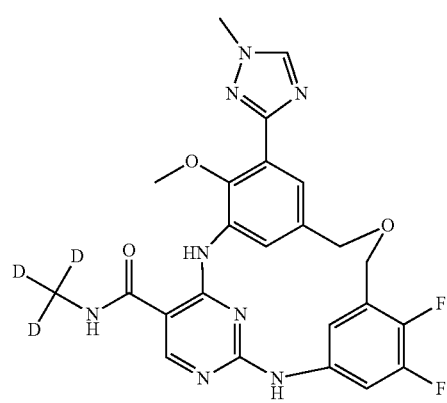 [SMILES: [2H]C([2H])([2H])NC(=O)c1cnc2nc1Nc1cc(cc(-c3ncn(C)n3)c1OC)COCc1cc(cc(F)c1F)N2]
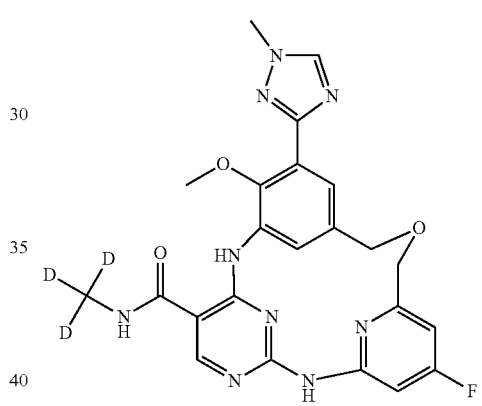
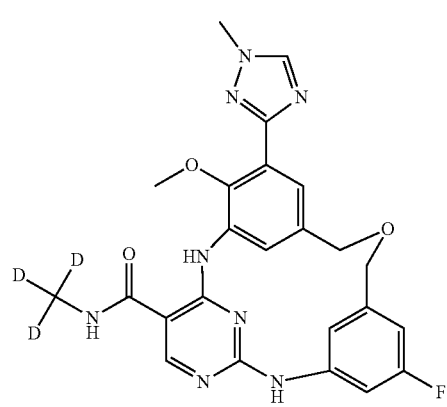 [SMILES: [2H]C([2H])([2H])NC(=O)c1cnc2nc1Nc1cc(cc(-c3ncn(C)n3)c1OC)COCc1cc(F)cc(c1)N2]
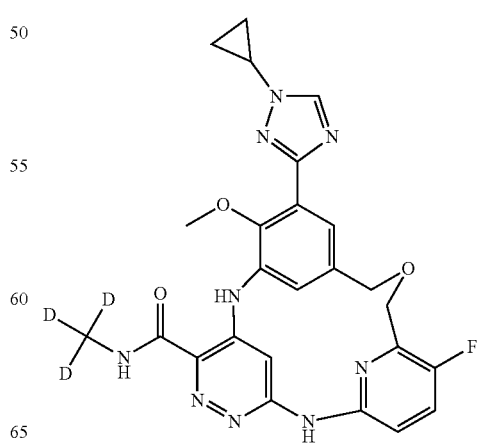

103
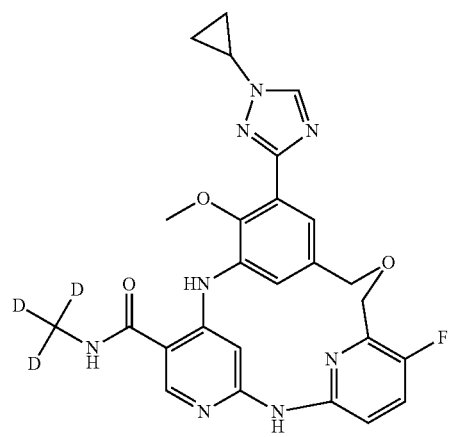
104
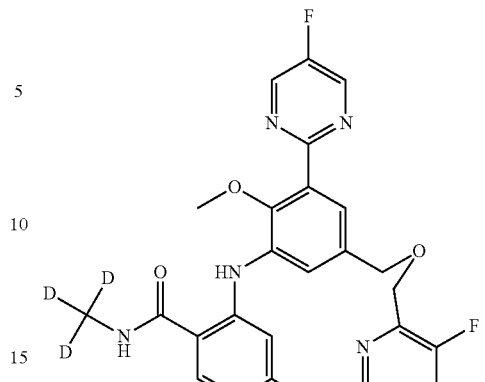
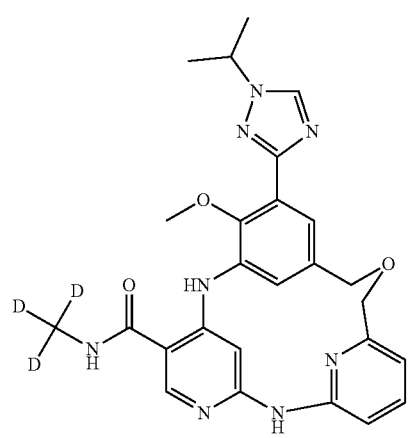 [SMILES: [2H]C([2H])([2H])NC(=O)c1cnc2cc1Nc1cc(cc(-c3ncn(C(C)C)n3)c1OC)COCc1cccc(n1)N2]
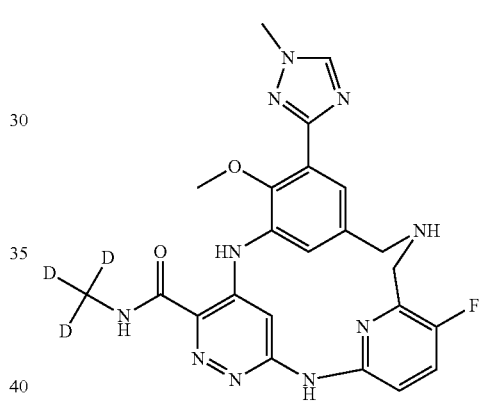
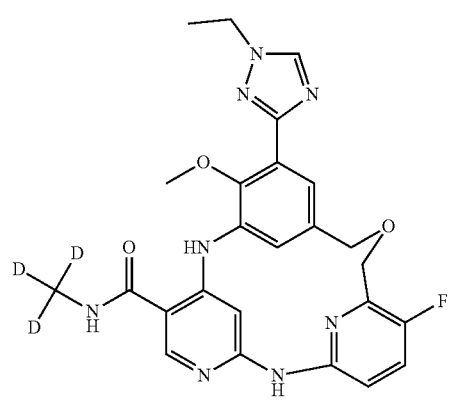 [SMILES: [2H]C([2H])([2H])NC(=O)c1cnc2cc1Nc1cc(cc(-c3ncn(CC)n3)c1OC)COCc1nc(ccc1F)N2]
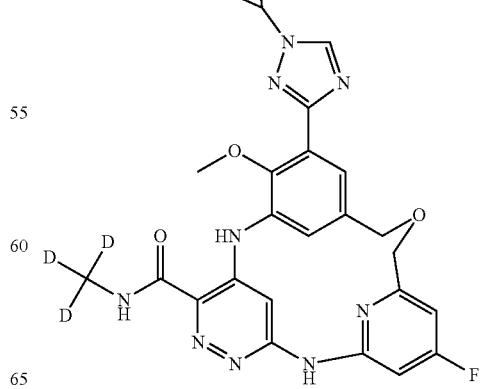

105
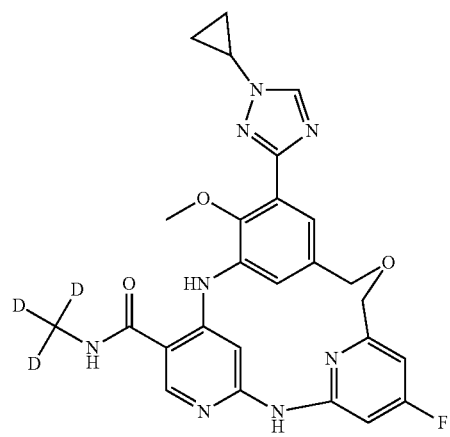
106
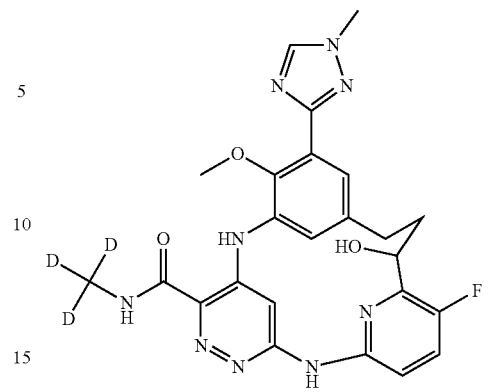
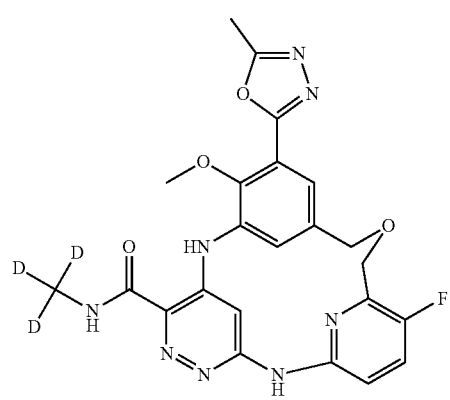 [SMILES: [2H]C([2H])([2H])NC(=O)c1nnc2cc1Nc1cc(cc(-c3nnc(C)o3)c1OC)COCc1nc(ccc1F)N2]
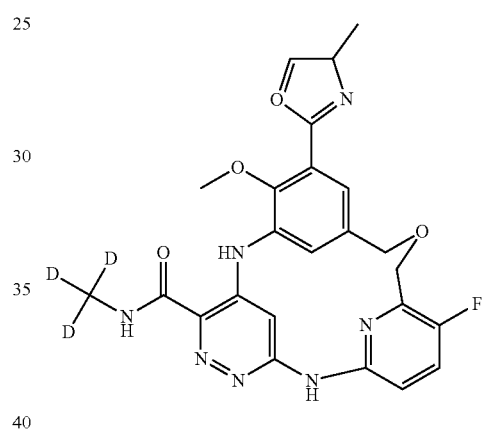
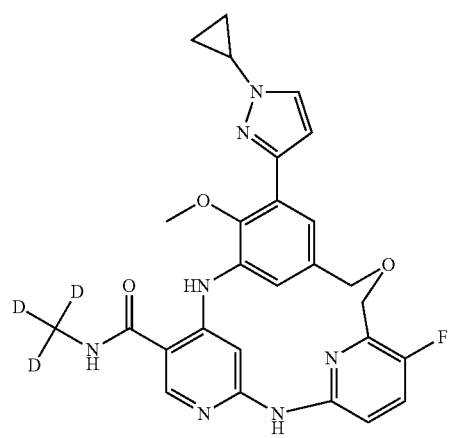 [SMILES: [2H]C([2H])([2H])NC(=O)c1cnc2cc1Nc1cc(cc(-c3ccn(C4CC4)n3)c1OC)COCc1nc(ccc1F)N2]
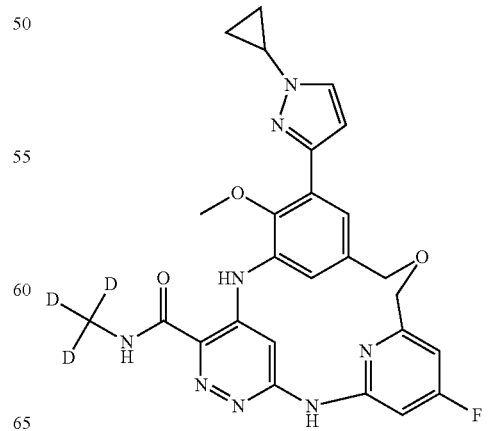

107
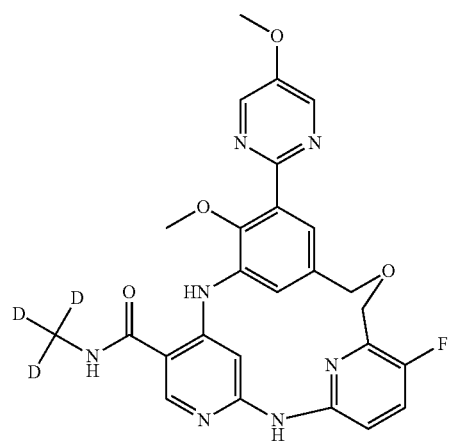 [SMILES: [2H]C([2H])([2H])NC(=O)c1cnc2cc1Nc1cc(cc(-c3ncc(OC)cn3)c1OC)COCc1nc(ccc1F)N2]
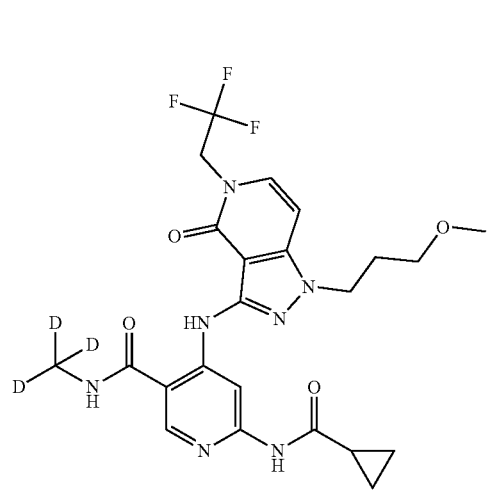 [SMILES: [2H]C([2H])([2H])NC(=O)c1cnc(NC(=O)C2CC2)cc1Nc1nn(CCCOC)c2ccn(CC(F)(F)F)c(=O)c12]
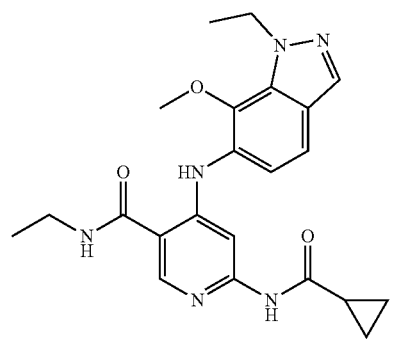 [SMILES: CCNC(=O)c1cnc(NC(=O)C2CC2)cc1Nc1ccc2cnn(CC)c2c1OC]
108
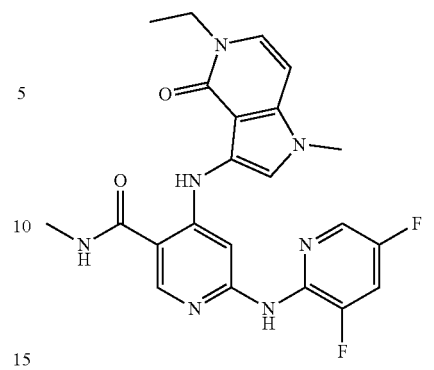
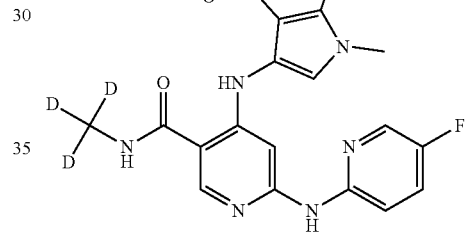
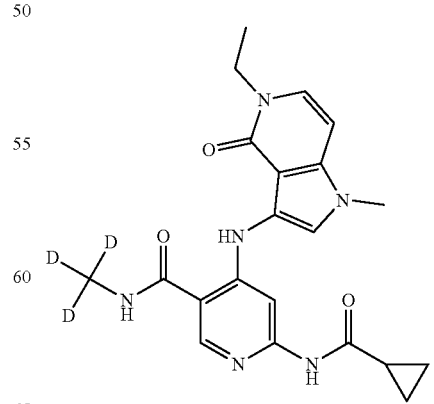

109
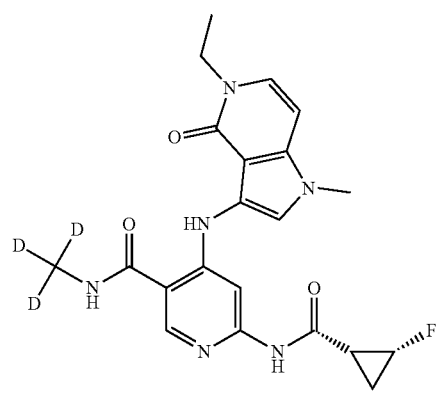
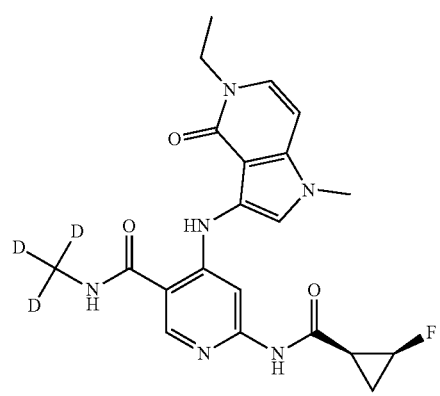 [SMILES: [2H]C([2H])([2H])NC(=O)c1cnc(NC(=O)[C@@H]2C[C@@H]2F)cc1Nc1cn(C)c2ccn(CC)c(=O)c12]
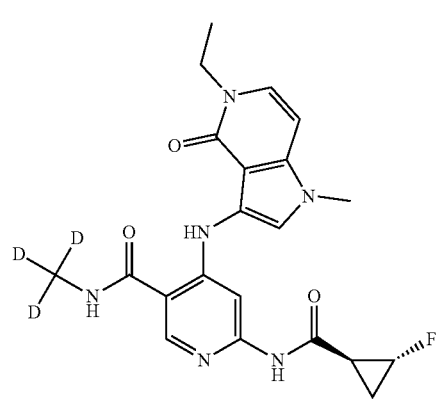 [SMILES: [2H]C([2H])([2H])NC(=O)c1cnc(NC(=O)[C@@H]2C[C@H]2F)cc1Nc1cn(C)c2ccn(CC)c(=O)c12]
110
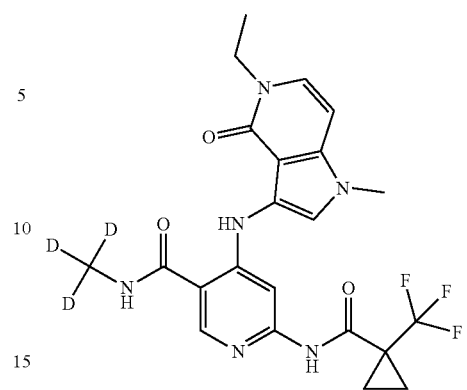
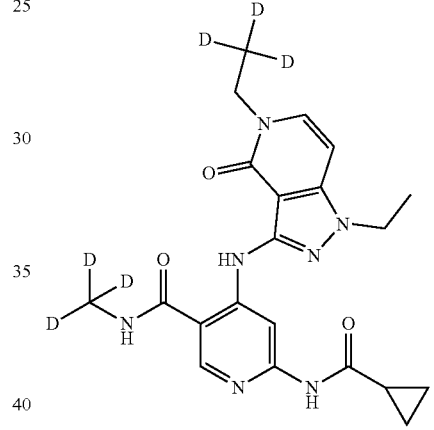
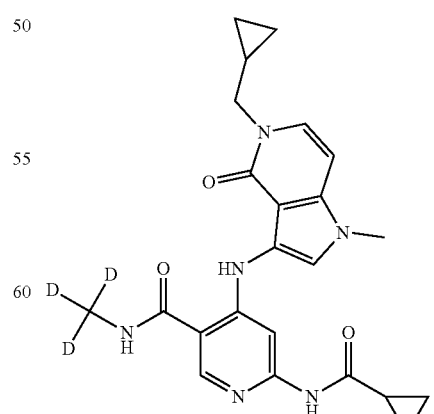

111
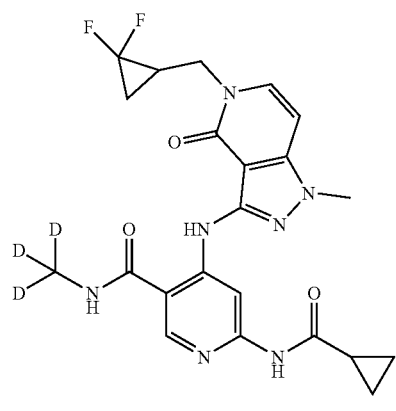 [SMILES: [2H]C([2H])([2H])NC(=O)c1cnc(NC(=O)C2CC2)cc1Nc1nn(C)c2ccn(CC3CC3(F)F)c(=O)c12]
112
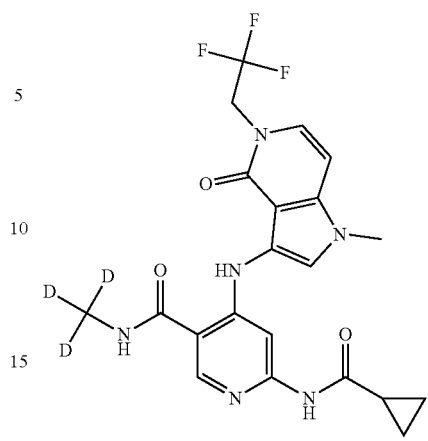
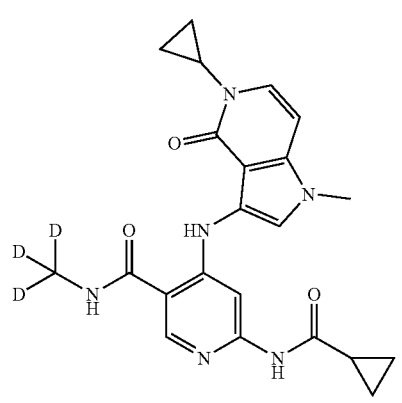 [SMILES: [2H]C([2H])([2H])NC(=O)c1cnc(NC(=O)C2CC2)cc1Nc1cn(C)c2ccn(C3CC3)c(=O)c12]
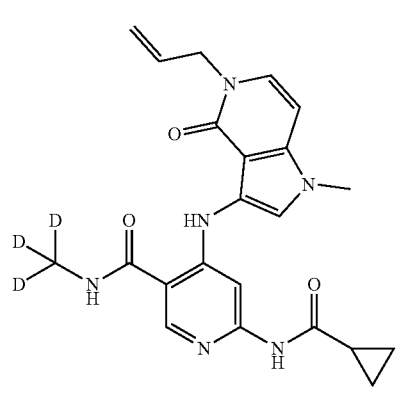 [SMILES: [2H]C([2H])([2H])NC(=O)c1cnc(NC(=O)C2CC2)cc1Nc1cn(C)c2ccn(CC=C)c(=O)c12]
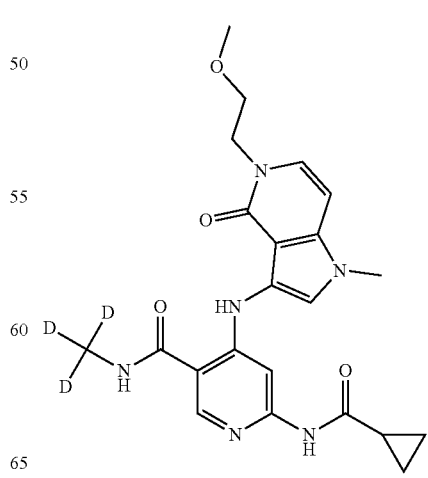

113
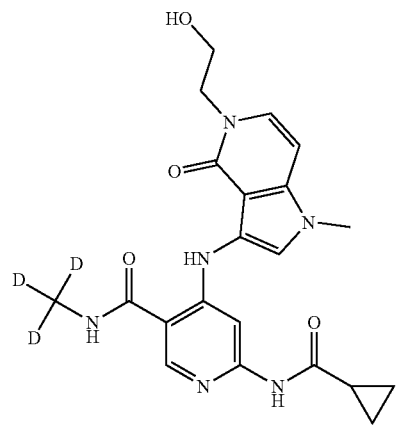 [SMILES: [2H]C([2H])([2H])NC(=O)c1cnc(NC(=O)C2CC2)cc1Nc1cn(C)c2ccn(CCO)c(=O)c12]
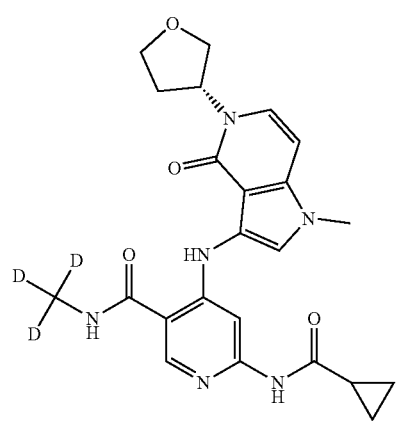 [SMILES: [2H]C([2H])([2H])NC(=O)c1cnc(NC(=O)C2CC2)cc1Nc1cn(C)c2ccn([C@@H]3CCOC3)c(=O)c12]
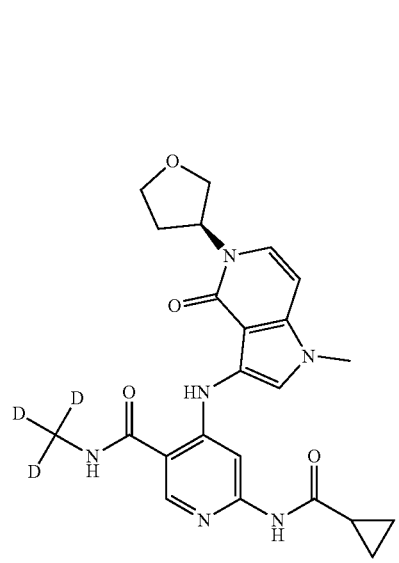 [SMILES: [2H]C([2H])([2H])NC(=O)c1cnc(NC(=O)C2CC2)cc1Nc1cn(C)c2ccn([C@H]3CCOC3)c(=O)c12]
114
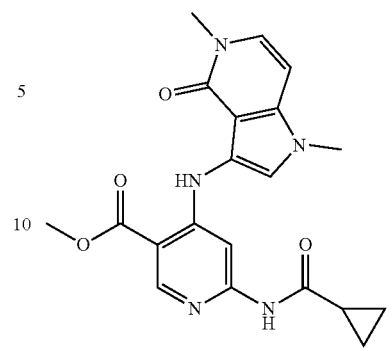
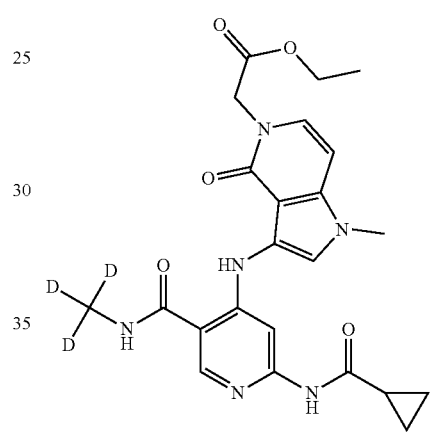
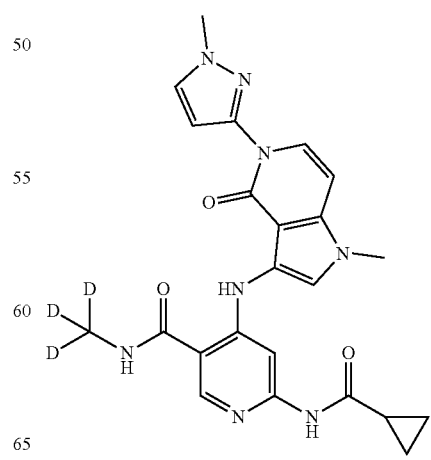

115
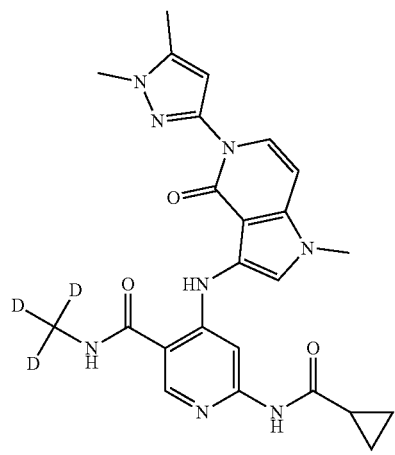 [SMILES: [2H]C([2H])([2H])NC(=O)c1cnc(NC(=O)C2CC2)cc1Nc1cn(C)c2ccn(-c3cc(C)n(C)n3)c(=O)c12]
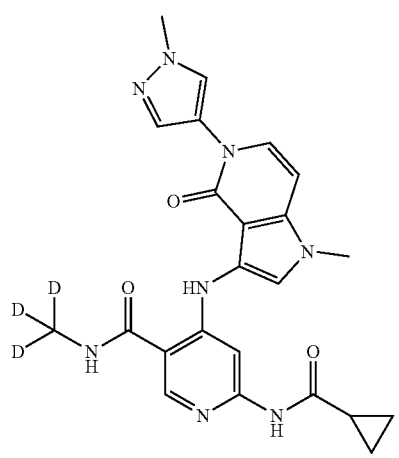 [SMILES: [2H]C([2H])([2H])NC(=O)c1cnc(NC(=O)C2CC2)cc1Nc1cn(C)c2ccn(-c3cnn(C)c3)c(=O)c12]
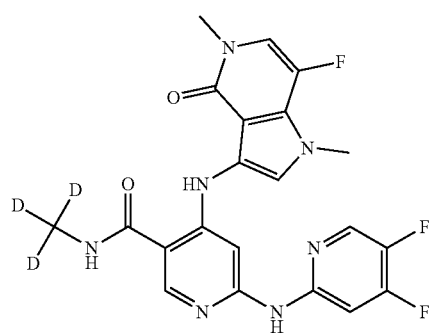 [SMILES: [2H]C([2H])([2H])NC(=O)c1cnc(Nc2cc(F)c(F)cn2)cc1Nc1cn(C)c2c(F)cn(C)c(=O)c12]
116
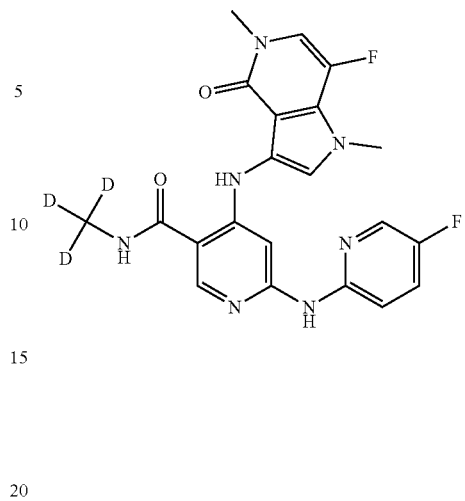
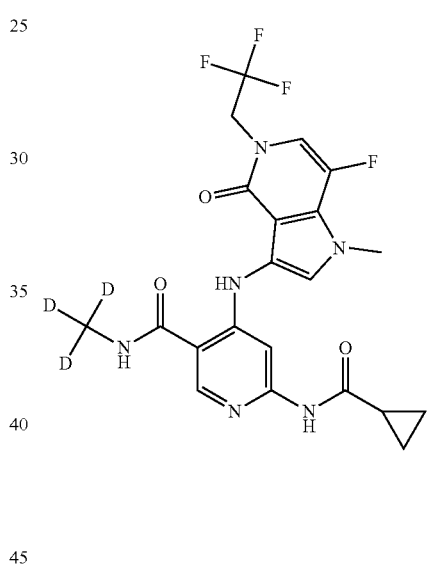
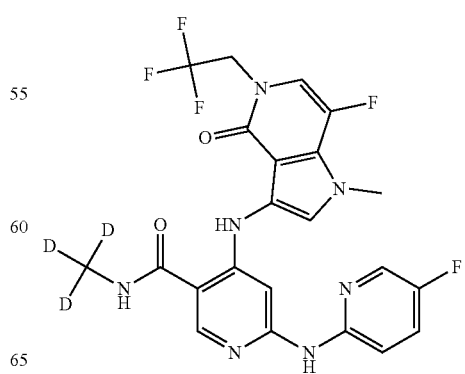

117
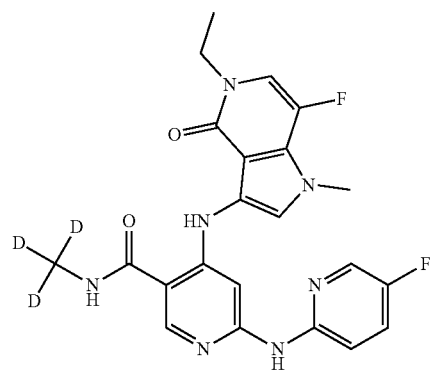
118
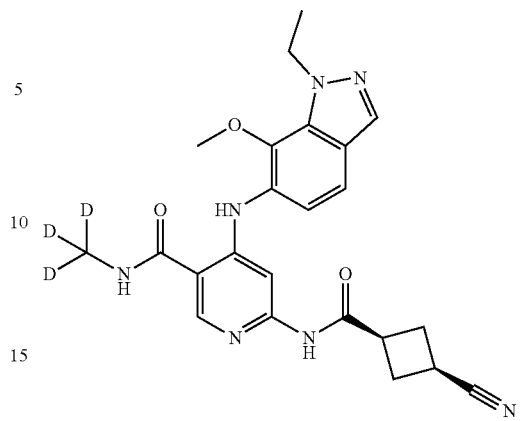
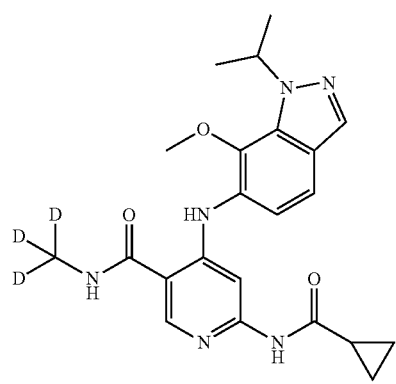
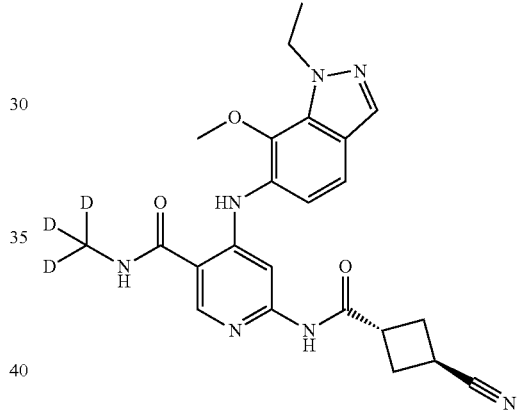
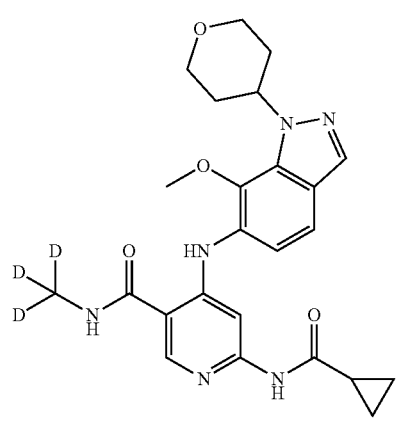 [SMILES: [2H]C([2H])([2H])NC(=O)c1cnc(NC(=O)C2CC2)cc1Nc1ccc2cnn(C3CCOCC3)c2c1OC]
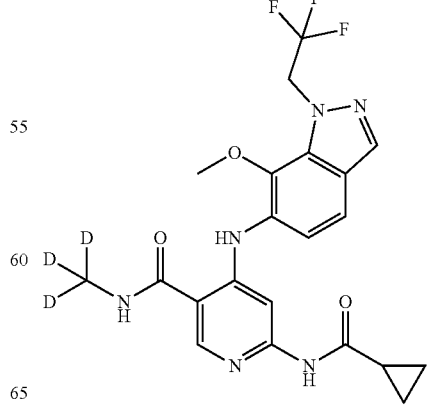

119
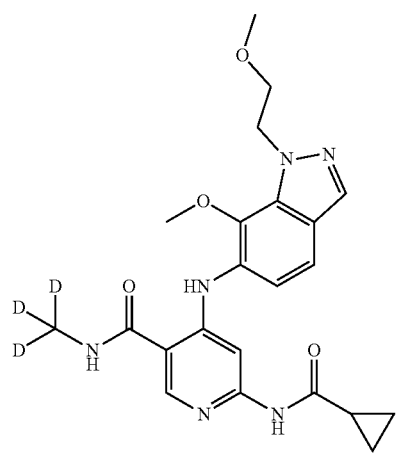 [SMILES: [2H]C([2H])([2H])NC(=O)c1cnc(NC(=O)C2CC2)cc1Nc1ccc2cnn(CCOC)c2c1OC]
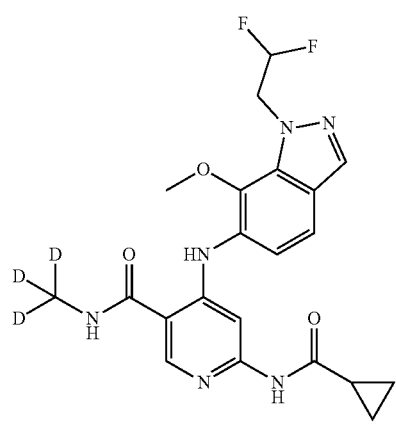 [SMILES: [2H]C([2H])([2H])NC(=O)c1cnc(NC(=O)C2CC2)cc1Nc1ccc2cnn(CC(F)F)c2c1OC]
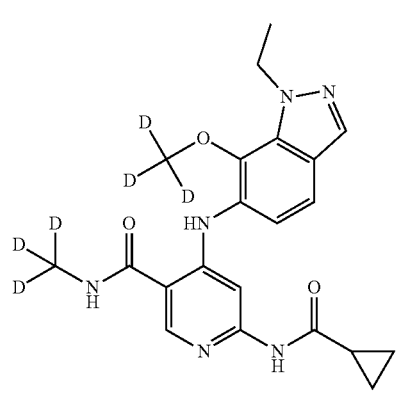 [SMILES: [2H]C([2H])([2H])NC(=O)c1cnc(NC(=O)C2CC2)cc1Nc1ccc2cnn(CC)c2c1OC([2H])([2H])[2H]]
120
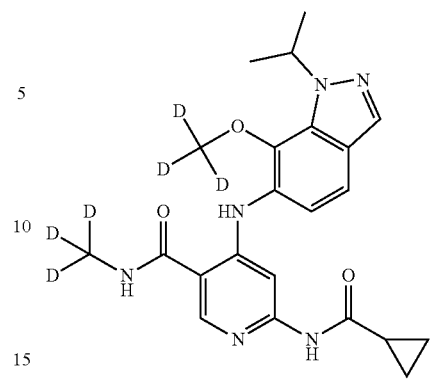
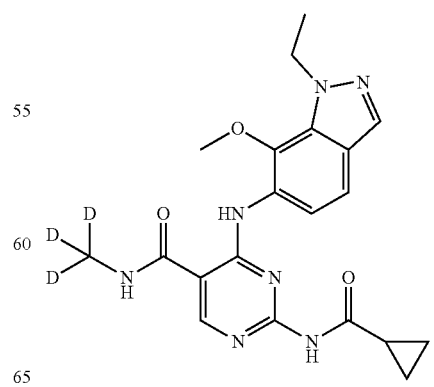

121
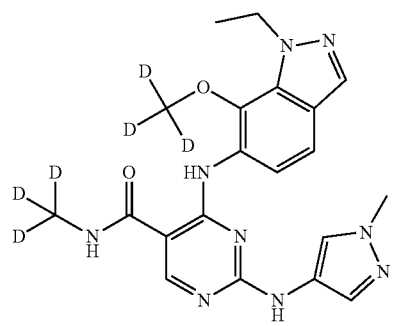 [SMILES: [2H]C([2H])([2H])NC(=O)c1cnc(Nc2cnn(C)c2)nc1Nc1ccc2cnn(CC)c2c1OC([2H])([2H])[2H]]
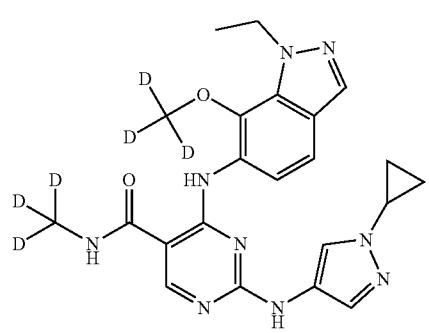 [SMILES: [2H]C([2H])([2H])NC(=O)c1cnc(Nc2cnn(C3CC3)c2)nc1Nc1ccc2cnn(CC)c2c1OC([2H])([2H])[2H]]
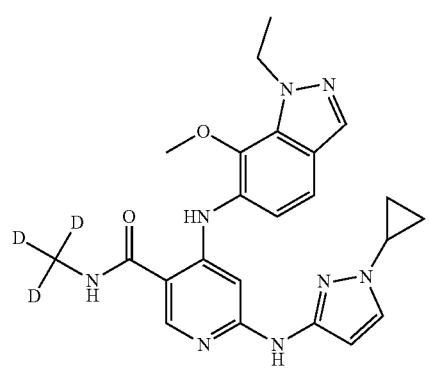 [SMILES: [2H]C([2H])([2H])NC(=O)c1cnc(Nc2ccn(C3CC3)n2)cc1Nc1ccc2cnn(CC)c2c1OC]
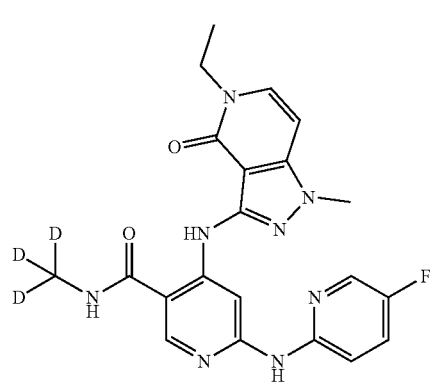 [SMILES: [2H]C([2H])([2H])NC(=O)c1cnc(Nc2ccc(F)cn2)cc1Nc1nn(C)c2ccn(CC)c(=O)c12]
122
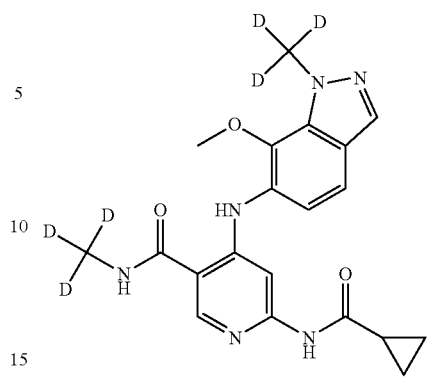
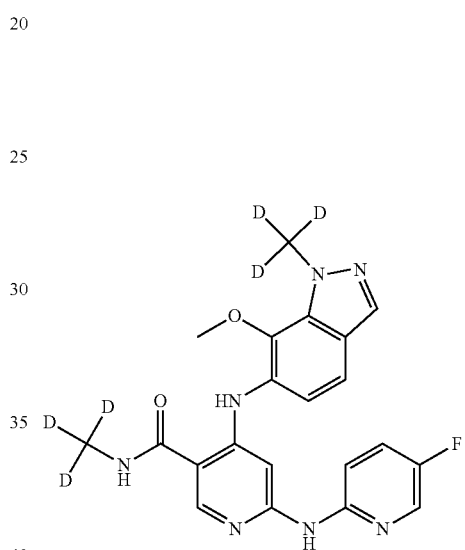
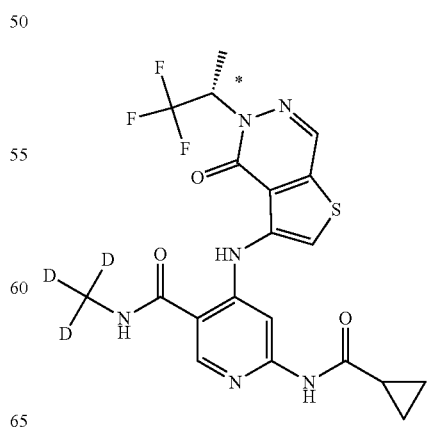

123
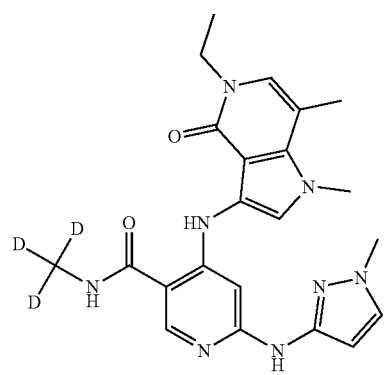 [SMILES: [2H]C([2H])([2H])NC(=O)c1cnc(Nc2ccn(C)n2)cc1Nc1cn(C)c2c(C)cn(CC)c(=O)c12]
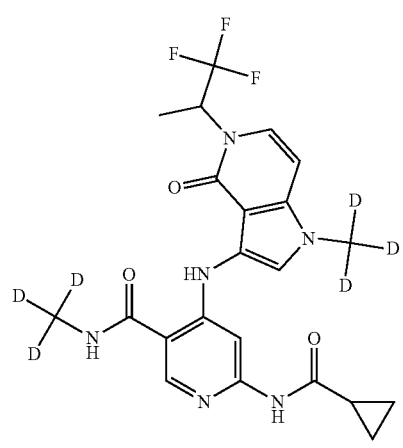 [SMILES: [2H]C([2H])([2H])NC(=O)c1cnc(NC(=O)C2CC2)cc1Nc1cn(C([2H])([2H])[2H])c2ccn(C(C)C(F)(F)F)c(=O)c12]
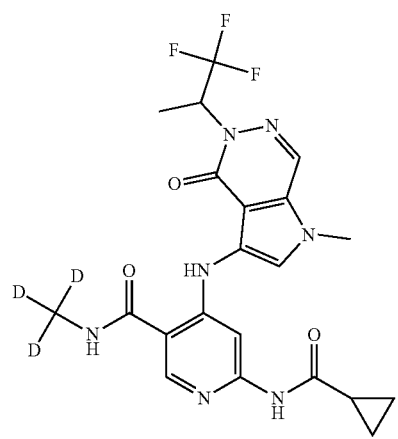 [SMILES: [2H]C([2H])([2H])NC(=O)c1cnc(NC(=O)C2CC2)cc1Nc1cn(C)c2cnn(C(C)C(F)(F)F)c(=O)c12]
124
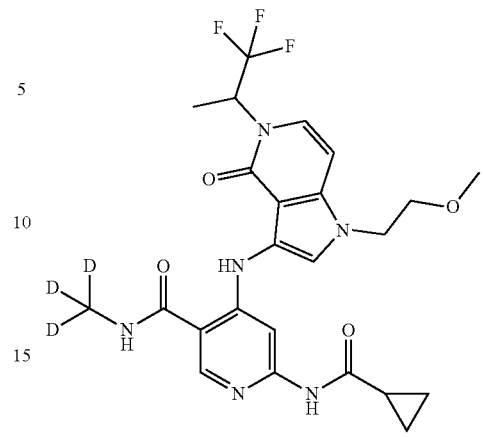
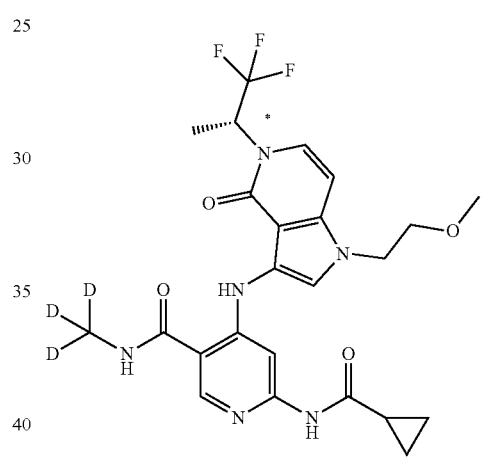
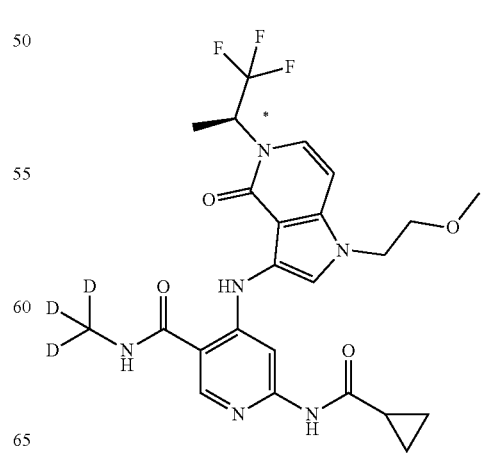

125
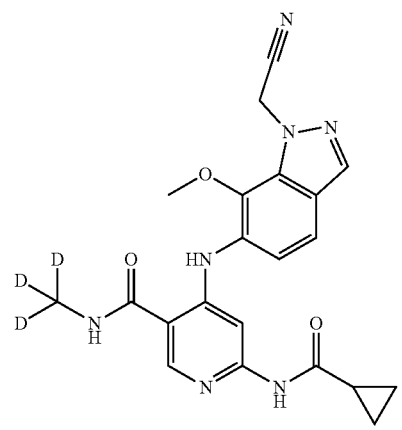
126
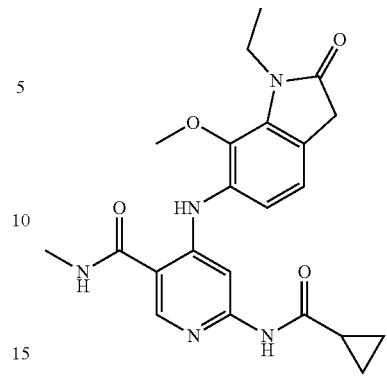
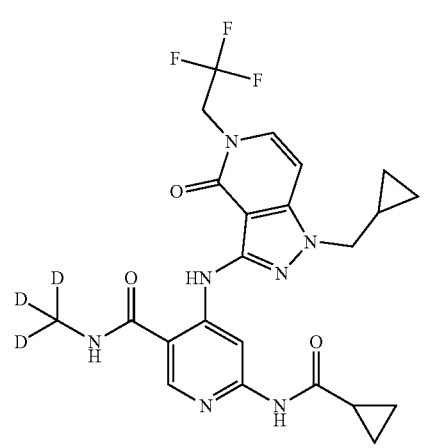 [SMILES: [2H]C([2H])([2H])NC(=O)c1cnc(NC(=O)C2CC2)cc1Nc1nn(CC2CC2)c2ccn(CC(F)(F)F)c(=O)c12]
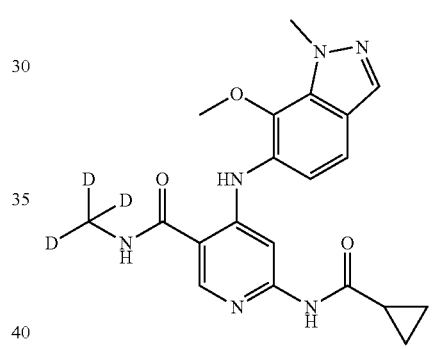
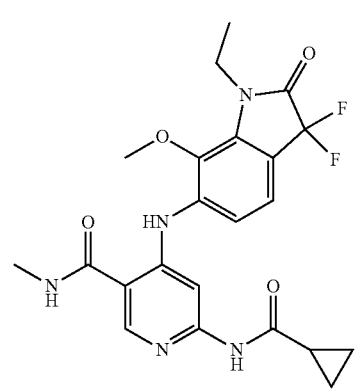 [SMILES: CCN1C(=O)C(F)(F)c2ccc(Nc3cc(NC(=O)C4CC4)ncc3C(=O)NC)c(OC)c21]
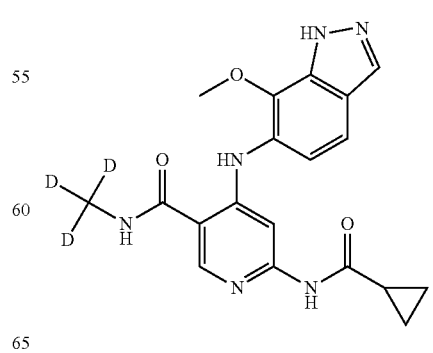

127
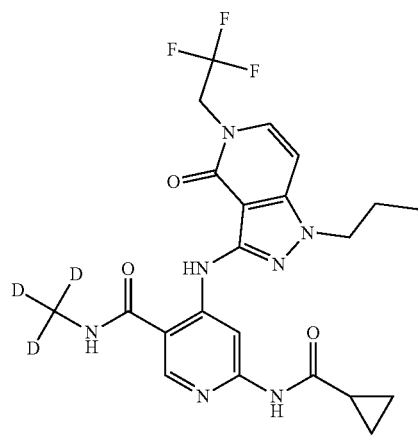 [SMILES: [2H]C([2H])([2H])NC(=O)c1cnc(NC(=O)C2CC2)cc1Nc1nn(CCC)c2ccn(CC(F)(F)F)c(=O)c12]
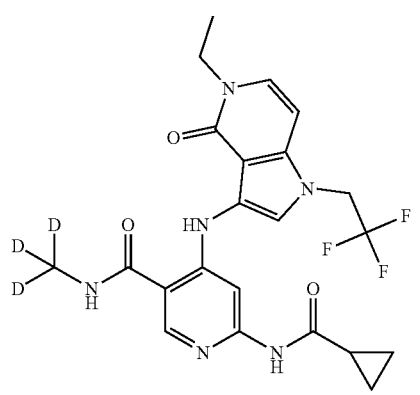 [SMILES: [2H]C([2H])([2H])NC(=O)c1cnc(NC(=O)C2CC2)cc1Nc1cn(CC(F)(F)F)c2ccn(CC)c(=O)c12]
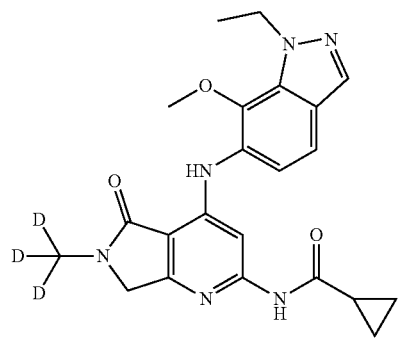 [SMILES: [2H]C([2H])([2H])N1Cc2nc(NC(=O)C3CC3)cc(Nc3ccc4cnn(CC)c4c3OC)c2C1=O]
128
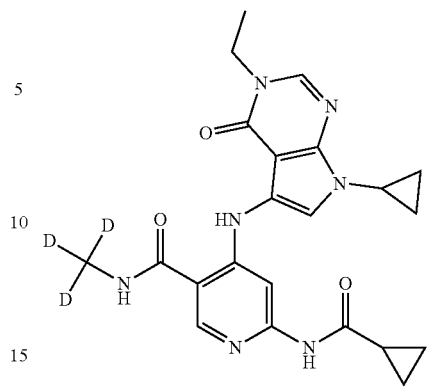
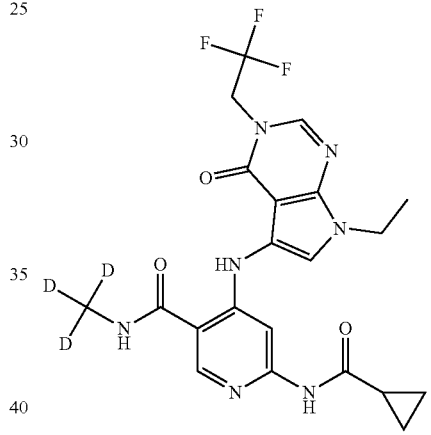
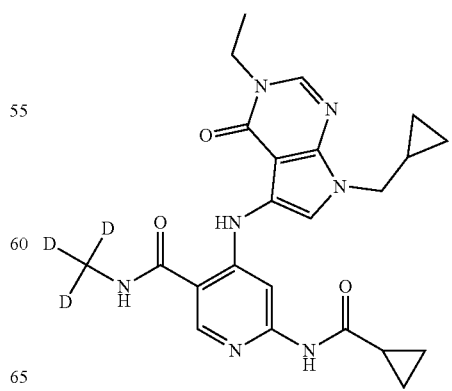

129
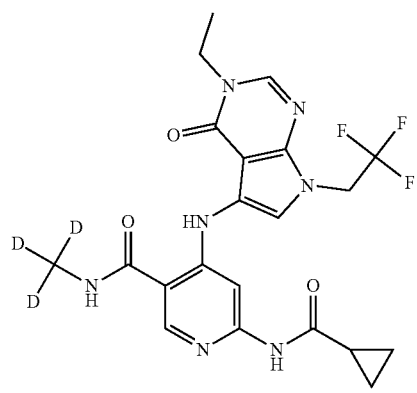 [SMILES: [2H]C([2H])([2H])NC(=O)c1cnc(NC(=O)C2CC2)cc1Nc1cn(CC(F)(F)F)c2ncn(CC)c(=O)c12]
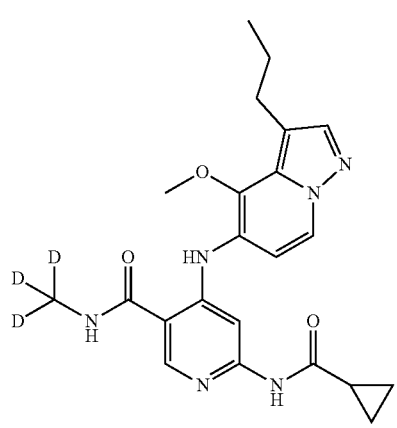 [SMILES: [2H]C([2H])([2H])NC(=O)c1cnc(NC(=O)C2CC2)cc1Nc1ccn2ncc(CCC)c2c1OC]
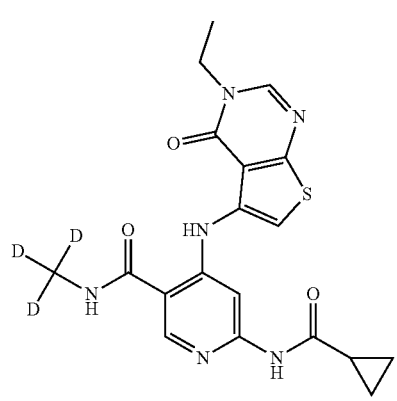
130
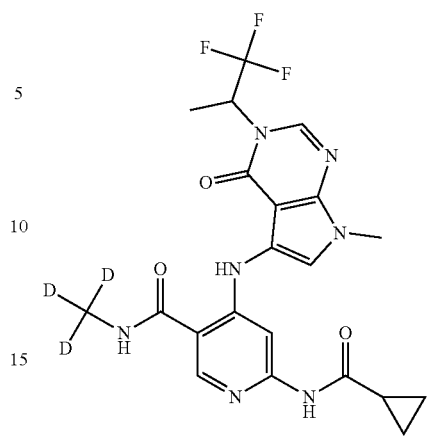
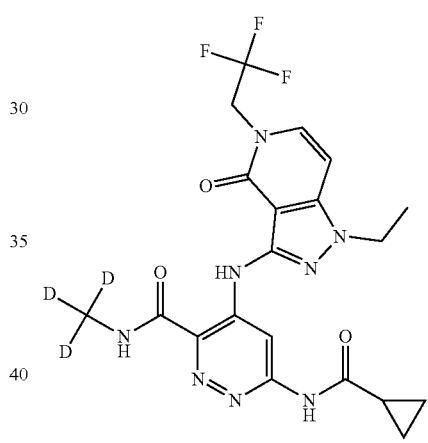
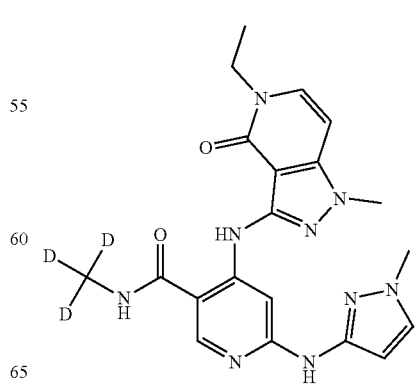

131
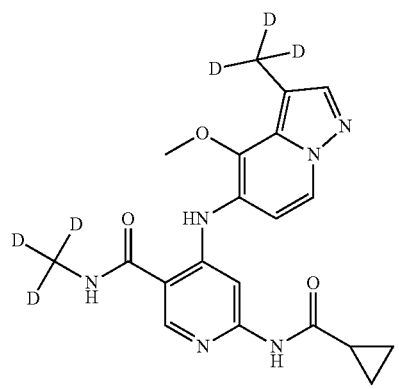 [SMILES: [2H]C([2H])([2H])NC(=O)c1cnc(NC(=O)C2CC2)cc1Nc1ccn2ncc(C([2H])([2H])[2H])c2c1OC]
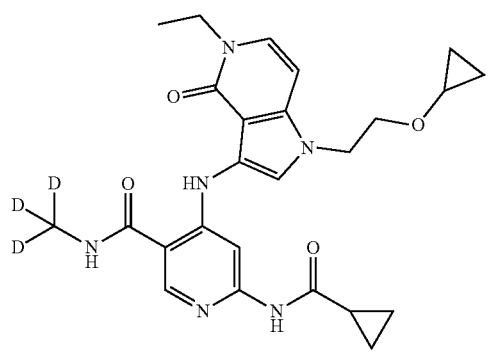 [SMILES: [2H]C([2H])([2H])NC(=O)c1cnc(NC(=O)C2CC2)cc1Nc1cn(CCOC2CC2)c2ccn(CC)c(=O)c12]
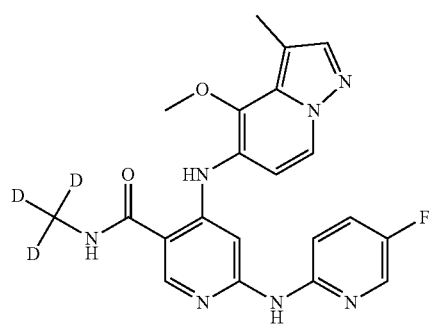 [SMILES: [2H]C([2H])([2H])NC(=O)c1cnc(Nc2ccc(F)cn2)cc1Nc1ccn2ncc(C)c2c1OC]
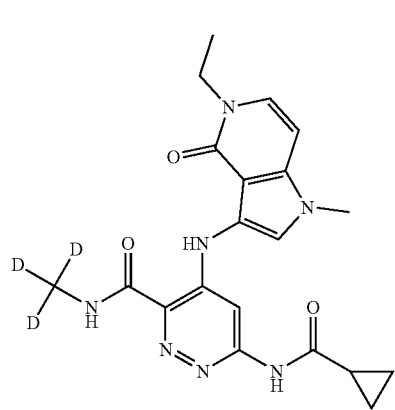
132
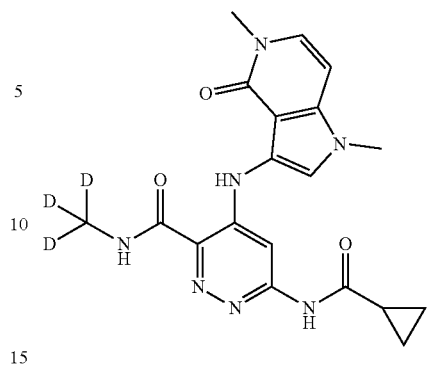
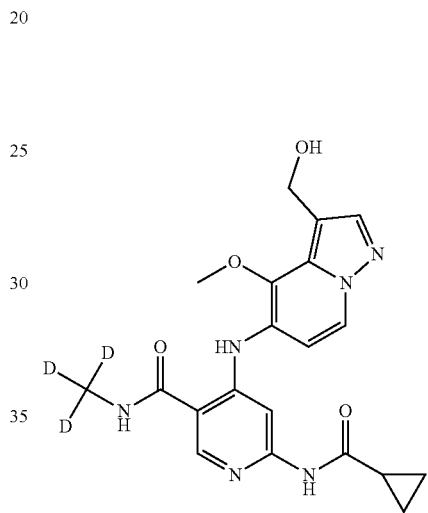
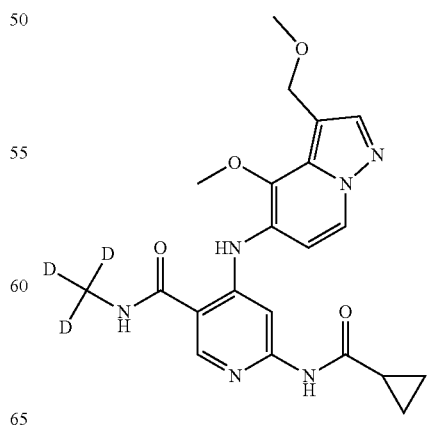

133
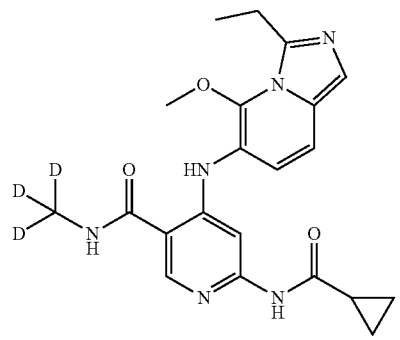 [SMILES: [2H]C([2H])([2H])NC(=O)c1cnc(NC(=O)C2CC2)cc1Nc1ccc2cnc(CC)n2c1OC]
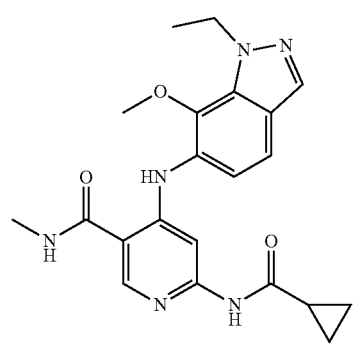 [SMILES: CCn1ncc2ccc(Nc3cc(NC(=O)C4CC4)ncc3C(=O)NC)c(OC)c21]
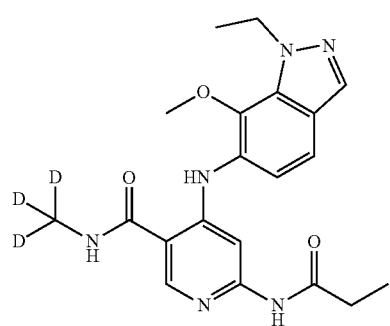 [SMILES: [2H]C([2H])([2H])NC(=O)c1cnc(NC(=O)CC)cc1Nc1ccc2cnn(CC)c2c1OC]
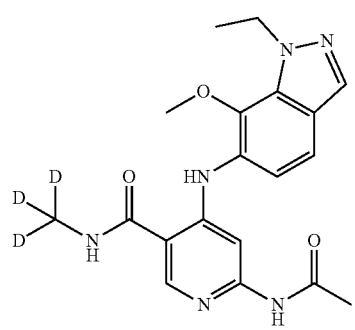 [SMILES: [2H]C([2H])([2H])NC(=O)c1cnc(NC(C)=O)cc1Nc1ccc2cnn(CC)c2c1OC]
134
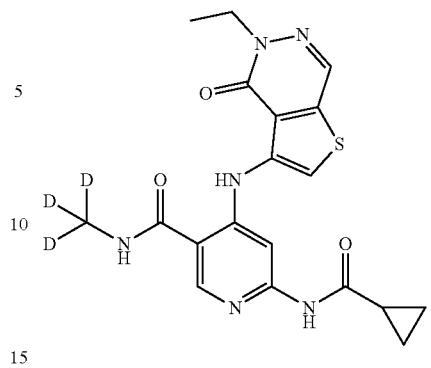
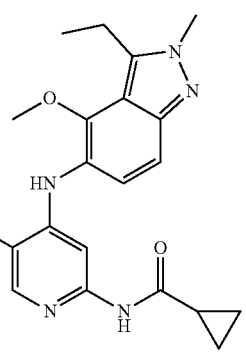
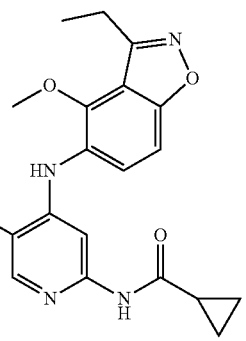

135
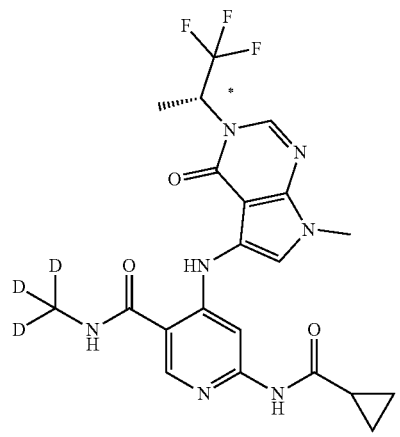 [SMILES: [2H]C([2H])([2H])NC(=O)c1cnc(NC(=O)C2CC2)cc1Nc1cn(C)c2ncn([C@H](C)C(F)(F)F)c(=O)c12]
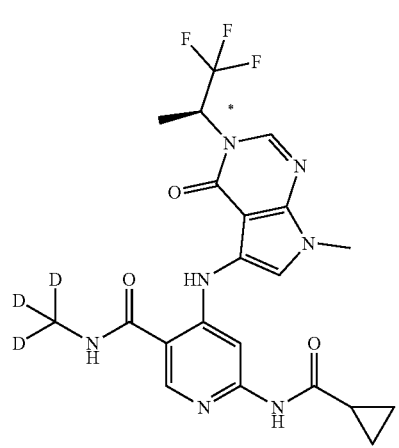 [SMILES: [2H]C([2H])([2H])NC(=O)c1cnc(NC(=O)C2CC2)cc1Nc1cn(C)c2ncn([C@@H](C)C(F)(F)F)c(=O)c12]
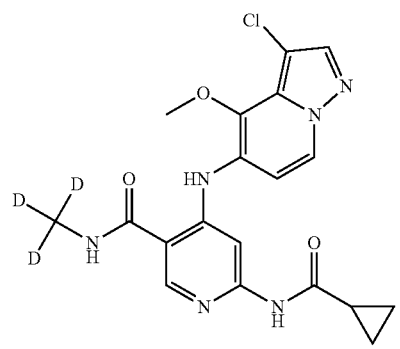 [SMILES: [2H]C([2H])([2H])NC(=O)c1cnc(NC(=O)C2CC2)cc1Nc1ccn2ncc(Cl)c2c1OC]
136
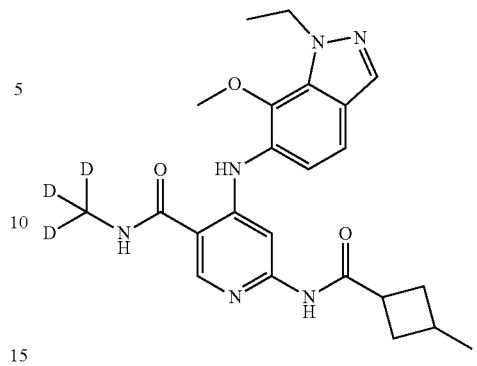
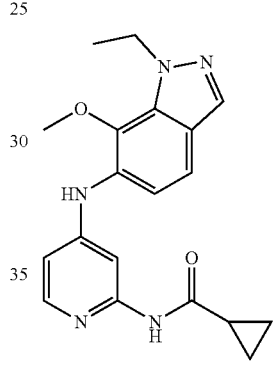
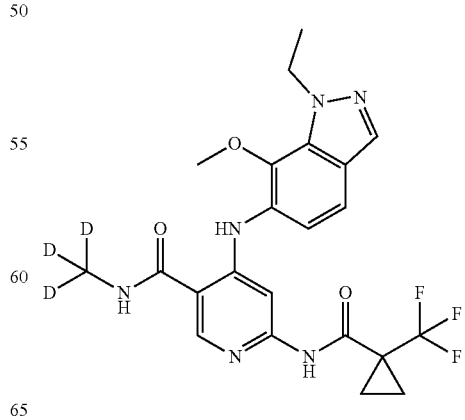

137
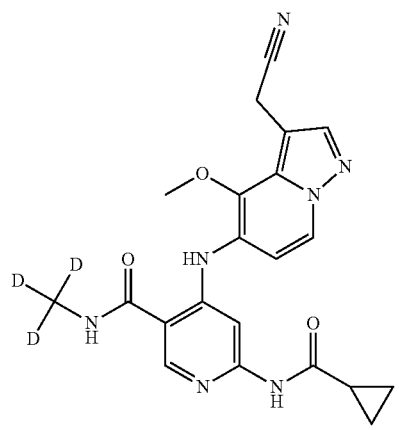 [SMILES: [2H]C([2H])([2H])NC(=O)c1cnc(NC(=O)C2CC2)cc1Nc1ccn2ncc(CC#N)c2c1OC]
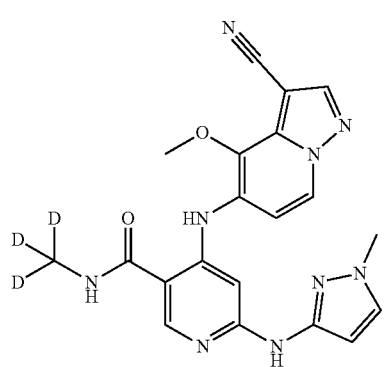 [SMILES: [2H]C([2H])([2H])NC(=O)c1cnc(Nc2ccn(C)n2)cc1Nc1ccn2ncc(C#N)c2c1OC]
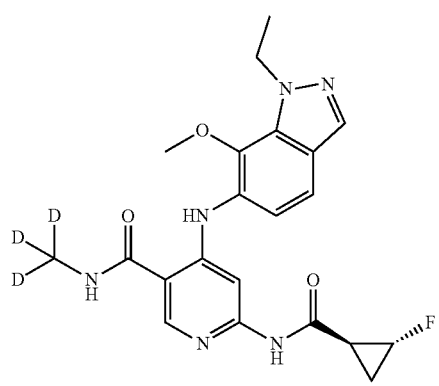 [SMILES: [2H]C([2H])([2H])NC(=O)c1cnc(NC(=O)[C@@H]2C[C@H]2F)cc1Nc1ccc2cnn(CC)c2c1OC]
138
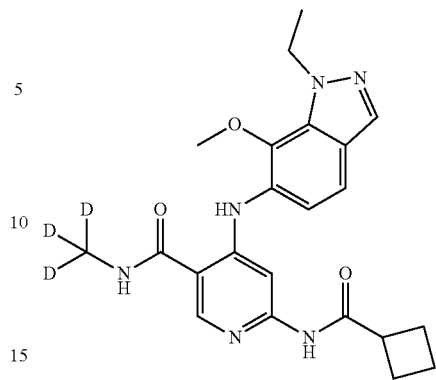
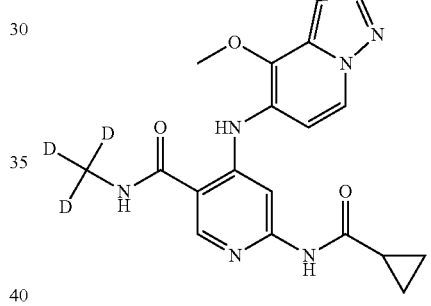
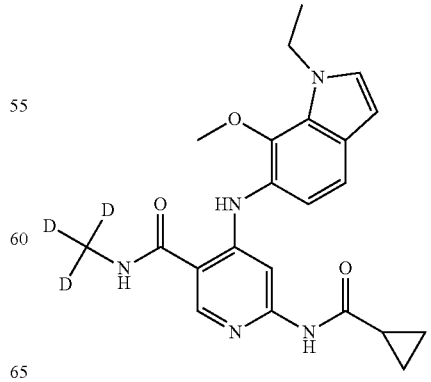

139
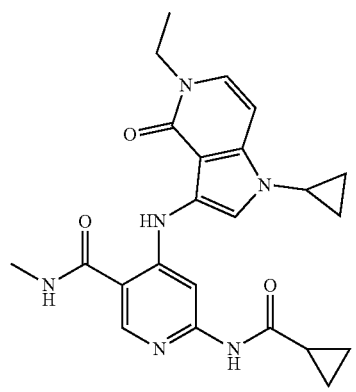 [SMILES: CCn1ccc2c(c(Nc3cc(NC(=O)C4CC4)ncc3C(=O)NC)cn2C2CC2)c1=O]
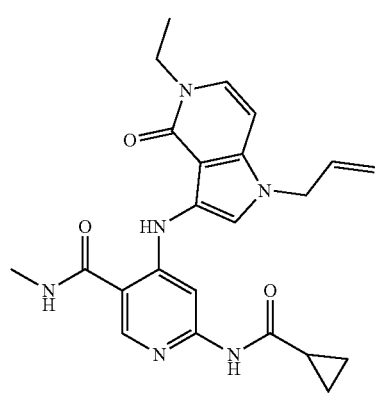 [SMILES: C=CCn1cc(Nc2cc(NC(=O)C3CC3)ncc2C(=O)NC)c2c(=O)n(CC)ccc21]
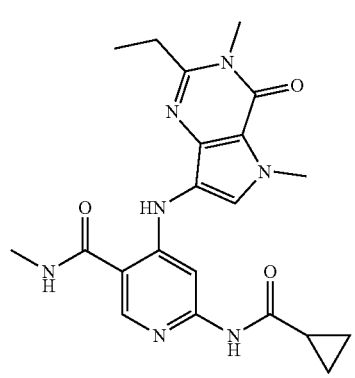 [SMILES: CCc1nc2c(Nc3cc(NC(=O)C4CC4)ncc3C(=O)NC)cn(C)c2c(=O)n1C]
140
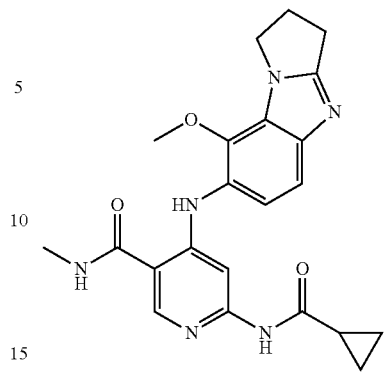
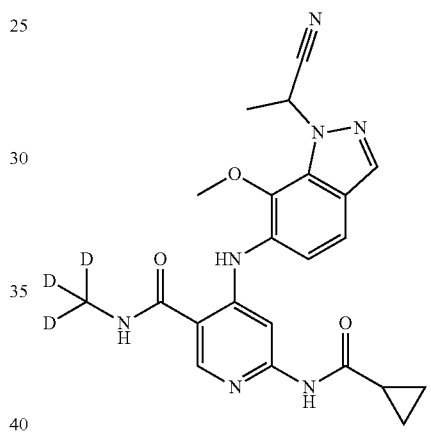
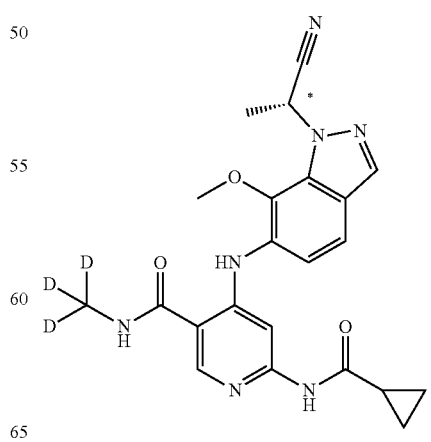

141
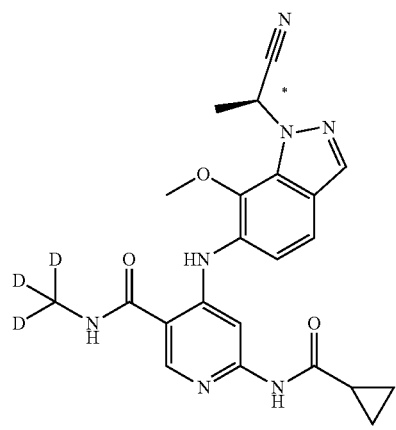 [SMILES: [2H]C([2H])([2H])NC(=O)c1cnc(NC(=O)C2CC2)cc1Nc1ccc2cnn([C@@H](C)C#N)c2c1OC]
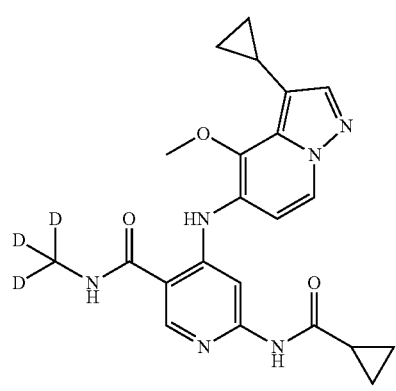 [SMILES: [2H]C([2H])([2H])NC(=O)c1cnc(NC(=O)C2CC2)cc1Nc1ccn2ncc(C3CC3)c2c1OC]
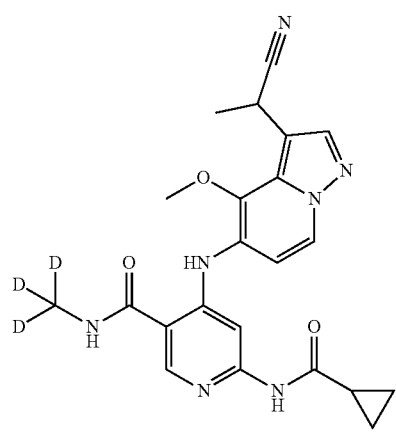 [SMILES: [2H]C([2H])([2H])NC(=O)c1cnc(NC(=O)C2CC2)cc1Nc1ccn2ncc(C(C)C#N)c2c1OC]
142
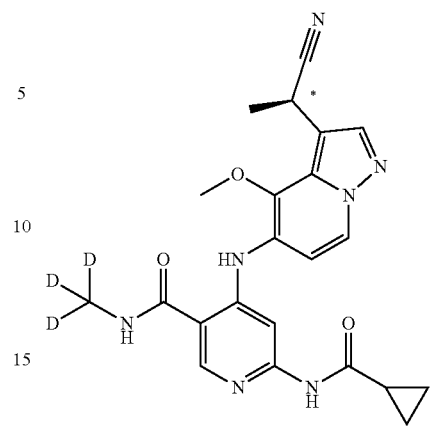
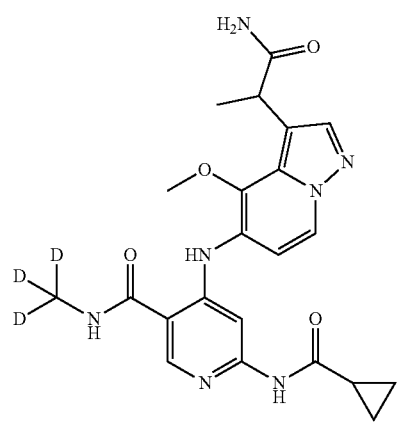 [SMILES: [2H]C([2H])([2H])NC(=O)c1cnc(NC(=O)C2CC2)cc1Nc1ccn2ncc(C(C)C(N)=O)c2c1OC]

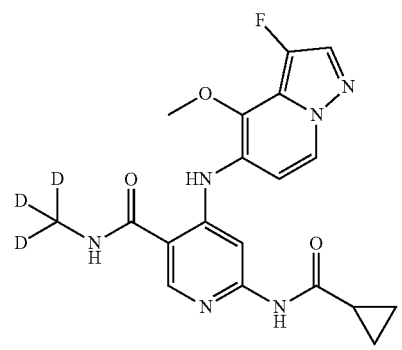
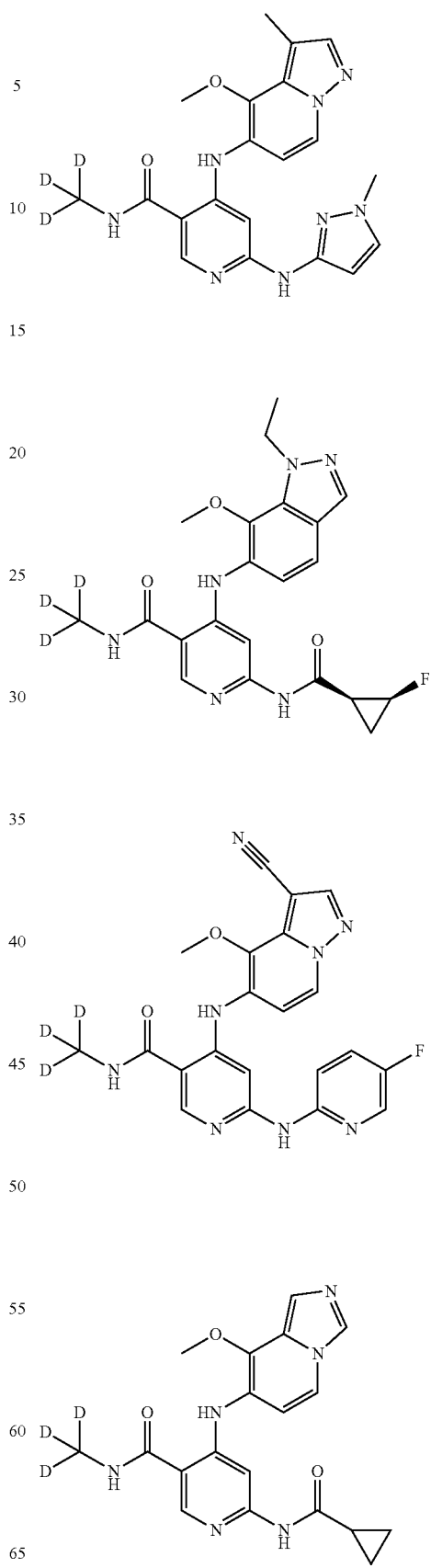

145
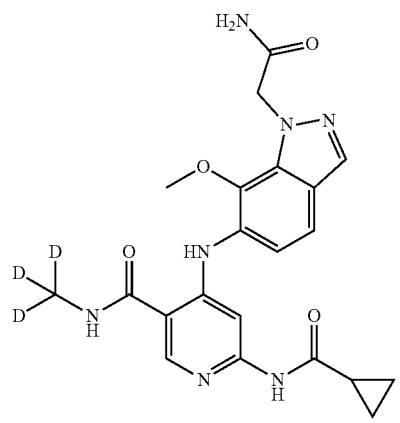
146
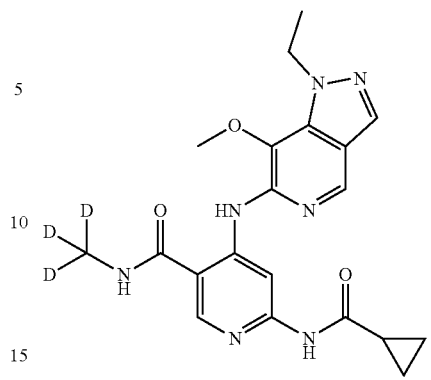
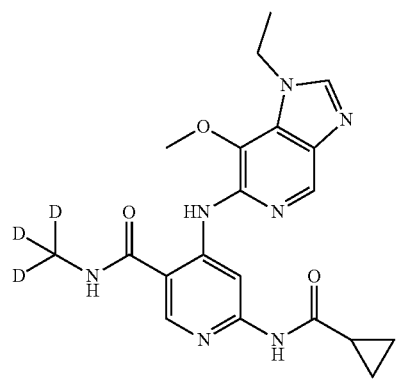 [SMILES: [2H]C([2H])([2H])NC(=O)c1cnc(NC(=O)C2CC2)cc1Nc1ncc2ncn(CC)c2c1OC]
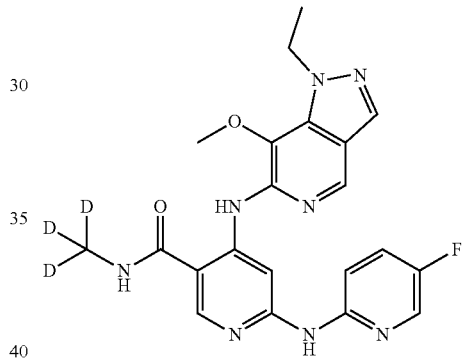
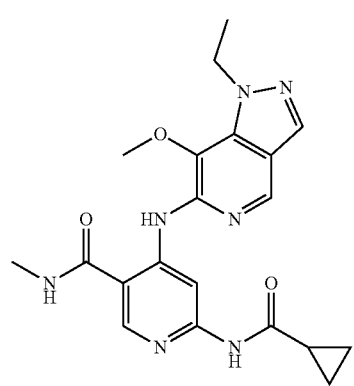 [SMILES: CCn1ncc2cnc(Nc3cc(NC(=O)C4CC4)ncc3C(=O)NC)c(OC)c21]
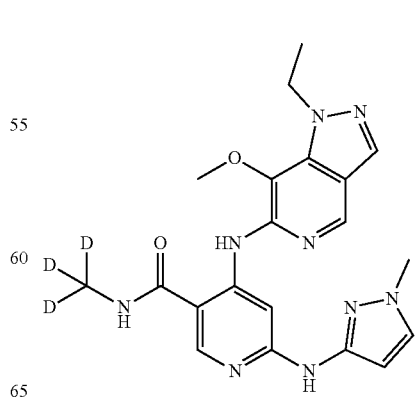

| 147 | 148 |
|---|---|
| 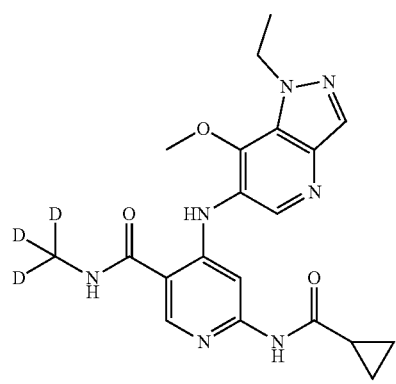 | 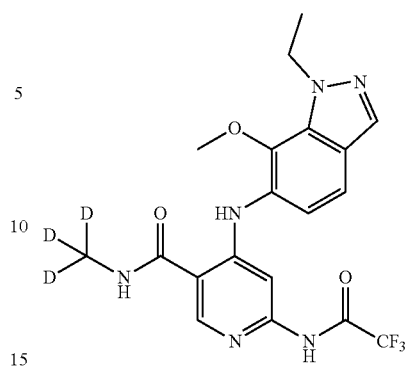 |
| 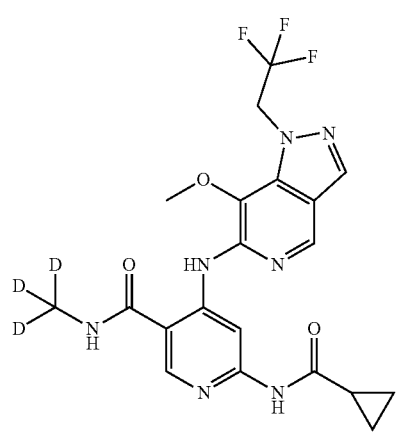 [SMILES: [2H]C([2H])([2H])NC(=O)c1cnc(NC(=O)C2CC2)cc1Nc1ncc2cnn(CC(F)(F)F)c2c1OC]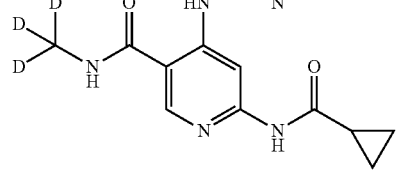 | 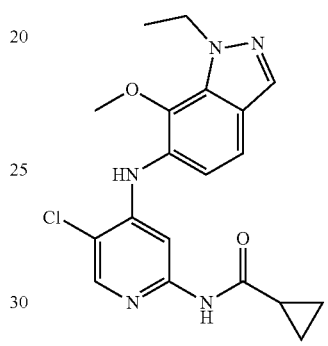<br>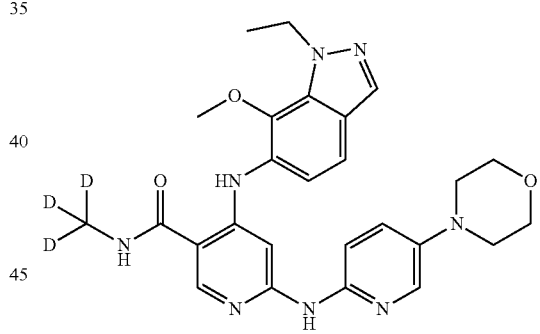 |
| 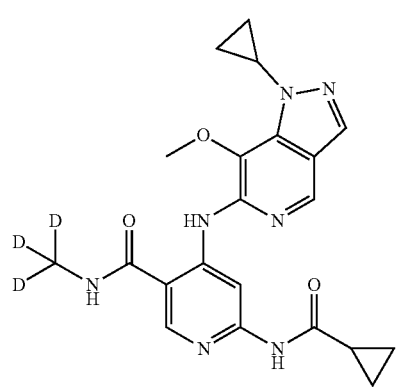 [SMILES: [2H]C([2H])([2H])NC(=O)c1cnc(NC(=O)C2CC2)cc1Nc1ncc2cnn(C3CC3)c2c1OC] | 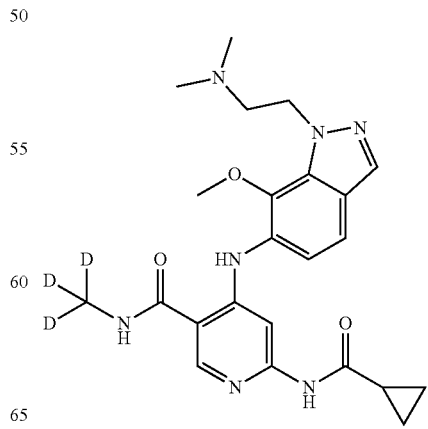 |

149
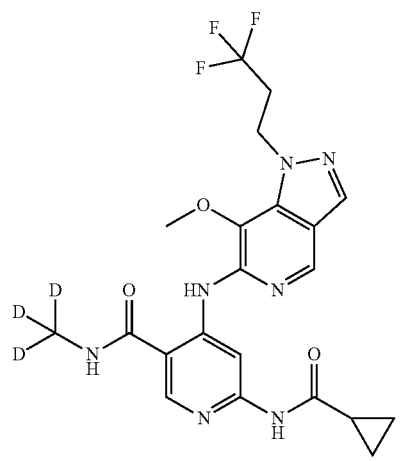 [SMILES: [2H]C([2H])([2H])NC(=O)c1cnc(NC(=O)C2CC2)cc1Nc1ncc2cnn(CCC(F)(F)F)c2c1OC]
150
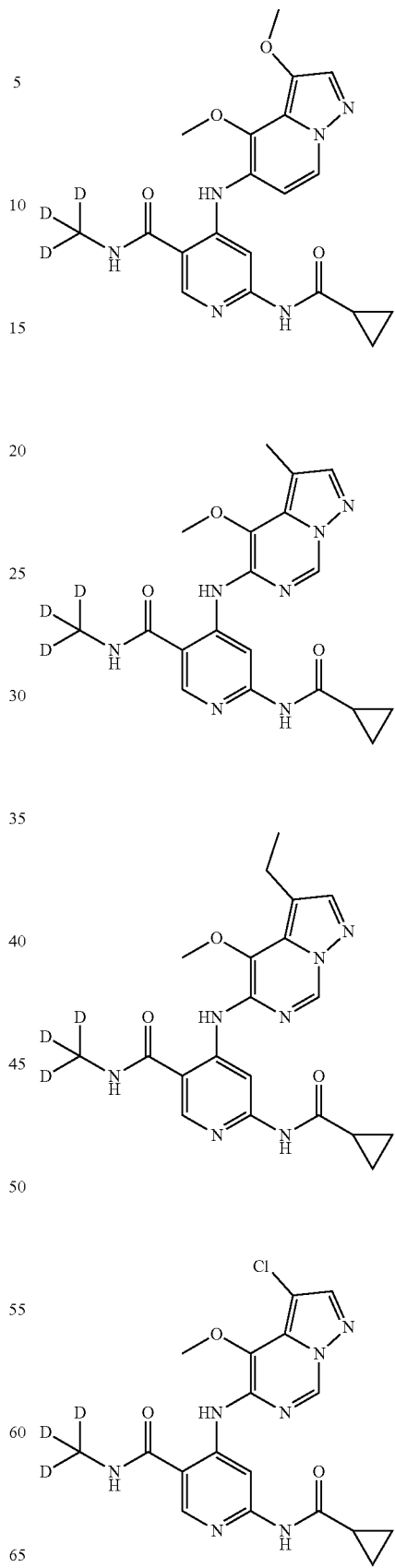

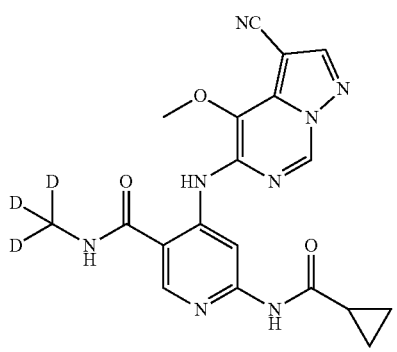 [SMILES: [2H]C([2H])([2H])NC(=O)c1cnc(NC(=O)C2CC2)cc1Nc1ncn2ncc(Cl)c2c1OC]

In yet another aspect, the invention generally relates to a method for preparing a compound disclosed herein, as exemplified by the synthetic schemes and experimental procedure disclosed herein.

In yet another aspect, the invention generally relates to a pharmaceutical composition comprising a compound disclosed herein, effective to treat or reduce one or more diseases or disorders, in a mammal, including a human, and a pharmaceutically acceptable excipient, carrier, or diluent.

In yet another aspect, the invention generally relates to a pharmaceutical composition comprising an amount of a compound having the structural formula of (I):

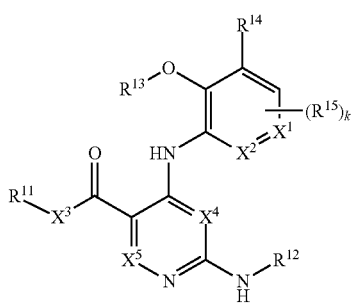

(I)

or a pharmaceutically acceptable form or an isotope derivative thereof,
wherein
each of $X^1$ and $X^2$ is independently selected from CH and N;
each of $X^4$ and $X^5$ is independently selected from CH, CF and N;
$X^3$ is NR, O, $CH_2$ or $CF_2$;
$R^{11}$ is a H, F, $C_1$-$C_3$ alkyl or $CD_3$, provided that $R^{11}$ is not F when $X^3$ is NR or O;
$R^{12}$ is C(=O)$R^{12'}$ or $R^{12'}$, wherein $R^{12'}$ is a $C_1$-$C_6$ alkyl, $C_3$-$C_6$ cycloalkyl or heterocycloalkyl, aryl or heteroaryl, each substituted with 0-2 $R^{12a}$, wherein $R^{12a}$ is selected from the group consisting of halogen, $CF_3$, CN, OR, amino, alkyl, cycloalkyl, heterocyclic, aryl and heteroaryl;
$R^{13}$ is a $C_1$-$C_3$ alkyl, $CD_3$ or $CF_3$;
$R^{14}$ is H, $C_1$-$C_6$ alkyl or heteroalkyl or a $C_3$-$C_6$ cycloalkyl or heterocycloalkyl, or a 5- or 6-membered heteroaryl group comprising 1, 2 or 3 hetero atoms selected from N, O and S, or $R^{14}$ is OR$^{14'}$, wherein $R^{14'}$ is $C_1$-$C_6$ alkyl or a $C_3$-$C_6$ cycloalkyl or heterocycloalkyl, each substituted with 0-2 $R^{14a}$, wherein $R^{14a}$ is selected from the group consisting of halogen, R, OR, amino, $CF_3$ and CN;
$R^{15}$ at each occurrence is independently selected from F, Cl, CN, OR, NRR', and a $C_1$-$C_3$ alkyl;
R at each occurrence is independently H or a $C_1$-$C_6$ alkyl; and
k is 0, 1, 2 or 3,
effective to treat, or reduce one or more diseases or disorders, in a mammal, including a human, and a pharmaceutically acceptable excipient, carrier, or diluent.

In yet another aspect, the invention generally relates to a pharmaceutical composition comprising an amount of a compound having the structural formula of (II):

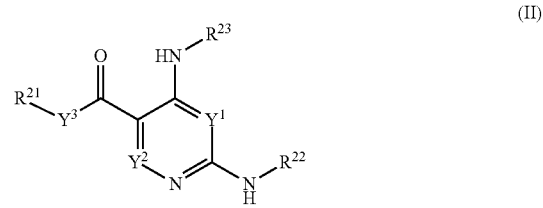

(II)

or a pharmaceutically acceptable form or an isotope derivative thereof,
wherein
$Y^1$ is CH, CF or N;
$Y^2$ is CH or N;
$Y^3$ is NR, O, $CH_2$ or $CF_2$;
$R^{21}$ is a H, F, $C_1$-$C_3$ alkyl and $CD_3$, provided that $R^{21}$ is not F when $Y^3$ is N or O;
$R^{22}$ is
$R^{22'}$, wherein $R^{22'}$ is a $C_1$-$C_6$ alkyl, $C_3$-$C_6$ cycloalkyl or heterocycloalkyl, aryl or heteroaryl, each substituted with 0-2 $R^{22a}$, wherein $R^{22a}$ is selected from the group consisting of halogen, CN, OR, amino, alkyl, cycloalkyl, heterocyclic;
an aryl or heteroaryl group, each substituted with 0-2 $R^{22a}$; or (C=O)$R^{27}$;
$R^{23}$ is
wherein

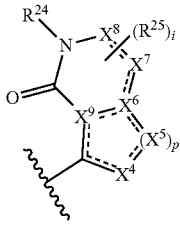

each of $X^4$, $X^5$, $X^6$, $X^7$, $X^8$ and $X^9$ is independently selected from O, C, CH, S, N and NR$^{26}$;
$R^{24}$ is H and $C_{1-6}$ alkyl, substituted with 0-3 $R^{24a}$, or $C_{3-10}$ cycloalkyl or heterocycloalkyl, $C_{5-10}$ aryl or heteroaryl, or a 4- to 10-membered heterocycle having 1-4 heteroatoms selected from N, O and S, each group is substituted with 0-4 $R^{24b}$;
$R^{24a}$ at each occurrence is independently H, D, halo, OH, OR, $CH_3$, $CF_3$, $CH_2CF_3$ or CN, NRR', $(CH_2)_n$NRR' or a 4- to 6-membered heterocycle having 1-4 heteroatoms selected from N, O and S;

$R^{24b}$ at each occurrence is independently H, halo, CN, OR, NRR', OCF$_3$, CF$_3$, C$_{1-6}$ alkyl, C$_{3-10}$ cycloalkyl, heterocycloalkyl, aryl, or heteroaryl, each substituted with 0-3 R$^{24a}$, C$_{1-6}$ haloalkyl, C$_{2-6}$ alkenyl substituted with 0-3 R$^{24a}$, C$_{2-6}$ alkynyl substituted with 0-3 R$^{24a}$;

$R^{25}$ is F, Cl, CN, CD$_3$, CH$_2$CF$_3$, CF$_3$, OR, NRR', C$_1$-C$_3$ alkyl, C$_3$-C$_5$ cycloalkyl, substituted with 0-2 R$^{24b}$;

$R^{26}$ is H, a C$_1$-C$_6$ alkyl, CD$_3$, or C$_3$-C$_6$ cycloalkyl, substituted with 0-3 R$^{24a}$;

$R^{27}$ is a C$_{1-6}$ alkyl or C$_{3-6}$ cycloalkyl, aryl or heteroaryl, each substituted with 0-2 R$^{24b}$;

each of R and R' is independently H or a C$_1$-C$_6$ alkyl, or R and R', together with the nitrogen atom to which they are bound, form a 4- to 7-membered ring comprising 0-2 heteroatoms selected from O, NR, S and SO$_2$;

n is 0, 1, 2, 3 or 4;

i is 0, 1 or 2; and p is 1 or 2, effective to treat, or reduce one or more diseases or disorders, in a mammal, including a human, and a pharmaceutically acceptable excipient, carrier, or diluent.

In yet another aspect, the invention generally relates to a pharmaceutical composition comprising an amount of a compound having the structural formula of (III):

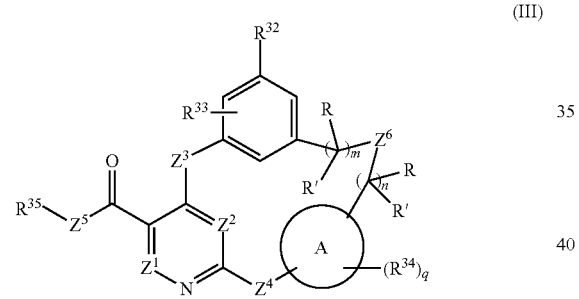

(III)

or a pharmaceutically acceptable form or an isotope derivative thereof, wherein

Ring A is a 5- or 6-membered aryl or heteroaryl;

$X^1$ is selected from NR, O, CH$_2$ and CF$_2$;

$Z^1$ is CH or N;

$Z^2$ is CH, CF or N;

each of $Z^3$ and $Z^4$ is independently selected from NR, CH$_2$ and CF$_2$;

$Z^6$ is NR$^{36}$, CH$_2$, O, S, SO or SO$_2$;

$R^{32}$ is R$^{32'}$ or OR$^{32'}$, wherein R$^{32'}$ is a C$_{1-12}$ alkyl, 3- to 6-membered cycloalkyl or heterocycloalkyl comprising 1, 2 or 3 heteroatoms selected from N, O and S, or a 5- or 6-membered aryl or heteroaryl group, each substituted with 0-3 R$^{32a}$;

$R^{32a}$ is independently at each occurrence, H, OCF$_3$, CN, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, (CH$_2$)$_r$NR$^g$R$^g$, —(CH$_2$)$_r$C(O)NR$^g$R$^g$, —(CH$_2$)$_r$NR$^b$C(O)R$^c$, —(CH$_2$)$_r$NR$^b$C(O)OR$^c$, —NR$^b$C(O)NR$^g$R$^g$, —S(O)$_v$NR$^g$R$^g$, —NR$^b$S(O)$_v$R$^c$, —S(O)$_v$R$^c$, C$_{1-6}$ alkyl substituted with 0-3 R$^a$, C$_{1-6}$ haloalkyl, C$_{2-6}$ alkenyl substituted with 0-3 R$^a$, 3- to 6-membered cycloalkyl substituted with 0-3 R$^a$, or 3- to 6-membered heterocycloalkyl comprising 1-3 heteroatoms selected from N, O and S substituted with 0-3 R$^a$;

each of $R^{33}$ and $R^{34}$ is independently selected from H, F, Cl, CN, OR$^g$, CH$_3$, CD$_3$, CF$_3$, OCD$_3$, OCF$_3$ and —(CH$_2$)$_p$-Q;

$R^{35}$ is H, F, a C$_1$-C$_3$ alkyl and CD$_3$, provided that R$^{35}$ is not F when $X^1$ is O or N;

$R^{36}$ is R substituted with 0-3 R$^d$;

$R^a$ at each occurrence is independently H, F, Cl, Br, OCF$_3$, CF$_3$, CHF$_2$, CN, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^g$R$^g$, —(CH$_2$)$_r$C(O)NR$^g$R$^g$, —(CH$_2$)$_r$NR$^b$C(O)R$^c$, —(CH$_2$)$_r$NR$^b$C(O)OR$^c$, —NR$^b$C(O)NR$^g$R$^g$, —S(O)$_v$NR$^g$R$^g$, —NR$^b$S(O)$_v$R$^c$, —S(O)R$^c$, —S(O)$_2$R$^c$, C$_{1-6}$ alkyl substituted with 0-3 R$^f$, C$_{1-6}$ haloalkyl, 3- to 6-membered cycloalkyl substituted with 0-3 R$^f$, or 3- to 6-membered heterocycloalkyl comprising 1-3 heteroatoms selected from N, O and S substituted with 0-3 R$^f$;

$R^b$ is H, C$_{1-6}$ alkyl substituted with 0-3 R$^d$, C$_{1-6}$ haloalkyl, C$_{3-6}$ cycloalkyl substituted with 0-2 R$^d$, or 5- to 7-membered heterocycloalkyl comprising 1-3 heteroatoms selected from N, O and S substituted with 0-3 R$^f$ or (CH$_2$)$_r$-phenyl substituted with 0-3 R$^d$;

$R^c$ is C$_{1-6}$ alkyl substituted with 0-3 R$^f$, (CH$_2$)$_r$—C$_{3-6}$ cycloalkyl substituted with 0-3 R$^f$ or (CH$_2$)$_r$-phenyl substituted with 0-3 R$^f$;

$R^d$ is independently at each occurrence, hydrogen, F, Cl, Br, OCF$_3$, CF$_3$, CN, NO$_2$, —OR$^e$, —(CH$_2$)$_r$C(O) R$^e$, —NR$^e$R$^e$, —NR$^e$C(O)OR$^e$, C$_{1-6}$ alkyl or (CH$_2$)$_r$-phenyl substituted with 0-3 R$^f$;

$R^e$ is independently at each occurrence, hydrogen, C$_{1-6}$ alkyl, C$_{3-6}$ cycloalkyl or (CH$_2$)$_r$-phenyl substituted with 0-3 R$^f$;

$R^f$ is independently at each occurrence, hydrogen, halo, CN, NH$_2$, OH, C$_{3-6}$ cycloalkyl, CF$_3$, O(C$_{1-6}$ alkyl) or a 5- to 7-membered heterocycloalkyl comprising 1-3 heteroatoms selected from N, O and S;

$R^g$ at each occurrence is independently H, C$_{1-4}$ alkyl substituted with 0-3 R$^f$, CF$_3$, C$_{3-10}$ cycloalkyl substituted with 0-1 R$^f$, (CH)$_r$-phenyl substituted with 0-3 R$^d$ or 5- to 7-membered heterocycloalkyl comprising 1-3 heteroatoms selected from N, O and S substituted with 0-3 R$^d$;

Q is a water solubilizing group, optionally selected from OH, OR, NRR', heterocyclic and heteroaryl groups, wherein R and R', together with the nitrogen atom to which they are bound, form a 4- to 7-membered ring comprising 0-2 heteroatoms selected from O, NR, S and SO$_2$;

R is H or a C$_1$-C$_6$ alkyl substituted with 0-3 R$^d$;

R' is H or a C$_1$-C$_6$ alkyl substituted with 0-3 R$^d$;

m is 0, 1, 2 and 3;

n is 0, 1, 2 and 3;

p is 0, 1, 2, 3 or 4;

q is 0, 1, 2, 3 or 4;

v is 0, 1, or 2; and r is 0, 1, 2, 3, 4 or 5, effective to treat, or reduce one or more diseases or disorders, in a mammal, including a human, and a pharmaceutically acceptable excipient, carrier, or diluent.

In yet another aspect, the invention generally relates to a pharmaceutical composition comprising an amount of a compound having the structural formula of (IV):

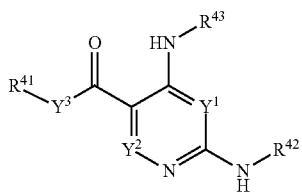

(IV)

or a pharmaceutically acceptable form or an isotope derivative thereof,
wherein
$Y^1$ is CH, CF or N;
$Y^2$ is CH or N;
$Y^3$ is NR, O, $CH_2$ or $CF_2$;
$R^{41}$ is a H, F, $C_1$-$C_3$ alkyl and $CD_3$, provided that $R^{41}$ is not F when $Y^3$ is NR or O;
$R^{42}$ is
$R^{42'}$, wherein $R^{42'}$ is a $C_1$-$C_6$ alkyl, $C_3$-$C_6$ cycloalkyl or heterocycloalkyl, aryl or heteroaryl, each substituted with 0-2 of halogen, CN, OR, amino, alkyl, cycloalkyl, heterocyclic, aryl and heteroaryl;
an aryl or heteroaryl group substituted with 0-2 $R^{42a}$; or
(C=O)$R^{42b}$;
$R^{43}$ is

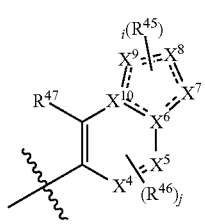

wherein
each of $X^4$, $X^5$, $X^6$, $X^7$, $X^8$, $X^9$ and $X^{10}$ is independently selected from C, CH, O, N and NH;
$R^{42a}$ at each occurrence is independently H, D, halo, OH, OR, $CH_3$, $CF_3$, $CH_2CF_3$, CN, C(O)NR, NRR', $(CH_2)_n$NRR' or a 4- to 6-membered heterocycle having 1-4 heteroatoms selected from N, O and S;
$R^{42b}$ is a $C_{1-6}$ alkyl or $C_{3-6}$ cycloalkyl, aryl or heteroaryl, each substituted with 0-2 $R^{42c}$;
$R^{42c}$ at each occurrence is independently H, halo, CN, OR, NRR', $OCF_3$, $CF_3$, $C_{1-6}$ alkyl substituted with 0-3 $R^{42a}$, $C_{1-6}$ haloalkyl, $C_{2-6}$ alkenyl substituted with 0-3 $R^{42a}$, $C_{2-6}$ alkynyl substituted with 0-3 $R^{42a}$;
$R^{45}$ each occurrence is independently H, halo, CN, OR, NRR', $OCF_3$, $CF_3$, $C_{1-6}$ alkyl, substituted with 0-3 $R^{42a}$, or $C_{3-10}$ cycloalkyl or heterocycloalkyl, $C_{5-10}$ aryl or heteroaryl, or a 4- to 10-membered heterocycle having 1-4 heteroatoms selected from N, O and S, each group is substituted with 0-4 $R^{42c}$, optionally two $R^{45}$s, along with the C or N atoms that they are attached to, form a 4- to 6-membered ring;
$R^{46}$ each occurrence is independently F, Cl, CN, OR, $C_1$-$C_3$ alkyl, $C_3$-$C_5$ cycloalkyl, $CD_3$, $CH_2CF_3$ or $CF_3$;
$R^{47}$ is H, $OCF_3$, $C_1$-$C_3$ alkyl, $C_1$-$C_3$ alkoxy or $OCD_3$;
each of R and R' is independently H or a $C_1$-$C_6$ alkyl, or R and R', together with the nitrogen atom to which they are bound, form a 4- to 7-membered ring comprising 0-2 heteroatoms selected from O, NR, S and $SO_2$;
n is 0, 1, 2, 3 or 4;
i is 0, 1 or 2; and
j is 0, 1 or 2,
effective to treat, or reduce one or more diseases or disorders, in a mammal, including a human, and a pharmaceutically acceptable excipient, carrier, or diluent.

In yet another aspect, the invention generally relates to a pharmaceutical composition comprising an amount of a compound having the structural formula of (V):

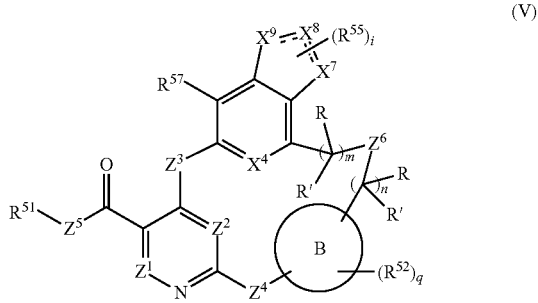

(V)

or a pharmaceutically acceptable form or an isotope derivative thereof,
wherein
Ring B is a 5- or 6-membered aryl or heteroaryl;
$Z^1$ is CH or N;
$Z^2$ is CH, CF or N;
each of $Z^3$ and $Z^4$ is independently selected from NR, $CH_2$ and $CF_2$;
$Z^5$ is selected from NR, O, $CH_2$ and $CF_2$;
$Z^6$ is $NR^{56}$, $CH_2$, O, S, SO or $SO_2$;
each of $X^4$, $X^7$, $X^8$ and $X^9$ is independently selected from CH, N and NH;
$R^{51}$ is a H, F, $C_1$-$C_3$ alkyl and $CD_3$, provided that $R^{51}$ is not F when $Z^5$ is N or O;
$R^{52}$ is independently selected from H, F, Cl, CN, $OR^g$, $CH_3$, $CF_3$, $OCF_3$ and —$(CH_2)_p$-Q;
$R^{52a}$ at each occurrence is independently H, D, halo, OH, OR, $CH_3$, $CF_3$, $CH_2CF_3$ or CN, NRR', $(CH_2)_n$NRR' or a 4- to 6-membered heterocycle having 1-4 heteroatoms selected from N, O and S;
$R^{52c}$ at each occurrence is independently H, halo, CN, OR, NRR', $OCF_3$, $CF_3$, $C_{1-6}$ alkyl substituted with 0-3 $R^{52a}$, $C_{1-6}$ haloalkyl, $C_{2-6}$ alkenyl substituted with 0-3 $R^{52a}$, $C_{2-6}$ alkynyl substituted with 0-3 $R^{52a}$;
$R^{55}$ each occurrence is independently H, $C_{1-6}$ alkyl, substituted with 0-3 $R^{52a}$, or $C_{3-10}$ cycloalkyl or heterocycloalkyl, $C_{5-10}$ aryl or heteroaryl, or a 4- to 10-membered heterocycle having 1-4 heteroatoms selected from N, O and S, each group is substituted with 0-4 $R^{52c}$;
$R^{56}$ is R substituted with 0-3 $R^d$;
$R^{57}$ is H, $C_1$-$C_3$ alkyl, $C_1$-$C_3$ alkoxy, $OCD_3$ or $OCF_3$;
$R^c$ is $C_{1-6}$ alkyl substituted with 0-3 $R^f$, $(CH_2)_r$—$C_{3-6}$ cycloalkyl substituted with 0-3 $R^f$ or $(CH_2)_r$-phenyl substituted with 0-3 $R^f$;
$R^d$ is independently at each occurrence, hydrogen, F, Cl, Br, $OCF_3$, $CF_3$, CN, $NO_2$, —$OR^e$, —$(CH_2)_r$C(O)

R$^c$, —NR$^e$R$^e$, —NR$^e$C(O)OR$^c$, C$_{1-6}$ alkyl or (CH$_2$)$_r$-phenyl substituted with 0-3 R$^f$;

R$^{Cc}$ is independently at each occurrence, hydrogen, C$_{1-6}$ alkyl, C$_{3-6}$ cycloalkyl or (CH$_2$)$_r$-phenyl substituted with 0-3 R$^f$;

R$^f$ is independently at each occurrence, hydrogen, halo, CN, NH$_2$, OH, C$_{3-6}$ cycloalkyl, CF$_3$, O(C$_{1-6}$ alkyl) or a 5- to 7-membered heterocycloalkyl comprising 1-3 heteroatoms selected from N, O and S;

R$^g$ at each occurrence is independently H, C$_{1-4}$ alkyl substituted with 0-3 R$^f$, CF$_3$, C$_{3-10}$ cycloalkyl substituted with 0-1 R$^f$, (CH)$_r$-phenyl substituted with 0-3 R$^d$ or 5- to 7-membered heterocycloalkyl comprising 1-3 heteroatoms selected from N, O and S substituted with 0-3 R$^d$;

Q is a water solubilizing group, optionally selected from OH, OR, NRR', heterocyclic and heteroaryl groups, wherein R and R', together with the nitrogen atom to which they are bound, form a 4- to 7-membered ring comprising 0-2 heteroatoms selected from O, NR, S and SO$_2$;

R is H or a C$_1$-C$_6$ alkyl substituted with 0-3 R$^d$;
R' is H or a C$_1$-C$_6$ alkyl substituted with 0-3 R$^d$;
i is 0, 1, 2 and 3;
m is 0, 1, 2 and 3;
n is 0, 1, 2 and 3;
p is 0, 1, 2, 3 or 4; and
q is 0, 1, 2, 3 or 4, effective to treat, or reduce one or more diseases or disorders, in a mammal, including a human, and a pharmaceutically acceptable excipient, carrier, or diluent.

In certain embodiments, a pharmaceutical composition disclosed herein is suitable for oral administration.

In certain embodiments, a pharmaceutical composition disclosed herein is suitable for topical administration.

In certain embodiments, a pharmaceutical composition disclosed herein is suitable for GI-restricted administration.

In certain embodiments, a pharmaceutical composition disclosed herein is useful to treat or reduce one or more of inflammatory diseases, immune-mediated diseases and cancers, or a related disease or disorder. In certain embodiments, the disease or disorder is an inflammatory disease. In certain embodiments, the disease or disorder is an immune-mediated disease. In certain embodiments, the disease or disorder is cancer. In certain embodiments, the disease or disorder is selected from: inflammatory bowel disease, psoriasis, vitiligo, atopic dermatitis, systemic lupus erythematosus, asthma, diabetic nephropathy, chronic myelogenous leukemia (CML), essential thrombocythemia (ET), polycythemia vera (PV), myelofibrosis (MF), breast cancer and ovarian cancer.

In yet another aspect, the invention generally relates to a unit dosage form comprising a pharmaceutical composition disclosed herein.

In certain embodiments, the unit dosage form is a tablet.
In certain embodiments, the unit dosage form is a capsule.
In certain embodiments, the unit dosage form is a topical formulation.

In yet another aspect, the invention generally relates to a method for treating, reducing or preventing a disease or disorder, comprising administering to a subject in need thereof a therapeutically effective amount of a compound disclosed herein.

In yet another aspect, the invention generally relates to a method for treating, reducing or preventing a disease or disorder, comprising administering to a subject in need thereof a therapeutically effective amount of a compound having the structural formula of (I):

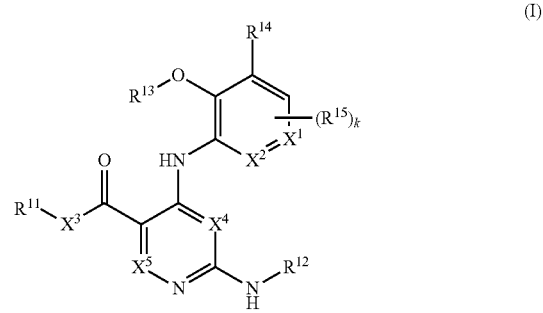

(I)

or a pharmaceutically acceptable form or an isotope derivative thereof, wherein
each of X$^1$ and X$^2$ is independently selected from CH and N;
each of X$^4$ and X$^5$ is independently selected from CH, CF and N;
X$^3$ is NR, O, CH$_2$ or CF$_2$;
R$^{11}$ is a H, F, C$_1$-C$_3$ alkyl or CD$_3$, provided that R$^{11}$ is not F when X$^3$ is NR or O;
R$^{12}$ is C(=O)R$^{12'}$ or R$^{12'}$, wherein R$^{12'}$ is a C$_1$-C$_6$ alkyl, C$_3$-C$_6$ cycloalkyl or heterocycloalkyl, aryl or heteroaryl, each substituted with 0-2 R$^{12a}$, wherein R$^{12a}$ is selected from the group consisting of halogen, CF$_3$, CN, OR, amino, alkyl, cycloalkyl, heterocyclic, aryl and heteroaryl;
R$^{13}$ is a C$_1$-C$_3$ alkyl, CD$_3$ or CF$_3$;
R$^{14}$ is H, C$_1$-C$_6$ alkyl or heteroalkyl or a C$_3$-C$_6$ cycloalkyl or heterocycloalkyl, or a 5- or 6-membered heteroaryl group comprising 1, 2 or 3 hetero atoms selected from N, O and S, or R$^{14}$ is OR$^{14'}$, wherein R$^{14'}$ is C$_1$-C$_6$ alkyl or heteroalkyl or a C$_3$-C$_6$ cycloalkyl or heterocycloalkyl, each substituted with 0-2 R$^{14a}$, wherein R$^{14a}$ is selected from the group consisting of halogen, R, OR, amino, CF$_3$ and CN;
R$^{15}$ at each occurrence is independently selected from F, Cl, CN, OR, NRR', and a C$_1$-C$_3$ alkyl;
R at each occurrence is independently H or a C$_1$-C$_6$ alkyl; and
k is 0, 1, 2 or 3, wherein the disease or disorder is selected from inflammatory diseases, immune-mediated diseases, cancer, or a related disease or disorder thereof, in a mammal, including a human.

In yet another aspect, the invention generally relates to a method for treating, reducing or preventing a disease or disorder, comprising administering to a subject in need thereof a therapeutically effective amount of a compound having the structural formula of (II):

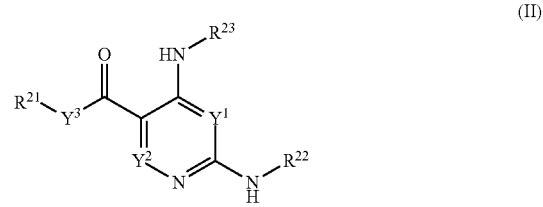

(II)

or a pharmaceutically acceptable form or an isotope derivative thereof,
wherein
$Y^1$ is CH, CF or N;
$Y^2$ is CH or N;
$Y^3$ is NR, O, $CH_2$ or $CF_2$;
$R^{21}$ is a H, F, $C_1$-$C_3$ alkyl and $CD_3$, provided that $R^{21}$ is not F when $Y^3$ is N or O;
$R^{22}$ is
  $R^{22'}$, wherein $R^{22'}$ is a $C_1$-$C_6$ alkyl, $C_3$-$C_6$ cycloalkyl or heterocycloalkyl, aryl or heteroaryl, each substituted with 0-2 $R^{22a}$, wherein $R^{22a}$ is selected from the group consisting of halogen, CN, OR, amino, alkyl, cycloalkyl, heterocyclic;
  an aryl or heteroaryl group, each substituted with 0-2 $R^{22a}$; or
  (C=O)$R^{27}$;
$R^{23}$ is wherein
  each of $X^4$, $X^5$, $X^6$, $X^7$, $X^8$ and $X^9$ is independently selected from O, C, CH, S, N and $NR^{26}$;
  $R^{24}$ is H and $C_{1-6}$ alkyl, substituted with 0-3 $R^{24a}$, or $C_{3-10}$ cycloalkyl or heterocycloalkyl, $C_{5-10}$ aryl or heteroaryl, or a 4- to 10-membered heterocycle having 1-4 heteroatoms selected from N, O and S, each group is substituted with 0-4 $R^{24b}$;
  $R^{24a}$ at each occurrence is independently H, D, halo, OH, OR, $CH_3$, $CF_3$, $CH_2CF_3$ or CN, NRR', $(CH_2)_n$NRR' or a 4- to 6-membered heterocycle having 1-4 heteroatoms selected from N, O and S;
  $R^{24b}$ at each occurrence is independently H, halo, CN, OR, NRR', $OCF_3$, $CF_3$, $C_{1-6}$ alkyl, $C_{3-10}$ cycloalkyl, heterocycloalkyl, aryl, or heteroaryl, each substituted with 0-3 $R^{24a}$, $C_{1-6}$ haloalkyl, $C_{2-6}$ alkenyl substituted with 0-3 $R^{24a}$, $C_{2-6}$ alkynyl substituted with 0-3 $R^{24a}$;
  $R^{25}$ is F, Cl, CN, $CD_3$, $CH_2CF_3$, $CF_3$, OR, NRR', $C_1$-$C_3$ alkyl, $C_3$-$C_5$ cycloalkyl, substituted with 0-2 $R^{24b}$;
  $R^{26}$ is H, a $C_1$-$C_6$ alkyl, $CD_3$, or $C_3$-$C_6$ cycloalkyl, substituted with 0-3 $R^{24a}$;
  $R^{27}$ is a $C_{1-6}$ alkyl or $C_{3-6}$ cycloalkyl, aryl or heteroaryl, each substituted with 0-2 $R^{24b}$;
  each of R and R' is independently H or a $C_1$-$C_6$ alkyl, or R and R', together with the nitrogen atom to which they are bound, form a 4- to 7-membered ring comprising 0-2 heteroatoms selected from O, NR, S and $SO_2$;
  n is 0, 1, 2, 3 or 4;
  i is 0, 1 or 2; and
  p is 1 or 2,
wherein the disease or disorder is selected from inflammatory diseases, immune-mediated diseases, cancer, or a related disease or disorder thereof, in a mammal, including a human.

In yet another aspect, the invention generally relates to a method for treating, reducing or preventing a disease or disorder, comprising administering to a subject in need thereof a therapeutically effective amount of a compound having the structural formula (III):

(III)

or a pharmaceutically acceptable form or an isotope derivative thereof,
wherein
  Ring A is a 5- or 6-membered aryl or heteroaryl;
  $X^1$ is selected from NR, O, $CH_2$ and $CF_2$;
  $Z^1$ is CH or N;
  $Z^2$ is CH, CF or N;
  each of $Z^3$ and $Z^4$ is independently selected from NR, $CH_2$ and $CF_2$;
  $Z^6$ is $NR^{36}$, $CH_2$, O, S, SO or $SO_2$;
  $R^{32}$ is $R^{32'}$ or $OR^{32'}$, wherein $R^{32'}$ is a $C_{1-12}$ alkyl, 3- to 6-membered cycloalkyl or heterocycloalkyl comprising 1, 2 or 3 heteroatoms selected from N, O and S, or a 5- or 6-membered aryl or heteroaryl group, each substituted with 0-3 $R^{32a}$;
  $R^{32a}$ is independently at each occurrence, H, $OCF_3$, CN, —$(CH_2)_r OR^b$, —$(CH_2)_r SR^b$, —$(CH_2)_r C(O)R^b$, —$(CH_2)_r C(O)OR^b$, —$(CH_2)_r OC(O)R^b$, $(CH_2)_r NR^g R^g$, —$(CH_2)_r C(O)NR^g R^g$, —$(CH_2)_r NR^b C(O)R^c$, —$(CH_2)_r NR^b C(O)OR^c$, —$NR^b C(O)NR^g R^g$, —$S(O)_v NR^g R^g$, —$NR^b S(O)_v R^c$, —$S(O)_v R^c$, $C_{1-6}$ alkyl substituted with 0-3 $R^a$, $C_{1-6}$ haloalkyl, $C_{2-6}$ alkenyl substituted with 0-3 $R^a$, 3- to 6-membered cycloalkyl substituted with 0-3 $R^a$, or 3- to 6-membered heterocycloalkyl comprising 1-3 heteroatoms selected from N, O and S substituted with 0-3 $R^a$;
  each of $R^{33}$ and $R^{34}$ is independently selected from H, F, Cl, CN, $OR^e$, $CH_3$, $CD_3$, $CF_3$, $OCD_3$, $OCF_3$ and —$(CH_2)_p$-Q;
  $R^{35}$ is H, F, a $C_1$-$C_3$ alkyl and $CD_3$, provided that $R^{35}$ is not F when $X^1$ is O or N;
  $R^{36}$ is R substituted with 0-3 $R^d$;
  $R^a$ at each occurrence is independently H, F, Cl, Br, $OCF_3$, $CF_3$, $CHF_2$, CN, —$(CH_2)_r OR^b$, —$(CH_2)_r SR^b$, —$(CH_2)_r C(O)R^b$, —$(CH_2)_r C(O)OR^b$, —$(CH_2)_r OC(O)R^b$, —$(CH_2)_r NR^g R^g$, —$(CH_2)_r C(O)NR^g R^g$, —$(CH_2)_r NR^b C(O)R^c$, —$(CH_2)_r NR^b C(O)OR^c$, —$NR^b C(O)NR^g R^g$, —$S(O)_v NR^g R^g$, —$NR^b S(O)_v R^c$, —$S(O)R^c$, —$S(O)_2 R^c$, $C_{1-6}$ alkyl substituted with 0-3 $R^f$, $C_{1-6}$ haloalkyl, 3- to 6-membered cycloalkyl substituted with 0-3 $R^f$, or 3- to 6-membered heterocycloalkyl comprising 1-3 heteroatoms selected from N, O and S substituted with 0-3 $R^f$;
  $R^b$ is H, $C_{1-6}$ alkyl substituted with 0-3 $R^d$, $C_{1-6}$ haloalkyl, $C_{3-6}$ cycloalkyl substituted with 0-2 $R^d$, or 5- to 7-membered heterocycloalkyl comprising 1-3 heteroatoms selected from N, O and S substituted with 0-3 $R^f$ or $(CH_2)_r$-phenyl substituted with 0-3 $R^d$;

$R^c$ is $C_{1-6}$ alkyl substituted with 0-3 $R^f$, $(CH_2)_r$—$C_{3-6}$ cycloalkyl substituted with 0-3 $R^f$ or $(CH_2)_r$-phenyl substituted with 0-3 $R^f$;

$R^d$ is independently at each occurrence, hydrogen, F, Cl, Br, $OCF_3$, $CF_3$, CN, $NO_2$, —$OR^e$, —$(CH_2)_rC(O)R^e$, —$NR^eR^e$, —$NR^eC(O)OR^e$, $C_{1-6}$ alkyl or $(CH_2)_r$-phenyl substituted with 0-3 $R^f$;

$R^e$ is independently at each occurrence, hydrogen, $C_{1-6}$ alkyl, $C_{3-6}$ cycloalkyl or $(CH_2)_r$-phenyl substituted with 0-3 $R^f$;

$R^f$ is independently at each occurrence, hydrogen, halo, CN, $NH_2$, OH, $C_{3-6}$ cycloalkyl, $CF_3$, $O(C_{1-6}$ alkyl) or a 5- to 7-membered heterocycloalkyl comprising 1-3 heteroatoms selected from N, O and S;

$R^g$ at each occurrence is independently H, $C_{1-4}$ alkyl substituted with 0-3 $R^f$, $CF_3$, $C_{3-10}$ cycloalkyl substituted with 0-1 $R^f$, $(CH)_r$-phenyl substituted with 0-3 $R^d$ or 5- to 7-membered heterocycloalkyl comprising 1-3 heteroatoms selected from N, O and S substituted with 0-3 $R^d$;

Q is a water solubilizing group, optionally selected from OH, OR, NRR', heterocyclic and heteroaryl groups, wherein R and R', together with the nitrogen atom to which they are bound, form a 4- to 7-membered ring comprising 0-2 heteroatoms selected from O, NR, S and $SO_2$;

R is H or a $C_1$-$C_6$ alkyl substituted with 0-3 $R^d$;

R' is H or a $C_1$-$C_6$ alkyl substituted with 0-3 $R^d$;

m is 0, 1, 2 and 3;

n is 0, 1, 2 and 3;

p is 0, 1, 2, 3 or 4;

q is 0, 1, 2, 3 or 4;

v is 0, 1, or 2; and r is 0, 1, 2, 3, 4 or 5, wherein the disease or disorder is selected from inflammatory diseases, immune-mediated diseases, cancer, or a related disease or disorder thereof, in a mammal, including a human.

In yet another aspect, the invention generally relates to a method for treating, reducing or preventing a disease or disorder, comprising administering to a subject in need thereof a therapeutically effective amount of a compound having the structural formula (IV):

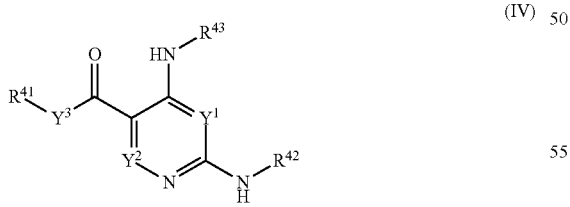

(IV)

or a pharmaceutically acceptable form or an isotope derivative thereof, wherein $Y^1$ is CH, CF or N;

$Y^2$ is CH or N;

$Y^3$ is NR, O, $CH_2$ or $CF_2$;

$R^{41}$ is a H, F, $C_1$-$C_3$ alkyl and $CD_3$, provided that $R^{41}$ is not F when $Y^3$ is NR or O;

$R^{42}$ is $R^{42'}$, wherein $R^{42'}$ is a $C_1$-$C_6$ alkyl, $C_3$-$C_6$ cycloalkyl or heterocycloalkyl, aryl or heteroaryl, each substituted with 0-2 of halogen, CN, OR, amino, alkyl, cycloalkyl, heterocyclic, aryl and heteroaryl;

an aryl or heteroaryl group substituted with 0-2 $R^{42a}$; or $(C=O)R^{42b}$;

$R^{43}$ is

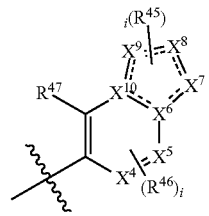

wherein each of $X^4$, $X^5$, $X^6$, $X^7$, $X^8$, $X^9$ and $X^{10}$ is independently selected from C, CH, O, N and NH;

$R^{42a}$ at each occurrence is independently H, D, halo, OH, OR, $CH_3$, $CF_3$, $CH_2CF_3$, CN, C(O)NR, NRR', $(CH_2)_nNRR'$ or a 4- to 6-membered heterocycle having 1-4 heteroatoms selected from N, O and S;

$R^{42b}$ is a $C_{1-6}$ alkyl or $C_{3-6}$ cycloalkyl, aryl or heteroaryl, each substituted with 0-2 $R^{42c}$;

$R^{42c}$ at each occurrence is independently H, halo, CN, OR, NRR', $OCF_3$, $CF_3$, $C_{1-6}$ alkyl substituted with 0-3 $R^{42a}$, $C_{1-6}$ haloalkyl, $C_{2-6}$ alkenyl substituted with 0-3 $R^{42a}$, $C_{2-6}$ alkynyl substituted with 0-3 $R^{42a}$;

$R^{45}$ each occurrence is independently H, halo, CN, OR, NRR', $OCF_3$, $CF_3$, $C_{1-6}$ alkyl, substituted with 0-3 $R^{42a}$, or $C_{3-10}$ cycloalkyl or heterocycloalkyl, $C_{5-10}$ aryl or heteroaryl, or a 4- to 10-membered heterocycle having 1-4 heteroatoms selected from N, O and S, each group is substituted with 0-4 $R^{42c}$, optionally two $R^{45}$s, along with the C or N atoms that they are attached to, form a 4- to 6-membered ring;

$R^{46}$ each occurrence is independently F, Cl, CN, OR, $C_1$-$C_3$ alkyl, $C_3$-$C_5$ cycloalkyl, $CD_3$, $CH_2CF_3$ or $CF_3$;

$R^{47}$ is H, $OCF_3$, $C_1$-$C_3$ alkyl, $C_1$-$C_3$ alkoxy or $OCD_3$;

each of R and R' is independently H or a $C_1$-$C_6$ alkyl, or R and R', together with the nitrogen atom to which they are bound, form a 4- to 7-membered ring comprising 0-2 heteroatoms selected from O, NR, S and $SO_2$;

n is 0, 1, 2, 3 or 4;

i is 0, 1 or 2; and j is 0, 1 or 2, wherein the disease or disorder is selected from inflammatory diseases, immune-mediated diseases, cancer, or a related disease or disorder thereof, in a mammal, including a human.

In yet another aspect, the invention generally relates to a method for treating, reducing or preventing a disease or disorder, comprising administering to a subject in need thereof a therapeutically effective amount of a compound having the structural formula (V):

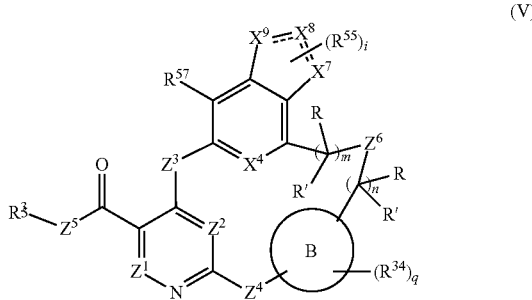

(V)

or a pharmaceutically acceptable form or an isotope derivative thereof,
wherein
Ring B is a 5- or 6-membered aryl or heteroaryl;
$Z^1$ is CH or N;
$Z^2$ is CH, CF or N;
each of $Z^3$ and $Z^4$ is independently selected from NR, $CH_2$ and $CF_2$;
$Z^5$ is selected from NR, O, $CH_2$ and $CF_2$;
$Z^6$ is $NR^{56}$, $CH_2$, O, S, SO or $SO_2$;
each of $X^4$, $X^7$, $X^8$ and $X^9$ is independently selected from CH, N and NH;
$R^{51}$ is a H, F, $C_1$-$C_3$ alkyl and $CD_3$, provided that $R^{51}$ is not F when $Z^5$ is N or O;
$R^{52}$ is independently selected from H, F, Cl, CN, $OR^g$, $CH_3$, $CF_3$, $OCF_3$ and $—(CH_2)_p$-Q;
$R^{52a}$ at each occurrence is independently H, D, halo, OH, OR, $CH_3$, $CF_3$, $CH_2CF_3$ or CN, NRR', $(CH_2)_n$NRR' or a 4- to 6-membered heterocycle having 1-4 heteroatoms selected from N, O and S;
$R^{52c}$ at each occurrence is independently H, halo, CN, OR, NRR', $OCF_3$, $CF_3$, $C_{1-6}$ alkyl substituted with 0-3 $R^{52a}$, $C_{1-6}$ haloalkyl, $C_{2-6}$ alkenyl substituted with 0-3 $R^{52a}$, $C_{2-6}$ alkynyl substituted with 0-3 $R^{52a}$;
$R^{55}$ each occurrence is independently H, $C_{1-6}$ alkyl, substituted with 0-3 $R^{52a}$, or $C_{3-10}$ cycloalkyl or heterocycloalkyl, $C_{5-10}$ aryl or heteroaryl, or a 4- to 10-membered heterocycle having 1-4 heteroatoms selected from N, O and S, each group is substituted with 0-4 $R^{52c}$;
$R^{56}$ is R substituted with 0-3 $R^d$;
$R^{57}$ is H, $C_1$-$C_3$ alkyl, $C_1$-$C_3$ alkoxy, $OCD_3$ or $OCF_3$;
$R^c$ is $C_{1-6}$ alkyl substituted with 0-3 $R^f$, $(CH_2)_r$—$C_{3-6}$ cycloalkyl substituted with 0-3 $R^f$ or $(CH_2)_r$-phenyl substituted with 0-3 $R^f$;
$R^d$ is independently at each occurrence, hydrogen, F, Cl, Br, $OCF_3$, $CF_3$, CN, $NO_2$, —OR', —$(CH_2)_rC(O)R^c$, —$NR^eR^e$, —$NR^eC(O)OR^c$, $C_{1-6}$ alkyl or $(CH_2)_r$-phenyl substituted with 0-3 $R^f$;
$R^e$ is independently at each occurrence, hydrogen, $C_{1-6}$ alkyl, $C_{3-6}$ cycloalkyl or $(CH_2)_r$-phenyl substituted with 0-3 $R^f$;
$R^f$ is independently at each occurrence, hydrogen, halo, CN, $NH_2$, OH, $C_{3-6}$ cycloalkyl, $CF_3$, $O(C_{1-6}$ alkyl) or a 5- to 7-membered heterocycloalkyl comprising 1-3 heteroatoms selected from N, O and S;
$R^g$ at each occurrence is independently H, $C_{1-4}$ alkyl substituted with 0-3 $R^1$, $CF_3$, $C_{3-10}$ cycloalkyl substituted with 0-1 $R^f$, $(CH)_r$-phenyl substituted with 0-3 $R^d$ or 5- to 7-membered heterocycloalkyl comprising 1-3 heteroatoms selected from N, O and S substituted with 0-3 $R^d$;

Q is a water solubilizing group, optionally selected from OH, OR, NRR', heterocyclic and heteroaryl groups, wherein R and R', together with the nitrogen atom to which they are bound, form a 4- to 7-membered ring comprising 0-2 heteroatoms selected from O, NR, S and $SO_2$;
R is H or a $C_1$-$C_6$ alkyl substituted with 0-3 $R^d$;
R' is H or a $C_1$-$C_6$ alkyl substituted with 0-3 $R^d$;
i is 0, 1, 2 and 3;
m is 0, 1, 2 and 3;
n is 0, 1, 2 and 3;
p is 0, 1, 2, 3 or 4; and
q is 0, 1, 2, 3 or 4,
wherein the disease or disorder is selected from inflammatory diseases, immune-mediated diseases, cancer, or a related disease or disorder thereof, in a mammal, including a human.

In certain embodiments, the method is used to treat an inflammatory disease. In certain embodiments, the method is used to treat an immune-mediated disease. In certain embodiments, the method is used to treat cancer. In certain embodiments, the method is used to treat a disease or disorder is selected from: inflammatory bowel disease, psoriasis, vitiligo, atopic dermatitis, systemic lupus erythematosus, asthma, diabetic nephropathy, chronic myelogenous leukemia (CML), essential thrombocythemia (ET), polycythemia vera (PV), myelofibrosis (MF), breast cancer and ovarian cancer.

In certain embodiments, administration of the compound is via oral administration.

In certain embodiments, administration of the compound is via topical administration.

In certain embodiments, administration of the compound administration is via GI-restricted administration.

In yet another aspect, the invention generally relates to use of a compound disclosed herein, and a pharmaceutically acceptable excipient, carrier, or diluent, in preparation of a medicament for treating a disease or disorder.

In certain embodiments, use of the compound is for treating one or more of inflammatory diseases, immune-mediated diseases and cancer. In certain embodiments, use of the compound is for treating an inflammatory disease. In certain embodiments, use of the compound is for treating an immune-mediated disease. In certain embodiments, use of the compound is for treating cancer. In certain embodiments, use of the compound is for treating a disease or disorder is selected from: inflammatory bowel disease, psoriasis, vitiligo, atopic dermatitis, systemic lupus erythematosus, asthma, diabetic nephropathy, chronic myelogenous leukemia (CML), essential thrombocythemia (ET), polycythemia vera (PV), myelofibrosis (MF), breast cancer and ovarian cancer.

In certain embodiments, use of the compound is via oral administration. In certain embodiments, use of the compound is via topical administration. In certain embodiments, use of the compound is via GI restriction administration.

A list of non-limiting examples of the compounds of the invention is provided in Table #. Certain exemplary data of select compounds are provided in Table #.

As discussed herein, isotope derivative compounds having one or more hydrogen atoms (e.g., 1, 2, 4, 5, 6, 7, 8, 9, 10, etc.) replaced with deuterium atoms are contemplated in the presented invention.

The term "inflammatory disease" refers to a disease or condition characterized by aberrant inflammation, e.g. an increased level of inflammation compared to a control such as a healthy person not suffering from a disease. Examples of inflammatory diseases that may be treated with a compound, pharmaceutical composition, or method described herein include autoimmune diseases, traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, and atopic dermatitis. Such conditions are frequently inextricably intertwined with other diseases, disorders and conditions. A non-limiting list of inflammatory-related diseases, disorders and conditions which may, for example, be caused by inflammatory cytokines, include, arthritis, kidney failure, lupus, asthma, psoriasis, colitis, pancreatitis, allergies, fibrosis, surgical complications (e.g., where inflammatory cytokines prevent healing), anemia, and fibromyalgia. Other diseases and disorders, which may be associated with chronic inflammation include Alzheimer's disease, congestive heart failure, stroke, aortic valve stenosis, arteriosclerosis, osteoporosis, Parkinson's disease, infections, inflammatory bowel disease (IBD), allergic contact dermatitis and other eczemas, systemic sclerosis, transplantation and multiple sclerosis. Some of the aforementioned diseases, disorders and conditions for which a compound of the present disclosure may be particularly efficacious (due to, for example, limitations of current therapies) are described in more detail hereafter.

The term "autoimmune disease" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include acne vulgaris, acute disseminated encephalomyelitis, acute necrotizing hemorrhagic leukoencephalitis, Addison's disease, agammaglobulinemia, Aicardi-Goutieres syndrome (AGS), alopecia areata, alopecia totalis, amyloidosis, ankylosing spondylitis, anti-GBM/anti-TBM nephritis, antiphospholipid syndrome, autoimmune angioedema, autoimmune aplastic anemia, autoimmune dysautonomia, autoimmune hepatitis, autoimmune hyperlipidemia, autoimmune immunodeficiency, autoimmune inner ear disease, autoimmune myocarditis, autoimmune oophoritis, autoimmune pancreatitis, autoimmune retinopathy, autoimmune thrombocytopenic purpura, autoimmune thyroid disease, autoimmune urticaria, axonal or neuronal neuropathies, balo disease, Behcet's disease, bullous pemphigoid, cardiomyopathy, Castleman disease, celiac disease, Chagas disease, chronic atypical neutrophilic dermatosis with lipodystrophy and elevated temperature (CANDLE), chronic active hepatitis, chronic fatigue syndrome, chronic inflammatory demyelinating polyneuropathy, chronic recurrent multifocal ostomyelitis, Churg-Strauss syndrome, cicatricial pemphigoid/benign mucosal pemphigoid, Crohn's disease, Cogans syndrome, cold agglutinin disease, congenital heart block, coxsackie myocarditis, CREST disease, Cushing's disease, demyelinating neuropathies, depression, dermatitis herpetiformis, dermatomyositis, Devic's disease (neuromyelitis optica), discoid lupus, Dressler's syndrome, dry eye syndrome DES (keratoconjunctivitis sicca), endometriosis, eosinophilic esophagitis, eosinophilic fasciitis, erythema nodosum, essential mixed cryoglobulinemia, experimental allergic encephalomyelitis, Evans syndrome, fibromyalgia, fibrosing alveolitis, giant cell arteritis (temporal arteritis), giant cell myocarditis, glomerulonephritis, Goodpasture's syndrome, granulomatosis with polyangiitis, graft-versus-host disease (GVDH), Graves' disease, Guillain-Barre syndrome, Hashimoto's encephalitis, Hashimoto's thyroiditis, hemolytic anemia, Henoch-Schonlein purpura, herpes gestationis, hidradenitis suppurativa, hypogammaglobulinemia, idiopathic thrombocytopenic purpura, IgA nephropathy, IgG4-related sclerosing disease, inflammatory bowel disease (IBD), immunoregulatory lipoproteins, inclusion body myositis, interstitial cystitis, juvenile arthritis, juvenile diabetes (Type 1 diabetes), juvenile dermatomyositis (JDM), juvenile myositis, Kawasaki syndrome, Lambert-Eaton syndrome, leukocytoclastic vasculitis, lichen planus, lichen sclerosus, ligneous conjunctivitis, linear IgA disease, lupus, lyme disease, chronic, Meniere's disease, microscopic polyangiitis, mixed connective tissue disease, Mooren's ulcer, Mucha-Habermann disease, multiple sclerosis (MS), myasthenia gravis, myositis, narcolepsy, neuromyelitis optica, neutropenia, ocular cicatricial pemphigoid, optic neuritis, palindromic rheumatism, pediatric autoimmune neuropsychiatric disorders associated with *streptococcus*, paraneoplastic cerebellar degeneration, paroxysmal nocturnal hemoglobinuria p, Parry Romberg syndrome, Parsonnage-Turner syndrome, Pars planitis (peripheral uveitis), pemphigus, peripheral neuropathy, perivenous encephalomyelitis, pernicious anemia, POEMS syndrome, polyarteritis nodosa, polycystic ovary syndrome (PCOS), Type I, II, & III autoimmune polyglandular syndromes, polymyalgia rheumatica, polymyositis, postmyocardial infarction syndrome, postpericardiotomy syndrome, progesterone dermatitis, primary biliary cirrhosis, primary sclerosing cholangitis, psoriasis, psoriatic arthritis, plaque psoriasis, idiopathic pulmonary fibrosis, pyoderma gangrenosum, pure red cell aplasia, Raynauds phenomenon, reactive Arthritis, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome, stimulator of interferon genes (STING)-associated vasculopathy with onset during infancy (SAVI), subacute bacterial endocarditis, Susac's syndrome, sympathetic ophthalmia, systemic lupus erythematosus (SLE), Takayasu's arteritis, temporal arteritis/Giant cell arteritis, thrombocytopenic purpura, Tolosa-Hunt syndrome, transplant rejection (allograft transplant rejection), transverse myelitis, Type 1 diabetes, ulcerative colitis, undifferentiated connective tissue disease, uveitis, vasculitis, vesiculobullous dermatosis, vitiligo, or Wegener's granulomatosis.

The term "immune-mediated disease" refers to chronic inflammatory diseases perpetuated by antibodies and cellular immunity. Immune-mediated diseases include, for example, but not limited to, asthma, allergies, arthritis (e.g., rheumatoid arthritis, psoriatic arthritis, and ankylosing spondylitis), juvenile arthritis, inflammatory bowel diseases (e.g., ulcerative colitis and Crohn's disease), endocrinopathies (e.g., type 1 diabetes and Graves' disease), neurodegenerative diseases (e.g., multiple sclerosis (MS)), autistic spectrum disorder, depression, Alzheimer's disease, Guillain-Barre syndrome, obsessive-compulsive disorder, optic neuritis, retinal degeneration, dry eye syndrome DES, Sjogren's syndrome, amyotrophic lateral sclerosis (ALS), Parkinson's disease, Huntington's Disease, Guillain-Barre syndrome, myasthenia gravis, and chronic idiopathic demyelinating disease (CID)), vascular diseases (e.g., autoimmune hearing loss, systemic vasculitis, and atherosclerosis), and skin diseases (e.g., acne vulgaris dermatomyositis, pemphigus, systemic lupus erythematosus (SLE), discoid lupus erthematosus, scleroderma, psoriasis, plaque psoriasis, vasculitics, vitiligo and alopecias). Hashimoto's thyroiditis, pernicious anemia, Cushing's disease, Addison's disease, chronic active hepatitis, polycystic ovary syndrome (PCOS), celiac disease, pemphigus, transplant rejection (allograft transplant rejection), graft-versus-host disease (GVDH).

The term "cancer" as used herein refers to all types of cancer, neoplasm or malignant tumors found in mammals, e.g., humans, including hematological cancers leukemia, and lymphomas, T-ALL, large B-cell lymphoma, solid cancers such as carcinomas and sarcomas. Exemplary cancers include blood cancer, brain cancer, glioma, glioblastoma, neuroblastoma, prostate cancer, colorectal cancer, pancreatic cancer, cervical cancer, gastric cancer, ovarian cancer, lung cancer, and cancer of the head. Exemplary cancers include cancer of the thyroid, endocrine system, brain, breast, cervix, colon, head & neck, liver, kidney, lung, non-small cell lung, melanoma, mesothelioma, ovary, sarcoma, stomach, uterus, medulloblastoma, colorectal cancer, pancreatic cancer. Additional examples include penile, skin—non-melanoma, anal, hepatobiliary, esophagogastric, uterine sarcoma, gastrointestinal stromal tumor, salivary gland, peripheral nervous system, soft tissue sarcoma, bone, renal, myeloproliferative neoplasms, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, metastatic leiomyosarcoma, synovial sarcoma, undifferentiated pleomorphic sarcoma, round cell liposarcoma or prostate cancer.

In certain embodiments of the use, the disease or disorder is selected from: inflammatory bowel disease, psoriasis, vitiligo, atopic dermatitis, systemic lupus erythematosus, asthma, diabetic nephropathy, chronic myelogenous leukemia (CML), essential thrombocythemia (ET), polycythemia vera (PV), myelofibrosis (MF), breast cancer and ovarian cancer.

Isotopically-labeled compounds are also within the scope of the present disclosure. As used herein, an "isotopically-labeled compound" refers to a presently disclosed compound including pharmaceutical salts and prodrugs thereof, each as described herein, in which one or more atoms are replaced by an atom having an atomic mass or mass number different from the atomic mass or mass number usually found in nature. Examples of isotopes that can be incorporated into compounds presently disclosed include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

By isotopically-labeling the presently disclosed compounds, the compounds may be useful in drug and/or substrate tissue distribution assays. Tritiated ($^{3}H$) and carbon-14 ($^{14}C$) labeled compounds are particularly preferred for their ease of preparation and detectability. Further, substitution with heavier isotopes such as deuterium ($^{2}H$) can afford certain therapeutic advantages resulting from greater metabolic stability, for example increased in vivo half-life or reduced dosage requirements and, hence, may be preferred in some circumstances. Isotopically labeled compounds presently disclosed, including pharmaceutical salts, esters, and prodrugs thereof, can be prepared by any means known in the art.

Further, substitution of normally abundant hydrogen ($^{1}H$) with heavier isotopes such as deuterium can afford certain therapeutic advantages, e.g., resulting from improved absorption, distribution, metabolism and/or excretion (ADME) properties, creating drugs with improved efficacy, safety, and/or tolerability. Benefits may also be obtained from replacement of normally abundant $^{12}C$ with $^{13}C$. (See, WO 2007/005643, WO 2007/005644, WO 2007/016361, and WO 2007/016431.)

Stereoisomers (e.g., cis and trans isomers) and all optical isomers of a presently disclosed compound (e.g., R and S enantiomers), as well as racemic, diastereomeric and other mixtures of such isomers are within the scope of the present disclosure.

Compounds of the present invention are, subsequent to their preparation, preferably isolated and purified to obtain a composition containing an amount by weight equal to or greater than 95% ("substantially pure"), which is then used or formulated as described herein. In certain embodiments, the compounds of the present invention are more than 99% pure. Solvates and polymorphs of the compounds of the invention are also contemplated herein. Solvates of the compounds of the present invention include, for example, hydrates.

Any appropriate route of administration can be employed, for example, parenteral, intravenous, subcutaneous, intramuscular, intraventricular, intracorporeal, intraperitoneal, rectal, or oral administration. Most suitable means of administration for a particular patient will depend on the nature and severity of the disease or condition being treated or the nature of the therapy being used and on the nature of the active compound.

Solid dosage forms for oral administration include capsules, tablets, pills, powders, and granules. In such solid dosage forms, the compounds described herein or derivatives thereof are admixed with at least one inert customary excipient (or carrier) such as sodium citrate or dicalcium phosphate or (i) fillers or extenders, as for example, starches, lactose, sucrose, glucose, mannitol, and silicic acid, (ii) binders, as for example, carboxymethylcellulose, alignates, gelatin, polyvinylpyrrolidone, sucrose, and acacia, (iii) humectants, as for example, glycerol, (iv) disintegrating agents, as for example, agar-agar, calcium carbonate, potato or tapioca starch, alginic acid, certain complex silicates, and sodium carbonate, (v) solution retarders, as for example, paraffin, (vi) absorption accelerators, as for example, quaternary ammonium compounds, (vii) wetting agents, as for example, cetyl alcohol, and glycerol monostearate, (viii) adsorbents, as for example, kaolin and bentonite, and (ix) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents. Solid compositions of a similar type may also be employed as fillers in soft and hard-filled gelatin capsules using such excipients as lactose or milk sugar as well as high molecular weight polyethyleneglycols, and the like. Solid dosage forms such as tablets, dragees, capsules, pills, and granules can be prepared with coatings and shells, such as enteric coatings and others known in the art.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, such as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like. Besides such inert diluents, the composition can also include additional agents, such as wetting, emulsifying, suspending, sweetening, flavoring, or perfuming agents.

Materials, compositions, and components disclosed herein can be used for, can be used in conjunction with, can be used in preparation for, or are products of the disclosed methods and compositions. It is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

The following examples are meant to be illustrative of the practice of the invention and not limiting in any way.

| Examples | |
|---|---|
| Abbreviations | |
| Methanol: | MeOH |
| Dichloromethane: | DCM |
| Petroleum ether: | PE |
| Ethyl acetate: | EtOAc |
| Acetonitrile: | ACN |
| Isopropanol: | IPA |
| Triethylamine: | TEA |
| Sodium hydroxide: | NaOH |
| Propylphosphonic Acid Anhydride: | $T_3P$ |

| Examples | |
|---|---|
| Abbreviations | |
| Nitrogen: | $N_2$ |
| Thin-Layer Chromatography: | TLC |
| High Performance Liquid Chromatography: | HPLC |
| N,N-Diisopropylethylamine: | DIPEA |
| N,N-Dimethylformamide: | DMF |
| 4-Methylbenzene-1-sulfonyl chloride: | TsCl |
| Room temperature: | RT/r.t. |
| Hours: | hrs |

Representative methods of prep-HPLC: Flow rate and gradient may change.

Exemplary methods for prep-HPLC are provided below.

Method A: $NH_4HCO_3$:

Column: Gilson2-Xbrige C18 19*150 mm, 5 μm; mobile phase: $CH_3CN$ in water (0.1% $NH_4HCO_3$) from 20% to 60%, flow rate: 15 ml/min.

Method B: TFA:

Column: waters-Xbridge C18 10*190 mm, 5 μm; mobile phase: $CH_3CN$ in water (0.1% TFA) from 15% to 40%, flow rate: 15 ml/min.

Method C: HCOOH:

Column: waters-Xbridge C18 10*190 mm, 5 μm; mobile phase: $CH_3CN$ in water (0.1% formic acid) from 15% to 40%, flow rate: 15 ml/min.

Method D: HCOOH:

Method E: $NH_4HCO_3$

Column: Waters Xbridge® Prep $C_{18}$ OBD™ (5 micron, 19*150 mm); Mobile phase: $CH_3CN$ in water (10 mM $NH_4HCO_3$) from 20% to 60%, Flow rate: 20 mL/min.

Column: Waters SunFire Prep C18 OBD™ (5 micron, 19*150 mm); mobile phase: $CH_3CN$ in water (0.1% formic acid) from 18% to 38%, flow rate: 20 ml/min.

Representative Methods of Analytical-HPLC

Method 1: Analysis was performed on an Agilent 1200_series HPLC-6120 MS. UHPLC Long Gradient Equivalent 5% to 95% acetonitrile (containing 0.02% NH4OAc) in water run time of 6.5 minutes with a flow rate of 1.5 mL/min. A Waters Xbridge C18 column (18.5 micron, 4.6*50 mm) was used at a temperature of 40° C.

Method 2: Analysis was performed on an Agilent 1200_series HPLC-6120 MS. UHPLC Long Gradient Equivalent 5% to 95% acetonitrile (containing 0.1%_trifluoroacetic acid) in water run time of 6.5 minutes with a flow rate of 1.5 mL/min. A Waters Xbridge C18 column (18.5 micron, 4.6*50 ram) was used at a temperature of 40° C.

Method 3: Analysis was performed on an Agilent 1260_series HPLC-6120 MS. UHPLC Long Gradient Equivalent 5% to 95% acetonitrile (containing 0.02% NH4OAc) in water run time of 2.5 minutes with a flow rate of 0.5 mL/min. A diamonsil Plus $C_{18}$ column (18.5 micron, 4.6*30 mm) was used at a temperature of 40° C.

Method 4: Analysis was performed on an Agilent 1260_series HPLC-6125C MS. HPLC Long Gradient Equivalent 20% to 100% acetonitrile in water (containing 0.1% FA) run time of 6 minutes with a flow rate of 0.8 mL/min. Agilent ZORBAX SB-C18 column (1.8 micron, 2.1*50 mm) was used at a temperature of 30° C.

Representative Method of Prep-Chiral HPLC:

Shimadzu LC-20A, Daicel Chiralpak IB N, 51 am, 4.6*250 mm; Mobile phase: Hexane/EtOH/Diethylamine=80/20/0.3, Flow rate: 25 mL/min.

Example 1

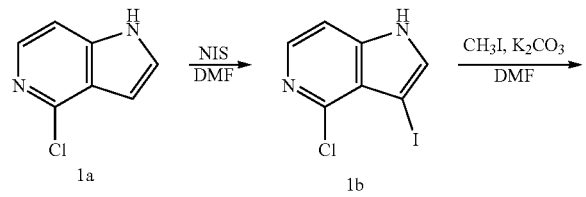

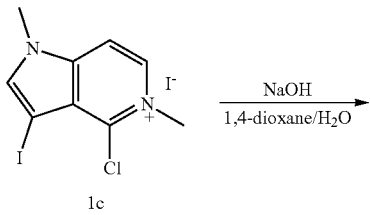

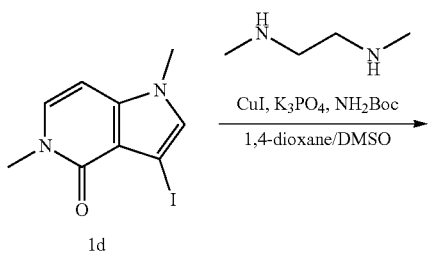

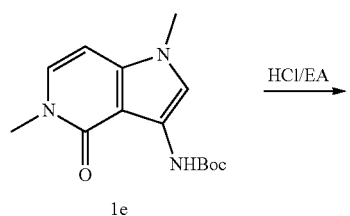

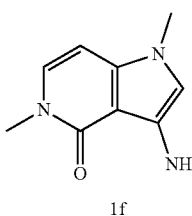

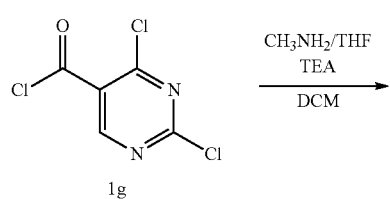

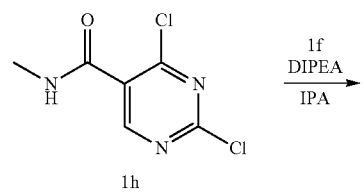

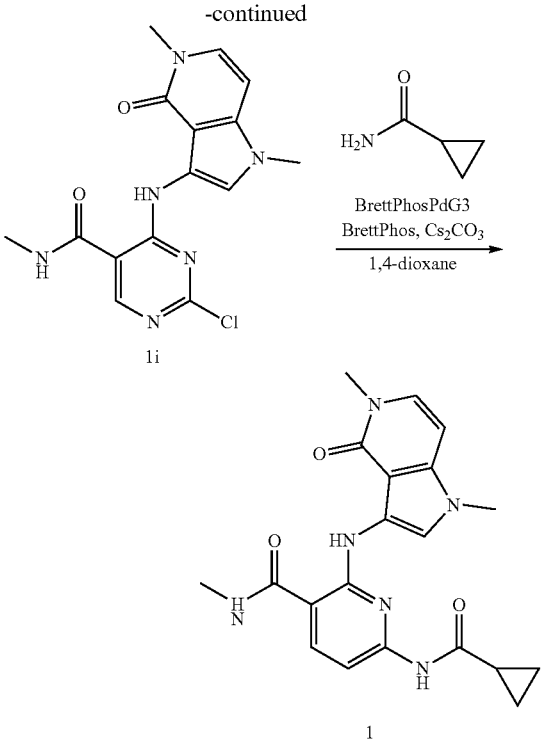

Step 1. 4-Chloro-3-iodo-1H-pyrrolo[3,2-c]pyridine (1b)

To a mixture of 4-chloro-1H-pyrrolo[3,2-c]pyridine 1a (17.00 g, 111.42 mmol) in DMF (350 mL) was added NIS (37.60 g, 167.12 mmol) portionwise at 0° C. After stirring for 2 h at r.t., the mixture was diluted with EtOAc (2 L) and washed with brine (500 mL*3). The separated organic layer was concentrated under reduced pressure to give the title compound 1b (23.2 g, 75% yield) as a brown solid. $^1$H NMR (400 MHz, CDCl$_3$) δ 8.89 (brs, 1H), 8.10 (d, J=5.6 Hz, 1H), 7.39 (d, J=2.4 Hz, 1H), 7.31 (d, J=5.6 Hz, 1H).

Step 2. 4-Chloro-3-iodo-1,5-dimethyl-1H-pyrrolo[3,2-c]pyridin-5-ium iodide (1c)

A mixture of 1b (2 g, 7.18 mmol), K$_2$CO$_3$ (2.97 g, 21.55 mmol) and CH$_3$I (5.10 g, 35.91 mmol) in DMF (20 mL) was stirred at r.t. for 16 h. The reaction solution was used in the next step without working up. LC-MS (Method 1) t$_R$=1.78 min, m/z M+=307.1.

Step 3. 3-Iodo-1,5-dimethyl-1H-pyrrolo[3,2-c]pyridin-4-((5H)-one (1d)

Compound 1c was dissolved in a mixture of water (10 mL) and 1,4-dioxane (10 mL). To the solution was added NaOH (1.44 g, 35.93 mmol). After stirring for 6 h at r.t., the reaction mixture was extracted with EtOAc (30 mL*2). The combined organic layer was washed with brine (30 mL), dried over Na$_2$SO$_4$ and concentrated to afford the title compound 1d (1.13 g, 55% yield) as a black solid. $^1$H NMR (400 MHz, CDCl$_3$) δ 7.05 (d, J=7.6 Hz, 1H), 6.89 (s, 1H), 6.27 (d, J=7.6 Hz, 1H), 3.68 (s, 3H), 3.56 (s, 3H).

Step 4. Tert-butyl (1,5-dimethyl-4-oxo-4,5-dihydro-1H-pyrrolo[3,2-c]pyridin-3-yl)carbamate (1e)

A mixture of 1d (1.13 g, 3.92 mmol), tert-butyl carbamate (4.60 g, 39.22 mmol), N, N'-dimethylenediamine (173 mg, 1.96 mmol), CuI (374 mg, 1.96 mmol), $K_3PO_4$ (1.67 g, 7.84 mmol) in 1,4-dioxane/DMSO (2 mL, v/v=10/1) was stirred at 90° C. under $N_2$. The reaction mixture was cooled down to r.t., concentrated and the residue was purified by chromatography on silica gel (PE/EtOAc from 1/10 to 1/1) to give the title compound 1e (400 mg, 37% yield) as a white solid. $^1$H NMR (400 MHz, DMSO-$d_6$) δ 8.27 (s, 1H), 7.20 (d, J=7.2 Hz, 1H), 7.13 (s, 1H), 6.51 (d, J=7.2 Hz, 1H), 3.64 (s, 3H), 3.43 (s, 3H), 1.47 (s, 9H).

Step 5. 3-Amino-1,5-dimethyl-1H-pyrrolo[3,2-c]pyridin-4-((5H)-one hydrochloride (1f)

Compound 1e (279 mg, 1 mmol) was dissolved in a solution of HCl (g) in EtOAc (5 mL, 2 M). The resulting mixture was stirred for 2 h at r.t. The formed solid was filtered. The filter cake was dried to give the title compound 1f (179 mg, 82% yield) as a white solid. $^1$H NMR (400 MHz, DMSO-$d_6$) δ 10.22 (s, 2H), 7.45 (d, J=7.6 Hz, 1H), 7.27 (s, 1H), 6.61 (d, J=7.6 Hz, 1H), 3.71 (s, 3H), 3.48 (s, 3H).

Step 6. 2,4-Dichloro-N-methylpyrimidine-5-carboxamide (1h)

To a solution of 2,4-dichloropyrimidine-5-carbonyl chloride 1g (500 mg, 2.36 mmol) in DCM (5 mL) was added TEA (478 mg, 4.73 mmol) and methylamine (2.36 mmol, 1.2 mL, 2 M in THF) sequentially at −70° C. The mixture was stirred at −70° C. for 1 h. The mixture was diluted with DCM (20 mL) and washed with sat. NaHCO$_3$ (20 mL). The separated organic layer was washed with brine (20 mL), dried over Na$_2$SO$_4$ and filtered. The filtrate was concentrated. The residue was purified by flash chromatography on silica gel (PE/EtOAc=3/1) to give the title compound 1h (170 mg, 35% yield). $^1$H NMR (400 MHz, CDCl$_3$) δ 8.98 (s, 1H), 6.49 (s, 1H), 3.07 (d, J=4.8 Hz, 3H).

Step 7. 2-Chloro-4-((1,5-dimethyl-4-oxo-4,5-dihydro-1H-pyrrolo[3,2-c]pyridin-3-yl)amino)-N-methylpyrimidine-5-carboxamide (1i)

Compound 1f (50 mg, 0.23 mmol), 1h (58 mg, 0.28 mmol) and DIPEA (91 mg, 0.70 mmol) were dissolved in IPA (1 mL). The resulting reaction was stirred at 60° C. for 3 h. The reaction mixture was cooled down to r.t. and concentrated to dryness. The solid was treated with EtOAc (5 mL). The formed solid was collected by filtering and the filter cake was dried to give the title compound 1i (51.5 mg, 63% yield) as a white solid. LC-MS (Method 3) $t_R$=1.30 min, m/z (M+H)$^+$=347.2.

Step 8. 2-(Cyclopropanecarboxamido)-4-((1,5-dimethyl-4-oxo-4,5-dihydro-1H-pyrrolo[3,2-c]pyridin-3-yl)amino)-N-methylpyrimidine-S-carboxamide (1)

Compound 1i (50 mg, 0.14 mmol), cyclopropanecarboxamide (61 mg, 0.72 mmol), BrettPhos (15 mg, 0.02 mmol), BrettPhos Pd G3 (26 mg, 0.02 mmol) and Cs$_2$CO$_3$ (94 mg, 0.29 mmol) were dissolved in 1,4-dioxane (1 mL). The mixture was stirred at 100° C. for 5 h under $N_2$. The reaction mixture was cooled down to r.t. and evaporated to dryness. The residue was purified by Prep-HPLC (Method A) to give the title compound 1 (22.5 mg, 39% yield). LC-MS (Method 2) $t_R$=2.52 min, m/z (M+H)$^+$=396.2. $^1$H NMR (400 MHz, DMSO-$d_6$) δ 11.82 (s, 1H), 10.86 (s, 1H), 8.62 (d, J=7.6 Hz, 2H), 8.46 (d, J=4.4 Hz, 1H), 7.30 (d, J=7.2 Hz, 1H), 6.52 (d, J=7.6 Hz, 1H), 3.70 (s, 3H), 3.46 (s, 3H), 2.80 (d, J=4.8 Hz, 3H), 2.20-2.17 (m, 1H), 0.93-0.83 (m, 4H).

Example 2

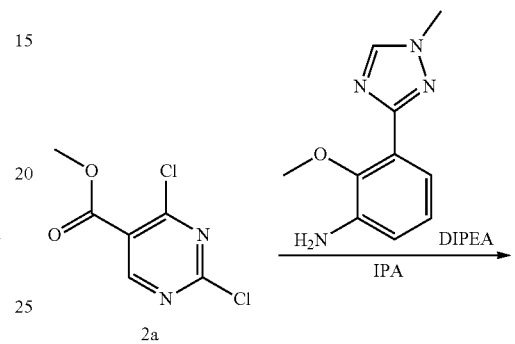

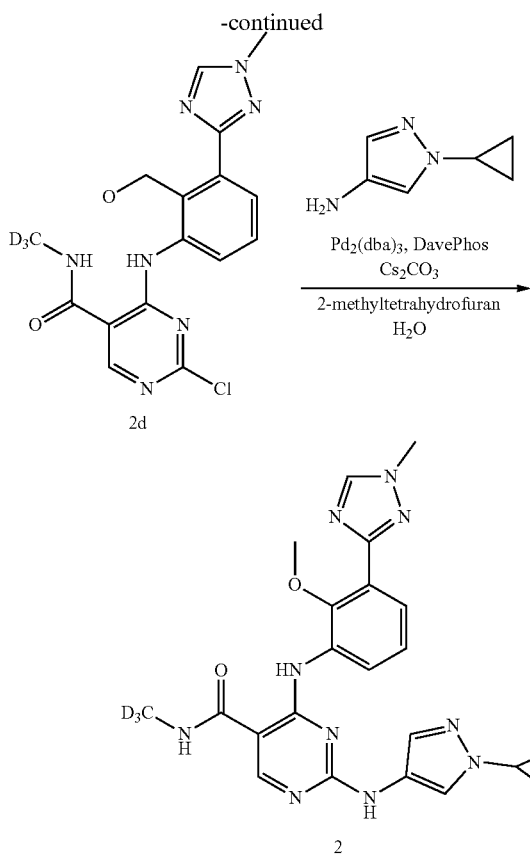

mmol, 50% in DMF) and DIPEA (1.32 g, 4.16 mmol) were dissolved in DMF (8 mL). The resulting solution was stirred at r.t. for 1 h. The mixture was basified with 20% aq. Na₂CO₃ solution to pH>8 and extracted with EtOAc (30 mL*2). The combined organic layer was washed with water (20 mL) and brine (20 mL), dried over anhydrous Na₂SO₄ and filtered. The filtrate was concentrated to give the title compound 2d (190 mg, 36% yield) as a yellow solid. ¹H NMR (400 MHz, DMSO-d₆) δ 11.89 (s, 1H), 8.91 (s, 1H), 8.76 (s, 1H), 8.57 (s, 1H), 8.45 (d, J=7.6 Hz, 1H), 8.60 (d, J=7.6 Hz, 1H), 7.27 (t, J=8.0 Hz, 1H), 3.95 (s, 3H), 3.80 (s, 3H).

Step 4. 2-[(1-Cyclopropylpyrazol-4-yl)amino]-4-[2-methoxy-3-(1-methyl-1,2,4-triazol-3-yl)anilino]-N-(trideuteromethyl)pyrimidine-5-carboxamide (2)

Compound 2d (20 mg, 0.53 mmol), 1-cyclopropylpyrazol-4-amine (20 mg, 0.15 mmol), DavePhos (5 mg, 0.011 mmol), Cs₂CO₃ (35 mg, 0.16 mmol) and Pd₂(dba)₃ (5 mg, 0.005 mmol) were dissolved in a mixture of 2-methyltetrahydrofuran (1 mL) and H₂O (0.5 mL). The mixture was stirred at 80° C. for 2 h. After cooling to r.t., the mixture was filtered and the filtrate was concentrated to dryness. The residue was purified by Prep-HPLC (Method A) to afford the title compound 2 (7 mg, 28% yield) as a white solid. LC-MS (Method 1) t$_R$=2.89 min, m/z (M+H)⁺=464.2. ¹H NMR (400 MHz, DMSO-d₆) δ 11.77-11.60 (m, 1H), 9.50 (s, 1H), 8.67-8.61 (m, 1H), 8.55 (s, 1H), 8.36 (s, 1H), 8.25-8.23 (m, 1H), 7.95-7.79 (m, 1H), 7.59-7.38 (m, 2H), 7.20 (t, J=8.0 Hz, 1H), 3.95 (s, 3H), 3.78 (s, 3H), 3.59-3.50 (m, 1H), 1.00-0.85 (m, 4H).

Example 3

Step 1. Methyl 2-chloro-4-((2-methoxy-3-(1-methyl-1H-1,2,4-triazol-3-yl)phenyl)amino)pyrimidine-5-carboxylate (2b)

To a solution of 2-methoxy-3-(1-methyl-1,2,4-triazol-3-yl)aniline (1.4 g, 6.86 mmol) and 2a (1.42 g, 6.86 mmol) in IPA (20 mL) was added DIPEA (1.77 g, 13.71 mmol) dropwise. The reaction mixture was stirred at 80° C. overnight. After cooling to r.t., the reaction mixture was diluted with water (50 mL) and extracted with EtOAc (50 mL*3). The combined organic layer was dried over Na₂SO₄ and filtered. The filtrate was concentrated to dryness to give the title compound 2b (1.3 g, 51% yield) as a red oil. ¹H NMR (400 MHz, DMSO-d₆) δ 11.00 (s, 1H), 8.87 (s, 1H), 8.58 (s, 1H), 8.47 (d, J=8.0 Hz, 1H), 7.65 (d, J=8.8 Hz, 1H), 7.31 (t, J=7.6 Hz 1H), 3.96 (s, 3H), 3.93 (s, 3H), 3.81 (s, 3H).

Step 2. 2-Chloro-4-((2-methoxy-3-(1-methyl-1H-1,2,4-triazol-3-yl)phenyl)amino)pyrimidine-5-carboxylic acid (2c)

Compound 2b (1 g, 2.67 mmol) and NaOH (214 mg, 5.34 mmol) were dissolved in THF (8 mL) and H₂O (4 mL). The resulting mixture was stirred at 50° C. for 3 h. The mixture was acidified with 1 N HCl to pH=2. The formed solid was filtered and the filter cake was dried to give the title compound 2c (840 mg, 87% yield) as a yellow solid. LC-MS (Method 3) t$_R$=1.12 min, m/z (M+H)⁺=361.1.

Step 3. 2-Chloro-4-[2-methoxy-3-(1-methyl-1,2,4-triazol-3-yl)anilino]-N-(trideuteromethyl)pyrimidine-5-carboxamide (2d)

Compound 2c (500 mg, 1.39 mmol), methyl-d₃-amine hydrochloride (127 mg, 1.80 mmol), T₃P (716 mg, 5.54

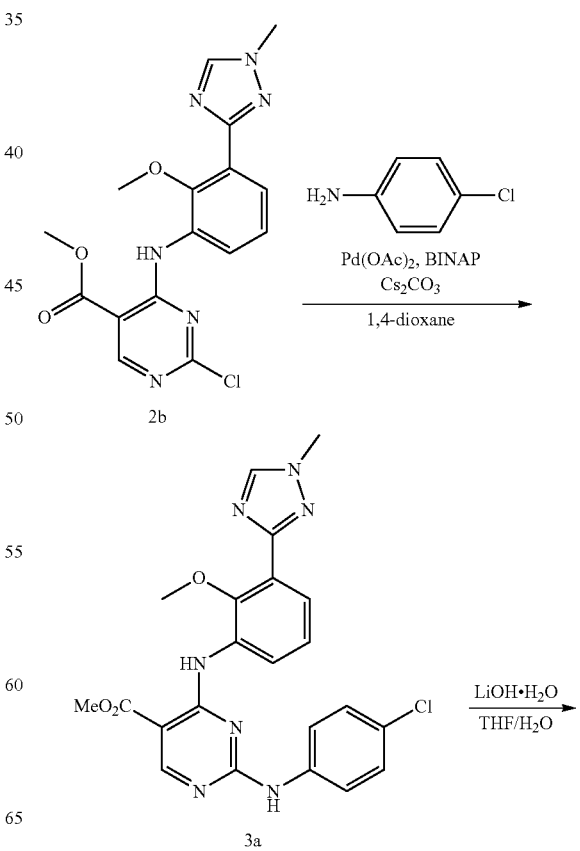

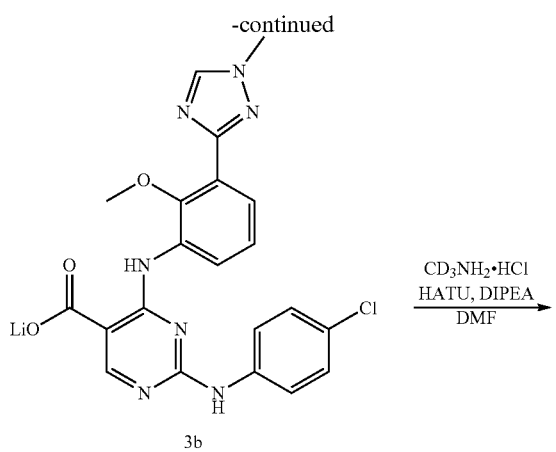

Step 1. Methyl 2-((4-chlorophenyl)amino)-4-((2-methoxy-3-(1-methyl-1H-1,2,4-triazol-3-yl) phenyl)amino)pyrimidine-5-carboxylate (3a)

A mixture of 2b (40 mg, 0.108 mmol), 4-chloroaniline (15 mg, 0.119 mmol), Cs$_2$CO$_3$ (70 mg, 0.216 mmol), BINAP (13.7 mg, 0.022 mmol) and Pd(OAc) 2 (2.5 mg, 0.011 mmol) in 1,4-dioxane (1.2 mL) was stirred at 85° C. under N$_2$ overnight. The mixture was cooled down to r.t., then filtered through a pad of celite and concentrated. The residue was purified by Prep-TLC (DCM/MeOH=10/1) to give the product 3a (15 mg, 27% yield) as a light-yellow oil. LC-MS (Method 4) $t_R$=4.54 min, m/z (M+H)$^+$=466.2.

Step 2. Lithium 2-((4-chlorophenyl) amino)-4-((2-methoxy-3-(1-methyl-1H-1,2,4-triazol-3-yl)phenyl)amino)pyrimidine-5-carboxylate (3b)

To a stirred mixture of 3a (15 mg, 0.032 mmol) in THF (0.6 mL) and water (0.3 mL) was added lithium hydroxide monohydrate (3 mg, 0.064 mmol). The reaction was stirred for 12 h at r.t. The mixture was concentrated under reduced pressure to give the crude product 3b (18 mg, yield given) as a brown-yellow solid. LC-MS (Method 4) $t_R$=3.24 min, m/z (M+H)$^+$=452.2.

Step 3. 2-((4-Chlorophenyl) amino)-4-((2-methoxy-3-(1-methyl-1H-1,2,4-triazol-3-yl) phenyl) amino)-N-(methyl-d$_3$)pyrimidine-5-carboxamide (3)

To a stirred mixture of 3b (18 mg, 0.04 mmol) in DMF (1.0 mL) were added methyl-d$_3$-amine hydrochloride (8.5 mg, 0.12 mmol), HATU (46 mg, 0.12 mmol) and DIPEA (31 mg, 0.24 mmol). The mixture was stirred overnight at r.t. The mixture was purified by Prep-HPLC (Method E) to afford the title product 3 (3.4 mg, 18% yield) as an off-white solid. LC-MS (Method 4) $t_R$=3.56 min, m/z (M+H)$^+$=468.3. $^1$H NMR (400 MHz, CDCl$_3$) δ 11.53 (s, 1H), 8.32 (s, 1H), 8.15-8.07 (m, 2H), 7.97 (s, 1H), 7.74 (dd, J=8.0, 1.6 Hz, 1H), 7.32 (d, J=8.8 Hz, 2H), 7.20 (t, J=8.0 Hz, 1H), 7.14 (d, J=8.8 Hz, 2H), 6.46 (s, 1H), 4.05 (s, 3H), 3.83 (s, 3H).

Example 4

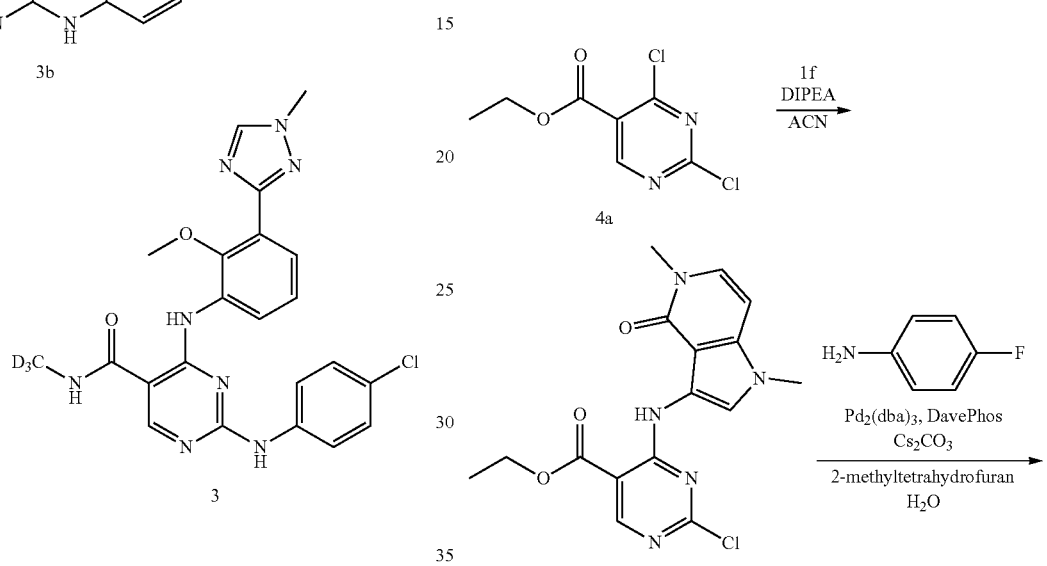

min, m/z (M+H)$^+$=425.1. $^1$H NMR (400 MHz, DMSO-d$_6$) δ 11.80 (s, 1H), 9.49 (s, 1H), 8.53 (s, 1H), 8.24 (s, 1H), 7.68-7.64 (m, 3H), 7.32 (d, J=7.2 Hz, 1H), 7.23 (t, J=8.6 Hz, 2H), 6.51 (d, J=7.6 Hz, 1H), 3.63 (s, 3H), 3.45 (s, 3H).

Example 5

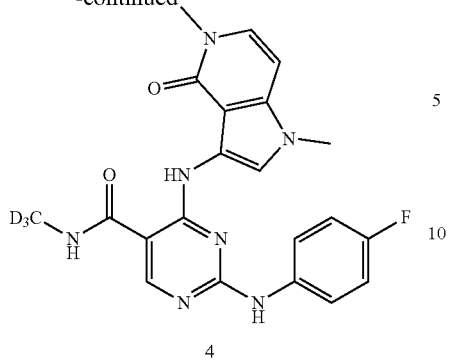

4

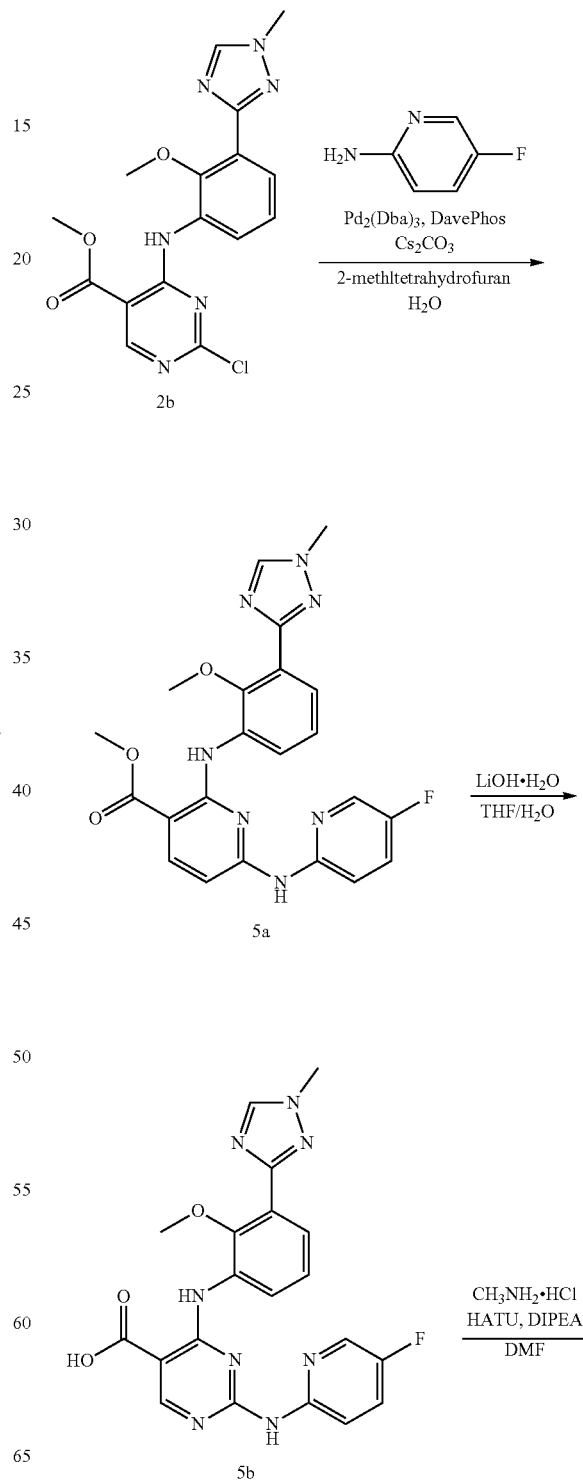

Step 1. Ethyl 2-chloro-4-((1,5-dimethyl-4-oxo-4,5-dihydro-1H-pyrrolo[3,2-c]pyridin-3-yl)amino)pyrimidine-5-carboxylate (4b)

Compound 1f (200 mg, 0.94 mmol), DIPEA (603 mg, 4.68 mmol) and ethyl 2,4-dichloropyrimidine-5-carboxylate 4$^a$ (207 mg, 0.94 mmol) were dissolved in ACN (4 mL). The resulting mixture was stirred at 80° C. for 2 h. After cooling to r.t., the formed solid was filtered. The filter cake was dried to give the title compound 4b (223 mg, 66% yield). $^1$H NMR (400 MHz, DMSO-d$_6$) δ 11.63 (s, 1H), 8.76 (s, 1H), 7.65 (s, 1H), 7.39 (d, J=6.4 Hz, 1H), 6.60 (d, J=7.2 Hz, 1H), 4.42-4.39 (m, 2H), 3.75 (s, 3H), 3.49 (s, 3H), 1.37 (t, J=7.2 Hz, 3H).

Step 2. Ethyl 4-((1,5-dimethyl-4-oxo-4,5-dihydro-1H-pyrrolo[3,2-c]pyridin-3-yl)amino)-2-((4-fluorophenyl)amino)pyrimidine-5-carboxylate (4c)

Compound 4c (184 mg, 76% yield), a yellow solid, was synthesized by utilizing a similar preparative procedure of Step 4 in Example 2 with 4b (200 mg, 0.55 mmol) and 4-fluoroaniline (92 mg, 0.83 mmol) as starting materials. LC-MS (Method 3) $t_R$=1.46 min, m/z (M+H)$^+$=437.2.

Step 3. 4-((1,5-Dimethyl-4-oxo-4,5-dihydro-1H-pyrrolo[3,2-c]pyridin-3-yl)amino)-2-((4-fluorophenyl)amino)pyrimidine-5-carboxylic acid (4d)

A mixture of 4c (150 mg, 0.34 mmol) and LiOH·H$_2$O (29 mg, 0.69 mmol) in THF (5 mL) and H$_2$O (2.5 mL) was stirred at 50° C. for 16 h. After cooling to r.t., the mixture was adjusted to pH=3 with 1 M HCl and extracted with EtOAc (50 mL*3). The combined organic layer was dried with Na$_2$SO$_4$, filtered and concentrated to afford 4d (100 mg, 71% yield) as a yellow solid. LC-MS (Method 3) $t_R$=0.98 min, m/z (M+H)$^+$=409.1.

Step 4. 4-((1,5-Dimethyl-4-oxo-4,5-dihydro-1H-pyrrolo[3,2-c]pyridin-3-yl)amino)-2-((4-fluorophenyl)amino)-N-(methyl-d$_3$)pyrimidine-5-carboxamide (4)

Compound 4d (30 mg, 0.07 mmol), methyl-d$_3$-amine hydrochloride (21 mg, 0.29 mmol), HATU (84 mg, 0.22 mmol) and DIPEA (47 mg, 0.37 mmol) were dissolved in DMF (2 mL). The reaction mixture was stirred at 25° C. for 2 h and then concentrated to dryness. The residue was purified by Prep-HPLC (Method A) to give the title compound 4 (9.2 mg, 29% yield). LC-MS (Method 1) $t_R$=3.31

-continued

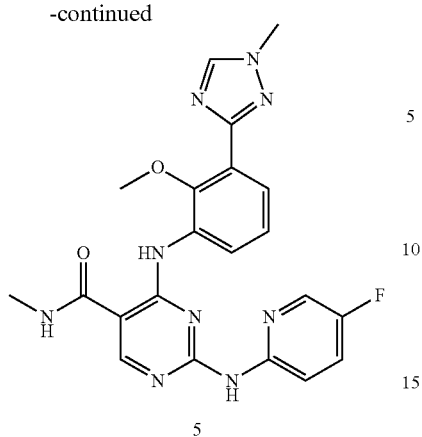

5

Step 1. Methyl 2-((5-fluoropyridin-2-yl)amino)-4-((2-methoxy-3-(1-methyl-1H-1,2,4-triazol-3-yl)phenyl)amino)pyrimidine-5-carboxylate (5a)

Compound 5a (230 mg, 95% yield), a yellow solid, was synthesized by utilizing a similar preparative procedure of Step 4 in Example 2 with 2b (200 mg, 0.53 mmol) and 5-fluoropyridin-2-amine (60 mg, 0.53 mmol) as starting materials. LC-MS (Method 3) $t_R$=1.29 min, m/z $(M+H)^+$=451.1.

Step 2. 2-((5-Fluoropyridin-2-yl)amino)-4-((2-methoxy-3-(1-methyl-1H-1,2,4-triazol-3-yl)phenyl)amino)pyrimidine-5-carboxylic acid (5b)

Compound 5b (222 mg, 98% yield), a yellow solid, was synthesized by utilizing a similar preparative procedure of Step 3 in Example 4 with 5a (230 mg, 0.51 mmol) as the starting material. LC-MS (Method 3) $t_R$=1.06 min, m/z $(M+H)^+$=437.1.

Step 3. 2-((5-Fluoropyridin-2-yl)amino)-4-((2-methoxy-3-(1-methyl-1H-1,2,4-triazol-3-yl)phenyl)amino)-N-methylpyrimidine-5-carboxamide (5)

Compound 5 (6 mg, 12% yield), a white solid, was synthesized by utilizing a similar preparative procedure of Step 3 in Example 2 with 5b (50 mg, 0.11 mmol) and $CH_3NH_2 \cdot HCl$ (15 mg, 0.22 mmol) as starting materials. LC-MS (Method 2) $t_R$=2.84 min, m/z $(M+H)^+$=450.0. $^1H$ NMR (400 MHz, $CDCl_3$) δ 11.23 (s, 1H), 8.37 (s, 1H), 8.33-8.27 (m, 2H), 8.13-8.11 (m, 2H), 7.84 (s, 1H), 7.73 (dd, J=8.0, 2.0 Hz, 1H), 7.35-7.28 (m, 1H), 7.19 (t, J=8.0 Hz, 1H), 5.99 (d, J=4.0, Hz, 1H), 4.01 (s, 3H), 3.89 (s, 3H), 3.01 (d, J=4.8 Hz, 3H).

Example 6

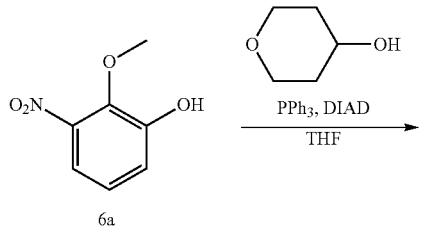

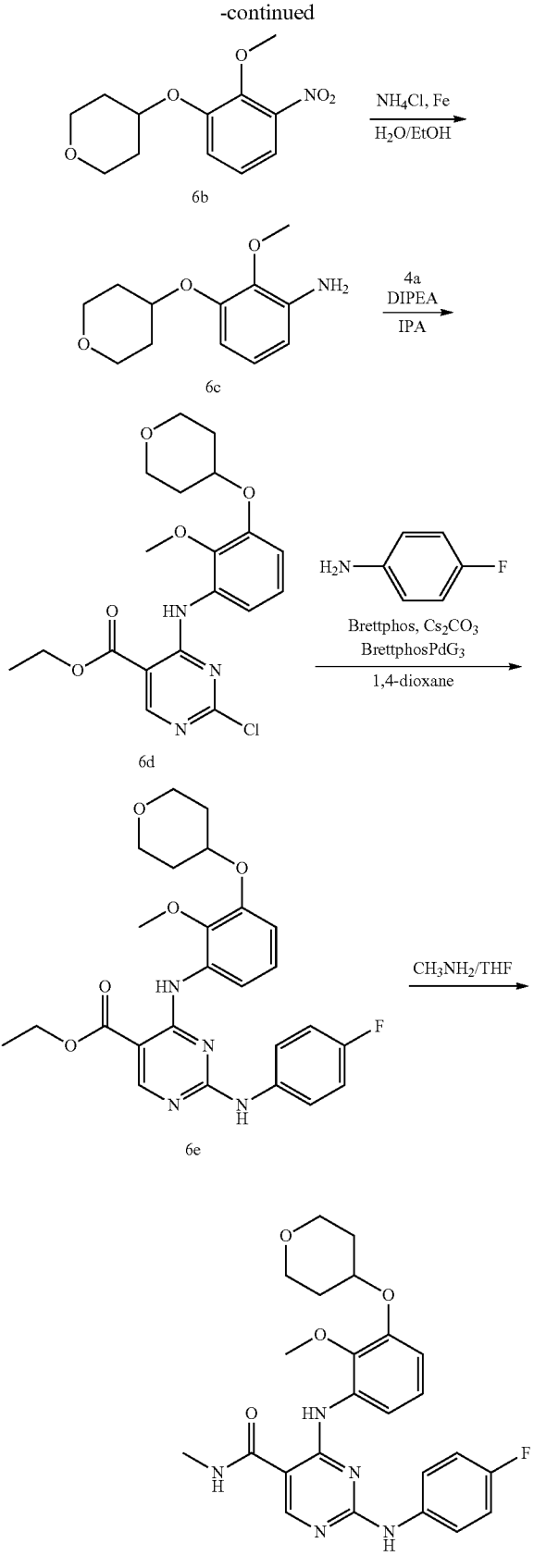

Step 1. 4-(2-Methoxy-3-nitrophenoxy)tetrahydro-2H-pyran (6b)

To a solution of 6a (2 g, 11.82 mmol), tetrahydropyran-4-ol (1.45 g, 14.18 mmol) and triphenylphosphine (6.20 g, 23.64 mmol) in THF (40 mL) was added DIAD (4.78 g, 23.64 mmol) dropwise at 0° C. After stirring at r.t. overnight, the reaction mixture was diluted with EtOAc (100 mL). The resultant mixture was washed with water (20 mL*2) and brine (20 mL). The separated organic layer was dried over anhydrous Na$_2$SO$_4$ and filtered. The filtrate was concentrated to dryness. The residue was purified by flash chromatography on silica gel (PE/EtOAc=5/1) to give the title compound 6b (1.79 g, 60% yield) as a yellow oil. $^1$H NMR (400 MHz, DMSO-d$_6$) δ 7.38-7.35 (m, 2H), 7.25-7.21 (m, 1H), 4.49-4.45 (m, 1H), 3.89 (s, 3H), 3.87-3.77 (m, 2H), 3.39-3.33 (m, 2H), 1.85-1.82 (m, 2H), 1.58-1.55 (m, 2H).

Step 2. 2-Methoxy-3-((tetrahydro-2H-pyran-4-yl)oxy)aniline (6c)

Compound 6b (1.25 g, 4.93 mmol), Fe powder (1.38 g, 24.68 mmol) and NH$_4$Cl (1.31 g, 24.68 mmol) were dissolved in a mixture of EtOH (5 mL) and H$_2$O (5 mL). The reaction solution was stirred at 80° C. for 2 h. The reaction mixture was cooled and filtered. The filtrate was concentrated to dryness. The residue was purified by flash chromatography on silica gel (PE/EtOAc=5/1) to give the title compound 6c (450 mg, 41% yield) as a red oil. LC-MS (Method 3) t$_R$=1.18 min, m/z (M+H)$^+$=224.1.

Step 3. Ethyl 2-chloro-4-((2-methoxy-3-((tetrahydro-2H-pyran-4-yl)oxy)phenyl)amino)pyrimidine-5-carboxylate (6d)

Compound 6d (80 mg, 11% yield), a white solid, was synthesized by utilizing a similar preparative procedure of Step 1 in Example 2 with 6c (400 mg, 1.79 mmol) and 4a (475 mg, 2.15 mmol) as starting materials. $^1$H NMR (300 MHz, DMSO-d$_6$) δ 10.91 (s, 1H), 8.87 (s, 1H), 8.06 (d, J=8.4 Hz, 1H), 7.16 (t, J=8.4 Hz, 1H), 6.93 (d, J=8.4 Hz, 1H), 4.48-4.40 (m, 4H), 3.89-3.85 (m, 5H), 3.32-3.28 (m, 1H), 2.01-1.71 (m, 4H), 1.39 (t, J=7.2 Hz, 3H).

Step 4. Ethyl 2-((4-fluorophenyl)amino)-4-((2-methoxy-3-((tetrahydro-2H-pyran-4-yl)oxy)phenyl)amino)pyrimidine-5-carboxylate (6e)

Compound 6e (57 mg, 66% yield), a white solid, was synthesized by utilizing a similar preparative procedure of Step 8 in Example 1 with 6d (80 mg, 0.20 mmol) and 4-fluoroaniline (33 mg, 0.30 mmol) as starting materials. $^1$H NMR (400 MHz, DMSO-d$_6$) δ 10.70 (s, 1H), 9.94 (s, 1H), 8.75 (s, 1H), 8.01 (brs, 1H), 7.67 (s, 2H), 7.15 (t, J=9.0 Hz, 2H), 7.02 (t, J=8.2 Hz, 1H), 6.82 (d, J=7.2 Hz, 1H), 4.41-4.30 (m, 3H), 3.86-3.82 (m, 5H), 3.27-3.24 (m, 2H), 1.35-1.23 (m, 2H), 1.19-1.03 (m, 2H), 1.34 (t, J=7.0 Hz, 3H).

Step 5. 2-((4-Fluorophenyl)amino)-4-((2-methoxy-3-((tetrahydro-2H-pyran-4-yl)oxy)phenyl)amino)-N-methylpyrimidine-5-carboxamide (6)

A mixture of 6e (50 mg, 0.10 mmol) in methylamine (2 mL, 2 M in THF) was stirred at 80° C. for 2 days. After cooling to r.t., the reaction mixture was concentrated and the residue was purified by Prep-HPLC (Method A) to afford compound 6 (6.5 mg, 13% yield) as a white solid. LC-MS (Method 1) T$_R$=3.89 min, m/z (M+H)$^+$=468.2. $^1$H NMR (400 MHz, DMSO-d$_6$) δ 11.46 (s, 1H), 9.62 (s, 1H), 8.60 (s, 1H), 8.44 (s, 1H), 8.10 (s, 1H), 7.68-7.66 (m, 2H), 7.12 (t, J=8.8 Hz, 2H), 7.00 (t, J=8.0 Hz, 1H), 6.76 (d, J=7.2 Hz, 1H), 4.30-4.28 (m, 1H), 3.87-3.84 (m, 2H), 3.81 (s, 3H), 3.30-3.23 (m, 2H), 2.79 (d, J=4.4 Hz, 3H), 1.81-1.78 (m, 4H).

Example 7

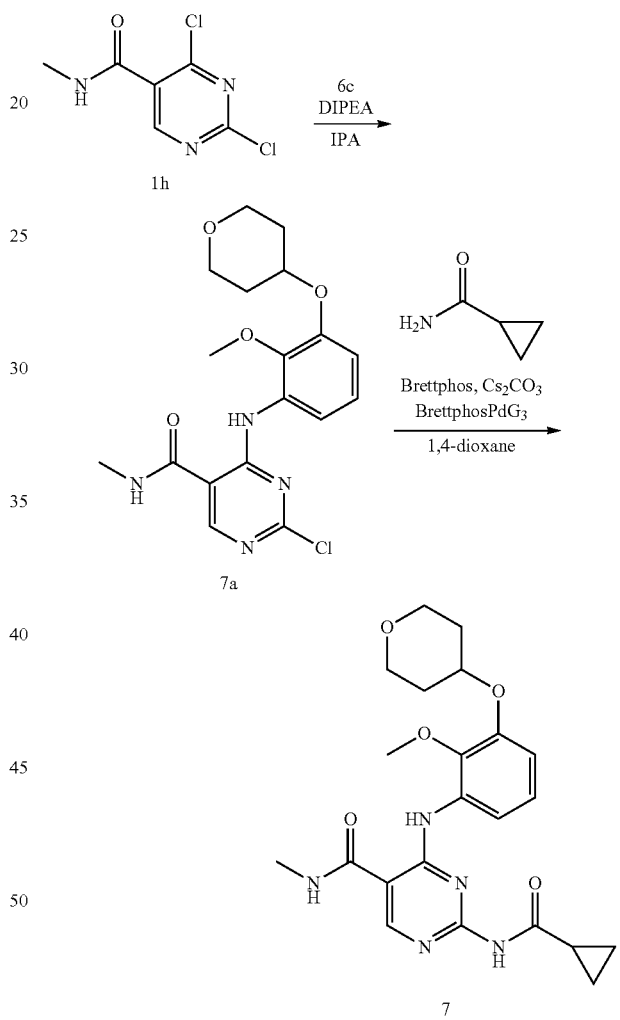

Step 1. 2-Chloro-4-((2-methoxy-3-((tetrahydro-2H-pyran-4-yl)oxy)phenyl)amino)-N-methylpyrimidine-5-carboxamide (7a)

Compound 7a (50 mg, 52% yield), a white solid, was synthesized by utilizing a similar preparative procedure of Step 1 in Example 2 with 1h (50 mg, 0.24 mmol) and 6c (65 mg, 0.29 mmol) as starting materials. LC-MS (Method 3) t$_R$=1.37 min, m/z (M+H)$^+$=393.1.

Step 2. 2-(Cyclopropanecarboxamido)-4-((2-methoxy-3-((tetrahydro-2H-pyran-4-yl)oxy)phenyl)amino)-N-methylpyrimidine-5-carboxamide (7)

Compound 7 (10 mg, 18% yield), a white solid, was synthesized by utilizing a similar preparative procedure of Step 8 in Example 1 with 7a (50 mg, 0.12 mmol) and cyclopropanecarboxamide (64 mg, 0.64 mmol) as starting materials. LC-MS (Method 1) $t_R$=3.11 min, m/z (M+H)$^+$=442.2. $^1$H NMR (400 MHz, DMSO-d$_6$) δ 11.56 (s, 1H), 10.82 (s, 1H), 8.77 (d, J=8.4 Hz, 1H), 8.68 (s, 1H), 8.62 (d, J=4.8 Hz, 1H), 7.00 (t, J=8.4 Hz, 1H), 6.75 (d, J=8.0 Hz, 1H), 4.35-4.30 (m, 1H), 3.92-3.70 (m, 2H), 3.76 (s, 3H), 3.11-3.00 (m, 2H), 2.81 (t, J=4.4 Hz, 3H), 2.33-2.32 (m, 1H), 2.15-2.13 (m, 4H), 0.87-0.82 (m, 4H).

Example 8

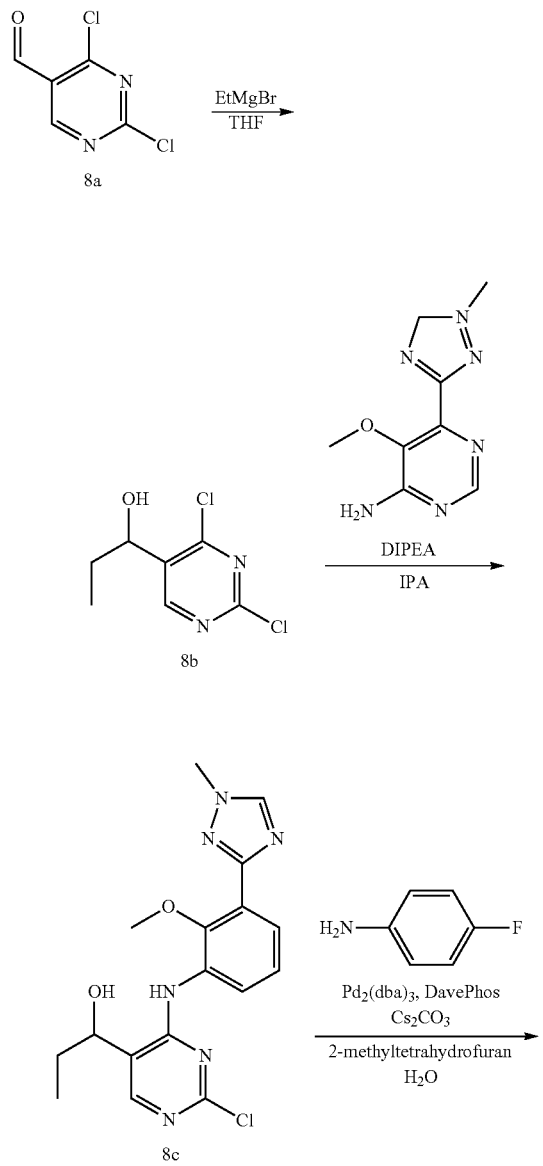

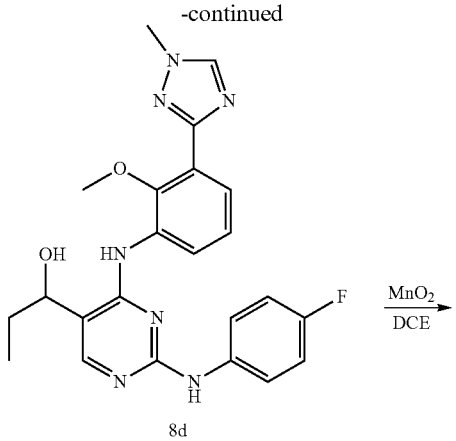

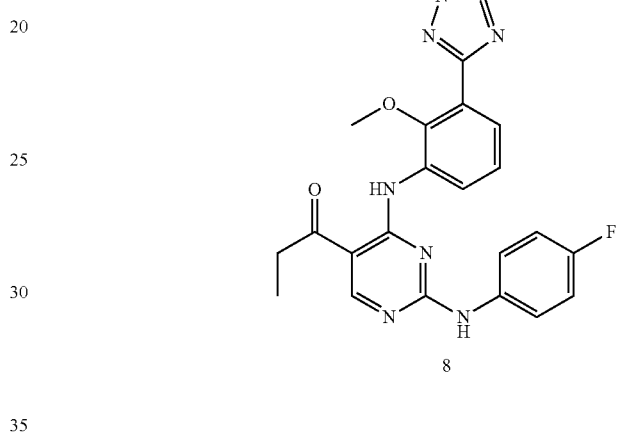

Step 1. 1-(2,4-Dichloropyrimidin-5-yl)propan-1-ol (8b)

To a solution of 8a (1 g, 5.65 mmol) in THF (7 mL) was added EtMgBr (8 mL, 8.48 mmol, 1 M in THF) at −55° C. After stirring at −55° C. for 4 h, the reaction mixture was quenched with 1 N aq. HCl and extracted with EtOAc (50 mL*2). The combined organic phase was concentrated to dryness. The residue was purified by flash chromatography on silica gel (DCM/MeOH=50/1) to afford the title compound 8b (256 mg, 22% yield) as yellow oil. $^1$H NMR (400 MHz, DMSO-d$_6$) δ 8.80 (s, 1H), 4.75-4.72 (m, 1H), 1.74-1.72 (m, 1H), 1.66-1.60 (m, 2H), 0.90 (t, J=7.2 Hz, 3H).

Step 2. 1-(2-Chloro-4-((2-methoxy-3-(1-methyl-1H-1,2,4-triazol-3-yl)phenyl)amino)pyrimidin-5-yl)propan-1-ol (8c)

Compound 8c (50 mg, 18% yield), a yellow oil, was synthesized by utilizing a similar preparative procedure of Step 1 in Example 2 with 8b (150 mg, 0.72 mmol) and 2-methoxy-3-(1-methyl-1,2,4-triazol-3-yl)aniline (221 mg, 1.09 mmol) as starting materials. LC-MS (Method 3) $t_R$=1.38 min, m/z (M+H)$^+$=375.2.

Step 3. 1-(2-((4-Fluorophenyl)amino)-4-((2-methoxy-3-(1-methyl-1H-1,2,4-triazol-3-yl)phenyl)amino)pyrimidin-5-yl)propan-1-ol (8d)

Compound 8d (50 mg, 69% yield), a yellow oil, was synthesized by utilizing a similar preparative procedure of Step 4 in Example 2 with 8c (60 mg, 0.16 mmol) and 4-fluoroaniline (35 mg, 0.32 mmol) as starting materials. LC-MS (Method 3) $t_R$=1.51 min, m/z (M+H)⁺=450.5.

Step 4. 1-(2-((4-Fluorophenyl)amino)-4-((2-methoxy-3-(1-methyl-1H-1,2,4-triazol-3-yl)phenyl)amino)pyrimidin-5-yl)propan-1-one (8)

A suspension solution of 8d (30 mg, 66.74 mmol) and MnO₂ (29.01 mg, 0.33 mmol) in 1,2-dichloroethane (2 mL) was stirred at 100° C. for 4 h. The reaction mixture was cooled and filtered. The filter cake was purified by Prep-HPLC (Method A) to give compound 8 (3 mg, 10% yield) as a white solid. LC-MS (Method 1) $t_R$=2.32 min, m/z (M+H)⁺=448.2. ¹H NMR (400 MHz, DMSO-d₆) δ 11.90 (s, 1H), 10.02 (s, 1H), 8.97 (s, 1H), 8.57 (s, 2H), 7.69 (s, 2H), 7.57 (d, J=7.6 Hz, 1H), 7.17 (t, J=8.8 Hz, 3H), 3.96 (s, 3H), 3.80 (s, 3H), 3.02 (q, J=7.2 Hz, 2H), 1.12 (t, J=7.2 Hz, 3H).

Example 9

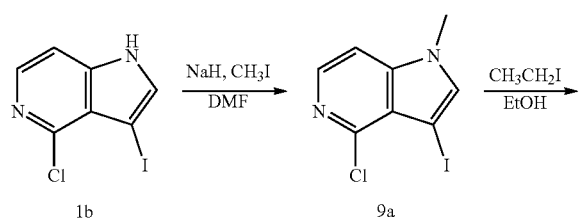

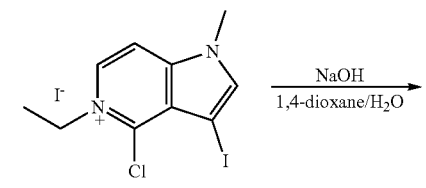

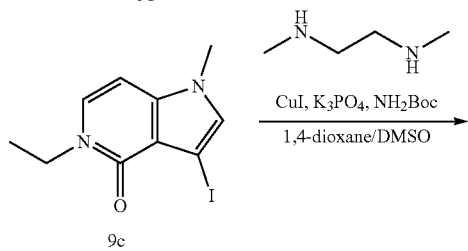

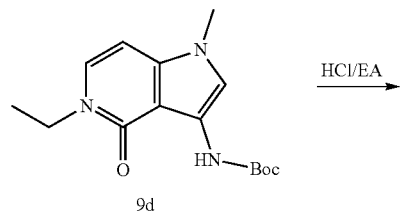

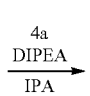

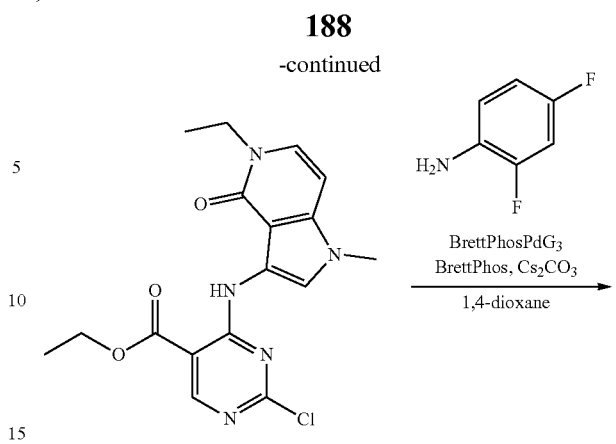

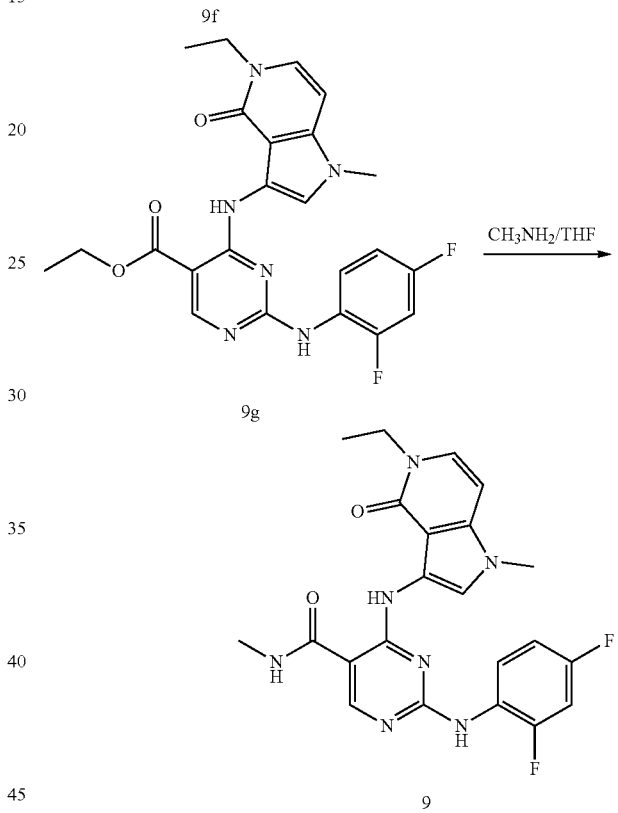

Step 1. 4-Chloro-3-iodo-1-methyl-1H-pyrrolo[3,2-c]pyridine (9a)

To a solution of 1b (15 g, 53.86 mmol) in DMF (80 mL) was added sodium hydride (2.48 g, 64.64 mmol, 60% in mineral oil) portionwise at 0° C. After stirring at this temperature for 0.5 h, iodomethane (6.88 g, 48.48 mmol) was added to the reaction mixture. The reaction mixture was stirred at 0° C. for 1 h and then poured into water (200 mL) with stirring. The formed solid was collected by filtering and the filter cake was dried to afford the title compound 9a (11 g, 70% yield) as a brown solid. ¹H NMR (400 MHz, DMSO-d₆) δ 8.04 (d, J=6.4 Hz, 1H), 7.77 (s, 1H), 7.63 (d, J=6.4 Hz, 1H), 3.83 (s, 3H).

Step 2. 4-Chloro-5-ethyl-3-iodo-1-methyl-1H-pyrrolo[3,2-c]pyridin-5-ium iodide (9b)

Compound 9a (5 g, 17.09 mmol) and C₂H₅I (10 mL) were dissolved in EtOH (10 mL) in a sealed tube. The resulting mixture was stirred at 80° C. for 18 h. After cooling to r.t., the reaction mixture was cooled and concentrated to dryness. The residue was used to the next step without purification. LC-MS (Method 3) $t_R$=1.48 min, m/z M$^+$=321.1.

Step 3. 5-Ethyl-3-iodo-1-methyl-1H-pyrrolo[3,2-c]pyridin-4-(5H)-one (9c)

Compound 9c (2.0 g, 40% yield), a brown solid, was synthesized by utilizing a similar preparative procedure of Step 3 in Example 1 with 9b (5.4 g, 16.79 mmol) and NaOH (2.02 g, 50.38 mmol) as starting materials. $^1$H NMR (300 MHz, DMSO-d$_6$) δ 7.32 (d, J=7.5 Hz, 1H), 7.16 (s, 1H), 6.49 (d, J=7.5 Hz, 1H), 3.84 (q, J=6.6 Hz, 2H), 3.61 (s, 3H), 1.12 (t, J=6.6 Hz, 3H).

Step 4. Tert-butyl (5-ethyl-1-methyl-4-oxo-4,5-dihydro-1H-pyrrolo[3,2-c]pyridin-3-yl)carbamate (9d)

Compound 9d (1.5 g, 71% yield), a white solid, was synthesized by utilizing a similar preparative procedure of Step 4 in Example 1 with 9c (2.19 g, 7.25 mmol) and tert-butyl carbamate (8.49 g, 72.49 mmol) as starting materials. $^1$H NMR (400 MHz, DMSO-d$_6$) δ 8.32 (s, 1H), 7.31 (d, J=7.2 Hz, 1H), 7.14 (s, 1H), 6.54 (d, J=7.2 Hz, 1H), 3.92 (q, J=7.2 Hz, 2H), 3.65 (s, 3H), 1.47 (s, 9H), 1.18 (t, J=7.2 Hz, 3H).

Step 5. 3-Amino-5-ethyl-1-methyl-1H-pyrrolo[3,2-c]pyridin-4-((5H)-one hydrochloride (9e)

Compound 9e (1.3 g, 83% yield), a white solid, was synthesized by utilizing a similar preparative procedure of Step 5 in Example 1 with 9d (2.0 g, 6.86 mmol) as the starting material. $^1$H NMR (400 MHz, DMSO-d$_6$) δ 10.21 (brs, 3H), 7.46 (d, J=7.6 Hz, 1H), 7.27 (s, 1H), 6.53 (d, J=7.6 Hz, 1H), 3.97 (q, J=7.6 Hz, 2H), 3.71 (s, 3H), 1.22 (t, J=7.6 Hz, 3H).

Step 6. Ethyl 2-chloro-4-((5-ethyl-1-methyl-4-oxo-4,5-dihydro-1H-pyrrolo[3,2-c]pyridin-3-yl)amino)pyrimidine-5-carboxylate (9f)

Compound 9f (160 mg, 63% yield), a white solid, was synthesized by utilizing a similar preparative procedure of Step 1 in Example 2 with 9e (130 mg, 0.86 mmol) and 2,4-dichloropyrimidine-5-carboxylate (150 mg, 0.86 mmol) as starting materials. $^1$H NMR (400 MHz, DMSO-d$_6$) δ 8.75 (s, 1H), 7.63 (s, 1H), 7.39 (d, J=7.6 Hz, 1H), 6.58 (d, J=7.6 Hz, 1H), 4.40 (q, J=7.2 Hz, 2H), 3.97 (t, J=7.2 Hz, 2H), 3.75 (s, 3H), 1.37 (t, J=7.2 Hz, 3H), 1.25 (t, J=7.2 Hz, 3H).

Step 7. Ethyl 2-((2,4-difluorophenyl)amino)-4-((5-ethyl-1-methyl-4-oxo-4,5-dihydro-1H-pyrrolo[3,2-e]pyridin-3-yl)amino)pyrimidine-5-carboxylate (9g)

Compound 9g (30 mg, 70% yield), a yellow solid, was synthesized by utilizing a similar preparative procedure of Step 8 in Example 1 with 9f (50 mg, 0.13 mmol) and 2,4-difluoroaniline (35 mg, 0.26 mmol) as starting materials. LC-MS (Method 3) $t_R$=1.57 min, m/z (M+H)$^+$=469.3.

Step 8. 2-((2,4-Difluorophenyl)amino)-4-((5-ethyl-1-methyl-4-oxo-4,5-dihydro-1H-pyrrolo[3,2-c]pyridin-3-yl)amino)-N-methylpyrimidine-5-carboxamide (9)

Compound 9 (6 mg, 18% yield), a yellow solid, was synthesized by utilizing a similar preparative procedure of Step 5 in Example 6 with 9g (35 mg, 0.07 mmol) as the starting material. The crude product was purified by Prep-HPLC (Method C). LC-MS (Method 2) $t_R$=3.10 min, m/z (M+H)$^+$=454.1. $^1$H NMR (400 MHz, DMSO-d$_6$) δ 11.77 (s, 1H), 9.18 (s, 1H), 8.49 (s, 1H), 8.25-8.20 (m, 1H), 7.60-7.58 (m, 1H), 7.43 (t, J=8.4 Hz, 1H), 7.30 (d, J=7.2 Hz, 1H), 7.19 (t, J=7.6 Hz, 1H), 6.49 (d, J=7.2 Hz, 1H), 3.93 (q, J=6.4 Hz, 2H), 3.50 (s, 3H), 2.77 (d, J=4.4 Hz, 3H), 1.20 (t, J=6.8 Hz, 3H).

Example 10

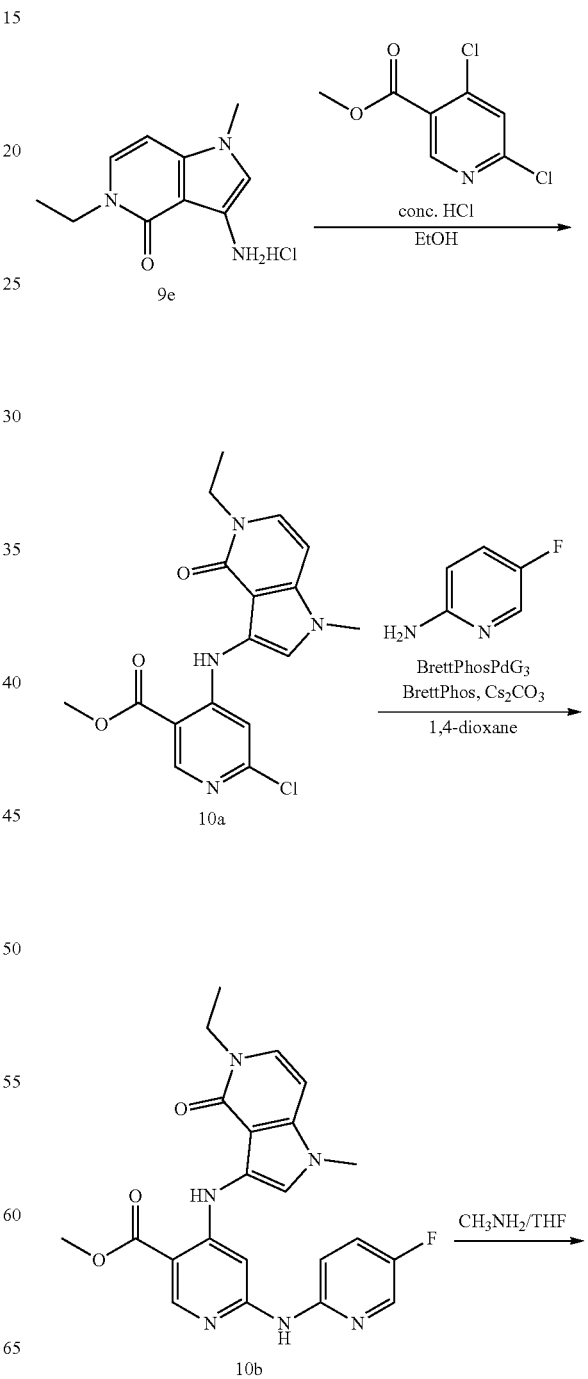

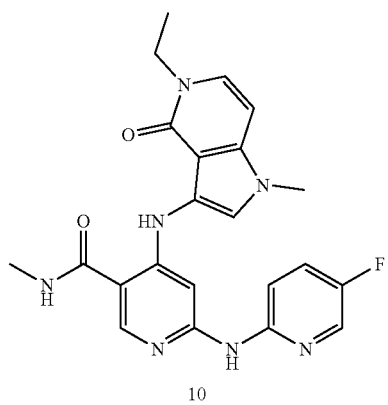

Step 1. Methyl 6-chloro-4-((5-ethyl-1-methyl-4-oxo-4,5-dihydro-1H-pyrrolo[3,2-c]pyridin-3-yl)amino)nicotinate (10a)

Compound 9e (100 mg, 0.43 mmol), methyl 4,6-dichloropyridine-3-carboxylate (136 mg, 0.66 mmol) and conc. HCl (0.1 mL) were dissolved in EtOH (1 mL). The resulting mixture was stirred at 90° C. for 4 h. The suspension was cooled and filtered. The filter cake was dried to afford 10a (120 mg, 69% yield) as a white solid. $^1$H NMR (400 MHz, DMSO-$d_6$) δ 10.74 (s, 1H), 8.66 (s, 1H), 7.43 (s, 1H), 7.39 (d, J=7.2 Hz, 1H), 7.15 (s, 1H), 6.57 (d, J=7.2 Hz, 1H), 3.99-3.89 (m, 5H), 3.72 (s, 3H), 1.20 (t, J=6.8 Hz, 3H).

Step 2. Methyl 4-((5-ethyl-1-methyl-4-oxo-4,5-dihydro-1H-pyrrolo[3,2-c]pyridin-3-yl)amino)-6-((5-fluoropyridin-2-yl)amino)nicotinate (10b)

Compound 10b (61 mg, 56% yield), a yellow solid, was synthesized by utilizing a similar preparative procedure of Step 8 in Example 1 with 10a (100 mg, 0.25 mmol) and 5-fluoropyridin-2-amine (34 mg, 0.30 mmol) as starting materials. $^1$H NMR (400 MHz, DMSO-$d_6$) δ 10.88 (s, 1H), 10.04 (s, 1H), 8.65 (s, 1H), 8.32 (s, 1H), 7.80 (s, 1H), 7.71-7.68 (m, 2H), 7.38 (d, J=7.2 Hz, 1H), 7.28 (s, 1H), 6.59 (d, J=7.2 Hz, 1H), 3.94 (d, J=7.6 Hz, 2H), 3.87 (s, 3H), 3.78 (s, 3H), 1.22 (t, J=7.6 Hz, 3H).

Step 3. 4-((5-Ethyl-1-methyl-4-oxo-4,5-dihydro-1H-pyrrolo[3,2-c]pyridin-3-yl)amino)-6-((5-fluoropyridin-2-yl)amino)-N-methylnicotinamide (10)

Compound 10 (15 mg, 30% yield), a white solid, was synthesized by utilizing a similar preparative procedure of Step 5 in Example 6 with 10b (50 mg, 0.11 mmol) as the starting material. The crude product was purified by Prep-HPLC (Method C). LC-MS (Method 3) $t_R$=3.26 min, m/z (M+H)$^+$=436.1. $^1$H NMR (400 MHz, DMSO-$d_6$) δ 11.00 (s, 1H), 9.80 (s, 1H), 8.39 (s, 1H), 8.30-8.29 (m, 1H), 8.26 (d, J=2.8 Hz, 1H), 7.77-7.74 (m, 1H), 7.68-7.65 (m, 2H), 7.35 (d, J=7.6 Hz, 1H), 7.22 (s, 1H), 6.55 (d, J=7.2 Hz, 1H), 3.94 (q, J=7.6 Hz, 2H), 3.76 (s, 3H), 2.77 (d, J=4.4 Hz, 3H), 1.21 (t, J=7.6 Hz, 3H).

Example 11

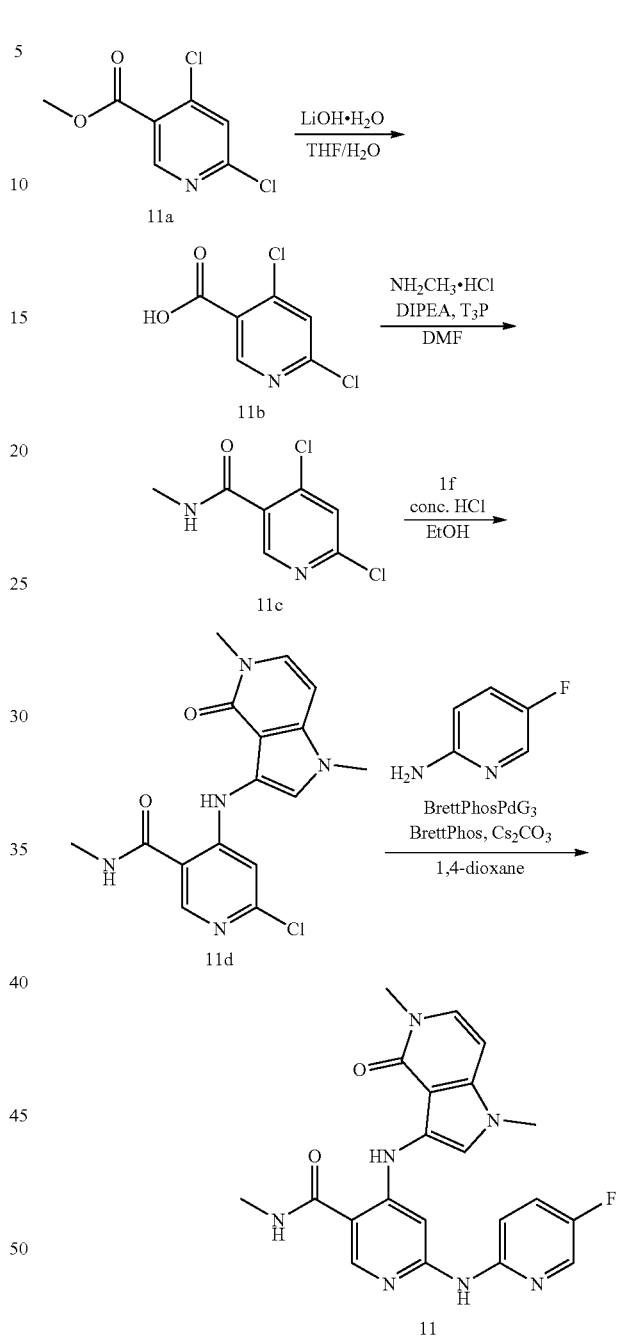

Step 1. 4,6-Dichloronicotinic acid (11b)

Compound 11a (10 g, 48.54 mmol) and LiOH·H$_2$O (6.12 g, 145.61 mmol) were dissolved in THF/H$_2$O (100 mL, v/v=1/1). The mixture was stirred at r.t. for 2 h. The reaction mixture was acidified with 1 N HCl to pH<7 and extracted with EtOAc (10 mL*2). The combined organic phase was concentrated to afford 11b (9.2 g, 99% yield) as a white solid. $^1$H NMR (400 MHz, DMSO-$d_6$) δ 13.95 (brs, 1H), 8.82 (s, 1H), 7.93 (s, 1H).

Step 2. 4,6-Dichloro-N-methylnicotinamide (11c)

Compound 11b (4.15 g, 21.61 mmol), methylamine hydrochloride (1.90 g, 28.10 mmol), DIPEA (11.17 g, 86.46 mmol) and T$_3$P (27.51 g, 86.46 mmol, 50% wt in DMF) were dissolved in DMF (20 mL). The resulting mixture was stirred at r.t. for 8 h. The reaction mixture was diluted with EtOAc (60 mL), washed with brine (30 mL), dried over anhydrous Na$_2$SO$_4$ and filtered. The filtrate was concentrated under vacuum. The residue was purified by flash chromatography on silica gel (PE/EtOAc=2/1) to give 11c (3.9 g, 88% yield) as a white solid. $^1$H NMR (400 MHz, DMSO-d$_6$) δ 8.62 (s, 1H), 7.42 (s, 1H), 6.38 (brs, 1H), 3.03 (d, J=4.4 Hz, 3H).

Step 3. 6-Chloro-4-((1,5-dimethyl-4-oxo-4,5-dihydro-1H-pyrrolo[3,2-c]pyridin-3-yl)amino)-N-methylnicotinamide (11d)

Compound 1f (90 mg, 0.51 mmol), 11c (156 mg, 0.76 mmol) and conc. HCl (0.2 mL) were dissolved in EtOH (1 mL) and the resulting reaction mixture was stirred at 90° C. for 6 h. The suspension was cooled and filtered. The filter cake was dried to afford 11d (100 mg, 52% yield) as a yellow solid. $^1$H NMR (400 MHz, DMSO-d$_6$) δ 10.81 (s, 1H), 8.68 (d, J=4.4 Hz, 1H), 8.44 (s, 1H), 7.36 (d, J=7.6 Hz, 1H), 7.33 (s, 1H), 7.04 (s, 1H), 6.53 (d, J=7.6 Hz, 1H), 3.71 (s, 3H), 3.42 (s, 3H), 2.79 (d, J=3.6 Hz, 3H).

Step 4. 4-((1,5-Dimethyl-4-oxo-4,5-dihydro-1H-pyrrolo[3,2-c]pyridin-3-yl)amino)-6-((5-fluoropyridin-2-yl)amino)-N-methylnicotinamide (1H)

Compound 11 (9 mg, 15% yield), a white solid, was synthesized by utilizing a similar preparative procedure of Step 8 in Example 1 with 11d (50 mg, 0.14 mmol) and 5-fluoropyridin-2-amine (24 mg, 0.21 mmol) as starting materials. LCMS (Method 1) t$_R$=3.01 min, m/z (M+H)$^+$=422.2. $^1$H NMR (400 MHz, DMSO-d$_6$) δ 10.98 (s, 1H), 9.77 (s, 1H), 8.38 (s, 1H), 8.28-8.28 (m, 2H), 7.78-7.75 (m, 1H), 7.67-7.62 (m, 2H), 7.33 (d, J=7.6 Hz, 1H), 7.21 (s, 1H), 6.52 (d, J=7.6 Hz, 1H), 3.75 (s, 3H), 3.44 (s, 3H), 2.77 (d, J=4.4 Hz, 3H).

Example 12

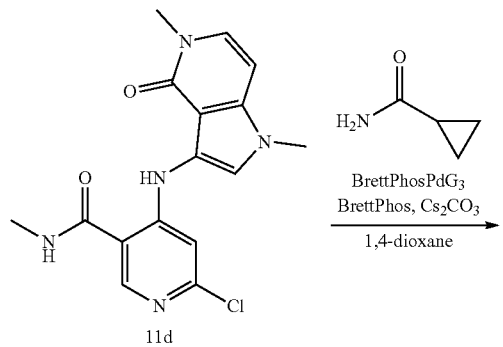

Step 1. 6-(Cyclopropanecarboxamido)-4-((1,5-dimethyl-4-oxo-4,5-dihydro-1H-pyrrolo[3,2-c]pyridin-3-yl)amino)-N-methylnicotinamide (12)

Compound 12 (12.5 mg, 22% yield), a white solid, was synthesized by utilizing a similar preparative procedure of Step 8 in Example 1 with 11d (50 mg, 0.14 mmol) and cyclopropanecarboxamide (61 mg. 0.72 mmol) as starting materials. LCMS (Method 1) t$_R$=2.18 min, m/z (M+H)$^+$=395.1. $^1$H NMR (400 MHz, DMSO-d$_6$) δ 10.88 (s, 1H), 10.73 (s, 1H), 8.42-8.40 (m, 2H), 7.98 (s, 1H), 7.34 (d, J=7.2 Hz, 1H), 7.01 (s, 1H), 6.51 (d, J=7.2 Hz, 1H), 3.68 (s, 3H), 3.42 (s, 3H), 2.78 (d, J=4.4 Hz, 3H), 2.02-2.00 (m, 1H), 0.83-0.79 (m, 4H).

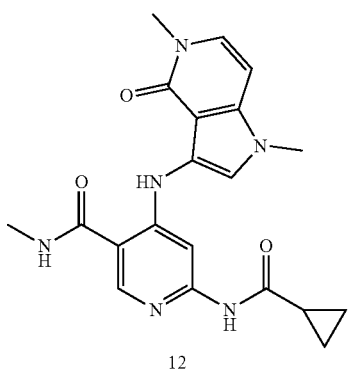

12

Example 13

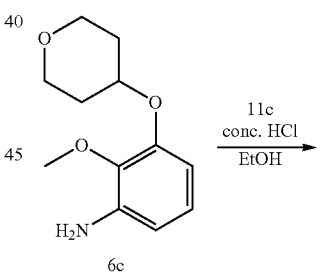

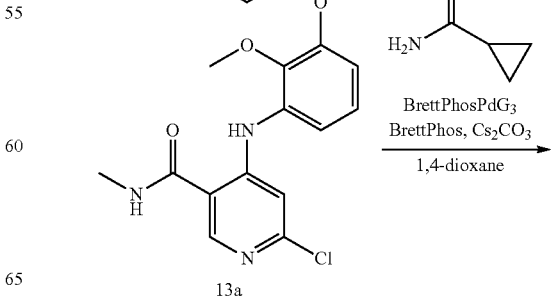

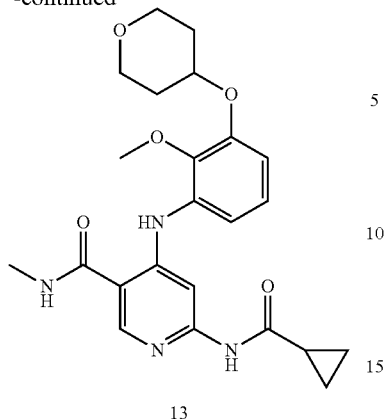

13

Step 1. 6-Chloro-4-((2-methoxy-3-((tetrahydro-2H-pyran-4-yl)oxy)phenyl)amino)-N-methylnicotinamide (13a)

Compound 13a (8.6 mg, 35% yield), a white solid, was synthesized by utilizing a similar preparative procedure of Step 1 in Example 10 with 6c (200 mg, 0.90 mmol) and 11c (202 mg, 0.99 mmol) as starting materials. (Method 3) $t_R$=1.49 min, m/z (M+H)$^+$=392.3.

Step 2. 6-(Cyclopropanecarboxamido)-4-((2-methoxy-3-((tetrahydro-2H-pyran-4-yl)oxy)phenyl)amino)-N-methylnicotinamide (13)

Compound 13 (35 mg, 45% yield), a white solid, was synthesized by utilizing a similar preparative procedure of Step 8 in Example 1 with 13a (70 mg, 0.18 mmol) and cyclopropanecarboxamide (76 mg, 0.90 mmol) as starting materials. LCMS (Method 1) $t_R$=3.24 min, m/z (M+H)$^+$=441.2. $^1$H NMR (400 MHz, DMSO-d$_6$) δ 10.70 (s, 1H), 10.40 (s, 1H), 8.54 (d, J=4.4 Hz, 1H), 8.45 (s, 1H), 8.04 (s, 1H), 7.08-7.00 (m, 2H), 6.81 (d, J=7.6 Hz, 1H), 4.24-4.20 (m, 1H), 3.82-3.80 (m, 5H), 3.30-3.24 (m, 2H), 2.78 (d, J=4.4 Hz, 2H), 1.98-1.95 (m, 2H), 1.79-1.77 (m, 2H), 1.68-1.60 (m, 2H), 0.78-0.75 (m, 4H).

Example 14

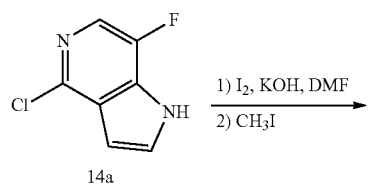
14a

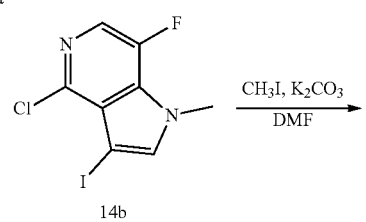
14b

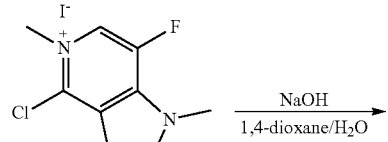
14c

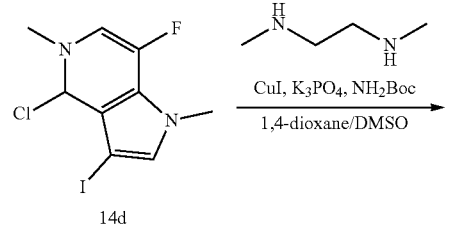
14d

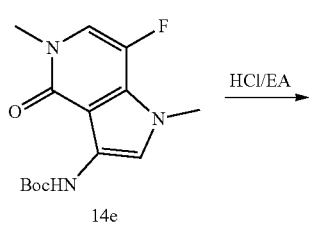
14e

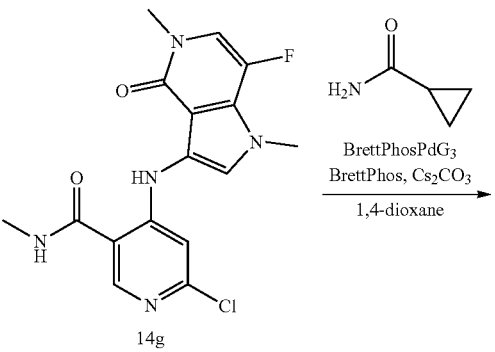
11c
14f

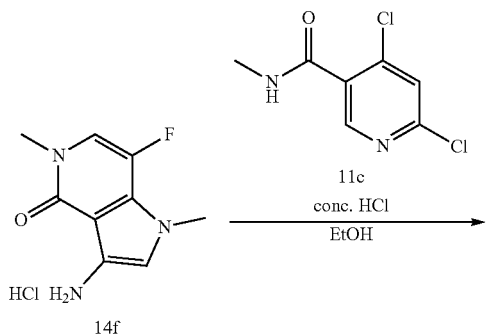
14g

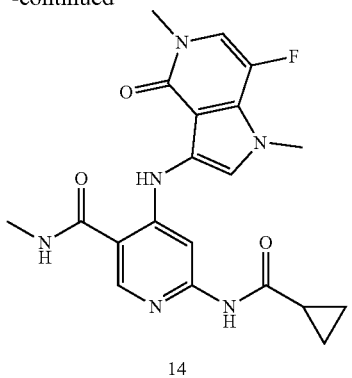

14

Step 1. 4-Chloro-7-fluoro-3-iodo-1-methyl-1H-pyrrolo[3,2-c]pyridine (14b)

To a mixture of 14a (450 mg, 2.64 mmol) and KOH (296 mg, 5.28 mmol) in DMF (5 mL) was added $I_2$ (668 mg, 2.64 mmol) at 0° C. After stirring at this temperature for 1 h, $CH_3I$ (418 mg, 2.95 mmol) was added to the reaction mixture. The black reaction mixture was stirred at 0° C. for 1 h. The mixture was poured into ice-water (30 mL) and the formed solid was filtered. The filter cake was dried to afford 14b (550 mg, 72% yield) as a brown solid. $^1H$ NMR (300 MHz, $CDCl_3$) δ 7.97 (d, J=3.0 Hz, 1H), 7.24 (s, 1H), 4.05 (s, 3H).

Step 2. 4-Chloro-7-fluoro-3-iodo-1,5-dimethyl-1H-pyrrolo[3,2-c]pyridin-5-ium iodide (14c)

Compound 14c (570 mg, yield given), a yellow solid, was synthesized by utilizing a similar preparative procedure of Step 2 in Example 1 with 14b (550 mg, 1.77 mmol) as the starting material. LC-MS (Method 3) $t_R$=1.13 min, m/z $M^+$=325.1.

Step 3. 7-Fluoro-3-iodo-1,5-dimethyl-1H-pyrrolo[3,2-c]pyridin-4-(5H)-one (14d)

Compound 14d (460 mg, 86% yield), a yellow solid, was synthesized by utilizing a similar preparative procedure of Step 3 in Example 1 with 14c (570 mg, 1.75 mmol) as the starting material. $^1H$ NMR (400 MHz, DMSO-$d_6$) δ 7.58 (d, J=8.0 Hz, 1H), 7.31 (s, 1H), 3.83 (d, J=2.0 Hz, 3H), 3.36 (s, 3H).

Step 4. Tert-butyl (7-fluoro-1,5-dimethyl-4-oxo-4,5-dihydro-1H-pyrrolo[3,2-c]pyridin-3-yl)carbamate (14e)

Compound 14e (110 mg, 50% yield), a yellow solid, was synthesized by utilizing a similar preparative procedure of Step 4 in Example 1 with 14d (230 mg, 0.75 mmol) and tert-butyl carbamate (880 mg, 7.51 mmol) as starting materials. $^1H$ NMR (400 MHz, DMSO-$d_6$) δ 8.35 (s, 1H), 7.53 (d, J=8.0 Hz, 1H), 7.23 (s, 1H), 3.80 (s, 3H), 3.38 (s, 3H), 1.47 (s, 9H).

Step 5. 3-Amino-7-fluoro-1,5-dimethyl-1H-pyrrolo[3,2-c]pyridin-4(5H)-one hydrochloride (14f)

Compound 14f (80 mg, 93% yield), a white solid, was synthesized by utilizing a similar preparative procedure of Step 5 in Example 1 with 14e (110 mg, 0.37 mmol) as the starting material. $^1H$ NMR (400 MHz, DMSO-$d_6$) δ 10.10 (brs, 2H), 7.69 (d, J=8.0 Hz, 1H), 7.33 (s, 1H), 3.86 (s, 3H), 3.42 (s, 3H).

Step 6. 6-Chloro-4-((7-fluoro-1,5-dimethyl-4-oxo-4,5-dihydro-1H-pyrrolo[3,2-c]pyridin-3-yl)amino)-N-methylnicotinamide (14g)

Compound 14g (68 mg, 46% yield), a brown solid, was synthesized by utilizing similar preparative procedure of Step 1 in Example 10 with 14f (80 mg, 0.41 mmol) and 11c (126 mg, 0.61 mmol) as starting materials. LC-MS (Method 3) $t_R$=1.32 min, m/z $(M+H)^+$=364.3.

Step 7. 6-(Cyclopropanecarboxamido)-4-((7-fluoro-1,5-dimethyl-4-oxo-4,5-dihydro-1H-pyrrolo[3,2-c]pyridin-3-yl)amino)-N-methylnicotinamide (14)

Compound 14 (10 mg, 18% yield), a white solid, was synthesized by utilizing a similar preparative procedure of Step 8 in Example 1 with 14g (50 mg, 0.14 mmol) and cyclopropanecarboxamide (47 mg, 0.55 mmol) as starting materials. LC-MS (Method 1) $t_R$=2.69 min, m/z $(M+H)^+$=413.1. $^1H$ NMR (400 MHz, DMSO-$d_6$) δ 10.88 (s, 1H), 10.73 (s, 1H), 8.42 (s, 1H), 8.40 (s, 1H), 7.99 (s, 1H), 7.56 (d, J=8.0 Hz, 1H), 7.10 (s, 1H), 3.84 (s, 3H), 3.59 (s, 3H), 2.78 (d, J=4.4 Hz, 3H), 2.03-2.11 (m, 1H), 0.85-0.88 (m, 4H).

Example 15

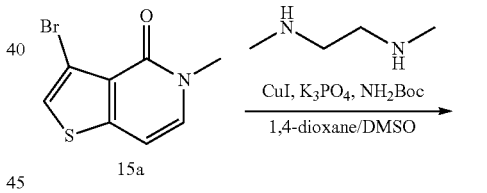

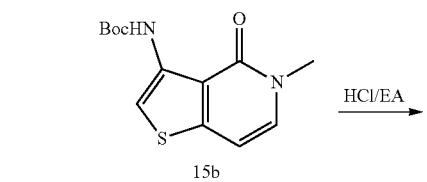

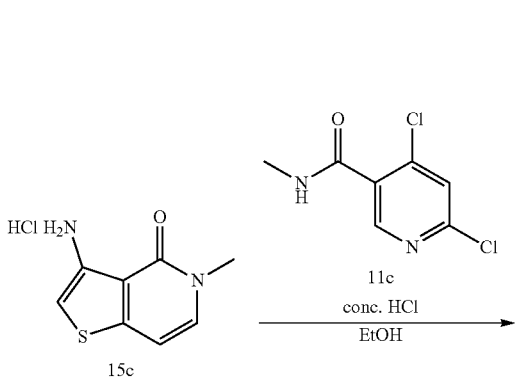

-continued

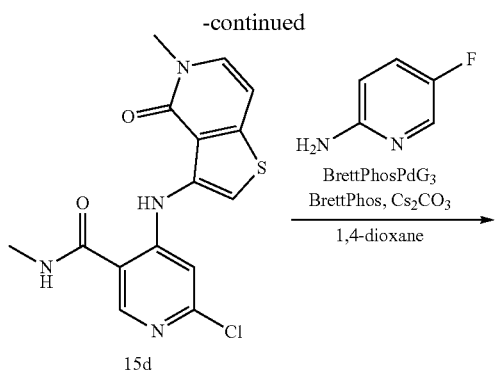

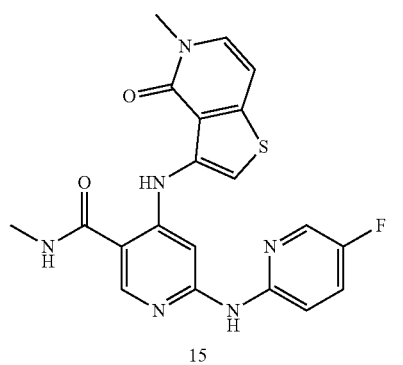

Step 1. Tert-butyl (5-methyl-4-oxo-4,5-dihydrothieno[3,2-c]pyridin-3-yl)carbamate (15b)

Compound 15b (92 mg, 27% yield), a white solid, was synthesized by utilizing a similar preparative procedure of Step 4 in Example 1 with 15a (300 mg, 1.23 mmol) and tert-butyl carbamate (719 mg, 6.14 mmol) as starting materials. $^1$H NMR (400 MHz, DMSO-$d_6$) 9.88 (s, 1H), 7.58 (d, J=7.2 Hz, 1H), 7.38 (s, 1H), 6.94 (d, J=7.2 Hz, 1H), 3.50 (s, 3H), 1.49 (s, 9H).

Step 2. 3-Amino-5-methylthieno[3,2-c]pyridin-4-(5H)-one hydrochloride (15c)

Compound 15c (71 mg, yield given), a white solid, was synthesized by utilizing a similar preparative procedure of Step 5 in Example 1 with 15b (59 mg, 0.33 mmol) as the starting material. LCMS (Method 3) $t_R$=1.15 min, m/z (M+H)$^+$=181.2.

Step 3. 6-Chloro-N-methyl-4-((5-methyl-4-oxo-4,5-dihydrothieno[3,2-c]pyridin-3-yl)amino)nicotinamide (15d)

A mixture of 15c (71 mg, 0.33 mmol) and 11c (67 mg, 0.33 mmol) in EtOH (2 mL) and conc. HCl (0.2 mL) was stirred overnight at 80° C. After cooling to r.t., the formed solid was filtered and the filter cake was dried to afford 15d (60 mg, 53% yield) as a yellow solid.

Step 4. 6-((5-Fluoropyridin-2-yl)amino)-N-methyl-4-((5-methyl-4-oxo-4,5-dihydrothieno[3,2-c]pyridin-3-yl)amino)nicotinamide (15)

Compound 15 (5.6 mg, 9% yield), a white solid, was synthesized by utilizing a similar preparative procedure of Step 8 in Example 1 with 15d (50 mg, 0.14 mmol) and 5-fluoropyridin-2-amine (48 mg, 0.43 mmol) as starting materials. LCMS (Method 1) $t_R$=3.34 min, m/z (M+H)$^+$=425.1. $^1$H NMR (400 MHz, DMSO-$d_6$) δ 11.44 (s, 1H), 9.84 (s, 1H), 8.40 (s, 1H), 8.33 (d, J=4.4 Hz, 1H), 8.24 (d, J=2.8 Hz, 1H), 7.99 (s, 1H), 7.78 (dd, J=8.8, 3.6 Hz, 1H), 7.65 (td, J=8.4, 2.8 Hz, 1H), 7.58 (d, J=7.6 Hz, 1H), 7.20 (s, 1H), 6.87 (d, J=7.6 Hz, 1H), 3.52 (s, 3H), 2.77 (d, J=4.4 Hz, 3H).

Example 16

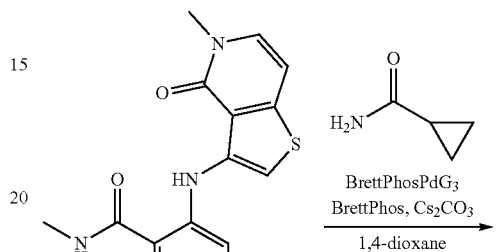

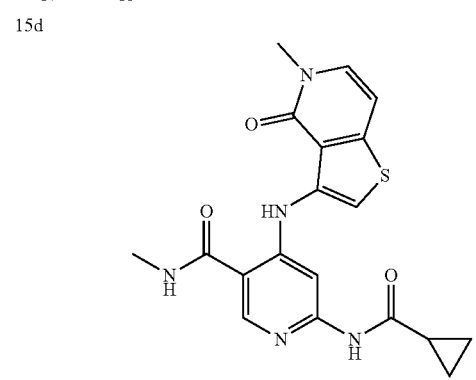

Step 1. 6-(Cyclopropanecarboxamido)-N-methyl-4-((5-methyl-4-oxo-4,5-dihydrothieno[3,2-c]pyridin-3-yl)amino)nicotinamide (16)

Compound 16 (4 mg, 7% yield), a white solid, was synthesized by utilizing a similar preparative procedure of Step 8 in Example 1 with 15d (50 mg, 0.14 mmol) and cyclopropanecarboxamide (85 mg, 0.61 mmol) as starting materials. LCMS (Method 1) $t_R$=3.07 min, m/z (M+H)$^+$=398.1. $^1$H NMR (400 MHz, DMSO-$d_6$) δ 11.44 (s, 1H), 10.85 (s, 1H), 8.45 (s, 2H), 8.40 (s, 1H), 7.58 (d, J=7.6 Hz, 1H), 7.05 (s, 1H), 6.85 (d, J=7.6 Hz, 1H), 3.50 (s, 3H), 2.77 (d, J=4.8 Hz, 3H), 2.12-1.99 (m, 1H), 0.83-0.80 (m, 4H).

Example 17

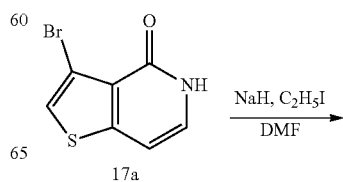

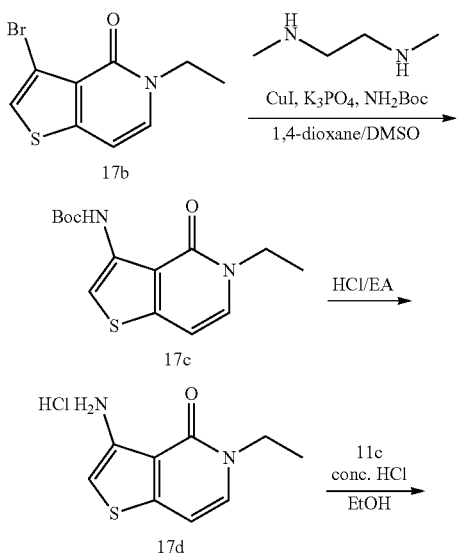

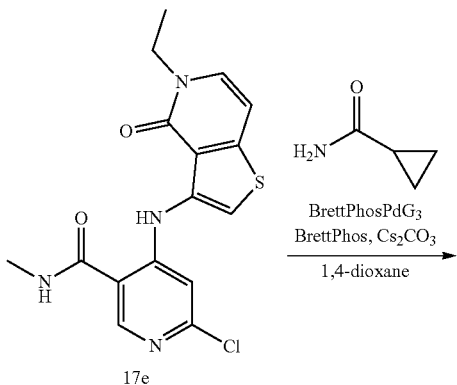

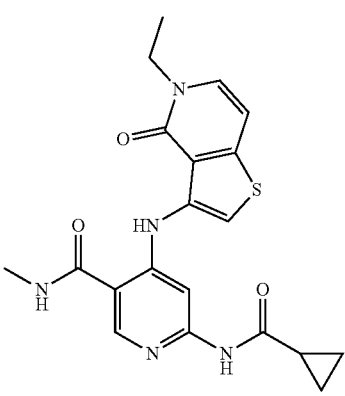

Step 1. 3-Bromo-5-ethylthieno[3,2-c]pyridin-4-(5H)-one (17b)

To a solution of 17a (1 g, 4.35 mmol) in DMF (10 mL) was added NaH (150 mg, 6.52 mmol, 60% in mineral oil) at 0° C. The resulting mixture was stirred at r.t. for 0.5 h. Then CH$_3$CH$_2$I (813 mg, 5.22 mmol) was added to the mixture. After stirring at r.t. overnight, the reaction mixture was poured into water (30 mL) and extracted with EtOAc (50 mL*2). The combined organic layer was dried over Na$_2$SO$_4$, filtered and evaporated under vacuum. The crude product was purified by silica gel flash flash chromatography (PE/EtOAc=4/1) to afford 17b (810 mg, 72%) as a black oil. LCMS (Method 3) $t_R$=1.43 min, m/z (M+H)$^+$=260.1.

Step 2. Tert-butyl (5-ethyl-4-oxo-4,5-dihydrothieno[3,2-c]pyridin-3-yl)carbamate (17c)

Compound 17c (500 mg, 71% yield), a yellow oil, was synthesized by utilizing a similar preparative procedure of Step 4 in Example 1 with 17b (620 mg, 2.40 mmol) and tert-butyl carbamate (2.81 g, 24.02 mmol) as starting materials. LCMS (Method 3) $t_R$=1.70 min, m/z (M+H)$^+$=295.3.

Step 3. 3-Amino-5-ethylthieno[3,2-c]pyridin-4-(5H)-one hydrochloride (17d)

Compound 17d (390 mg, yield given), a yellow solid, was synthesized by utilizing a similar preparative procedure of Step 5 in Example 1 with 17c (500 mg, 1.7 mmol) as the starting material. LCMS (Method 3) $t_R$=1.31 min, m/z (M+H)$^+$=195.1.

Step 4. 6-Chloro-4-((5-ethyl-4-oxo-4,5-dihydrothieno[3,2-c]pyridin-3-yl)amino)-N-methylnicotinamide (17e)

Compound 17e (160 mg, 43% yield), a brown solid, was synthesized by utilizing a similar preparative procedure of Step 1 in Example 10 with 17d (200 mg, 1.03 mmol) and 11c (316 mg, 1.54 mmol) as starting materials. LCMS (Method 3) $t_R$=1.31 min, m/z (M+H)$^+$=363.0.

Step 5. 6-(Cyclopropanecarboxamido)-4-((5-ethyl-4-oxo-4,5-dihydrothieno[3,2-c]pyridin-3-yl)amino)-N-methylnicotinamide (17)

Compound 17 (18 mg, 26% yield), a white solid, was synthesized by utilizing a similar preparative procedure of Step 8 in Example 1 with 17e (60 mg, 0.17 mmol) and cyclopropanecarboxamide (28 mg, 0.33 mmol) as starting materials. LCMS (Method 1) $t_R$=3.28 min, m/z (M+H)$^+$=412.1. $^1$H NMR (400 MHz, DMSO-d$_6$) δ 11.45 (s, 1H), 10.85 (s, 1H), 8.46 (s, 2H), 8.42 (s, 1H), 7.61 (d, J=7.2 Hz, 1H), 7.08 (s, 1H), 6.91 (d, J=7.2 Hz, 1H), 4.02 (q, J=6.4 Hz, 2H), 2.80 (d, J=4.4 Hz, 3H), 2.02-1.98 (m, 1H), 1.27 (t, J=6.8 Hz, 3H), 0.85-0.82 (m, 4H).

Example 18

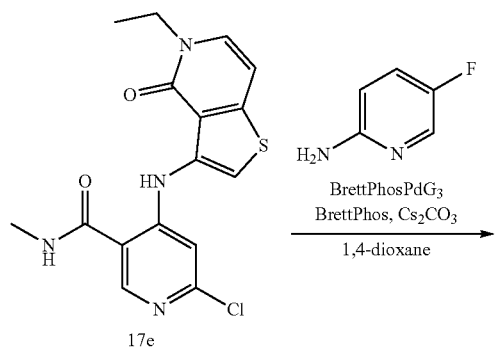

Step 1. 4-((5-Ethyl-4-oxo-4,5-dihydrothieno[3,2-c]pyridin-3-yl)amino)-6-((5-fluoropyridin-2-yl)amino)-N-methylnicotinamide (18)

Compound 18 (3.5 mg, 5% yield), a white solid, was synthesized by utilizing a similar preparative procedure of Step 8 in Example 1 with 17e (60 mg, 0.17 mmol) and 5-fluoropyridin-2-amine (37 mg, 0.33 mmol) as starting materials. LCMS (Method 1) $t_R$=2.99 min, m/z (M+H)$^+$=439.1. $^1$H NMR (400 MHz, DMSO-d$_6$) δ 11.46 (s, 1H), 9.86 (s, 1H), 8.43 (s, 1H), 8.36 (s, 1H), 8.26 (s, 1H), 8.03 (s, 1H), 7.79-7.61 (m, 3H), 7.23 (s, 1H), 6.92 (d, J=9.2 Hz, 1H), 4.04 (q, J=6.4 Hz, 2H), 2.81 (d, J=4.4 Hz, 3H), 1.29 (t, J=6.8 Hz, 3H).

Example 19

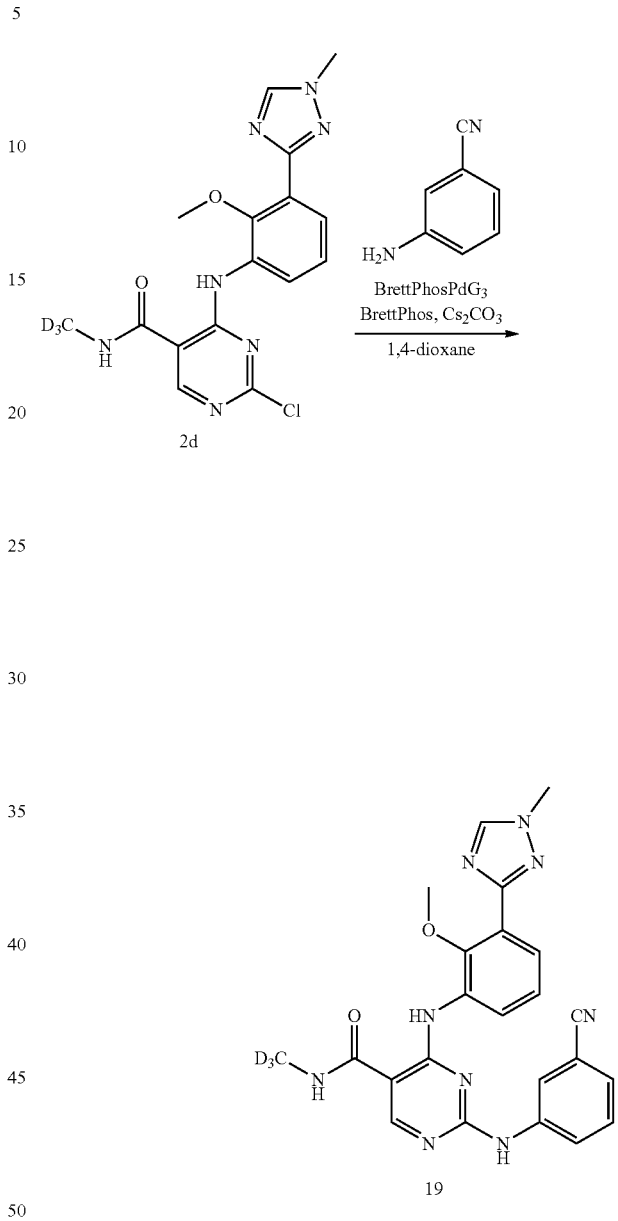

Step 1. 2-(3-Cyanoanilino)-4-[2-methoxy-3-(1-methyl-1,2,4-triazol-3-yl)anilino]-N-(trideuteriomethyl)pyrimidine-5-carboxamide (19)

Compound 19 (8.6 mg, 35% yield), a white solid, was synthesized by utilizing a similar preparative procedure of Step 8 in Example 1 with 2d (20 mg, 0.05 mmol) and 3-aminobenzonitrile (7 mg, 0.05 mmol) as starting materials. LCMS (Method 2) $t_R$=4.10 min, m/z (M+H)$^+$=459.2. $^1$H NMR (400 MHz, DMSO-d$_6$) δ 11.82 (s, 1H), 10.01 (s, 1H), 8.72 (s, 1H), 8.55-8.51 (m, 3H), 8.27 (s, 1H), 7.91 (d, J=8.4 Hz, 1H), 7.54-7.42 (m, 3H), 7.22 (t, J=8.0 Hz, 1H), 3.95 (s, 3H), 3.79 (s, 3H).

Example 20

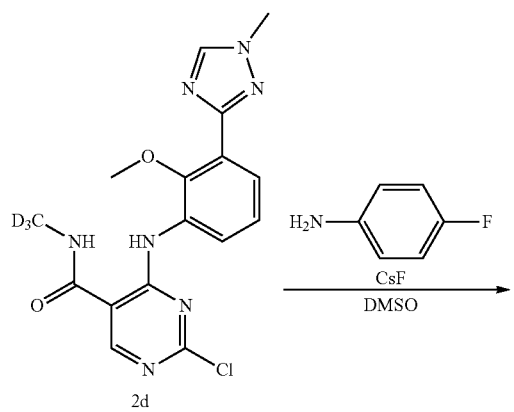

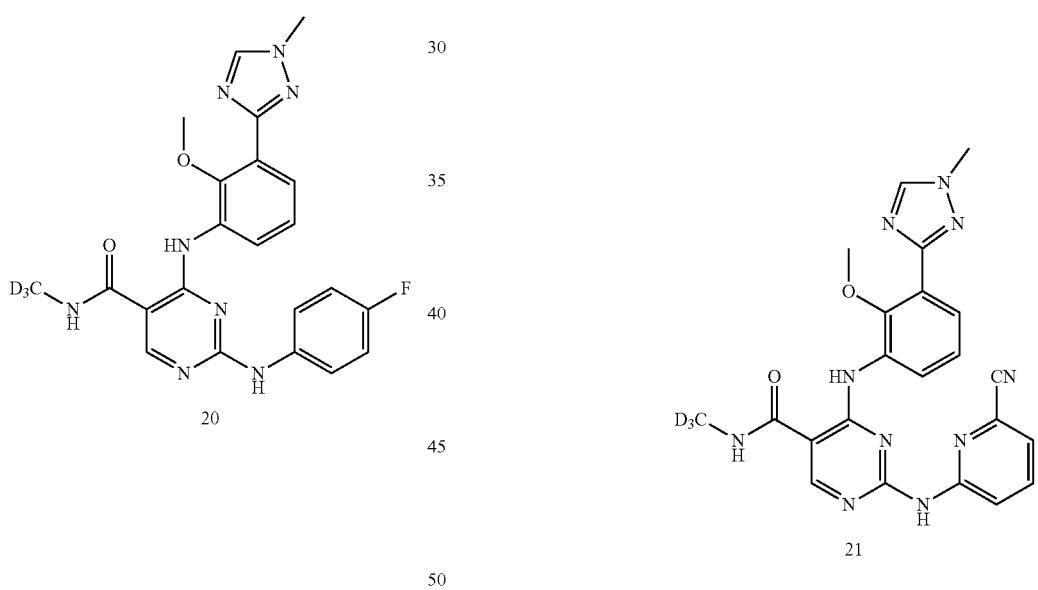

Step 1. 2-(4-Fluoroanilino)-4-[2-methoxy-3-(1-methyl-1,2,4-triazol-3-yl)anilino]-N-(trideuteriomethyl)pyrimidine-5-carboxamide (20)

Compound 2d (50 mg, 0.13 mmol), 4-fluoroaniline (15 mg, 0.13 mmol) and CsF (18 mg, 0.26 mmol) were dissolved in DMSO (1 mL). The reaction was stirred at 60° C. for 3 days. The mixture was cooled, diluted with H$_2$O (5 mL) and extracted with EtOAc (5 mL). The organic layer was concentrated to dryness. The residue was purified by Prep-HPLC (Method A) to give 20 (1.4 mg, 2% yield) as a white solid. LCMS (Method 1) t$_R$=3.77 min, m/z (M+H)$^+$=452.3. $^1$H NMR (400 MHz, DMSO-d$_6$) δ 11.78 (s, 1H), 9.68 (s, 1H), 8.65 (s, 1H), 8.58 (s, 2H), 8.44 (s, 1H), 7.70-7.67 (m, 2H), 7.51 (dd, J=9.2, 4.4 Hz, 1H), 7.17-7.12 (m, 3H), 3.94 (s, 3H), 3.78 (s, 3H).

Example 21

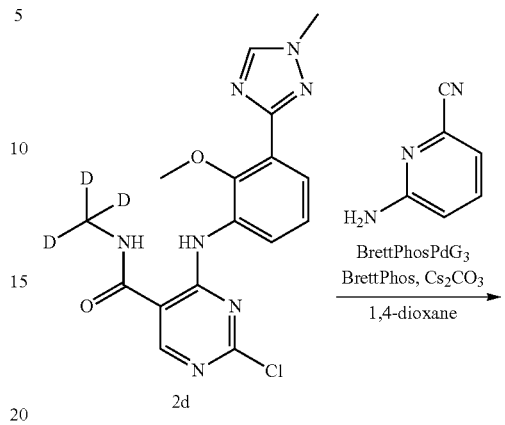

Step 1. 2-[(6-Cyano-2-pyridyl)amino]-4-[2-methoxy-3-(1-methyl-1,2,4-triazol-3-yl)anilino]-N-(trideuteriomethyl)pyrimidine-5-carboxamide (21)

Compound 21 (3.4 mg, 7% yield), a white solid, was synthesized by utilizing a similar preparative procedure of Step 8 in Example 1 with 2d (40 mg, 0.1 mmol) and 6-aminopicolinonitrile (25 mg, 0.21 mmol) as starting materials. LCMS (Method 1) t$_R$=3.44 min, m/z (M+H)$^+$=460.2. $^1$H NMR (400 MHz, DMSO-d$_6$) δ 11.82 (s, 1H), 10.63 (s, 1H), 8.84 (d, J=8.4 Hz, 1H), 8.72 (s, 1H), 8.59 (s, 1H), 8.55 (s, 1H), 8.44 (d, J=8.4 Hz, 1H), 7.95 (t, J=8.0 Hz, 1H), 7.63 (dd, J=7.6 Hz, 1H), 7.51 (t, J=7.6, 1.2 Hz, 1H), 7.22 (t, J=7.6 Hz, 1H), 3.95 (s, 3H), 3.79 (s, 3H).

Example 22
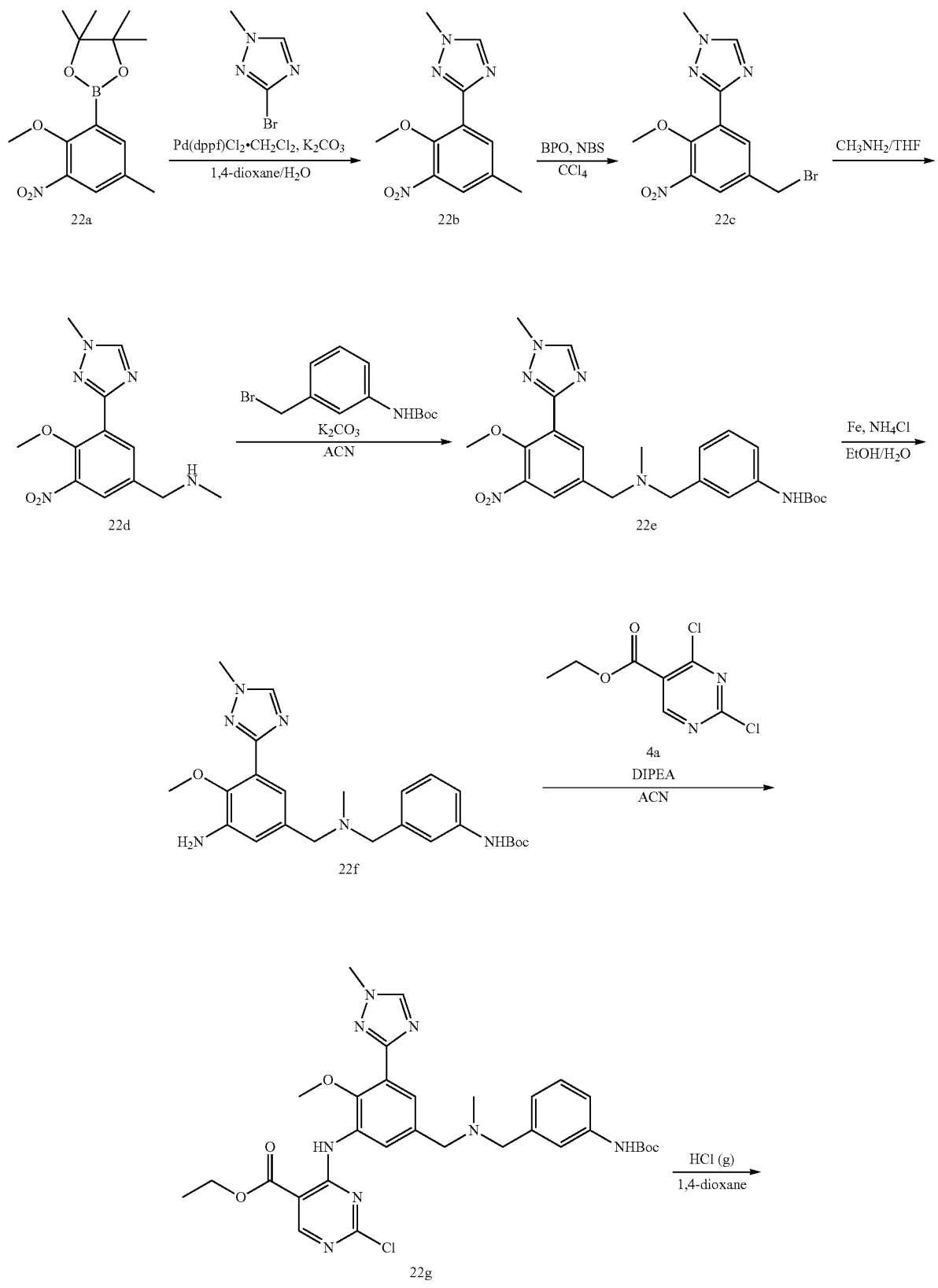

-continued

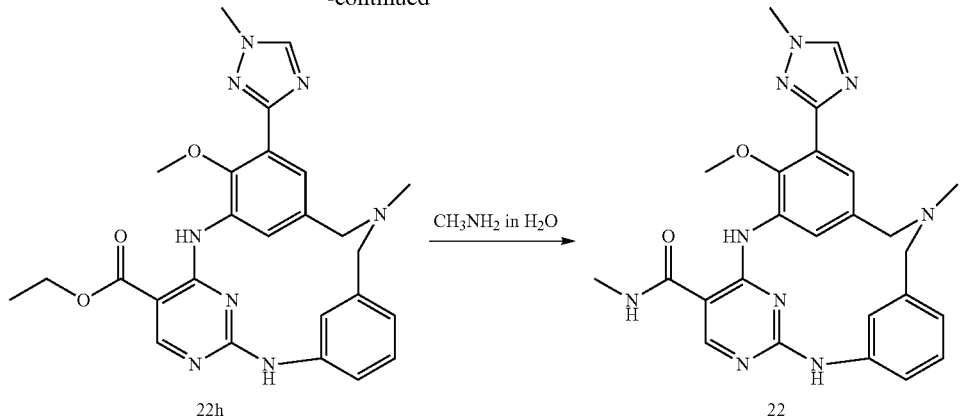

Step 1. 3-(2-Methoxy-5-methyl-3-nitrophenyl)-1-methyl-1H-1,2,4-triazole (22b)

Compound 22a (15.49 g, 52.84 mmol), 3-bromo-1-methyl-1H-1,2,4-triazole (9.42 g, 58.13 mmol), Pd(dppf)Cl$_2$·CH$_2$Cl$_2$ (2.16 g, 2.64 mmol) and K$_2$CO$_3$ (21.88 g, 158.53 mmol) were mixed in 1,4-dioxane (160 mL) and H$_2$O (16 mL). The above reaction was stirred at 110° C. for 2 h. The mixture was diluted with water (20 mL) and extracted with EtOAc (30 mL*2). The combined organic layer was concentrated to dryness. The residue was purified by flash chromatography on silica gel (PE/EtOAc from 3/1 to EtOAc) to give the title compound 22b (8.3 g, 63% yield) as a brown solid. $^1$H NMR (400 MHz, CDCl$_3$) δ 8.12 (s, 1H), 8.02 (d, J=2.0 Hz, 1H), 7.60 (d, J=1.6 Hz, 1H), 4.02 (s, 3H), 3.91 (s, 3H), 2.42 (s, 3H).

Step 2. 3-(5-(Bromomethyl)-2-methoxy-3-nitrophenyl)-1-methyl-1H-1,2,4-triazole (22c)

To a mixture of 22b (2.0 g, 8.06 mmol) in CCl$_4$ (20 mL) was added BPO (199 mg, 3.22 mmol) and NBS (1.58 g, 8.86 mmol). The mixture was irradiated for 16 h. The mixture was diluted with H$_2$O (50 mL) and extracted with DCM (100 mL*3). The combined organic layer was dried over Na$_2$SO$_4$ and filtered. The filtrate was concentrated. The residue was purified by flash chromatography on silica gel (PE/EtOAc=2/1) to give the title compound 22c (1.1 g, 42% yield) as a yellow solid. $^1$H NMR (400 MHz, CDCl$_3$) δ 8.27 (d, J=2.0 Hz, 1H), 8.16 (s, 1H), 7.84 (d, J=2.0 Hz, 1H), 4.51 (s, 2H), 4.04 (s, 3H), 3.95 (s, 3H).

Step 3. 1-(4-Methoxy-3-(1-methyl-1H-1,2,4-triazol-3-yl)-5-nitrophenyl)-N-methylmethanamine (22d)

Compound 22c (1.32 g, 4.04 mmol) was dissolved in a solution of methanamine in THF (2.0 M, 20 mL) was stirred at r.t. overnight. The mixture was concentrated to dryness. The residue was purified by flash chromatography on silica gel (DCM/MeOH=10/1) to give the title compound 22d (500 mg, 45% yield) as a yellow solid. $^1$H NMR (400 MHz, CDCl$_3$) δ 8.17 (d, J=2.0 Hz, 1H), 8.13 (s, 1H), 7.81 (d, J=2.0 Hz, 1H), 4.02 (s, 3H), 3.92 (s, 3H), 3.83 (s, 2H), 2.47 (s, 3H).

Step 4. Tert-butyl (3-(((4-methoxy-3-(1-methyl-1H-1,2,4-triazol-3-yl)-5-nitrobenzyl)(methyl)amino)methyl)phenyl)carbamate (22e)

Compound 22d (128 mg, 0.46 mmol), tert-butyl (3-(bromomethyl)phenyl)carbamate (139 mg, 0.48 mmol) and K$_2$CO$_3$ (191 mg, 1.38 mmol) were dissolved in ACN (3 mL). The above mixture was stirred at r.t. for 16 h. The mixture was concentrated to dryness. The residue was purified by flash chromatography on silica gel (PE/EtOAc=2/1) to give the title compound 22e (160 mg, 72% yield) as a yellow oil. LC-MS (Method 3) t$_R$=1.67 min, m/z (M+H)$^+$=483.3.

Step 5. Tert-butyl (3-(((3-amino-4-methoxy-5-(1-methyl-1H-1,2,4-triazol-3-yl)benzyl)(methyl)amino)methyl)phenyl)carbamate (22f)

Compound 22f (135 mg, 90% yield), a yellow solid, was synthesized by utilizing a similar preparative procedure of Step 2 in Example 6 with 22e (160 mg, 0.33 mmol) as the starting material. LC-MS (Method 3) t$_R$=1.49 min, m/z (M+H)$^+$=453.3.

Step 6. Ethyl 4-((5-(((3-((tert-butoxycarbonyl)amino)benzyl)(methyl)amino)methyl)-2-methoxy-3-(1-methyl-1H-1,2,4-triazol-3-yl)phenyl)amino)-2-chloropyrimidine-5-carboxylate (22g)

A mixture of 22f (156 mg, 0.35 mmol), ethyl 2,4-dichloropyrimidine-5-carboxylate (80 mg, 0.36 mmol) and DIPEA (89 mg, 0.69 mmol) in ACN (3 mL) was stirred at 85° C. for 2 h. The mixture was concentrated and the residue was purified by flash chromatography on silica gel (DCM/MeOH=30/1) to afford 22g (144 mg, 66% yield) as a yellow solid. LC-MS (Method 3) t$_R$=1.77 min, m/z (M+H)$^+$=637.6.

Step 7. Ethyl 10-methoxy-15-methyl-11-(1-methyl-1,2,4-triazol-3-yl)-2,4,8,15,23-pentazatetracyclo[15.3.1.1$^{3,7}$.1$^{9,13}$]tricosa-1(21),3(23),4,6,9,11,13(22),17,19-nonaene-6-carboxylate (22h)

Compound 22g (124 mg, 0.19 mmol) was dissolved in a solution of HCl (g) in 1,4-dioxane (40 mL, 2.0 M). The above reaction was stirred at 60° C. for 2 h. The mixture was concentrated to give the title compound 22h (120 mg, purity 40%, 46% yield) as a yellow oil. LC-MS (Method 3) t$_R$=1.56 min, m/z (M+H)$^+$=501.5.

Step 8. 10-Methoxy-N,15-dimethyl-11-(1-methyl-1,2,4-triazol-3-yl)-2,4,8,15,23-pentazatetracyclo[15.3.1.1$^{3,7}$.1$^{9,13}$]tricosa-1(21),3(23),4,6,9,11,13(22),17,19-nonaene-6-carboxamide (22)

A mixture of 22h (120 mg, 0.24 mmol) and methanamine (18 mL, 40% in water) was stirred at 100° C. for 18 h. The mixture was concentrated to dryness. The residue was purified by Prep-HPLC (Method A) to give the title compound 22 (11 mg, 9% yield) as a yellow solid. LC-MS (Method 2) $t_R$=2.53 min, m/z (M+H)$^+$=486.2. $^1$H NMR (400 MHz, DMSO-$d_6$) δ 11.70 (s, 1H), 9.73 (s, 1H), 8.86 (d, J=1.6 Hz, 1H), 8.68 (s, 1H), 8.54 (s, 1H), 8.47-8.44 (m, 2H), 7.37 (d, J=2.0 Hz, 1H), 7.21 (t, J=8.0 Hz, 1H), 7.02 (d, J=8.0 Hz, 1H), 6.92 (d, J=7.6 Hz, 1H), 3.94 (s, 3H), 3.78 (s, 3H), 3.50 (s, 2H), 3.42 (s, 2H), 2.80 (d, J=4.4 Hz, 3H), 2.40 (s, 3H).

Example 23

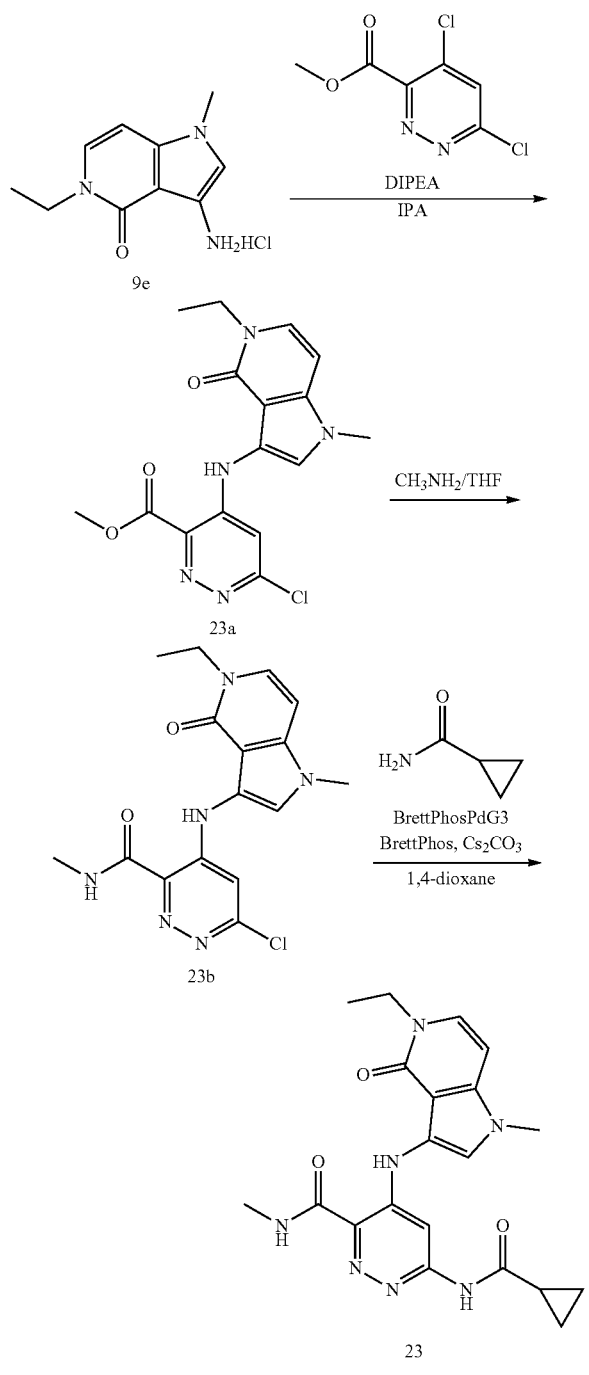

Step 1. Methyl 6-chloro-4-((5-ethyl-1-methyl-4-oxo-4,5-dihydro-1H-pyrrolo[3,2-c]pyridin-3-yl)amino)pyridazine-3-carboxylate (23a)

Compound 23a (120 mg, 50% yield), a yellow solid, was synthesized by utilizing a similar preparative procedure of Step 1 in Example 2 with 9e (150 mg, 0.66 mmol) and methyl 4,6-dichloropyridazine-3-carboxylate (136 mg, 0.66 mmol) as starting materials. LC-MS (Method 3) $t_R$=1.22 min, m/z (M+H)$^+$=362.1.

Step 2. 6-Chloro-4-((5-ethyl-1-methyl-4-oxo-4,5-dihydro-1H-pyrrolo[3,2-c]pyridin-3-yl)amino)-N-methylpyridazine-3-carboxamide (23b)

Compound 23a (100 mg, 0.28 mmol) was dissolved in a solution of methanamine (5 mL, 2 M in THF). The reaction mixture was stirred at r.t. for 2 h. The reaction was washed with water (5 mL) and extracted with EtOAc (10 mL*3). The combined organic layer was dried over sodium sulfate and filtered. The filtrate was concentrated under reduced pressure to afford the title compound 23b (80 mg, 80% yield). LC-MS (Method 3) $t_R$=1.25 min, m/z (M+H)$^+$=361.1.

Step 3. 6-(Cyclopropanecarboxamido)-4-((5-ethyl-1-methyl-4-oxo-4,5-dihydro-1H-pyrrolo[3,2-c]pyridin-3-yl)amino)-N-methylpyridazine-3-carboxamide (23)

Compound 23 (4.2 mg, 19% yield), a light-yellow solid, was synthesized by utilizing a similar preparative procedure of Step 8 in Example 1 with 23b (20 mg, 0.06 mmol) and cyclopropanecarboxamide (24 mg, 0.28 mmol) as starting materials. LC-MS (Method 1) $t_R$=3.12 min, m/z (M+H)$^+$=410.1. $^1$H NMR (400 MHz, DMSO-$d_6$) δ 11.28-11.26 (m, 2H), 8.98 (s, 1H), 8.09-8.07 (m, 1H), 7.38 (d, J=7.6 Hz, 1H), 7.06 (s, 1H), 6.58-6.55 (m, 1H), 3.92 (q, J=7.2 Hz, 2H), 3.71 (s, 3H), 2.85 (d, J=4.4 Hz, 3H), 2.11-2.08 (m, 1H), 1.23 (t, J=7.2 Hz, 3H), 0.95-0.73 (m, 4H).

Example 24

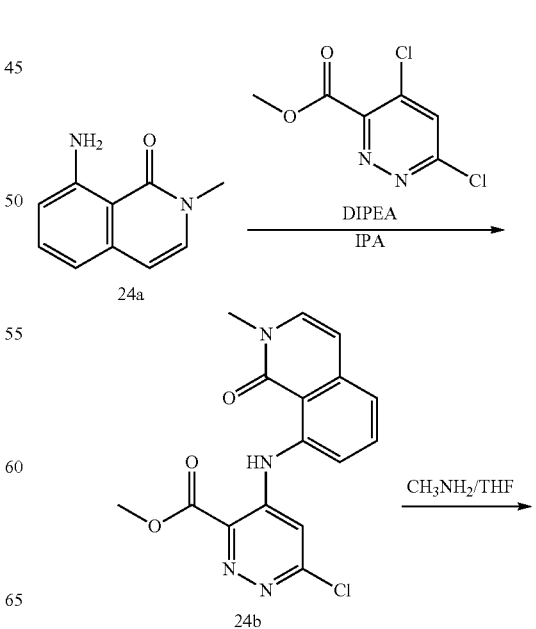

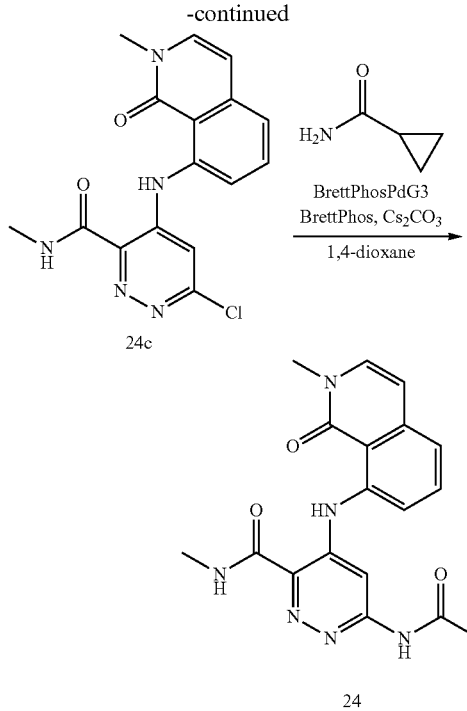

Step 1. Methyl 6-chloro-4-((2-methyl-1-oxo-1,2-dihydroisoquinolin-8-yl)amino)pyridazine-3-carboxylate (24b)

Compound 24b (100 mg, 21% yield), a yellow solid, was synthesized by utilizing a similar preparative procedure of Step 1 in Example 2 with 24a (240 mg, 1.38 mmol) and methyl 4,6-dichloropyridazine-3-carboxylate (342 mg, 1.65 mmol) as starting materials. $^1$H NMR (400 MHz, DMSO-$d_6$) δ 12.39 (s, 1H), 7.78 (s, 1H), 7.69-7.63 (m, 2H), 7.53 (d, J=8.4 Hz, 1H), 7.39 (dd, J=2.0, 6.8 Hz, 1H), 6.67 (d, J=7.2 Hz, 1H), 4.00 (s, 3H), 3.50 (s, 3H).

Step 2. 6-Chloro-N-methyl-4-((2-methyl-1-oxo-1,2-dihydroisoquinolin-8-yl)amino)pyridazine-3-carboxamide (24c)

Compound 24c (100 mg, 63% yield, 50% purity), a yellow solid, was synthesized by utilizing a similar preparative procedure of Step 2 in Example 23 with 24b (80 mg, 0.23 mmol) as the starting material. LC-MS (Method 3) $t_R$=1.39 min, m/z (M+H)$^+$=344.8.

Step 3. 6-(Cyclopropanecarboxamido)-N-methyl-4-((2-methyl-1-oxo-1,2-dihydroisoquinolin-8-yl)amino)pyridazine-3-carboxamide (24)

Compound 24 (11.6 mg, 20% yield), a yellow solid, was synthesized by utilizing a similar preparative procedure of Step 8 in Example 1 with 24c (50 mg, 0.15 mmol) and cyclopropanecarboxamide (25 mg, 0.29 mmol) as starting materials. LC-MS (Method 1) $t_R$=3.64 min, m/z (M+H)$^+$=393.2. $^1$H NMR (400 MHz, DMSO-$d_6$) δ 12.40 (s, 1H), 11.31 (s, 1H), 8.95-8.92 (m, 1H), 8.48 (s, 1H), 7.62-7.58 (m, 1H), 7.52 (d, J=8.0 Hz, 1H), 7.48 (d, J=6.8 Hz, 1H), 7.30 (d, J=7.6 Hz, 1H), 6.60 (d, J=7.2 Hz, 1H), 3.47 (s, 3H), 2.85 (d, J=4.8 Hz, 3H), 2.09-2.05 (m, 1H), 0.87-0.80 (m, 4H).

Example 25

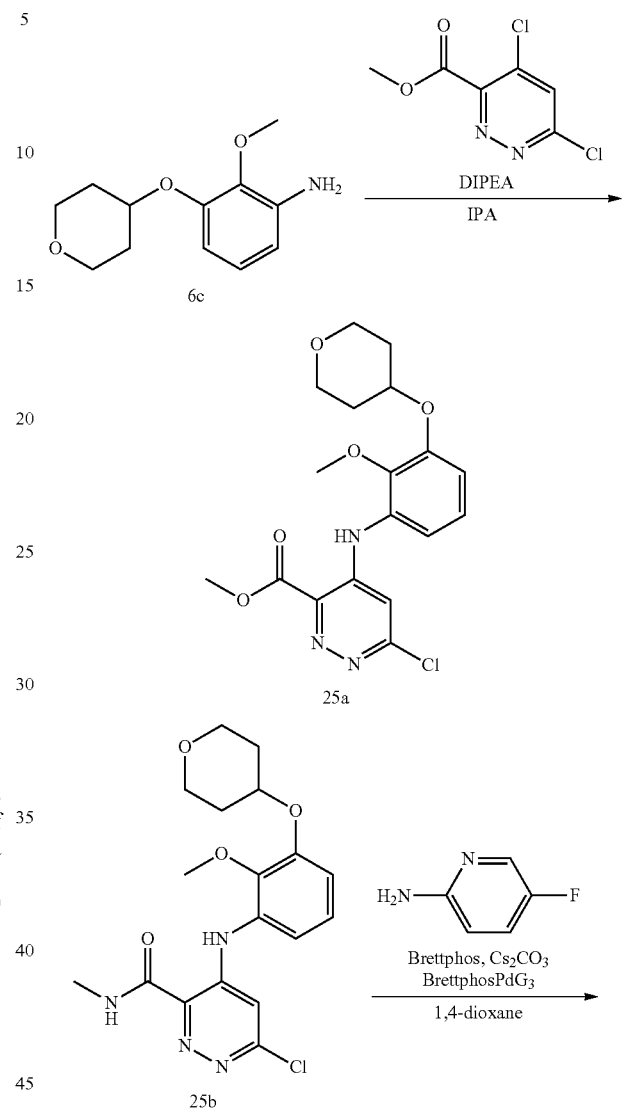

Step 1. Methyl 6-chloro-4-((2-methoxy-3-((tetrahydro-2H-pyran-4-yl)oxy)phenyl)amino)pyridazine-3-carboxylate (25a)

Compound 25a (100 mg, 13% yield), a yellow solid, was synthesized by utilizing a similar preparative procedure of Step 1 in Example 2 with 6c (450 mg, 2.02 mmol) and methyl 4,6-dichloropyridazine-3-carboxylate (500 mg, 2.42 mmol) as starting materials. $^1$H NMR (400 MHz, CDCl$_3$) δ 9.82 (s, 1H), 7.14-7.10 (m, 2H), 6.92 (d, J=8.0 Hz, 1H), 6.86 (d, J=7.6 Hz, 1H), 4.37-4.32 (m, 1H), 4.09 (s, 3H), 3.98-3.91 (m, 2H), 3.90 (s, 3H), 3.43-3.37 (m, 2H), 1.89-1.84 (m, 2H), 1.77-1.68 (m, 2H).

Step 2. 6-Chloro-4-((2-methoxy-3-((tetrahydro-2H-pyran-4-yl)oxy)phenyl)amino)-N-methylpyridazine-3-carboxamide (25b)

Compound 25b (60 mg, 60% yield), a white solid, was synthesized by utilizing a similar preparative procedure of Step 2 in Example 23 with 25a (100 mg, 0.25 mmol) as the starting material. LC-MS (Method 3) t$_R$=1.58 min, m/z (M+H)$^+$=393.4.

Step 3. 6-((5-Fluoropyridin-2-yl)amino)-4-((2-methoxy-3-((tetrahydro-2H-pyran-4-yl)oxy)phenyl)amino)-N-methylpyridazine-3-carboxamide (25)

Compound 25 (12.5 mg, 23% yield), an off-white solid, was synthesized by utilizing a similar preparative procedure of Step 8 in Example 1 with 25b (45 mg, 0.11 mmol) and 5-fluoropyridin-2-amine (39 mg, 0.34 mmol) as starting materials. LC-MS (Method 1) t$_R$=3.85 min, m/z (M+H)$^+$=469.2. $^1$H NMR (400 MHz, DMSO-d$_6$) δ 10.79 (s, 1H), 10.18 (s, 1H), 9.08-9.04 (m, 1H), 8.20-8.18 (m, 1H), 8.00 (s, 1H), 7.70-7.68 (m, 2H), 7.03-7.14 (m, 2H), 6.88 (dd, J=2.0, 7.6 Hz, 1H), 4.30-4.25 (m, 1H), 3.84 (s, 3H), 3.83-3.79 (m, 2H), 3.29-3.25 (m, 2H), 2.84 (d, J=4.8 Hz, 3H), 1.82-1.77 (m, 2H), 1.69-1.60 (m, 2H).

Example 26

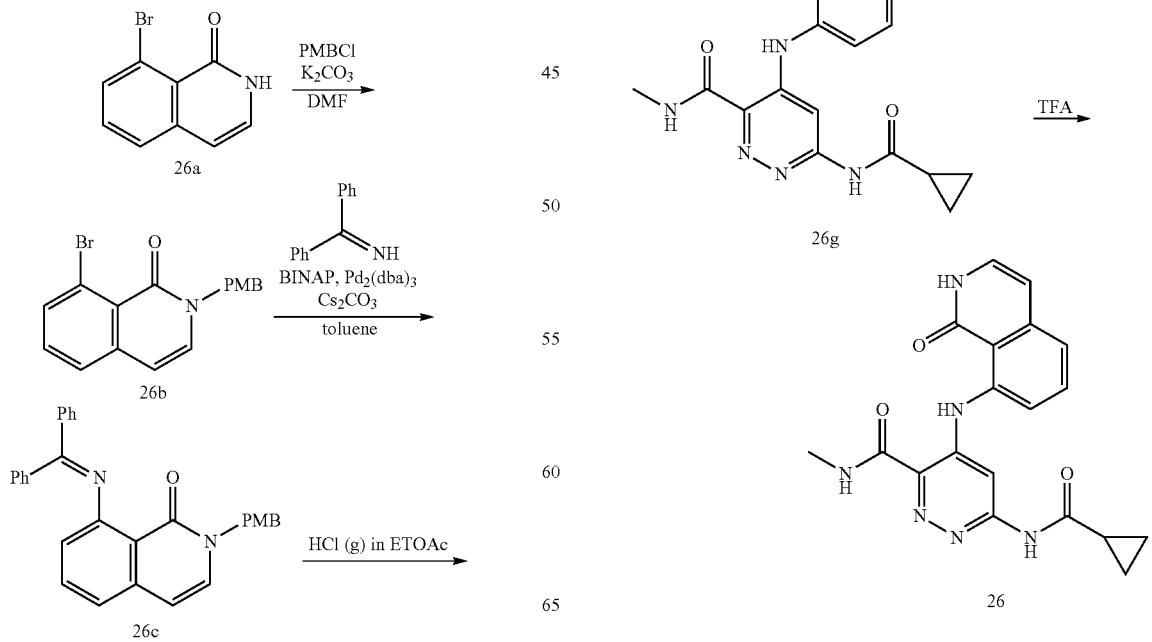

Step 1. 8-Bromo-2-(4-methoxybenzyl)isoquinolin-1(2H)-one (26b)

A mixture of 26a (1 g, 4.46 mmol), 1-(chloromethyl)-4-methoxybenzene (1.05 g, 6.69 mmol) and K$_2$CO$_3$ (1.23 g, 8.93 mmol) in DMF (10 mL) was stirred at 50° C. overnight. After cooling to r.t., the mixture was poured into water (30 mL) and extracted with EtOAc (20 mL*3). The combined organic layer was concentrated and the residue was purified by flash chromatography on silical gel (PE/EtOAc=3/1) to afford 26b (1.54 g, 97% yield) as a yellow oil. LC-MS (Method 3) t$_R$=1.61 min, m/z (M+H)$^+$=344.2.

Step 2. 8-((Diphenylmethylene)amino)-2-(4-methoxybenzyl)isoquinolin-1(2H)-one (26c)

A mixture of 26b (1.5 g, 4.36 mmol), diphenylmethanimine (2.37 g, 13.07 mmol), Pd$_2$(dba)$_3$ (399 mg, 0.44 mmol), BINAP (814 mg, 1.31 mmol) and Cs$_2$CO$_3$ (2.83 g, 8.72 mmol) in toluene (15 mL) was stirred at 100° C. overnight under N$_2$. After cooling to r.t., the reaction mixture was diluted with water (20 mL) and extracted with EtOAc (20 mL*3). The combined organic layer was concentrated and the residue was purified by flash chromatography on silica gel (PE/EtOAc=1/1) to afford 26c (870 mg, 45% yield) as a red solid. LC-MS (Method 3) t$_R$=1.78 min, m/z (M+H)$^+$=445.3.

Step 3. 8-Amino-2-(4-methoxybenzyl)isoquinolin-1(2H)-one hydrochloride (26d)

A mixture of 26c (830 mg, 1.87 mmol) in HCl/EtOAc (10 mL, 1 M) was stirred for 3 h at r.t. The formed solid was filtered and the filter cake was dried to afford 26d (380 mg, 64% yield) as a yellow solid. LC-MS (Method 3) t$_R$=1.55 min, m/z (M+H)$^+$=281.1.

Step 4. Methyl 6-chloro-4-((2-(4-methoxybenzyl)-1-oxo-1,2-dihydroisoquinolin-8-yl)amino)pyridazine-3-carboxylate (26e)

A mixture of 26d (310 mg, 0.98 mmol), methyl 4,6-dichloropyridazine-3-carboxylate (304 mg, 1.47 mmol) and DIPEA (379 mg, 2.94 mmol) in $^i$PrOH (5 mL) was stirred at 80° C. for 12 h. After cooling to r.t., the formed solid was filtered and dried to afford 26e (100 mg, 23% yield) as a yellow solid. LC-MS (Method 3) t$_R$=1.56 min, m/z (M+H)$^+$=451.2.

Step 5. 6-Chloro-4-((2-(4-methoxybenzyl)-1-oxo-1,2-dihydroisoquinolin-8-yl)amino)-N-methylpyridazine-3-carboxamide (26f)

A mixture of 26e (90 mg, 0.20 mmol) and CH$_3$NH$_2$ (2 mmol, 2 mL, 1 M in THF) was stirred at r.t. for 1 h. The solid was filtered and dried to afford 26f (80 mg, 89% yield) as a yellow solid. LC-MS (Method 3) t$_R$=1.61 min, m/z (M+H)$^+$=450.2.

Step 6. 6-(Cyclopropanecarboxamido)-4-((2-(4-methoxybenzyl)-1-oxo-1,2-dihydroisoquinolin-8-yl)amino)-N-methylpyridazine-3-carboxamide (26g)

A mixture of 26f (90 mg, 0.20 mmol), cyclopropanecarboxamide (51 mg, 0.60 mmol), BrettPhos Pd G3 (18 mg, 0.02 mmol), BrettPhos (21 mg, 0.04 mmol) and Cs$_2$CO$_3$ (130 mg, 0.40 mmol) in 1,4-dioxane (1 mL) was stirred at 100° C. for 3 h under N$_2$ atmosphere. After cooling to r.t., the mixture was concentrated and the residue was purified by flash chromatography on silica gel (DCM/MeOH=20/1) to afford 26g (25 mg, 32% yield) as a white solid. LC-MS (Method 3) t$_R$=1.50 min, m/z (M+H)$^+$=499.5.

Step 7. 6-(Cyclopropanecarboxamido)-N-methyl-4-((1-oxo-1,2-dihydroisoquinolin-8-yl)amino)pyridazine-3-carboxamide (26)

A mixture of 26g (50 mg, 0.10 mmol) and TFA (2 mL) was stirred at 110° C. for 18 h. The mixture was concentrated and the residue was purified by Prep-HPLC (Method A) to afford 26 (3 mg, 8% yield) as a white solid. LC-MS (Method 1) t$_R$=2.81 min, m/z (M+H)$^+$=379.2. $^1$H NMR (400 MHz, DMSO-d$_6$) δ 12.30 (s, 1H), 11.32 (s, 1H), 11.20 (d, J=6.4 Hz, 1H), 8.92 (d, J=4.0 Hz, 1H), 8.49 (s, 1H), 7.57 (t, J=8.0 Hz, 1H), 7.50 (d, J=8.0 Hz, 1H), 7.29 (d, J=8.0 Hz, 1H), 7.15 (t, J=6.8 Hz, 1H), 6.53 (d, J=6.8 Hz, 1H), 2.83 (d, J=4.8 Hz, 3H), 2.09-2.05 (m, 1H), 0.87-0.80 (m, 4H).

Example 27

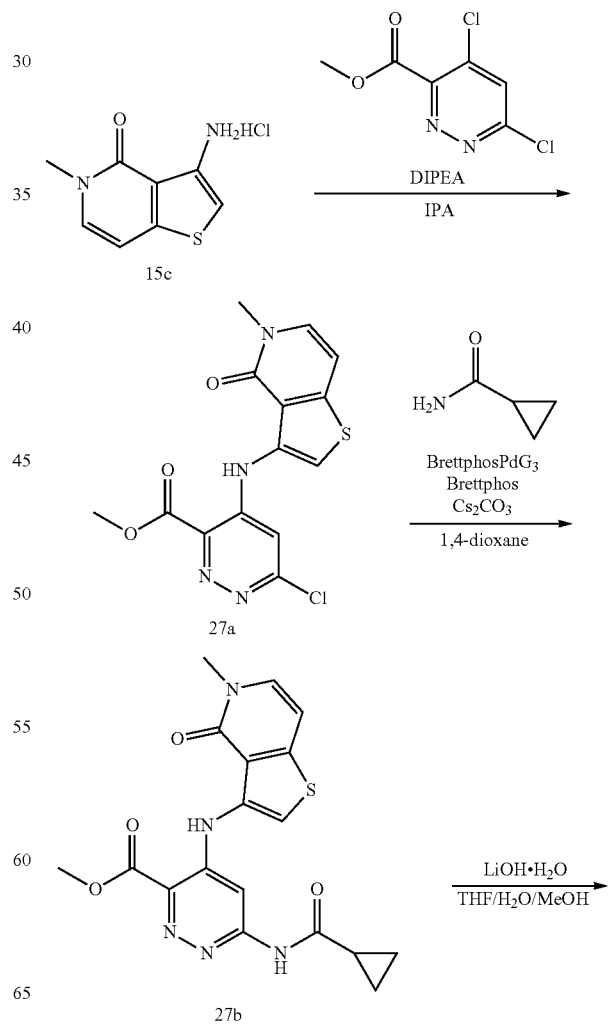

-continued

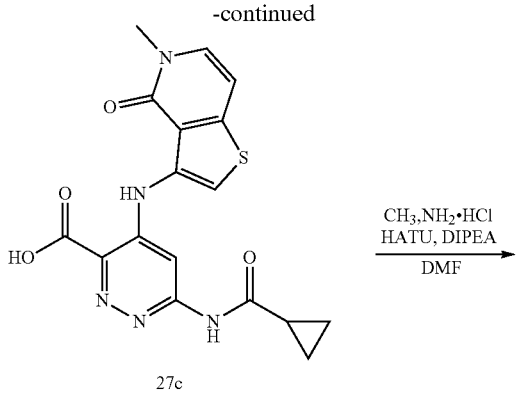

27c

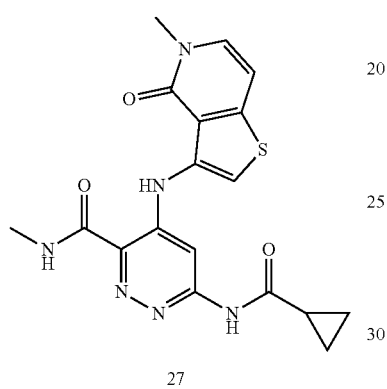

27

Step 1. Methyl 6-chloro-4-((5-methyl-4-oxo-4,5-dihydrothieno[3,2-c]pyridin-3-yl)amino)pyridazine-3-carboxylate (27a)

Compound 27a (100 mg, 34% yield), a blue solid, was synthesized by utilizing a similar preparative procedure of Step 1 in Example 2 with 15c (150 mg, 0.83 mmol) and methyl 4,6-dichloropyridazine-3-carboxylate (258 mg, 1.25 mmol) as starting materials. $^1$H NMR (400 MHz, DMSO-d$_6$) δ 11.50 (s, 1H), 7.81 (s, 1H), 7.67-7.65 (m, 2H), 6.96 (d, J=7.6 Hz, 1H), 4.01 (s, 3H), 3.54 (s, 3H).

Step 2. Methyl 6-(cyclopropanecarboxamido)-4-((5-methyl-4-oxo-4,5-dihydrothieno[3,2-c]pyridin-3-yl)amino)pyridazine-3-carboxylate (27b)

Compound 27b (100 mg, 59% yield), a yellow solid, was synthesized by utilizing a similar preparative procedure of Step 8 in Example 1 with 27a (150 mg, 0.43 mmol) and cyclopropanecarboxamide (73 mg, 0.86 mmol) as starting materials. LC-MS (Method 3) t$_R$=1.36 min, m/z (M+H)$^+$=400.2.

Step 3. 6-(Cyclopropanecarboxamido)-4-((5-methyl-4-oxo-4,5-dihydrothieno[3,2-c]pyridin-3-yl)amino)pyridazine-3-carboxylic acid (27c)

A mixture of 27b (30 mg, 0.08 mmol), LiOH·H$_2$O (10 mg, 0.24 mmol) in THF/MeOH/H$_2$O (0.6 mL, v/v/v=1/1/1) was stirred at r.t. for 3 h. The mixture was diluted with water (5 mL) and acidified with 1 N HCl to pH=4, and concentrated to afford compound 27c (28 mg, 97% yield) as a white solid. LC-MS (Method 3) t$_R$=1.04 min, m/z (M+H)$^+$=386.1.

Step 4. 6-(Cyclopropanecarboxamido)-N-methyl-4-((5-methyl-4-oxo-4,5-dihydrothieno[3,2-c]pyridin-3-yl)amino)pyridazine-3-carboxamide (27)

A mixture of 27c (28 mg, 0.07 mmol), methanamine hydrochloride (15 mg, 0.22 mmol), HATU (138 mg, 0.36 mumol), DIPEA (94 mg, 0.73 mmol) in DMF (1 mL) was stirred at r.t. for 2 h. The mixture was diluted with water (5 mL), extracted with EtOAc (5 mL). The organic layer was concentrated. The residue was purified by Prep-HPLC (Method A) to afford 27 (1.2 mg, 4% yield) as a white solid. LC-MS (Method 1) t$_R$=3.03 min, m/z (M+H)$^+$=399.1. $^1$H NMR (400 MHz, CD$_3$OD) δ 8.62 (s, 1H), 7.47 (d, J=7.2 Hz, 1H), 7.23 (s, 1H), 6.85 (d, J=6.8 Hz, 1H), 3.62 (s, 3H), 3.00 (s, 3H), 2.00-1.92 (m, 1H), 1.03-1.01 (m, 2H), 0.96-0.93 (m, 2H).

Example 28

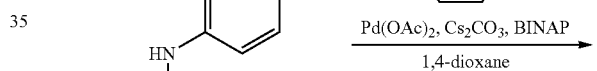
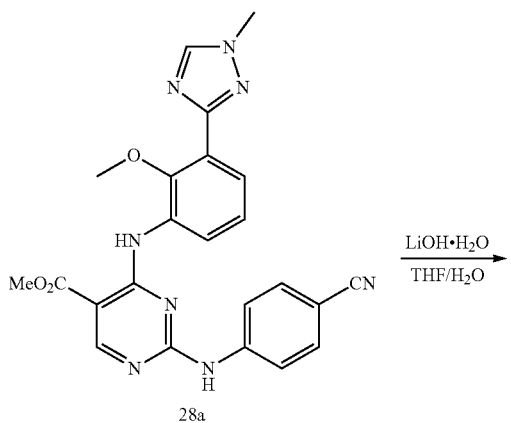

28a

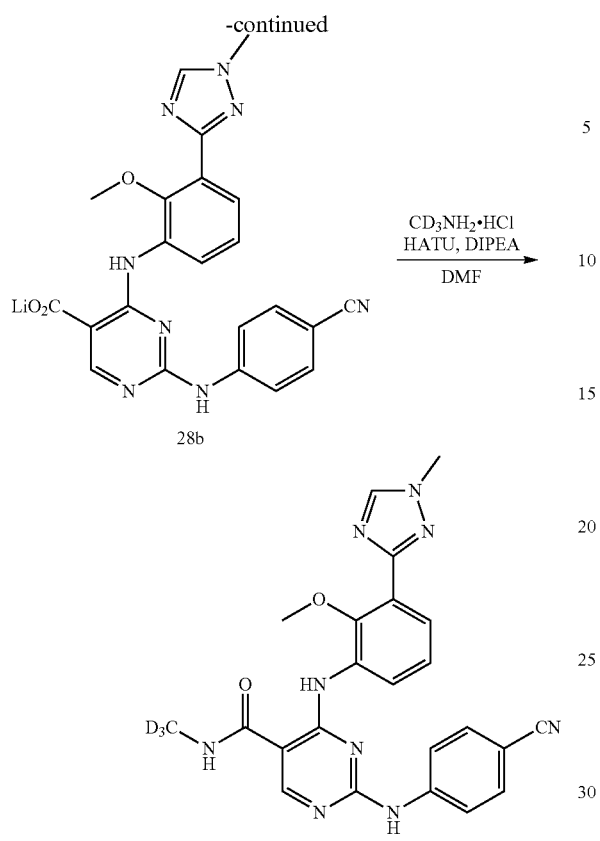

mg, 0.18 mmol), HATU (70 mg, 0.18 mmol) and DIPEA (47 mg, 0.36 mmol). The mixture was stirred overnight at r.t. The mixture was purified by Prep-HPLC (Method E) to afford compound 28 (8.5 mg, 31% yield) as an off-white solid. LC-MS (Method 4) $t_R$=3.20 min, m/z (M+H)$^+$=459.3. $^1$H NMR (400 MHz, DMSO-$d_6$) δ 11.76 (s, 1H), 10.17 (s, 1H), 8.72 (s, 1H), 8.57-8.54 (m, 3H), 7.94 (d, J=8.8 Hz, 2H), 7.72 (d, J=8.8 Hz, 2H), 7.57 (dd, J=8.0, 1.6 Hz, 1H), 7.26 (t, J=8.0 Hz, 1H), 3.95 (s, 3H), 3.79 (s, 3H).

Example 29

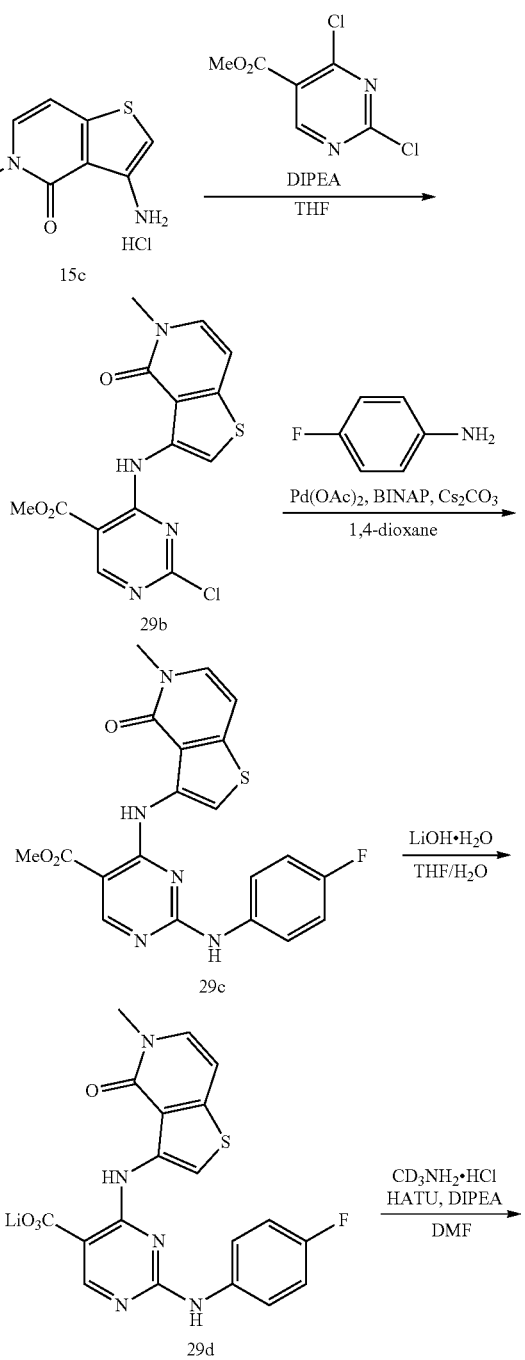

Step 1. Methyl 2-((4-cyanophenyl) amino)-4-((2-methoxy-3-(1-methyl-1H-1,2,4-triazol-3-yl) phenyl) amino)pyrimidine-5-carboxylate (28a)

A mixture of 2b (50 mg, 0.133 mmol), 4-aminobenzonitrile (17 mg, 0.146 mmol), Cs$_2$CO$_3$ (87 mg, 0.266 mmol), BINAP (16.2 mg, 0.026 mmol) and Pd(OAc)$_2$ (2.9 mg, 0.013 mmol) in 1,4-dioxane (1.4 mL) was stirred at 85° C. under N$_2$ overnight. The mixture was cooled down to r.t., then filtered through a pad of celite and concentrated. The residue was purified by Prep-TLC (DCM/MeOH=10/1) to give the compound 28a (21 mg, 35% yield) as a brown-yellow oil. LC-MS (Method 4) $t_R$=4.16 min, m/z (M+H)$^+$=457.3.

Step 2. Lithium 2-((4-cyanophenyl) amino)-4-((2-methoxy-3-(1-methyl-1H-1,2,4-triazol-3-yl)phenyl) amino)pyrimidine-5-carboxylate (28b)

To a stirred mixture of 28a (21 mg, 0.046 mmol) in THF (0.6 mL) and water (0.3 mL) was added lithium hydroxide monohydrate (4 mg, 0.092 mmol) for 12 h at r.t. The mixture was concentrated under reduced pressure to give the crude compound 28b (27 mg, yield given) as a brown-yellow solid. LC-MS (Method 4) $t_R$=3.34 min, m/z (M+H)$^+$=443.2.

Step 3. 2-((4-Cyanophenyl) amino)-4-((2-methoxy-3-(1-methyl-1H-1,2,4-triazol-3-yl) phenyl) amino)-N-(methyl-d$_3$)pyrimidine-5-carboxamide (28)

To a stirred mixture of 28b (27 mg, 0.06 mmol) in DMF (1.0 mL) were added methyl-d$_3$-amine hydrochloride (13

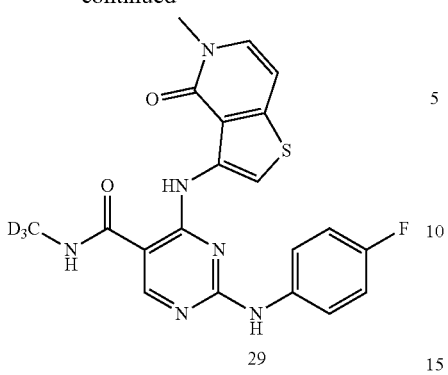

¹H NMR (400 MHz, DMSO-d₆) δ 12.46 (s, 1H), 9.67 (s, 1H), 8.56 (s, 1H), 8.30 (s, 1H), 7.72-7.70 (m, 2H), 7.58 (d, J=7.2 Hz, 1H), 7.20-7.16 (m, 2H), 6.88 (d, J=7.2 Hz, 1H), 3.53 (s, 3H).

Example 30

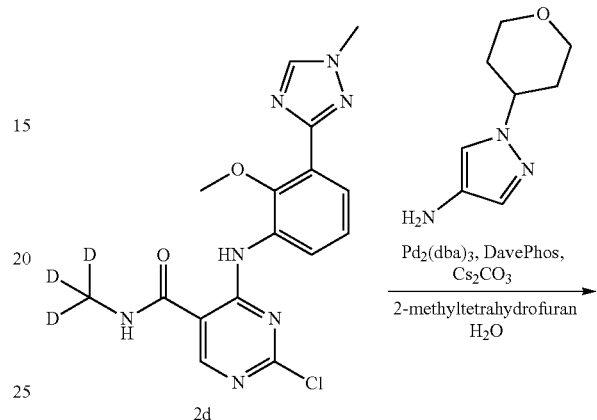

Step 1. Methyl 2-chloro-4-((5-methyl-4-oxo-4,5-dihydrothieno[3,2-c]pyridin-3-yl) amino) pyrimidine-5-carboxylate (29b)

To a stirred mixture of 15c (36 mg, 0.167 mmol) and methyl 2,4-dichloropyrimidine-5-carboxylate (37 mg, 0.184 mmol) in THF (0.8 mL) was added DIPEA (43 mg, 0.334 mmol) at r.t. The mixture was stirred for 6 h at r.t. The mixture was concentrated and purified by Prep-TLC (PE/EtOAc=1/4) to give the product 29b (16 mg, 27% yield) as a light-yellow solid. LC-MS (Method 4) $t_R$=4.46 min, m/z (M+H)⁺=351.1.

Step 2. Methyl 2-((4-fluorophenyl) amino)-4-((5-methyl-4-oxo-4,5-dihydrothieno[3,2-c]pyridin-3-yl) amino)pyrimidine-5-carboxylate (29c)

A mixture of 29b (32 mg, 0.091 mmol), 4-fluoroaniline (12 mg, 0.11 mmol), Cs₂CO₃ (59 mg, 0.182 mmol), BINAP (16.2 mg, 0.026 mmol) and Pd(OAc)₂ (2.9 mg, 0.013 mmol) in 1,4-dioxane (1.0 mL) was stirred at 85° C. under N₂ overnight. The mixture was cooled down to r.t., then filtered through a pad of celite and concentrated. The residue was purified by Prep-TLC (DCM/MeOH=10/1) to give the product 29c (30 mg, 77% yield) as a brown-yellow oil. LC-MS (Method4) $t_R$=4.53 min, m/z (M+H)⁺=426.2.

Step 3. Lithium 2-((4-fluorophenyl) amino)-4-((5-methyl-4-oxo-4,5-dihydrothieno[3,2-c]pyridin-3-yl) amino)pyrimidine-5-carboxylate (29d)

To a stirred mixture of 29c (30 mg, 0.07 mmol) in THF (0.6 mL) and water (0.3 mL) was added lithium hydroxide monohydrate (8 mg, 0.21 mmol) for 12 h at r.t. The mixture was concentrated under reduced pressure to give the crude compound 29d (35 mg, yield given) as a brown-yellow solid. LC-MS (Method 4) $t_R$=3.63 min, m/z (M+H)⁺=412.1.

Step 4. 2-((4-Fluorophenyl) amino)-N-(methyl-d₃)-4-((5-methyl-4-oxo-4,5-dihydrothieno[3,2-c]pyridin-3-yl) amino)pyrimidine-5-carboxamide (29)

To a stirred mixture of 29d (35 mg, 0.08 mmol) in DMF (1.0 mL) was added methyl-d₃-amine hydrochloride (17 mg, 0.24 mmol), HATU (91 mg, 0.24 mmol) and DIPEA (62 mg, 0.48 mmol). The mixture was stirred overnight at r.t. The mixture was purified by Prep-HPLC (Method E) to afford the title product 29 (2.7 mg, 8% yield) as a light-yellow solid. LC-MS (Method 4) $t_R$=3.48 min, m/z (M+H)⁺=428.1.

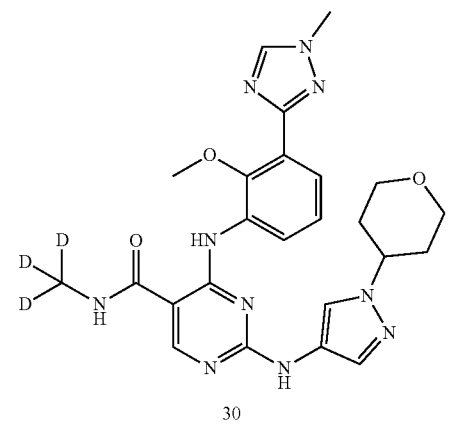

Step 1. 4-((2-Methoxy-3-(1-methyl-1H-1,2,4-triazol-3-yl)phenyl)amino)-N-(methyl-d₃)-2-((1-(tetrahydro-2H-pyran-4-yl)-1H-pyrazol-4-yl)amino)pyrimidine-5-carboxamide (30)

Compound 30 (32.2 mg, 48% yield), an off-white solid, was synthesized by utilizing a similar preparative procedure of Step 4 in Example 2 with 2d (50 mg, 0.13 mmol) and 1-(tetrahydro-2H-pyran-4-yl)-1H-pyrazol-4-amine (33 mg, 0.20 mmol) as starting materials. LC-MS (Method 4) $t_R$=3.48 min, m/z (M+H)⁺=508.2. ¹H NMR (400 MHz, CDCl₃) δ 11.22 (s, 1H), 8.31 (s, 1H), 8.10 (s, 1H), 7.75-7.73 (m, 2H), 7.46-7.44 (m, 1H), 7.17 (t, J=8.0 Hz, 1H), 6.92-6.90 (m, 1H), 5.93 (s, 1H), 4.22-4.20 (m, 1H), 4.09-4.06 (m, 2H), 4.01 (s, 3H), 3.89 (s, 3H), 3.52-3.50 (m, 2H), 2.05-1.92 (m, 4H).

Example 31

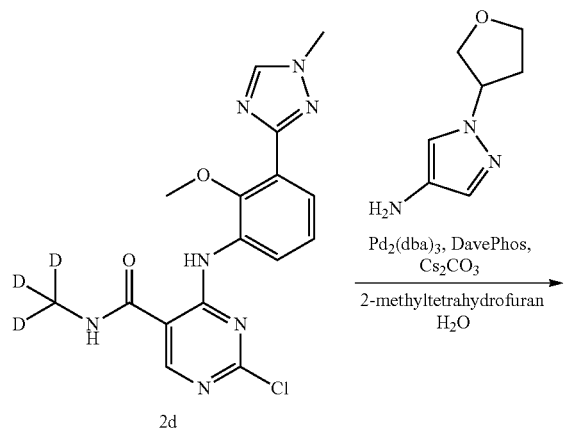

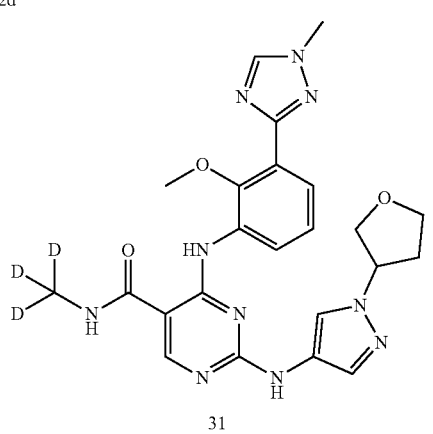

Step 1. 4-((2-Methoxy-3-(1-methyl-1H-1,2,4-triazol-3-yl)phenyl)amino)-N-(methyl-d₃)-2-((1-(tetrahydrofuran-3-yl)-1H-pyrazol-4-yl)amino)pyrimidine-5-carboxamide (31)

Compound 31 (6 mg, 9% yield), an off-white solid, was synthesized by utilizing a similar preparative procedure of Step 4 in Example 2 with 2d (50 mg, 0.13 mmol) and 1-(tetrahydrofuran-3-yl)-1H-pyrazol-4-amine (31 mg, 0.20 mmol) as starting materials. LC-MS (Method 4) $t_R$=3.33 min, m/z (M+H)⁺=494.2. ¹H NMR (400 MHz, CDCl₃) δ 11.27 (s, 1H), 8.32 (s, 1H), 8.11 (s, 1H), 7.71-7.69 (m, 2H), 7.48 (s, 1H), 7.16 (t, J=8.0 Hz, 1H), 6.11 (s, 1H), 4.83-4.81 (m, 1H), 4.07-4.00 (m, 6H), 3.93-3.82 (m, 4H), 2.39-2.34 (m, 2H).

Example 32

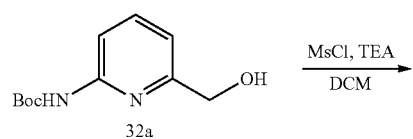

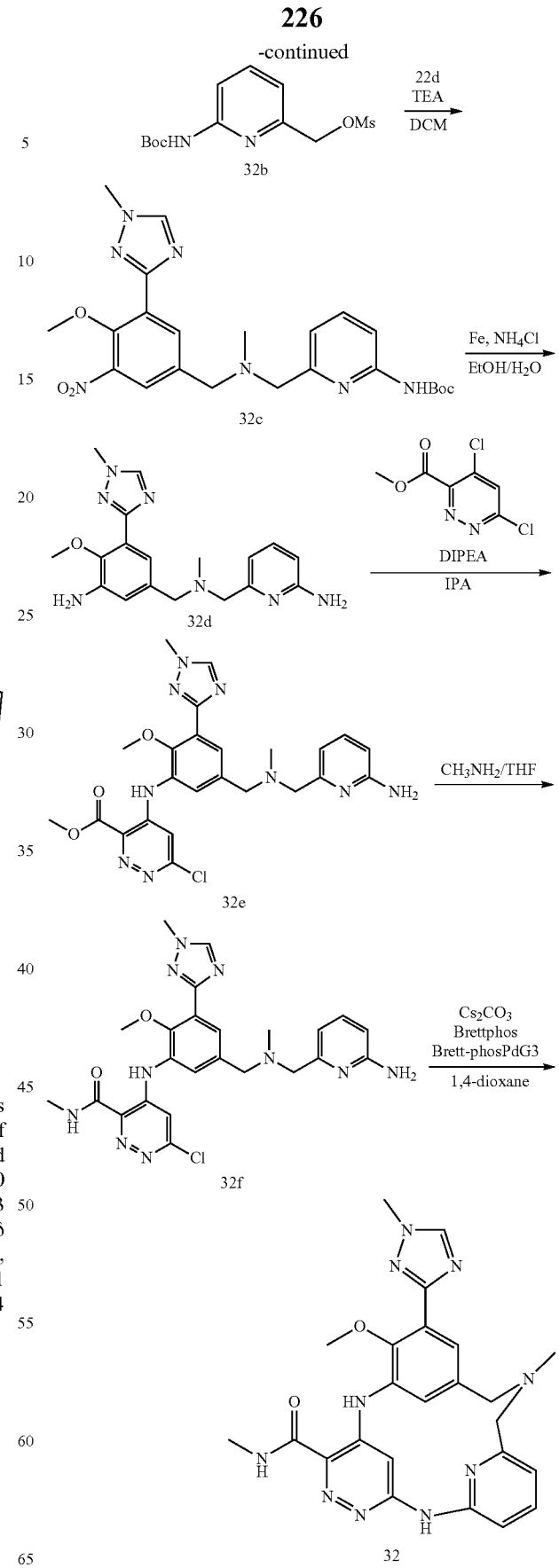

Step 1. (6-((Tert-butoxycarbonyl)amino)pyridin-2-yl)methyl methanesulfonate (32b)

To a solution of 32a (300 mg, 1.34 mmol) and TEA (406 mg, 4.01 mmol) in DCM (3 mL) was added MSCl (161 mg, 1.40 mmol) at 0° C. After stirring for 2 h at this temperature, the mixture was used for next step without working up. LC-MS (Method 3) $t_R$=1.12 min, m/z (M+H)$^+$=303.2.

Step 2. Tert-butyl (6-(((4-methoxy-3-(1-methyl-1H-1,2,4-triazol-3-yl)-5-nitrobenzyl)(methyl)amino)methyl)pyridin-2-yl)carbamate (32c)

To a solution of 32b (400 mg, 1.32 mmol) and TEA (402 mg, 3.97 mmol) in DCM (5 mL) was added 22d (275 mg, 0.99 mmol) in DCM (5 mL) at 0° C. The reaction mixture was stirred at r.t. overnight. The mixture was concentrated. The residue was purified by flash chromatography on silica gel (DCM/MeOH=30/1) to afford the title compound 32c (213 mg, 33% yield) as a yellow oil. $^1$H NMR (400 MHz, DMSO-d$_6$) δ 9.62 (s, 1H), 8.63 (s, 1H), 8.22 (d, J=2.0 Hz, 1H), 7.89 (d, J=2.0 Hz, 1H), 7.71-7.64 (m, 2H), 7.11 (d, J=6.4 Hz, 1H), 3.97 (s, 3H), 3.82 (s, 3H), 3.66 (s, 2H), 3.57 (s, 2H), 2.18 (s, 3H), 1.46 (s, 9H).

Step 3. 6-(((3-Amino-4-methoxy-5-(1-methyl-1H-1,2,4-triazol-3-yl)benzyl)(methyl)amino)methyl)pyridin-2-amine (32d)

Compound 32d (300 mg, purity 35%, 62% yield), a yellow solid, was synthesized by utilizing a similar preparative procedure of Step 2 in Example 6 with 32c (230 mg, 0.48 mmol) as the starting material. LC-MS (Method 3) $t_R$=1.12 min, m/z (M+H)$^+$=354.2.

Step 4. Methyl 4-((5-(((((6-aminopyridin-2-yl)methyl)(methyl)amino)methyl)-2-methoxy-3-(1-methyl-1H-1,2,4-triazol-3-yl)phenyl)amino)-6-chloropyridazine-3-carboxylate (32e)

Compound 32e (45 mg, 24% yield), a yellow oil, was synthesized by utilizing a similar preparative procedure of Step 1 in Example 2 with 32d (270 mg, 60% purity, 0.36 mmol) and methyl 4,6-dichloropyridazine-3-carboxylate (89 mg, 0.43 mmol) as starting materials. $^1$H NMR (400 MHz, DMSO-d$_6$) δ 9.87 (s, 1H), 8.82 (s, 1H), 8.00-7.97 (m, 1H), 7.76-7.73 (m, 1H), 7.53-7.50 (m, 1H), 7.25-7.23 (m, 1H), 6.69 (s, 1H), 6.56 (brs, 2H), 4.25 (s, 2H), 4.08 (s, 2H), 4.00 (s, 3H), 3.96 (s, 3H), 3.72 (s, 3H), 3.14 (s, 3H).

Step 5. 4-((5-(((((6-Aminopyridin-2-yl)methyl)(methyl)amino)methyl)-2-methoxy-3-(1-methyl-1H-1,2,4-triazol-3-yl)phenyl)amino)-6-chloro-N-methylpyridazine-3-carboxamide (32f)

Compound 32f (25 mg, 83% yield), a yellow oil, was synthesized by utilizing a similar preparative procedure of Step 2 in Example 23 with 32e (30 mg, 0.06 mmol) and methylamine (2.36 mmol, 1.2 mL, 2 M in THF) as starting materials. LC-MS (Method 3) $t_R$=1.27 min, m/z (M+H)$^+$=523.5.

Step 6. 10-Methoxy-N,15-dimethyl-11-(1-methyl-1,2,4-triazol-3-yl)-2,4,5,8,15,21-hexazatetracyclo[15.3.1.13,7.19,13]tricosa-1(21),3(23),4,6,9,11,13(22),17,19-nonaene-6-carboxamide (32)

Compound 32f (25 mg, 0.05 mmol), BrettPhos (3 mg, 0.005 mmol), BrettPhos Pd G3 (4 mg, 0.005 mmol) and Cs$_2$CO$_3$ (47 mg, 0.14 mmol) were dissolved in 1,4-dioxane (15 mL). The resulting mixture was stirred at 100° C. for 3 h under N$_2$. The mixture was filtered. The filtrate was concentrated. The residue was purified by Prep-HPLC (Method A) to give the title compound 32 (4 mg, 17% yield) as a yellow solid. LC-MS (Method 2) $t_R$=2.80 min, m/z (M+H)$^+$=487.2. $^1$H NMR (400 MHz, DMSO-d$_6$) δ 10.67 (s, 1H), 10.44 (brs, 1H), 9.89 (s, 1H), 9.06-9.03 (m, 1H), 8.56 (s, 1H), 8.27 (s, 1H), 7.63 (t, J=8.0 Hz, 1H), 7.44 (d, J=2.0 Hz, 1H), 7.05 (d, J=8.0 Hz, 1H), 6.84 (d, J=7.2 Hz, 1H), 3.95 (s, 3H), 3.78 (s, 3H), 3.69 (s, 2H), 3.19 (s, 2H), 2.87 (d, J=4.8 Hz, 3H), 2.30 (s, 3H).

Example 33

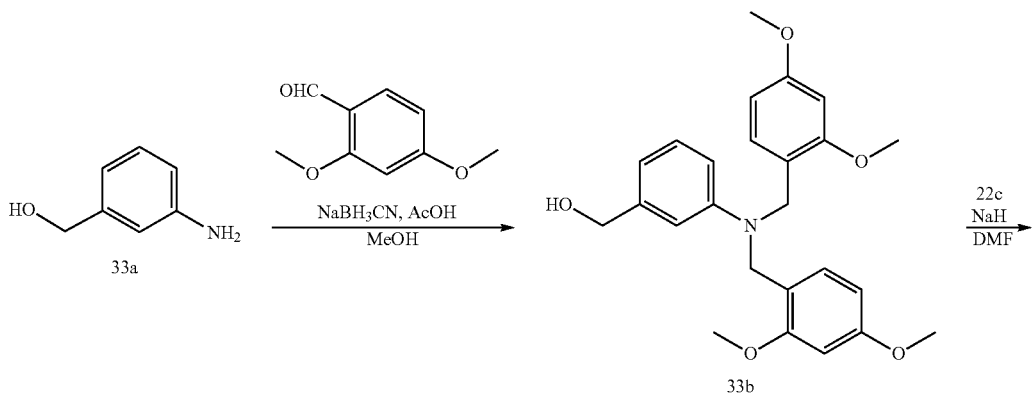

-continued
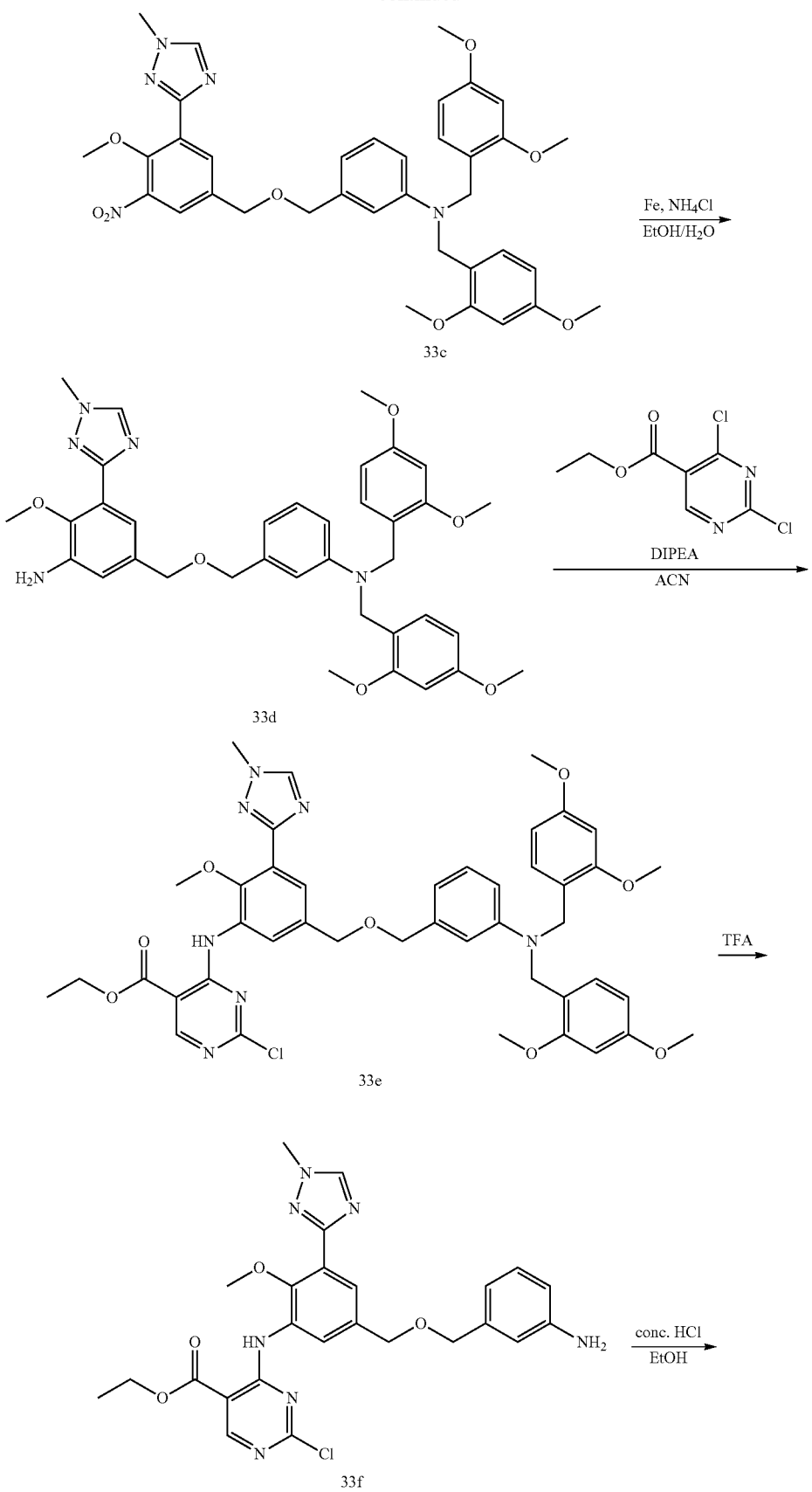

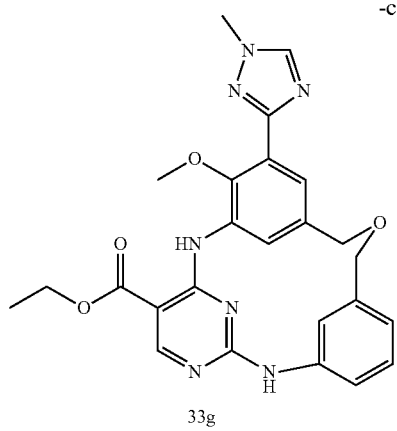

33g

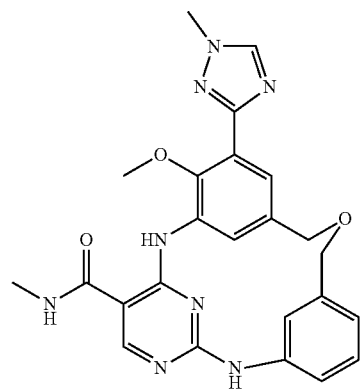

33

Step 1. (3-(Bis(2,4-dimethoxybenzyl)amino)phenyl)methanol (33b)

Compound 33a (2.0 g, 16.24 mmol), 2,4-dimethoxybenzaldehyde (8.10 g, 48.72 mmol) and AcOH (975 mg, 16.24 mmol) were dissolved in MeOH (30 mL). The above reaction was stirred at r.t. for 10 min. Then NaBH$_3$CN (5.10 g, 81.20 mmol) was added to the mixture. The mixture was stirred at r.t. for 4 h. The mixture was diluted with H$_2$O (30 mL) and extracted with EtOAc (50 mL*2). The combined organic layer was concentrated to dryness. The residue was purified by flash chromatography on silica gel (PE/EtOAc=30/1) to give the title compound 33b (1.1 g, 16% yield) as a yellow oil. LC-MS (Method 3) $t_R$=1.66 min, m/z (M+H)$^+$=424.3.

Step 2. N,N-Bis(2,4-dimethoxybenzyl)-3-(((4-methoxy-3-(1-methyl-1H-1,2,4-triazol-3-yl)-5-nitrobenzyl)oxy)methyl)aniline (33c)

To a mixture of 33b (311 mg, 0.73 mmol) in DMF (2 mL) was added NaH (35 mg, 0.88 mmol, 60% in mineral oil) at 0° C. The mixture was stirred at r.t. for 30 min. Then 22c (200 mg, 0.61 mmol) was added at 0° C. The mixture was stirred at r.t. for 3 h. The mixture was quenched with H$_2$O (5 mL) and extracted with EtOAc (15 mL*2). The combined organic layer was washed with brine (15 mL), dried over Na$_2$SO$_4$ and filtered. The filtrate was concentrated. The residue was purified by flash chromatography on silica gel (EtOAc) to give the title compound 33c (150 mg, 37% yield) as a yellow solid. LC-MS (Method 3) $t_R$=1.78 min, m/z (M+H)$^+$=670.4.

Step 3. 3-(((3-Amino-4-methoxy-5-(1-methyl-1H-1,2,4-triazol-3-yl)benzyl)oxy)methyl)-N,N-bis(2,4-dimethoxybenzyl)aniline (33d)

Compound 33d (150 mg, 50% purity, 52% yield), a yellow solid, was synthesized by utilizing a similar preparative procedure of Step 2 of Example 6 with 33c (150 mg, 0.22 mmol) as the starting material. LC-MS (Method 3) $t_R$=1.67 min, m/z (M+H)$^+$=640.8.

Step 4. Ethyl 4-((5-(((3-(bis(2,4-dimethoxybenzyl)amino)benzyl)oxy)methyl)-2-methoxy-3-(1-methyl-1H-1,2,4-triazol-3-yl)phenyl)amino)-2-chloropyrimidine-5-carboxylate (33e)

A mixture of ethylethyl 2,4-dichloropyrimidine-5-carboxylate (45 mg, 0.20 mmol), 33d (100 mg, 0.16 mmol) and DIPEA (61 mg, 0.47 mmol) in ACN (4 mL) was stirred at 80° C. for 3 h. The mixture was concentrated and the residue was purified by flash chromatography on silica gel (PE/EtOAc=1/1) to afford 33e (37 mg, 29% yield) as a yellow solid. LC-MS (Method 3) $t_R$=1.92 min, m/z (M−H)$^-$=822.6.

Step 5. Ethyl 4-((5-(((3-aminobenzyl)oxy)methyl)-2-methoxy-3-(1-methyl-1H-1,2,4-triazol-3-yl)phenyl)amino)-2-chloropyrimidine-5-carboxylate (33f)

Compound 33e (37 mg, 0.05 mmol) was dissolved in TFA (3 mL) and the resulting mixture was stirred at 50° C. for 3 h. The mixture was concentrated to give the crude compound 33f (30 mg, yield given) as a red solid. LC-MS (Method 3) $t_R$=1.55 min, m/z (M+H)$^+$=524.5.

Step 6. Ethyl 10-methoxy-11-(1-methyl-1,2,4-triazol-3-yl)-15-oxa-2,4,8,23-tetrazatetracyclo [15.3.1.13,7.19,13]tricosa-1(21),3(23),4,6,9,11,13(22),17,19-nonaene-6-carboxylate (33g)

To a mixture of 33f (20 mg, 0.04 mmol) in EtOH (6 mL) was added 1 drop of conc. HCl. The mixture was stirred at 60° C. for 2 h. The mixture was concentrated to give the crude title compound 33g (20 mg, 99% yield) as a yellow solid. LC-MS (Method 3) $t_R$=1.56 min, m/z (M−H)$^-$=486.5.

Step 7. 10-Methoxy-N-methyl-11-(1-methyl-1,2,4-triazol-3-yl)-15-oxa-2,4,8,23-tetrazatetracyclo [15.3.1.13,7.19,13]tricosa-1(21),3(23),4,6,9,11,13(22),17,19-nonaene-6-carboxamide (33)

A mixture of 33g (25 mg, 0.05 mmol) in methylamine (4 mL, 30% wt in ethanol solution) was stirred at 90° C. for 16 h. The mixture was concentrated. And the residue was purified by Prep-HPLC (Method A) to afford 33 (3.2 mg, 13% yield) as a yellow solid. LC-MS (Method 1) $t_R$=2.94 min, m/z (M+H)$^+$=473.2. $^1$H NMR (400 MHz, CD$_3$OD) δ 8.92 (d, J=1.2 Hz, 1H), 8.52 (s, 1H), 8.47 (s, 1H), 8.41 (d, J=1.6 Hz, 1H), 7.46 (d, J=1.6 Hz, 1H), 7.33-7.27 (m, 1H), 7.06-7.03 (m, 2H), 4.59 (s, 2H), 4.51 (s, 2H), 4.01 (s, 3H), 3.78 (s, 3H), 2.91 (s, 3H).

Example 34

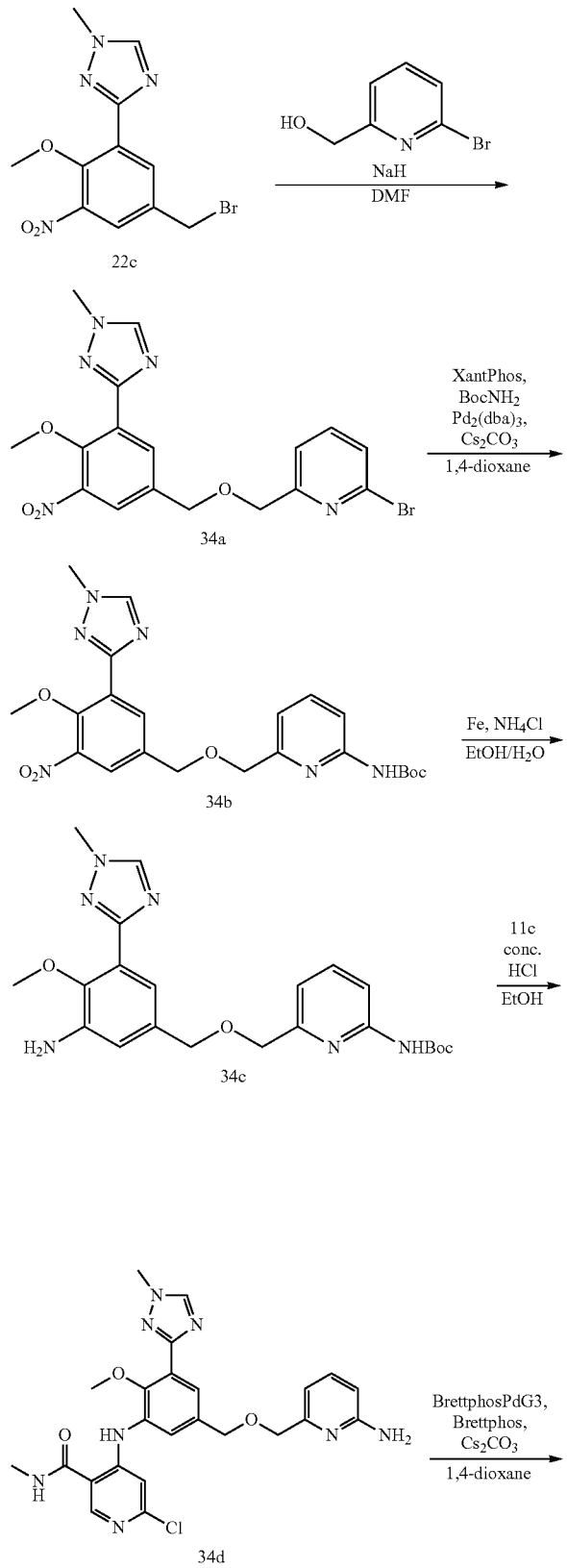

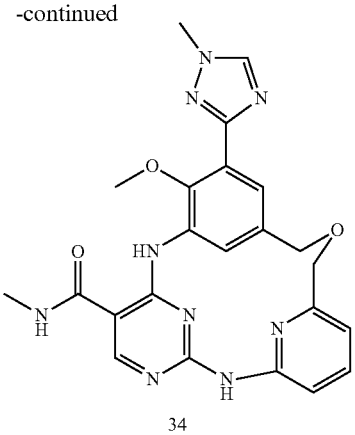

Step 1. 2-Bromo-6-(((4-methoxy-3-(1-methyl-1H-1,2,4-triazol-3-yl)-5-nitrobenzyl)oxy)methyl)pyridine (34a)

Compound 34a (269 mg, 34% yield), a yellow solid, was synthesized by utilizing a similar preparative procedure of Step 2 in Example 33 with 22c (600 mg, 1.83 mmol) and (6-bromopyridin-2-yl)methanol (517 mg, 2.75 mmol) as starting materials. LC-MS (Method 3) $t_R$=1.56 min, m/z (M+H)$^+$=436.3.

Step 2. Tert-butyl (6-(((4-methoxy-3-(1-methyl-1H-1,2,4-triazol-3-yl)-5-nitrobenzyl)oxy)methyl)pyridin-2-yl)carbamate (34b)

Compound 34a (269 mg, 0.62 mmol), tert-butyl carbamate (363 mg, 3.10 mmol), XantPhos (72 mg, 0.12 mmol), Pd$_2$(dba)$_3$ (57 mg, 0.06 mmol) and Cs$_2$CO$_3$ (404 mg, 1.24 mmol) were dissolved in 1,4-dioxane (4 mL). The above reaction was stirred at 90° C. for 3 h. The mixture was concentrated. The residue was purified by flash chromatography on silica gel (PE/EtOAc=1/1) to give the title compound 34b (266 mg, 91% yield) as a yellow solid. $^1$H NMR (400 MHz, CDCl$_3$) δ 8.33 (d, J=2.0 Hz, 1H), 8.17 (s, 1H), 7.86-7.82 (m, 2H), 7.67 (t, J=8.0 Hz, 1H), 7.48 (brs, 1H), 7.08 (d, J=7.6 Hz, 1H), 4.65 (s, 2H), 4.56 (s, 2H), 4.03 (s, 3H), 3.94 (s, 3H), 1.53 (s, 9H).

Step 3. Tert-butyl (6-(((3-amino-4-methoxy-5-(1-methyl-1H-1,2,4-triazol-3-yl)benzyl)oxy)methyl)pyridin-2-yl)carbamate (34c)

Compound 34c (241 mg, 97% yield), a white solid, was synthesized by utilizing a similar preparative procedure of Step 2 of Example 6 with 34b (266 mg, 0.57 mmol) as the starting material. LC-MS (Method 3) $t_R$=1.50 min, m/z (M+H)$^+$=441.5.

Step 4. 4-((5-(((6-Aminopyridin-2-yl)methoxy)methyl)-2-methoxy-3-(1-methyl-1H-1,2,4-triazol-3-yl)phenyl)amino)-6-chloro-N-methylnicotinamide (34d)

Compound 34d (36 mg, 62% yield), a yellow solid, was synthesized by utilizing a similar preparative procedure of Step 1 of Example 10 with 34c (50 mg, 0.11 mmol) and 11c (35 mg, 0.17 mmol) as starting materials. $^1$H NMR (400 MHz, DMSO-d$_6$) δ 10.60 (s, 1H), 8.86-8.76 (m, 1H), 8.56

(s, 1H), 8.51 (s, 1H), 7.67 (d, J=2.0 Hz, 1H), 7.48 (d, J=2.0 Hz, 1H), 7.36 (t, J=8.0 Hz, 1H), 6.95 (s, 1H), 6.59 (d, J=7.2 Hz, 1H), 6.33 (d, J=8.0 Hz, 1H), 5.87 (s, 2H), 4.60 (s, 2H), 4.40 (s, 2H), 3.95 (s, 3H), 3.71 (s, 3H), 2.81 (d, J=4.8 Hz, 3H).

Step 5. 10-Methoxy-N-methyl-11-(1-methyl-1,2,4-triazol-3-yl)-15-oxa-2,4,8,21-tetrazatetracyclo[15.3.1.1³,⁷.1⁹,¹³]tricosa-1(21),3(23),4,6,9,11,13(22),17,19-nonaene-6-carboxamide (34)

Compound 34 (8 mg, 36% yield), a yellow solid, was synthesized by utilizing a similar preparative procedure of Step 6 of Example 32 with 34d (24 mg, 0.05 mmol) as the starting material. LC-MS (Method 1) $t_R$=3.40 min, m/z (M+H)$^+$=473.2. $^1$H NMR (400 MHz, DMSO-$d_6$) δ 10.72 (s, 1H), 9.92 (s, 1H), 9.46 (s, 1H), 8.56 (s, 1H), 8.52-8.49 (m, 2H), 8.23 (d, J=2.0 Hz, 1H), 7.61 (t, J=7.6 Hz, 1H), 7.41 (d, J=2.0 Hz, 1H), 7.00 (d, J=8.0 Hz, 1H), 6.91 (d, J=7.2 Hz, 1H), 4.65 (s, 2H), 4.35 (s, 2H), 3.95 (s, 3H), 3.79 (s, 3H), 2.80 (d, J=4.0 Hz, 3H).

Example 35

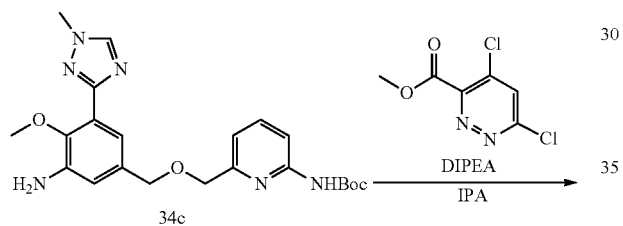

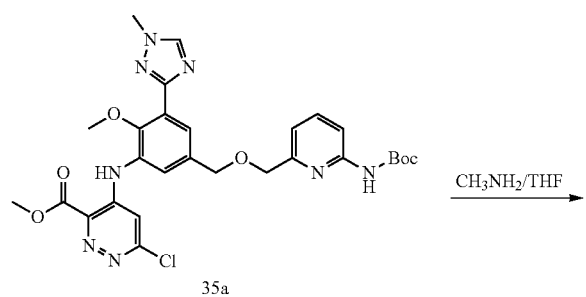

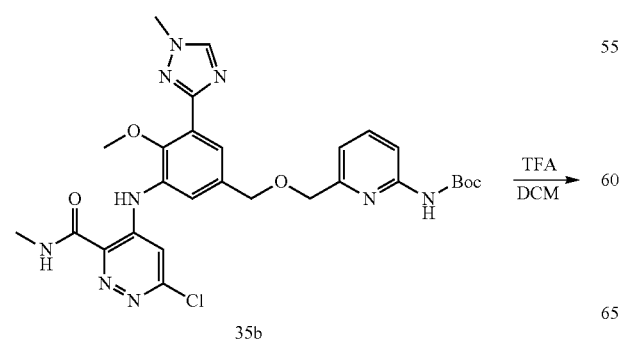

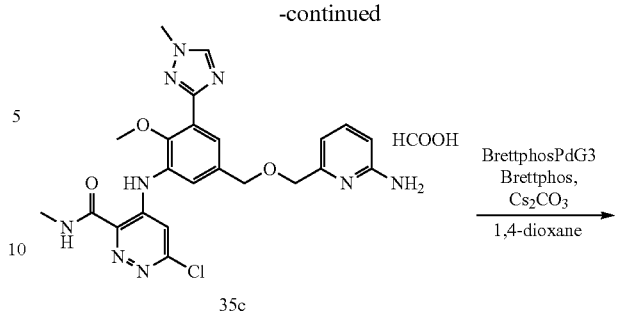

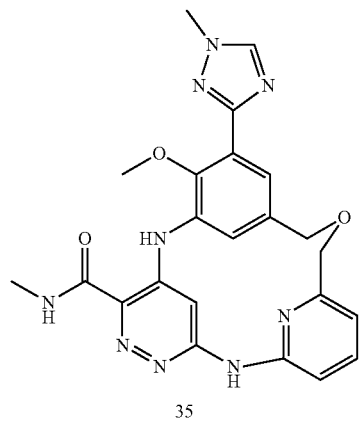

Step 1. Methyl 4-((5-(((6-((tert-butoxycarbonyl)amino)pyridin-2-yl)methoxy)methyl)-2-methoxy-3-(1-methyl-1H-1,2,4-triazol-3-yl)phenyl)amino)-6-chloropyridazine-3-carboxylate (35a)

Compound 35a (25 mg, 30% yield), a yellow solid, was synthesized by utilizing a similar preparative procedure of Step 7 of Example 1 with 34c (60 mg, 0.14 mmol) and methyl 4,6-dichloropyridazine-3-carboxylate (56 mg, 0.27 mmol) as starting materials. LC-MS (Method 3) $t_R$=1.23 min, m/z (M+H)$^+$=611.1.

Step 2. Tert-butyl (6-(((3-((6-chloro-3-(methylcarbamoyl)pyridazin-4-yl)amino)-4-methoxy-5-(1-methyl-1H-1,2,4-triazol-3-yl)benzyl)oxy)methyl)pyridin-2-yl)carbamate (35b)

Compound 35b (50 mg, yield given), a yellow solid, was synthesized by utilizing a similar preparative procedure of Step 2 in Example 23 with 35a (50 mg, 0.08 mmol) as the starting material. LC-MS (Method 3) $t_R$=1.55 min, m/z (M+H)$^+$=610.3.

Step 3. 4-((5-(((6-Aminopyridin-2-yl)methoxy)methyl)-2-methoxy-3-(1-methyl-1H-1,2,4-triazol-3-yl)phenyl)amino)-6-chloro-N-methylpyridazine-3-carboxamide formate (35c)

Compound 35b (50 mg, 0.08 mmol) was dissolved in a solution consisting of TFA (0.5 mL) and DCM (0.5 mL). The resulting reaction was stirred at r.t. for 1 h. The reaction mixture was purified by Prep-HPLC (Method C) to give the title compound 35c (45 mg, 99% yield) as a yellow solid. LC-MS (Method 3) $t_R$=1.31 min, m/z (M+H)$^+$=510.5.

Step 4. 10-Methoxy-N-methyl-11-(1-methyl-1H-1,2,4-triazol-3-yl)-15-oxa-2,4,5,8,21-pentaazatetracyclo[15.3.1.1^{3,7}.1^{9,13}]tricosa-1(21),3,5,7(23),9(22),10,12,17,19-nonaene-6-carboxamide (35)

Compound 35 (10 mg, 26% yield), a white solid, was synthesized by utilizing a similar preparative procedure of Step 6 of Example 32 with 35c (50 mg, 0.08 mmol) as the starting material. LC-MS (Method 1) $t_R$=3.18 min, m/z (M+H)$^+$=474.0. $^1$H NMR (400 MHz, DMSO-d$_6$) δ10.77 (s, 1H), 10.47 (s, 1H), 9.74 (s, 1H), 9.07 (d, J=4.8 Hz, 1H), 8.57 (s, 1H), 8.22 (s, 1H), 7.68 (t, J=7.6 Hz, 1H), 7.48 (s, 1H), 7.11 (d, J=8.4 Hz, 1H), 6.98 (d, J=7.2 Hz, 1H), 4.67 (s, 2H), 4.39 (s, 2H), 3.96 (s, 3H), 3.81 (s, 3H), 2.87 (d, J=4.8 Hz, 3H).

Example 36

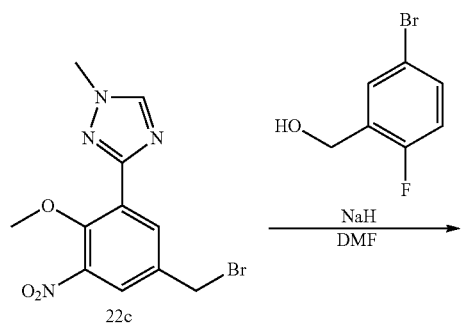

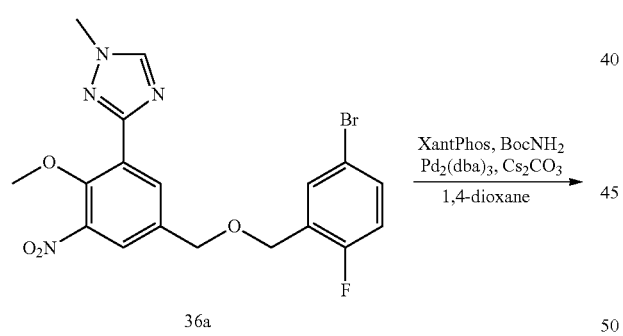

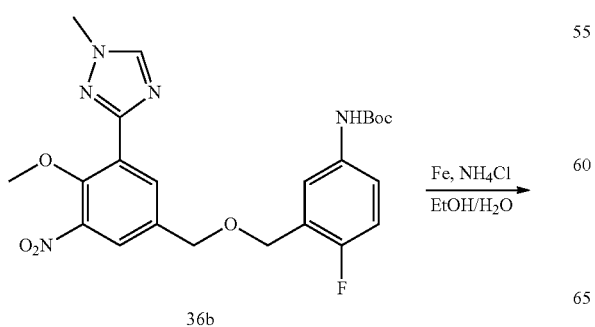

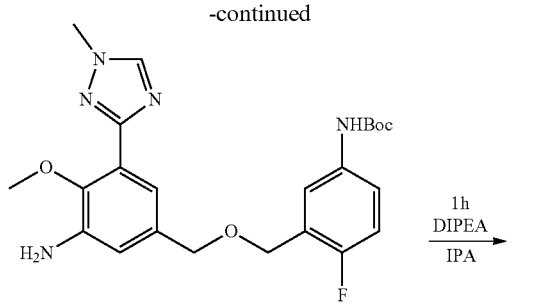

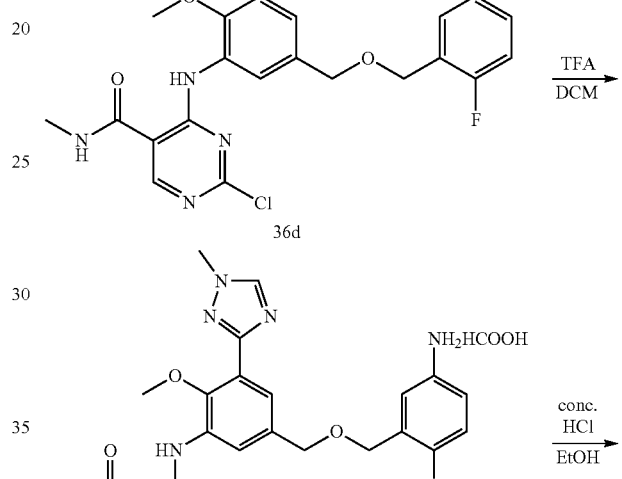

Step 1. 3-(5-(((5-Bromo-2-fluorobenzyl)oxy)methyl)-2-methoxy-3-nitrophenyl)-1-methyl-1H-1,2,4-triazole (36a)

Compound 36a (160 mg, 29% yield), a brown solid, was synthesized by utilizing a similar preparative procedure of Step 2 in Example 33 with 22c (400 mg, 1.22 mmol) and (5-bromo-2-fluorophenyl)methanol (376 mg, 1.83 mmol) as starting materials. LC-MS (Method 3) $t_R$=1.60 min, m/z (M+H)$^+$=451.5.

Step 2. Tert-butyl (4-fluoro-3-(((4-methoxy-3-(1-methyl-1H-1,2,4-triazol-3-yl)-5-nitrobenzyl)oxy)methyl)phenyl)carbamate (36b)

Compound 36b (80 mg, 74% yield), a brown solid, was synthesized by utilizing a similar preparative procedure of Step 2 in Example 34 with 36a (100 mg, 0.22 mmol) as the starting material. LC-MS (Method 3) $t_R$=1.59 min, m/z (M+H)$^+$=488.3.

Step 3. Tert-butyl (3-(((3-amino-4-methoxy-5-(1-methyl-1H-1,2,4-triazol-3-yl)benzyl)oxy)methyl)-4-fluorophenyl)carbamate (36c)

Compound 36c (30 mg, 40% yield), a yellow solid, was synthesized by utilizing a similar preparative procedure of Step 2 in Example 6 with 36b (80 mg, 0.16 mmol) as the starting material. LC-MS (Method 3) $t_R$=1.53 min, m/z (M−H)$^−$=456.7.

Step 4. Tert-butyl (3-(((3-((2-chloro-5-(methylcarbamoyl)pyrimidin-4-yl)amino)-4-methoxy-5-(1-methyl-1H-1,2,4-triazol-3-yl)benzyl)oxy)methyl)-4-fluorophenyl)carbamate (36d)

Compound 36d (48 mg, 92% yield), a yellow solid, was synthesized by utilizing a similar preparative procedure of Step 7 in Example 1 with 36c (38 mg, 0.08 mmol) and 1h (26 mg, 0.12 mmol) as starting materials. LC-MS (Method 3) $t_R$=1.59 min, m/z (M+H)$^+$=627.7.

Step 5. 4-((5-(((5-Amino-2-fluorobenzyl)oxy)methyl)-2-methoxy-3-(1-methyl-1H-1,2,4-triazol-3-yl)phenyl)amino)-2-chloro-N-methylpyrimidine-5-carboxamide formate (36e)

A solution of 36d (103 mg, 0.16 mmol) in DCM (1 mL) and TFA (1 mL) was stirred at r.t. for 1 h. The reaction was completed and the residue was purified by Prep-HPLC (Method C) to afford 36$^e$ (87 mg, 92% yield) as a yellow solid. LC-MS (Method 3) $t_R$=1.40 min, m/z (M+H)$^+$=527.5.

Step 6. 18-Fluoro-10-methoxy-N-methyl-11-(1-methyl-1H-1,2,4-triazol-3-yl)-15-oxa-2,4,8,23-tetraazatetracyclo[15.3.1.1^{3,7}.1 ^{9,13}]tricosa-1(20),3,5,7(23),9(22),10,12,17(21),18-nonaene-6-carboxamide (36)

Compound 36 (18 mg, 28% yield), an off-white solid, was synthesized by utilizing a similar preparative procedure of Step 6 in Example 33 with 36e (70 mg, 0.13 mmol) as the starting material. LC-MS (Method 1) $t_R$=3.07 min, m/z (M+H)$^+$=491.3. $^1$H NMR (400 MHz, DMSO-d$_6$) δ 11.76 (s, 1H), 9.81 (s, 1H), 8.74 (d, J=2.0 Hz, 1H), 8.69 (s, 1H), 8.55 (s, 1H), 8.49-8.45 (m, 2H), 7.47 (d, J=2.0 Hz, 1H), 7.13-7.11 (m, 2H), 4.60 (s, 2H), 4.51 (s, 2H), 3.95 (s, 3H), 3.79 (s, 3H), 2.80 (d, J=4.4 Hz, 3H).

Example 37

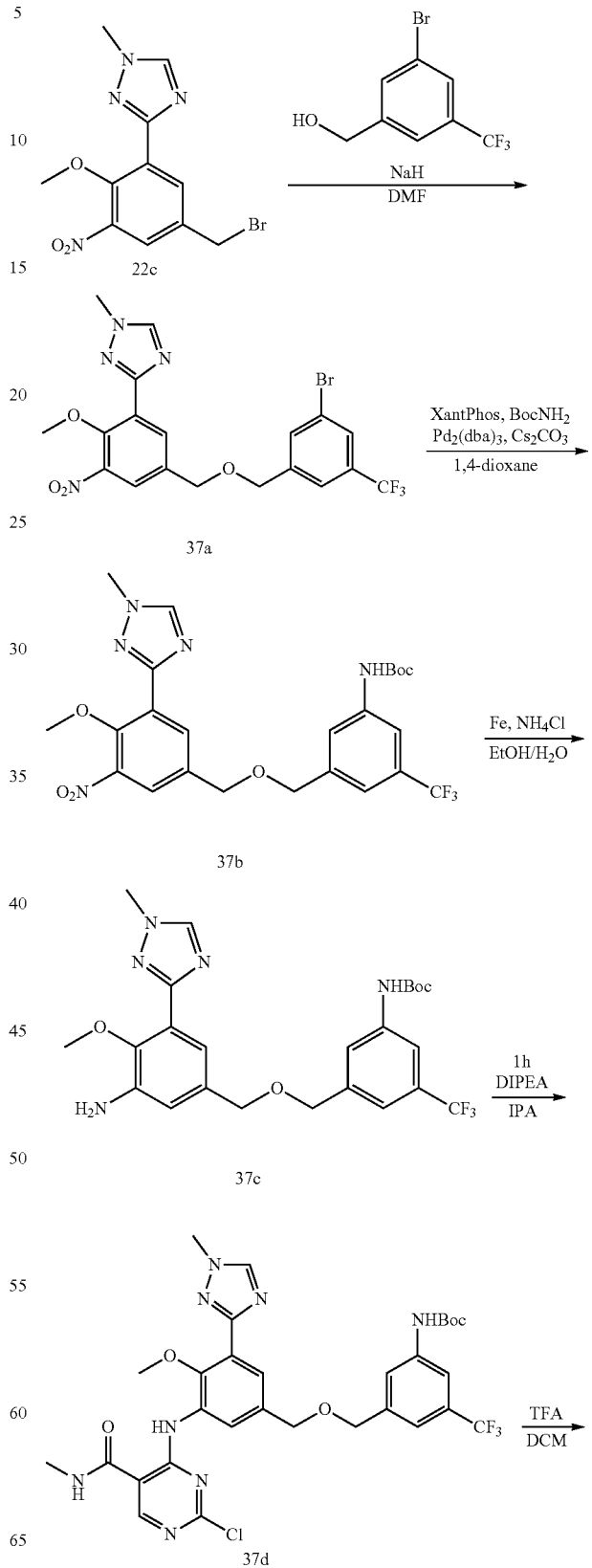

-continued

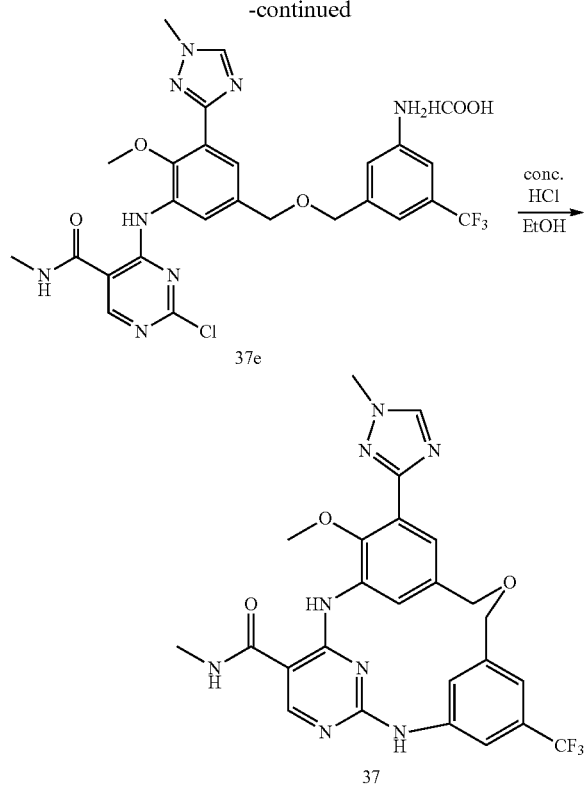

Step 1. 3-(5-(((3-Bromo-5-(trifluoromethyl)benzyl)oxy)methyl)-2-methoxy-3-nitrophenyl)-1-methyl-1H-1,2,4-triazole (37a)

Compound 37a (16 mg, 10% yield), a yellow solid, was synthesized by utilizing a similar preparative procedure of Step 2 in Example 33 with 22c (100 mg, 0.31 mmol) and (3-bromo-5-(trifluoromethyl)phenyl)methanol (117 mg, 0.46 mmol) as starting materials. LC-MS (Method 3) $t_R$=1.67 min, m/z (M+H)$^+$=503.1.

Step 2. Tert-butyl (3-(((4-methoxy-3-(1-methyl-1H-1,2,4-triazol-3-yl)-5-nitrobenzyl)oxy)methyl)-5-(trifluoromethyl)phenyl)carbamate (37b)

Compound 37b (85 mg, 56% purity, 37% yield), a brown solid, was synthesized by utilizing a similar preparative procedure of Step 2 in Example 34 with 37a (120 mg, 0.24 mmol) as the starting material. LC-MS (Method 3) $t_R$=1.68 min, m/z (M+H)$^+$=538.3.

Step 3. Tert-butyl (3-(((3-amino-4-methoxy-5-(1-methyl-1H-1,2,4-triazol-3-yl)benzyl)oxy)methyl)-5-(trifluoromethyl)phenyl)carbamate (37c)

Compound 37c (36 mg, 45% yield), a yellow solid, was synthesized by utilizing a similar preparative procedure of Step 2 in Example 6 with 37b (85 mg, 0.16 mmol) as the starting material. LC-MS (Method 3) $t_R$=1.62 min, m/z (M+H)$^+$=508.6.

Step 4. Tert-butyl (3-(((3-((2-chloro-5-(methylcarbamoyl)pyrimidin-4-yl)amino)-4-methoxy-5-(1-methyl-1H-1,2,4-triazol-3-yl)benzyl)oxy)methyl)-5-(trifluoromethyl)phenyl)carbamate (37d)

Compound 37d (40 mg, 85% yield), a white solid, was synthesized by utilizing a similar preparative procedure of Step 7 in Example 1 with 37c (36 mg, 0.07 mmol) and 1h (22 mg, 0.11 mmol) as starting materials. LC-MS (Method 3) $t_R$=1.64 min, m/z (M+H)$^+$=677.3.

Step 5. 4-((5-(((3-Amino-5-(trifluoromethyl)benzyl)oxy)methyl)-2-methoxy-3-(1-methyl-1H-1,2,4-triazol-3-yl)phenyl)amino)-2-chloro-N-methylpyrimidine-5-carboxamide formate (37e)

Compound 37e (30 mg, 64% yield), a white solid, was synthesized by utilizing a similar preparative procedure of Step 3 in Example 35 with 37d (51 mg, 0.08 mmol) as the starting material. LC-MS (Method 3) $t_R$=1.19 min, m/z (M+H)$^+$=577.1.

Step 6. 10-Methoxy-N-methyl-11-(1-methyl-1H-1,2,4-triazol-3-yl)-19-(trifluoromethyl)-15-oxa-2,4,8,23-tetraazatetracyclo[15.3.1.1^{3,7}.1^{9,13}]tricosa-1(20),3,5,7(23),9(22),10,12,17(21),18-nonaene-6-carboxamide (37)

Compound 37 (15 mg, 53% yield), an off-white solid, was synthesized by utilizing a similar preparative procedure of Step 6 in Example 33 with 37e (30 mg, 0.05 mmol) as the starting material. LC-MS (Method 2) $t_R$=3.04 min, m/z (M+H)$^+$=541.2. $^1$H NMR (400 MHz, DMSO-d$_6$) δ 11.77 (s, 1H), 10.07 (s, 1H), 8.86 (s, 1H), 8.72 (s, 1H), 8.66 (d, J=2.0 Hz, 1H), 8.56-8.54 (m, 2H), 7.49 (d, J=2.0 Hz, 1H), 7.44 (s, 1H), 7.29 (s, 1H), 4.60 (s, 2H), 4.56 (s, 2H), 3.95 (s, 3H), 3.79 (s, 3H), 2.81 (d, J=4.4 Hz, 3H).

Example 38

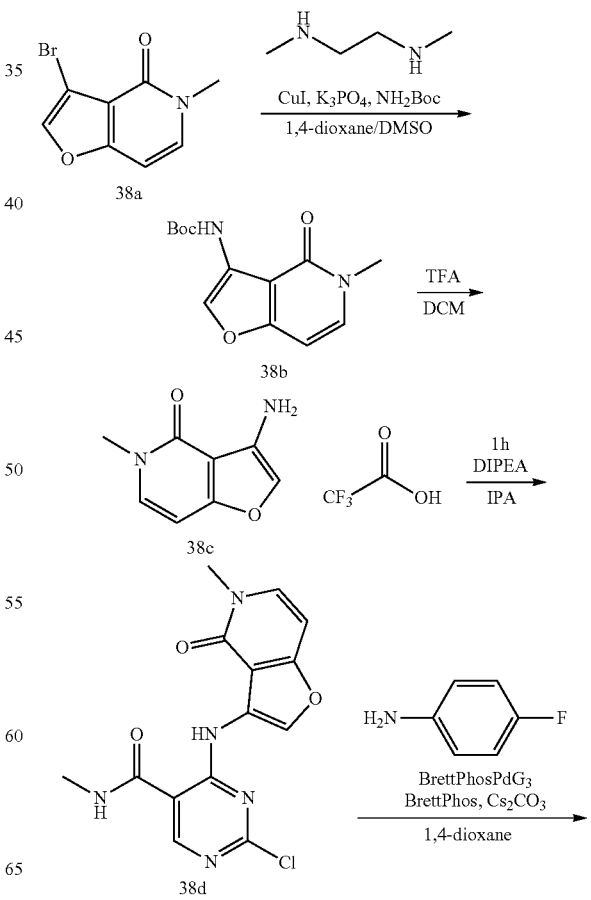

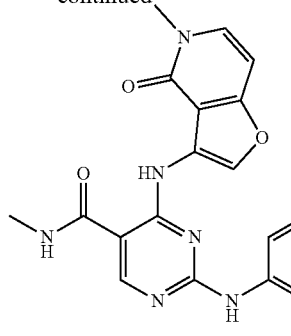

38

Step 1. Tert-butyl (5-methyl-4-oxo-4,5-dihydrofuro[3,2-c]pyridin-3-yl)carbamate (38b)

Compound 38b (447 mg, 48% yield), a white solid, was synthesized by utilizing a similar preparative procedure of Step 4 in Example 1 with 38a (800 mg, 3.51 mmol) and tert-butyl carbamate (822 mg, 7.02 mmol) as starting materials. $^1$H NMR (400 MHz, DMSO-$d_6$) δ 7.99 (s, 1H), 7.90 (s, 1H), 7.67 (d, J=7.6 Hz, 1H), 6.71 (d, J=7.6 Hz, 1H), 3.52 (s, 3H), 1.51 (s, 9H).

Step 2. 3-Amino-5-methylfuro[3,2-c]pyridin-4-(5H)-one trifluoromethanesulfonate (38c)

Compound 38b (100 mg, 0.38 mmol) was dissolved in a mixture of TFA and DCM (2 mL, v/v=1/3). The above solution was stirred at r.t. for 2 h. The reaction mixture was concentrated to dryness to give 38c (105 mg, yield given) as a brown oil. LC-MS (Method 3) $t_R$=0.29 min, m/z (M+H)$^+$=165.1.

Step 3. 2-Chloro-N-methyl-4-((5-methyl-4-oxo-4,5-dihydrofuro[3,2-c]pyridin-3-yl)amino)pyrimidine-5-carboxamide (38d)

A mixture of 1h (78 mg, 0.38 mmol), 38c (105 mg, 0.37 mmol) and DIPEA (244 mg, 1.89 mmol) in IPA (2 mL) was stirred at 40° C. for 6 h. The mixture was concentrated and the residue was purified by flash chromatography on silica gel (EtOAc) to afford 38d (38 mg, 30% yield) as a yellow solid. LCMS (Method 3) $t_R$=1.03 min, m/z (M+H)$^+$=334.3.

Step 4. 2-((4-Fluorophenyl)amino)-N-methyl-4-((5-methyl-4-oxo-4,5-dihydrofuro[3,2-c]pyridin-3-yl)amino)pyrimidine-5-carboxamide (38)

Compound 38 (9 mg, 19% yield), a yellow solid, was synthesized by utilizing a similar preparative procedure of Step 8 in Example 1 with 38d (38 mg, 0.11 mmol) and 4-fluoroaniline (63 mg, 0.60 mmol) as starting materials. LCMS (Method 1) $t_R$=3.13 min, m/z (M+H)$^+$=408.9. $^1$H NMR (400 MHz, DMSO-$d_6$) δ 11.74 (s, 1H), 9.69 (s, 1H), 8.63 (s, 1H), 8.38 (d, J=4.4 Hz, 1H), 7.71-7.64 (m, 2H), 7.63 (d, J=7.2 Hz, 1H), 7.19 (t, J=8.8 Hz, 2H), 6.67 (d, J=7.6 Hz, 1H), 3.49 (s, 3H), 2.79 (d, J=4.4 Hz, 3H).

Example 39

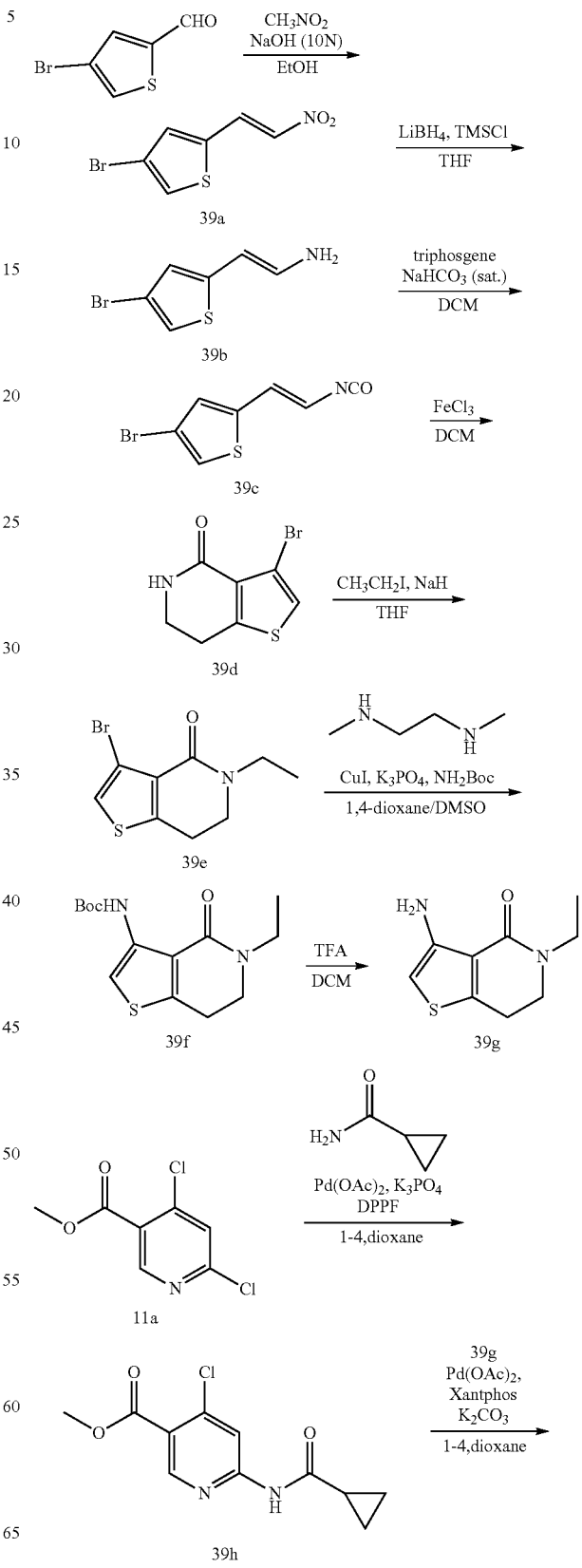

-continued

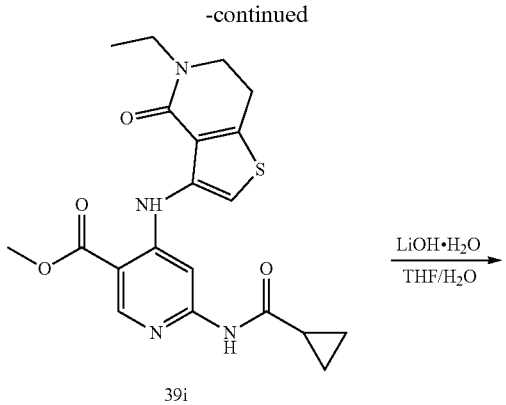

39i

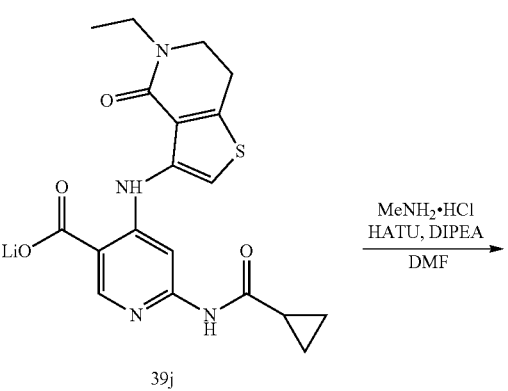

39j

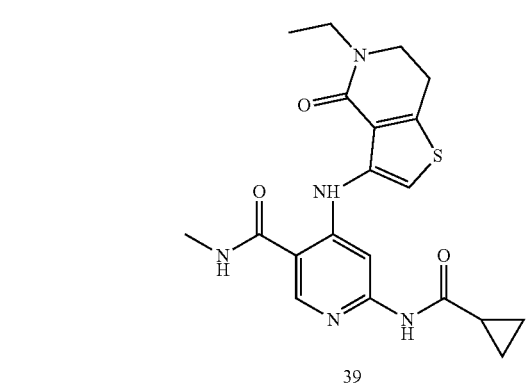

39

Step 1. (E)-4-bromo-2-(2-nitrovinyl) thiophene (39a)

To a mixture of 4-bromothiophene-2-carbaldehyde (5 g, 26.2 mmol) in ethanol (100 mL) was added nitromethane (2 g, 32.7 mmol) dropwise. The reaction was stirred at 0° C., followed by the addition of NaOH (10 N, 2.6 mL, 27.4 mmol) dropwise at the same condition. After stirring for 2 h at r.t., the mixture was quenched with 6 N HCl (100 mL). The formed solid was collected and dried under reduced pressure to afford compound 39a (2.3 g, 37% yield) as a light-yellow solid. $^1$H NMR (400 MHz, CDCl$_3$) δ 8.04 (d, J=13.6 Hz, 1H), 7.49-7.43 (m, 2H), 7.36-7.35 (m, 1H). LC-MS (Method 4) $t_R$=3.67 min, m/z (M+H−46)$^+$=188.0.

Step 2. 2-(4-Bromothiophen-2-yl) ethan-1-amine (39b)

A solution of LiBH$_4$ (4.1 mL, 8.2 mmol, 2 M in THF) in THF (3.0 mL) was treated with trimethylchlorosilane (1.78 g, 16.4 mmol) dropwise at r.t. under nitrogen atmosphere, followed by the addition of 39a (480 mg, 2.05 mmol) dropwise in THF (6 mL). The resulting mixture was stirred overnight at r.t. The mixture was quenched with MeOH and basified by 4 N NaOH to pH=8 to 9 and extracted with EA. The organic phases were combined, dried over Na$_2$SO$_4$, concentrated under reduced pressure to afford compound 39b (280 mg, 68% yield) as a light-yellow oil. LC-MS (Method 4) $t_R$=1.25 min, m/z (M+H)$^+$=206.1.

Step 3. 4-Bromo-2-(2-isocyanatoethyl) thiophene (39c)

A solution of 39b (210 mg, 1.01 mmol) in DCM (9 mL) was treated with triphosgene (120 mg, 0.4 mmol) in DCM (0.5 mL) dropwise at 0° C., followed by the addition of saturated sodium bicarbonate (2.5 mL) solution dropwise at 0° C. The resulting mixture was stirred for 1 h at 0° C., dried over Na$_2$SO$_4$ and concentrated to afford the crude compound 39c (250 mg, yield given). The crude was used for next step without purification.

Step 4. 3-Bromo-6,7-dihydrothieno[3,2-c]-pyridin-4-(5H)-one (39d)

To a stirred solution of 39c (250 mg, 1.08 mmol) in DCM (9 mL) was added FeCl$_3$ (192.18 mg, 1.18 mmol) at r.t. The mixture was stirred for 3 h at 50° C. The residue was purified by Prep-TLC (PE/EtOAc=1/1) to afford compound 39d (80 mg, 32% yield) as a light-yellow oil. LC-MS (Method 4) $t_R$=2.63 min, m/z (M+H)$^+$=231.9.

Step 5. 3-Bromo-5-ethyl-6,7-dihydrothieno[3,2-c] pyridin-4-(5H)-one (39e)

To a stirred solution of 39d (75 mg, 0.323 mmol) in DMF (6 mL) was added NaH (26 mg, 0.646 mmol, 60% purity in mineral oil) and iodoethane (76 mg, 0.485 mmol) dropwise at r.t. The mixture was stirred overnight at 65° C. The residue was purified by Prep-TLC (PE/EtOAc=1/3) to afford compound 39e (50 mg, 59% yield) as a light-yellow oil. LC-MS (Method 4) $t_R$=3.40 min, m/z (M+H)$^+$=259.9.

Step 6. Tert-butyl (5-ethyl-4-oxo-4,5,6,7-tetrahydrothieno[3,2-c]pyridin-3-yl) carbamate (39l)

A mixture of 39e (50 mg, 0.19 mmol), tert-butyl carbamate (45 mg, 0.38 mmol), N,N-dimethylenediamine (7 mg, 0.076 mmol), CuI (8 mg, 0.04 mmol), K$_3$PO$_4$ (81 mg, 0.38 mmol) in 1,4-dioxane (1 mL) and DMSO (0.4 mL) was stirred at 90° C. under N$_2$. The reaction mixture was cooled down to r.t., concentrated and the residue was purified by Prep-TLC (PE/EtOAc=1/2) to afford compound 39f (21 mg, 37% yield) as a light-yellow oil. LC-MS (Method 4) $t_R$=4.82 min, m/z (M+H)$^+$=297.1.

Step 7. 3-Amino-5-ethyl-6,7-dihydrothieno[3,2-c]pyridin-4-(5H)-one (39g)

To a stirred solution of 39f (20 mg, 0.067 mmol) in DCM (0.5 mL) was added TFA (148.00 mg, 1.30 mmol, 0.1 mL) dropwise at 0° C. The mixture was stirred for 2 h at r.t. The mixture was dilute with DCM and concentrated under reduced pressure to get the crude compound 39g (25 mg, yield given). The crude was used for next step without purification. LC-MS (Method 4) $t_R$=1.83 min, m/z (M+H)$^+$=197.1.

Step 8. Methyl 4-chloro-6-(cyclopropanecarboxamido) nicotinate (39h)

A solution of 11a (42 mg, 0.2 mmol), Pd(OAc)$_2$ (4.58 mg, 0.02 mmol), DPPF (33 mg, 0.06 mmol), K$_3$PO$_4$ (85 mg, 0.4 mmol) and cyclopropanecarboxamide (85 mg, 0.2 mmol) in 1,4-dioxane (1 mL) was stirred overnight at 75° C. The reaction mixture was cooled down to r.t., concentrated and the residue was purified by Prep-TLC (PE/EtOAc=1/2) to afford compound 39h (40 mg, 78% yield) as an off-white solid. LC-MS (Method 4) $t_R$=3.80 min, m/z (M+H)$^+$=255.1.

Step 9. Methyl 6-(cyclopropanecarboxamido)-4-((5-ethyl-4-oxo-4,5,6,7-tetrahydro thieno[3,2-c]pyridin-3-yl) amino) nicotinate (39i)

A mixture of 39g (239 mg, 0.068 mmol), 39h (23 mg, 0.088 mmol), K$_2$CO$_3$ (40 mg, 0.136 mmol), XantPhos (8 mg, 0.014 mmol) and Pd(OAc)$_2$ (2.0 mg, 0.007 mmol) in 1,4-dioxane (0.8 mL) was stirred at 85° C. under N$_2$ overnight. The mixture was cooled down to r.t., then filtered through a celite pad and concentrated. The residue was concentrated and purified by Prep-TLC (PE/EtOAc=1/1) to give compound 39i (12 mg, 43% yield) as a brown-yellow oil. LC-MS (Method 4) $t_R$=3.56 min, m/z (M+H)$^+$=415.1.

Step 10. Lithium 6-(cyclopropanecarboxamido)-4-((5-ethyl-4-oxo-4,5,6,7-tetra hydrothieno[3,2-c]pyridin-3-yl) amino) nicotinate (39j)

To a stirred mixture of 39i (12 mg, 0.029 mmol) in THF (0.9 mL) and water (0.3 mL) was added lithium hydroxide monohydrate (8 mg, 0.21 mmol). The reaction was stirred for 12 h at r.t. The mixture was concentrated under reduced pressure to give the crude compound 39j (19 mg, yield given) as a brown-yellow solid. LC-MS (Method 4) $t_R$=2.89 min, m/z (M+H)$^+$=401.1.

Step 11. 6-(Cyclopropanecarboxamido)-4-((5-ethyl-4-oxo-4,5,6,7-tetrahydrothieno[3,2-c]pyridin-3-yl) amino)-N-methyl-nicotinamide (39)

To a stirred mixture of 39j (19 mg, 0.05 mmol) in DMF (1.0 mL) were added methyl-d$_3$-amine hydrochloride (10 mg, 0.14 mmol), HATU (54 mg, 0.14 mmol) and DIEA (37 mg, 0.28 mmol). The mixture was stirred overnight at r.t. The mixture was purified by Prep-HPLC (Method E) to afford the title product 39 (1.6 mg, 8% yield) as a yellow solid. LC-MS (Method 4) $t_R$=2.90 min, m/z (M+H)$^+$=414.1.
$^1$H NMR (400 MHz, CDCl$_3$) δ 11.47 (s, 1H), 8.63 (s, 1H), 8.36 (s, 1H), 8.24 (s, 1H), 6.95 (s, 1H), 6.27 (s, 1H), 3.65-3.59 (m, 4H), 3.06-2.99 (m, 5H), 1.55-1.53 (m, 1H), 1.19 (t, J=7.2 Hz, 3H), 1.10-1.08 (m, 2H), 0.92-0.88 (m, 2H).

Example 40

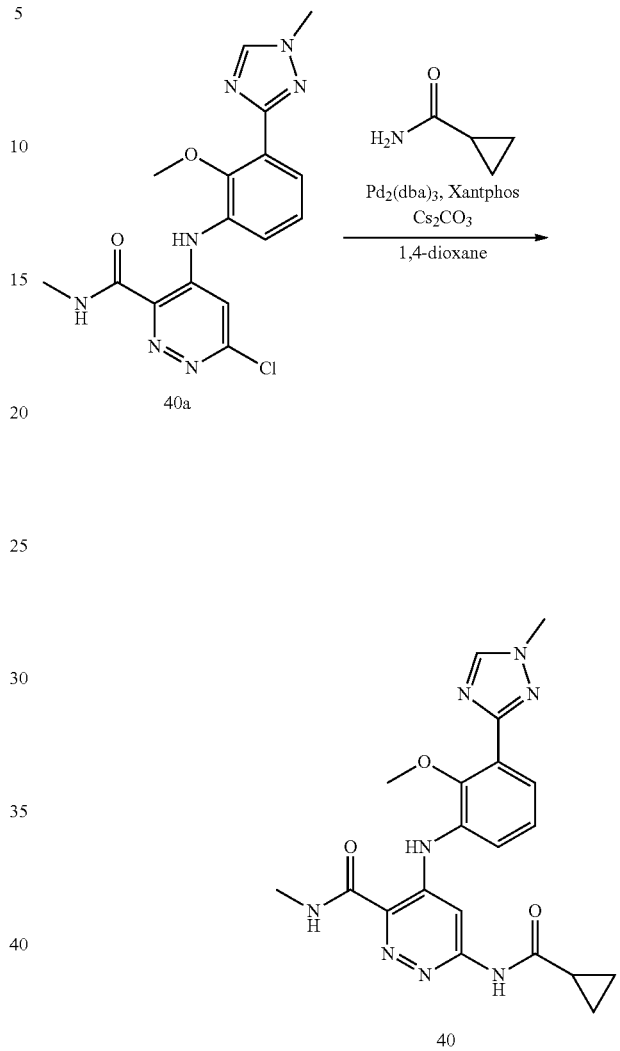

Step 1. 6-(Cyclopropanecarboxamido)-4-((2-methoxy-3-(1-methyl-1H-1,2,4-triazol-3-yl)phenyl) amino)-N-methylpyridazine-3-carboxamide (40)

Compound 40a (35 mg, 0.09 mmol), cyclopropanecarboxamide (16 mg, 0.19 mmol), Pd$_2$(dba)$_3$ (9 mg, 0.009 mmol), XantPhos (7 mg, 0.014 mmol) and Cs$_2$CO$_3$ (61 mg, 0.19 mmol) were dissolved in 1,4-dioxane (1 mL). The above reaction was stirred at 100° C. for 4 h. The reaction mixture was diluted with water (5 mL) and extracted with EtOAc (10 mL*3). The combined organic layer was concentrated to dryness. The residue was purified by Prep-HPLC (Method A) to give the title compound 40 (9 mg, 16% yield) as a white solid. LC-MS (Method 1) $t_R$=3.16 min, m/z (M+H)$^+$=423.1. $^1$H NMR (400 MHz, CDCl$_3$) δ 11.10 (s, 1H), 9.12 (brs, 1H), 8.18 (s, 1H), 8.10-8.04 (m, 2H), 7.82 (d, J=6.8 Hz, 1H), 7.50 (d, J=7.6 Hz, 1H), 7.30-7.23 (m, 1H), 4.00 (s, 3H), 3.81 (s, 3H), 3.04 (d, J=5.2 Hz, 3H), 1.27-1.23 (m, 1H), 1.12-1.08 (m, 2H), 0.95-0.88 (m, 2H).

Example 41

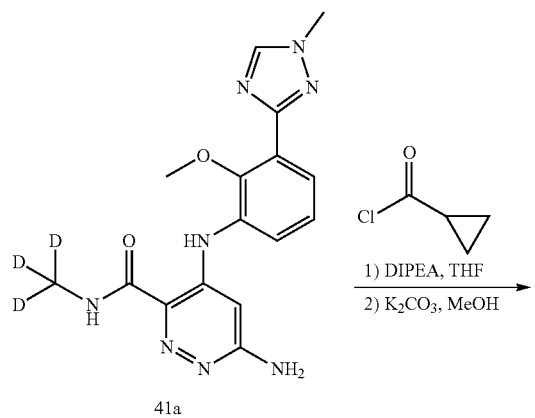

Example 42

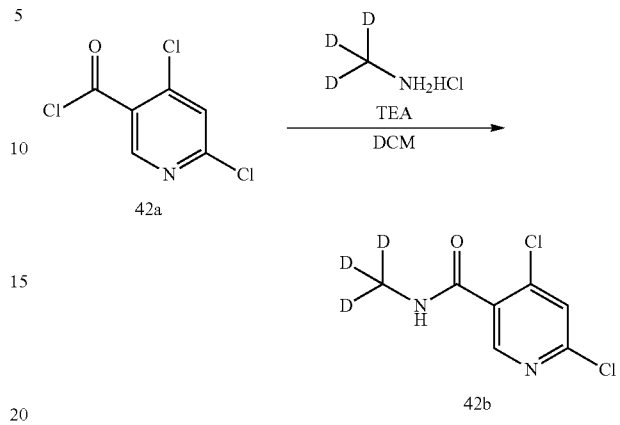

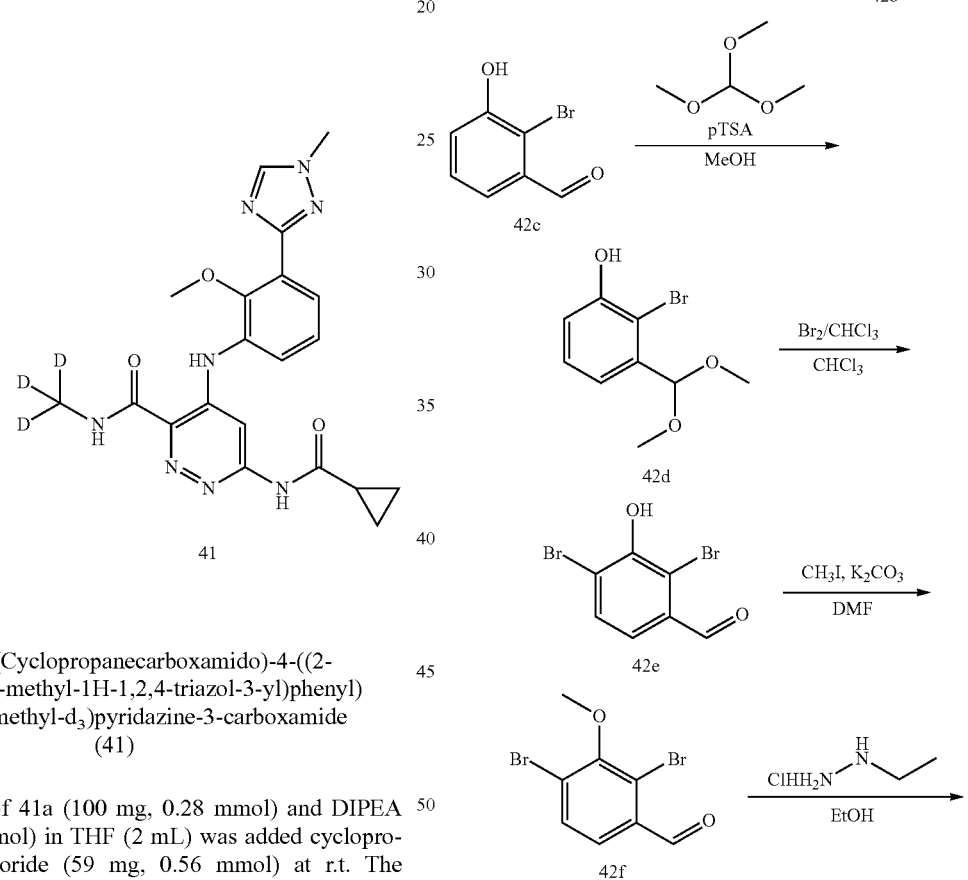

Step 1. 6-(Cyclopropanecarboxamido)-4-((2-methoxy-3-(1-methyl-1H-1,2,4-triazol-3-yl)phenyl)amino)-N-(methyl-d₃)pyridazine-3-carboxamide (41)

To a mixture of 41a (100 mg, 0.28 mmol) and DIPEA (108 mg, 0.84 mmol) in THF (2 mL) was added cyclopropanecarbonyl chloride (59 mg, 0.56 mmol) at r.t. The mixture was stirred at r.t. for 2 h and then concentrated to dryness. The residue was dissolved in MeOH (4 mL), then $K_2CO_3$ (116 mg, 0.84 mmol) was added to the mixture. The mixture was stirred at r.t. for 40 min. The mixture was diluted with $H_2O$ (8 mL) and extracted with DCM (15 mL*2). The combined organic layer was concentrated to dryness. The residue was purified by Prep-HPLC (Method A) to give the title compound 41 (40 mg, 33% yield) as a white solid. LC-MS (Method 2) $t_R$=3.21 min, m/z (M+H)⁺ 426.3. ¹H NMR (400 MHz, CDCl₃) δ 11.05 (s, 1H), 9.25 (brs, 1H), 8.19 (s, 1H), 8.11 (s, 1H), 8.06 (brs, 1H), 7.81 (dd, J=8.0, 1.6 Hz, 1H), 7.50 (dd, J=8.0, 1.6 Hz, 1H), 7.29-7.25 (m, 1H), 4.01 (s, 3H), 3.80 (s, 3H), 1.72-1.68 (m, 1H), 1.12-1.08 (m, 2H), 0.94-0.89 (m, 2H).

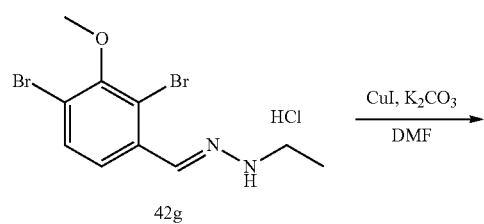

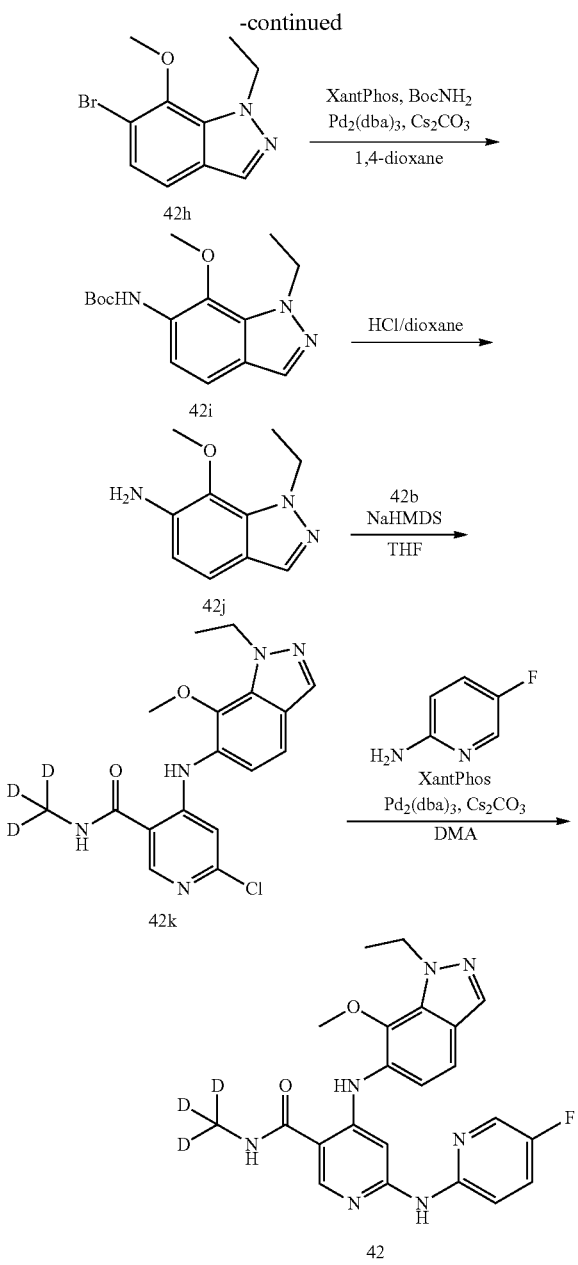

Step 1. 4,6-Dichloro-N-(methyl-d₃)nicotinamide (42b)

To a solution of 42$^a$ (1.1 g, 5.23 mmol) in DCM (20 mL) was added methan-d₃-amine hydrochloride (406 mg, 5.75 mmol) and TEA (2.64 g, 26.14 mmol) at 0° C. Then the mixture was stirred at r.t. for 1 h. The mixture was diluted with H₂O (20 mL) and extracted with DCM (20 mL). The organic layer was separated and washed with brine (20 mL), dried over Na₂SO₄ and filtered. The filtrate was concentrated to dryness to give the title compound 42b (800 mg, 74% yield) as an off-white solid. LC-MS (Method 4) $t_R$=2.18 min, m/z (M+H)⁺=208.0.

Step 2. 2-Bromo-3-(dimethoxymethyl)phenol (42d)

To a solution of 42$^c$ (2 g, 9.95 mmol) and trimethoxymethane (5.28 g, 49.75 mmol, 5.45 mL) in MeOH (30 mL) was added pTSA (172 mg, 1.00 mmol). The mixture was stirred at 100° C. for 16 h. The solvent was removed under vacuum to give crude product 42d (2.5 g, yield given) as a yellow oil. LC-MS (Method 4) $t_R$=3.54 min, m/z (M+H)⁺=215.0.

Step 3. 2,4-Dibromo-3-hydroxybenzaldehyde (42e)

To a solution of 42d (500 mg, 2.02 mmol) in CHCl₃ (5 mL) was added a solution of molecular bromine (323 mg, 2.02 mmol) in CHCl₃ (5 mL) at 0° C. The reaction was stirred at 25° C. for 16 h. The reaction was quenched by aq. Na₂S₂O₃ (40 mL) and extracted with EtOAc (25 mL*3). The combined organic layer was washed with brine (25 mL), dried over Na₂SO₄, filtered and concentrated. The residue was purified by flash silica gel chromatography (PE/EtOAc=10/1 to 3/1) to give the title compound 42e (300 mg, 53% yield) as a white solid. LC-MS (Method 4) $t_R$=2.915 min, m/z (M+H)⁺=280.9. ¹H NMR (400 MHz, DMSO-d₆) δ 10.44 (s, 1H), 10.17 (d, J=0.8 Hz, 1H), 7.83-7.65 (m, 1H), 7.27 (d, J=8.4 Hz, 1H).

Step 4. 2,4-Dibromo-3-methoxybenzaldehyde (42f)

To a solution of 42e (300 mg, 1.07 mmol) and K₂CO₃ (296 mg, 2.14 mmol) in DMF (3 mL) was added iodomethane (228 mg, 1.61 mmol). The mixture was stirred at 25° C. for 2 h, then poured into water (20 mL) and extracted with EtOAc (20 mL*3). The combined organic layer was washed with brine (30 mL), dried over Na₂SO₄, filtered and concentrated under vacuum to give the title product 42f (300 mg, 95% yield) as a yellow solid. LC-MS (Method 4) $t_R$=4.00 min, m/z (M+H)⁺=294.9.

Step 5. (E)-1-(2,4-Dibromo-3-methoxybenzylidene)-2-ethylhydrazine hydrochloride (42g)

Compound 42f (300 mg, 1.02 mmol) and ethylhydrazine hydrochloride (128 mg, 1.33 mmol) were dissolved in EtOH (5 mL). The resulting mixture was stirred at 25° C. for 1 h and then cooled to 0° C. The cloudy mixture was filtered and the solid was washed with EtOH (1 mL) to afford the title compound 42g (270 mg, 71% yield) as an off-white solid. LC-MS (Method 4) $t_R$=4.62 min, m/z (M+H)⁺=337.0.

Step 6. 6-Bromo-1-ethyl-7-methoxy-1H-indazole (42h)

To a solution of 42g (270 mg, 0.72 mmol) in DMF (2.5 mL) was added K₂CO₃ (300 mg, 2.17 mmol) and CuI (14 mg, 0.072 mmol). The mixture was stirred at 100° C. for 16 h. Water (40 mL) was added to the above mixture. The solution was extracted with EtOAc (20 mL*3). The combined organic layer was washed with brine (20 mL), dried over Na₂SO₄, filtered and concentrated under vacuum to give crude compound 42h (150 mg, 81% yield) as a pale-yellow solid. LC-MS (Method 4) $t_R$=3.99 min, m/z (M+H)⁺=255.0.

Step 7. Tert-butyl (1-ethyl-7-methoxy-1H-indazol-6-yl)carbamate (42i)

Compound 42h (45 mg, 0.18 mmol), tert-butyl carbamate (41 mg, 0.35 mmol), Pd₂(dba)₃ (16 mg, 0.018 mmol), XantPhos (21 mg, 0.035 mmol) and Cs₂CO₃ (144 mg, 0.44 mmol) were dissolved in dioxane (1 mL). The resulting mixture was stirred at 100° C. for 16 h under N₂. The mixture was diluted with H₂O, extracted with EtOAc, washed with brine, dried over Na₂SO₄ and filtered. The filtration was concentrated to dryness. The residue was purified by flash chromatography (PE/EtOAc=10/1 to 1/1) to give the title compound 42i (35 mg, 68% yield) as a pale-yellow solid. LC-MS (Method 4) $t_R$=3.99 min, m/z (M+H)⁺=292.3.

Step 8. 1-Ethyl-7-methoxy-1H-indazol-6-amine (42j)

To a solution of 42i (31 mg, 0.1 mmol) in dioxane (0.5 mL) was added a solution of HCl (g) in dioxane (4 M, 0.5 mL). The mixture was stirred at r.t. for 30 min. The mixture was concentrated to dryness. The residue was diluted with H₂O (10 mL) and adjusted to pH>7 with aq Na₂CO₃, then extracted with EtOAc (10 mL*3). The organic layers were washed with aq. Na₂CO₃ (15 mL) and brine (15 mL) and separated. The solution was dried over Na₂SO₄ and filtered. The filtrate was concentrated to give the title compound 42j (20 mg, 98% yield) as a yellow solid. LC-MS (Method 4) $t_R$=1.73 min, m/z (M+H)⁺=192.3.

Step 9. 6-Chloro-4-((1-ethyl-7-methoxy-1H-indazol-6-yl)amino)-N-(methyl-d₃)nicotinamide (42k)

To a solution of 42j (20 mg, 0.10 mmol) and 42b (26 mg, 0.13 mmol) in THF (1 mL) was added NaHMDS (0.35 mL, 0.7 mmol, 2 M in THF) at 0° C., then the mixture was stirred at r.t. for 30 min. The mixture was diluted with H₂O (20 mL) and extracted with EtOAc (20 mL). The organic layer was washed with brine (20 mL), dried over Na₂SO₄ and filtered. The filtrate was concentrated to dryness to give the title compound 42k (30 mg, 79% yield) as a yellow solid. LC-MS (Method 4) $t_R$=3.52 min, m/z (M+H)⁺=363.2.

Step 10. 4-((1-Ethyl-7-methoxy-1H-indazol-6-yl)amino)-6-((5-fluoropyridin-2-yl)amino)-N-(methyl-d₃)nicotinamide (42)

Compound 42k (30 mg, 0.082 mmol), 5-fluoropyridin-2-amine (19 mg, 0.17 mmol), XantPhos (9.7 mg, 0.016 mmol), Cs₂CO₃ (67 mg, 0.20 mmol) and Pd₂(dba)₃ (7.6 mg, 0.008 mmol) were dissolved in DMA (1 mL). The resulting mixture was stirred at 145° C. for 2 h. The mixture was concentrated to dryness and purified by Prep-HPLC (Method D) to give the title compound 42 (2.2 mg, 6% yield) as an off-white solid. ¹H NMR (400 MHz, DMSO-d₆) δ 10.54 (s, 1H), 9.71 (s, 1H), 8.47 (s, 1H), 8.44 (s, 1H), 8.03 (d, J=1.6 Hz, 1H), 8.01 (s, 1H), 7.68-7.65 (m, 1H), 7.60-7.56 (m, 1H), 7.54 (d, J=8.8 Hz, 1H), 7.46 (m, 1H), 7.21 (d, J=8.8 Hz, 1H), 4.52 (q, J=7.2 Hz, 2H), 3.78 (s, 3H), 1.37 (t, J=7.2 Hz, 3H). LC-MS (Method 4) $t_R$=2.66 min, m/z (M+H)⁺=439.2.

Example 43

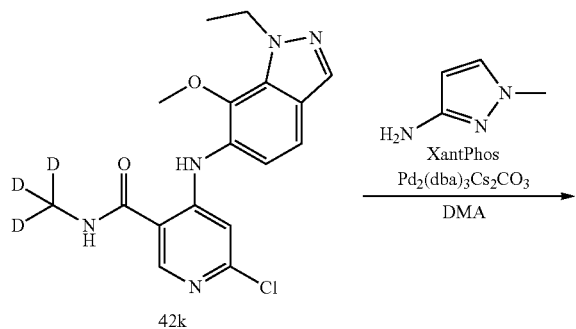

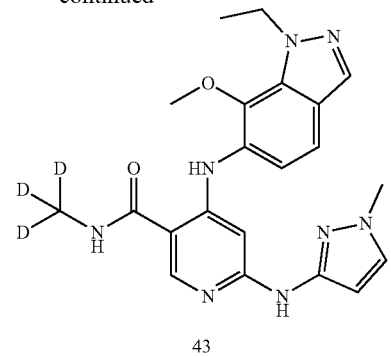

Step 1. 4-((1-Ethyl-7-methoxy-1H-indazol-6-yl)amino)-N-(methyl-d₃)-6-((1-methyl-1H-pyrazol-3-yl)amino)nicotinamide (43)

Compound 42k (20 mg, 55.1 μmol), 1-methyl-1H-pyrazol-3-amine (11 mg, 0.11 mmol), XantPhos (6 mg, 0.011 mmol), Cs₂CO₃ (44.9 mg, 0.14 mmol) and Pd₂(dba)₃ (5 mg, 0.005 mmol) were dissolved in DMA (1 mL). The resulting mixture was stirred at 160° C. for 1 h under N₂ atmosphere. The mixture was concentrated to dryness and purified by Prep-HPLC (Method D) to give the compound 43 (2.0 mg, 9% yield) as an off-white solid. LC-MS (Method 4) $t_R$=2.42 min, m/z (M+H)⁺=424.3. ¹H NMR (400 MHz, DMSO-d₆) δ 10.57 (s, 1H), 9.20 (s, 1H), 8.40 (s, 1H), 8.03 (s, 1H), 7.53 (d, J=8.4 Hz, 1H), 7.45 (d, J=1.6 Hz, 1H), 7.24 (d, J=8.4 Hz, 1H), 7.20 (s, 1H), 6.06 (d, J=1.6 Hz, 1H), 4.55 (q, J=7.2 Hz, 2H), 3.81 (s, 3H), 3.62 (s, 3H), 1.40 (t, J=7.2 Hz, 3H).

Example 44

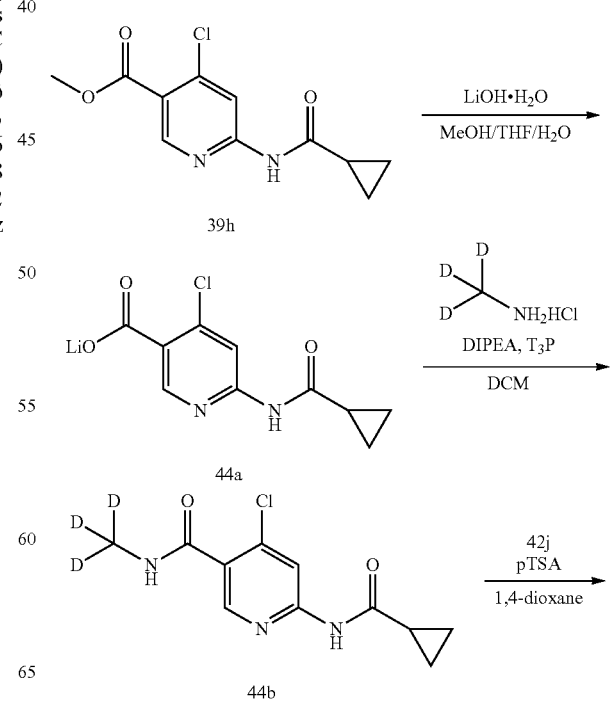

Example 45

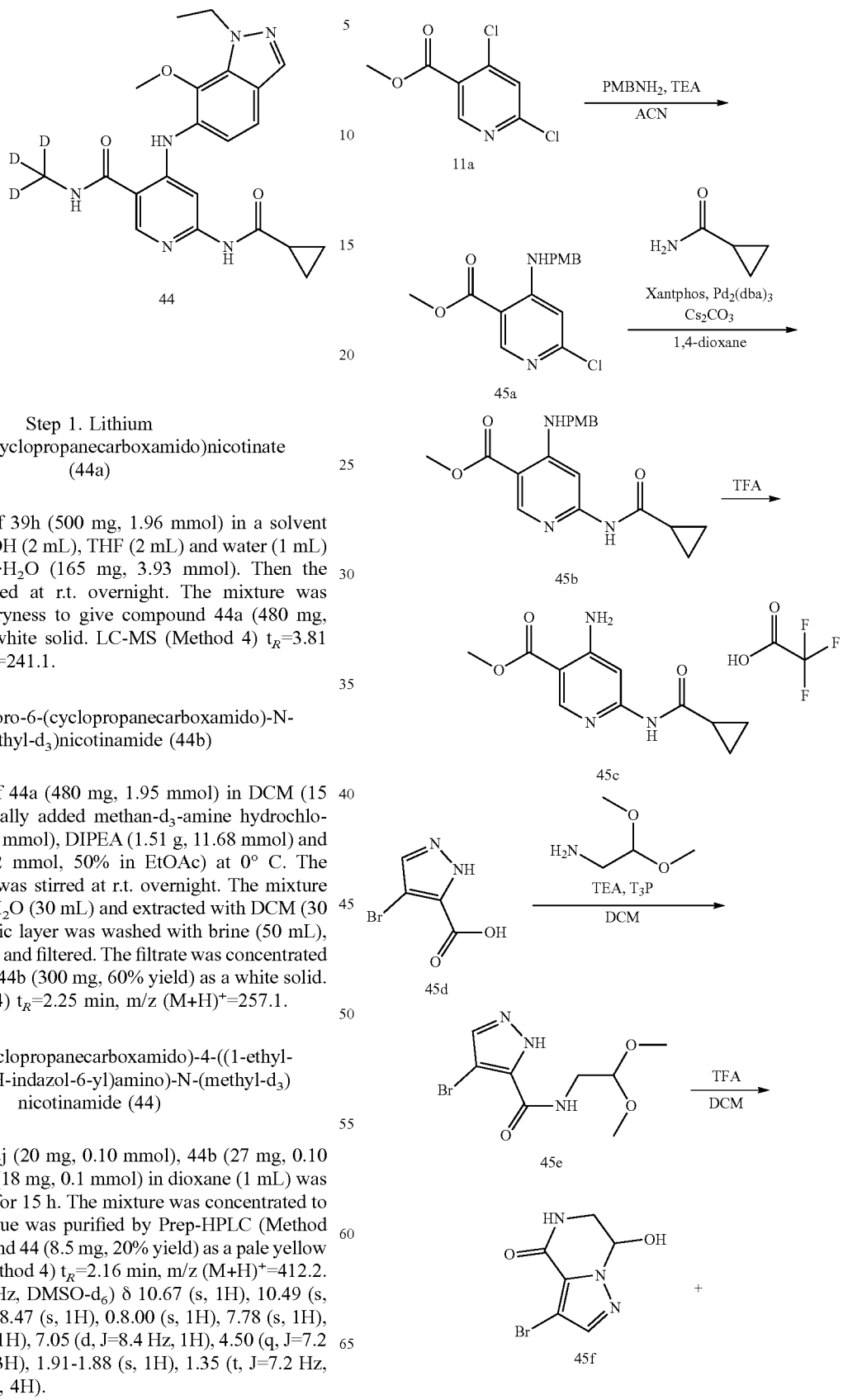

Step 1. Lithium 4-chloro-6-(cyclopropanecarboxamido)nicotinate (44a)

To a solution of 39h (500 mg, 1.96 mmol) in a solvent containing of MeOH (2 mL), THF (2 mL) and water (1 mL) was added LiOH·H$_2$O (165 mg, 3.93 mmol). Then the mixture was stirred at r.t. overnight. The mixture was concentrated to dryness to give compound 44a (480 mg, 99% yield) as a white solid. LC-MS (Method 4) $t_R$=3.81 min, m/z (M+H)$^+$=241.1.

Step 2. 4-Chloro-6-(cyclopropanecarboxamido)-N-(methyl-d$_3$)nicotinamide (44b)

To a solution of 44a (480 mg, 1.95 mmol) in DCM (15 mL) was sequentially added methan-d$_3$-amine hydrochloride (275 mg, 3.89 mmol), DIPEA (1.51 g, 11.68 mmol) and T$_3$P (1.86 g, 2.92 mmol, 50% in EtOAc) at 0° C. The resulting mixture was stirred at r.t. overnight. The mixture was diluted with H$_2$O (30 mL) and extracted with DCM (30 mL*3). The organic layer was washed with brine (50 mL), dried over Na$_2$SO$_4$ and filtered. The filtrate was concentrated to dryness to give 44b (300 mg, 60% yield) as a white solid. LC-MS (Method 4) $t_R$=2.25 min, m/z (M+H)$^+$=257.1.

Step 3. 6-(Cyclopropanecarboxamido)-4-((1-ethyl-7-methoxy-1H-indazol-6-yl)amino)-N-(methyl-d$_3$)nicotinamide (44)

A mixture of 42j (20 mg, 0.10 mmol), 44b (27 mg, 0.10 mmol) and pTSA (18 mg, 0.1 mmol) in dioxane (1 mL) was stirred at 100° C. for 15 h. The mixture was concentrated to dryness. The residue was purified by Prep-HPLC (Method E) to give compound 44 (8.5 mg, 20% yield) as a pale yellow solid. LC-MS (Method 4) $t_R$=2.16 min, m/z (M+H)$^+$=412.2. $^1$H NMR (400 MHz, DMSO-d$_6$) δ 10.67 (s, 1H), 10.49 (s, 1H), 8.57 (s, 1H), 8.47 (s, 1H), 0.8.00 (s, 1H), 7.78 (s, 1H), 7.47 (d, J=8.4 Hz, 1H), 7.05 (d, J=8.4 Hz, 1H), 4.50 (q, J=7.2 Hz, 2H), 3.74 (s, 3H), 1.91-1.88 (s, 1H), 1.35 (t, J=7.2 Hz, 3H), 0.71-0.66 (m, 4H).

-continued

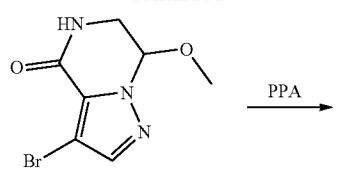

45g

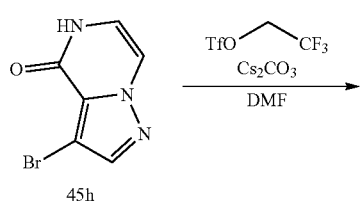

45h

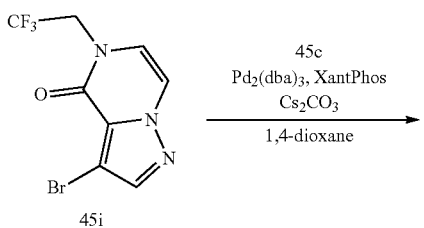

45i

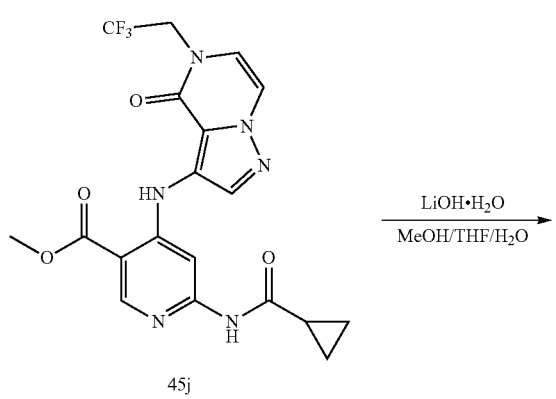

45j

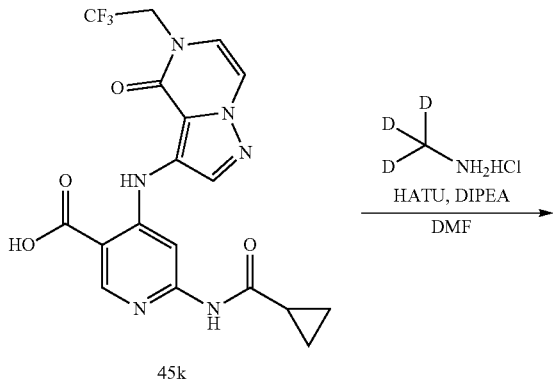

45k

-continued

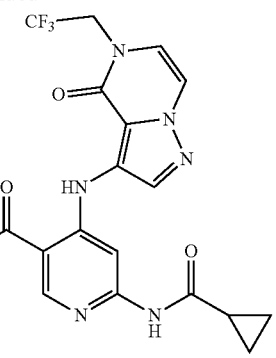

45

Step 1. Methyl 6-chloro-4-((4-methoxybenzyl)amino)nicotinate (45a)

To a solution of 11a (5 g, 24.27 mmol) in ACN (8 mL) was added (4-methoxyphenyl)methanamine (3.33 g, 24.27 mmol, 3.17 mL) and TEA (4.91 g, 48.54 mmol, 6.77 mL) then the mixture was stirred at r.t. for 24 h. The mixture was diluted with H$_2$O (100 mL), extracted with EA (50 mL*3), washed with brine, dried over Na$_2$SO$_4$, concentrated and purified by flash chromtography (PE/EtOAc=20/1 to 5/1) to get the compound 45a (6.5 g, 87% yield) as an off-white solid. LC-MS (Method4) t$_R$=4.18 min, m/z (M+H)$^+$=307.1.

Step 2. Methyl 6-(cyclopropanecarboxamido)-4-((4-methoxybenzyl)amino)nicotinate (45b)

A mixture of 45a (2 g, 6.52 mmol), cyclopropanecarboxamide (1.11 g, 13.04 mmol), XantPhos (754 mg, 1.30 mmol), Pd$_2$(dba)$_3$ (597 mg, 0.65 mmol), Cs$_2$CO$_3$ (5.31 g, 16.30 mmol) in 1,4-dioxane (30 mL) was stirred at 110° C. for 2 h. Then the mixture was diluted with H$_2$O (100 mL), extracted with EA (60 mL*3), washed with brine and dried over Na$_2$SO$_4$, concentrated to get the crude compound 45b (2.3 g, 99% yield) as a yellow solid. LC-MS (Method4) t$_R$=2.91 min, m/z (M+H)$^+$=356.2.

Step 3. Methyl 4-amino-6-(cyclopropanecarboxamido)nicotinate 2,2,2-trifluoroacetate (45c)

A solution of 45b (2.1 g, 5.91 mmol) in TFA (10 mL) was stirred at 80° C. for 16 h. Then the mixture was concentrated and diluted with EA (10 mL), filtered and wash with EA (5 mL*2), then the solid was dried to get the compound 45c (1.8 g, 87% yield, TFA salt) as an off-white solid. LC-MS (Method 4) t$_R$=1.28 min, m/z (M+H)$^+$=236.2.

Step 4. 4-Bromo-N-(2,2-dimethoxyethyl)-1H-pyrazole-5-carboxamide (45e)

To a stirred solution of 45d (1 g, 5.24 mmol) in DCM (30 mL) were added TEA (2.65 g, 26.18 mmol, 3.65 mL) and 2,2-dimethoxyethanamine (826 mg, 7.85 mmol) at room temperature. The reaction mixture was cooled to 0° C. and T$_3$P (4.7 mL, 7.85 mmol, 50% in ethyl acetate) was added and the reaction mixture was stirred at room temperature for 16 h. The reaction mixture was diluted with water (60 mL) and extracted with dichloromethane (30 mL*3). The com-

259 bined organic layer was dried over Na$_2$SO$_4$, filtered and concentrated and purified by flash chromatography (PE/EtOAc=10/1 to 1/1) to get the compound 45e (500 mg, 34% yield) as a white solid. LC-MS (Method 4) t$_R$=2.28 min, m/z (M−H)$^−$=276.0.

Step 5. 3-Bromo-7-hydroxy-6,7-dihydropyrazolo[1,5-a]pyrazin-4-(5H)-one (45f) and 3-bromo-7-methoxy-6,7-dihydropyrazolo[1,5-a]pyrazin-4-(5H)-one (45g)

To a solution of 45e (500 mg, 1.80 mmol) in DCM (2 mL) was added TFA (266 mg, 2.34 mmol) and the mixture was stirred at r.t. for 16 h. The mixture was concentrated to get a mixture of the compound 45f (300 mg, 72% yield) and 45g (120 mg, 27% yield) as a yellow oil. 45f: LC-MS (Method 4) t$_R$=1.32 min, m/z (M+H)$^+$=232.0; 45g: LC-MS (Method 4) t$_R$=2.12 min, m/z (M+H)$^+$=246.0.

Step 6. 3-Bromopyrazolo[1,5-a]pyrazin-4-(5H)-one (45h)

A mixture of 45f (300 mg, 1.29 mmol) and 45g (120 mg, 0.49 mmol) in PPA (1 mL) was stirred at 145° C. for 4 h. The mixture was diluted with H$_2$O (50 mL), extracted with DCM (50 mL*3), washed with brine, dried over Na$_2$SO$_4$, concentrated and purified by flash chromatography (DCM/MeOH=100/1 to 20/1) to get the compound 45h (200 mg, 52% yield) as an off-white solid. LC-MS (Method 4) t$_R$=1.69 min, m/z (M+H)$^+$=214.0.

Step 7. 3-Bromo-5-(2,2,2-trifluoroethyl)pyrazolo[1,5-a]pyrazin-4-(5H)-one (45i)

To a solution of 45h (150 mg, 0.70 mmol) in DMF (3 mL) added Cs$_2$CO$_3$ (571 mg, 1.75 mmol) and 2,2,2-trifluoroethyl trifluoromethanesulfonate (244 mg, 1.05 mmol) then the mixture was stirred at r.t. for 30 min. The mixture was diluted with H$_2$O (10 mL), extracted with EA (10 mL*3), washed with brine, dried over Na$_2$SO$_4$, concentrated to get the crude compound 45i (160 mg, 77% yield) as a yellow solid. LC-MS (Method 4) t$_R$=3.18 min, m/z (M+H)$^+$=296.0.

Step 8. Methyl 6-(cyclopropanecarboxamido)-4-((4-oxo-5-(2,2,2-trifluoroethyl)-4,5-dihydropyrazolo[1,5-a]pyrazin-3-yl)amino)nicotinate (45j)

A mixture of 45i (150 mg, 0.51 mmol), 45c (212 mg, 0.61 mmol), Cs$_2$CO$_3$ (660 mg, 2.03 mmol), Pd$_2$(dba)$_3$ (46 mg, 0.05 mmol), XantPhos (58 mg, 0.10 mmol) in 1,4-dioxane (1.5 mL) was stirred at 105° C. for 15 h. The mixture was diluted with H$_2$O (30 mL), extracted with EA (30 mL*3), washed with brine, dried over Na$_2$SO$_4$, concentrated and purified by flash chromatography (DCM/MeOH=100/1 to 30/1) to get the compound 45j (120 mg, 51% yield) as a pale yellow solid. LC-MS (Method 4) t$_R$=3.35 min, m/z (M+H)$^+$=451.2.

Step 9. 6-(Cyclopropanecarboxamido)-4-((4-oxo-5-(2,2,2-trifluoroethyl)-4,5-dihydropyrazolo[1,5-a]pyrazin-3-yl)amino)nicotinic acid (45k)

To a solution of methyl 45j (100 mg, 0.22 mmol) in the solvent (2.5 mL, MeOH/THF/H$_2$O=2/2/1) was added LiOH·H$_2$O (28 mg, 0.67 mmol), then the mixture was stirred at r.t. for 16 h. The mixture was diluted with H$_2$O (2 mL) and acidified to pH=2 with aq HCl (1 N), then concentrated to get the compound 45k (100 mg, yield given) as a white solid. LC-MS (Method 4) t$_R$=2.40 min, m/z (M+H)$^+$=437.1.

Step 10. 6-(Cyclopropanecarboxamido)-N-(methyl-d$_3$)-4-((4-oxo-5-(2,2,2-trifluoroethyl)-4,5-dihydropyrazolo[1,5-a]pyrazin-3-yl)amino)nicotinamide (45)

A mixture of 45k (100 mg, 0.23 mmol), methan-d$_3$-amine hydrochloride (97 mg, 1.38 mmol), DIPEA (296 mg, 2.3 mmol), HATU (174 mg, 0.45 mmol) in DMF (2 mL) was stirred at r.t. for 6 h. The mixture diluted with H$_2$O (10 mL), extracted with DCM (10 mL*3), washed with brine, dried over Na$_2$SO$_4$, concentrated and purified by Prep-HPLC (Method E) to get the compound 45 (19.6 mg, 19% yield) as a white solid. LC-MS (Method 4) t$_R$=2.51 min, m/z (M+H)$^+$=453.2. $^1$H NMR (400 MHz, DMSO-d$_6$) δ 11.11 (s, 1H), 10.85 (s, 1H), 8.50 (s, 1H), 8.49 (s, 1H), 8.11 (s, 1H), 8.04 (s, 1H), 7.73 (d, J=6.0 Hz, 1H), 7.03 (d, J=6.4 Hz, 1H), 4.77 (q, J=9.2 Hz, 2H), 2.00-1.95 (m, 1H), 0.82-0.76 (m, 4H).

Example 46

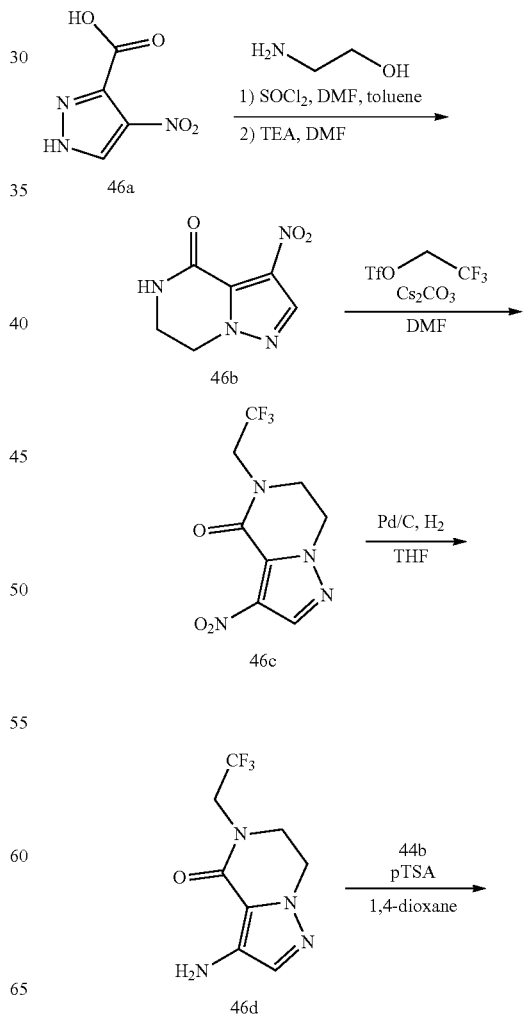

-continued

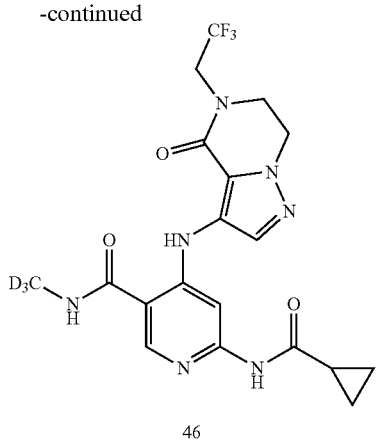

46

Step 1. 3-Nitro-6,7-dihydropyrazolo[1,5-a]pyrazin-4-(5-H)-one (46b)

To a solution of 46a (200 mg, 1.27 mmol) and 2-aminoethanol (93.33 mg, 1.53 mmol) in toluene was added SOCl$_2$ (454 mg, 3.82 mmol) and DMF (9 mg, 0.13 mmol) then the mixture was stirred at 50° C. for 2 h. Then stirred at 70° C. overnight. The mixture was concentrated and dissolved in DMF (10 mL) and TEA (644 mg, 6.37 mmol) was added into the mixture, then the mixture was stirred at 70° C. for 2 h. The mixture was diluted with H$_2$O (50 mL), extracted with EtOAc (20 mL*3), washed with brine, dried over Na$_2$SO$_4$, concentrated to get the crude product 46b (180 mg, 78% yield) as a yellow solid. LC-MS (Method 4) t$_R$=1.10 min, m/z (M+H)$^+$=183.0.

Step 2. 3-Nitro-5-(2,2,2-trifluoroethyl)-6,7-dihydropyrazolo[1,5-a]pyrazin-4-(5H)-one (46c)

To a solution of 46b (170 mg, 0.93 mmol) in DMF (3 mL) was added Cs$_2$CO$_3$ (912 mg, 2.80 mmol) and 2,2,2-trifluoroethyl trifluoromethanesulfonate (433 mg, 1.87 mmol) then the mixture was stirred at r.t. for 1 h. The mixture was diluted with H$_2$O (20 mL), extracted with EA (15 mL*3), washed with brine, dried over Na$_2$SO$_4$, concentrated and purified by flash chromatography (PE/EtOAc=10/1 to 2/1) to get the compound 46c (70 mg, 28% yield) as a yellow solid. LC-MS (Method 4) t$_R$=2.61 min, m/z (M+H)$^+$=265.0.

Step 3. 3-Amino-5-(2,2,2-trifluoroethyl)-6,7-dihydropyrazolo[1,5-a]pyrazin-4-(5H)-one (46d)

To a solution of 46c (70 mg, 0.26 mmol) in THF (2 mL) was added Pd/C (7 mg, 10% wt), then the mixture was stirred at r.t. under H$_2$ for 2 h. The mixture was filtered and the filtrate was concentrated to get the compound 46d (52 mg, 84% yield) as a colorless solid. LC-MS (Method 4) t$_R$=1.58 min, m/z (M+H)$^+$=235.1.

Step 4. 6-(Cyclopropanecarboxamido)-N-(methyl-d$_3$)-4-((4-oxo-5-(2,2,2-trifluoroethyl)-4,5,6,7-tetrahydropyrazolo[1,5-a]pyrazin-3-yl)amino) nicotinamide (46)

A mixture of 44b (38 mg, 0.15 mmol), 46d (35 mg, 0.15 mmol) and pTSA (25 mg, 0.15 mmol) in 1,4-dioxane (1 mL) was stirred at 100° C. for 16 h. The mixture was concentrated and purified by Prep-HPLC (Method E) to get the compound 46 (14 mg, 21% yield) as a white solid. LC-MS (Method 4) t$_R$=2.44 min, m/z (M+H)$^+$=455.2. $^1$H NMR (400 MHz, DMSO-d$_6$) δ 10.95 (s, 1H), 10.82 (s, 1H), 8.47-8.45 (m, 2H), 8.10 (s, 1H), 7.76 (s, 1H), 4.40-4.30 (m, 4H), 3.90-3.88 (m, 2H), 2.00-1.96 (m, 1H), 0.81-0.79 (m, 4H).

Example 47

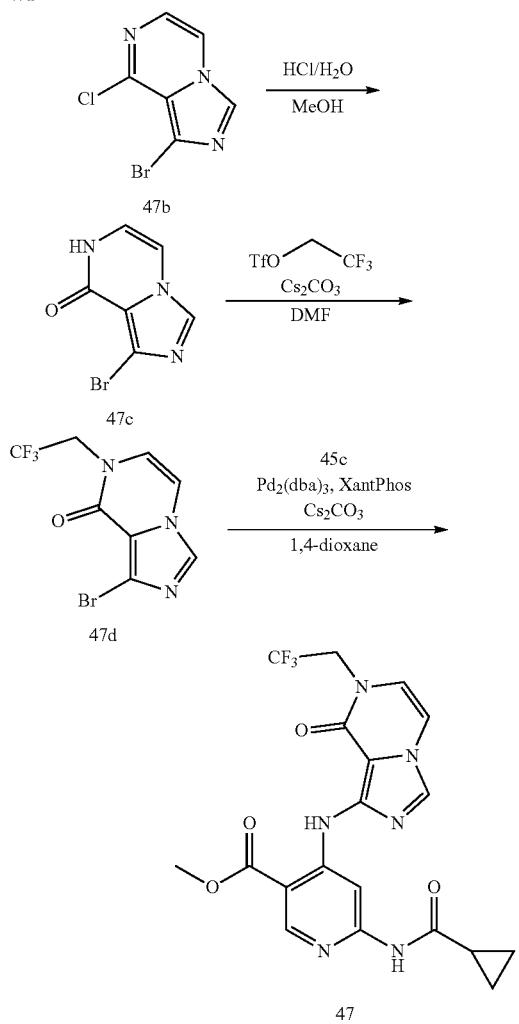

Step 1. 1-Bromo-8-chloroimidazo[1,5-a]pyrazine (47b)

To a solution of 47a (2.0 g, 13.02 mmol) in DMF (20 mL) was added NBS (2.32 g, 13.02 mmol) at −20° C., then the mixture was stirred at −20° C. for 2 h and stirred at r.t. for 16 h. The mixture was diluted with H$_2$O (100 mL), extracted with EA (30 mL*3), washed with brine, dried over Na$_2$SO$_4$, concentrated and purified by flash chromatography (PE/EtOAc=10/1 to 2/1) to get the compound 47b (1.4 g, 6.02 mmol, 46% yield) as a white solid. $^1$H NMR (400 MHz, CDCl$_3$) δ 8.16 (s, 1H), 7.76 (d, J=4.8 Hz, 1H), 7.36 (d, J=4.8 Hz, 1H). LC-MS (Method 4) t$_R$ 2.06 min, m/z (M+H)$^+$=234.0.

Step 2. 1-Bromoimidazo[1,5-a]pyrazin-8(7H)-one (47c)

To a solution of 47b (400 mg, 1.72 mmol) in MeOH (5 mL) was added HCl (2 N in H$_2$O, 1 mL). Then the mixture was stirred at 60° C. for 1 h. The mixture was concentrated to get the compound 47c (350 mg, 95% yield) as a white solid. LC-MS (Method 4) t$_R$=0.76 min, m/z (M+H)$^+$=214.0.

Step 3. 1-Bromo-7-(2,2,2-trifluoroethyl)imidazo[1,5-a]pyrazin-8(7H)-one (47d)

To a solution of 47c (250 mg, 1.17 mmol) in DMF (4 mL) was added Cs$_2$CO$_3$ (761 mg, 2.34 mmol) and 2,2,2-trifluoroethyl trifluoromethanesulfonate (407 mg, 1.75 mmol) then the mixture was stirred at r.t. for 30 min. The mixture was diluted with H$_2$O (20 mL), extracted with EA (10 mL*3), wash with brine, dried over Na$_2$SO$_4$, concentrated to get the compound 47d (200 mg, 58% yield) as a yellow solid. LC-MS (Method 4) t$_R$=1.83 min, m/z (M+H)$^+$=296.1.

Step 4. Methyl 6-(cyclopropanecarboxamido)-4-((8-oxo-7-(2,2,2-trifluoroethyl)-7,8-dihydroimidazo[1,5-a]pyrazin-1-yl)amino)nicotinate (47)

A mixture of 47d (50 mg, 0.17 mmol), 45c (59 mg, 0.17 mmol), Pd$_2$(dba)$_3$ (15 mg, 0.017 mmol), XantPhos (20 mg, 0.034 mmol), Cs$_2$CO$_3$ (165 mg, 0.51 mmol) in 1,4-dioxane (1 mL) was stirred at 105° C. for 16 h. The mixture was diluted with H$_2$O (20 mL), extracted with EA (10 mL*3), washed with brine, dried over Na$_2$SO$_4$, concentrated and purified by Prep-HPLC (Method E) to get the compound 47 (1.8 mg, 2.4% yield) as a yellow solid. LC-MS (Method 4) t$_R$=2.83 min, m/z (M+H)$^+$=451.2. $^1$H NMR (400 MHz, CDCl$_3$) δ 11.63 (s, 1H), 9.62 (s, 1H), 8.80 (s, 1H), 8.24 (s, 1H), 7.75 (s, 1H), 6.89 (d, J=6.0 Hz, 1H), 6.36 (d, J=6.0 Hz, 1H), 4.48 (q, J=8.4 Hz, 2H), 3.98 (s, 3H), 1.28-1.24 (m, 1H), 1.18-1.16 (m, 2H), 0.90-0.88 (m, 2H).

Example 48

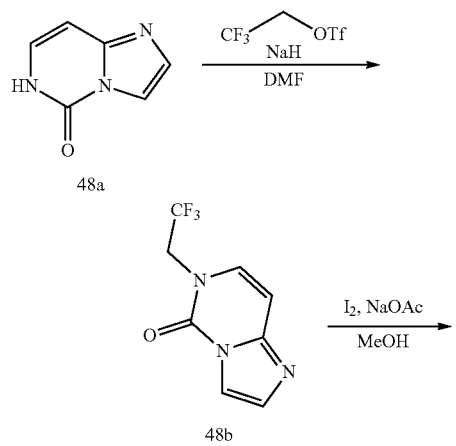

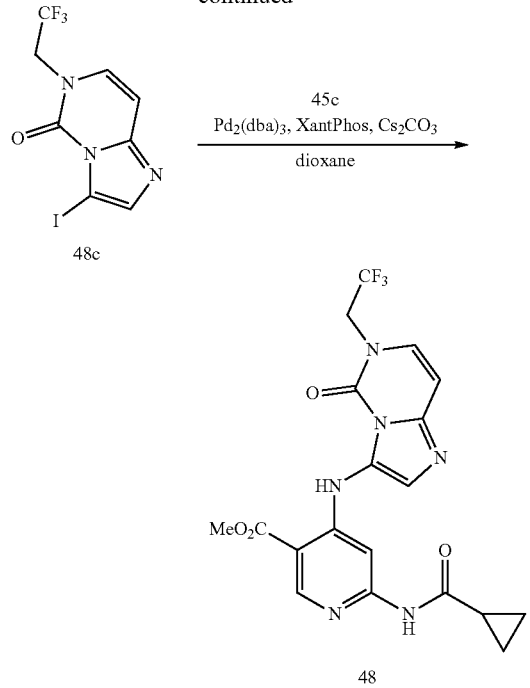

Step 1. 6-(2,2,2-Trifluoroethyl)imidazo[1,2-c]pyrimidin-5(6H)-one (48b)

To a solution of 48a (810 mg, 6.0 mmol) in DMF (60 mL) was added NaH (360 mg, 0.9 mmol, 60% purity) at 0° C., the mixture was stirred for 10 min at r.t. followed by the addition of 2,2,2-trifluoroethyl trifluoromethanesulfonate (1.67 g, 7.20 mmol) dropwise at r.t. The mixture was stirred overnight at r.t. The mixture was diluted with H$_2$O (200 mL), extracted with EtOAc (100 mL*3), washed with brine (100 mL), dried over Na$_2$SO$_4$, concentrated to get the compound 48b (1.3 g, 99% yield) as a yellow solid. LC-MS (Method 4) t$_R$=1.53 min, m/z (M+H)$^+$=218.1.

Step 2. 3-Iodo-6-(2,2,2-trifluoroethyl)imidazo[1,2-c]pyrimidin-5(6H)-one (48c)

To a stirred solution of 48b (150 mg, 0.69 mmol) in methanol (6 mL) was added I2 (265 mg, 2.07 mmol) at 0° C. The mixture was stirred for 48 h at 55° C. The mixture was quenched by addition of saturated sodium thiosulfate solution dropwise at r.t. The mixture was diluted with H$_2$O (30 mL), extracted with EtOAc (20 mL*3). The organic layer was concentrated and purified by Prep-HPLC (Method E) to obtain 48c (186 mg, 78% yield) as a light yellow solid. LC-MS (Method 4) t$_R$=2.94 min, m/z (M+H)$^+$=343.9.

Step 3. Methyl 6-(cyclopropanecarboxamido)-4-((5-oxo-6-(2,2,2-trifluoroethyl)-5,6-dihydroimidazo[1,2-c]pyrimidin-3-yl)amino)nicotinate (48)

A mixture of 48$^c$ (34 mg, 0.10 mmol), 45$^c$ (36 mg, 0.11 mmol), Pd$_2$(dba)$_3$ (9 mg, 0.01 mmol), XantPhos (12 mg, 0.02 mmol), Cs$_2$CO$_3$ (114 mg, 0.35 mmol) in dioxane (1 mL) was stirred at 95° C. for 16 h. The mixture was purified by Prep-HPLC (Method E) to get the compound 48 (5 mg, 11% yield) as an off-white solid. LC-MS (Method 4) t$_R$=3.08 min, m/z (M+H)$^+$=451.2. $^1$H NMR (400 MHz, CD$_3$OD) δ 8.74 (s, 1H), 8.2 (s, 1H), 7.63 (s, 1H), 7.46 (d, J=8.0 Hz, 1H), 6.63 (d, J=8.0 Hz, 1H), 4.81 (q, J=8.4 Hz, 2H), 3.92 (s, 3H), 1.90-1.84 (m, 1H), 0.99-0.95 (m, 2H), 0.90-0.86 (m, 2H).

Example 49

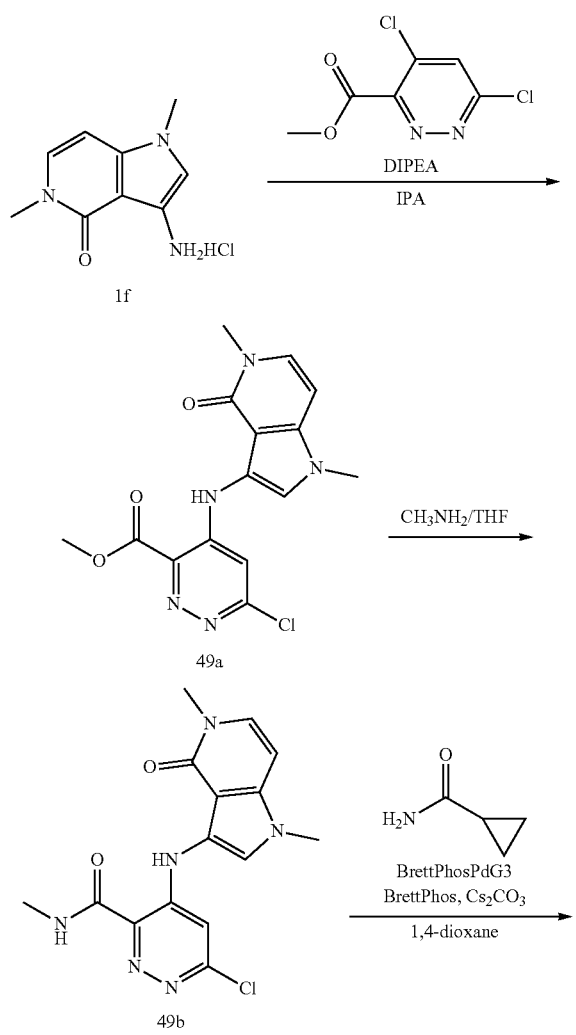

Step 1. Methyl 6-chloro-4-((1,5-dimethyl-4-oxo-4,5-dihydro-1H-pyrrolo[3,2-c]pyridin-3-yl)amino)pyridazine-3-carboxylate (49a)

A mixture of 1f (314 mg, 1.47 mmol), methyl 4,6-dichloropyridazine-3-carboxylate (365 mg, 1.76 mmol) and DIPEA (948 mg, 7.35 mmol) in IPA (6 mL) was stirred at 50° C. for 18 h. The mixture was concentrated. The residue was purified by flash chromatography on silica gel (PE/EtOAc=1/1) to give the title compound 49a (300 mg, 59% yield) as a yellow solid. $^1$H NMR (400 MHz, CDCl$_3$) δ 11.15 (s, 1H), 7.18 (s, 1H), 7.09 (d, J=7.6 Hz, 1H), 6.86 (s, 1H), 6.30 (d, J=7.6 Hz, 1H), 4.11 (s, 3H), 3.75 (s, 3H), 3.61 (s, 3H).

Step 2. 6-Chloro-4-((1,5-dimethyl-4-oxo-4,5-dihydro-1H-pyrrolo[3,2-c]pyridin-3-yl)amino)-N-methylpyridazine-3-carboxamide (49b)

A solution of 49a (300 mg, 0.86 mmol) and methylamine (5 mL, 2.0 M in THF) was stirred at 50° C. overnight in a sealed tube. The mixture was cooled to r.t. and concentrated to afford the title compound 49b (210 mg, 70% yield) as a yellow solid. LC-MS (Method 3) $t_R$=1.26 min, m/z (M+H)$^+$=347.0.

Step 3. 6-(Cyclopropanecarboxamido)-4-((1,5-dimethyl-4-oxo-4,5-dihydro-1H-pyrrolo[3,2-c]pyridin-3-yl)amino)-N-methylpyridazine-3-carboxamide (49)

A mixture of 49b (50 mg, 0.14 mmol), cyclopropanecarboxamide (61 mg, 0.72 mmol), BrettPhos (8 mg, 0.014 mmol), BrettPhos Pd G3 (13 mg, 0.014 mmol) and Cs$_2$CO$_3$ (141 mg, 0.43 mmol) in 1,4-dioxane (2 mL) was stirred at 140° C. for 4 h. The reaction mixture was concentrated. The residue was purified by Prep-HPLC (Method A) to afford the title compound 49 (7 mg, 12% yield) as an off-white solid. LC-MS (Method 1) $t_R$=3.09 min, m/z (M+H)$^+$=396.2. $^1$H NMR (400 MHz, DMSO-d$_6$) δ 11.25 (s, 1H), 11.23 (s, 1H), 8.95 (s, 1H), 8.07 (s, 1H), 7.37 (d, J=7.2 Hz, 1H), 7.06 (s, 1H), 6.54 (d, J=6.8 Hz, 1H), 3.71 (s, 3H), 3.42 (s, 3H), 2.84 (s, 3H), 2.10-2.08 (m, 1H), 0.85-0.80 (m, 4H).

Example 50

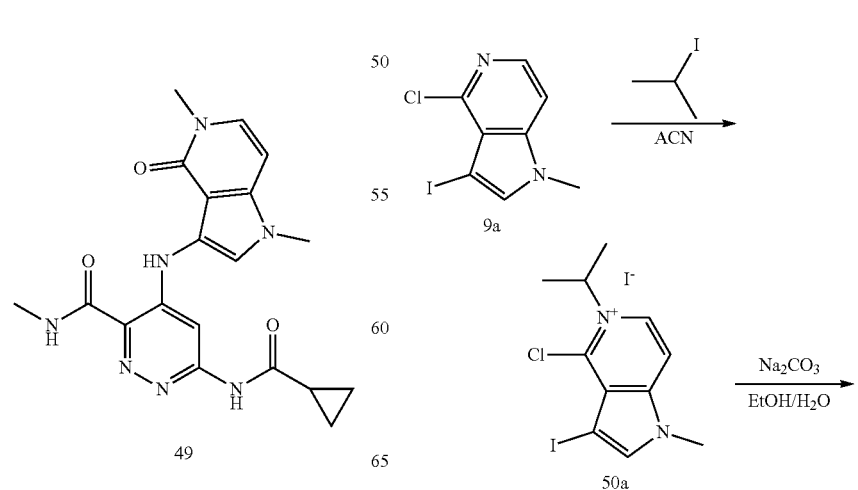

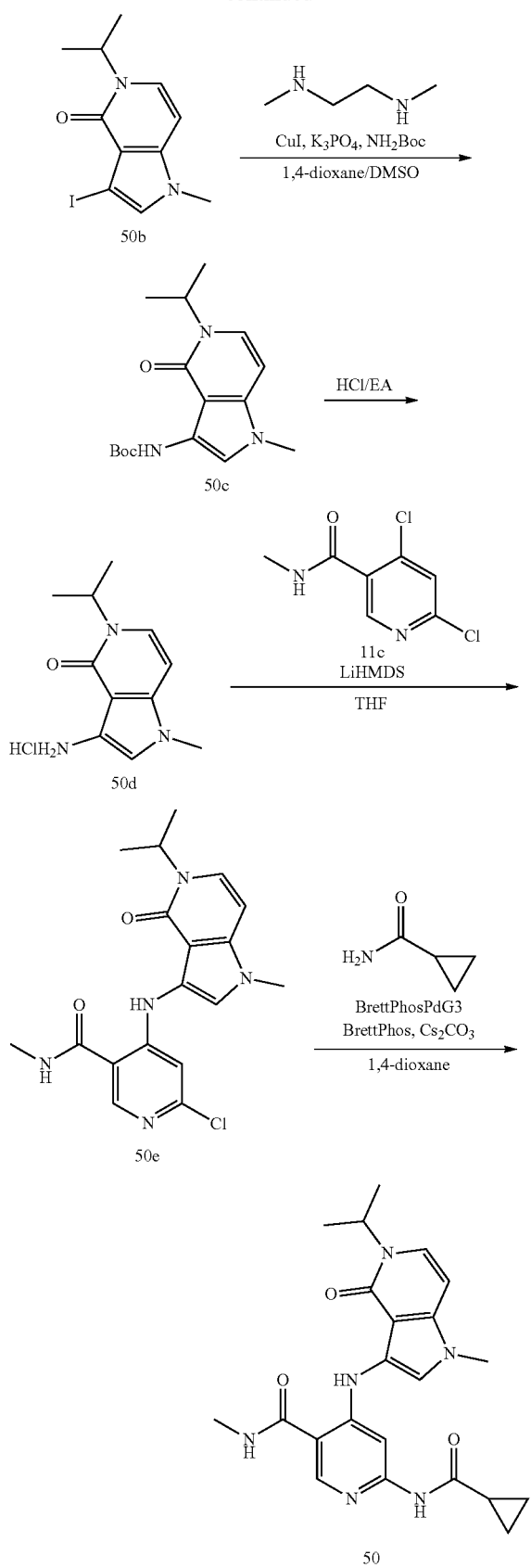

Step 1. 4-Chloro-3-iodo-5-isopropyl-1-methyl-1H-pyrrolo[3,2-e]pyridin-5-ium iodide (50a)

A mixture of 9a (2.0 g, 6.84 mmol) in ACN (15 mL) and 2-iodopropane (15 mL) was stirred at 80° C. for 48 h. The mixture was concentrated and dried to the title compound 50a (2.0 g, 87% yield) as a brown solid. LC-MS (Method 3) $t_R$=1.62 min, m/z (M+H)$^+$=335.2.

Step 2. 3-Iodo-5-isopropyl-1-methyl-1,5-dihydro-4H-pyrrolo[3,2-c]pyridin-4-one (50b)

A mixture of 50a (2.0 g, 5.96 mmol) and Na$_2$CO$_3$ (1.89 g, 17.88 mmol) in EtOH/H$_2$O (15 mL/15 mL) was stirred at 60° C. for 30 minutes. The mixture was concentrated to remove EtOH, extracted with EtOAc (20 mL*3). The combined organic layer was concentrated and the residue was purified by flash chromatography on silica gel (PE/EtOAc=3/1) to give title compound 50b (450 mg, 24% yield) as a yellow solid. $^1$H NMR (400 MHz, DMSO-d$_6$) δ 7.40 (d, J=7.6 Hz, 1H), 7.22 (s, 1H), 6.58 (d, J=7.6 Hz, 1H), 5.18-5.13 (m, 1H), 3.68 (s, 3H), 1.27 (d, J=6.8 Hz, 6H).

Step 3. Tert-butyl (5-isopropyl-1-methyl-4-oxo-4,5-dihydro-1H-pyrrolo[3,2-e]pyridin-3-yl)carbamate (50c)

Compound 50c (260 mg, 90% yield), a yellow solid, was synthesized by utilizing a similar preparative procedure of Step 4 in Example 1 with 50b (300 mg, 0.95 mmol) and tert-butyl carbamate (889 mg, 7.59 mmol) as starting materials. LC-MS (Method 3) $t_R$=1.58 min, m/z (M+H)$^+$=306.3.

Step 4. 3-Amino-5-isopropyl-1-methyl-1,5-dihydro-4H-pyrrolo[3,2-c]pyridin-4-one hydrochloride (50d)

Compound 50d (150 mg, 86% yield), a blue solid, was synthesized by utilizing a similar preparative procedure of Step 5 in Example 1 with 50c (260 mg, 0.85 mmol) as the starting material. LC-MS (Method 3) $t_R$=1.18 min, m/z (M+H)$^+$=206.3.

Step 5. 6-Chloro-4-((5-isopropyl-1-methyl-4-oxo-4,5-dihydro-1H-pyrrolo[3,2-c]pyridin-3-yl)amino)-N-methylnicotinamide (50e)

To a solution of 50d (130 mg, 0.63 mmol) and 11$^c$ (130 mg, 0.63 mmol) in THF (1 mL) was added LiHMDS (2.53 mL, 2.53 mmol, 1.0 M in THF) at 0° C. The mixture was stirred at r.t. for 1 h. The mixture was quenched with saturated NH$_4$Cl solution (5 mL) and extracted with EtOAc (10 mL*2). The combined organic layer was concentrated. The title compound was purified by Prep-HPLC (Method A) to give the title compound 50e (120 mg, 51% yield) as a brown solid. LC-MS (Method 3) $t_R$=1.36 min, m/z (M+H)$^+$=374.3.

Step 6. 6-(Cyclopropanecarboxamido)-4-((5-isopropyl-1-methyl-4-oxo-4,5-dihydro-1H-pyrrolo[3,2-c]pyridin-3-yl)amino)-N-methylnicotinamide (50)

Compound 50 (26 mg, 46% yield), a white solid, was synthesized by utilizing a similar preparative procedure of Step 8 in Example 1 with 50e (50 mg, 0.13 mmol) and cyclopropanecarboxamide (11 mg, 0.13 mmol) as starting materials. LC-MS (Method 1) $t_R$=3.01 min, m/z (M+H)$^+$=423.2. $^1$H NMR (400 MHz, DMSO-d$_6$) δ 10.92 (s, 1H), 10.72 (s, 1H), 8.42 (s, 1H), 8.40 (d, J=4.4 Hz, 1H), 8.00 (s, 1H), 7.38 (d, J=7.6 Hz, 1H), 7.02 (s, 1H), 6.56 (d, J=7.6 Hz, 1H), 5.19-5.16 (m, 1H), 3.69 (s, 3H), 2.76 (d, J=6.8 Hz, 3H), 2.03-2.01 (m, 1H), 1.28 (d, J=6.8 Hz, 6H), 0.85-0.79 (m, 4H).

Example 51

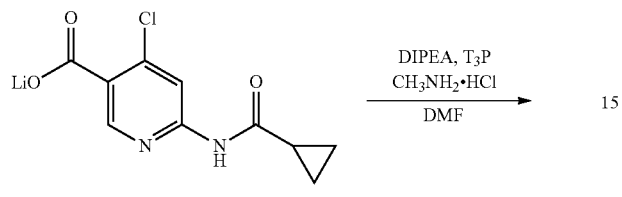

44a

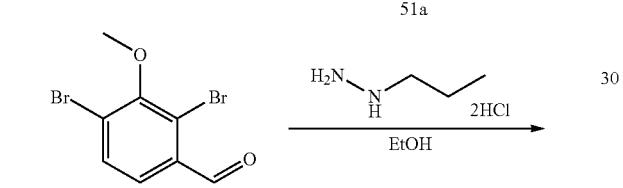

51a

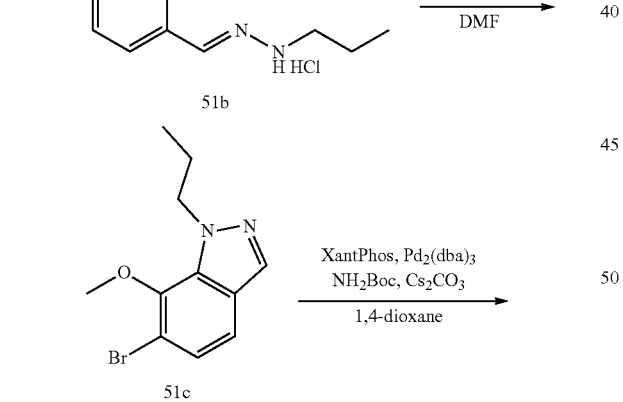

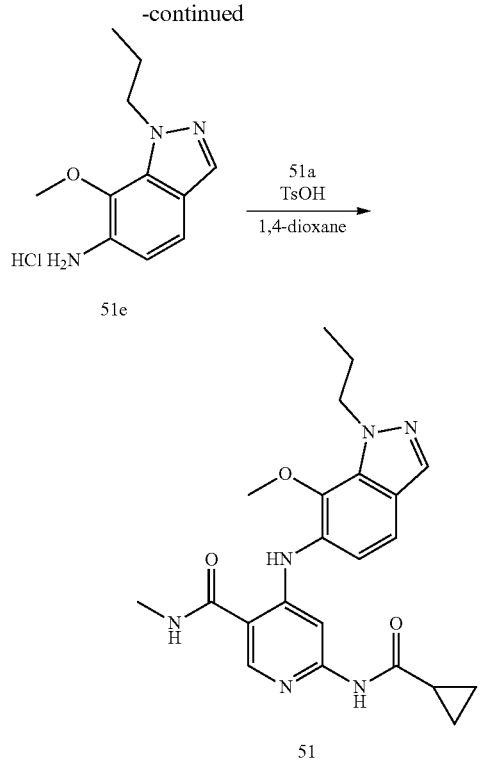

Step 1. 4-Chloro-6-(cyclopropanecarboxamido)-N-methylnicotinamide (51a)

A mixture of 44a (338 mg, 1.37 mmol), DIPEA (1.06 g, 8.23 mmol), methylamine hydrochloride (184 mg, 2.75 mmol) and $T_3P$ (1.75 g, 2.74 mmol, 50% wt in DMF) in DMF (2 mL) was stirred at 50° C. for 24 h. The reaction mixture was poured into water (5 mL) and extracted with EtOAc (20 mL*3). The separated organic layer was washed with water (5 mL) and concentrated under reduced pressure. The residue was purified by flash chromatography on silica gel (DCM/MeOH=10/1) to afford the tile compound 51a (120 mg, 34% yield) as a white solid. $^1$H NMR (400 MHz, DMSO-$d_6$) δ 11.19 (s, 1H), 8.46 (s, 1H), 8.37 (s, 1H), 8.19 (s, 1H), 2.75 (d, J=5.2 Hz, 3H), 2.02-1.99 (m, 1H), 0.85-0.82 (m, 4H).

Step 2. (E)-1-(2,4-dibromo-3-methoxybenzylidene)-2-propylhydrazine hydrochloride (51b)

A mixture of 42f (700 mg, 2.38 mmol) and propylhydrazine dihydrochloride (290 mg, 2.62 mmol) in EtOH (3 mL) was stirred at rt for 0.5 h. The reaction mixture was cooled to 0° C. and filtered. The filter cake was washed with EtOH (2 mL) and dried to afford afford the title compound 51b (500 mg, 60% yield) as a yellow solid. LC-MS (Method 3) $t_R$=1.41 min, m/z (M+H)$^+$=349.1.

Step 3. 6-Bromo-7-methoxy-1-propyl-1H-indazole (51c)

A mixture of 51b (400 mg, 1.03 mmol), $K_2CO_3$ (429 mg, 3.10 mmol) and CuI (79 mg, 0.41 mmol) in DMF (10 mL) was stirred at 100° C. for 8 h. The reaction mixture was filtered and the filtrate was diluted with water (10 mL). The mixture was extracted with EtOAc (20 mL*2). The combined organic phase was washed brine (20 mL*2), concentrated and the residue was purified by flash chromatography on silica gel (PE/EtOAc=30/1) to afford the title compound 51c (120 mg, 43% yield) as a yellow oil. $^1$H NMR (400 MHz, CDCl$_3$) δ 7.94 (s, 1H), 7.33 (d, J=8.8 Hz, 1H), 7.22 (d, J=8.8 Hz, 1H), 4.52 (t, J=7.2 Hz, 2H), 4.00 (s, 3H), 1.98-1.89 (m, 2H), 0.92 (t, J=7.6 Hz, 3H).

Step 4. Tert-butyl (7-methoxy-1-propyl-1H-indazol-6-yl)carbamate (51d)

A mixture of 51c (120 mg, 0.45 mmol), tert-butyl carbamate (104 mg, 0.89 mmol), XantPhos (77 mg, 0.13 mmol)), Pd$_2$(dba)$_3$ (61 mg, 0.67 mmol) and Cs$_2$CO$_3$ (291 mg, 0.89 mmol) in 1,4-dioxane (3 mL) was stirred at 100° C. for 24 h under N$_2$. After cooling to r.t., the reaction mixture was diluted with water (5 mL) and extracted with EtOAc (10 mL*2). The combined organic phase was concentrated and the residue was purified by flash chromatography on silica gel (PE/EtOAc=20/1) to afford the title compound 51d (57 mg, 42% yield) as a yellow oil. $^1$H NMR (400 MHz, CDCl$_3$) δ 7.90 (s, 1H), 7.85 (d, J=8.4 Hz, 1H), 7.42 (d, J=8.8 Hz, 1H), 6.94 (s, 1H), 4.47 (t, J=7.6 Hz, 1H), 3.87 (s, 3H), 1.94-1.89 (m, 2H), 1.55 (s, 9H), 0.89 (t, J=7.6 Hz, 3H).

Step 5. 7-Methoxy-1-propyl-1H-indazol-6-amine hydrochloride (51e)

To a mixture of 51d (62 mg, 0.20 mmol) in EtOH (1 mL) was added HCl (g) in EtOH (2 mL, 1.5 M) at 0° C. After stirring at r.t. for 2 h, the reaction mixture was concentrated to afford the title compound 51e (45 mg, 92% yield) as a yellow solid. LC-MS (Method 3) t$_R$=0.94 min, m/z (M+H)$^+$=206.4.

Step 6. 6-(Cyclopropanecarboxamido)-4-((7-methoxy-1-propyl-1H-indazol-6-yl)amino)-N-methylnicotinamide (51)

A mixture of 51e (19 mg, 0.079 mmol), 51a (20 mg, 0.079 mmol) and TsOH (3 mg, 0.017 mmol) in 1,4-dioxane (2 mL) was stirred at 100° C. for 20 h. The reaction mixture was concentrated and purified by Prep-HPLC (Method A) to afford 51 (17 mg, 51% yield) as a white solid. LC-MS (Method 2) t$_R$=2.78 min, m/z (M+H)$^+$=423.1. $^1$H NMR (400 MHz, DMSO-d$_6$) δ 10.69 (s, 1H), 10.53 (s, 1H), 8.62 (d, J=4.8 Hz, 1H), 8.51 (s, 1H), 8.03 (s, 1H), 7.62 (s, 1H), 7.50 (d, J=8.8 Hz, 1H), 7.09 (d, J=8.8 Hz, 1H), 4.46 (t, J=6.8 Hz, 2H), 3.78 (s, 3H), 2.81 (d, J=4.4 Hz, 3H), 1.97-1.91 (m, 1H), 1.88-1.79 (m, 2H), 0.84 (t, J=7.6 Hz, 3H), 0.76-0.68 (m, 4H).

Example 52

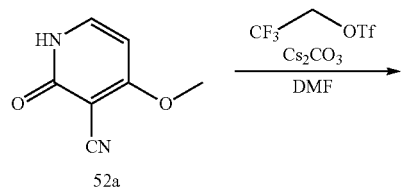

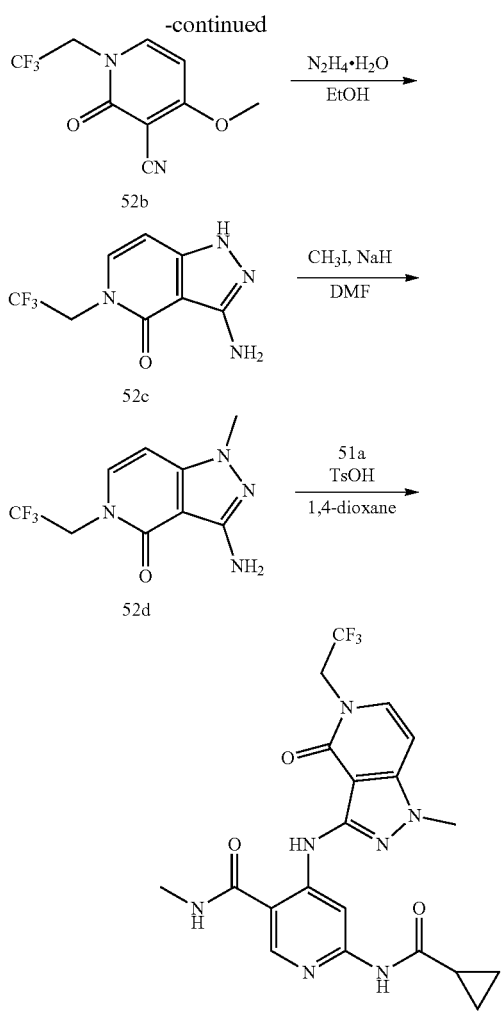

Step 1. 4-Methoxy-2-oxo-1-(2,2,2-trifluoroethyl)-1,2-dihydropyridine-3-carbonitrile (52b)

To a solution of 52a (5 g, 33.3 mmol) and Cs$_2$CO$_3$ (21.7 g, 66.6 mmol) in DMF (100 mL) was added 2,2,2-trifluoroethyl trifluoromethanesulfonate (23.2 g, 99.9 mmol) at 0° C., then the mixture was stirred at 25° C. for 14 h. The mixture was diluted with H$_2$O (200 mL), extracted with EA (100 mL*3), washed with brine, dried over Na$_2$SO$_4$, concentrated to get the crude product 52b (8.0 g, yield given) as a yellow oil. LC-MS (Method 4) t$_R$=2.34 min, m/z (M+H)$^+$=233.0.

Step 2. 3-Amino-5-(2,2,2-trifluoroethyl)-1,5-dihydro-4H-pyrazolo[4,3-c]pyridin-4-one (52c)

To a solution of 52b (8 g, 34.5 mmol) in EtOH (80 mL) was added N$_2$H$_4$·H$_2$O (26.5 g, 425 mmol, 80% wt in H$_2$O) at 0° C., then the mixture was stirred at 80° C. for 14 h. The mixture was concentrated and slurried with (MTBE/EA, 25 ml/25 mL) to get the compound 52c (4 g, 46.4 mmol) as a yellow solid. LC-MS (Method 4) t$_R$=1.42 min, m/z (M+H)$^+$=233.0.

Step 3. 3-Amino-1-methyl-5-(2,2,2-trifluoroethyl)-1,5-dihydro-4H-pyrazolo[4,3-c]pyridin-4-one (52d)

To a solution of 52c (250 mg, 1.1 mmol) in DMF (2 mL) was added NaH (60 mg, 1.55 mmol, 60% in oil) at 0° C., the mixture was stirred at 25° C. for 30 min, then CH$_3$I (550 mg, 3.88 mmol) was added and stirred at 25° C. for 4 h. The mixture was diluted with H$_2$O (5 mL), extracted with EA (5 mL*3), washed with brine, dried over Na$_2$SO$_4$, concentrated to get the crude compound 52d (250 mg, 95% yield) as a brown oil. LC-MS (Method 4) t$_R$=2.06 min, m/z (M+H)$^+$=247.1.

Step 4. 6-(Cyclopropanecarboxamido)-N-methyl-4-((1-methyl-4-oxo-5-(2,2,2-trifluoroethyl)-4,5-dihydro-1H-pyrazolo[4,3-c]pyridin-3-yl)amino)nicotinamide (52)

A mixture of 52d (30 mg, 0.12 mmol), 51a (33 mg, 0.12 mmol) and pTSA (25 mg, 0.15 mmol) in 1,4-dioxane (1 mL) was stirred at 100° C. for 16 h. The mixture was concentrated and purified by Prep-HPLC (Method D) to get the compound 52 (2 mg, 4% yield) as a white solid. LC-MS (Method 4) t$_R$=2.65 min, m/z (M+H)$^+$=464.2. $^1$H NMR (400 MHz, DMSO-d$_6$) δ 11.69 (s, 1H), 10.69 (s, 1H), 9.24 (s, 1H), 8.54-8.50 (m, 2H), 7.47 (dd, J=7.6, 0.9 Hz, 1H), 6.68 (d, J=7.6 Hz, 1H), 4.83 (q, J=9.2 Hz, 2H), 3.81 (s, 3H), 2.77 (d, J=4.4 Hz, 3H), 2.02-1.95 (m, 1H), 0.83-0.74 (m, 4H).

Example 53 was stirred at 100° C. for 16 h. The mixture was concentrated and purified by Prep-HPLC (Method D) to get the compound 53 (20.4 mg, 22% yield) as a white solid. LC-MS (Method 4) t$_R$=2.65 min, m/z (M+H)$^+$=467.2. $^1$H NMR (400 MHz, DMSO-d$_6$) δ 11.68 (s, 1H), 10.68 (s, 1H), 9.24 (s, 1H), 8.50 (s, 1H), 8.49 (s, 1H), 7.47 (d, J=7.6 Hz, 1H), 6.68 (d, J=7.6 Hz, 1H), 4.83 (q, J=9.2 Hz, 2H), 3.81 (s, 3H), 2.01-1.94 (m, 1H), 0.82-0.75 (m, 4H).

Example 54

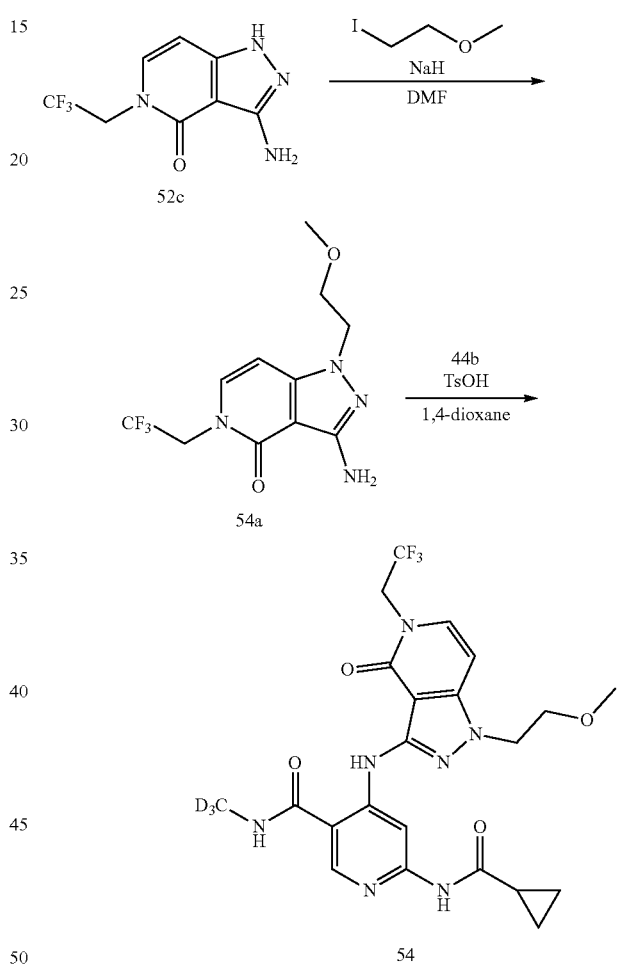

Step 1. 3-Amino-1-(2-methoxyethyl)-5-(2,2,2-trifluoroethyl)-1,5-dihydro-4H-pyrazolo[4,3-c]pyridin-4-one (54a)

To a solution of 52c (500 mg, 2.2 mmol) in DMF (5 mL) was added NaH (107 mg, 2.8 mmol, 60% in mineral oil) at 0° C., the mixture was stirred at 25° C. for 30 min, then 2-iodoethyl methyl ether (801 mg, 4.3 mmol) was added, and stirred at 25° C. for 4 h. The mixture was was diluted with H$_2$O (15 mL), extracted with EA (15 mL*3), washed with brine, dried over Na$_2$SO$_4$, concentrated to get the compound 54a (500 mg, 80%) as a brown oil. LC-MS (Method 4) t$_R$=2.25 min, m/z (M+H)$^+$=291.2.

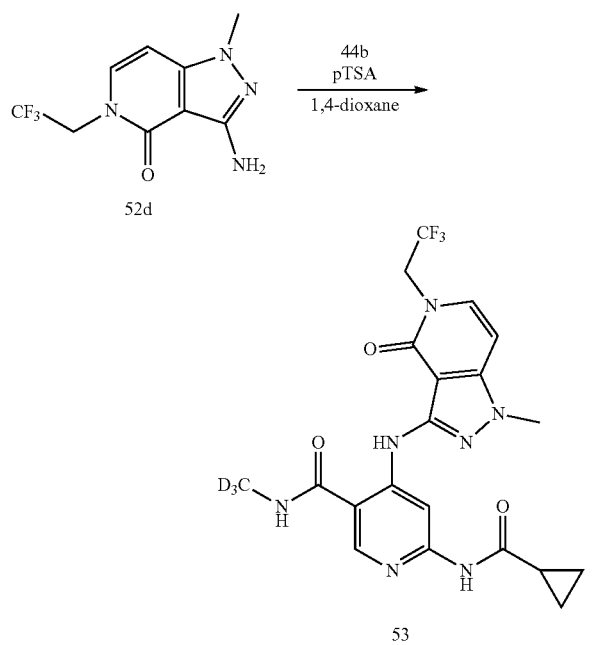

Step 1. 6-(Cyclopropanecarboxamido)-N-(methyl-d$_3$)-4-((1-methyl-4-oxo-5-(2,2,2-trifluoroethyl)-4,5-dihydro-1H-pyrazolo[4,3-c]pyridin-3-yl)amino)nicotinamide (53)

A mixture of 52d (50 mg, 0.19 mmol), 44b (48 mg, 0.19 mmol) and pTSA (37 mg, 0.19 mmol) in 1,4-dioxane (1 mL)

Step 2 6-(Cyclopropanecarboxamido)-4-((1-(2-methoxyethyl)-4-oxo-5-(2,2,2-trifluoroethyl)-4,5-dihydro-1H-pyrazolo[4,3-c]pyridin-3-yl)amino)-N-(methyl-d₃)nicotinamide (54)

A mixture of 54ᵃ (56.52 mg, 0.19 mmol), 44b (50 mg, 0.19 mmol) and pTSA (37 mg, 0.19 mmol) in 1,4-dioxane (1 mL) was stirred at 100° C. for 16 h. The mixture was concentrated and DIPEA (0.2 mL), MeOH (2 mL) was added. The mixture was stirred at 25° C. for 1 h, filtered to get the compound 54 (36.5 mg, 37% yield) as a white solid. LC-MS (Method 4) $t_R$=3.03 min, m/z (M+H)⁺=511.3. ¹H NMR (400 MHz, DMSO-$d_6$) δ 11.68 (s, 1H), 10.72 (s, 1H), 9.35 (s, 1H), 8.52 (s, 1H), 8.51 (s, 1H), 7.46 (d, J=7.6 Hz, 1H), 6.72 (d, J=7.6 Hz, 1H), 4.82 (q, J=9.2 Hz, 2H), 4.27 (t, J=5.4 Hz, 2H), 3.87 (t, J=5.4 Hz, 2H), 3.19 (s, 3H), 2.02-1.96 (m, 1H), 0.81-0.76 (m, 4H).

Example 55

Na₂SO₄, concentrated to get compound 55a (60 mg, 85% yield) as a yellow solid. LC-MS (Method 4) $t_R$=3.47 min, m/z (M+H)⁺=360.1.

Step 2. 6-((5-Fluoropyridin-2-yl)amino)-4-((2-methoxy-3-(trifluoromethyl)phenyl)amino)-N-methylnicotinamide (55)

A mixture of 55a (20 mg, 0.056 mmol), 5-fluoropyridin-2-amine (9.35 mg, 0.083 mmol), Cs₂CO₃ (45 mg, 0.14 mmol), Pd₂(dba)₃ (5 mg, 0.006 mmol), XantPhos (6 mg, 0.011 mmol) in DMA (1 mL) was stirred at 145° C. for 2 h. The mixture was filtered and purified by Prep-HPLC (Method E) to get the compound 55 (2.2 mg, 9% yield) as an off-white solid. LC-MS (Method 4) $t_R$=3.25 min, m/z (M+H)⁺=436.1. ¹H NMR (400 MHz, CDCl₃) δ 10.66 (s, 1H), 8.28 (s, 1H), 8.04 (s, 1H), 7.66 (d, J=7.6 Hz, 1H), 7.40-7.32 (m, 5H), 7.24-7.20 (m, 1H), 6.12 (s, 1H), 3.85 (s, 3H), 3.02 (d, J=4.8 Hz, 3H).

Example 56

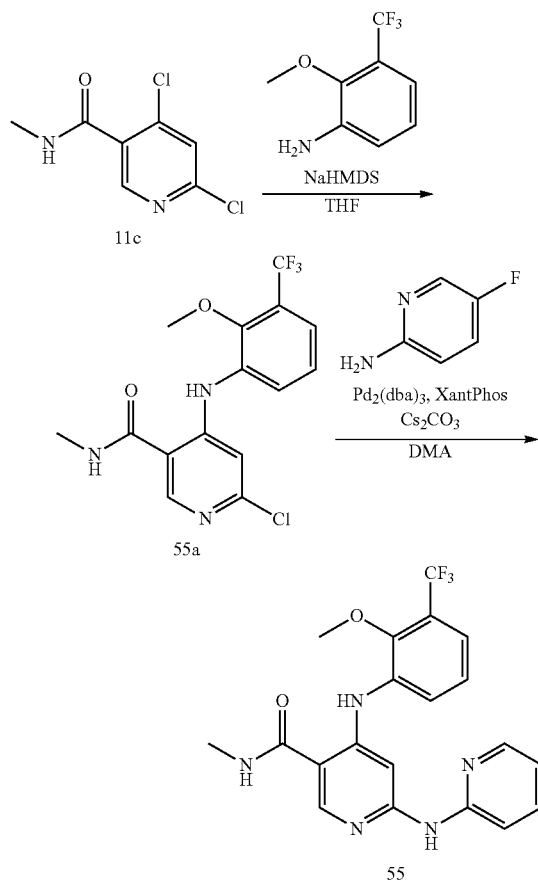

Step 1. 6-Chloro-4-((2-methoxy-3-(trifluoromethyl)phenyl)amino)-N-methylnicotinamide (55a)

To a solution of 11c (40 mg, 0.20 mmol), 2-methoxy-3-(trifluoromethyl)aniline (41 mg, 0.21 mmol) in THF (1 mL) was added NaHMDS (0.86 mL, 1.71 mmol, 2 M in THF) at an ice-bath, then the mixture was stirred at r.t. for 2 h. The mixture was diluted with H₂O (10 mL), extracted with EtOAc (10 mL*3), washed with brine (10 mL), dried over

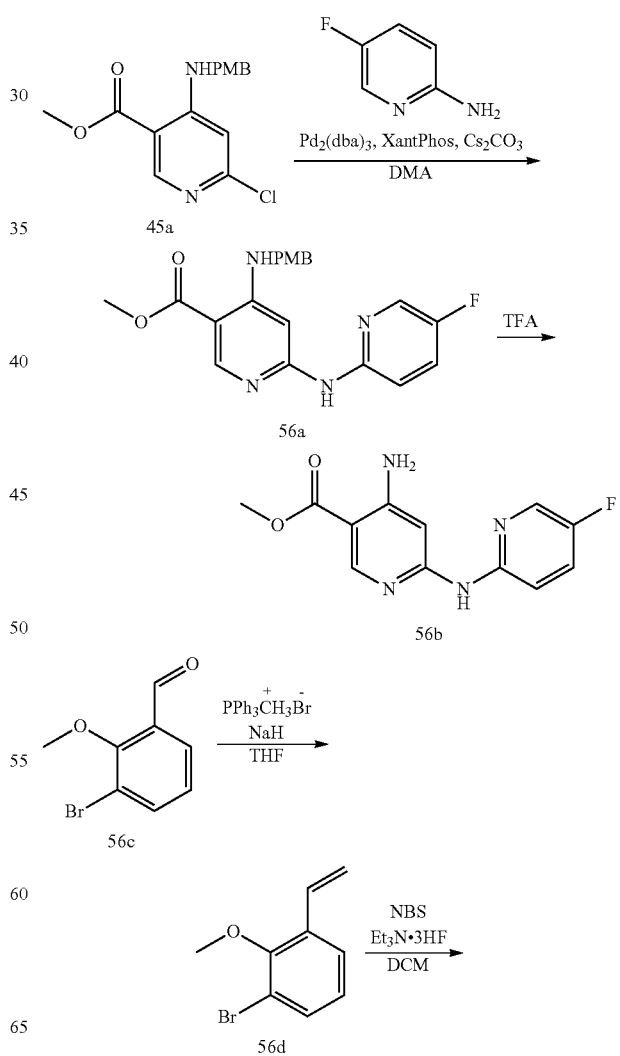

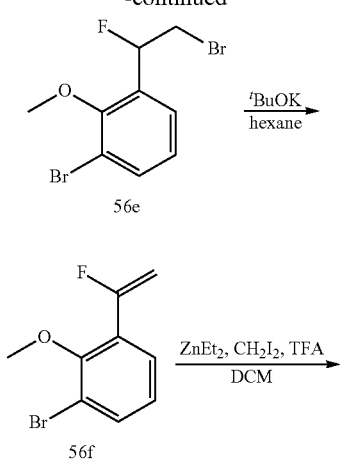

56e

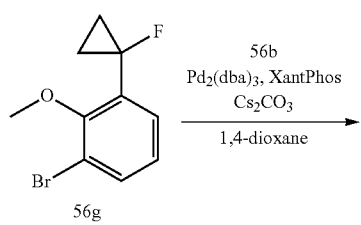

56f

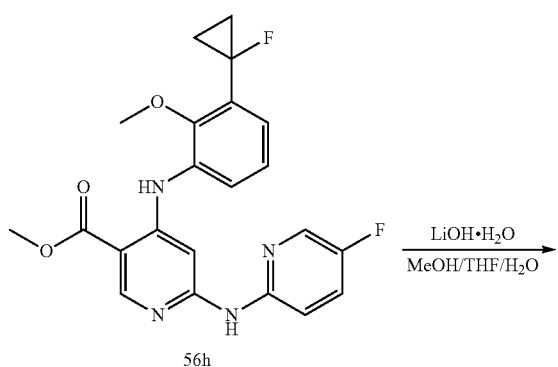

56g

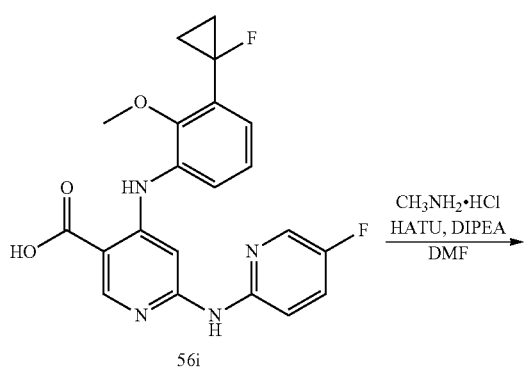

56h

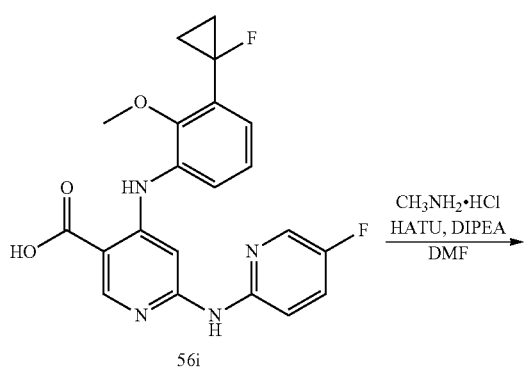

56i

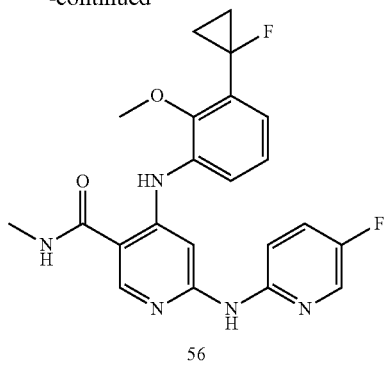

56

Step 1. Methyl 6-((5-fluoropyridin-2-yl)amino)-4-((4-methoxybenzyl)amino)nicotinate (56a)

A mixture of 45a (200 mg, 0.65 mol), 5-fluoropyridin-2-amine (110 mg, 0.98 mmol), $Pd_2(dba)_3$ (36 mg, 0.039 mmol), XantPhos (75 mg, 0.13 mmol), $Cs_2CO_3$ (531 mg, 1.63 mmol) in DMA (3 mL) was stirred at 145° C. (M.W.) for 1.5 h. The mixture was diluted with $H_2O$ (10 mL), extracted with EtOAc (10 mL*3), washed with brine (20 mL), dried over $Na_2SO_4$, concentrated and purified by flash chromatography (DCM/MeOH=100/1 to 30/1) to get the compound 56a (200 mg, 80% yield) as a yellow solid. LC-MS (Method 4) $t_R$=3.09 min, m/z $(M+H)^+$=383.2.

Step 2. Methyl 4-amino-6-((5-fluoropyridin-2-yl)amino)nicotinate (56b)

A solution of methyl 56a (200 mg, 0.52 mmol) in TFA (4 mL) was stirred at 40° C. for 2 h. The mixture was concentrated and then diluted with $H_2O$ (20 mL), adjusted pH to 7-9 with aq $Na_2CO_3$, extracted with EtOAc (15 mL*3), washed with brine (20 mL), dried over $Na_2SO_4$, concentrated and purified by flash chromatography (DCM/MeOH=100/1 to 25/1) to get the compound 56b (55 mg, 40% yield) as a yellow solid. LC-MS (Method 4) $t_R$=2.13 min, m/z $(M+H)^+$=263.1.

Step 3. 1-Bromo-2-methoxy-3-vinylbenzene (56d)

To a suspension of 56c (3.0 g, 13.95 mmol) and methyl (triphenyl)phosphonium bromide (6.00 g, 16.74 mmol) in THF (50 mL) was added NaH (2.23 g, 55.80 mmol, 60% in mineral oil) at 0° C., then the mixture was stirred at r.t. for 16 h. The mixture was diluted with $H_2O$ (100 mL), extracted with EtOAc (60 mL*3), washed with brine (100 mL), dried over $Na_2SO_4$, concentrated and purified by flash chromatography (PE/EtOAc=50/1 to 20/1) to get the compound 56d (2.2 g, 74% yield) as a colorless oil. $^1H$ NMR (400 MHz, $CDCl_3$) δ 7.45 (d, J=8.0 Hz, 2H), 7.04-6.95 (m, 2H), 5.78 (dd, J=44 Hz, J=1.2 Hz, 1H), 5.35 (dd, J=44 Hz, J=1.2 Hz, 1H), 3.81 (s, 3H).

Step 4. 1-Bromo-3-(2-bromo-1-fluoroethyl)-2-methoxybenzene (56e)

Compound 56d (2.2 g, 10.33 mmol) was dissolved in DCM (20 mL) and the mixture was cooled to 5° C., triethylamine trihydrofluoride (4.99 g, 30.98 mmol) and NBS (2.21 g, 12.39 mmol) were added to the mixture in one portion and the mixture was stirred at r.t. overnight. The mixture was washed with 10% aq. solution of NaHCO₃ (200 mL*2) and brine (100 mL), dried over Na₂SO₄, and evaporated in vacuo at 45° C. to get the compound 56e (2.5 g, 78% yield) as a colorless oil.

Step 5. 1-Bromo-3-(1-fluorovinyl)-2-methoxybenzene (56f)

tBuOK (1.80 g, 16.03 mmol) was suspended in hexane (20 mL). The mixture was cooled to 0° C. and 56e (2.50 g, 8.01 mmol) in hexane (20 mL) was added dropwise to the mixture. The mixture was slowly heated up to room temperature and stirred at this temperature for 1 h. EtOAc (200 mL) was added and the mixture was washed with brine (100 mL*2), dried over Na₂SO₄, concentrated and purified by flash chromatography (PE/EtOAc=100/1 to 20/1) to get the crude compound 56f (1.1 g, 59% yield) as a colorless oil. ¹H NMR (400 MHz, CDCl₃) δ 7.55 (dd, J=8.0 Hz, J=1.6 Hz, 1H), 7.46 (dd, J=7.6 Hz, J=1.6 Hz, 1H), 7.01 (t, J=8.0 Hz, 1H), 5.39 (dd, J=52.0 Hz, J=2.8 Hz, 1H), 5.08 (dd, J=19.6 Hz, J=2.8 Hz, 1H), 3.83 (s, 3H).

Step 6. 1-Bromo-3-(1-fluorocyclopropyl)-2-methoxybenzene (56g)

To a solution of diethylzinc (10 mL, 10.00 mmol, 1 M in hexane) in DCM (20 mL) was added diiodomethane (2.87 g, 10.71 mmol) in DCM (5 mL) at −5° C. Then the mixture was stirred at −5° C. for 30 min, then a solution of TFA (1.09 g, 9.52 mmol) in DCM (5 mL) was added and stirred at −5° C. for 30 min. A solution of 56g (550 mg, 2.38 mmol) in DCM (5 mL) was added. After 5 min, the mixture was warmed to room temperature and stirred overnight. The mixture was treated with 1 N HCl (100 mL) and extracted with DCM (50 mL*3), washed with brine (100 mL), dried over Na₂SO₄, concentrated and purified by flash chromatography (PE/EtOAc=100/1) to get the compound 56e (100 mg, 17% yield) as a yellow oil. ¹H NMR (400 MHz, CDCl₃) δ 7.59-7.56 (m, 1H), 7.43-7.40 (m, 1H), 7.02-6.98 (m, 1H), 3.97 (s, 3H), 1.55-1.36 (m, 2H), 1.03-0.87 (m, 2H).

Step 7. Methyl 4-((3-(1-fluorocyclopropyl)-2-methoxyphenyl)amino)-6-((5-fluoropyridin-2-yl)amino)nicotinate (56h)

A mixture of 56g (30 mg, 0.11 mmol), 56b (28 mg, 0.11 mmol), Pd₂(dba)₃ (16 mg, 0.017 mmol), XantPhos (19.86 mg, 0.034 mmol), Cs₂CO₃ (112 mg, 0.34 mmol) in 1,4-dioxane (1 mL) was stirred at 95° C. for 16 h. The mixture was concentrated and purified by flash chromatography (DCM/MeOH=20/1) to get the compound 56h (10 mg, 20% yield) as a yellow solid. LC-MS (Method 4) t$_R$=3.73 min, m/z (M+H)⁺=427.2.

Step 8. 4-((3-(1-Fluorocyclopropyl)-2-methoxyphenyl)amino)-6-((5-fluoropyridin-2-yl)amino)nicotinic acid (56i)

To a solution of 56h (10 mg, 0.023 mmol) in the solvent (MeOH/THF/H₂O=2/2/1, 0.5 mL) was added LiOH·H₂O (3 mg, 0.070 mmol), then the mixture was stirred at r.t. for 4 h. The mixture was acidified to pH=4 with 1 N HCl, then the mixture was concentrated to get the crude compound 56i (9 mg, 93% yield) as a yellow solid. LC-MS (Method 4) t$_R$=3.44 min, m/z (M+H)⁺=413.1.

Step 9. 4-((3-(1-Fluorocyclopropyl)-2-methoxyphenyl)amino)-6-((5-fluoropyridin-2-yl)amino)-N-methylnicotinamide (56)

To a solution of 56i (9 mg, 0.022 mmol) in DMF (0.5 mL) was added DIPEA (25 mg, 0.20 mol), methanamine hydrochloride (9 mg, 0.13 mmol) and HATU (17 mg, 0.044 mmol) at an ice-bath. The the mixture was stirred at r.t. for 16 h. The mixture was purified by Prep-HPLC (Method E) to get the compound 56 (0.7 mg, 7% yield) as a white solid. LC-MS (Method 4) t$_R$=3.33 min, m/z (M+H)⁺=426.2. ¹H NMR (400 MHz, CDCl₃) δ 10.47 (s, 1H), 8.22 (s, 1H), 8.00 (s, 1H), 7.65 (s, 1H), 7.52 (d, J=8.0 Hz, 1H), 7.34-7.27 (m, 3H), 7.18-6.99 (m, 1H), 6.33 (brs, 1H), 3.91 (s, 3H), 3.00 (d, J=4.8 Hz, 3H), 1.45-1.38 (m, 2H), 1.08-1.04 (m, 2H).

Example 57

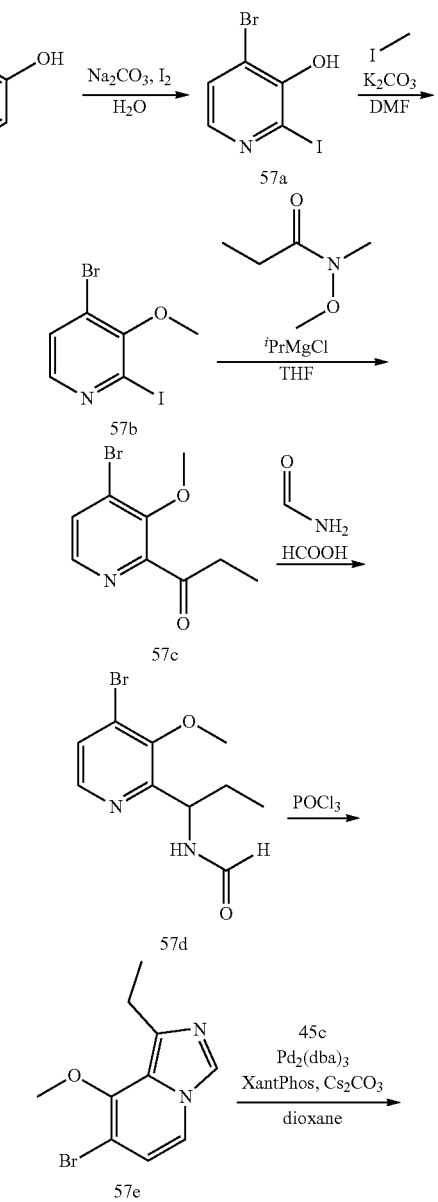

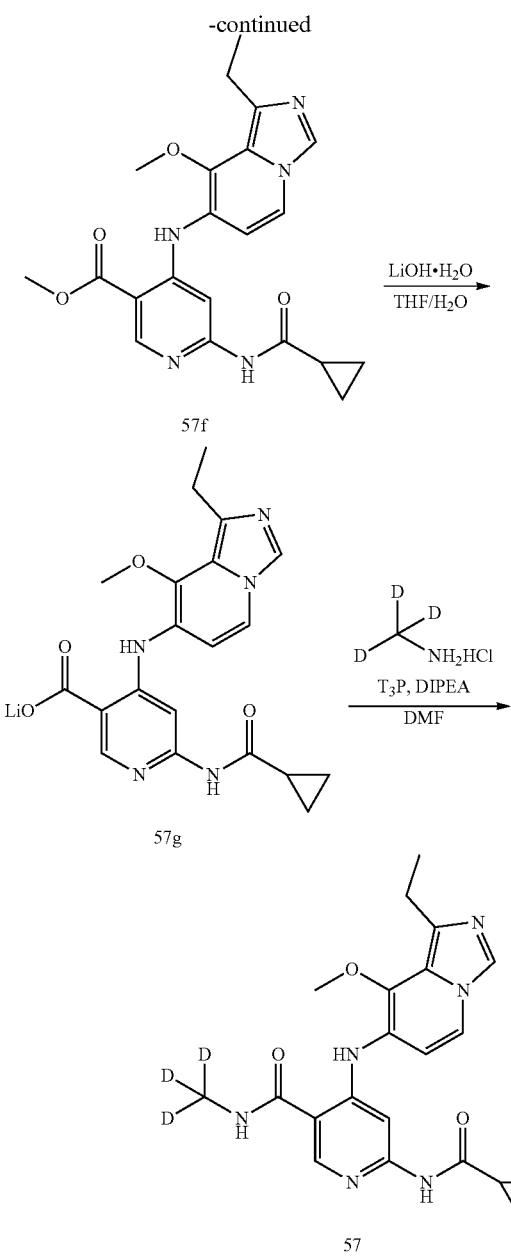

Step 1. 4-Bromo-2-iodopyridin-3-ol (57a)

To a solution of 4-bromopyridin-3-ol (3.0 g, 17.24 mmol) in H$_2$O (30 mL) was added Na$_2$CO$_3$ (3.91 g, 36.21 mmol) and I$_2$ (4.38 g, 17.24 mmol), then the mixture was stirred at r.t. for 16 h. The mixture was adjusted to pH=4 with aq HCl (2 N), the mixture was filtered and the solid was dried to get the compound 57a (5.1 g, 99% yield) as a white solid. LC-MS (Method 4) t$_R$=2.67 min, m/z (M+H)$^+$=299.9.

Step 2. 4-Bromo-2-iodo-3-methoxypyridine (57b)

To a solution of 57a (5 g, 16.67 mmol) in DMF (50 mL) was added K$_2$CO$_3$ (6.90 g, 50.02 mmol), and iodomethane (3.31 g, 23.34 mmol, 1.45 mL), then the mixture was stirred at r.t. for 2 h. The mixture was diluted with H$_2$O (200 mL), extracted with EtOAc (60 mL*3), washed with brine (60 mL), dried over Na$_2$SO$_4$, concentrated and purified by flash chromatography (PE/EA=100/1 to 2/1) to get the compound 57b (4.5 g, 86% yield) as a white solid. LC-MS (Method 4) t$_R$=3.43 min, m/z (M+H)$^+$=313.9.

Step 3. 1-(4-Bromo-3-methoxypyridin-2-yl)propan-1-one (57c)

To a solution of 57b (4 g, 12.74 mmol) in THF (40 mL) was added $^i$PrMgCl (7.7 mL, 15.4 mmol, 2 M in THF) at 0° C., and the mixture was stirred at 0° C. for 1 h. A solution of N-methoxy-N-methyl-propanamide (1.81 g, 15.4 mmol) in THF (5 mL) was added into the mixture at 0° C. and stirred at 0° C. for 1 h and stirred at r.t. for 4 h. The mixture was diluted with H$_2$O (200 mL), extracted with EtOAc (60 mL*3), washed with brine (60 mL), dried over Na$_2$SO$_4$, concentrated and purified by flash chromatography (PE/EA=100/1 to 2/1) to get the compound 57c (2.7 g, 87% yield) as a colorless oil. LC-MS (Method 4) t$_R$=3.80 min, m/z (M+H)$^+$=244.0.

Step 4. N-(1-(4-bromo-3-methoxypyridin-2-yl)propyl)formamide (57d)

To a solution of 57c (2.7 g, 11.06 mmol) in formamide (49.82 g, 1.11 mol, 44 mL) was added formic acid (10.18 g, 221.2 mmol, 8 mL), then the mixture was stirred at 135° C. for 16 h. The mixture was diluted with H$_2$O (200 mL), extracted with EtOAc (70 mL*3). The organic layers were washed with brine (50 mL*2), dried over Na$_2$SO$_4$, concentrated and purified by flash chromatography (PE/EA=10/1 to 1/2) to get the compound 57d (600 mg, 20% yield) as a yellow oil. LC-MS (Method 4) t$_R$=2.94 min, m/z (M+H)$^+$=273.1.

Step 5. 7-Bromo-1-ethyl-8-methoxyimidazo[1,5-a]pyridine (57e)

A solution of 57d (600 mg, 2.20 mmol) in POCl$_3$ (6 mL) was stirred at 100° C. for 1.5 h. The mixture was concentrated and diluted with H$_2$O (20 mL) at 5° C., extracted with EtOAc (15 mL*3), washed with brine (15 mL), dried over Na$_2$SO$_4$, concentrated and purified by flash chromatography (PE/EA=20/1 to 1/2) to get the compound 57e (500 mg, 89% yield) as a yellow solid. LC-MS (Method 4) t$_R$=1.23 min, m/z (M+H)$^+$=255.1.

Step 6. Methyl 6-(cyclopropanecarboxamido)-4-((1-ethyl-8-methoxyimidazo[1,5-a]pyridin-7-yl)amino)nicotinate (57f)

A mixture of 57e (102 mg, 0.4 mmol), 45c (140 mg, 0.4 mmol), Pd$_2$(dba)$_3$ (37 mg, 0.04 mmol), XantPhos (47 mg, 0.08 mmol), Cs$_2$CO$_3$ (522 mg, 1.60 mmol) in dioxane (2 mL) was stirred at 100° C. for 16 h. The mixture was concentrated and purified by flash chromatography (DCM/MeOH=100/1 to 20/1) to get the compound 57f (30 mg, 18% yield) as a yellow solid. LC-MS (Method 4) t$_R$=2.49 min, m/z (M+H)$^+$=410.3.

Step 7. Lithium 6-(cyclopropanecarboxamido)-4-((1-ethyl-8-methoxyimidazo[1,5-a]pyridin-7-yl)amino)nicotinate (57g)

To a solution of 57f (30 mg, 0.073 mmol) in THF (2 mL) and H$_2$O (0.5 mL) was added LiOH·H$_2$O (9 mg, 0.22 mmol), the mixture was stirred at r.t. for 16 h. The mixture was concentrated to get the crude compound 57g (29 mg, 99% yield) as an off-white solid. LC-MS (Method 4) $t_R$=1.07 min, m/z (M+H)$^+$=396.3.

Step 8. 6-(Cyclopropanecarboxamido)-4-((1-ethyl-8-methoxyimidazo[1,5-a]pyridin-7-yl)amino)-N-(methyl-d$_3$)nicotinamide (57)

To a solution of 57g (29 mg, 0.072 mmol) in DMF (2 mL) was added methan-d$_3$-amine hydrochloride (15 mg, 0.4 mmol), DIPEA (140 mg, 1.08 mmol) and T$_3$P (138 mg, 0.22 mmol, 50% wt. in EA) at an ice-bath, then the mixture was stirred at r.t. for 16 h. The mixture was quenched with H$_2$O (0.5 mL) and stirred for 15 min at r.t., the mixture was concentrated and purified by Prep-HPLC (Method E) to get the compound 57 (3.2 mg, 11% yield) as an off-white solid. LC-MS (Method 4) $t_R$=1.20 min, m/z (M+H)$^+$=412.3. $^1$H NMR (400 MHz, DMSO-d$_6$) δ 10.65 (s, 1H), 10.21 (s, 1H), 8.52 (s, 1H), 8.46 (s, 1H), 8.20 (s, 1H), 8.01 (d, J=7.6 Hz, 1H), 7.60 (s, 1H), 6.47 (d, J=7.6 Hz, 1H), 3.72 (s, 3H), 2.85 (q, J=7.6 Hz, 2H), 1.97-1.92 (m, 1H), 1.20 (t, J=7.6 Hz, 3H), 0.71-0.69 (m, 4H).

Example 58

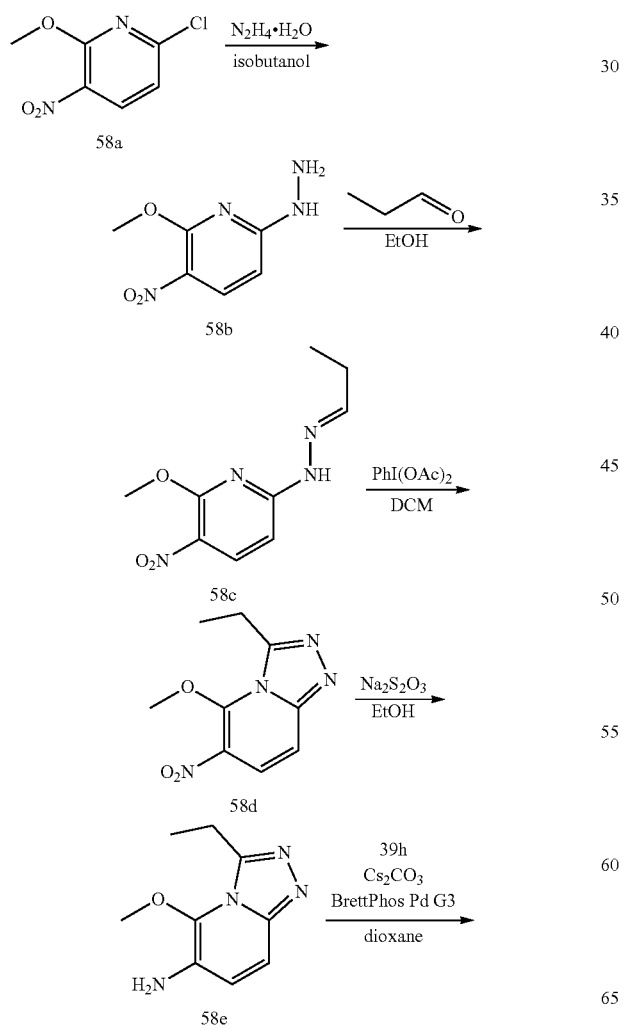

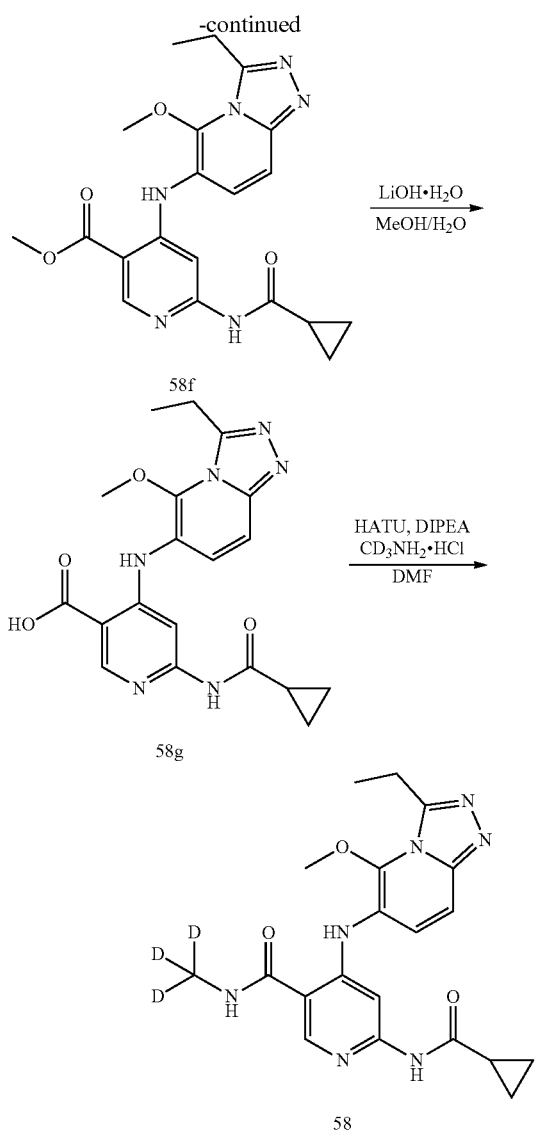

Step 1. 6-Hydrazineyl-2-methoxy-3-nitropyridine (58b)

A mixture of 58a (7.00 g, 37.12 mmol) and N$_2$H$_4$·H$_2$O (5.57 g, 111.37 mmol) in isobutanol (5 mL) was stirred at 80° C. for 2 h. A yellow suspension was formed. The reaction mixture was concentrated and triturated with MeCN (30 mL) to give 58b as a pale brown solid (6.8 g, yield given), which was used for the next step directly without further purification. LC-MS (Method 4) $t_R$=0.61 min, m/z (M+H)$^+$=185.1.

Step 2. 2-Methoxy-3-nitro-6-(2-propylidenehydrazineyl)pyridine (58c)

A mixture of 58b (3.00 g, 16.29 mmol) in ethanol (60 mL) was added propanal (870 mg, 14.99 mmol, 1.07 mL). The resulting mixture was stirred at 80° C. for 1 h. A yellow suspension was formed. The reaction mixture was concentrated and purified by flash chromatography (EA in PE is 10-50%) to give 58c (1.20 g, 33% yield) as a yellow solid. LC-MS (Method 4) $t_R$=3.87 min, m/z (M+H)$^+$=225.1.

Step 3. 3-Ethyl-5-methoxy-6-nitro-[1,2,4]triazolo[4,3-a]pyridine (58d)

To a mixture of 58c (1.20 g, 5.35 mmol) in DCM (15 mL) and MeOH (5 mL), was added PhI(AcO)$_2$ (1.72 g, 5.35 mmol) at 20° C. The resulting mixture was stirred at 20° C. for 12 h. A yellow solution was formed. The reaction mixture was quenched with water (50 mL) and extracted with DCM (50 mL*3). The combined organic layer was washed with brine (50 mL*2), dried over anhydrous Na$_2$SO$_4$, filtered and concentrated. The residue was purified by column chromatograph (EA in PE is 10-60%) to give 58d as a yellow solid (410 mg, 34% yield). LC-MS (Method 4) $t_R$=2.95 min, m/z (M+H)$^+$=223.1.

Step 4. 3-Ethyl-5-methoxy-[1,2,4]triazolo[4,3-a]pyridin-6-amine (58e)

To a solution of 58d (130 mg, 0.585 mmol) in ethanol (10 mL) was added aq. Na$_2$S$_2$O$_4$ (1 M, 5 mL). The resulting mixture was stirred at 80° C. under N$_2$ atmosphere for 10 min. A white suspension was formed. The reaction mixture was diluted with water (50 mL) and extracted with EtOAc (30 mL*3). The combined organic layer was washed with brine (50 mL*2), dried over anhydrous Na$_2$SO$_4$, filtered and concentrated. The residue was purified by column chromatograph (MeOH in DCM is 0-10%) to give 58e (40 mg, 36% yield) as a brown solid. LC-MS (Method 4) $t_R$=0.72 min, m/z (M+H)$^+$=193.1.

Step 5. Methyl 6-(cyclopropanecarboxamido)-4-((3-ethyl-5-methoxy-[1,2,4]triazolo[4,3-a]pyridin-6-yl)amino)nicotinate (58f)

A mixture of 58e (40 mg, 0.208 mol), 39h (53 mg, 0.208 mmol), BrettPhos (22 mg, 0.042 mmol), Cs$_2$CO$_3$ (136 mg, 0.416 mmol) and BrettPhos Pd G3 (19 mg, 0.021 mmol) in dioxane (3 mL) was stirred at 100° C. for 6 h under N$_2$ atmosphere. A brown solution was formed. The reaction mixture was diluted with EtOAc (50 mL) and filtered through a pad of celite. The filtrate was concentrated and purified by Prep-TLC (DCM/MeOH=10/1) to give 58f (80 mg, 94% yield) as a yellow solid. LC-MS (Method 4) $t_R$=2.77 min, m/z (M+H)$^+$=411.2.

Step 6. 6-(Cyclopropanecarboxamido)-4-((3-ethyl-5-methoxy-[1,2,4]triazolo[4,3-a]pyridin-6-yl)amino)nicotinic acid (58g)

A mixture of 58f (80 mg, 0.195 mmol) and LiOH·H$_2$O (25 mg, 0.585 mmol) in co-solvent of methanol (4 mL) and water (1 mL) was stirred at 40° C. for 12 h. A yellow solution was formed. The reaction mixture was concentrated and dried in vacuo to give 58g (80 mg, yield given) as a yellow solid, which was used for the next step directly without further purification. LC-MS (Method 4) $t_R$=2.05 min, m/z (M+H)$^+$=397.2.

Step 7. 6-(Cyclopropanecarboxamido)-4-((3-ethyl-5-methoxy-[1,2,4]triazolo[4,3-a]pyridin-6-yl)amino)-N-(methyl-d$_3$)nicotinamide (58)

A mixture of 58g (80 mg, crude), HATU (154 mg, 0.404 mmol) and methan-d$_3$-amine hydrochloride (14 mg, 0.201 mmol), DIPEA (78 mg, 0.605 mmol) in DMF (3 mL) was stirred at 0° C. for 1 h. A white suspension was formed. The reaction mixture was diluted with water (40 mL) and extracted with EtOAc (40 mL*3). The combined organic layer was washed with water (40 mL*3), brine (40 mL*2), dried over anhydrous Na$_2$SO$_4$, filtered and concentrated. The residue was purified by Prep-HPLC (Method E) to give 58 (10 mg, 12% yield) as a white solid. LC-MS (Method 4) $t_R$=2.19 min, m/z (M+H)$^+$=413.3. $^1$H NMR (400 MHz, DMSO-d$_6$) δ 10.70 (s, 1H), 10.15 (s, 1H), 8.58 (s, 1H), 8.50 (s, 1H), 7.60 (d, J=9.2 Hz, 1H), 7.52 (d, J=9.2 Hz, 1H), 7.38 (s, 1H), 4.09 (s, 3H), 2.86 (q, J=7.6 Hz, 2H), 1.95-1.87 (m, 1H), 1.33 (t, J=7.6 Hz, 3H), 0.72-0.64 (m, 4H).

Example 59

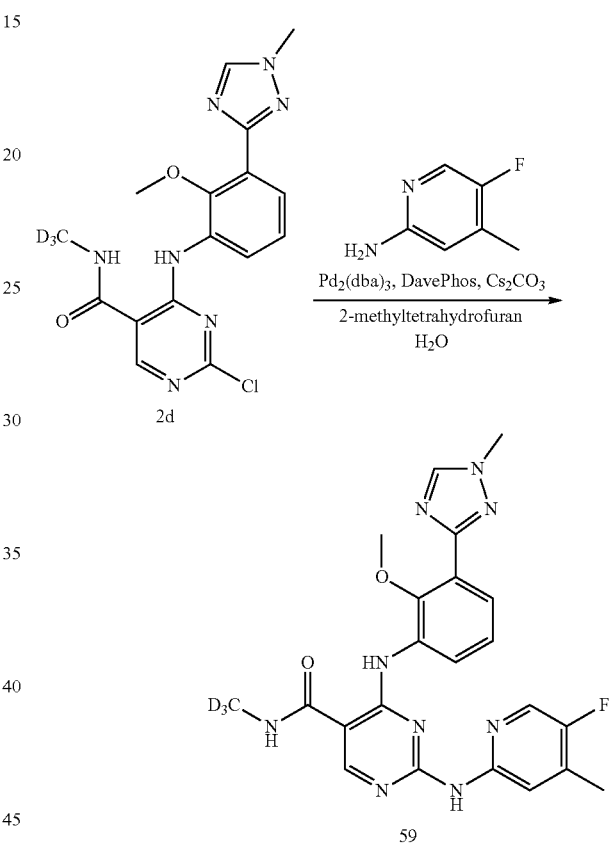

Step 1. 2-((5-Fluoro-4-methylpyridin-2-yl)amino)-4-((2-methoxy-3-(1-methyl-1H-1,2,4-triazol-3-yl)phenyl)amino)-N-(methyl-d$_3$)pyrimidine-5-carboxamide (59)

A mixture of 2d (40 mg, 0.16 mmol), 5-fluoro-4-methylpyridin-2-amine (18 mg, 0.14 mmol), DavePhos (7 mg, 0.02 mmol), Cs$_2$CO$_3$ (69 mg, 0.21 mmol) and Pd$_2$(dba)$_3$ (10 mg, 0.01 mmol) in 2-methyltetrahydrofuran (1 mL) and H$_2$O (0.5 mL) was stirred at 80° C. for 2 h. After cooling to r.t., the reaction mixture was filtered and the filtrate was concentrated. The residue was purified by Prep-HPLC (Method A) to afford compound 59 (10.2 mg, 21% yield) as a white solid. LC-MS (Method 1) $t_R$=3.31 min, m/z (M+H)$^+$=467.1. $^1$H NMR (400 MHz, DMSO-d$_6$) δ 11.80 (s, 1H), 10.02 (s, 1H), 8.73-8.70 (m, 2H), 8.55 (s, 1H), 8.50 (s, 1H), 8.21 (s, 1H), 8.04 (d, J=5.2 Hz, 1H), 7.53 (dd, J=7.6 Hz, 1.2 Hz, 1H), 7.17 (q, J=8.0 Hz, 1H), 3.95 (s, 3H), 3.79 (s, 3H), 2.25 (s, 3H).

Example 60

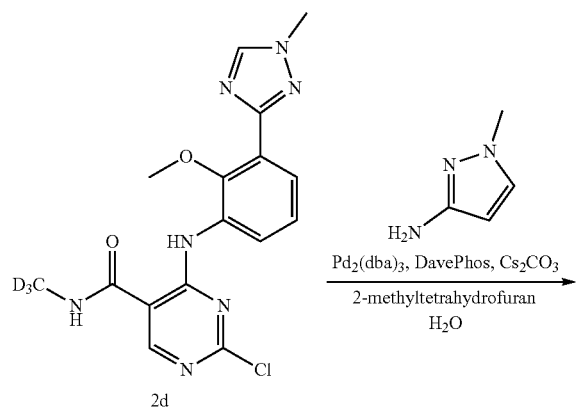

Example 61

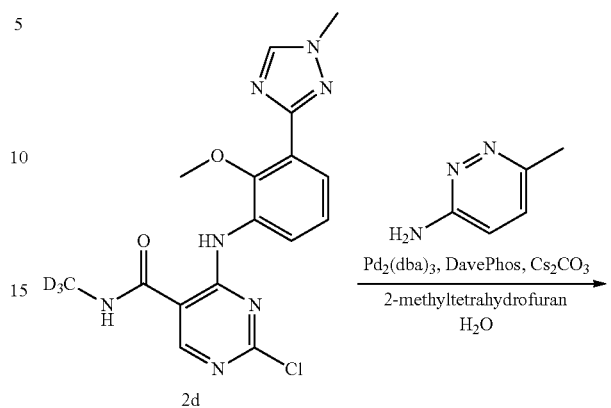

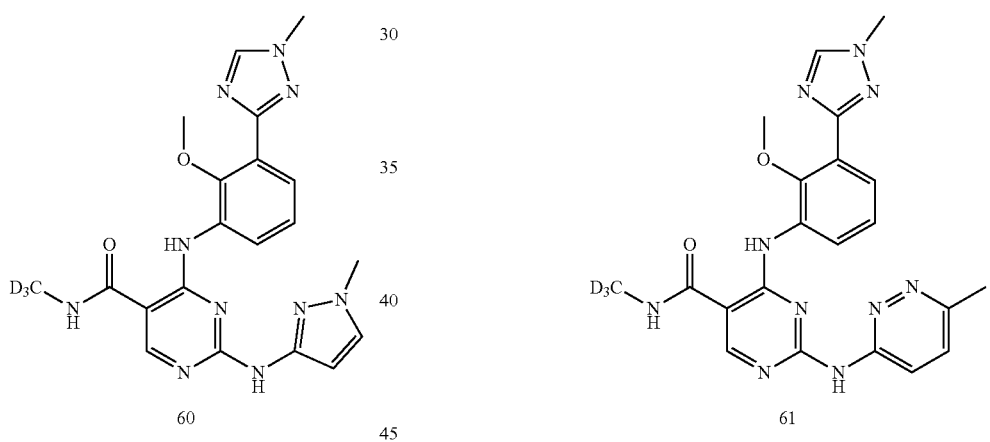

Step 1. 4-((2-Methoxy-3-(1-methyl-1H-1,2,4-triazol-3-yl)phenyl)amino)-N-(methyl-d₃)-2-((1-methyl-1H-pyrazol-3-yl)amino)pyrimidine-5-carboxamide (60)

Compound 60 (16.1 mg, 28% yield), a white solid, was synthesized by utilizing a similar preparative procedure in Example 59 with 2d (50 mg, 0.13 mmol) and 1-methyl-1H-pyrazol-3-amine (19 mg, 0.20 mmol) as starting materials. LC-MS (Method 1) $t_R$=3.24 min, m/z (M+H)$^+$=438.2. $^1$H NMR (400 MHz, DMSO-d₆) δ 11.80 (s, 1H), 9.85 (s, 1H), 8.86 (s, 1H), 8.63 (s, 1H), 8.54 (s, 1H), 8.41 (s, 1H), 7.58 (d, J=1.2 Hz, 1H), 7.48 (dd, J=7.6, 1.2 Hz, 1H), 7.11 (q, J=7.2 Hz, 1H), 6.43 (s, 1H), 3.95 (s, 3H), 3.79 (s, 3H), 3.78 (s, 3H).

Step 1. 4-((2-Methoxy-3-(1-methyl-1H-1,2,4-triazol-3-yl)phenyl)amino)-N-(methyl-d₃)-2-((6-methylpyridazin-3-yl)amino)pyrimidine-5-carboxamide (61)

Compound 61 (5 mg, 8% yield), a white solid, was synthesized by utilizing a similar preparative procedure in Example 59 with 2d (50 mg, 0.13 mmol) and 6-methylpyridazin-3-amine (22 mg, 0.20 mmol) as starting materials. LC-MS (Method 1) $t_R$=2.87 min, m/z (M+H)$^+$=450.3. $^1$H NMR (400 MHz, DMSO-d₆) δ 11.80 (s, 1H), 10.57 (s, 1H), 8.78 (d, J=8.4 Hz, 1H), 8.70 (s, 1H), 8.55 (s, 2H), 8.29 (d, J=9.2 Hz, 1H), 7.53-7.49 (m, 2H), 7.19-7.15 (m, 1H), 3.95 (s, 3H), 3.79 (s, 3H), 2.57 (s, 3H).

Example 62

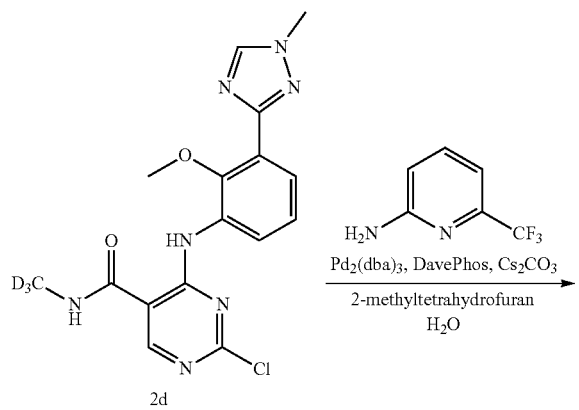

Step 1. 4-((2-Methoxy-3-(1-methyl-1H-1,2,4-triazol-3-yl)phenyl)amino)-N-(methyl-d₃)-2-((6-(trifluoromethyl)pyridin-2-yl)amino)pyrimidine-5-carboxamide (62)

Compound 62 (9.0 mg, 23% yield), a white solid, was synthesized by utilizing a similar preparative procedure in Example 59 with 2d (30 mg, 0.08 mmol) and 6-(trifluoromethyl)pyridin-2-amine (19 mg, 0.12 mmol) as starting materials. LC-MS (Method 1) $t_R$=3.35 min, m/z (M+H)⁺=503.3. ¹H NMR (400 MHz, DMSO-d₆) δ 11.83 (s, 1H), 10.58 (s, 1H), 8.98 (d, J=4.0 Hz, 1H), 8.73 (s, 1H), 8.58-8.51 (m, 3H), 8.01 (t, J=8.0 Hz, 1H), 7.54-7.48 (m, 2H), 7.18 (t, J=8.0 Hz, 1H), 3.95 (s, 3H), 3.80 (s, 3H).

Example 63

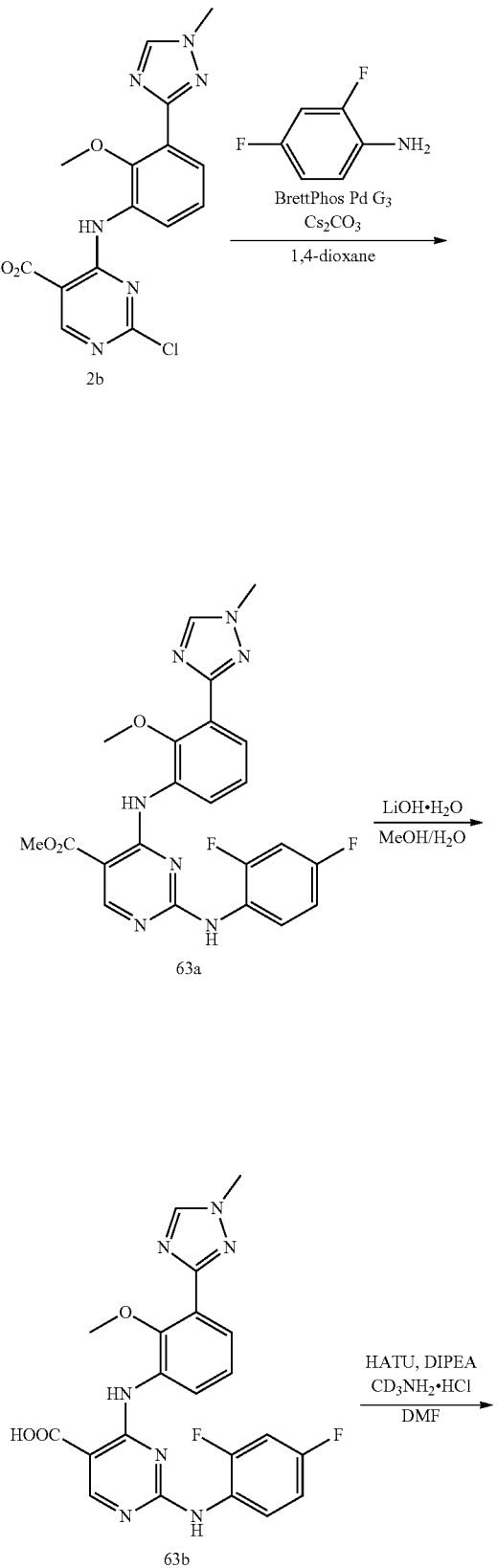

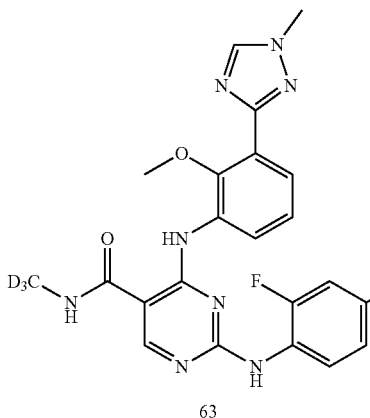

63

Step 1. Methyl 2-((2,4-difluorophenyl)amino)-4-((2-methoxy-3-(1-methyl-1H-1,2,4-triazol-3-yl)phenyl)amino)pyrimidine-5-carboxylate (63a)

To a solution of 2b (60 mg, 0.16 mmol) in 1,4-dioxane (1 mL) was added 2,4-difluoroaniline (26 mg, 0.18 mmol), BrettPhos Pd G3 (14 mg, 0.02 mmol) and $Cs_2CO_3$ (104 mg, 0.32 mmol). The mixture was stirred at 80° C. under $N_2$ for 16 h. The mixture was filtered and concentrated, then purified by Prep-TLC (DCM/MeOH=20/1) to get the compound 63a (46 mg, 60% yield) as a yellow solid.

Step 2. 2-((2,4-Difluorophenyl)amino)-4-((2-methoxy-3-(1-methyl-1H-1,2,4-triazol-3-yl)phenyl)amino)pyrimidine-5-carboxylic acid (63b)

To a solution of 63a (46 mg, 0.1 mmol) in $MeOH/H_2O$ (1 mL/0.5 mL) was added $LiOH \cdot H_2O$ (8.5 mg, 0.2 mmol) and the mixture was stirred at r.t. for 16 h. The mixture was diluted with 0.5 N HCl aq. (2 mL), extracted with EA (3 mL*3), washed with brine, dried over $Na_2SO_4$, concentrated to get the compound 63b (50 mg, yield given) as an off-white solid.

Step 3. 2-((2,4-Difluorophenyl)amino)-4-((2-methoxy-3-(1-methyl-1H-1,2,4-triazol-3-yl)phenyl)amino)-N-(methyl-$d_3$)pyrimidine-5-carboxamide (63)

A mixture of 63b (50 mg, 0.11 mmol), methan-$d_3$-amine hydrochloride (23 mg, 0.33 mmol), DIPEA (71 mg, 0.55 mmol), HATU (125 mg, 0.33 mmol) in DMF (2 mL) was stirred at r.t. for 6 h. The mixture diluted with $H_2O$ (10 mL), extracted with DCM (10 mL*3), washed with brine, dried over $Na_2SO_4$, concentrated and purified by Prep-HPLC (Method E) to get the compound 63 (1 mg, 2% yield) as a white solid. LC-MS (Method 4) $t_R$=2.32 min, m/z $(M+H)^+$=470.2. $^1$H NMR (400 MHz, DMSO-$d_6$) δ 11.77 (s, 1H), 9.29 (s, 1H), 8.57 (s, 1H), 8.49 (s, 1H), 8.39 (s, 1H), 7.53 (m, 1H), 7.40 (dd, J=12.0, 6.4 Hz, 1H), 7.37-7.31 (m, 2H), 7.11-7.06 (m, 1H), 6.91 (t, J=6.4 Hz 1H), 3.90 (s, 3H), 3.72 (s, 3H).

Example 64

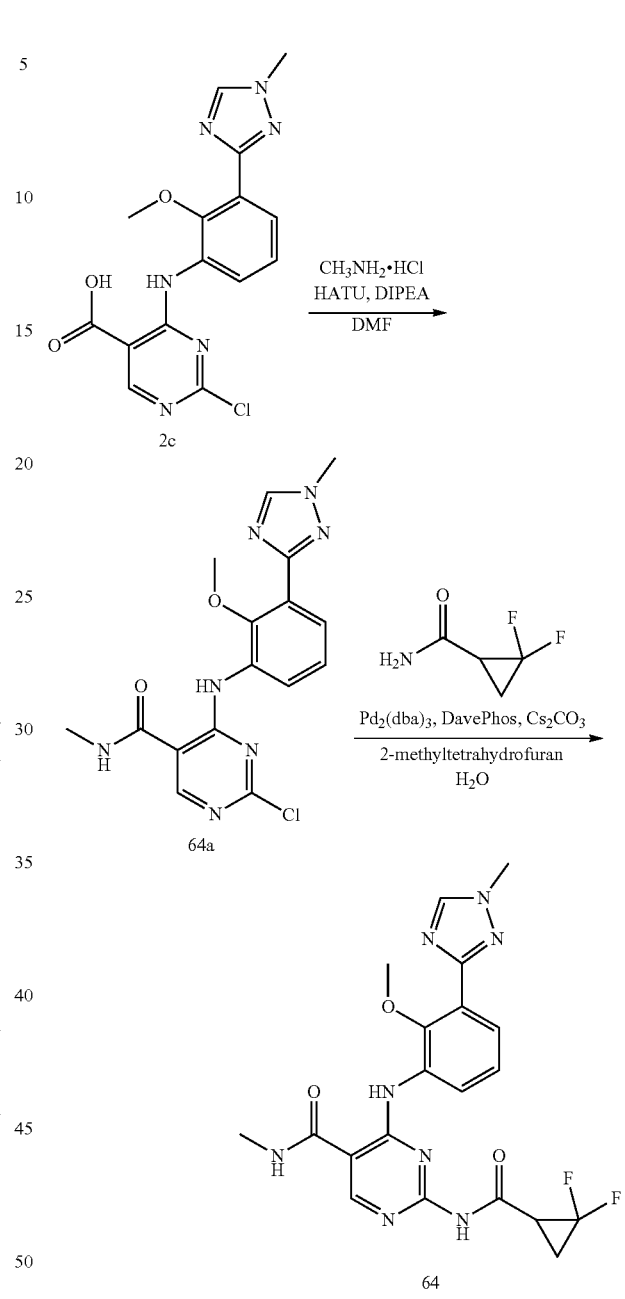

Step 1. 2-Chloro-4-((2-methoxy-3-(1-methyl-1H-1,2,4-triazol-3-yl)phenyl)amino)-N-methylpyrimidine-5-carboxamide (64a)

A mixture of 2c (100 mg, 0.28 mmol), HATU (316 mg, 0.83 mmol), DIPEA (107.28 mg, 0.83 mmol) and methylamine hydrochloride (37 mg, 0.55 mmol) in DMF (1 mL) was stirred at room temperature for 1 h. The mixture was diluted with EtOAc (20 mL) and washed with brine (5 mL*2), dried over $Na_2SO_4$, filtered and concentrated under vacuum. The reaction mixture was purified by flash chromatography on silica gel (DCM/MeOH=10/1) to afford 64$^a$ (15 mg, 14% yield) as a yellow solid. LC-MS (Method 3) $t_R$=1.30 min, m/z $(M+H)^+$=374.1.

Step 2. 2-(2,2-Difluorocyclopropane-1-carboxamido)-4-((2-methoxy-3-(1-methyl-1H-1,2,4-triazol-3-yl)phenyl)amino)-N-methylpyrimidine-5-carboxamide (64)

Compound 64 (1 mg, 5% yield), a white solid, was synthesized by utilizing a similar preparative procedure in Example 59 with 64a (15 mg, 0.04 mmol) and 2,2-difluorocyclopropane-1-carboxamide (7 mg, 0.06 mmol) as starting materials. LC-MS (Method 1) t$_R$=4.06 min, m/z (M+H)$^+$=459.2. $^1$H NMR (400 MHz, CD$_3$OD) δ 9.02 (dd, J=8.4, 1.6 Hz, 1H), 8.62 (s, 1H), 8.49 (s, 1H), 7.53 (dd, J=8.0, 1.6 Hz, 1H), 7.29-7.25 (m, 1H), 4.04 (s, 3H), 3.81 (s, 3H), 2.94 (s, 3H), 1.82-1.77 (m, 1H), 1.33 (m, 2H).

Example 65

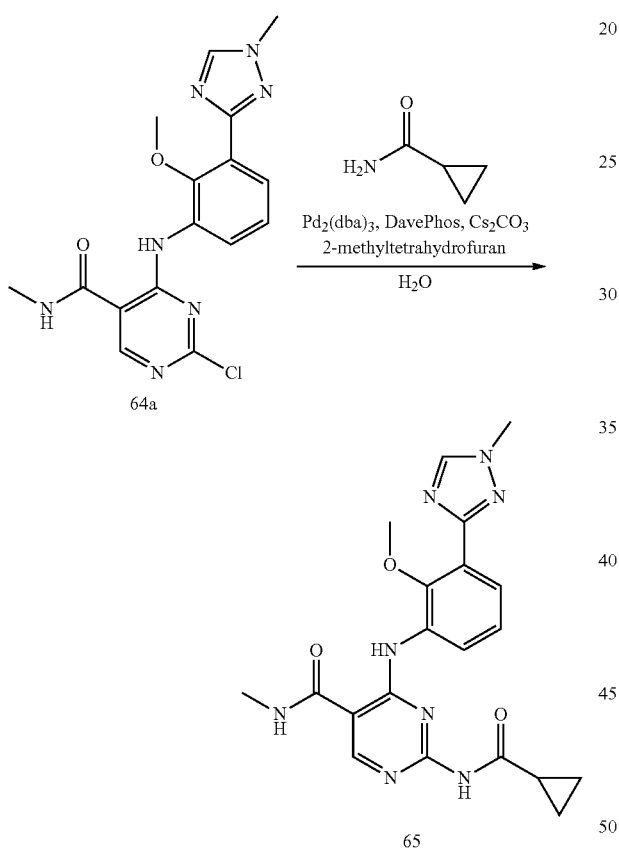

Step 1. 2-(Cyclopropanecarboxamido)-4-((2-methoxy-3-(1-methyl-1H-1,2,4-triazol-3-yl)phenyl)amino)-N-methylpyrimidine-5-carboxamide (65)

Compound 65 (8.2 mg, 15% yield), a white solid, was synthesized by utilizing a similar preparative procedure in Example 59 with 64a (50 mg, 0.13 mmol) and cyclopropanecarboxamide (57 mg, 0.66 mmol) as starting materials. LC-MS (Method 2) t$_R$=3.84 min, m/z (M+H)$^+$=423.2. $^1$H NMR (400 MHz, DMSO-d$_6$) δ 11.89 (s, 1H), 10.89 (brs, 1H), 9.25 (d, J=7.6 Hz, 1H), 8.75 (s, 1H), 8.65 (d, J=4.4 Hz, 1H), 8.54 (s, 1H), 7.49 (d, J=8.0 Hz, 1H), 7.15 (t, J=8.0 Hz, 1H), 3.95 (s, 3H), 3.80 (s, 3H), 2.81 (d, J=4.0 Hz, 3H), 2.10-2.13 (m, 1H), 0.91-0.81 (m, 4H).

Example 66

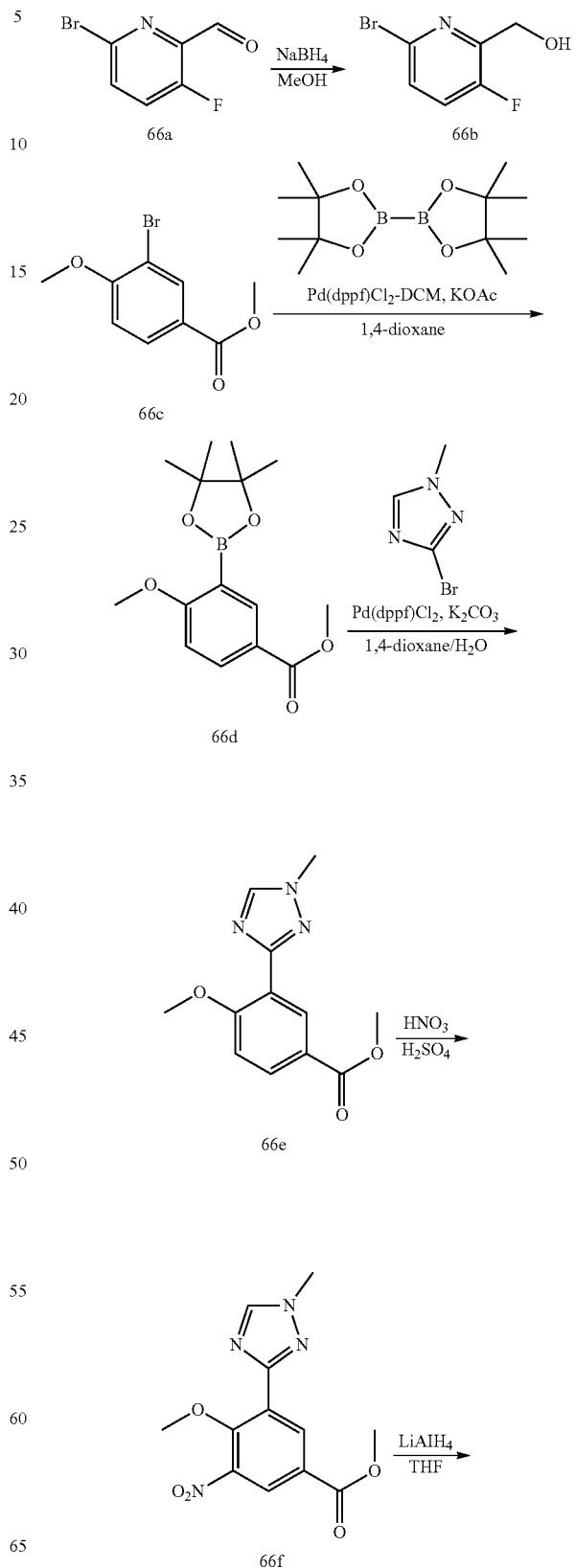

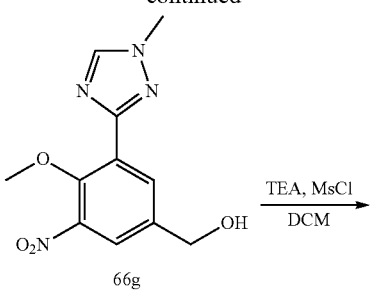

66g

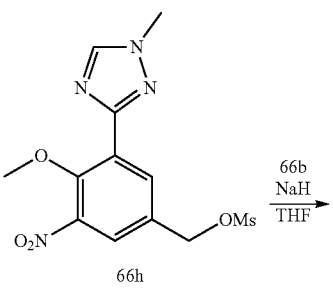

66h

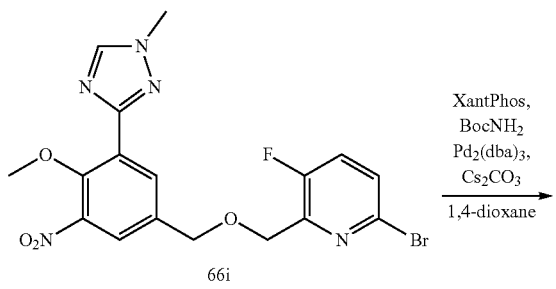

66i

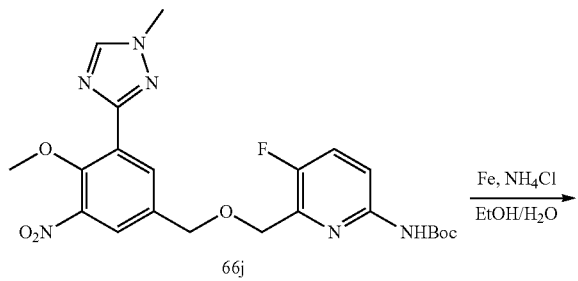

66j

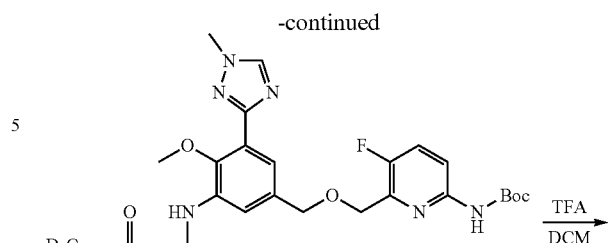

66l

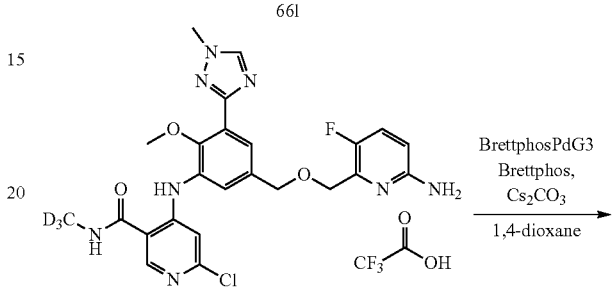

66m

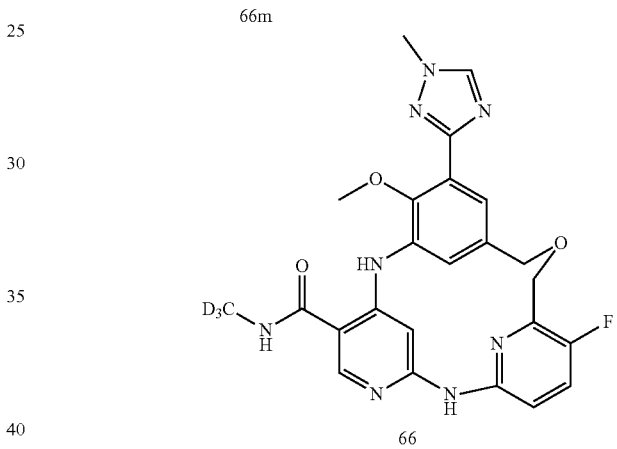

66

Step 1. (6-Bromo-3-fluoropyridin-2-yl)methanol (66b)

To a mixture of 6-bromo-3-fluoropicolinaldehyde (1.0 g, 4.90 mmol) in MeOH (15 mL) was added NaBH$_4$ (278 mg, 7.35 mmol) at 0° C. The reaction mixture was stirred at 0° C. for 0.5 h. The reaction mixture was diluted with ice-water (15 mL) and extracted with EtOAc (30 mL*2). The combined organic phase was dried over Na$_2$SO$_4$ and filtered. The filtrate was concentrated to afford the title compound 66b (970 mg, 96% yield) as a white solid. $^1$H NMR (300 MHz, CDCl$_3$) δ 7.44-7.40 (m, 1H), 7.30 (d, J=8.4 Hz, 1H), 4.80 (s, 2H), 3.28 (brs, 1H).

Step 2. Methyl 4-methoxy-3-(4,4,5,5-tetramethyl-1,3,2-dioxaborolan-2-yl)benzoate (66d)

A mixture of methyl 3-bromo-4-methoxybenzoate (9.0 g, 36.72 mmol), 4,4,4',4',5,5,5',5'-octamethyl-2,2'-bi(1,3,2-dioxaborolane) (10.26 g, 40.40 mmol), Pd(dppf)Cl$_2$·DCM (3.00 g, 3.67 mmol) and KOAc (10.81 g, 110.17 mmol) in 1,4-dioxane (100 mL) was stirred at 110° C. for 16 h under N$_2$. The reaction mixture was cooled to r.t., diluted with H$_2$O (80 mL) and extracted with EtOAc (150 mL*2). The organic phase was combined and washed with brine (100 mL), dried over $Na_2SO_4$, filtered and concentrated to give compound 66d (10.7 g, yield given) as a black solid. LC-MS (Method 3) $t_R$=1.58 min, m/z $(M+H)^+$=293.3.

Step 3. Methyl 4-methoxy-3-(1-methyl-1H-1,2,4-triazol-3-yl)benzoate (66e)

A mixture of 3-bromo-1-methyl-1H-1,2,4-triazole (7.5 g, 46.30 mmol), 66d (14.88 g, 50.93 mmol), Pd(dppf)Cl$_2$ (1.69 g, 2.31 mmol) and K$_2$CO$_3$ (12.80 g, 92.60 mmol) in H$_2$O (10 mL) and 1,4-dioxane (100 mL) was stirred at 110° C. for 12 h under N$_2$. The mixture was cooled to r.t. and filtered through celatom. The filter cake was washed EtOAc (100 mL). The filtrate was concentrated. The residue was purified by flash chromatography on silica gel (EtOAc) to afford the title compound 66e (5.9 g, 52% yield) as a brown oil. LC-MS (Method 3) $t_R$=1.14 min, m/z $(M+H)^+$=248.3.

Step 4. Methyl 4-methoxy-3-(1-methyl-1H-1,2,4-triazol-3-yl)-5-nitrobenzoate (66f)

To a mixture of 66e (5.9 g, 23.86 mmol) in conc. H$_2$SO$_4$ (30 mL) was added dropwise conc. HNO$_3$ (1.80 g, 28.64 mmol) at 0° C. The reaction mixture was stirred at 0° C. for 1 h. The reaction mixture was poured into ice-water (70 mL) and MeOH (50 mL). The mixture was heated to 45° C. Ammonium hydroxide (25% wt, 100 mL) was added. The mixture was stirred at 20° C. for 10 min. The mixture was filtered. The filter cake was washed with water (50 mL) and dried to give 66f (5.5 g, 79% yield) as a brown solid. $^1$H NMR (400 MHz, DMSO-d$_6$) δ 8.72 (d, J=2.8 Hz, 1H), 8.68 (s, 1H), 8.42 (d, J=2.8 Hz, 1H), 3.99 (s, 3H), 3.91 (s, 3H), 3.89 (s, 3H).

Step 5. (4-Methoxy-3-(1-methyl-1H-1,2,4-triazol-3-yl)-5-nitrophenyl)methanol (66g)

To a mixture of 66f (3.9 g, 13.34 mmol) in THF (40 mL) was added LiAlH$_4$ (557 mg, 14.68 mmol) at 0° C. The reaction mixture was stirred at 0° C. for 0.5 h under N$_2$. The reaction mixture was quenched with ice-water (4 mL) followed by 15% aq. NaOH (4 mL), water (12 mL). To the mixture was added Na$_2$SO$_4$ (40 g) and EtOAc (150 mL) and the mixture was stirred at r.t. for 16 h. The mixture was filtered and the filter cake was washed with EtOAc (100 mL). The filtrate was concentrated and the residue was purified by flash chromatography on silica gel (EtOAc) to afford the title compound 66g (1.7 g, 48% yield) as a yellow solid. LC-MS (Method 3) $t_R$=1.26 min, m/z $(M+H)^+$=265.2.

Step 6. 4-Methoxy-3-(1-methyl-1H-1,2,4-triazol-3-yl)-5-nitrobenzyl methanesulfonate (66h)

To a mixture of 66g (2.09 g, 7.91 mmol) and TEA (2.40 g, 23.73 mmol) in DCM (20 mL) was added methanesulfonyl chloride (1.36 g, 11.86 mmol) dropwise at 0° C. The reaction was stirred at 0° C. for 1 h under N$_2$ and diluted with ice-water (10 mL). The mixture was extracted with DCM (30 mL*2) and the combined organic layer was dried over Na$_2$SO$_4$ and filtered. The filtrate was concentrated to afford the title compound 66h (2.71 g, yield given) as a yellow oil. LC-MS (Method 3) $t_R$=1.38 min, m/z $(M+H)^+$=343.2.

Step 7. 6-Bromo-3-fluoro-2-(((4-methoxy-3-(1-methyl-1H-1,2,4-triazol-3-yl)-5-nitrobenzyl)oxy)methyl)pyridine (66i)

To a solution of 66h (500 mg, 1.46 mmol) and 66b (316 mg, 1.53 mmol) in THF (5 mL) was added NaH (84 mg, 2.19 mmol, 60% purity in mineral oil) at 0° C. After stirring at r.t. for 30 min, the mixture was quenched with brine (8 mL) and extracted with EtOAc (10 mL*3). The combined organic layer was concentrated and the residue was purified by flash chromatography on silica gel (PE/EtOAc=1/1) to afford the title compound 66i (400 mg, 61% yield) as a yellow oil. LC-MS (Method 3) $t_R$=1.58 min, m/z $(M+H)^+$=452.2.

Step 8. Tert-butyl (5-fluoro-6-(((4-methoxy-3-(1-methyl-1H-1,2,4-triazol-3-yl)-5-nitrobenzyl)oxy)methyl)pyridin-2-yl)carbamate (66j)

A mixture of 66i (406 mg, 0.90 mmol), tert-butyl carbamate (316 mg, 2.69 mmol), XantPhos (104 mg, 0.18 mmol), Pd$_2$(dba)$_3$ (82 mg, 0.09 mmol) and Cs$_2$CO$_3$ (585 mg, 1.80 mmol) in 1,4-dioxane (7 mL) was stirred at 90° C. for 2 h under N$_2$. The reaction mixture was cooled and concentrated. The residue was purified by flash chromatography on silica gel (PE/EtOAc=1/1) to afford the title compound 66j (365 mg, 83% yield) as a yellow solid. $^1$H NMR (400 MHz, DMSO-d$_6$) δ 9.86 (s, 1H), 8.63 (s, 1H), 8.18 (d, J=2.0 Hz, 1H), 7.88 (d, J=2.0 Hz, 1H), 7.78 (dd, J=3.2, 9.2 Hz, 1H), 7.68 (t, J=9.2 Hz, 1H), 4.68 (s, 2H), 4.60 (d, J=2.0 Hz, 2H), 3.97 (s, 3H), 3.82 (s, 3H), 1.46 (s, 9H).

Step 9. Tert-butyl (6-(((3-amino-4-methoxy-5-(1-methyl-1H-1,2,4-triazol-3-yl)benzyl)oxy)methyl)-5-fluoropyridin-2-yl)carbamate (66k)

A mixture of 66j (360 mg, 0.74 mmol), Fe powder (206 mg, 3.68 mmol) and NH$_4$Cl (394 mg, 7.37 mmol) in EtOH/H$_2$O (3 mL/0.6 mL) was stirred at 95° C. for 1 h. The reaction mixture was cooled and filtered. The filtrate was concentrated and the residue was purified by flash chromatography on silica gel (DCM/MeOH=20/1) to afford the title compound 66k (310 mg, 92% yield) as a yellow oil. LC-MS (Method 3) $t_R$=1.43 min, m/z $(M+H)^+$=459.3.

Step 10. Tert-butyl (6-(((3-((2-chloro-5-((methyl-d$_3$)carbamoyl)pyridin-4-yl)amino)-4-methoxy-5-(1-methyl-1H-1,2,4-triazol-3-yl)benzyl)oxy)methyl)-5-fluoropyridin-2-yl)carbamate (66l)

Compound 66l (150 mg, 91% yield), a yellow oil, as synthesized by utilizing a similar preparative procedure of Step 5 in Example 50 with 66k (120 mg, 0.26 mmol) and 42b (60 mg, 0.29 mmol) as starting materials. LC-MS (Method 3) $t_R$=1.51 min, m/z $(M+H)^+$630.3.

Step 11. 4-((5-(((6-Amino-3-fluoropyridin-2-yl)methoxy)methyl)-2-methoxy-3-(1-methyl-1H-1,2,4-triazol-3-yl)phenyl)amino)-6-chloro-N-(methyl-d$_3$)nicotinamide 2,2,2-trifluoroacetic acid (66m)

A mixture of 66l (150 mg, 0.24 mmol) in TFA/DCM (1.5 mL/1.5 mL) was stirred at r.t. for 1 h. The solvent was removed by pumping through N$_2$ and the residue was purified by Prep-HPLC (Method B) to afford the title compound 66m (52 mg, 34% yield) as a yellow solid. LC-MS (Method 3) $t_R$=1.20 min, m/z $(M+H)^+$=530.2.

Step 12. 18-Fluoro-10-methoxy-N-(methyl-d$_3$)-11-(1-methyl-1H-1,2,4-triazol-3-yl)-15-oxa-2,4,8,21-tetraazatetracyclo[15.3.1.1^{3,7}.1^{9,13}]tricosa-1(20),3,5,7(23),9(22),10,12,17(21),18-nonaene-6-carboxamide (66)

A mixture of 66m (50 mg, 0.08 mmol), BrettPhos (4 mg, 0.008 mmol), BrettPhos Pd G3 (7 mg, 0.008 mmol) and Cs$_2$CO$_3$ (76 mg, 0.23 mmol) was stirred at 100° C. for 3 h under N$_2$. The reaction mixture was cooled, filtered and concentrated. The residue was purified by Prep-HPLC (Method A) to afford the title compound 66 (24 mg, 62% yield) as a white solid. LC-MS (Method 1) t$_R$=2.76 min, m/z (M+H)$^+$=494.2. $^1$H NMR (400 MHz, DMSO-d$_6$) δ 10.73 (s, 1H), 9.98 (s, 1H), 9.33 (s, 1H), 8.56 (s, 1H), 8.51 (s, 1H), 8.47 (s, 1H), 8.15 (s, 1H), 7.61 (t, J=9.2 Hz, 1H), 7.42 (s, 1H), 7.07-7.05 (m, 1H), 4.68 (s, 2H), 4.45 (s, 2H), 3.95 (s, 3H), 3.79 (s, 3H).

Example 67

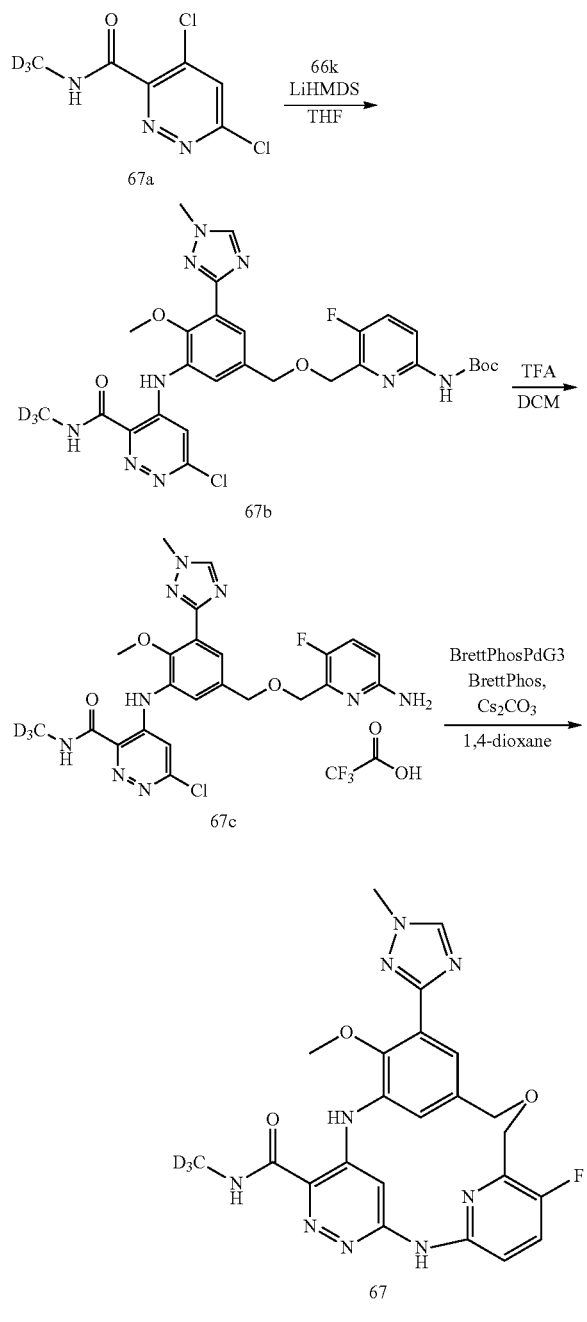

Step 1. Tert-butyl (6-(((3-((6-chloro-3-((methyl-d$_3$) carbamoyl)pyridazin-4-yl)amino)-4-methoxy-5-(1-methyl-1H-1,2,4-triazol-3-yl)benzyl)oxy)methyl)-5-fluoropyridin-2-yl)carbamate (67b)

Compound 67b (165 mg, yield given), a brown solid, was synthesized by utilizing a similar preparative procedure of Step 5 in Example 50 with 66k (120 mg, 0.26 mmol) and 67a (60 mg, 0.29 mmol) as starting materials. LC-MS (Method 3) t$_R$=1.64 min, m/z (M+H)$^+$=631.5.

Step 2. 4-((5-(((6-Amino-3-fluoropyridin-2-yl)methoxy)methyl)-2-methoxy-3-(1-methyl-1H-1,2,4-triazol-3-yl)phenyl)amino)-6-chloro-N-(methyl-d$_3$)pyridazine-3-carboxamide 2,2,2-trifluoroacetic acid (67c)

Compound 67c (150 mg, yield given), a brown gum, was synthesized by utilizing a similar preparative procedure of Step 11 in Example 66 with 67b (147 mg, 0.23 mmol) as the starting material. LC-MS (Method 3) t$_R$=1.17 min, m/z (M+H)$^+$=531.2.

Step 3. 18-Fluoro-10-methoxy-N-(methyl-d$_3$)-11-(1-methyl-1H-1,2,4-triazol-3-yl)-15-oxa-2,4,5,8,21-pentaazatetracyclo[15.3.1.1^{3,7}.1^{9,13}]tricosa-1(20),3,5,7(23),9(22),10,12,17(21),18-nonaene-6-carboxamide (67)

Compound 67 (26 mg, 23% yield), a white solid, was synthesized by utilizing a similar preparative procedure of the final step in Example 66 with 67c (150 mg, 0.23 mmol) as the starting material. LC-MS (Method 1) t$_R$=2.82 min, m/z (M$^+$)$^+$=495.2. $^1$H NMR (400 MHz, DMSO-d$_6$) δ 10.78 (s, 1H), 10.54 (s, 1H), 9.60 (s, 1H), 9.04 (s, 1H), 8.57 (s, 1H), 8.14 (d, J=1.2 Hz, 1H), 7.68 (t, J=9.2 Hz, 1H), 7.50 (d, J=1.6 Hz, 1H), 7.18 (dd, J=2.8, 9.2 Hz, 1H), 4.70 (s, 2H), 4.49 (d, J=2.4 Hz, 2H), 3.95 (s, 3H), 3.80 (s, 3H).

Example 68

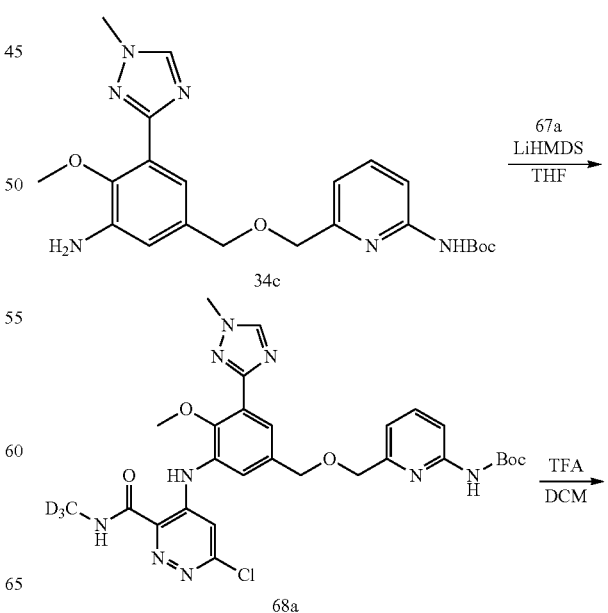

Example 69

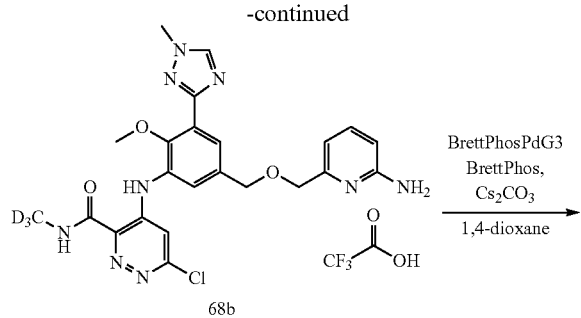
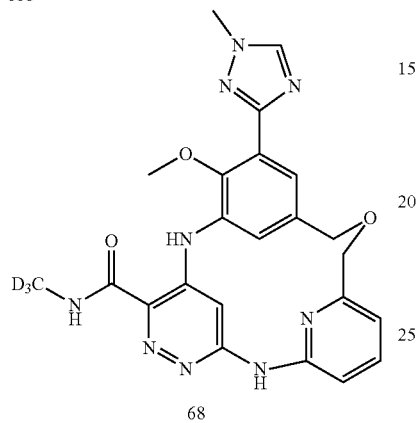
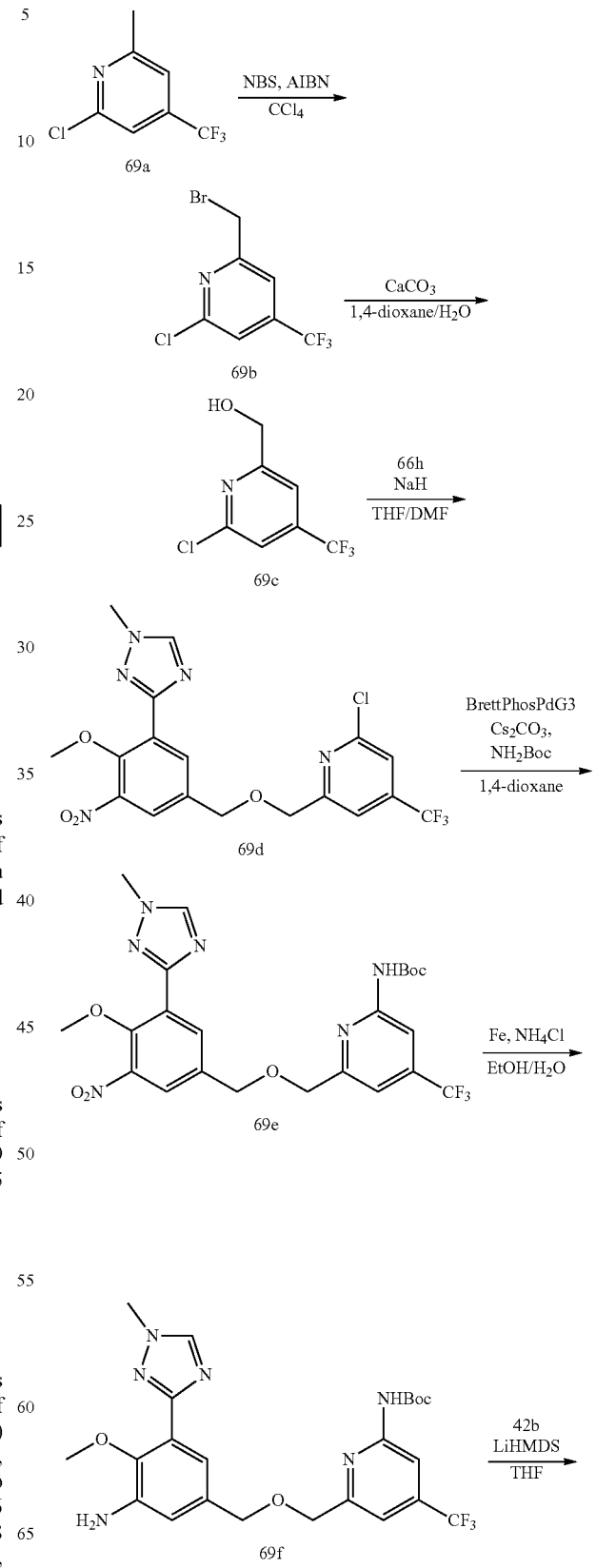

Step 1. Tert-butyl (6-(((3-((6-chloro-3-((methyl-d₃) carbamoyl)pyridazin-4-yl)amino)-4-methoxy-5-(1-methyl-1H-1,2,4-triazol-3-yl)benzyl)oxy)methyl) pyridin-2-yl)carbamate (68a)

Compound 68a (237 mg, 73% yield), a yellow solid, was synthesized by utilizing a similar preparative procedure of Step 5 in Example 50 with 34c (234 mg, 0.53 mmol) and 67a (133 mg, 0.64 mmol) as starting materials. LC-MS (Method 3) $t_R$=1.64 min, m/z (M+H)⁺=613.6.

Step 2. 4-((5-(((6-Aminopyridin-2-yl)methoxy) methyl)-2-methoxy-3-(1-methyl-1H-1,2,4-triazol-3-yl)phenyl)amino)-6-chloro-N-(methyl-d₃)pyridazine-3-carboxamide 2,2,2-trifluoroacetic acid (68b)

Compound 68b (210 mg, 87% yield), a yellow solid, was synthesized by utilizing a similar preparative procedure of the eleventh step in Example 66 with 68a (237 mg, 0.39 mmol) as the starting material. LC-MS (Method 3) $t_R$=1.35 min, m/z (M+H)⁺=513.5.

Step 3. 10-Methoxy-N-(methyl-d₃)-11-(1-methyl-1H-1,2,4-triazol-3-yl)-15-oxa-2,4,5,8,21-pentaazatetracyclo[15.3.1.1^{3,7}.1^{9,13}]tricosa-1(21),3,5,7(23),9(22),10,12,17,19-nonaene-6-carboxamide (68)

Compound 68 (64 mg, 50% yield), a yellow solid, was synthesized by utilizing a similar preparative procedure of the final step in Example 66 with 68b (170 mg, 0.27 mmol) as the starting material. LC-MS (Method 1) $t_R$=3.28 min, m/z (M+H)⁺=477.2. ¹H NMR (400 MHz, DMSO-d₆) δ 10.77 (s, 1H), 10.47 (s, 1H), 9.73 (s, 1H), 9.04 (s, 1H), 8.56 (s, 1H), 8.21 (d, J=1.6 Hz, 1H), 7.67 (t, J=8.0 Hz, 1H), 7.48 (d, J=1.6 Hz, 1H), 7.12 (d, J=8.4 Hz, 1H), 6.98 (d, J=7.2 Hz, 1H), 4.67 (s, 2H), 4.39 (s, 2H), 3.95 (s, 3H), 3.80 (s, 3H).

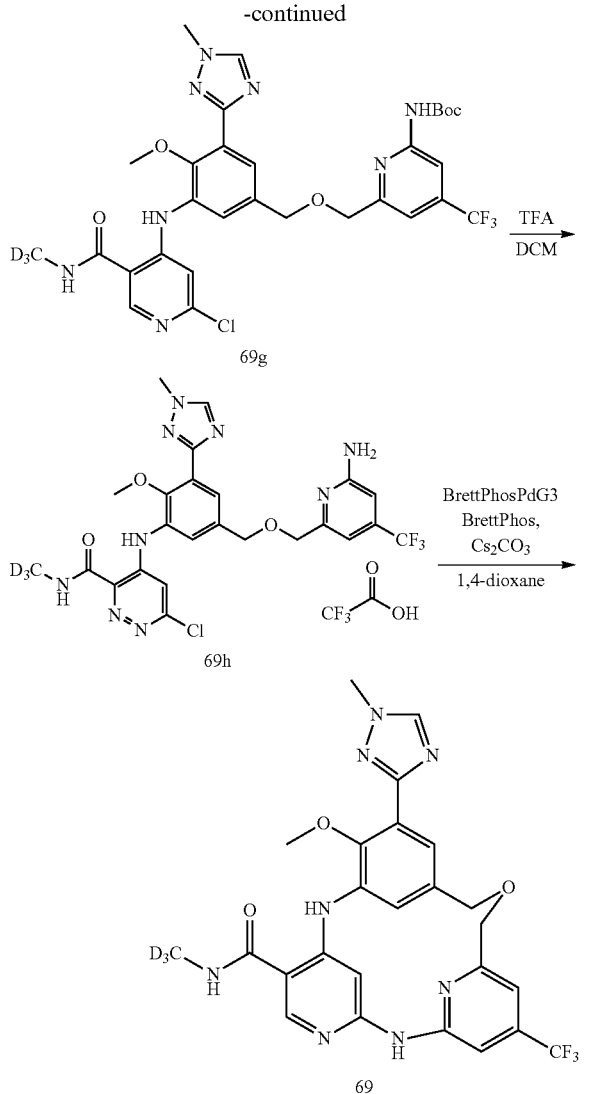

pressure to afford the title compound 69c (900 mg, 72% yield) as a yellow solid. LC-MS (Method 3) $t_R$=1.46 min, m/z (M+H)$^+$=212.0.

Step 3. 2-Chloro-6-(((4-methoxy-3-(1-methyl-1H-1, 2,4-triazol-3-yl)-5-nitrobenzyl)oxy)methyl)-4-(trifluoromethyl)pyridine (69d)

To a mixture of 66h (150 mg, 0.44 mmol) and 69c (121 mg, 0.57 mmol) in THF (1.5 mL) and DMF (0.5 mL) was added NaH (32 mg, 0.79 mmol, 60% purity in mineral oil) at 0° C. The reaction mixture was stirred at 0° C. for 0.5 h. The reaction mixture was poured into sat. NH$_4$Cl (10 mL) and extracted with EtOAc (20 mL*2). The combined organic layer was concentrated. The residue was purified by flash chromatography on silica gel (PE/EtOAc=1/1) to afford the title compound 69d (125 mg, 62% yield) as a yellow solid. $^1$H NMR (400 MHz, CDCl$_3$) δ 8.24 (d, J=2.4 Hz, 1H), 8.13 (s, 1H), 7.84 (d, J=2.0 Hz, 1H), 7.66 (s, 1H), 7.47 (s, 1H), 4.73 (s, 4H), 4.03 (s, 3H), 3.95 (s, 3H).

Step 4. Tert-butyl (6-(((4-methoxy-3-(1-methyl-1H-1,2,4-triazol-3-yl)-5-nitrobenzyl)oxy)methyl)-4-(trifluoromethyl)pyridin-2-yl)carbamate (69e)

A mixture of 69d (123 mg, 0.27 mmol), Cert-butyl carbamate (94 mg, 0.81 mmol), BrettPhos Pd G3 (24 mg, 0.027 mmol) and Cs$_2$CO$_3$ (263 mg, 0.81 mmol) in 1,4-dioxane (3 mL) was stirred at 90° C. for 2 h under N$_2$. The reaction mixture was cooled, diluted with H$_2$O (8 mL) and extracted with EtOAc (15 mL*2). The combined organic layer was dried over Na$_2$SO$_4$, filtered and concentrated to give the title compound 69e (144 mg, yield given) as a yellow solid. LC-MS (Method 3) $t_R$=1.79 min, m/z (M+H–100)$^+$=439.3.

Step 5. Tert-butyl (6-(((3-amino-4-methoxy-5-(1-methyl-1H-1,2,4-triazol-3-yl)benzyl)oxy)methyl)-4-(trifluoromethyl)pyridin-2-yl)carbamate (69f)

Compound 69f (99 mg, 75% yield), a brown solid, was synthesized by utilizing a similar preparative procedure of Step 9 in Example 66 with 69e (139 mg, 0.26 mmol) as the starting material. LC-MS (Method 3) $t_R$=1.46 min, m/z (M+H)$^+$=509.3.

Step 6. Tert-butyl (6-(((3-((2-chloro-5-((methyl-d$_3$) carbamoyl)pyridin-4-yl)amino)-4-methoxy-5-(1-methyl-1H-1,2,4-triazol-3-yl)benzyl)oxy)methyl)-4-(trifluoromethyl)pyridin-2-yl)carbamate (69g)

Compound 69g (119 mg, 100% yield), a brown solid, was synthesized by utilizing a similar preparative procedure of Step 5 in Example 50 with 69f (89 mg, 0.18 mmol) and 42b (40 mg, 0.19 mmol) as starting materials. LC-MS (Method 3) $t_R$=1.73 min, m/z (M+H)$^+$=680.5.

Step 7. 4-((5-(((6-Amino-4-(trifluoromethyl)pyridin-2-yl)methoxy)methyl)-2-methoxy-3-(1-methyl-1H-1, 2,4-triazol-3-yl)phenyl)amino)-6-chloro-N-(methyl-d$_3$)nicotinamide 2,2,2-trifluoroacetic acid (69h)

Compound 69h (63 mg, 56% yield), a white solid, was synthesized by utilizing a similar preparative procedure of Step 11 in Example 66 with 69g (110 mg, 0.16 mmol) as the starting material. LC-MS (Method 3) $t_R$=1.27 min, m/z (M+H)$^+$=580.2.

Step 1. 2-(Bromomethyl)-6-chloro-4-(trifluoromethyl)pyridine (69b)

A mixture of 2-chloro-6-methyl-4-(trifluoromethyl)pyridine (3.0 g, 15.34 mmol), AIBN (252 mg, 1.53 mmol) and NBS (2.46 g, 13.81 mmol) in CCl$_4$ (60 mL) was heated to reflux for 16 h. The reaction mixture was cooled to 0° C. and filtered. The filtrate was concentrated and the residue was purified by flash chromatography on silica gel (PE) to give the title compound 69b (1.5 g, 36% yield) as a yellow oil. $^1$H NMR (400 MHz, CDCl$_3$) δ 7.61 (s, 1H), 7.50 (s, 1H), 4.55 (s, 2H).

Step 2. (6-Chloro-4-(trifluoromethyl)pyridin-2-yl) methanol (69c)

A mixture of 69b (1.62 g, 5.92 mmol) and CaCO$_3$ (2.96 g, 29.60 mmol) in H$_2$O/1,4-dioxane (10 mL/10 mL) was stirred at 115° C. for 36 h. The reaction mixture was cooled, diluted with water (15 mL) and extracted with EtOAc (20 mL*3). The combined organic layer was dried over anhydrous Na$_2$SO$_4$, filtered and concentrated under the reduced Step 8. 10-Methoxy-N-(methyl-d$_3$)-11-(1-methyl-1H-1,2,4-triazol-3-yl)-19-(trifluoromethyl)-15-oxa-2,4,8,21-tetraazatetracyclo[15.3.1.1^{3,7}.1^{9,13}]tricosa-1(21),3,5,7(23),9(22),10,12,17,19-nonaene-6-carboxamide (69)

Compound 69 (38 mg, 77% yield), a white solid, was synthesized by utilizing a similar preparative procedure of Step 12 in Example 66 with 69h (63 mg, 0.09 mmol) as the starting material. LC-MS (Method 2) $t_R$=3.60 min, m/z (M+H)$^+$=544.2. $^1$H NMR (400 MHz, DMSO-d$_6$) δ 10.73 (s, 1H), 10.28 (s, 1H), 9.35 (s, 1H), 8.56 (s, 1H), 8.54 (s, 1H), 8.51 (s, 1H), 8.19 (d, J=1.6 Hz, 1H), 7.44 (d, J=2.0 Hz, 1H), 7.33 (s, 1H), 7.26 (s, 1H), 4.67 (s, 2H), 4.44 (s, 2H), 3.95 (s, 3H), 3.79 (s, 3H).

Example 70

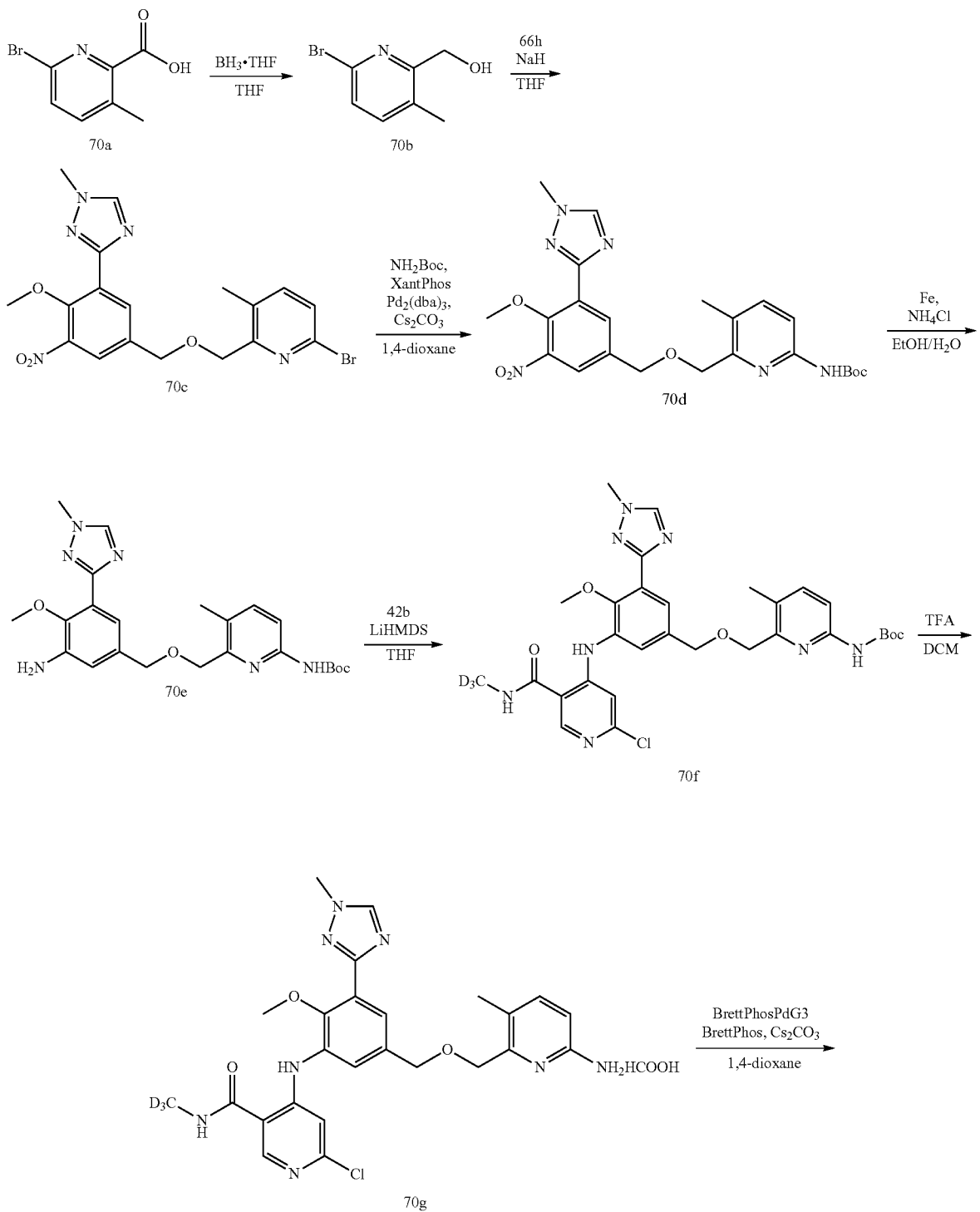

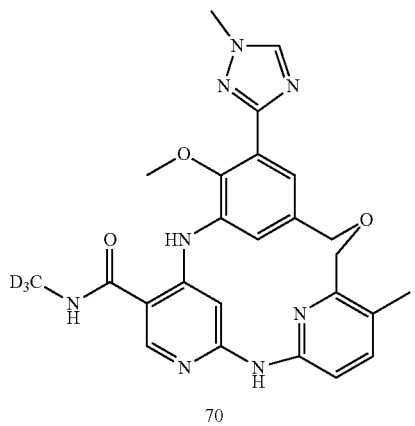

70

Step 1. (6-Bromo-3-methylpyridin-2-yl)methanol (70b)

A mixture of 6-bromo-3-methylpicolinic acid (1.0 g, 4.63 mmol) in THF (10 mL) was added BH$_3$·THF (9.2 mL, 9.26 mmol, 1.0 M in THF) at 0° C. The reaction mixture was stirred at 55° C. for 24 h. The reaction mixture was diluted with MeOH (10 mL) and 6 M HCl (10 mL) and stirred at 60° C. for 1 h. The reaction mixture was cooled to room temperature and extracted with EtOAc (30 mL*2). The combined organic phase was dried over Na$_2$SO$_4$, filtered and concentrated. The residue was purified by flash chromatography on silica gel (PE/EtOAc=4/1) to afford the title compound 70b (280 mg, 30% yield) as a colorless oil. LC-MS (Method 3) $t_R$=1.12 min, m/z (M+H)$^+$=202.1.

Step 2. 6-Bromo-2-(((4-methoxy-3-(1-methyl-1H-1,2,4-triazol-3-yl)-5-nitrobenzyl)oxy)methyl)-3-methylpyridine (70c)

Compound 70c (154 mg, 59% yield), a yellow solid, was synthesized by utilizing a similar preparative procedure of Step 7 in Example 66 with 66h (200 mg, 0.58 mmol) and 70b (142 mg, 0.70 mmol) as starting materials. LC-MS (Method 3) $t_R$=1.60 min, m/z (M+H)$^+$=448.3.

Step 3. Tert-butyl (6-(((4-methoxy-3-(1-methyl-1H-1,2,4-triazol-3-yl)-5-nitrobenzyl)oxy)methyl)-5-methylpyridin-2-yl)carbamate (70d)

Compound 70d (160 mg, 96% yield), a yellow solid, was synthesized by utilizing a similar preparative procedure of Step 8 in Example 66 with 70c (154 mg, 0.34 mmol) and tert-butyl carbamate (121 mg, 1.03 mmol) as starting materials. LC-MS (Method 3) $t_R$=1.69 min, m/z (M+H−100)$^+$=385.4.

Step 4. Tert-butyl (6-(((3-amino-4-methoxy-5-(1-methyl-1H-1,2,4-triazol-3-yl)benzyl)oxy)methyl)-5-methylpyridin-2-yl)carbamate (70e)

Compound 70e (147 mg, 80% yield), a yellow solid, was synthesized by utilizing a similar preparative procedure of Step 9 in Example 66 with 70d (195 mg, 0.40 mmol) as the starting material. LC-MS (Method 3) $t_R$=1.52 min, m/z (M+H)$^+$=455.5.

Step 5. Tert-butyl (6-(((3-((2-chloro-5-((methyl-d$_3$) carbamoyl)pyridin-4-yl)amino)-4-methoxy-5-(1-methyl-1H-1,2,4-triazol-3-yl)benzyl)oxy)methyl)-5-methylpyridin-2-yl)carbamate (70f)

Compound 70f (170 mg, 97% yield), a yellow solid, was synthesized by utilizing a similar preparative procedure of Step 5 in Example 50 with 70e (127 mg, 0.28 mmol) and 42b (76 mg, 0.36 mmol) as starting materials. LC-MS (Method 3) $t_R$=1.51 min, m/z (M+H)$^+$=626.0.

Step 6. 4-((5-(((6-Amino-3-methylpyridin-2-yl)methoxy)methyl)-2-methoxy-3-(1-methyl-1H-1,2,4-triazol-3-yl)phenyl)amino)-6-chloro-N-(methyl-d$_3$) nicotinamide formic acid (70g)

A solution of 70f (175 mg, 0.28 mmol) in TFA (3 mL) and DCM (3 mL) was stirred at r.t. for 1 h. The solvent was removed by pumping through N$_2$ and the residue was purified by Prep-HPLC (Method C) to afford the title compound 70g (112 mg, 70% yield) as a yellow solid. LC-MS (Method 3) $t_R$=1.30 min, m/z (M+H)$^+$=526.2.

Step 7. 10-Methoxy-N-(methyl-d$_3$)-18-methyl-11-(1-methyl-1H-1,2,4-triazol-3-yl)-15-oxa-2,4,8,21-tetraazatetracyclo[15.3.1.1^{3,7}.1^{9,13}]tricosa-1(20),3,5,7(23),9(22),10,12,17(21),18-nonaene-6-carboxamide (70)

Compound 70 (42 mg, 35% yield), a white solid, was synthesized by utilizing a similar preparative procedure of Step 12 in Example 66 with 70g (140 mg, 0.24 mmol) as the starting material. LC-MS (Method 1) $t_R$=2.79 min, m/z (M+H)$^+$=490.2. $^1$H NMR (400 MHz, DMSO-d$_6$) δ 10.75 (s, 1H), 9.74 (s, 1H), 9.47 (s, 1H), 8.55 (s, 1H), 8.49 (s, 1H), 8.43 (s, 1H), 8.17 (d, J=1.2 Hz, 1H), 7.46 (d, J=8.8 Hz, 1H), 7.40 (d, J=1.6 Hz, 1H), 6.94 (d, J=8.0 Hz, 1H), 4.66 (s, 2H), 4.41 (s, 2H), 3.95 (s, 3H), 3.80 (s, 3H), 2.29 (s, 3H).

Example 71
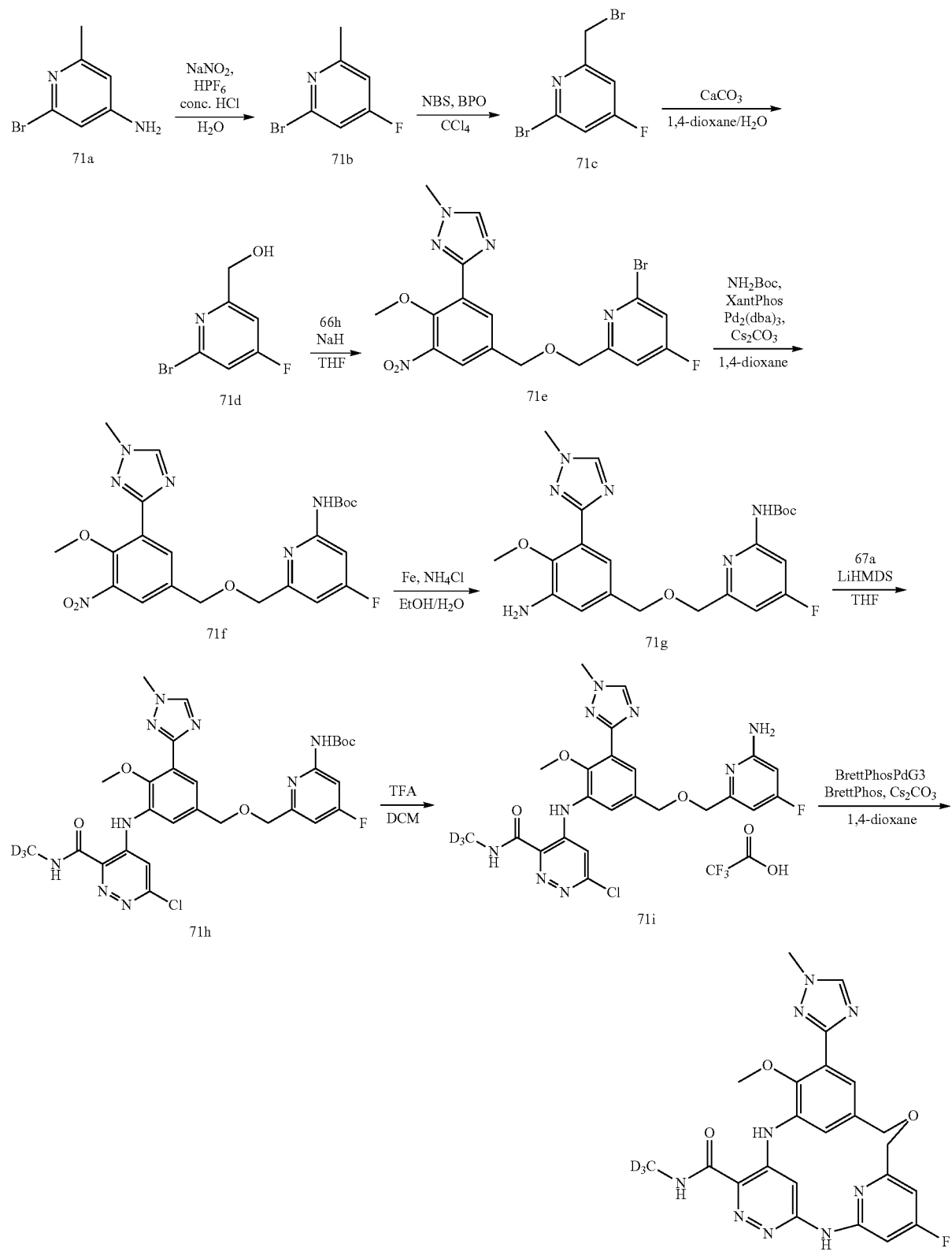

Step 1. 2-Bromo-4-fluoro-6-methylpyridine (71b)

To a mixture of 2-bromo-6-methylpyridin-4-amine (5.0 g, 26.73 mmol) in H$_2$O (40 mL) and conc. HCl (25 mL) was added NaNO$_2$ (3.69 g, 53.47 mmol) at 0° C. over 10 min. After stirring for 10 min at this temperature, to the reaction mixture was added hexafluorophosphoric acid solution (8.58 g, 58.81 mmol, 65% purity) dropwise. The reaction mixture was stirred at 0° C. for 0.5 h and the formed solid was collected by filtering. The filter cake was washed with ice-water (30 mL), diethyl ether (30 mL) and dried in the air for 24 h. The solid was slowly heated to 100° C. and a dark-red oily material was formed after 10 min. After cooling to r.t., the oil was basified with 1M aq. NaOH to pH=10 and extracted with DCM (50 mL*2). The combined organic layer was dried over Na$_2$SO$_4$, filtered and concentrated to afford the title compound 71b (1.24 g, 24% yield) as a black oil. $^1$H NMR (400 MHz, CDCl$_3$) δ 7.10-7.07 (m, 1H), 6.87 (dd, J=9.2 Hz, 2.0 Hz, 1H), 2.54 (s, 3H).

Step 2. 2-Bromo-6-(bromomethyl)-4-fluoropyridine (71c)

A mixture of 71b (1.1 g, 5.79 mmol), NBS (1.03 g, 5.79 mmol) and BPO (70 mg, 0.29 mmol) in CCl$_4$ (10 mL) was stirred at illumination for 2 h. The reaction mixture was diluted with water (10 mL) and extracted with DCM (20 mL*2). The combined organic phase was concentrated and the residue was purified by flash chromatography on silica gel (PE/EtOAc=10/1) to afford the title compound 71c (710 mg, 46% yield) as a colorless oil. LC-MS (Method 3) $t_R$=1.48 min, m/z (M+H)$^+$=267.9.

Step 3. (6-Bromo-4-fluoropyridin-2-yl)methanol (71d)

A mixture of 71c (710 mg, 2.64 mmol) and CaCO$_3$ (1.32 g, 13.20 mmol) in 1,4-dioxane (10 mL) and H$_2$O (5 mL) was stirred at 110° C. for 20 h. The reaction mixture was cooled and concentrated and the residue was purified by flash chromatography on silica gel (PE/EtOAc=4/1) to afford the title compound 71d (88 mg, 16% yield) as a colorless oil. LC-MS (Method 3) $t_R$=1.12 min, m/z (M+H)$^+$=205.9.

Step 4. 2-Bromo-4-fluoro-6-(((4-methoxy-3-(1-methyl-1H-1,2,4-triazol-3-yl)-5-nitrobenzyl)oxy)methyl)pyridine (71e)

Compound 71e (66 mg, 19% yield), a white solid, was synthesized by utilizing a similar preparative procedure of Step 7 in Example 66 with 66h (270 mg, 0.79 mmol) and 71d (179 mg, 0.87 mmol) as starting materials. LC-MS (Method 3) $t_R$=1.64 min, m/z (M+H)$^+$=452.2.

Step 5. Tert-butyl (4-fluoro-6-(((4-methoxy-3-(1-methyl-1H-1,2,4-triazol-3-yl)-5-nitrobenzyl)oxy)methyl)pyridin-2-yl)carbamate (71f)

Compound 71f (71 mg, yield given), a brown solid, was synthesized by utilizing a similar preparative procedure of Step 8 in Example 66 with 71e (66 mg, 0.15 mmol) and tert-butyl carbamate (51 mg, 0.44 mmol) as starting materials. LC-MS (Method 3) $t_R$=1.71 min, m/z (M+H-100)$^+$=389.3.

Step 6. Tert-butyl (6-(((3-amino-4-methoxy-5-(1-methyl-1H-1,2,4-triazol-3-yl)benzyl)oxy)methyl)-4-fluoropyridin-2-yl)carbamate (71g)

Compound 71g (43 mg, 65% yield), a yellow solid, was synthesized by utilizing a similar preparative procedure of Step 9 in Example 66 with 71f (70 mg, 0.14 mmol) as the starting material. LC-MS (Method 3) $t_R$=1.50 min, m/z (M+H)$^+$=459.3.

Step 7. Tert-butyl (6-(((3-((6-chloro-3-((methyl-d$_3$)carbamoyl)pyridazin-4-yl)amino)-4-methoxy-5-(1-methyl-1H-1,2,4-triazol-3-yl)benzyl)oxy)methyl)-4-fluoropyridin-2-yl)carbamate (71h)

Compound 71h (50 mg, 84% yield), a yellow solid, was synthesized by utilizing a similar preparative procedure of Step 5 in Example 50 with 71g (43 mg, 0.09 mmol) and 67a (20 mg, 0.09 mmol) as starting materials. LC-MS (Method 3) $t_R$=1.53 min, m/z (M+H)$^+$=631.2.

Step 8. 4-((5-(((6-Amino-4-fluoropyridin-2-yl)methoxy)methyl)-2-methoxy-3-(1-methyl-1H-1,2,4-triazol-3-yl)phenyl)amino)-6-chloro-N-(methyl-d$_3$)pyridazine-3-carboxamide 2,2,2-trifluoroacetic acid (71i)

Compound 71i (30 mg, 59% yield), a white solid, was synthesized by utilizing a similar preparative procedure of Step 11 in Example 66 with 71h (50 mg, 0.08 mmol) as the starting material. LC-MS (Method 3) $t_R$=1.38 min, m/z (M+H)$^+$=531.3.

Step 9. 19-Fluoro-10-methoxy-N-(methyl-d$_3$)-11-(1-methyl-1H-1,2,4-triazol-3-yl)-15-oxa-2,4,5,8,21-pentaazatetracyclo[15.3.1.1^{3,7}.1^{9,13}]tricosa-1(21),3,5,7(23),9(22),10,12,17,19-nonaene-6-carboxamide (71)

Compound 71 (3 mg, 13% yield), a yellow solid, was synthesized by utilizing a similar preparative procedure of Step 12 in Example 66 with 71i (30 mg, 0.05 mmol) as the starting material. LC-MS (Method 2) $t_R$=3.37 min, m/z (M+H)$^+$=495.2. $^1$H NMR (400 MHz, DMSO-d$_6$) δ 10.77 (s, 1H), 10.61 (s, 1H), 9.63 (s, 1H), 9.07 (s, 1H), 8.57 (s, 1H), 8.18 (d, J=1.6 Hz, 1H), 7.49 (d, J=1.6 Hz, 1H), 6.99 (dd, J=2.0, 9.2 Hz, 1H), 6.90 (dd, J=2.0 Hz, 11.2 Hz, 1H), 4.67 (s, 2H), 4.39 (s, 2H), 3.95 (s, 3H), 3.80 (s, 3H).

Example 72
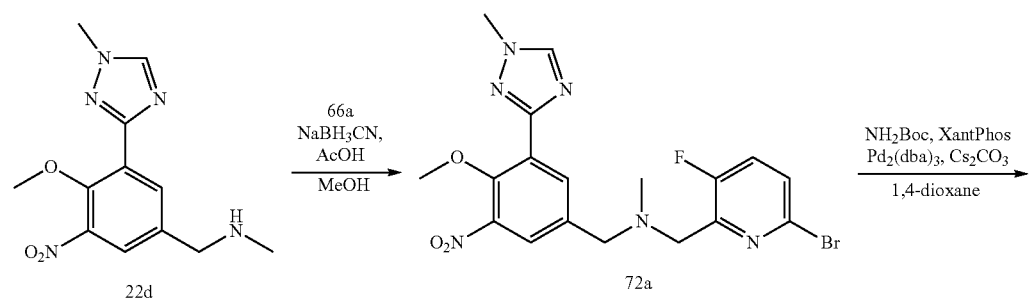
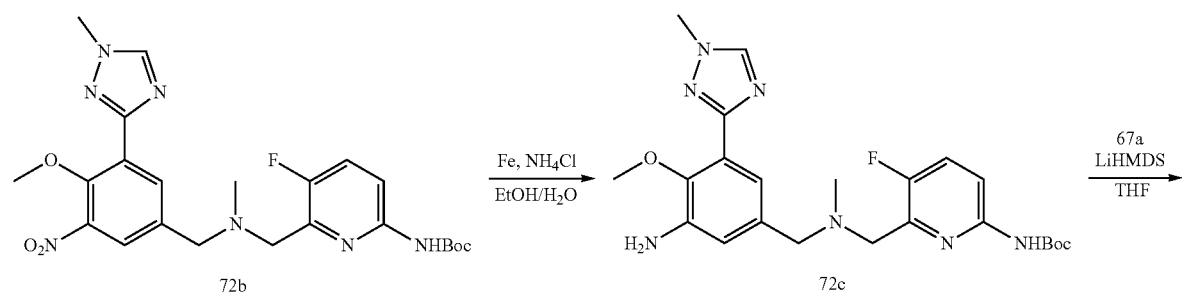
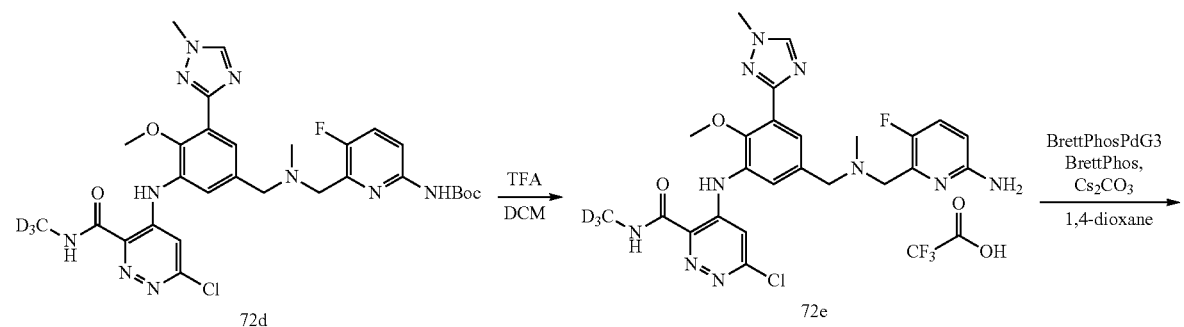
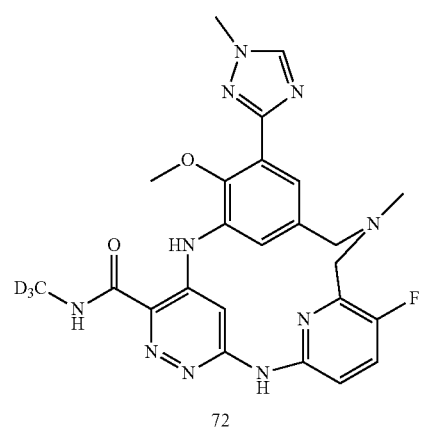

Step 1. 1-(6-Bromo-3-fluoropyridin-2-yl)-N-(4-methoxy-3-(1-methyl-1H-1,2,4-triazol-3-yl)-5-nitrobenzyl)-N-methylmethanamine (72a)

To a solution of 22d (90 mg, 0.32 mmol) and 66a (66 mg, 0.32 mmol) in MeOH (2 mL) was added NaBH$_3$CN (102 mg, 1.62 mmol). The reaction mixture was stirred at r.t. for 5 min. Then AcOH (2 mg, 0.03 mmol) was added to the solution. After stirring at r.t. for 2 h, the reaction mixture was quenched with water (5 mL) and extracted with EtOAc (20 mL*3). The combined organic layer was dried over anhydrous Na$_2$SO$_4$, filtered and concentrated. The residue was purified by flash chromatography on silica gel (PE/EtOAc=1/1) to afford the title compound 72a (80 mg, 53% yield) as a yellow oil. LC-MS (Method 3) $t_R$=1.51 min, m/z (M+H)$^+$=465.1.

Step 2. Tert-butyl (5-fluoro-6-(((4-methoxy-3-(1-methyl-1H-1,2,4-triazol-3-yl)-5-nitrobenzyl)(methyl)amino)methyl)pyridin-2-yl)carbamate (72b)

Compound 72b (60 mg, 93% yield), a yellow solid, was synthesized by utilizing a similar preparative procedure of Step 8 in Example 66 with 72a (60 mg, 0.13 mmol) and tert-butyl carbamate (45 mg, 0.39 mmol) as starting materials. LC-MS (Method 3) $t_R$=1.74 min, m/z (M+H−100)$^+$=402.3.

Step 3. Tert-butyl (6-(((3-amino-4-methoxy-5-(1-methyl-1H-1,2,4-triazol-3-yl)benzyl)(methyl)amino)methyl)-5-fluoropyridin-2-yl)carbamate (72c)

Compound 72c (23 mg, 38% yield), a yellow oil, was synthesized by utilizing a similar preparative procedure of Step 9 in Example 66 with 72b (65 mg, 0.13 mmol) as the starting material. LC-MS (Method 3) $t_R$=1.33 min, m/z (M+H)$^+$=472.3.

Step 4. Tert-butyl (6-(((3-((6-chloro-3-((methyl-d$_3$)carbamoyl)pyridazin-4-yl)amino)-4-methoxy-5-(1-methyl-1H-1,2,4-triazol-3-yl)benzyl)(methyl)amino)methyl)-5-fluoropyridin-2-yl)carbamate (72d)

Compound 72d (30 mg, 100% yield), a yellow solid, was synthesized by utilizing a similar preparative procedure of Step 5 in Example 50 with 72c (22 mg, 0.05 mmol) and 67a (13 mg, 0.06 mmol) as starting materials. LC-MS (Method 3) $t_R$=1.67 min, m/z (M+H)$^+$=644.6.

Step 5. 4-((5-(((((6-Amino-3-fluoropyridin-2-yl)methyl)(methyl)amino)methyl)-2-methoxy-3-(1-methyl-1H-1,2,4-triazol-3-yl)phenyl)amino)-6-chloro-N-(methyl-d$_3$)pyridazine-3-carboxamide 2,2,2-trifluoroacetic acid (72e)

Compound 72e (30 mg, 98% yield), a yellow solid, was synthesized by utilizing a similar preparative procedure of Step 11 in Example 66 with 72d (30 mg, 0.05 mmol) as the starting material. LC-MS (Method 3) $t_R$=1.33 min, m/z (M+H)$^+$=544.5.

Step 6. 18-Fluoro-10-methoxy-N-(methyl-d$_3$)-15-methyl-11-(1-methyl-1H-1,2,4-triazol-3-yl)-2,4,5,8,15,21-hexaazatetracyclo[15.3.1.1^{3,7}.1^{9,13}]tricosa-1(20),3,5,7(23),9(22),10,12,17(21),18-nonaene-6-carboxamide (72)

Compound 72 (5 mg, 22% yield), a white solid, was synthesized by utilizing a similar preparative procedure of Step 12 in Example 66 with 72e (30 mg, 0.05 mmol) as the starting material. LC-MS (Method 2) $t_R$=3.34 min, m/z (M+H)$^+$=508.2. $^1$H NMR (400 MHz, DMSO-d 6) δ 10.69 (s, 1H), 10.50 (s, 1H), 9.75 (s, 1H), 9.02 (s, 1H), 8.56 (s, 1H), 8.21 (s, 1H), 7.63 (t, J=9.2 Hz, 1H), 7.45 (s, 1H), 7.11 (dd, J=8.8, 2.4 Hz, 1H), 3.95 (s, 3H), 3.77 (s, 3H), 3.72 (s, 2H), 3.37 (s, 2H), 2.32 (s, 3H).

Example 73

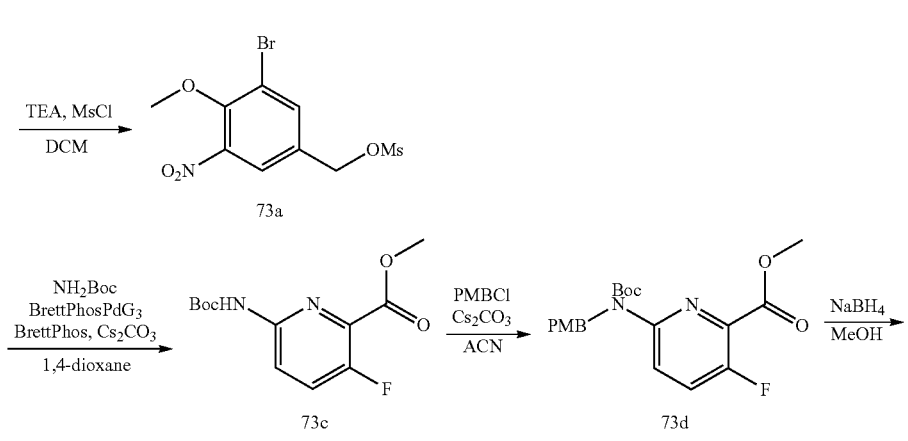

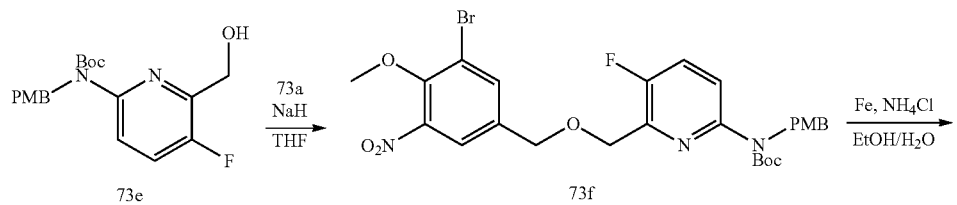

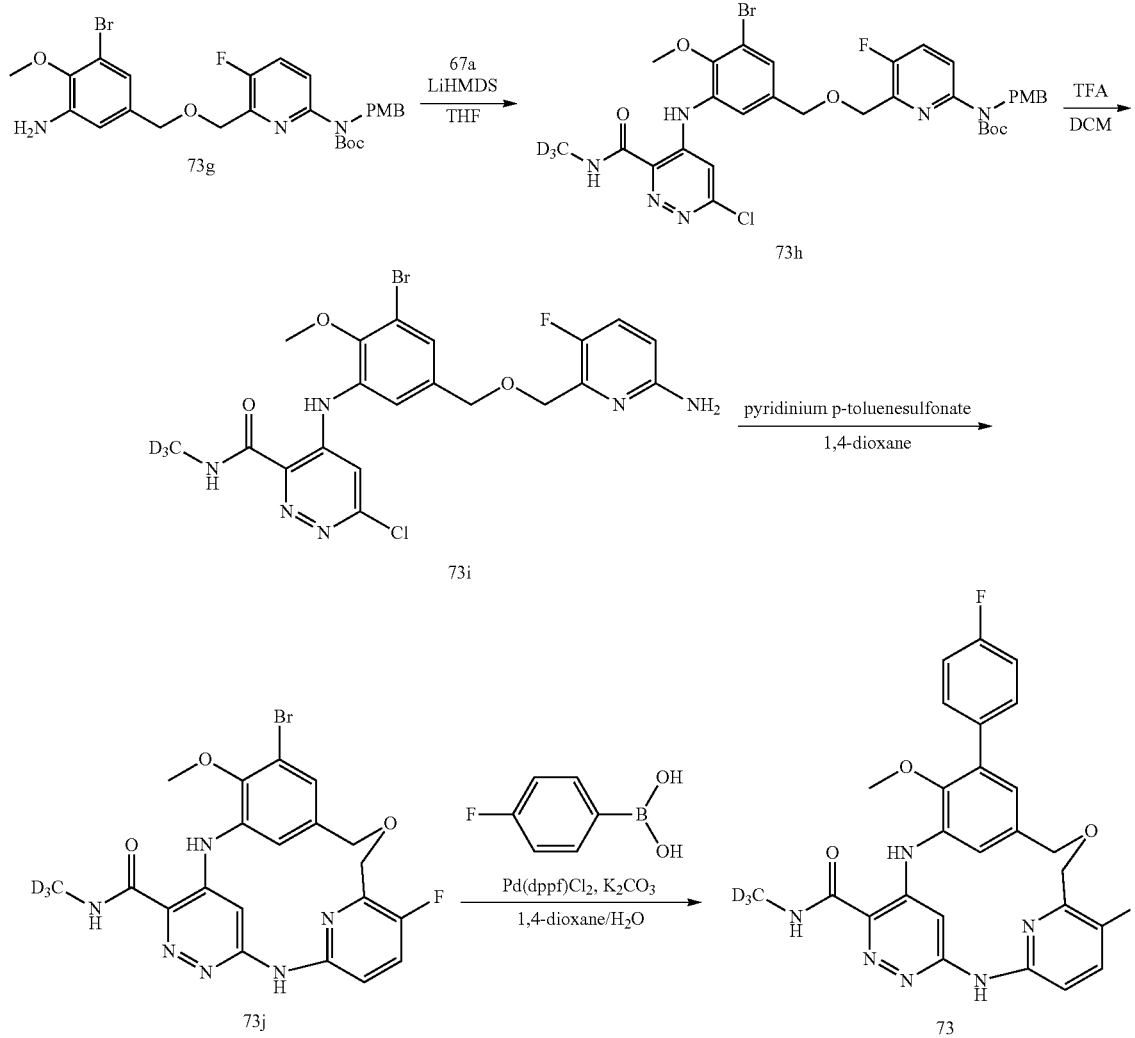

Step 1. 3-Bromo-4-methoxy-5-nitrobenzyl methanesulfonate (73a)

Compound 73a (5.6 g, 48% yield), a yellow oil, was synthesized by utilizing a similar preparative procedure of Step 6 in Example 66 with (3-bromo-4-methoxy-5-nitrophenyl)methanol (9.0 g, 34.34 mmol) and methanesulfonyl chloride (5.9 g, 51.52 mmol) as starting materials. $^1$H NMR (400 MHz, CDCl$_3$) δ 7.85 (d, J=2.0 Hz, 1H), 7.80 (d, J=2.0 Hz, 1H), 5.19 (s, 2H), 4.02 (s, 3H), 3.14 (s, 3H).

Step 2. Methyl 6-((tert-butoxycarbonyl)amino)-3-fluoropicolinate (73c)

Compound 73b (5.5 g, 77% yield), a yellow solid, was synthesized by utilizing a similar preparative procedure of Step 3 in Example 49 with 73b (5.0 g, 26.38 mmol) and tert-butyl carbamate (3.71 g, 31.65 mmol) as starting materials. $^1$H NMR (400 MHz, DMSO-d$_6$) δ 10.18 (s, 1H), 8.03 (dd, J=9.2, 3.2 Hz, 1H), 7.86 (t, J=9.6 Hz, 1H), 4.02 (s, 3H), 1.46 (s, 9H).

Step 3. Methyl 6-((tert-butoxycarbonyl)(4-methoxybenzyl)amino)-3-fluoropicolinate (73d)

To a mixture of 73c (4.6 g, 17.02 mmol) and Cs$_2$CO$_3$ (11.10 g, 34.04 mmol) in ACN (40 mL) was added PMBCl (3.98 g, 25.53 mmol) at 0° C. The reaction mixture was stirred at r.t. for 2 h. The reaction mixture was quenched with ice water (30 mL) and extracted with EtOAc (30 mL*3). The combined organic layer was conentrated to afford the title compound 73d (6.6 g, 99% yield) as a white solid. LC-MS (Method 3) t$_R$=1.78 min, m/z (M+H−56)$^+$=335.3.

Step 4. Methyl 6-((tert-butoxycarbonyl)(4-methoxybenzyl)amino)-3-fluoropicolinate (73e)

To a solution of 73d (6.65 g, 17.03 mmol) in MeOH (65 mL) was added NaBH$_4$ (1.29 g, 34.06 mmol) portionwise at 0° C. The reaction mixture was stirred at r.t. for 1 h. The reaction mixture was quenched with water (80 mL) and extracted with EtOAc (70 mL*3). The combined organic layer was concentrated to afford the title compound 73e (5.4 g, 87% yield) as a white solid. LC-MS (Method 1) t$_R$=1.55 min, m/z (M+H)$^+$=363.3.

Step 5. Tert-butyl (6-((3-bromo-4-methoxy-5-nitrobenzyl)oxy)methyl)-5-fluoropyridin-2-yl)(4-methoxybenzyl)carbamate (73f)

Compound 73f (500 mg, 60% yield), a yellow oil, was synthesized by utilizing a similar preparative procedure of Step 7 in Example 66 with 73e (500 mg, 1.38 mmol) and 73a (470 mg, 1.38 mmol) as starting materials. LC-MS (Method 3) $t_R$=1.53 min, m/z (M+H)$^+$=607.1.

Step 6. Tert-butyl (6-(((3-amino-5-bromo-4-methoxybenzyl)oxy)methyl)-5-fluoropyridin-2-yl)(4-methoxybenzyl)carbamate (73g)

Compound 73g (700 mg, 74% yield), a brown oil, was synthesized by utilizing a similar preparative procedure of Step 9 in Example 66 with 73f (1.0 g, 1.65 mmol) as the starting material. LC-MS (Method 3) $t_R$=1.75 min, m/z (M+H)$^+$=576.1.

Step 7. Tert-butyl (6-(((3-bromo-5-((6-chloro-3-((methyl-d$_3$)carbamoyl)pyridazin-4-yl)amino)-4-methoxybenzyl)oxy)methyl)-5-fluoropyridin-2-yl)(4-methoxybenzyl)carbamate (73h)

Compound 73h (1.17 g, yield given), a yellow solid, was synthesized by utilizing a similar preparative procedure of Step 5 in Example 50 with 73g (900 mg, 1.56 mmol) and 67a (326 mg, 1.56 mmol) as starting materials. LC-MS (Method 3) $t_R$=1.99 min, m/z (M+H)$^+$=748.3.

Step 8. 4-((5-((6-Amino-3-fluoropyridin-2-yl)methoxy)methyl)-3-bromo-2-methoxyphenyl)amino)-6-chloro-N-(methyl-d$_3$)pyridazine-3-carboxamide (73i)

Compound 73i (700 mg, 72% yield), a yellow solid, was synthesized by utilizing a similar preparative procedure of Step 11 in Example 66 with 73h (1.37 g, 1.83 mmol) as the starting material. LC-MS (Method 3) $t_R$=1.52 min, m/z (M+H)$^+$=528.0.

Step 9. 11-Bromo-18-fluoro-10-methoxy-N-(methyl-d$_3$)-15-oxa-2,4,5,8,21-pentaazatetracyclo[15.3.1.1^{3,7}.1^{9,13}]tricosa-1(20),3,5,7(23),9(22),10,12,17(21),18-nonaene-6-carboxamide (73j)

A mixture of 73i (30 mg, 0.056 mmol) and pyridinium p-toluenesulfonate (43 mg, 0.17 mmol) in 1,4-dioxane (10 mL) was stirred at 110° C. for 18 h under N$_2$. The reaction mixture was cooled and concentrated. The residue was purified by flash chromatography on silica gel (DCM/MeOH=20/1) to afford the title compound 73j (15 mg, 54% yield) as a yellow solid. LC-MS (Method 3) $t_R$=1.78 min, m/z (M+H)$^+$=492.2.

Step 10. 18-Fluoro-11-(4-fluorophenyl)-10-methoxy-N-(methyl-d$_3$)-15-oxa-2,4,5,8,21-pentaazatetracyclo[15.3.1.1^{3,7}.1^{9,13}]tricosa-1(20),3,5,7(23),9(22),10,12,17(21),18-nonaene-6-carboxamide (73)

A mixture of 73j (15 mg, 0.03 mmol), (4-fluorophenyl)boronic acid (9 mg, 0.61 mmol), Pd(dppf)Cl$_2$ (4 mg, 0.006 mmol) and K$_2$CO$_3$ (13 mg, 0.09 mmol) in 1,4-dioxane (0.5 mL) and H$_2$O (0.1 mL) was stirred at 100° C. for 5 h under N$_2$. Then the reaction mixture was cooled, filtered and concentrated. The residue was purified by Prep-HPLC (Method A) to afford the title compound 73 (2.1 mg, 14% yield) as a yellow solid. LC-MS (Method 2) $t_R$=3.20 min, m/z (M+H)$^+$=508.2. $^1$H NMR (400 MHz, CDCl$_3$) δ 10.73 (s, 1H), 9.68 (s, 1H), 8.39 (s, 1H), 8.22 (s, 1H), 8.07 (s, 1H), 7.60-7.57 (m, 2H), 7.38 (t, J=8.8 Hz, 1H), 7.15-7.13 (m, 2H), 6.93 (s, 1H), 6.85 (dd, J=9.2, 2.0 Hz, 1H), 4.73 (s, 2H), 4.64 (s, 2H), 3.50 (s, 3H).

Example 74

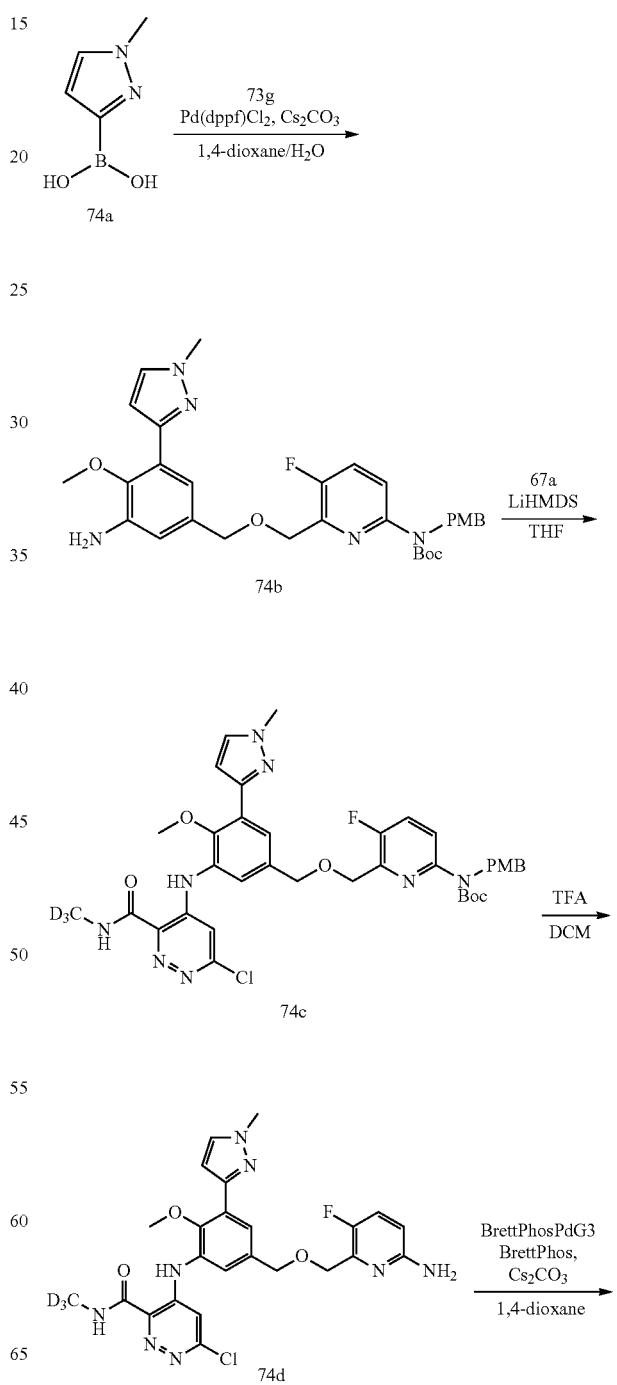

321

-continued

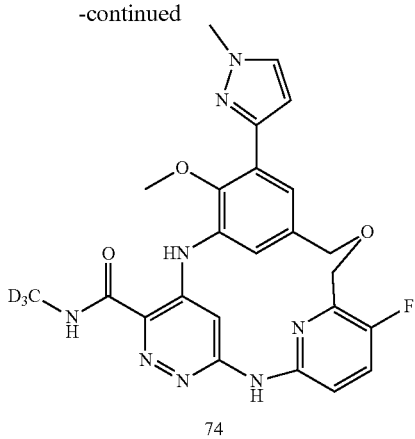

74

Step 1. Tert-butyl (6-(((3-amino-4-methoxy-5-(1-methyl-1H-pyrazol-3-yl)benzyl)oxy)methyl)-5-fluoropyridin-2-yl)(4-methoxybenzyl)carbamate (74b)

A mixture of 73g (200 mg, 0.35 mmol), 74a (108 mg, 0.52 mmol), Cs₂CO₃ (226 mg, 0.69 mmol) and Pd(dppf)Cl₂ (26 mg, 0.035 mmol) in 1,4-dioxane/H₂O (1.8 mL, v/v=5/1) was stirred at 100° C. for 12 h under N₂. After cooling to r.t., the reaction mixture was filtered and concentrated. The residue was purified by flash chromatography on silica gel (PE/EtOAc=1/1) to afford the title product 74b (120 mg, 60% yield) as a yellow solid. LC-MS (Method 3) $t_R$=1.83 min, m/z (M+H)⁺=578.2.

Step 2. Tert-butyl (6-(((3-((6-chloro-3-((methyl-d₃)carbamoyl)pyridazin-4-yl)amino)-4-methoxy-5-(1-methyl-1H-pyrazol-3-yl)benzyl)oxy)methyl)-5-fluoropyridin-2-yl)(4-methoxybenzyl)carbamate (74c)

Compound 74c (101 mg, 71% yield), a yellow solid, was synthesized by utilizing a similar preparative procedure of

322

Step 5 in Example 50 with 74b (110 mg, 0.19 mmol) and 67a (48 mg, 0.23 mmol) as starting materials. LC-MS (Method 3) $t_R$=1.85 min, m/z (M+H)⁺=750.5.

Step 3. 4-((5-(((6-Amino-3-fluoropyridin-2-yl)methoxy)methyl)-2-methoxy-3-(1-methyl-1H-pyrazol-3-yl)phenyl)amino)-6-chloro-N-(methyl-d₃)pyridazine-3-carboxamide (74d)

Compound 74d (69 mg, 97% yield), a yellow solid, was synthesized by utilizing a similar preparative procedure of Step 11 in Example 66 with 74c (101 mg, 0.13 mmol) as the starting material. LC-MS (Method 3) $t_R$=1.48 min, m/z (M+H)⁺=530.3.

Step 4. 18-Fluoro-10-methoxy-N-(methyl-d₃)-11-(1-methyl-1H-pyrazol-3-yl)-15-oxa-2,4,5,8,21-pentaazatetracyclo[15.3.1.1^{3,7}.1^{9,13}]tricosa-1(20),3,5,7(23),9(22),10,12,17(21),18-nonaene-6-carboxamide (74)

Compound 74 (6 mg, 9% yield), a white solid, was synthesized by utilizing a similar preparative procedure of Step 12 in Example 66 with 74d (69 mg, 0.13 mmol) as the starting material. LC-MS (Method 2) $t_R$=2.88 min, m/z (M+H)⁺=494.2. ¹H NMR (400 MHz, DMSO-d₆) δ 10.75 (s, 1H), 10.53 (s, 1H), 9.62 (s, 1H), 9.04 (s, 1H), 8.24 (d, J=1.6 Hz, 1H), 7.79 (d, J=2.4 Hz, 1H), 7.68 (q, J=9.2 Hz, 1H), 7.53 (d, J=1.6 Hz, 1H), 7.17 (dd, J=9.2 Hz, 3.2 Hz, 1H), 6.76 (d, J=2.4 Hz, 1H), 4.68 (s, 2H), 4.48 (d, J=2.4 Hz, 2H), 3.91 (s, 3H), 3.65 (s, 3H).

Example 75

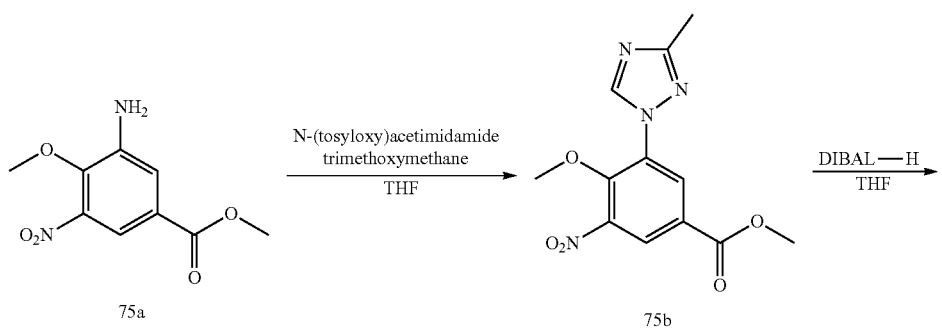

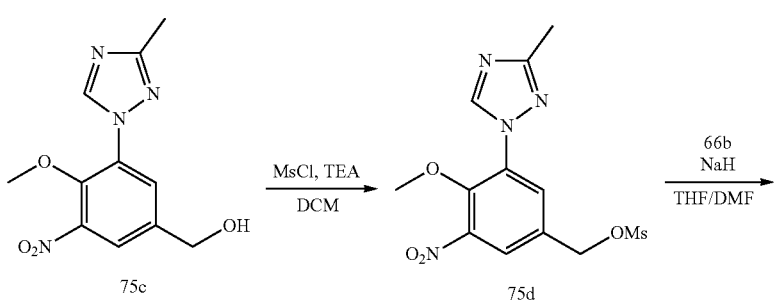

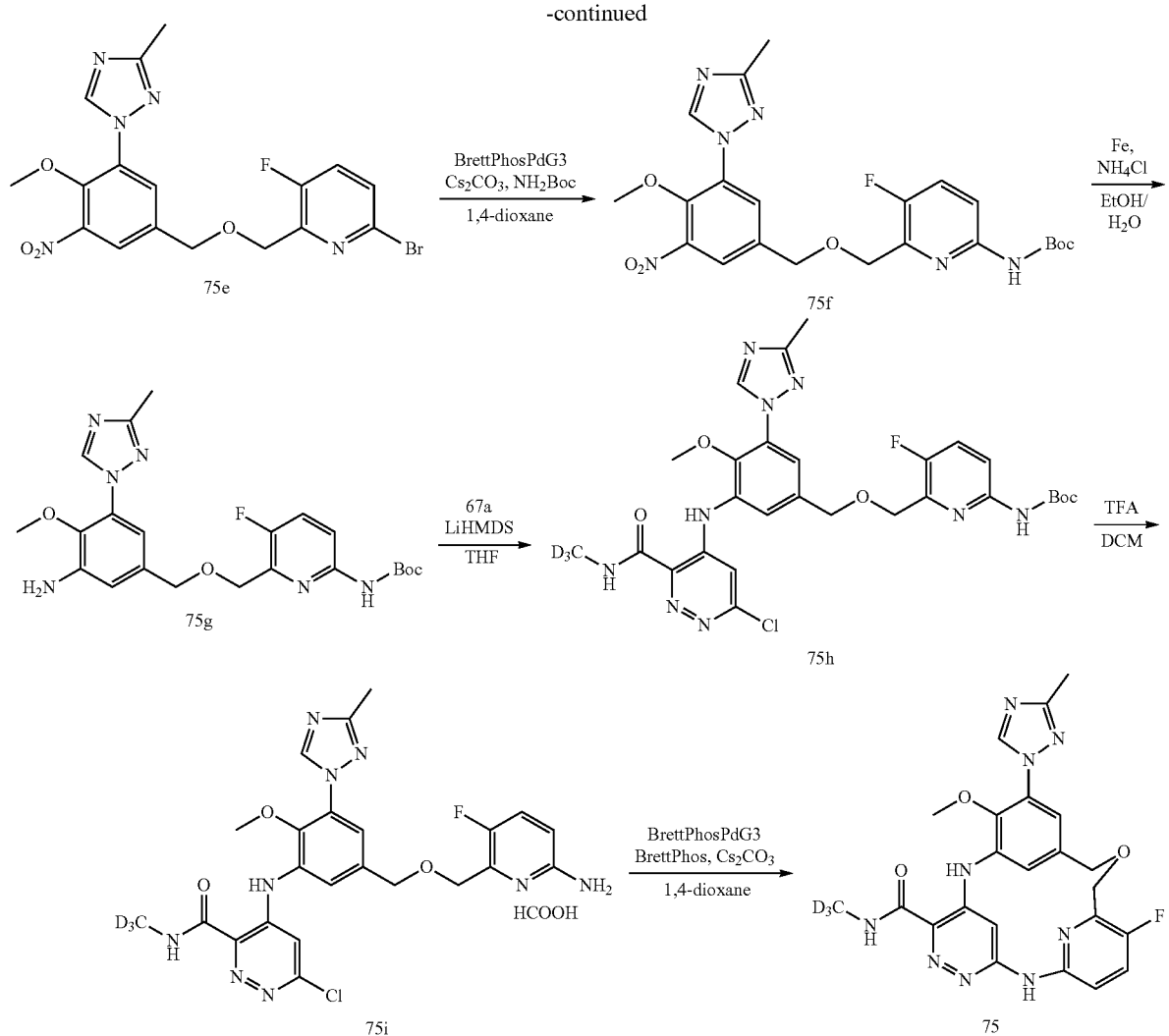

Step 1. Methyl 4-methoxy-3-(3-methyl-1H-1,2,4-triazol-1-yl)-5-nitrobenzoate (75b)

To a solution of methyl 3-amino-4-methoxy-5-nitrobenzoate (1.3 g, 5.75 mmol) in THF (15 mL) was added N-(tosyloxy)acetimidamide (1.44 g, 6.32 mmol) followed by trimethoxymethane (915 mg, 8.62 mmol). After the reaction mixture was stirred at 60° C. for 2 h, the reaction mixture was cooled and concentrated. The residue was dissolved in DCM (50 mL), washed with sat. NaHCO₃ (50 mL), dried over Na₂SO₄, filtered and concentrated. The residue was purified by flash chromatography on silica gel (PE/EtOAc=1/1) to afford the title compound 75b (1.68 g, yield given) as a yellow solid. LC-MS (Method 3) $t_R$=1.53 min, m/z (M+H)⁺=293.0.

Step 2. (4-Methoxy-3-(3-methyl-1H-1,2,4-triazol-1-yl)-5-nitrophenyl)methanol (75c)

To a solution of 75b (1 g, 3.42 mmol) in THF (40 mL) was added diisobutylaluminum hydride (20 mL, 20.53 mmol, 1.0 M in hexane) at −70° C. The reaction mixture was stirred at −70° C. for 30 min and then stirred at r.t. for 4 h. The reaction mixture was quenched with sat. NH₄Cl (50 mL) and the temperature was maintained below 25° C. The separated aqueous phase was extracted with DCM (100 mL*2). The combined organic layer was dried over Na₂SO₄, filtered and concentrated. The residue was purified by flash chromatography on silica gel (EtOAc) to afford the title compound 75c (450 mg, 50% yield) as a colorless oil. LC-MS (Method 3) $t_R$=1.31 min, m/z (M+H)⁺=265.0.

Step 3. 4-Methoxy-3-(3-methyl-1H-1,2,4-triazol-1-yl)-5-nitrobenzyl methanesulfonate (75d)

Compound 75d (300 mg, 51% yield), a yellow solid, was synthesized by utilizing a similar preparative procedure of Step 6 in Example 66 with 75c (450 mg, 1.70 mmol) and methanesulfonyl chloride (233 mg, 2.04 mmol) as starting materials. LC-MS (Method 3) $t_R$=1.35 min, m/z (M+H)⁺=342.9.

Step 4. 6-Bromo-3-fluoro-2-(((4-methoxy-3-(3-methyl-1H-1,2,4-triazol-1-yl)-5-nitrobenzyl)oxy)methyl)pyridine (75e)

Compound 75e (190 mg, 48% yield), a yellow oil, was synthesized by utilizing a similar preparative procedure of Step 3 in Example 69 with 75d (300 mg, 0.88 mmol) and 66b (181 mg, 0.88 mmol) as starting materials. $^1$H NMR (400 MHz, DMSO-$d_6$) δ 8.88 (s, 1H), 7.98 (d, J=2.0 Hz, 1H), 7.94 (d, J=2.0 Hz, 1H), 7.78-7.69 (m, 2H), 4.69 (s, 4H), 3.62 (s, 3H), 2.39 (s, 3H).

Step 5. Tert-butyl (5-fluoro-6-(((4-methoxy-3-(3-methyl-1H-1,2,4-triazol-1-yl)-5-nitrobenzyl)oxy)methyl)pyridin-2-yl)carbamate (75f)

A mixture of 75e (190 mg, 0.42 mmol), tert-butyl carbamate (148 mg, 1.26 mmol), BrettPhos Pd G3 (76 mg, 0.084 mmol) and $Cs_2CO_3$ (274 mg, 0.84 mmol) in 1,4-dioxane (2 mL) was stirred at 90° C. for 4 h under $N_2$ atmosphere. The reaction mixture was diluted with EtOAc (10 mL) and filtered. The filtrate was concentrated to afford the title compound 75f (200 mg, 97% yield) as a yellow oil. LC-MS (Method 3) $t_R$=1.78 min, m/z (M+H−100)$^+$=388.9.

Step 6. Tert-butyl (6-(((3-amino-4-methoxy-5-(3-methyl-1H-1,2,4-triazol-1-yl)benzyl)oxy)methyl)-5-fluoropyridin-2-yl)carbamate (75g)

Compound 75g (120 mg, 64% yield), a yellow oil, was synthesized by utilizing a similar preparative procedure of Step 9 in Example 66 with 75f (200 mg, 0.41 mmol) as the starting material. LC-MS (Method 3) $t_R$=1.65 min, m/z (M+H)$^+$=459.0.

Step 7. Tert-butyl (6-(((3-((6-chloro-3-(methylcarbamoyl)pyridazin-4-yl)amino)-4-methoxy-5-(3-(methyl-$d_3$)-1H-1,2,4-triazol-1-yl)benzyl)oxy)methyl)-5-fluoropyridin-2-yl)carbamate (75h)

Compound 75h (120 mg, 64% yield), a yellow solid, was synthesized by utilizing a similar preparative procedure of Step 5 in Example 50 with 75g (60 mg, 0.13 mmol) and 67a (27 mg, 0.13 mmol) as starting materials. LC-MS (Method 3) $t_R$=1.60 min, m/z (M+H−100)$^+$=531.3.

Step 8. 4-((5-(((6-Amino-3-fluoropyridin-2-yl)methoxy)methyl)-2-methoxy-3-(3-(methyl-$d_3$)-1H-1,2,4-triazol-1-yl)phenyl)amino)-6-chloro-N-methylpyridazine-3-carboxamide formate (75i)

Compound 75i (55 mg, 73% yield), a yellow solid, was synthesized by utilizing a similar preparative procedure of Step 11 in Example 66 with 75h (82 mg, 0.13 mmol) as the starting material. LC-MS (Method 3) $t_R$=1.34 min, m/z (M+H)$^+$=531.3.

Step 9. 18-Fluoro-10-methoxy-N-(methyl-$d_3$)-11-(3-methyl-1H-1,2,4-triazol-1-yl)-15-oxa-2,4,5,8,21-pentaazatetracyclo[15.3.1.1^{3,7}.1^{9,13}]tricosa-1(20),3,5,7(23),9(22),10,12,17(21),18-nonaene-6-carboxamide (75)

Compound 75 (24.7 mg, 48% yield), a white solid, was synthesized by utilizing a similar preparative procedure of Step 12 in Example 66 with 75i (60 mg, 0.10 mmol) as the starting material. LC-MS (Method 1) $t_R$=3.85 min, m/z (M+H)$^+$=495.1. $^1$H NMR (400 MHz, DMSO-$d_6$) δ 10.90 (s, 1H), 10.60 (s, 1H), 9.59 (s, 1H), 9.09 (s, 1H), 8.86 (s, 1H), 8.19 (s, 1H), 7.69 (t, J=9.2 Hz, 1H), 7.31 (s, 1H), 7.19 (dd, J=9.2, 2.4 Hz, 1H), 4.71 (s, 2H), 4.50 (s, 2H), 3.60 (s, 3H), 2.38 (s, 3H).

Example 76

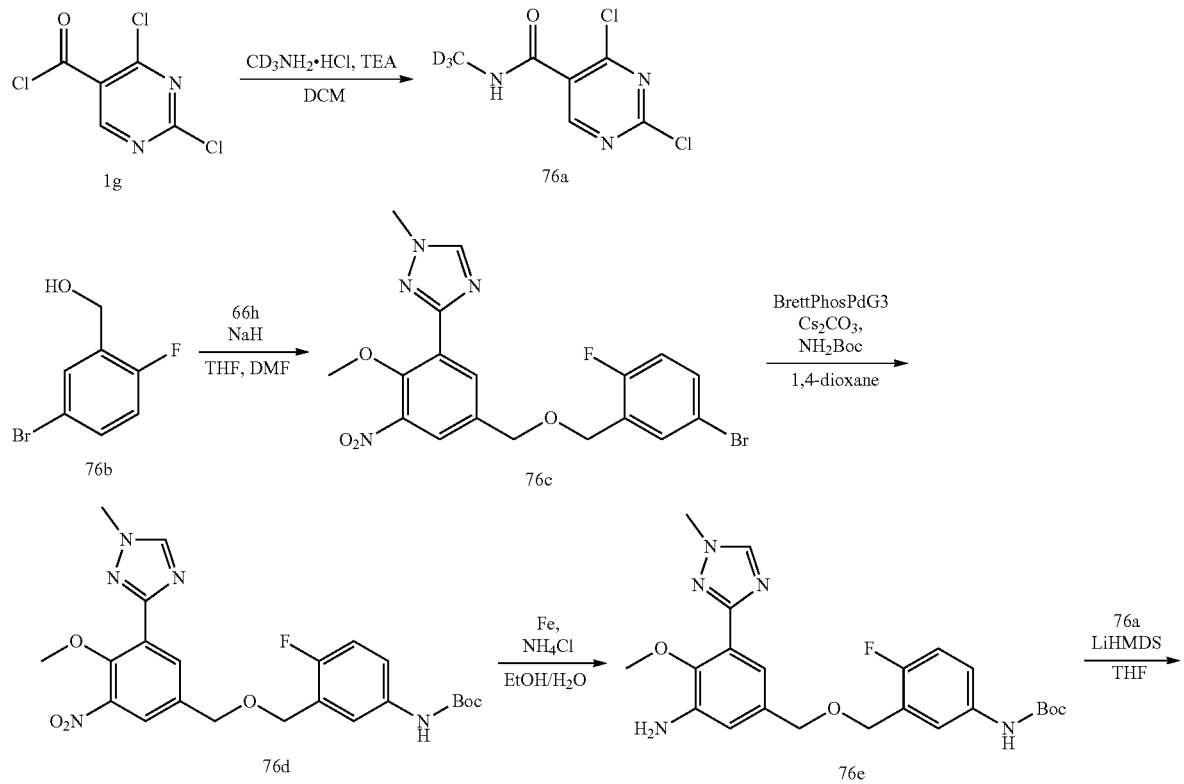

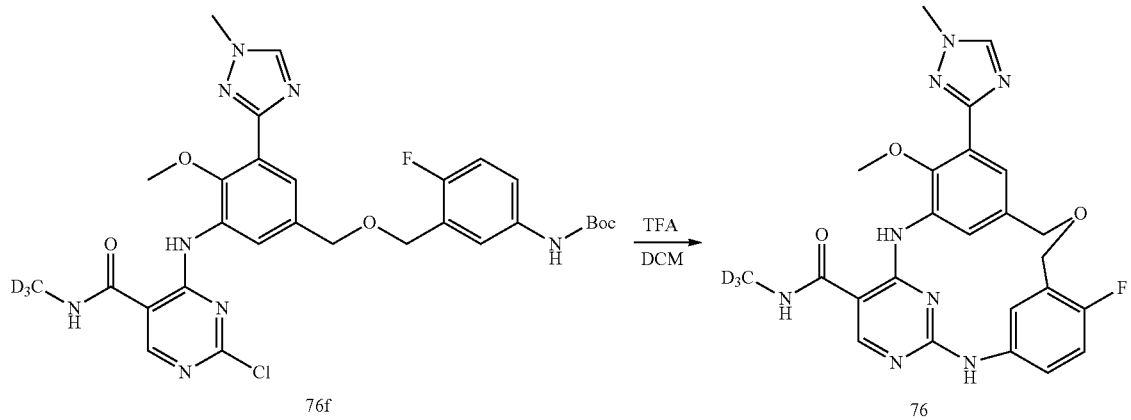

Step 1. 2,4-Dichloro-N-(methyl-d$_3$)pyrimidine-5-carboxamide (76a)

To a mixture of methan-d$_3$-amine hydrochloride (1.40 g, 19.86 mmol) in DCM (200 mL) was added 1g (3.5 g, 16.55 mmol) slowly followed by TEA (1.68 g, 16.55 mmol, 2.31 mL) at −78° C. After stirring for 1 h at this temperature, the reaction was quenched with water (30 mL). The organic layer was separated and concentrated. The residue was purified by flash chromatography using silica gel (PE/EtOAc=5/1) to afford the title compound 76a (1.38 g, 35% yield) as a white solid. $^1$H NMR (400 MHz, DMSO-d$_6$) δ 8.88 (s, 1H), 8.85 (s, 1H).

Step 2. 3-(5-(((5-Bromo-2-fluorobenzyl)oxy)methyl)-2-methoxy-3-nitrophenyl)-1-methyl-1H-1,2,4-triazole (76c)

Compound 76c (288 mg, 84% yield), a brown solid, was synthesized by utilizing a similar preparative procedure of Step 3 in Example 69 with 76b (156 mg, 0.76 mmol) and 66h (260 mg, 0.76 mmol) as starting materials. LC-MS (Method 3) t$_R$=1.62 min, m/z (M+H)$^+$=451.1.

Step 3. Tert-butyl (4-fluoro-3-(((4-methoxy-3-(1-methyl-1H-1,2,4-triazol-3-yl)-5-nitrobenzyl)oxy)methyl)phenyl)carbamate (76d)

A mixture of 76c (288 mg, 0.64 mmol), tert-butyl carbamate (97 mg, 0.83 mmol), BrettPhos Pd G3 (59 mg, 0.064 mmol) and Cs$_2$CO$_3$ (416 mg, 1.28 mmol) in 1,4-dioxane (3 mL) was stirred at 90° C. for 3 h. After cooling to r.t., the reaction mixture was diluted with water (10 mL) and extracted with EtOAc (20 mL*2). The combined organic layer was concentrated to afford the title compound 76d (311 mg, yield given) as a brown solid. LC-MS (Method 3) t$_R$=1.62 min, m/z (M+H)$^+$=488.3.

Step 4. Tert-butyl (3-(((3-amino-4-methoxy-5-(1-methyl-1H-1,2,4-triazol-3-yl)benzyl)oxy)methyl)-4-fluorophenyl)carbamate (76e)

Compound 76e (260 mg, 89% yield), a brown solid, was synthesized by utilizing a similar preparative procedure of Step 9 in Example 66 with 76d (311 mg, 0.64 mmol) as the starting material. LC-MS (Method 3) t$_R$=1.53 min, m/z (M+H)$^+$=458.3.

Step 5. Tert-butyl (3-(((3-((2-chloro-5-((methyl-d$_3$)carbamoyl)pyrimidin-4-yl)amino)-4-methoxy-5-(1-methyl-1H-1,2,4-triazol-3-yl)benzyl)oxy)methyl)-4-fluorophenyl)carbamate (76f)

Compound 76f (110 mg, yield given), a white solid, was synthesized by utilizing a similar preparative procedure of Step 5 in Example 50 with 76e (80 mg, 0.17 mmol) and 76a (48 mg, 0.23 mmol) as starting materials. LC-MS (Method 3) t$_R$=1.60 min, m/z (M+H)$^+$=630.3.

Step 6. 18-Fluoro-10-methoxy-N-(methyl-d$_3$)-11-(1-methyl-1H-1,2,4-triazol-3-yl)-15-oxa-2,4,8,23-tetraazatetracyclo[15.3.1.1^{3,7}.1^{9,13}]tricosa-1(20),3,5,7(23),9(22),10,12,17(21),18-nonaene-6-carboxamide (76)

To a mixture of 76f (110 mg, 0.17 mmol) in DCM (1 mL) was added TFA (1 mL) dropwise at 0° C. After stirring at 35° C. for 1 h, the reaction mixture was pumped through N$_2$ to remove the solvent and the residue was purified with by Prep-HPLC (Method A) to afford the title compound 76 (26 mg, 30% yield) as a white solid. LC-MS (Method 2) t$_R$=3.32 min, m/z (M+H)$^+$=494.1. $^1$H NMR (400 MHz, DMSO-d$_6$) δ 11.76 (s, 1H), 9.81 (s, 1H), 8.74 (s, 1H), 8.69 (s, 1H), 8.55 (s, 1H), 8.47-8.45 (m, 2H), 7.47 (s, 1H), 7.13-7.11 (m, 2H), 4.60 (s, 2H), 4.51 (s, 2H), 3.95 (s, 3H), 3.79 (s, 3H).

Example 77

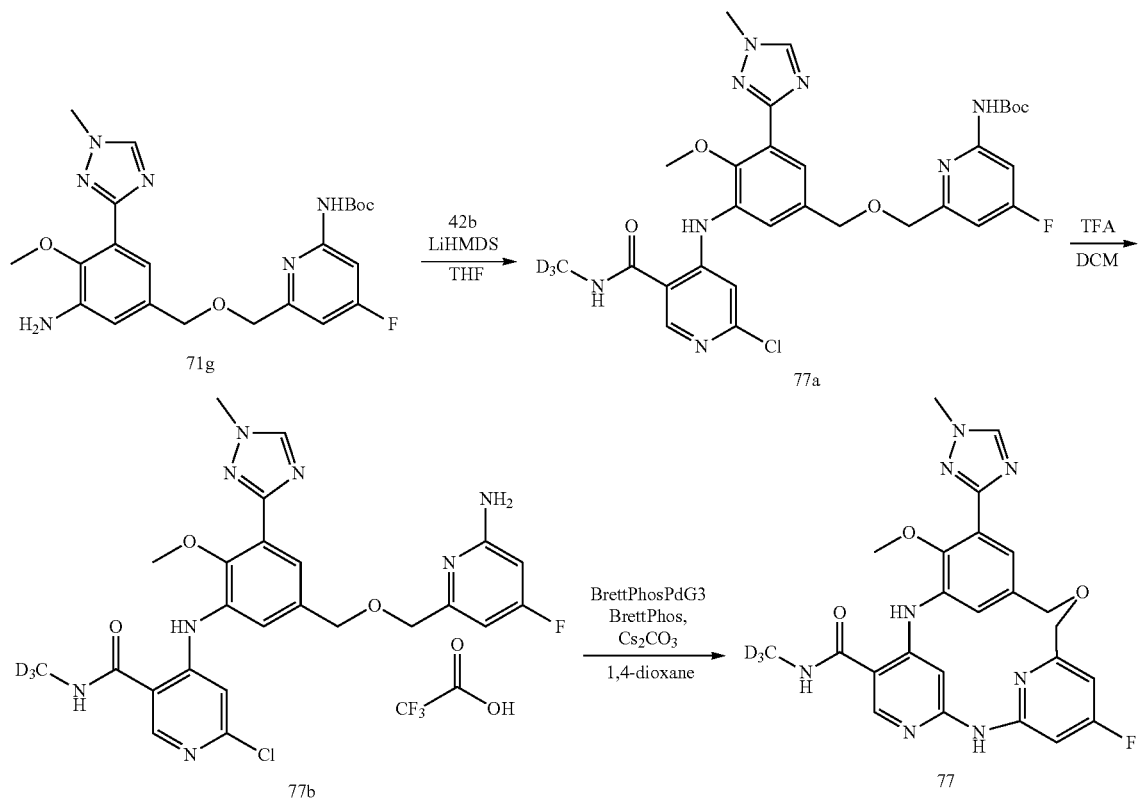

Step 1. Tert-butyl (6-(((3-((2-chloro-5-((methyl-d₃)carbamoyl)pyridin-4-yl)amino)-4-methoxy-5-(1-methyl-1H-1,2,4-triazol-3-yl)benzyl)oxy)methyl)-4-fluoropyridin-2-yl)carbamate (77a)

Compound 77a (54 mg, yield given), a yellow solid, was synthesized by utilizing a similar preparative procedure of Step 5 in Example 50 with 71g (40 mg, 0.087 mmol) and 42b (18 mg, 0.087 mmol) as starting materials. LC-MS (Method 3) $t_R$=1.58 min, m/z (M+H)⁺=630.3.

Step 2. 4-((5-(((6-Amino-4-fluoropyridin-2-yl)methoxy)methyl)-2-methoxy-3-(1-methyl-1H-1,2,4-triazol-3-yl)phenyl)amino)-6-chloro-N-(methyl-d₃) nicotinamide trifluoroacetate (77b)

Compound 77b (20 mg, 36% yield), a yellow solid, was synthesized by utilizing a similar preparative procedure of Step 11 in Example 66 with 77a (60 mg, 0.086 mmol) as the starting material. LC-MS (Method 3) $t_R$=1.32 min, m/z (M+H)⁺=530.3.

Step 3. 19-Fluoro-10-methoxy-N-(methyl-d₃)-11-(1-methyl-1H-1,2,4-triazol-3-yl)-15-oxa-2,4,8,21-tetraazatetracyclo[15.3.1.1^{3,7}.1^{9,13}]tricosa-1(21),3,5,7(23),9(22),10,12,17,19-nonaene-6-carboxamide (77)

Compound 77 (3.0 mg, 19% yield), a white solid, was synthesized by utilizing a similar preparative procedure of Step 12 in Example 66 with 77b (20 mg, 0.031 mmol) as the starting material. LC-MS (Method 1) $t_R$=2.83 min, m/z (M+H)⁺=494.1. ¹H NMR (400 MHz, DMSO-d₆) δ 10.71 (s, 1H), 10.05 (s, 1H), 9.37 (s, 1H), 8.55-8.49 (m, 3H), 8.18 (s, 1H), 7.41 (s, 1H), 6.89 (dd, J=9.2, 1.6 Hz, 1H), 6.78 (dd, J=11.6, 2.0 Hz, 1H), 4.65 (s, 2H), 4.35 (s, 2H), 3.95 (s, 3H), 3.78 (s, 3H).

Example 78

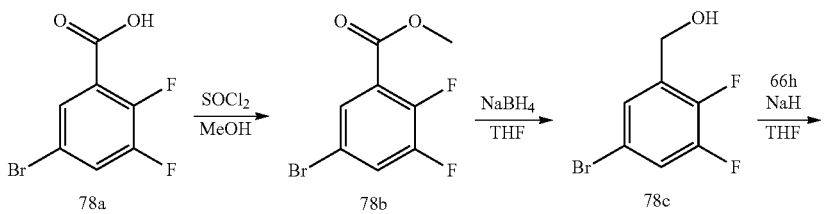

-continued
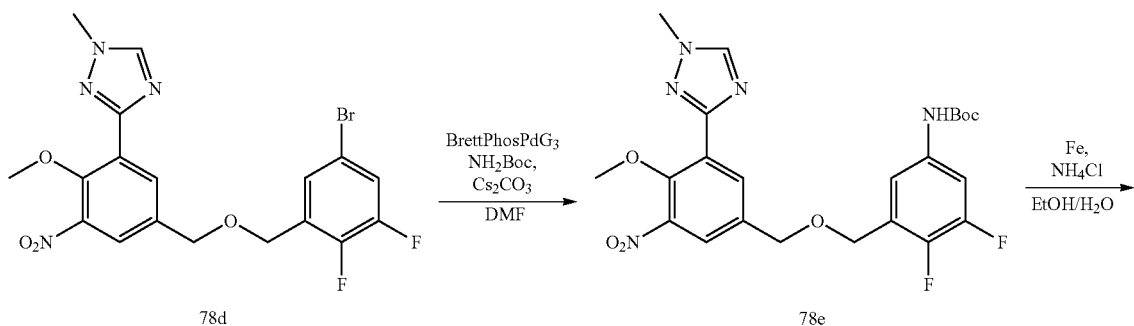
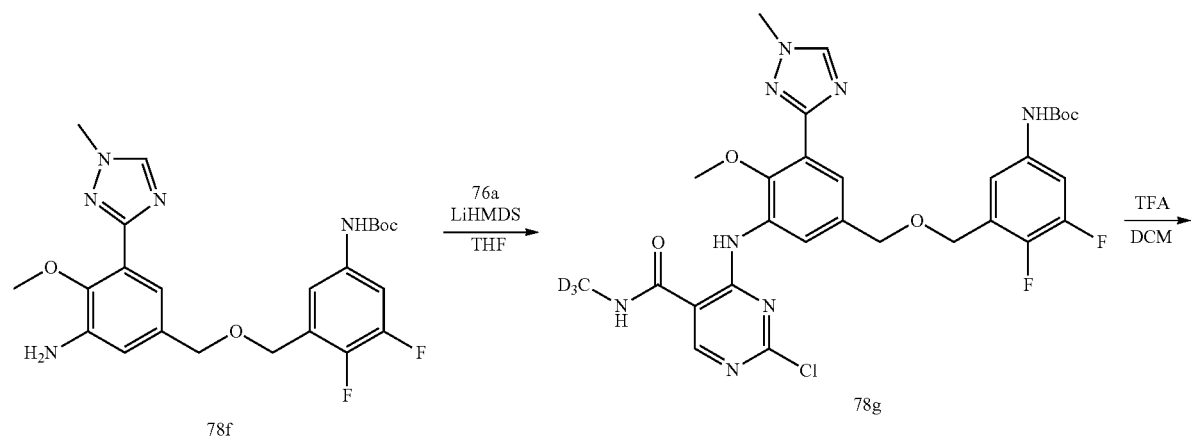
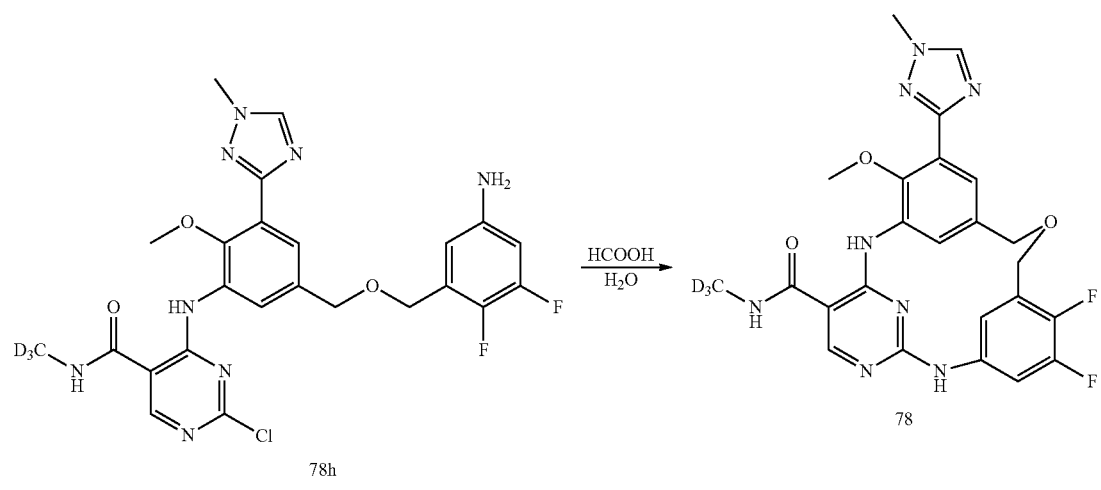

Step 1. Methyl 5-bromo-2,3-difluorobenzoate (78b)

A solution of 78a (500 mg, 2.11 mmol) and SOCl$_2$ (1 mL) in MeOH (5 mL) was stirred at 85° C. for 6 h. The reaction mixture was concentrated and residue was diluted with water (5 mL) and EtOAc (40 mL). The separated organic layer was washed with brine (10 mL), dried over Na$_2$SO$_4$, filtered and concentrated to afford the title compound 78b (500 mg, 94% yield) as a yellow oil. $^1$H NMR (400 MHz, CDCl$_3$) δ 7.83-7.83 (m, 1H), 7.54-7.50 (m, 1H), 3.95 (s, 3H).

Step 2. (5-Bromo-2,3-difluorophenyl)methanol (78c)

To a solution of 78b (550 mg, 2.19 mmol) in THF (8 mL) was added NaBH$_4$ (166 mg, 1.38 mmol) portionwise at 0° C. The reaction mixture was stirred at 0° C. for 2 h. The reaction mixture was quenched with water (20 mL) and extracted with EtOAc (20 mL*3). The separated organic layer was washed with brine (20 mL), dried over Na$_2$SO$_4$, filtered and concentrated to afford the title compound 78c (200 mg, 41% yield) as a yellow oil. $^1$H NMR (400 MHz, CDCl$_3$) δ 7.40-7.38 (m, 1H), 7.29-7.25 (m, 1H), 4.77 (s, 2H), 1.93 (brs, 1H).

Step 3. 3-(5-(((5-Bromo-2,3-difluorobenzyl)oxy) methyl)-2-methoxy-3-nitrophenyl)-1-methyl-1H-1,2, 4-triazole (78d)

Compound 78d (280 mg, 83% yield), a yellow solid, was synthesized by utilizing a similar preparative procedure of Step 7 in Example 66 with 78c (160 mg, 0.72 mmol) and 66h (246 mg, 0.72 mmol) as starting materials. LC-MS (Method 3) $t_R$=1.64 min, m/z (M+H)$^+$=468.9.

Step 4. Tert-butyl (3,4-difluoro-5-(((4-methoxy-3-(1-methyl-1H-1,2,4-triazol-3-yl)-5-nitrobenzyl)oxy) methyl)phenyl)carbamate (78e)

A mixture of 78d (280 mg, 0.60 mmol), tert-butyl carbamate (91 mg, 0.78 mmol), BrettPhos Pd G3 (559 mg, 0.06 mmol) and Cs$_2$CO$_3$ (389 mg, 1.19 mmol) in DMF (5 mL) was stirred at 90° C. for 3 h. After cooling to r.t., the reaction mixture was diluted with water (10 mL) and extracted with EtOAc (20 mL*2). The combined organic layer was concentrated to afford the title compound 78e (302 mg, yield given) as a brown solid. LC-MS (Method 3) $t_R$=1.67 min, m/z (M+H)$^+$=506.3.

Step 5. Tert-butyl (3-(((3-amino-4-methoxy-5-(1-methyl-1H-1,2,4-triazol-3-yl)benzyl)oxy)methyl)-4, 5-difluorophenyl)carbamate (78f)

Compound 78f (160 mg, 57% yield), a yellow solid, was synthesized by utilizing a similar preparative procedure of Step 9 in Example 66 with 78e (300 mg, 0.59 mmol) as the starting material. LC-MS (Method 3) $t_R$=1.55 min, m/z (M+H)$^+$=476.2.

Step 6. Tert-butyl (3-(((3-((2-chloro-5-((methyl-d$_3$) carbamoyl)pyrimidin-4-yl)amino)-4-methoxy-5-(1-methyl-1H-1,2,4-triazol-3-yl)benzyl)oxy)methyl)-4, 5-difluorophenyl)carbamate (78g)

Compound 78g (60 mg, 80% yield), a yellow solid, was synthesized by utilizing a similar preparative procedure of Step 5 in Example 50 with 78f (50 mg, 0.11 mmol) and 76a (31 mg, 0.15 mmol) as starting materials. LC-MS (Method 3) $t_R$=1.59 min, m/z (M+H)$^+$=648.3.

Step 7. 18,19-Difluoro-10-methoxy-N-(methyl-d$_3$)-11-(1-methyl-1H-1,2,4-triazol-3-yl)-15-oxa-2,4,8,23-tetraazatetracyclo[15.3.1.1^{3,7}.1^{9,13}]tricosa-1 (20),3,5,7(23),9(22),10,12,17(21),18-nonaene-6-carboxamide (78)

A mixture of 78g (60 mg, 0.09 mmol) in TFA (1 mL) and DCM (3 mL) was stirred at 35° C. for 1 h. The solvent was removed by pumping through N$_2$. The residue was purified by Prep-HPLC (Method C) and the eluent was concentrated at 50° C. for 1 h. The crude product was was purified by Prep-HPLC (Method A) to afford the title compound 78 (15 mg, 32% yield) as a yellow solid. LC-MS (Method 1) $t_R$=3.23 min, m/z (M+H)$^+$=512.1. $^1$H NMR (400 MHz, DMSO-d$_6$) δ 11.76 (s, 1H), 9.89 (s, 1H), 8.70 (s, 1H), 8.67 (d, J=2.0 Hz, 1H), 8.55 (s, 1H), 8.50 (s, 1H), 8.37 (d, J=5.2 Hz, 1H), 7.50 (d, J=2 Hz, 1H), 7.13-7.08 (m, 1H), 4.62 (s, 2H), 4.55 (s, 2H), 3.95 (s, 3H), 3.79 (s, 3H).

Example 79

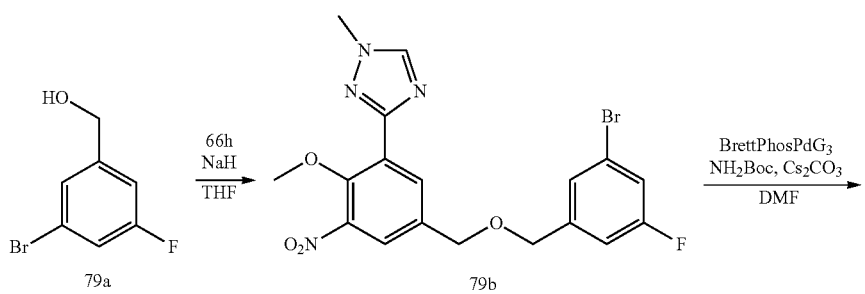

-continued
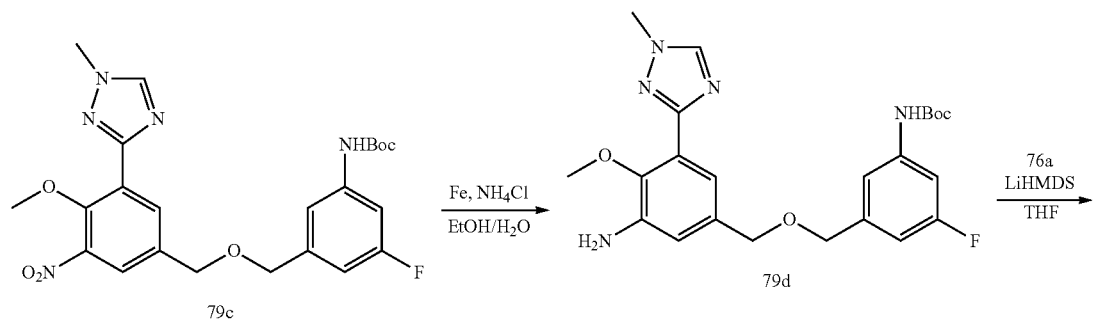
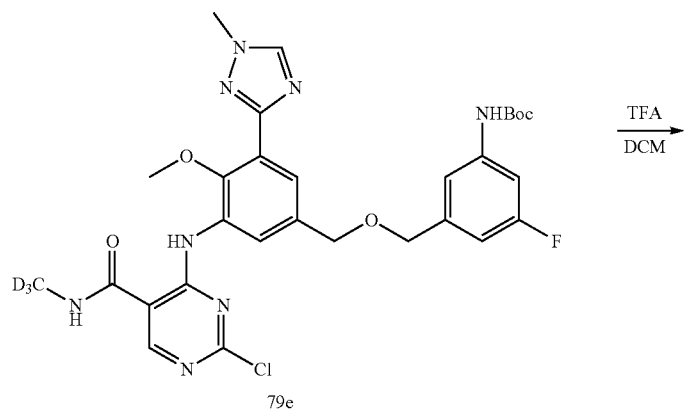
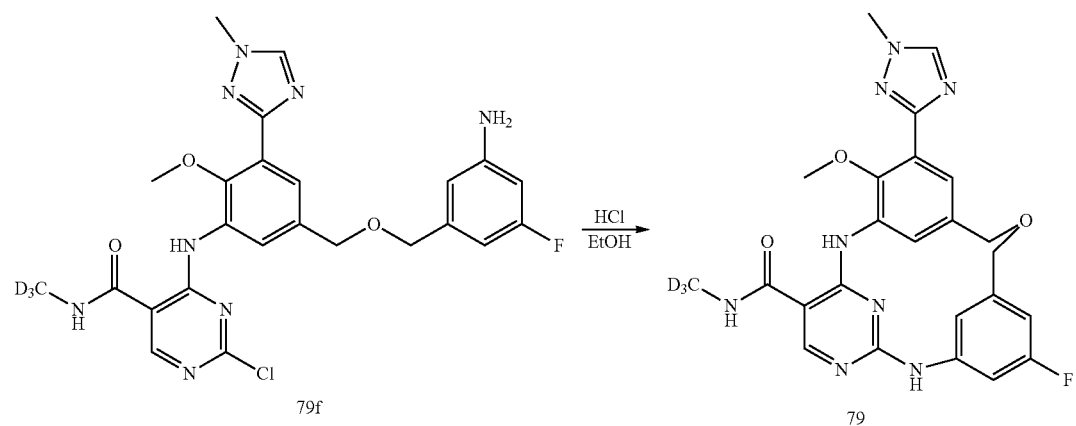

Step 1. 3-(5-(((3-Bromo-5-fluorobenzyl)oxy) methyl)-2-methoxy-3-nitrophenyl)-1-methyl-1H-1,2, 4-triazole (79b)

Compound 79b (300 mg, 76% yield), a brown oil, was synthesized by utilizing a similar preparative procedure of Step 7 in Example 66 with 66h (300 mg, 0.88 mmol) and 79a (180 mg, 0.88 mmol) as starting materials. LC-MS (Method 3) $t_R$=1.64 min, m/z (M+H)$^+$=451.1.

Step 2. Tert-butyl (3-fluoro-5-(((4-methoxy-3-(1-methyl-1H-1,2,4-triazol-3-yl)-5-nitrobenzyl)oxy) methyl)phenyl)carbamate (79c)

Compound 79c (160 mg, 49% yield), a yellow solid, was synthesized by utilizing a similar preparative procedure of Step 4 in Example 78 with 79b (300 mg, 0.66 mmol) and tert-butyl carbamate (99 mg, 0.86 mmol) as starting materials. LC-MS (Method 3) $t_R$=1.68 min, m/z (M+H)$^+$=488.3.

Step 3. Tert-butyl (3-(((3-amino-4-methoxy-5-(1-methyl-1H-1,2,4-triazol-3-yl)benzyl)oxy)methyl)-5-fluorophenyl)carbamate (79d)

Compound 79d (30 mg, 64% yield), a yellow solid, was synthesized by utilizing a similar preparative procedure of Step 9 in Example 66 with 79c (50 mg, 0.10 mmol) as the starting material. LC-MS (Method 3) $t_R$=1.49 min, m/z (M+H)$^+$=458.3.

Step 4. Tert-butyl (3-(((3-((2-chloro-5-((methyl-d$_3$) carbamoyl)pyrimidin-4-yl)amino)-4-methoxy-5-(1-methyl-1H-1,2,4-triazol-3-yl)benzyl)oxy)methyl)-5-fluorophenyl)carbamate (79e)

Compound 79e (20 mg, 73% yield), a yellow oil, was synthesized by utilizing a similar preparative procedure of Step 5 in Example 50 with 79d (20 mg, 0.04 mmol) and 76a (18 mg, 0.09 mmol) as starting materials. LC-MS (Method 3) $t_R$=1.59 min, m/z (M+H)$^+$=630.2.

Step 5. 4-((5-(((3-Amino-5-fluorobenzyl)oxy) methyl)-2-methoxy-3-(1-methyl-1H-1,2,4-triazol-3-yl)phenyl)amino)-2-chloro-N-(methyl-d$_3$)pyrimidine-5-carboxamide (79f)

A mixture of 79e (120 mg, 0.19 mmol) in DCM (1 mL) and TFA (1 mL) was stirred at 30° C. for 1 h. The solvent was removed by pumping through N$_2$ and the residue was purified by Prep-HPLC (Method A) to afford the title compound 79f (20 mg, 20% yield) as a yellow solid. LC-MS (Method 3) $t_R$=1.37 min, m/z (M+H)$^+$=530.3.

Step 6. 19-Fluoro-10-methoxy-N-(methyl-d$_3$)-11-(1-methyl-1H-1,2,4-triazol-3-yl)-15-oxa-2,4,8,23-tetraazatetracyclo[15.3.1.1^{3,7}.1^{9,13}]tricosa-1 (21),3,5,7(23),9(22),10,12,17,19-nonaene-6-carboxamide (79)

To a solution of 79f (20 mg, 0.04 mmol) in EtOH (0.5 mL) was added conc. HCl (0.04 mmol). The mixture was stirred at 60° C. for 1 h and then concentrated. The residue was purified by Prep-HPLC (Method A) to afford the title compound 79 (9 mg, 48% yield) as a white solid. LC-MS (Method 1) $t_R$=3.60 min, m/z (M+H)$^+$=494.1. $^1$H NMR (400 MHz, DMSO-d$_6$) δ 11.76 (s, 1H), 9.92 (s, 1H), 8.74 (d, J=2.4 Hz, 1H), 8.70 (s, 1H), 8.55 (s, 1H), 8.50 (s, 1H), 8.41 (s, 1H), 7.47 (d, J=2.0 Hz, 1H), 6.91-6.81 (m, 1H), 6.80 (d, J=9.2 Hz, 1H), 4.52 (s, 2H), 4.51 (s, 2H), 3.95 (s, 3H), 3.79 (s, 3H).

Example 80

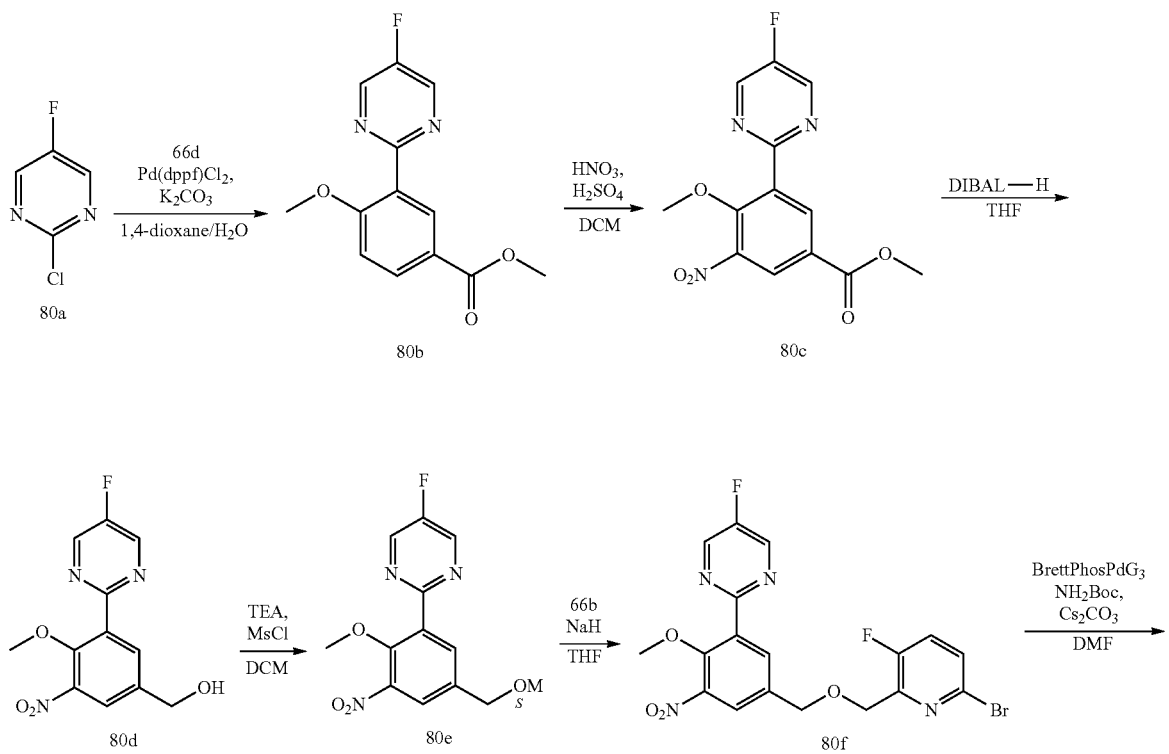

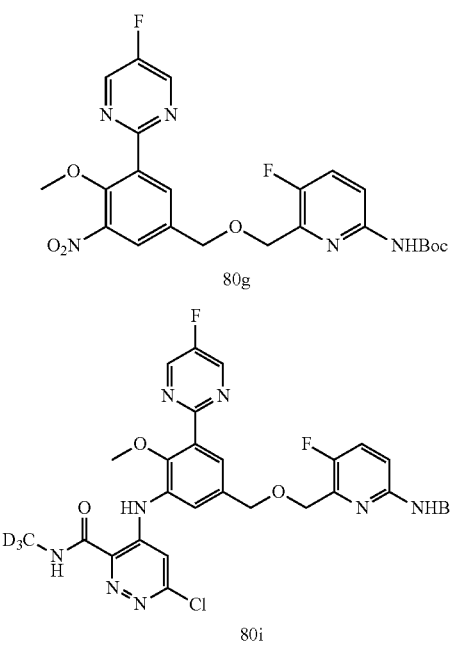
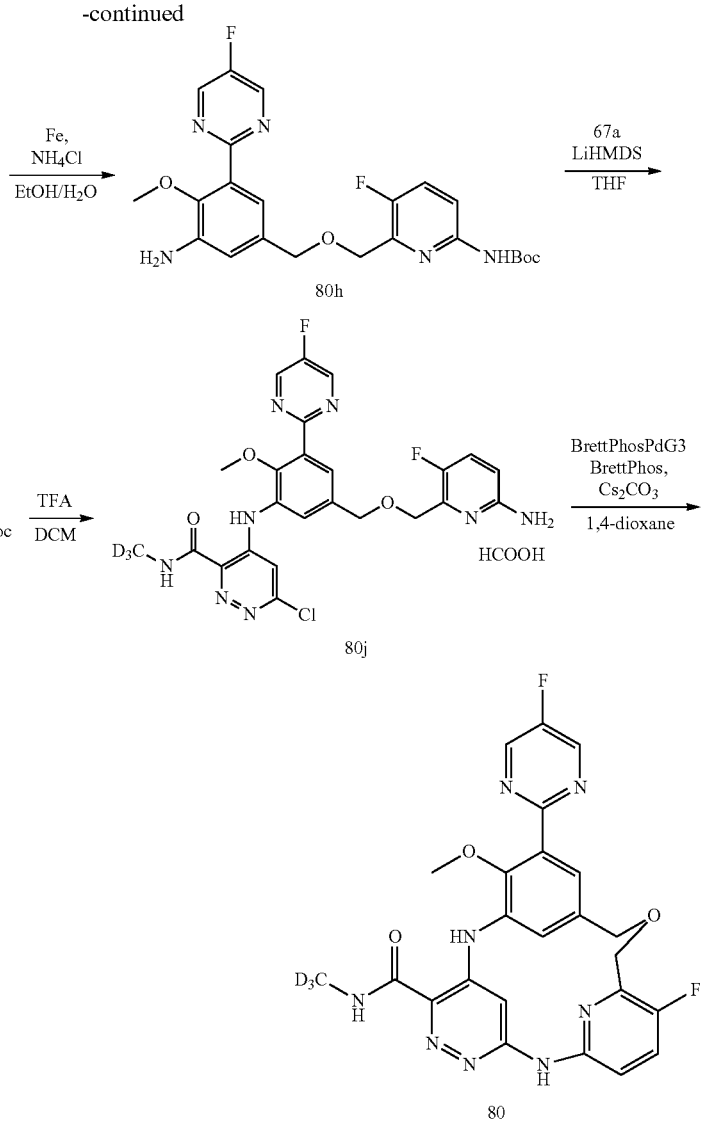

Step 1. Methyl 3-(5-fluoropyrimidin-2-yl)-4-methoxybenzoate (80b)

Compound 80b (7.3 g, 68% yield), a white solid, was synthesized by utilizing a similar preparative procedure of Step 2 in Example 66 with 66d (12.0 g, 41.08 mmol) and 80a (5.44 g, 41.08 mmol) as starting materials. LC-MS (Method 3) $t_R$=1.35 min, m/z (M+H)$^+$=263.1.

Step 2. Methyl 3-(5-fluoropyrimidin-2-yl)-4-methoxy-5-nitrobenzoate (80c)

A mixture of 80b (500 mg, 1.91 mmol) in conc. $H_2SO_4$ (1 mL) and DCM (1 mL) was added conc. $HNO_3$ (400 mg, 3.81 mmol) dropwise at 0° C. The reaction was stirred at 0° C. for 0.5 h. The reaction mixture was poured into ice-water (6 mL) and MeOH (4 mL). Ammonium hydroxide (25% wt, 10 mL) was added into the mixture to adjust pH to 10. The mixture was filtrated. The filter cake was washed with water (20 mL) and purified by flash chromatography on silica gel (PE/EtOAc=7/1) to afford the title compound 80c (320 mg, 55% yield) as a white solid. $^1$H NMR (400 MHz, DMSO-$d_6$) δ 9.11 (s, 2H), 8.56 (d, J=2.0 Hz, 1H), 8.51 (d, J=2.0 Hz, 1H), 3.91 (s, 3H), 3.74 (s, 3H).

Step 3. (3-(5-Fluoropyrimidin-2-yl)-4-methoxy-5-nitrophenyl)methanol (80d)

Compound 80d (260 mg, 89% yield), a yellow solid, was synthesized by utilizing a similar preparative procedure of Step 2 in Example 75 with 80c (320 mg, 1.04 mmol) as the starting material. $^1$H NMR (400 MHz, DMSO-$d_6$) δ 9.08 (s, 2H), 7.98 (d, J=2.0 Hz, 1H), 7.94 (d, J=2.0 Hz, 1H), 5.52 (t, J=6.0 Hz, 1H), 4.59 (d, J=5.6 Hz, 2H), 3.67 (s, 3H).

Step 4. 3-(5-Fluoropyrimidin-2-yl)-4-methoxy-5-nitrobenzyl methanesulfonate (80e)

Compound 80e (310 mg, 93% yield), a yellow gum, was synthesized by utilizing a similar preparative procedure of Step 6 in Example 66 with 80d (260 mg, 0.93 mmol) as the starting material. LC-MS (Method 3) $t_R$=1.38 min, m/z (M+H)$^+$=358.1.

Step 5. 2-(5-((((6-Bromo-3-fluoropyridin-2-yl)methoxy)methyl)-2-methoxy-3-nitrophenyl)-5-fluoropyrimidine (80f)

Compound 80f (283 mg, 70% yield), a yellow oil, was synthesized by utilizing a similar preparative procedure of Step 7 in Example 66 with 80e (310 mg, 0.87 mmol) and 66b (197 mg, 0.95 mmol) as starting materials. LC-MS (Method 3) $t_R$=1.62 min, m/z (M+H)$^+$=467.0.

Step 6. Tert-butyl (5-fluoro-6-(((3-(5-fluoropyrimidin-2-yl)-4-methoxy-5-nitrobenzyl)oxy)methyl)pyridin-2-yl)carbamate (80g)

Compound 80g (300 mg, 98% yield), a yellow solid, was synthesized by utilizing a similar preparative procedure of Step 4 in Example 78 with 80f (283 mg, 0.61 mmol) and tert-butyl carbamate (213 mg, 1.82 mmol) as starting materials. LC-MS (Method 3) $t_R$=1.68 min, m/z (M+H−100)$^+$=404.2.

Step 7. Tert-butyl (6-(((3-amino-5-(5-fluoropyrimidin-2-yl)-4-methoxybenzyl)oxy)methyl)-5-fluoropyridin-2-yl)carbamate (80h)

Compound 80h (280 mg, 99% yield), a yellow solid, was synthesized by utilizing a similar preparative procedure of Step 9 in Example 66 with 80g (300 mg, 0.60 mmol) as the starting material. LC-MS (Method 3) $t_R$=1.55 min, m/z (M+H)$^+$=474.3.

Step 8. Tert-butyl (6-(((3-((6-chloro-3-((methyl-d$_3$)carbamoyl)pyridazin-4-yl)amino)-5-(5-fluoropyrimidin-2-yl)-4-methoxybenzyl)oxy)methyl)-5-fluoropyridin-2-yl)carbamate (80i)

Compound 80i (380 mg, 99% yield), a yellow solid, was synthesized by utilizing a similar preparative procedure of Step 5 in Example 50 with 80h (280 mg, 0.59 mmol) and 67a (148 mg, 0.71 mmol) as starting materials. LC-MS (Method 3) $t_R$=1.67 min, m/z (M+H)$^+$=646.3.

Step 9. 4-((5-((((6-Amino-3-fluoropyridin-2-yl)methoxy)methyl)-3-(5-fluoropyrimidin-2-yl)-2-methoxyphenyl)amino)-6-chloro-N-(methyl-d$_3$)pyridazine-3-carboxamide formic acid (80j)

Compound 80j (215 mg, 56% yield), a yellow solid, was synthesized by utilizing a similar preparative procedure of Step 11 in Example 66 with 80i (420 mg, 0.65 mmol) as the starting material. LC-MS (Method 3) $t_R$=1.45 min, m/z (M+H)$^+$=546.3.

Step 10. 18-Fluoro-11-(5-fluoropyrimidin-2-yl)-10-methoxy-N-(methyl-d$_3$)-15-oxa-2,4,5,8,21-pentaazatetracyclo[15.3.1.1^{3,7}.1^{9,13}]tricosa-1(20),3,5,7(23),9(22),10,12,17(21),18-nonaene-6-carboxamide (80)

Compound 80 (63 mg, 34% yield), a yellow solid, was synthesized by utilizing a similar preparative procedure of Step 12 in Example 66 with 80j (215 mg, 0.36 mmol) as the starting material. LC-MS (Method 1) $t_R$=3.42 min, m/z (M+H)$^+$=510.1. $^1$H NMR (400 MHz, DMSO-d$_6$) δ 10.79 (s, 1H), 10.57 (s, 1H), 9.60 (s, 1H), 9.12-9.01 (m, 3H), 8.21 (s, 1H), 7.69 (t, J=8.0 Hz, 1H), 7.37 (s, 1H), 7.18 (d, J=8.0 Hz, 1H), 4.71 (s, 2H), 4.49 (s, 2H), 3.74 (s, 3H).

Example 81

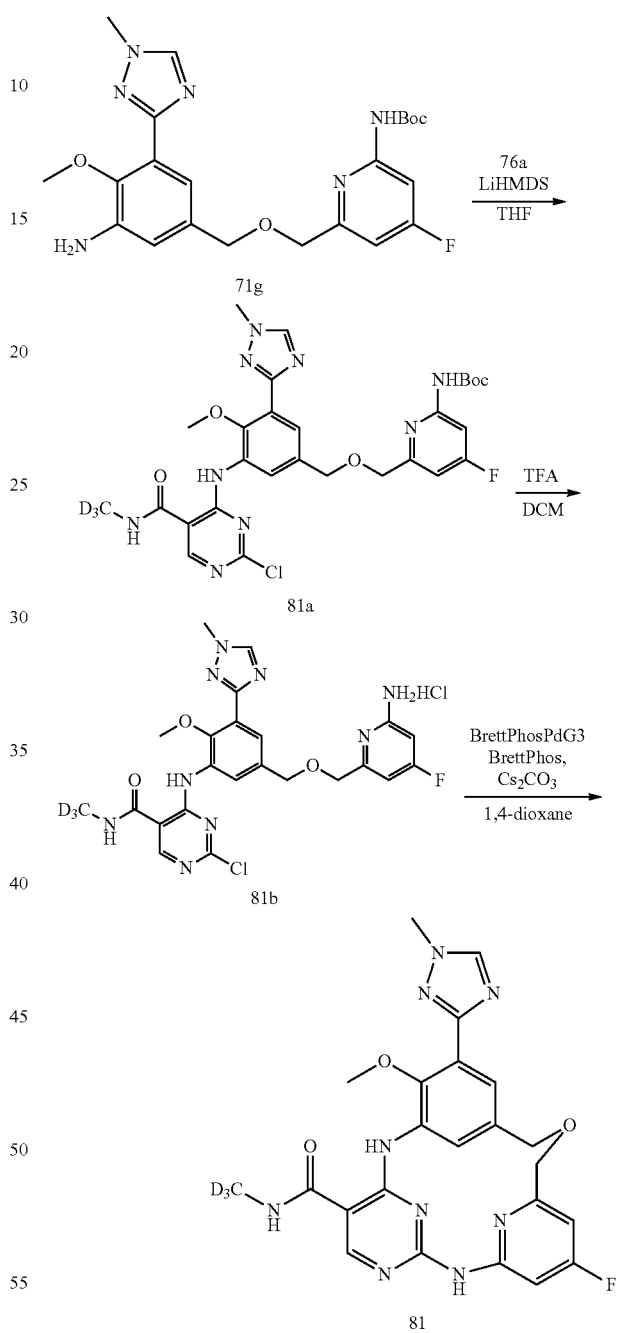

Step 1. Tert-butyl (6-(((3-((2-chloro-5-((methyl-d$_3$)carbamoyl)pyrimidin-4-yl)amino)-4-methoxy-5-(1-methyl-1H-1,2,4-triazol-3-yl)benzyl)oxy)methyl)-4-fluoropyridin-2-yl)carbamate (81a)

Compound 81a (41 mg, 99% yield), a yellow solid, was synthesized by utilizing a similar preparative procedure of Step 5 in Example 50 with 71g (30 mg, 0.07 mmol) and 76a (18 mg, 0.09 mmol) as starting materials. LC-MS (Method 3) $t_R$=1.58 min, m/z (M+H)$^+$=631.3.

Step 2. 4-((5-((((6-Amino-4-fluoropyridin-2-yl) methoxy)methyl)-2-methoxy-3-(1-methyl-1H-1,2,4-triazol-3-yl)phenyl)amino)-2-chloro-N-(methyl-d$_3$) pyrimidine-5-carboxamide hydrochloride (81b)

A mixture of 81a (41 mg, 0.06 mmol) in TFA (0.5 mL) and DCM (1.5 mL) was stirred at 35° C. for 0.5 h. The solvent was removed by pumping through N$_2$ and the residue was purified via reverse flash (C-18) (5% to 95% acetonitrile in water containing 0.1% HCl) to afford the title compound 81b (36 mg, 98% yield) as a yellow solid. LC-MS (Method 3) $t_R$=1.35 min, m/z (M+H)$^+$=531.3.

Step 3. 19-Fluoro-10-methoxy-N-(methyl-d$_3$)-11-(1-methyl-1H-1,2,4-triazol-3-yl)-15-oxa-2,4,8,21,23-pentaazatetracyclo[15.3.1.1^{3,7}.1^{9,13}]tricosa-1(21),3,5,7(23),9(22),10,12,17,19-nonaene-6-carboxamide (81)

Compound 81 (8 mg, 26% yield), a white solid, was synthesized by utilizing a similar preparative procedure of Step 12 in Example 66 with 81b (36 mg, 0.06 mmol) as the starting material. LC-MS (Method 2) $t_R$=3.41 min, m/z (M+H)$^+$=495.2. $^1$H NMR (400 MHz, DMSO-d$_6$) δ 11.94 (s, 1H), 10.38 (s, 1H), 9.89 (s, 1H), 8.73 (s, 1H), 8.54 (s, 1H), 8.52 (s, 1H), 7.30 (s, 1H), 7.01 (d, J=8.8 Hz, 1H), 6.88 (d, J=10.8 Hz, 1H), 4.71 (s, 2H), 4.53 (s, 2H), 3.94 (s, 3H), 3.80 (s, 3H).

Example 82

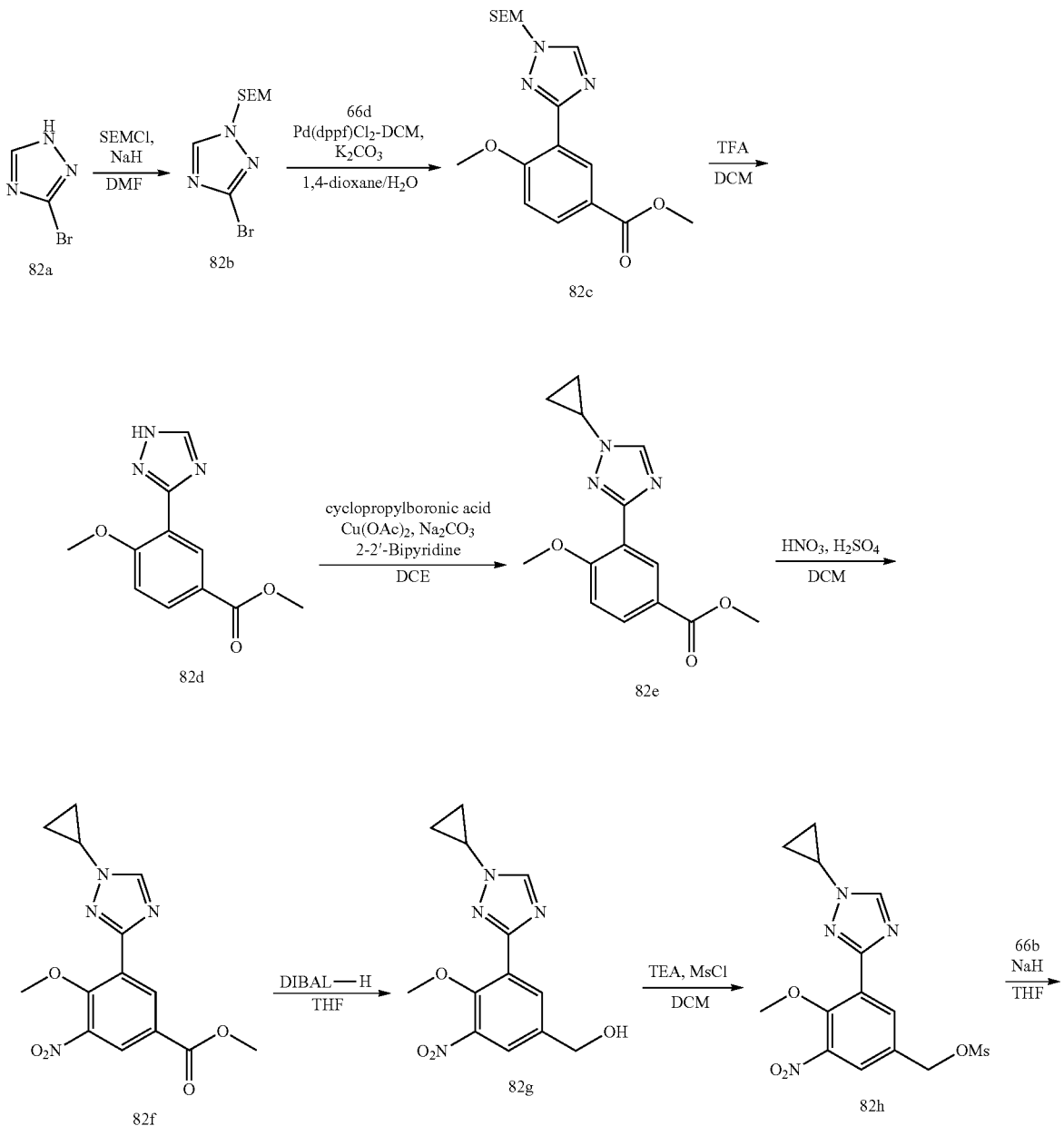

-continued

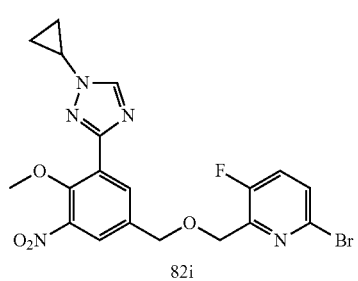
82i

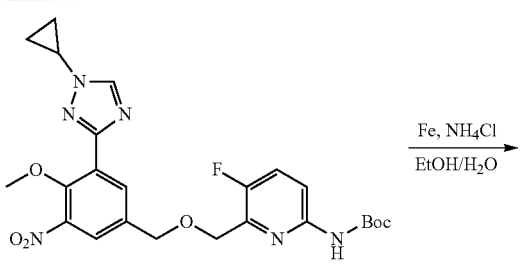
82j

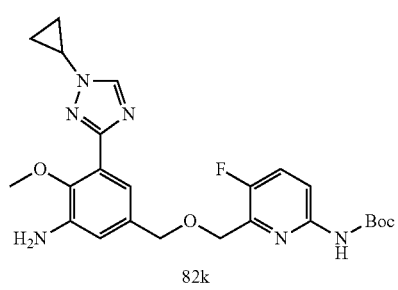
82k

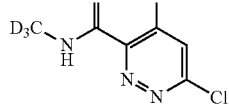
82l

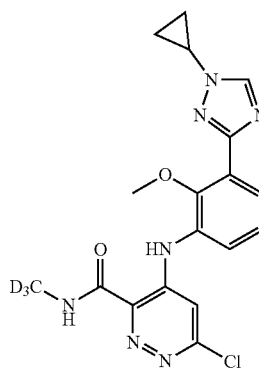
82m

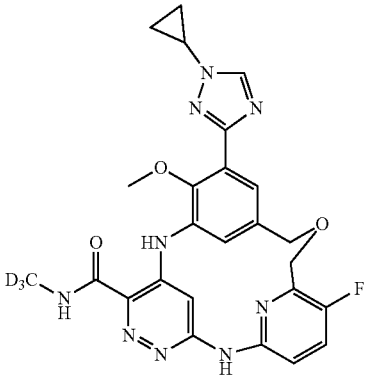
82

Step 1. 3-Bromo-1-((2-(trimethylsilyl)ethoxy)methyl)-1H-1,2,4-triazole (82b)

To a solution of 82a (918 mg, 6.2 mmol) in DMF (10 mL) was added NaH (311 mg, 8.11 mmol, 60% purity in mineral oil) at 0° C. The mixture was stirred at 0° C. for 30 min. The mixture was added SEMCl (1.35 g, 8.11 mmol) at 0° C. Then the mixture was stirred at r.t. overnight. The mixture was diluted with $H_2O$ (10 mL), extracted with DCM (10 mL). The organic layer was dried over $Na_2SO_4$ and filtered. The filtrate was concentrated. The residue was purified by flash chromatography on silica gel (PE/EtOAc=5/1) to afford the title compound 82b (1.0 g, 53% yield) as a colorless oil. $^1$H NMR (400 MHz, DMSO-$d_6$) δ 8.79 (s, 1H), 5.52 (s, 2H), 3.62 (t, J=7.6 Hz, 2H), 0.88 (t, J=8.0 Hz, 2H), 0.02 (s, 9H).

Step 2. Methyl 4-methoxy-3-(1-((2-(trimethylsilyl)ethoxy)methyl)-1H-1,2,4-triazol-3-yl)benzoate (82c)

A mixture of 82b (18.25 g, 65.59 mmol), 66d (14.74 g, 50.34 mmol), Pd(dppf)Cl$_2$-DCM (2.04 g, 2.52 mmol), $K_2CO_3$ (13.93 g, 100.91 mmol) in 1,4-dioxane (200 mL) and water (40 mL) was stirred at 90° C. for 3 h. The mixture was filtered. The filtrate was concentrated. The residue was purified by flash chromatography on silica gel (PE/EtOAc=1/1) to afford the title compound 82c (8.2 g, 45% yield) as a yellow oil. LC-MS (Method 3) $t_R$=1.75 min, m/z (M+H)$^+$=364.0.

Step 3. Methyl 4-methoxy-3-(1H-1,2,4-triazol-3-yl)benzoate (82d)

To a solution of 82c (8.2 g, 22.56 mmol) in DCM (10 mL) was added TFA (30 mL) at 0° C. The mixture was stirred at rt for 5 h. After the reaction was completed, saturated NaHCO$_3$ solution (100 mL) was added. The mixture was stirred at r.t. for 20 min. DCM (100 mL) was added to the mixture. The organic layer was separated, washed with brine (100 mL), dried over Na$_2$SO$_4$ and filtered. The filtrate was concentrated to afford the title compound 82d (5.2 g, 99% yield) as a white solid. LC-MS (Method 3) $t_R$=1.31 min, m/z (M+H)$^+$=234.0.

Step 4. Methyl 3-(1-cyclopropyl-1H-1,2,4-triazol-3-yl)-4-methoxybenzoate (82e)

To a solution of 82d (3 g, 12.86 mmol), Cu(OAc)$_2$ (2.80 g, 15.44 mmol), 2,2'-bipyridine (2.41 g, 15.44 mmol), Na$_2$CO$_3$ (2.73 g, 25.73 mmol) in DCE (30 mL) was added cyclopropylboronic acid (3.31 g, 38.59 mmol). The mixture was stirred at 85° C. for 16 h. The mixture was concentrated. The residue was purified by flash chromatography on silica gel (EtOAc) to afford the title compound 82e (710 mg, 20% yield) as a yellow oil. LC-MS (Method 3) $t_R$=1.33 min, m/z (M+H)$^+$=274.0.

Step 5. Methyl 3-(1-cyclopropyl-1H-1,2,4-triazol-3-yl)-4-methoxy-5-nitrobenzoate (82f)

Compound 82f (440 mg, 53% yield), a yellow solid, was synthesized by utilizing a similar preparative procedure of Step 2 in Example 80 with 82e (710 mg, 2.60 mmol) as the starting material. LC-MS (Method 3) $t_R$=1.40 min, m/z (M+H)$^+$=319.1.

Step 6. (3-(1-Cyclopropyl-1H-1,2,4-triazol-3-yl)-4-methoxy-5-nitrophenyl)methanol (82g)

Compound 82g (280 mg, 88% yield), a yellow gum, was synthesized by utilizing a similar preparative procedure of Step 2 in Example 75 with 82f (350 mg, 1.10 mmol) as the starting material. $^1$H NMR (400 MHz, CDCl$_3$) δ 8.21 (s, 1H), 8.14 (d, J=2.0 Hz, 1H), 7.80 (d, J=2.4 Hz, 1H), 4.75 (s, 2H), 3.91 (s, 3H), 3.72-3.67 (m, 1H), 1.25-1.21 (m, 4H).

Step 7. 3-(1-Cyclopropyl-1H-1,2,4-triazol-3-yl)-4-methoxy-5-nitrobenzyl methanesulfonate (82h)

Compound 82h (400 mg, 99% yield), a yellow gum, was synthesized by utilizing a similar preparative procedure of Step 6 in Example 66 with 82g (320 mg, 1.10 mmol) as the starting material. LC-MS (Method 3) $t_R$=1.33 min, m/z (M+H)$^+$=369.1.

Step 8. 6-Bromo-2-(((3-(1-cyclopropyl-1H-1,2,4-triazol-3-yl)-4-methoxy-5-nitrobenzyl)oxy)methyl)-3-fluoropyridine (82i)

Compound 82i (300 mg, 67% yield), a yellow oil, was synthesized by utilizing a similar preparative procedure of Step 7 in Example 66 with 82h (345 mg, 0.94 mmol) and 66b (212 mg, 1.03 mmol) as starting materials. LC-MS (Method 3) $t_R$=1.55 min, m/z (M+H)$^+$=478.1.

Step 9. Tert-butyl (6-(((3-(1-cyclopropyl-1H-1,2,4-triazol-3-yl)-4-methoxy-5-nitrobenzyl)oxy)methyl)-5-fluoropyridin-2-yl)carbamate (82j)

Compound 82j (368 mg, 100% yield), a yellow oil, was synthesized by utilizing a similar preparative procedure of Step 4 in Example 78 with 82i (343 mg, 0.72 mmol) and tert-butyl carbamate (168 mg, 1.43 mmol) as starting materials. LC-MS (Method 3) $t_R$=1.65 min, m/z (M+H)$^+$=515.1.

Step 10. Tert-butyl (6-(((3-amino-5-(1-cyclopropyl-1H-1,2,4-triazol-3-yl)-4-methoxybenzyl)oxy)methyl)-5-fluoropyridin-2-yl)carbamate (82k)

Compound 82k (306 mg, 88% yield), a yellow solid, was synthesized by utilizing a similar preparative procedure of Step 9 in Example 66 with 82j (368 mg, 0.72 mmol) as the starting material. LC-MS (Method 3) $t_R$=1.50 min, m/z (M+H)$^+$=485.3.

Step 11. Tert-butyl (6-(((3-((6-chloro-3-((methyl-d$_3$)carbamoyl)pyridazin-4-yl)amino)-5-(1-cyclopropyl-1H-1,2,4-triazol-3-yl)-4-methoxybenzyl)oxy)methyl)-5-fluoropyridin-2-yl)carbamate (82l)

Compound 82l (140 mg, 98% yield), a yellow solid, was synthesized by utilizing a similar preparative procedure of Step 5 in Example 50 with 82k (105 mg, 0.22 mmol) and 67a (45 mg, 0.22 mmol) as starting materials. LC-MS (Method 3) $t_R$=1.61 min, m/z (M+H)$^+$=657.3.

Step 12. 4-((5-(((6-Amino-3-fluoropyridin-2-yl)methoxy)methyl)-3-(1-cyclopropyl-1H-1,2,4-triazol-3-yl)-2-methoxyphenyl)amino)-6-chloro-N-(methyl-d$_3$)pyridazine-3-carboxamide formic acid (82m)

Compound 82m (120 mg, 79% yield), a yellow solid, was synthesized by utilizing a similar preparative procedure of Step 6 in Example 70 with 82l (165 mg, 0.25 mmol) as the starting material. LC-MS (Method 3) $t_R$=1.37 min, m/z (M+H)$^+$=557.3.

Step 13. 11-(1-Cyclopropyl-1H-1,2,4-triazol-3-yl)-18-fluoro-10-methoxy-N-(methyl-d$_3$)-15-oxa-2,4,5,8,21-pentaazatetracyclo[15.3.1.1^{3,7}.1^{9,13}]tricosa-1(20),3,5,7(23),9(22),10,12,17(21),18-nonaene-6-carboxamide (82)

Compound 82 (34 mg, 33% yield), a white solid, was synthesized by utilizing a similar preparative procedure of Step 12 in Example 66 with 82m (120 mg, 0.20 mmol) as the starting material. LC-MS (Method 1) $t_R$=3.08 min, m/z (M+H)$^+$=521.2. $^1$H NMR (400 MHz, DMSO-d$_6$) δ 10.78 (s, 1H), 10.54 (s, 1H), 9.60 (s, 1H), 9.04 (s, 1H), 8.70 (s, 1H), 8.14 (d, J=2.0 Hz, 1H), 7.68 (t, J=9.2 Hz, 1H), 7.49 (d, J=2.0 Hz, 1H), 7.18 (dd, J=9.2, 2.8 Hz, 1H), 4.70 (s, 2H), 4.48 (d, J=2.4 Hz, 2H), 3.90-3.85 (m, 1H), 3.79 (s, 3H), 1.19-1.05 (m, 4H).

Example 83

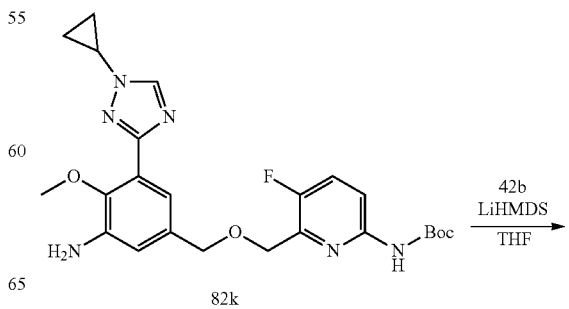

82k

-continued

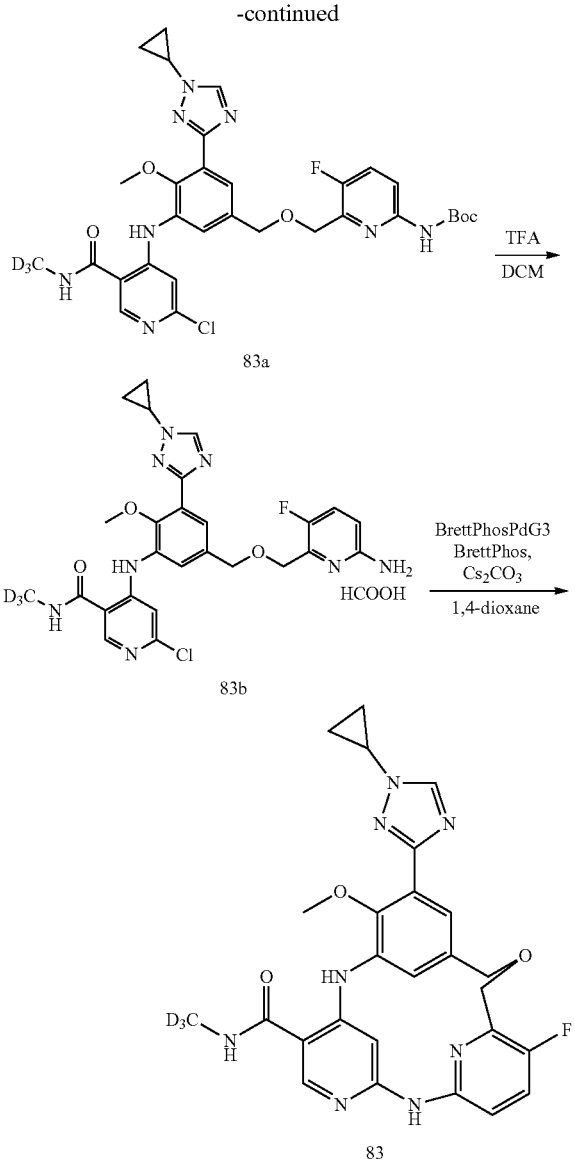

Step 1. Tert-butyl (6-(((3-((2-chloro-5-((methyl-d₃)carbamoyl)pyridin-4-yl)amino)-5-(1-cyclopropyl-1H-1,2,4-triazol-3-yl)-4-methoxybenzyl)oxy)methyl)-5-fluoropyridin-2-yl)carbamate (83a)

Compound 83a (210 mg, 97% yield), a yellow solid, was synthesized by utilizing a similar preparative procedure of Step 5 in Example 50 with 82k (160 mg, 0.33 mmol) and 42b (69 mg, 0.33 mmol) as starting materials. LC-MS (Method 3) $t_R$=1.58 min, m/z (M+H)⁺=656.3.

Step 2. 4-((5-(((6-Amino-3-fluoropyridin-2-yl)methoxy)methyl)-3-(1-cyclopropyl-1H-1,2,4-triazol-3-yl)-2-methoxyphenyl)amino)-6-chloro-N-(methyl-d₃) nicotinamide formate (83b)

Compound 83b (150 mg, 70% yield), a yellow solid, was synthesized by utilizing a similar preparative procedure of Step 6 in Example 70 with 83a (235 mg, 0.36 mmol) as the starting material. LC-MS (Method 3) $t_R$=1.34 min, m/z (M+H)⁺=556.3.

Step 3. 11-(1-Cyclopropyl-1H-1,2,4-triazol-3-yl)-18-fluoro-10-methoxy-N-(methyl-d₃)-15-oxa-2,4,8,21-tetraazatetracyclo[15.3.1.1^{3,7}.1^{9,13}]tricosa-1(20),3,5,7(23),9(22),10,12,17(21),18-nonaene-6-carboxamide (83)

Compound 83 (34 mg, 26% yield), a white solid, was synthesized by utilizing a similar preparative procedure of Step 12 in Example 66 with 83b (150 mg, 0.25 mmol) as the starting material. LC-MS (Method 2) $t_R$=2.71 min, m/z (M+H)⁺=520.2. ¹H NMR (400 MHz, DMSO-d₆) δ 10.73 (s, 1H), 9.98 (s, 1H), 9.33 (s, 1H), 8.68 (s, 1H), 8.51 (s, 1H), 8.46 (s, 1H), 8.15 (d, J=1.2 Hz, 1H), 7.61 (t, J=9.2 Hz, 1H), 7.41 (d, J=1.6 Hz, 1H), 7.07 (dd, J=9.2, 3.2 Hz, 1H), 4.67 (s, 2H), 4.45 (d, J=2.0 Hz, 2H), 3.90-3.84 (m, 1H), 3.77 (s, 3H), 1.19-1.05 (m, 4H).

Example 84

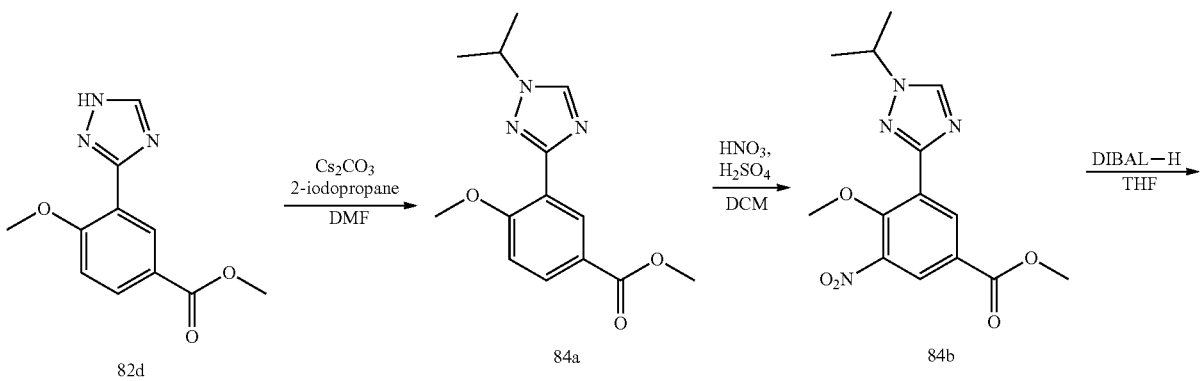

-continued

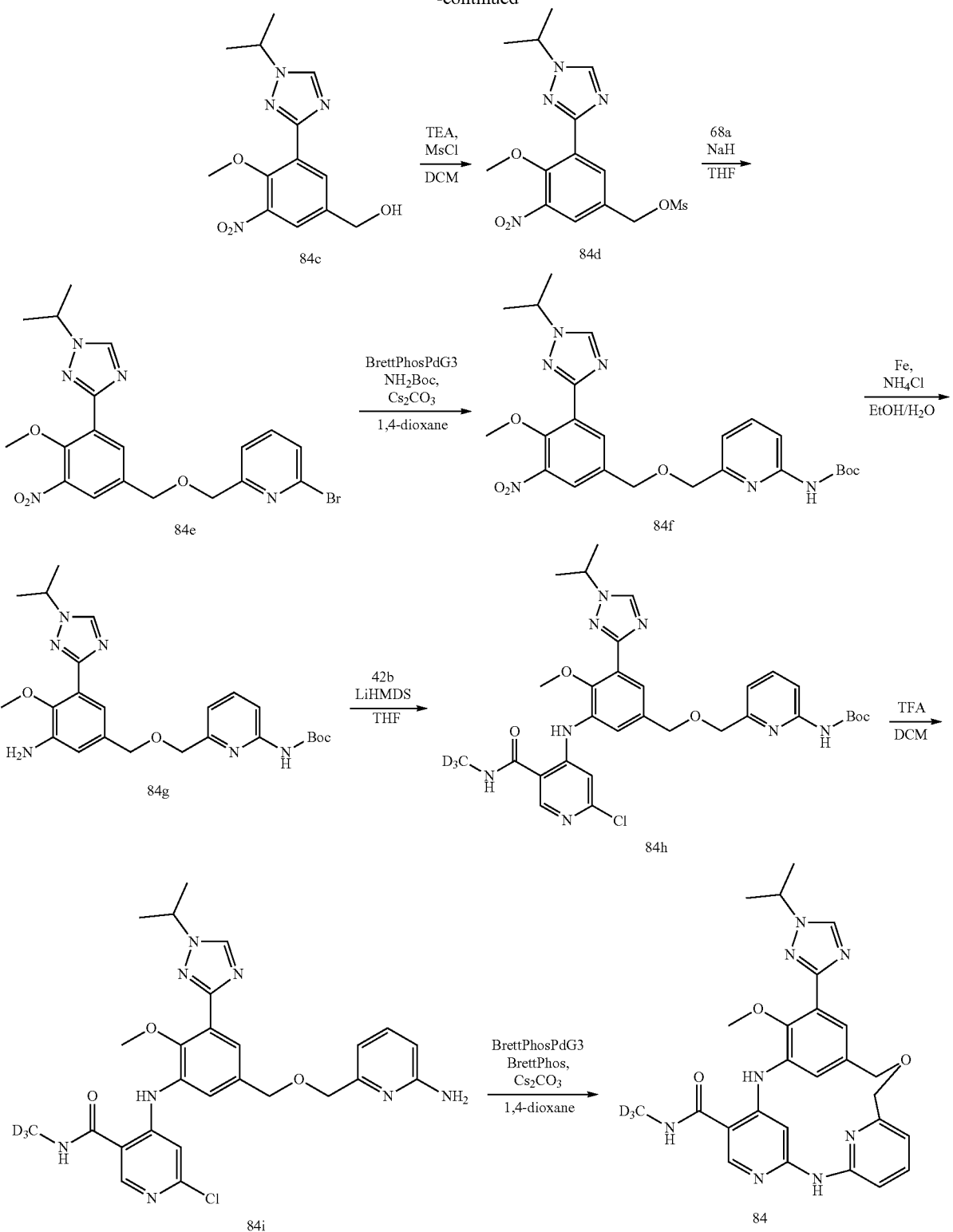

Step 1. Methyl 3-(1-isopropyl-1H-1,2,4-triazol-3-yl)-4-methoxybenzoate (84a)

A mixture of 82d (1.0 g, 4.29 mmol), $Cs_2CO_3$ (2.79 g, 8.58 mmol) and 2-iodopropane (1.09 g, 6.43 mmol) in DMF (10 mL) was stirred at 90° C. for 16 h in a sealed tube. The reaction mixture was diluted with water (20 mL) and extracted with EtOAc (30 mL*2). The combined organic phase was washed with brine (30 mL) and concentrated. The residue was purified by flash chromatography on silica gel (PE/EtOAc=1/1) to afford the title compound 84a (320 mg, 27% yield) as a white solid. $^1$H NMR (400 MHz, CDCl$_3$) δ 8.20 (dd, J=8.8, 2.4 Hz, 1H), 8.10 (d, J=2.0 Hz, 1H), 8.01 (s, 1H), 7.05 (d, J=8.8 Hz, 1H), 4.33-4.23 (m, 1H), 3.90 (s, 3H), 3.89 (s, 3H), 1.45 (d, J=6.8 Hz, 6H).

Step 2. Methyl 3-(1-isopropyl-1H-1,2,4-triazol-3-yl)-4-methoxy-5-nitrobenzoate (84b)

Compound 84b (370 mg, 99% yield), a brown gum, was synthesized by utilizing a similar preparative procedure of Step 2 in Example 80 with 84a (320 mg, 1.16 mmol) as the starting material. LC-MS (Method 3) $t_R$=1.45 min, m/z (M+H)$^+$=321.1.

Step 3. (3-(1-Isopropyl-1H-1,2,4-triazol-3-yl)-4-methoxy-5-nitrophenyl)methanol (84c)

Compound 84c (90 mg, 39% yield), a yellow gum, was synthesized by utilizing a similar preparative procedure of Step 2 in Example 75 with 84b (250 mg, 0.78 mmol) as the starting material. $^1$H NMR (400 MHz, CDCl$_3$) δ 8.06 (s, 1H), 8.00 (s, 1H), 7.66 (s, 1H), 4.78 (s, 2H), 4.39-4.33 (m, 1H), 3.63 (s, 3H), 1.45 (d, J=6.8 Hz, 6H).

Step 4. 3-(1-Isopropyl-1H-1,2,4-triazol-3-yl)-4-methoxy-5-nitrobenzyl methanesulfonate (84d)

Compound 84d (110 mg, 96% yield), a yellow oil, was synthesized by utilizing a similar preparative procedure of Step 6 in Example 66 with 84c (90 mg, 0.31 mmol) as the starting material. LC-MS (Method 3) $t_R$=1.39 min, m/z (M+H)$^+$=371.1.

Step 5. 2-Bromo-6-(((3-(1-isopropyl-1H-1,2,4-triazol-3-yl)-4-methoxy-5-nitrobenzyl)oxy)methyl)pyridine (84e)

Compound 84e (108 mg, 79% yield), a yellow gum, was synthesized by utilizing a similar preparative procedure of Step 7 in Example 66 with 84d (110 mg, 0.30 mmol) and 68a (84 mg, 0.45 mmol) as starting materials. LC-MS (Method 3) $t_R$=1.55 min, m/z (M+H)$^+$=462.0.

Step 6. Tert-butyl (6-(((3-(1-isopropyl-1H-1,2,4-triazol-3-yl)-4-methoxy-5-nitrobenzyl)oxy)methyl)pyridin-2-yl)carbamate (84f)

Compound 84f (115 mg, 99% yield), a yellow solid, was synthesized by utilizing a similar preparative procedure of Step 4 in Example 69 with 84e (108 mg, 0.23 mmol) and tert-butyl carbamate (109 mg, 0.93 mmol) as starting materials. LC-MS (Method 3) $t_R$=1.71 min, m/z (M+H−100)$^+$=399.2.

Step 7. Tert-butyl (6-(((3-amino-5-(1-isopropyl-1H-1,2,4-triazol-3-yl)-4-methoxybenzyl)oxy)methyl)pyridin-2-yl)carbamate (84g)

Compound 84g (70 mg, 62% yield), a white solid, was synthesized by utilizing a similar preparative procedure of Step 9 in Example 66 with 84f (121 mg, 0.24 mmol) as the starting material. LC-MS (Method 3) $t_R$=1.60 min, m/z (M+H)$^+$=469.3.

Step 8. Tert-butyl (6-(((3-((2-chloro-5-((methyl-d$_3$)carbamoyl)pyridin-4-yl)amino)-5-(1-isopropyl-1H-1,2,4-triazol-3-yl)-4-methoxybenzyl)oxy)methyl)pyridin-2-yl)carbamate (84h)

Compound 84h (90 mg, 94% yield), a white solid, was synthesized by utilizing a similar preparative procedure of Step 5 in Example 50 with 84g (70 mg, 0.15 mmol) and 42b (31 mg, 0.15 mmol) as starting materials. LC-MS (Method 3) $t_R$=1.66 min, m/z (M+H)$^+$=640.3.

Step 9. 4-((5-(((6-Aminopyridin-2-yl)methoxy)methyl)-3-(1-isopropyl-1H-1,2,4-triazol-3-yl)-2-methoxyphenyl)amino)-6-chloro-N-(methyl-d$_3$)nicotinamide (84i)

Compound 84i (56 mg, 74% yield), a white solid, was synthesized by utilizing a similar preparative procedure of Step 5 in Example 79 with 84h (90 mg, 0.14 mmol) as the starting material. LC-MS (Method 3) $t_R$=1.36 min, m/z (M+H)$^+$=540.1.

Step 10. 10-Methoxy-N-(methyl-d$_3$)-11-[1-(propan-2-yl)-1H-1,2,4-triazol-3-yl]-15-oxa-2,4,8,21-tetraazatetracyclo[15.3.1.1ˆ{3,7}.1ˆ{9,13}]tricosa-1(21),3,5,7(23),9(22),10,12,17,19-nonaene-6-carboxamide (84)

Compound 84 (33 mg, 63% yield), a white solid, was synthesized by utilizing a similar preparative procedure of Step 12 in Example 66 with 84i (56 mg, 0.10 mmol) as the starting material. LC-MS (Method 2) $t_R$=3.26 min, m/z (M+H)$^+$=504.2. $^1$H NMR (400 MHz, DMSO-d$_6$) δ 10.79 (s, 1H), 9.96 (s, 1H), 9.48 (s, 1H), 8.53 (s, 1H), 8.50 (s, 1H), 8.39 (s, 1H), 8.10 (s, 1H), 7.62 (t, J=8.0 Hz, 1H), 7.02 (d, J=8.0 Hz, 1H), 6.98 (s, 1H), 6.93 (d, J=7.2 Hz, 1H), 4.67 (s, 2H), 4.41-4.35 (m, 3H), 3.48 (s, 3H), 1.37 (d, J=6.4 Hz, 6H).

Example 85

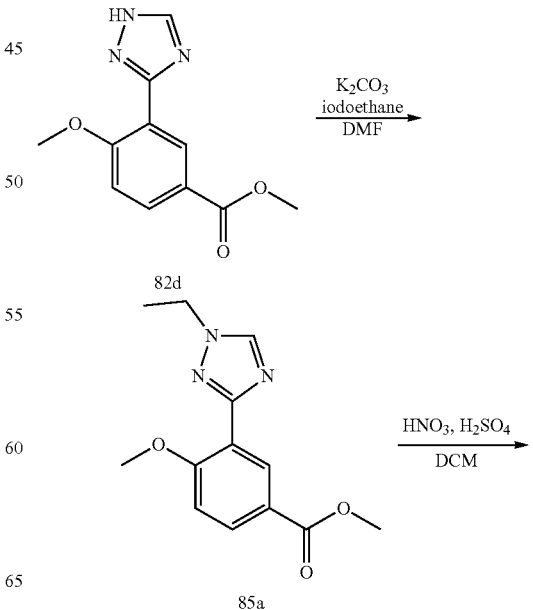

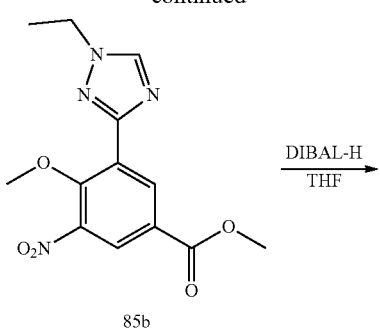

85b

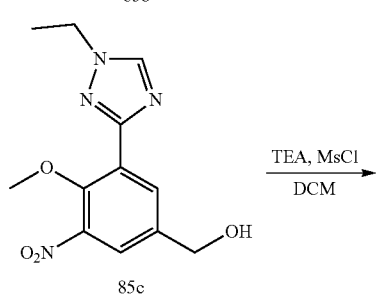

85c

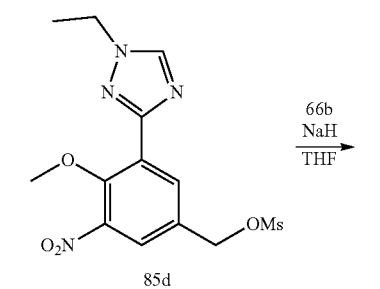

85d

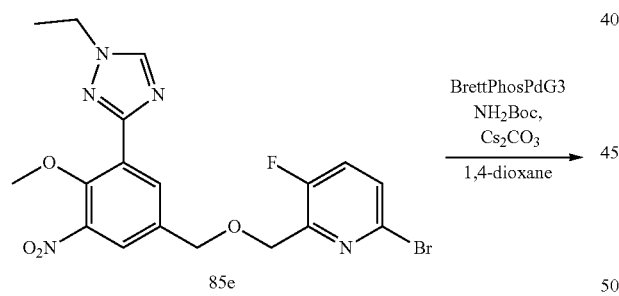

85e

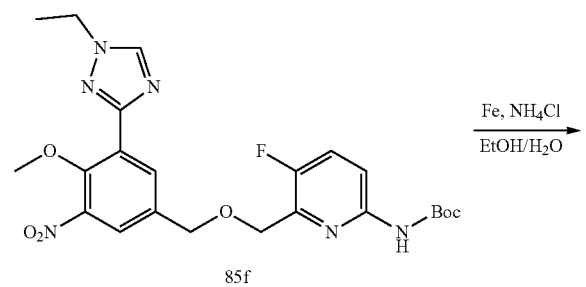

85f

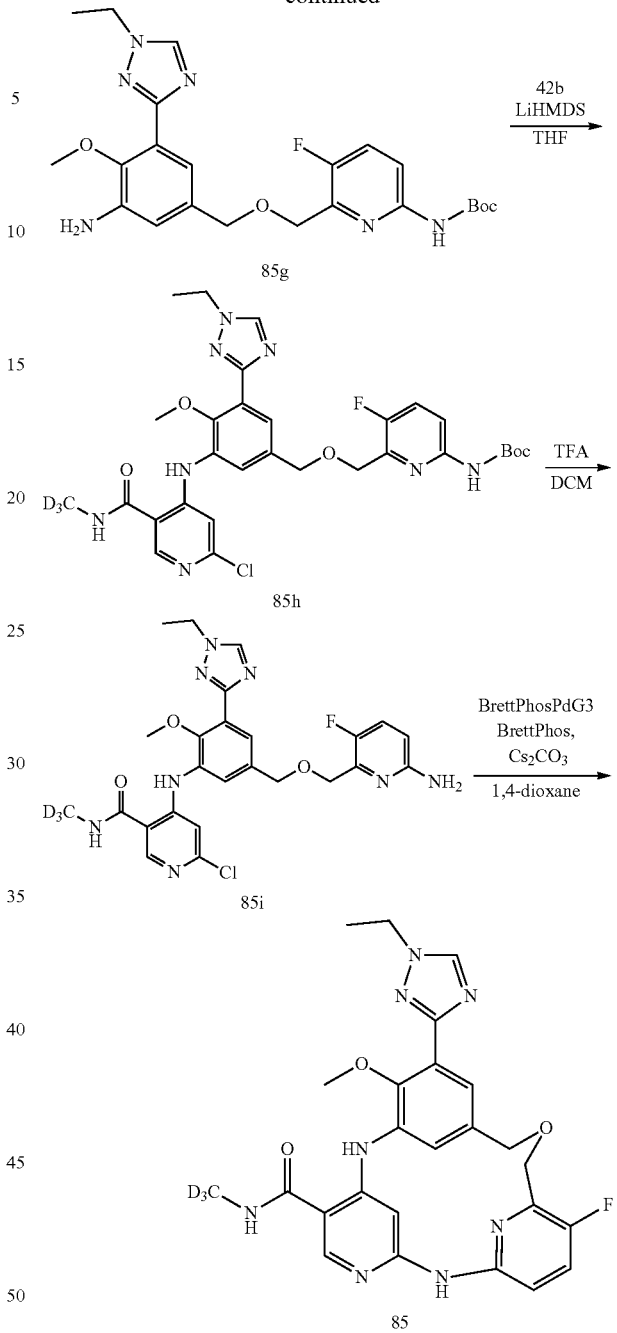

Step 1. Methyl 3-(1-ethyl-1H-1,2,4-triazol-3-yl)-4-methoxybenzoate (85a)

A mixture of iodoethane (1.00 g, 6.43 mmol), 82d (1.00 g, 4.29 mmol), K₂CO₃ (1.78 g, 12.86 mmol) in DMF (10 mL) was stirred at 60° C. for 12 h. Ice-water (15 mL) was added to the mixture and the mixture was extracted with EtOAc (30 mL*2). The organic layer was concentrated and the residue was purified by flash chromatography on silica gel (PE/EtOAc=5/1) to afford the title compound 85a (300 mg, 27% yield) as a yellow solid. ¹H NMR (400 MHz, DMSO-d₆) δ 8.57 (s, 1H), 8.38 (d, J=2.4 Hz, 1H), 8.01 (dd, J=8.8, 2.4 Hz, 1H), 7.26 (d, J=8.4 Hz, 1H), 4.26 (q, J=7.2 Hz, 2H), 3.90 (s, 3H), 3.84 (s, 3H), 1.43 (t, J=7.2 Hz, 3H).

Step 2. Methyl 3-(1-ethyl-1H-1,2,4-triazol-3-yl)-4-methoxy-5-nitrobenzoate (85b)

Compound 85b (200 mg, 55% yield), a yellow oil, was synthesized by utilizing a similar preparative procedure of Step 2 in Example 80 with 85a (310 mg, 1.19 mmol) as the starting material. LC-MS (Method 3) $t_R$=1.37 min, m/z (M+H)$^+$=307.1.

Step 3. (3-(1-Ethyl-1H-1,2,4-triazol-3-yl)-4-methoxy-5-nitrophenyl)methanol (85c)

Compound 85c (60 mg, 33% yield), a yellow solid, was synthesized by utilizing a similar preparative procedure of Step 2 in Example 75 with 85b (200 mg, 0.65 mmol) as the starting material. LC-MS (Method 3) $t_R$=1.23 min, m/z (M+H)$^+$=279.0.

Step 4. 3-(1-Ethyl-1H-1,2,4-triazol-3-yl)-4-methoxy-5-nitrobenzyl methanesulfonate (85d)

Compound 85d (40 mg, 52% yield), a yellow oil, was synthesized by utilizing a similar preparative procedure of Step 6 in Example 66 with 85c (60 mg, 0.22 mmol) as the starting material. LC-MS (Method 3) $t_R$=1.35 min, m/z (M+H)$^+$=357.1.

Step 5. 6-Bromo-2-(((3-(1-ethyl-1H-1,2,4-triazol-3-yl)-4-methoxy-5-nitrobenzyl)oxy)methyl)-3-fluoropyridine (85e)

Compound 85e (40 mg, 40% yield), a colorless oil, was synthesized by utilizing a similar preparative procedure of Step 7 in Example 66 with 85d (76 mg, 0.21 mmol) and 66b (48 mg, 0.23 mmol) as starting materials. LC-MS (Method 3) $t_R$=1.50 min, m/z (M+H)$^+$=466.1.

Step 6. Tert-butyl (6-(((3-(1-ethyl-1H-1,2,4-triazol-3-yl)-4-methoxy-5-nitrobenzyl)oxy)methyl)-5-fluoropyridin-2-yl)carbamate (85f)

Compound 85f (40 mg, 93% yield), a yellow solid, was synthesized by utilizing a similar preparative procedure of Step 4 in Example 69 with 85e (40 mg, 0.09 mmol) and tert-butyl carbamate (49 mg, 0.43 mmol) as starting materials. LC-MS (Method 3) $t_R$=1.60 min, m/z (M+H−100)$^+$=403.2.

Step 7. Tert-butyl (6-(((3-amino-5-(1-ethyl-1H-1,2,4-triazol-3-yl)-4-methoxybenzyl)oxy)methyl)-5-fluoropyridin-2-yl)carbamate (85g)

Compound 85g (40 mg, 99% yield), a white solid, was synthesized by utilizing a similar preparative procedure of Step 9 in Example 66 with 85f (43 mg, 0.09 mmol) as the starting material. LC-MS (Method 3) $t_R$=1.52 min, m/z (M+H)$^+$=473.3.

Step 8. Tert-butyl (6-(((3-((2-chloro-5-((methyl-d$_3$)carbamoyl)pyridin-4-yl)amino)-5-(1-ethyl-1H-1,2,4-triazol-3-yl)-4-methoxybenzyl)oxy)methyl)-5-fluoropyridin-2-yl)carbamate (85h)

Compound 85h (30 mg, 79% yield), a white solid, was synthesized by utilizing a similar preparative procedure of Step 5 in Example 50 with 85g (28 mg, 0.06 mmol) and 42b (12 mg, 0.06 mmol) as starting materials. LC-MS (Method 3) $t_R$=1.53 min, m/z (M+H)$^+$=644.3.

Step 9. 4-((5-(((6-Amino-3-fluoropyridin-2-yl)methoxy)methyl)-3-(1-ethyl-1H-1,2,4-triazol-3-yl)-2-methoxyphenyl)amino)-6-chloro-N-(methyl-d$_3$)nicotinamide (85i)

Compound 85i (40 mg, 95% yield), a white solid, was synthesized by utilizing a similar preparative procedure of Step 11 in Example 66 with 85h (50 mg, 0.08 mmol) as the starting material. LC-MS (Method 3) $t_R$=1.31 min, m/z (M+H)$^+$=544.1.

Step 10. 11-(1-Ethyl-1H-1,2,4-triazol-3-yl)-18-fluoro-10-methoxy-N-(methyl-d$_3$)-15-oxa-2,4,8,21-tetraazatetracyclo[15.3.1.1^{3,7}.1^{9,13}]tricosa-1(20),3,5,7(23),9,11,13(22),17(21),18-nonaene-6-carboxamide (85)

Compound 85 (4 mg, 11% yield), a white solid, was synthesized by utilizing a similar preparative procedure of Step 12 in Example 66 with 85i (40 mg, 0.07 mmol) as the starting material. LC-MS (Method 2) $t_R$=3.42 min, m/z (M+H)$^+$=508.2. $^1$H NMR (400 MHz, DMSO-d$_6$) δ 10.81 (s, 1H), 10.03 (s, 1H), 9.36 (s, 1H), 8.53 (s, 1H), 8.50 (s, 1H), 8.32 (d, J=1.2 Hz, 1H), 8.10 (s, 1H), 7.63 (t, J=9.2 Hz, 1H), 7.08 (dd, J=9.2, 2.8 Hz, 1H), 7.01 (d, J=1.6 Hz, 1H), 4.69 (s, 2H), 4.49 (d, J=2.4 Hz, 2H), 4.03 (q, J=7.2 Hz, 2H), 3.48 (s, 3H), 1.33 (t, J=7.2 Hz, 3H).

Example 86

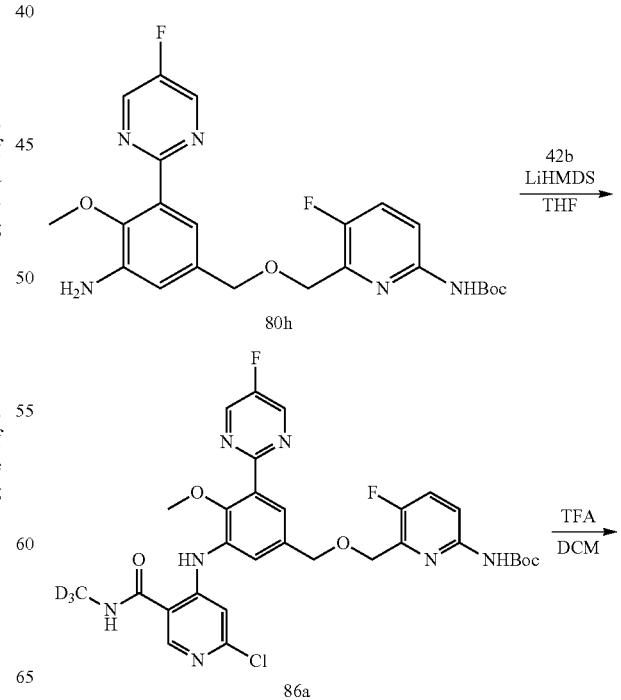

-continued

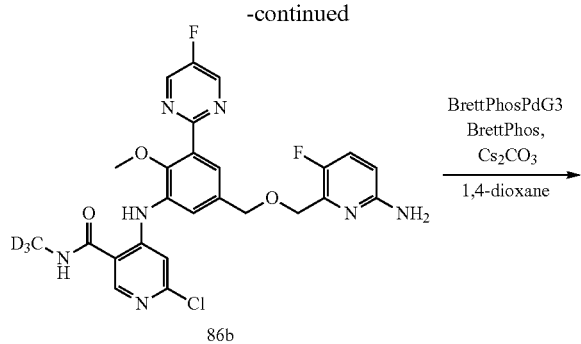

Step 1. Tert-butyl (6-(((3-((2-chloro-5-((methyl-d₃)carbamoyl)pyridin-4-yl)amino)-5-(5-fluoropyrimidin-2-yl)-4-methoxybenzyl)oxy)methyl)-5-fluoropyridin-2-yl)carbamate (86a)

Compound 86a (90 mg, 86% yield), a white solid, was synthesized by utilizing a similar preparative procedure of Step 5 in Example 50 with 80h (77 mg, 0.16 mmol) and 42b (37 mg, 0.18 mmol) as starting materials. LC-MS (Method 3) $t_R$=1.64 min, m/z (M+H)⁺=645.1.

Step 2. 4-((5-((((6-Amino-3-fluoropyridin-2-yl)methoxy)methyl)-3-(5-fluoropyrimidin-2-yl)-2-methoxyphenyl)amino)-6-chloro-N-(methyl-d₃)nicotinamide (86b)

Compound 86b (60 mg, 91% yield), a white solid, was synthesized by utilizing a similar preparative procedure of Step 11 in Example 66 with 86a (78 mg, 0.12 mmol) as the starting material. LC-MS (Method 3) $t_R$=1.41 min, m/z (M+H)⁺=545.3.

Step 3. 18-Fluoro-11-(5-fluoropyrimidin-2-yl)-10-methoxy-N-(methyl-d₃)-15-oxa-2,4,8,21-tetraazatetracyclo[15.3.1.1^{3,7}.1^{9,13}]tricosa-1(20),3,5,7(23),9(22),10,12,17(21),18-nonaene-6-carboxamide (86)

Compound 86 (4 mg, 6% yield), a white solid, was synthesized by utilizing a similar preparative procedure of Step 12 in Example 66 with 86b (71 mg, 0.13 mmol) as the starting material. LC-MS (Method 1) $t_R$=3.40 min, m/z (M+H)⁺=509.0. ¹H NMR (400 MHz, DMSO-d₆) δ 10.73 (s, 1H), 10.00 (s, 1H), 9.33 (s, 1H), 9.04 (s, 2H), 8.52 (s, 1H), 8.48 (s, 1H), 8.23 (s, 1H), 7.62 (t, J=9.2 Hz, 1H), 7.29 (s, 1H), 7.08 (dd, J=9.2, 2.8 Hz, 1H), 4.69 (s, 2H), 4.45 (s, 2H), 3.73 (s, 3H).

Example 87

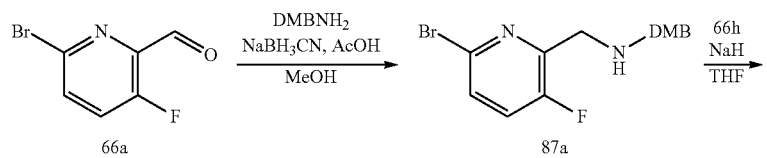

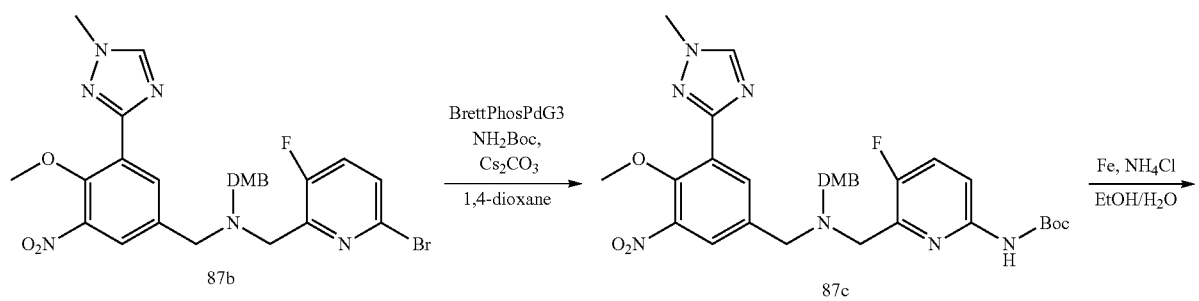

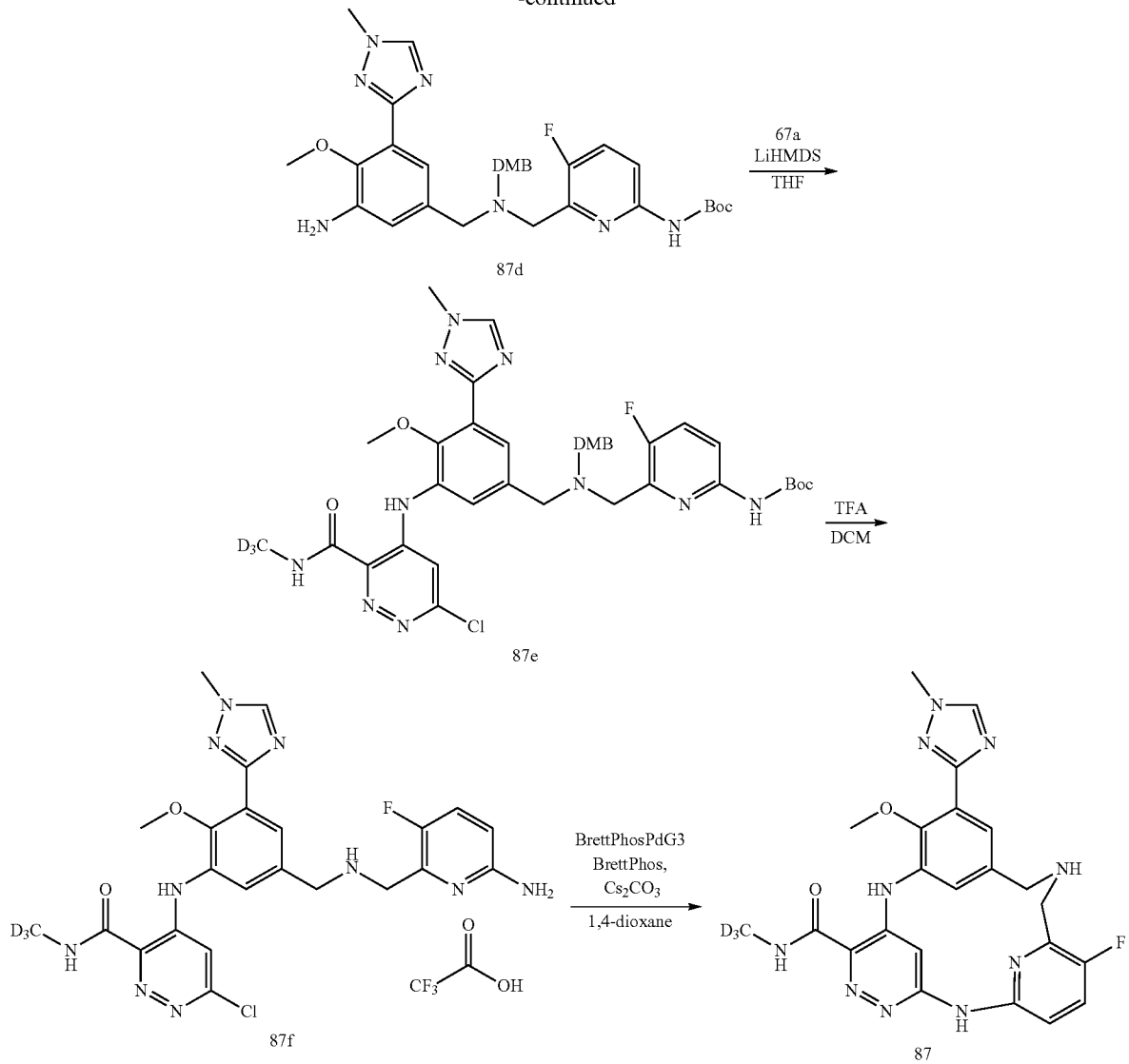

Step 1. 1-(6-Bromo-3-fluoropyridin-2-yl)-N-(2,4-dimethoxybenzyl)methanamine (87a)

To a solution of 66a (500 mg, 2.45 mmol), (2,4-dimethylphenyl)methanamine (410 mg, 2.45 mmol) in MeOH (5 mL) was added acetic acid (14.71 mg, 0.245 mmol). After stirring at 0° C. for 15 min, NaBH$_3$CN (616 mg, 9.80 mmol) was added to the mixture. The mixture was stirred for 2 h at r.t. Then the reaction was quenched with water (5 mL) and extracted with EtOAc (8 mL*3). The combined organic layer was concentrated to afford the title compound 87a (375 mg, 43% yield) as a yellow oil. LC-MS (Method 3) t$_R$=1.64 min, m/z (M+H)$^+$=355.1.

Step 2. 1-(6-Bromo-3-fluoropyridin-2-yl)-N-(2,4-dimethoxybenzyl)-N-(4-methoxy-3-(1-methyl-1H-1,2,4-triazol-3-yl)-5-nitrobenzyl)methanamine (87b)

Compound 87b (500 mg, 81% yield), a yellow gum, was synthesized by utilizing a similar preparative procedure of Step 7 in Example 66 with 87a (363 mg, 1.02 mmol) and 66h (350 mg, 1.02 mmol) as starting materials. LC-MS (Method 3) t$_R$=1.67 min, m/z (M+H)$^+$=601.0.

Step 3. Tert-butyl (6-(((2,4-dimethoxybenzyl)(4-methoxy-3-(1-methyl-1H-1,2,4-triazol-3-yl)-5-nitrobenzyl)amino)methyl)-5-fluoropyridin-2-yl)carbamate (87c)

Compound 87c (530 mg, yield given), a brown gum, was synthesized by utilizing a similar preparative procedure of Step 3 in Example 76 with 87b (500 mg, 0.83 mmol) and tert-butyl carbamate (127 mg, 1.08 mmol) as starting materials. LC-MS (Method 3) t$_R$=1.84 min, m/z (M+H)$^+$=638.3.

Step 4. Tert-butyl (6-(((3-amino-4-methoxy-5-(1-methyl-1H-1,2,4-triazol-3-yl)benzyl)(2,4-dimethoxybenzyl)amino)methyl)-5-fluoropyridin-2-yl)carbamate (87d)

Compound 87d (349 mg, 79% yield), a yellow solid, was synthesized by utilizing a similar preparative procedure of Step 9 in Example 66 with 87c (450 mg, 0.64 mmol) as the starting material. LC-MS (Method 3) $t_R$=1.69 min, m/z (M+H)$^+$=608.3.

Step 5. Tert-butyl (6-(((3-((6-chloro-3-((methyl-d$_3$) carbamoyl)pyridazin-4-yl)amino)-4-methoxy-5-(1-methyl-1H-1,2,4-triazol-3-yl)benzyl)(2,4-dimethoxybenzyl)amino)methyl)-5-fluoropyridin-2-yl) carbamate (87e)

Compound 87e (380 mg, 92% yield), a brown solid, was synthesized by utilizing a similar preparative procedure of Step 5 in Example 50 with 87d (320 mg, 0.53 mmol) and 67a (121 mg, 0.58 mmol) as starting materials. LC-MS (Method 3) $t_R$=1.74 min, m/z (M+H)$^+$=780.2.

Step 6. 4-((5-((((6-Amino-3-fluoropyridin-2-yl) methyl)amino)methyl)-2-methoxy-3-(1-methyl-1H-1,2,4-triazol-3-yl)phenyl)amino)-6-chloro-N-(methyl-d$_3$)pyridazine-3-carboxamide trifluoroacetate (87f)

Compound 87f (150 mg, 61% yield), a brown solid, was synthesized by utilizing a similar preparative procedure of Step 11 in Example 66 with 87e (360 mg, 0.46 mmol) as the starting material. LC-MS (Method 3) $t_R$=1.39 min, m/z (M+H)$^+$=530.3.

Step 7. 18-Fluoro-10-methoxy-N-(methyl-d$_3$)-11-(1-methyl-1H-1,2,4-triazol-3-yl)-2,4,5,8,15,21-hexaazatetracyclo[15.3.1.1^{3,7}.1^{9,13}]tricosa-1(20),3,5,7(23),9(22),10,12,17(21),18-nonaene-6-carboxamide (87)

Compound 87 (150 mg, 61% yield), a light-yellow solid, was synthesized by utilizing a similar preparative procedure of Step 12 in Example 66 with 87f (360 mg, 0.46 mmol) as the starting material. LC-MS (Method 2) $t_R$=2.70 min, m/z (M+H)$^+$=494.1. $^1$H NMR (400 MHz, DMSO-d$_6$) δ 10.72 (s, 1H), 10.46 (s, 1H), 9.70 (s, 1H), 9.01 (s, 1H), 8.55 (s, 1H), 8.31 (s, 1H), 7.60 (t, J=8.8 Hz, 1H), 7.45 (s, 1H), 7.09 (d, J=8.4 Hz, 1H), 3.95 (s, 3H), 3.85 (s, 2H), 3.78 (s, 3H). 3.61 (s, 2H).

Example 88

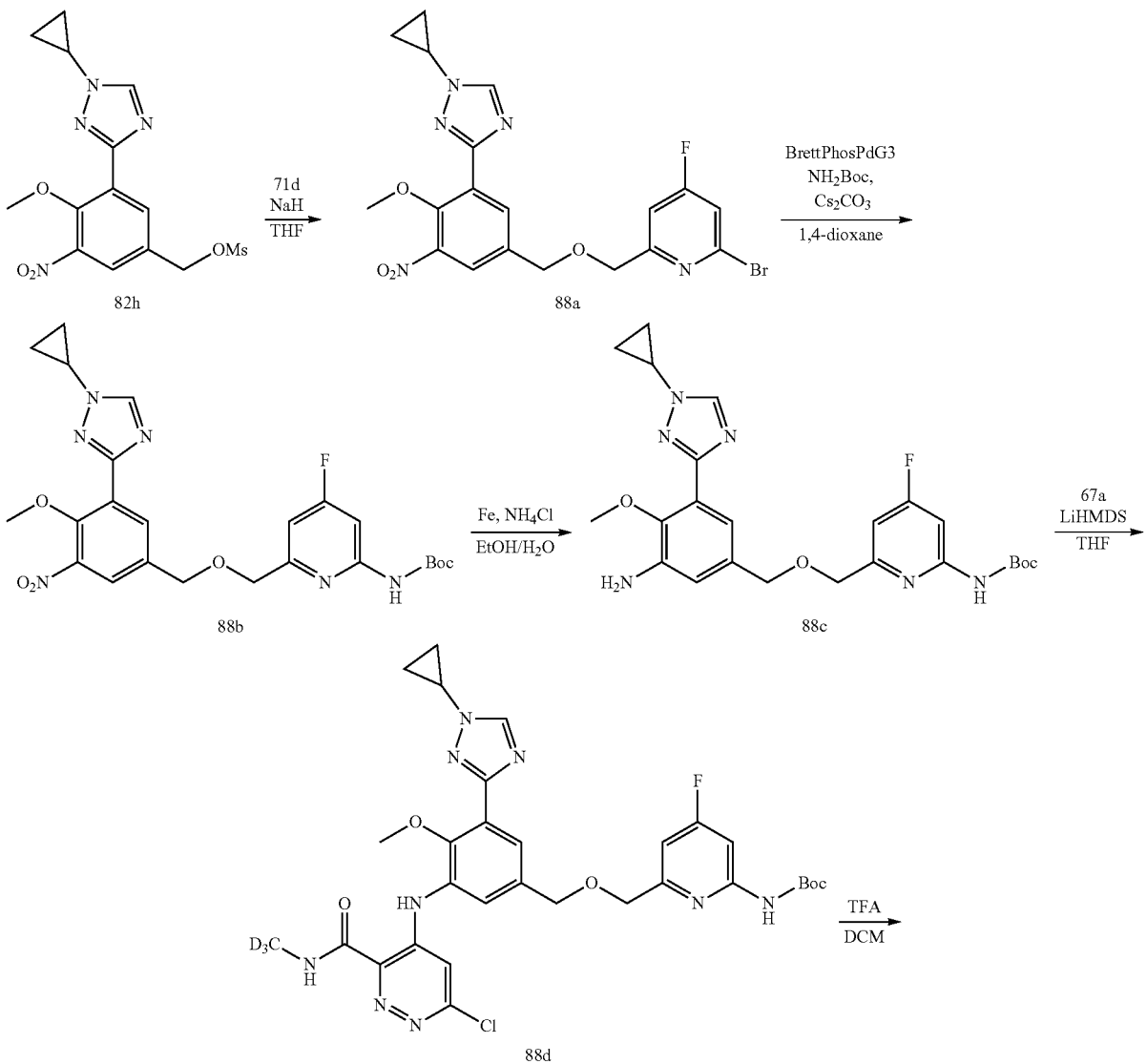

-continued

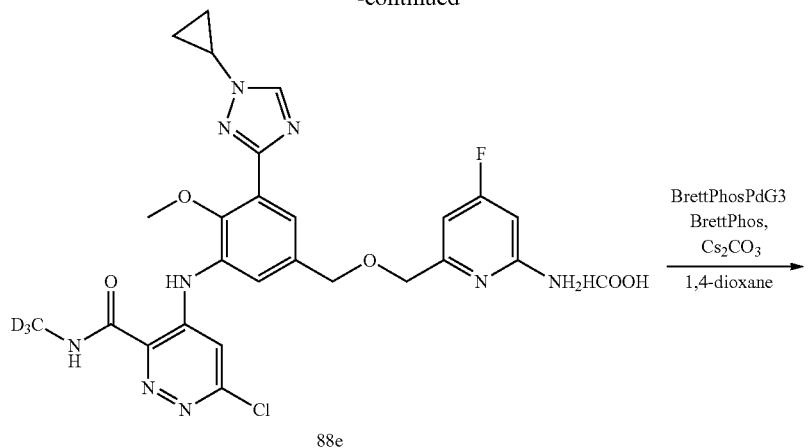

88e

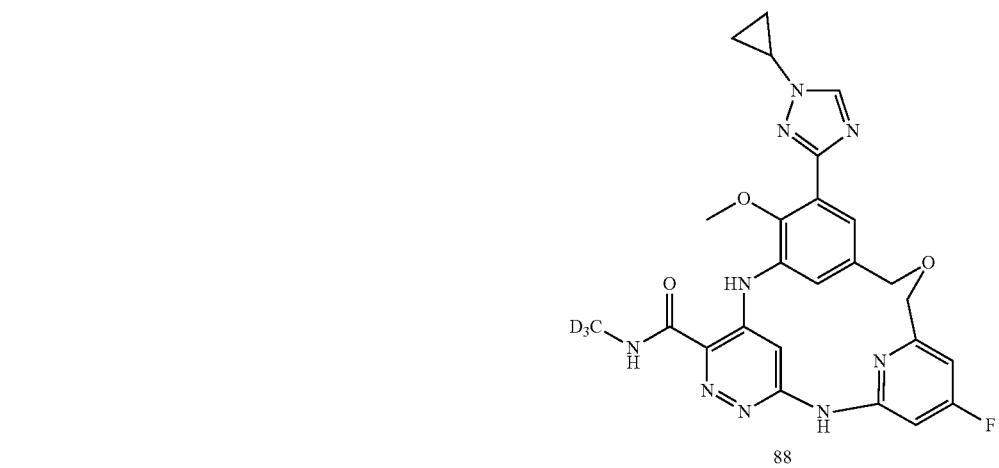 [SMILES: [2H]C([2H])([2H])NC(=O)c1nnc2cc1Nc1cc(cc(-c3ncn(C4CC4)n3)c1OC)COCc1cc(F)cc(n1)N2]

88

Step 1. 2-Bromo-6-(((3-(1-cyclopropyl-1H-1,2,4-triazol-3-yl)-4-methoxy-5-nitrobenzyl)oxy)methyl)-4-fluoropyridine (88a)

Compound 88a (293 mg, 65% yield), a yellow solid, was synthesized by utilizing a similar preparative procedure of Step 7 in Example 66 with 82h (349 mg, 0.95 mmol) and 71d (195 mg, 0.95 mmol) as starting materials. LC-MS (Method 3) $t_R$=1.57 min, m/z (M+H)$^+$=478.0.

Step 2. Tert-butyl (6-(((3-(1-cyclopropyl-1H-1,2,4-triazol-3-yl)-4-methoxy-5-nitrobenzyl)oxy)methyl)-4-fluoropyridin-2-yl)carbamate (88b)

Compound 88b (315 mg, yield given), a brown gum, was synthesized by utilizing a similar preparative procedure of Step 4 in Example 69 with 88a (293 mg, 0.61 mmol) and tert-butyl carbamate (93 mg, 0.80 mmol) as starting materials. LC-MS (Method 3) $t_R$=1.74 min, m/z (M+H−100)$^+$=415.2.

Step 3. Tert-butyl (6-(((3-amino-5-(1-cyclopropyl-1H-1,2,4-triazol-3-yl)-4-methoxybenzyl)oxy)methyl)-4-fluoropyridin-2-yl)carbamate (88c)

Compound 88c (186 mg, 63% yield), a brown solid, was synthesized by utilizing a similar preparative procedure of Step 9 in Example 66 with 88b (315 mg, 0.61 mmol) as the starting material. LC-MS (Method 3) $t_R$=1.58 min, m/z (M+H)$^+$=485.3.

Step 4. Tert-butyl (6-(((3-((6-chloro-3-((methyl-d$_3$)carbamoyl)pyridazin-4-yl)amino)-5-(1-cyclopropyl-1H-1,2,4-triazol-3-yl)-4-methoxybenzyl)oxy)methyl)-4-fluoropyridin-2-yl)carbamate (88d)

Compound 88d (122 mg, yield given), a yellow solid, was synthesized by utilizing a similar preparative procedure of Step 5 in Example 50 with 88c (90 mg, 0.19 mmol) and 67a (47 mg, 0.22 mmol) as starting materials. LC-MS (Method 3) $t_R$=1.63 min, m/z (M+H)$^+$=657.3.

Step 5. 4-((5-(((6-Amino-4-fluoropyridin-2-yl)methoxy)methyl)-3-(1-cyclopropyl-1H-1,2,4-triazol-3-yl)-2-methoxyphenyl)amino)-6-chloro-N-(methyl-d$_3$)pyridazine-3-carboxamide formic acid (88e)

Compound 88e (58 mg, 53% yield), a yellow solid, was synthesized by utilizing a similar preparative procedure of Step 6 in Example 70 with 88d (120 mg, 0.18 mmol) as the starting material. LC-MS (Method 3) $t_R$=1.39 min, m/z (M+H)$^+$=557.2.

Step 6. 11-(1-Cyclopropyl-1H-1,2,4-triazol-3-yl)-19-fluoro-10-methoxy-N-(methyl-d$_3$)-15-oxa-2,4,5,8,21-pentaazatetracyclo[15.3.1.1^{3,7}.1^{9,13}]tricosa-1(21),3,5,7(23),9(22),10,12,17,19-nonaene-6-carboxamide (88)

Compound 88 (15 mg, 30% yield), a white solid, was synthesized by utilizing a similar preparative procedure of Step 12 in Example 66 with 88e (58 mg, 0.10 mmol) as the starting material. The title compound was purified by Prep-HPLC (Method C). LC-MS (Method 2) t$_R$=2.88 min, m/z (M+H)$^+$=521.1. $^1$H NMR (400 MHz, DMSO-d$_6$) δ 10.77 (s, 1H), 10.61 (s, 1H), 9.63 (s, 1H), 9.07 (s, 1H), 8.69 (s, 1H), 8.17 (s, 1H), 7.48 (s, 1H), 6.99 (d, J=8.8 Hz, 1H), 6.90 (d, J=11.2 Hz, 1H), 4.67 (s, 2H), 4.38 (s, 2H), 3.89-3.85 (m, 1H), 3.79 (s, 3H), 1.19-1.05 (m, 4H).
Example 89
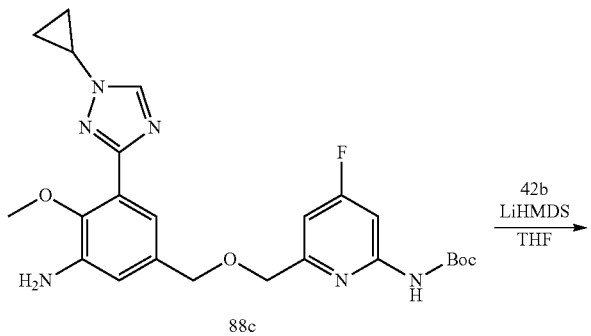
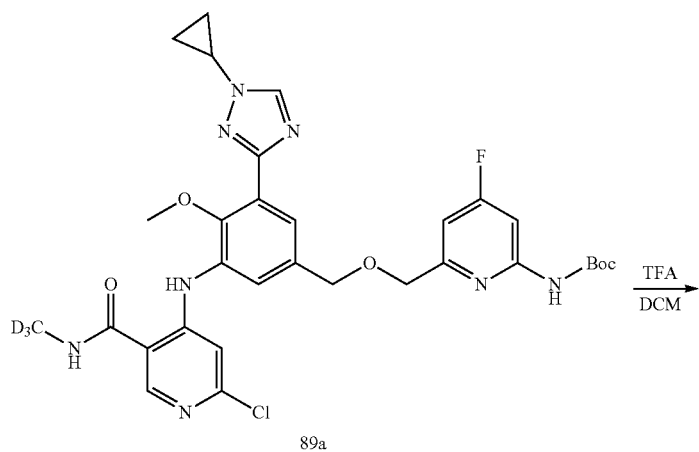
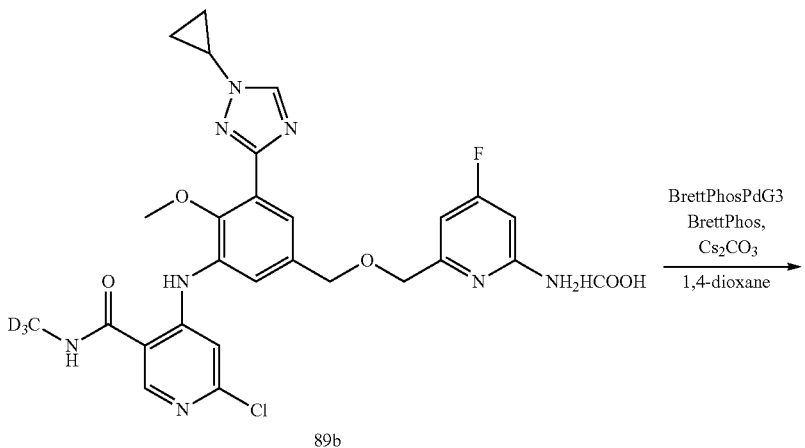

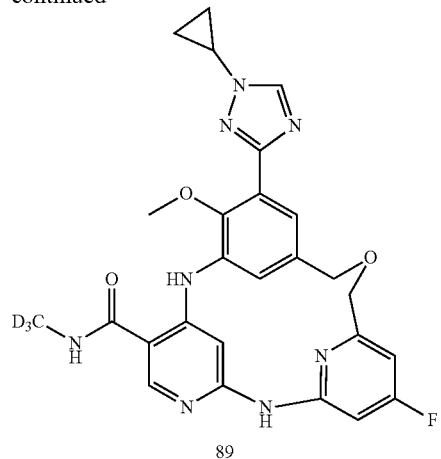

89

Step 1. Tert-butyl (6-(((3-((2-chloro-5-((methyl-d₃)carbamoyl)pyridin-4-yl)amino)-5-(1-cyclopropyl-1H-1,2,4-triazol-3-yl)-4-methoxybenzyl)oxy)methyl)-4-fluoropyridin-2-yl)carbamate (89a)

Compound 89a (130 mg, 96% yield), a yellow solid, was synthesized by utilizing a similar preparative procedure of Step 5 in Example 50 with 88c (100 mg, 0.21 mmol) and 42b (43 mg, 0.21 mmol) as starting materials. LC-MS (Method 3) $t_R$=1.64 min, m/z (M+H)⁺=656.3.

Step 2. 4-((5-((((6-Amino-4-fluoropyridin-2-yl)methoxy)methyl)-3-(1-cyclopropyl-1H-1,2,4-triazol-3-yl)-2-methoxyphenyl)amino)-6-chloro-N-(methyl-d₃)nicotinamide formic acid (89b)

Compound 89b (86 mg, 72% yield), a yellow solid, was synthesized by utilizing a similar preparative procedure of Step 6 in Example 70 with 89a (130 mg, 0.20 mmol) as the starting material. The title compound was purified by Prep-HPLC (Method C). LC-MS (Method 3) $t_R$=1.37 min, m/z (M+H)⁺=556.3.

Step 3. 11-(1-Cyclopropyl-1H-1,2,4-triazol-3-yl)-19-fluoro-10-methoxy-N-(methyl-d₃)-15-oxa-2,4,8,21-tetraazatetracyclo[15.3.1.1ˆ{3,7}.1ˆ{9,13}]tricosa-1(21),3,5,7(23),9(22),10,12,17,19-nonaene-6-carboxamide (89)

Compound 89 (24 mg, 32% yield), a white solid, was synthesized by utilizing a similar preparative procedure of Step 12 in Example 66 with 89b (86 mg, 0.14 mmol) as starting material. LC-MS (Method 1) $t_R$=3.16 min, m/z (M+H)⁺=520.1. ¹H NMR (400 MHz, DMSO-d₆) δ 10.71 (s, 1H), 10.05 (s, 1H), 9.37 (s, 1H), 8.68 (s, 1H), 8.52 (s, 1H), 8.49 (s, 1H), 8.18 (s, 1H), 7.40 (s, 1H), 6.91 (d, J=8.0 Hz, 1H), 6.79 (d, J=11.2 Hz, 1H), 4.65 (s, 2H), 4.34 (s, 2H), 3.89-3.84 (m, 1H), 3.77 (s, 3H), 1.19-1.05 (m, 4H).

Example 90

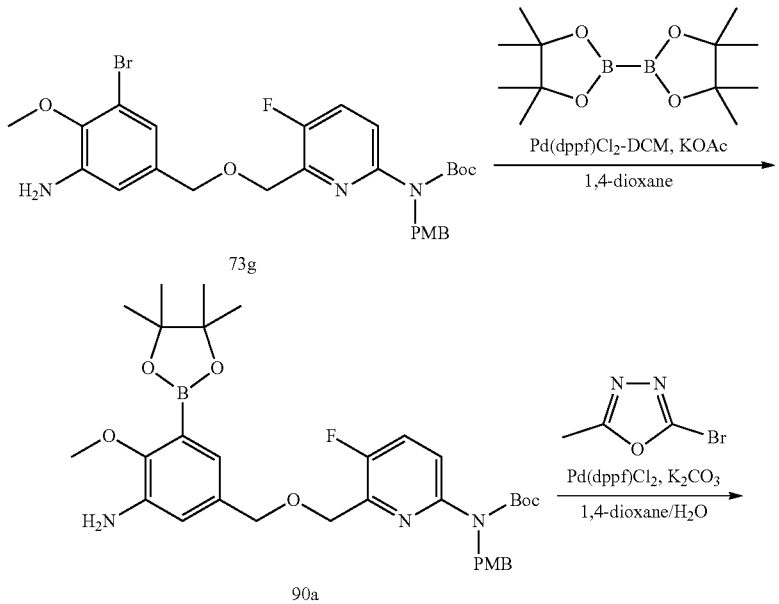

-continued
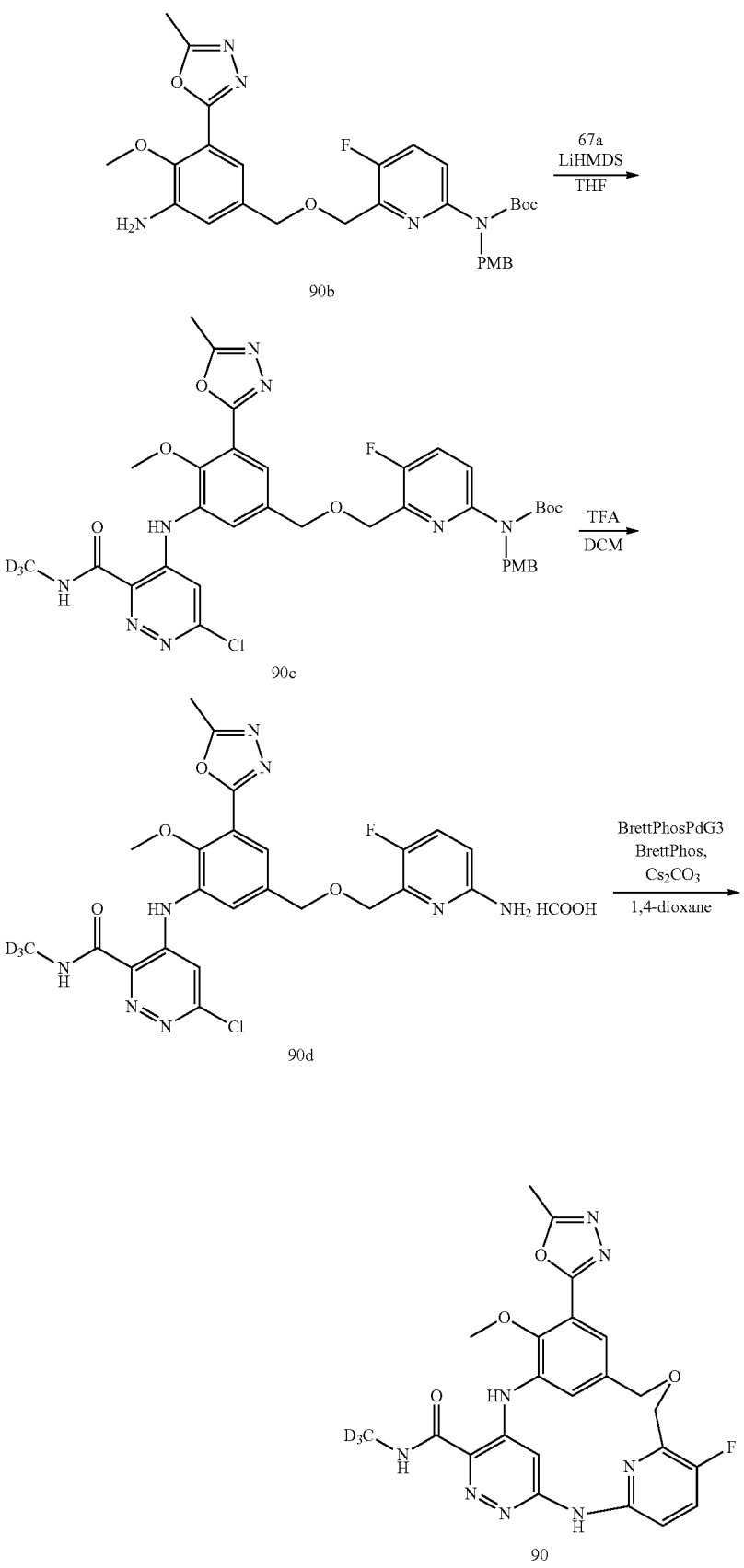

Step 1. Tert-butyl (6-(((3-amino-4-methoxy-5-(4,4,5,5-tetramethyl-1,3,2-dioxaborolan-2-yl)benzyl)oxy)methyl)-5-fluoropyridin-2-yl)(4-methoxybenzyl)carbamate (90a)

Compound 90a (800 mg, 46% yield), a yellow solid, was synthesized by utilizing a similar preparative procedure of Step 2 in Example 66 with 73g (1.6 g, 2.78 mmol) and 4,4,4',4',5,5,5',5'-octamethyl-2,2'-bi(1,3,2-dioxaborolane) (916 mg, 3.61 mmol) as starting materials. LC-MS (Method 3) $t_R$=1.90 min, m/z (M+H)$^+$=624.3.

Step 2. Tert-butyl (6-(((3-amino-, 1-methoxy-5-(5-methyl-1,3,4-oxadiazol-2-yl)benzyl)oxy)methyl)-5-fluoropyridin-2-yl)(4-methoxybenzyl)carbamate (90b)

Compound 90b (80 mg, 74% yield), a yellow solid, was synthesized by utilizing a similar preparative procedure of Step 3 in Example 66 with 90a (101 mg, 0.19 mmol) and 2-bromo-5-methyl-1,3,4-oxadiazole (36 mg, 0.22 mmol) as starting materials. LC-MS (Method 3) $t_R$=1.63 min, m/z (M+H)$^+$=580.2.

Step 3. Tert-butyl (6-(((3-((6-chloro-3-((methyl-d$_3$)carbamoyl)pyridazin-4-yl)amino)-4-methoxy-5-(5-methyl-1,3,4-oxadiazol-2-yl)benzyl)oxy)methyl)-5-fluoropyridin-2-yl)(4-methoxybenzyl)carbamate (90c)

To a mixture of 90b (140 mg, 0.24 mmol) and 67a (50 mg, 0.24 mmol) in anhydrous THF (14 mL) was added LiHMDS (0.48 mL, 0.48 mmol, 1.0 M in THF) at −40° C. The mixture was stirred at −40° C. for 1 h. The mixture was diluted with H$_2$O (5 mL), extracted with EtOAc (15 mL*2). The separated organic layer was dried over MgSO$_4$, filtered and concentrated to afford the crude title compound 90c (180 mg, 99% yield) as a yellow solid which was used directly in next step without further purification. LC-MS (Method 3) $t_R$=1.67 min, m/z (M+H)$^+$=752.3.

Step 4. 4-((5-(((6-Amino-3-fluoropyridin-2-yl)methoxy)methyl)-2-methoxy-3-(5-methyl-1,3,4-oxadiazol-2-yl)phenyl)amino)-6-chloro-N-(methyl-d$_3$)pyridazine-3-carboxamide formic acid (90d)

Compound 90d (80 mg, 69% yield), a yellow solid, was synthesized by utilizing a similar preparative procedure of Step 6 in Example 70 with 90c (150 mg, 0.20 mmol) as the starting material. The title compound was purified by Prep-HPLC (Method C). LC-MS (Method 3) $t_R$=1.40 min, m/z (M+H)$^+$=532.2.

Step 5. 18-Fluoro-10-methoxy-N-(methyl-d$_3$)-11-(5-methyl-1,3,4-oxadiazol-2-yl)-15-oxa-2,4,5,8,21-pentaazatetracyclo[15.3.1.1^{3,7}.1^{9,13}]tricosa-1(20),3,5,7(23),9(22),10,12,17(21),18-nonaene-6-carboxamide (90)

Compound 90 (13 mg, 19% yield), a white solid, was synthesized by utilizing a similar preparative procedure of Step 12 in Example 66 with 90d (80 mg, 0.14 mmol) as the starting material. LC-MS (Method 1) $t_R$=3.11 min, m/z (M+H)$^+$=496.1. $^1$H NMR (400 MHz, DMSO-d$_6$) δ 10.91 (s, 1H), 10.61 (s, 1H), 9.56 (s, 1H), 9.10 (s, 1H), 8.33 (s, 1H), 7.70 (t, J=9.2 Hz, 1H), 7.53 (s, 1H), 7.19 (dd, J=9.6 Hz, 3.2 Hz, 1H), 4.74 (s, 2H), 4.50 (s, 2H), 3.84 (s, 3H), 2.61 (s, 3H).

Example 91

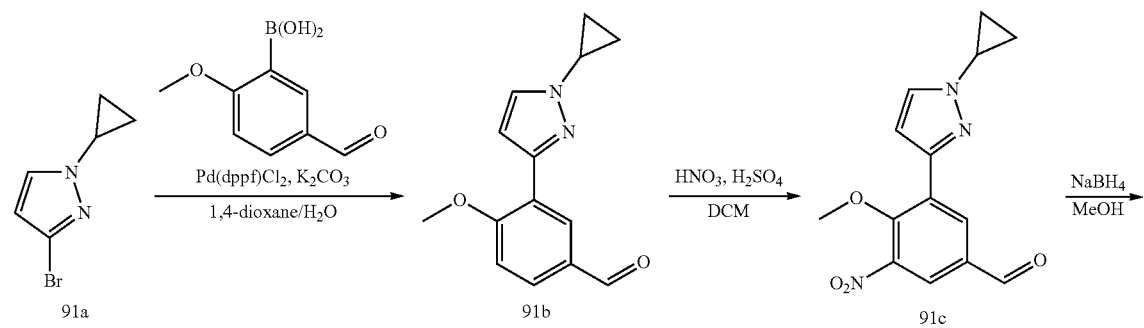

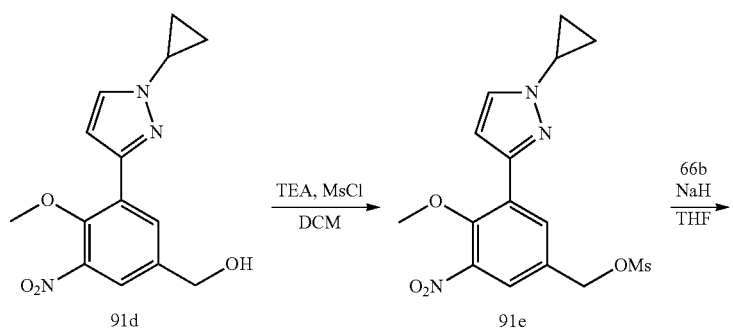

-continued
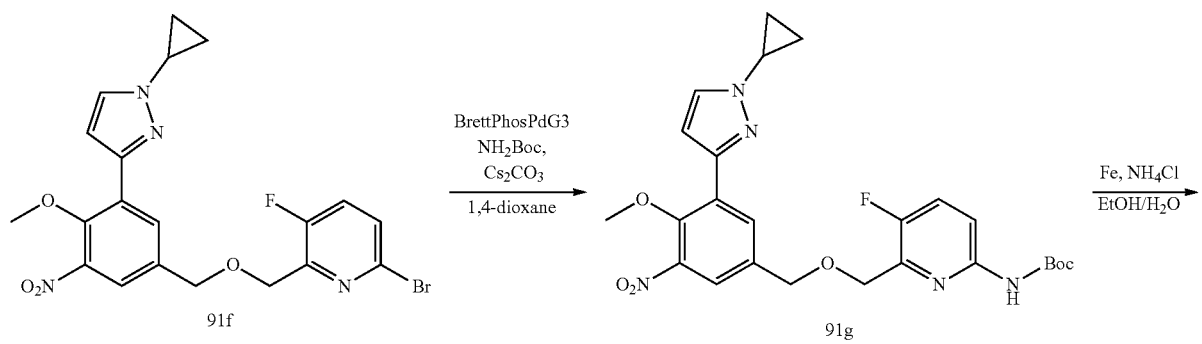
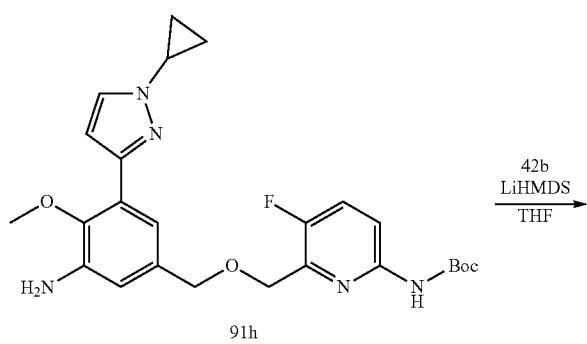
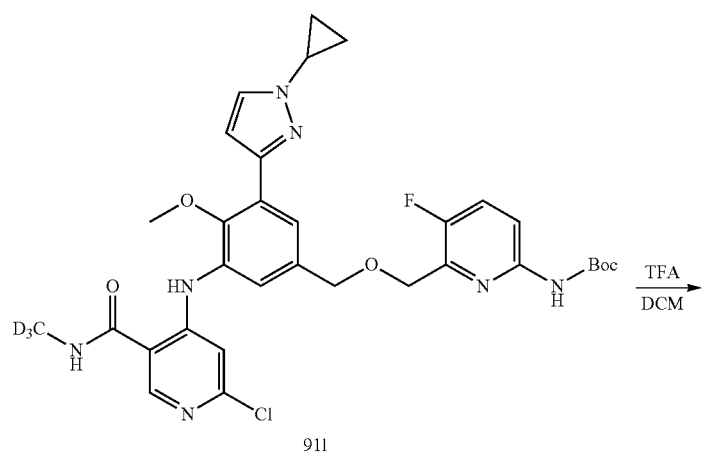
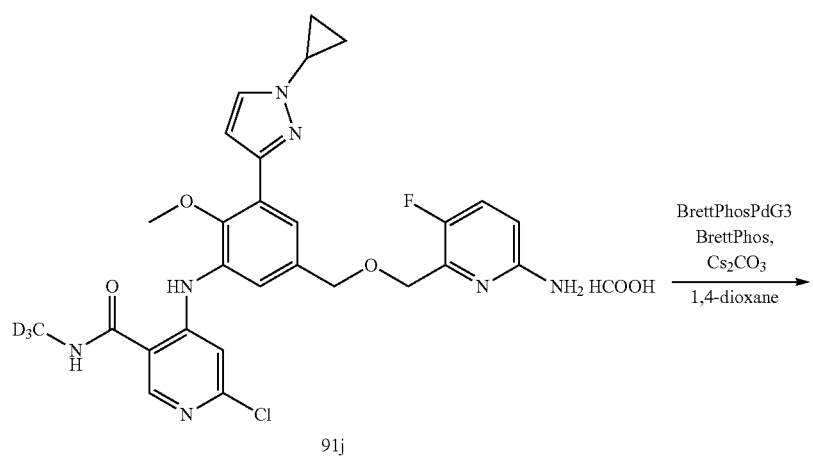

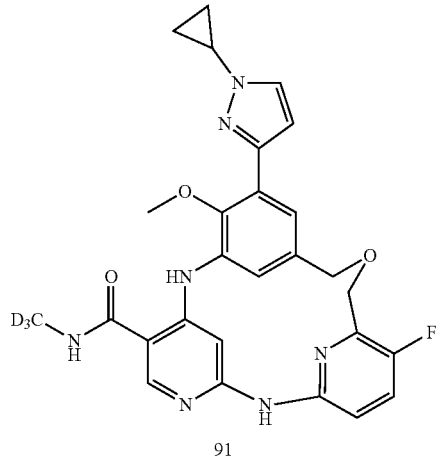

91

Step 1. 3-(1-Cyclopropyl-1H-pyrazol-3-yl)-4-methoxybenzaldehyde (91b)

Compound 91b (1.26 g, 88% yield), a yellow solid, was synthesized by utilizing a similar preparative procedure of Step 3 in Example 66 with 91a (1.10 g, 5.88 mmol) and (5-formyl-2-methoxyphenyl)boronic acid (2.12 g, 11.76 mmol) as starting materials. $^1$H NMR (400 MHz, DMSO-$d_6$) δ 9.93 (s, 1H), 8.40 (d, J=2.4 Hz, 1H), 7.86 (dd, J=2.4, 8.8 Hz, 1H), 7.82 (d, J=2.4 Hz, 1H), 7.30 (d, J=8.4 Hz, 1H), 6.73 (d, J=2.0 Hz, 1H), 3.97 (s, 3H), 3.80-3.75 (m, 1H), 1.12-1.08 (m, 2H), 1.02-0.97 (m, 2H).

Step 2. 3-(1-Cyclopropyl-1H-pyrazol-3-yl)-4-methoxy-5-nitrobenzaldehyde (91c)

Compound 91c (260 mg, 28% yield), a yellow solid, was synthesized by utilizing a similar preparative procedure of Step 2 in Example 80 with 91b (770 mg, 3.18 mmol) as the starting material. $^1$H NMR (400 MHz, DMSO-$d_6$) δ 10.05 (s, 1H), 8.63 (d, J=2.0 Hz, 1H), 8.35 (d, J=2.0 Hz, 1H), 7.97 (d, J=2.4 Hz, 1H), 6.79 (d, J=2.4 Hz, 1H), 3.87-3.82 (m, 1H), 3.79 (s, 3H), 1.19-1.12 (m, 2H), 1.06-1.01 (m, 2H).

Step 3. (3-(1-Cyclopropyl-1H-pyrazol-3-yl)-4-methoxy-5-nitrophenyl)methanol (91d)

Compound 91d (250 mg, 95% yield), a yellow oil, was synthesized by utilizing a similar preparative procedure of Step 1 in Example 66 with 91c (260 mg, 0.91 mmol) as the starting material. LC-MS (Method 3) $t_R$=1.41 min, m/z (M+H)$^+$=290.1.

Step 4. 3-(1-Cyclopropyl-1H-pyrazol-3-yl)-4-methoxy-5-nitrobenzyl methanesulfonate (91e)

Compound 91e (310 mg, 98% yield), a yellow oil, was synthesized by utilizing a similar preparative procedure of Step 6 in Example 66 with 91d (250 mg, 0.86 mmol) as the starting material. LC-MS (Method 3) $t_R$=1.55 min, m/z (M+H)$^+$=368.1.

Step 5. 6-Bromo-2-(((3-(1-cyclopropyl-1H-pyrazol-3-yl)-4-methoxy-5-nitrobenzyl)oxy)methyl)-3-fluoropyridine (91f)

Compound 91f (310 mg, 75% yield), a yellow oil, was synthesized by utilizing a similar preparative procedure of Step 7 in Example 66 with 91e (320 mg, 0.87 mmol) and 66b (215 mg, 1.05 mmol) as starting materials. LC-MS (Method 3) $t_R$=1.70 min, m/z (M+H)$^+$=477.0.

Step 6. Tert-butyl (6-(((3-(1-cyclopropyl-1H-pyrazol-3-yl)-4-methoxy-5-nitrobenzyl)oxy)methyl)-5-fluoropyridin-2-yl)carbamate (91g)

Compound 91g (333 mg, yield given), a brown oil, was synthesized by utilizing a similar preparative procedure of Step 4 in Example 69 with 91f (310 mg, 0.65 mmol) and tert-butyl carbamate (380 mg, 3.25 mmol) as starting materials. LC-MS (Method 3) $t_R$=1.73 min, m/z (M+H)$^+$=514.1.

Step 7. Tert-butyl (6-(((3-amino-5-(1-cyclopropyl-1H-pyrazol-3-yl)-4-methoxybenzyl)oxy)methyl)-5-fluoropyridin-2-yl)carbamate (91h)

Compound 91h (166 mg, 50% yield), a yellow oil, was synthesized by utilizing a similar preparative procedure of Step 9 in Example 66 with 91g (350 mg, 0.68 mmol) as the starting material. LC-MS (Method 3) $t_R$=1.69 min, m/z (M+H)$^+$=484.3.

Step 8. Tert-butyl (6-(((3-((2-chloro-5-((methyl-$d_3$)carbamoyl)pyridin-4-yl)amino)-5-(1-cyclopropyl-1H-pyrazol-3-yl)-4-methoxybenzyl)oxy)methyl)-5-fluoropyridin-2-yl)carbamate (91i)

Compound 91i (112 mg, yield given), a brown solid, was synthesized by utilizing a similar preparative procedure of Step 5 in Example 50 with 91h (83 mg, 0.17 mmol) and 42b (43 mg, 0.21 mmol) as starting materials. LC-MS (Method 3) $t_R$=1.77 min, m/z (M+H)$^+$=655.2.

Step 9. 4-((5-(((6-Amino-3-fluoropyridin-2-yl)methoxy)methyl)-3-(1-cyclopropyl-1H-pyrazol-3-yl)-2-methoxyphenyl)amino)-6-chloro-N-(methyl-$d_3$)nicotinamide formic acid (91j)

Compound 91j (52 mg, 48% yield), a white solid, was synthesized by utilizing a similar preparative procedure of Step 6 in Example 70 with 91i (118 mg, 0.18 mmol) as the starting material. The title compound was purified by Prep-HPLC (Method C). LC-MS (Method 3) $t_R$=1.52 min, m/z (M+H)$^+$=555.2.

Step 10. 11-(1-Cyclopropyl-1H-pyrazol-3-yl)-18-fluoro-10-methoxy-N-(methyl-d₃)-15-oxa-2,4,8,21-tetraazatetracyclo[15.3.1.1ˆ{3,7}.1ˆ{9,13}]tricosa-1(20),3,5,7(23),9(22),10,12,17(21),18-nonaene-6-carboxamide (91)

Compound 91 (10 mg, 22% yield), an off-white solid, was synthesized by utilizing a similar preparative procedure of Step 12 in Example 66 with 91j (52 mg, 0.87 mmol) as the starting material. LC-MS (Method 1) $t_R$=3.95 min, m/z (M+H)⁺=519.1. ¹H NMR (400 MHz, DMSO-d₆) δ 10.70 (s, 1H), 9.97 (s, 1H), 9.36 (s, 1H), 8.50 (s, 1H), 8.46 (s, 1H), 8.04 (s, 1H), 7.86 (d, J=2.0 Hz, 1H), 7.61 (t, J=9.2 Hz, 1H), 7.45 (s, 1H), 7.06 (dd, J=2.8, 8.8 Hz, 1H), 6.74 (d, J=2.0 Hz, 1H), 4.67 (s, 2H), 4.45 (s, 2H), 3.81-3.75 (m, 1H), 3.63 (s, 3H), 1.11-0.99 (m, 4H).

Example 92

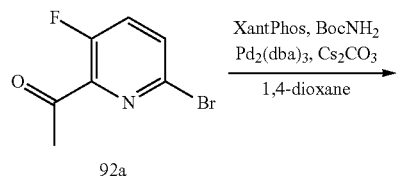

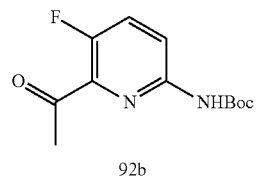

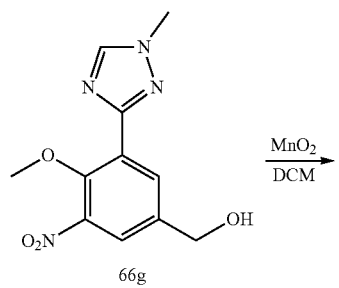

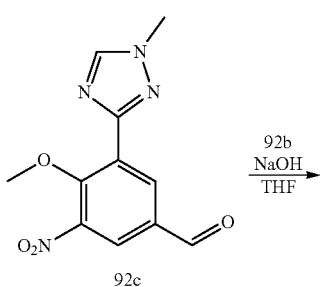

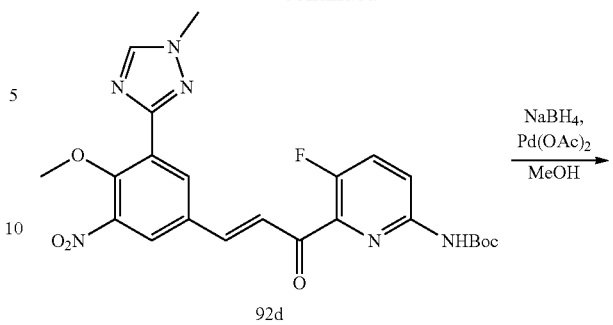

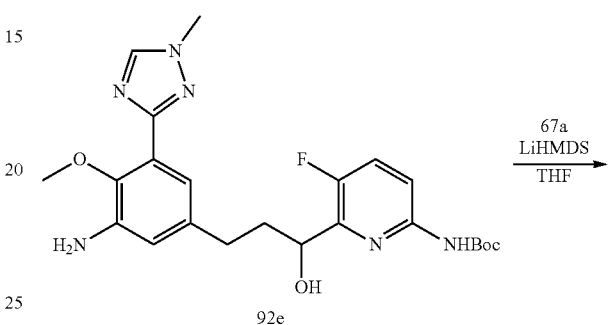

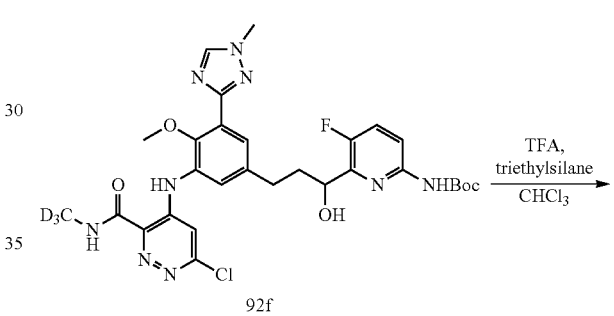

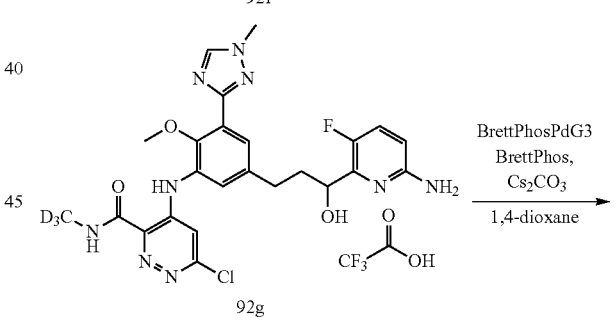

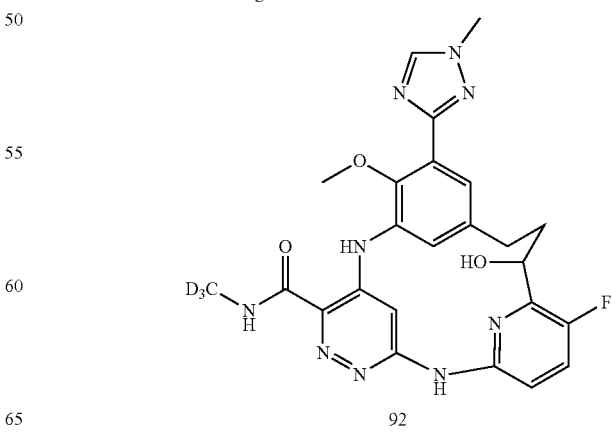

Step 1. Tert-butyl (6-acetyl-5-fluoropyridin-2-yl)carbamate (92b)

Compound 92b (550 mg, 94% yield), a yellow solid, was synthesized by utilizing a similar preparative procedure of Step 8 in Example 66 with 92a (500 mg, 2.29 mmol) and tert-butyl carbamate (1.34 g, 11.47 mmol) as starting materials. $^1$H NMR (400 MHz, DMSO-$d_6$) δ 10.06 (s, 1H), 8.00 (dd, J=3.2, 9.2 Hz, 1H), 7.08 (t, J=10.0 Hz, 1H), 2.56 (s, 3H), 1.48 (s, 9H).

Step 2. 4-Methoxy-3-(1-methyl-1H-1,2,4-triazol-3-yl)-5-nitrobenzaldehyde (92c)

A mixture of 66g (100 mg, 0.38 mmol) and MnO$_2$ (329 mg, 3.78 mmol) in DCM (3 mL) was stirred at 30° C. for 18 h. The reaction mixture was filtered and the filter cake was washed with DCM (15 mL). The filtrate was concentrated to afford the title compound 92c (93 mg, 94% yield) as a yellow solid. $^1$H NMR (400 MHz, DMSO-$d_6$) δ 10.06 (s, 1H), 8.69 (s, 1H), 8.68 (d, J=2.0 Hz, 1H), 8.47 (d, J=2.0 Hz, 1H), 3.99 (s, 3H), 3.90 (s, 3H).

Step 3. Tert-butyl (E)-(5-fluoro-6-(3-(4-methoxy-3-(1-methyl-1H-1,2,4-triazol-3-yl)-5-nitrophenyl)acryloyl)pyridin-2-yl)carbamate (92d)

To a mixture of 92c (420 mg, 1.60 mmol) and 92b (407 mg, 1.60 mmol) in THF (20 mL) was added 1.5 M NaOH (1.60 mL, 2.4 mmol) at 0° C. The reaction mixture was stirred at r.t. for 4 h. The reaction mixture was diluted with H$_2$O (10 mL) and extracted with EtOAc (30 mL*2). The combined organic layer was concentrated. The residue was purified by flash chromatography on silica gel (PE/EtOAc=1/1) to afford the title compound 92d (444 mg, 56% yield) as a yellow solid. LC-MS (Method 3) $t_R$=1.70 min, m/z (M+H)$^+$=499.2.

Step 4. Tert-butyl (6-(3-(3-amino-4-methoxy-5-(1-methyl-1H-1,2,4-triazol-3-yl)phenyl)-1-hydroxypropyl)-5-fluoropyridin-2-yl)carbamate (92e)

The mixture of 92d (300 mg, 0.60 mmol), NaBH$_4$ (23 mg, 0.60 mmol) and Pd(OAc)$_2$ (7 mg, 0.03 mmol) were combined in a round-bottom flask. MeOH (6 mL) was slowly added into the flask through a syringe under H$_2$ atmosphere. The reaction mixture was stirred at r.t. for 18 h. The reaction mixture was concentrated and the residue was purified by flash chromatography on silica gel (DCM/MeOH=20/1) to afford the title compound 92e (80 mg, 28% yield) as a yellow solid. LC-MS (Method 3) $t_R$=1.38 min, m/z (M+H)$^+$=473.2.

Step 5. Tert-butyl (6-(3-(3-((6-chloro-3-((methyl-$d_3$)carbamoyl)pyridazin-4-yl)amino)-4-methoxy-5-(1-methyl-1H-1,2,4-triazol-3-yl)phenyl)-1-hydroxypropyl)-5-fluoropyridin-2-yl)carbamate (92f)

Compound 92f (30 mg, 31% yield), a yellow solid, was synthesized by utilizing a similar preparative procedure of Step 5 in Example 50 with 92e (72 mg, 0.15 mmol) and 67a (32 mg, 0.15 mmol) as starting materials. LC-MS (Method 3) $t_R$=1.50 min, m/z (M+H)$^+$=645.3.

Step 6. 4-((5-(3-(6-Amino-3-fluoropyridin-2-yl)-3-hydroxypropyl)-2-methoxy-3-(1-methyl-1H-1,2,4-triazol-3-yl)phenyl)amino)-6-chloro-N-(methyl-$d_3$)pyridazine-3-carboxamide 2,2,2-trifluoroacetic acid (92g)

A mixture of 92f (30 mg, 0.05 mmol), TFA (32 mg, 0.28 mmol) and triethylsilane (16 mg, 0.14 mmol) in CHCl$_3$ (1 mL) was stirred at 50° C. for 3 h. The reaction mixture was cooled and concentrated to afford the crude compound 92g (30 mg, 98% yield) as a yellow oil which was used directly in next step without further purification. LC-MS (Method 3) $t_R$=1.37 min, m/z (M+H)$^+$=545.3.

Step 7. 18-Fluoro-16-hydroxy-10-methoxy-N-(methyl-$d_3$)-11-(1-methyl-1H-1,2,4-triazol-3-yl)-2,4,5,8,21-pentaazatetracyclo[15.3.1.1^{3,7}.1^{9,13}]tricosa-1(20),3,5,7(23),9(22),10,12,17(21),18-nonaene-6-carboxamide (92)

Compound 92 (2 mg, 9% yield), a white solid, was synthesized by utilizing a similar preparative procedure of Step 12 in Example 66 with 92g (30 mg, 0.05 mmol) as the starting material. LC-MS (Method 2) $t_R$=2.98 min, m/z (M+H)$^+$=509.1. $^1$H NMR (400 MHz, DMSO-$d_6$) δ 10.66 (s, 1H), 10.41 (s, 1H), 9.45 (s, 1H), 9.00 (s, 1H), 8.56 (s, 1H), 7.71 (s, 1H), 7.57-7.52 (m, 1H), 7.49 (s, 1H), 7.06 (dd, J=9.2 Hz, 2.4 Hz, 1H), 5.43 (d, J=5.2 Hz, 1H), 4.46-4.43 (m, 1H), 3.95 (s, 3H), 3.75 (s, 3H), 2.95-2.79 (m, 2H), 2.40-2.29 (m, 1H), 2.11-2.05 (m, 1H).

Example 93

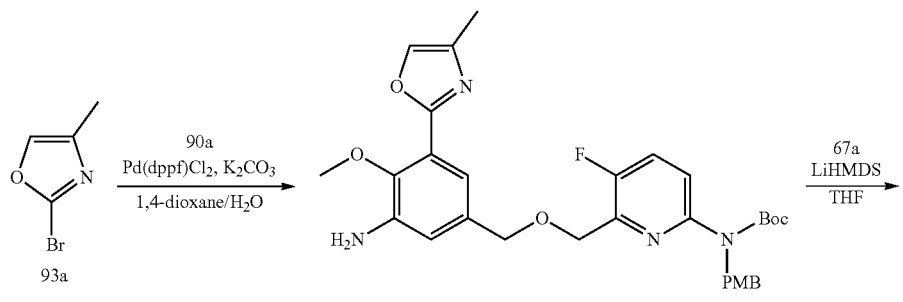

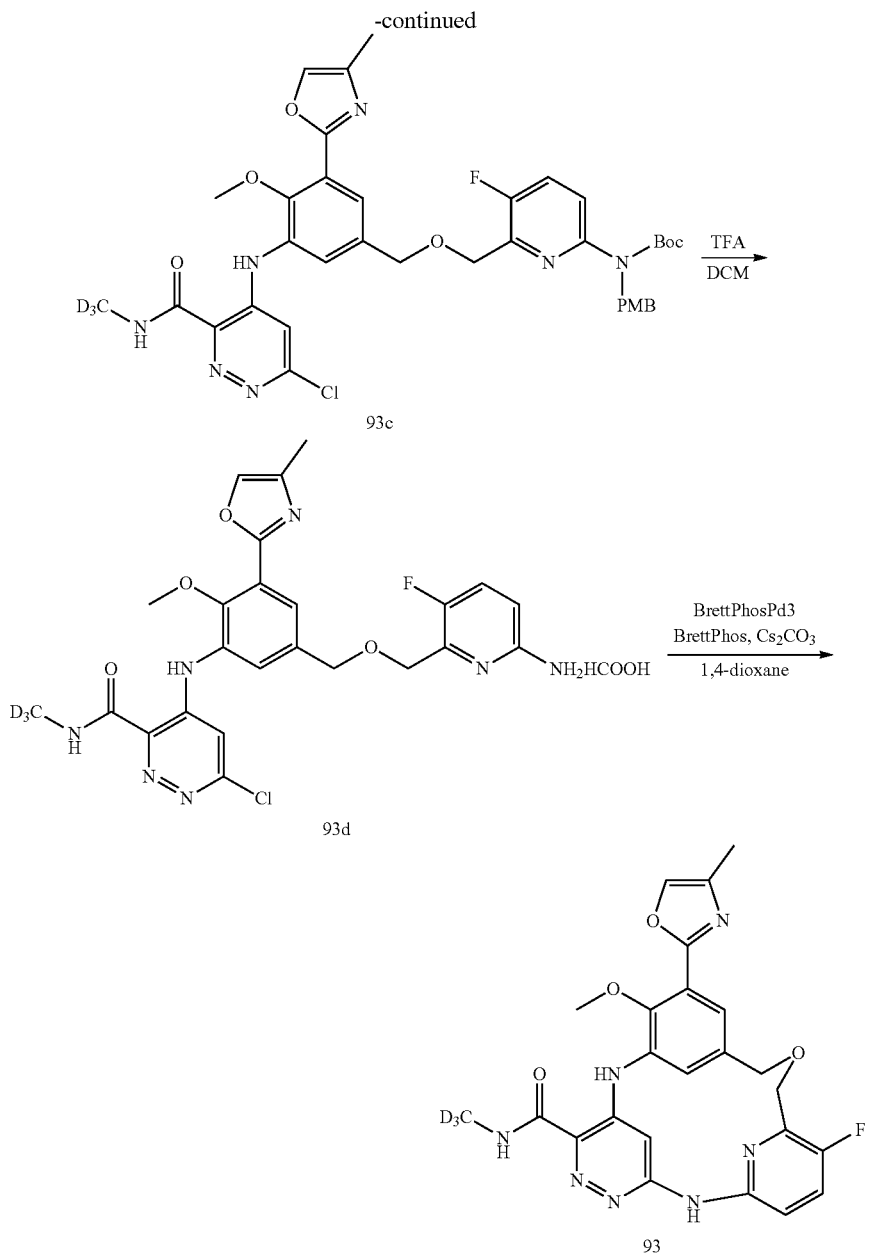

Step 1. Tert-butyl (6-(((3-amino-4-methoxy-5-(4-methyloxazol-2-yl)benzyl)oxy)methyl)-5-fluoropyridin-2-yl)(4-methoxybenzyl)carbamate (93b)

Compound 93b (137 mg, 85% yield), a yellow oil, was synthesized by utilizing a similar preparative procedure of Step 3 in Example 66 with 90a (173 mg, 0.28 mmol) and 93a (58 mg, 0.36 mmol) as starting materials. LC-MS (Method 3) $t_R$=1.75 min, m/z (M+H−100)$^+$=479.2.

Step 2. Tert-butyl (6-(((3-((6-chloro-3-((methyl-d$_3$)carbamoyl)pyridazin-4-yl)amino)-4-methoxy-5-(4-methyloxazol-2-yl)benzyl)oxy)methyl)-5-fluoropyridin-2-yl)(4-methoxybenzyl)carbamate (93c)

Compound 93c (270 mg, 99% yield), a yellow solid, was synthesized by utilizing a similar preparative procedure of Step 3 in Example 90 with 93b (210 mg, 0.36 mmol) and 67a (76 mg, 0.36 mmol) as starting materials. The title compound was purified by Prep-HPLC (Method C). LC-MS (Method 3) $t_R$=1.83 min, m/z (M+H−100)$^+$=651.3.

Step 3. 4-((5-(((6-Amino-3-fluoropyridin-2-yl)methoxy)methyl)-2-methoxy-3-(4-methyloxazol-2-yl)phenyl)amino)-6-chloro-N-(methyl-d$_3$)pyridazine-3-carboxamide formic acid (93d)

Compound 93d (85 mg, 50% yield), a yellow solid, was synthesized by utilizing a similar preparative procedure of Step 6 in Example 70 with 93c (220 mg, 0.29 mmol) as the starting material. LC-MS (Method 3) $t_R$=1.51 min, m/z (M+H)$^+$=531.2.

Step 4. 18-Fluoro-10-methoxy-N-(methyl-d₃)-11-(4-methyl-1,3-oxazol-2-yl)-15-oxa-2,4,5,8,21-pentaazatetracyclo[15.3.1.1^{3,7}.1^{9,13}]tricosa-1(20),3,5,7(23),9(22),10,12,17(21),18-nonaene-6-carboxamide (93)

Compound 93 (20 mg, 23% yield), a white solid, was synthesized by utilizing a similar preparative procedure of Step 12 in Example 66 with 93d (100 mg, 0.17 mmol) as the starting material. LC-MS (Method 1) $t_R$=1.78 min, m/z (M+H)⁺=495.1. ¹H NMR (400 MHz, DMSO-d₆) δ 10.84 (s, 1H), 10.57 (s, 1H), 9.56 (s, 1H), 9.06 (s, 1H), 8.22 (d, J=1.6 Hz, 1H), 7.98 (s, 1H), 7.68 (t, J=9.2 Hz, 1H), 7.55 (d, J=1.6 Hz, 1H), 7.18 (dd, J=3.2, 9.2 Hz, 1H), 4.71 (s, 2H), 4.48 (d, J=2.4 Hz, 2H), 3.81 (s, 3H), 2.20 (s, 3H).

Example 94

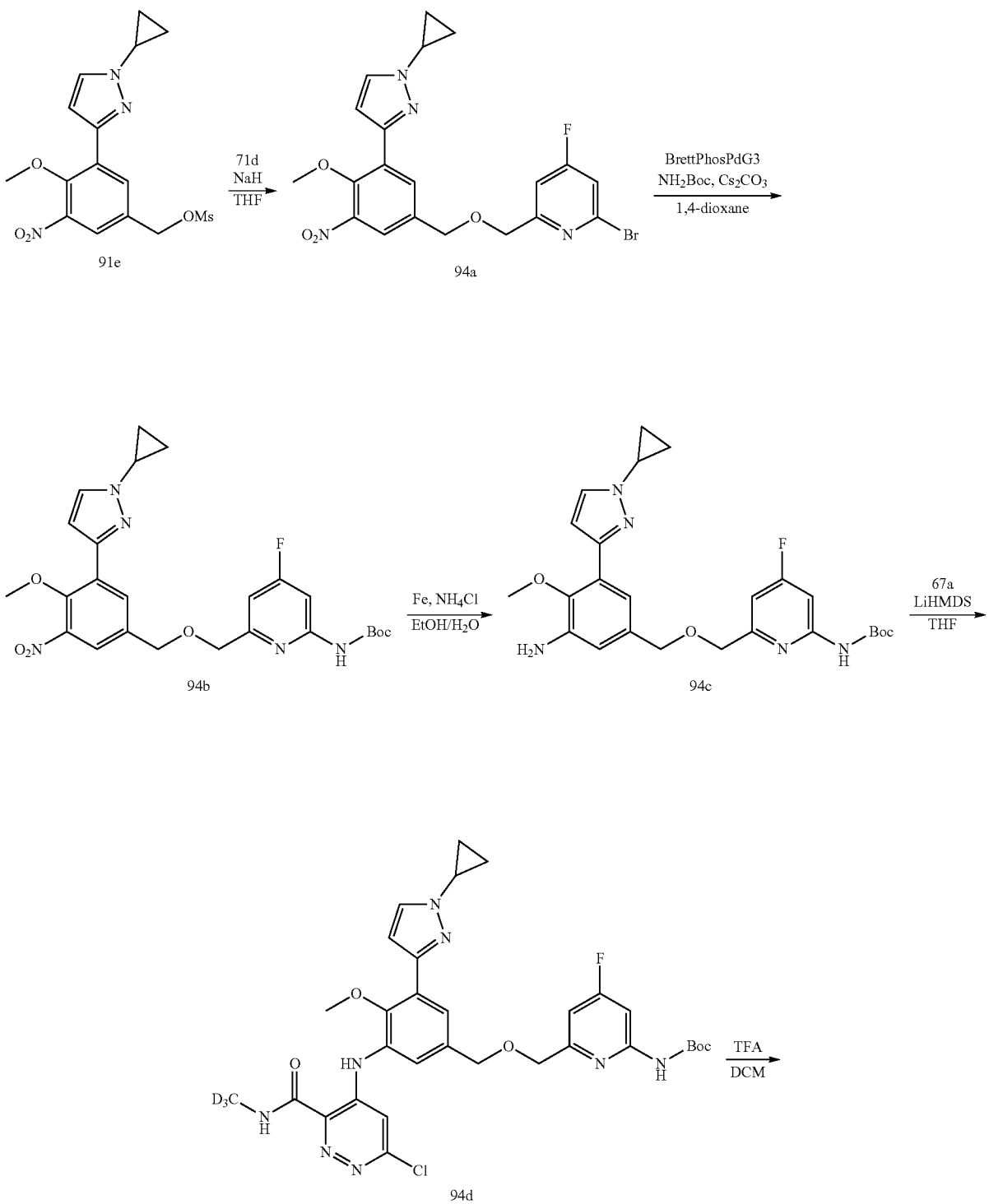

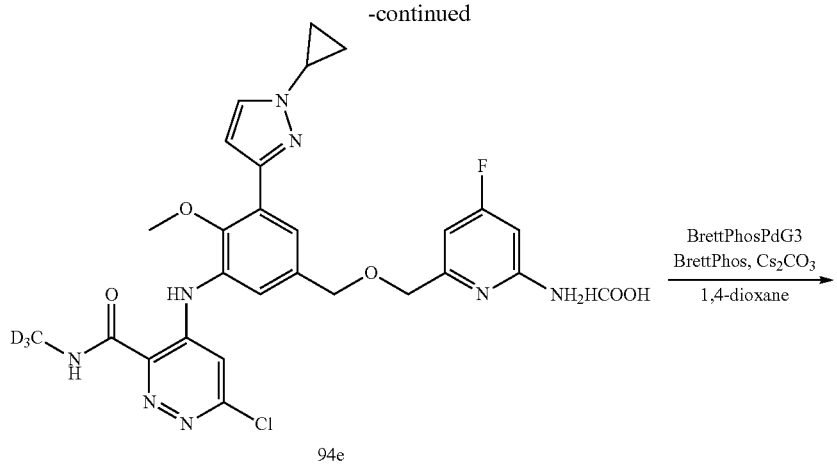

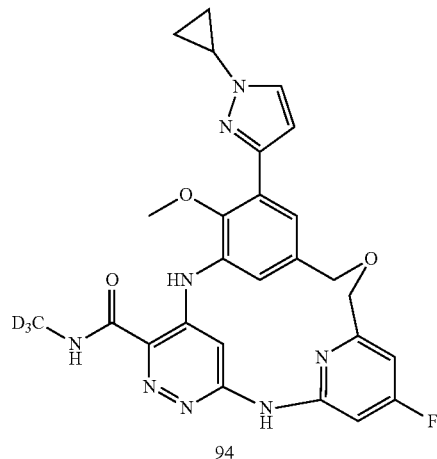 [SMILES: [2H]C([2H])([2H])NC(=O)c1nnc2cc1Nc1cc(cc(-c3ccn(C4CC4)n3)c1OC)COCc1cc(F)cc(n1)N2]

Step 1. 2-Bromo-6-(((3-(1-cyclopropyl-1H-pyrazol-3-yl)-4-methoxy-5-nitrobenzyl)oxy)methyl)-4-fluoropyridine (94a)

Compound 94a (180 mg, 71% yield), a yellow solid, was synthesized by utilizing a similar preparative procedure of Step 7 in Example 66 with 91e (255 mg, 0.69 mmol) and 71d (110 mg, 0.53 mmol) as starting materials. LC-MS (Method 3) $t_R$=1.71 min, m/z (M+H)$^+$=477.0.

Step 2. Tert-butyl (6-(((3-(1-cyclopropyl-1H-pyrazol-3-yl)-4-methoxy-5-nitrobenzyl)oxy)methyl)-4-fluoropyridin-2-yl)carbamate (94b)

Compound 94b (322 mg, 99% yield), a brown oil, was synthesized by utilizing a similar preparative procedure of Step 4 in Example 69 with 94a (300 mg, 0.63 mmol) and tert-butyl carbamate (147 mg, 1.26 mmol) as starting materials. LC-MS (Method 3) $t_R$=1.82 min, m/z (M+H−100)$^+$=414.2.

Step 3. Tert-butyl (6-(((3-amino-5-(1-cyclopropyl-1H-pyrazol-3-yl)-4-methoxybenzyl)oxy)methyl)-4-fluoropyridin-2-yl)carbamate (94c)

Compound 94c (70 mg, 23% yield), a yellow oil, was synthesized by utilizing a similar preparative procedure of Step 9 in Example 66 with 94b (320 mg, 0.62 mmol) as the starting material. LC-MS (Method 3) $t_R$=1.71 min, m/z (M+H)$^+$=484.2.

Step 4. Tert-butyl (6-(((3-((6-chloro-3-((methyl-d$_3$)carbamoyl)pyridazin-4-yl)amino)-5-(1-cyclopropyl-1H-pyrazol-3-yl)-4-methoxybenzyl)oxy)methyl)-4-fluoropyridin-2-yl)carbamate (94d)

Compound 94d (95 mg, 100% yield), a brown solid, was synthesized by utilizing a similar preparative procedure of Step 5 in Example 50 with 94c (70 mg, 0.14 mmol) and 67a (39 mg, 0.19 mmol) as starting materials. LC-MS (Method 3) $t_R$=1.83 min, m/z (M+H)$^+$=656.2.

Step 5. 4-((5-(((6-Amino-4-fluoropyridin-2-yl)methoxy)methyl)-3-(1-cyclopropyl-1H-pyrazol-3-yl)-2-methoxyphenyl)amino)-6-chloro-N-(methyl-d$_3$)pyridazine-3-carboxamide formic acid (94e)

Compound 94e (69 mg, 75% yield), a white solid, was synthesized by utilizing a similar preparative procedure of Step 6 in Example 70 with 94d (100 mg, 0.15 mmol) as the starting material. The title compound was purified by Prep-HPLC (Method C). LC-MS (Method 3) $t_R$=1.59 min, m/z (M+H)$^+$=556.2.

Step 6. 11-(1-Cyclopropyl-1H-pyrazol-3-yl)-19-fluoro-10-methoxy-N-(methyl-d$_3$)-15-oxa-2,4,5,8,21-pentaazatetracyclo[15.3.1.1ˆ{3,7}.1ˆ{9,13}]tricosa-1(21),3,5,7(23),9(22),10,12,17,19-nonaene-6-carboxamide (94)

Compound 94 (13 mg, 22% yield), a white solid, was synthesized by utilizing a similar preparative procedure of Step 12 in Example 66 with 94e (69 mg, 0.11 mmol) as the starting material. LC-MS (Method 1) $t_R$=3.27 min, m/z (M+H)$^+$=520.2. $^1$H NMR (400 MHz, DMSO-d$_6$) δ 10.74 (s, 1H), 10.60 (s, 1H), 9.65 (s, 1H), 9.06 (s, 1H), 8.06 (s, 1H), 7.87-7.82 (m, 1H), 7.52 (s, 1H), 6.99 (d, J=8.8 Hz, 1H), 6.91 (d, J=10.8 Hz, 1H), 6.74 (d, J=2.4 Hz, 1H), 4.66 (s, 2H), 4.38 (s, 2H), 3.81-3.76 (m, 1H), 3.65 (s, 3H), 1.11-0.99 (m, 4H).

Example 95

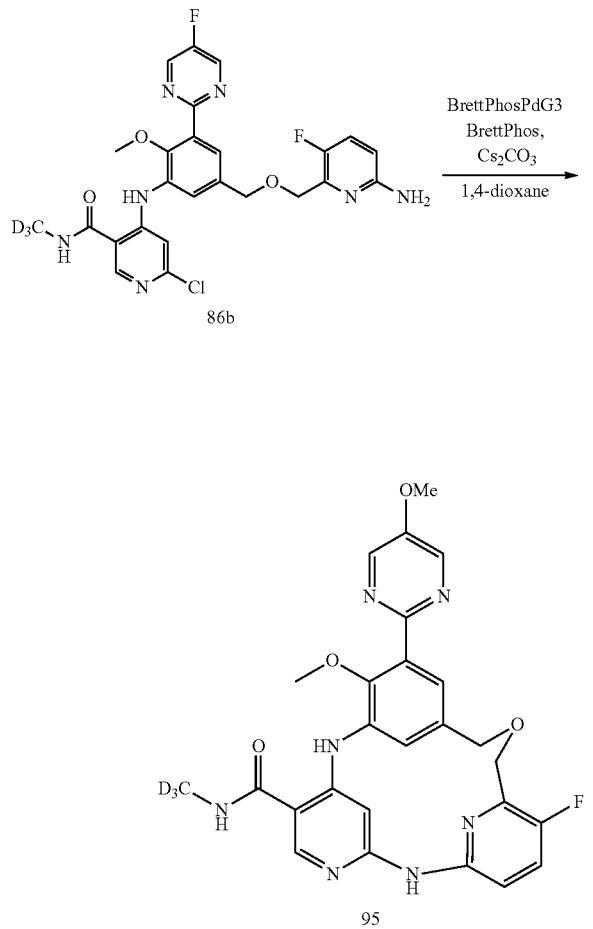

Step 1. 18-Fluoro-10-methoxy-11-(5-methoxypyrimidin-2-yl)-N-(methyl-d$_3$)-15-oxa-2,4,8,21-tetraazatetracyclo[15.3.1.1^{3,7}.1^{9,13}]tricosa-1(20),3,5,7(23),9(22),10,12,17(21),18-nonaene-6-carboxamide (95)

Compound 95 (5 mg, 7% yield), a white solid, was synthesized by utilizing a similar preparative procedure of Step 12 in Example 66 with 86b (71 mg, 0.13 mmol) as the starting material. LC-MS (Method 1) $t_R$=3.27 min, m/z (M+H)$^+$=521.1. $^1$H NMR (400 MHz, DMSO-d$_6$) δ 10.70 (s, 1H), 9.98 (s, 1H), 9.34 (s, 1H), 8.68 (s, 2H), 8.51 (s, 1H), 8.47 (s, 1H), 8.17 (s, 1H), 7.61 (t, J=9.2 Hz, 1H), 7.26 (d, J=2.4 Hz, 1H), 7.07 (dd, J=8.8 Hz, 2.8 Hz, 1H), 4.68 (s, 2H), 4.46 (d, J=2.0 Hz, 2H), 3.98 (s, 3H), 3.72 (s, 3H).

Example 96

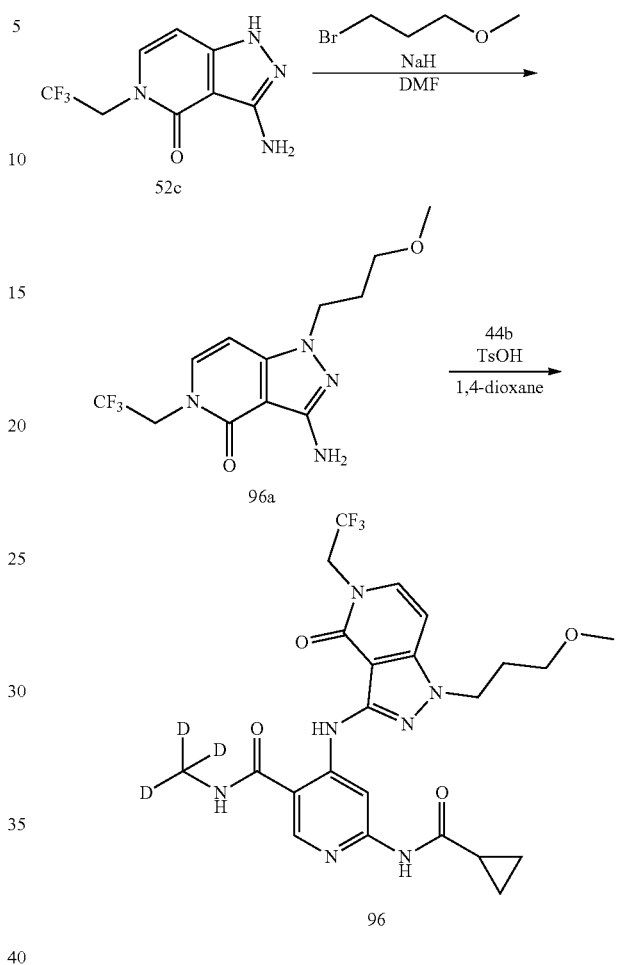

Step 1. 3-Amino-1-(3-methoxypropyl)-5-(2,2,2-trifluoroethyl)-1,5-dihydro-4H-pyrazolo[4,3-c]pyridin-4-one (96a)

To a solution of 52c (500 mg, 2.15 mmol) in DMF (5 mL) was added NaH (90 mg, 2.4 mmol, 60% in oil) at 0° C., the mixture was stirred at 25° C. for 30 min, then 1-bromo-3-methoxy-propane (329 mg, 2.15 mmol) was added, and stirred at 25° C. for 4 h. The mixture was was diluted with H$_2$O (15 mL), extracted with EA (15 mL*3), washed with brine, dried over Na$_2$SO$_4$, concentrated to get the compound 96a (480 mg, 73% yield) as a brown oil. LC-MS (Method 4) $t_R$=2.58 min, m/z (M+H)$^+$=305.2.

Step 2 6-(Cyclopropanecarboxamido)-4-((1-(3-methoxypropyl)-4-oxo-5-(2,2,2-trifluoroethyl)-4,5-dihydro-1H-pyrazolo[4,3-c]pyridin-3-yl)amino)-N-(methyl-d$_3$)nicotinamide (96)

A mixture of 96a (59.26 mg, 0.19 mmol), 44b (50 mg, 0.19 mmol) and pTSA (37 mg, 0.19 mmol) in 1,4-dioxane (1 mL) was stirred at 100° C. for 16 h. The mixture was concentrated and DIPEA (0.2 mL) and MeOH (2 mL) was added. The mixture was stirred at 25° C. for 1 h and filtered to get the compound 96 (26.1 mg, 25% yield) as a white solid. LC-MS (Method 4) $t_R$=3.91 min, m/z (M+H)$^+$=525.4.

¹H NMR (400 MHz, DMSO-d₆) δ 11.67 (s, 1H), 10.69 (s, 1H), 9.31 (s, 1H), 8.51 (s, 1H), 8.50 (s, 1H), 7.46 (d, J=7.6 Hz, 1H), 6.65 (d, J=7.7 Hz, 1H), 4.83 (q, J=9.2 Hz, 2H), 4.15 (t, J=6.7 Hz, 2H), 3.25 (t, J=6.1 Hz, 2H), 3.15 (s, 3H), 2.16-2.09 (m, 2H), 2.01-1.95 (m, 1H), 0.81-0.74 (m, 4H).

Example 97

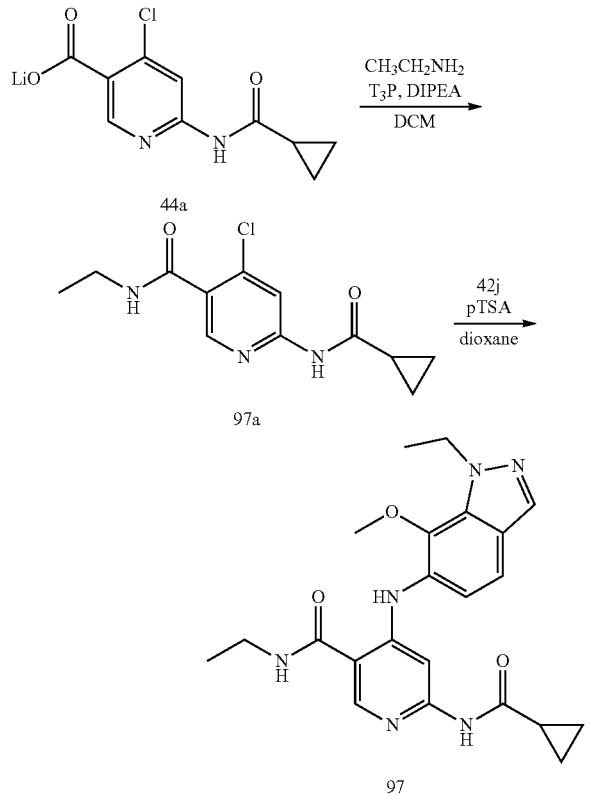

Example 98

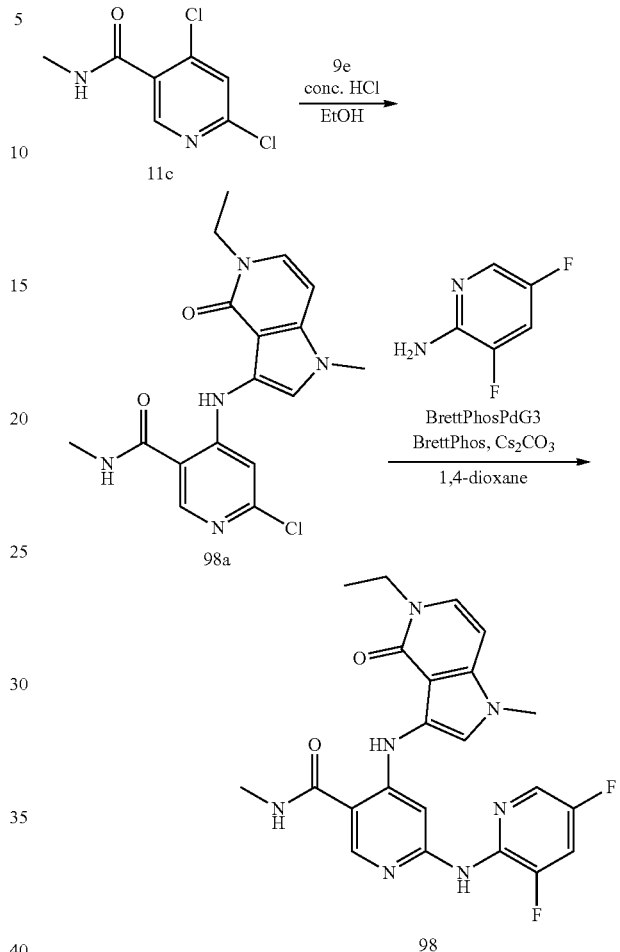

Step 1. 4-Chloro-6-(cyclopropanecarboxamido)-N-ethylnicotinamide (97a)

Compound 97a (100 mg, 45% yield), an off-white solid, was synthesized by utilizing a similar preparative procedure of Step 2 in Example 44 with 44a (205 mg, 0.83 mmol) and ethylamine (281 mg, 6.23 mmol) as starting materials. LC-MS (Method 4) $t_R$=1.56 min, m/z (M+H)⁺=268.1.

Step 2. 6-(Cyclopropanecarboxamido)-N-ethyl-4-((1-ethyl-7-methoxy-1H-indazol-6-yl)amino)nicotinamide (97)

Compound 97 (33.5 mg, 42% yield), a white solid, was synthesized by utilizing a similar preparative procedure of Step 3 in Example 44 with 97a (50 mg, 0.19 mmol) and 42j (46.4 mg, 0.24 mmol) as starting materials. LC-MS (Method 4) $t_R$=2.16 min, m/z (M+H)⁺=423.3. ¹H NMR (400 MHz, DMSO-d₆) δ 10.73 (s, 1H), 10.52 (s, 1H), 8.66 (t, J=5.5 Hz, 1H), 8.53 (s, 1H), 8.03 (s, 1H), 7.84 (s, 1H), 7.51 (d, J=8.6 Hz, 1H), 7.10 (d, J=8.6 Hz, 1H), 4.54 (q, J=7.2 Hz, 2H), 3.79 (s, 3H), 3.35-3.26 (m, 2H), 2.00-1.89 (m, 1H), 1.39 (t, J=7.2 Hz, 3H), 1.16 (t, J=7.2 Hz, 3H), 0.78-0.66 (m, 4H).

Step 1. 6-Chloro-4-((5-ethyl-1-methyl-4-oxo-4,5-dihydro-1H-pyrrolo[3,2-c]pyridin-3-yl)amino)-N-methylnicotinamide (98a)

To a mixture of 9e (150 mg, 0.66 mmol), 11c (203 mg, 0.99 mmol) in EtOH (3 mL) was added conc. HCl (64 mg, 0.66 mmol). The reaction mixture was stirred at 80° C. for 12 h. The solvent was evaporated under reduced pressure and the residue was purified by flash chromatography on silica gel (DCM/MeOH=50/1) to give the title compound 98a (50 mg, 21% yield) as a yellow solid. LC-MS (Method 3) $t_R$=1.65 min, m/z (M+H)⁺=360.3.

Step 2. 6-((3,5-Difluoropyridin-2-yl)amino)-4-((5-ethyl-1-methyl-4-oxo-4,5-dihydro-1H-pyrrolo[3,2-c]pyridin-3-yl)amino)-N-methylnicotinamide (98)

Compound 98 (20 mg, 32% yield), a white solid, was synthesized by utilizing a similar preparative procedure of Step 3 in Example 49 with 98a (50 mg, 0.14 mmol) and 3,5-difluoropyridin-2-amine (36 mg, 0.28 mmol) as starting materials. LC-MS (Method 1) $t_R$=3.25 min, m/z (M+H)⁺=454.2. ¹H NMR (400 MHz, DMSO-d₆) δ 10.99 (s, 1H), 9.13 (s, 1H), 8.38 (s, 1H), 8.32 (d, J=4.8 Hz, 1H), 8.25

(d, J=2.4 Hz, 1H), 7.95-7.90 (m, 1H), 7.85 (s, 1H), 7.35 (d, J=7.6 Hz, 1H), 7.14 (s, 1H), 6.54 (d, J=7.6 Hz, 1H), 3.93 (q, J=7.2 Hz, 2H), 3.75 (s, 3H), 2.77 (d, J=4.8 Hz, 3H), 1.21 (t, J=7.2 Hz, 3H).

Example 99

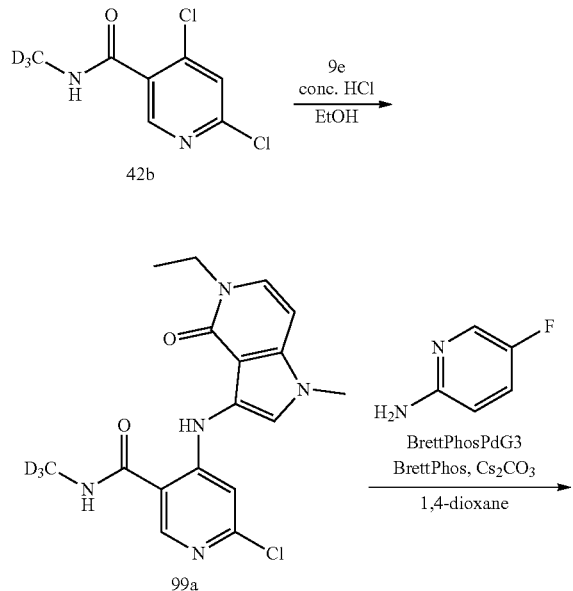

Step 1. 6-Chloro-4-[(5-ethyl-1-methyl-4-oxo-pyrrolo[3,2-c]pyridin-3-yl)amino]-N-(methyl-d₃)pyridine-3-carboxamide (99a)

Compound 99a (124 mg, 35% yield), a yellow solid, was synthesized by utilizing a similar preparative procedure of Step 1 in Example 98 with 42b (313 mg, 1.05 mmol) and 9e (200 mg, 0.88 mmol) as starting materials. LC-MS (Method 3) $t_R$=1.15 min, m/z (M+H)⁺=363.1.

Step 2. 4-[(5-Ethyl-1-methyl-4-oxo-pyrrolo[3,2-c]pyridin-3-yl)amino]-6-[(5-fluoro-2-pyridyl)amino]-N-(methyl-d₃)pyridine-3-carboxamide (99)

Compound 99 (15 mg, 25% yield), a white solid, was synthesized by utilizing a similar preparative procedure of Step 3 in Example 49 with 99a (50 mg, 0.14 mmol) and 5-fluoropyridin-2-amine (31 mg, 0.28 mmol) as starting materials. LC-MS (Method 1) $t_R$=3.24 min, m/z (M+H)⁺=439.2. ¹H NMR (400 MHz, DMSO-d₆) δ 10.99 (s, 1H), 9.78 (s, 1H), 8.39 (s, 1H), 8.25 (d, J=3.2 Hz, 2H), 7.77-7.74 (m, 1H), 7.68-7.63 (m, 2H), 7.34 (d, J=7.6 Hz, 1H), 7.22 (s, 1H), 6.54 (d, J=7.2 Hz, 1H), 3.93 (q, J=6.8 Hz, 2H), 3.75 (s, 3H), 1.21 (t, J=6.8 Hz, 3H).

Example 100

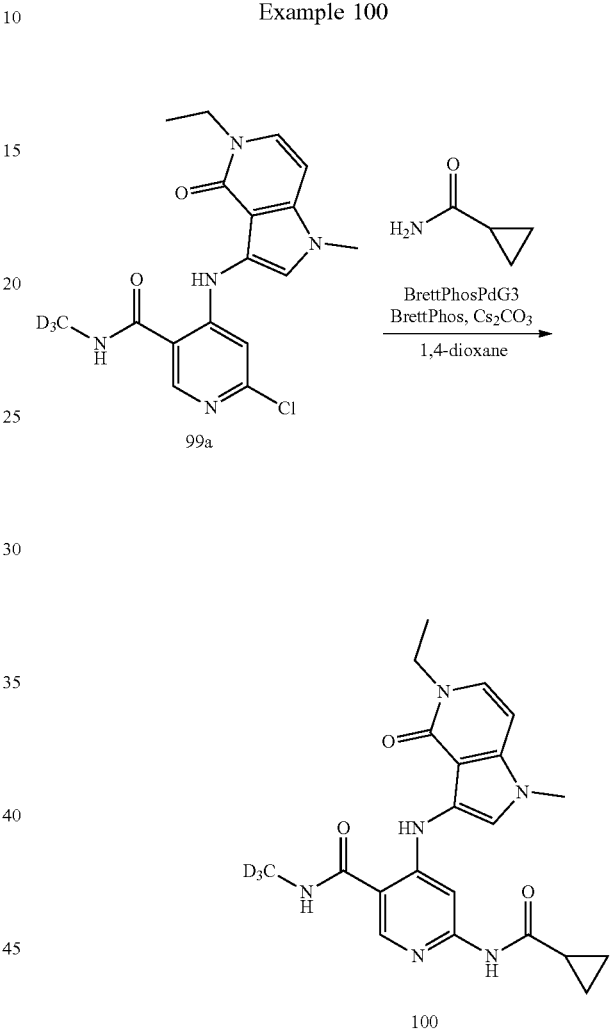

Step 1. 6-(Cyclopropanecarbonylamino)-4-[(5-ethyl-1-methyl-4-oxo-pyrrolo[3,2-c]pyridin-3-yl)amimo]-N-(methyl-d₃)pyridine-3-carboxamide (100)

Compound 100 (10 mg, 22% yield), a white solid, was synthesized by utilizing a similar preparative procedure of Step 3 in Example 49 with 99a (40 mg, 0.11 mmol) and cyclopropanecarboxamide (19 mg, 0.22 mmol) as starting materials. LC-MS (Method 1) $t_R$=2.60 min, m/z (M+H)⁺=412.2. ¹H NMR (400 MHz, DMSO-d₆) δ 10.89 (s, 1H), 10.71 (s, 1H), 8.42 (s, 1H), 8.37 (s, 1H), 8.00 (s, 1H), 7.34 (d, J=7.2 Hz, 1H), 7.02 (s, 1H), 6.53 (d, J=7.2 Hz, 1H), 3.93 (q, J=6.8 Hz, 2H), 3.68 (s, 3H), 2.02-2.01 (m, 1H), 1.20 (t, J=6.8 Hz, 3H), 0.83-0.79 (m, 4H).

Example 101

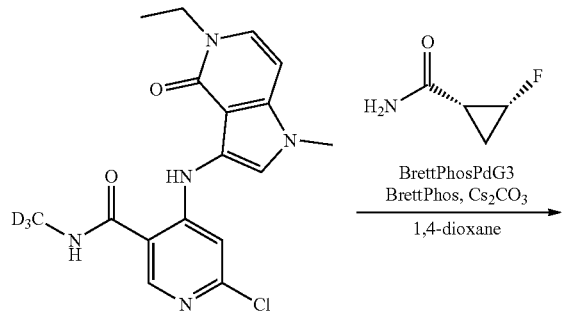

Step 1. 4-[(5-Ethyl-1-methyl-4-oxo-pyrrolo[3,2-c]pyridin-3-yl)amino]-6-[[(1R,2R)-2-fluorocyclopropanecarbonyl]amino]-N-(methyl-d₃)pyridine-3-carboxamide (101)

Compound 101 (2.3 mg, 4% yield), a white solid, was synthesized by utilizing a similar preparative procedure of Step 3 in Example 49 with 99a (50 mg, 0.14 mmol) and (1R,2R)-2-fluorocyclopropanecarboxamide (57 mg, 0.57 mmol) as starting materials. LC-MS (Method 1) $t_R$=2.87 min, m/z (M+H)⁺=430.2. ¹H NMR (400 MHz, DMSO-$d_6$) δ 10.90 (s, 1H), 10.87 (s, 1H), 8.44 (s, 1H), 8.40 (s, 1H), 7.93 (s, 1H), 7.35 (d, J=7.6 Hz, 1H), 7.00 (s, 1H), 6.54 (d, J=7.2 Hz, 1H), 4.98-4.81 (m, 1H), 3.92 (q, J=7.2 Hz, 2H), 3.67 (s, 3H), 1.54-1.46 (m, 1H), 1.29-1.18 (m, 5H).

Example 102

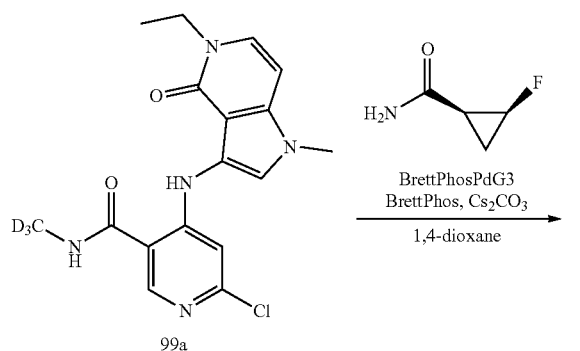

Step 1. 4-[(5-Ethyl-1-methyl-4-oxo-pyrrolo[3,2-c]pyridin-3-yl)amino]-6-[[(1S,2S)-2-fluorocyclopropanecarbonyl]amino]-N-(methyl-d₃)pyridine-3-carboxamide (102)

Compound 102 (2.8 mg, 5% yield), a white solid, was synthesized by utilizing a similar preparative procedure of Step 3 in Example 49 with 99a (50 mg, 0.14 mmol) and (1S,2S)-2-fluorocyclopropanecarboxamide (71 mg, 0.69 mmol) as starting materials. LC-MS (Method 1) $t_R$=2.56 min, m/z (M+H)⁺=430.1. ¹H NMR (400 MHz, DMSO-$d_6$) δ 10.90 (s, 1H), 10.76 (s, 1H), 8.43 (s, 1H), 8.40 (s, 1H), 7.97 (s, 1H), 7.35 (d, J=7.6 Hz, 1H), 7.04 (s, 1H), 6.54 (d, J=7.2 Hz, 1H), 5.02-4.81 (m, 1H), 3.92 (q, J=6.8 Hz, 2H), 3.70 (s, 3H), 2.23-2.07 (m, 1H), 1.70-1.60 (m, 1H), 1.23-1.12 (m, 4H).

Example 103

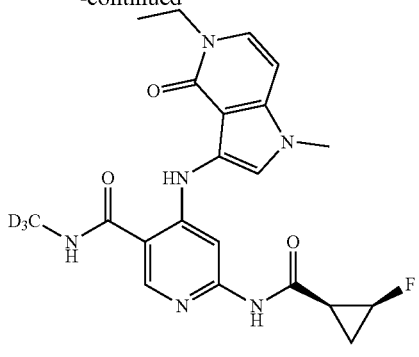

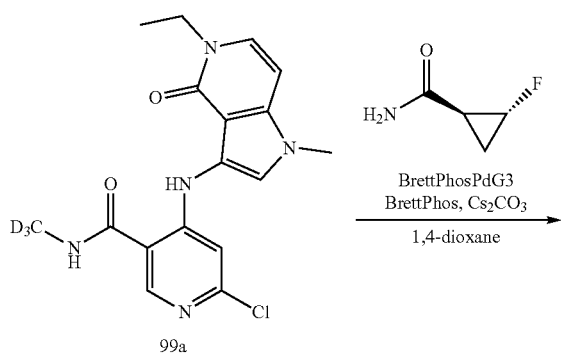

Step 1. 4-[(5-Ethyl-1-methyl-4-oxo-pyrrolo[3,2-c]pyridin-3-yl)amino]-6-[[(1S,2R)-2-fluorocyclopropanecarbonyl]amino]-N-(methyl-d₃)pyridine-3-carboxamide (103)

Compound 103 (6 mg, 10% yield), a white solid, was synthesized by utilizing a similar preparative procedure of Step 3 in Example 49 with 99a (50 mg, 0.14 mmol) and (1S,2R)-2-fluorocyclopropanecarboxamide (71 mg, 0.69 mmol) as starting materials. LC-MS (Method 1) $t_R$=2.96 min, m/z (M+H)⁺=430.2. ¹H NMR (400 MHz, DMSO-d₆) δ 10.89 (s, 1H), 10.88 (s, 1H), 8.44 (s, 1H), 8.40 (s, 1H), 7.93 (s, 1H), 7.34 (d, J=7.2 Hz, 1H), 7.00 (s, 1H), 6.53 (d, J=7.0 Hz, 1H), 4.99-4.81 (m, 1H), 3.92 (q, J=7.2 Hz, 2H), 3.67 (s, 3H), 2.63-2.52 (m, 1H), 1.56-1.46 (m, 1H), 1.30-1.18 (m, 4H).

Example 104

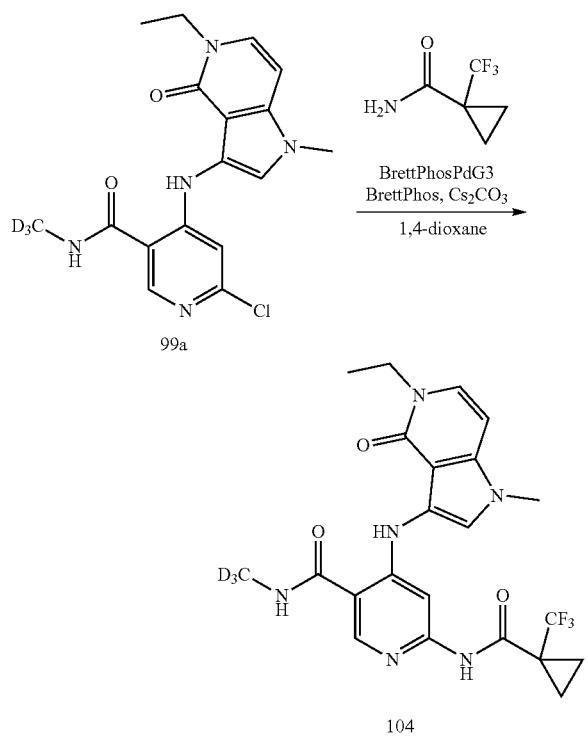

Step 1. 4-[(5-Ethyl-1-methyl-4-oxo-pyrrolo[3,2-c]pyridin-3-yl)amino]-N-(methyl-d₃)-6-[[1-(trifluoromethyl)cyclopropanecarbonyl]amino]pyridine-3-carboxamide (104)

Compound 104 (28 mg, 42% yield), a white solid, was synthesized by utilizing a similar preparative procedure of Step 3 in Example 49 with 99a (50 mg, 0.14 mmol) and 1-(trifluoromethyl)cyclopropanecarboxamide (105 mg, 0.69 mmol) as starting materials. LC-MS (Method 1) $t_R$=2.49 min, m/z (M+H)⁺=480.2. ¹H NMR (400 MHz, DMSO-d₆) δ 10.90 (s, 1H), 10.17 (s, 1H), 8.45 (s, 2H), 7.90 (s, 1H), 7.35 (d, J=8.0 Hz, 1H), 7.06 (s, 1H), 6.54 (d, J=7.2 Hz, 1H), 3.92 (q, J=7.2 Hz, 2H), 3.70 (s, 3H), 1.50-1.49 (m, 2H), 1.30-1.27 (m, 2H), 1.20 (t, J=7.2 Hz, 3H).

Example 105

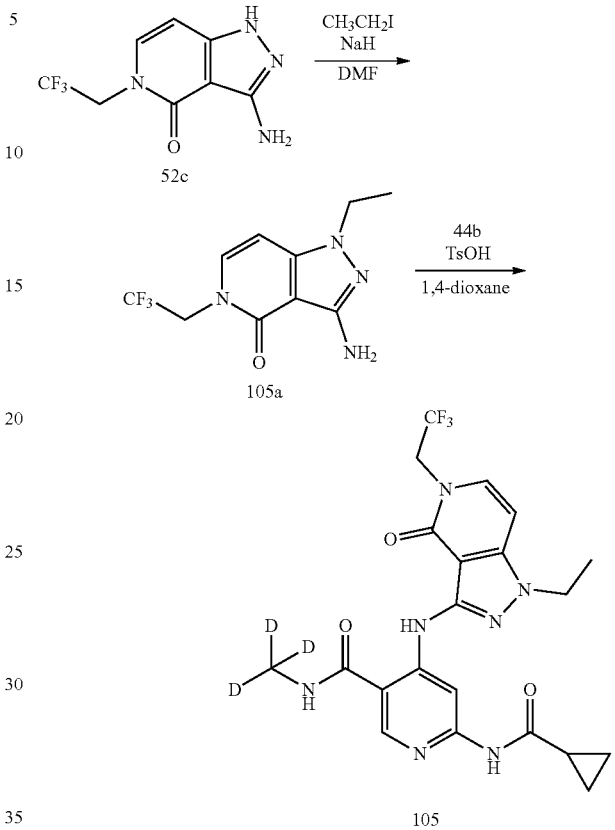

Step 1. 3-Amino-1-ethyl-5-(2,2,2-trifluoroethyl)-1,5-dihydro-4H-pyrazolo[4,3-c]pyridin-4-one (105a)

To a solution of 52c (200 mg, 0.86 mmol) in DMF (2 mL) was added NaH (39.6 mg, 1.0 mmol, 60% purity in mineral oil) at 0° C., the mixture was stirred at 25° C. for 30 min, then iodoethane (161 mg, 1.0 mmol) was added, and stirred at 25° C. for 4 h. The mixture was diluted with H₂O (10 mL), extracted with EA (10 mL*3), washed with brine, dried over Na₂SO₄ and concentrated to get the crude compound 176a (190 mg, 84% yield) as a brown oil. LC-MS (Method 4) $t_R$=2.46 min, m/z (M+H)⁺=261.1.

Step 2 6-(Cyclopropanecarboxamido)-4-((1-ethyl-4-oxo-5-(2,2,2-trifluoroethyl)-4,5-dihydro-1H-pyrazolo[4,3-c]pyridin-3-yl)amino)-N-(methyl-d₃)nicotinamide (105)

A mixture of 105a (50.68 mg, 0.19 mmol), 44b (50 mg, 0.19 mmol) and pTSA (37 mg, 0.19 mmol) in 1,4-dioxane (1 mL) was stirred at 100° C. for 16 h. The mixture was concentrated and DIPEA (0.2 mL) and MeOH (2 mL) was added. The mixture was stirred at 25° C. for 1 h and filtered to get the compound 105 (35 mg, 37% yield) as a white solid. LC-MS (Method 4) $t_R$=3.14 min, m/z (M+H)⁺=481.3. ¹H NMR (400 MHz, DMSO-d₆) δ 11.69 (s, 1H), 10.69 (s, 1H), 9.33 (s, 1H), 8.51 (s, 1H), 8.50 (s, 1H), 7.46 (d, J=7.6 Hz, 1H), 6.71 (d, J=7.6 Hz, 1H), 4.83 (q, J=9.2 Hz, 2H), 4.15 (q, J=7.2 Hz, 2H), 2.02-1.96 (m, 1H), 1.43 (t, J=7.2 Hz, 3H), 0.81-0.75 (m, 4H).

Example 106

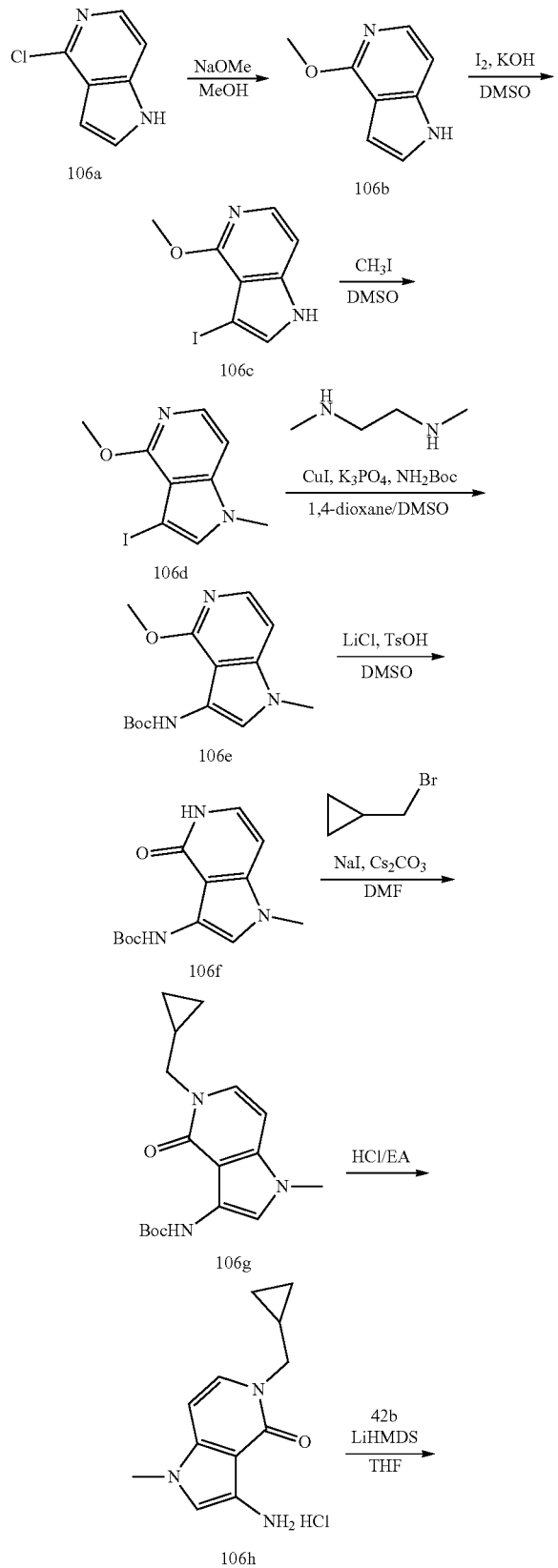

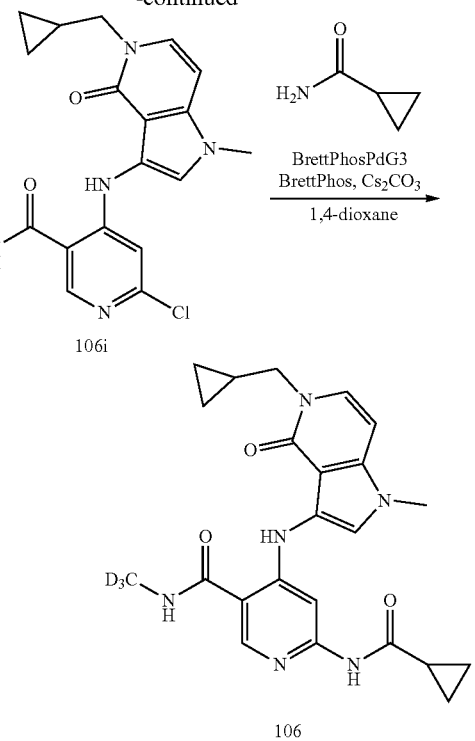

Step 1. 4-Methoxy-1H-pyrrolo[3,2-c]pyridine (106b)

To a mixture of 106a (50.0 g, 327.69 mmol) and sodium methoxide (30.0 g, 555.56 mmol) in MeOH (100 mL) was stirred at 120° C. overnight. The solvent was evaporated under reduced pressure. The residue was purified by flash chromatography on silica gel (PE/EtOAc=10/1) to give the title compound 106b (10.8 g, 22% yield) as a white solid. $^1$H NMR (400 MHz, DMSO-$d_6$) δ 11.49 (s, 1H), 7.71 (d, J=6.4 Hz, 1H), 7.30 (t, J=2.4 Hz, 1H), 7.04 (d, J=6.0 Hz, 1H), 6.48 (t, J=2.0 Hz, 1H), 3.96 (s, 3H).

Step 2. 3-Iodo-4-methoxy-1H-pyrrolo[3,2-c]pyridine (106c)

To a solution of 106b (10.8 g, 72.89 mmol) in DMF (80 mL) was added KOH (8.18 g, 145.79 mmol) at 0° C. for 5 min. Then I2 (18.44 g, 72.89 mmol) was added to the mixture. The reaction mixture was stirred at 0° C. for 30 minutes. The reaction mixture was used directly in next step without working up. LC-MS (Method 3) $t_R$=1.33 min, m/z (M+H)$^+$=275.1.

Step 3. 3-Iodo-4-methoxy-1-methyl-1H-pyrrolo[3,2-c]pyridine (106d)

To a solution of 106c (19.98 g, 72.90 mmol) in DMF (80 mL) was added CH$_3$I (15.52 g, 109.36 mmol) at 0° C. The mixture was stirred at 0° C. for 30 min. The reaction mixture was diluted with water (400 mL) and the formed solid was filtered to afford 106d (19.8 g, 94% yield) as a brown solid. LC-MS (Method 3) $t_R$=1.28 min, m/z (M+H)$^+$=289.1.

Step 4. Tert-butyl (4-methoxy-1-methyl-1H-pyrrolo[3,2-c]pyridin-3-yl)carbamate (106e)

Compound 106e (5.66 g, 68% yield), a yellow solid, was synthesized by utilizing a similar preparative procedure of Step 4 in Example 1 with 106d (8.6 g, 29.85 mmol) and tert-butyl carbamate (6.99 g, 59.70 mmol) as starting materials. LC-MS (Method 3) $t_R$=1.65 min, m/z (M+H)$^+$=278.3.

Step 5. Tert-butyl (1-methyl-4-oxo-4,5-dihydro-1H-pyrrolo[3,2-c]pyridin-3-yl)carbamate (106f)

A mixture of 106e (6.0 g, 21.64 mmol), LiCl (1.19 g, 28.13 mmol) and TsOH·H$_2$O (5.34 g, 28.13 mmol) in DMSO (50 mL) was stirred at 60° C. for 1 h. The reaction mixture was diluted with water (150 mL) and extracted with EtOAc (50 mL*3). The combined organic phase were dried over anhydrous Na$_2$SO$_4$, filtered and concentrated. The residue was purified by flash chromatography on silica gel (PE/EtOAc=2/1) to give the title compound 106f (4.1 g, 72% yield) as a white solid. LC-MS (Method 3) $t_R$=1.28 min, m/z (M+H)$^+$=264.2.

Step 6. Tert-butyl (5-(cyclopropylmethyl)-1-methyl-4-oxo-4,5-dihydro-1H-pyrrolo[3,2-c]pyridin-3-yl)carbamate (106g)

A mixture of 106f (300 mg, 0.80 mmol), (bromomethyl)cyclopropane (215 mg, 1.60 mmol), NaI (24 mg, 0.16 mmol) and Cs$_2$CO$_3$ (780 mg, 2.40 mmol) in DMF (5 mL) was stirred at 70° C. for 4 h. The reaction mixture was diluted with water (10 mL) and extracted with EtOAc (20 mL*3). The combined organic phase was dried over anhydrous Na$_2$SO$_4$ and filtered. The filtrate was concentrated to give the title compound 106g (127 mg, 50% yield) as a yellow solid. LC-MS (Method 3) $t_R$=1.61 min, m/z (M+H−56)$^+$=262.2.

Step 7. 3-Amino-5-(cyclopropylmethyl)-1-methyl-1,5-dihydro-4H-pyrrolo[3,2-c]pyridin-4-one hydrochloride (106h)

Compound 106h (101 mg, 50% yield), a yellow solid, was synthesized by utilizing a similar preparative procedure of Step 5 in Example 1 with 106g (253 mg, 0.80 mmol) as the starting material. LC-MS (Method 3) $t_R$=1.25 min, m/z (M+H)$^+$=218.2.

Step 8. 6-Chloro-4-((5-(cyclopropylmethyl)-1-methyl-4-oxo-4,5-dihydro-1H-pyrrolo[3,2-c]pyridin-3-yl)amino)-N-(methyl-d$_3$)nicotinamide (106i)

Compound 106i (100 mg, 52% yield), a brown solid, was synthesized by utilizing a similar preparative procedure of Step 5 in Example 50 with 106h (125 mg, 0.49 mmol) and 42b (103 mg, 0.49 mmol) as starting materials. LC-MS (Method 3) $t_R$=1.44 min, m/z (M+H)$^+$=389.5.

Step 9. 6-(Cyclopropanecarboxamido)-4-((5-(cyclopropylmethyl)-1-methyl-4-oxo-4,5-dihydro-1H-pyrrolo[3,2-c]pyridin-3-yl)amino)-N-(methyl-d$_3$)nicotinamide (106)

Compound 106 (6 mg, 11% yield), a white solid, was synthesized by utilizing a similar preparative procedure of Step 3 in Example 49 with 106i (50 mg, 0.13 mmol) and cyclopropanecarboxamide (55 mg, 0.64 mmol) as starting materials. LC-MS (Method 1) $t_R$=3.18 min, m/z (M+H)$^+$=438.3. $^1$H NMR (400 MHz, DMSO-d$_6$) δ 10.89 (s, 1H), 10.70 (s, 1H), 8.43 (s, 1H), 8.37 (s, 1H), 8.00 (s, 1H), 7.37 (d, J=7.2 Hz, 1H), 7.02 (s, 1H), 6.52 (d, J=7.2 Hz, 1H), 3.76 (d, J=7.2 Hz, 2H), 3.69 (s, 3H), 2.03-1.99 (m, 1H), 1.24-1.18 (m, 1H), 0.86-0.79 (m, 4H), 0.45-0.42 (m, 2H), 0.38-0.36 (m, 2H).

Example 107

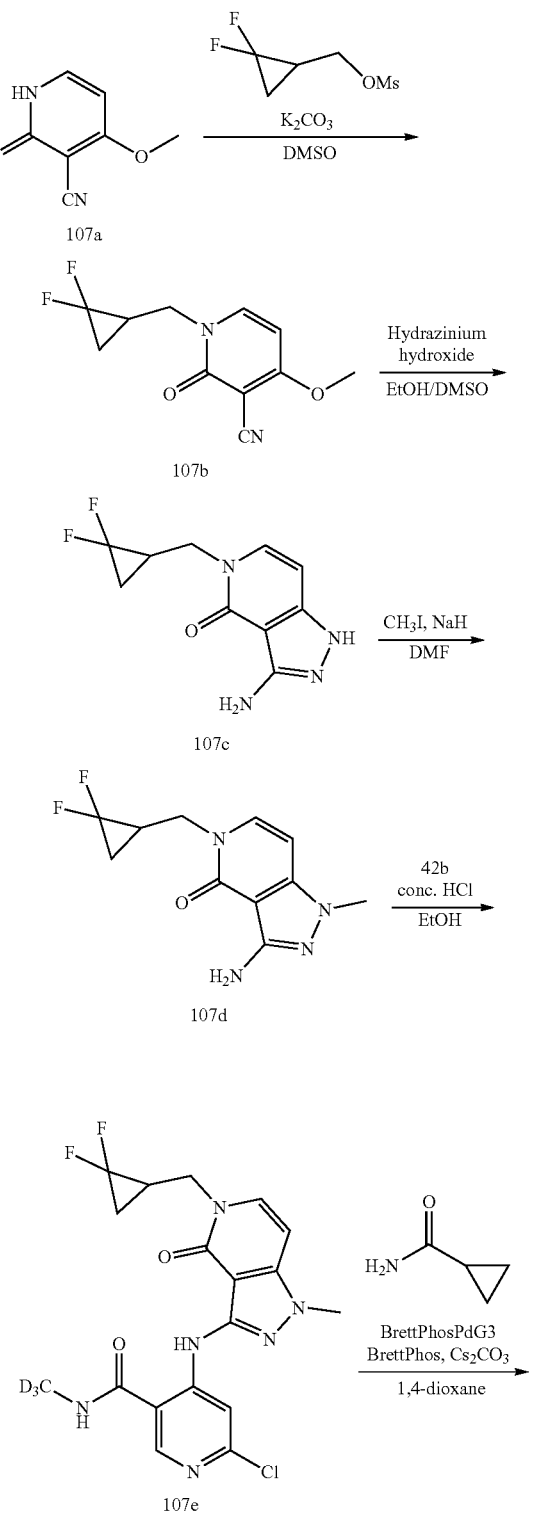

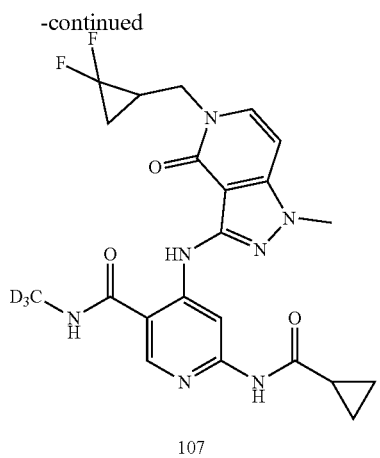

107

Step 1. 1-((2,2-Difluorocyclopropyl)methyl)-4-methoxy-2-oxo-1,2-dihydropyridine-3-carbonitrile (107b)

A mixture of 107a (2.42 g, 16.11 mmol), (2,2-difluorocyclopropyl)methyl methanesulfonate (1.5 g, 8.06 mmol), $K_2CO_3$ (2.22 g, 16.11 mmol) in DMSO (30 mL) was stirred at 40° C. for 4 h. After cooling to r.t., the reaction mixture was used in next step without purification. LC-MS (Method 3) $t_R$=1.27 min, m/z (M+H)⁺=241.0.

Step 2. 3-Amino-5-((2,2-difluorocyclopropyl)methyl)-1H-pyrazolo[4,3-c]pyridin-4-(5H)-one (107c)

A mixture of 107b (1.94 g, 8.08 mmol), hydrazinium hydroxide solution (2 mL) in EtOH/DMSO (50 mL, v/v=2/3) was stirred at 100° C. for 12 h. The mixture was concentrated. The title compound was purified by Prep-HPLC (Method A) to afford 107c (500 mg, 26% yield) as a yellow solid. LC-MS (Method 3) $t_R$=1.25 min, m/z (M+H)⁺=241.0.

Step 3. 3-Amino-5-((2,2-difluorocyclopropyl)methyl)-1-methyl-1H-pyrazolo[4,3-c]pyridin-4-(5H)-one (107d)

To a solution of 107c (500 mg, 2.08 mmol) in anhydrous DMF (5 mL) was added NaH (74.9 mg, 1.87 mmol, 60% purity in mineral oil) at 0° C. After stirring at 0° C. for 30 min, to the mixture was added iodomethane (265.9 mg, 1.87 mmol) at 0° C. The reaction was stirred at r.t. for 5 h. The reaction mixture was diluted with $H_2O$ (5 mL) and extracted with EtOAc (5 mL*2). The organic layer was dried over $Na_2SO_4$, filtered, and the filtrate was concentrated. The title compound was purified by Prep-HPLC (Method A) to afford 107d (130 mg, 25% yield) as a yellow oil. LC-MS (Method 3) $t_R$=1.27 min, m/z (M+H)⁺=255.0.

Step 4. 6-Chloro-4-((5-((2,2-difluorocyclopropyl)methyl)-1-methyl-4-oxo-4,5-dihydro-1H-pyrazolo[4,3-c]pyridin-3-yl)amino)-N-(methyl-d₃)nicotinamide (107e)

Compound 107e (10 mg, 5% yield), a white solid, was synthesized by utilizing a similar preparative procedure of Step 1 in Example 98 with 107d (130 mg, 0.5 mmol) and 42b (117 mg, 0.56 mmol) as starting materials. LC-MS (Method 3) $t_R$=1.61 min, m/z (M+H)⁺=425.9.

Step 5. 6-(Cyclopropanecarboxamido)-4-((5-((2,2-difluorocyclopropyl)methyl)-1-methyl-4-oxo-4,5-dihydro-1H-pyrazolo[4,3-c]pyridin-3-yl)amino)-N-(methyl-d₃)nicotinamide (107)

Compound 107 (2.5 mg, 11% yield), a white solid, was synthesized by utilizing a similar preparative procedure of Step 3 in Example 49 with 107e (20 mg, 0.047 mmol) and cyclopropanecarboxamide (20 mg, 0.23 mmol) as starting materials. LC-MS (Method 2) $t_R$=3.20 min, m/z (M+H)⁺=475.1. ¹H NMR (400 MHz, DMSO-d₆) δ 11.66 (s, 1H), 10.70 (s, 1H), 9.25 (s, 1H), 8.56 (s, 1H), 8.55 (s, 1H), 7.52 (d, J=7.6 Hz, 1H), 6.63 (d, J=7.6 Hz, 1H), 4.05-4.04 (m, 2H), 3.84 (s, 3H), 2.33-2.32 (m, 2H), 2.22-2.19 (m, 1H), 2.03-1.99 (m, 1H), 0.82-0.80 (m, 4H).

Example 108

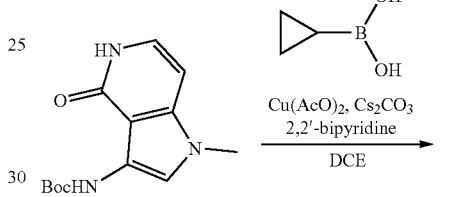

108f

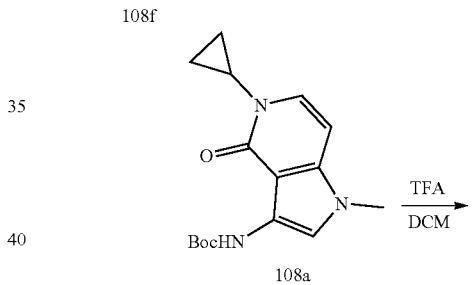

108a

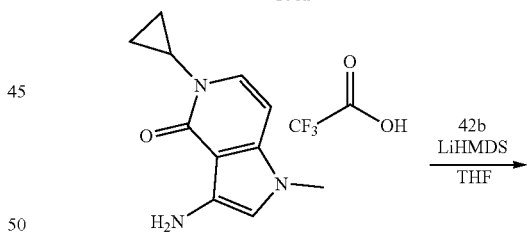

108b

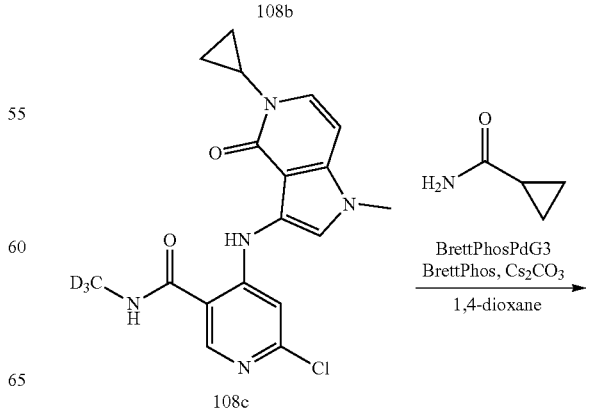

108c

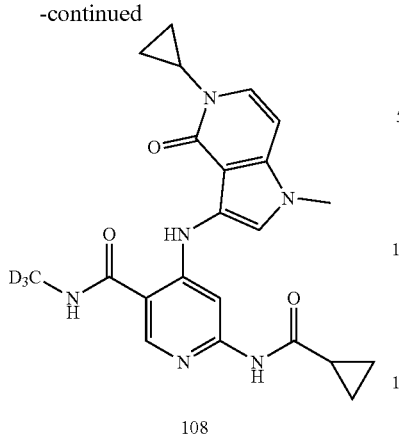

108

Step 1. Tert-butyl (5-cyclopropyl-1-methyl-4-oxo-4,5-dihydro-1H-pyrrolo[3,2-c]pyridin-3-yl)carbamate (108a)

A mixture of 106f (440 mg, 1.67 mmol), cyclopropylboronic acid (359 mg, 4.18 mmol), $Na_2CO_3$ (709 mg, 6.68 mmol), 2,2'-bipyridine (1.04 g, 6.68 mmol) and copper (II) acetate (455 mg, 2.51 mmol) in 10 mL of 1,2-dichloroethane was stirred at 70° C. overnight. The mixture was diluted with $H_2O$ (10 mL) and extracted with EtOAc (15 mL*2). The combined organic layer was concentrated. The residue was purified by flash chromatography on silica gel (PE/EtOAc=4/1) to give the title compound 108a (340 mg, 67% yield) as a yellow solid. LC-MS (Method 3) $t_R$=1.49 min, m/z $(M+H)^+$=304.3.

Step 2. 3-Amino-5-cyclopropyl-1-methyl-1,5-dihydro-4H-pyrrolo[3,2-c]pyridin-4-one trifluoroacetic acid (108b)

To a solution of 108a (400 mg, 1.32 mmol) in DCM (4 mL) was added TFA (1 mL). The mixture was stirred at r.t. for 1 h. The mixture was concentrated to give the title compound 108b (400 mg, 96% yield) as a brown solid. LC-MS (Method 3) $t_R$=0.29 min, m/z $(M+H)^+$=204.3.

Step 3. 6-Chloro-4-((5-cyclopropyl-1-methyl-4-oxo-4,5-dihydro-1H-pyrrolo[3,2-c]pyridin-3-yl)amino)-N-(methyl-$d_3$)nicotinamide (108c)

Compound 108c (60 mg, 18% yield), a yellow solid, was synthesized by utilizing a similar preparative procedure of Step 5 in Example 50 with 108b (282 mg, 0.89 mmol) and 42b (184 mg, 0.89 mmol) as starting materials. LC-MS (Method 3) $t_R$=1.30 min, m/z $(M+H)^+$=375.3.

Step 4. 6-(Cyclopropanecarboxamido)-4-((5-cyclopropyl-1-methyl-4-oxo-4,5-dihydro-1H-pyrrolo[3,2-c]pyridin-3-yl)amino)-N-(methyl-$d_3$)nicotinamide (108)

Compound 108 (10 mg, 15% yield), a white solid, as synthesized by utilizing a similar preparative procedure of Step 3 in Example 49 with 108c (60 mg, 0.16 mmol) and cyclopropanecarboxamide (34 mg, 0.40 mmol) as starting materials. LC-MS (Method 2) $t_R$=2.97 min, m/z $(M+H)^+$=424.2. $^1$H NMR (400 MHz, DMSO-$d_6$) δ 10.90 (s, 1H), 10.72 (s, 1H), 8.43 (s, 1H), 8.38 (s, 1H), 7.99 (s, 1H), 7.20 (d, J=7.2 Hz, 1H), 7.01 (s, 1H), 6.47 (d, J=7.2 Hz, 1H), 3.68 (s, 3H), 3.24-3.21 (m, 1H), 2.07-1.97 (m, 1H), 1.02-0.94 (m, 2H), 0.87-0.77 (m, 6H).

Example 109

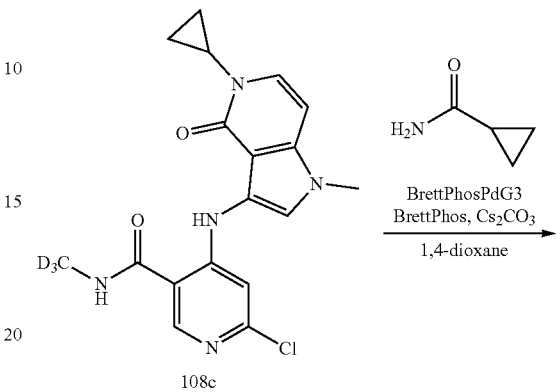

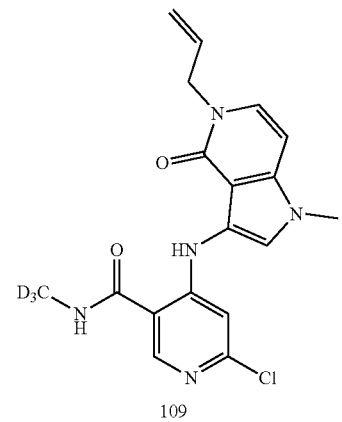

Step 1. 4-((5-Allyl-1-methyl-4-oxo-4,5-dihydro-1H-pyrrolo[3,2-e]pyridin-3-yl)amino)-6-(cyclopropanecarboxamido)-N-(methyl-$d_3$)nicotinamide (109)

Compound 109 (2 mg, 3% yield), a white solid, was synthesized by utilizing a similar preparative procedure of Step 3 in Example 49 with 108c (60 mg, 0.16 mmol) and cyclopropanecarboxamide (34 mg, 0.40 mmol) as starting materials. LC-MS (Method 2) $t_R$=3.07 min, m/z $(M+H)^+$=424.2. $^1$H NMR (400 MHz, DMSO-$d_6$) δ 10.88 (s, 1H), 10.70 (s, 1H), 8.42 (s, 1H), 8.37 (s, 1H), 7.99 (s, 1H), 7.25 (d, J=7.2 Hz, 1H), 7.03 (s, 1H), 6.56 (d, J=7.6 Hz, 1H), 5.97-5.90 (m, 1H), 5.13 (d, J=10.4 Hz, 1H), 5.02 (d, J=17.2 Hz, 1H), 4.53 (d, J=5.2 Hz, 2H), 3.68 (s, 3H), 2.03-1.99 (m, 1H), 0.85-0.78 (m, 4H).

Example 110

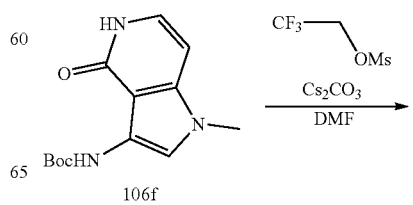

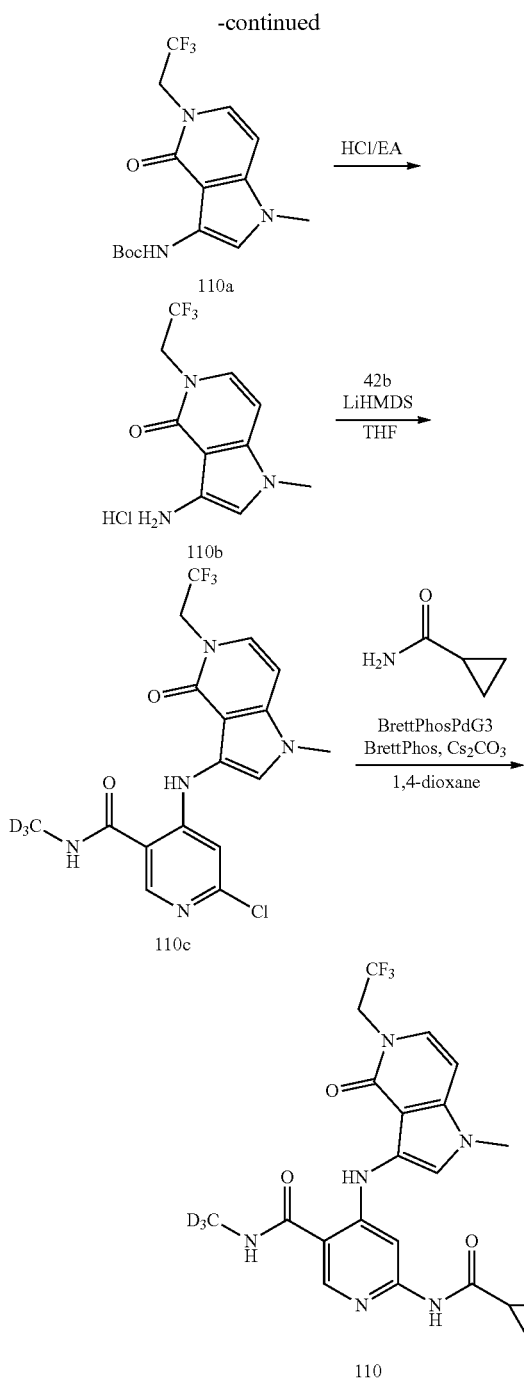

compound 110a (135 mg, 37% yield) as a yellow solid. LC-MS (Method 3) $t_R$=1.51 min, m/z (M+H)⁺=346.3.

Step 2. 3-Amino-1-methyl-5-(2,2,2-trifluoroethyl)-1,5-dihydro-4H-pyrrolo[3,2-c]pyridin-4-one hydrochloride (110b)

Compound 110b (91 mg, 83% yield), a white solid, was synthesized by utilizing a similar preparative procedure of Step 5 in Example 1 with 110a (135 mg, 0.39 mmol) as the starting material. LC-MS (Method 3) $t_R$=0.95 min, m/z (M+H)⁺=246.1.

Step 3. 6-Chloro-N-(methyl-d₃)-4-((1-methyl-4-oxo-5-(2,2,2-trifluoroethyl)-4,5-dihydro-1H-pyrrolo[3,2-c]pyridin-3-yl)amino)nicotinamide (110c)

Compound 110c (124 mg, 81% yield), a brown solid, was synthesized by utilizing a similar preparative procedure of Step 5 in Example 50 with 110b (90 mg, 0.37 mmol) and 42b (82 mg, 0.37 mmol) as starting materials. LC-MS (Method 3) $t_R$=1.24 min, m/z (M+H)⁺=417.1.

Step 4. 6-(Cyclopropanecarboxamido)-N-(methyl-d₃)-4-((1-methyl-4-oxo-5-(2,2,2-trifluoroethyl)-4,5-dihydro-1H-pyrrolo[3,2-e]pyridin-3-yl)amino)nicotinamide (110)

Compound 110 (4 mg, 5% yield), a white solid, as synthesized by utilizing a similar preparative procedure of Step 3 in Example 49 with 110c (75 mg, 0.18 mmol) and cyclopropanecarboxamide (46 mg, 0.54 mmol) as starting materials. LC-MS (Method 2) $t_R$=3.24 min, m/z (M+H)⁺=466.2. ¹H NMR (400 MHz, DMSO-d₆) δ 10.92 (s, 1H), 10.73 (s, 1H), 8.45 (s, 1H), 8.41 (s, 1H), 8.01 (s, 1H), 7.34 (d, J=7.2 Hz, 1H), 7.08 (s, 1H), 6.66 (d, J=7.2 Hz, 1H), 4.85 (q, J=9.2 Hz, 2H), 3.72 (s, 3H), 2.06-1.87 (m, 1H), 0.87-0.75 (m, 4H).

Example 111

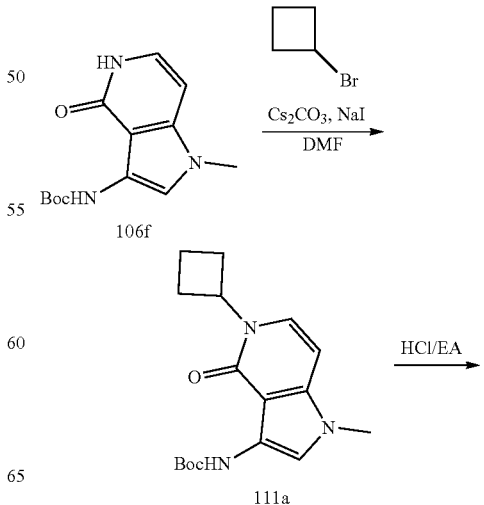

Step 1. Tert-butyl (1-methyl-4-oxo-5-(2,2,2-trifluoroethyl)-4,5-dihydro-1H-pyrrolo[3,2-c]pyridin-3-yl)carbamate (110a)

To a solution of 106f (400 mg, 1.06 mmol) and Cs₂CO₃ (1.04 g, 3.19 mmol) in DMF (4 mL) was added 2,2,2-trifluoroethyl methanesulfonate (227 mg, 1.28 mmol) at r.t. The mixture was stirred at 80° C. for 16 h. The reaction mixture was diluted with H₂O (5 mL) and extracted with EtOAc (8 mL*3). The combined organic phase was concentrated and the residue was purified by flash chromatography on silica gel (PE/EtOAc=5/1) to afford the title

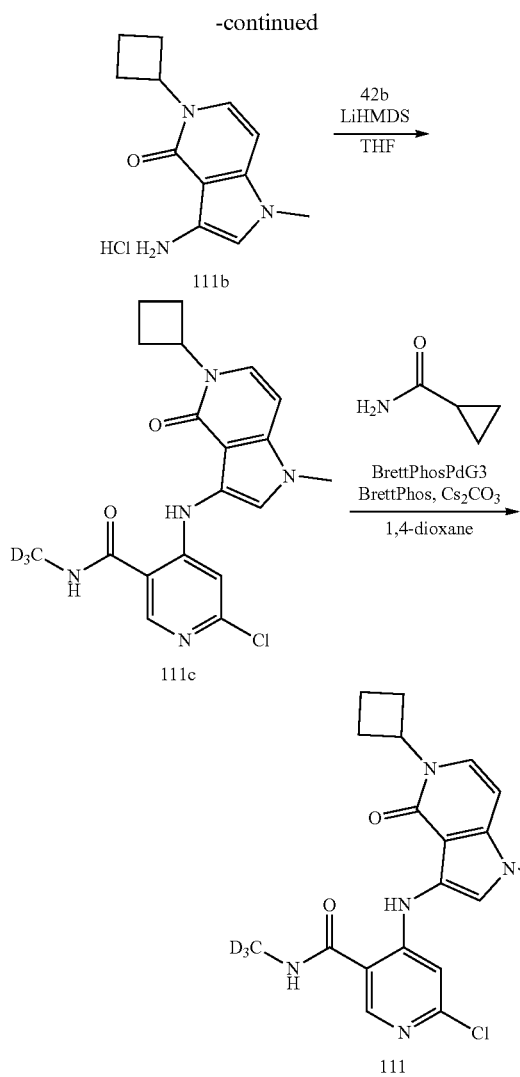

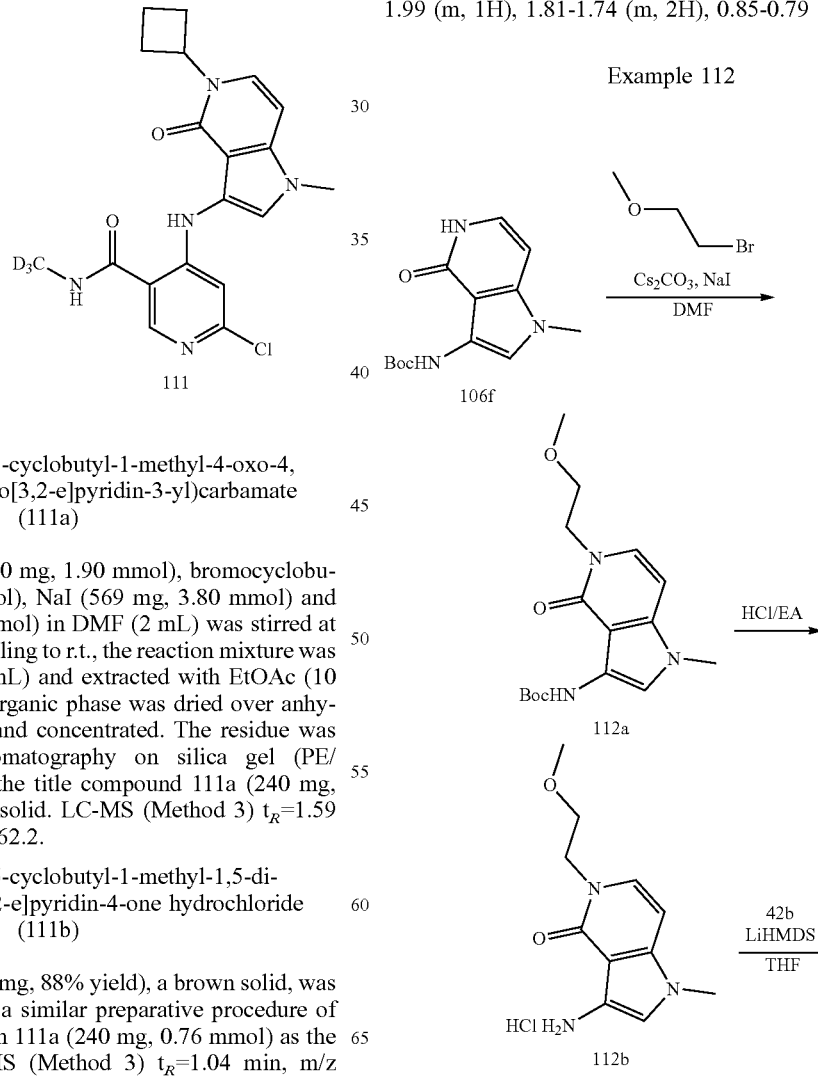

Step 3. 6-Chloro-4-((5-cyclobutyl-1-methyl-4-oxo-4,5-dihydro-1H-pyrrolo[3,2-e]pyridin-3-yl)amino)-N-(methyl-d$_3$)nicotinamide (111c)

Compound 111c (96 mg, 45% yield), a brown solid, was synthesized by utilizing a similar preparative procedure of Step 5 in Example 50 with 111b (120 mg, 0.55 mmol) and 42b (115 mg, 0.55 mmol) as starting materials. LC-MS (Method 3) $t_R$=1.37 min, m/z (M+H)$^+$=389.4.

Step 4. 4-((5-Cyclobutyl-1-methyl-4-oxo-4,5-dihydro-1H-pyrrolo[3,2-e]pyridin-3-yl)amino)-6-(cyclopropanecarboxamido)-N-(methyl-d$_3$)nicotinamide (111)

Compound 111 (15 mg, 27% yield), a white solid, was synthesized by utilizing a similar preparative procedure of Step 3 in Example 49 with 111c (50 mg, 0.13 mmol) and cyclopropanecarboxamide (55 mg, 0.64 mmol) as starting materials. LC-MS (Method 2) $t_R$=2.65 min, m/z (M+H)$^+$=438.2. $^1$H NMR (400 MHz, DMSO-d$_6$) δ 10.88 (s, 1H), 10.71 (s, 1H), 8.42 (s, 1H), 8.37 (s, 1H), 7.99 (s, 1H), 7.51 (d, J=8.0 Hz, 1H), 7.01 (s, 1H), 6.57 (d, J=7.6 Hz, 1H), 5.21-5.17 (m, 1H), 3.69 (s, 3H), 2.31-2.24 (m, 4H), 2.02-1.99 (m, 1H), 1.81-1.74 (m, 2H), 0.85-0.79 (m, 4H).

Example 112

Step 1. Tert-butyl (5-cyclobutyl-1-methyl-4-oxo-4,5-dihydro-1H-pyrrolo[3,2-e]pyridin-3-yl)carbamate (111a)

A mixture of 106f (500 mg, 1.90 mmol), bromocyclobutane (513 mg, 3.80 mmol), NaI (569 mg, 3.80 mmol) and Cs$_2$CO$_3$ (1.86 g, 5.70 mmol) in DMF (2 mL) was stirred at 90° C. for 36 h. After cooling to r.t., the reaction mixture was diluted with water (20 mL) and extracted with EtOAc (10 mL*3). The combined organic phase was dried over anhydrous Na$_2$SO$_3$, filtered and concentrated. The residue was purified by flash chromatography on silica gel (PE/EtOAc=10/1) to afford the title compound 111a (240 mg, 40% yield) as a yellow solid. LC-MS (Method 3) $t_R$=1.59 min, m/z (M+H−56)$^+$=262.2.

Step 2. 3-Amino-5-cyclobutyl-1-methyl-1,5-dihydro-4H-pyrrolo[3,2-e]pyridin-4-one hydrochloride (111b)

Compound 111b (170 mg, 88% yield), a brown solid, was synthesized by utilizing a similar preparative procedure of Step 5 in Example 1 with 111a (240 mg, 0.76 mmol) as the starting material. LC-MS (Method 3) $t_R$=1.04 min, m/z (M+H)$^+$=218.2.

-continued

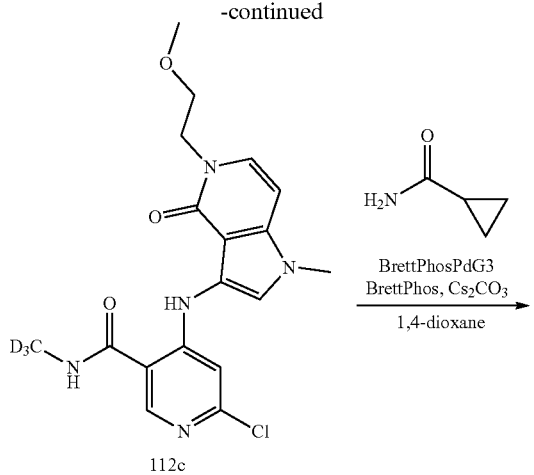

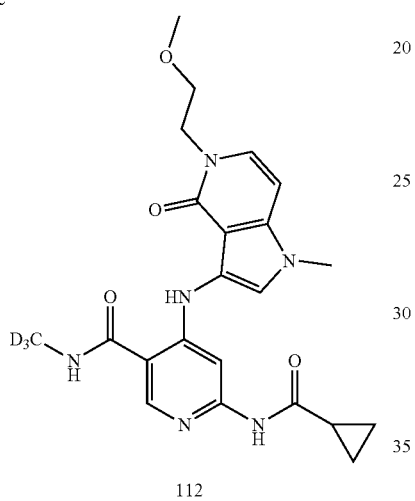

Step 1. Tert-butyl (5-(2-methoxyethyl)-1-methyl-4-oxo-4,5-dihydro-1H-pyrrolo[3,2-c]pyridin-3-yl)carbamate (112a)

Compound 112a (210 mg, 69% yield), a yellow solid, was synthesized by utilizing a similar preparative procedure of Step 6 in Example 106 with 106f (250 mg, 0.95 mmol) and 1-bromo-2-methoxyethane (198 mg, 1.42 mmol) as starting materials. LC-MS (Method 3) $t_R$=1.33 min, m/z $(M+H)^+$=322.2.

Step 2. 3-Amino-5-(2-methoxyethyl)-1-methyl-1,5-dihydro-4H-pyrrolo[3,2-c]pyridin-4-one hydrochloride (112b)

Compound 112b (170 mg, 88% yield), a white solid, was synthesized by utilizing a similar preparative procedure of Step 5 in Example 1 with 112a (210 mg, 0.65 mmol) as the starting material. LC-MS (Method 3) $t_R$=0.33 min, m/z $(M+H)^+$=222.2.

Step 3. 6-Chloro-4-((5-(2-methoxyethyl)-1-methyl-4-oxo-4,5-dihydro-1H-pyrrolo[3,2-c]pyridin-3-yl)amino)-N-(methyl-d$_3$)nicotinamide (112c)

Compound 112c (160 mg, 75% yield), a yellow solid, was synthesized by utilizing a similar preparative procedure of Step 5 in Example 50 with 112b (160 mg, 0.54 mmol) and 42b (136 mg, 0.65 mmol) as starting materials. LC-MS (Method 3) $t_R$=1.18 min, m/z $(M+H)^+$=393.2.

Step 4. 6-(Cyclopropanecarboxamido)-4-((5-(2-methoxyethyl)-1-methyl-4-oxo-4,5-dihydro-1H-pyrrolo[3,2-c]pyridin-3-yl)amino)-N-(methyl-d$_3$) nicotinamide (112)

Compound 112 (40 mg, 71% yield), a white solid, was synthesized by utilizing a similar preparative procedure of Step 3 in Example 49 with 16d (50 mg, 0.13 mmol) and cyclopropanecarboxamide (54 mg, 0.64 mmol) as starting materials. LC-MS (Method 2) $t_R$=2.64 min, m/z $(M+H)^+$=442.2. $^1$H NMR (400 MHz, DMSO-d$_6$) δ 10.88 (s, 1H), 10.71 (s, 1H), 8.43 (s, 1H), 8.37 (s, 1H), 8.00 (s, 1H), 7.28 (d, J=7.2 Hz, 1H), 7.02 (s, 1H), 6.50 (d, J=7.6 Hz, 1H), 4.06 (t, J=5.2 Hz, 2H), 3.68 (s, 3H), 3.55 (t, J=5.2 Hz, 2H), 3.23 (s, 3H), 2.03-1.99 (m, 1H), 0.84-0.78 (m, 4H).

Example 113

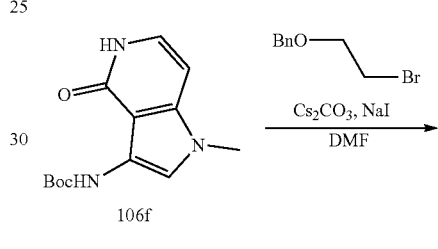

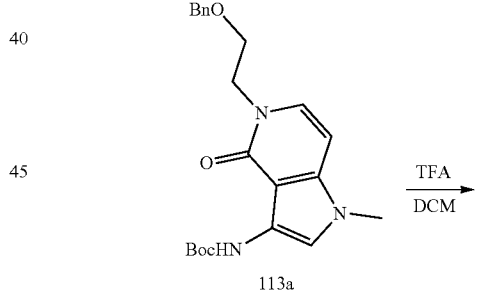

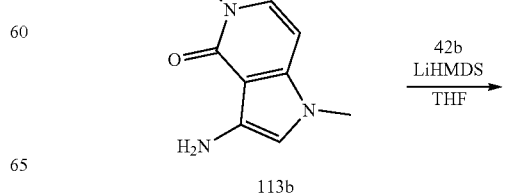

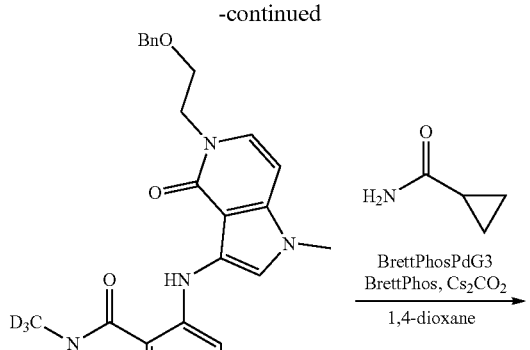

Step 2. 3-Amino-5-(2-(benzyloxy)ethyl)-1-methyl-1,5-dihydro-4H-pyrrolo[3,2-c]pyridin-4-one trifluoroacetic acid (113b)

Compound 113b (300 mg, 58% yield), a brown oil, was synthesized by utilizing a similar preparative procedure of Step 2 in Example 108 with 113a (500 mg, 1.26 mmol) as the starting material. LC-MS (Method 3) $t_R$=1.28 min, m/z $(M+H)^+$=298.2.

Step 3. 4-((5-(2-(Benzyloxy)ethyl)-1-methyl-4-oxo-4,5-dihydro-1H-pyrrolo[3,2-c]pyridin-3-yl)amino)-6-chloro-N-(methyl-$d_3$)nicotinamide (113c)

Compound 113c (85 mg, 30% yield), a yellow solid, was synthesized by utilizing a similar preparative procedure of Step 5 in Example 50 with 113b (250 mg, 0.61 mmol) and 42b (140 mg, 0.67 mmol) as starting materials. LC-MS (Method 3) $t_R$=1.40 min, m/z $(M+H)^+$=469.0.

Step 4. 4-((5-(2-(Benzyloxy)ethyl)-1-methyl-4-oxo-4,5-dihydro-1H-pyrrolo[3,2-c]pyridin-3-yl)amino)-6-(cyclopropanecarboxamido)-N-(methyl-$d_3$)nicotinamide (113d)

Compound 113d (90 mg, 96% yield), a yellow solid, was synthesized by utilizing a similar preparative procedure of Step 3 in Example 49 with 113c (85 mg, 0.18 mmol) and cyclopropanecarboxamide (77 mg, 0.91 mmol) as starting materials. LC-MS (Method 3) $t_R$=1.50 min, m/z $(M+H)^+$=518.7.

Step 5. 6-(Cyclopropanecarboxamido)-4-((5-(2-hydroxyethyl)-1-methyl-4-oxo-4,5-dihydro-1H-pyrrolo[3,2-c]pyridin-3-yl)amino)-N-(methyl-$d_3$)nicotinamide (113)

A solution of 113d (85 mg, 0.16 mmol) in TFA (1 mL) was stirred at 60° C. for 5 h. The reaction was cooled to r.t. and the solvent was evaporated. The reaction was purified by flash chromatography (DCM/MeOH=10/1) to give the title compound 113 (7 mg, 10% yield) as a white solid. LC-MS (Method 1) $t_R$=2.21 min, m/z $(M+H)^+$=428.2. $^1$H NMR (400 MHz, DMSO-$d_6$) δ 10.91 (s, 1H), 10.72 (s, 1H), 8.42 (s, 1H), 8.37 (s, 1H), 8.00 (s, 1H), 7.28 (d, J=7.6 Hz, 1H), 7.01 (s, 1H), 6.50 (d, J=7.2 Hz, 1H), 4.83 (t, J=4.4 Hz, 1H), 3.94 (t, J=4.8 Hz, 2H), 3.68 (s, 3H), 3.61 (d, J=5.2 Hz, 2H), 2.03-1.98 (m, 1H), 0.84-0.76 (m, 4H).

Example 114

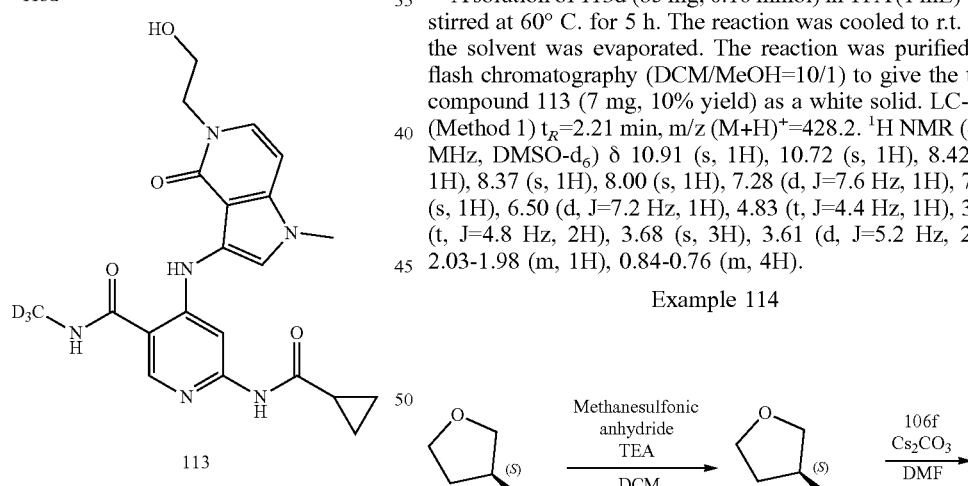

Step 1. Tert-butyl (5-(2-(benzyloxy)ethyl)-1-methyl-4-oxo-4,5-dihydro-1H-pyrrolo[3,2-c]pyridin-3-yl)carbamate (113a)

Compound 113a (500 mg, 66% yield), a yellow oil, was synthesized by utilizing a similar preparative procedure of Step 6 in Example 106 with 106f (500 mg, 1.90 mmol) and ((2-bromoethoxy)methyl)benzene (613 mg, 2.85 mmol) as starting materials. LC-MS (Method 3) $t_R$=1.57 min, m/z $(M+H)^+$=398.2.

-continued

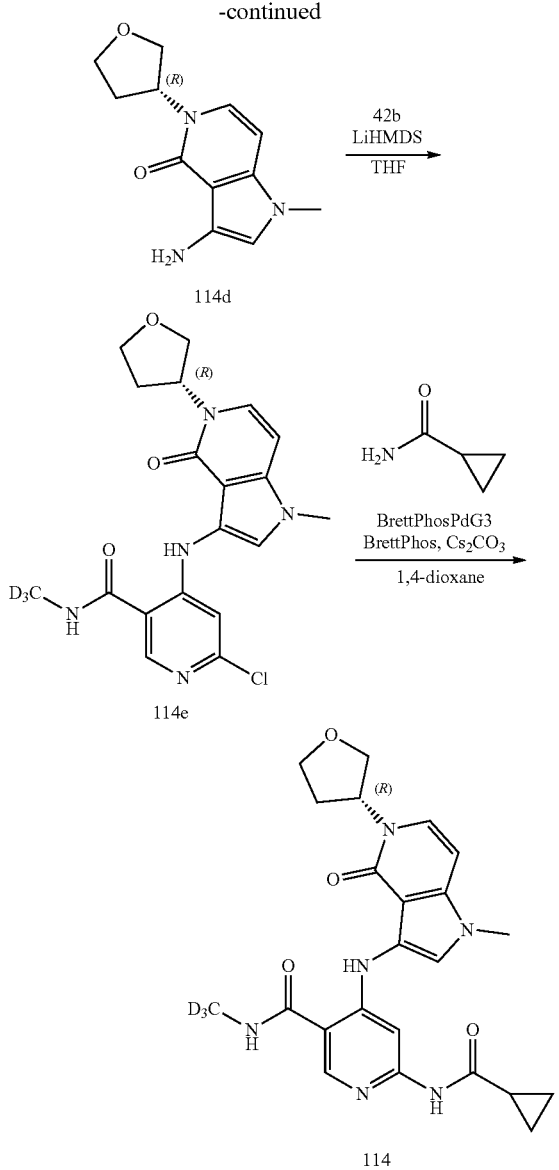

procedure of Step 1 in Example 110 with 106f (500 mg, 1.90 mmol) and 114b (473 mg, 2.85 mmol) as starting materials. LC-MS (Method 3) $t_R$=1.64 min, m/z (M+H)$^+$=334.4.

Step 3. (R)-3-amino-1-methyl-5-(tetrahydrofuran-3-yl)-1,5-dihydro-4H-pyrrolo[3,2-c]pyridin-4-one (114d)

Compound 114d (150 mg, 71% yield), a green oil, was synthesized by utilizing a similar preparative procedure of Step 2 in Example 108 with 114c (300 mg, 0.90 mmol) as the starting material. LC-MS (Method 3) $t_R$=0.31 min, m/z (M+H)$^+$=234.3.

Step 4. (R)-6-chloro-N-(methyl-d$_3$)-4-((1-methyl-4-oxo-5-(tetrahydrofuran-3-yl)-4,5-dihydro-1H-pyrrolo[3,2-c]pyridin-3-yl)amino)nicotinamide (114e)

Compound 114e (36 mg, 14% yield), a black solid, was synthesized by utilizing a similar preparative procedure of Step 5 in Example 50 with 114d (150 mg, 0.64 mmol) and 42b (134 mg, 0.64 mmol) as starting materials. LC-MS (Method 3) $t_R$=1.32 min, m/z (M+H)$^+$=405.3.

Step 5. (R)-6-(cyclopropanecarboxamido)-N-(methyl-d$_3$)-4-((1-methyl-4-oxo-5-(tetrahydrofuran-3-yl)-4,5-dihydro-1H-pyrrolo[3,2-c]pyridin-3-yl)amino)nicotinamide (114)

Compound 114 (3 mg, 8% yield), a white solid, was synthesized by utilizing a similar preparative procedure of Step 3 in Example 49 with 114e (35 mg, 0.09 mmol) and cyclopropanecarboxamide (37 mg, 0.43 mmol) as starting materials. LC-MS (Method 1) $t_R$=2.50 min, m/z (M+H)$^+$=454.3. $^1$H NMR (400 MHz, DMSO-d$_6$) δ 10.91 (s, 1H), 10.71 (s, 1H), 8.42 (s, 1H), 8.37 (s, 1H), 7.99 (s, 1H), 7.26 (d, J=7.6 Hz, 1H), 7.03 (s, 1H), 6.60 (d, J=7.6 Hz, 1H), 5.55-5.52 (m, 1H), 4.08-4.04 (m, 1H), 3.88-3.84 (m, 1H), 3.80-3.72 (m, 2H), 3.69 (s, 3H), 2.44-2.38 (m, 1H), 2.06-1.98 (m, 1H), 1.94-1.88 (m, 1H), 0.86-0.78 (m, 4H).

Step 1. (S)-tetrahydrofuran-3-yl methanesulfonate (114b)

To a solution of (S)-tetrahydrofuran-3-ol 114a (1.0 g, 11.35 mmol) in DCM (10 mL) was added methylsulfonyl methanesulfonate (3.95 g, 22.70 mmol) and TEA (3.45 g, 34.05 mmol) at −10° C. The mixture was stirred at r.t. overnight. The solution was diluted with DCM (20 mL), washed with saturated aq·NaHCO$_3$, dried over Na$_2$SO$_4$ and filtered. The filtrate was concentrated to give the title compound 114b (1.5 g, 79% yield) as a yellow oil. $^1$H NMR (400 MHz, CDCl$_3$) δ 5.31 (d, J=4.0 Hz, 1H), 4.04-3.86 (m, 4H), 3.06 (s, 3H), 2.77-2.23 (m, 2H).

Step 2. Tert-butyl (R)-(1-methyl-4-oxo-5-(tetrahydrofuran-3-yl)-4,5-dihydro-1H-pyrrolo[3,2-c]pyridin-3-yl)carbamate (114c)

Compound 114c (200 mg, 32% yield), a light-yellow solid, was synthesized by utilizing a similar preparative Example 115

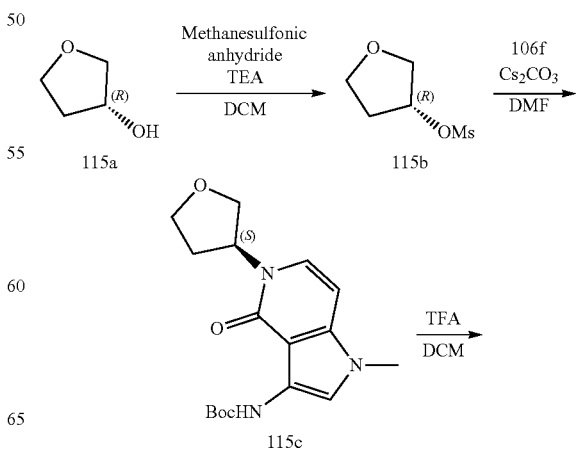

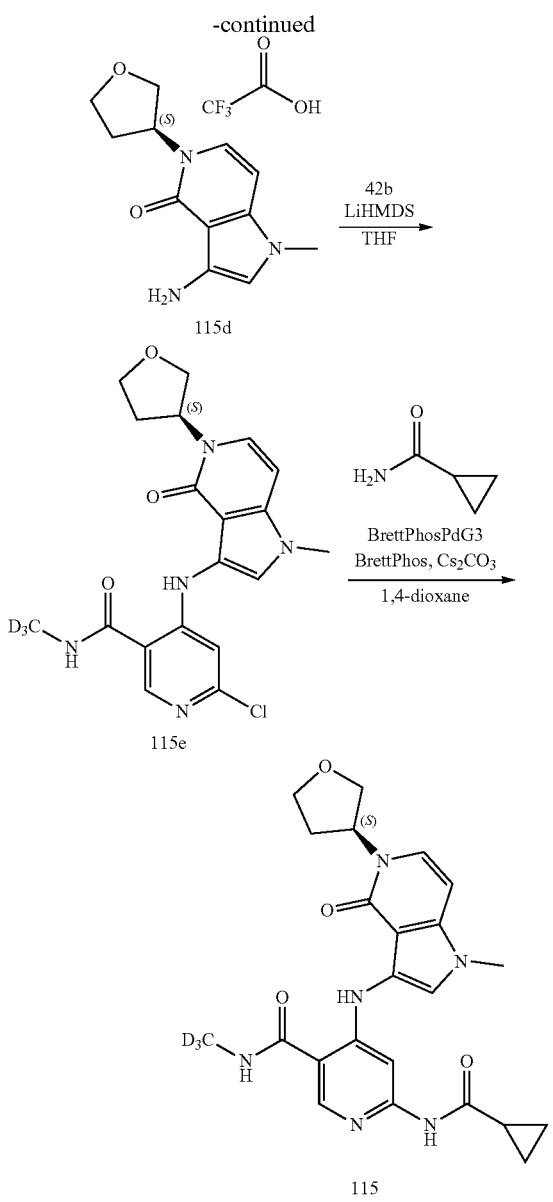

mmol) and 115b (473 mg, 2.85 mmol) as starting materials. LC-MS (Method 3) $t_R$=1.45 min, m/z (M+H)$^+$=334.3.

Step 3. (S)-3-amino-1-methyl-5-(tetrahydrofuran-3-yl)-1H-pyrrolo[3,2-c]pyridin-4-(5H)-one trifluoroacetic acid (115d)

Compound 115d (357 mg, 98% yield), a green oil, was synthesized by utilizing a similar preparative procedure of Step 2 in Example 108 with 115c (350 mg, 1.05 mmol) as the starting material. LC-MS (Method 3) $t_R$=0.99 min, m/z (M+H)$^+$=234.3.

Step 4. 6-Chloro-4-[[1-methyl-4-oxo-5-[(3S)-tetrahydrofuran-3-yl]pyrrolo[3,2-c]pyridin-3-yl]amino]-N-(methyl-d$_3$)pyridine-3-carboxamide (115e)

Compound 115e (75 mg, 18% yield), a brown solid, was synthesized by utilizing a similar preparative procedure of Step 5 in Example 50 with 115d (357 mg, 1.03 mmol) and 42b (214 mg, 1.03 mmol) as starting materials. LC-MS (Method 3) $t_R$=1.38 min, m/z (M+H)$^+$=405.4.

Step 5. 6-(Cyclopropanecarbonylamino)-4-[[1-methyl-4-oxo-5-[(3S)-tetrahydrofuran-3-yl]pyrrolo[3,2-c]pyridin-3-yl]amino]-N-(methyl-d$_3$)pyridine-3-carboxamide (115)

Compound 115 (26 mg, 31% yield), a yellow solid, was synthesized by utilizing a similar preparative procedure of Step 3 in Example 49 with 115e (75 mg, 0.19 mmol) and cyclopropanecarboxamide (79 mg, 0.93 mmol) as starting materials. LC-MS (Method 2) $t_R$=2.72 min, m/z (M+H)$^+$=454.2. $^1$H NMR (400 MHz, DMSO-d$_6$) δ 10.92 (s, 1H), 10.71 (s, 1H), 8.42 (s, 1H), 8.37 (s, 1H), 7.99 (s, 1H), 7.26 (d, J=7.6 Hz, 1H), 7.03 (s, 1H), 6.60 (d, J=7.6 Hz, 1H), 5.56-5.51 (m, 1H), 4.10-4.04 (m, 1H), 3.88-3.84 (m, 1H), 3.80-3.72 (m, 2H), 3.69 (s, 3H), 2.47-2.40 (m, 1H), 2.03-1.99 (m, 1H), 1.97-1.88 (m, 1H), 0.84-0.79 (m, 4H).

Example 116

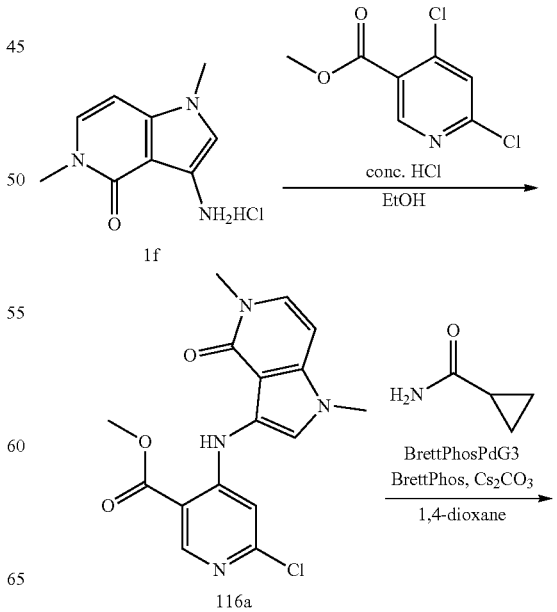

Step 1. (R)-tetrahydrofuran-3-yl methanesulfonate (115b)

Compound 115b (1.6 g, 85% yield), a yellow oil, was synthesized by utilizing a similar preparative procedure of Step 1 in Example 114 with 115a (1.0 g, 11.35 mmol) and methylsulfonyl methanesulfonate (5.93 g, 34.05 mmol) as starting materials. $^1$H NMR (400 MHz, CDCl$_3$) δ 5.32-5.29 (m, 1H), 3.88-3.71 (m, 4H), 3.21 (s, 3H), 2.24-2.19 (m, 1H), 2.10-2.08 (m, 1H).

Step 2. (S)-tert-butyl (1-methyl-4-oxo-5-(tetrahydrofuran-3-yl)-4,5-dihydro-1H-pyrrolo[3,2-c]pyridin-3-yl)carbamate (115c)

Compound 115c (350 mg, 55% yield), a light-yellow solid, was synthesized by utilizing a similar preparative procedure of Step 1 in Example 110 with 106f (500 mg, 1.90

-continued

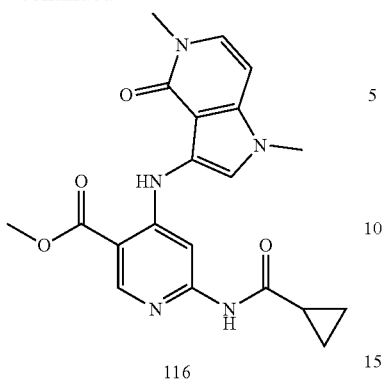

116

Step 1. Methyl 6-chloro-4-((1,5-dimethyl-4-oxo-4,5-dihydro-1H-pyrrolo[3,2-c]pyridin-3-yl)amino)nicotinate (116a)

Compound 116a (150 mg, 57% yield), a brown solid, was synthesized by utilizing a similar preparative procedure of Step 1 in Example 98 with 1f (280 mg, 0.76 mmol) and methyl 4,6-dichloronicotinate (187 mg, 0.91 mmol) as starting materials. LC-MS (Method 3) $t_R$=1.40 min, m/z (M+H)$^+$=347.2.

Step 2. Methyl 6-(cyclopropanecarboxamido)-4-((1,5-dimethyl-4-oxo-4,5-dihydro-1H-pyrrolo[3,2-c]pyridin-3-yl)amino)nicotinate (116)

Compound 116 (150 mg, 88% yield), a brown solid, was synthesized by utilizing a similar preparative procedure of Step 3 in Example 49 with 116a (150 mg, 0.43 mmol) and cyclopropanecarboxamide (184 mg, 2.16 mmol) as starting materials. LC-MS (Method 1) $t_R$=2.86 min, m/z (M+H)$^+$=396.2. $^1$H NMR (400 MHz, DMSO-d$_6$) δ 10.93 (s, 1H), 10.76 (s, 1H), 8.67 (s, 1H), 8.07 (s, 1H), 7.37 (d, J=7.2 Hz, 1H), 7.07 (s, 1H), 6.56 (d, J=7.2 Hz, 1H), 3.88 (s, 3H), 3.71 (s, 3H), 3.45 (s, 3H), 2.04-1.99 (m, 1H), 0.86-0.82 (m, 4H).

Example 117

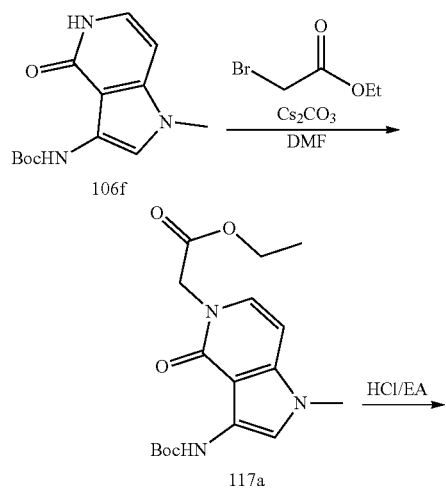

-continued

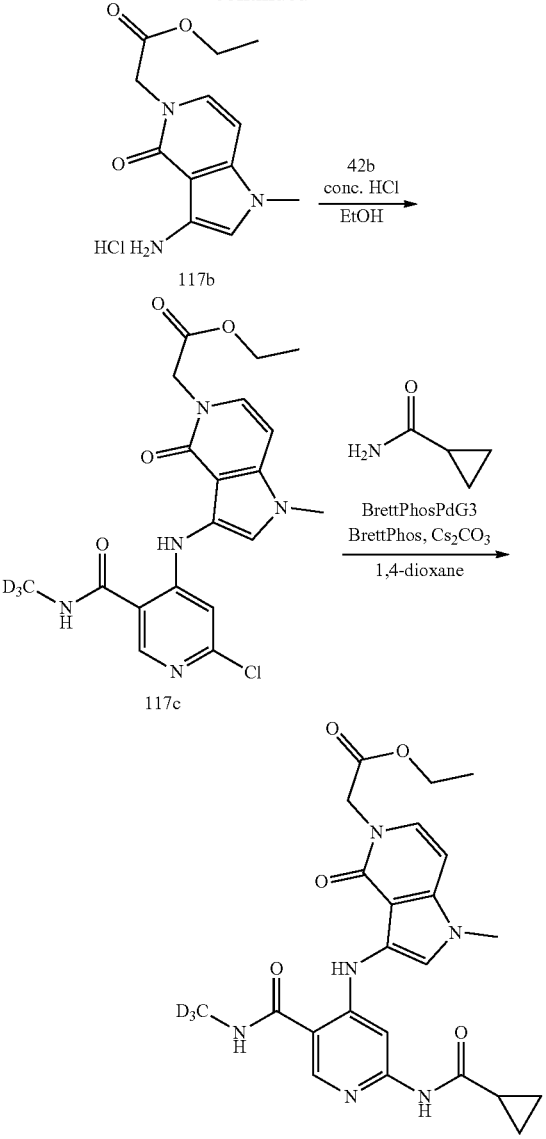

Step 1. Ethyl 2-(3-((tert-butoxycarbonyl)amino)-1-methyl-4-oxo-1H-pyrrolo[3,2-c]pyridin-5(4H)-yl)acetate (117a)

Compound 117a (600 mg, 90% yield), a yellow solid, was synthesized by utilizing a similar preparative procedure of Step 1 in Example 110 with 11f (500 mg, 1.90 mmol) and ethyl 2-bromoacetate (634 mg, 3.80 mmol) as starting materials. LC-MS (Method 3) $t_R$=1.47 min, m/z (M+H)$^+$=350.2.

Step 2. Ethyl 2-(3-amino-1-methyl-4-oxo-1H-pyrrolo[3,2-c]pyridin-5(4H)-yl)acetate hydrochloride (117b)

Compound 117b (430 mg, 88% yield), a yellow solid, was synthesized by utilizing a similar preparative procedure of Step 5 in Example 1 with 117a (600 mg, 1.72 mmol) as the starting material. $^1$H NMR (400 MHz, DMSO-d$_6$) δ 10.13

(brs, 2H), 7.45 (d, J=7.2 Hz, 1H), 7.26 (s, 1H), 6.68 (d, J=7.6 Hz, 1H), 4.76 (s, 2H), 4.14 (q, J=7.2 Hz, 2H), 3.73 (s, 3H), 1.21 (t, J=7.2 Hz, 3H).

Step 3. Ethyl 2-(3-((2-chloro-5-((methyl-d₃)carbamoyl)pyridin-4-yl)amino)-1-methyl-4-oxo-1,4-dihydro-5H-pyrrolo[3,2-c]pyridin-5-yl)acetate (117c)

Compound 117c (140 mg, 41% yield), a yellow solid, was synthesized by utilizing a similar preparative procedure of Step 1 in Example 98 with 42b (167 mg, 0.80 mmol) and 117b (229 mg, 0.80 mmol) as starting materials. LC-MS (Method 3) $t_R$=1.21 min, m/z (M+H)⁺=421.1.

Step 4. Ethyl 2-(3-((2-(cyclopropanecarboxamido)-5-((methyl-d₃)carbamoyl)pyridin-4-yl)amino)-1-methyl-4-oxo-1,4-dihydro-5H-pyrrolo[3,2-c]pyridin-5-yl)acetate (117)

Compound 117 (95 mg, 61% yield), a white solid, was synthesized by utilizing a similar preparative procedure of Step 3 in Example 49 with 117c (140 mg, 0.33 mmol) and cyclopropanecarboxamide (142 mg, 1.66 mmol) as starting materials. LC-MS (Method 2) $t_R$=2.65 min, m/z (M+H)⁺=470.1. ¹H NMR (400 MHz, DMSO-d₆) δ 10.87 (s, 1H), 10.72 (s, 1H), 8.43 (s, 1H), 8.38 (s, 1H), 8.01 (s, 1H), 7.33 (d, J=7.6 Hz, 1H), 7.05 (s, 1H), 6.57 (d, J=7.2 Hz, 1H), 4.70 (s, 2H), 4.14 (q, J=7.2 Hz, 2H), 3.71 (s, 3H), 2.03-2.00 (m, 1H), 1.22 (t, J=7.2 Hz, 3H), 0.85-0.78 (m, 4H).

Example 118

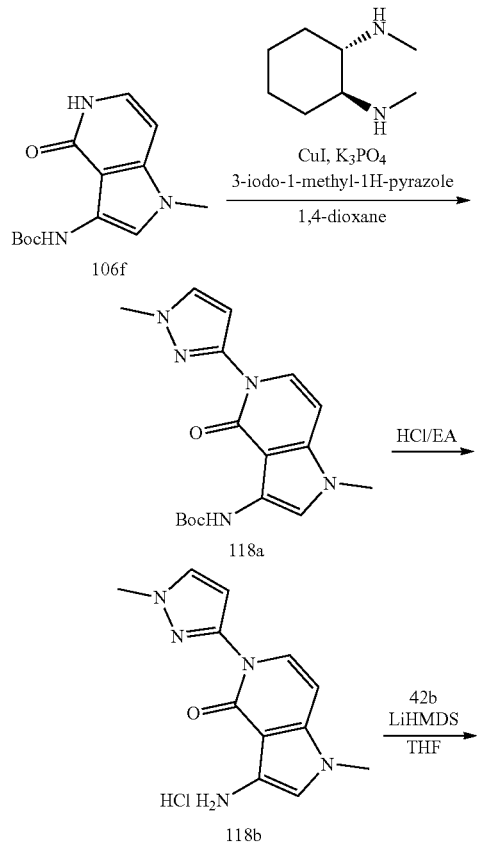

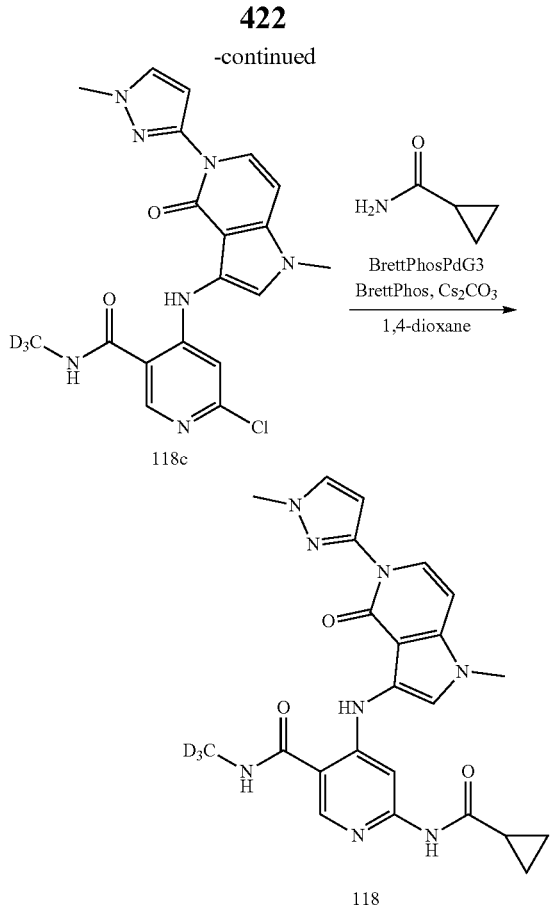

Step 1. Tert-butyl (1-methyl-5-(1-methyl-1H-pyrazol-3-yl)-4-oxo-4,5-dihydro-1H-pyrrolo[3,2-c]pyridin-3-yl)carbamate (118a)

A mixture of 106f (400 mg, 1.52 mmol), 3-iodo-1-methyl-1H-pyrazole (474 mg, 2.28 mmol), CuI (145 mg, 0.76 mmol), K₃PO₄ (967 mg, 4.56 mmol) and (1S,2S)—N,N-dimethylcyclohexane-1,2-diamine (108 mg, 0.76 mmol) in 1,4-dioxane (4 mL) was stirred at 110° C. overnight under N₂. The mixture was concentrated and the residue was purified by flash chromatography on silica gel (PE/EtOAc=4/1) to give the title compound 118a (350 mg, 67% yield) as a yellow solid. LC-MS (Method 3) $t_R$=1.48 min, m/z (M+H)⁺=344.3.

Step 2. 3-Amino-1-methyl-5-(1-methyl-1H-pyrazol-3-yl)-1H-pyrrolo[3,2-c]pyridin-4-(5H)-one hydrochloride (118b)

Compound 118b (280 mg, 98% yield), a white solid, was synthesized by utilizing a similar preparative procedure of Step 5 in Example 1 with 118a (350 mg, 1.02 mmol) as the starting material. ¹H NMR (400 MHz, DMSO-d₆) δ 10.23 (brs, 3H), 7.79 (s, 1H), 7.74 (d, J=7.2 Hz, 1H), 7.29 (d, J=2.4 Hz, 1H), 6.76 (d, J=7.6 Hz, 1H), 6.64 (d, J=2.0 Hz, 1H), 3.87 (s, 3H), 3.76 (s, 3H).

Step 3. 6-Chloro-4-[[1-methyl-5-(1-methylpyrazol-3-yl)-4-oxo-pyrrolo[3,2-c]pyridin-3-yl]amino]-N-(methyl-d₃)pyridine-3-carboxamide (118c)

Compound 118c (70 mg, 29% yield), a brown solid, was synthesized by utilizing a similar preparative procedure of Step 5 in Example 50 with 118b (161 mg, 0.58 mmol) and 42b (120 mg, 0.58 mmol) as starting materials. LC-MS (Method 3) $t_R$=1.26 min, m/z (M+H)$^+$=415.3.

Step 4. 6-(Cyclopropanecarbonylamino)-4-[[1-methyl-5-(1-methylpyrazol-3-yl)-4-oxo-pyrrolo[3,2-c]pyridin-3-yl]amino]-N-(methyl-d₃)pyridine-3-carboxamide (118)

Compound 118 (26 mg, 33% yield), a white solid, was synthesized by utilizing a similar preparative procedure of Step 3 in Example 49 with 118c (70 mg, 0.17 mmol) and cyclopropanecarboxamide (29 mg, 0.34 mmol) as starting materials. LC-MS (Method 2) $t_R$=2.68 min, m/z (MA-1)$^+$=464.2. $^1$H NMR (400 MHz, DMSO-d₆) δ 10.88 (s, 1H), 10.72 (s, 1H), 8.43 (s, 1H), 8.38 (s, 1H), 8.01 (s, 1H), 7.75 (d, J=2.4 Hz, 1H), 7.59 (d, J=8.0 Hz, 1H), 7.07 (s, 1H), 6.66 (d, J=7.6 Hz, 1H), 6.60 (d, J=2.4 Hz, 1H), 3.86 (s, 3H), 3.73 (s, 3H), 2.03-2.00 (m, 1H), 0.84-0.78 (m, 4H).

Example 119

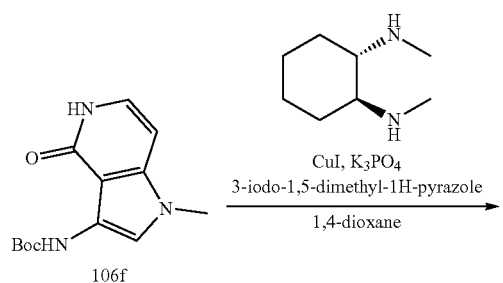

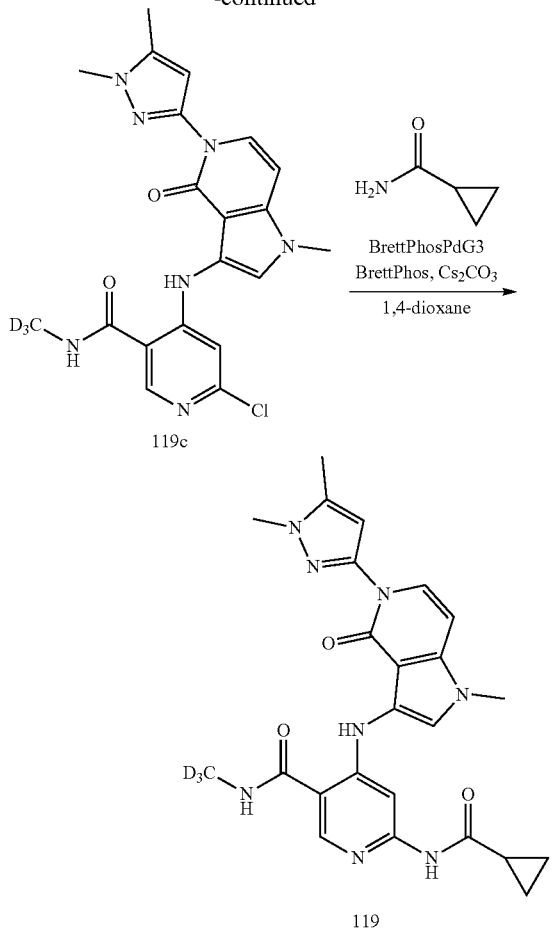

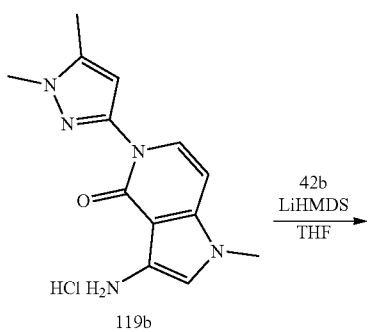

Step 1. Tert-butyl (5-(1,5-dimethyl-1H-pyrazol-3-yl)-1-methyl-4-oxo-4,5-dihydro-1H-pyrrolo[3,2-e]pyridin-3-yl)carbamate (119a)

Compound 119a (405 mg, 75% yield), a white solid, was synthesized by utilizing a similar preparative procedure of Step 1 in Example 118 with 106f (400 mg, 1.52 mmol) and 3-iodo-1,5-dimethyl-1H-pyrazole (532 mg, 3.04 mmol) as starting materials. LC-MS (Method 3) $t_R$=1.49 min, m/z (M+H)$^+$=358.3.

Step 2. 3-Amino-5-(1,5-dimethyl-1H-pyrazol-3-yl)-1-methyl-1H-pyrrolo[3,2-e]pyridin-4-((5H)-one hydrochloride (119b)

Compound 119b (400 mg, 99% yield), a white solid, was synthesized by utilizing a similar preparative procedure of Step 5 in Example 1 with 119a (490 mg, 1.37 mmol) as the starting material. $^1$H NMR (300 MHz, DMSO-d₆) δ 10.25 (brs, 3H), 7.73 (d, J=7.5 Hz, 1H), 7.33 (s, 1H), 6.76 (d, J=7.5 Hz, 1H), 6.49 (s, 1H), 3.78 (s, 6H), 2.33 (s, 3H).

Step 3. 6-Chloro-4-[[5-(1,5-dimethylpyrazol-3-yl)-1-methyl-4-oxo-pyrrolo[3,2-e]pyridin-3-yl]amino]-N-(methyl-d₃)pyridine-3-carboxamide (119c)

Compound 119c (130 mg, 39% yield), a white solid, was synthesized by utilizing a similar preparative procedure of Step 5 in Example 50 with 119b (228 mg, 0.78 mmol) and 42b (162 mg, 0.78 mmol) as starting materials. LC-MS (Method 3) $t_R$=1.32 min, m/z (M+H)$^+$=429.3.

Step 4. 6-(Cyclopropanecarbonylamino)-4-[[5-(1,5-dimethylpyrazol-3-yl)-1-methyl-4-oxo-pyrrolo[3,2-e]pyridin-3-yl]amino]-N-(methyl-d$_3$)pyridine-3-carboxamide (119)

Compound 119 (29 mg, 33% yield), a yellow solid, was synthesized by utilizing a similar preparative procedure of Step 3 in Example 49 with 119c (80 mg, 0.19 mmol) and cyclopropanecarboxamide (79 mg, 0.93 mmol) as starting materials. LC-MS (Method 2) $t_R$=2.78 min, m/z (M+H)$^+$=478.2. $^1$H NMR (400 MHz, DMSO-d$_6$) δ 10.91 (s, 1H), 10.72 (s, 1H), 8.44 (s, 1H), 8.38 (s, 1H), 8.02 (s, 1H), 7.58 (d, J=7.6 Hz, 1H), 7.06 (s, 1H), 6.64 (d, J=7.6 Hz, 1H), 6.44 (s, 1H), 3.73 (s, 3H), 3.72 (s, 3H), 2.30 (s, 3H), 2.02-2.00 (m, 1H), 0.85-0.79 (m, 4H).

Example 120

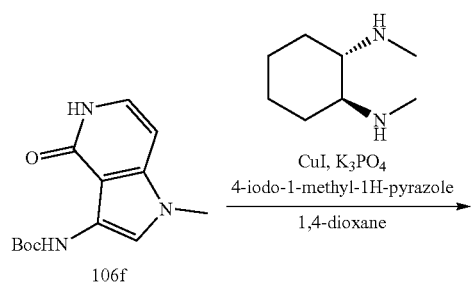

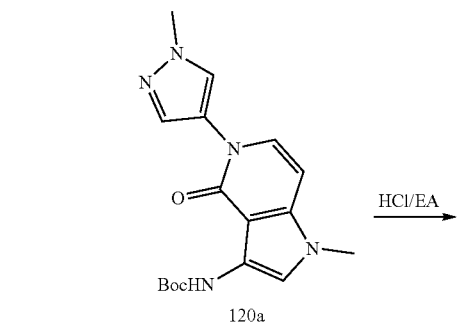

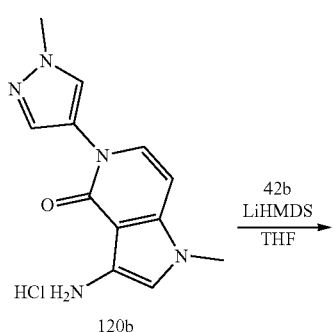

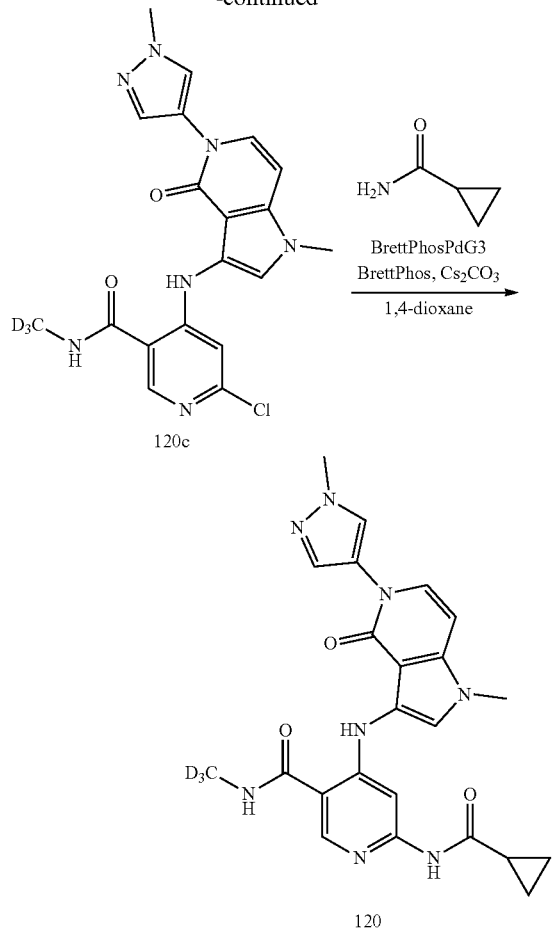

Step 1. Tert-butyl (1-methyl-5-(1-methyl-1H-pyrazol-4-yl)-4-oxo-4,5-dihydro-1H-pyrrolo[3,2-c]pyridin-3-yl)carbamate (120a)

Compound 120a (280 mg, 61% yield), a yellow solid, was synthesized by utilizing a similar preparative procedure of Step 1 in Example 118 with 106f (350 mg, 1.33 mmol) and 4-iodo-1-methyl-1H-pyrazole (553 mg, 2.66 mmol) as starting materials. LC-MS (Method 3) $t_R$=1.40 min, m/z (M+H)$^+$=344.3.

Step 2. 3-Amino-1-methyl-5-(1-methyl-1H-pyrazol-4-yl)-1H-pyrrolo[3,2-e]pyridin-4-(5H)-one hydrochloride (120b)

Compound 120b (170 mg, 83% yield), a white solid, was synthesized by utilizing a similar preparative procedure of Step 5 in Example 1 with 120a (250 mg, 0.73 mmol) as the starting material. $^1$H NMR (400 MHz, DMSO-d$_6$) δ 10.21 (brs, 3H), 8.17 (s, 1H), 7.78 (s, 1H), 7.57 (d, J=7.6 Hz, 1H), 7.30 (s, 1H), 6.76 (d, J=7.6 Hz, 1H), 3.89 (s, 3H), 3.76 (s, 3H).

Step 3. 6-Chloro-N-(methyl-d$_3$)-4-(O-methyl-5-(1-methyl-1H-pyrazol-4-yl)-4-oxo-4,5-dihydro-1H-pyrrolo[3,2-c]pyridin-3-yl)amino)nicotinamide (120c)

Compound 120c (70 mg, 29% yield), a brown solid, was synthesized by utilizing a similar preparative procedure of Step 5 in Example 50 with 120b (160 mg, 0.57 mmol) and 42b (119 mg, 0.57 mmol) as starting materials. LC-MS (Method 3) $t_R$=1.22 min, m/z (M+H)⁺=415.3.

Step 4. 6-(Cyclopropanecarboxamido)-N-(methyl-d₃)-4-((1-methyl-5-(1-methyl-1H-pyrazol-4-yl)-4-oxo-4,5-dihydro-1H-pyrrolo[3,2-c]pyridin-3-yl)amino)nicotinamide (120)

Compound 120 (40 mg, 51% yield), a yellow solid, was synthesized by utilizing a similar preparative procedure of Step 3 in Example 49 with 120c (70 mg, 0.17 mmol) and cyclopropanecarboxamide (14 mg, 0.17 mmol) as starting materials. LC-MS (Method 2) $t_R$=2.99 min, m/z (M+H)⁺=464.3. ¹H NMR (400 MHz, DMSO-d₆) δ 10.90 (s, 1H), 10.73 (s, 1H), 8.44 (s, 1H), 8.38 (s, 1H), 8.17 (s, 1H), 8.01 (s, 1H), 7.72 (s, 1H), 7.46 (d, J=8.0 Hz, 1H), 7.08 (s, 1H), 6.67 (d, J=7.6 Hz, 1H), 3.88 (s, 3H), 3.73 (s, 3H), 2.03-1.99 (m, 1H), 0.86-0.79 (m, 4H).

Example 121

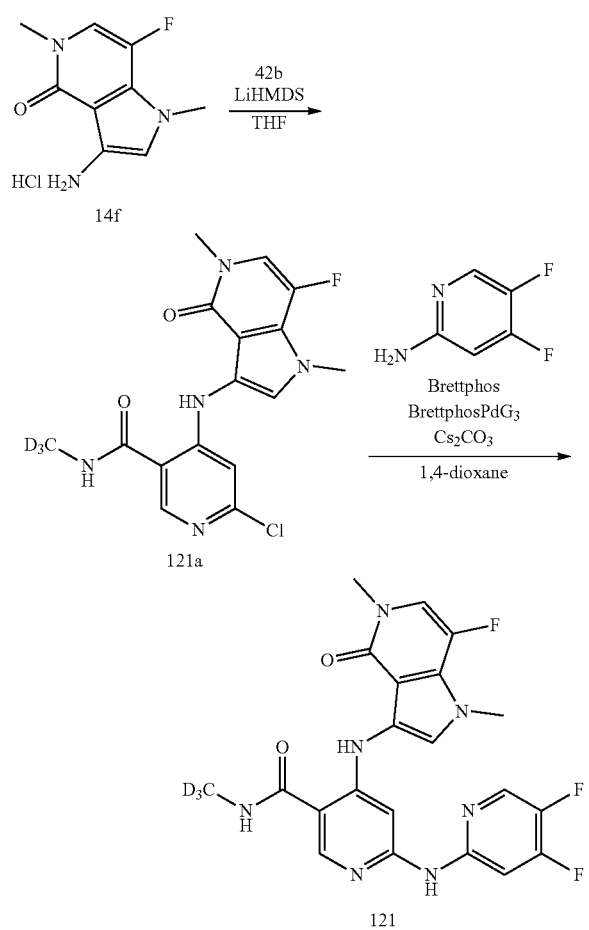

121

Step 1. 6-Chloro-4-((7-fluoro-1,5-dimethyl-4-oxo-4,5-dihydro-1H-pyrrolo[3,2-c]pyridin-3-yl)amino)-N-(methyl-d₃)nicotinamide (121a)

Compound 121a (130 mg, 90% yield), a brown solid, was synthesized by utilizing a similar preparative procedure of Step 5 in Example 50 with 14f (77 mg, 0.39 mmol) and 42b (82 mg, 0.39 mmol) as starting materials. LC-MS (Method 3) $t_R$=1.32 min, m/z (M+H)⁺=367.2.

Step 2. 6-((4,5-Difluoropyridin-2-yl)amino)-4-((7-fluoro-1,5-dimethyl-4-oxo-4,5-dihydro-1H-pyrrolo[3,2-c]pyridin-3-yl)amino)-N-(methyl-d₃)nicotinamide (121)

Compound 121 (29.5 mg, 21% yield), a white solid, was synthesized by utilizing a similar preparative procedure Step 3 in Example 49 with 121a (110 mg, 0.30 mmol) and 4,5-difluoropyridin-2-amine (58.5 mg, 0.45 mmol) as starting materials. LC-MS (Method 2) $t_R$=2.60 min, m/z (M+H)⁺=461.2. ¹H NMR (400 MHz, DMSO-d₆) δ 11.00 (s, 1H), 9.96 (s, 1H), 8.46-8.42 (m, 2H), 8.31-8.28 (m, 1H), 8.04-7.99 (m, 1H), 7.58 (d, J=8.0 Hz, 1H), 7.41 (s, 1H), 7.28 (s, 1H), 3.90 (s, 3H), 3.39 (s, 3H).

Example 122

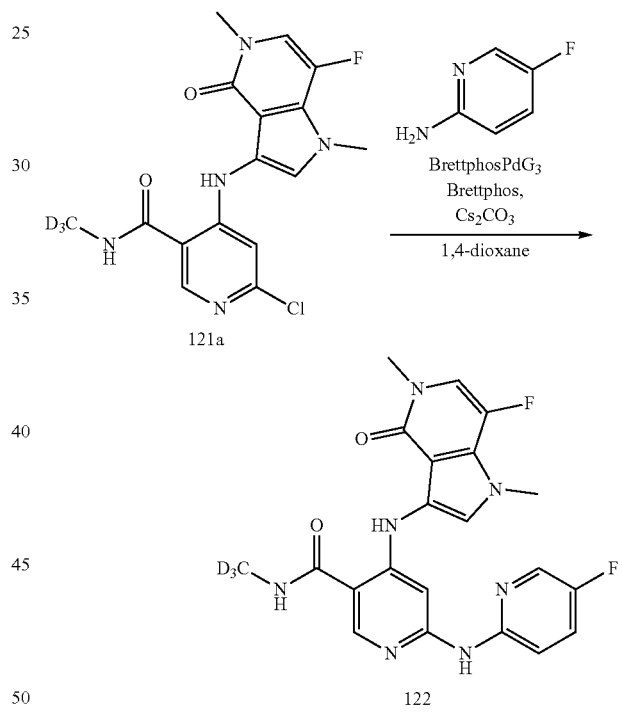

Step 1. 4-((7-Fluoro-1,5-dimethyl-4-oxo-4,5-dihydro-1H-pyrrolo[3,2-c]pyridin-3-yl)amino)-6-((5-fluoropyridin-2-yl)amino)-N-(methyl-d₃)nicotinamide (122)

Compound 122 (29.5 mg, 28% yield), a white solid, was synthesized by utilizing a similar preparative procedure Step 3 in Example 49 with 121a (90 mg, 0.24 mmol) and 5-fluoropyridin-2-amine (33 mg, 0.29 mmol) as starting materials. LC-MS (Method 2) $t_R$=2.60 min, m/z (M+H)⁺=443.1. ¹H NMR (400 MHz, DMSO-d₆) δ 11.02 (s, 1H), 9.78 (s, 1H), 8.40 (s, 1H), 8.27-8.26 (m, 2H), 7.80-7.76 (m, 1H), 7.69-7.63 (m, 2H), 7.57 (d, J=8.0 Hz, 1H), 7.29 (s, 1H), 3.91 (s, 3H), 3.40 (s, 3H).

Example 123

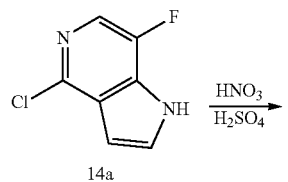

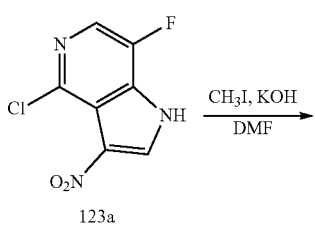

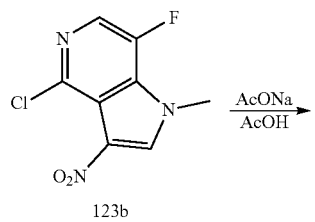

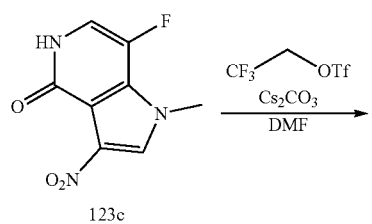

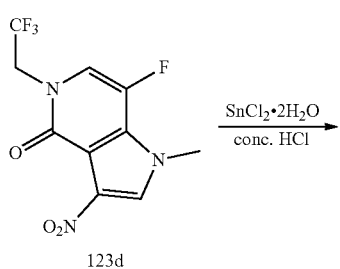

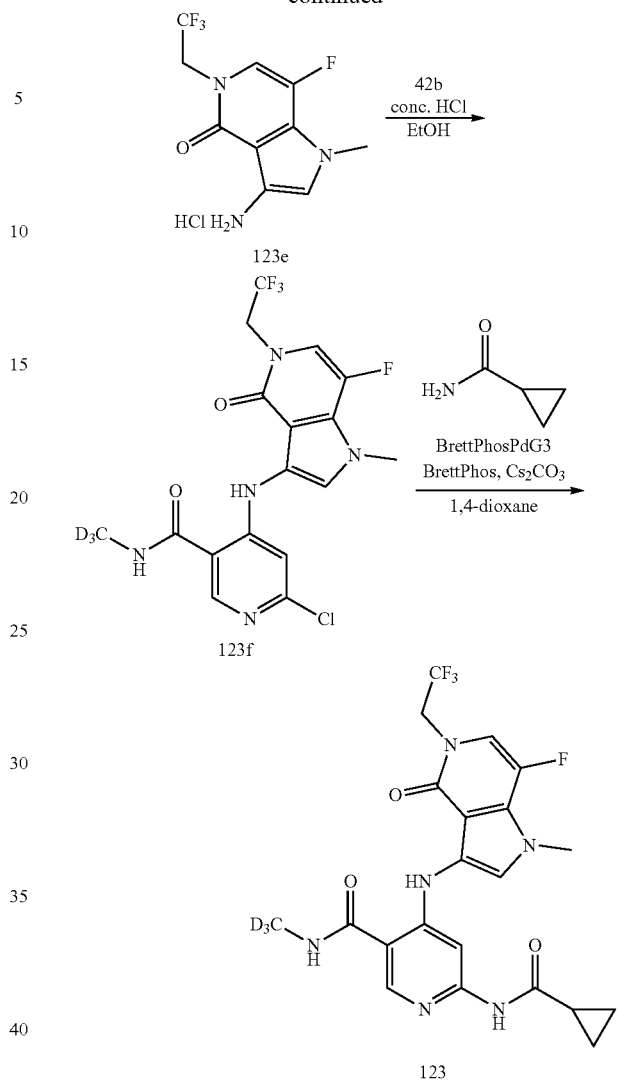

Step 1. 4-Chloro-7-fluoro-3-nitro-1H-pyrrolo[3,2-c]pyridine (123a)

To a solution of 14a (400 mg, 2.35 mmol) in conc. $H_2SO_4$ (4 mL) was added $HNO_3$ (273 mg, 2.81 mmol, 65% wt) slowly at 0° C. After stirring for 1 h at 0° C., the reaction mixture was poured into ice water and the formed solid was filtered. The filter cake was dried to afford 123a (300 mg, 59% yield) as a brown solid. $^1$H NMR (400 MHz, DMSO-$d_6$) δ 11.94 (s, 1H), 8.90 (s, 1H), 8.31 (d, J=2.8 Hz, 1H).

Step 2. 4-Chloro-7-fluoro-1-methyl-3-nitro-1H-pyrrolo[3,2-c]pyridine (123b)

To a solution of 123a (300 mg, 1.39 mmol) in DMF (3 mL) was added KOH (156 mg, 2.78 mmol). After stirring at 0° C. for 5 min, to it was added iodomethane (296 mg, 2.09 mmol). The resultant mixture was stirred at 0° C. for 30 min. The reaction mixture was diluted with water and the formed solid was collected by filtering. The filter cake was dried to afford 123b (220 mg, 69% yield) as a brown solid. $^1$H NMR (400 MHz, DMSO-$d_6$) δ 8.90 (s, 1H), 8.31 (d, J=2.8 Hz, 1H), 4.05 (s, 3H).

Step 3. 7-Fluoro-1-methyl-3-nitro-1H-pyrrolo[3,2-c]pyridin-4-(5H)-one (123c)

A mixture of 123b (230 mg, 1.00 mmol) and sodium acetate (246 mg, 3.01 mmol) in acetic acid (3 mL) was stirred at 130° C. for 20 h. After cooling to r.t., the reaction was diluted with H₂O (3 mL) and filtered. The filter cake was wash with H₂O (5 mL) and dried under reduced pressure to afford 123c (156 mg, 74% yield) as a brown solid. $^1$H NMR (400 MHz, DMSO-$d_6$) δ 11.08 (s, 1H), 8.90 (s, 1H), 7.41 (d, J=6.8 Hz, 1H), 3.91 (s, 3H).

Step 4. 7-Fluoro-1-methyl-3-nitro-5-(2,2,2-trifluoroethyl)-1H-pyrrolo[3,2-c]pyridin-4-(5H)-one (123d)

A solution of 123c (150 mg, 0.71 mmol), Cs₂CO₃ (463 mg, 1.42 mmol) and 2,2,2-trifluoroethyl trifluoromethanesulfonate (495 mg, 2.13 mmol) in DMF (0.5 mL) was stirred at 50° C. for 12 h. After cooling to r.t., the reaction was diluted with H₂O (3 mL) and filtered. The filter cake was dried to afford 123d (155 mg, 74% yield) as a white solid. $^1$H NMR (400 MHz, DMSO-$d_6$) δ 8.46 (s, 1H), 7.86 (d, J=7.6 Hz, 1H), 4.82 (q, J=8.8 Hz, 2H), 3.92 (s, 3H).

Step 5. 3-Amino-7-fluoro-1-methyl-5-(2,2,2-trifluoroethyl)-1H-pyrrolo[3,2-c]pyridin-4-(5H)-one hydrochloride (123e)

To a solution of 123d (450 mg, 1.53 mmol) in conc. HCl (10 mL) was added SnCl₂·2H₂O (694 mg, 3.07 mmol) at 0° C. After stirring at 0° C. for 30 min, the reaction mixture was concentrated to dryness to afford crude 123e (400 mg, 87% yield) as a light-yellow solid, which was used for the next step without purification. LC-MS (Method 3) $t_R$=1.31 min, m/z (M+H)⁺=264.0.

Step 6. 6-Chloro-4-((7-fluoro-1-methyl-4-oxo-5-(2,2,2-trifluoroethyl)-4,5-dihydro-1H-pyrrolo[3,2-c]pyridin-3-yl)amino)-N-(methyl-$d_3$)nicotinamide (123f)

Compound 123f (84 mg, 39% yield), a yellow solid, was synthesized by utilizing a similar preparative procedure of Step 1 in Example 98 with 123e (130 mg, 0.49 mmol) and 42b (103 mg, 0.49 mmol) as starting materials. LC-MS (Method 3) $t_R$=1.40 min, m/z (M+H)⁺=435.2.

Step 7. 6-(Cyclopropanecarboxamido)-4-((7-fluoro-1-methyl-4-oxo-5-(2,2,2-trifluoroethyl)-4,5-dihydro-1H-pyrrolo[3,2-c]pyridin-3-yl)amino)-N-(methyl-$d_3$)nicotinamide (123)

Compound 123 (26 mg, 28% yield), a white solid, was synthesized by utilizing a similar preparative procedure of Step 3 in Example 49 with 123f (84 mg, 0.19 mmol) and cyclopropanecarboxamide (82 mg, 0.97 mmol) as starting materials. LC-MS (Method 2) $t_R$=3.25 min, m/z (M+H)⁺=484.0. $^1$H NMR (400 MHz, DMSO-$d_6$) δ 10.94 (s, 1H), 10.76 (s, 1H), 8.46 (s, 1H), 8.42 (s, 1H), 8.02 (s, 1H), 7.58 (d, J=7.6 Hz, 1H), 7.16 (s, 1H), 4.77 (q, J=9.2 Hz, 2H), 3.86 (s, 3H), 2.03-2.00 (m, 1H), 0.84-0.79 (m, 4H).

Example 124

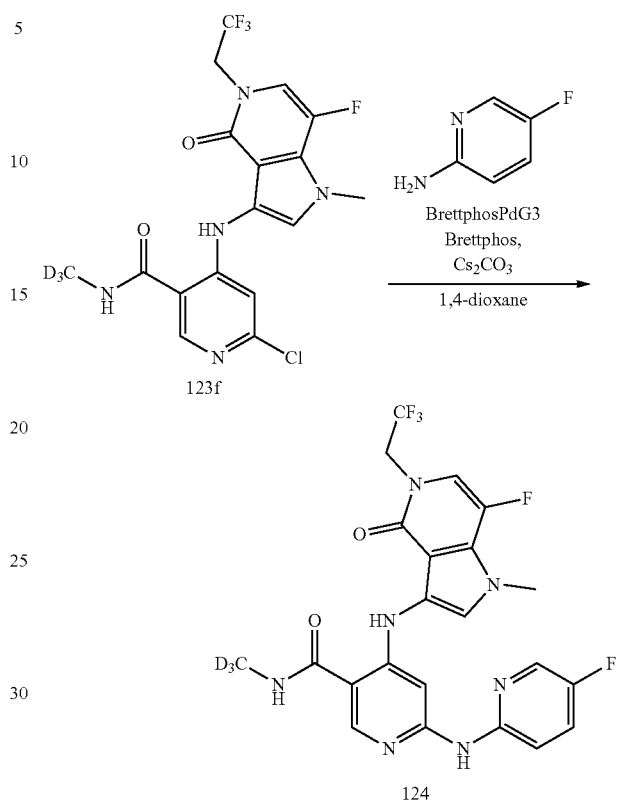

Step 1. 4-((7-Fluoro-1-methyl-4-oxo-5-(2,2,2-trifluoroethyl)-4,5-dihydro-1H-pyrrolo[3,2-c]pyridin-3-yl)amino)-6-((5-fluoropyridin-2-yl)amino)-N-(methyl-$d_3$)nicotinamide (124)

Compound 124 (14 mg, 9% yield), a white solid, was synthesized by utilizing a similar preparative procedure of Step 3 in Example 49 with 123f (130 mg, 0.30 mmol) and 5-fluoropyridin-2-amine (67 mg, 0.60 mmol) as starting materials. LC-MS (Method 1) $t_R$=3.88 min, m/z (M+H)⁺=511.0. $^1$H NMR (400 MHz, DMSO-$d_6$) δ 11.06 (s, 1H), 9.81 (s, 1H), 8.43 (s, 1H), 8.31 (s, 1H), 8.27 (d, J=3.2 Hz, 1H), 7.79-7.76 (m, 1H), 7.68-7.59 (m, 2H), 7.58 (d, J=8.0 Hz, 1H), 7.35 (s, 1H), 4.81 (q, J=9.2 Hz, 2H), 3.93 (s, 3H).

Example 125

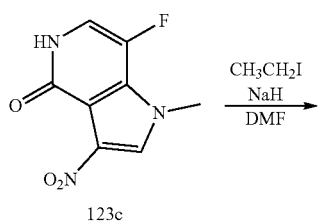

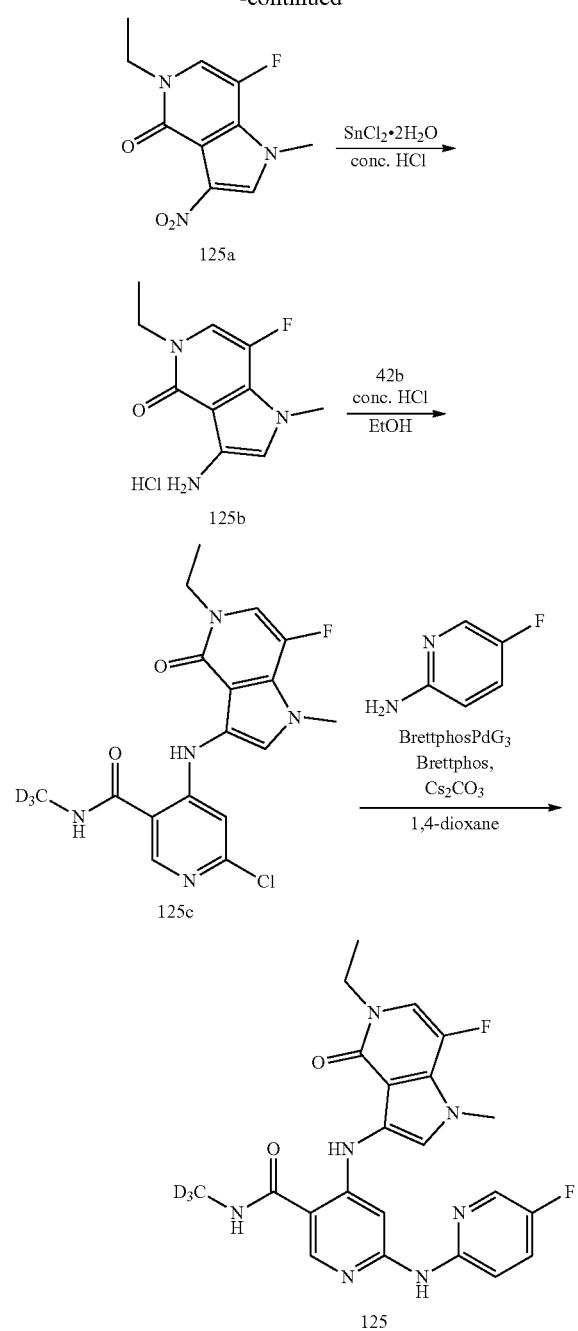

Step 2. 3-Amino-5-ethyl-7-fluoro-1-methyl-1H-pyrrolo[3,2-c]pyridin-4-(5H)-one hydrochloride (125b)

Compound 125b (500 mg, 97% yield), a brown solid, was synthesized by utilizing a similar preparative procedure of Step 5 in Example 123 with 125a (500 mg, 2.09 mmol) as the starting material. LC-MS (Method 3) $t_R$=1.14 min, m/z (M+H)$^+$=210.0.

Step 3. 6-Chloro-4-((5-ethyl-7-fluoro-1-methyl-4-oxo-4,5-dihydro-1H-pyrrolo[3,2-c]pyridin-3-yl)amino)-N-(methyl-d$_3$)nicotinamide (125c)

Compound 125c (200 mg, 25% yield), a yellow solid, was synthesized by utilizing a similar preparative procedure of Step 1 in Example 98 with 125b (513 mg, 2.09 mmol) and 42b (434 mg, 2.09 mmol) as starting materials. LC-MS (Method 3) $t_R$=1.37 min, m/z (M+H)$^+$=381.2.

Step 4. 4-((5-Ethyl-7-fluoro-1-methyl-4-oxo-4,5-dihydro-1H-pyrrolo[3,2-c]pyridin-3-yl)amino)-6-((5-fluoropyridin-2-yl)amino)-N-(methyl-d$_3$)nicotinamide (125)

Compound 125 (16 mg, 13% yield), a yellow solid, was synthesized by utilizing a similar preparative procedure of Step 3 in Example 49 with 125c (100 mg, 0.26 mmol) and 5-fluoropyridin-2-amine (35 mg, 0.32 mmol) as starting materials. LC-MS (Method 1) $t_R$=1.95 min, m/z (M+H)$^+$=457.0. $^1$H NMR (400 MHz, DMSO-d$_6$) δ 11.03 (s, 1H), 9.79 (s, 1H), 8.40 (s, 1H), 8.28-8.26 (m, 2H), 7.80-7.76 (m, 1H), 7.68-7.63 (m, 2H), 7.58 (d, J=7.6 Hz, 1H), 7.29 (s, 1H), 3.91 (s, 3H), 3.89 (q, J=7.6 Hz, 2H), 1.21 (t, J=7.2 Hz, 3H).

Example 126

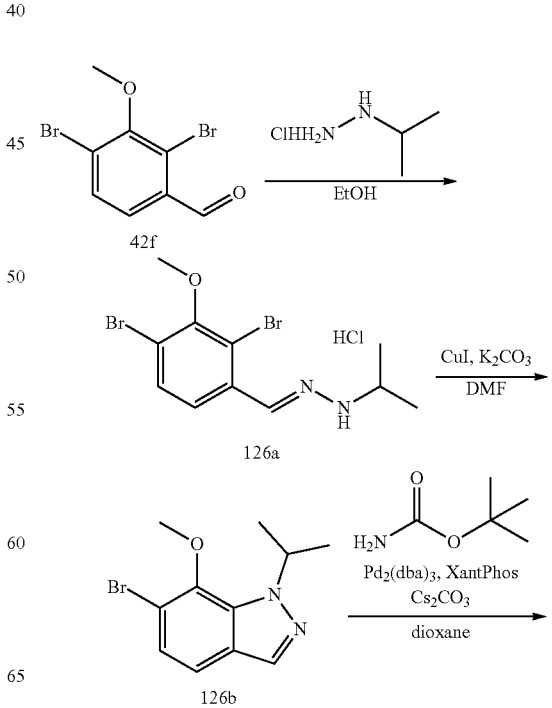

Step 1. 5-Ethyl-7-fluoro-1-methyl-3-nitro-1H-pyrrolo[3,2-c]pyridin-4-(5H)-one (125a)

To a stirred solution of 123c (500 mg, 2.37 mmol) in DMF (5 mL) was added NaH (181 mg, 4.74 mmol, 60% in mineral oil). After stirring for 30 min at r.t., to it was added iodoethane (554 mg, 3.55 mmol). The reaction mixture was stirred at r.t. for 3 h. The reaction mixture was diluted with H$_2$O (30 mL) and extracted with EtOAc (50 mL*3). The organic phase was evaporated under reduced pressure to afford 125a (500 mg, 88% yield) as a brown solid. LC-MS (Method 3) $t_R$=1.10 min, m/z (M+H)$^+$=240.0.

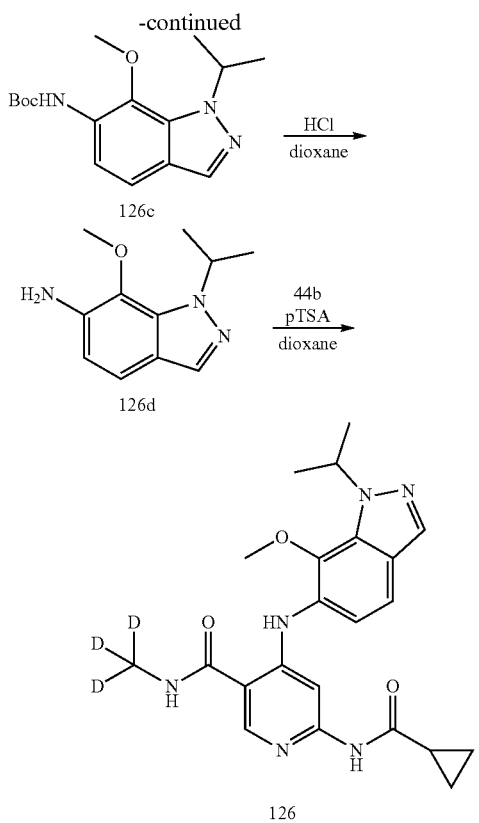

Step 1. (E)-1-(2,4-dibromo-3-methoxybenzylidene)-2-isopropylhydrazine hydrochloride (126a)

Compound 42f (1.0 g, 3.40 mmol) and isopropylhydrazine hydrochloride (451 mg, 4.08 mmol) were dissolved in EtOH (12 mL). The resulting mixture was stirred at 25° C. for 1 h and then cooled to 0° C. The cloudy mixture was filtered and washed with EtOH (2 mL) to afford the title compound 126a (1.1 g, 2.85 mmol, 84% yield) as an off-white solid. LC-MS (Method 4) $t_R$=5.22 min, m/z $(M+H)^+$=349.0.

Step 2. 6-Bromo-1-isopropyl-7-methoxy-1H-indazole (126b)

To a solution of 126a (1.1 g, 2.85 mmol) in DMF (15 mL) was added $K_2CO_3$ (982 mg, 7.11 mmol) and CuI (54 mg, 0.28 mmol). The mixture was stirred at 100° C. for 16 h. Water (50 mL) was added to above mixture. The solution was extracted with EtOAc (20 mL*3). The combined organic layer was washed with brine (50 mL), dried over $Na_2SO_4$, filtered and concentrated under vacuum to give crude compound 126b (700 mg, 2.60 mmol, 91% yield) as a yellow oil. LC-MS (Method 4) $t_R$=4.69 min, m/z $(M+H)^+$=269.0.

Step 3. Tert-butyl (1-isopropyl-7-methoxy-1H-indazol-6-yl)carbamate (126c)

A mixture of 126b (700 mg, 2.60 mmol), tert-butyl carbamate (609 mg, 5.20 mmol), $Pd_2(dba)_3$ (238 mg, 0.26 mmol), XantPhos (305 mg, 0.52 mmol), $Cs_2CO_3$ (2.12 g, 6.50 mmol) in dioxane (10 mL) was stirred at 100° C. for 16 h under $N_2$. The mixture was diluted with $H_2O$ (30 mL), extracted with EA (20 mL*3), washed with brine (30 mL), dried over $Na_2SO_4$, concentrated to get the crude compound 126c (600 mg, 1.96 mmol, 75% yield) as a yellow solid. LC-MS (Method 4) $t_R$=4.58 min, m/z $(M+H)^+$=306.3.

Step 4. 1-Isopropyl-7-methoxy-1H-indazol-6-amine (126d)

To a solution of 126c (600 mg, 1.96 mmol) in dioxane (6 mL) was added a solution of HCl (g) in dioxane (4 M, 6 mL). The mixture was stirred at r.t. for 30 min. The mixture was concentrated to dryness. The residue was diluted with $H_2O$ (30 mL), adjusted pH to 7-9 with aq $Na_2CO_3$, and extracted with EtOAc (30 mL*3). The organic layers were washed with aq $Na_2CO_3$ (30 mL) and brine (30 mL), dried over $Na_2SO_4$ and filtered. The filtrate was concentrated to give the title compound 126d (350 mg, 87% yield) as a yellow solid. LC-MS (Method 4) $t_R$=2.80 min, m/z $(M+H)^+$=206.1.

Step 5. 6-(Cyclopropanecarboxamido)-4-((1-isopropyl-7-methoxy-1H-indazol-6-yl)amino)-N-(methyl-$d_3$)nicotinamide (126)

A mixture of 126d (50 mg, 0.24 mmol), 44b (69 mg, 0.27 mmol), pTSA (42 mg, 0.24 mmol) in dioxane (2 mL) was stirred at 100° C. for 15 h. The mixture was concentrated and purified by Prep-HPLC (Method E) to get the compound 126 (66 mg, 64% yield) as a white solid. LC-MS (Method 4) $t_R$=3.18 min, m/z $(M+H)^+$=426.3. $^1$H NMR (400 MHz, DMSO-$d_6$) δ 10.72 (s, 1H), 10.54 (s, 1H), 8.61 (s, 1H), 8.52 (s, 1H), 0.8.07 (s, 1H), 7.84 (s, 1H), 7.51 (d, J=8.4 Hz, 1H), 7.10 (d, J=8.4 Hz, 1H), 5.28-5.25 (m, 1H), 3.78 (s, 3H), 1.97-1.93 (m, 1H), 1.49 (d, J=6.8 Hz, 6H), 0.86-0.70 (m, 4H).

Example 127

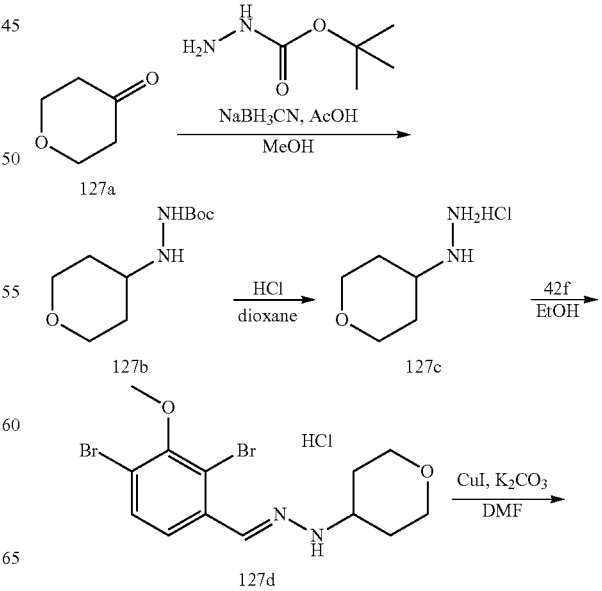

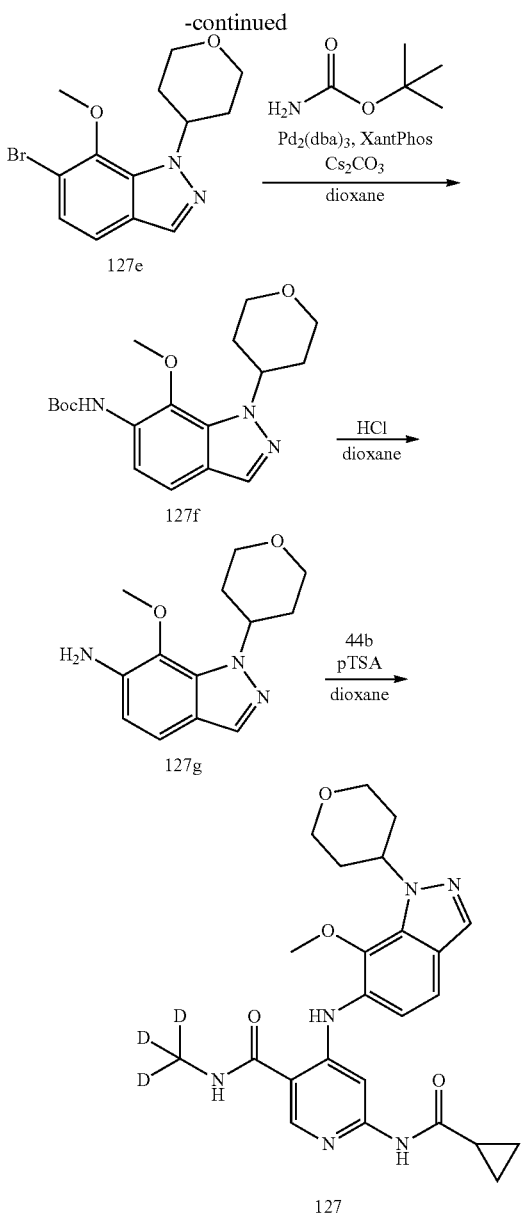

Step 1. Tert-butyl 2-(tetrahydro-2H-pyran-4-yl)hydrazine-1-carboxylate (127b)

To a solution of 127a (1 g, 9.99 mmol) in MeOH (10 mL) was added tert-butyl hydrazinecarboxylate (1.58 g, 11.99 mmol) then the mixture was stirred at r.t. for 3 h. Then acetic acid (30 mg, 0.5 mmol) and NaBH$_3$CN (1.26 g, 19.98 mmol) was added into the mixture and the mixture was stirred at r.t. for 16 h. The mixture was diluted with H$_2$O (50 mL), extracted with EtOAc (30 mL*3), washed with brine (50 mL), dried over Na$_2$SO$_4$ and concentrated to get compound 127b (2.16 g, 9.99 mmol) as a white solid. LC-MS (Method 4) t$_R$=2.30 min, m/z (M+H−56)$^+$=161.2.

Step 2. (Tetrahydro-2H-pyran-4-yl)hydrazine hydrochloride (127c)

To a solution of 127b (2.16 g, 9.99 mmol) in 1,4-dioxane (10 mL) was added HCl/1,4-dioxane (4 M, 10 mL) then the mixture was stirred at r.t for 2 h. The mixture was concentrated to get the crude compound 127c (1.5 g, 98% yield) as a white solid. LC-MS (Method 4) t$_R$=0.83 min, m/z (M+H)$^+$ =117.1.

Step 3. (E)-1-(2,4-dibromo-3-methoxybenzylidene)-2-(tetrahydro-2H-pyran-4-yl)hydrazine hydrochloride (127d)

Compound 42f (500 mg, 1.70 mmol) and 127c (286 mg, 1.87 mmol) were dissolved in EtOH (5 mL). The resulting mixture was stirred at 25° C. for 1 h and then cooled to 0° C. The cloudy mixture was filtered and washed with EtOH (1 mL) to afford the title compound 127d (600 mg, 1.40 mmol, 82% yield) as an off-white solid. LC-MS (Method 4) t$_R$=4.99 min, m/z (M+H)$^+$=391.1.

Step 4. 6-Bromo-7-methoxy-1-(tetrahydro-2H-pyran-4-yl)-1H-indazole (127e)

To a solution of 127d (600 mg, 1.40 mmol) in DMF (10 mL) was added K$_2$CO$_3$ (580 mg, 4.20 mmol) and CuI (27 mg, 0.14 mmol). The mixture was stirred at 100° C. for 16 h. Water (30 mL) was added to above mixture. The solution was extracted with EtOAc (20 mL*3). The combined organic layer was washed with brine (50 mL), dried over Na$_2$SO$_4$, filtered and concentrated under vacuum to give crude compound 127e (250 mg, 57% yield) as a yellow oil. LC-MS (Method 4) t$_R$=4.72 min, m/z (M+H)$^+$=311.2.

Step 5. Tert-butyl (7-methoxy-1-(tetrahydro-2H-pyran-4-yl)-1H-indazol-6-yl)carbamate (127f)

A mixture of 127e (250 mg, 0.80 mmol), tert-butyl carbamate (235 mg, 2.01 mmol), Pd$_2$(dba)$_3$ (74 mg, 0.08 mmol), XantPhos (94 mg, 1.60 mmol), Cs$_2$CO$_3$ (654 mg, 2.01 mmol) in dioxane (5 mL) was stirred at 100° C. for 16 h under N$_2$. The mixture was diluted with H$_2$O (20 mL), extracted with EA (20 mL*3), washed with brine (30 mL), dried over Na$_2$SO$_4$, concentrated to get the crude compound 127f (210 mg, 75% yield) as a yellow solid. LC-MS (Method 4) t$_R$=4.22 min, m/z (M+H)$^+$=348.3.

Step 6. 7-Methoxy-1-(tetrahydro-2H-pyran-4-yl)-1H-indazol-6-amine (127g)

To a solution of 127f (200 mg, 0.58 mmol) in dioxane (2 mL) was added a solution of HCl (g) in dioxane (4 M, 2 mL). The mixture was stirred at r.t. for 2 h. The mixture was concentrated to dryness. The residue was diluted with H$_2$O (30 mL), adjusted pH to 7-9 with aq Na$_2$CO$_3$, and extracted with EtOAc (30 mL*3). The organic layers were washed with aq Na$_2$CO$_3$ (30 mL) and brine (30 mL), dried over Na$_2$SO$_4$ and filtered. The filtrate was concentrated and purified by flash chromatography (PE/EA from 1/1 to 1/10) to give the title compound 127g (130 mg, 91% yield) as a yellow solid. LC-MS (Method 4) t$_R$=2.40 min, m/z (M+H)$^+$=248.2.

Step 7. 6-(Cyclopropanecarboxamido)-4-((7-methoxy-1-(tetrahydro-2H-pyran-4-yl)-1H-indazol-6-yl)amino)-N-(methyl-d$_3$)nicotinamide (127)

A mixture of 127g (40 mg, 0.16 mmol), 44b (41 mg, 0.16 mmol), pTSA (28 mg, 0.16 mmol) in dioxane (1.5 mL) was stirred at 100° C. for 15 h. The mixture was concentrated and purified by Prep-HPLC (Method E) to get the compound 127

(45 mg, 59% yield) as a white solid. LC-MS (Method 4) $t_R$=2.84 min, m/z (M+H)$^+$=468.4. $^1$H NMR (400 MHz, DMSO-d$_6$) δ 10.69 (s, 1H), 10.53 (s, 1H), 8.57 (s, 1H), 8.48 (s, 1H), 0.8.05 (s, 1H), 7.80 (s, 1H), 7.49 (d, J=8.4 Hz, 1H), 7.07 (d, J=8.4 Hz, 1H), 5.06-5.00 (m, 1H), 3.99-3.96 (m, 2H), 3.76 (s, 3H), 3.52-3.45 (m, 2H), 2.13-2.07 (m, 2H), 1.97-1.89 (m, 3H), 0.71-0.65 (m, 4H).

Example 128

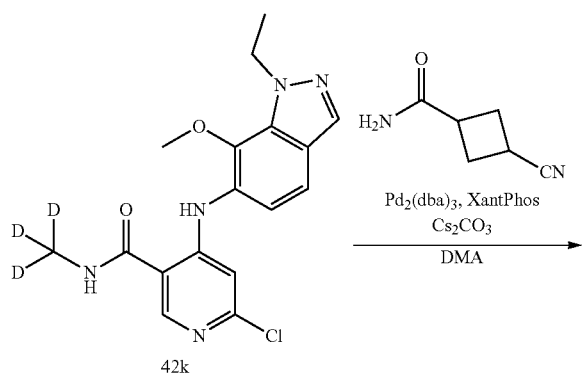

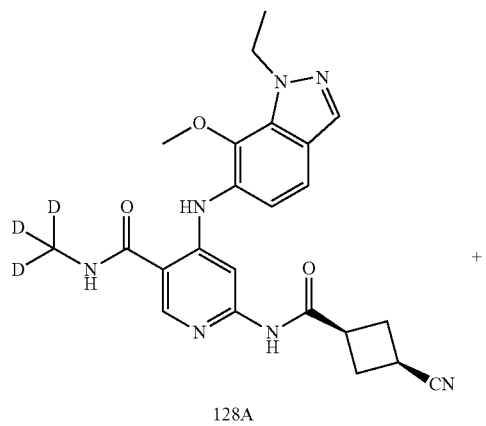

128A

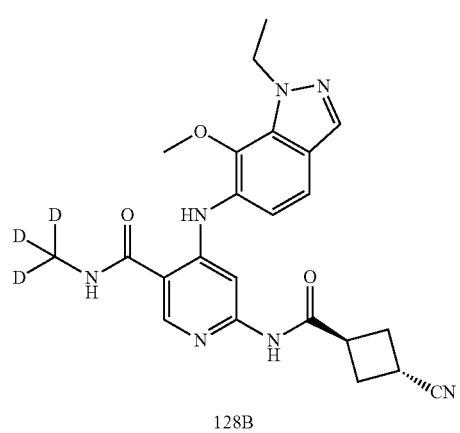

128B

Step 1. 6-((Cis)-3-cyanocyclobutane-1-carboxamido)-4-((1-ethyl-7-methoxy-1H-indazol-6-yl)amino)-N-(methyl-d$_3$)nicotinamide (128A) and 6-((Trans)-3-cyanocyclobutane-1-carboxamido)-4-((1-ethyl-7-methoxy-1H-indazol-6-yl)amino)-N-(methyl-d$_3$)nicotinamide (128B)

A mixture of 42k (60 mg, 0.16 mmol), 3-cyanocyclobutanecarboxamide (51 mg, 0.41 mmol), XantPhos (19 mg, 0.033 mol), Pd$_2$(dba)$_3$ (15 mg, 0.016 mmol), Cs$_2$CO$_3$ (135 mg, 0.41 mmol) in DMA (1 mL) was stirred at 145° C. at M.W. for 1.5 h. Then the mixture was diluted with H$_2$O (10 mL), extracted with EtOAc (10 mL*3), washed with brine (10 mL), dried over Na$_2$SO$_4$, concentrated and purified by Prep-HPLC (Method E) to get the compound 128A (2.3 mg, 3% yield) as an off-white solid and 128B (2.0 mg, 2.7% yield) as a white solid.

128A: LC-MS (Method 4) $t_R$=2.88 min, m/z (M+H)$^+$=451.4.
$^1$H NMR (400 MHz, CDCl$_3$) δ 10.27 (s, 1H), 8.23 (s, 1H), 7.94-7.93 (m, 2H), 7.81 (s, 1H), 7.51 (d, J=8.4 Hz, 1H), 7.16 (d, J=8.4 Hz, 1H), 6.16 (s, 1H), 4.63 (q, J=7.2 Hz, 2H), 3.89 (s, 3H), 3.13-3.01 (m, 2H), 2.77-2.69 (m, 2H), 2.66-2.53 (m, 2H), 1.51 (t, J=7.2 Hz, 3H).

128B: LC-MS (Method 4) $t_R$=2.97 min, m/z (M+H)$^+$=451.4.
$^1$H NMR (400 MHz, CDCl$_3$) δ 10.27 (s, 1H), 8.25 (s, 1H), 8.04 (s, 1H), 7.94-7.93 (m, 2H), 7.50 (d, J=8.4 Hz, 1H), 7.17 (d, J=8.4 Hz, 1H), 6.22 (s, 1H), 4.63 (q, J=7.2 Hz, 2H), 3.89 (s, 3H), 3.34-3.27 (m, 1H), 3.23-3.18 (m, 1H), 2.77-2.70 (m, 2H), 2.60-2.53 (m, 2H), 1.51 (t, J=7.2 Hz, 3H).

Example 129

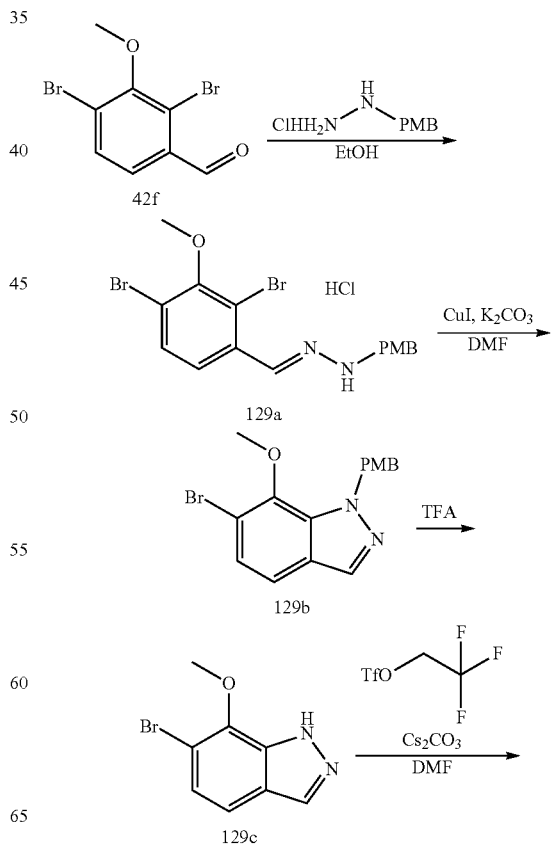

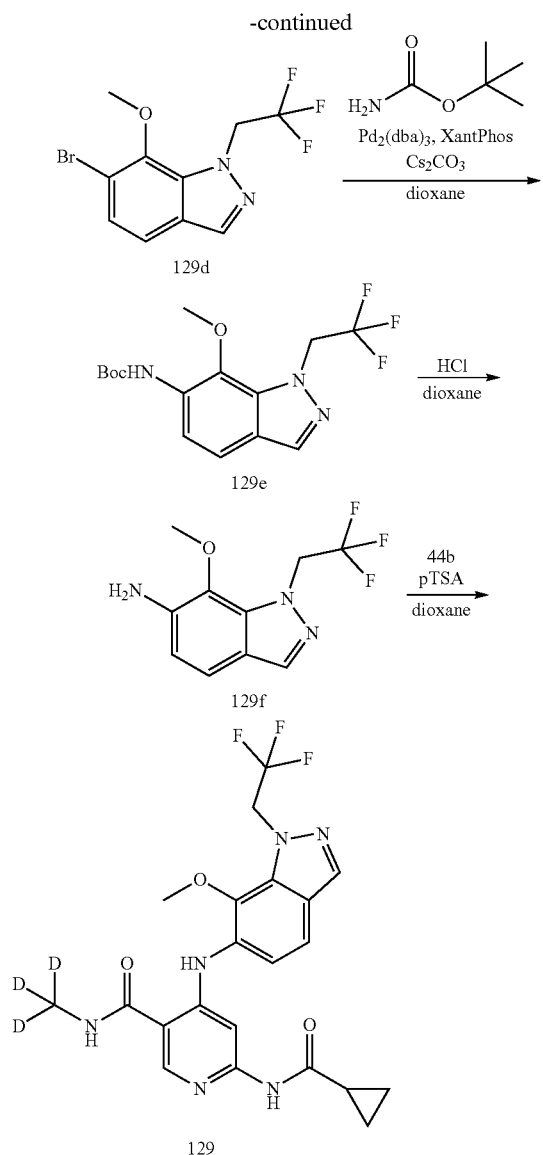

Step 1. (E)-1-(2,4-dibromo-3-methoxybenzylidene)-2-(4-methoxybenzyl)hydrazine hydrochloride (129a)

Compound 42f (3.0 g, 10.21 mmol) and (4-methoxybenzyl)hydrazine hydrochloride (2.12 g, 11.23 mmol) were dissolved in EtOH (30 mL). The resulting mixture was stirred at 25° C. for 16 h and then cooled to 0° C. The cloudy mixture was filtered and washed with EtOH (5 mL) to afford the title compound 129a (3.5 g, 74% yield) as a pale yellow solid. LC-MS (Method 4) $t_R$=5.22 min, m/z $(M+H)^+$=427.0.

Step 2. 6-Bromo-7-methoxy-1-(4-methoxybenzyl)-1H-indazole (129b)

To a solution of 129a (3.5 g, 7.53 mmol) in DMF (50 mL) was added $K_2CO_3$ (2.6 g, 18.83 mmol) and CuI (143 mg, 0.75 mmol). The mixture was stirred at 100° C. for 16 1h. Water (200 mL) was added to above mixture. The solution was extracted with EtOAc (60 mL*3). The combined organic layer was washed with brine (100 mL), dried over $Na_2SO_4$, filtered and concentrated under vacuum to give crude compound 129b (2.4 g, 91% yield) as a yellow oil. LC-MS (Method 4) $t_R$=4.81 min, m/z $(M+H)^+$=347.1.

Step 3. 6-Bromo-7-methoxy-1H-indazole (129c)

129b (2.4 g, 6.91 mmol) was dissolved in TFA (20 mL), then the mixture was stirred at 90° C. for 4 h. Then the mixture was concentrated, and diluted with $H_2O$ (50 mL), adjusted pH to 7 with aq $NaHCO_3$, then extracted with EtOAc (50 mL*3), washed with brine (50 mL), dried over $Na_2SO_4$, concentrated and purified by flash chromatography (PE/EA=1/1 to 1/10) to get the compound 129c (1.4 g, 89% yield) as a yellow solid.
LC-MS (Method 4) $t_R$=3.39 min, m/z $(M+H)^+$=226.9.

Step 4. 6-Bromo-7-methoxy-1-(2,2,2-trifluoroethyl)-1H-indazole (129d)

To a solution of 129c (400 mg, 1.76 mmol) in DMF (5 mL) was added $Cs_2CO_3$ (1.15 g, 3.52 mmol) and 2,2,2-trifluoroethyl trifluoromethanesulfonate (613 mg, 2.64 mmol, 0.38 mL) at r.t., then the mixture was stirred at r.t. for 2 h. The mixture was diluted with $H_2O$ (20 mL), extracted with EtOAc (20 mL*3), washed with brine (30 mL), dried over $Na_2SO_4$, concentrated to get the compound 129d (80 mg, 15% yield) and 6-bromo-7-methoxy-2-(2,2,2-trifluoroethyl)-2H-indazole (300 mg, 55% yield) both as a yellow oil. LC-MS (Method 4) $t_R$=4.50 min, m/z $(M+H)^+$=309.0.
$^1$H NMR (400 MHz, $CDCl_3$) δ 8.06 (s, 1H), 7.35 (d, J=8.4 Hz, 1H), 7.31 (d, J=8.4 Hz, 1H), 5.19 (q, 2H), 4.06 (s, 3H).

Step 5. Tert-butyl (7-methoxy-1-(2,2,2-trifluoroethyl)-1H-indazol-6-yl)carbamate (129e)

A mixture of 129d (60 mg, 0.19 mmol), tert-butyl carbamate (57 mg, 0.49 mmol), $Pd_2(dba)_3$ (18 mg, 0.02 mmol), XantPhos (23 mg, 0.04 mmol), $Cs_2CO_3$ (190 mg, 0.60 mmol) in dioxane (1 mL) was stirred at 100° C. for 16 h under $N_2$. The mixture was diluted with $H_2O$ (20 mL), extracted with EA (20 mL*3), washed with brine (30 mL), dried over $Na_2SO_4$, concentrated to get the crude compound 129e (42 mg, 63% yield) as a yellow solid. LC-MS (Method 4) $t_R$=4.48 min, m/z $(M+H)^+$=346.2.

Step 6. 7-Methoxy-1-(2,2,2-trifluoroethyl)-1H-indazol-6-amine (129f)

To a solution of 129e (42 mg, 0.12 mmol) in dioxane (0.5 mL) was added a solution of HCl (g) in dioxane (4 M, 0.5 mL). The mixture was stirred at r.t. for 2 h. The mixture was concentrated to dryness. The residue was diluted with $H_2O$ (20 mL), adjusted pH to 7-9 with aq $Na_2CO_3$, extracted with EtOAc (20 mL*3). The organic layers were washed with aq $Na_2CO_3$ (20 mL) and brine (20 mL), dried over $Na_2SO_4$ and filtered. The filtrate was concentrated and purified by flash chromatography (PE/EA=1/1 to 1/10) to give the title compound 129f (20 mg, 67% yield) as a yellow solid. LC-MS (Method 4) $t_R$=3.06 min, m/z $(M+H)^+$=246.1.

Step 7. 6-(Cyclopropanecarboxamido)-4-((7-methoxy-1-(2,2,2-trifluoroethyl)-1H-indazol-6-yl)amino)-N-(methyl-$d_3$)nicotinamide (129)

A mixture of 129f (20 mg, 0.082 mmol), 44b (41 mg, 0.082 mmol), pTSA (14 mg, 0.082 mmol) in dioxane (1 mL) was stirred at 100° C. for 15 h. The mixture was concentrated and purified by Prep-HPLC (Method E) to get the compound 129 (5.1 mg, 13% yield) as a pale yellow solid. LC-MS (Method 4) $t_R$=3.22 min, m/z (M+H)$^+$=466.3. $^1$H NMR (400 MHz, CDCl$_3$) δ 10.28 (s, 1H), 8.27-8.26 (m, 2H), 8.01 (s, 1H), 7.92 (s, 1H), 7.48 (d, J=8.4 Hz, 1H), 7.23 (d, J=8.4 Hz, 1H), 6.19 (s, 1H), 5.19 (q, J=8.4 Hz, 2H), 3.90 (s, 3H), 1.52-1.50 (m, 1H), 1.25-1.02 (m, 2H), 0.88-0.84 (m, 2H).

Example 130

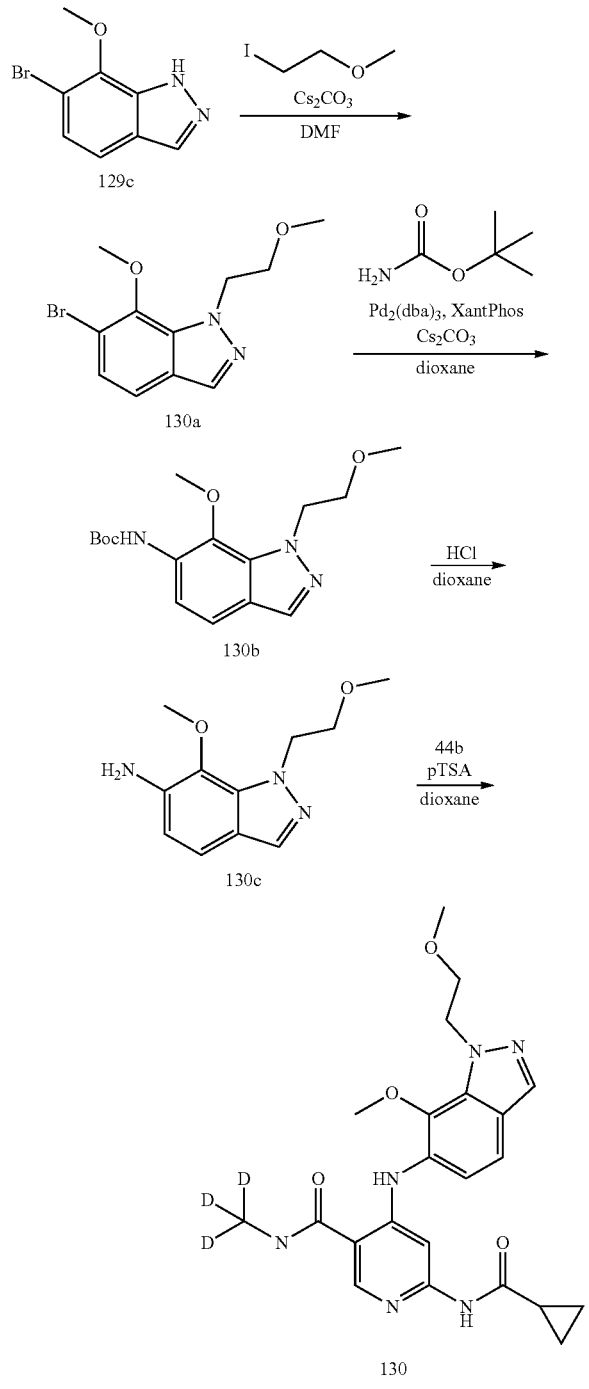

Step 1. 6-Bromo-7-methoxy-1-(2-methoxyethyl)-1H-indazole (130a)

To a solution of 129c (400 mg, 1.76 mmol) in DMF (5 mL) was added Cs$_2$CO$_3$ (1.15 g, 3.52 mmol) and 1-iodo-2-methoxyethane (98 mg, 0.53 mmol) at r.t. then the mixture was stirred at r.t. for 2 h. The mixture was diluted with H$_2$O (20 mL), extracted with EtOAc (20 mL*3), washed with brine (30 mL), dried over Na$_2$SO$_4$, concentrated to get the compound 130a (200 mg, 40% yield) and 6-bromo-7-methoxy-2-(2-methoxyethyl)-2H-indazole (200 mg, 40% yield) both as a yellow oil. LC-MS (Method 4) $t_R$=3.15 min, m/z (M+H)$^+$=285.1. $^1$H NMR (400 MHz, CDCl$_3$) δ 7.97 (s, 1H), 7.32 (d, J=8.4 Hz, 1H), 7.42 (d, J=8.4 Hz, 1H), 4.75 (t, J=5.6 Hz, 2H), 4.03 (s, 3H), 3.87 (t, J=5.6 Hz, 2H), 3.00 (s, 3H).

Step 2. Tert-butyl (7-methoxy-1-(2-methoxyethyl)-1H-indazol-6-yl)carbamate (130b)

A mixture of 130a (200 mg, 0.70 mmol), tert-butyl carbamate (164 mg, 1.40 mmol), Pd$_2$(dba)$_3$ (64 mg, 0.07 mmol), XantPhos (82 mg, 0.14 mmol), Cs$_2$CO$_3$ (571 mg, 1.75 mmol) in dioxane (2.5 mL) was stirred at 100° C. for 16 h under N$_2$. The mixture was diluted with H$_2$O (20 mL), extracted with EA (20 mL*3), washed with brine (30 mL), dried over Na$_2$SO$_4$, concentrated to get the crude compound 130b (200 mg, 88% yield) as a yellow solid. LC-MS (Method 4) $t_R$=4.09 min, m/z (M+H)$^+$=322.2.

Step 3. 7-Methoxy-1-(2-methoxyethyl)-1H-indazol-6-amine (130c)

To a solution of 130b (200 mg, 0.62 mmol) in dioxane (2 mL) was added a solution of HCl (g) in dioxane (4 M, 2 mL). The mixture was stirred at r.t. for 2 h. The mixture was concentrated to dryness. The residue was diluted with H$_2$O (20 mL), adjusted pH to 7-9 with aq Na$_2$CO$_3$, and extracted with EtOAc (20 mL*3). The organic layers were washed with aq Na$_2$CO$_3$ (20 mL) and brine (20 mL) and separated. The solution was dried over Na$_2$SO$_4$ and filtered. The filtrate was concentrated and purified by flash chromatography (PE/EA=1/1 to 1/10) to give the title compound 130c (90 mg, 65% yield) as a yellow solid. LC-MS (Method 4) $t_R$=2.13 min, m/z (M+H)$^+$=222.1.

Step 4. 6-(Cyclopropanecarboxamido)-4-((7-methoxy-1-(2-methoxyethyl)-1H-indazol-6-yl)amino)-N-(methyl-d$_3$)nicotinamide (130)

A mixture of 130c (40 mg, 0.18 mmol), 44b (51 mg, 0.20 mmol), pTSA (31 mg, 0.18 mmol) in dioxane (1 mL) was stirred at 100° C. for 2 h. The mixture was concentrated and purified by Prep-HPLC (Method E) to get the compound 130 (37 mg, 46% yield) as an off-white solid. LC-MS (Method 4) $t_R$=2.61 min, m/z (M+H)$^+$=442.4. $^1$H NMR (400 MHz, CDCl$_3$) 10.22 (s, 1H), 8.24 (s, 1H), 8.10 (s, 1H), 7.94-7.93 (m, 2H), 7.46 (d, J=8.4 Hz, 1H), 7.17 (d, J=8.4 Hz, 1H), 6.15 (s, 1H), 4.75 (t, J=6.0 Hz, 2H), 3.88 (s, 3H), 3.85 (t, J=6.0 Hz, 2H), 3.31 (s, 3H), 1.65-1.46 (m, 1H), 1.04-1.02 (m, 2H), 0.86-0.83 (m, 2H).

Example 131

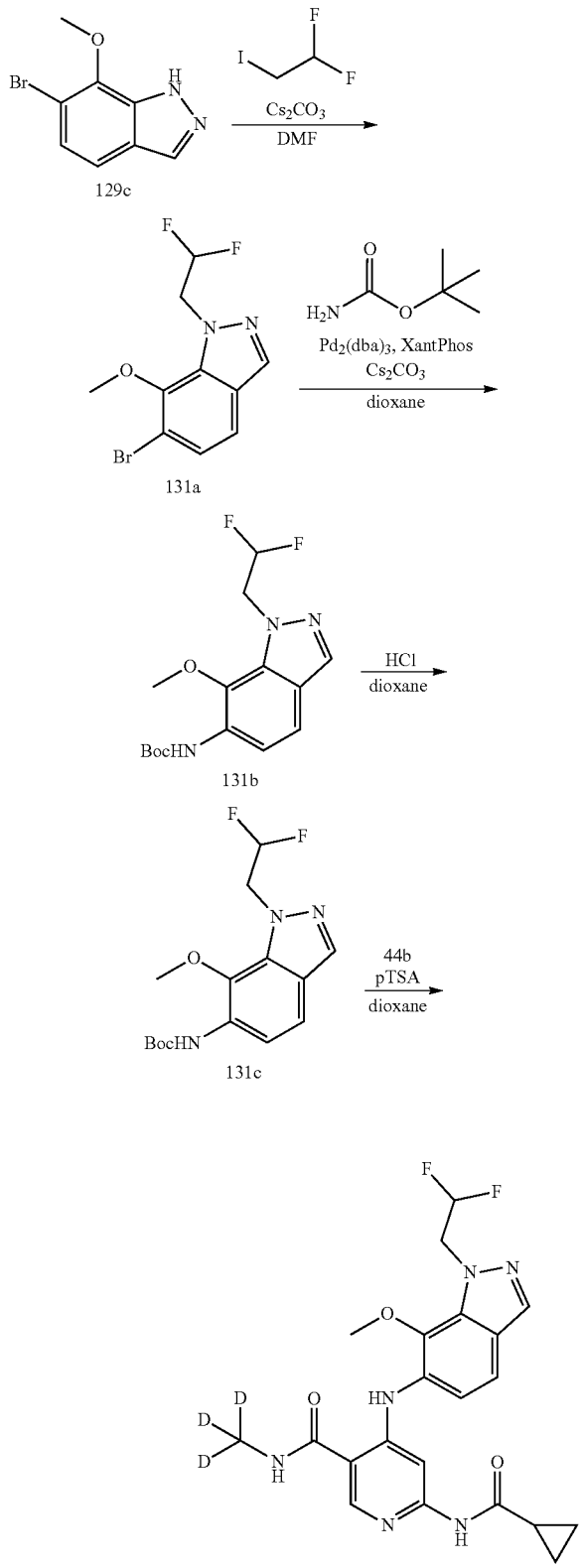

Step 1. 6-Bromo-7-methoxy-1-(2,2-difluoroethyl)-1H-indazole (131a)

To a solution of 129c (200 mg, 0.88 mmol) in DMF (2 mL) was added $Cs_2CO_3$ (574 mg, 1.76 mmol) and 1,1-difluoro-2-iodoethane (253 mg, 1.32 mmol) at r.t., then the mixture was stirred at r.t. for 2 h. The mixture was diluted with $H_2O$ (20 mL), extracted with EtOAc (20 mL*3), washed with brine (30 mL), dried over $Na_2SO_4$, concentrated to get the compound 131a (110 mg, 43% yield) and 6-bromo-2-(2,2-difluoroethyl)-7-methoxy-2H-indazole (110 mg, 43% yield) both as a yellow oil. LC-MS (Method 4) $t_R$=4.28 min, m/z (M+H)$^+$=291.1. $^1$H NMR (400 MHz, CDCl$_3$) δ 8.02 (s, 1H), 7.34 (d, J=8.4 Hz, 1H), 7.29 (d, J=8.4 Hz, 1H), 6.25 (tt, J=56 Hz, J=4.4 Hz, 1H), 4.93 (td, J=13.2 Hz, J=4.4 Hz, 2H), 4.05 (s, 3H).

Step 2. Tert-butyl (1-(2,2-difluoroethyl)-7-methoxy-1H-indazol-6-yl)carbamate (131b)

A mixture of 131a (110 mg, 0.38 mmol), tert-butyl carbamate (117 mg, 0.94 mmol), Pd$_2$(dba)$_3$ (38 mg, 0.042 mmol), XantPhos (47 mg, 0.079 mmol), Cs$_2$CO$_3$ (369 mg, 1.13 mmol) in dioxane (1.5 mL) was stirred at 100° C. for 16 h under N$_2$. The mixture was diluted with H$_2$O (20 mL), extracted with EA (20 mL*3), washed with brine (30 mL), dried over Na$_2$SO$_4$, concentrated to get the crude compound 131b (100 mg, 88% yield) as a yellow solid. LC-MS (Method 4) $t_R$=4.26 min, m/z (M+H)$^+$=328.2.

Step 3. 1-(2,2-Difluoroethyl)-7-methoxy-1H-indazol-6-amine (131c)

To a solution of 131b (100 mg, 0.31 mmol) in dioxane (2 mL) was added a solution of HCl (g) in dioxane (4 M, 2 mL). The mixture was stirred at r.t. for 2 h. The mixture was concentrated to dryness. The residue was diluted with H$_2$O (20 mL), adjusted pH to 7-9 with aq Na$_2$CO$_3$, and extracted with EtOAc (20 mL*3). The organic layers were washed with aq Na$_2$CO$_3$ (20 mL) and brine (20 mL) and separated. The solution was dried over Na$_2$SO$_4$ and filtered. The filtrate was concentrated and purified by flash chromatography (PE/EA=1/1 to 1/10) to give the title compound 131c (50 mg, 72% yield) as a yellow solid. LC-MS (Method 4) $t_R$=2.66 min, m/z (M+H)$^+$=228.1.

Step 4. 6-(Cyclopropanecarboxamido)-4-((1-(2,2-difluoroethyl)-7-methoxy-1H-indazol-6-yl)amino)-N-(methyl-d$_3$)nicotinamide (131)

A mixture of 131c (50 mg, 0.22 mmol), 44b (56 mg, 0.22 mmol), pTSA (38 mg, 0.22 mmol) in dioxane (1 mL) was stirred at 100° C. for 2 h. The mixture was concentrated and purified by Prep-HPLC (Method E) to get the compound 131 (33 mg, 33% yield) as a pale yellow solid. LC-MS (Method 4) $t_R$=2.93 min, m/z (M+H)$^+$=448.3. $^1$H NMR (400 MHz, CDCl$_3$) δ 10.26 (s, 1H), 8.25-8.24 (m, 2H), 7.97 (s, 1H), 7.90 (s, 1H), 7.47 (d, J=8.4 Hz, 1H), 7.21 (d, J=8.4 Hz, 1H), 6.40-6.10 (m, 2H), 4.92 (td, J=13.2 Hz, J=4.4 Hz, 2H), 3.88 (s, 3H), 1.51-1.47 (m, 1H), 1.05-1.01 (m, 2H), 0.87-0.82 (m, 2H).

Example 132

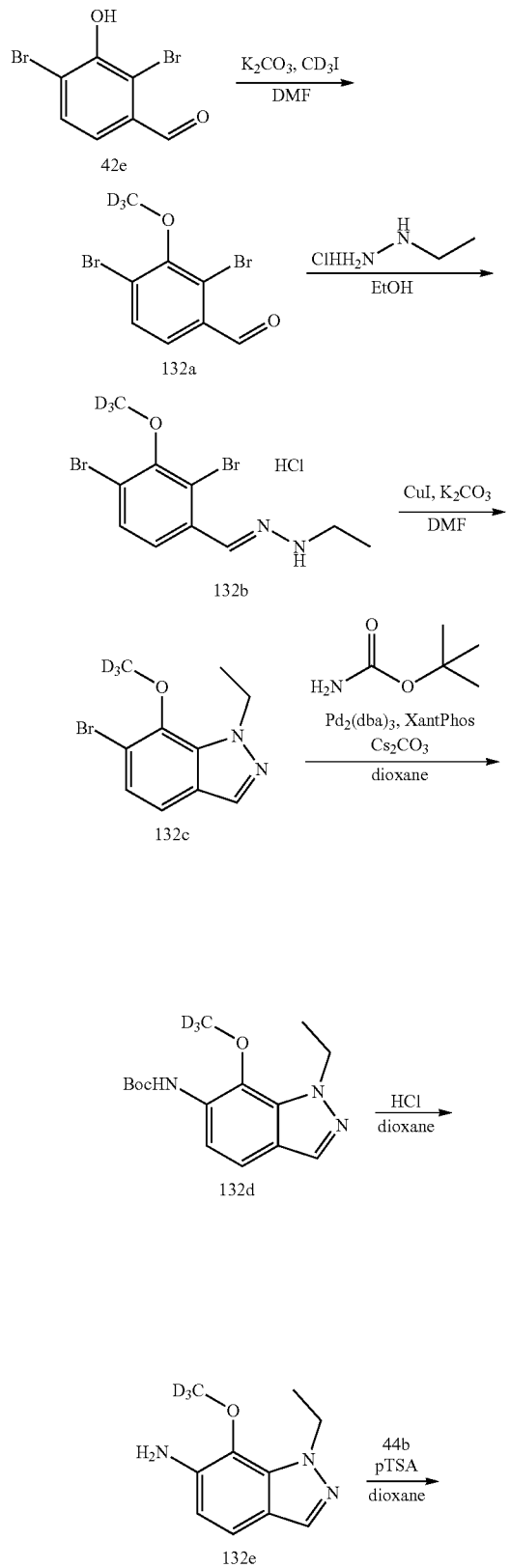

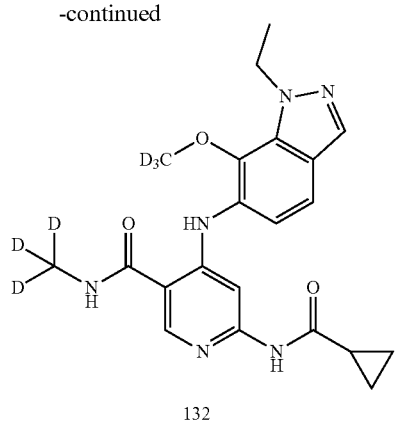

132

Step 1. 2,4-Dibromo-3-(methoxy-d₃)benzaldehyde (132a)

To a solution of 42e (1.5 g, 5.36 mmol) and K₂CO₃ (1.48 g, 10.72 mmol) in DMF (20 mL) was added iodomethane-d₃ (1.17 g, 8.04 mmol). The mixture was stirred at 25° C. for 2 h, then poured into water (40 mL) and extracted with EtOAc (30 mL*3). The combined organic layer was washed with brine (30 mL), dried over Na₂SO₄, filtered and concentrated under vacuum to give crude compound 132a (1.5 g, 94% yield) as a yellow solid. LC-MS (Method 4) $t_R$=4.49 min. m/z (M+H)⁺=296.3.

Step 2. (E)-1-(2,4-dibromo-3-(methoxy-d₃)benzylidene)-2-ethylhydrazine hydrochloride (132b)

Compound 132a (500 mg, 1.68 mmol) and ethylhydrazine hydrochloride (179 mg, 1.85 mmol) were dissolved in EtOH (6 mL). The resulting mixture was stirred at 25° C. for 1 h and then cooled to 0° C. The cloudy mixture was filtered and washed with EtOH (1 mL) to afford the title compound 132b (410 mg, 65% yield) as an off-white solid. LC-MS (Method 4) $t_R$=5.05 min, m/z (M+H)⁺=338.0.

Step 3. 6-Bromo-1-ethyl-7-(methoxy-d₃)-1H-indazole (132c)

To a solution of 132b (400 mg, 1.07 mmol) in DMF (15 mL) was added K₂CO₃ (515 mg, 3.73 mmol) and CuI (20 mg, 0.11 mmol). The mixture was stirred at 100° C. for 16 h. Water (50 mL) was added to above mixture. The solution was extracted with EtOAc (20 mL*3). The combined organic layer was washed with brine (50 mL), dried over Na₂SO₄, filtered and concentrated under vacuum to give crude compound 132c (250 mg, 91% yield) as a yellow oil. LC-MS (Method 4) $t_R$=4.49 min, m/z (M+H)⁺=258.1.

Step 4. Tert-butyl (1-ethyl-7-(methoxy-d₃)-1H-indazol-6-yl)carbamate (132d)

A mixture of 132c (100 mg, 0.39 mmol), tert-butyl carbamate (91 mg, 0.77 mmol), Pd₂(dba)₃ (35 mg, 0.04 mmol), XantPhos (46 mg, 0.08 mmol), Cs₂CO₃ (315 mg, 0.97 mmol) in dioxane (10 mL) was stirred at 100° C. for 16 h under N₂. The mixture was diluted with H₂O (30 mL), extracted with EA (20 mL*3), washed with brine (30 mL), dried over Na₂SO₄, concentrated to get the crude compound

449

132d (110 mg, 96% yield) as a yellow solid. LC-MS (Method 4) $t_R$=4.40 min, m/z (M+H)$^+$=295.2.

Step 5. 1-Ethyl-7-(methoxy-d$_3$)-1H-indazol-6-amine (132e)

To a solution of 132d (110 mg, 0.37 mmol) in dioxane (2 mL) was added a solution of HCl (g) in dioxane (4 M, 2 mL). The mixture was stirred at r.t. for 30 min. The mixture was concentrated to dryness. The residue was diluted with H$_2$O (30 mL), adjusted pH to 7-9 with aq Na$_2$CO$_3$ and extracted with EtOAc (30 mL*3). The organic layers were washed with aq Na$_2$CO$_3$ (30 mL) and brine (30 mL) and separated. The solution was dried over Na$_2$SO$_4$ and filtered. The filtrate was concentrated to give the title compound 132e (40 mg, 55% yield) as a yellow solid. LC-MS (Method 4) $t_R$=2.34 min, m/z (M+H)$^+$=195.3.

Step 6. 6-(Cyclopropanecarboxamido)-4-((1-ethyl-7-(methoxy-d$_3$)-1H-indazol-6-yl)amino)-N-(methyl-d$_3$)nicotinamide (132)

A mixture of 132e (40 mg, 0.21 mmol), 44b (53 mg, 0.21 mmol), pTSA (35 mg, 0.21 mmol) in dioxane (2 mL) was stirred at 100° C. for 15 h. The mixture was concentrated and purified by Prep-HPLC (Method E) to get the compound 132 (23 mg, 27% yield) as a pale yellow solid. LC-MS (Method 4) $t_R$=2.83 min, m/z (M+H)$^+$=415.3. $^1$H NMR (400 MHz, DMSO-d$_6$) δ 10.72 (s, 1H), 10.54 (s, 1H), 8.61 (s, 1H), 8.52 (s, 1H), 8.04 (s, 1H), 7.83 (s, 1H), 7.50 (d, J=8.4 Hz, 1H), 7.09 (d, J=8.4 Hz, 1H), 4.54 (q, J=7.2 Hz, 2H), 1.95-1.93 (m, 1H), 1.40 (t, J=7.2 Hz, 3H), 0.74-0.70 (m, 4H).

Example 133

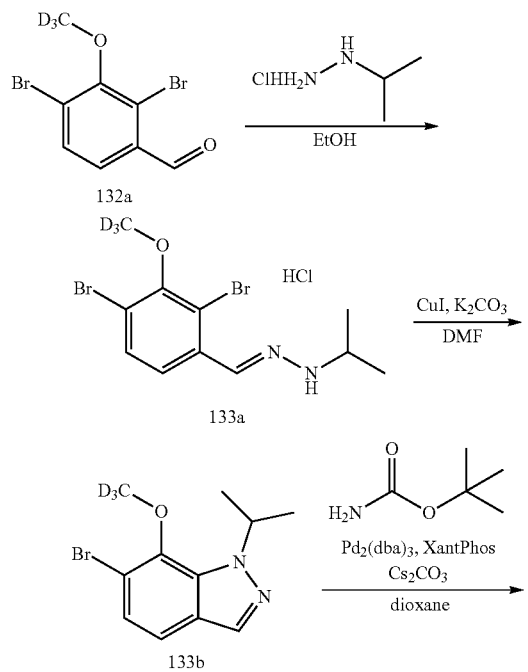

-continued

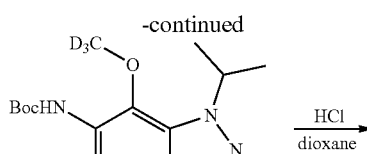

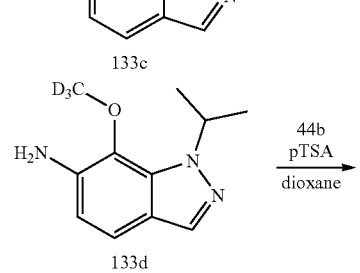

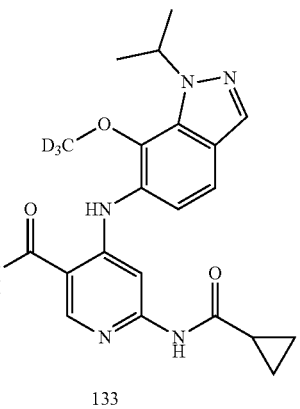

Step 1. (E)-1-(2,4-dibromo-3-(methoxy-d$_3$)benzylidene)-2-isopropylhydrazine hydrochloride (133a)

Compound 132a (1.0 g, 3.40 mmol) and isopropylhydrazine hydrochloride (447 mg, 4.04 mmol) were dissolved in EtOH (10 mL). The resulting mixture was stirred at 25° C. for 1 h and then cooled to 0° C. The cloudy mixture was filtered and washed with EtOH (2 mL) to afford the title compound 133a (1.19 g, 91% yield) as an off-white solid. LC-MS (Method 4) $t_R$=5.22 min, m/z (M+H)$^+$=352.0.

Step 2. 6-Bromo-1-isopropyl-7-(methoxy-d$_3$)-1H-indazole (133b)

To a solution of 133a (1.19 g, 3.06 mmol) in DMF (15 mL) was added K$_2$CO$_3$ (1.56 mg, 7.65 mmol) and CuI (59 mg, 0.31 mmol). The mixture was stirred at 100° C. for 16 h. Water (50 mL) was added to above mixture. The solution was extracted with EtOAc (20 mL*3). The combined organic layer was washed with brine (50 mL), dried over Na$_2$SO$_4$, filtered and concentrated under vacuum to give crude compound 133b (700 mg, 2.60 mmol, 85% yield) as a yellow oil. LC-MS (Method 4) $t_R$=4.69 min, m/z (M+H)$^+$=272.0.

Step 3. Tert-butyl (1-isopropyl-7-(methoxy-d$_3$)-1H-indazol-6-yl)carbamate (133c)

A mixture of 133b (700 mg, 2.60 mmol), tert-butyl carbamate (609 mg, 5.20 mmol), Pd$_2$(dba)$_3$ (238 mg, 0.26 mmol), XantPhos (305 mg, 0.52 mmol), Cs$_2$CO$_3$ (2.12 g, 6.50 mmol) in dioxane (10 mL) was stirred at 100° C. for 16 h under N₂. The mixture was diluted with H₂O (30 mL), extracted with EA (20 mL*3), washed with brine (30 mL), dried over Na₂SO₄, concentrated to get the crude compound 133c (600 mg, 1.96 mmol, 75% yield) as a yellow solid. LC-MS (Method 4) $t_R$=4.58 min, m/z (M+H)⁺=309.3.

Step 4. 1-Isopropyl-7-(methoxy-d₃)-1H-indazol-6-amine (133d)

To a solution of 133c (600 mg, 1.96 mmol) in dioxane (6 mL) was added a solution of HCl (g) in dioxane (4 M, 6 mL). The mixture was stirred at r.t. for 30 min. The mixture was concentrated to dryness. The residue was diluted with H₂O (30 mL), adjusted pH to 7-9 with aq Na₂CO₃, and extracted with EtOAc (30 mL*3). The organic layers were washed with aq Na₂CO₃ (30 mL) and brine (30 mL) and separated. The solution was dried over Na₂SO₄ and filtered. The filtrate was concentrated to give the title compound 133d (350 mg, 87% yield) as a yellow solid. LC-MS (Method 4) $t_R$=2.80 min, m/z (M+H)⁺=209.1.

Step 5. 6-(Cyclopropanecarboxamido)-4-((1-isopropyl-7-(methoxy-d₃)-1H-indazol-6-yl)amino)-N-(methyl-d₃)nicotinamide (133)

A mixture of 133d (100 mg, 0.48 mmol), 44b (148 mg, 0.57 mmol), pTSA (83 mg, 0.48 mmol) in dioxane (8 mL) was stirred at 100° C. for 3 h. The mixture was concentrated and purified by Prep-HPLC (Method E) to get the compound 133 (62.5 mg, 30% yield) as a white solid. LC-MS (Method 4) $t_R$=3.19 min, m/z (M+H)⁺=429.3. ¹H NMR (400 MHz, CDCl₃) δ 10.24 (s, 1H), 8.03 (s, 1H), 8.24 (s, 1H), 7.94-7.93 (m, 2H), 7.46 (d, J=8.4 Hz, 1H), 7.15 (d, J=8.4 Hz, 1H), 6.24 (s, 1H), 5.36-5.29 (m, 1H), 1.57 (d, J=6.8 Hz, 6H), 1.53-1.48 (m, 1H), 1.04-1.00 (m, 2H), 0.88-0.81 (m, 2H).

Example 134

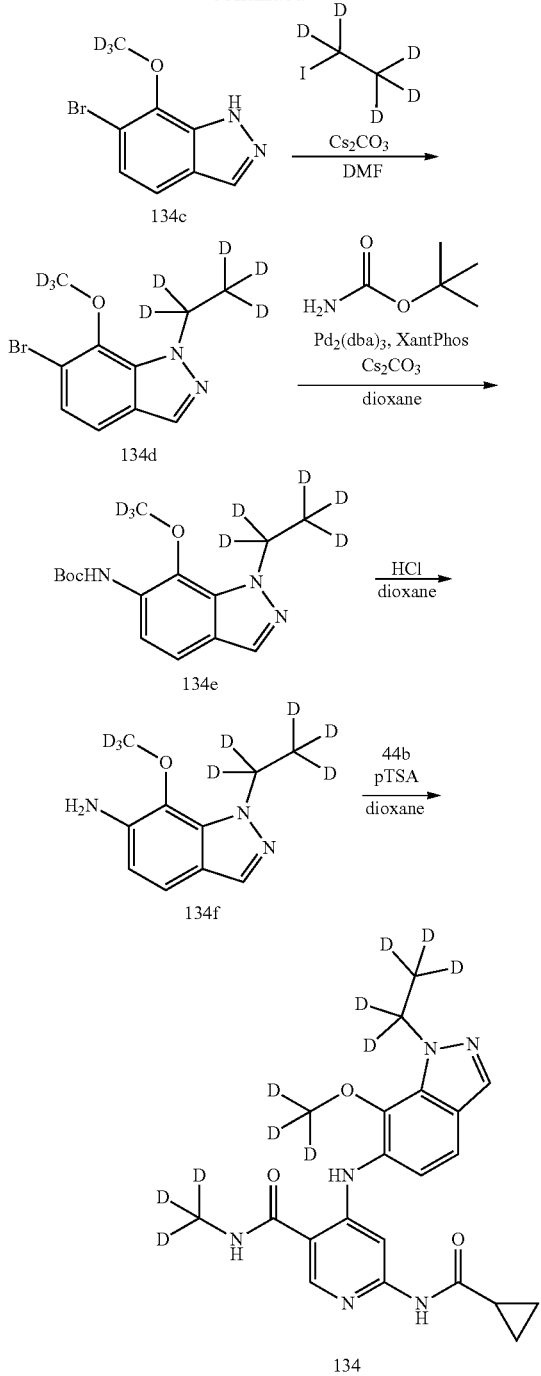

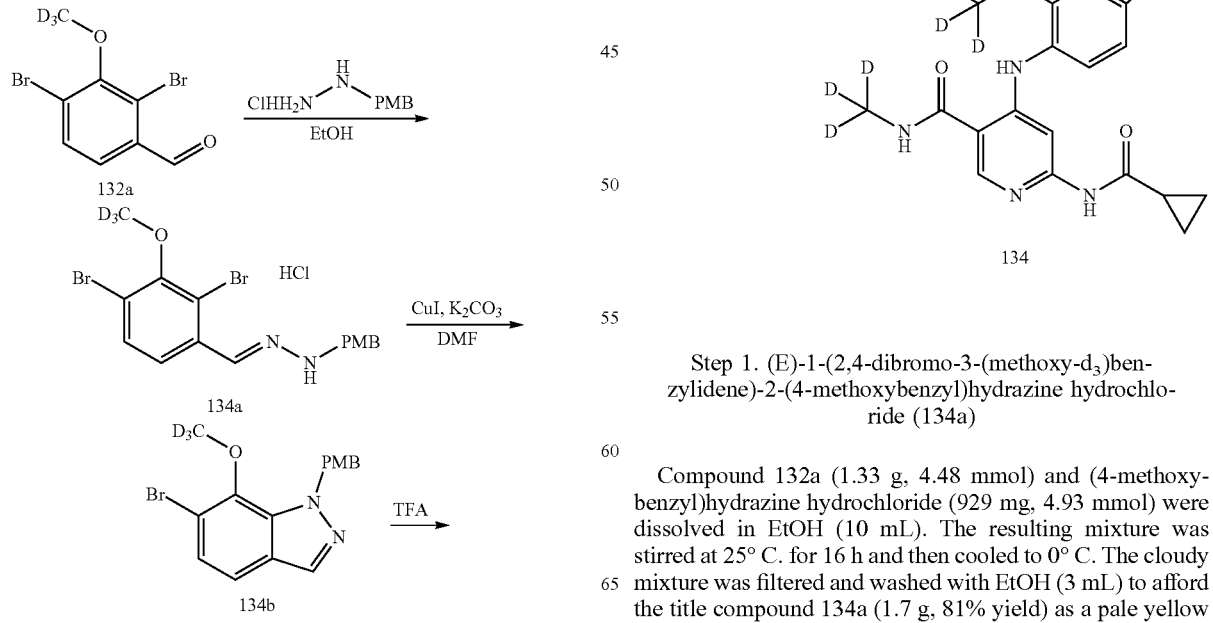

Step 1. (E)-1-(2,4-dibromo-3-(methoxy-d₃)benzylidene)-2-(4-methoxybenzyl)hydrazine hydrochloride (134a)

Compound 132a (1.33 g, 4.48 mmol) and (4-methoxybenzyl)hydrazine hydrochloride (929 mg, 4.93 mmol) were dissolved in EtOH (10 mL). The resulting mixture was stirred at 25° C. for 16 h and then cooled to 0° C. The cloudy mixture was filtered and washed with EtOH (3 mL) to afford the title compound 134a (1.7 g, 81% yield) as a pale yellow solid. LC-MS (Method 4) $t_R$=5.26 min, m/z (M+H)⁺=430.0.

Step 2. 6-Bromo-7-(methoxy-d₃)-1-(4-methoxybenzyl)-1H-indazole (134b)

To a solution of 134a (1.7 g, 3.94 mmol) in DMF (20 mL) was added K₂CO₃ (1.36 g, 18.83 mmol) and CuI (75 mg, 0.39 mmol). The mixture was stirred at 100° C. for 16 h. Water (200 mL) was added to above mixture. The solution was extracted with EtOAc (60 mL*3). The combined organic layer was washed with brine (100 mL), dried over Na₂SO₄, filtered and concentrated under vacuum to give crude compound 134b (1.0 g, 72% yield) as a yellow oil. LC-MS (Method 4) $t_R$=4.84 min, m/z (M+H)⁺=350.1.

Step 3. 6-Bromo-7-(methoxy-d₃)-1H-indazole (134c)

134b (1.0 g, 2.86 mmol) was dissolved in TFA (10 mL), then the mixture was stirred at 90° C. for 4 h. Then the mixture was concentrated and diluted with H₂O (50 mL), adjusted pH to 7 with aq NaHCO₃, then extracted with EtOAc (50 mL*3), washed with brine (50 mL), dried over Na₂SO₄, concentrated and purified by flash chromatography (PE/EA=1/1 to 1/10) to get the compound 134c (500 mg, 76% yield) as a yellow solid.
LC-MS (Method 4) $t_R$=3.40 min, m/z (M+H)⁺=230.0.

Step 4. 6-Bromo-1-(ethyl-d₅)-7-(methoxy-d₃)-1H-indazole (134d)

To a solution of 134c (500 mg, 2.17 mmol) in DMF (5 mL) was added Cs₂CO₃ (1.42 g, 4.35 mmol) and 1-bromoethane-1,1,2,2,2-d₅ (322 mg, 2.83 mmol) at r.t. Then the mixture was stirred at r.t. for 2 h. The mixture was diluted with H₂O (20 mL), extracted with EtOAc (20 mL*3), washed with brine (30 mL), dried over Na₂SO₄, concentrated to get the compound 134d (200 mg, 35% yield) and 6-bromo-2-(ethyl-d₅)-7-(methoxy-d₃)-2H-indazole (280 mg, 49% yield) both as a yellow oil. LC-MS (Method 4) $t_R$=4.36 min, m/z (M+H)⁺=263.1. ¹H NMR (400 MHz, CDCl₃) δ 7.95 (s, 1H), 7.32 (d, J=8.4 Hz, 1H), 7.22 (d, J=8.4 Hz, 1H).

Step 5. Tert-butyl (1-(ethyl-d₅)-7-(methoxy-d₃)-1H-indazol-6-yl)carbamate (134e)

A mixture of 134d (200 mg, 0.76 mmol), tert-butyl carbamate (178 mg, 1.52 mmol), Pd₂(dba)₃ (70 mg, 0.076 mmol), XantPhos (89 mg, 0.15 mmol), Cs₂CO₃ (619 mg, 1.90 mmol) in dioxane (2 mL) was stirred at 100° C. for 16 h under N₂. The mixture was diluted with H₂O (20 mL), extracted with EtOAc (20 mL*3), washed with brine (30 mL), dried over Na₂SO₄, concentrated to get the crude compound 134e (200 mg, 88% yield) as a yellow solid. LC-MS (Method 4) $t_R$=4.30 min, m/z (M+H)⁺=300.2.

Step 6. 1-(Ethyl-d₅)-7-(methoxy-d₃)-1H-indazol-6-amine (134f)

To a solution of 134e (200 mg, 0.67 mmol) in dioxane (2 mL) was added a solution of HCl (g) in dioxane (4 M, 2 mL). The mixture was stirred at r.t. for 2 h. The mixture was concentrated to dryness. The residue was diluted with H₂O (20 mL), adjusted pH to 7-9 with aq Na₂CO₃, and extracted with EtOAc (20 mL*3). The organic layers were washed with aq Na₂CO₃ (20 mL) and brine (20 mL) and separated. The solution was dried over Na₂SO₄ and filtered. The filtrate was concentrated and purified by flash chromatography (PE/EA=1/1 to 1/10) to give the title compound 134f (120 mg, 90% yield) as a yellow solid. LC-MS (Method 4) $t_R$=2.32 min, m/z (M+H)⁺=200.3.

Step 7. 6-(Cyclopropanecarboxamido)-4-((1-(ethyl-d₅)-7-(methoxy-d₃)-1H-indazol-6-yl)amino)-N-(methyl-d₃)nicotinamide (134)

A mixture of 134f (40 mg, 0.20 mmol), 44b (57 mg, 0.22 mmol), pTSA (34 mg, 0.20 mmol) in dioxane (1 mL) was stirred at 100° C. for 3 h. The mixture was concentrated and purified by Prep-HPLC (Method E) to get the compound 134 (46 mg, 55% yield) as an off-white solid. LC-MS (Method 4) $t_R$=2.84 min, m/z (M+H)⁺=420.4. ¹H NMR (400 MHz, DMSO-d₆) δ 10.72 (s, 1H), 10.54 (s, 1H), 8.61 (s, 1H), 8.52 (s, 1H), 8.03 (s, 1H), 7.83 (s, 1H), 7.50 (d, J=8.4 Hz, 1H), 7.09 (d, J=8.4 Hz, 1H), 1.96-1.92 (m, 1H), 0.74-0.70 (m, 4H).

Example 135

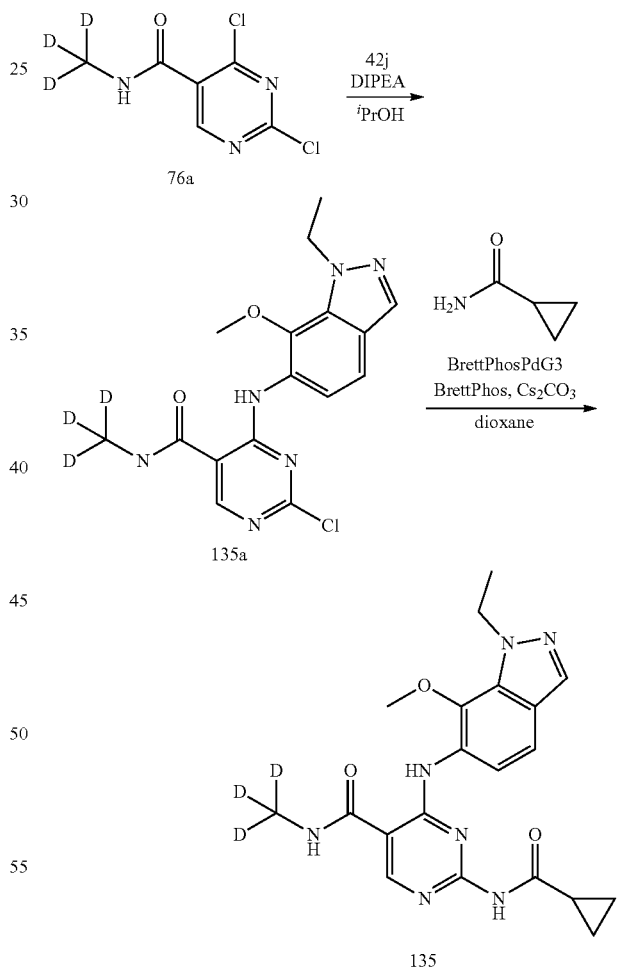

Step 1. 2-Chloro-4-((1-ethyl-7-methoxy-1H-indazol-6-yl)amino)-N-(methyl-d₃)pyrimidine-5-carboxamide (135a)

To a solution of 76a (36 mg, 0.17 mmol) and 42j (30 mg, 0.16 mol) in ⁱPrOH (1 mL) was added DIPEA (41 mg, 0.31 mmol), then the mixture was stirred at 60° C. for 4 h. The mixture was diluted with water (20 mL), extracted with EtOAc (20 mL*3), washed with brine (30 mL), dried over $Na_2SO_4$, concentrated to get the crude compound 135a (40 mg, 70% yield) as a yellow solid. LC-MS (Method 4) $t_R$=3.86 min, m/z (M+H)$^+$=364.2.

Step 2. 2-(Cyclopropanecarboxamido)-4-((1-ethyl-7-methoxy-1H-indazol-6-yl)amino)-N-(methyl-d$_3$)pyrimidine-5-carboxamide (135)

A mixture of 135a (20 mg, 0.055 mmol), cyclopropanecarboxamide (47 mg, 0.55 mmol), BrettPhos (4.43 mg, 0.008 mmol), BrettPhos Pd G3 (7 mg, 0.008 mmol), $Cs_2CO_3$ (36 mg, 0.11 mmol) in dioxane (1 mL) was stirred at 100° C. for 16 h. The mixture was diluted with water (10 mL), extracted with EtOAc (10 mL*3), washed with brine (20 mL), dried over $Na_2SO_4$, concentrated and purified by Prep-HPLC (Method E) to get the compound 135 (4.4 mg, 19% yield) as an off-white solid. LC-MS (Method 4) $t_R$=2.94 min, m/z (M+H)$^+$=413.3. $^1$H $^1$H NMR (400 MHz, DMSO-d$_6$) δ 10.84 (s, 1H), 10.85 (s, 1H), 8.87 (d, J=8.8 Hz, 1H), 8.75 (s, 1H), 8.69 (s, 1H), 8.00 (s, 1H), 7.44 (d, J=8.4 Hz, 1H), 4.54 (q, J=7.2 Hz, 2H), 3.89 (s, 3H), 2.18-2.16 (m, 1H), 1.41 (t, J=7.2 Hz, 3H), 0.87-0.80 (m, 4H).

Example 136

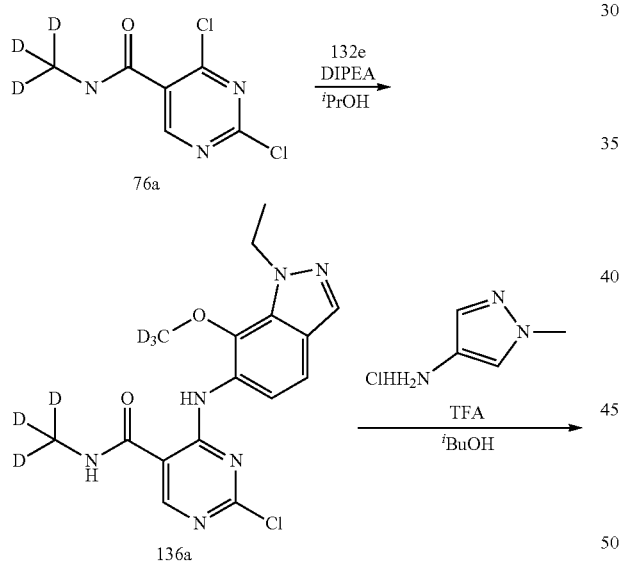

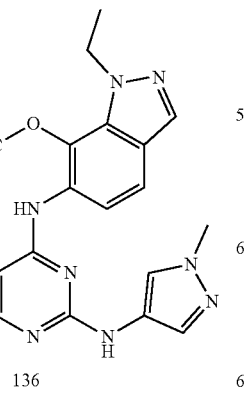

Step 1. 2-Chloro-4-((1-ethyl-7-(methoxy-d$_3$)-1H-indazol-6-yl)amino)-N-(methyl-d$_3$)pyrimidine-5-carboxamide (136a)

To a solution of 76a (83 mg, 0.40 mmol) and 132e (70 mg, 0.36 mol) in $^i$PrOH (2 mL) was added DIPEA (93 mg, 0.72 mmol), then the mixture was stirred at 60° C. for 4 h. The mixture was diluted with water (20 mL), extracted with EtOAc (20 mL*3), washed with brine (30 mL), dried over $Na_2SO_4$, concentrated to get the crude compound 136a (120 mg, 91% yield) as a yellow solid. LC-MS (Method 4) $t_R$=3.89 min, m/z (M+H)$^+$=367.2.

Step 2. 4-((1-Ethyl-7-(methoxy-d$_3$)-1H-indazol-6-yl)amino)-N-(methyl-d$_3$)-2-((1-methyl-1H-pyrazol-4-yl)amino)pyrimidine-5-carboxamide (136)

To a solution of 136a (40 mg, 0.11 mmol), 1-methyl-1H-pyrazol-4-amine hydrochloride (17 mg, 0.13 mmol) in $^i$BuOH (1 mL) was added TFA (12 mg, 0.11 mmol) and the mixture was stirred at 90° C. for 6 h. Then the mixture was concentrated and purified by Prep-HPLC (Method E) to get the compound 136 (20 mg, 43% yield) as a white solid. LC-MS (Method 4) $t_R$=2.86 min, m/z (M+H)$^+$=428.2. $^1$H NMR (400 MHz, DMSO-d$_6$) δ 11.67-11.36 (m, 1H), 9.58-9.50 (m, 1H), 8.61 (s, 1H), 8.41 (s, 1H), 8.07 (s, 1H), 7.72-7.79 (m, 1H), 7.55-7.46 (m, 2H), 7.32-7.20 (m, 1H), 4.55 (q, J=7.2 Hz, 2H), 3.81-3.52 (m, 3H), 1.40 (t, J=7.2, 3H).

Example 137

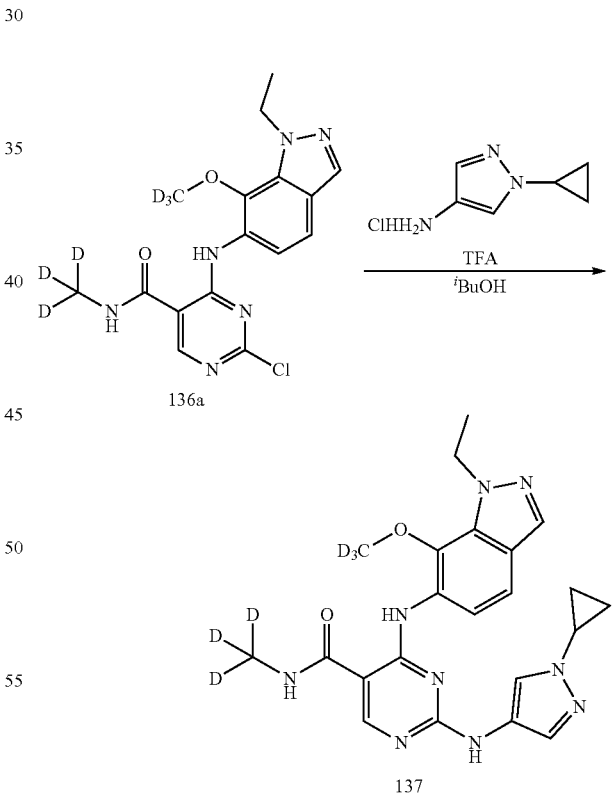

Step 1. 2-((1-Cyclopropyl-1H-pyrazol-4-yl)amino)-4-((1-ethyl-7-(methoxy-d$_3$)-1H-indazol-6-yl)amino)-N-(methyl-d$_3$)pyrimidine-5-carboxamide (137)

To a solution of 136a (40 mg, 0.11 mmol), 1-cyclopropyl-1H-pyrazol-4-amine hydrochloride (21 mg, 0.13 mmol) in i-BuOH (1 mL) was added TFA (12 mg, 0.11 mmol). Then the mixture was stirred at 90° C. for 6 h. Then the mixture was concentrated and purified by Prep-HPLC (Method E) to get the compound 137 (10 mg, 20% yield) as a white solid. LC-MS (Method 4) $t_R$=3.07 min, m/z (M+H)$^+$=454.3. $^1$H NMR (400 MHz, DMSO-d$_6$) δ 11.66-11.35 (m, 1H), 9.59-9.51 (m, 1H), 8.67-8.61 (m, 1H), 8.42 (s, 1H), 8.07-8.02 (m, 1H), 7.68-7.66 (m, 1H), 7.56-7.50 (m, 2H), 7.30-7.21 (m, 1H), 4.56 (q, J=7.2 Hz, 2H), 2.49-2.44 (m, 1H), 1.41 (t, J=7.2 Hz, 3H), 0.75-0.72 (m, 4H).

Example 138

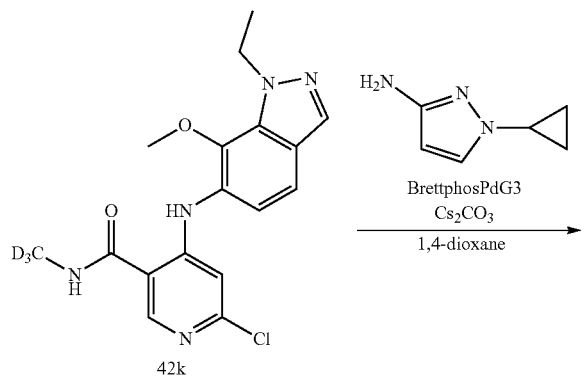

Step 1. 6-((1-Cyclopropyl-1H-pyrazol-3-yl)amino)-4-((1-ethyl-7-methoxy-1H-indazol-6-yl)amino)-N-(methyl-d$_3$)nicotinamide (138)

Compound 138 (11 mg, 18% yield), a white solid, was synthesized by utilizing a similar preparative procedure of Step 3 in Example 49 with 42k (50 mg, 0.14 mmol) and 1-cyclopropyl-1H-pyrazol-3-amine (34 mg, 0.28 mmol) as starting materials. LC-MS (Method 2) $t_R$=3.52 min, m/z (M+H)$^+$=450.1. $^1$H NMR (400 MHz, DMSO-d$_6$) δ 10.54 (s, 1H), 9.19 (s, 1H), 8.40 (s, 1H), 8.37 (s, 1H), 8.03 (s, 1H), 7.54-7.52 (m, 2H), 7.21-7.17 (m, 2H), 6.02 (s, 1H), 4.56 (q, J=7.2 Hz, 2H), 3.82 (s, 3H), 3.46-3.43 (m, 1H), 1.41 (t, J=7.2 Hz, 3H), 0.76-0.72 (m, 4H).

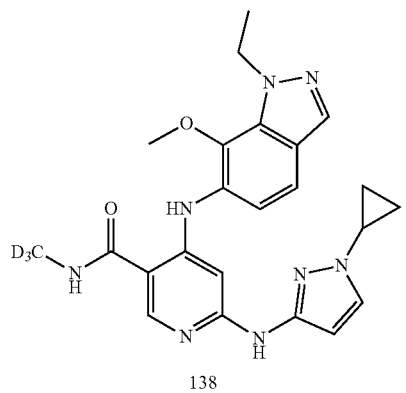

138

Example 139

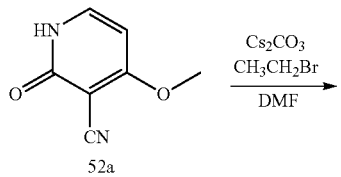

-continued

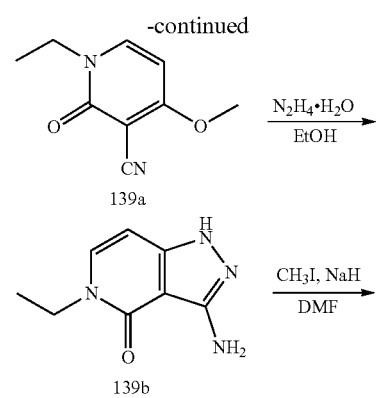

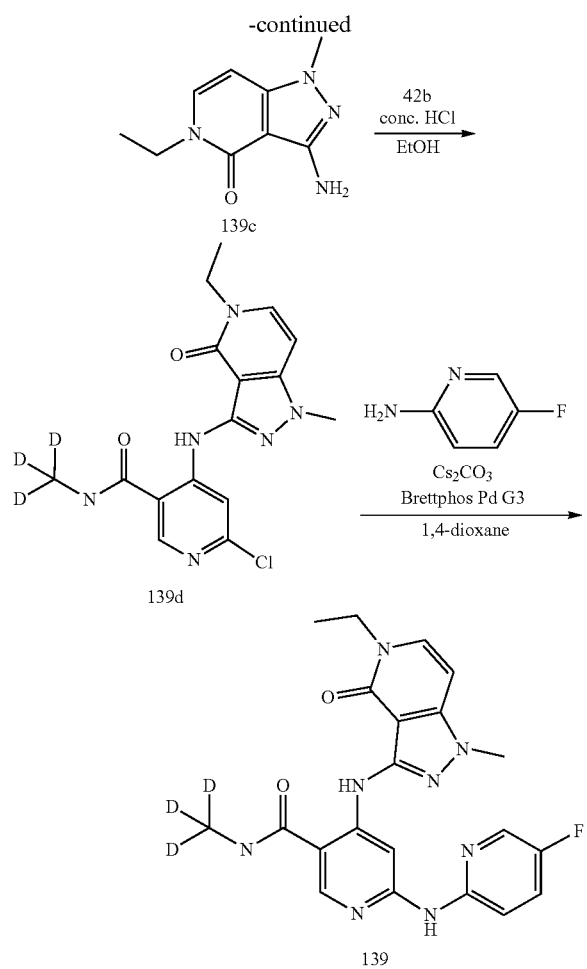

(449.2 mg, 3.17 mmol) was added, and stirred at 25° C. for 4 h. The mixture was diluted with $H_2O$ (15 mL), extracted with EA (15 mL*3), washed with brine, dried over $Na_2SO_4$, concentrated to get the crude compound 139c (250 mg, 51% yield) as a brown oil. LC-MS (Method 4) $t_R$=1.28 min, m/z $(M+H)^+$=193.1.

Step 4. 6-Chloro-4-((5-ethyl-1-methyl-4-oxo-4,5-dihydro-1H-pyrazolo[4,3-c]pyridin-3-yl)amino)-N-(methyl-$d_3$)nicotinamide (139d)

A mixture of 139c (234 mg, 1.22 mmol), 42b (253 mg, 1.22 mmol) and cone. HCl (1 mL) in EtOH (2.5 mL) was stirred at 80° C. for 16 h. The mixture was cooled to 25° C. and filtered to get the compound 139d (150 mg, 34% yield) as a white solid. LC-MS (Method 4) $t_R$=3.35 min, m/z $(M+H)^+$=364.2.

Step 5. 4-((5-Ethyl-1-methyl-4-oxo-4,5-dihydro-1H-pyrazolo[4,3-c]pyridin-3-yl)amino)-6-((5-fluoropyridin-2-yl)amino)-N-(methyl-$d_3$)nicotinamide (139)

To a solution of 139d (100 mg, 0.27 mmol) in 1,4-dioxane (2 mL) was added 5-fluoropyridin-2-amine (92.44 mg, 0.82 mmol), BrettPhos Pd G3 (25 mg, 0.03 mmol) and $Cs_2CO_3$ (268 mg, 0.82 mmol). The mixture was stirred at 80° C. under $N_2$ for 16 h. The reaction mixture was concentrated and purified by Prep-HPLC (Method E) to get the compound 139 (43 mg, 37% yield) as a white solid. LC-MS (Method 4) $t_R$=2.77 min, m/z $(M+H)^+$=440.3. $^1$H NMR (400 MHz, DMSO-$d_6$) δ 11.62 (s, 1H), 9.86 (s, 1H), 9.02 (s, 1H), 8.45 (s, 1H), 8.36 (s, 1H), 8.24 (t, J=1.8 Hz, 1H), 7.63-7.61 (m, 2H), 7.49 (d, J=7.5 Hz, 1H), 6.55 (d, J=7.5 Hz, 1H), 3.90 (q, J=7.2 Hz, 2H), 3.86 (s, 3H) 1.18 (t, J=7.2 Hz, 3H).

Example 140

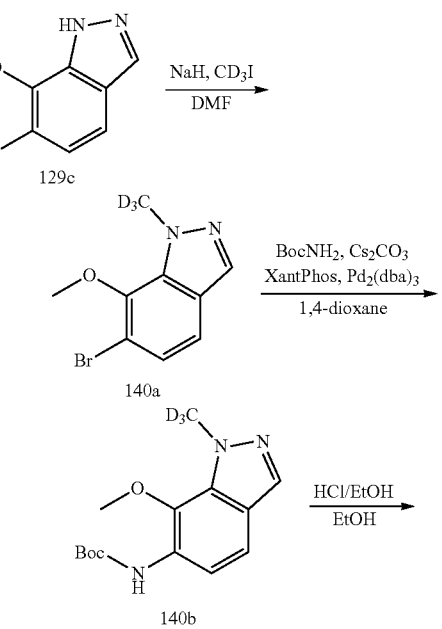

Step 1. 1-Ethyl-4-methoxy-2-oxo-1,2-dihydropyridine-3-carbonitrile (139a)

To a solution of 139a (0.8 g, 5.3 mmol) and $Cs_2CO_3$ (3.47 g, 10.6 mmol) in DMF (10 mL) was added bromoethane (2.49 g, 15.9 mmol) at 0° C., then the mixture was stirred at 25° C. for 14 h. The mixture was diluted with $H_2O$ (20 mL), extracted with EA (20 mL*3), washed with brine, dried over $Na_2SO_4$ and concentrated to get the crude product 139a (1 g, yield given) as a yellow oil. LC-MS (Method 4) $t_R$=1.21 min, m/z $(M+H)^+$=179.1

Step 2. 3-Amino-5-ethyl-1,5-dihydro-4H-pyrazolo[4,3-c]pyridin-4-one (139b)

To a solution of 139a (1 g, 5.61 mmol) in EtOH (10 mL) was added $N_2H_4·H_2O$ (2.1 g, 41.5 mmol) at 0° C., then the mixture was stirred at 80° C. for 14 h. The mixture was concentrated and slurried with MTBE/EA (10 mL/10 mL) to get the compound 139b (0.5 g, 50% yield) as an off-white solid. LC-MS (Method 4) $t_R$=0.73 min, m/z $(M+H)^+$=179.1.

Step 3. 3-Amino-5-ethyl-1-methyl-1,5-dihydro-4H-pyrazolo[4,3-c]pyridin-4-one (139c)

To a solution of 139b (470 mg, 2.64 mmol) in DMF (5 mL) was added NaH (121 mg, 3.17 mmol, 60% in oil) at 0° C., the mixture was stirred at 25° C. for 30 min, then $CH_3I$

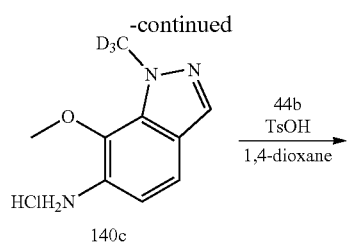

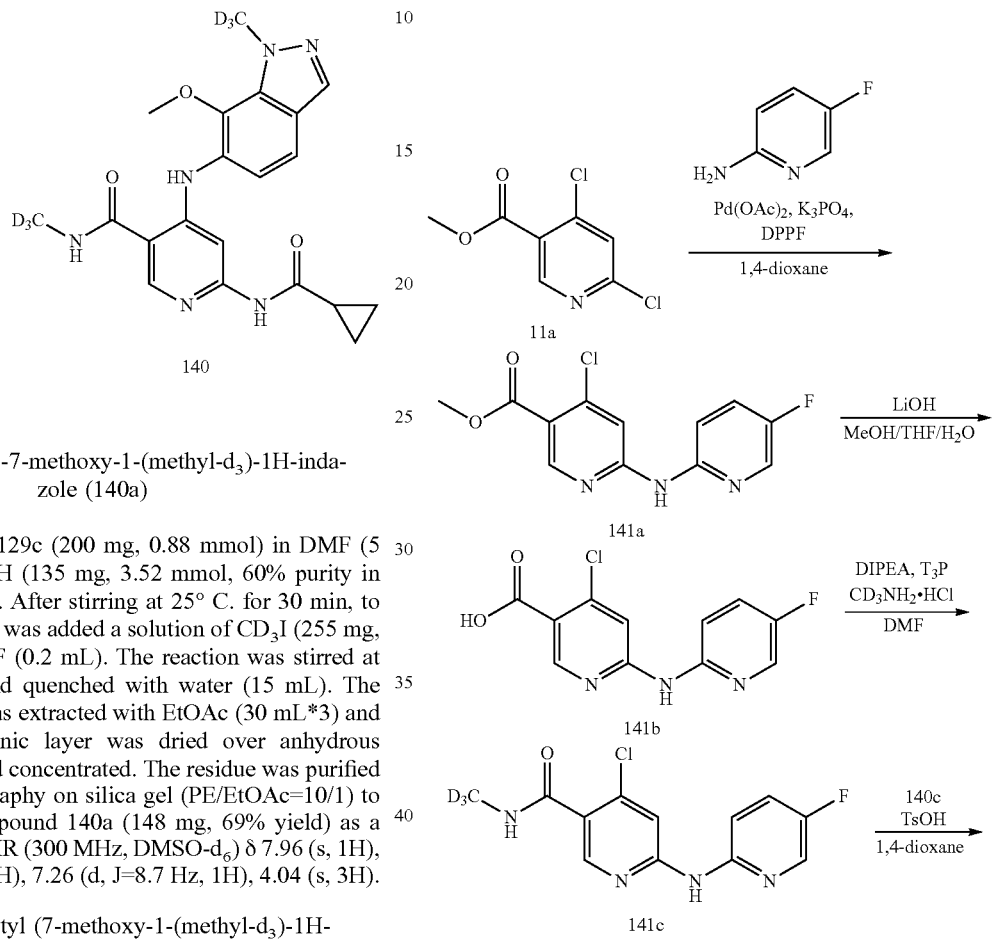

Step 1. 6-Bromo-7-methoxy-1-(methyl-d₃)-1H-indazole (140a)

To a solution of 129c (200 mg, 0.88 mmol) in DMF (5 mL) was added NaH (135 mg, 3.52 mmol, 60% purity in mineral oil) at 0° C. After stirring at 25° C. for 30 min, to the reaction mixture was added a solution of CD₃I (255 mg, 1.76 mmol) in DMF (0.2 mL). The reaction was stirred at 25° C. for 16 h and quenched with water (15 mL). The resultant mixture was extracted with EtOAc (30 mL*3) and the combined organic layer was dried over anhydrous Na₂SO₄, filtered and concentrated. The residue was purified by flash chromatography on silica gel (PE/EtOAc=10/1) to afford the title compound 140a (148 mg, 69% yield) as a yellow solid. $^1$H NMR (300 MHz, DMSO-d₆) δ 7.96 (s, 1H), 7.36 (d, J=8.7 Hz, 1H), 7.26 (d, J=8.7 Hz, 1H), 4.04 (s, 3H).

Step 2. Tert-butyl (7-methoxy-1-(methyl-d₃)-1H-indazol-6-yl)carbamate (140b)

Compound 140b (102 mg, 85% yield), a yellow solid, was synthesized by utilizing a similar preparative procedure of Step 4 in Example 51 with 140a (105 mg, 0.45 mmol) and tert-butyl carbamate (101 mg, 0.86 mmol) as starting materials. LC-MS (Method 3) $t_R$=1.22 min, m/z (M+H)⁺=281.2.

Step 3. 7-Methoxy-1-(methyl-d₃)-1H-indazol-6-amine hydrochloride (140c)

Compound 140c (102 mg, 95% yield), a yellow solid, was synthesized by utilizing a similar preparative procedure of Step 5 in Example 51 with 140b (102 mg, 0.36 mmol) as the starting material. LC-MS (Method 3) $t_R$=0.85 min, m/z (M+H)⁺=181.1.

Step 7. 6-(Cyclopropanecarboxamido)-4-((7-methoxy-1-(methyl-d₃)-1H-indazol-6-yl)amino)-N-(methyl-d₃)nicotinamide (140)

Compound 140 (16 mg, 41% yield), a white solid, was synthesized by utilizing a similar preparative procedure of Step 6 in Example 51 with 140c (21 mg, 0.097 mmol) and 44b (25 mg, 0.097 mmol) as starting materials. LC-MS (Method 1) $t_R$=2.71 min, m/z (M+H)⁺=401.1. $^1$H NMR (400 MHz, DMSO-d₆) δ 10.69 (s, 1H), 10.55 (s, 1H), 8.59 (s, 1H), 8.52 (s, 1H), 8.01 (s, 1H), 7.83 (s, 1H), 7.51 (d, J=8.4 Hz, 1H), 7.11 (d, J=8.8 Hz, 1H), 3.80 (s, 3H), 1.96-1.93 (m, 1H), 0.75-0.73 (m, 4H).

Example 141

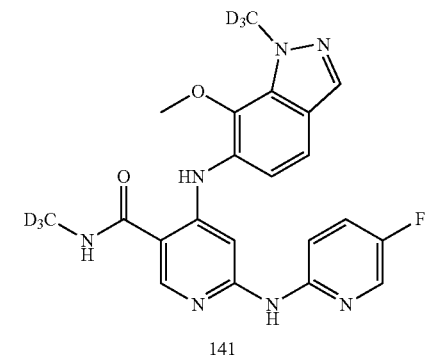

Step 1. Methyl 4-chloro-6-((5-fluoropyridin-2-yl)amino)nicotinate (141a)

A mixture of 11a (2.0 g, 9.71 mmol), 5-fluoropyridin-2-amine (1.31 g, 11.65 mmol), K₃PO₄ (4.12 g, 19.42 mmol), DPPF (807 mg, 1.46 mmol) and Pd(OAc)2 (327 mg, 1.46 mmol) in anhydrous dioxane (20 mL) was stirred at 90° C.

for 12 h. After cooling to r.t., the mixture was filtered and the filtrate was concentrated. The residue was purified by flash chromatography on silica gel (PE/EtOAc=7/1) to afford the title compound 141a (2.0 g, 73% yield) as a yellow solid. LC-MS (Method 3) $t_R$=1.11 min, m/z (M+H)$^+$=282.4.

Step 2. 4-Chloro-6-((5-fluoropyridin-2-yl)amino)nicotinic acid (141b)

To a solution of 141a (2.0 g, 7.10 mmol) in MeOH/THF/H$_2$O (20 mL, v/v/v=2/2/1) was added LiOH·H$_2$O (1.49 g, 35.50 mmol). After stirring at r.t. for 12 h, the reaction mixture was concentrated to dryness and acidified with 1 N HCl to pH=2. The formed solid was collected by filtering and filter cake was dried to give the crude compound 141b (1.8 g, 95% yield) as a yellow solid. LC-MS (Method 3) $t_R$=0.88 min, m/z (M+H)$^+$=268.2.

Step 3. 4-Chloro-6-((5-fluoropyridin-2-yl)amino)-N-(methyl-d$_3$)nicotinamide (141c)

A mixture of 141b (400 mg, 1.50 mmol), trideuteriomethanamine hydrochloride (529 mg, 7.50 mmol) and DIPEA (1.16 g, 9.00 mmol) in T$_3$P (2 mL, 50% wt in DMF) was stirred at 50° C. for 16 h. After cooling to r.t., the reaction mixture was poured into water (10 mL) and the formed solid was collected by filtering. The filter cake was slurried with MeOH (5 mL) for 30 min. The solid was filtered and dried to afford the title compound 141c (380 mg, 90% yield) as a yellow solid. MS (Method 3) $t_R$=1.10 min, m/z (M+H)$^+$=284.1.

Step 4. 6-((5-Fluoropyridin-2-yl)amino)-4-((7-methoxy-1-(methyl-d$_3$)-1H-indazol-6-yl)amino)-N-(methyl-d$_3$)nicotinamide (141)

Compound 141 (5 mg, 6% yield), a white solid, was synthesized by utilizing a similar preparative procedure of Step 6 in Example 51 with 141c (40 mg, 0.18 mmol) and 140c (52 mg, 0.18 mmol) as starting materials. LC-MS (Method 2) $t_R$=3.06 min, m/z (M+H)$^+$=428.0. $^1$H NMR (400 MHz, DMSO-d$_6$) δ 10.57 (s, 1H), 9.72 (s, 1H), 8.48 (s, 1H), 8.47 (s, 1H), 8.06-8.07 (m, 1H), 8.01 (s, 1H), 7.72-7.69 (m, 1H), 7.63-7.60 (m, 1H), 7.57 (d, J=8.8 Hz, 1H), 7.49 (s, 1H), 7.52 (d, J=8.4 Hz, 1H), 3.82 (s, 3H).

Example 142

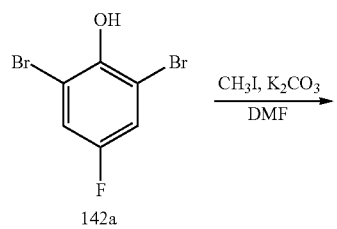

142a

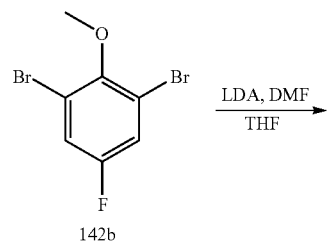

142b

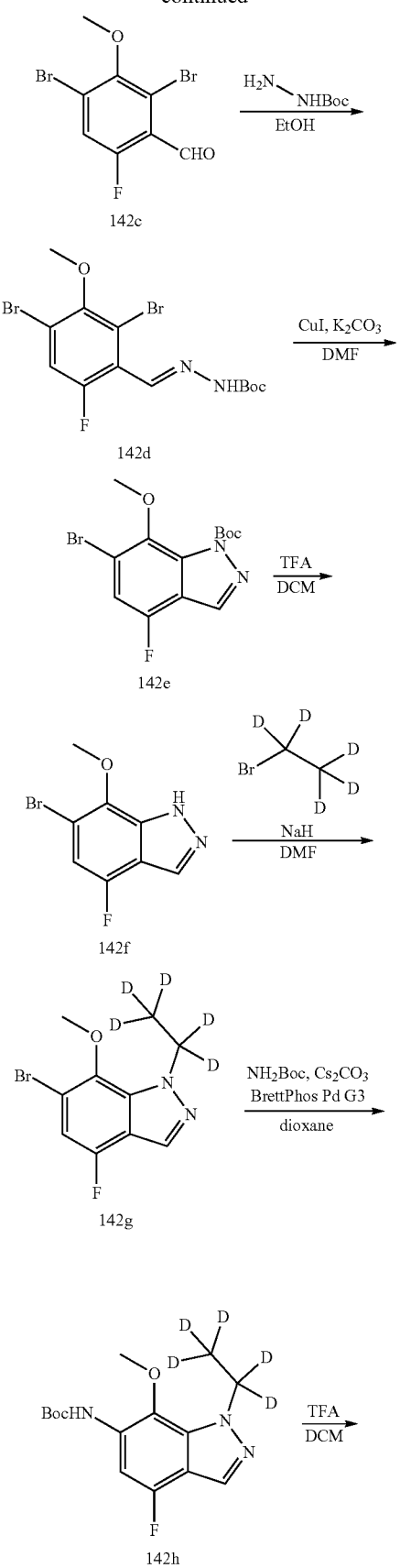

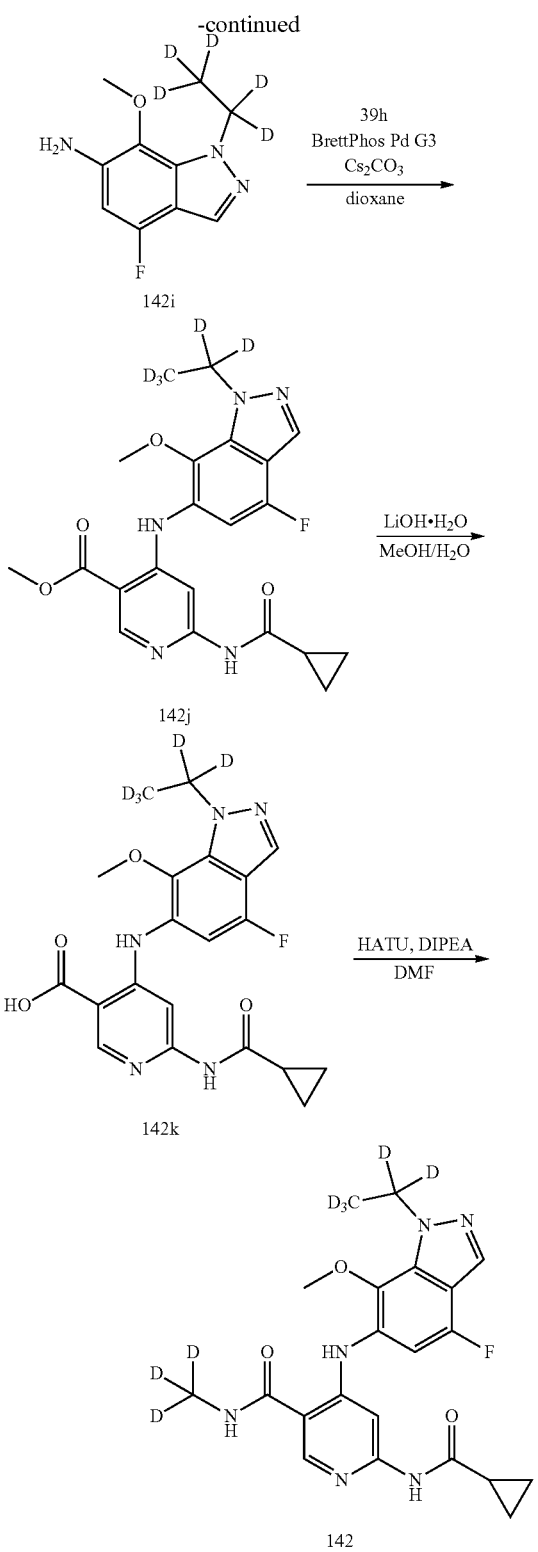

was stirred at 20° C. for 1 h. A yellow solution was formed. The reaction mixture was quenched with water (50 mL) and extracted with EtOAc (50 mL*3). The combined organic layer was washed with brine (50 mL*2), dried over anhydrous $Na_2SO_4$, filtered and concentrated. The residue was purified by column chromatograph (EA in PE is 0-10%) to give 142b (710 mg, 96% yield) as a white solid. LC-MS (Method 4) $t_R$=3.82 min, ink (M+H)$^+$=283.9.

Step 2. 2,4-Dibromo-6-fluoro-3-methoxy-benzaldehyde (142c)

To a mixture of 142b (710 mg, 2.50 mmol) in THF (10 mL), was added LDA (2 M, 1.50 mL) at −78° C. The resulting mixture was stirred at −78° C. for 15 min. Then the DMF (192 mg, 2.63 mmol, 203 μL) was added into the above mixture at −78° C. The reaction mixture was further stirred at −78° C. for 1 h. A yellow solution was formed. The reaction mixture was quenched with water (50 mL) and extracted with EtOAc (50 mL*3). The combined organic layer was washed with brine (50 mL*2), dried over anhydrous $Na_2SO_4$, filtered and concentrated. The residue was purified by column chromatograph (EA in PE is 0-20%) to give 142c (564 mg, 72% yield) as a yellow solid. LC-MS (Method 4) $t_R$=3.52 min, m/z (M+H)$^+$=311.9.

Step 3. Tert-butyl-2-(2,4-dibromo-6-fluoro-3-methoxybenzylidene)hydrazine-1-carboxylate (142d)

A mixture of 142c (364 mg, 1.17 mmol) and tert-butyl N-aminocarbamate (170 mg, 1.28 mmol) in ethanol (10 mL) was stirred at 80° C. for 2 h. A yellow suspension was formed. The reaction mixture was concentrated to give a yellow solid, which was further purified by flash chromatography (EA in PE is 10-30%) to give 142d (497 mg, 99% yield) as a light-yellow solid. LC-MS (Method 4) $t_R$=4.66 min, m/z (M+H)$^+$=425.9.

Step 4. Tert-butyl 6-bromo-4-fluoro-7-methoxy-indazole-1-carboxylate (142e)

A solution of 142d (200 mg, 0.469 mmol), $K_2CO_3$ (130 mg, 0.934 mmol) and CuI (45 mg, 0.235 mmol) in DMF (2 mL) was degassed and purged with nitrogen for 3 times. The resulting mixture was stirred at 100° C. under $N_2$ atmosphere for 12 h. A black suspension was formed. The reaction mixture was quenched with water (50 mL) and extracted with EtOAc (30 mL*3). The combined organic layer was washed with brine (50 mL*2), dried over anhydrous $Na_2SO_4$, filtered and concentrated. The residue was dried in vacuo to give 142e (162 mg, crude) as a yellow solid, which was used for the next step directly without further purification. LC-MS (Method 4) $t_R$=4.52 min, m/z (M+H)$^+$=345.0.

Step 5. 6-Bromo-4-fluoro-7-methoxy-1H-indazole (142f)

To a mixture of 142e (162 mg, 0.469 mmol) in DCM (3 mL), was added TFA (1 mL). The resulting mixture was stirred at 20° C. for 1 h. A brown suspension was formed. The reaction mixture was quenched with aq. $NaHCO_3$(40 mL) and extracted with DCM (30 mL*3). The combined organic layer was washed with brine (50 mL*2), dried over anhydrous $Na_2SO_4$, filtered and concentrated. The residue Step 1. 1,3-Dibromo-5-fluoro-2-methoxy-benzene (142b)

To a mixture of 142a (700 mg, 2.59 mmol) and $K_2CO_3$ (537.68 mg, 3.89 mmol) in DMF (10 mL) was added $CH_3I$ (405 mg, 2.85 mmol) and at 20° C. The resulting mixture was purified by column chromatograph (EA in PE is 20-50%) to give 142f (67 mg, 58% yield for 2 steps) as a yellow solid. LC-MS (Method 4) $t_R$=3.75 min, m/z (M+H)$^+$ =245.0.

Step 6. 6-Bromo-4-fluoro-7-methoxy-1-(1,1,2,2,2-pentadeuterioethyl)indazole (142g)

To a mixture of 142f (67 mg, 0.273 mmol) and in DMF (3 mL) was added NaH (32 mg, 0.786 mmol, 60% in mineral oil) and 1-bromo-1,1,2,2,2-pentadeuterio-ethane (41 mg, 0.355 mmol) at 0° C. The resulting mixture was stirred at 0-10° C. for 1 h. A yellow suspension was formed. The reaction mixture was quenched with water (50 mL) and extracted with EtOAc (30 mL*3). The combined organic layer was washed with brine (50 mL*2), dried over anhydrous $Na_2SO_4$, filtered and concentrated. The residue was purified by column chromatograph (EA in PE is 10-30%) to give 142g (40 mg, 52% yield) as a yellow solid. LC-MS (Method 4) $t_R$=4.70 min, m/z (M+H)$^+$=278.1. $^1$H NMR (400 MHz, CDCl$_3$) δ 8.00 (s, 1H), 6.91 (d, J=8.8 Hz, 1H), 3.97 (s, 3H).

Step 7. Tert-butyl N-[4-fluoro-7-methoxy-1-(1,1,2,2,2-pentadeuterioethyl)indazol-6-yl]carbamate (142h)

A solution of 142g (40 mg, 0.144 mmol), tert-butyl carbamate (25 mg, 0.216 mmol), BrettPhos Pd G3 (13 mg, 0.014 mmol), BrettPhos (15 mg, 0.029 mmol) and $Cs_2CO_3$ (117 mg, 0.36 mmol) in dioxane (2 mL) was degassed and purged with nitrogen for 3 times. The resulting mixture was stirred at 100° C. under $N_2$ atmosphere for 12 h. A black suspension was formed. The reaction mixture was diluted with water (50 mL), then extracted with EtOAc (50 mL*2). The combined organic layer was washed with water (50 mL*2), brine (50 mL*2), dried over anhydrous $Na_2SO_4$, filtered and concentrated. The residue was purified by Prep-TLC (SiO$_2$, EtOAc in PE is 30%) to give 142h (38 mg, 84% yield) as a yellow solid. LC-MS (Method 4) $t_R$=4.71 min, m/z (M+H)$^+$=315.2

Step 8. 4-Fluoro-7-methoxy-1-(1,1,2,2,2-pentadeuterioethyl)indazol-6-amine (142i)

To a mixture of 142h (38 mg, 0.121 mmol) in DCM (3 mL), was added TFA (1 mL). The resulting mixture was stirred at 20° C. for 1 h. A brown suspension was formed. The reaction mixture was quenched with aq. NaHCO$_3$ (40 mL) and extracted with DCM (30 mL*3). The combined organic layer was washed with brine (50 mL*2), dried over anhydrous Na$_2$SO$_4$, filtered and concentrated. The residue was purified by column chromatograph (EA in PE is 10-50%) to give 142i (15 mg, 58% yield) as a yellow solid. LC-MS (Method 4) $t_R$=3.07 min, m/z (M+H)$^+$=215.1.

Step 9. Methyl 6-(cyclopropanecarboxamido)-4-((1-(ethyl-d$_5$)-4-fluoro-7-methoxy-1H-indazol-6-yl)amino)nicotinate (142j)

A solution of 142i (15 mg, 0.07 mmol), methyl 4-chloro-6-(cyclopropanecarbonylamino)pyridine-3-carboxylate (18 mg, 0.070 mmol), BrettPhos (8 mg, 0.014 mmol), Cs$_2$CO$_3$ (57 mg, 0.175 mmol) and BrettPhos Pd G3 (6 mg, 0.007 mmol) in dioxane (2 mL) was degassed and purged with nitrogen for 3 times. The resulting mixture was stirred at 100° C. under N$_2$ atmosphere for 12 h. A black suspension was formed. The reaction was diluted with EtOAc (50 mL) and filtered through a pad of celite. The filtrate was concentrated and purified by Prep-TLC (MeOH in DCM=1/10) to give 142j (30 mg, 0.069 mmol, 99% yield) as a yellow solid. LC-MS (Method 4) $t_R$=4.08 min, m/z (M+H)$^+$=433.2. $^1$H NMR (400 MHz, DMSO-d$_6$) δ 10.92 (s, 1H), 9.75 (s, 1H), 8.72 (s, 1H), 8.20 (s, 1H), 7.80 (s, 1H), 6.99 (d, J=10.4 Hz, 1H), 3.90 (s, 3H), 3.76 (s, 3H), 1.99-1.90 (m, 1H), 0.80-0.70 (m, 4H).

Step 10. 6-(Cyclopropanecarboxamido)-4-((1-(ethyl-d$_5$)-4-fluoro-7-methoxy-1H-indazol-6-yl)amino)nicotinic acid (142k)

A mixture of methyl 142j (30 mg, 0.069 mmol) and LiOH·H$_2$O (9 mg, 0.208 mmol) in co-solvent of MeOH (3 mL) and water (1 mL) was stirred at 40° C. for 12 h. A yellow solution was formed. The reaction mixture was diluted with water (5 mL), adjusted to pH=6 with 1 M aq. HCl, concentrated and dried in vacuo to give 142k (29 mg, yield given) as a yellow solid, which was used for the next step directly without further purification. LC-MS (Method 4) $t_R$=3.10 min, m/z (M+H)$^+$=419.2.

Step 11. 6-(Cyclopropanecarboxamido)-4-((1-(ethyl-d$_5$)-4-fluoro-7-methoxy-1H-indazol-6-yl)amino)-N-(methyl-d$_3$)nicotinamide (142)

A mixture of 142k (29 mg, 0.069 mmol), HATU (40 mg, 0.104 mmol) and trideuteriomethanamine (10 mg, 0.139 mmol), DIPEA (27 mg, 0.208 mmol, 0.036 mL) in DMF (3 mL) was stirred at 0° C. for 1 h. A white suspension was formed. The reaction mixture was diluted with water (40 mL) and extracted with EtOAc (40 mL*3). The combined organic layer was washed with water (40 mL*3), brine (40 mL*2), dried over anhydrous Na$_2$SO$_4$, filtered and concentrated. The residue was purified by Prep-HPLC (Method E) to give 142 (5.3 mg, 0.012 mmol, 17.6% yield) as a white solid. LC-MS (Method 4) $t_R$=3.29 min, m/z (M+H)$^+$=435.3. $^1$H NMR (400 MHz, DMSO-d$_6$) δ 10.81 (s, 1H), 10.66 (s, 1H), 8.65 (s, 1H), 8.53 (s, 1H), 8.16 (s, 1H), 7.84 (s, 1H), 6.96 (d, J=10.8 Hz, 1H), 3.78 (s, 3H), 1.99-1.90 (m, 1H), 0.85-0.70 (m, 4H).

Example 143

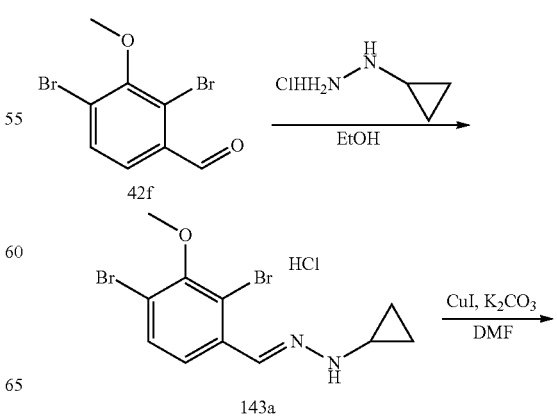

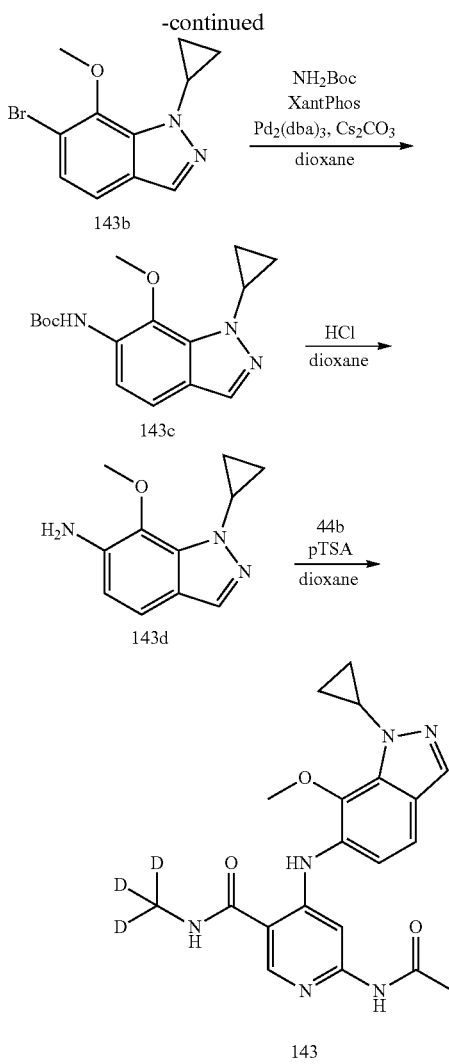

Step 1. (E)-1-Cyclopropyl-2-(2,4-dibromo-3-methoxybenzylidene)hydrazine hydrochloride (143a)

To a stirred solution of 42f (1.0 g, 3.42 mmol) in EtOH (20 mL) was added cyclopropylhydrazine hydrochloride (500 mg, 4.26 mmol) at room temperature. The reaction mixture was stirred at room temperature for 16 h. The reaction mixture was concentrated and slurried with EtOH (10 mL) to give 143a (1.0 g, 84% yield) as a white solid. LCMS (Method 4) $t_R$=4.58 min, m/z (M+H)$^+$=347.0.

Step 2. 6-Bromo-1-cyclopropyl-7-methoxy-1H-indazole (143b)

To a solution of 143a (500 mg, 1.45 mmol) in DMF (10 mL) was added CuI (55 mg, 0.29 mmol) and K$_2$CO$_3$ (400 mg, 2.9 mmol), the mixture was stirred at 100° C. for 16 h under N$_2$ atmosphere. The mixture was diluted with H$_2$O (10 mL), extracted with EA (20 mL*3), washed with brine (20 mL), dried over Na$_2$SO$_4$, concentrated and purified by flash chromatography (DCM/MeOH=100/1 to 10/1) to get the compound 143b (40 mg, 10% yield) as a yellow oil. LC-MS (Method 4) $t_R$=4.52 min, m/z (M+H)$^+$=267.0.

Step 3. Tert-butyl (1-cyclopropyl-7-methoxy-1H-indazol-6-yl)carbamate (143c)

To a mixture of 143b (40 mg, 0.15 mmol) and tert-butyl carbamate (120 mg, 0.49 mmol) in 1,4-dioxane (1 mL) was added XantPhos (173 mg, 0.03 mmol), Pd$_2$(dba)$_3$ (14 mg, 0.015 mmol) and Cs$_2$CO$_3$ (98 mg, 0.30 mmol), the reaction mixture was stirred at 100° C. for 12 h. The mixture was diluted with H$_2$O (50 mL), extracted with EtOAc (20 mL*3), washed with brine, dried over Na$_2$SO$_4$, concentrated and purified by flash chromatography (DCM/MeOH=100/1 to 10/1) to get the compound 143c (30 mg, 60% yield) as an off-white solid. LC-MS (Method 4) $t_R$=4.45 min, m/z (M+H)$^+$=304.2.

Step 4. 1-Cyclopropyl-7-methoxy-1H-indazol-6-amine hydrochloride (143d)

To a solution of 143c (30 mg, 0.09 mmol) in ACN (1 mL) was added HCl/1,4-dioxane (1 mL), the reaction mixture was stirred at 25° C. for 3 h. The mixture was concentrated to give the compound 143d (21 mg, 99% yield) as a yellow solid. LC-MS (Method 4) $t_R$=2.53 min, m/z (M+H)$^+$=204.2.

Step 5. 6-(Cyclopropanecarboxamido)-4-((1-cyclopropyl-7-methoxy-1H-indazol-6-yl)amino)-N-(methyl-d$_3$)nicotinamide (143)

To a solution of 143d (21 mg, 0.09 mmol) and 44b (30 mg, 0.012 mmol) in 1,4-dioxane (2 mL) was added pTSA (15 mg, 0.09 mmol), the reaction mixture was stirred at 100° C. for 5 h. The reaction mixture was concentrated and purified by Prep-HPLC (Method E) to give the compound 143 (5.7 mg, 14% yield) as an off-white solid. LC-MS (Method 4) $t_R$=3.03 min, m/z (M+H)$^+$=424.2. $^1$H NMR (400 MHz, CDCl$_3$) δ 10.28 (s, 1H), 8.24 (s, 1H), 8.12 (s, 1H), 7.99 (s, 1H), 7.81 (s, 1H), 7.45 (d, J=8.4 Hz, 1H), 7.19 (d, J=8.8 Hz, 1H), 6.16 (s, 1H), 4.04-3.95 (m, 1H), 3.90 (s, 3H). 1.51-1.41 (m, 1H), 1.39-1.30 (m, 2H), 1.10-0.98 (m, 4H), 0.90-0.81 (m, 2H).

Example 144

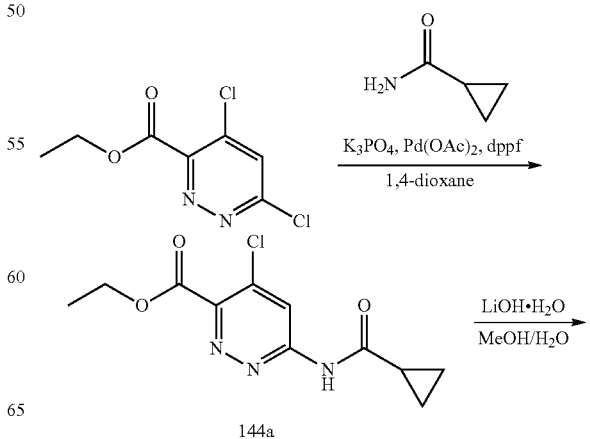

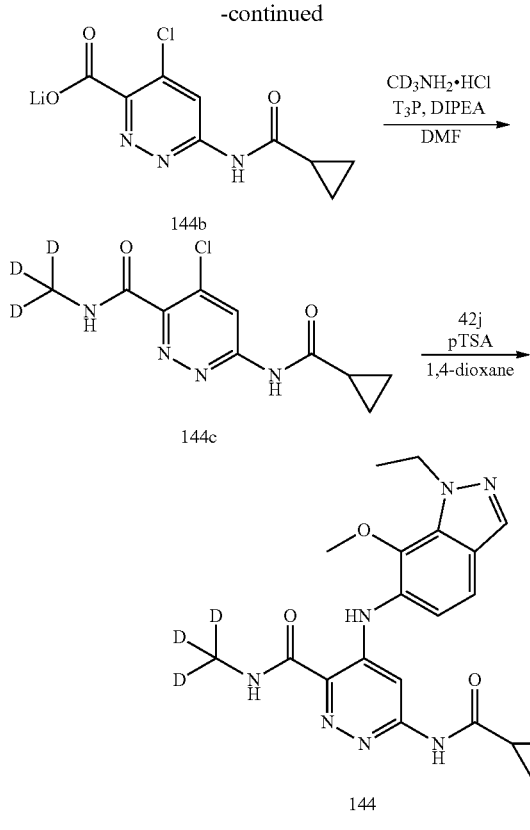

Step 1. Methyl 4-chloro-6-(cyclopropanecarbox-amido)pyridazine-3-carboxylate (144a)

To a solution of ethyl 4,6-dichloropyridazine-3-carboxylate (500 mg, 2.4 mmol) and cyclopropanecarboxamide (408 mg, 4.8 mmol) in 1,4-dioxane (20 mL) was added Pd(OAc)$_2$ (54 mg, 0.24 mmol), dppf (265 mg, 0.48 mmol) and K$_3$PO$_4$ (1.01 g, 4.8 mmol), then the mixture was stirred at 90° C. for 4 h under N$_2$ atmosphere. The mixture was diluted with H$_2$O (50 mL), extracted with EtOAc (30 mL*3), washed with brine (30 mL), dried over Na$_2$SO$_4$, concentrated and purified by flash chromatography (DCM/MeOH=100/1 to 10/1) to get the compound 144a (200 mg, 33% yield) as an off-white solid. LC-MS (Method 4) t$_R$=3.46 min, m/z (M+H)$^+$=270.1.

Step 2. Lithium 4-chloro-6-(cyclopropanecarbox-amido)pyridazine-3-carboxylate (144b)

To a solution of 144a (100 mg, 0.41 mmol) in MeOH (1 mL) and H$_2$O (1 mL) was added LiOH·H$_2$O (34 mg, 0.82 mmol), then the mixture was stirred at r.t. for 2 h. The reaction mixture was concentrated and used for next step directly without further purification. LC-MS (Method 4) t$_R$=1.44 min, m/z (M+H)$^+$=242.1.

Step 3. 4-Chloro-6-(cyclopropanecarboxamido)-N-(methyl-d$_3$)pyridazine-3-carboxamide (144c)

To a solution of 144b (132 mg, crude) in DMF (1 mL) was added methan-d$_3$-amine hydrochloride (58 mg, 0.82 mmol) and DIPEA (251 mg, 1.95 mmol), the mixture was stirred at r.t. under for 20 min, then T$_3$P (368 mg, 0.58 mmol, 50% in EtOAc) was added to the reaction mixture, the reaction mixture was stirred at r.t. for 3 h. The mixture was diluted with H$_2$O (50 mL), extracted with EtOAc (30 mL*3), washed with brine (30 mL), dried over Na$_2$SO$_4$, concentrated and purified by flash chromatography (DCM/MeOH=100/1 to 10/1) to get the compound 144c (15 mg, 14% yield, over two steps) as an off-white solid. LC-MS (Method 4) t$_R$=2.24 min, m/z (M+H)$^+$=258.1.

Step 4. 6-(Cyclopropanecarboxamido)-4-((1-ethyl-7-methoxy-1H-indazol-6-yl)amino)-N-(methyl-d$_3$) pyridazine-3-carboxamide (144)

A mixture of 144c (15 mg, 0.058 mmol), 42j (10 mg, 0.05 mmol) and pTSA (9 mg, 0.05 mmol) in 1,4-dioxane (1 mL) was stirred at 100° C. for 5 h. The mixture was concentrated and purified by Prep-HPLC (Method E) to get the compound 144 (3.7 mg, 15% yield) as a white solid. LC-MS (Method 4) t$_R$=3.03 min, m/z (M+H)$^+$=413.4.

1H NMR (400 MHz, CDCl$_3$) δ 10.81 (s, 1H), 8.98 (s, 1H), 8.12 (s, 1H), 7.99 (s, 1H), 7.94 (s, 1H), 7.47 (d, J=8.4 Hz, 1H), 7.07 (d, J=8.8 Hz, 1H), 4.61 (q, J=7.2 Hz, 2H), 3.84 (s, 3H), 2.02-1.98 (m, 1H), 1.48 (t, J=7.2 Hz, 3H), 1.08-1.01 (m, 2H), 0.92-0.85 (m, 2H).

Example 145

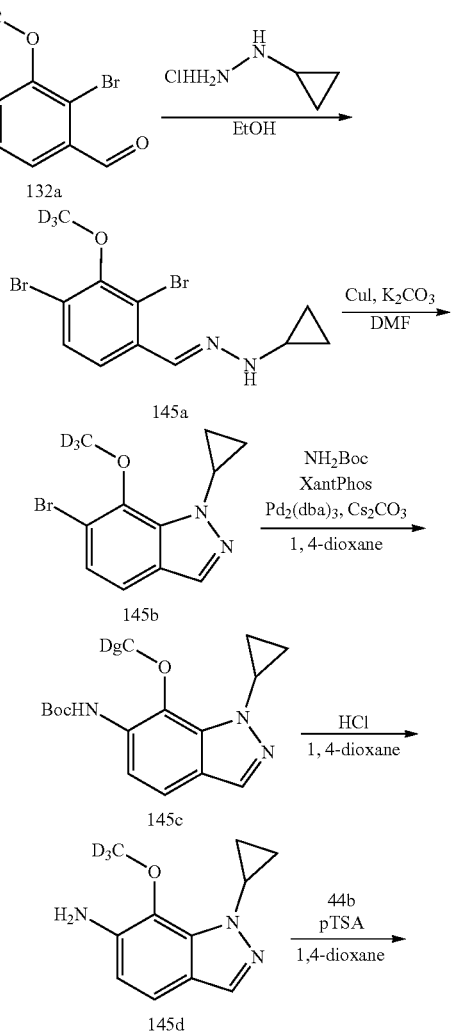

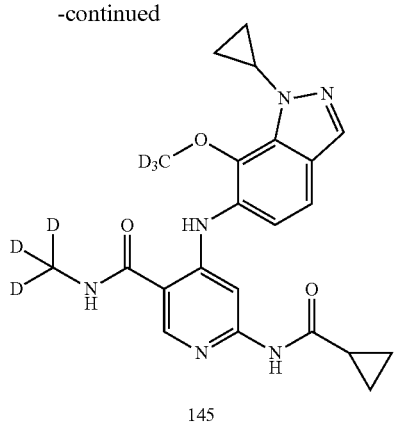

145

Step 1. (E)-1-cyclopropyl-2-(2,4-dibromo-3-(methoxy-d₃)benzylidene)hydrazine hydrochloride (145a)

To a stirred solution of 132a (1 g, 3.38 mmol) in EtOH (20 mL) was added cyclopropylhydrazine hydrochloride (500 mg, 4.26 mmol) at room temperature. The reaction mixture was stirred at room temperature for 16 h. The reaction mixture was concentrated and slurried with EtOH (2 mL) to give the compound 145a (1 g, 77% yield) as a white solid. $t_R$=4.58 min, m/z (M+H)⁺=350.0.

Step 2. 6-Bromo-1-cyclopropyl-7-(methoxy-d₃)-1H-indazole (145b)

To a solution of 145a (1 g, 2.6 mmol) in DMF (10 mL) was added CuI (49.4 mg, 0.26 mmol) and K₂CO₃ (717 mg, 5.2 mmol), the mixture was stirred at 100° C. for 16 h under N₂ atmosphere. The mixture was diluted with H₂O (10 mL), extracted with EA (20 mL*3), washed with brine (20 mL), dried over Na₂SO₄, concentrated and purified by flash chromatography (DCM/MeOH=100/1 to 10/1) to get the compound 145b (110 mg, 0.40 mmol, 15% yield) as a yellow oil. LC-MS (Method 4) $t_R$=4.52 min, m/z (M+H)⁺=270.0.

Step 3. Tert-butyl (1-cyclopropyl-7-(methoxy-d₃)-1H-indazol-6-yl)carbamate (145c)

A mixture of 145b (110 mg, 0.40 mmol) and tert-butyl carbamate (94 mg, 0.80 mmol) in 1,4-dioxane (1 mL) was added XantPhos (46 mg, 0.08 mmol), Pd₂(dba)₃ (36 mg, 0.04 mmol) and Cs₂CO₃ (260 mg, 0.8 mmol). The reaction mixture stirred at 100° C. for 12 h. The mixture was diluted with H₂O (50 mL), extracted with EtOAc (20 mL*3), washed with brine (30 mL), dried over Na₂SO₄, concentrated and purified by flash chromatography (DCM/MeOH=100/1 to 10/1) to get the compound 145c (40 mg, 33% yield) as an off-white solid. LC-MS (Method 4) $t_R$=4.45 min, m/z (M+H)⁺=307.2.

Step 4. 1-Cyclopropyl-7-(methoxy-d₃)-1H-indazol-6-amine (145d)

To a solution of 145c (40 mg, 0.13 mmol) in CH₃CN (2 mL) was added HCl/dioxane (2 mL, 4 M). The reaction mixture was stirred at 25° C. for 3 h, aq NaHCO₃ (10 mL, 3 M) was added to adjust pH to above 7, and the reaction mixture was extracted with DCM (10 mL*5), washed with brine (5 mL), dried over Na₂SO₄, concentrated to give the compound 145d (28 mg, 99% yield) as a yellow solid. LC-MS (Method 4) $t_R$=2.53 min, m/z (M+H)⁺=207.2.

Step 5. 6-(Cyclopropanecarboxamido)-4-((1-cyclopropyl-7-(methoxy-d₃)-1H-indazol-6-yl)amino)-N-(methyl-d₃)nicotinamide (145)

To a solution of 145d (28 mg, 0.13 mmol) and 44b (31 mg, 0.013 mmol) in 1,4-dioxane (2 mL) was added pTSA (22 mg, 0.13 mmol), the reaction mixture was stirred at 100° C. for 5 h. The reaction mixture was concentrated and purified by Prep-HPLC (Method E) to give the compound 145 (5.7 mg, 10% yield) as an off-white solid. LC-MS (Method 4) $t_R$=3.06 min, m/z (M+H)⁺=427.2. ¹H NMR (400 MHz, CDCl₃) δ 10.27 (s, 1H), 8.22 (s, 1H), 8.02 (s, 1H), 7.96 (s, 1H), 7.81 (s, 1H), 7.45 (d, J=8.8 Hz, 1H), 7.19 (d, J=8.4 Hz, 1H), 6.11 (s, 1H), 4.02-3.96 (m, 1H), 1.51-1.42 (m, 1H), 1.39-1.30 (m, 2H), 1.12-1.10 (m, 4H), 0.98-0.80 (m, 2H).

Example 146

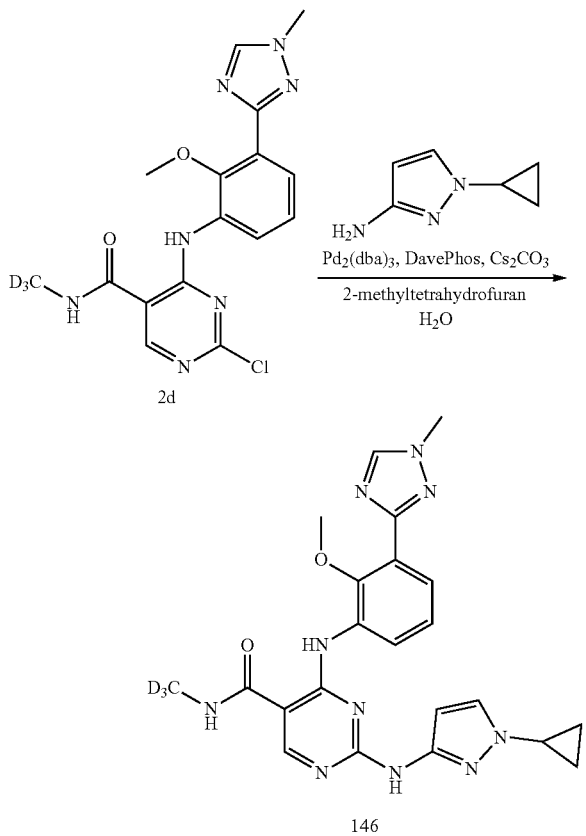 [SMILES: [2H]C([2H])([2H])NC(=O)c1cnc(Cl)nc1Nc1cccc(-c2ncn(C)n2)c1OC ; Nc1ccn(C2CC2)n1 ; [2H]C([2H])([2H])NC(=O)c1cnc(Nc2ccn(C3CC3)n2)nc1Nc1cccc(-c2ncn(C)n2)c1OC]

146

Step 1. 2-((1-Cyclopropyl-1H-pyrazol-3-yl)amino)-4-((2-methoxy-3-(1-methyl-1H-1,2,4-triazol-3-yl)phenyl)amino)-N-(methyl-d₃)pyrimidine-5-carboxamide (146)

Compound 146 (9.9 mg, 40% yield), a white solid, was synthesized by utilizing a similar preparative procedure of Step 4 in Example 2 with 2d (20 mg, 0.05 mmol) and 1-cyclopropyl-1H-pyrazol-3-amine (13 mg, 0.11 mmol) as starting materials. LC-MS (Method 1) $t_R$=2.92 min, m/z (M+H)⁺=464.3. ¹H NMR (400 MHz, DMSO-$d_6$) δ 11.79 (s, 1H), 9.91-9.84 (m, 1H), 8.86-8.80 (m, 1H), 8.62 (s, 1H), 8.54 (s, 1H), 8.40 (s, 1H), 7.66 (d, J=2.0 Hz, 1H), 7.48 (dd, J=8.0, 1.6 Hz, 1H), 7.11 (t, J=8.0 Hz, 1H), 6.53-6.39 (m, 1H), 3.94 (s, 3H), 3.78 (s, 3H), 3.66-3.60 (m, 1H), 1.01-0.92 (m, 4H).

Example 147

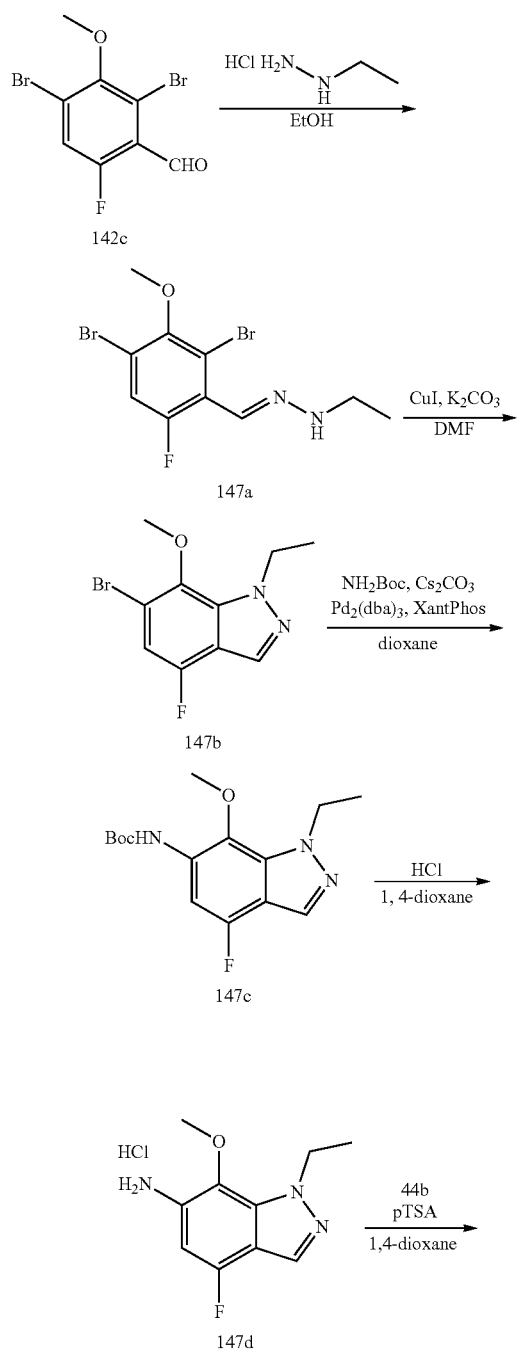

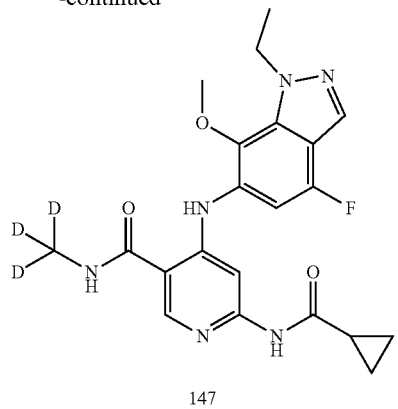

Step 1. (E)-1-(2,4-dibromo-6-fluoro-3-methoxybenzylidene)-2-ethylhydrazine hydrochloride (147a)

To a solution of 142c (108 mg, 0.35 mmol) in EtOH (10 mL) was added ethylhydrazine hydrochloride (43 mg, 0.45 mmol). The resulting mixture was stirred at r.t. for 1 h. Then the solvent was removed under vacuum, and the residue was purified by flash chromatography on silica gel (PE/EA=10/1) to afford compound 147a (104 mg, 77% yield) as a white solid. LC-MS (Method 4) $t_R$=4.67 min, m/z (M+H)⁺=352.9.

Step 2. 6-Bromo-1-ethyl-4-fluoro-7-methoxy-1H-indazole (147b)

To a solution of 147a (240 mg, 0.61 mmol) in DMF (5 mL) was added CuI (13 mg, 0.07 mmol) and $K_2CO_3$ (260 mg, 1.88 mmol). The resulting mixture was stirred at 100° C. under nitrogen for 16 h. Then the mixture was allowed to cooled down to r.t. and quenched with water (10 mL), extracted with EtOAc (10 mL*3). The organic layers were combined, dried over anhydrous $Na_2SO_4$ and concentrated. The residue was purified by chromatography on silica gel (PE/EA=8/1) to give the compound 147b (95 mg, 57% yield) as a light-yellow oil. LC-MS (Method 4) $t_R$=4.70 min, m/z (M+H)⁺273.0.

Step 3. Tert-butyl (1-ethyl-4-fluoro-7-methoxy-1H-indazol-6-yl)carbamate (147c)

To a solution of 147b (95 mg, 0.35 mmol) and tert-butyl carbamate (54 mg, 0.46 mmol) in anhydrous 1,4-dioxane (5 mL) was added $Pd_2(dba)_3$ (16 mg, 0.02 mmol), XantPhos (24 mg, 0.04 mmol) and $Cs_2CO_3$ (230 mg, 0.70 mmol). The resulting mixture was stirred at 100° C. under nitrogen for 16 h. Then the mixture was allowed to cooled down to r.t. The solid was removed by filtration, and the filtrate was concentrated. The residue was purified by chromatography on silica gel (PE/EA=6/1) to provide the compound 147c (83 mg, 77% yield) as a light-yellow oil. LC-MS (Method 4) $t_R$=4.71 min, m/z (M+H)⁺=310.2.

Step 4. 1-Ethyl-4-fluoro-7-methoxy-1H-indazol-6-amine hydrochloride (147d)

To a solution of 147c (83 mg, 0.27 mmol) in 1,4-dioxane (1 mL) was added HCl/1,4-dioxane (4 M, 1.5 mL, 6 mmol). After stirred at r.t. for 3 h, the solvent was removed to afford compound 147d (60 mg, 90% yield) as a yellow solid. LC-MS (Method 4) $t_R$=3.14 min, m/z (M+H)$^+$=210.1.

Step 5. 6-(Cyclopropanecarboxamido)-4-((1-ethyl-4-fluoro-7-methoxy-1H-indazol-6-yl)amino)-N-(methyl-d$_3$)nicotinamide (147)

To a solution of 147d (83 mg, 0.34 mmol) and 44d (80 mg, 0.31 mmol) in 1,4-dioxane (2 mL) was added pTSA (86 mg, 0.5 mmol). The resulting mixture was stirred at 85° C. for 3 h. After cooled down to r.t., the solvent was removed and the residue was purified by Prep-HPLC (Method E) to afford compound 147 (7.0 mg, 4.8% yield) as a white solid. LC-MS (Method 4) $t_R$=3.26 min, m/z (M+H)$^+$=430.3. $^1$H NMR (400 MHz, CD$_3$OD) δ 8.39 (s, 1H), 8.01 (s, 1H), 7.87 (s, 1H), 6.88 (d, J=12 Hz, 1H), 4.61 (q, J=7.2 Hz, 2H), 3.82 (s, 3H), 1.81 (s, 1H), 1.45 (t, J=8.0 Hz, 3H), 0.90-0.80 (m, 4H).

Example 148

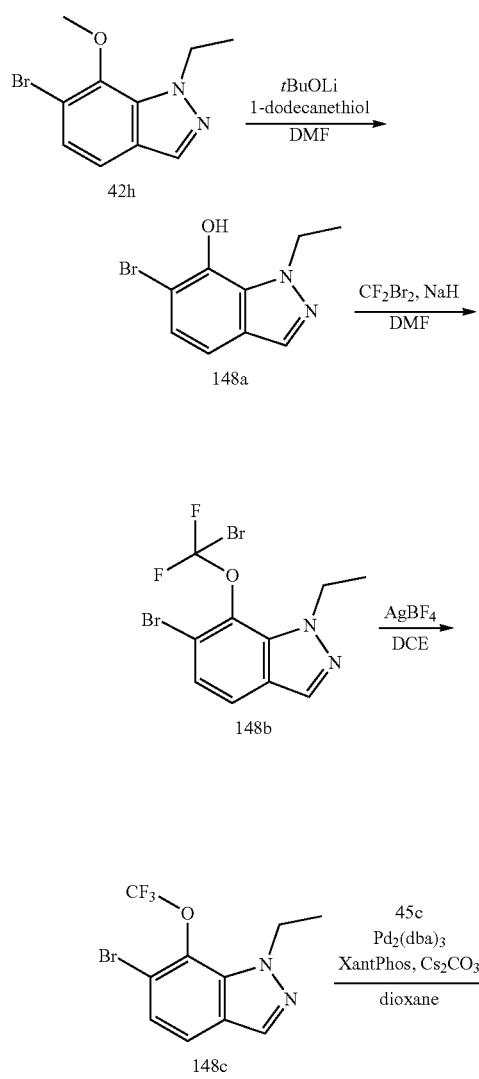

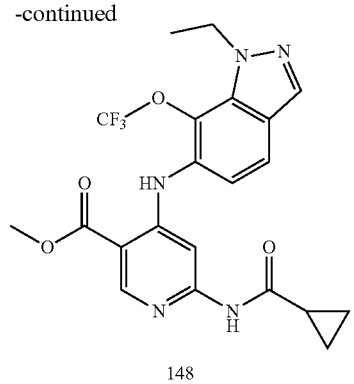

Step 1. 6-Bromo-1-ethyl-1H-indazol-7-ol (148a)

To a stirred solution of compound 42h (0.5 g, 1.96 mmol) and 1-dodecanethiol (845 mg, 4.17 mmol) in DMF (5 mL) was added t-BuOLi (343 mg, 4.28 mmol). The resulting mixture was stirred at 100° C. for 2.5 h. Then the mixture was cooled to room temperature and quenched with water (20 mL). The pH was adjusted to 5 with 2 N HCl aqueous solution and extracted with EtOAc (13 mL*3). The organic layers were combined, dried over anhydrous Na$_2$SO$_4$ and concentrated. The residue was purified by chromatography on silica gel (PE/EA=10/1) to give the compound 148a (0.45 g, 95% yield) as a light-yellow solid. LC-MS (Method 4) $t_R$=3.62 min, m/z (M+H)$^+$=241.0.

Step 2. 6-Bromo-7-(bromodifluoromethoxy)-1-ethyl-1H-indazole (148b)

To a solution of 148a (0.45 g, 1.87 mmol) in DMF (5 mL) was added NaH (247 mg, 6.17 mmol, 60% in mineral oil) at 0° C. After stirred at r.t. for 0.5 h, dibromodifluoromethane (3.92 g, 18.6 mmol) was added, and the resulting reaction mixture was stirred at r.t. for 16 h. Then it was quenched with water (20 mL) and extracted with EtOAc (15 mL*3). The organic layers were combined, dried over anhydrous Na$_2$SO$_4$ and concentrated. The residue was purified by chromatography on silica gel (PE/EA=15/1) to give the compound 148b (0.60 g, 87% yield) as a yellow solid. LC-MS (Method 4) $t_R$=5.11 min, m/z (M+H)$^+$=369.0.

Step 3. 6-Bromo-1-ethyl-7-(trifluoromethoxy)-1H-indazole (148c)

To a solution of 148b (0.6 g, 1.62 mmol) in DCE (10 mL) was added AgBF$_4$ (1.1 g, 5.64 mmol) at 0° C. Then the mixture was stirred at 65° C. for 4 h under nitrogen atmosphere. Then it was quenched with water (10 mL) and extracted with DCM (20 mL*3). The organic layers were combined, dried over anhydrous Na$_2$SO$_4$ and concentrated. The residue was purified by chromatography on silica gel (PE/EA=9/1) to give the compound 148c (428 mg, 77% yield) as a dark-yellow solid. LC-MS (Method 4) $t_R$=5.15 min, m/z (M+H)$^+$=309.0.

Step 4. Methyl 6-(cyclopropanecarboxamido)-4-((1-ethyl-7-(trifluoromethoxy)-1H-indazol-6-yl)amino)nicotinate (148)

To a solution of 148c (407 mg, 1.32 mmol) and 45c (312 mg, 0.94 mmol) in anhydrous 1,4-dioxane (12 mL) was added Pd$_2$(dba)$_3$ (65 mg, 0.07 mmol), XantPhos (100 mg, 0.17 mmol) and Cs$_2$CO$_3$ (1.12 g, 3.44 mmol). The resulting mixture was refluxed at 100° C. under nitrogen for 8 h. Then the mixture was allowed to cooled down to r.t. The solid was removed by filtration, and the filtrate was concentrated. The residue was purified by Prep-HPLC (Method E) to afford compound 148 (83 mg, 12% yield) as a white solid. LC-MS (Method 4) t$_R$=4.40 min, m/z (M+H)$^+$=464.2. $^1$H-NMR (400 MHz, CDCl$_3$) δ 10.03 (s, 1H), 8.75 (s, 1H), 8.31 (s, 1H), 7.99 (s, 1H), 7.88 (s, 1H), 7.70 (d, J=8.8 Hz, 1H), 7.26 (d, J=8.8 Hz, 1H), 4.55 (q, J=8.0 Hz, 2H), 3.94 (s, 3H), 1.53-1.48 (m, 1H) 1.47 (t, J=7.2 Hz, 3H), 1.03-0.99 (m, 2H), 0.87-0.82 (m, 2H).

Example 149

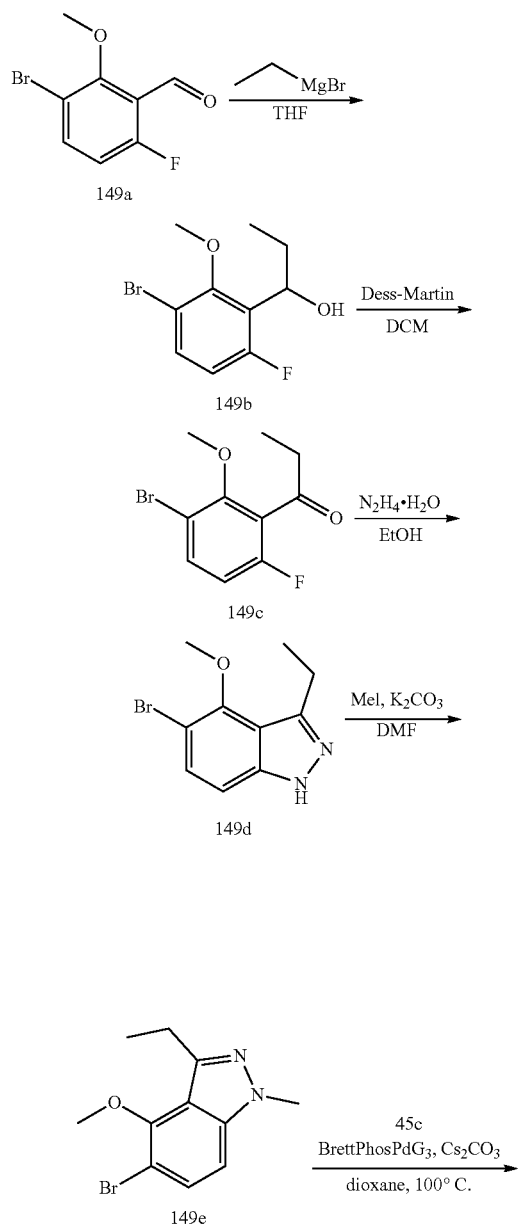

-continued

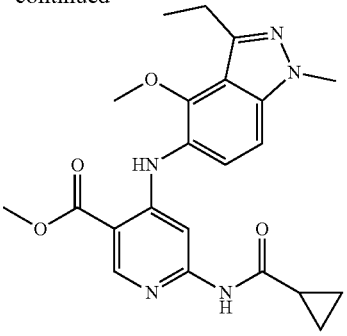

149

Step 1. 1-(3-Bromo-6-fluoro-2-methoxyphenyl)propan-1-ol (149b)

To a solution of 149a (2.0 g, 8.58 mmol) in anhydrous THF (25 mL) was added EtMgBr (2 M in THF, 6.5 mL, 13 mmol) dropwise at 0° C. under nitrogen atmosphere. Then the mixture was allowed to warm up to r.t. and stirred for 1 h, cautiously quenched with sat. NH$_4$Cl (20 mL). After the separation of the layers, the aqueous layer was extracted with DCM (20 mL*3). The organic layers were combined, dried over anhydrous Na$_2$SO$_4$ and concentrated. The residue was purified by silica gel chromatography (PE/EA=5/1) to give 149b (1.11 g, 49% yield) as a colorless liquid. LC-MS (Method 4) t$_R$=3.86 min, m/z (M+H−18)$^+$=245.0.

Step 2. 1-(3-Bromo-6-fluoro-2-methoxyphenyl)propan-1-one (149c)

To a solution of 149b (1.11 g, 4.22 mmol) in DCM (15 mL) was added Dess-Martin (2.3 g, 5.42 mmol), and the mixture was stirred at r.t. for 3 h. The resulting reaction mixture was concentrated under vacuum. The residue was purified by chromatography on silica gel (PE/EA=5/1) to give 149c (880 mg, 80% yield) as a colorless liquid.

Step 3. 5-Bromo-3-ethyl-4-methoxy-1H-indazole (149d)

A solution of 149c (880 mg, 3.37 mmol) and hydrazine hydrate (6 mL, 80% in H$_2$O) in EtOH (15 mL) was stirred at 90° C. for 3 h. Then the reaction solution was cooled down to r.t. and concentrated under vacuum. The residue was purified by chromatography on silica gel (PE/EA=7/1) to afford 149d (215 mg, 25% yield) as a light yellow solid. LC-MS (Method 4) t$_R$=3.94 min, m/z (M+H)$^+$=255.0.

Step 4. 5-Bromo-3-ethyl-4-methoxy-1-methyl-1H-indazole (149e)

To a stirred mixture of 149d (215 mg, 0.84 mmol) and K$_2$CO$_3$ (242 mg, 1.75 mmol) in DMF (6 mL) was added MeI (136 mg, 0.95 mmol). After stirred at 70° C. for 2 h, the mixture was quenched with water (15 mL), extracted with EA (12 mL*3) and The combined organic layer was dried over anhydrous Na$_2$SO$_4$ and concentrated. The residue was purified by chromatography on silica gel (PE/EA=7/1) to give 149e (144 mg, 64% yield) as a yellow oil. LC-MS (Method 4) t$_R$=4.48 min, m/z (M+H)$^+$=269.0.

Step 5. Methyl 6-(cyclopropanecarboxamido)-4-((3-ethyl-4-methoxy-1-methyl-1H-indazol-5-yl)amino)nicotinate (149)

To a solution of 149e (144 mg, 0.53 mmol) and 45c (133 mg, 0.40 mmol) in anhydrous 1,4-dioxane (12 mL) was added BrettPhos Pd G3 (63 mg, 0.07 mmol) and $Cs_2CO_3$ (486 mg, 1.49 mmol). The resulting mixture was refluxed at 100° C. under nitrogen atmosphere for 16 h. Then the mixture was allowed to cooled down to r.t. The solvent was removed, and the residue was purified by Prep-HPLC (Method E) to afford compound 149 (25 mg, 11% yield) as a white solid. LC-MS (Method 4) $t_R$=3.50 min, m/z $(M+H)^+$=424.3. $^1$H-NMR (400 MHz, $CDCl_3$) δ 9.60 (s, 1H), 8.71 (s, 1H), 8.27 (s, 1H), 7.60 (s, 1H), 7.37 (d, J=9.0 Hz, 1H), 7.11 (d, J=9.0 Hz, 1H), 4.07 (s, 3H), 3.92 (s, 3H), 3.82 (s, 3H), 3.13 (q, J=7.6 Hz, 2H), 1.50-1.44 (m, 1H), 1.30 (t, J=7.6 Hz, 3H), 1.01-0.97 (m, 2H), 0.84-0.80 (m, 2H).

Example 150

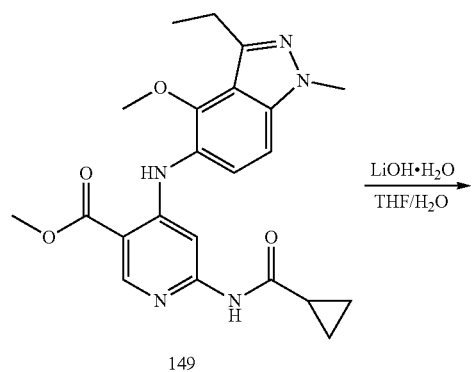

Step 1. 6-(Cyclopropanecarboxamido)-4-((3-ethyl-4-methoxy-1-methyl-1H-indazol-5-yl)amino)nicotinic acid (150a)

To a solution of 149 (22 mg, 0.05 mmol) in THF (0.8 mL) and $H_2O$ (0.2 mL) was added $LiOH \cdot H_2O$ (52 mg, 1.24 mmol), and the mixture was stirred at 65° C. for 16 h. Then it was cooled down to r.t. and adjusted pH to 5 with 2 N HCl aqueous solution. The acidified solution was extracted with DCM/MeOH=6:1 (3 mL*7) and The combined organic layer was dried over anhydrous $Na_2SO_4$. Then it was concentrated to afford the crude product 150a (15 mg, 71% yield) as a light yellow solid. LC-MS (Method 4) $t_R$=2.64 min, m/z $(M+H)^+$=410.3.

Step 2. 6-(Cyclopropanecarboxamido)-4-((3-ethyl-4-methoxy-1-methyl-1H-indazol-5-yl)amino)-N-(methyl-$d_3$)nicotinamide (150)

To a solution of 150a (15 mg, 0.04 mmol) and HATU (15 mg, 0.04 mmol) in DMF (1 mL) was added DIPEA (18 mg, 0.14 mmol). After stirred at r.t. for 10 min, methyl-$d_3$-amine hydrochloride (5.4 mg, 0.08 mmol) was added and the final mixture was stirred at r.t. for 1 h. Then the mixture was filtered and the filtrate was purified by Prep-HPLC (Method E) to afford 150 (4.2 mg, 27% yield) as a white solid. LC-MS (Method 4) $t_R$=2.83 min, m/z $(M+H)^+$=426.3. $^1$H NMR (400 MHz, $CDCl_3$) δ 9.94 (s, 1H), 8.20 (s, 1H), 8.18 (s, 1H), 7.64 (s, 1H), 7.29 (d, J=8.8 Hz, 1H), 7.07 (d, J=8.8 Hz, 1H), 6.17 (s, 1H), 3.95 (s, 3H), 3.86 (s, 3H), 3.03 (q, J=7.6 Hz, 2H), 1.49-1.43 (m, 1H), 1.35 (t, J=7.6 Hz, 3H), 1.01-0.97 (m, 2H), 0.83-0.78 (m, 2H).

Example 151

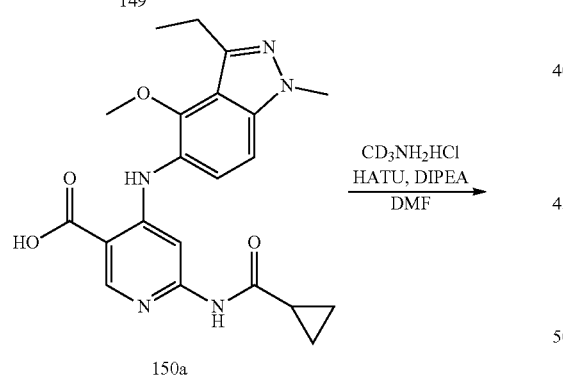

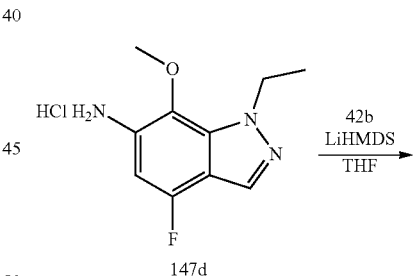

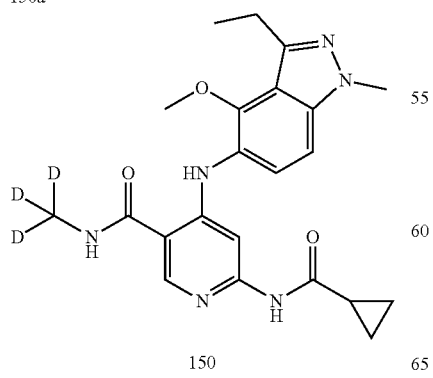

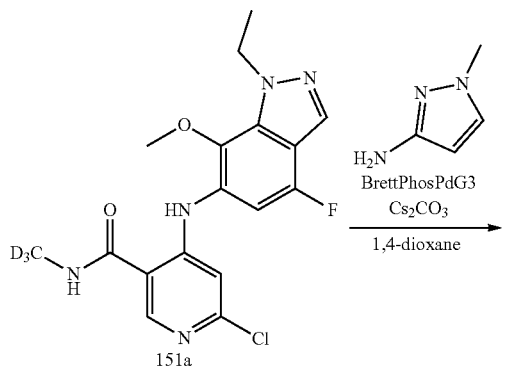

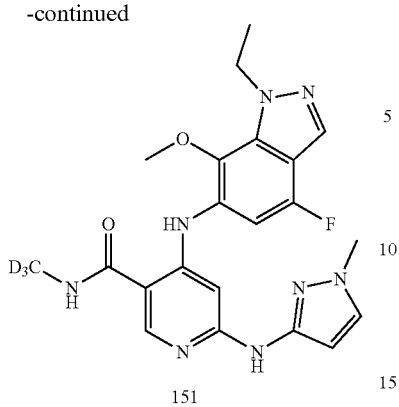

151

Step 1. 6-Chloro-4-((1-ethyl-4-fluoro-7-methoxy-1H-indazol-6-yl)amino)-N-(methyl-d₃)nicotinamide (151a)

To a mixture of 147d (280 mg, 1.14 mmol), 42b (237 mg, 1.14 mmol) in THF (5 mL) was added LiHMDS (9.12 mL, 1 M in THF) at −60° C. After stirring for 20 min at 20° C., the reaction was quenched with ice water (5 mL) and the organic layer was removed under vacuo. The formed solid was collected by filtering and dried to afford the title compound 151a (340 mg, 81% yield) as a brown solid. LC-MS (Method 3) $t_R$=1.71 min, m/z (M+H)⁺=381.1.

Step 2. 4-((1-Ethyl-4-fluoro-7-methoxy-1H-indazol-6-yl)amino)-N-(methyl-d₃)-6-((1-methyl-1H-pyrazol-3-yl)amino)nicotinamide (151)

A mixture of 151a (22 mg, 0.058 mmol), 1-methyl-1H-pyrazol-3-amine (11 mg, 0.16 mmol), BrettPhos Pd G3 (26 mg, 0.028 mmol), Cs₂CO₃ (38 mg, 0.12 mmol) in anhydrous dioxane (1 mL) was stirred at 100° C. for 16 h under N₂. The mixture was cooled, concentrated and the residue was purified by Prep-HPLC (Method A) to afford compound 151 (6 mg, 24% yield) as a white solid. LC-MS (Method 2) $t_R$=3.43 min, m/z (M+H)⁺=442.2. ¹H NMR (400 MHz, DMSO-d₆) δ 10.77 (s, 1H), 9.30 (s, 1H), 8.42 (s, 2H), 8.14 (s, 1H), 7.48 (d, J=2.4 Hz, 1H), 7.41 (s, 1H), 7.13 (d, J=11.2 Hz, 1H), 6.06 (s, 1H), 4.55 (q, J=6.8 Hz, 2H), 3.81 (s, 3H), 3.66 (s, 3H), 1.42 (t, J=6.8 Hz, 3H).

Example 152

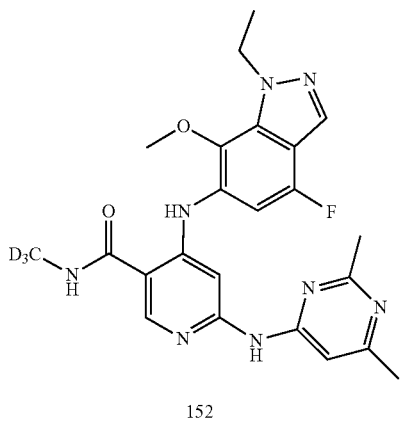

152

Step 1. 6-((2,6-Dimethylpyrimidin-4-yl)amino)-4-((1-ethyl-4-fluoro-7-methoxy-1H-indazol-6-yl)amino)-N-(methyl-d₃)nicotinamide (152)

A mixture of 151a (36 mg, 0.095 mmol), 2,6-dimethylpyrimidin-4-amine (23 mg, 0.19 mmol), BrettPhos Pd G3 (34 mg, 0.038 mmol), Cs₂CO₃ (62 mg, 0.19 mmol) in anhydrous dioxane (1 mL) was stirred at 100° C. for 3 h under N₂. The mixture was concentrated and the residue was purified by Prep-HPLC (Method A) to afford the title compound 152 (22 mg, 50% yield) as a white solid. LC-MS (Method 2) $t_R$=2.60 min, m/z (M+H)⁺=468.1. ¹H NMR (400 MHz, DMSO-d₆) δ 10.72 (s, 1H), 10.02 (s, 1H), 8.57 (s, 1H), 8.53 (s, 1H), 8.16 (s, 1H), 7.94 (s, 1H), 7.11-7.09 (m, 2H), 4.56 (q, J=7.2 Hz, 2H), 3.81 (s, 3H), 2.22 (s, 3H), 2.23 (s, 3H), 1.42 (t, J=7.2 Hz, 3H).

Example 153

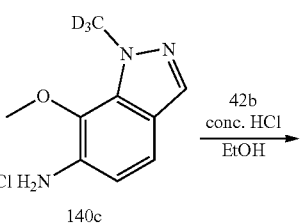

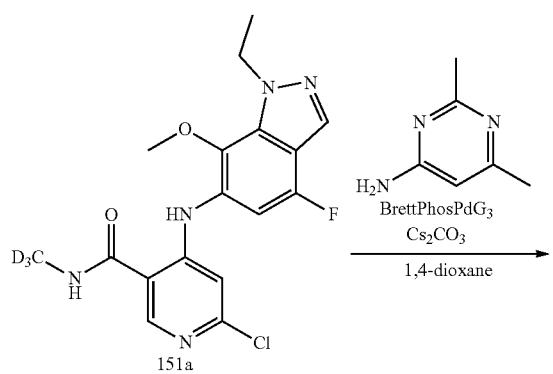

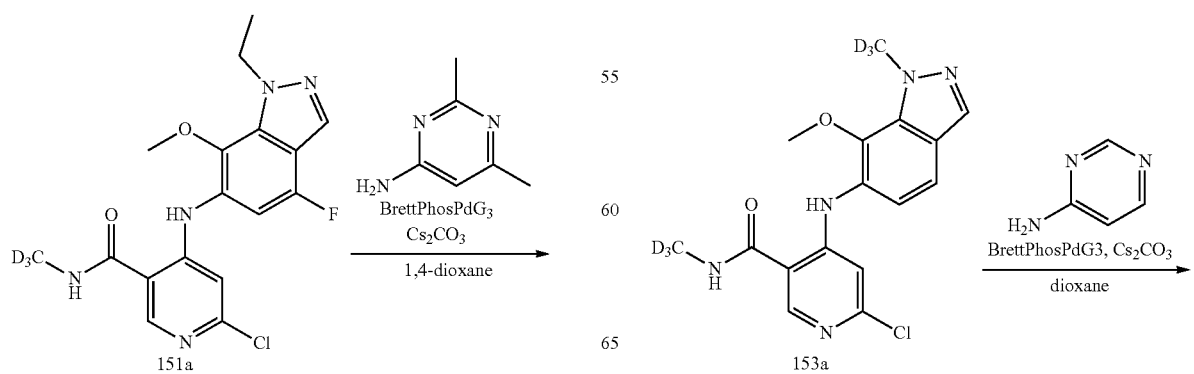

485

-continued

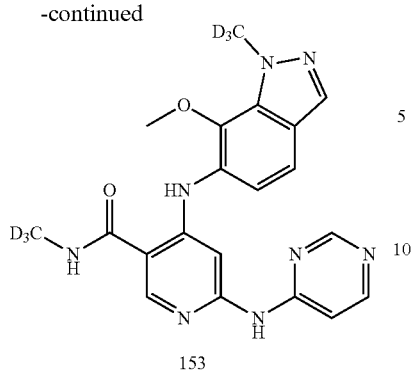

153

Step 1. 6-Chloro-4-((7-methoxy-1-(methyl-d₃)-1H-indazol-6-yl)amino)-N-(methyl-d 3)nicotinamide (153a)

A mixture of 140c (70 mg, 0.32 mmol), 42b (74 mg, 0.36 mmol) and conc. HCl (1.18 mg, 0.032 mmol) in EtOH (1 mL) was stirred at 80° C. for 24 h. The mixture was concentrated and the residue was purified by flash chromatography on silica gel (DCM/MeOH=20/1) to afford the title compound 153a (100 mg, 88% yield) as a yellow solid. LC-MS (Method 2) $t_R$=1.19 min, m/z (M+H)$^+$=352.2.

Step 2. 4-((7-Methoxy-1-(methyl-d₃)-1H-indazol-6-yl)amino)-N-(methyl-d₃)-6-(pyrimidin-4-ylamino)nicotinamide (153)

A mixture of 153a (50 mg, 0.14 mmol), pyrimidin-4-amine (27 mg, 0.28 mmol), BrettPhos Pd G3 (26 mg, 0.028 mmol) and Cs₂CO₃ (93 mg, 0.28 mmol) in anhydrous dioxane (1 mL) was stirred at stirred at 100° C. for 16 h under N₂. After cooling to r.t., the reaction mixture was concentrated under reduced pressure. The residue was purified by flash chromatography on silica gel (DCM/MeOH=20/1) to afford the title compound 153 (25 mg, 42% yield) as a white solid. LC-MS (Method 2) $t_R$=2.23 min, m/z (M+H)$^+$=411.1. $^1$H NMR (300 MHz, DMSO-d₆) δ 10.63 (s, 1H), 10.17 (s, 1H), 8.62 (s, 2H), 8.56 (s, 1H), 8.43 (d, 0.1=6.0 Hz, 1H), 8.06 (s, 1H), 7.73 (d, J=6.0 Hz, 1H), 7.60 (d, J=8.7 Hz, 1H), 7.57 (s, 1H), 7.27 (d, J=8.7 Hz, 1H), 3.85 (s, 3H).

Example 154

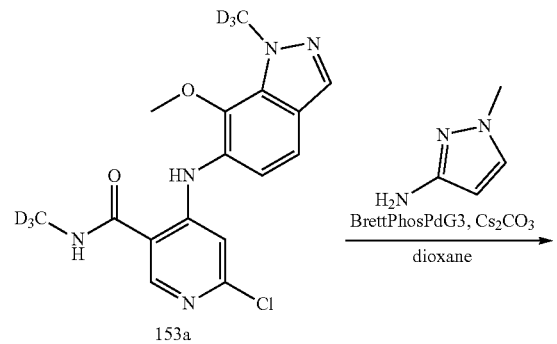

486

-continued

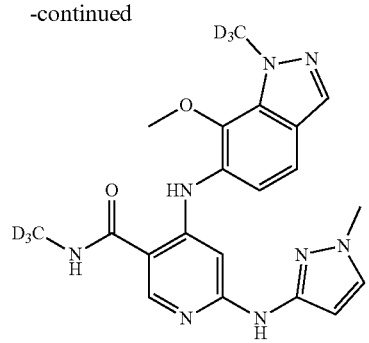

154

Step 1. 4-((7-Methoxy-1-(methyl-d₃)-1H-indazol-6-yl)amino)-N-(methyl-d₃)-6-((1-methyl-1H-pyrazol-3-yl)amino)nicotinamide (154)

A mixture of 153a (50 mg, 0.14 mmol), pyrimidin-4-amine (28 mg, 0.28 mmol), BrettPhos Pd G3 (26 mg, 0.028 mmol) and Cs₂CO₃ (93 mg, 0.28 mmol) in anhydrous dioxane (1 mL) was stirred at 100° C. for 16 h under N₂. After cooling to r.t., the reaction mixture was concentrated under reduced pressure. The residue was purified by flash chromatography on silica gel (DCM/MeOH=20/1) to afford the title compound 154 (20 mg, 34% yield) as a white solid. LC-MS (Method 2) $t_R$=2.49 min, m/z (M+H)$^+$=413.1. $^1$H NMR (400 MHz, DMSO-d₆) δ 10.57 (s, 1H), 9.17 (s, 1H), 8.40 (s, 1H), 8.38 (s, 1H), 8.00 (s, 1H), 7.54 (d, J=8.4 Hz, 1H), 7.46 (s, 1H), 7.26 (d, J=8.8 Hz, 1H), 7.22 (s, 1H), 6.07 (s, 1H), 3.82 (s, 3H), 3.63 (s, 3H).

Example 155

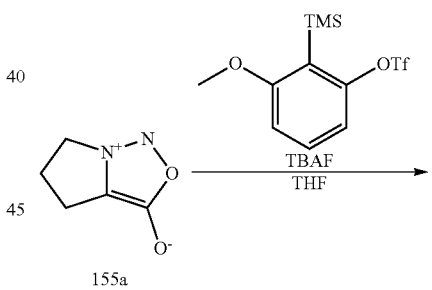

155a

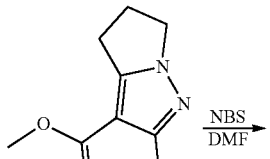

155b

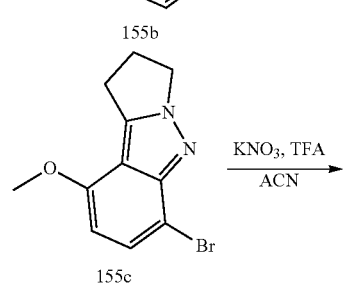

155c

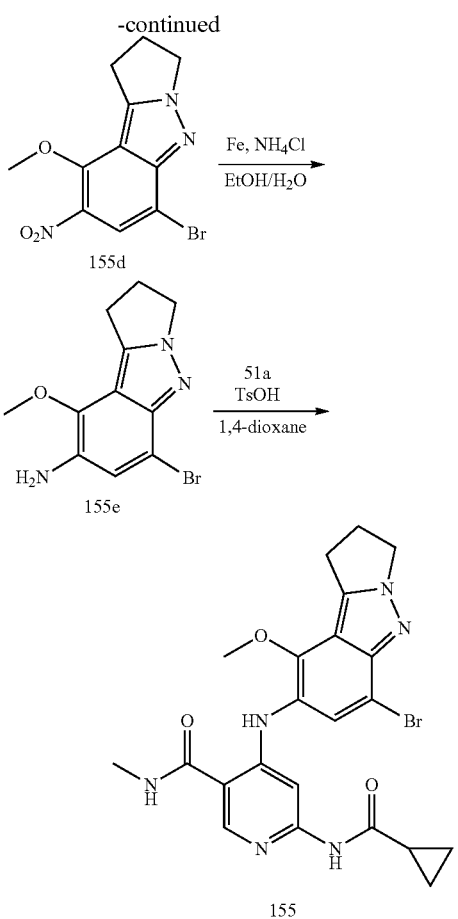

Step 1. 9-Methoxy-2,3-dihydro-1H-pyrrolo[1,2-b]indazole (155b)

To a solution of 155a (2.30 g, 18.27 mmol) and (3-methoxy-2-trimethylsilyl-phenyl) trifluoromethanesulfonate (5 g, 15.23 mmol) in THF (20 mL) was added TBAF (6.37 g, 24.36 mmol) at 0° C. After stirring at r.t. for 16 h, the mixture was poured into sat. NaHCO$_3$ (20 mL) and extracted with EtOAc (20 mL*2). The separated organic layer was concentrated and the residue was purified by flash chromatography on silica gel (PE/EtOAc=3/1) to afford the title compound 155b (1.5 g, 52% yield) as a white solid. LC-MS (Method 3) t$_R$=1.17 min, m/z (M+H)$^+$=189.1.

Step 2. 6-Bromo-9-methoxy-2,3-dihydro-1H-pyrrolo[1,2-b]indazole (155c)

To a solution of 155b (450 mg, 2.39 mmol) in DMF (5 mL) was added NBS (426 mg, 2.39 mmol) at 0° C. After stirring at 5° C. for 30 min, the mixture was poured into ice water (10 mL) and the formed solid was filtered. The filter cake was dried to afford the title compound 155c (600 mg, 94% yield) as a brown solid. $^1$H NMR (400 MHz, CDCl$_3$) δ 7.36 (d, J=7.8 Hz, 1H), 6.22 (d, J=7.8 Hz, 1H), 4.48 (t, J=7.6 Hz, 2H), 3.93 (s, 3H), 3.32 (t, J=7.6 Hz, 2H), 2.83-2.76 (m, 2H).

Step 3. 6-Bromo-9-methoxy-8-nitro-2,3-dihydro-1H-pyrrolo[1,2-b]indazole (155d)

To a mixture of 155c (200 mg, 0.75 mmol) in ACN (8 mL) was added TFA (2 mL) followed by KNO$_3$ (76 mg, 0.75 mmol) at 0° C. After stirring at 50° C. for 3 h, the reaction mixture was poured into sat. Na$_2$CO$_3$ (10 mL) to adjust pH to 8-9 and extracted with EtOAc (20 mL*2). The combined organic phase was concentrated and the residue was purified by flash chromatography on silica gel (DCM/MeOH=100/1) to afford the title compound 155d (150 mg, 64% yield) as a yellow solid. $^1$H NMR (400 MHz, CDCl$_3$) δ 8.52 (s, 1H), 4.60 (t, J=7.6 Hz, 2H), 4.12 (s, 3H), 3.38 (t, J=7.6 Hz, 2H), 2.87-2.84 (m, 2H).

Step 4. 6-Bromo-9-methoxy-2,3-dihydro-1H-pyrrolo[1,2-b]indazol-8-amine (155e)

A mixture of 155d (110 mg, 0.35 mmol), Fe (98 mg, 1.76 mmol) and NH$_4$Cl (189 mg, 3.52 mmol) in EtOH (5 mL) and H$_2$O (2.5 mL) was stirred at 50° C. for 1 h. The reaction mixture was filtered and the filter cake was washed with MeOH (10 mL). The filtrate was concentrated and the residue was purified by flash chromatography on silica gel (DCM/MeOH=100/1) to afford the title compound 155e (32 mg, 32% yield) as a yellow solid. $^1$H NMR (400 MHz, DMSO-d$_6$) δ 6.28 (s, 1H), 5.23 (s, 2H), 4.33 (t, J=7.2 Hz, 2H), 3.73 (s, 3H), 3.18 (t, J=7.2 Hz, 2H), 2.70-2.67 (m, 2H).

Step 5. 4-((6-Bromo-9-methoxy-2,3-dihydro-1H-pyrrolo[1,2-b]indazol-8-yl)amino)-6-(cyclopropanecarboxamido)-N-methylnicotinamide (155)

Compound 155 (30 mg, 63% yield) was synthesized by utilizing a similar preparative procedure of Step 6 in Example 51 with 155e (27 mg, 0.96 mmol) and 51a (27 mg, 0.11 mmol) as starting materials. LC-MS (Method 1) t$_R$=3.23 min, m/z (M+H)$^+$=499.0. $^1$H NMR (400 MHz, DMSO-d$_6$) δ 10.98 (s, 1H), 10.77 (s, 1H), 8.61 (d, J=4.0 Hz, 1H), 8.54 (s, 1H), 8.19 (s, 1H), 7.26 (s, 1H), 4.42 (t, J=6.8 Hz, 2H), 3.89 (s, 3H), 3.27-3.25 (m, 2H), 2.79 (d, J=4.4 Hz, 3H), 2.76-2.68 (m, 2H), 2.02-1.97 (m, 1H), 0.83-0.74 (m, 4H).

Example 156

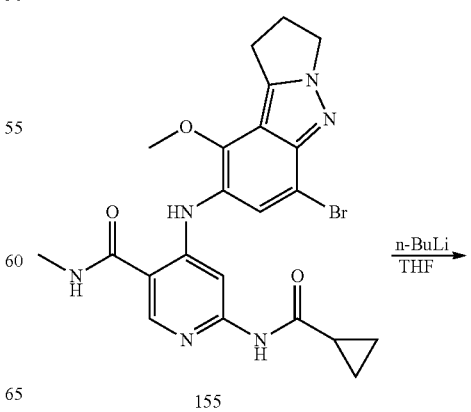

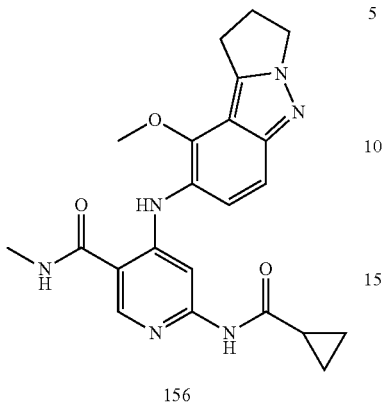

156

Step 1. 6-(Cyclopropanecarboxamido)-4-((9-methoxy-2,3-dihydro-1H-pyrrolo[1,2-b]indazol-8-yl)amino)-N-methylnicotinamide (156)

To a mixture of 155 (22 mg, 0.044 mmol) in THF (0.5 mL) was added n-BuLi (1.76 mL, 4.4 mmol, 2.5 M in THF) at −60° C. After stirring at r.t. for 10 min, the reaction was quenched with H$_2$O (2 mL) at 0° C. The reaction mixture was extracted with EtOAc (5 mL*2). The combined organic phase was concentrated and the residue was purified by Prep-HPLC (Method A) to afford the title compound 156 (4.4 mg, 24% yield) as a yellow solid. LC-MS (Method 2) t$_R$=3.40 min, m/z (M+H)$^+$=421.1. $^1$H NMR (400 MHz, DMSO-d$_6$) δ 10.64 (s, 1H), 10.60 (s, 1H), 8.53 (d, J=4.4 Hz, 1H), 8.48 (s, 1H), 7.98 (s, 1H), 7.05 (d, J=8.0 Hz, 1H), 6.34 (d, J=7.6 Hz, 1H), 4.34 (t, J=7.2 Hz, 2H), 3.66 (s, 3H), 3.19 (t, J=6.8 Hz, 2H), 2.79 (d, J=4.0 Hz, 3H), 2.71-2.65 (m, 2H), 1.99-1.94 (m, 1H), 0.75-0.74 (m, 4H).

Example 157

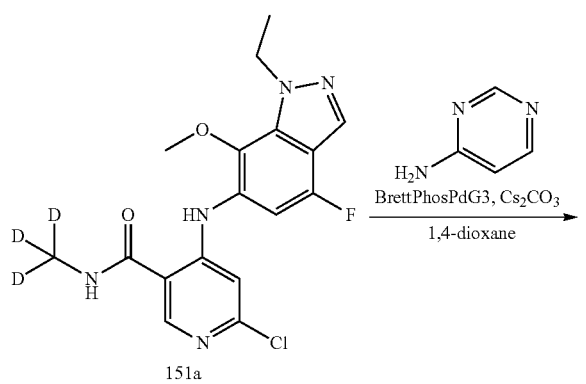

151a

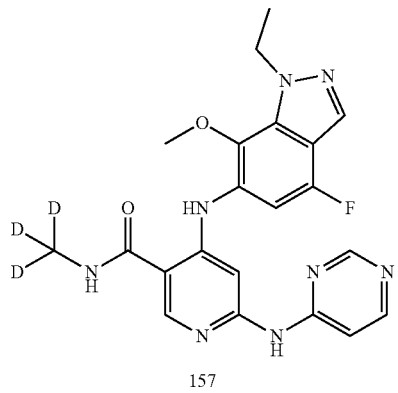

157

Step 1. 4-((1-Ethyl-4-fluoro-7-methoxy-1H-indazol-6-yl)amino)-N-(methyl-d$_3$)-6-(pyrimidin-4-ylamino)nicotinamide (157)

A mixture of 151a (50 mg, 0.13 mmol), pyrimidin-4-amine (25 mg, 0.26 mmol), BrettPhos Pd G3 (24 mg, 0.03 mmol) and Cs$_2$CO$_3$ (86 mg, 0.26 mmol) in anhydrous 1,4-dioxane (1 mL) was stirred at 100° C. for 3 h under N$_2$ atmosphere. The reaction mixture was cooled and concentrated. The residue was purified by Prep-HPLC (Method A) to afford 157 (25 mg, 43% yield) as a white solid. LC-MS (Method 2) t$_R$=2.60 min, m/z (M+H)$^+$=440.1. $^1$H NMR (400 MHz, DMSO-d$_6$) δ 10.71 (s, 1H), 10.20 (s, 1H), 8.61 (s, 1H), 8.59 (s, 1H), 8.55 (s, 1H), 8.42 (d, J=6.0 Hz, 1H), 8.17 (s, 1H), 7.74 (d, J=5.6 Hz, 1H), 7.60 (s, 1H), 7.12 (d, J=11.2 Hz, 1H), 4.58 (q, J=7.2 Hz, 2H), 3.81 (s, 3H), 1.43 (t, J=7.2 Hz, 3H).

Example 158

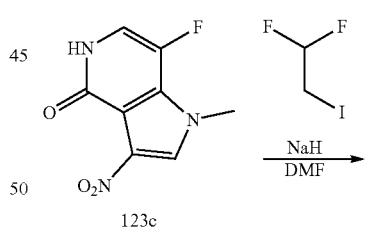

123c

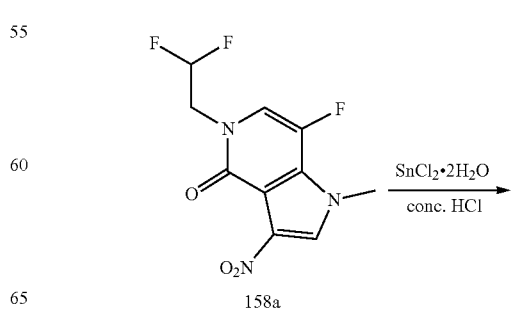

158a

-continued

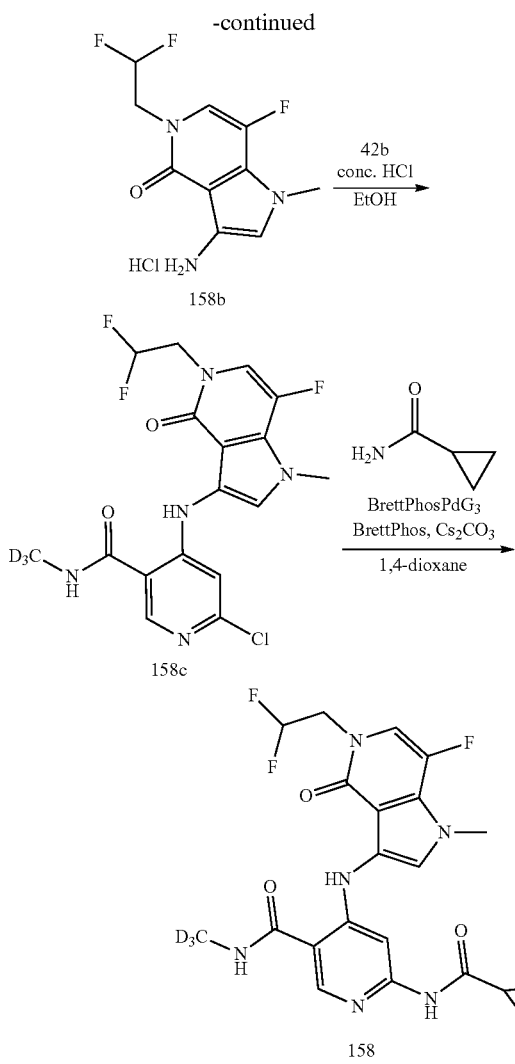

Step 1 in Example 98 with 158b (60 mg, 0.21 mmol) and 42b (53 mg, 0.26 mmol) as starting materials. LC-MS (Method 2) $t_R$=2.97 min, m/z (M+H)$^+$=417.0.

Step 4. 6-(Cyclopropanecarboxamido)-4-((5-(2,2-difluoroethyl)-7-fluoro-1-methyl-4-oxo-4,5-dihydro-1H-pyrrolo[3,2-c]pyridin-3-yl)amino)-N-(methyl-d$_3$) nicotinamide (158)

Compound 158 (10 mg, 15% yield), a yellow solid, was synthesized by utilizing a similar preparative procedure of Step 3 in Example 49 with 158c (30 mg, 0.14 mmol) and cyclopropanecarboxamide (61 mg, 0.72 mmol) as starting materials. LC-MS (Method 1) $t_R$=3.22 min, m/z (M+H)$^+$=466.1. $^1$H NMR (400 MHz, DMSO-d$_6$) δ 10.90 (s, 1H), 10.75 (s, 1H), 8.45 (s, 1H), 8.41 (s, 1H), 8.00 (s, 1H), 7.57 (d, J=7.6 Hz, 1H), 7.14 (s, 1H), 6.27 (t, J=15.6 Hz, 1H), 4.30-4.27 (m, 2H), 3.38 (s, 3H), 2.04-1.98 (m, 1H), 0.83-0.79 (m, 4H).

Example 159

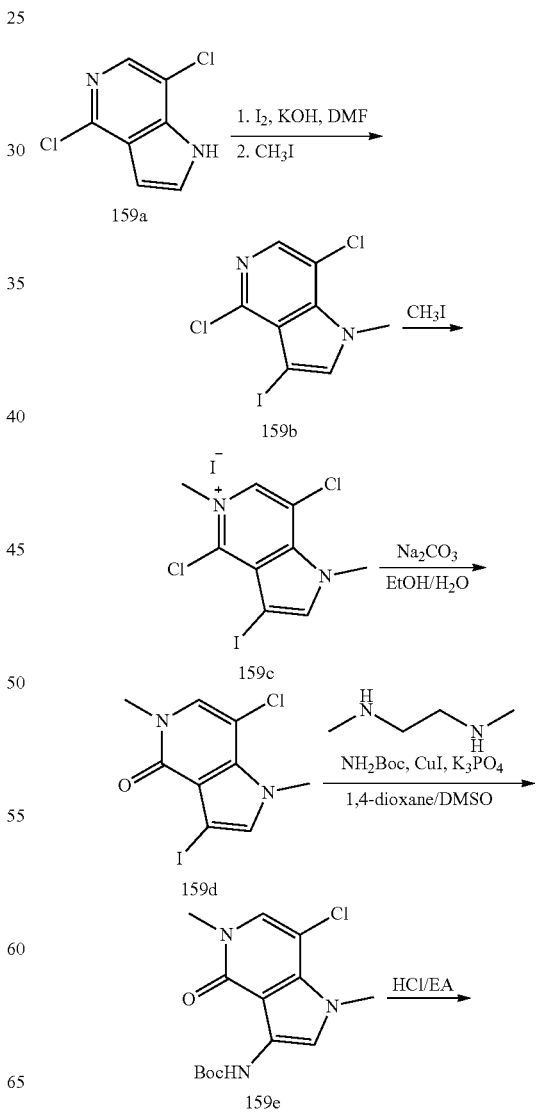

Step 1. 5-(2,2-Difluoroethyl)-7-fluoro-1-methyl-3-nitro-1H-pyrrolo[3,2-c]pyridin-4-(5H)-one (158a)

Compound 158a (200 mg, 61% yield), a yellow solid, was synthesized by utilizing a similar preparative procedure of Step 1 in Example 125 with 123c (250 mg, 1.18 mmol) and 1,1-difluoro-2-iodoethane (341 mg, 1.78 mmol) as starting materials. LC-MS (Method 3) $t_R$=1.21 min, m/z (M+H)$^+$=276.0.

Step 2. 3-Amino-5-(2,2-difluoroethyl)-7-fluoro-1-methyl-1,5-dihydro-4H-pyrrolo[3,2-c]pyridin-4-one hydrochloride (158b)

Compound 158b (60 mg, 29% yield), a yellow solid, was synthesized by utilizing a similar preparative procedure of Step 5 in Example 123 with 158a (200 mg, 0.72 mmol) as the starting material. LC-MS (Method 3) $t_R$=1.27 min, m/z (M+H)$^+$=246.1.

Step 3. 6-Chloro-4-((5-(2,2-difluoroethyl)-7-fluoro-1-methyl-4-oxo-4,5-dihydro-1H-pyrrolo[3,2-c]pyridin-3-yl)amino)-N-(methyl-d$_3$)nicotinamide (158c)

Compound 158c (60 mg, 68% yield), a white solid, was synthesized by utilizing a similar preparative procedure of

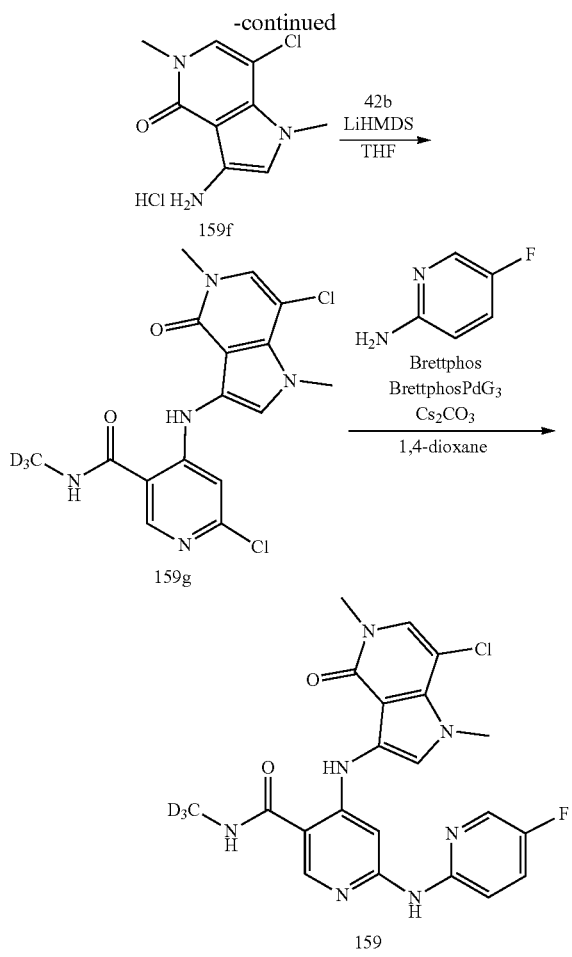

Step 1. 4,7-Dichloro-3-iodo-1-methyl-1H-pyrrolo[3,2-c]pyridine (159b)

To a mixture of 159a (836 mg, 2.67 mmol) and KOH (299 mg, 5.34 mmol) in DMF (5 mL) was added CH$_3$I (569 mg, 4.01 mmol). After stirring for 30 min at r.t., the reaction mixture was diluted with water and filtered. The filter cake was dried to afford 159b (460 mg, 53% yield) as a brown solid. $^1$H NMR (300 MHz, DMSO-d$_6$) b 8.04 (s, 1H), 7.04 (s, 1H), 4.10 (s, 3H).

Step 2. 4,7-Dichloro-3-iodo-1,5-dimethyl-1H-pyrrolo[3,2-c]pyridin-5-ium iodide (159c)

A mixture of 159b (680 mg, 2.08 mmol) in CH$_3$I (15 mL) was stirred at 80° C. for 5 h. After cooling to r.t., the mixture was concentrated under reduced pressure to afford 159c (711 mg, yield given) as a yellow solid. LC-MS (Method 3) t$_R$=1.36 min, m/z M$^+$=341.0.

Step 3. 7-Chloro-3-iodo-1,5-dimethyl-1H-pyrrolo[3,2-c]pyridin-4-(5H)-one (159d)

A solution of 159c (100 mg, 0.29 mmol) and Na$_2$CO$_3$ (93 mg, 0.88 mmol) in EtOH/H$_2$O (1 mL/1 mL) was stirred at 60° C. for 2 h. After cooling to r.t., the reaction mixture was diluted with H$_2$O (25 mL) and extracted with EtOAc (20 mL*2). The organic phase was concentrated under reduced pressure to afford 159d (43 mg, 99% yield) as a yellow solid. $^1$H NMR (400 MHz, DMSO-d$_6$) δ 7.59 (s, 1H), 7.31 (s, 1H), 3.96 (s, 3H), 3.39 (s, 3H).

Step 4. Tert-butyl (7-chloro-1,5-dimethyl-4-oxo-4,5-dihydro-1H-pyrrolo[3,2-c]pyridin-3-yl)carbamate (159e)

Compound 159e (208 mg, 61% yield), a brown solid, was synthesized by utilizing a similar preparative procedure of Step 4 in Example 1 with 159d (350 mg, 1.09 mmol) and tert-butyl carbamate (636 mg, 5.43 mmol) as starting materials. $^1$H NMR (400 MHz, DMSO-d$_6$) δ 8.40 (s, 1H), 7.54 (s, 1H), 7.21 (s, 1H), 3.92 (s, 3H), 3.41 (s, 3H), 1.47 (s, 9H).

Step 5. 3-Amino-7-chloro-1,5-dimethyl-1H-pyrrolo[3,2-c]pyridin-4-(5H)-one hydrochloride (159f)

Compound 159f (148 mg, 93% yield), a white solid, was synthesized by utilizing a similar preparative procedure of Step 5 in Example 1 with 159e (200 mg, 0.64 mmol) as the starting material. LC-MS (Method 3) t$_R$=0.85 min, m/z (M+H)$^+$=212.2.

Step 6. 6-Chloro-4-((7-chloro-1,5-dimethyl-4-oxo-4,5-dihydro-1H-pyrrolo[3,2-c]pyridin-3-yl)amino)-N-(methyl-d$_3$)nicotinamide (159g)

Compound 159g (130 mg, 94% yield), a brown solid, was synthesized by utilizing a similar preparative procedure of Step 5 in Example 50 with 159f (90 mg, 0.36 mmol) and 42b (75 mg, 0.36 mmol) as starting materials. LC-MS (Method 3) t$_R$=1.42 min, m/z (M+H)$^+$=383.1.

Step 7. 4-((7-Chloro-1,5-dimethyl-4-oxo-4,5-dihydro-1H-pyrrolo[3,2-c]pyridin-3-yl)amino)-6-((5-fluoropyridin-2-yl)amino)-N-(methyl-d$_3$)nicotinamide (159)

Compound 159 (13 mg, 21% yield), a white solid, was synthesized by utilizing a similar preparative procedure of Step 3 in Example 49 with 159g (100 mg, 0.26 mmol) and 5-fluoropyridin-2-amine (35 mg, 0.31 mmol) as starting materials. LC-MS (Method 1) t$_R$=3.37 min, m/z (M+H)$^+$=459.0. $^1$H NMR (400 MHz, DMSO-d$_6$) δ 11.03 (s, 1H), 9.77 (s, 1H), 8.40 (s, 1H), 8.27-8.26 (m, 2H), 7.81-7.78 (m, 1H), 7.69-7.63 (m, 2H), 7.57 (s, 1H), 7.26 (s, 1H), 4.04 (s, 3H), 3.43 (s, 3H).

Example 160

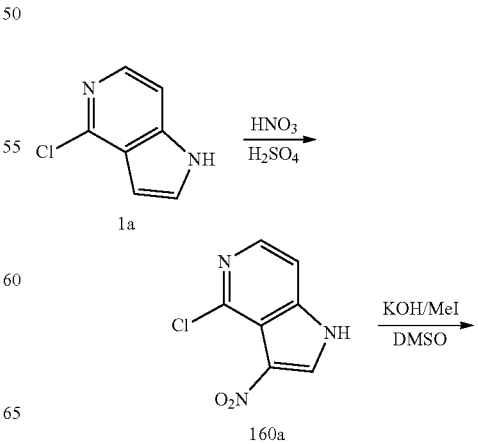

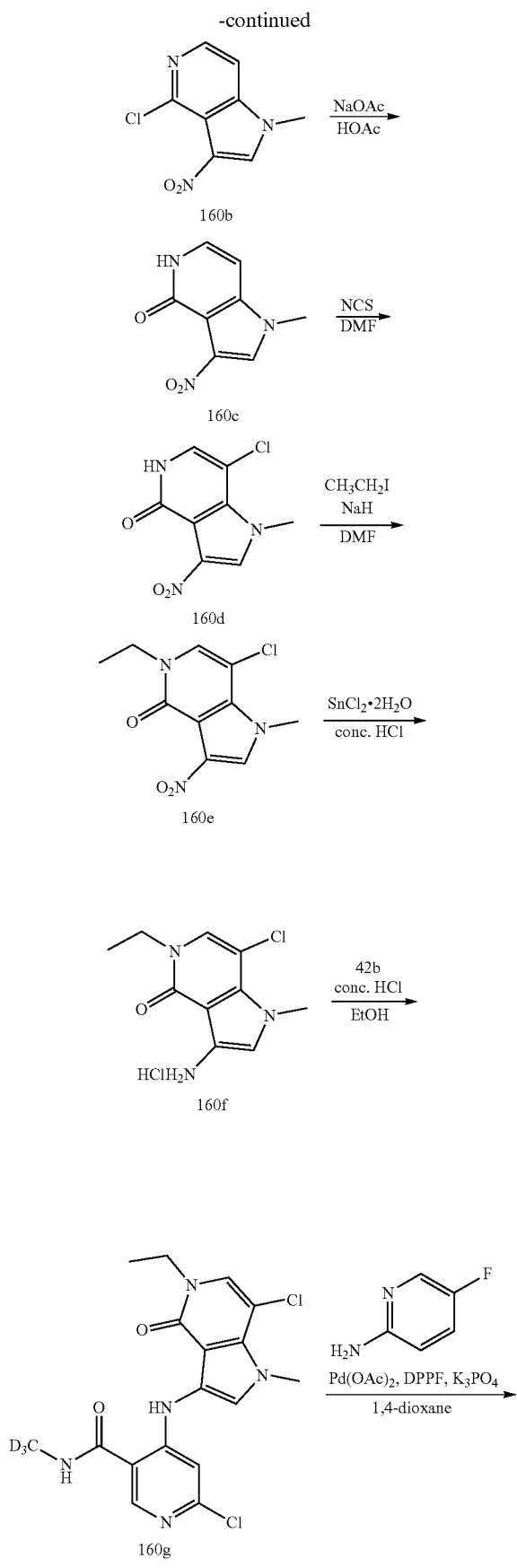

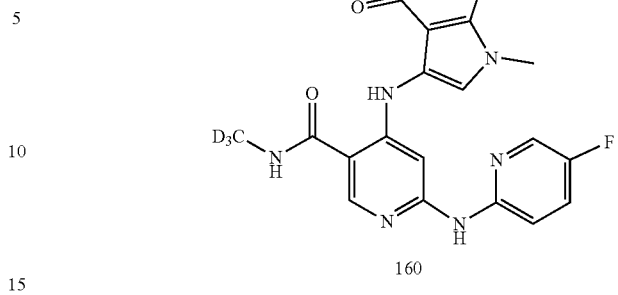

Step 1. 4-Chloro-3-nitro-1H-pyrrolo[3,2-c]pyridine (160a)

Compound 160a (11 g, 85% yield), a white solid, was synthesized by utilizing a similar preparative procedure of Step 1 in Example 123 with 1a (10 g, 65.5 mmol) as the starting material. $^1$H NMR (400 MHz, DMSO-$d_6$) δ 12.17 (brs, 1H), 8.80 (d, J=2.0 Hz, 1H), 8.21 (d, J=5.6 Hz, 1H), 7.60 (d, J=5.6 Hz, 1H).

Step 2. 4-Chloro-1-methyl-3-nitro-1H-pyrrolo[3,2-c]pyridine (160b)

Compound 160b (8.5 g, 72% yield), a yellow solid, was synthesized by utilizing a similar preparative procedure of Step 2 in Example 123 with 160a (11 g, 55.6 mmol) as the starting material. $^1$H NMR (400 MHz, DMSO-$d_6$) δ 8.87 (s, 1H), 6.28 (d, J=6.0 Hz, 1H), 7.77 (d, J=6.0 Hz, 1H), 3.92 (s, 3H).

Step 3. 1-Methyl-3-nitro-1H-pyrrolo[3,2-c]pyridin-4-(5H)-one (160c)

Compound 160c (712 mg, 78% yield), a yellow solid, was synthesized by utilizing a similar preparative procedure of Step 3 in Example 123 with 160b (1 g, 4.73 mmol) as the starting material. $^1$H NMR (400 MHz, DMSO-$d_6$) δ 12.24 (brs, 1H), 8.32 (s, 1H), 7.24 (d, J=7.2 Hz, 1H), 6.55 (d, J=7.2 Hz, 1H), 3.77 (s, 3H).

Step 4. 7-Chloro-1-methyl-3-nitro-1,5-dihydro-4H-pyrrolo[3,2-c]pyridin-4-one (160d)

A solution of 160c (3.25 g, 16.83 mmol) and NCS (2.47 g, 18.51 mmol) in DMF (40 mL) was stirred at 35° C. for 12 h. The reaction mixture was diluted with H$_2$O (120 mL) and filtered. The filter cake was dried under reduced pressure to afford 160d (2.9 g, 76% yield) as a yellow solid. $^1$H NMR (400 MHz, DMSO-$d_6$) δ 11.57 (brs, 1H), 8.29 (s, 1H), 7.40 (s, 1H), 4.05 (s, 3H).

Step 5. 7-Chloro-5-ethyl-1-methyl-3-nitro-1H-pyrrolo[3,2-c]pyridin-4-(5H)-one (160e)

Compound 160e (1.89 g, 84% yield), a yellow solid, was synthesized by utilizing a similar preparative procedure of Step 1 in Example 125 with 160d (2.0 g, 8.79 mmol) and iodoethane (5.48 g, 35.15 mmol) as starting materials. $^1$H NMR (400 MHz, DMSO-$d_6$) δ 8.38 (s, 1H), 7.87 (s, 1H), 4.05 (s, 3H), 3.93 (q, J=7.2 Hz, 2H), 1.21 (t, J=7.2 Hz, 3H).

Step 6. 3-Amino-7-chloro-5-ethyl-1-methyl-1H-pyrrolo[3,2-c]pyridin-4-(5H)-one hydrochloride (160f)

Compound 160f (1.85 g, 92% yield), a yellow solid, was synthesized by utilizing a similar preparative procedure of Step 5 in Example 123 with 160e (1.95 g, 7.63 mmol) as the starting material. LC-MS (Method 3) $t_R$=1.21 min, m/z (M+H)$^+$=226.1.

Step 7. 6-Chloro-4-((7-chloro-5-ethyl-1-methyl-4-oxo-4,5-dihydro-1H-pyrrolo[3,2-c]pyridin-3-yl)amino)-N-(methyl-d$_3$)nicotinamide (160g)

Compound 160g (1.84 g, 66% yield), a yellow solid, was synthesized by utilizing a similar preparative procedure of Step 1 in Example 98 with 160f (1.85 g, 7.06 mmol) and 42b (1.47 g, 7.06 mmol) as starting materials. LC-MS (Method 3) $t_R$=1.44 min, m/z (M+H)$^+$=397.1.

Step 8. 4-((7-Chloro-5-ethyl-1-methyl-4-oxo-4,5-dihydro-1H-pyrrolo[3,2-c]pyridin-3-yl)amino)-6-((5-fluoropyridin-2-yl)amino)-N-(methyl-d$_3$)nicotinamide (160)

A mixture of 160g (50 mg, 0.13 mmol), 5-fluoropyridin-2-amine (17 mg, 0.15 mmol) Pd(OAc)$_2$ (3 mg, 12.59 umol), DPPF (2 mg, 25.17 umol) and K$_3$PO$_4$ (27 mg, 0.13 mmol) in dioxane (1 mL) was stirred at 100° C. for 16 h. After cooling to r.t., the reaction mixture was concentrated and the residue was purified by Prep-HPLC (Method A) to afford 160 (15 mg, 25% yield) as a yellow solid. LC-MS (Method 1) $t_R$=3.10 min, m/z (M+H)$^+$=473.0. $^1$H NMR (400 MHz, DMSO-d$_6$) δ 11.04 (s, 1H), 9.77 (s, 1H), 8.40 (s, 1H), 8.27-8.25 (m, 2H), 7.80-7.77 (m, 1H), 7.69-7.63 (m, 2H), 7.59 (s, 1H), 7.26 (s, 1H), 4.04 (s, 3H), 3.94 (q, J=7.2 Hz, 2H), 1.22 (t, J=7.2 Hz, 3H).

Example 161

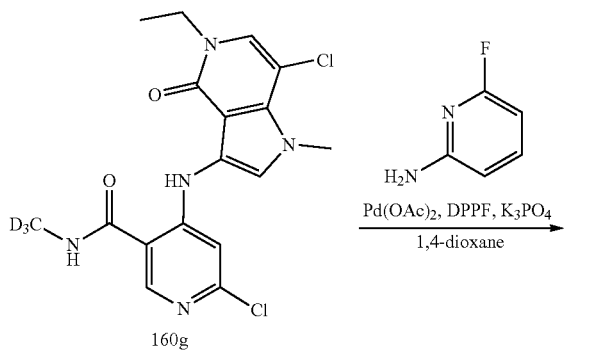

Step 1. 4-((7-Chloro-5-ethyl-1-methyl-4-oxo-4,5-dihydro-1H-pyrrolo[3,2-c]pyridin-3-yl)amino)-6-((6-fluoropyridin-2-yl)amino)-N-(methyl-d$_3$)nicotinamide (161)

Compound 161 (12 mg, 10% yield), a brown solid, was synthesized by utilizing a similar preparative procedure of Step 8 in Example 160 with 160g (100 mg, 0.25 mmol) and 6-fluoropyridin-2-amine (34 mg, 0.30 mmol) as starting materials. LC-MS (Method 1) $t_R$=3.63 min, m/z (M+H)$^+$=473.0. $^1$H NMR (400 MHz, DMSO-d$_6$) 11.14 (s, 1H), 10.02 (s, 1H), 8.42 (s, 1H), 8.31 (s, 1H), 7.83 (d, J=8.4 Hz, 1H), 7.80 (s, 1H), 7.59 (s, 1H), 7.44 (d, J=6.8 Hz, 1H), 7.32 (s, 1H), 6.60 (dd, J=2.0, 8.0 Hz, 1H), 4.02 (s, 3H), 3.95 (q, J=7.2 Hz, 2H), 1.22 (t, J=7.2 Hz, 3H).

Example 162

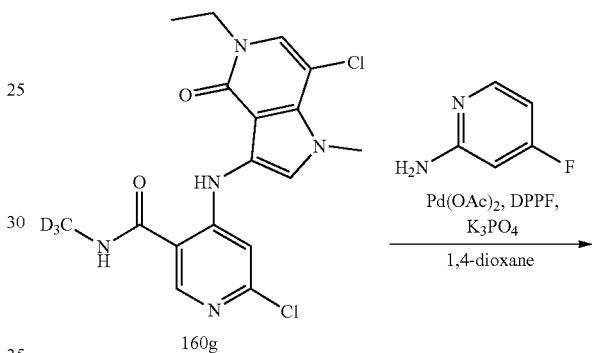

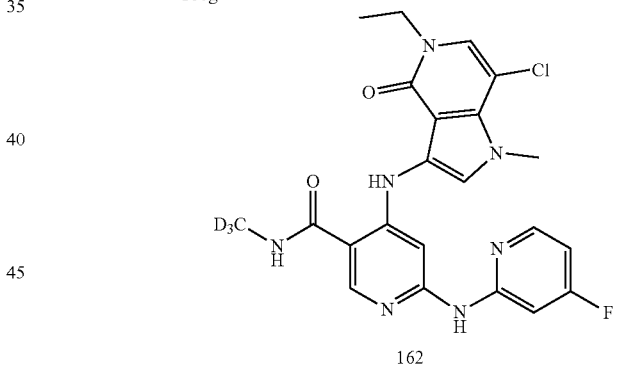

Step 1. 4-((7-Chloro-5-ethyl-1-methyl-4-oxo-4,5-dihydro-1H-pyrrolo[3,2-c]pyridin-3-yl)amino)-6-((4-fluoropyridin-2-yl)amino)-N-(methyl-d$_3$)nicotinamide (162)

Compound 162 (25 mg, 21% yield), a brown solid, was synthesized by utilizing a similar preparative procedure of Step 8 in Example 160 with 160g (100 mg, 0.25 mmol) and 4-fluoropyridin-2-amine (37 mg, 0.33 mmol) as starting materials. LC-MS (Method 1) $t_R$=3.08 min, m/z (M+H)$^+$=473.0. $^1$H NMR (400 MHz, DMSO-d$_6$) δ 11.05 (s, 1H), 9.95 (s, 1H), 8.42 (s, 1H), 8.32-8.28 (m, 2H), 7.73 (d, J=12.4 Hz, 1H), 7.60-7.58 (m, 2H), 7.29 (s, 1H), 6.85-6.82 (m, 1H), 4.03 (s, 3H), 3.93 (q, J=6.8 Hz, 2H), 1.22 (t, J=6.8 Hz, 3H).

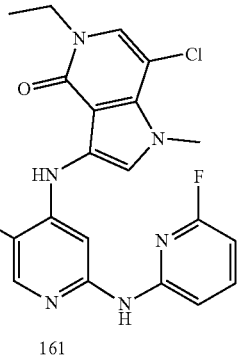

Example 163

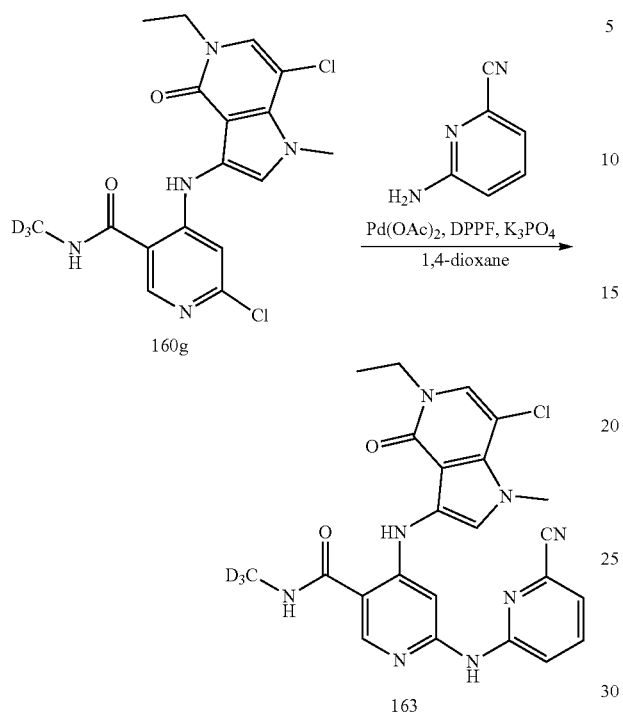

Step 1. 4-((7-Chloro-5-ethyl-1-methyl-4-oxo-4,5-dihydro-1H-pyrrolo[3,2-c]pyridin-3-yl)amino)-6-((6-cyanopyridin-2-yl)amino)-N-(methyl-d₃)nicotinamide (163)

Compound 163 (1.5 mg, 1% yield), a white solid, was synthesized by utilizing a similar preparative procedure of Step 8 in Example 160 with 160g (100 mg, 0.25 mmol) and 6-aminopicolinonitrile (36 mg, 0.30 mmol) as starting materials. LC-MS (Method 1) $t_R$=3.50 min, m/z (M+H)⁺=480.1. ¹H NMR (400 MHz, DMSO-d₆) δ 11.05 (s, 1H), 10.15 (s, 1H), 8.42 (s, 1H), 8.33 (s, 1H), 7.93-7.84 (m, 2H), 7.73 (s, 1H), 7.58 (s, 1H), 7.50 (d, J=7.6 Hz, 1H), 7.24 (s, 1H), 4.00 (s, 3H), 3.91 (q, J=7.6 Hz, 2H), 1.21 (t, J=7.6 Hz, 3H).

Example 164

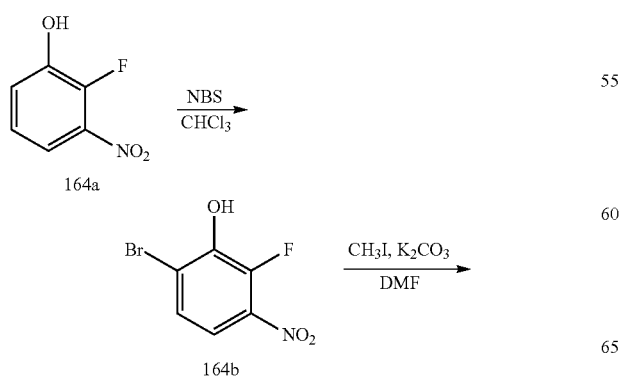

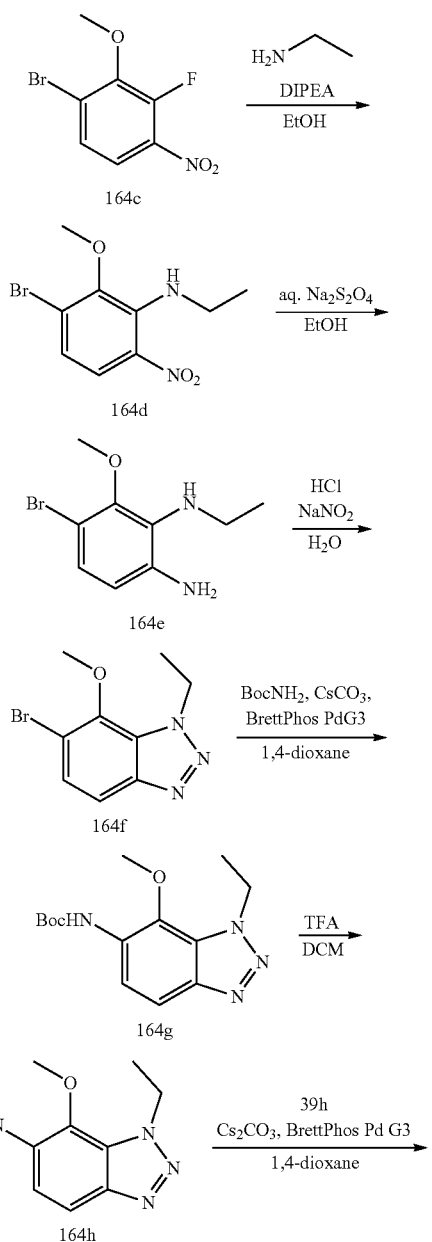

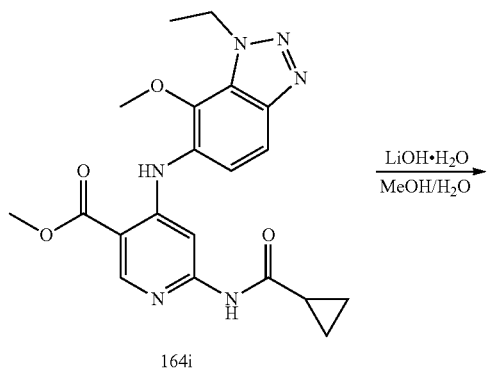

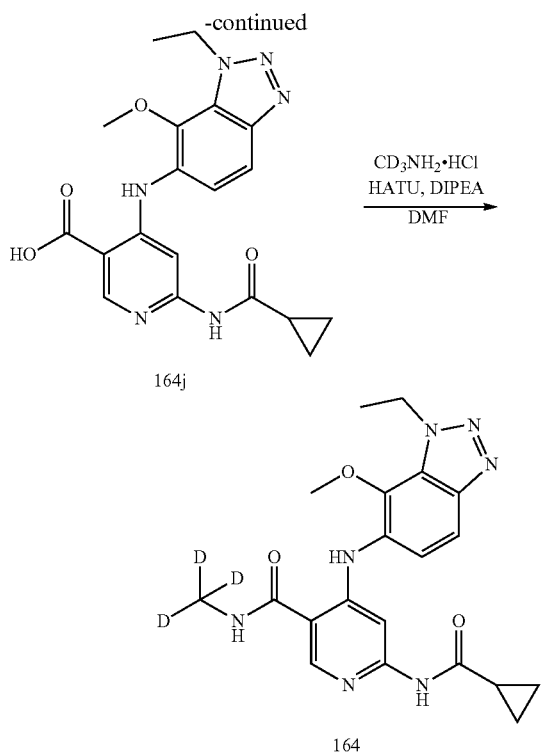

Step 1. 6-Bromo-2-fluoro-3-nitro-phenol (164b)

A mixture of 164a (300 mg, 1.91 mmol), NBS (340 mg, 1.91 mmol) in CHCl$_3$ (5 mL) was stirred at 20° C. for 12 h. A yellow solution was formed. The reaction mixture was diluted with water (40 mL) and extracted with DCM (30 mL*3). The combined organic layer was washed with brine (50 mL*2), dried over anhydrous Na$_2$SO$_4$, filtered and concentrated. The residue was purified by column chromatograph (EA in PE is 10-30%) to give 164b (300 mg, 48% yield) as a yellow solid. LC-MS (Method 4) t$_R$=3.44 min, m/z (M+H)$^+$=235.9. $^1$H NMR (400 MHz, DMSO-d$_6$) δ 11.60 (brs, 1H), 7.60 (dd, J=9.2 Hz, 2.0 Hz, 1H), 7.52 (dd, J=9.2 Hz, 6.8 Hz, 1H).

Step 2. 1-Bromo-3-fluoro-2-methoxy-4-nitro-benzene (164c)

A mixture of 164b (1.10 g, 4.66 mmol), CH$_3$I (860 mg, 6.06 mmol) and K$_2$CO$_3$ (837 mg, 6.06 mmol) in DMF (15 mL) was stirred at 20° C. for 3 h. A yellow suspension was formed. The reaction mixture was diluted with water (40 mL) and extracted with EtOAc (40 mL*3). The combined organic layer was washed with water (40 mL*3), brine (40 mL*2), dried over anhydrous Na$_2$SO$_4$, filtered and concentrated. The residue was purified by flash chromatography (EtOAc in PE is 0-10%) to give 164c (746 mg, 64% yield) as a yellow solid. LC-MS (Method 4) t$_R$=5.03 min, m/z [M−H]$^−$=248.0. $^1$H NMR (400 MHz, DMSO-d$_6$) δ 7.68 (dd, J=9.2 Hz, 7.2 Hz, 1H), 7.48 (dd, J=9.2 Hz, 2.0 Hz, 1H), 4.04 (d, J=1.6 Hz, 3H).

Step 3. 3-Bromo-N-ethyl-2-methoxy-6-nitro-aniline (164d)

A mixture of 164c (550 mg, 2.20 mmol), DIPEA (569 mg, 4.40 mmol) and ethanamine (1.32 mL, 2.64 mmol, 2.0 M in THF) in ethanol (10 mL) was stirred at 20° C. for 12 h. A white suspension was formed. The reaction mixture was diluted with water (40 mL) and extracted with EtOAc (40 mL*3). The combined organic layer was washed with water (40 mL*3) and brine (40 mL*2), dried over anhydrous Na$_2$SO$_4$, filtered and concentrated. The residue was purified by flash chromatography (EtOAc in PE is 0-10%) to give 164d (600 mg, 99% yield) as an orange oil. LCMS (Method 4) t$_R$=4.82 min, m/z (M+H)$^+$=275.0.

Step 4. 5-Bromo-N$^1$-ethyl-6-methoxybenzene-1,2-diamine (164e)

To a solution of 164d (600 mg, 2.18 mmol) in ethanol (10 mL), was added aq. Na$_2$S$_2$O 4 (8.55 mL, 8.55 mmol, 1 M). The resulting mixture was stirred at 80° C. under N$_2$ atmosphere for 10 min. A white suspension was formed. The reaction mixture was diluted with water (50 mL) and extracted with EtOAc (30 mL*3). The combined organic layer was washed with brine (50 mL*2), dried over anhydrous Na$_2$SO$_4$, filtered and concentrated. The residue was purified by column chromatograph (MeOH in DCM is 0-10%) to give 164e (248 mg, 35% yield) as a brown solid. LCMS (Method 4) t$_R$=2.23 min, m/z (M+H)$^+$=247.0.

Step 5. 6-Bromo-1-ethyl-7-methoxy-benzotriazole (164f)

To a mixture of NaNO$_2$ (84 mg, 1.22 mmol) in HCl (0.2 M, 12.24 mL) was added 164e (200 mg, 0.816 mmol) in HCl (0.2 M, 12 mL) at 0° C. The resulting mixture was stirred at 0-5° C. for 2 h. A brown suspension was formed. The reaction mixture was diluted with water (30 mL), adjusted pH to 12 with NaOH (2 M), and extracted with EtOAc (40 mL*3). The combined organic layer was washed with water (40 mL*3), brine (40 mL*2), dried over anhydrous Na$_2$SO$_4$, filtered and concentrated. The residue was purified by flash chromatography (EtOAc in PE is 10-30%) to give 164f (164 mg, 78% yield) as a yellow oil. LCMS (Method 4) t$_R$=3.94 min, m/z (M+H)$^+$=257.0. $^1$H NMR (400 MHz, CDCl$_3$) δ 7.67 (d, J=8.8 Hz, 1H), 7.45 (d, J=8.8 Hz, 1H), 4.81 (q, J=7.2 Hz, 2H), 4.04 (s, 3H), 1.63 (t, J=7.2 Hz, 3H).

Step 6. Tert-butyl N-(3-ethyl-4-methoxy-benzotriazol-5-yl) carbamate (164g)

A solution of 164f (150 mg, 0.585 mmol), tert-butyl carbamate (103 mg, 0.878 mmol), BrettPhos Pd G3 (53 mg, 0.058 mmol) and Cs$_2$CO$_3$ (477 mg, 1.46 mmol) in dioxane (1 mL) was degassed and purged with nitrogen for 3 times. The resulting mixture was stirred at 100° C. under N$_2$ atmosphere for 12 h. A black suspension was formed. The reaction mixture was diluted with EtOAc (50 mL) and filtered through a pad of celite. The filtrate was concentrated to give a yellow oil. The residue was purified by flash chromatography (EtOAc in PE is 10-50%) to give 164g (170 mg, 99% yield) as a yellow gum. LCMS (Method 4) t$_R$=3.95 min, m/z (M+H)$^+$=293.1.

Step 7. 3-Ethyl-4-methoxy-benzotriazol-5-amine (164h)

To a mixture of 164g (170 mg, 0.581 mmol) in DCM (3 mL) was added TFA (740 mg, 6.49 mmol, 0.5 mL) at 0° C. The resulting mixture was stirred at 0-10° C. for 1 h. A yellow solution was formed. The reaction mixture was concentrated under reduced pressure, diluted with H$_2$O (20 mL) basified by aq Na₂CO₃, extracted with EtOAc (20 mL*3) washed with brine (20 mL), dried over Na₂SO₄, concentrated and purified by column chromatograph (EA in PE is 10-30%) to give 164h (110 mg, 98% yield) as a yellow solid. LCMS (Method 4) $t_R$=2.08 min, m/z (M+H)⁺=193.0. ¹H NMR (400 MHz, CDCl₃) δ 7.59 (d, J=8.8 Hz, 1H), 6.81 (d, J=8.8 Hz, 1H), 4.74 (q, J=7.2 Hz, 2H), 4.00 (brs, 2H), 3.88 (s, 3H), 1.61 (t, J=7.2 Hz, 3H).

Step 8. Methyl 6-(cyclopropanecarbonylamino)-4-[(3-ethyl-4-methoxy-benzotriazol-5-yl)amino]pyridine-3-carboxylate (164i)

A mixture of 164h (60 mg, 0.312 mmol), 39h (79 mg, 0.312 mmol), BrettPhos (33 mg, 0.062 mmol), Cs₂CO₃ (254 mg, 0.78 mmol) and BrettPhos Pd G3 (28 mg, 0.031 mmol) in dioxane (3 mL) was stirred at 100° C. for 12 h. A brown solution was formed. The reaction mixture was diluted with EtOAc (50 mL) and filtered through a pad of celite. The filtrate was concentrated and purified by Prep-TLC (DCM/MeOH=10/1) to give 164i (110 mg, 85% yield) as a yellow solid. LCMS (Method 4) $t_R$=3.36 min, m/z (M+H)⁺=411.2.

Step 9. 6-(Cyclopropanecarbonylamino)-4-[(3-ethyl-4-methoxy-benzotriazol-5-yl)amino]pyridine-3-carboxylic acid (164j)

A mixture of 164i (110 mg, 0.268 mmol) and LiOH·H₂O (34 mg, 0.804 mmol) in co-solvent of MeOH (6 mL) and water (2 mL) was stirred at 40° C. for 12 h. A yellow solution was formed. The mixture was adjusted pH=2 with 2N HCl, The reaction mixture was concentrated and dried in vacuo to give 164j (106 mg, crude) as a yellow solid, which was used for the next step directly without further purification. LCMS (Method 4) $t_R$=2.51 min, m/z (M+H)⁺=397.1.

Step 10. 6-(Cyclopropanecarbonylamino)-4-[(3-ethyl-4-methoxy-benzotriazol-5-yl)amino]-N-(trideuteriomethyl)pyridine-3-carboxamide (164)

A mixture of methan-d₃-amine hydrochloride (19 mg, 0.268 mmol), HATU (203 mg, 0.535 mmol) and 164j (106 mg, 0.267 mmol), DIPEA (104 mg, 0.802 mmol, 0.14 mL) in DMF (3 mL) was stirred at 0° C. for 1 h. A white suspension was formed. The reaction mixture was diluted with water (40 mL) and extracted with EtOAc (40 mL*3). The combined organic layer was washed with water (40 mL*3) and brine (40 mL*2), dried over anhydrous Na₂SO₄, filtered and concentrated. The residue was purified by Prep-HPLC (Method E) to give 164 (1.8 mg, 1.6% yield) as a white solid. LCMS (Method 4) $t_R$=2.62 min, m/z (M+H)⁺=413.2. ¹H NMR (400 MHz, CDCl₃) δ 10.32 (s, 1H), 8.42 (s, 1H), 8.25 (s, 1H), 7.91 (s, 1H), 7.79 (d, J=8.8 Hz, 1H), 7.36 (d, J=8.8 Hz, 1H), 6.20 (s, 1H), 4.81 (q, J=7.2 Hz, 2H), 3.90 (s, 3H), 1.60 (t, J=7.2 Hz, 3H), 1.58-1.48 (m, 1H), 1.04-0.98 (m, 2H), 0.88-0.80 (m, 2H).

Example 165

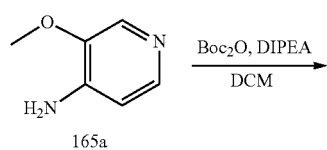

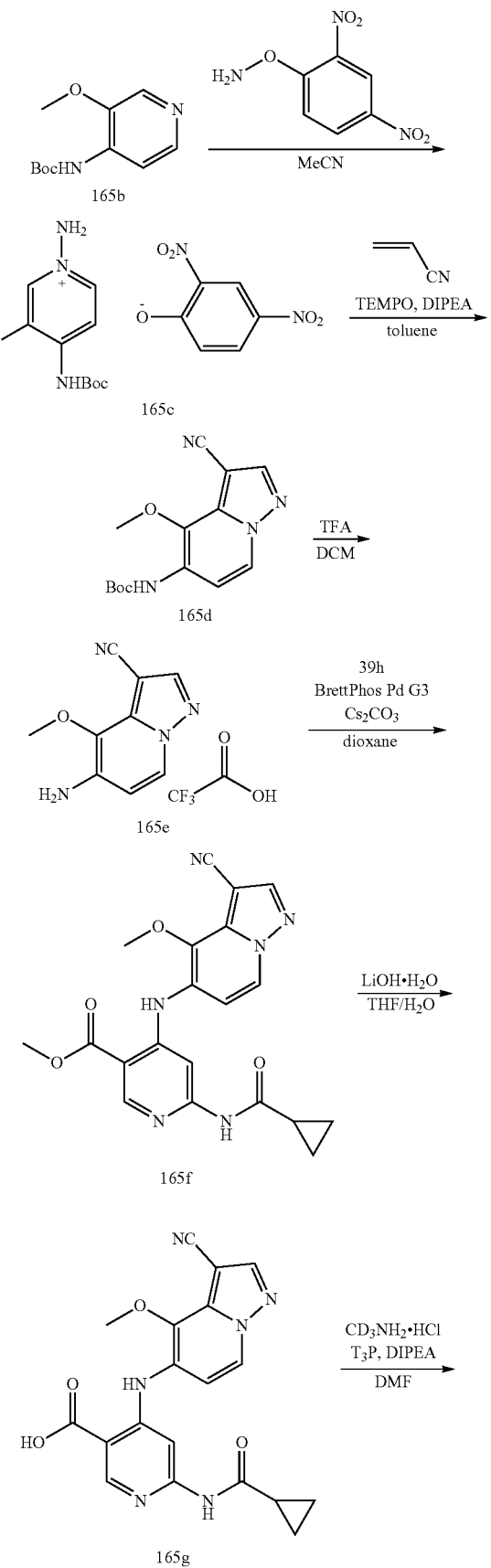

505

-continued

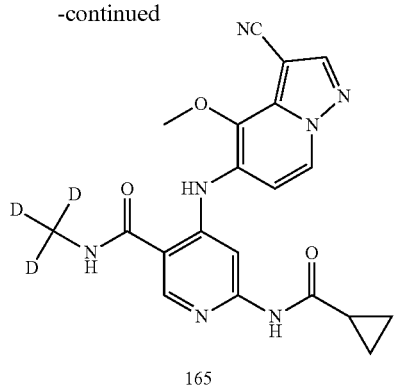

165

Step 1. Tert-butyl (3-methoxypyridin-4-yl)carbamate (165b)

A solution of 165a (800 mg, 6.44 mmol), Boc₂O (1.83 g, 8.38 mmol, 1.9 mL) and DIPEA (1.67 g, 12.89 mmol, 2.24 mL) in DCM (15 mL) was stirred at 20° C. for 12 h. A yellow solution was formed. The reaction mixture was concentrated and purified by flash chromatography (EtOAc in PE is 10-50%) to give 165b (1.45 g, yield given) as a white solid. LC-MS (Method 4) $t_R$=1.92 min, m/z (M+H)⁺=225.1.

Step 2. 1-Amino-4-((tert-butoxycarbonyl)amino)-3-methoxypyridin-1-ium 2,4-dinitrophenolate (165c)

A mixture of 165b (1.45 g, 6.47 mmol) and O-(2,4-dinitrophenyl) hydroxylamine (1.42 g, 7.11 mmol) in MeCN (50 mL) was stirred at 50° C. for 16 h. A yellow solution was formed. The reaction was concentrated to give 165c (2.73 g, crude) as a yellow solid, which was used for the next step directly without further purification. LC-MS (Method 4) $t_R$=1.66 min, m/z M⁺=240.1.

Step 3. Tert-butyl (3-cyano-4-methoxypyrazolo[1,5-a]pyridin-5-yl) carbamate (165d)

A mixture of 165e (88 mg, 0.208 mmol), acrylonitrile (27 mg, 0.312 mmol), TEMPO (40 mg, 0.25 mmol) and DIPEA (54 mg, 0.416 mmol, 73 μL) in toluene (1 mL) was stirred at 40° C. for 12 h. A black solution was formed. The reaction mixture was diluted with water (30 mL) and extracted with EtOAc (30 mL*2). The combined organic layer was washed with brine (40 mL*2), dried over anhydrous Na₂SO₄, filtered and concentrated. The residue was purified by column chromatograph (EtOAc in PE is 10-50%) to give 165d (30 mg, 50% yield over 2 steps) as a yellow solid. LC-MS (Method 4) $t_R$=4.02 min, m/z (M+H)⁺=289.1. ¹H NMR (400 MHz, CDCl₃): δ 8.30 (d, J=7.2 Hz, 1H), 8.14 (s, 1H), 8.08 (d, J=7.6 Hz, 1H), 7.22 (brs, 1H), 4.04 (s, 3H), 1.56 (s, 9H).

Step 4. 5-Amino-4-methoxypyrazolo[1,5-a]pyridine-3-carbonitrile 2,2,2-trifluoroacetate (165e)

To a mixture of 165d (30 mg, 0.104 mmol) in DCM (3 mL) was added TFA (1.49 g, 13.1 mmol, 1 mL) at 0° C. The resulting mixture was stirred at 20° C. for 1 h. A yellow solution was formed. The reaction mixture was concentrated and dried in vacuo to give 165e (20 mg, crude) as a yellow solid. LC-MS (Method 4) $t_R$=1.97 min, m/z (M+H)⁺=189.0.

Step 5. Methyl 4-((3-cyano-4-methoxypyrazolo[1,5-a]pyridin-5-yl)amino)-6-(cyclopropanecarboxamido) nicotinate (165f)

A mixture of 165e (20 mg, 0.106 mmol), 39h (54 mg, 0.212 mmol), BrettPhos (11 mg, 0.021 mmol), Cs₂CO₃ (104 mg, 0.319 mmol) and BrettPhos Pd G3 (10 mg, 0.011 mmol) in dioxane (3 mL) was stirred at 100° C. for 12 h. A brown solution was formed. The reaction mixture was diluted with EtOAc (50 mL) and filtered through a pad of celite. The filtrate was concentrated and purified by Prep-TLC (DCM/MeOH=10/1) to give 165f (50 mg, crude) as a yellow solid. LC-MS (Method 4) $t_R$=3.54 min, m/z (M+H)⁺=407.2. ¹H NMR (400 MHz, DMSO-d₆): δ 11.08 (s, 1H), 10.05 (s, 1H), 8.83 (d, J=7.2 Hz, 1H), 8.77 (s, 1H), 8.62 (s, 1H), 8.01 (s, 1H), 7.34 (d, J=7.6 Hz, 1H), 3.90 (s, 3H), 2.05-1.94 (m, 1H), 0.85-0.72 (m, 4H).

Step 6. 4-((3-Cyano-4-methoxypyrazolo[1,5-a]pyridin-5-yl)amino)-6-(cyclopropanecarboxamido)nicotinic acid (165g)

A mixture of 165f (40 mg, 0.098 mmol) and LiOH·H₂O (9 mg, 0.208 mmol) in co-solvent of THF (3 mL) and water (1 mL) was stirred at 40° C. for 12 h. A yellow solution was formed. The reaction mixture was adjusted pH=2 with 1 N HCl and concentrated and dried in vacuo to 165g (40 mg, yield given) as a yellow solid, which was used for the next step directly without further purification. LC-MS (Method 4) $t_R$=2.35 min, m/z (M+H)⁺=393.2.

Step 7. 4-((3-Cyano-4-methoxypyrazolo[1,5-a]pyridin-5-yl)amino)-6-(cyclopropanecarboxamido)-N-(methyl-d₃)nicotinamide (165)

A mixture of trideuteriomethanamine hydrochloride (13 mg, 0.184 mmol), 165g (36 mg, 0.092 mmol), DIPEA (36 mg, 0.275 mmol) and T₃P (117 mg, 0.184 mmol, 130 uL, 50% in EtOAc) in DMF (3 mL) was stirred at 20° C. for 12 h. A yellow solution was formed. The reaction mixture was filtered and purified by Prep-HPLC (Method E) to give 165 (4.3 mg, 11.5% yield) as a white solid. LC-MS (Method 4) $t_R$=2.74 min, m/z (M+H)⁺=409.2. ¹H NMR (400 MHz, DMSO-d₆) δ 11.01 (s, 1H), 10.90 (s, 1H), 8.75 (d, J=7.6 Hz, 1H), 8.70 (s, 1H), 8.56 (s, 1H), 8.53 (s, 1H), 8.03 (s, 1H), 7.28 (d, J=7.2 Hz, 1H), 3.87 (s, 3H), 2.01-1.93 (m, 1H), 0.80-0.72 (m, 4H).

Example 166

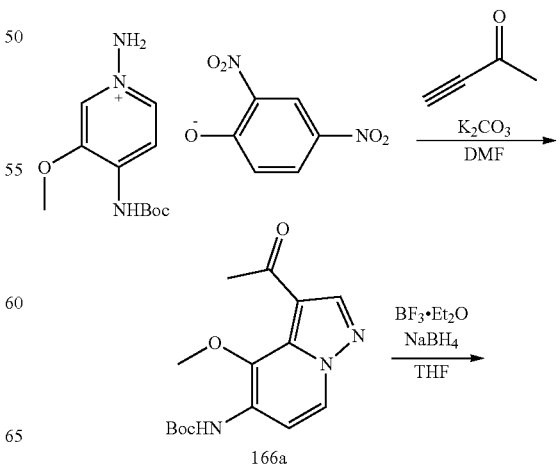

166a

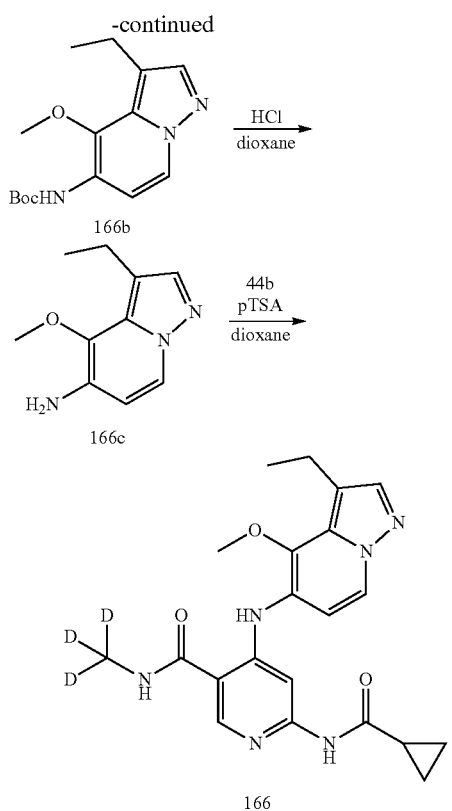

The mixture was stirred at r.t. for 16 h. The mixture was concentrated to dryness. The residue was diluted with H₂O (20 mL), adjusted pH to 7-9 with aq Na$_2$CO$_3$, and extracted with EtOAc (20 mL*3). The organic layers were washed with aq Na$_2$CO$_3$ (20 mL) and brine (20 mL) and separated. The solution was dried over Na$_2$SO$_4$ and filtered. The filtrate was concentrated to give the title compound 166c (80 mg, 93% yield) as a brown solid. LC-MS (Method 4) $t_R$=2.75 min, m/z (M+H)$^+$=192.1.

Step 4. 6-(Cyclopropanecarboxamido)-4-((3-ethyl-4-methoxypyrazolo[1,5-a]pyridin-5-yl)amino)-N-(methyl-d$_3$)nicotinamide (166)

A mixture of 166c (40 mg, 0.21 mmol), 44b (54 mg, 0.21 mmol), pTSA (36 mg, 0.21 mmol) in dioxane (2 mL) was stirred at 100° C. for 15 h. The mixture was concentrated and purified by Prep-HPLC (Method E) to get the compound 166 (20 mg, 23% yield) as an off-white solid. LC-MS (Method 4) $t_R$=2.96 min, m/z (M+H)$^+$=412.3. $^1$H NMR (400 MHz, DMSO-d6): δ 10.78 (s, 1H), 10.51 (s, 1H), 8.63 (s, 1H), 8.53 (s, 1H), 8.42 (d, J=7.6 Hz, 1H), 7.82 (s, 1H), 7.80 (s, 1H), 6.79 (d, J=7.6 Hz, 1H), 3.77 (s, 3H), 2.81 (q, J=7.6 Hz, 2H), 1.97-1.95 (m, 1H), 1.25 (t, J=7.6 Hz, 3H), 0.76-0.74 (m, 4H).

Example 167

Step 1. Tert-butyl (3-acetyl-4-methoxypyrazolo[1,5-a]pyridin-5-yl)carbamate (166a)

To a solution of 165c (969 mg, 2.29 mmol) in DMF (10 mL) was added K$_2$CO$_3$ (632 mg, 4.58 mmol) and but-3-yn-2-one (187 mg, 2.75 mmol) at r.t. Then the mixture was stirred at r.t. for 2 h. The mixture was diluted with H$_2$O (30 mL), extracted with EtOAc (20 mL*3), washed with brine (20 mL), dried over Na$_2$SO$_4$, concentrated and purified by flash chromatography (PE/EA=10/1 to 1/1) to get the compound 166a (180 mg, 25% yield) as a yellow oil and tert-butyl (3-acetyl-6-methoxypyrazolo[1,5-a]pyridin-5-yl) carbamate (290 mg, 41% yield) as a yellow solid. LC-MS (Method 4) $t_R$=3.59 min, m/z (M+H)$^+$=306.2. $^1$H NMR (400 MHz, CDCl$_3$) δ 8.31 (s, 1H), 8.30 (dd, J=7.6 Hz, J=0.4 Hz, 1H), 8.07 (d, J=7.6 Hz, 1H), 7.39 (s, 1H), 3.84 (s, 3H), 2.59 (s, 3H), 1.55 (s, 9H).

Step 2. Tert-butyl (3-ethyl-4-methoxypyrazolo[1,5-a]pyridin-5-yl)carbamate (166b)

To a solution of 166b (140 mg, 0.46 mmol) in THF (2 mL) was added BF$_3$·Et$_2$O (130 mg, 0.92 mmol) and NaBH$_4$ (17 mg, 0.46 mmol) at an ice-bath, then the mixture was stirred at r.t. for 2 h. The mixture was quenched with MeOH (0.5 mL) and concentrated to get the crude product 166b (130 mg, 97% yield) as a yellow oil. LC-MS (Method 4) $t_R$=4.45 min, m/z (M+H)$^+$=292.2.

Step 3. 3-Ethyl-4-methoxypyrazolo[1,5-a]pyridin-5-amine (166c)

To a solution of 166b (130 mg, 0.45 mmol) in dioxane (2 mL) was added a solution of HCl (g) in dioxane (4 M, 2 mL).

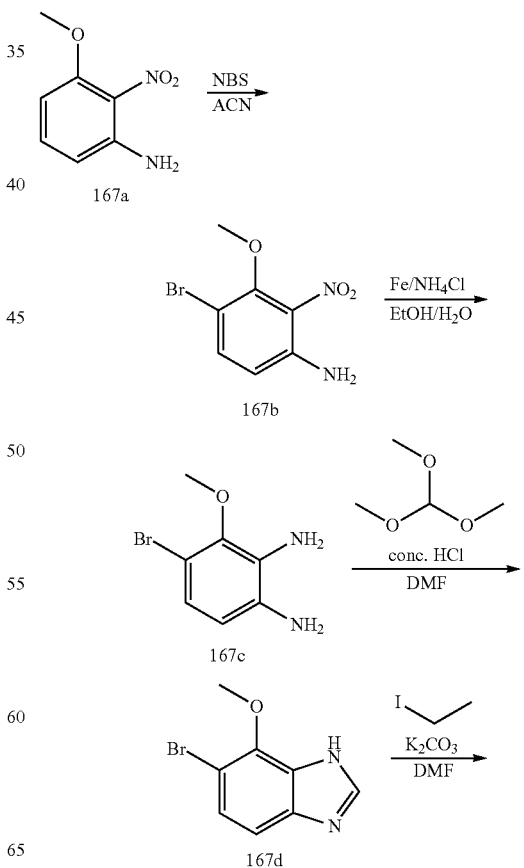

-continued

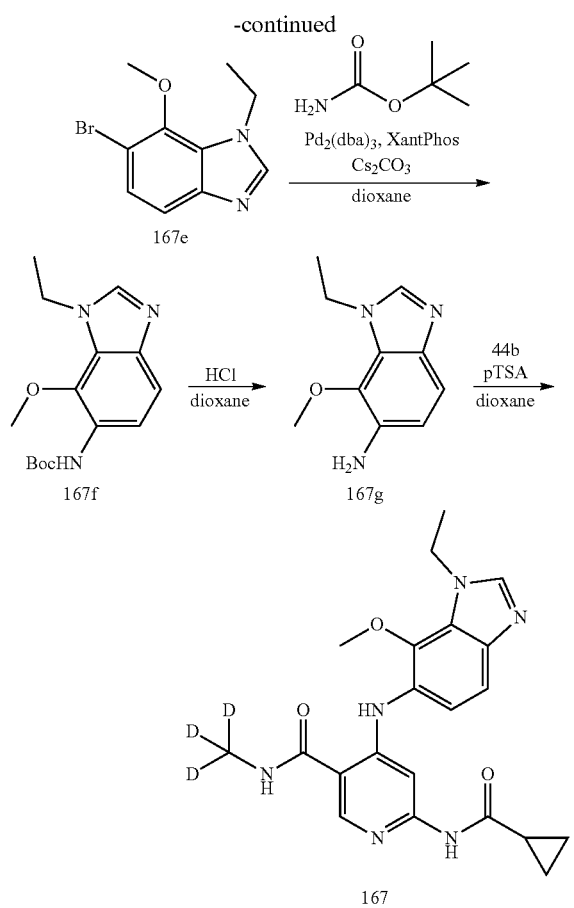

Step 1. 4-Bromo-3-methoxy-2-nitroaniline (167b)

To a solution of 167a (4.0 g, 23.79 mmol) in ACN (60 mL) was added NBS (4.23 g, 23.79 mmol), then the mixture was stirred at r.t. for 4 h. The mixture was diluted with H₂O (100 mL), extracted with EtOAc (50 mL*3), washed with brine (50 mL), dried over Na₂SO₄, concentrated and purified by flash chromatpraphy (PE/EA=20/1 to 1/1) to get the compound 167b (590 mg, 10% yield) and 6-bromo-3-methoxy-2-nitroaniline (3.5 g, 14.17 mmol, 60% yield) both as a yellow solid. LC-MS (Method 4) $t_R$=3.82 min, m/z (M+H)⁺=247.0. ¹H NMR (400 MHz, CDCl₃) δ 7.38 (d, J=8.8 Hz, 1H), 6.48 (d, J=8.8 Hz, 1H), 4.99 (s, 2H), 3.98 (s, 3H).

Step 2. 4-Bromo-3-methoxybenzene-1,2-diamine (167c)

To a solution of 167b (580 mg, 2.35 mmol) in H₂O (2 mL) and EtOH (10 mL) was added Fe (656 mg, 11.74 mmol) and NH₄Cl (628 mg, 11.74 mmol), then the mixture was stirred at 80° C. for 4 h. The mixture was diluted with H₂O (30 mL), extracted with EtOAc (30 mL*3), washed with brine (50 mL), dried over Na₂SO₄, concentrated to get the crude product 167c (500 mg, 98% yield) as a yellow solid. LC-MS (Method 4) $t_R$=2.22 min, m/z (M+H)⁺=217.0.

Step 3. 6-Bromo-7-methoxy-1H-benzo[d]imidazole (167d)

To a solution of 167c (400 mg, 1.85 mmol) in DMF (5 mL) was added trimethoxymethane (980 mg, 9.24 mmol, 1.01 mL) and conc. HCl (0.1 mL) and the mixture was stirred at 100° C. for 30 min. The mixture was concentrated and diluted with H₂O (30 mL), adjusted pH to 7-9, extracted with EtOAc (30 mL*3), washed with brine (30 mL), dried over Na₂SO₄, concentrated to get the compound 167d (300 mg, 71% yield) as a yellow solid. LC-MS (Method 4) $t_R$=3.26 min, m/z (M+H)⁺=227.0.

Step 4. 6-Bromo-1-ethyl-7-methoxy-1H-benzo[d]imidazole (167e)

To a solution of 167d (300 mg, 1.32 mmol) in DMF (3 mL) was added K₂CO₃ (365 mg, 2.64 mmol) and iodoethane (268 mg, 1.72 mmol), then the mixture was stirred at r.t. for 2 h. The mixture was diluted with H₂O (20 mL), extracted with EtOAc (15 mL*3), washed with brine (20 mL), dried over Na₂SO₄, concentrated and purified by flash chromatography (PE/EA=20/1 to 1/2) to get the compound 167e (80 mg, 24% yield) and 5-bromo-1-ethyl-4-methoxy-1H-benzo[d]imidazole (240 mg, 71% yield) both as a yellow oil. LC-MS (Method 4) $t_R$=2.74 min, m/z (M+H)⁺=255.0. ¹H NMR (400 MHz, CDCl₃) δ 7.83 (s, 1H), 7.43 (d, J=8.8 Hz, 1H), 7.38 (d, J=8.8 Hz, 1H), 4.40 (q, J=7.2 Hz, 2H), 4.00 (s, 3H), 1.54 (t, J=7.2 Hz, 3H).

Step 5. Tert-butyl (1-ethyl-7-methoxy-1H-benzo[d]imidazol-6-yl)carbamate (167f)

A mixture of 167e (80 mg, 0.31 mmol), tert-butyl carbamate (74 mg, 0.63 mmol), Pd₂(dba)₃ (29 mg, 0.03 mmol), XantPhos (37 mg, 0.62 mmol), Cs₂CO₃ (255 mg, 0.78 mmol) in dioxane (1 mL) was stirred at 100° C. for 16 h under N₂. The mixture was diluted with H₂O (10 mL), extracted with EtOAc (10 mL*3), washed with brine (20 mL), dried over Na₂SO₄, concentrated and purified by flash chromatography (PE/EA=10/1 to 1/2) to get the compound 167f (40 mg, 44% yield) as a yellow solid. LC-MS (Method 4) $t_R$=3.98 min, m/z (M+H)⁺=292.2.

Step 6. 1-Ethyl-7-methoxy-1H-benzo[d]imidazol-6-amine (167g)

To a solution of 167f (40 mg, 0.14 mmol) in dioxane (1 mL) was added HCl/dioxane (4 M, 1 mL). The mixture was stirred at r.t. for 2 h. The mixture was concentrated to dryness. The residue was diluted with H₂O (10 mL), adjusted pH to 7-9 with aq Na₂CO₃, and extracted with EtOAc (10 mL*3). The organic layers were washed with aq Na₂CO₃ (10 mL) and brine (10 mL) and separated. The solution was dried over Na₂SO₄ and filtered. The filtrate was concentrated to give the title compound 167g (25 mg, 80% yield) as a yellow solid. LC-MS (Method 4) $t_R$=1.07 min, m/z (M+H)⁺=192.1.

Step 7. 6-(Cyclopropanecarboxamido)-4-((1-ethyl-7-methoxy-1H-benzo[d]imidazol-6-yl)amino)-N-(methyl-d₃)nicotinamide (167)

A mixture of 167g (20 mg, 0.13 mmol), 44b (34 mg, 0.13 mmol), pTSA (23 mg, 0.13 mmol) in dioxane (1 mL) was stirred at 100° C. for 15 h. The mixture was concentrated and purified by Prep-HPLC (Method E) to get the compound 167 (5.8 mg, 10.8% yield) as a pale yellow solid. LC-MS (Method 4) $t_R$=1.50 min, m/z (M+H)⁺=412.3. ¹H NMR (400 MHz, DMSO-d₆) δ 10.66 (s, 1H), 10.39 (s, 1H), 8.57 (s, 1H), 8.50 (s, 1H), 8.20 (s, 1H), 7.70 (s, 1H), 7.41 (d, J=8.4

Hz, 1H), 7.11 (d, J=8.4 Hz, 1H), 4.38 (q, J=7.2 Hz, 2H), 3.76 (s, 3H), 1.93-1.92 (m, 1H), 1.41 (t, J=7.2 Hz, 3H), 0.73-0.68 (m, 4H).

Example 168

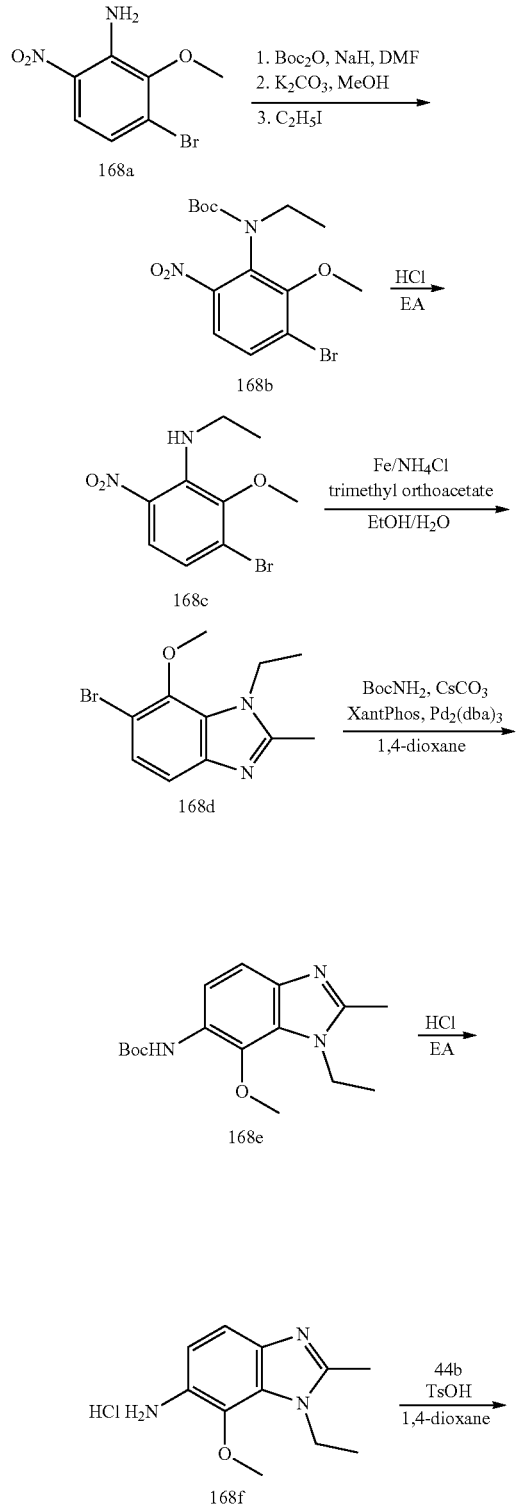

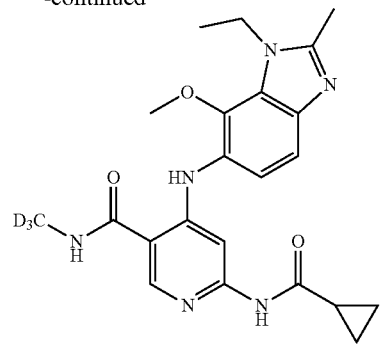

168

Step 1. Tert-butyl (3-bromo-2-methoxy-6-nitrophenyl)(ethyl)carbamate (168b)

To a solution of 168a (1.6 g, 6.48 mmol, CAS 89677-51-0) in DMF (8 mL) was added NaH (993 mg, 25.91 mmol, 60% purity in mineral oil) at 0° C. After stirring at 25° C. for 30 min, to it was added a solution of Boc$_2$O (4.24 g, 19.43 mmol) in DMF (0.5 mL). The reaction mixture was stirred at 25° C. for 16 h and quenched with water (30 mL). The resultant mixture was extracted with EtOAc (50 mL*3). The combined organic layer was washed with brine (30 mL*3), dried over anhydrous Na$_2$SO$_4$, filtered and concentrated under reduced pressure. The residue was dissolved in MeOH (20 mL) and to it was added K$_2$CO$_3$ (1.73 g, 12.52 mmol). The reaction mixture was stirred at 50° C. for 16 h. After cooling to r.t., iodoethane (3.03 g, 19.44 mmol) was added to the reaction. The reaction was stirred at stirred at 70° C. for 16 h. After cooling to r.t., the reaction mixture was concentrated and the residue was diluted with water (30 mL) and extracted with EtOAc (30 mL*3). The combined organic layer was concentrated under reduced pressure and the residue was purified by flash chromatography on silica gel (PE/EtOAc=10/1) to afford the title compound 168b (780 mg, 32% yield) as a yellow oil. $^1$H NMR (400 MHz, DMSO-d$_6$) δ 7.88 (d, J=8.8 Hz, 1H), 7.76 (d, J=8.8 Hz, 1H), 3.76 (s, 3H), 3.64-3.61 (m, 1H), 3.46-3.60 (m, 1H), 1.23 (s, 9H), 1.07 (t, J=7.2 Hz, 3H).

Step 2. 3-Bromo-N-ethyl-2-methoxy-6-nitroaniline hydrochloride (168c)

A mixture of 168b (780 mg, 2.08 mmol) in HCl/EtOAc (10 mL, 2 M) was stirred at 25° C. for 16 h. The mixture was concentrated to afford 168c (585 mg, 90% yield) as a yellow oil. LC-MS (Method 3) t$_R$=1.34 min, m/z (M+H)$^+$=275.1.

Step 3. 6-Bromo-1-ethyl-7-methoxy-2-methyl-1H-benzo[d]imidazole (168d)

A mixture of 168c (500 mg, 1.82 mmol), trimethyl orthoacetate (2.18 g, 18.18 mmol), Fe powder (508 mg, 9.09 mmol) and NH$_4$Cl (583 mg, 10.91 mmol) in EtOH (4 mL) and H$_2$O (0.8 mL) was stirred at 50° C. for 2 h. The reaction mixture was diluted with water (20 mL) and extracted with EtOAc (20 mL*3). The combined organic phase was dried over anhydrous Na$_2$SO$_4$, filtered and concentrated and the residue was purified by flash chromatography on silica gel (PE/EtOAc=10/1) to afford the title compound 168d (300 mg, 61% yield) as a yellow oil. LC-MS (Method 3) $t_R$=1.15 min, m/z (M+H)$^+$=269.0.

Step 4. Tert-butyl (1-ethyl-7-methoxy-2-methyl-1H-benzo[d]imidazol-6-yl)carbamate (168e)

Compound 168e (200 mg, 59% yield), a black solid, was synthesized by utilizing a similar preparative procedure of Step 4 in Example 51 with 168d (300 mg, 1.11 mmol) and tert-butyl carbamate (196 mg, 1.67 mmol) as starting materials. LC-MS (Method 3) $t_R$=0.75 min, m/z (M+H)$^+$=306.0.

Step 5. 1-Ethyl-7-methoxy-2-methyl-1H-benzo[d]imidazol-6-amine (168f)

A solution of 168e (200 mg, 0.66 mmol) in HCl/EtOAc (2 mL, 2 M) was stirred at r.t. for 2 h. The reaction was concentrated to afford 168f (100 mg, 63% yield) as a black solid. LC-MS (Method 3) $t_R$=0.85 min, m/z (M+H)$^+$=206.1.

Step 6. 6-(Cyclopropanecarboxamido)-4-((1-ethyl-7-methoxy-2-methyl-1H-benzo[d]imidazol-6-yl)amino)-N-(methyl-d$_3$)nicotinamide (168)

Compound 168 (4 mg, 7% yield), a brown solid, was synthesized by utilizing a similar preparative procedure of Step 6 in Example 51 with 168f (43 mg, 0.017 mmol) and 44b (25 mg, 0.014 mmol) as starting materials. LC-MS (Method 1) $t_R$=3.51 min, m/z (M+H)$^+$=426.1. $^1$H NMR (400 MHz, DMSO-d$_6$) δ 10.61 (s, 1H), 10.34 (s, 1H), 8.56 (s, 1H), 8.49 (s, 1H), 7.88 (s, 1H), 7.28 (d, J=8.8 Hz, 1H), 7.04 (d, J=8.8 Hz, 1H), 4.30 (q, J=6.4 Hz, 2H), 3.75 (s, 3H), 2.52 (s, 3H), 1.95-1.90 (m, 1H), 1.32 (t, J=6.8 Hz, 3H), 0.73-0.68 (m, 4H).

Example 169

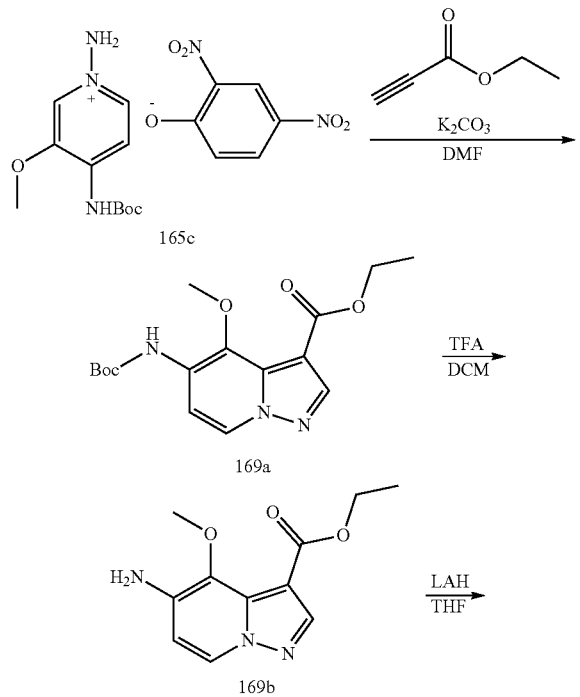

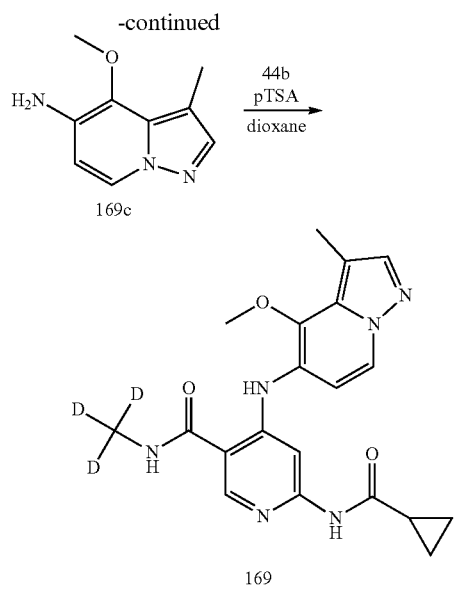

Step 1. Ethyl 5-((tert-butoxycarbonyl)amino)-4-methoxypyrazolo[1,5-a]pyridine-3-carboxylate (169a)

To a solution of 165c (1.50 g, 3.12 mmol) in DMF (15 mL) was added K$_2$CO$_3$ (647 mg, 4.69 mmol) and stirred at 25° C. for 1 h. Then ethyl propiolate (460 mg, 4.69 mmol) was added and the reaction mixture was stirred at 25° C. for 16 h. The mixture was diluted with water (50 mL) and extracted with EtOAc (20 mL*3). The combined organic layer was washed by brine (20 mL*2), dried over Na$_2$SO$_4$ and evaporated in vacuo, purified by flash chromatography on silica gel eluted with (PE/EA-10/1) to give 169a (150 mg, 14% yield) as a yellow solid. LC-MS (Method 5) $t_R$=2.91 min, m/z (M+H)$^+$=336.2. $^1$H NMR (400 MHz, DMSO-d$_6$) δ 9.02 (s, 1H), 8.59 (d, J=7.6 Hz, 1H), 8.36 (s, 1H), 7.70 (d, J=7.6 Hz, 1H), 4.23 (q, J=6.8 Hz, 2H), 3.74 (s, 3H), 1.50 (s, 9H), 1.31 (t, J=6.8 Hz, 3H).

Step 2. Ethyl 5-amino-4-methoxypyrazolo[1,5-a]pyridine-3-carboxylate (169b)

To a solution of 169a (150 mg, 0.448 mmol) in DCM (5 mL) was cooled to 0° C. and added TFA (1 mL) dropwise and then stirred at 25° C. for 2 h. The mixture was concentrated and the residue was diluted with DCM (10 mL), added sat. NaHCO$_3$ solution to adjust pH to 8 and extracted with DCM (10 mL*3). The combined organic layer was washed by brine (10 mL*2), dried over sodium sulphate and evaporated in vacuo to give 169b (70.0 mg, 66% yield) as a yellow solid. LC-MS (Method 5) $t_R$=1.40 min, m/z (M+H)$^+$=236.2.

Step 3. 4-Methoxy-3-methylpyrazolo[1,5-a]pyridin-5-amine (169c)

To a solution of 169b (70.0 mg, 0.298 mmol) in THF (3 mL) was added LiAlH$_4$ (113 mg, 2.98 mmol) portionwise under N$_2$ and then stirred at 70° C. for 2 h. The mixture was quenched with Na$_2$SO$_4$·10H$_2$O (500 mg) and filtered, the filtrate was evaporated in vacuo to give the crude product. The residue was purified by Prep-TLC (PE/EA=1/1) to give 169c (30.0 mg, 57% yield) as a yellow solid. LC-MS (Method 5) $t_R$=1.82 min, m/z (M+H)$^+$178.2. $^1$H NMR (400 MHz, CDCl$_3$) δ 8.04 (d, J=7.2 Hz, 1H), 7.54 (s, 1H), 6.24 (d, J=7.2 Hz, 1H), 3.83 (s, 3H), 2.33 (s, 3H).

Step 4. 6-(Cyclopropanecarboxamido)-4-((4-methoxy-3-methylpyrazolo[1,5-a]pyridin-5-yl)amino)-N-(methyl-d$_3$)nicotinamide (169)

To a solution of 169c (30 mg, 0.169 mmol) and 44b (43.4 mg, 0.169 mmol) in dioxane (3 mL) was added pTSA (58.1 mg, 0.338 mmol) and stirred at 100° C. for 16 h. It was cooled to 25° C. and purified by Prep-TLC (DCM/MeOH=15/1) to give 169 (24.0 mg, 36% yield) as an off-white solid. LC-MS (Method 6), $t_R$=2.83 min, m/z (M+H)$^+$=398.0. $^1$H NMR (400 MHz, DMSO-d$_6$) δ 10.79 (s, 1H), 10.53 (s, 1H), 8.63 (s, 1H), 8.53 (s, 1H), 8.42 (d, J=7.2 Hz, 1H), 7.81 (s, 1H), 7.77 (s, 1H), 6.79 (d, J=7.6 Hz, 1H), 3.78 (s, 3H), 2.38 (s, 3H), 2.01-1.94 (m, 1H), 0.77-0.75 (m, 4H).

Example 170

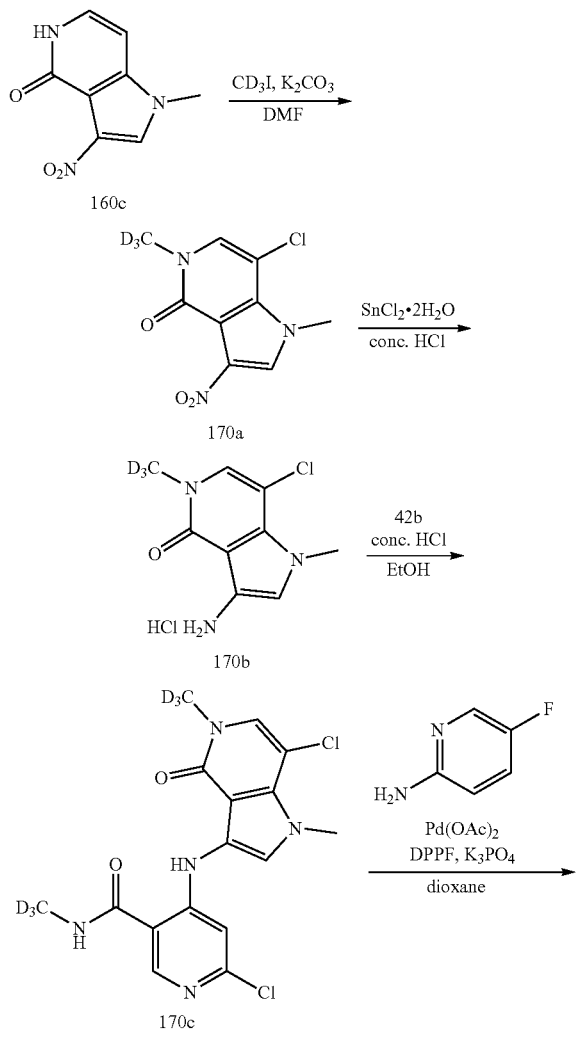

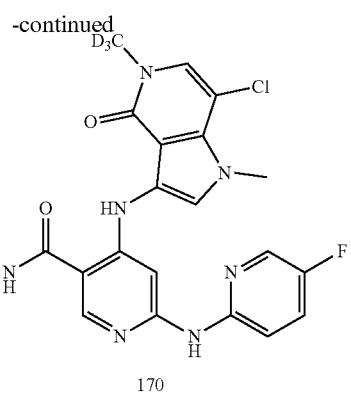

170

Step 1. 7-Chloro-1-methyl-5-(methyl-d$_3$)-3-nitro-1,5-dihydro-4H-pyrrolo[3,2-c]pyridin-4-one (170a)

A mixture of 160c (198 mg, 0.87 mmol), K$_2$CO$_3$ (240 mg, 1.74 mmol) and CD$_3$I (189 mg, 1.30 mmol) in DMF (2 mL) was stirred at 50° C. overnight. After cooling to r.t., the mixture was diluted with H$_2$O (8 mL), extracted with DCM (10 mL*2) and washed with brine (5 mL). The combined organic layer was dried over Na$_2$SO$_4$, filtered and the filtrate was concentrated. The residue was slurried with EtOAc (5 mL) and filtered. The filter cake was dried to afford the title compound 170a (199 mg, 94% yield) as a green solid. LC-MS (Method 3) $t_R$=1.12 min, m/z (M+H)$^+$=245.0.

Step 2. 3-Amino-7-chloro-1-methyl-5-(methyl-d$_3$)-1,5-dihydro-4H-pyrrolo[3,2-c]pyridin-4-one hydrochloride (170b)

Compound 170b (160 mg, 94% yield), a yellow solid, was synthesized by utilizing a similar preparative procedure of Step 5 in Example 123 with 170a (195 mg, 0.80 mmol) and SnCl$_2$.2H$_2$O (180 mg, 0.80 mmol) as starting materials. LC-MS (Method 3) $t_R$=1.18 min, m/z (M+H)$^+$=215.2.

Step 3. 6-Chloro-4-((7-chloro-1-methyl-5-(methyl-d$_3$)-4-oxo-4,5-dihydro-1H-pyrrolo[3,2-c]pyridin-3-yl)amino)-N-(methyl-d$_3$)nicotinamide (170c)

Compound 170c (160 mg, 47% yield), a yellow solid, was synthesized by utilizing a similar preparative procedure of Step 1 in Example 98 with 170b (180 mg, 0.72 mmol) and 42b (149 mg, 0.72 mmol) as starting materials. LC-MS (Method 3) $t_R$=1.36 min, m/z (M+H)$^+$=386.1.

Step 4. 4-((7-Chloro-1-methyl-5-(methyl-d$_3$)-4-oxo-4,5-dihydro-1H-pyrrolo[3,2-c]pyridin-3-yl)amino)-6-((5-fluoropyridin-2-yl)amino)-N-(methyl-d$_3$)nicotinamide (170)

Compound 170 (4.5 mg, 8% yield), a white solid, was synthesized by utilizing a similar preparative procedure of Step 8 in Example 160 with 170c (50 mg, 0.13 mmol) and 5-fluoropyridin-2-amine (29 mg, 0.26 mmol) as starting materials. LC-MS (Method 3) $t_R$=3.36 min, m/z (M+H)$^+$=462.1. $^1$H NMR (400 MHz, DMSO-d$_6$) δ 11.04 (s, 1H), 9.77 (s, 1H), 8.40 (s, 1H), 8.28-8.26 (m, 2H), 7.81-7.78 (m, 1H), 7.66-7.63 (m, 2H), 7.57 (s, 1H), 7.26 (s, 1H), 4.04 (s, 3H).

Example 171

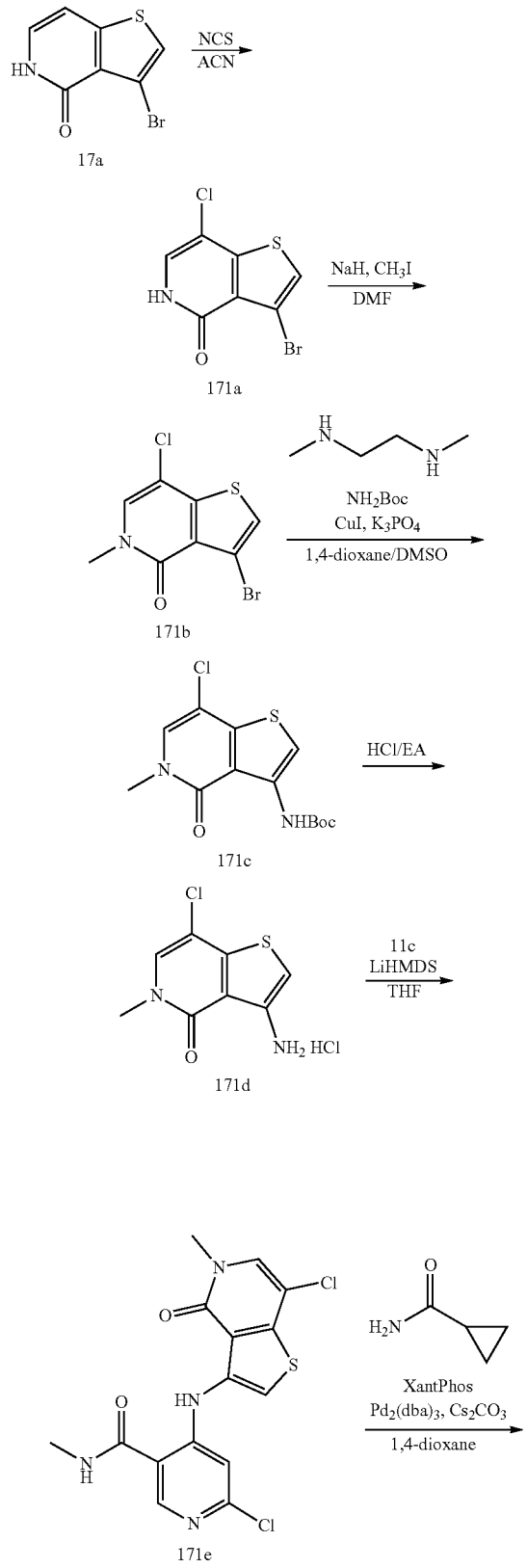

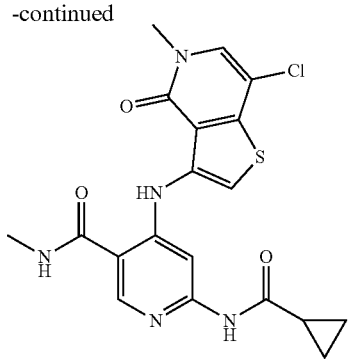

Step 1. 3-Bromo-7-chlorothieno[3,2-c]pyridin-4-(5H)-one (171a)

A mixture of 17a (1.5 g, 6.52 mmol) and NCS (1.13 g, 8.48 mmol) in ACN (10 mL) was stirred at 90° C. for 5 h. The reaction mixture was cooled, poured into ice-water (20 mL) and extracted with EtOAc (50 mL*2). The combined organic phase was dried over $Na_2SO_4$, filtered and concentrated to give the title compound 171a (2.0 g, yield given) as a brown solid. LC-MS (Method 3) $t_R$=1.34 min, m/z (M+H)$^+$=264.0.

Step 2. 3-Bromo-7-chloro-5-methylthieno[3,2-c]pyridin-4-(5H)-one (171b)

A mixture of 171a (500 mg, 1.89 mmol) in DMF (5 mL) was added NaH (145 mg, 6.05 mmol, 60% in mineral oil) at 0° C. After stirring at r.t. for 30 min, to it was added MeI (537 mg, 3.78 mmol). The reaction was stirred at r.t. for 1 h and poured into ice-water. The mixture was extracted with EtOAc (50 mL*2) and the combined organic phase was washed with brine (20 mL), dried over anhydrous $Na_2SO_4$, filtered, concentrated. The residue was purified by flash chromatography on silica gel (PE/EtOAc=5/1) to afford 171b (310 mg, 59% yield) as a brown solid. $^1$H NMR (400 MHz, DMSO-$d_6$) δ 8.06 (s, 1H), 7.87 (s, 1H), 3.51 (s, 3H).

Step 3. Tert-butyl (7-chloro-5-methyl-4-oxo-4,5-dihydrothieno[3,2-c]pyridin-3-yl)carbamate (171c)

Compound 171c (229 mg, 23% yield), a yellow solid, was synthesized by utilizing a similar preparative procedure of Step 4 in Example 1 with 171b (900 mg, 3.23 mmol) and tert-butyl carbamate (3.78 g, 32.31 mmol) as starting materials. $^1$H NMR (400 MHz, DMSO-$d_6$) δ 9.72 (s, 1H), 7.96 (s, 1H), 7.50 (s, 1H), 3.50 (s, 3H), 1.49 (s, 9H).

Step 4. 3-Amino-7-chloro-5-methylthieno[3,2-c]pyridin-4-(5H)-one hydrochloride (171d)

Compound 171d (79 mg, 99% yield), a yellow solid, was synthesized by utilizing a similar preparative procedure of Step 5 in Example 1 with 171c (100 mg, 0.32 mmol) as the starting material. LC-MS (Method 3) $t_R$=1.14 min, m/z (M+H)$^+$=215.0.

Step 5. 6-Chloro-4-((7-chloro-5-methyl-4-oxo-4,5-dihydrothieno[3,2-c]pyridin-3-yl)amino)-N-methylnicotinamide (171e)

Compound 171e (55 mg, 39% yield), a yellow solid, was synthesized by utilizing a similar preparative procedure of Step 5 in Example 50 with 171d (92 mg, 0.37 mmol) and 11c (91 mg, 0.44 mmol) as starting materials. LC-MS (Method 3) $t_R$=1.38 min, m/z (M+H)$^+$=383.0.

Step 6. 4-((7-Chloro-5-methyl-4-oxo-4,5-dihydrothieno[3,2-c]pyridin-3-yl)amino)-6-(cyclopropanecarboxamido)-N-methylnicotinamide (171)

A mixture of 171 (50 mg, 0.13 mmol), cyclopropanecarboxamide (56 mg, 0.65 mmol), Pd$_2$(dba)$_3$ (12 mg, 0.013 mmol), XantPhos (15 mg, 0.026 mmol) and Cs$_2$CO$_3$ (85 mg, 0.26 mmol) in 1,4-dioxane (4 mL) was stirred at 70° C. for 18 h under N$_2$. The reaction mixture was cooled and concentrated. The residue was purified by Prep-HPLC (Method A) to give the title compound 171 (3 mg, 5% yield) as a white solid. LC-MS (Method 1) $t_R$=3.35 min, m/z (M+H)$^+$=432.1. $^1$H NMR (400 MHz, DMSO-d$_6$) δ 11.44 (s, 1H), 10.87 (s, 1H), 8.48-8.46 (m, 2H), 8.39 (s, 1H), 7.98 (s, 1H), 7.19 (s, 1H), 3.51 (s, 3H), 2.78 (d, J=3.6 Hz, 3H), 2.03-1.94 (m, 1H), 0.91-0.71 (m, 4H).

Example 172

Step 5 in Example 50 with 171d (40 mg, 0.16 mmol) and 42b (33 mg, 0.16 mmol) as starting materials. LC-MS (Method 3) $t_R$=1.46 min, m/z (M+H)$^+$=386.1.

Step 2. 4-((7-Chloro-5-methyl-4-oxo-4,5-dihydrothieno[3,2-c]pyridin-3-yl)amino)-6-(cyclopropanecarboxamido)-N-(methyl-d$_3$)nicotinamide (172)

Compound 172 (3.5 mg, 10% yield), a white solid, was synthesized by utilizing a similar preparative procedure of Step 3 in Example 49 with 172a (30 mg, 0.08 mmol) and cyclopropanecarboxamide (33 mg, 0.39 mmol) as starting materials. LC-MS (Method 1) $t_R$=3.10 min, m/z (M+H)$^+$=435.0. $^1$H NMR (400 MHz, DMSO-d$_6$) δ 11.43 (s, 1H), 10.85 (s, 1H), 8.47 (s, 1H), 8.44 (s, 1H), 8.39 (s, 1H), 7.97 (s, 1H), 7.19 (s, 1H), 3.51 (s, 3H), 2.03-1.98 (m, 1H), 0.85-0.79 (m, 4H).

Example 173

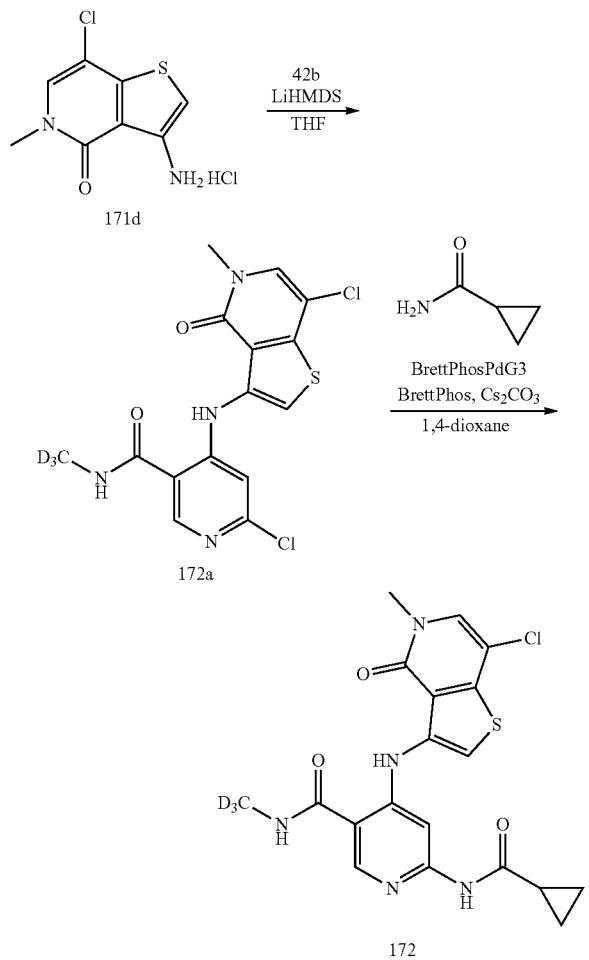
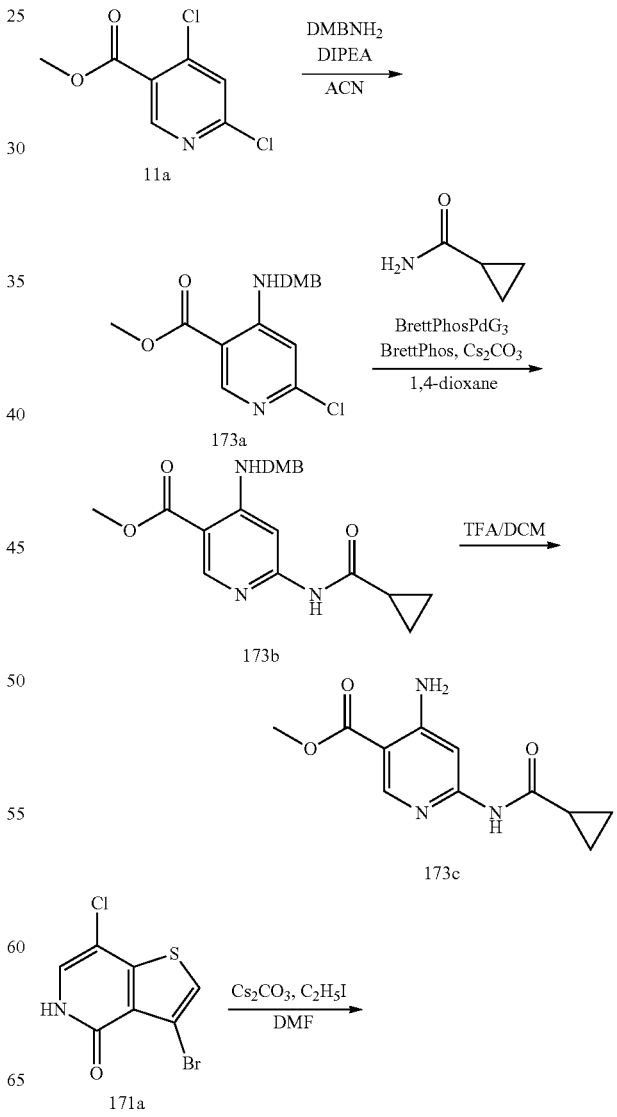

Step 1. 6-Chloro-4-((7-chloro-5-methyl-4-oxo-4,5-dihydrothieno[3,2-c]pyridin-3-yl)amino)-N-(methyl-d$_3$)nicotinamide (172a)

Compound 172a (40 mg, 65% yield), a brown solid, was synthesized by utilizing a similar preparative procedure of

521

-continued

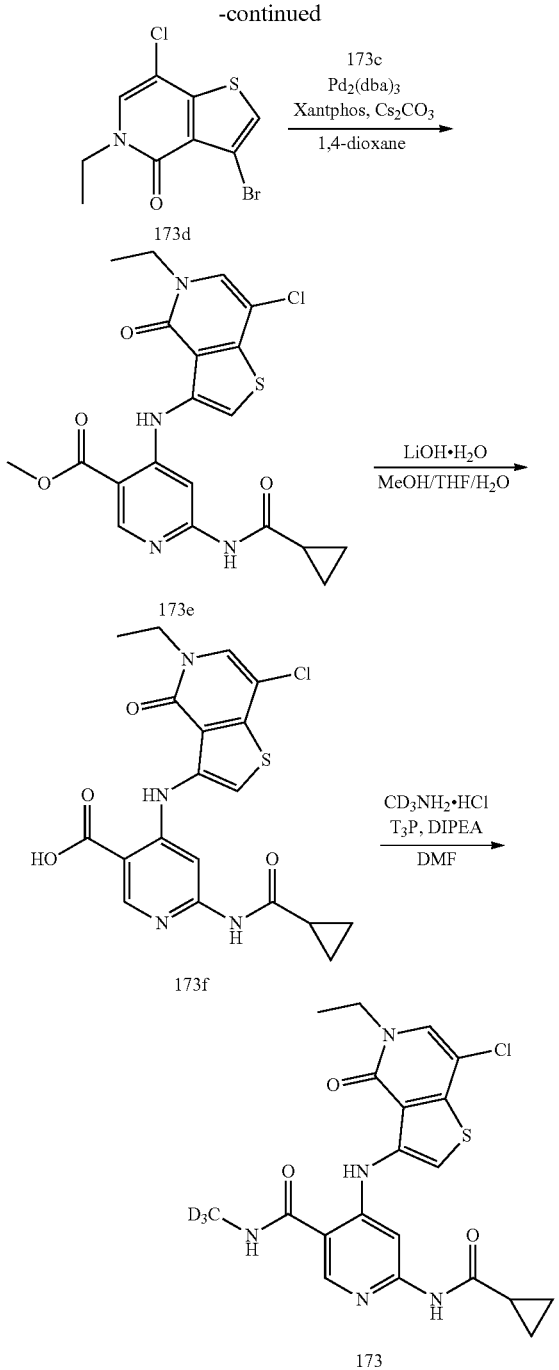

Step 1. Methyl
6-chloro-4-((2,4-dimethoxybenzyl)amino)nicotinate
(173a)

To a solution of 11a (5.0 g, 24.27 mmol) and DIPEA (9.39 g, 72.81 mmol) in ACN (50 mL) was added (2,4-dimethoxyphenyl)methanamine (4.46 g, 26.70 mmol). The reaction mixture was stirred at 50° C. for 16 h. After cooling to r.t., the reaction mixture was diluted with $H_2O$ (100 mL) and extracted with EtOAc (100 mL*2). The combined organic layer was concentrated to afford the title compound 173a (8.10 g, 99% yield) as a white solid. LC-MS (Method 3) $t_R$=1.25 min, m/z $(M+H)^+$=336.9.

522

Step 2. Methyl 6-(cyclopropanecarboxamido)-4-((2, 4-dimethoxybenzyl)amino)nicotinate (173b)

Compound 173b (3.1 g, 68% yield), an off-white solid, was synthesized by utilizing a similar preparative procedure of Step 3 in Example 49 with 173a (4.0 g, 1.89 mmol) and cyclopropanecarboxamide (2.53 g, 29.69 mmol) as starting materials. LC-MS (Method 3) $t_R$=1.56 min, m/z $(M+H)^+$=386.2.

Step 3. Methyl
4-amino-6-(cyclopropanecarboxamido)nicotinate
(173c)

To a solution of 173b (4 g, 10.38 mmol) in DCM (30 mL) was added TFA (10 mL) at 0° C. The reaction mixture was stirred at 30° C. for 2 h. The solvent was removed by pumping through $N_2$. The residue was diluted in water (20 mL) and basified with saturated $Na_2CO_3$ to adjust pH to above 7. The mixture was extracted with EtOAc (80 mL*3). The combined organic layer was dried over anhydrous $Na_2SO_4$, filtered and concentrated to afford the title compound 173c (1.4 g, 57% yield) as an off-white solid. LC-MS (Method 3) $t_R$=1.29 min, m/z $(M+H)^+$=236.0.

Step 4. 3-Bromo-7-chloro-5-ethylthieno[3,2-c]pyridin-4-(5H)-one (173d)

Compound 173d (480 mg, 87% yield), a brown solid, was synthesized by utilizing a similar preparative procedure of Step 1 in Example 110 with 171a (500 mg, 1.89 mmol) and iodoethane (884 mg, 5.67 mmol) as starting materials. $^1$H NMR (400 MHz, DMSO-$d_6$) δ 8.04 (s, 1H), 7.84 (s, 1H), 3.98 (q, J=7.2 Hz, 2H), 1.25 (t, J=7.2 Hz, 3H).

Step 5. Methyl 4-((7-chloro-5-ethyl-4-oxo-4,5-dihydrothieno[3,2-c]pyridin-3-yl)amino)-6-(cyclopropanecarboxamido)nicotinate (173e)

Compound 173e (200 mg, 44% yield), a yellow solid, was synthesized by utilizing a similar preparative procedure of Step 6 in Example 171 with 173d (300 mg, 1.03 mmol) and 173c (193 mg, 0.82 mmol) as starting materials. LC-MS (Method 3) $t_R$=1.59 min, m/z $(M+H)^+$=447.0.

Step 6. 4-((7-Chloro-5-ethyl-4-oxo-4,5-dihydrothieno[3,2-c]pyridin-3-yl)amino)-6-(cyclopropanecarboxamido)nicotinic acid (173f)

Compound 173f (120 mg, 62% yield), a yellow solid, was synthesized by utilizing a similar preparative procedure of Step 3 in Example 27 with 173e (200 mg, 0.45 mmol) as the starting material. LC-MS (Method 3) $t_R$=1.19 min, m/z $(M+H)^+$=433.0.

Step 7. 4-((7-Chloro-5-ethyl-4-oxo-4,5-dihydrothieno[3,2-c]pyridin-3-yl)amino)-6-(cyclopropanecarboxamido)-N-(methyl-$d_3$)nicotinamide (173)

Compound 173 (20 mg, 18% yield), a yellow solid, was synthesized by utilizing a similar preparative procedure of Step 2 in Example 11 with 173f (120 mg, 0.28 mmol) and trideuteriomethanamine hydrochloride (98 mg, 1.39 mmol) as starting materials. LC-MS (Method 2) $t_R$=3.35 min, m/z $(M+H)^+$=449.1. $^1$H NMR (400 MHz, DMSO-$d_6$) δ 11.44 (s, 1H), 10.85 (s, 1H), 8.48 (s, 1H), 8.45 (s, 1H), 8.39 (s, 1H), 7.99 (s, 1H), 7.20 (s, 1H), 4.00 (q, J=7.2 Hz, 2H), 2.02-1.98 (m, 1H), 1.26 (t, J=7.2 Hz, 3H), 0.84-0.81 (m, 4H).

Example 174

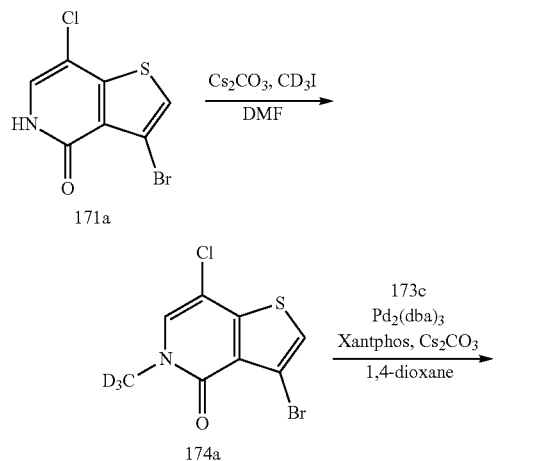

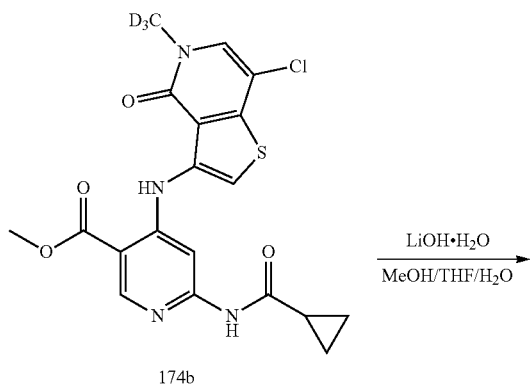

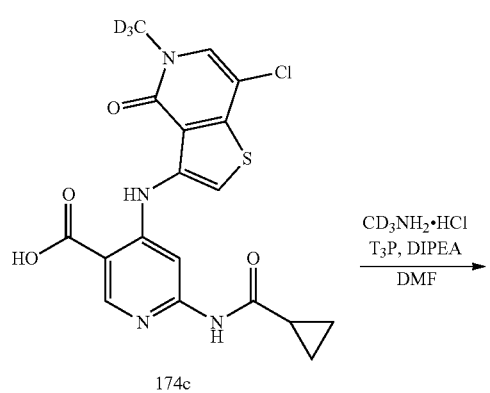

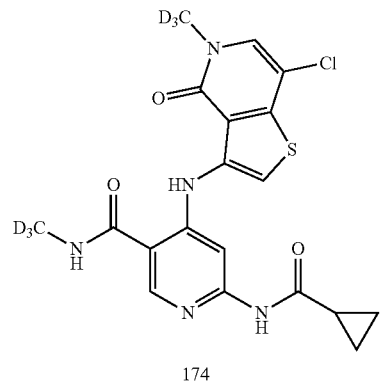

174

Step 1. 3-Bromo-7-chloro-5-(methyl-d₃)thieno[3,2-c]pyridin-4-(5H)-one (174a)

Compound 174a (430 mg, 81% yield), a white solid, was synthesized by utilizing a similar preparative procedure of Step 1 in Example 110 with 171a (500 mg, 1.89 mmol) and CD₃I (411 mg, 2.84 mmol) as starting materials. $^1$H NMR (400 MHz, DMSO-d₆) δ 8.02 (s, 1H), 7.84 (s, 1H).

Step 2. Methyl 4-((7-Chloro-5-(methyl-d₃)-4-oxo-4,5-dihydrothieno[3,2-c]pyridin-3-yl)amino)-6-(cyclopropanecarboxamido)nicotinate (174b)

Compound 174b (170 mg, 55% yield), a white solid, was synthesized by utilizing a similar preparative procedure of Step 6 in Example 171 with 174a (200 mg, 0.71 mmol) and 173c (134 mg, 0.57 mmol) as starting materials. LC-MS (Method 3) $t_R$=1.65 min, m/z (M+H)$^+$=436.1.

Step 3. 4-((7-Chloro-5-(methyl-d₃)-4-oxo-4,5-dihydrothieno[3,2-c]pyridin-3-yl)amino)-6-(cyclopropanecarboxamido)nicotinic acid (174c)

Compound 174c (158 mg, 96% yield), a white solid, was synthesized by utilizing similar preparative procedure of Step 3 in Example 27 with 174b (170 mg, 0.39 mmol) as the starting material. LC-MS (Method 3) $t_R$=1.16 min, m/z (M+H)$^+$=422.1.

Step 4. 4-((7-Chloro-5-(methyl-d₃)-4-oxo-4,5-dihydrothieno[3,2-c]pyridin-3-yl)amino)-6-(cyclopropanecarboxamido)-N-(methyl-d₃)nicotinamide (174)

Compound 174 (7 mg, 4% yield), a white solid, was synthesized by utilizing a similar preparative procedure of Step 2 in Example 11 with 174c (158 mg, 0.37 mmol) and trideuteriomethanamine hydrochloride (32 mg, 0.45 mmol) as starting materials. LC-MS (Method 1) $t_R$=3.17 min, m/z (M+H)$^+$=438.0. $^1$H NMR (400 MHz, DMSO-d₆) δ 11.44 (s, 1H), 10.85 (s, 1H), 8.47 (s, 1H), 8.44 (s, 1H), 8.39 (s, 1H), 7.97 (s, 1H), 7.19 (s, 1H), 2.03-1.99 (m, 1H), 0.85-0.80 (m, 4H).

Example 175

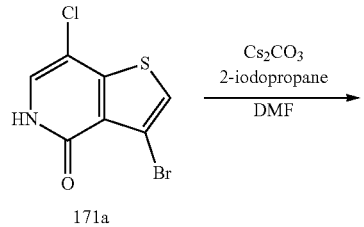

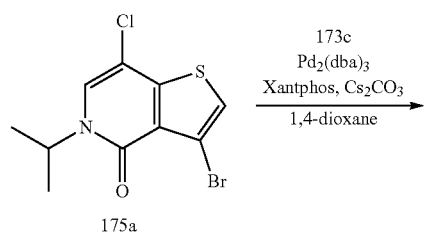

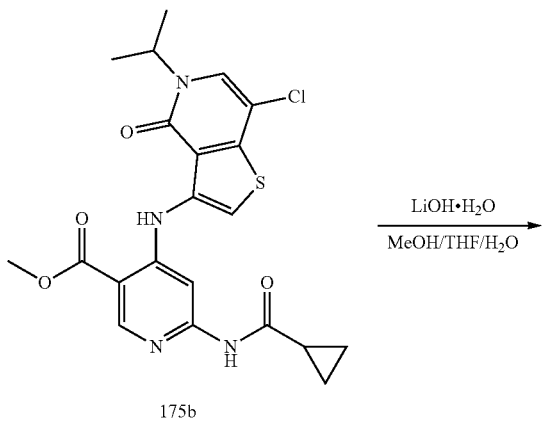

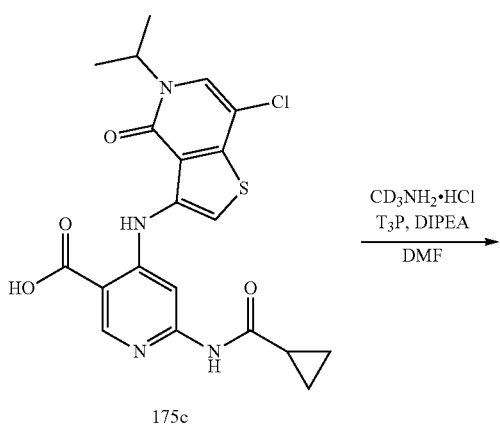

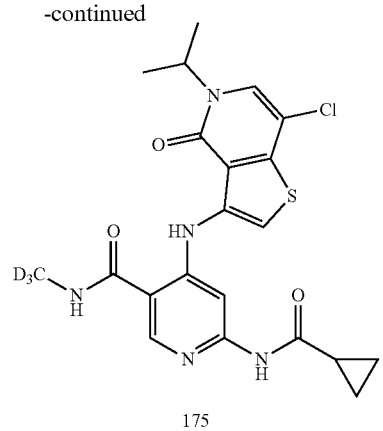

Step 1. 3-Bromo-7-chloro-5-isopropylthieno[3,2-c]pyridin-4-(5H)-one (175a)

Compound 175a (1.0 g, 86% yield), a brown solid, was synthesized by utilizing a similar preparative procedure of Step 1 in Example 110 with 171a (1.0 g, 3.78 mmol) and 2-iodopropane (1.29 g, 7.56 mmol) as starting materials. LC-MS (Method 3) $t_R$=1.62 min, m/z (M+H)$^+$=305.9.

Step 2. Methyl 4-((7-chloro-5-isopropyl-4-oxo-4,5-dihydrothieno[3,2-c]pyridin-3-yl)amino)-6-(cyclopropanecarboxamido)nicotinate (175b)

Compound 175b (600 mg, 80% yield), a yellow solid, was synthesized by utilizing a similar preparative procedure of Step 6 in Example 171 with 175a (500 mg, 1.63 mmol) and 173c (235 mg, 1.30 mmol) as starting materials. LC-MS (Method 3) $t_R$=1.96 min, m/z (M+H)$^+$=461.0.

Step 3. 4-((7-Chloro-5-isopropyl-4-oxo-4,5-dihydrothieno[3,2-c]pyridin-3-yl)amino)-6-(cyclopropanecarboxamido)nicotinic acid (175c)

Compound 175c (60 mg, 80% yield), a white solid, was synthesized by utilizing a similar preparative procedure of Step 3 in Example 27 with 175b (83 mg, 0.19 mmol) as the starting material. LC-MS (Method 3) $t_R$=1.47 min, m/z (M+H)$^+$=447.1.

Step 4. 4-((7-Chloro-5-isopropyl-4-oxo-4,5-dihydrothieno[3,2-c]pyridin-3-yl)amino)-6-(cyclopropanecarboxamido)-N-(methyl-d$_3$)nicotinamide (175)

Compound 175 (5 mg, 6% yield), a white solid, was synthesized by utilizing a similar preparative procedure of Step 2 in Example 11 with 175c (77 mg, 0.17 mmol) and trideuteriomethanamine hydrochloride (24 mg, 0.34 mmol) as starting materials. LC-MS (Method 2) $t_R$=3.89 min, m/z (M+H)$^+$=463.0. $^1$H NMR (400 MHz, DMSO-d$_6$) δ 11.46 (s, 1H), 10.85 (s, 1H), 8.47 (s, 1H), 8.44 (s, 1H), 8.38 (s, 1H), 7.94 (s, 1H), 7.19 (s, 1H), 5.20-5.17 (m, 1H), 2.02-1.98 (m, 1H), 1.35 (d, J=6.8 Hz, 3H), 1.25 (d, J=6.8 Hz, 3H), 0.83-0.81 (m, 4H).

Example 176

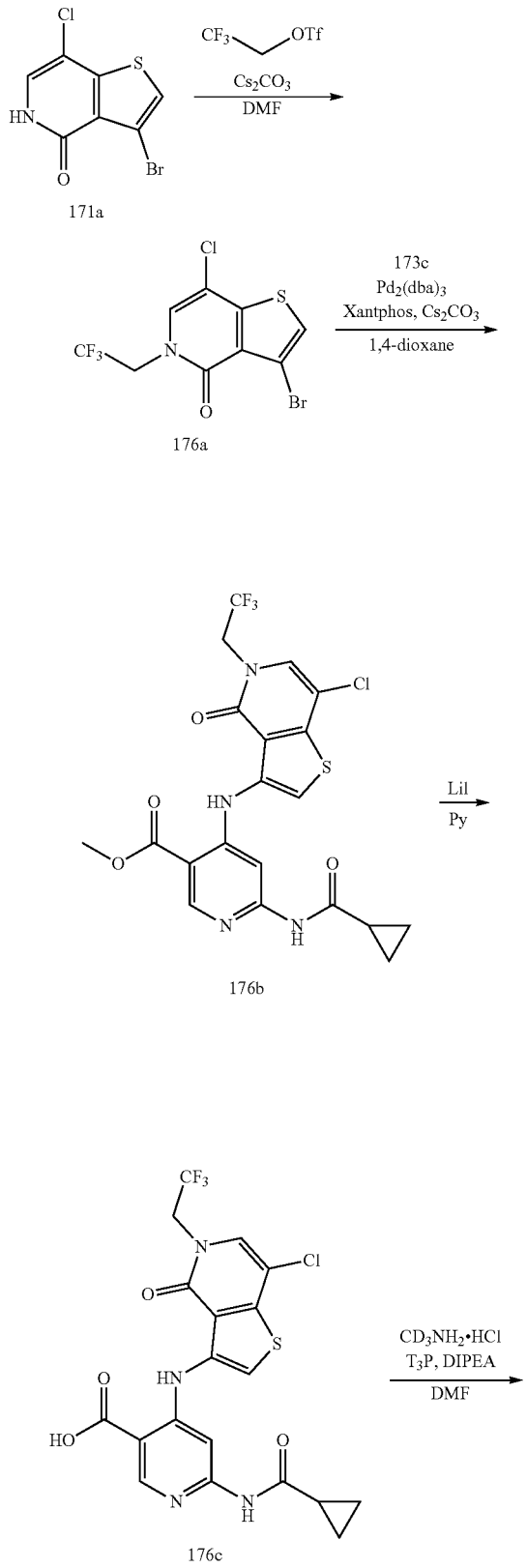

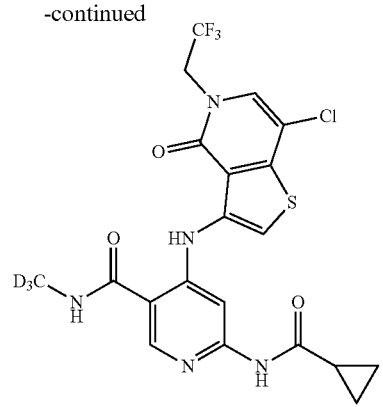

Step 1. 3-Bromo-7-chloro-5-(2,2,2-trifluoroethyl)thieno[3,2-c]pyridin-4-(5H)-one (176a)

Compound 176a (0.98 g, 75% yield), a white solid, was synthesized by utilizing a similar preparative procedure of Step 1 in Example 110 with 171a (1.0 g, 3.78 mmol) and 2,2,2-trifluoroethyl trifluoromethanesulfonate (1.75 g, 7.56 mmol) as starting materials. LC-MS (Method 3) $t_R$=1.08 min, m/z (M+H)$^+$=345.8.

Step 2. Methyl 4-((7-chloro-4-oxo-5-(2,2,2-trifluoroethyl)-4,5-dihydrothieno[3,2-c]pyridin-3-yl)amino)-6-(cyclopropanecarboxamido)nicotinate (176b)

Compound 176b (130 mg, 31% yield), a yellow solid, was synthesized by utilizing a similar preparative procedure of Step 6 in Example 171 with 176a (200 mg, 0.85 mmol) and 173c (589 mg, 1.70 mmol) as starting materials. LC-MS (Method 3) $t_R$=1.78 min, m/z (M+H)$^+$=501.1.

Step 3. 4-((7-Chloro-4-oxo-5-(2,2,2-trifluoroethyl)-4,5-dihydrothieno[3,2-c]pyridin-3-yl)amino)-6-(cyclopropanecarboxamido)nicotinic acid (176c)

A mixture of 176b (120 mg, 0.24 mmol) and LiI (144 mg, 1.08 mmol) in pyridine (0.5 mL) was stirred at 140° C. under microwave for 1 h. The reaction mixture was cooled, diluted with water (5 mL) and filtered. The filter cake was dried to afford 176c (77 mg, 66% yield) as a yellow solid. LC-MS (Method 3) $t_R$=1.78 min, m/z (M−H)$^-$=485.0.

Step 4. 4-((7-Chloro-4-oxo-5-(2,2,2-trifluoroethyl)-4,5-dihydrothieno[3,2-c]pyridin-3-yl)amino)-6-(cyclopropanecarboxamido)-N-(methyl-d$_3$)nicotinamide (176)

Compound 176 (2.4 mg, 4% yield), a white solid, was synthesized by utilizing a similar preparative procedure of Step 2 in Example 11 with 176c (50 mg, 0.12 mmol) and trideuteriomethanamine hydrochloride (33 mg, 0.47 mmol) as starting materials. LC-MS (Method 2) $t_R$=3.66 min, m/z (M+H)$^+$=502.9. $^1$H NMR (400 MHz, DMSO-d$_6$) δ 11.41 (s, 1H), 10.87 (s, 1H), 8.50 (s, 1H), 8.49 (s, 1H), 8.38 (s, 1H), 7.97 (s, 1H), 7.30 (s, 1H), 4.93 (q, J=9.2 Hz, 2H), 2.03-1.99 (m, 1H), 0.92-0.81 (m, 4H).

Example 177

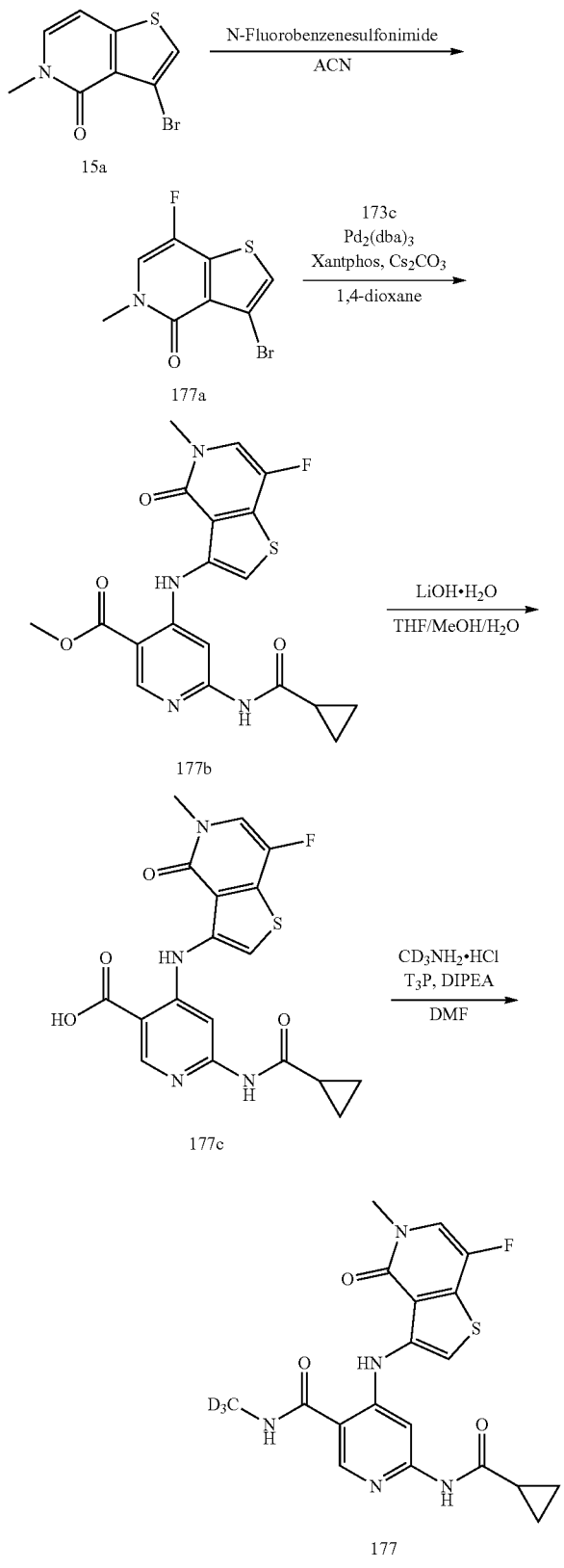

Step 1. 3-Bromo-7-fluoro-5-methylthieno[3,2-c]pyridin-4-(5H)-one (177a)

The mixture of 15a (117 mg, 0.48 mmol) and N-fluorobenzenesulfonimide (185 mg, 0.96 mmol) in ACN (1 mL) was stirred at 60° C. for 16 h. The reaction mixture was concentrated. The residue was purified by flash chromatography on silica gel (PE/EtOAc=4/1) to afford 177a (30 mg, 24% yield) as a red solid. LC-MS (Method 3) $t_R$=1.39 min, m/z $(M+H)^+$=261.8.

Step 3. Methyl 6-(cyclopropanecarboxamido)-4-((7-fluoro-5-methyl-4-oxo-4,5-dihydrothieno[3,2-c]pyridin-3-yl)amino)nicotinate (177b)

Compound 177b (81 mg, 32% yield), a brown solid, was synthesized by utilizing a similar preparative procedure of Step 6 in Example 171 with 177a (120 mg, 0.46 mmol) and 173c (108 mg, 0.46 mmol) as starting materials. LC-MS (Method 3) $t_R$=1.49 min, m/z $(M+H)^+$=417.0.

Step 4. 6-(Cyclopropanecarboxamido)-4-((7-fluoro-5-methyl-4-oxo-4,5-dihydrothieno[3,2-c]pyridin-3-yl)amino)nicotinic acid (177c)

Compound 177c (65 mg, 84% yield), a white solid, was synthesized by utilizing a similar preparative procedure of Step 3 in Example 27 with 177b (80 mg, 0.19 mmol) as the starting material. LC-MS (Method 3) $t_R$=1.30 min, m/z $(M+H)^+$=402.9.

Step 5. 6-(Cyclopropanecarboxamido)-4-((7-fluoro-5-methyl-4-oxo-4,5-dihydrothieno[3,2-c]pyridin-3-yl)amino)-N-(methyl-d₃)nicotinamide (177)

Compound 177 (2.4 mg, 19% yield), a white solid, was synthesized by utilizing a similar preparative procedure of Step 2 in Example 11 with 177c (65 mg, 0.16 mmol) and trideuteriomethanamine hydrochloride (23 mg, 0.32 mmol) as starting materials. LC-MS (Method 1) $t_R$=2.64 min, m/z $(M+H)^+$=419.0. $^1$H NMR (400 MHz, Trifluoroacetic acid-d) δ 8.87 (s, 1H), 7.90 (s, 1H), 7.89 (s, 1H), 7.13 (s, 1H), 4.23 (s, 3H), 3.64-3.67 (m, 1H), 1.62-1.66 (m, 4H).

Example 178

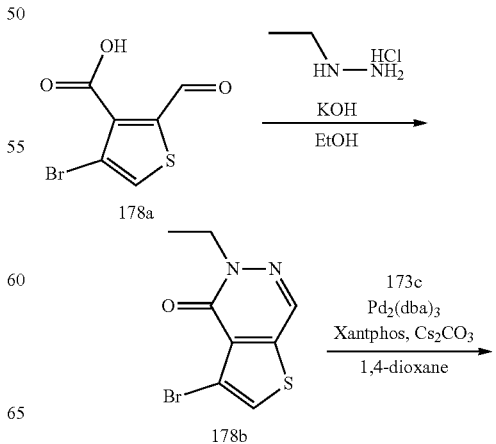

531
-continued

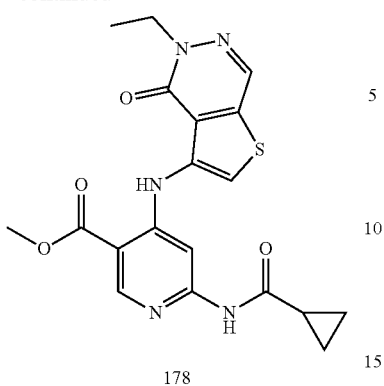
178

Step 1. 3-Bromo-5-ethylthieno[2,3-d]pyridazin-4-(5H)-one (178b)

A mixture of ethylhydrazine hydrochloride (1.71 g, 17.72 mmol) and KOH (994 mg, 17.72 mmol) in EtOH (20 mL) was stirred at r.t. for 0.5 h. The white solid was filtered off and the filtrate was added to the solution of 178a (3.5 g, 14.76 mmol) in 10 mL of EtOH. The resultant mixture was stirred at 100° C. for 16 h. The reaction mixture was cooled and concentrated under reduced pressure. The residue was purified by chromatography on silica gel (DCM/MeOH=20/1) to afford 178b (3.15 g, 82% yield) as a yellow solid. $^1$H NMR (400 MHz, DMSO-$d_6$) δ 8.63 (s, 1H), 8.16 (s, 1H), 4.15 (q, J=7.2 Hz, 2H), 1.29 (t, J=7.2 Hz, 3H).

Step 2. Methyl 6-(cyclopropanecarboxamido)-4-((5-ethyl-4-oxo-4,5-dihydrothieno[2,3-d]pyridazin-3-yl)amino)nicotinate (178)

Compound 178 (670 mg, 84% yield), a white solid, was synthesized by utilizing a similar preparative procedure of Step 2 in Example 11 with 178b (500 mg, 1.93 mmol) and 173c (454 mg, 1.93 mmol) as starting materials. LC-MS (Method 1) $t_R$=3.54 min, m/z (M+H)$^+$=414.0. $^1$H NMR (400 MHz, DMSO-$d_6$) δ 11.31 (s, 1H), 10.07 (s, 1H), 8.76 (s, 1H), 8.62 (s, 1H), 8.45 (s, 1H), 7.62 (s, 1H), 4.19 (q, J=7.2 Hz, 2H), 3.90 (s, 3H), 2.02-2.05 (m, 1H), 1.30 (t, J=6.8 Hz, 3H), 0.83-0.85 (m, 4H).

Example 179

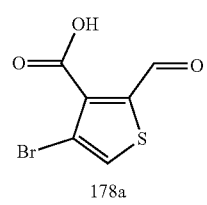
178a

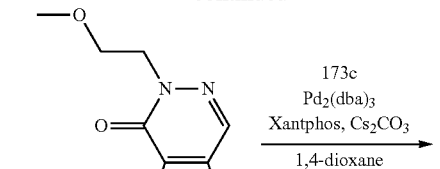

532
-continued

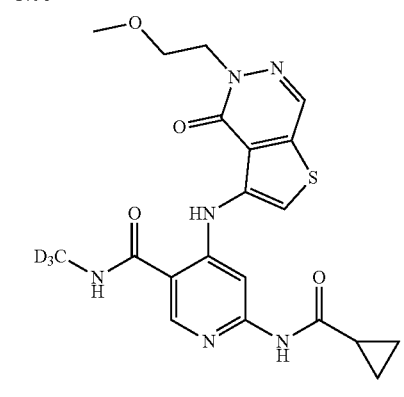

Step 1. 3-Bromo-5-(2-methoxyethyl)thieno[2,3-d]pyridazin-4-(5H)-one (179a)

Compound 179a (290 mg, 24% yield), a yellow solid, was synthesized by utilizing a similar preparative procedure of Step 1 in Example 178 with 178a (1.0 g, 4.25 mmol) and (2-methoxyethyl)hydrazine hydrochloride (539 mg, 4.25 mmol) as starting materials. LC-MS (Method 1) $t_R$=1.34 min, m/z (M+H)$^+$=288.9.

Step 2. Methyl 6-(cyclopropanecarboxamido)-4-((5-(2-methoxyethyl)-4-oxo-4,5-dihydrothieno[2,3-d]pyridazin-3-yl)amino)nicotinate (179b)

Compound 179b (315 mg, 71% yield), a white solid, was synthesized by utilizing a similar preparative procedure of Step 6 in Example 171 with 179a (290 mg, 1.00 mmol) and 173c (236 mg, 1.00 mmol) as starting materials. LC-MS (Method 3) $t_R$=0.75 min, m/z (M+H)$^+$=443.8.

Step 3. 6-(Cyclopropanecarboxamido)-4-((5-(2-methoxyethyl)-4-oxo-4,5-dihydrothieno[2,3-d]pyridazin-3-yl)amino)nicotinic acid (179c)

Compound 179c (270 mg, 89% yield), a white solid, was synthesized by utilizing a similar preparative procedure of Step 3 in Example 27 with 179b (315 mg, 0.71 mmol) as the starting material. LC-MS (Method 3) $t_R$=0.23 min, m/z (M+H)$^+$=429.9.

Step 4. 6-(Cyclopropanecarboxamido)-4-((5-(2-methoxyethyl)-4-oxo-4,5-dihydrothieno[2,3-d]pyridazin-3-yl)amino)-N-(methyl-d$_3$)nicotinamide (179)

Compound 179 (80 mg, 29% yield), a white solid, was synthesized by utilizing a similar preparative procedure of Step 2 in Example 11 with 179c (270 mg, 0.63 mmol) and trideuteriomethanamine hydrochloride (221 mg, 3.14 mmol) as starting materials. LC-MS (Method 2) $t_R$=2.27 min, m/z (M+H)$^+$=446.0. $^1$H NMR (400 MHz, DMSO-d$_6$) δ 11.41 (s, 1H), 10.86 (s, 1H), 8.58 (s, 1H), 8.51 (s, 1H), 8.47 (s, 1H), 8.38 (s, 1H), 7.53 (s, 1H), 4.31 (t, J=5.6 Hz, 2H), 3.71 (t, J=5.6 Hz, 2H), 3.25 (s, 3H), 2.04-1.98 (m, 1H), 0.87-0.80 (m, 4H).

Example 180

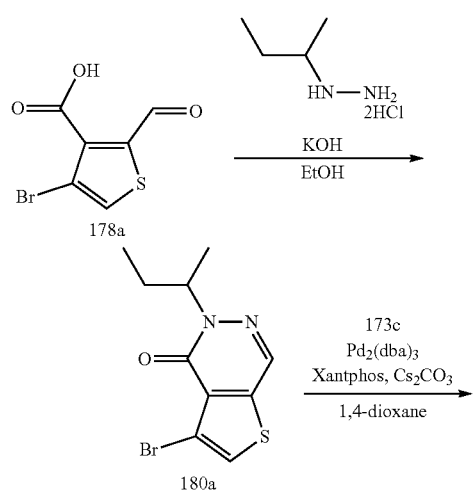

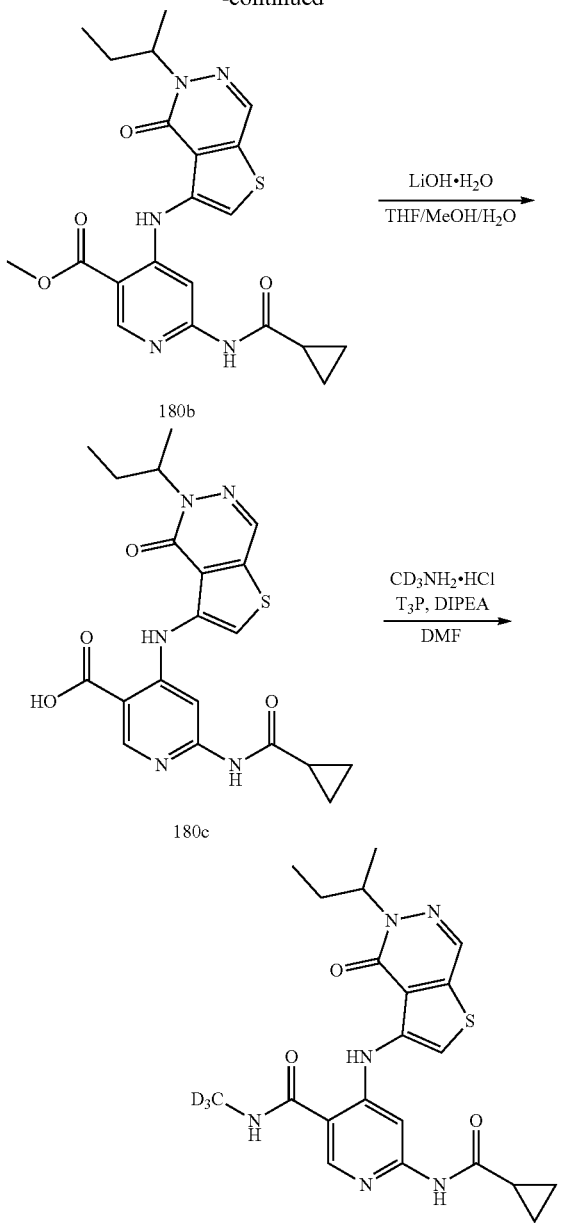

Step 1. 3-Bromo-5-(sec-butyl)thieno[2,3-d]pyridazin-4-(5H)-one (180a)

Compound 180a (150 mg, 15% yield), a white solid, was synthesized by utilizing a similar preparative procedure of Step 1 in Example 178 with 178a (800 mg, 3.37 mmol) and sec-butylhydrazine dihydrochloride (761 mg, 4.72 mmol) as starting materials. LC-MS (Method 1) $t_R$=1.34 min, m/z (M+H)$^+$=287.0. $^1$H NMR (400 MHz, DMSO-d$_6$) δ 8.68 (s, 1H), 8.15 (s, 1H), 5.07-5.02 (m, 1H), 1.82-1.66 (in, 2H), 1.27 (d, J=6.8 Hz, 3H), 0.75 (t, J=7.6 Hz, 3H).

Step 2. Methyl 4-((5-(sec-butyl)-4-oxo-4,5-dihydrothieno[2,3-d]pyridazin-3-yl)amino)-6-(cyclopropanecarboxamido)nicotinate (180b)

Compound 180b (110 mg, 51% yield) a white solid, was synthesized by utilizing a similar preparative procedure of Step 6 in Example 171 with 180a (140 mg, 0.49 mmol) and 173c (126 mg, 0.54 mmol) as starting materials. LC-MS (Method 2) $t_R$=3.27 min, m/z (M+H)$^+$=442.0.

Step 3. 4-((5-(Sec-butyl)-4-oxo-4,5-dihydrothieno[2,3-d]pyridazin-3-yl)amino)-6-(cyclopropanecarboxamido)nicotinic acid (180c)

Compound 180c (83 mg, 78% yield), a white solid, was synthesized by utilizing a similar preparative procedure of Step 3 in Example 27 with 180b (110 mg, 0.25 mmol) as the starting material. LC-MS (Method 3) $t_R$=0.66 min, m/z (M+H)$^+$=427.8.

Step 4. 4-((5-(Sec-butyl)-4-oxo-4,5-dihydrothieno[2,3-d]pyridazin-3-yl)amino)-6-(cyclopropanecarboxamido)-N-(methyl-d$_3$)nicotinamide (180)

Compound 180 (6.2 mg, 7% yield), a white solid, was synthesized by utilizing a similar preparative procedure of Step 2 in Example 11 with 180c (83 mg, 0.19 mmol) and trideuteriomethanamine hydrochloride (27 mg, 0.39 mmol) as starting materials. LC-MS (Method 2) $t_R$=3.16 min, m/z (M+H)$^+$=444.1. $^1$H NMR (400 MHz, DMSO-d$_6$) δ 11.43 (s, 1H), 10.87 (s, 1H), 8.63 (s, 1H), 8.51-8.48 (m, 2H), 8.38 (s, 1H), 7.52 (s, 1H), 5.11-5.06 (m, 1H), 2.04-1.98 (m, 1H), 1.86-1.77 (m, 1H), 1.74-1.66 (m, 1H), 1.30 (d, J=6.0 Hz, 3H), 0.87-0.80 (m, 4H), 0.77 (t, J=7.2 Hz, 3H).

Example 181

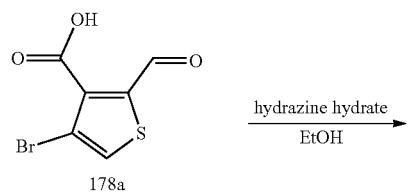

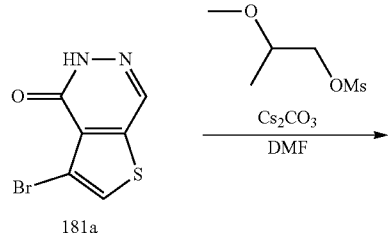

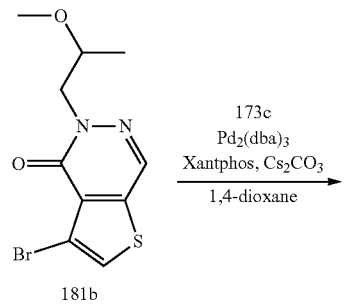

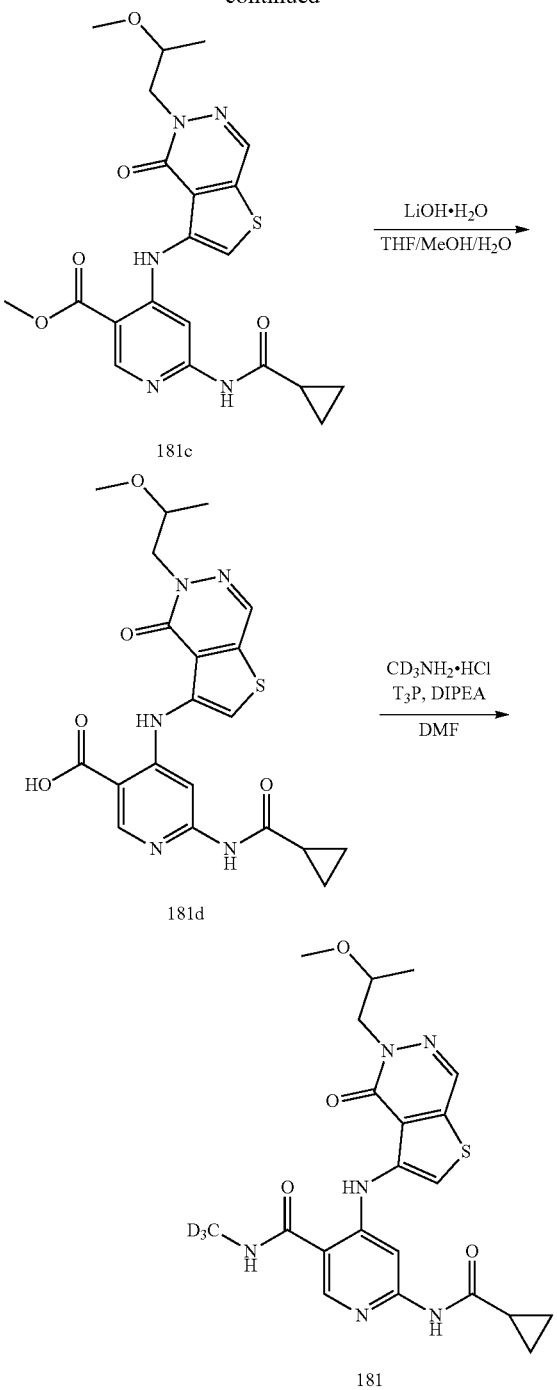

Step 1. 3-Bromothieno[2,3-d]pyridazin-4-(5H)-one (181a)

To a solution of 178a (8.4 g, 35.43 mmol) in EtOH (60 mL) was added hydrazine hydrate (8.86 g, 177.16 mmol) at r.t. The reaction mixture was stirred at 100° C. overnight. After cooling to r.t., the formed solid was filtered and the filter cake was dried to afford 181a (4.9 g, 60% yield) as a yellow solid. $^1$H NMR (400 MHz, DMSO-d$_6$) δ 12.84 (s, 1H), 8.58 (s, 1H), 8.14 (s, 1H).

Step 2. 3-Bromo-5-(2-methoxypropyl)thieno[2,3-d]pyridazin-4-(5H)-one (181b)

A mixture of 181a (300 mg, 1.30 mmol), 2-methoxypropyl methanesulfonate (328 mg, 1.95 mmol) and Cs₂CO₃ (847 mg, 2.60 mmol) in DMF (2 mL) was stirred at 70° C. for 12 h. After cooling to r.t., the reaction mixture was diluted with water (10 mL). The formed solid was filtered and the filter cake was dried to afford 181b (350 mg, 89% yield) as a yellow solid. LC-MS (Method 3) $t_R$=1.38 min, m/z (M+H)⁺=303.0.

Step 3. 4-((5-(Sec-butyl)-4-oxo-4,5-dihydrothieno[2,3-d]pyridazin-3-yl)amino)-6-(cyclopropanecarboxamido)nicotinic acid (181c)

Compound 181c (400 mg, 76% yield), a yellow solid, was synthesized by utilizing a similar preparative procedure of Step 6 in Example 171 with 181b (350 mg, 1.15 mmol) and 173c (272 mg, 1.15 mmol) as starting materials. LC-MS (Method 3) $t_R$=1.60 min, m/z (M+H)⁺=458.2.

Step 4. 6-(Cyclopropanecarboxamido)-4-((5-(2-methoxypropyl)-4-oxo-4,5-dihydrothieno[2,3-d]pyridazin-3-yl)amino)nicotinic acid (181d)

Compound 181d (300 mg, 77% yield), a yellow solid, was synthesized by utilizing a similar preparative procedure of Step 3 in Example 27 with 181c (400 mg, 0.87 mmol) as the starting material. LC-MS (Method 3) $t_R$=1.16 min, m/z (M+H)⁺=444.1.

Step 5. 6-(Cyclopropanecarboxamido)-4-((5-(2-methoxypropyl)-4-oxo-4,5-dihydrothieno[2,3-d]pyridazin-3-yl)amino)-N-(methyl-d₃)nicotinamide (181)

Compound 181 (100 mg, 32% yield), a gray solid, was synthesized by utilizing a similar preparative procedure of Step 2 in Example 11 with 181d (300 mg, 0.68 mmol) and trideuteriomethanamine hydrochloride (239 mg, 3.38 mmol) as starting materials. LC-MS (Method 1) $t_R$=2.61 min, m/z (M+H)⁺=460.1. ¹H NMR (400 MHz, DMSO-d₆) δ 11.39 (s, 1H), 10.88 (s, 1H), 8.58 (s, 1H), 8.51 (s, 1H), 8.49 (s, 1H), 8.37 (s, 1H), 7.54 (s, 1H), 4.29-4.27 (m, 1H), 4.01-3.99 (m, 1H), 3.88-3.76 (m, 1H), 3.21 (s, 3H), 2.00-1.98 (m, 1H), 1.14 (d, J=6.4 Hz, 3H), 0.82-0.80 (m, 4H).

Example 182

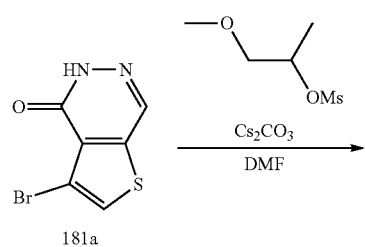

181a

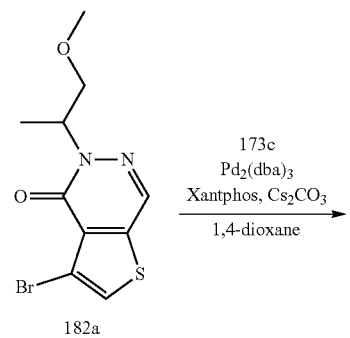

182a

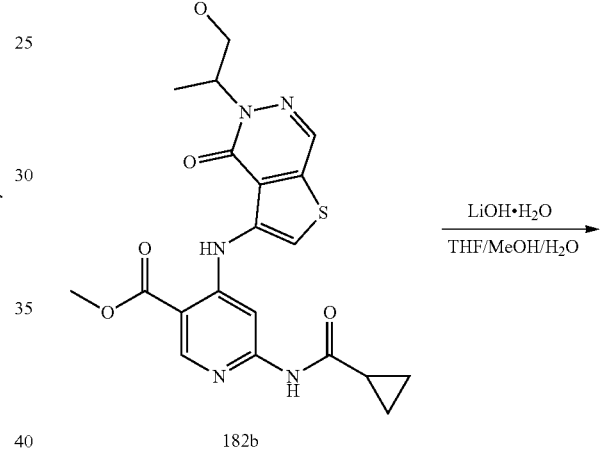

182b

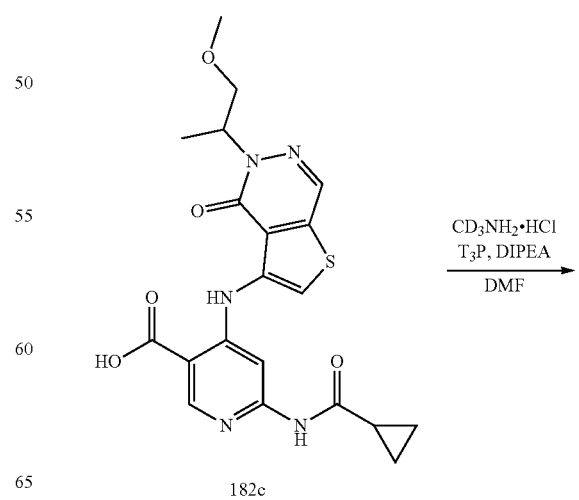

182c

1H), 3.53-3.49 (m, 1H), 3.20 (s, 3H), 2.02-1.96 (m, 1H), 1.26 (d, J=6.8 Hz, 3H), 0.99-0.91 (m, 4H).

Example 183

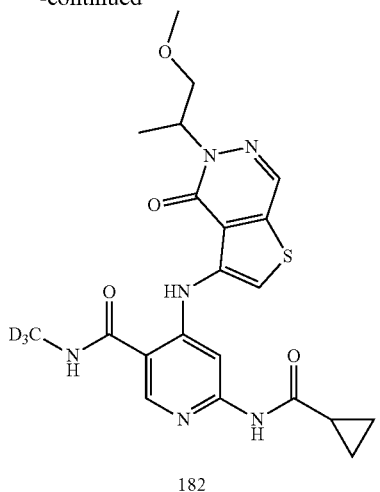

182

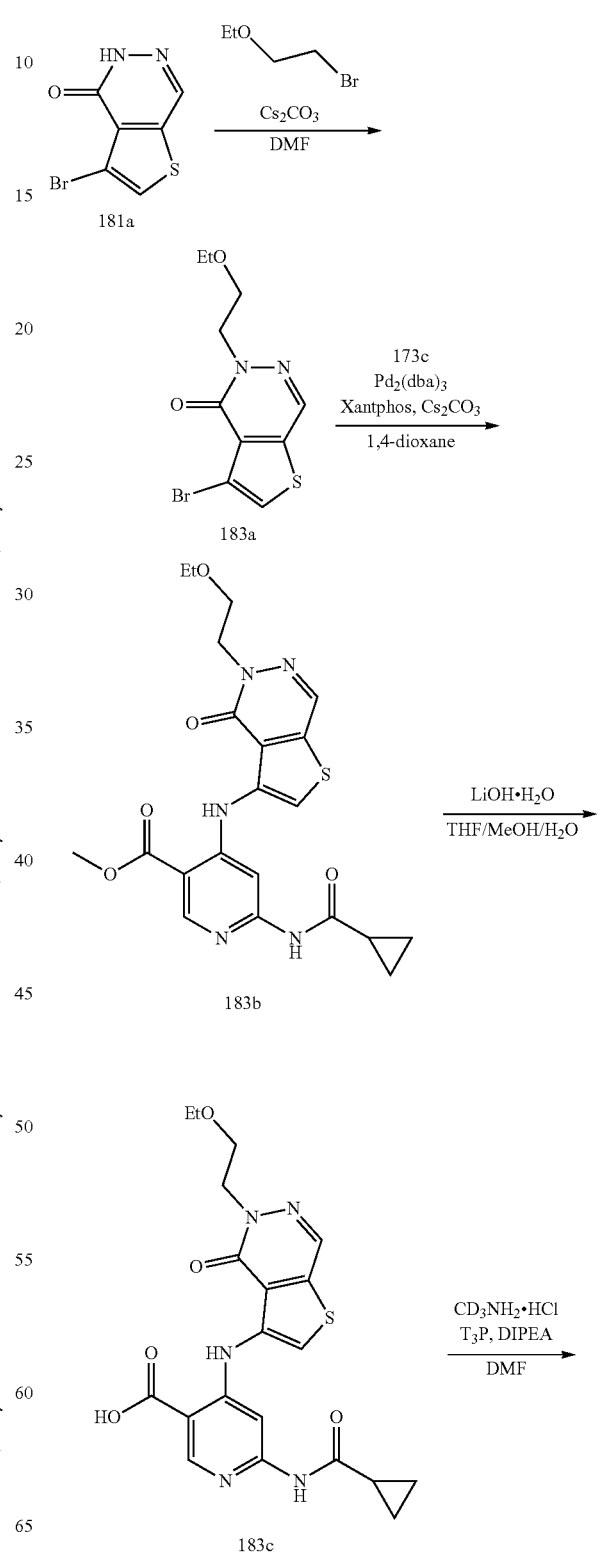

Step 1. 3-Bromo-5-(1-methoxypropan-2-yl)thieno[2,3-d]pyridazin-4-(5H)-one (182a)

Compound 182a (400 mg, 69% yield), a yellow solid, was synthesized by utilizing a similar preparative procedure of Step 1 in Example 110 with 181a (300 mg, 1.30 mmol) and 1-methoxypropan-2-yl methanesulfonate (327 mg, 1.95 mmol) as starting materials. $^1$H NMR (400 MHz, DMSO-$d_6$) δ 8.67 (s, 1H), 8.16 (s, 1H), 5.38-5.33 (m, 1H), 3.71-3.66 (m, 1H), 3.50-3.46 (m, 1H), 3.20 (s, 3H), 1.24 (d, J=6.8 Hz, 3H).

Step 2. Methyl 6-(cyclopropanecarboxamido)-4-((5-(1-methoxypropan-2-yl)-4-oxo-4,5-dihydrothieno[2,3-d]pyridazin-3-yl)amino)nicotinate (182b)

Compound 182b (210 mg, 52% yield), a yellow solid, was synthesized by utilizing a similar preparative procedure of Step 6 in Example 171 with 182a (270 mg, 0.89 mmol) and 173c (209 mg, 0.89 mmol) as starting materials. LC-MS (Method 3) $t_R$=1.62 min, m/z (M+H)$^+$=458.2.

Step 3. 6-(Cyclopropanecarboxamido)-4-((5-(1-methoxypropan-2-yl)-4-oxo-4,5-dihydrothieno[2,3-d]pyridazin-3-yl)amino)nicotinic acid (182c)

Compound 182c (195 mg, 96% yield), a yellow solid, was synthesized by utilizing a similar preparative procedure of Step 3 in Example 27 with 182b (210 mg, 0.46 mmol) as the starting material. LC-MS (Method 3) $t_R$=1.21 min, m/z (M+H)$^+$=444.1.

Step 4. 6-(Cyclopropanecarboxamido)-4-((5-(1-methoxypropan-2-yl)-4-oxo-4,5-dihydrothieno[2,3-d]pyridazin-3-yl)amino)-N-(methyl-$d_3$)nicotinamide (182)

Compound 182 (90 mg, 45% yield), a yellow solid, was synthesized by utilizing a similar preparative procedure of Step 2 in Example 11 with 182c (194 mg, 0.44 mmol) and trideuteriomethanamine hydrochloride (124 mg, 1.76 mmol) as starting materials. LC-MS (Method 2) $t_R$=3.16 min, m/z (M+H)$^+$=460.1. $^1$H NMR (400 MHz, DMSO-$d_6$) δ 12.06 (s, 1H), 11.68 (s, 1H), 8.87 (s, 1H), 8.69 (s, 1H), 8.47 (s, 1H), 7.92 (s, 1H), 7.83 (s, 1H), 5.39-5.34 (m, 1H), 3.73-3.68 (m,

541

-continued

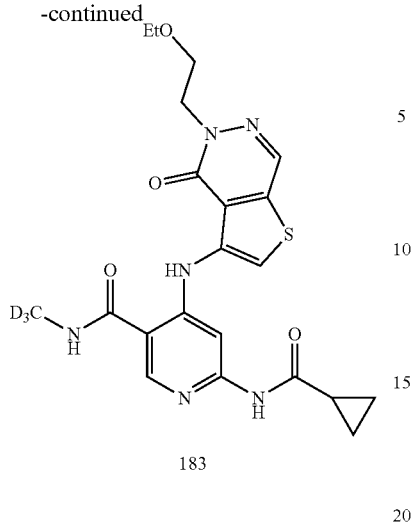

183

Step 1. 3-Bromo-5-(2-ethoxyethyl)thieno[2,3-d]pyridazin-4-(5H)-one (183a)

Compound 183a (390 mg, 99% yield), a yellow solid, was synthesized by utilizing a similar preparative procedure of Step 1 in Example 110 with 181a (300 mg, 1.30 mmol) and 1-bromo-2-ethoxyethane (298 mg, 1.95 mmol) as starting materials. LC-MS (Method 3) $t_R$=1.48 min, m/z (M+H)$^+$=305.1.

Step 2. Methyl 6-(cyclopropanecarboxamido)-4-((5-(2-ethoxyethyl)-4-oxo-4,5-dihydrothieno[2,3-d]pyridazin-3-yl)amino)nicotinate (183b)

Compound 183b (500 mg, 85% yield), a yellow solid, was synthesized by utilizing a similar preparative procedure of Step 6 in Example 171 with 183a (390 mg, 1.29 mmol) and 173c (363 mg, 1.54 mmol) as starting materials. LC-MS (Method 3) $t_R$=1.45 min, m/z (M+H)$^+$=458.1.

Step 3. 6-(Cyclopropanecarboxamido)-4-((5-(2-ethoxyethyl)-4-oxo-4,5-dihydrothieno[2,3-d]pyridazin-3-yl)amino)nicotinic acid (183c)

Compound 183c (227 mg, 78% yield), a white solid, was synthesized by utilizing a similar preparative procedure of Step 3 in Example 27 with 183b (300 mg, 0.66 mmol) as the starting material. LC-MS (Method 3) $t_R$=1.15 min, m/z (M+H)$^+$=444.1.

Step 4. 6-(Cyclopropanecarboxamido)-4-((5-(2-ethoxyethyl)-4-oxo-4,5-dihydrothieno[2,3-d]pyridazin-3-yl)amino)-N-(methyl-d₃)nicotinamide (183)

Compound 183 (40 mg, 17% yield), a white solid, was synthesized by utilizing a similar preparative procedure of Step 2 in Example 11 with 183c (225 mg, 0.51 mmol) and trideuteriomethanamine hydrochloride (143 mg, 2.03 mmol) as starting materials. LC-MS (Method 2) $t_R$=2.58 min, m/z (M+H)$^+$=460.1. $^1$H NMR (400 MHz, DMSO-$d_6$) δ 11.41 (s, 1H), 10.88 (s, 1H), 8.58 (s, 1H), 8.51 (s, 1H), 8.49 (s, 1H), 8.38 (s, 1H), 7.53 (s, 1H), 4.29 (t, J=6.0 Hz, 2H), 3.74 (t, J=5.6 Hz, 2H), 3.45 (q, J=7.2 Hz, 2H), 2.03-2.01 (m, 1H), 1.06 (t, J=7.2 Hz, 3H), 0.84-0.81 (m, 4H).

542

Example 184

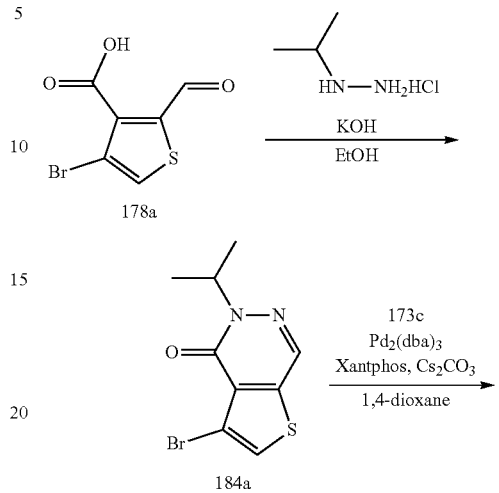

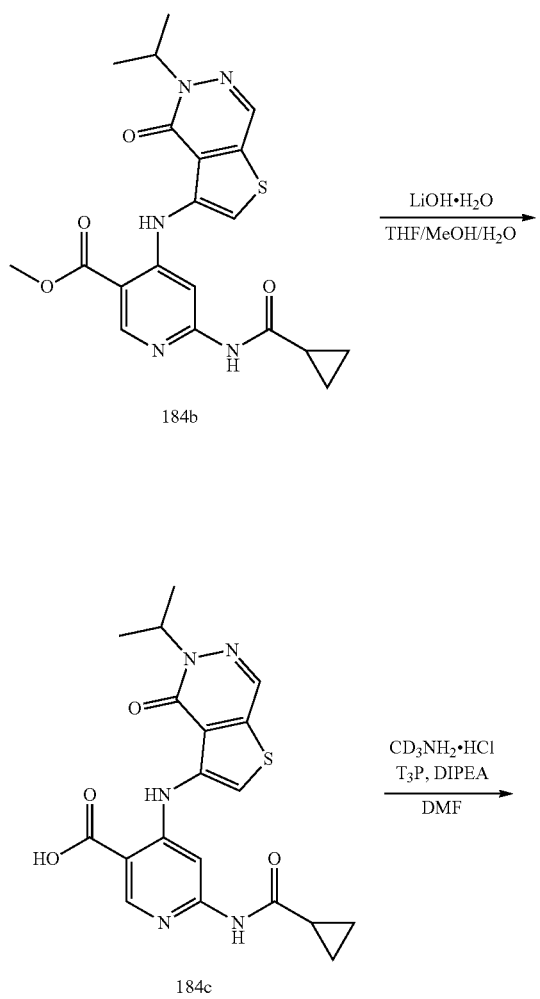

543

-continued

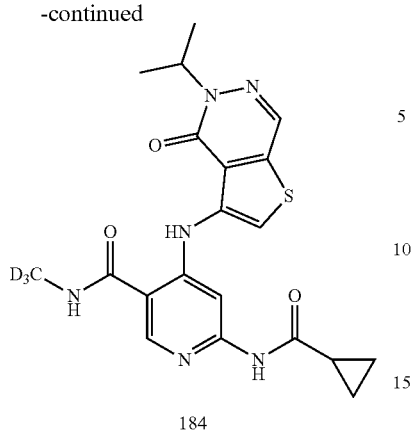

184

Step 1. 3-Bromo-5-isopropylthieno[2,3-d]pyridazin-4-(5H)-one (184a)

Compound 184a (2.8 g, 97% yield), a yellow solid, was synthesized by utilizing a similar preparative procedure of Step 1 in Example 178 with 178a (2.5 g, 10.55 mmol) and isopropylhydrazine hydrochloride (1.75 g, 15.82 mmol) as starting materials. LC-MS (Method 1) $t_R$=1.52 min, m/z (M+H)$^+$=274.9.

Step 2. Methyl 6-(cyclopropanecarboxamido)-4-((5-isopropyl-4-oxo-4,5-dihydrothieno[2,3-d]pyridazin-3-yl)amino)nicotinate (184b)

Compound 184b (500 mg, 64% yield), a yellow solid, was synthesized by utilizing a similar preparative procedure of Step 6 in Example 171 with 184a (500 mg, 1.83 mmol) and 173c (344 mg, 1.46 mmol) as starting materials. LC-MS (Method 3) $t_R$=1.78 min, m/z (M+H)$^+$=427.9.

Step 3. 6-(Cyclopropanecarboxamido)-4-((5-isopropyl-4-oxo-4,5-dihydrothieno[2,3-d]pyridazin-3-yl)amino)nicotinic acid (184c)

Compound 184c (195 mg, 78% yield), a yellow solid, was synthesized by utilizing a similar preparative procedure of Step 3 in Example 27 with 184b (269 mg, 0.61 mmol) as the starting material. LC-MS (Method 3) $t_R$=1.18 min, m/z (M+H)$^+$=414.1.

Step 4. 6-(Cyclopropanecarboxamido)-4-((5-isopropyl-4-oxo-4,5-dihydrothieno[2,3-d]pyridazin-3-yl)amino)-N-(methyl-d$_3$)nicotinamide (184)

Compound 184 (80 mg, 48% yield), a white solid, was synthesized by utilizing a similar preparative procedure of Step 2 in Example 11 with 184c (195 mg, 0.47 mmol) and trideuteriomethanamine hydrochloride (133 mg, 1.89 mmol) as starting materials. LC-MS (Method 1) $t_R$=3.31 min, m/z (M+H)$^+$=430.1. $^1$H NMR (400 MHz, DMSO-d$_6$) δ 12.12 (s, 1H), 11.68 (s, 1H), 8.85 (s, 1H), 8.68 (s, 1H), 8.46 (s, 1H), 7.89 (s, 1H), 7.83 (s, 1H), 5.28-5.23 (m, 1H), 2.00-1.96 (m, 1H), 1.33 (d, J=6.4 Hz, 6H), 0.96-0.92 (m, 4H).

544

Example 185

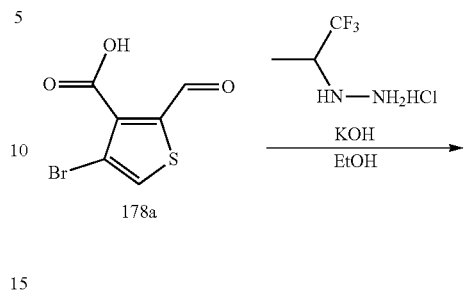

178a

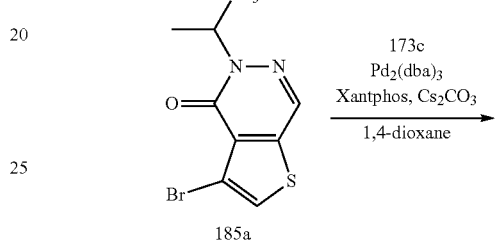

185a

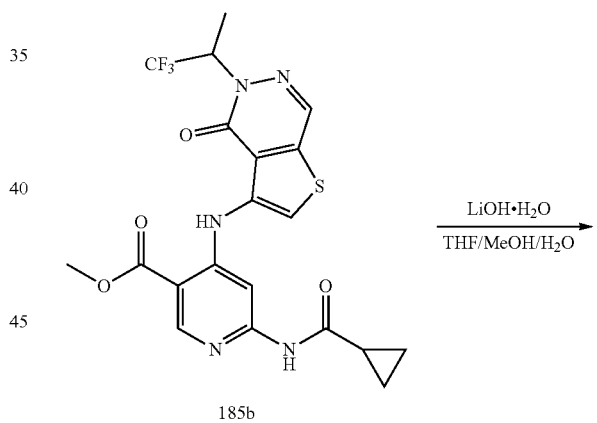

185b

185c

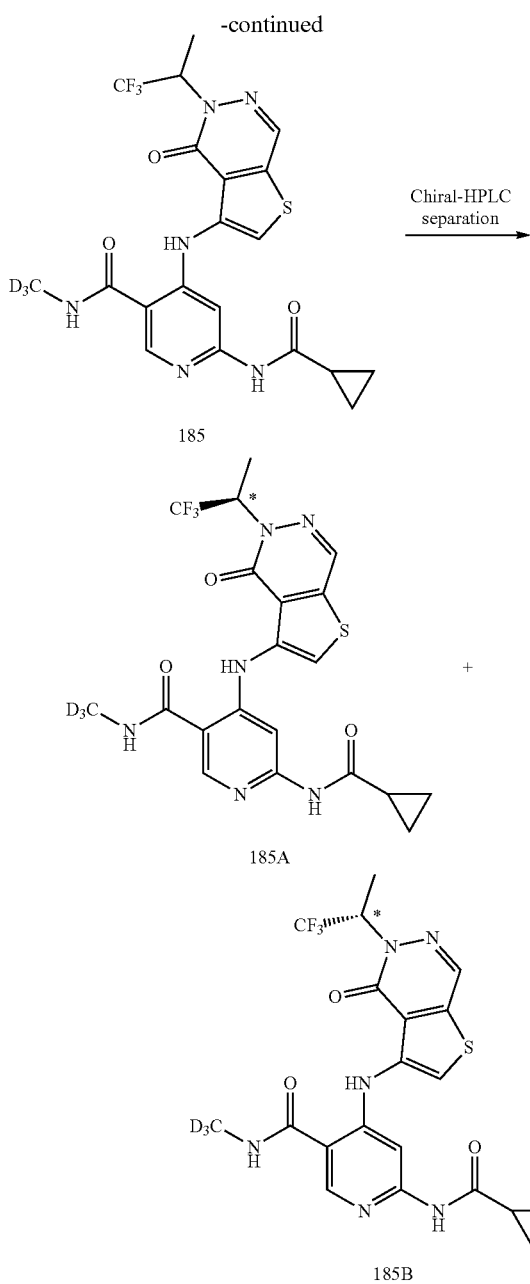

185

Chiral-HPLC separation →

185A

+

185B

Step 1. 3-Bromo-5-(1,1,1-trifluoropropan-2-yl) thieno[2,34]pyridazin-4-(5H)-one (185a)

Compound 185a (3.4 g, 65% yield), a yellow solid, was synthesized by utilizing a similar preparative procedure of Step 1 in Example 178 with 178a (5.0 g, 15.95 mmol) and (1,1,1-trifluoropropan-2-yl)hydrazine hydrochloride (2.63 g, 15.95 mmol) as starting materials. LC-MS (Method 1) $t_R$=1.48 min, m/z (M+H)$^+$=328.9.

Step 2. Methyl 6-(cyclopropanecarboxamido)-4-((4-oxo-5-(1,1,1-trifluoropropan-2-yl)-4,5-dihydrothieno [2,3-d]pyridazin-3-yl)amino)nicotinate (185b)

Compound 185b (560 mg, 76% yield), a yellow solid, was synthesized by utilizing a similar preparative procedure of Step 6 in Example 171 with 185a (500 mg, 1.53 mmol) and 173c (323 mg, 1.38 mmol) as starting materials. LC-MS (Method 3) $t_R$=1.63 min, m/z (M+H)$^+$=482.0.

Step 3. 6-(Cyclopropanecarboxamido)-4-((4-oxo-5-(1,1,1-trifluoropropan-2-yl)-4,5-dihydrothieno[2,3-d] pyridazin-3-yl)amino)nicotinic acid (185c)

To a solution of 185b (250 mg, 0.52 mmol) and LiOH·H$_2$O (109 mg, 2.60 mmol) in THF/MeOH/H$_2$O (5 mL, v/v/v=3/1/1 mL) was stirred at 60° C. for 12 h. The organic solvent was removed under reduced pressure and the aqueous layer was acidified with 1 N HCl to pH=2. The formed solid was collected by filtering and was dried to afford compound 185c (230 mg, 95% yield) as a yellow solid. LC-MS (Method 3) $t_R$=1.23 min, m/z (M+H)$^+$=468.0.

Step 4. 6-(Cyclopropanecarboxamido)-N-(methyl-d$_3$)-4-((4-oxo-5-(1,1,1-trifluoropropan-2-yl)-4,5-dihydrothieno[2,3-d]pyridazin-3-yl)amino)nicotinamide (185)

Compound 185 (120 mg, 50% yield), a light-yellow solid, was synthesized by utilizing a similar preparative procedure of Step 2 in Example 11 with 185c (230 mg, 0.49 mmol) and trideuteriomethanamine hydrochloride (174 mg, 2.46 mmol) as starting materials. LC-MS (Method 2) $t_R$=3.52 min, m/z (M+H)$^+$=484.1. $^1$H NMR (400 MHz, DMSO-d$_6$) δ 11.45 (s, 1H), 10.89 (s, 1H), 8.71 (s, 1H), 8.53 (s, 1H), 8.50 (s, 1H), 8.37 (s, 1H), 7.61 (s, 1H), 5.94-5.91 (m, 1H), 2.02-1.98 (m, 1H), 1.61 (d, J=6.8 Hz, 3H), 0.83-0.81 (m, 4H).

Step 5. (R*)-6-(cyclopropanecarboxamido)-N-(methyl-d$_3$)-4-((4-oxo-5-(1,1,1-trifluoropropan-2-yl)-4,5-dihydrothieno[2,3-d]pyridazin-3-yl)amino) nicotinamide (185A) and (S*)-6-(Cyclopropanecarboxamido)-N-(methyl-d$_3$)-4-((4-oxo-5-(1,1,1-trifluoropropan-2-yl)-4,5-dihydrothieno [2,3-d]pyridazin-3-yl)amino)nicotinamide (185B)

Compound 185 (40 mg) was separated by Prep-Chiral HPLC to afford 185A (14.5 mg, 36% yield) as a yellow solid, and 185B (15.0 mg, 37% yield) as a yellow solid.

185A: LC-MS (Method 2) $t_R$=3.39 min, m/z (M+H)$^+$=484.0. $^1$H NMR (400 MHz, DMSO-d$_6$) δ 11.46 (s, 1H), 10.90 (s, 1H), 8.71 (s, 1H), 8.53 (s, 1H), 8.51 (s, 1H), 8.37 (s, 1H), 7.61 (s, 1H), 5.94-5.91 (m, 1H), 2.00-1.98 (m, 1H), 1.60 (d, J=6.8 Hz, 3H), 0.83-0.81 (m, 4H).

185B: LC-MS (Method 2) $t_R$=3.44 min, m/z (M+H)$^+$=484.0. $^1$H NMR (400 MHz, DMSO-d$_6$) δ 11.46 (s, 1H), 10.90 (s, 1H), 8.71 (s, 1H), 8.53 (s, 1H), 8.51 (s, 1H), 8.37 (s, 1H), 7.61 (s, 1H), 5.94-5.91 (m, 1H), 2.00-1.98 (m, 1H), 1.60 (d, J=6.8 Hz, 3H), 0.83-0.81 (m, 4H).

Example 186

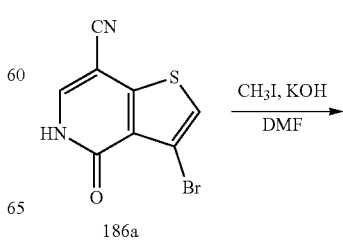

186a

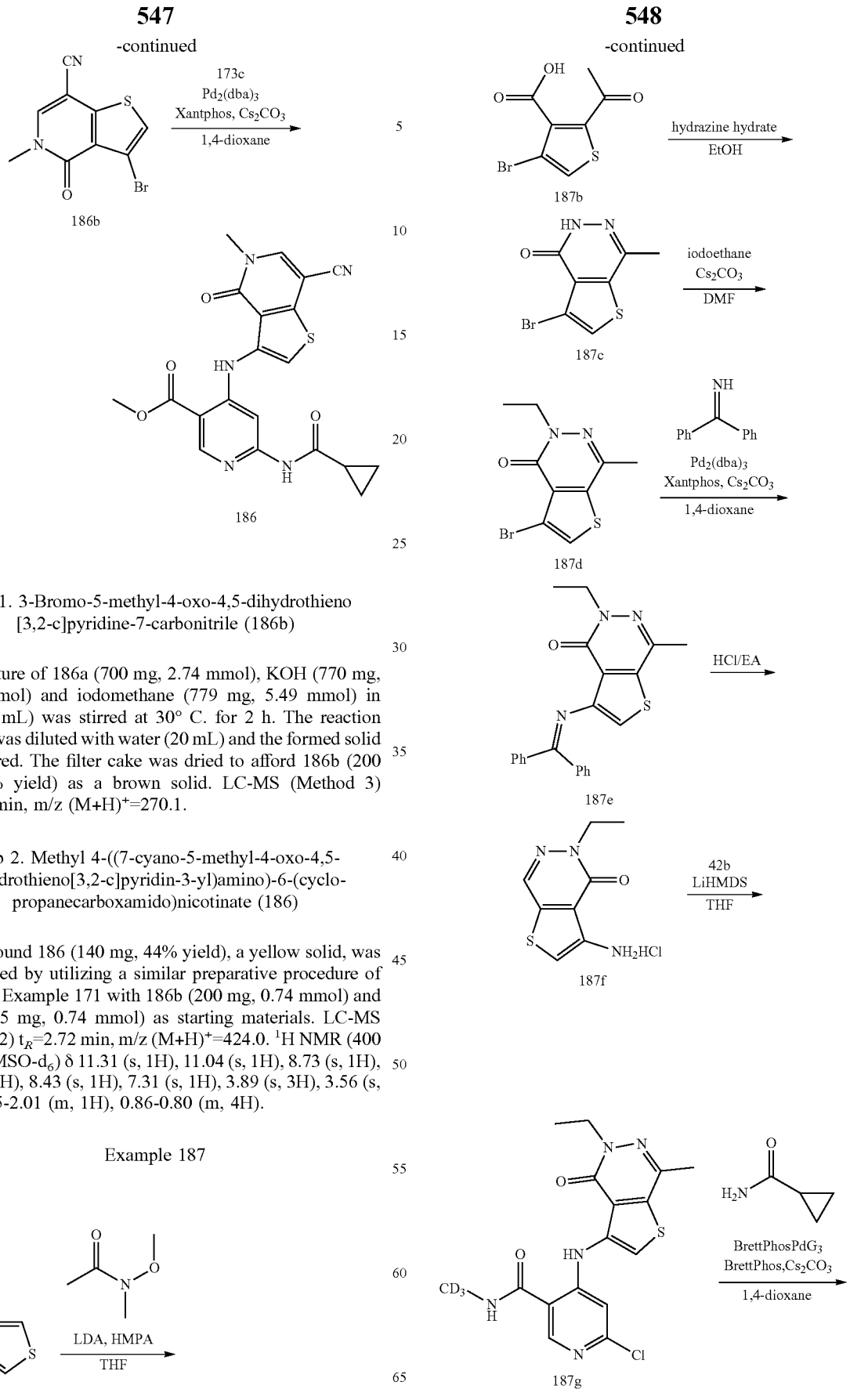

Step 1. 3-Bromo-5-methyl-4-oxo-4,5-dihydrothieno[3,2-c]pyridine-7-carbonitrile (186b)

A mixture of 186a (700 mg, 2.74 mmol), KOH (770 mg, 13.72 mmol) and iodomethane (779 mg, 5.49 mmol) in DMF (8 mL) was stirred at 30° C. for 2 h. The reaction mixture was diluted with water (20 mL) and the formed solid was filtered. The filter cake was dried to afford 186b (200 mg, 27% yield) as a brown solid. LC-MS (Method 3) $t_R$=0.65 min, m/z (M+H)$^+$=270.1.

Step 2. Methyl 4-((7-cyano-5-methyl-4-oxo-4,5-dihydrothieno[3,2-c]pyridin-3-yl)amino)-6-(cyclopropanecarboxamido)nicotinate (186)

Compound 186 (140 mg, 44% yield), a yellow solid, was synthesized by utilizing a similar preparative procedure of Step 6 in Example 171 with 186b (200 mg, 0.74 mmol) and 173c (175 mg, 0.74 mmol) as starting materials. LC-MS (Method 2) $t_R$=2.72 min, m/z (M+H)$^+$=424.0. $^1$H NMR (400 MHz, DMSO-d$_6$) δ 11.31 (s, 1H), 11.04 (s, 1H), 8.73 (s, 1H), 8.62 (s, 1H), 8.43 (s, 1H), 7.31 (s, 1H), 3.89 (s, 3H), 3.56 (s, 3H), 2.05-2.01 (m, 1H), 0.86-0.80 (m, 4H).

Example 187

-continued

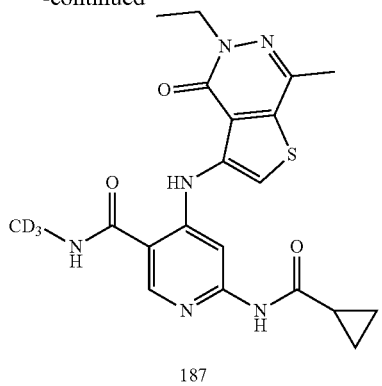

187

Step 1. 2-Acetyl-4-bromothiophene-3-carboxylic acid (187b)

To a solution of 187a (5 g, 23.92 mmol) and hexamethylphosphoramide (857 mg, 4.78 mmol) in THF (100 mL) was added LDA dropwise (26.3 mL, 52.62 mmol, 2 M in THF) at −60° C. After stirring for 1 h at −60° C., to the reaction mixture was added N-methoxy-N-methyl-acetamide (4.19 g, 40.66 mmol) at the same temperature. Then the reaction mixture was stirred at r.t. for 1 h. The reaction mixture was quenched with 1 N HCl to adjust to pH=1 and extracted with EtOAc (50 mL*2). The combined organic layer was washed with brine (30 mL) and dried over $Na_2SO_4$ and filtered. The filtrate was concentrated to afford 187b (3.5 g, 58% yield) as a yellow solid. $^1$H NMR (400 MHz, DMSO-$d_6$) δ 8.14 (s, 1H), 3.62 (s, 3H).

Step 2. 3-Bromo-7-methylthieno[2,3-d]pyridazin-4-(5H)-one (187c)

Compound 187c (1.0 g, 51% yield), a yellow solid, was synthesized by utilizing a similar preparative procedure of Step 1 in Example 181 with 187b (2.0 g, 7.97 mmol) and hydrazinium hydroxide (1.99 g, 40 mmol) as starting materials. $^1$H NMR (400 MHz, DMSO-$d_6$) δ 12.78 (s, 1H), 8.27 (s, 1H), 2.62 (s, 3H).

Step 3. 3-Bromo-5-ethyl-7-methylthieno[2,3-d]pyridazin-4-(5H)-one (187d)

A mixture of 187c (500 mg, 2.04 mmol), iodoethane (477 mg, 3.06 mmol) and $Cs_2CO_3$ (1.33 g, 4.08 mmol) in DMF (5 mL) was stirred at 80° C. for 2 h. After cooling to r.t., the reaction mixture was diluted with $H_2O$ (20 mL) and the formed solid was filtered. The filter cake was dried to afford 187d (485 mg, 87% yield) as a brown solid. LC-MS (Method 1) $t_R$=1.42 min, m/z (M+H)$^+$=274.0.

Step 4. 3-((Diphenylmethylene)amino)-5-ethyl-7-methylthieno[2,3-d]pyridazin-4-(5H)-one (187e)

A mixture of 187d (435 mg, 1.59 mmol), diphenylmethanimine (433 mg, 2.39 mmol), $Pd_2(dba)_3$ (73 mg, 0.08 mmol), XantPhos (46 mg, 0.08 mmol) and $Cs_2CO_3$ (1.04 g, 3.19 mmol) in 1,4-dioxane (4 mL) was stirred at 90° C. for 4 h under $N_2$. The reaction mixture was concentrated and the residue was purified by Prep-HPLC (Method A) to afford 187e (344 mg, 58% yield) as a white solid. LC-MS (Method 3) $t_R$=1.87 min, m/z (M+H)$^+$=374.1.

Step 5. 3-Amino-5-ethylthieno[2,3-d]pyridazin-4-(5H)-one hydrochloride (187f)

A solution of 187e (344 mg, 0.92 mmol) in HCl/EtOAc (7 mL, 2 M) was stirred at r.t. for 4 h. The reaction mixture was filtered. The filter cake was dried to afford 187f (170 mg, 75% yield) as a white solid. LC-MS (Method 3) $t_R$=2.46 min, m/z (M+H)$^+$=196.1.

Step 6. 6-Chloro-4-((5-ethyl-7-methyl-4-oxo-4,5-dihydrothieno[2,3-d]pyridazin-3-yl)amino)-N-(methyl-$d_3$)nicotinamide (187g)

Compound 187g (145 mg, 62% yield), a brown solid, was synthesized by utilizing a similar preparative procedure of Step 5 in Example 50 with 187f (150 mg, 0.61 mmol) and 42b (127 mg, 0.61 mmol) as starting materials. LC-MS (Method 3) $t_R$=0.82 min, m/z (M+H)$^+$=381.1.

Step 7. 6-(Cyclopropanecarboxamido)-4-((5-ethyl-7-methyl-4-oxo-4,5-dihydrothieno[2,3-d]pyridazin-3-yl)amino)-N-(methyl-$d_3$)nicotinamide (187)

Compound 187 (80 mg, 51% yield), a white solid, was synthesized by utilizing a similar preparative procedure of Step 3 in Example 49 with 187g (140 mg, 0.37 mmol) and cyclopropanecarboxamide (156 mg, 1.84 mmol) as starting materials. LC-MS (Method 1) $t_R$=3.58 min, m/z (M+H)$^+$=430.1. $^1$H NMR (400 MHz, DMSO-$d_6$) δ 11.45 (s, 1H), 10.90 (s, 1H), 8.51 (s, 1H), 8.49 (s, 1H), 8.39 (s, 1H), 7.51 (s, 1H), 4.14 (q, J=7.2 Hz, 2H), 2.47 (s, 3H), 2.02-1.99 (m, 1H), 1.29 (t, J=7.2 Hz, 3H), 0.83-0.81 (m, 4H).

Example 188

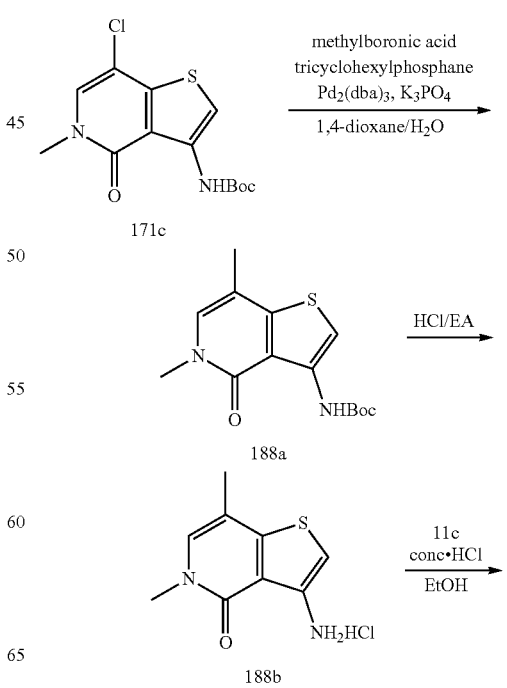

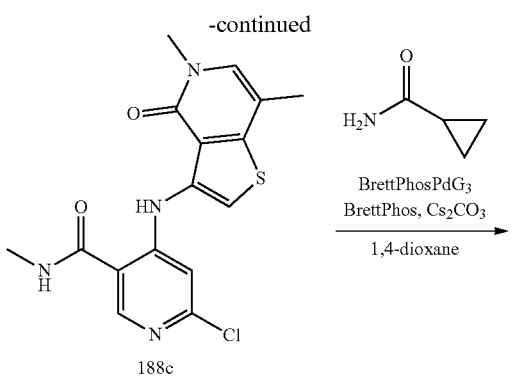

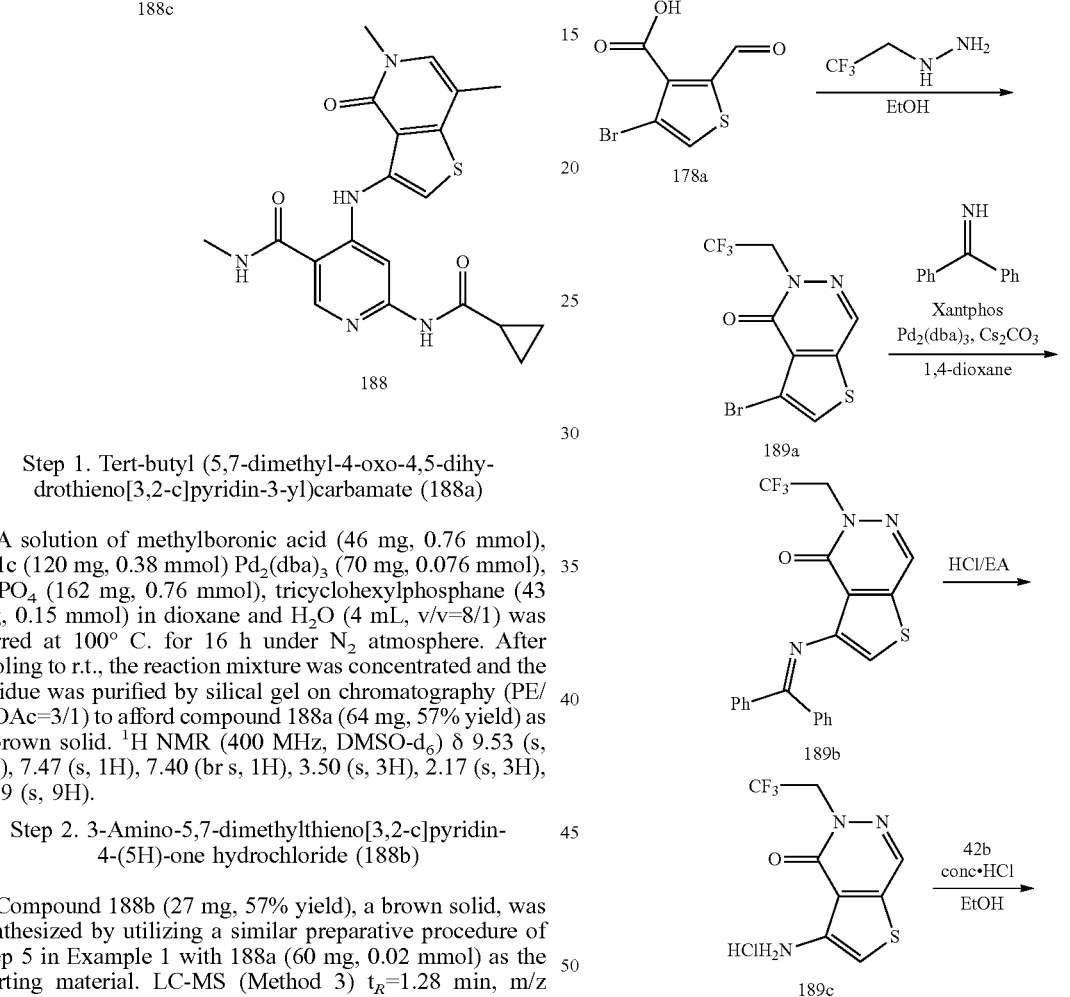

Step 3 in Example 49 with 188c (15 mg, 0.04 mmol) and cyclopropanecarboxamide (16 mg, 0.20 mmol) as starting materials. LC-MS (Method 1) $t_R$=3.07 min, m/z (M+H)$^+$=412.1. $^1$H NMR (400 MHz, DMSO-d$_6$) δ 11.45 (s, 1H), 10.84 (s, 1H), 8.46-8.44 (m, 2H), 8.41 (s, 1H), 7.45 (s, 1H), 7.09 (s, 1H), 3.48 (s, 3H), 2.78 (d, J=4.8 Hz, 3H), 2.17 (s, 3H), 2.03-1.99 (m, 1H), 0.85-0.79 (m, 4H).

Example 189

Step 1. Tert-butyl (5,7-dimethyl-4-oxo-4,5-dihydrothieno[3,2-c]pyridin-3-yl)carbamate (188a)

A solution of methylboronic acid (46 mg, 0.76 mmol), 171c (120 mg, 0.38 mmol) Pd$_2$(dba)$_3$ (70 mg, 0.076 mmol), K$_3$PO$_4$ (162 mg, 0.76 mmol), tricyclohexylphosphane (43 mg, 0.15 mmol) in dioxane and H$_2$O (4 mL, v/v=8/1) was stirred at 100° C. for 16 h under N$_2$ atmosphere. After cooling to r.t., the reaction mixture was concentrated and the residue was purified by silical gel on chromatography (PE/EtOAc=3/1) to afford compound 188a (64 mg, 57% yield) as a brown solid. $^1$H NMR (400 MHz, DMSO-d$_6$) δ 9.53 (s, 1H), 7.47 (s, 1H), 7.40 (br s, 1H), 3.50 (s, 3H), 2.17 (s, 3H), 1.49 (s, 9H).

Step 2. 3-Amino-5,7-dimethylthieno[3,2-c]pyridin-4-(5H)-one hydrochloride (188b)

Compound 188b (27 mg, 57% yield), a brown solid, was synthesized by utilizing a similar preparative procedure of Step 5 in Example 1 with 188a (60 mg, 0.02 mmol) as the starting material. LC-MS (Method 3) $t_R$=1.28 min, m/z (M+H)$^+$=195.1.

Step 3. 6-Chloro-4-((5,7-dimethyl-4-oxo-4,5-dihydrothieno[3,2-c]pyridin-3-yl)amino)-N-methylnicotinamide (188c)

Compound 188c (17 mg, 43% yield), a brown solid, was synthesized by utilizing a similar preparative procedure of Step 1 in Example 98 with 188b (25 mg, 0.11 mmol) and 11c (27 mg, 0.13 mmol) as starting materials. LC-MS (Method 3) $t_R$=1.36 min, m/z (M+H)$^+$=363.1.

Step 4. 6-(Cyclopropanecarboxamido)-4-((5,7-dimethyl-4-oxo-4,5-dihydrothieno[3,2-c]pyridin-3-yl)amino)-N-methylnicotinamide (188)

Compound 188 (1.0 mg, 6% yield), a white solid, was synthesized by utilizing a similar preparative procedure of

Step 5. 6-(Cyclopropanecarboxamido)-N-(methyl-d₃)-4-((4-oxo-5-(2,2,2-trifluoroethyl)-4,5-dihydrothieno[2,3-d]pyridazin-3-yl)amino)nicotinamide (189)

Compound 189 (101 mg, 50% yield), a white solid, was synthesized by utilizing a similar preparative procedure of Step 3 in Example 49 with 189d (180 mg, 0.43 mmol) and cyclopropanecarboxamide (182 mg, 2.14 mmol) as starting materials. LC-MS (Method 2) $t_R$=2.88 min, m/z (M+H)⁺=470.0. ¹H NMR (400 MHz, DMSO-d₆) δ 11.43 (s, 1H), 10.91 (s, 1H), 8.68 (s, 1H), 8.53-8.52 (m, 2H), 8.38 (s, 1H), 7.61 (s, 1H), 5.05-4.98 (m, 2H), 1.45-1.40 (m, 1H), 0.85-0.83 (m, 4H).

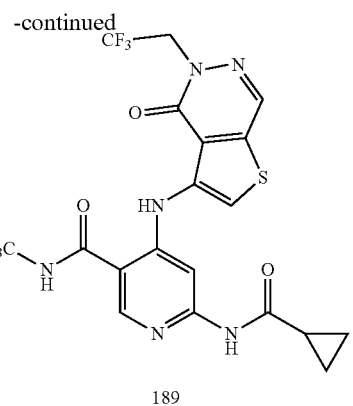

189

Example 190

Step 1. 3-Bromo-5-(2,2,2-trifluoroethyl)thieno[2,3-d]pyridazin-4-(5H)-one (189a)

A mixture of (2,2,2-trifluoroethyl)hydrazine (2.27 g, 19.91 mmol) and 178a (2.6 g, 6.64 mmol) in 30 mL of EtOH was stirred at 100° C. for 4 h. The reaction mixture was cooled and concentrated under reduced pressure. The residue was dissolved in EtOAc (100 mL) and washed with sat. Na₂CO₃ (20 mL*2), brine (20 mL), dried over Na₂SO₄, filtered and concentrated to afford compound 189a (1.64 g, 79% yield) as an off-white solid. ¹H NMR (400 MHz, DMSO-d₆) δ 8.73 (s, 1H), 8.24 (s, 1H), 4.15 (q, J=9.2 Hz, 2H).

Step 2. 3-((Diphenylmethylene)amino)-5-(2,2,2-trifluoroethyl)thieno[2,3-d]pyridazin-4-(5H)-one (189b)

A mixture of 189a (680 mg, 2.17 mmol), diphenylmethanimine (787 mg, 4.34 mmol), Pd₂(dba)₃ (199 mg, 0.22 mmol), XantPhos (126 mg, 0.22 mmol) and Cs₂CO₃ (1.42 g, 4.34 mmol) in 1,4-dioxane (4 mL) was stirred at 80° C. for 2 h under N₂. The reaction mixture was cooled and concentrated. The residue was purified by Prep-HPLC (Method A) to afford the compound 189b (600 mg, 67% yield) as a yellow solid. ¹H NMR (400 MHz, DMSO-d₆) δ 8.51 (s, 1H), 7.84-7.80 (m, 2H), 7.71-7.69 (m, 2H), 7.60-7.40 (m, 3H), 7.37-7.36 (m, 2H), 7.28-7.14 (m, 2H), 4.93 (q, J=8.4 Hz, 2H).

Step 3. 3-Amino-5-(2,2,2-trifluoroethyl)thieno[2,3-d]pyridazin-4-(5H)-one hydrochloride (189c)

A mixture of 189b (600 mg, 1.45 mmol) in HCl/EtOAc (12 mL, 2 M) was stirred for 2 h at r.t. The formed solid was filtered and the filter cake was dried to afford the title compound 189c (260 mg, 63% yield) as a yellow solid. LC-MS (Method 3) $t_R$=1.52 min, m/z (M+H)⁺=249.9.

Step 4. 6-Chloro-N-(methyl-d₃)-4-((4-oxo-5-(2,2,2-trifluoroethyl)-4,5-dihydrothieno[2,3-d]pyridazin-3-yl)amino)nicotinamide (189d)

Compound 189d (160 mg, 49% yield), a white solid, was synthesized by utilizing a similar preparative procedure of Step 1 in Example 98 with 189c (220 mg, 0.77 mmol) and 42b (160 mg, 0.77 mmol) as starting materials. LC-MS (Method 3) $t_R$=1.51 min, m/z (M+H)⁺=421.1.

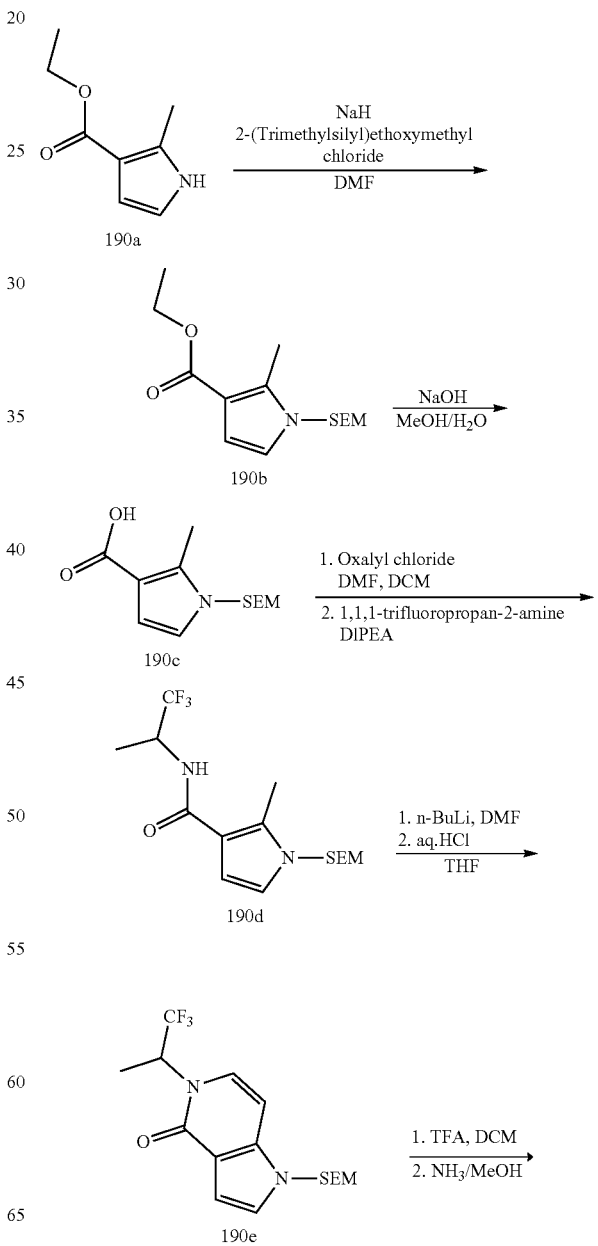

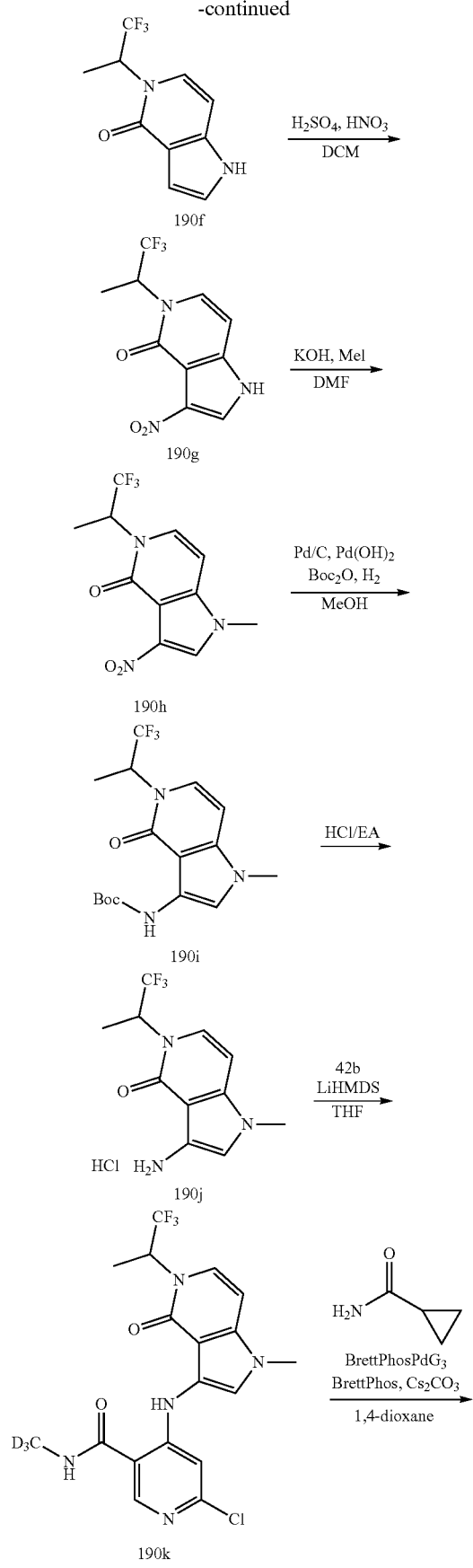

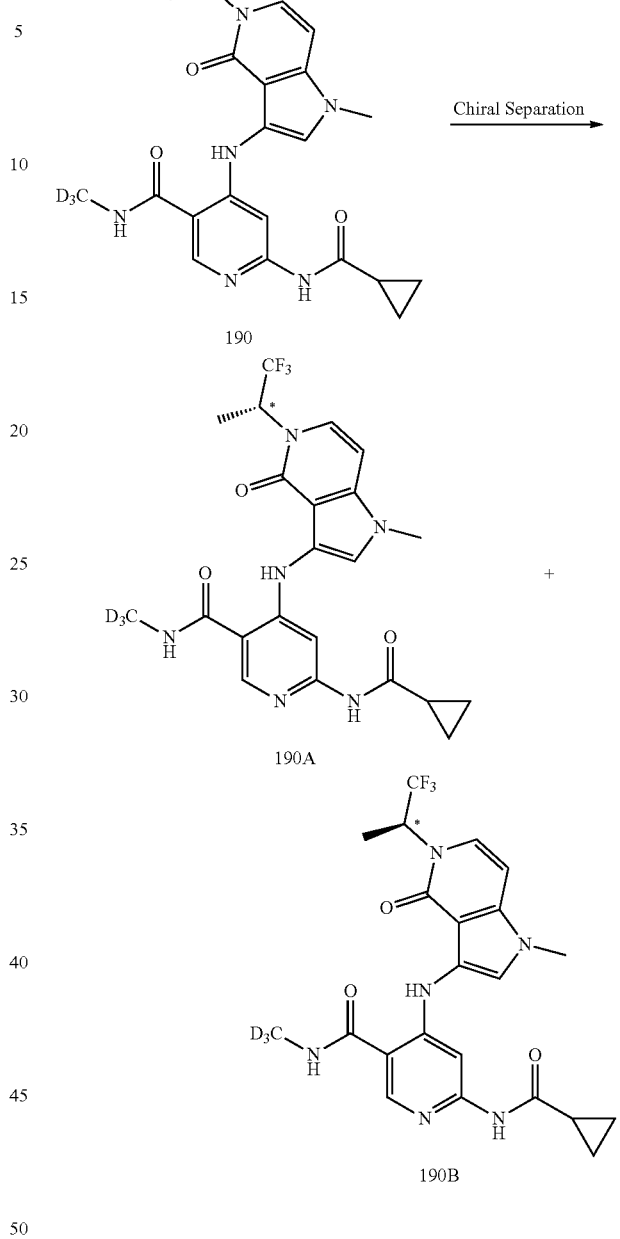

Step 1. Ethyl 2-methyl-1-((2-(trimethylsilyl)ethoxy)methyl)-1H-pyrrole-3-carboxylate (190b)

To a solution of ethyl 2-methyl-1H-pyrrole-3-carboxylate 190a (20 g, 130.57 mmol) in DMF (200 mL) was added NaH (3.60 g, 150.10 mmol, 60% purity in mineral oil) at 0° C. After stirring for 30 min, to the reaction was added 2-(trimethylsilyl)ethoxymethyl chloride (26.28 g, 156.68 mmol) dropwise at 0° C. The reaction mixture was stirred at r.t. for 1 h. Then the reaction mixture was poured into water (50 mL) and extracted with EtOAc (100 mL*3). The combined organic layer was washed with brine (50 mL), dried over $Na_2SO_4$, filtered and concentrated to afford compound 190b (28.8 g, 78% yield) as a yellow oil. $^1$H NMR (400 MHz, DMSO-$d_6$) δ 6.54 (d, J=3.2 Hz, 1H), 6.47 (d, J=3.2 Hz, 1H), 5.13 (s, 2H), 4.23 (q, J=6.8 Hz, 2H), 3.43 (t, J=7.6 Hz, 2H), 2.50 (s, 3H), 1.30 (t, J=6.8 Hz, 3H), 0.87 (t, J=8.0 Hz, 2H), 0.01 (s, 9H).

Step 2. 2-Methyl-1-((2-(trimethylsilyl)ethoxy) methyl)-1H-pyrrole-3-carboxylic acid (190c)

A solution of 190b (3 g, 10.58 mmol) and NaOH (2.12 g, 52.92 mmol) in MeOH (30 mL) and $H_2O$ (10 mL) was stirred at 90° C. for 16 h. After cooling to r.t., the solution was concentrated and the residue was diluted with water (30 mL). The aqueous layer was adjust to pH=3 with 2 M HCl and extracted with EtOAc (50 mL*3). The combined organic layer was washed with brine (30 mL), dried over $Na_2SO_4$, filtered and concentrated to afford compound 190c (2.7 g, yield given) as a white solid. $^1$H NMR (400 MHz, DMSO-$d_6$) δ 11.95 (brs, 1H), 6.84 (d, J=3.2 Hz, 1H), 6.37 (d, J=3.2 Hz, 1H), 5.27 (s, 2H), 3.49 (t, J=8.0 Hz, 2H), 2.55 (s, 3H), 0.87 (t, J=8.0 Hz, 2H), 0.02 (s, 9H).

Step 3. 2-Methyl-N-(1,1,1-trifluoropropan-2-yl)-1-((2-(trimethylsilyl)ethoxy)methyl)-1H-pyrrole-3-carboxamide (190d)

To a solution of 190c (1.6 g, 6.27 mmol) and DMF (46 mg, 0.62 mmol) in DCM (20 mL) was added oxalyl chloride (2.39 g, 18.80 mmol) at 0° C. After stirring at 0° C. for 2 h, the reaction solution was concentrated and the residue was dissolved in DCM (20 mL). To the solution was added DIPEA (3.23 g, 25.06 mmol) followed by 1,1,1-trifluoropropan-2-amine (709 mg, 6.27 mmol) at 0° C. The reaction mixture was stirred for 1 h at r.t. and diluted with DCM (50 mL). The solution was washed with water (15 mL), brine (15 mL), dried over $Na_2SO_4$, filtered and concentrated. The residue was purified by flash chromatography on silica gel (PE/EtOAc=5/1) to afford compound 190d (1.12 g, 51% yield) as a yellow oil. $^1$H NMR (400 MHz, DMSO-$d_6$) δ 7.98 (d, J=8.8 Hz, 1H), 6.84 (d, J=3.2 Hz, 1H), 6.62 (d, J=3.2 Hz, 1H), 5.25 (s, 2H), 4.82-4.73 (m, 1H), 3.48 (t, J=7.6 Hz, 2H), 2.54 (s, 3H), 1.34 (d, J=7.2 Hz, 3H), 0.87 (t, J=8.0 Hz, 2H), 0.01 (s, 9H).

Step 4. 5-(1,1,1-Trifluoropropan-2-yl)-1-((2-(trimethylsilyl)ethoxy)methyl)-1H-pyrrolo[3,2-c]pyridin-4-(5 1i)-one (190e)

A solution of 190d (3 g, 8.56 mmol) in THF (30 mL) was added n-BuLi (7 mL, 17.5 mmol, 2.5 M in THF) dropwise at −30° C. After stirring for 30 min at this temperature, to it was added anhydrous DMF (1.25 g, 17.12 mmol). The reaction mixture was stirred for 30 mins at −30° C. Then aq. HCl (6.5 mL, 2 M) was added to the reaction mixture slowly and the temperature was kept below −5° C. The reaction mixture was stirred for 2 h at r.t. and poured into water (50 mL). The solution was extracted with EtOAc (50 mL*3). The combined organic layer was washed with brine (50 mL), dried over $Na_2SO_4$, filtered and concentrated to afford compound 190e (2.85 g, 92% yield) as a black oil. LC-MS (Method 3) $t_R$=0.75 min, m/z (M+H)$^+$=360.8.

Step 5. 5-(1,1,1-Trifluoropropan-2-yl)-1H-pyrrolo[3,2-c]pyridin-4-(5H)-one (190f)

A solution of 190e (2.85 g, 7.91 mmol) in TFA/DCM (15 mL, v/v=1/3) was stirred at 50° C. for 2 h. After cooling to r.t., the reaction solution was concentrated and the residue was dissolved in $NH_3$ (g) in MeOH (20 mL, 2 M). The reaction mixture was stirred at r.t. for 2 h. The reaction mixture was concentrated and the residue was purified by flash chromatography on silica gel (PE/EtOAc=2/1) to afford compound 190f (788 mg, 43% yield) as a brown solid. $^1$H NMR (400 MHz, DMSO-$d_6$) δ 11.54 (brs, 1H), 7.30 (d, J=7.6 Hz, 1H), 7.12 (t, J=2.8 Hz, 1H), 6.57-6.55 (m, 2H), 5.99-5.92 (m, 1H), 1.57 (d, J=7.2 Hz, 3H).

Step 6. 3-Nitro-5-(1,1,1-trifluoropropan-2-yl)-1,5-dihydro-4H-pyrrolo[3,2-c]pyridin-4-one (190g)

To a solution of 190f (200 mg, 0.87 mmol) in DCM (2 mL) was added conc. sulfuric acid (109 mg, 1.09 mmol) followed by nitric acid (21 mg, 0.22 mmol) at 0° C. The reaction mixture was stirred for 1 h at r.t. The reaction mixture was poured into water (5 mL) and the formed solid was collected by filtering and dried to afford compound 190g (200 mg, 84% yield). LC-MS (Method 3) $t_R$=0.63 min, m/z (M+H)$^+$=275.8.

Step 7. 1-Methyl-3-nitro-5-(1,1,1-trifluoropropan-2-yl)-1H-pyrrolo[3,2-c]pyridin-4-(5H)-one (190h)

To a solution of 190g (250 mg, 0.91 mmol) in DMF (2 mL) was added KOH (102 mg, 1.82 mmol) at 0° C. After stirring for 30 min at 0° C., to it was added MeI (258 mg, 1.82 mmol). The reaction mixture was stirred for 1 h at 0° C. and poured into water (5 mL). The mixture was extracted with EtOAc (5 mL*3). The combined organic layer was concentrated to afford compound 190h (150 mg, 57% yield) as a yellow solid. $^1$H NMR (400 MHz, DMSO-$d_6$) δ 8.39 (s, 1H), 7.66 (d, J=7.6 Hz, 1H), 6.78 (d, J=7.6 Hz, 1H), 5.97-5.91 (m, 1H), 3.80 (s, 3H), 1.61 (d, J=7.2 Hz, 3H).

Step 8. Tert-butyl (1-methyl-4-oxo-5-(1,1,1-trifluoropropan-2-yl)-4,5-dihydro-1H-pyrrolo[3,2-c]pyridin-3-yl)carbamate (190i)

A mixture of 190h (100 mg, 0.35 mmol), Pd(OH)2 (10 mg, 10% wt), Pd/C (10 mg, 10% wt) and di-tert-butyl dicarbonate (151 mg, 0.69 mmol) in MeOH (2 mL) was stirred at 50° C. for 16 h under $H_2$ (1 atm). The reaction mixture was filtered and the filtrate was concentrated to afford compound 190i (124 mg, yield given) as a brown solid. LC-MS (Method 3) $t_R$=1.81 min, m/z (M+H)$^+$=360.0.

Step 9. 3-Amino-1-methyl-5-(1,1,1-trifluoropropan-2-yl)-1H-pyrrolo[3,2-c]pyridin-4-(5H)-one hydrochloride (190j)

A solution of 190i (124 mg, 0.35 mmol) in HCl/EtOAc (2 mL, 2 M) was stirred at 50° C. for 1 h. After cooling to r.t., the reaction was filtered and filter cake was dried to afford compound 190j (77 mg, 75% yield). LC-MS (Method 3) $t_R$=1.67 min, m/z (M+H)$^+$=360.0.

Step 10. 6-Chloro-N-(methyl-$d_3$)-4-((1-methyl-4-oxo-5-(1,1,1-trifluoropropan-2-yl)-4,5-dihydro-1H-pyrrolo[3,2-c]pyridin-3-yl)amino)nicotinamide (190k)

Compound 190k (18 mg, 22% yield), a white solid, was synthesized by utilizing a similar preparative procedure of Step 5 in Example 50 with 190j (55 mg, 0.19 mmol) and 42b (39 mg, 0.19 mmol) as starting materials. LC-MS (Method 3) $t_R$=1.36 min, m/z (M+H)$^+$=431.0.

Step 11. 6-(Cyclopropanecarboxamido)-N-(methyl-d₃)-4-((1-methyl-4-oxo-5-(1,1,1-trifluoropropan-2-yl)-4,5-dihydro-1H-pyrrolo[3,2-c]pyridin-3-yl)amino)nicotinamide (190)

Compound 190 (3.0 mg, 15% yield), a white solid, was synthesized by utilizing a similar preparative procedure of Step 3 in Example 49 with 190k (18 mg, 0.04 mmol) and cyclopropanecarboxamide (18 mg, 0.21 mmol) as starting materials. LC-MS (Method 2) $t_R$=2.71 min, m/z (M+H)⁺=480.1. ¹H NMR (400 MHz, DMSO-$d_6$) δ, 10.95 (s, 1H), 10.73 (s, 1H), 8.44 (s, 1H), 8.39 (s, 1H), 8.00 (s, 1H), 7.39 (d, J=7.6 Hz 1H), 7.07 (s, 1H), 6.68 (d, J=7.6 Hz 1H), 5.95-5.85 (m, 1H), 5.92 (s, 3H), 2.11-2.09 (m, 1H), 1.58 (d, J=7.2 Hz, 3H), 0.85-0.79 (m, 4H).

Step 12. (R*)-6-(Cyclopropanecarboxamido)-N-(methyl-d₃)-4-((1-methyl-4-oxo-5-(1,1,1-trifluoropropan-2-yl)-4,5-dihydro-1H-pyrrolo[3,2-c]pyridin-3-yl)amino)nicotinamide (190A) and (S*)-6-(Cyclopropanecarboxamido)-N-(methyl-d₃)-4-((1-methyl-4-oxo-5-(1,1,1-trifluoropropan-2-yl)-4,5-dihydro-1H-pyrrolo[3,2-c]pyridin-3-yl)amino)nicotinamide (190B)

Compound 190 (17.2 mg) was separated by Prep-Chiral HPLC to afford the title compound 190A (8.1 mg) as a white solid and 190B (8.2 mg) as a white solid.

190A: LC-MS (Method 1) $t_R$=2.70 min, m/z (M+H)⁺=480.0. ¹H NMR (400 MHz, DMSO-$d_6$) δ 10.95 (s, 1H), 10.73 (s, 1H), 8.44 (s, 1H), 8.40 (s, 1H), 8.01 (s, 1H), 7.39 (d, J=7.6 Hz, 1H), 7.07 (s, 1H), 6.69 (d, J=7.6 Hz, 1H), 5.94-5.89 (m, 1H), 3.72 (s, 3H), 2.02-1.99 (m, 1H), 1.58 (d, J=5.2 Hz, 3H), 0.85-0.79 (m, 4H).

190B: LC-MS (Method 1) $t_R$=2.71 min, m/z (M+H)⁺=480.1. ¹H NMR (400 MHz, DMSO-$d_6$) δ 10.96 (s, 1H), 10.73 (s, 1H), 8.45 (s, 1H), 8.41 (s, 1H), 8.01 (s, 1H), 7.39 (d, J=7.6 Hz, 1H), 7.07 (s, 1H), 6.68 (d, J=7.6 Hz, 1H), 5.94-5.89 (m, 1H), 3.72 (s, 3H), 2.02-1.99 (m, 1H), 1.58 (d, J=5.2 Hz, 3H), 0.85-0.79 (m, 4H).

Example 191

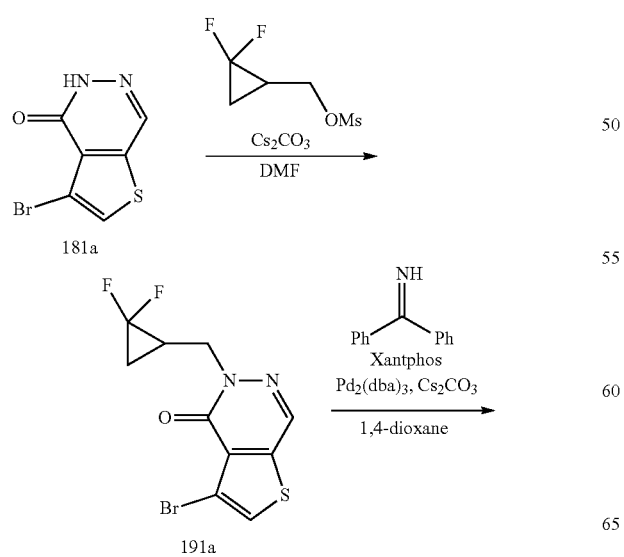

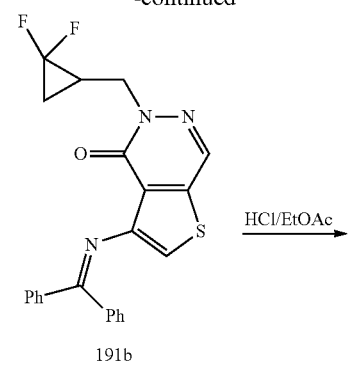

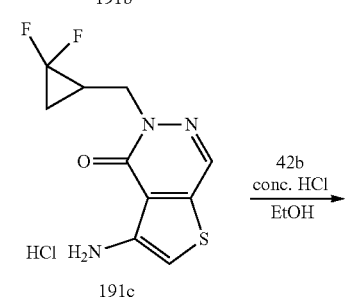

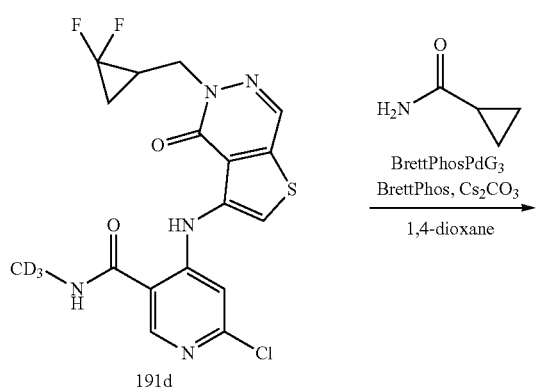

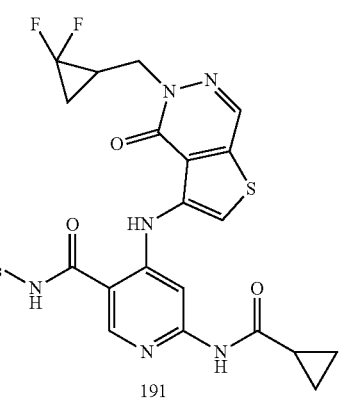

Step 1. 3-Bromo-5-((2,2-difluorocyclopropyl)methyl)thieno[2,3-d]pyridazin-4-(5H)-one (191a)

A mixture of 181a (400 mg, 1.73 mmol), (2,2-difluorocyclopropyl)methyl methanesulfonate (387 mg, 2.08 mmol) and Cs₂CO₃ (1.13 g, 3.46 mmol) in DMF (0.5 mL) was stirred at 70° C. for 30 min. After cooling to r.t., the mixture was diluted with ice-water (10 mL) and the formed solid was filtered. The filter cake was dried to afford 191a (500 mg, 90% yield) as a brown solid. LC-MS (Method 3) $t_R$=1.45 min, m/z (M+H)$^+$=321.0.

Step 2. 5-((2,2-Difluorocyclopropyl)methyl)-3-((diphenylmethylene)amino)thieno[2,3-d]pyridazin-4-(5H)-one (191b)

Compound 191b (250 mg, 38% yield), a brown solid, was synthesized by utilizing a similar preparative procedure of Step 2 in Example 189 with 191a (500 mg, 1.56 mmol) and diphenylmethanimine (296 mg, 1.63 mmol) as starting materials. LC-MS (Method 3) $t_R$=1.67 min, m/z (M+H)$^+$=422.1.

Step 3. 3-Amino-5-((2,2-difluorocyclopropyl) methyl)thieno[2,3d]pyridazin-4-(5H)-one hydrochloride (191c)

Compound 191c (120 mg, 69% yield), a yellow solid, was synthesized by utilizing a similar preparative procedure of Step 3 in Example 189 with 191b (250 mg, 0.59 mmol) as the starting material. LC-MS (Method 3) $t_R$=1.46 min, m/z (M+H)$^+$=258.1.

Step 4. 6-Chloro-4-((5-((2,2-difluorocyclopropyl) methyl)-4-oxo-4,5-dihydrothieno[2,3-d]pyridazin-3-yl)amino)-N-(methyl-d$_3$)nicotinamide (191d)

A mixture of 191c (120 mg, 0.41 mmol) and 42b (85 mg, 0.41 mmol) in EtOH (3 mL) was stirred at 80° C. for 12 h. After cooling to r.t, the formed solid was collected by filtering and dried to afford 191d (127 mg, 72% yield) as a yellow solid. LC-MS (Method 3) $t_R$=1.42 min, m/z (M+H)$^+$ =429.0.

Step 5. 6-(Cyclopropanecarboxamido)-4-((5-((2,2-difluorocyclopropyl)methyl)-4-oxo-4,5-dihydrothieno[2,3-d]pyridazin-3-yl)amino)-N-(methyl-d$_3$) nicotinamide (191)

Compound 191 (5 mg, 10% yield) was synthesized by utilizing a similar preparative procedure of Step 3 in Example 49 with 191d (47 mg, 0.11 mmol) and cyclopropanecarboxamide (47 mg, 0.55 mmol) as starting materials. LC-MS (Method 2) $t_R$=3.20 min, m/z (M+H)$^+$=478.1. $^1$H NMR (400 MHz, DMSO-d$_6$) δ 11.41 (s, 1H), 11.88 (s, 1H), 8.62 (s, 1H), 8.51 (s, 1H), 8.49 (s, 1H), 8.37 (s, 1H), 7.55 (s, 1H), 4.29-4.24 (m, 2H), 2.25-2.24 (m, 1H), 2.02-1.99 (m, 1H), 1.68-1.65 (m, 1H), 1.46-1.43 (m, 1H), 0.82-0.80 (m, 4H).

Example 192

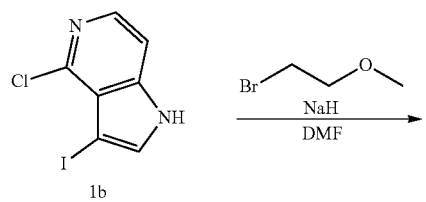

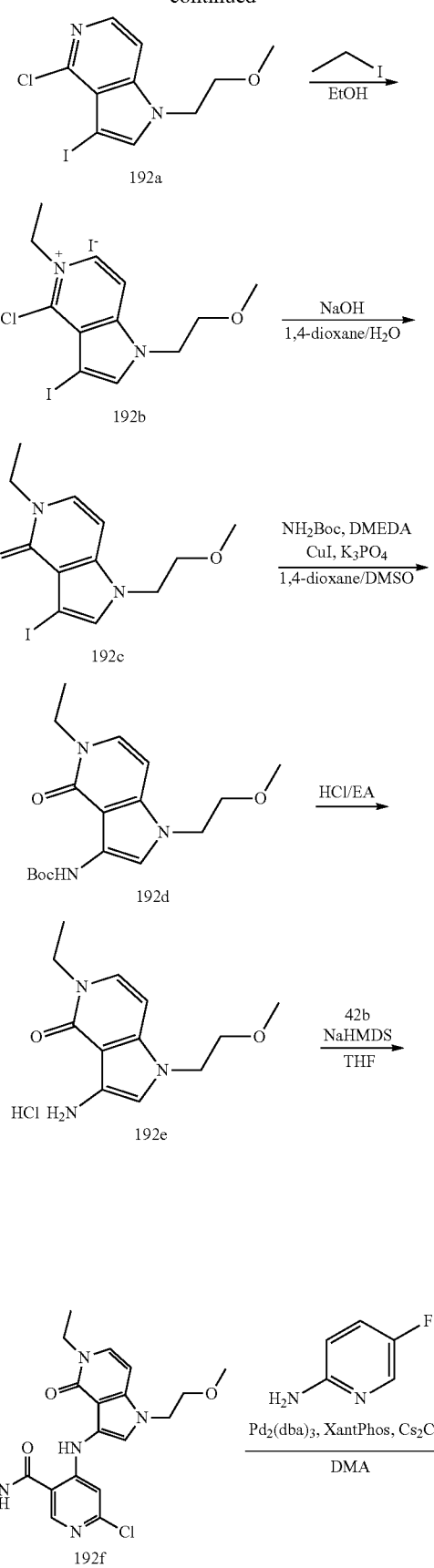

563

-continued

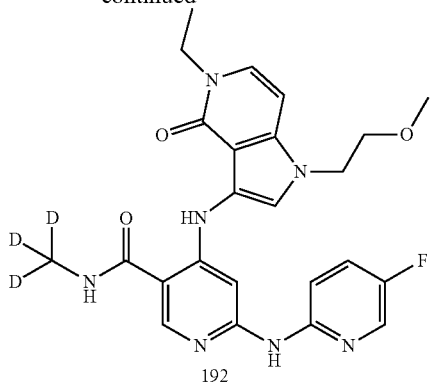

192

Step 1. 4-Chloro-3-iodo-1-(2-methoxyethyl)-1H-pyrrolo[3,2-c]pyridine (192a)

Compound 192a (1.30 g, 77% yield), a light yellow solid, was synthesized by utilizing a similar preparative procedure of Step 1 in Example 9 with 1b (1.4 g, 5.03 mmol) and 1-bromo-2-methoxyethane (629 mg, 4.53 mmol) as starting materials. LC-MS (Method 4) $t_R$=3.33 min, m/z (M+H)$^+$=337.2.

Step 2. 4-Chloro-5-ethyl-3-iodo-1-(2-methoxyethyl)-1H-pyrrolo[3,2-c]pyridin-5-ium iodide (192b)

Compound 192b (1.90 g, yield given), a red solid, was synthesized by utilizing a similar preparative procedure of Step 2 in Example 9 with 192a (1.3 g, 3.86 mmol) and iodoethane (4.82 g, 30.88 mmol) as starting materials. LC-MS (Method 4) $t_R$=1.09 min, m/z M+=365.2.

Step 3. 5-Ethyl-3-iodo-1-(2-methoxyethyl)-1,5-dihydro-4H-pyrrolo[3,2-c]pyridin-4-one (192c)

Compound 192c (760 mg, 2.19 mmol), a grey solid, was synthesized by utilizing a similar preparative procedure of Step 3 in Example 1 with 192b (1.61 g, 4.4 mmol) and NaOH (528 mg, 13.2 mmol) as starting materials. LC-MS (Method 4) $t_R$=3.29 min, m/z (M+H)$^+$=347.2.

Step 4. Tert-butyl (5-ethyl-1-(2-methoxyethyl)-4-oxo-4,5-dihydro-1H-pyrrolo[3,2-c]pyridin-3-yl)carbamate (192d)

Compound 192d (400 mg, 54% yield), a light-yellow solid, was synthesized by utilizing a similar preparative procedure of Step 4 in Example 1 with 192c (760 mg, 2.19 mmol) and tert-butyl carbamate (512 mg, 4.38 mmol) as starting materials. LC-MS (Method 4) $t_R$=3.58 min, m/z (M+H)$^+$=336.2.

Step 5. 3-Amino-5-ethyl-1-(2-methoxyethyl)-1,5-dihydro-4H-pyrrolo[3,2-c]pyridin-4-one hydrochloride (192e)

Compound 192e (276 mg, 85% yield), a brown solid, was synthesized by utilizing a similar preparative procedure of Step 5 in Example 1 with 192d (400 mg, 1.19 mmol) as the starting material. LC-MS (Method 4) $t_R$=3.58 min, m/z (M+H)$^+$=236.2.

564

Step 6. 6-Chloro-4-((5-ethyl-1-(2-methoxyethyl)-4-oxo-4,5-dihydro-1H-pyrrolo[3,2-c]pyridin-3-yl)amino)-N-(methyl-d$_3$)nicotinamide (192f)

To a stirred solution of 192e (141 mg, 0.52 mmol) and 42b (130 mg, 0.62 mmol) in THF (5 mL) was added NaHMDS (1.30 mL, 2.6 mmol, 2 M in THF) dropwise at 0° C. The mixture was stirred 1 h at 0° C. The mixture was diluted with H$_2$O (10 mL) and extracted with EtOAc (10 mL*2). The organic layer was washed with brine (15 mL), dried over Na$_2$SO$_4$ and filtered. The filtrate was concentrated to dryness to give the title compound 192f (150 mg, 71% yield) as a yellow solid. LC-MS (Method 4) $t_R$=2.64 min, m/z (M+H)$^+$=407.2.

Step 7. 4-((5-Ethyl-1-(2-methoxyethyl)-4-oxo-4,5-dihydro-1H-pyrrolo[3,2-c]pyridin-3-yl)amino)-6-((5-fluoropyridin-2-yl)amino)-N-(methyl-d$_3$)nicotinamide (192)

To a stirred solution of 192f (28 mg, 0.07 mmol) and 5-fluoropyridin-2-amine (15 mg, 0.14 mmol) in DMA (1.5 mL) was added Pd$_2$(dba)$_3$ (6 mg, 0.007 mmol), XantPhos (8 mg, 0.014 mmol) and Cs$_2$CO$_3$ (45 mg, 0.14 mmol) at r.t. The mixture was stirred overnight at 100° C. The mixture was purified with Prep-HPLC (Method E) to afford compound 192 (12.5 mg, 37% yield) as a light-yellow solid. LC-MS (Method 4) $t_R$=2.38 min, m/z (M+H)$^+$=483.4. $^1$H NMR (400 MHz, DMSO-d$_6$) δ 11.00 (s, 1H), 9.76 (s, 1H), 8.35 (s, 1H), 8.24-8.23 (m, 1H), 7.69 (s, 1H), 7.67-7.59 (m, 1H), 7.29 (d, J=7.2 Hz, 1H), 7.24 (m, 1H), 6.54 (d, J=7.2 Hz, 1H), 4.22 (t, J=5.2 Hz, 2H), 3.90 (q, J=7.2 Hz, 2H), 3.63 (t, J=5.2 Hz, 2H), 3.20 (s, 3H), 1.18 (t, J=7.2 Hz, 3H).

Example 193

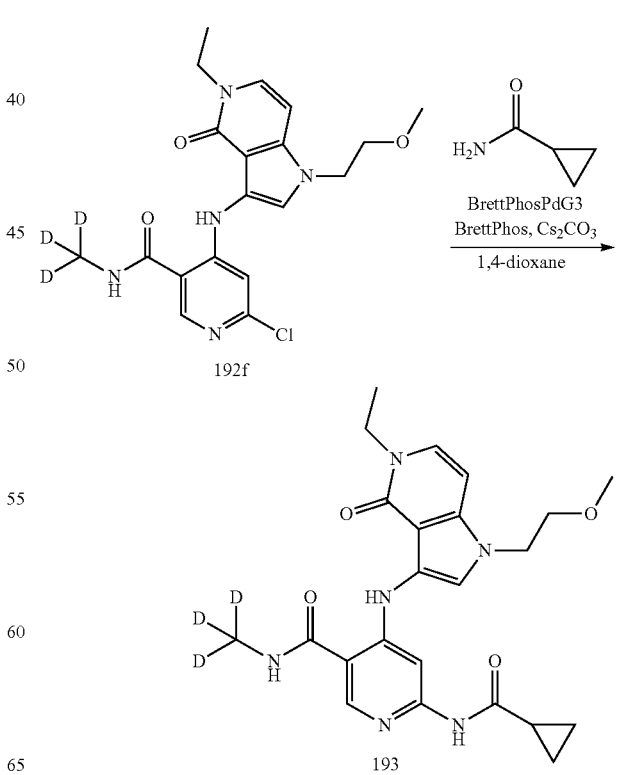

193

Step 1. 6-(Cyclopropanecarboxamido)-4-((5-ethyl-1-(2-methoxyethyl)-4-oxo-4,5-dihydro-1H-pyrrolo[3,2-c]pyridin-3-yl)amino)-N-(methyl-d₃)nicotinamide (193)

A mixture of 192f (10 mg, 0.024 mmol), cyclopropanecarboxamide (10 mg, 0.12 mmol), BrettPhos (2.6 mg, 0.005 mmol), BrettPhos Pd G3 (2.2 mg, 2.4 μmol) and Cs₂CO₃ (16 mg, 0.048 mmol) in dioxane (1.2 mL) was stirred overnight at 100° C. for 15 h. The mixture was purified by Prep-HPLC (Method E) to get compound 193 (3.0 mg, 26.8% yield) as a light-yellow solid. LC-MS (Method 4) $t_R$=2.44 min, m/z (M+H)⁺=456.3. ¹H NMR (400 MHz, CD₃OD) δ 8.28 (s, 1H), 8.02 (s, 1H), 7.23 (d, J=7.2 Hz, 1H), 7.16 (s, 1H), 6.59 (d, J=7.2 Hz, 1H), 4.24 (t, J=5.2 Hz, 2H), 4.00 (q, J=7.2 Hz, 2H), 3.70 (t, J=5.2 Hz, 2H), 3.28 (s, 3H), 1.87-1.85 (m, 1H), 1.27 (t, J=7.2 Hz, 3H), 0.98-0.96 (m, 2H), 0.91-0.86 (m, 2H).

Example 194

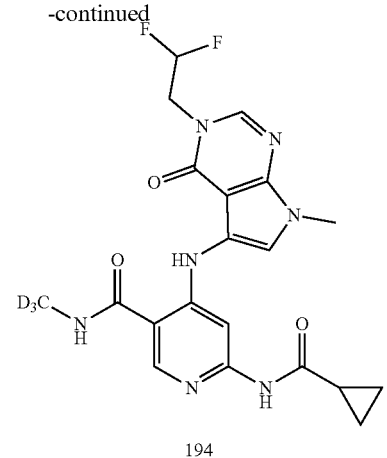

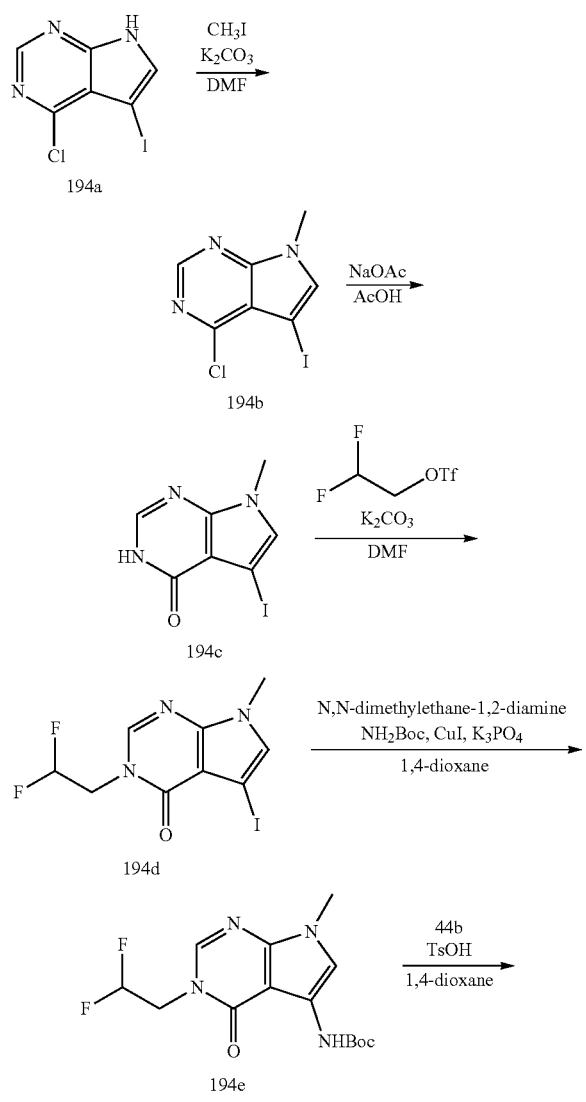

Step 1. 4-Chloro-5-iodo-7-methyl-7H-pyrrolo[2,3-d]pyrimidine (194b)

To a mixture of 194a (2 g, 7.16 mmol) and K₂CO₃ (1.98 g, 14.31 mmol) in DMF (20 mL) was added CH₃I (1.52 g, 10.73 mmol). After stirring at r.t. for 16 h, the mixture was diluted with water (10 mL) and extracted with EtOAc (30 mL*3). The combined organic layer was washed with brine (30 mL), dried over Na₂SO₄ and filtered. The filtrate was concentrated and the residue was purified by flash chromatography on silica gel (PE/EtOAc=5/1) to afford the title compound 194b (408 mg, 19% yield) as a yellow solid. ¹H NMR (400 MHz, DMSO-d₆) δ 8.64 (s, 1H), 7.95 (s, 1H), 3.82 (s, 3H).

Step 2. 5-Iodo-7-methyl-3H-pyrrolo[2,3-d]pyrimidin-4-(7H)-one (194c)

A mixture of 194b (408 mg, 1.39 mmol) and NaOAc (378 mg, 2.78 mmol) in AcOH (5 mL) was stirred at 100° C. for 16 h. After cooling to r.t., the mixture was concentrated to afford the title compound 194c (380 mg, 99% yield) as a black solid. ¹H NMR (400 MHz, DMSO-d₆) δ 11.94 (s, 1H), 7.90 (s, 1H), 7.28 (s, 1H), 3.70 (s, 3H).

Step 3. 3-(2,2-Difluoroethyl)-5-iodo-7-methyl-3H-pyrrolo[2,3-d]pyrimidin-4-(7H)-one (194d)

To a mixture of 194c (220 mg, 0.80 mmol) and K₂CO₃ (221 mg, 1.60 mmol) in DMF (3 mL) was added 2,2-difluoroethyl trifluoromethanesulfonate (257 mg, 1.2 mmol). After stirring at r.t. for 16 h, the mixture was diluted with water (20 mL) and extracted with EtOAc (80 mL*3). The combined organic layer was washed with brine (50 mL), dried over Na₂SO₄ and filtered. The filtrate was concentrated and the residue was purified by flash chromatography on silica gel (PE/EtOAc=5/1) to afford the title compound 194d (200 mg, 74% yield) as a colorless oil. ¹H NMR (400 MHz, DMSO-d₆) δ 8.24 (s, 1H), 7.36 (s, 1H), 6.47-6.20 (m, 1H), 4.47-4.38 (m, 2H), 3.69 (s, 3H).

Step 4. Tert-butyl (3-(2,2-difluoroethyl)-7-methyl-4-oxo-4,7-dihydro-3H-pyrrolo[2,3-d]pyrimidin-5-yl)carbamate (194e)

A mixture of 194d (150 mg, 0.44 mmol), tert-butyl carbamate (104 mg, 0.88 mmol), N,N-dimethylethane-1,2- diamine (20 mg, 0.22 mmol), CuI (42 mg, 0.22 mmol) and K₃PO₄ (188 mg, 0.88 mmol) in 1,4-dioxane (2 mL) was stirred at 90° C. for 12 h. The reaction mixture was cooled and concentrated. The residue was purified by flash chromatography on silica gel (PE/EtOAc=3/1) to afford the title compound 194e (65 mg, 45% yield) as a white solid. LC-MS (Method 1) $t_R$=1.29 min, m/z (M+H)⁺=329.3.

Step 5. 6-(Cyclopropanecarboxamido)-4-((3-(2,2-difluoroethyl)-7-methyl-4-oxo-4,7-dihydro-3H-pyrrolo[2,3-d]pyrimidin-5-yl)amino)-N-(methyl-d₃) nicotinamide (194)

A mixture of 194e (45 mg, 0.14 mmol), 44b (35 mg, 0.14 mmol) and TsOH (2 mg, 0.014 mmol) in 1,4-dioxane (0.5 mL) was stirred at 100° C. for 12 h in a sealed tube. The reaction mixture was cooled and concentrated. The residue was purified by flash chromatography on silica gel (DCM/MeOH=20/1) to afford the title compound 194 (20 mg, 33% yield) as a white solid. LC-MS (Method 2) $t_R$=2.83 min, m/z (M+H)⁺=449.0. ¹H NMR (400 MHz, DMSO-d₆) δ 10.75 (s, 1H), 10.73 (s, 1H), 8.47 (s, 1H), 8.45 (s, 1H), 8.21 (s, 1H), 7.91 (s, 1H), 7.08 (s, 1H), 6.44-6.16 (m, 1H), 4.46-4.38 (m, 2H), 3.71 (s, 3H), 2.00-1.98 (m, 1H), 0.79-0.77 (m, 4H).

Example 195

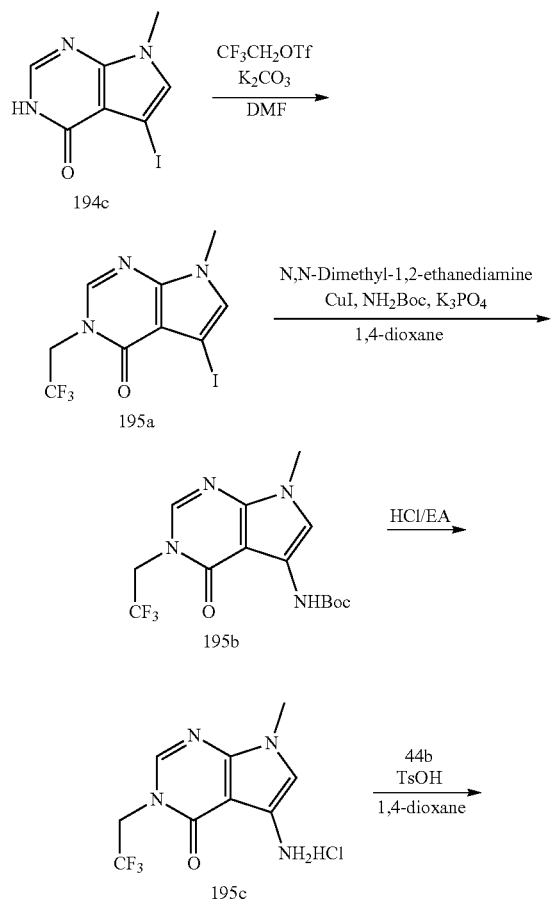

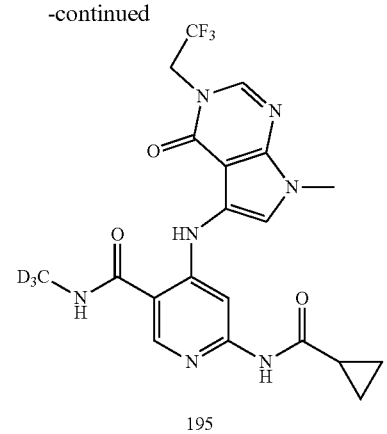

Step 1. 5-Iodo-7-methyl-3-(2,2,2-trifluoroethyl)-3,7-dihydro-4H-pyrrolo[2,3-d]pyrimidin-4-one (195a)

To a mixture of 194c (700 mg, 2.55 mmol) and K₂CO₃ (704 mg, 5.09 mmol) in DMF (10 mL) was added 2,2,2-trifluoroethyl trifluoromethanesulfonate (1.77 g, 7.64 mmol) at r.t. After stirring at r.t. for 16 h, the reaction mixture was diluted with water (20 mL) and extracted with EtOAc (80 mL*3). The combined organic phase was washed with brine (50 mL), dried over Na₂SO₄, filtered and concentrated. The residue was purified by flash chromatography (PE/EtOAc=5/1) to afford the title compound 195a (300 mg, 33% yield) as a yellow solid. ¹H NMR (400 MHz, CDCl₃) δ 7.87 (s, 1H), 6.96 (s, 1H), 4.65 (q, J=8.4 Hz, 2H), 3.76 (s, 3H).

Step 2. Tert-butyl (7-methyl-4-oxo-3-(2,2,2-trifluoroethyl)-4,7-dihydro-3H-pyrrolo[2,3-d]pyrimidin-5-yl)carbamate (195b)

A mixture of 195a (250 mg, 0.70 mmol), tert-butyl carbamate (123 mg, 1.05 mmol), N,N-dimethyl-1,2-ethanediamine (31 mg, 0.35 mmol), CuI (67 mg, 0.35 mmol) and K₃PO₄ (446 mg, 2.10 mmol) in anhydrous 1,4-dioxane (3 mL) was stirred at 90° C. for 16 h. The reaction mixture was cooled and concentrated. The residue was purified by flash chromatography on silica gel (PE/EtOAc=5/1) to afford the title compound 195b (107 mg, 54% yield) as a white solid. ¹H NMR (400 MHz, CDCl₃) δ 7.77 (s, 1H), 7.67 (s, 1H), 7.22 (s, 1H), 4.62 (q, J=8.4 Hz, 2H), 3.71 (s, 3H), 1.50 (s, 9H).

Step 3. 5-Amino-7-methyl-3-(2,2,2-trifluoroethyl)-3,7-dihydro-4H-pyrrolo[2,3-d]pyrimidin-4-one hydrochloride (195c)

A mixture of 195b (118 mg, 0.34 mmol) in HCl/EtOAc (2 mL, 2 M) was stirred at r.t. for 2 h. The reaction mixture was concentrated to afford the title compound 195c (95 mg, 99% yield) as a white solid. LC-MS (Method 2) $t_R$=0.49 min, m/z (M+H)⁺=247.1.

Step 4. 6-(Cyclopropanecarboxamido)-N-(methyl-d₃)-4-((7-methyl-4-oxo-3-(2,2,2-trifluoroethyl)-4,7-dihydro-3H-pyrrolo[2,3-d]pyrimidin-5-yl)amino) nicotinamide (195)

A mixture of 195c (80 mg, 0.28 mmol), 44b (80 mg, 0.31 mmol) and TsOH (10 mg, 0.057 mmol) in 1,4-dioxane (1.5 mL) was stirred at 100° C. for 16 h in a sealed tube. The reaction mixture was cooled and filtered. The filter cake was washed with EtOAc (2 mL) to give the crude product. The crude product was slurried in MeOH (2 mL) and filtered to afford the title compound 195 (58 mg, 44% yield) as a white solid. LC-MS (Method 2) $t_R$=2.41 min, m/z (M+H)$^+$=467.0. $^1$H NMR (400 MHz, DMSO-$d_6$) δ 11.49 (s, 1H), 10.97 (s, 1H), 8.76 (s, 1H), 8.42 (s, 1H), 8.30 (s, 1H), 7.43-7.31 (m, 2H), 4.91 (q, J=8.8 Hz, 2H), 3.75 (s, 3H), 1.96-1.88 (m, 1H), 0.91-0.85 (m, 4H).

Example 196

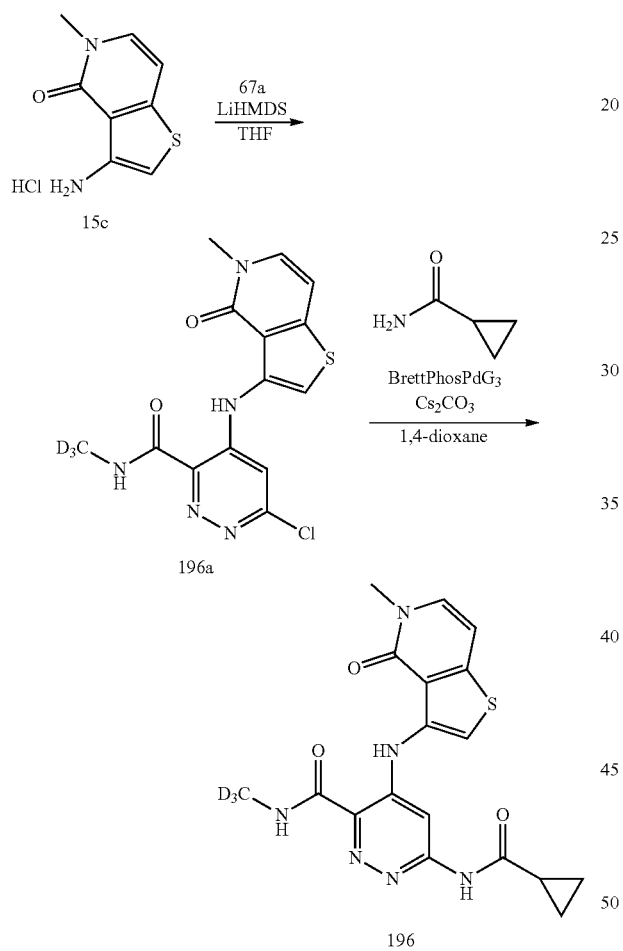

Step 1. 6-Chloro-N-(methyl-$d_3$)-4-((5-methyl-4-oxo-4,5-dihydrothieno[3,2-c]pyridin-3-yl)amino)pyridazine-3-carboxamide (196a)

To a solution of 15c (270 mg, 1.50 mmol) and 67a (313 mg, 1.50 mmol) in THF (2 mL) was added LiHMDS (6.0 mL, 6.00 mmol, 1 M in THF) at −60° C. and stirred at 0° C. for 15 min. The reaction was quenched with ice-water (3 mL) and the organic solvent was removed under vacuo. The formed solid was filtered and dried to afford the title compound 196a (300 mg, 57% yield) as a yellow solid. LC-MS (Method 3) $t_R$=1.12 min, m/z (M+H)$^+$=353.2.

Step 2. 6-(Cyclopropanecarboxamido)-N-(methyl-$d_3$)-4-((5-methyl-4-oxo-4,5-dihydrothieno[3,2-c]pyridin-3-yl)amino)pyridazine-3-carboxamide (196)

A mixture of 196a (150 mg, 0.43 mmol), cyclopropanecarboxamide (181 mg, 2.13 mmol), BrettPhos Pd G3 (78 mg, 0.085 mmol) and Cs$_2$CO$_3$ (277 mg, 0.85 mmol) in anhydrous 1,4-dioxane (3 mL) was stirred at 90° C. for 16 h under N$_2$. After cooling to r.t., the reaction mixture was poured into water (10 mL) and extracted with EtOAc (20 ml*3). The combined organic layer was concentrated under reduced pressure. The residue was purified by flash chromatography on silica gel (DCM/MeOH=20/1) to afford the title compound 196 (30 mg, 18% yield) as a white solid. LC-MS (Method 2) $t_R$=2.54 min, m/z (M+H)$^+$=402.0. $^1$H NMR (400 MHz, DMSO-$d_6$) δ 11.92 (s, 1H), δ 11.38 (s, 1H), 8.95 (s, 1H), 8.54 (s, 1H), 7.61 (d, J=7.2 Hz, 1H), 7.19 (s, 1H), 6.90 (d, J=7.2 Hz, 1H), 3.51 (s, 3H), 2.12-2.07 (m, 1H), 0.87-0.86 (m, 4H).

Example 197

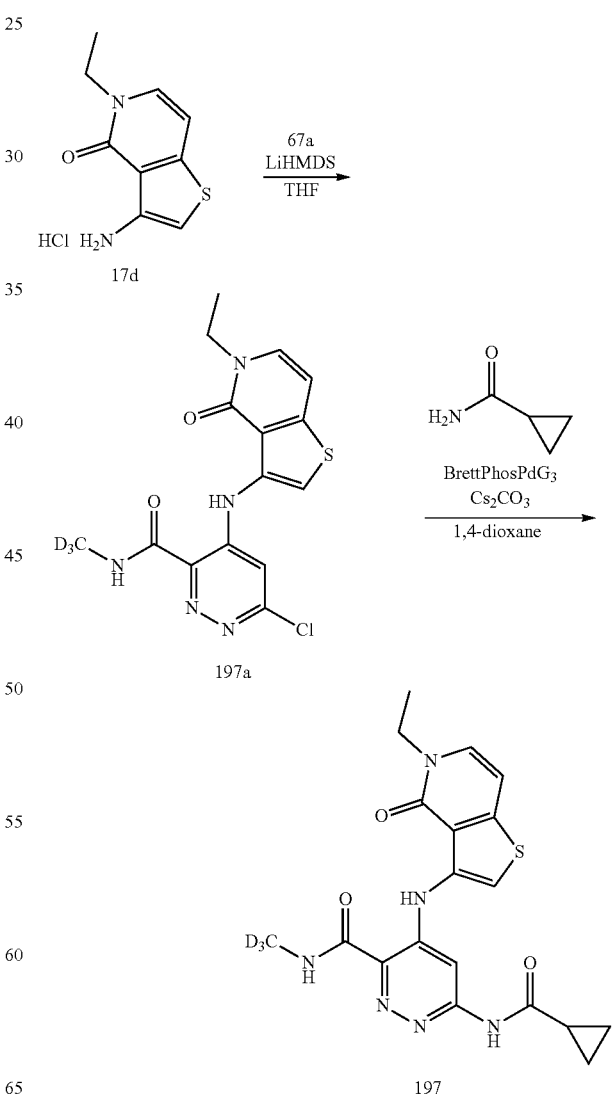

Step 1. 6-Chloro-N-(methyl-d₃)-4-((5-ethyl-4-oxo-4,5-dihydrothieno[3,2-c]pyridin-3-yl)amino)pyridazine-3-carboxamide (197a)

To a solution of 17d (400 mg, 2.06 mmol) and 67a (344 mg, 1.65 mmol) in THF (4 mL) was added LiHMDS (8.2 mL, 8.2 mmol, 1 M in THF) at −60° C. and stirred at r.t. for 30 min. The reaction was quenched with ice-water (0.5 mL) and the organic solvent was removed under vacuo. The formed solid was filtered and dried to afford the title compound 197a (500 mg, 66% yield) as a yellow solid. LC-MS (Method 3) $t_R$=1.21 min, m/z (M+H)⁺=367.3.

Step 2. 6-(Cyclopropanecarboxamido)-N-(methyl-d₃)-4-((5-ethyl-4-oxo-4,5-dihydrothieno[3,2-c]pyridin-3-yl)amino)pyridazine-3-carboxamide (197)

A mixture of 197a (200 mg, 0.55 mmol), cyclopropanecarboxamide (70 mg, 0.82 mmol), BrettPhos Pd G3 (74 mg, 0.08 mmol) and Cs₂CO₃ (355 mg, 1.09 mmol) in anhydrous 1,4-dioxane (3 mL) was stirred at 90° C. for 12 h. After cooling to r.t., the reaction mixture was concentrated under reduced pressure. The residue was purified by flash chromatography on silica gel (DCM/MeOH=20/1) to afford the title compound 197 (70 mg, 31% yield) as a white solid. LC-MS (Method 2) $t_R$=3.37 min, m/z (M+H)⁺=416.0. ¹H NMR (400 MHz, DMSO-d₆) δ 11.91 (s, 1H), 11.37 (s, 1H), 8.95 (s, 1H), 8.54 (s, 1H), 7.52 (d, J=7.6 Hz, 1H), 7.19 (s, 1H), 6.92 (d, J=7.2 Hz, 1H), 4.01 (q, J=7.2 Hz, 2H), 2.11-2.09 (m, 1H), 1.25 (t, J=6.8 Hz, 3H), 0.87-0.85 (m, 4H).

Example 198

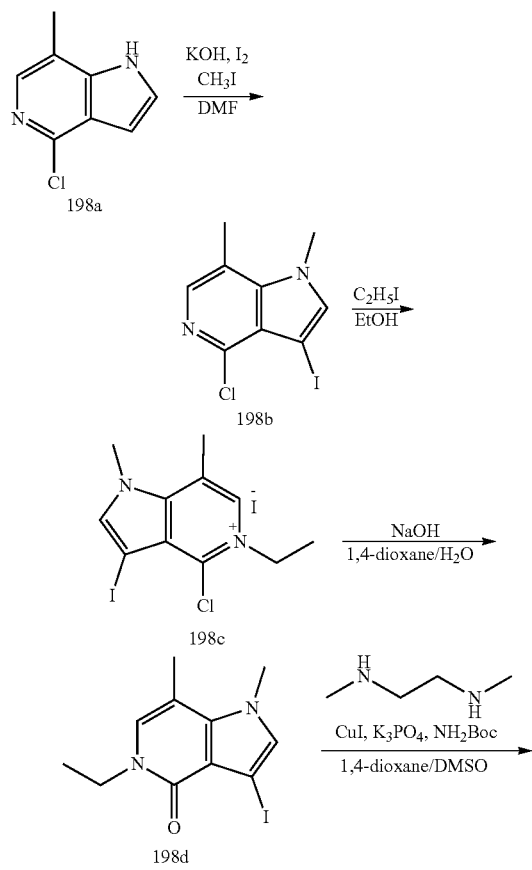

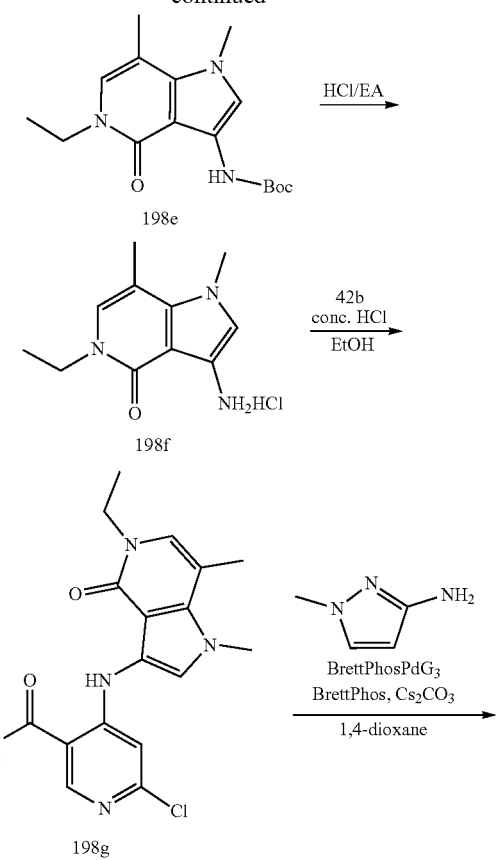

Step 1. 4-Chloro-3-iodo-1,7-dimethyl-1H-pyrrolo[3,2-c]pyridine (198b)

To a solution of 198a (1 g, 6.00 mmol) in DMF (10 mL) was added KOH (674 mg, 12.0 mmol) at 0° C. for 5 min. Then I₂ (1.52 g, 6.0 mmol) was added to the reaction and the reaction mixture was stirred at 0° C. for 30 min. To the reaction mixture was added iodomethane (1.28 g, 9.03 mmol). After stirring at 0° C. for 30 min, the reaction mixture was quenched with water (20 mL) and the formed solid was collected by filtering. The filter cake was dried to afford the title compound 198b (1.55 g, 84% yield) as a white solid. ¹H NMR (400 MHz, DMSO-d₆) δ 7.73 (s, 1H), 7.68 (s, 1H), 4.05 (s, 3H), 2.63 (s, 3H).

Step 2. 4-Chloro-5-ethyl-3-iodo-1,7-dimethyl-1H-pyrrolo[3,2-c]pyridin-5-ium iodide (198c)

Compound 198c (0.72 g, 51% yield), a white solid, was synthesized by utilizing a similar preparative procedure of Step 2 in Example 9 with 198b (1.3 g, 4.24 mmol) as the starting material. LC-MS (Method 3) $t_R$=1.43 min, m/z $M^+$=335.0.

Step 3. 5-Ethyl-3-iodo-1,7-dimethyl-1H-pyrrolo[3,2-c]pyridin-4-(5H)-one (198d)

Compound 198d (0.60 g, 45% yield), a yellow solid, was synthesized by utilizing a similar preparative procedure of Step 3 in Example 192 with 198c (1.4 g, 4.17 mmol) as the starting material. $^1$H NMR (400 MHz, DMSO-$d_6$) δ 7.17 (s, 1H), 7.04 (s, 1H), 3.89 (s, 3H), 3.84 (q, J=7.2 Hz, 2H), 2.34 (s, 3H), 1.17 (t, J=6.8 Hz, 3H).

Step 4. Tert-butyl (5-ethyl-1,7-dimethyl-4-oxo-4,5-dihydro-1H-pyrrolo[3,2-c]pyridin-3-yl)carbamate (198e)

Compound 198e (330 mg, 62% yield), a yellow solid, was synthesized by utilizing a similar preparative procedure of Step 4 in Example 1 with 198d (550 mg, 1.74 mmol) and tert-butyl carbamate (611 mg, 5.22 mmol) as starting materials. LC-MS (Method 3) $t_R$=1.53 min, m/z $(M+H)^+$=306.2.

Step 5. 3-Amino-5-ethyl-1,7-dimethyl-1H-pyrrolo[3,2-c]pyridin-4-(5H)-one hydrochloride (198f)

Compound 198f (261 mg, 94% yield), a white solid, was synthesized by utilizing a similar preparative procedure of Step 5 in Example 1 with 198e (330 mg, 1.08 mmol) as the starting material. LC-MS (Method 3) $t_R$=1.27 min, m/z $(M+H)^+$=206.2.

Step 6. 6-Chloro-4-((5-ethyl-1,7-dimethyl-4-oxo-4,5-dihydro-1H-pyrrolo[3,2-c]pyridin-3-yl)amino)-N-(methyl-$d_3$)nicotinamide (198g)

Compound 198g (162 mg, 55% yield), a brown solid, was synthesized by utilizing a similar preparative procedure of Step 1 in Example 98 with 198f (190 mg, 0.79 mmol) and 42b (180 mg, 0.86 mmol) as starting materials. $^1$H NMR (400 MHz, DMSO-$d_6$) δ 10.80 (s, 1H), 8.57 (s, 1H), 8.38 (s, 1H), 7.28 (s, 1H), 7.05 (s, 1H), 7.04 (s, 1H), 3.92 (s, 3H), 3.85 (q, J=6.8 Hz, 2H), 2.37 (s, 3H), 1.17 (t, J=6.8 Hz, 3H).

Step 7. 4-((5-Ethyl-1,7-dimethyl-4-oxo-4,5-dihydro-1H-pyrrolo[3,2-c]pyridin-3-yl)amino)-N-(methyl-$d_3$)-6-((1-methyl-1H-pyrazol-3-yl)amino)nicotinamide (198)

Compound 198 (8 mg, 23% yield), a white solid, was synthesized by utilizing a similar preparative procedure of Step 3 in Example 49 with 198g (30 mg, 0.08 mmol) and 1-methyl-1H-pyrazol-3-amine (15 mg, 0.16 mmol) as starting materials. LC-MS (Method 2) $t_R$=2.58 min, m/z $(M+H)^+$=438.1. $^1$H NMR (400 MHz, DMSO-$d_6$) δ 11.04 (s, 1H), 9.25 (s, 1H), 8.30 (s, 1H), 8.14 (s, 1H), 7.53 (d, J=2.0 Hz, 1H), 7.46 (s, 1H), 7.16 (s, 1H), 7.02 (s, 1H), 6.08 (s, 1H), 3.95 (s, 3H), 3.87 (q, J=6.8 Hz, 2H), 3.82 (s, 3H), 2.32 (s, 3H), 1.19 (t, J=6.8 Hz, 3H).

Example 199

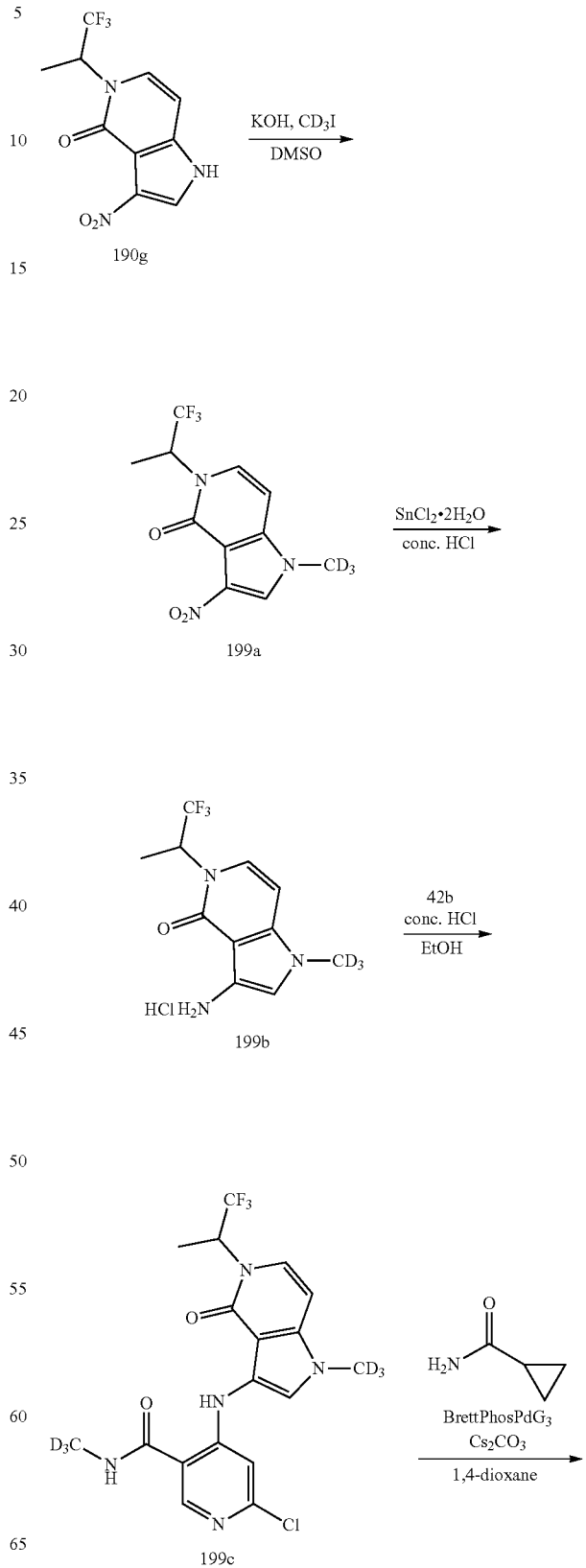

$t_R$=3.47 min, m/z (M+H)$^+$=483.1. $^1$H NMR (400 MHz, DMSO-d$_6$) δ 10.92 (s, 1H), 10.71 (s, 1H), 8.43 (s, 1H), 8.40 (s, 1H), 8.00 (s, 1H), 7.38 (d, J=7.6 Hz, 1H), 7.07 (s, 1H), 6.67 (d, J=7.6 Hz, 1H), 5.94-5.89 (m, 1H), 2.01-2.00 (m, 1H), 1.58 (d, J=6.8 Hz, 3H), 0.83-0.81 (m, 4H).

Example 200

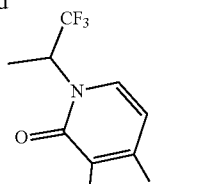

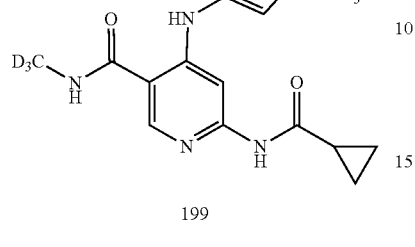

199

Step 1. 1-(Methyl-d$_3$)-3-nitro-5-(1,1,1-trifluoropropan-2-yl)-1H-pyrrolo[3,2-c]pyridin-4-((5H)-one (199a)

To a mixture of 190g (800 mg, 2.91 mmol) and KOH (326 mg, 5.81 mmol) in DMSO (6 mL) was added CD$_3$I (632 mg, 4.36 mmol) at 0° C. After stirring for 1 h at 0° C., the reaction mixture was poured into water (20 mL). The formed solid was collected by filtering and the filter cake was dried to afford the title compound 199a (620 mg, 73% yield) as a brown solid. $^1$H NMR (400 MHz, DMSO-d$_6$) δ 8.39 (s, 1H), 7.66 (d, J=7.6 Hz, 1H), 6.78 (d, J=7.6 Hz, 1H), 5.97-5.91 (m, 1H), 1.61 (d, J=7.2 Hz, 3H).

Step 2. 3-Amino-1-(methyl-d$_3$)-5-(1,1,1-trifluoropropan-2-yl)-1H-pyrrolo[3,2-c]pyridin-4-((5H)-one hydrochloride (199b)

Compound 199b (500 mg, 90% yield), a brown solid, was synthesized by utilizing a similar preparative procedure of Step 5 in Example 123 with 199a (620 mg, 2.12 mmol) and SnCl$_2$·2H$_2$O (922 mg, 4.09 mmol) as starting materials. LC-MS (Method 3) $t_R$=1.34 min, m/z (M+H)$^+$=263.3.

Step 3. 6-Chloro-N-(methyl-d$_3$)-4-((1-(methyl-d$_3$)-4-oxo-5-(1,1,1-trifluoropropan-2-yl)-4,5-dihydro-1H-pyrrolo[3,2-c]pyridin-3-yl)amino)nicotinamide (199c)

Compound 199c (400 mg, 10% yield), a brown solid, was synthesized by utilizing a similar preparative procedure of Step 1 in Example 98 with 199b (450 mg, 1.72 mmol) and 42b (357 mg, 1.72 mmol) as starting materials. LC-MS (Method 3) $t_R$=1.47 min, m/z (M+H)$^+$=434.3.

Step 4. 6-(Cyclopropanecarboxamido)-N-(methyl-d$_3$)-4-((1-(methyl-d$_3$)-4-oxo-5-(1,1,1-trifluoropropan-2-yl)-4,5-dihydro-1H-pyrrolo[3,2-c]pyridin-3-3/1)amino)nicotinamide (199)

A mixture of 199c (100 mg, 0.23 mmol), cyclopropanecarboxamide (98 mg, 1.15 mmol), BrettPhos Pd G3 (42 mg, 0.023 mmol) and Cs$_2$CO$_3$ (150 mg, 0.46 mmol) in 1,4-dioxane (0.5 mL) was stirred at 90° C. for 12 h under N$_2$ atmosphere. The reaction mixture was concentrated and the residue was purified by Prep-HPLC (Method A) to afford the title compound 199 as a white solid. LC-MS (Method 2)

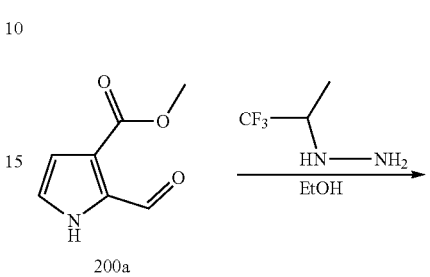

200a

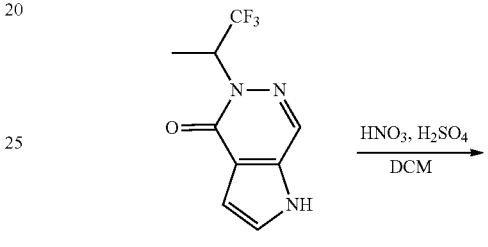

200b

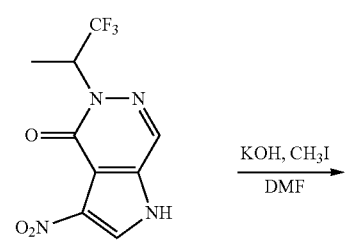

200c

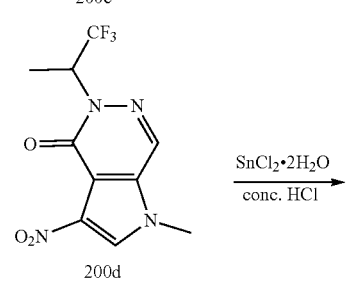

200d

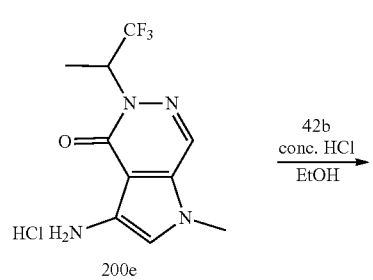

200e

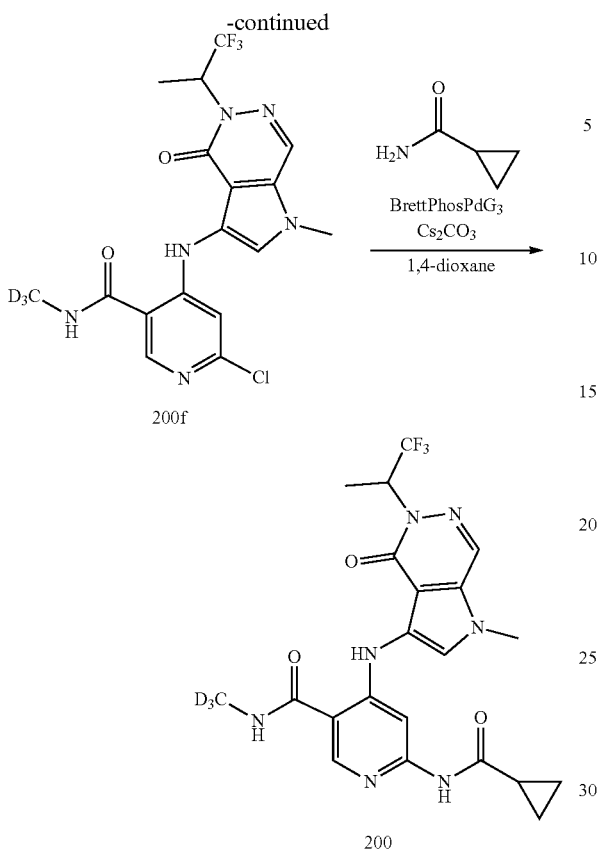

Step 1. 5-(1,1,1-Trifluoropropan-2-yl)-1H-pyrrolo[2,3-d]pyridazin-4-(5H)-one (200b)

A mixture of 200a (1.3 g, 8.49 mmol) and (2,2,2-trifluoro-1-methyl-ethyl)hydrazine (1.09 g, 8.49 mmol) in EtOH (15 mL) was stirred at 80° C. for 16 h. After cooling to r.t., the mixture was concentrated. The residue was purified by Prep-HPLC (Method A) to afford the title compound 200b (860 mg, 44% yield) as a yellow oil. $^1$H NMR (300 MHz, DMSO-$d_6$) δ 11.42 (s, 1H), 8.48 (s, 1H), 6.73 (d, J=5.4 Hz, 1H), 6.41 (d, J=5.4 Hz, 1H), 4.09-3.99 (m, 1H), 1.61 (d, J=7.2 Hz, 3H).

Step 2. 3-Nitro-5-(1,1,1-trifluoropropan-2-yl)-1,5-dihydro-4H-pyrrolo[2,3-d]pyridazin-4-one (200c)

Compound 200c (160 mg, 12% yield), a yellow solid, was synthesized by utilizing a similar preparative procedure of Step 6 in Example 190 with 200b (1.1 g, 4.76 mmol) as the starting material. $^1$H NMR (400 MHz, DMSO-$d_6$) δ 13.24 (s, 1H), 8.21 (s, 1H), 7.36 (s, 1H), 4.19-4.13 (m, 1H), 1.37 (d, J=6.8 Hz, 3H).

Step 3. 1-Methyl-3-nitro-5-(1,1,1-trifluoropropan-2-yl)-1,5-dihydro-4H-pyrrolo[2,3-d]pyridazin-4-one (200d)

To a mixture of 200c (160 mg, 0.058 mmol) and KOH (165 mg, 1.16 mmol) in DMF (2 mL) was added MeI (164 mg, 1.16 mmol) at 0° C. After stirring for 2 h at 0° C., the reaction mixture was poured into water (5 mL). The mixture was extracted with DCM (5 mL*2). The combined organic layer was washed with brine (10 mL), dried over $Na_2SO_4$, filtered and concentrated. The residue was purified by flash chromatography on silica gel (PE/EtOAc=5/1) to afford the title compound 200d (90 mg, 54% yield) as a yellow solid. $^1$H NMR (400 MHz, DMSO-$d_6$) δ 8.79 (s, 1H), 7.75 (s, 1H), 5.91-5.88 (m, 1H), 4.12 (s, 3H), 1.57 (d, J=7.2 Hz, 3H).

Step 4. 3-Amino-1-methyl-5-(1,1,1-trifluoropropan-2-yl)-1,5-dihydro-4H-pyrrolo[2,3-d]pyridazin-4-one hydrochloride (200e)

Compound 200e (80 mg, 87% yield), a yellow solid, was synthesized by utilizing a similar preparative procedure of Step 5 in Example 123 with 200d (900 mg, 0.31 mmol) and $SnCl_2·2H_2O$ (140 mg, 0.62 mmol) as starting materials. LC-MS (Method 3) $t_R$=1.31 min, m/z (M+H)$^+$=261.0.

Step 5. 6-Chloro-N-(methyl-$d_3$)-4-((1-methyl-4-oxo-5-(1,1,1-trifluoropropan-2-yl)-4,5-dihydro-1H-pyrrolo[2,3-d]pyridazin-3-yl)amino)nicotinamide (200f)

Compound 200f (7 mg, 5% yield), a brown solid, was synthesized by utilizing a similar preparative procedure of Step 1 in Example 98 with 200e (80 mg, 0.27 mmol) and 42b (64 mg, 0.31 mmol) as starting materials. LC-MS (Method 3) $t_R$=1.50 min, m/z (M+H)$^+$=432.2.

Step 6. 6-(Cyclopropanecarboxamido)-N-(methyl-$d_3$)-4-((1-methyl-4-oxo-5-(1,1,1-trifluoropropan-2-yl)-4,5-dihydro-1H-pyrrolo[2,3-d]pyridazin-3-yl)amino)nicotinamide (200)

Compound 200 (2 mg, 25% yield), a white solid, was synthesized by utilizing a similar preparative procedure of Step 4 in Example 199 with 200f (7 mg, 0.016 mmol) and cyclopropanecarboxamide (3 mg, 0.035 mmol) as starting materials. LC-MS (Method 1) $t_R$=3.17 min, m/z (M+H)$^+$=481.1. $^1$H NMR (400 MHz, DMSO-$d_6$) δ 10.90 (s, 1H), 10.78 (s, 1H), 8.51-8.48 (m, 3H), 7.96 (s, 1H), 7.37 (s, 1H), 5.89-5.85 (m, 1H), 3.88 (s, 3H), 2.02-1.97 (m, 1H), 1.56 (d, J=6.8 Hz, 3H), 0.85-0.78 (m, 4H).

Example 201

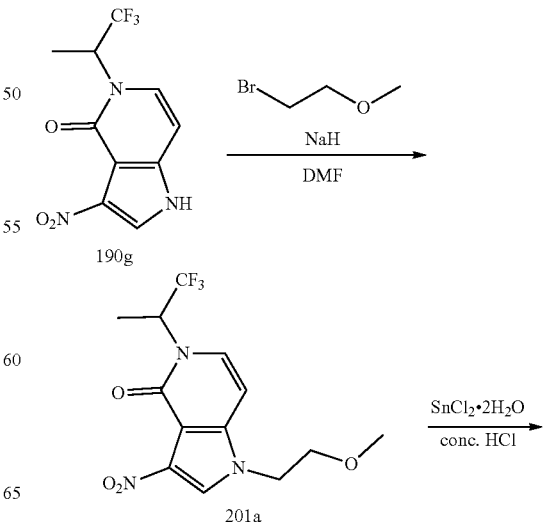

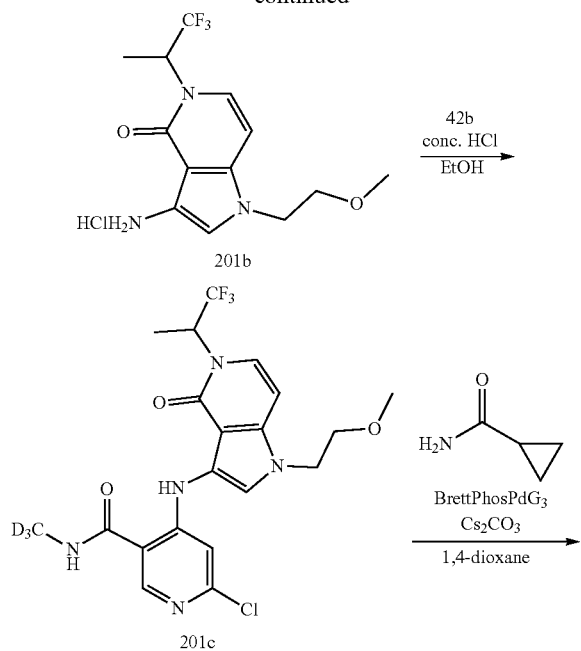

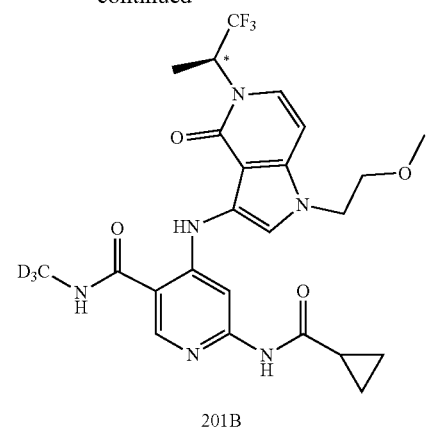

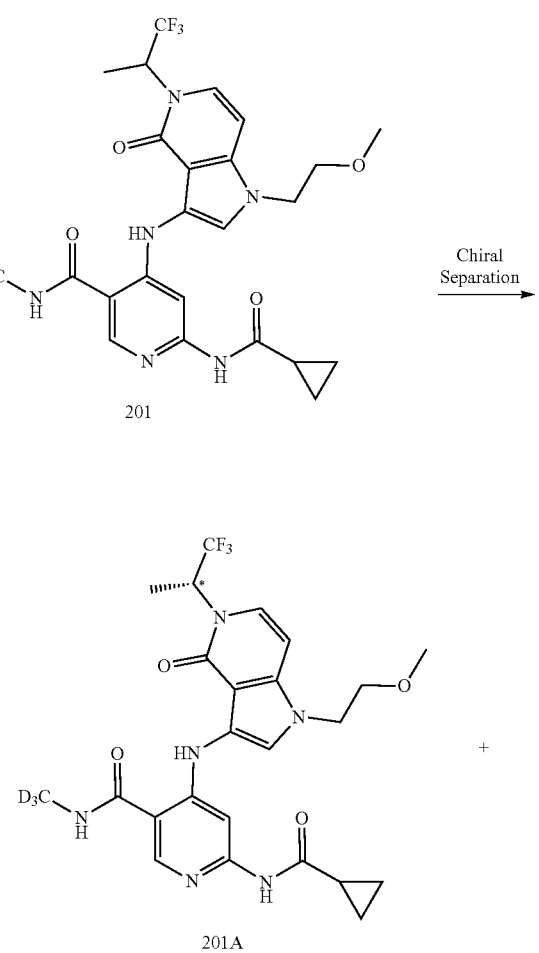

Step 1. 1-(2-Methoxyethyl)-3-nitro-5-(1,1,1-trifluoropropan-2-yl)-1,5-dihydro-4H-pyrrolo[3,2-c]pyridin-4-one (201a)

To a mixture of 190g (1.0 g, 3.63 mmol) in DMF (15 mL) was added NaH (291 mg, 7.27 mmol, 60% in mineral oil) at 0° C. After stirring for 30 min at 25° C., to the reaction was added 1-bromo-2-methoxyethane (758 mg, 5.45 mmol). The reaction was stirred at 50° C. for 16 h. After cooling to r.t., the reaction mixture was poured into water (30 mL). The formed solid was collected by filtering and the filter cake was dried to afford the title compound 201a (300 mg, 25% yield) as a brown solid. LC-MS (Method 3) $t_R$=1.25 min, m/z (M+H)$^+$=334.3.

Step 2. 3-Amino-1-(2-methoxyethyl)-5-(1,1,1-trifluoropropan-2-yl)-1,5-dihydro-4H-pyrrolo[3,2-c]pyridin-4-one hydrochloride (201b)

Compound 201b (200 mg, 66% yield), a brown solid, was synthesized by utilizing a similar preparative procedure of Step 5 in Example 123 with 201a (300 mg, 0.90 mmol) and SnCl$_2$·2H$_2$O (405 mg, 1.80 mmol) as starting materials. LC-MS (Method 3) $t_R$=1.19 min, m/z (M+H)$^+$=304.3.

Step 3. 6-Chloro-4-((1-(2-methoxyethyl)-4-oxo-5-(1,1,1-trifluoropropan-2-yl)-4,5-dihydro-1H-pyrrolo[3,2-c]pyridin-3-yl)amino)-N-(methyl-d$_3$)nicotinamide (201c)

Compound 201c (100 mg, 24% yield), a yellow solid, was synthesized by utilizing a similar preparative procedure of Step 1 in Example 98 with 201b (300 mg, 0.89 mmol) and 42b (184 mg, 0.89 mmol) as starting materials. LC-MS (Method 3) $t_R$=1.25 min, m/z (M+H)$^+$=475.3.

Step 4. 6-(Cyclopropanecarboxamido)-4-((1-(2-methoxyethyl)-4-oxo-5-(1,1,1-trifluoropropan-2-yl)-4,5-dihydro-1H-pyrrolo[3,2-c]pyridin-3-yl)amino)-N-(methyl-d$_3$)nicotinamide (201)

Compound 201 (11 mg, 10% yield), a yellow solid, was synthesized by utilizing a similar preparative procedure of Step 4 in Example 199 with 201c (100 mg, 0.21 mmol) and cyclopropanecarboxamide (54 mg, 0.63 mmol) as starting materials. LC-MS (Method 1) $t_R$ 3.16 min, m/z (M+H)$^+$=524.1. $^1$H NMR (400 MHz, DMSO-d$_6$) δ 10.93 (s, 1H), 10.72 (s, 1H), 8.44 (s, 1H), 8.39 (s, 1H), 8.07 (s, 1H), 7.37 (d, J=7.6 Hz, 1H), 7.18 (s, 1H), 6.71 (d, J=7.6 Hz, 1H), 5.89-5.85 (m, 1H), 4.22 (t, J=4.8 Hz, 2H), 3.65 (t, J=4.8 Hz, 2H), 3.24 (s, 3H), 2.02-1.98 (m, 1H), 1.58 (d, J=7.2 Hz, 3H), 0.81-0.78 (m, 4H).

Step 5. (R*)-6-(Cyclopropanecarboxamido)-4-((1-(2-methoxyethyl)-4-oxo-5-(1,1,1-trifluoropropan-2-yl)-4,5-dihydro-1H-pyrrolo[3,2-c]pyridin-3-yl)amino)-N-(methyl-d₃)nicotinamide (201A) and (S*)-6-(Cyclopropanecarboxamido)-4-((1-(2-methoxyethyl)-4-oxo-5-(1,1,1-trifluoropropan-2-yl)-4,5-dihydro-1H-pyrrolo[3,2-c]pyridin-3-yl)amino)-N-(methyl-d₃)nicotinamide (201B)

Compound 201 (11 mg) was separated by Prep-Chiral HPLC to afford the title compound 201A (4.7 mg, 43% yield) as a yellow solid and 201B (4.1 mg, 37% yield) as a yellow solid.

Example 202

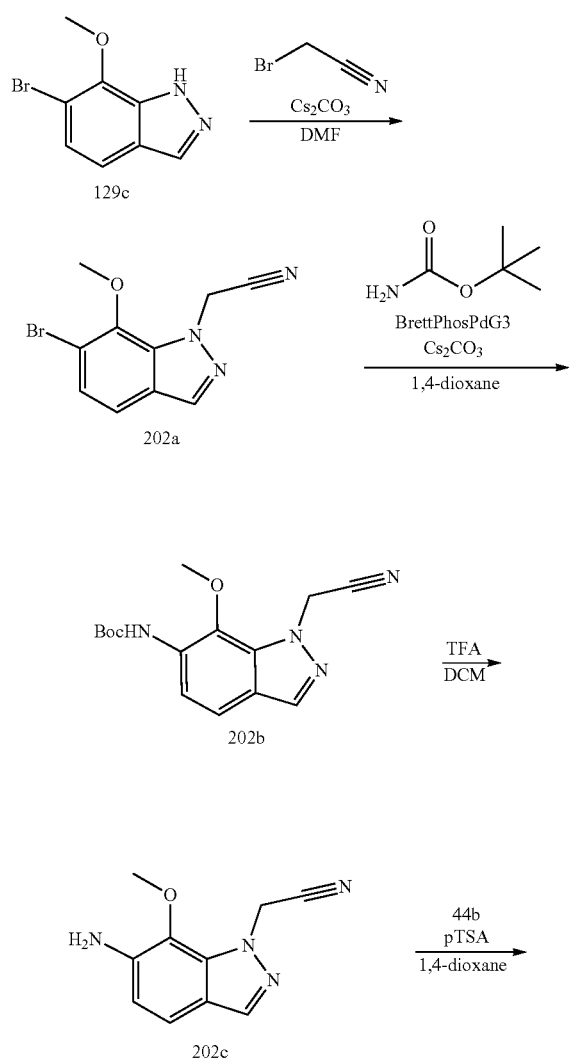

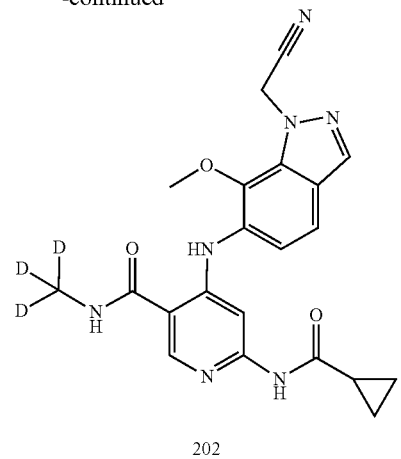

Step 1. 2-(6-Bromo-7-methoxy-1H-indazol-1-yl)acetonitrile (202a)

To a solution of 129c (200 mg, 0.88 mmol) in DMF (5 mL) was added Cs₂CO₃ (861 mg, 2.64 mmol) and 2-bromoacetonitrile (211 mg, 1.76 mmol) at r.t. Then the mixture was stirred at r.t. for 2 h. The mixture was diluted with H₂O (20 mL), extracted with EtOAc (20 mL*3), washed with brine (30 mL), dried over Na₂SO₄, concentrated to get the compound 202a (130 mg, 55% yield) as a yellow solid. LC-MS (Method 4) $t_R$=2.54 min, m/z (M+H)⁺=266.0. ¹H NMR (400 MHz, CDCl₃) δ 8.03 (s, 1H), 7.36 (d, J=8.4 Hz, 1H), 7.33 (d, J=8.4 Hz, 1H), 5.53 (s, 2H), 4.14 (s, 3H).

Step 2. Tert-butyl (1-(cyanomethyl)-7-methoxy-1H-indazol-6-yl)carbamate (202b)

A mixture of 202a (100 mg, 0.36 mmol), tert-butyl carbamate (110 mg, 0.94 mmol), BrettPhos Pd G3 (68 mg, 0.75 mmol), Cs₂CO₃ (306 mg, 0.94 mmol) in 1,4-dioxane (1.5 mL) was stirred at 95° C. for 16 h under N₂. The mixture was diluted with H₂O (10 mL), extracted with EA (10 mL*3), washed with brine (20 mL), dried over Na₂SO₄, concentrated to get the crude compound 202b (100 mg, 88% yield) as a yellow solid. LC-MS (Method 4) $t_R$=2.85 min, m/z (M+H)⁺=303.2.

Step 3. 2-(6-Amino-7-methoxy-1H-indazol-1-yl)acetonitrile (202c)

To a solution of 202b (80 mg, 0.26 mmol) in DCM (1 mL) was added TFA (0.5 mL), then the mixture was stirred at r.t. for 2 h. The mixture was concentrated to dryness. The residue was diluted with H₂O (10 mL), adjusted pH to 7-9 with aq Na₂CO₃, and extracted with EtOAc (10 mL*3). The organic layers were washed with aq Na₂CO₃ (10 mL) and brine (10 mL) and separated. The solution was dried over Na₂SO₄ and filtered. The filtrate was concentrated and purified by flash chromatography (PE/EA=1/1 to 1/10) to give the title compound 202c (30 mg, 56% yield) as a yellow solid. LC-MS (Method 4) $t_R$=1.30 min, m/z (M+H)⁺=203.1.

Step 4. 4-((1-(Cyanomethyl)-7-methoxy-1H-indazol-6-yl)amino)-6-(cyclopropanecarboxamido)-N-(methyl-d₃)nicotinamide (202)

A mixture of 202c (30 mg, 0.15 mmol), 44b (38 mg, 0.15 mmol), pTSA (26 mg, 0.15 mmol) in 1,4-dioxane (1 mL)

was stirred at 100° C. for 4 h. The mixture was concentrated and purified by Prep-HPLC (Method E) to get the compound 202 (16.3 mg, 26% yield) as an off-white solid. LC-MS (Method 4) $t_R$=1.81 min, m/z (M+H)$^+$=423.4. $^1$H NMR (400 MHz, DMSO-d$_6$) δ 10.76 (s, 1H), 10.62 (s, 1H), 8.64 (s, 1H), 8.54 (s, 1H), 8.20 (s, 1H), 7.88 (s, 1H), 7.58 (d, J=8.4 Hz, 1H), 7.22 (d, J=8.4 Hz, 1H), 5.74 (s, 2H), 3.85 (s, 3H), 1.96-1.93 (m, 1H), 0.75-0.72 (m, 4H).

Example 203

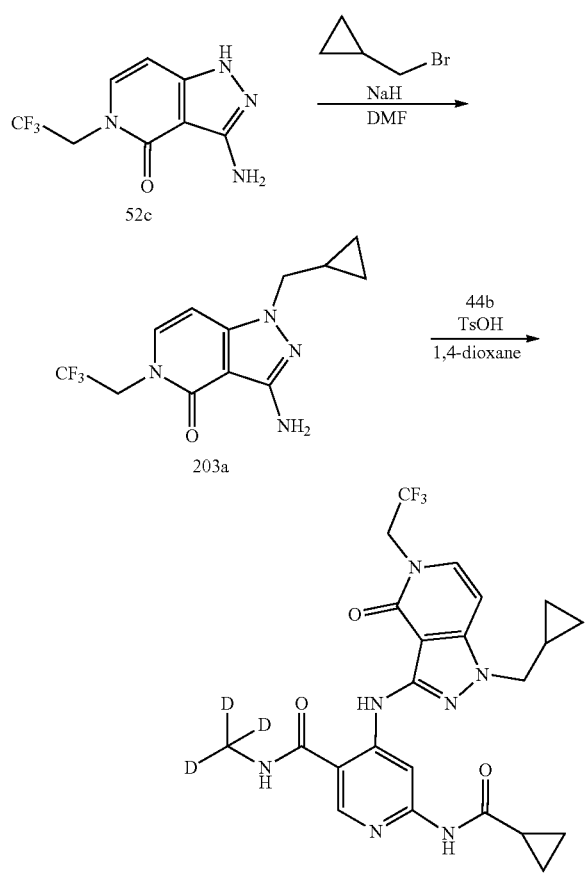

Step 1. 3-Amino-1-(cyclopropylmethyl)-5-(2,2,2-trifluoroethyl)-1,5-dihydro-4H-pyrazolo[4,3-c]pyridin-4-one (203a)

To a solution of 52c (200 mg, 0.86 mmol) in DMF (2 mL) was added NaH (40 mg, 1.0 mmol, 60% in mineral oil) at 0° C., the mixture was stirred at 25° C. for 30 min, then (bromomethyl)cyclopropane (135 mg, 1.0 mmol) was added, and stirred at 25° C. for 4 h. The mixture was was diluted with H$_2$O (10 mL), extracted with EA (10 mL*3), washed with brine, dried over Na$_2$SO$_4$ and concentrated to get the crude compound 203a (150 mg, 74% yield) as a brown oil. LC-MS (Method 4) $t_R$=2.84 min, m/z (M+H)$^+$=287.1.

Step 2. 6-(Cyclopropanecarboxamido)-4-((1-(cyclopropylmethyl)-4-oxo-5-(2,2,2-trifluoroethyl)-4,5-dihydro-1H-pyrazolo[4,3-c]pyridin-3-yl)amino)-N-(methyl-d$_3$)nicotinamide (203)

A mixture of 203a (111 mg, 0.38 mmol), 44b (100 mg, 0.38 mmol) and pTSA (74 mg, 0.38 mmol) in 1,4-dioxane (2 mL) was stirred at 100° C. for 16 h. The mixture was concentrated and DIPEA (0.4 mL) and MeOH (4 mL) was added. The mixture was stirred at 25° C. for 1 h and filtered to get the compound 203 (48 mg, 24% yield) as a white solid. LC-MS (Method 4) $t_R$=2.39 min, m/z (M+H)$^+$=507.3. $^1$H NMR (400 MHz, DMSO-d$_6$) δ 11.69 (s, 1H), 10.69 (s, 1H), 9.31 (s, 1H), 8.51 (s, 1H), 8.50 (s, 1H), 7.46 (d, J=7.6 Hz, 1H), 6.74 (d, J=7.6 Hz, 1H), 4.83 (q, J=9.2 Hz, 2H), 4.00 (d, J=7.2 Hz, 2H), 2.01-1.95 (m, 1H), 1.36-1.29 (m, 1H), 0.79-0.75 (m, 4H), 0.49-0.41 (m, 4H).

Example 204

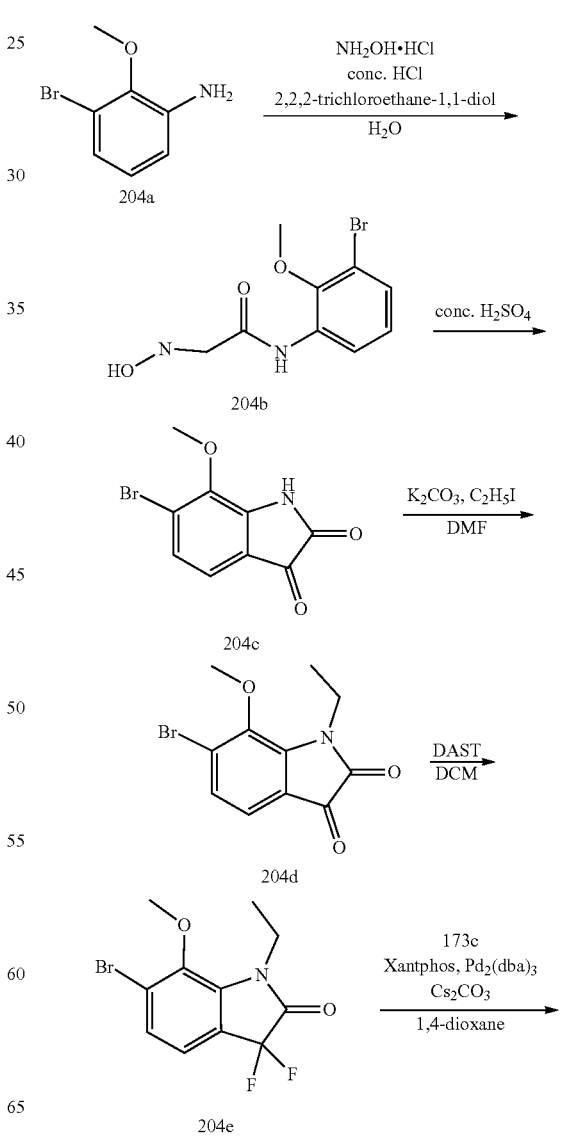

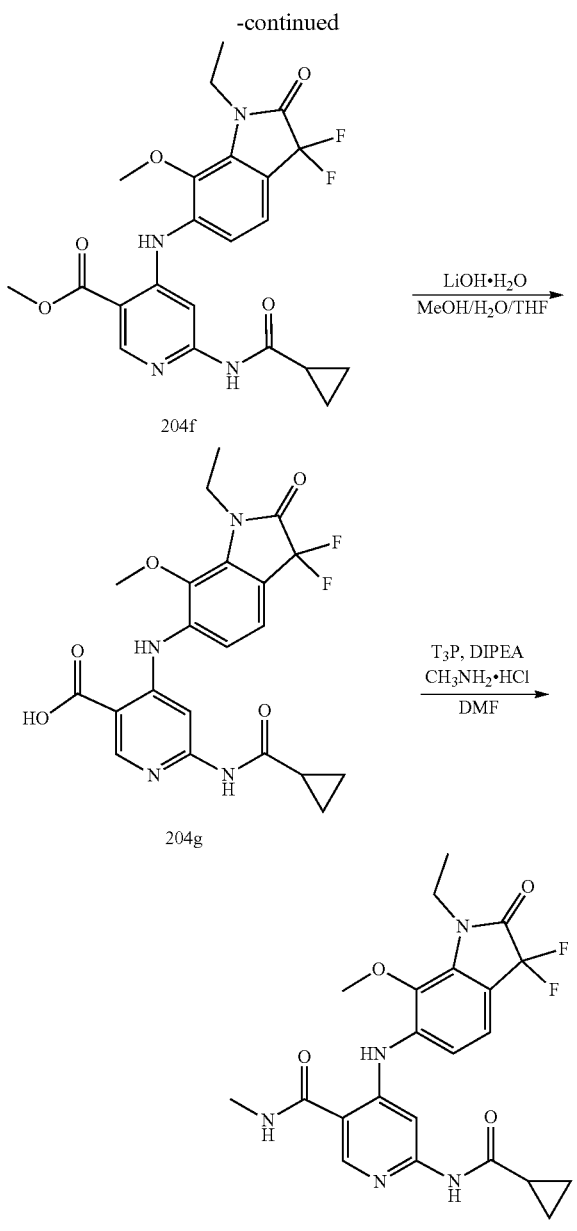

Step 1. N-(3-bromo-2-methoxyphenyl)-2-(hydroxy-imino)acetamide (204b)

To a solution of 204a (5 g, 24.75 mmol), NH₂OH·HCl (10.32 g, 148.48 mmol), conc. HCl (24.75 mmol, 2.5 mL) in H₂O (25 mL) was added 2,2,2-trichloroethane-1,1-diol (4.09 g, 24.75 mmol) slowly followed by Na₂SO₄ (21.09 g, 148.48 mmol) in H₂O (100 mL) at r.t. The reaction was stirred at 75° C. for 1 h. After cooling to r.t., the mixture was filtered and the filter cake was dried to afford the title compound 204b (6.0 g, 89% yield) as a white solid. LC-MS (Method 3) $t_R$=1.21 min, m/z (M–H)⁻=271.0.

Step 2. 6-Bromo-7-methoxyindoline-2,3-dione (204c)

A solution of 204b (5 g, 18.31 mmol) in conc. H₂SO₄ (30 mL) was stirred at r.t. for 12 h. The mixture was diluted with H₂O (40 mL) and the formed solid was collected by filtering. The filter cake was dried to afford the title compound 204c (3.19 g, 68% yield) as a brown solid. LC-MS (Method 3) $t_R$=1.01 min, m/z (M+H)⁺=256.2.

Step 3. 6-Bromo-1-ethyl-7-methoxyindoline-2,3-dione (204d)

A mixture of 204c (1.5 g, 5.86 mmol), K₂CO₃ (2.43 g, 17.57 mmol) and CH₃CH₂I (1.37 g, 8.79 mmol) in DMF (15 mL) was stirred at r.t. for 16 h. The mixture was diluted with water (10 mL) and extracted with EtOAc (50 mL). The separated organic layer was washed with brine (10 mL) and dried over Na₂SO₄, filtered and concentrated. The residue was purified by flash chromatography on silica gel (PE/EtOAc=5/1) to afford the title compound 204d (1.38 g, 83% yield) as a red oil. ¹H NMR (400 MHz, CDCl₃) δ 7.42 (d, J=8.0 Hz, 1H), 7.28 (d, J=8.0 Hz, 1H), 3.86 (s, 3H), 3.84 (t, J=6.8 Hz, 2H), 1.22 (t, J=6.8 Hz, 3H).

Step 4. 6-Bromo-1-ethyl-3,3-difluoro-7-methoxyindolin-2-one (204e)

To a solution of 204d (500 mg, 1.76 mmol) in DCM (5 mL) was added DAST (284 mg, 1.76 mmol) dropwise at 0° C. After stirring at r.t. for 16 h, the solution was diluted with DCM (20 mL) and washed with water (5 mL). The separated organic layer was washed with brine (10 mL) and dried over Na₂SO₄, filtered and concentrated. The residue was purified by flash chromatography on silica gel (PE/EtOAc=10/1) to afford the title compound 204e (240 mg, 45% yield) as a yellow oil. ¹H NMR (400 MHz, CDCl₃) δ 7.39 (d, J=8.0 Hz, 1H), 7.20-7.17 (m, 1H), 4.05-3.92 (m, 5H), 1.32 (t, J=6.8 Hz, 3H).

Step 5. Methyl 6-(cyclopropanecarboxamido)-4-((1-ethyl-3,3-difluoro-7-methoxy-2-oxoindolin-6-yl)amino)nicotinate (204f)

Compound 204f (110 mg, 37% yield), a light-yellow solid, was synthesized by utilizing a similar preparative procedure of Step 6 in Example 171 with 204e (200 mg, 0.65 mmol) and 173c (184 mg, 0.78 mmol) as starting materials. LC-MS (Method 3) $t_R$=1.17 min, m/z (M+H)⁺=461.3.

Step 6. 6-(Cyclopropanecarboxamido)-4-((1-ethyl-3,3-difluoro-7-methoxy-2-oxoindolin-6-yl)amino)nicotinic acid (204g)

Compound 204g (34 mg, 29% yield), a yellow solid, was synthesized by utilizing a similar preparative procedure of Step 3 in Example 27 with 204f (120 mg, 0.26 mmol) as the starting material. LC-MS (Method 3) $t_R$=0.98 min, m/z (M–H)⁻=445.3

Step 7. 6-(Cyclopropanecarboxamido)-4-((1-ethyl-3,3-difluoro-7-methoxy-2-oxoindolin-6-yl)amino)-N-methylnicotinamide (204)

Compound 204 (3.3 mg, 9% yield), a yellow solid, was synthesized by utilizing a similar preparative procedure of Step 2 in Example 11 with 204g (34 mg, 0.076 mmol) and methanamine hydrochloride (21 mg, 0.30 mmol) as starting materials. LC-MS (Method 2) $t_R$=2.94 min, m/z (M+H)⁺=460.1. ¹H NMR (400 MHz, DMSO-d₆) δ 10.93 (s, 1H), 10.87 (s, 1H), 8.73-8.70 (m, 1H), 8.57 (s, 1H), 8.17 (s, 1H), 7.52 (d, J=8.0 Hz, 1H), 7.26 (d, J=8.0 Hz, 1H), 3.89 (q, J=6.8 Hz, 2H), 3.77 (s, 3H), 2.80 (d, J=4.4 Hz, 3H), 2.03-1.98 (m, 1H), 1.24 (t, J=7.2 Hz, 3H), 0.87-0.76 (m, 4H).

Example 205

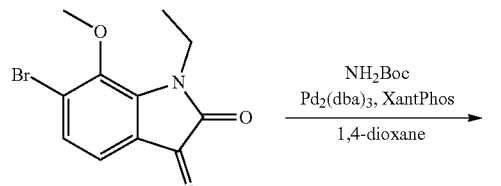

204d

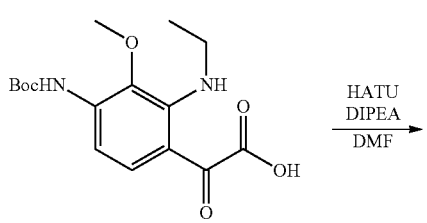

205a

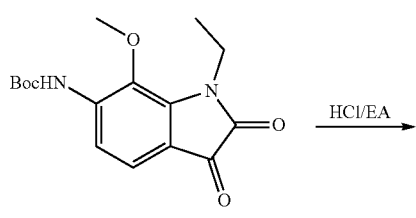

205b

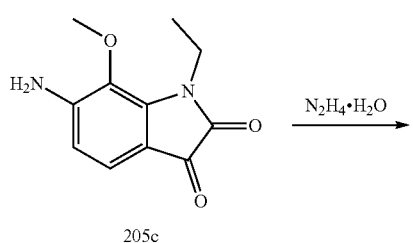

205c

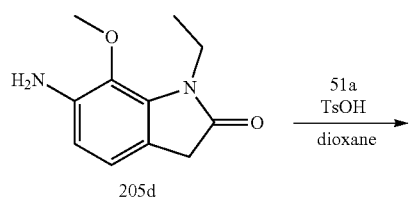

205d

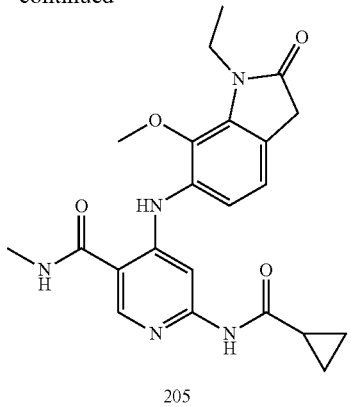

205

Step 1. 2-(4-((Tert-butoxycarbonyl)amino)-2-(ethylamino)-3-methoxyphenyl)-2-oxoacetic acid (205a)

A mixture of 204d (900 mg, 3.17 mmol), tert-butyl carbamate (557 mg, 4.75 mmol), XantPhos (366 mg, 0.63 mmol), $Pd_2(dba)_3$ (290 mg, 0.31 mmol) and $Cs_2CO_3$ (2.07 g, 6.34 mmol) in 1,4-dioxane (9 mL) was stirred at 100° C. for 4 h under $N_2$ atmosphere. After cooling to r.t., the reaction mixture was diluted with water (10 mL) and extracted with EtOAc (10 mL*2). The combined organic phase was concentrated and the residue was purified by Prep-HPLC (Method A) to afford the title compound 205a (440 mg, 41% yield) as a yellow solid. LC-MS (Method 3) $t_R$=1.42 min, m/z $(M+H)^+$=339.2.

Step 2. Tert-butyl (1-ethyl-7-methoxy-2,3-dioxoindolin-6-yl)carbamate (205b)

A mixture of 205a (350 mg, 1.03 mmol), HATU (787 mg, 2.07 mmol) and DIPEA (401 mg, 3.10 mmol) in DMF (3 mL) was stirred at r.t. for 16 h. The reaction was concentrated and the residue was purified by Prep-HPLC (Method A) to afford the title compound 205b (150 mg, 45% yield) as a yellow solid. LC-MS (Method 3) $t_R$=1.29 min, m/z $(M+H)^+$=321.0.

Step 3. 6-Amino-1-ethyl-7-methoxyindoline-2,3-dione (205c)

A solution of 205b (170 mg, 0.53 mmol) in HCl/EtOAc (4 mL, 2 M) was stirred at r.t. for 2 h. The solution was concentrated and the residue was purified by Prep-HPLC (Method A) to afford the title compound 205c (35 mg, 30% yield) as a yellow solid. LC-MS (Method 3) $t_R$=0.94 min, m/z $(M+H)^+$=221.1.

Step 4. 6-Amino-1-ethyl-7-methoxyindolin-2-one (205d)

A solution of 205c (30 mg, 0.13 mmol) in hydrazine hydrate (1 mL, 98% purity) was stirred at 130° C. for 4 h. The reaction mixture was cooled and concentrated. The residue was purified by reverse chromatography (Method A) to afford the title compound 205d (5 mg, 18% yield) as a yellow solid. LC-MS (Method 3) $t_R$=1.07 min, m/z $(M+H)^+$=207.4.

Step 5. 6-(Cyclopropanecarboxamido)-4-((1-ethyl-7-methoxy-2-oxoindolin-6-yl)amino)-N-methylnicotinamide (205)

A mixture of 205d (5 mg, 0.0024 mmol), 51a (6 mg, 0.0024 mmol) and TsOH (0.42 mg, 0.0024 mmol) in dioxane (1 mL) was stirred at 100° C. for 16 h. The reaction mixture was cooled and concentrated. The residue was purified by Prep-HPLC (Method A) to afford the title compound 205 (2 mg, 19% yield) as a white solid. LC-MS (Method 2) $t_R$=2.55 min, m/z (M+H)$^+$=424.1. $^1$H NMR (400 MHz, DMSO-d$_6$) δ 10.71 (s, 1H), 10.51 (s, 1H), 8.62-8.59 (m, 1H), 8.51 (s, 1H), 7.94 (s, 1H), 7.05 (d, J=7.6 Hz, 1H), 6.99 (d, J=7.6 Hz, 1H), 3.84 (q, J=7.2 Hz, 2H), 3.88 (s, 3H), 3.56 (s, 2H), 2.79 (d, J=4.4 Hz, 3H), 1.95-1.91 (m, 1H), 1.16 (t, J=7.2 Hz, 3H), 0.76-0.72 (m, 4H).

Example 206

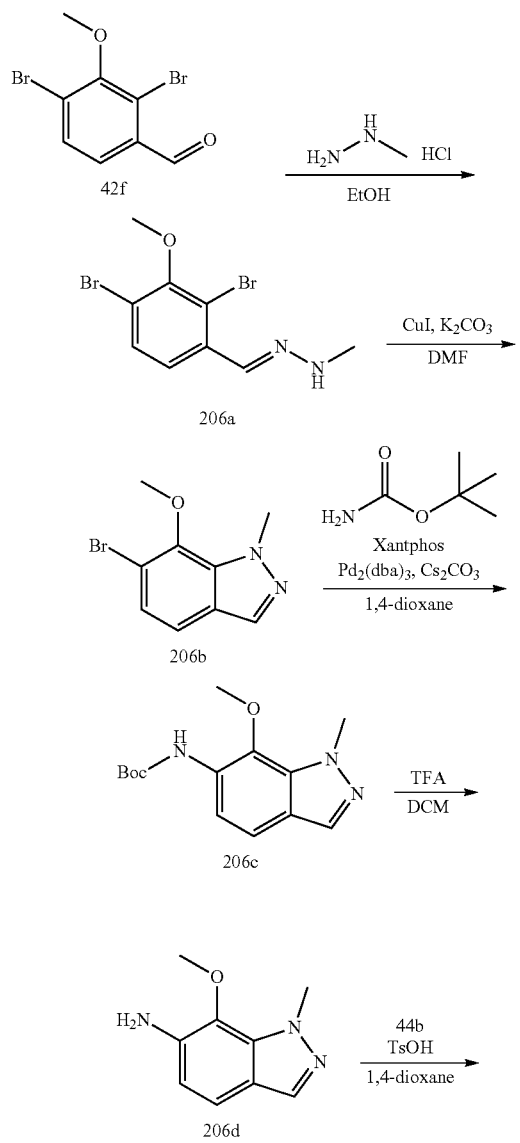

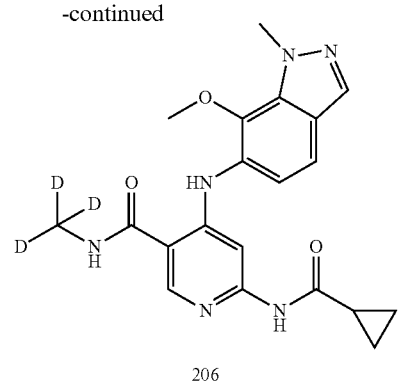

Step 1. (E)-1-(2,4-Dibromo-3-methoxybenzylidene)-2-methylhydrazine (206a)

To a solution of 42f (5.00 g, 17.0 mmol) in EtOH (20 mL) was added methylhydrazine hydrochloride (2.81 g, 34.0 mmol). The reaction mixture was stirred at 25° C. for 1 h. The solution was filtered. The filter cake was collected and washed with EtOH (5 mL). The solid was dried in vacuo to give the crude 206a (5.00 g, 91% yield) as a brown solid. LC-MS (Method 5) $t_R$=2.80 min, m/z (M+H)$^+$=322.8. $^1$H NMR (400 MHz, DMSO-d$_6$) δ 7.56 (d, J=8.8 Hz, 1H), 7.50-7.48 (m, 2H), 3.80 (s, 3H), 2.86 (s, 3H).

Step 2. 6-Bromo-7-methoxy-1-methyl-1H-indazole (206b)

To a solution of 206a (5.00 g, 13.9 mol) and potassium carbonate (13.6 g, 41.7 mol) in DMF (50 mL) was added copper(I) iodide (0.530 g, 2.78 mol) at 25° C. The reaction mixture was stirred at 100° C. for 16 h. The reaction mixture was cooled to 25° C. and poured into water (300 mL). The residue was extracted with EA (50 mL*3). The combined organic layer was washed with brine (50 mL*2), dried over sodium sulphate and evaporated in vacuo to give the crude product. The residue was purified by silica gel column and eluted with PE/EA=20/1 to 3/1 to give 206b (3.00 g, 74% yield) as a red oil. LC-MS (Method 6) $t_R$=2.68 min, m/z (M+H)$^+$=240.7. $^1$H NMR (400 MHz, DMSO-d$_6$) δ 8.08 (s, 1H), 7.47 (d, J=8.4 Hz, 1H), 7.26 (d, J=8.4 Hz, 1H), 4.20 (s, 3H), 3.94 (s, 3H).

Step 3. Tert-butyl (7-methoxy-1-methyl-1H-indazol-6-yl)carbamate (206c)

The mixture of 206b (1.00 g, 4.10 mmol), tert-butyl carbamate (1.44 g, 12.3 mmol) and cesium carbonate (3.34 g, 10.3 mmol) in 1,4-dioxane (15 ml) was stirred under nitrogen and to it was added Pd$_2$(dba)$_3$ (0.190 g, 0.205 mmol) and XantPhos (0.240 g, 0.410 mmol). The reaction mixture was stirred at 100° C. for 16 h. The reaction was cooled to 30° C. Water (30 mL) was added. The mixture was extracted with EA (50 mL*3). The combined organic layer was washed by brine (30 mL*2), dried over sodium sulphate and evaporated in vacuo to give the crude product. The crude product was purified via Prep-TLC (PE/EA=3/1) to give 206c (400 mg, 35% yield) as a yellow oil. LC-MS (Method 6) $t_R$=2.60 min, m/z (M+H)$^+$=277.8. $^1$H NMR (400 MHz, DMSO-d$_6$) δ 8.62 (s, 1H), 7.96 (s, 1H), 7.41 (d, J=8.6 Hz, 1H), 7.25 (d, J=8.6 Hz, 1H), 4.16 (s, 3H), 3.82 (s, 3H), 1.47 (s, 9H).

Step 4. 7-Methoxy-1-methyl-1H-indazol-6-amine (206d)

To a solution of 206c (400 mg, 1.44 mmol) in DCM (2 mL) was added trifluoroacetic (906 mg, 4.31 mmol) dropwise at 0° C. The reaction mixture was stirred at 25° C. for 1 h. The mixture was adjusted to pH=7-8 with saturated $Na_2CO_3$ aqueous solution, extracted with DCM (5 mL*3). The combined organic layer was dried over sodium sulphate and evaporated in vacuo to give the crude product. The crude product was purified via Prep-TLC (PE/EA=2/1) to give 206d (180 mg, 60% yield) as a red solid. LC-MS (Method 6) $t_R$=1.71 min, m/z (M+H)$^+$=177.8. $^1$H NMR (400 MHz, DMSO-$d_6$) δ 7.73 (s, 1H), 7.17 (d, J=8.4 Hz, 1H), 6.62 (d, J=8.4 Hz, 1H), 5.09 (brs, 2H), 4.04 (s, 3H), 3.74 (s, 3H).

Step 5. 6-(Cyclopropanecarboxamido)-4-((7-methoxy-1-methyl-1H-indazol-6-yl)amino)-N-(methyl-$d_3$)nicotinamide (206)

The mixture of 206d (180 mg, 1.02 mmol), 44b (261 mg, 1.02 mmol) and p-TSA (262 mg, 1.52 mmol) in 1,4-dioxane (3 mL) was stirred under $N_2$ at 100° C. for 16 h. Water (1 mL) was added. The residue was purified via Prep-HPLC (Columns: XBridge-1 5 μm 19-150 mm; Mobile phase: ACN/$H_2O$ (0.1% $NH_3H_2O$); Gradient: 20-35% ACN, 8 min; Flow rate: 20 mL/min) to give 206 (11.0 mg, 2.8% yield) as an off-white solid. LC-MS (Method 6) $t_R$=2.12 min, m/z (M+H)$^+$=398.1. $^1$H NMR (400 MHz, DMSO-$d_6$) δ 10.72 (s, 1H), 10.57 (s, 1H), 8.61 (s, 1H), 8.52 (s, 1H), 8.01 (s, 1H), 7.84 (s, 1H), 7.51 (d, J=8.6 Hz, 1H), 7.12 (d, J=8.6 Hz, 1H), 4.18 (s, 3H), 3.80 (s, 3H), 1.99-1.88 (m, 1H), 0.75-0.73 (m, 4H).

Example 207

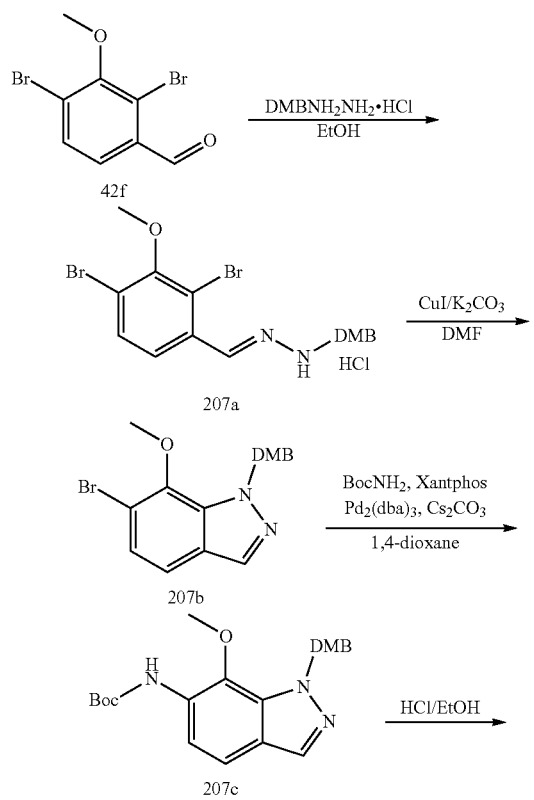

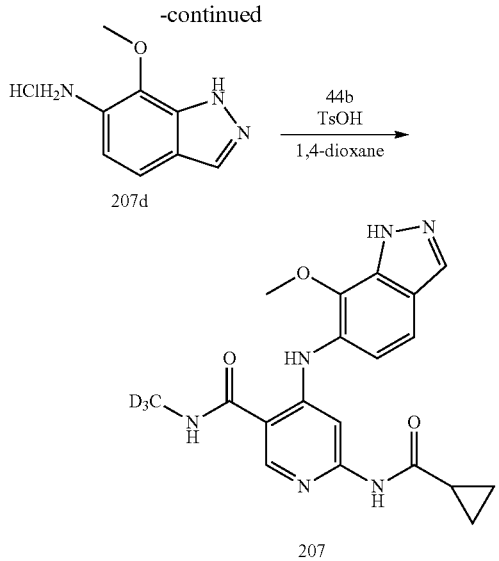

Step 1. (E)-1-(2,4-Dibromo-3-methoxybenzylidene)-2-(2,4-dimethoxybenzyl)hydrazine hydrochloride (207a)

To a solution of 42f (2 g, 6.80 mmol) in EtOH (2 mL) was added DMBNHNH$_2$·HCl (1.78 g, 8.16 mmol). The mixture was stirred at 25° C. for 16 h. The mixture was cooled down to 0° C. and filtered. The filter cake was dried to afford the title compound 207a (3.01 g, 97% yield) as a yellow solid. $^1$H NMR (300 MHz, DMSO-$d_6$) δ 7.73 (s, 1H), 7.58 (d, J=8.4 Hz, 1H), 7.49 (d, J=8.4 Hz, 1H), 6.92-6.88 (m, 2H), 7.19 (d, J=8.1 Hz, 1H), 6.58 (d, J=2.1 Hz, 1H), 6.52 (dd, J=8.4 Hz, 2.1 Hz, 1H), 4.30 (s, 2H), 3.83 (s, 3H), 3.80 (s, 3H), 3.77 (s, 3H).

Step 2. 6-Bromo-1-(2,4-dimethoxybenzyl)-7-methoxy-1H-indazole (207b)

To a solution of 207a (3 g, 6.11 mmol) in DMF (30 mL) was added $K_2CO_3$ (1.81 g, 13.10 mmol) and CuI (1.25 g, 6.55 mmol). The mixture was stirred at 100° C. for 10 h. The reaction mixture was diluted with water (10 mL) and extracted with EtOAc (50 mL*3). The combined organic layer was dried over anhydrous $Na_2SO_4$, filtered and concentrated. The residue was purified by flash chromatography on silica gel (PE/EtOAc=20/1) to afford the title compound 207b (801 mg, 35% yield) as a colorless oil. $^1$H NMR (300 MHz, CDCl$_3$) δ 8.06 (s, 1H), 7.40 (d, J=8.7 Hz, 1H), 7.29 (d, J=8.7 Hz, 1H), 6.59 (d, J=8.4 Hz, 1H), 6.53 (d, J=2.1 Hz, 1H), 6.38 (dd, J=2.1, 8.4 Hz, 1H), 5.83 (s, 2H), 3.89 (s, 3H), 3.85 (s, 3H), 3.81 (s, 3H).

Step 3. Tert-butyl (1-(2,4-dimethoxybenzyl)-7-methoxy-1H-indazol-6-yl)carbamate (207c)

A mixture of 207b (500 mg, 1.33 mmol), tert-butyl carbamate (310 mg, 2.65 mmol), XantPhos (153 mg, 0.27 mmol), $Cs_2CO_3$ (864 mg, 2.65 mmol) and Pd$_2$(dba)$_3$ (242 mg, 0.27 mmol) in 1,4-dioxane (10 mL) was stirred at 100° C. for 24 h under $N_2$ atmosphere. The reaction mixture was cooled and concentrated under reduced pressure. The residue was purified by flash chromatography on silica gel (PE/EtOAc=15/1) to afford 207c (450 mg, 82% yield) as a yellow oil. LC-MS (Method 3) $t_R$=1.42 min, m/z (M+H)$^+$=414.5.

Step 4. 7-Methoxy-1H-indazol-6-amine hydrochloride (207d)

A solution of 207c in HCl/EtOH (3 mL, 2 M) was stirred at 25° C. for 2 h. The formed solid was filtered and dried to afford 207d (70 mg, 71% yield) as a brown solid. LC-MS (Method 3) $t_R$=0.42 min, m/z (M+H)$^+$=164.3.

Step 5. 6-(Cyclopropanecarboxamido)-4-((7-methoxy-1H-indazol-6-yl)amino)-N-(methyl-d$_3$) nicotinamide (207)

A mixture of 207d (70 mg, 0.43 mmol), 44b (132 mg, 0.52 mmol) and TsOH (7 mg, 0.04 mmol) in 1,4-dioxane (1 mL) was stirred at 100° C. for 16 h. The reaction mixture was cooled and concentrated under reduced pressure. The residue was purified by flash chromatography on silica gel (DCM/MeOH=20/1) to afford 207 (16 mg, 10% yield) as a white solid. LC-MS (Method 2) $t_R$=2.76 min, m/z (M+H)$^+$=384.1. $^1$H NMR (400 MHz, DMSO-d$_6$) δ 13.28 (s, 1H), 10.66 (s, 1H), 10.48 (s, 1H), 8.55 (s, 1H), 8.49 (s, 1H), 8.07 (s, 1H), 7.79 (s, 1H), 7.49 (d, J=8.4 Hz, 1H), 7.08 (d, J=8.4 Hz, 1H), 3.87 (s, 3H), 1.95-1.92 (m, 1H), 0.73-0.71 (m, 4H).

Example 208

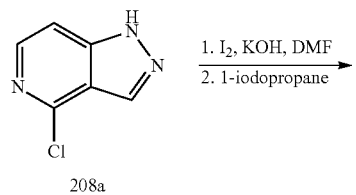

208a

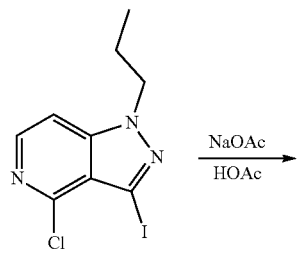

208b

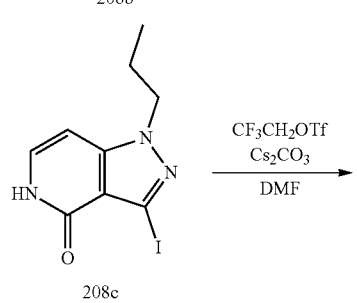

208c

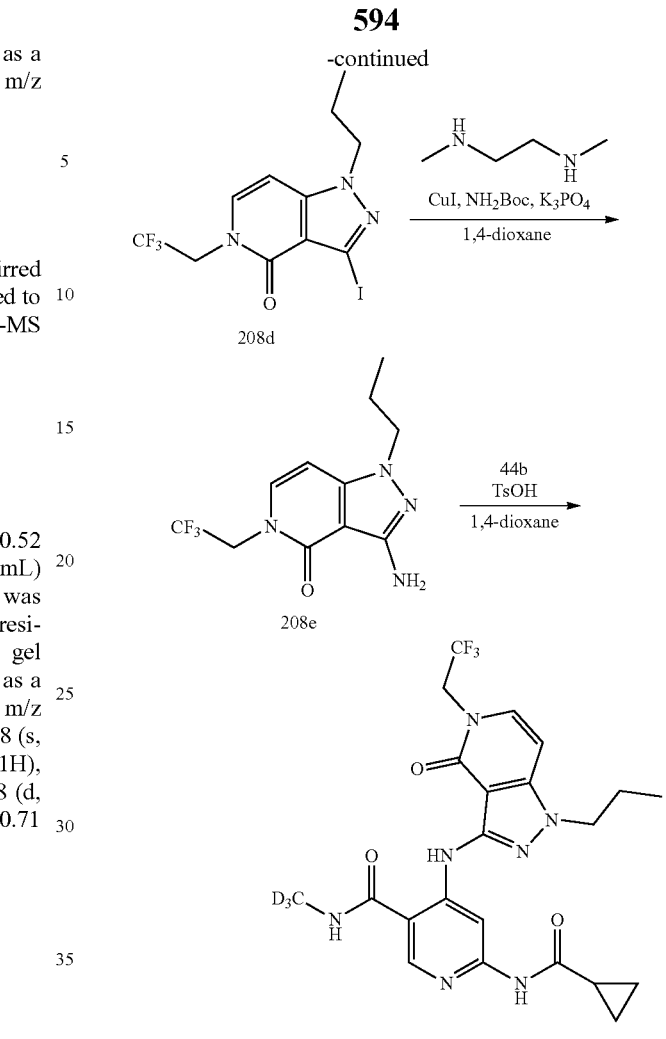

Step 1. 4-Chloro-3-iodo-1-propyl-1H-pyrazolo[4,3-c]pyridine (208b)

A mixture of 208a (400 mg, 2.60 mmol), KOH (585 mg, 10.42 mmol) and I$_2$ (1.32 g, 5.21 mmol) in DMF (5 mL) was stirred at 75° C. for 8 h. After cooling to r.t., to the reaction mixture was added 1-iodopropane (730 mg, 4.29 mmol). The reaction mixture was stirred at 40° C. for 24 h. After cooling to r.t., the reaction mixture was diluted with water (20 mL) and extracted with EtOAc (30 mL*2). The combined organic phase was washed with brine (30 mL) and concentrated. The residue was purified by flash chromatography on silica gel (PE/EtOAc=9/1) to afford 208b (400 mg, 58% yield) as a white solid. $^1$H NMR (400 MHz, CDCl$_3$) δ 8.16 (d, J=6.0 Hz, 1H), 7.28 (d, J=6.0 Hz, 1H), 4.32 (t, J=6.8 Hz, 2H), 2.00-1.91 (m, 2H), 0.93 (t, J=7.6 Hz, 3H).

Step 2. 3-Iodo-1-propyl-1,5-dihydro-4H-pyrazolo[4,3-c]pyridin-4-one (208c)

A mixture of 208b (530 mg, 1.65 mmol) and NaOAc (270 mg, 3.30 mmol) in AcOH (5 mL) was stirred at 100° C. for 16 h. The reaction mixture was concentrated. The residue was diluted with water (10 mL) and extracted with DCM (20 mL*2). The combined organic phase was dried over Na₂SO₄, filtered and concentrated to afford 208c (480 mg, 96% yield) as a white solid. LC-MS (Method 3) t_R=1.01 min, m/z (M+H)⁺=304.0.

Step 3. 3-Iodo-1-propyl-5-(2,2,2-trifluoroethyl)-1,5-dihydro-4H-pyrazolo[4,3-c]pyridin-4-one (208d)

A mixture of 208c (480 mg, 1.58 mmol), Cs₂CO₃ (1.03 g, 3.17 mmol) and 2,2,2-trifluoroethyl trifluoromethane-sulfonate (735 mg, 3.17 mmol) in DMF (6 mL) was stirred at 40° C. for 2 h. After cooling to r.t., the reaction mixture was diluted with water (20 mL) and extracted with EtOAc (30 mL*2). The combined organic phase was washed with brine (30 mL) and concentrated. The residue was purified by flash chromatography on silica gel (PE/EtOAc=4/1) to afford 208d (470 mg, 77% yield) as a white solid. ¹H NMR (400 MHz, CDCl₃) δ 7.12 (d, J=7.6 Hz, 1H), 6.37 (d, J=7.6 Hz, 1H), 4.61 (q, J=8.8 Hz, 2H), 4.17 (t, J=7.2 Hz, 2H), 1.97-1.88 (m, 2H), 0.93 (t, J=7.6 Hz, 3H).

Step 4. 3-Amino-1-propyl-5-(2,2,2-trifluoroethyl)-1,5-dihydro-4H-pyrazolo[4,3-c]pyridin-4-one (208e)

A mixture of 208d (250 mg, 0.65 mmol), tert-butyl carbamate (114 mg, 0.97 mmol), N,N'-dimethyl-1,2-ethane-diamine (29 mg, 0.33 mmol), CuI (62 mg, 0.33 mmol) and K₃PO₄ (413 mg, 1.95 mmol) in anhydrous 1,4-dioxane (3 mL) was stirred at 100° C. for 20 h under N₂ atmosphere. After cooling to r.t., the reaction mixture was concentrated. The residue was purified by flash chromatography on silica gel (PE/EtOAc=1/1) to afford 208e (40 mg, 22% yield) as a yellow solid. LC-MS (Method 3) t_R=1.12 min, m/z (M+H)⁺=275.1.

Step 5. 6-(Cyclopropanecarboxamido)-N-(methyl-d₃)-4-((4-oxo-1-propyl-5-(2,2,2-trifluoroethyl)-4,5-dihydro-1H-pyrazolo[4,3-c]pyridin-3-yl)amino)nicotinamide (208)

A mixture of 208e (40 mg, 0.15 mmol), 44b (45 mg, 0.18 mmol) and TsOH (13 mg, 0.07 mmol) in 1,4-dioxane (1 mL) was stirred at 100° C. for 24 h in a sealed tube. After cooling to r.t., the reaction mixture was filtered. The filter cake was washed with EtOAc (3 mL) to afford the crude product. The crude product was slurried with ACN (5 mL) for 30 min and filtered. The filter cake was dried to afford 208 (46 mg, 64% yield) as a white solid. LC-MS (Method 2) t_R=2.91 min, m/z (M+H)⁺=495.0. ¹H NMR (400 MHz, DMSO-d₆) δ 12.01 (s, 1H), 11.62 (br s, 1H), 8.96 (s, 1H), 8.80 (s, 1H), 8.53 (s, 1H), 7.54 (d, J=7.2 Hz, 1H), 6.81 (d, J=7.2 Hz, 1H), 4.88 (q, J=8.8 Hz, 2H), 4.19 (t, J=6.0 Hz, 2H), 2.09-2.01 (m, 1H), 1.98-1.88 (m, 2H), 0.97-0.87 (m, 4H), 0.83 (t, J=7.2 Hz, 3H).

Example 209

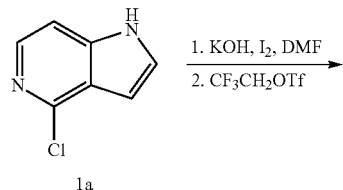

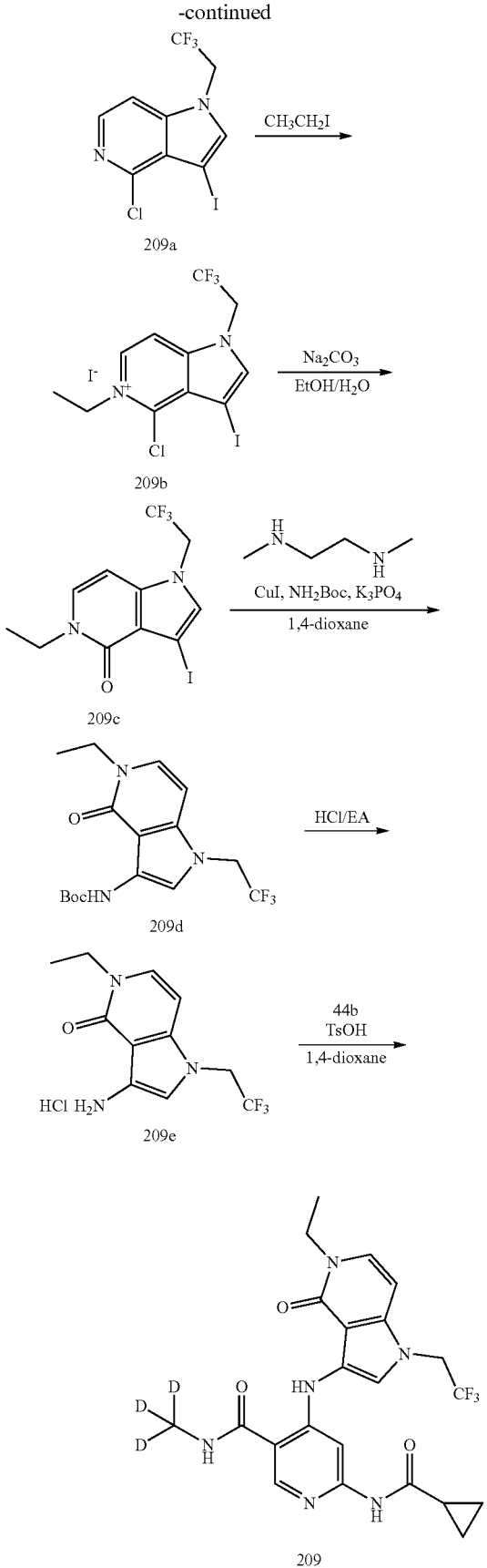

Step 1. 4-Chloro-3-iodo-1-(2,2,2-trifluoroethyl)-1H-pyrrolo[3,2-c]pyridine (209a)

To a solution of 1a (1.0 g, 6.55 mmol) and KOH (1.10 g, 19.66 mmol) in DMF (10 mL) was added 12 (1.66 g, 6.55 mmol) at 0° C. After stirring for 0.5 h at this temperature, to the reaction was added 2,2,2-trifluoroethyl methanesulfonate (1.73 g, 9.70 mmol). The resultant mixture was stirred at r.t. for 2 h and diluted with water (30 mL). The mixture was extracted with EtOAc (30 mL*3). The combined organic phase was washed with brine (30 mL) and concentrated. The residue was purified by flash chromatography on silica gel (PE/EtOAc=5/1) to afford 209a (2.2 g, 94% yield) as a yellow solid. LC-MS (Method 3) $t_R$=1.33 min, m/z (M+H)$^+$=361.0.

Step 2. 4-Chloro-5-ethyl-3-iodo-1-(2,2,2-trifluoroethyl)-1H-pyrrolo[3,2-c]pyridin-5-ium iodide (209b)

A mixture of 209a (950 mg, 2.64 mmol) and iodoethane (10 mL) was stirred at 70° C. for 5 h. After cooling to r.t., the mixture was concentrated to afford 209b (1.33 g, 98% yield) as a yellow solid. LC-MS (Method 3) $t_R$=1.07 min, m/z M$^+$=389.1.

Step 3. 5-Ethyl-3-iodo-1-(2,2,2-trifluoroethyl)-1,5-dihydro-4H-pyrrolo[3,2-c]pyridin-4-one (209c)

A mixture of 209b (1.33 g, 2.57 mmol) and Na$_2$CO$_3$ (816 mg, 7.70 mmol) in EtOH (10 mL) and H$_2$O (10 mL) was stirred at 70° C. for 5 h. The reaction mixture was cooled and concentrated. The residue was diluted with water (30 mL) and extracted with EtOAc (30 mL*3). The combined organic phase was washed with brine (30 mL) and concentrated. The residue was purified by flash chromatography on silica gel (PE/EtOAc=1/2) to afford 209c (600 mg, 63% yield) as a white solid. LC-MS (Method 3) $t_R$=1.14 min, m/z (M+H)$^+$=371.2.

Step 4. Tert-butyl (5-ethyl-4-oxo-1-(2,2,2-trifluoroethyl)-4,5-dihydro-1H-pyrrolo[3,2-c]pyridin-3-yl)carbamate (209d)

A mixture of 209c (600 mg, 1.62 mmol), tert-butyl carbamate (380 mg, 3.24 mmol), CuI (154 mg, 0.81 mmol), K$_3$PO$_4$ (688 mg, 3.24 mmol) and DMEDA (71 mg, 0.81 mmol) in anhydrous 1,4-dioxane (10 mL) was stirred at 90° C. overnight under N$_2$ atmosphere. The reaction mixture was cooled and concentrated. The residue was purified by flash chromatography on silica gel (PE/EtOAc=1/1) to give 209d (468 mg, 80% yield) as a yellow oil. $^1$H NMR (400 MHz, CDCl$_3$) δ 8.47 (s, 1H), 7.02 (d, J=7.2 Hz, 1H), 6.38 (d, J=7.2 Hz, 1H), 4.40 (q, J=8.4 Hz, 2H), 4.10 (q, J=7.2 Hz, 2H), 1.45 (s, 9H), 1.36 (t, J=7.2 Hz, 3H).

Step 5. 3-Amino-5-ethyl-1-(2,2,2-trifluoroethyl)-1,5-dihydro-4H-pyrrolo[3,2-c]pyridin-4-one hydrochloride (209e)

A mixture of 209d (468 mg, 1.30 mmol) in HCl/EtOAc (10 mL, 2.0 M) was stirred at r.t. for 4 h. The formed solid was collected by filtering and dried to afford 209e (268 mg, 70% yield) as a white solid. LC-MS (Method 3) $t_R$=0.91 min, m/z (M+H)$^+$=260.3.

Step 6. 6-(Cyclopropanecarboxamido)-4-((5-ethyl-4-oxo-1-(2,2,2-trifluoroethyl)-4,5-dihydro-1H-pyrrolo[3,2-c]pyridin-3-yl)amino)-N-(methyl-d$_3$)nicotinamide (209)

A mixture of 209e (250 mg, 0.85 mmol), 44b (217 mg, 0.85 mmol) and TsOH (29 mg, 0.17 mmol) in 1,4-dioxane (5 mL) was stirred at 100° C. overnight. After cooling to r.t., the mixture was concentrated. The residue was purified by flash chromatography on silical gel (DCM/MeOH=4/1) to afford the crude compound. The crude compound was purified by Prep-HPLC (Method A) to afford 209 (15 mg, 4% yield) as a white solid. LC-MS (Method 2) $t_R$=3.34 min, m/z (M+H)$^+$=480.1. $^1$H NMR (400 MHz, DMSO-d$_6$) δ 10.94 (s, 1H), 10.71 (s, 1H), 8.44 (s, 1H), 8.39 (s, 1H), 8.00 (s, 1H), 7.43 (d, J=7.6 Hz, 1H), 7.10 (s, 1H), 6.69 (d, J=7.6 Hz, 1H), 5.11 (q, J=9.2 Hz, 2H), 3.94 (q, J=7.2 Hz, 2H), 2.02-1.97 (m, 1H), 1.21 (t, J=6.8 Hz, 3H), 0.81-0.79 (m, 4H).

Example 210

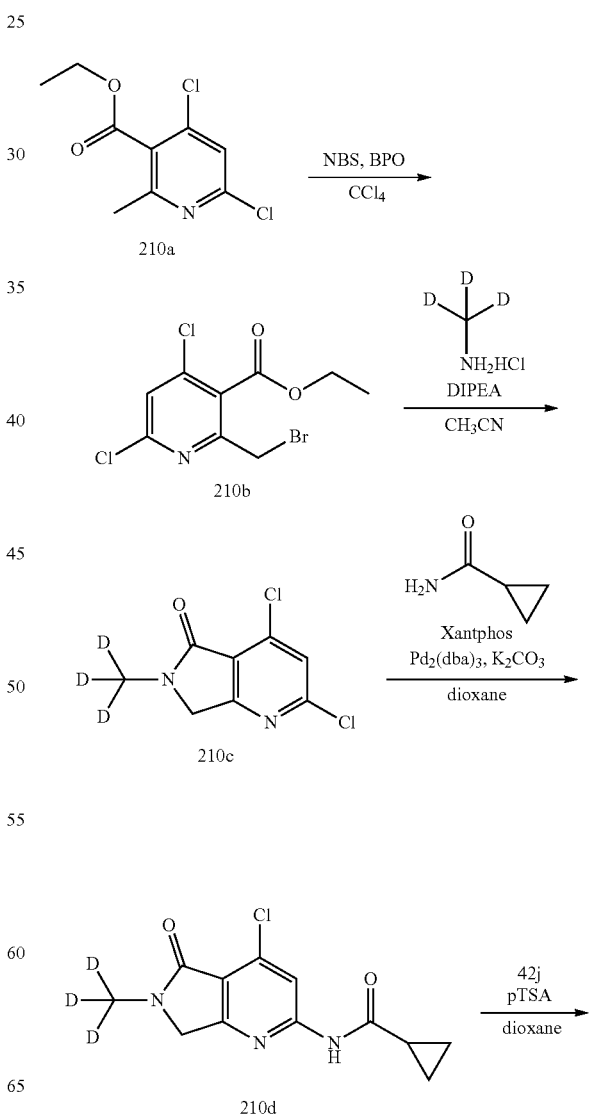

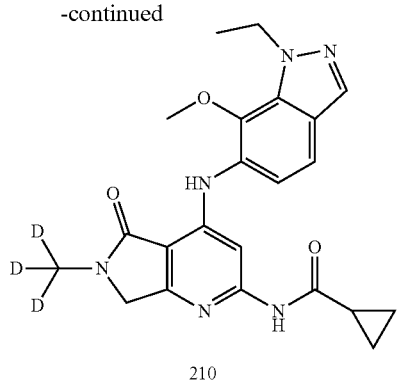

210

100° C. for 5 h. The mixture was diluted with H₂O (10 mL), extracted with EA (20 mL*3), washed with brine (20 mL), dried over Na₂SO₄ and concentrated. The residue was purified by Prep-HPLC (Method E) to give 210 (5.0 mg, 15% yield) as an off-white solid. LC-MS (Method 4) $t_R$=3.49 min, m/z (M+H)⁺=424.3. ¹H NMR (400 MHz, CDCl₃) δ 8.83 (s, 1H), 8.09 (s, 1H), 7.92 (s, 1H), 7.89 (s, 1H), 7.48 (d, J=8.4 Hz, 1H), 7.22 (d, J=8.4 Hz, 1H), 4.61 (q, J=7.2 Hz, 2H), 4.25 (s, 2H), 3.87 (s, 3H), 1.48 (t, J=7.2 Hz, 3H), 1.23 (m, 1H), 1.08-0.99 (m, 2H), 0.89-0.80 (m, 2H).

Example 211

Step 1. Ethyl 2-(bromomethyl)-4,6-dichloronicotinate (210b)

To a solution of 210a (5 g, 21.3 mmol) in CCl₄ (80 mL) was added N-bromosuccinimide (11.4 g, 64 mmol) and benzoyl peroxide (1.54 g, 6.4 mmol) and the mixture was stirred at 85° C. for 15 h. The mixture was cooled to room temperature and filtered, and the filtrate was concentrated. The residue was dissolved in ethyl acetate (100 mL), washed with brine (50 mL), dried over anhydrous sodium sulfate, filtered, concentrated and purified by flash chromatography on silica gel (PE/EtOAc=100/1 to 1/1) to give 210b (4 g, 60% yield) as a yellow solid. LC-MS (Method 4) $t_R$=4.21 min, m/z (M+H)⁺=312.0.

Step 2. 2,4-Dichloro-6-(methyl-d₃)-6,7-dihydro-5H-pyrrolo[3,4-b]pyridin-5-one (210c)

To a solution of 210b (3 g, 9.55 mmol) in CH₃CN (30 mL) was added DIPEA (2.46 g, 19.1 mmol) and methan-d₃-amine hydrochloride (1.2 g, 14.3 mmol) at 25° C. The mixture was stirred at 25° C. for 5 h. Then the reaction mixture was concentrated and purified by flash chromatography on silica gel (PE/EtOAc=10/1 to 1/3) to give the compound 210c (700 mg, 33% yield) as a yellow solid. LC-MS (Method 4) $t_R$=3.58 min, m/z (M+H)⁺=220.0.

Step 3. N-(4-chloro-6-(methyl-d₃)-5-oxo-6,7-dihydro-5H-pyrrolo[3,4-b]pyridin-2-yl)cyclopropanecarboxamide (210d)

To a solution of 210c (500 mg, 2.27 mmol) in dioxane (5 mL) was added XantPhos (262 mg, 0.454 mmol), Pd₂(dba)₃ (210 mg, 0.23 mmol), K₂CO₃ (626 mg, 4.54 mmol) and cyclopropanecarboxamide (459 mg, 4.54 mmol) at 25° C. The reaction mixture was stirred at 100° C. for 4 h under N₂ atmosphere. The mixture was diluted with H₂O (5 mL), extracted with EA (20 mL*3), washed with brine (20 mL), dried over Na₂SO₄, concentrated and purified by flash chromatography on silica gel (DCM/MeOH=100/1 to 10/1) to get the compound 210d (120 mg, 24% yield) as a yellow solid. LC-MS (Method 4) $t_R$=2.81 min, m/z (M+H)⁺=269.1.

Step 4. N-(4-((1-ethyl-7-methoxy-1H-indazol-6-yl)amino)-6-(methyl-d₃)-5-oxo-6,7-dihydro-5H-pyrrolo[3,4-b]pyridin-2-yl)cyclopropanecarboxamide (210)

To a solution of 210d (40 mg, 0.15 mmol) and 42j (28.8 mg, 0.15 mmol) in dioxane (1 mL) was added pTSA (25 mg, 0.15 mmol) at 25° C. The reaction mixture was stirred at

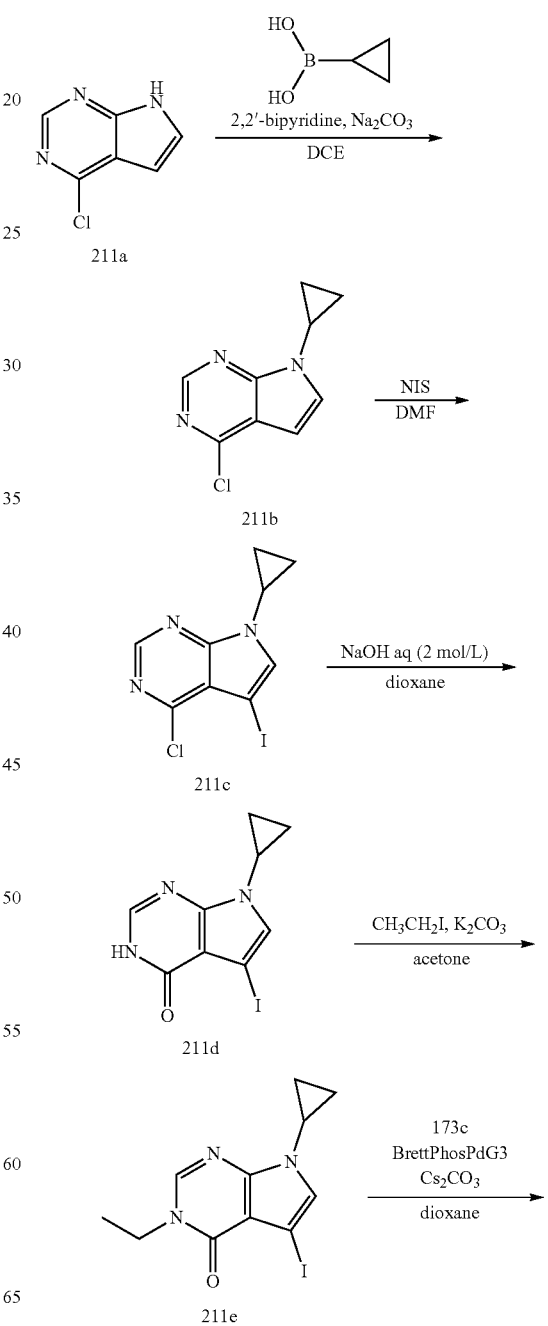

-continued

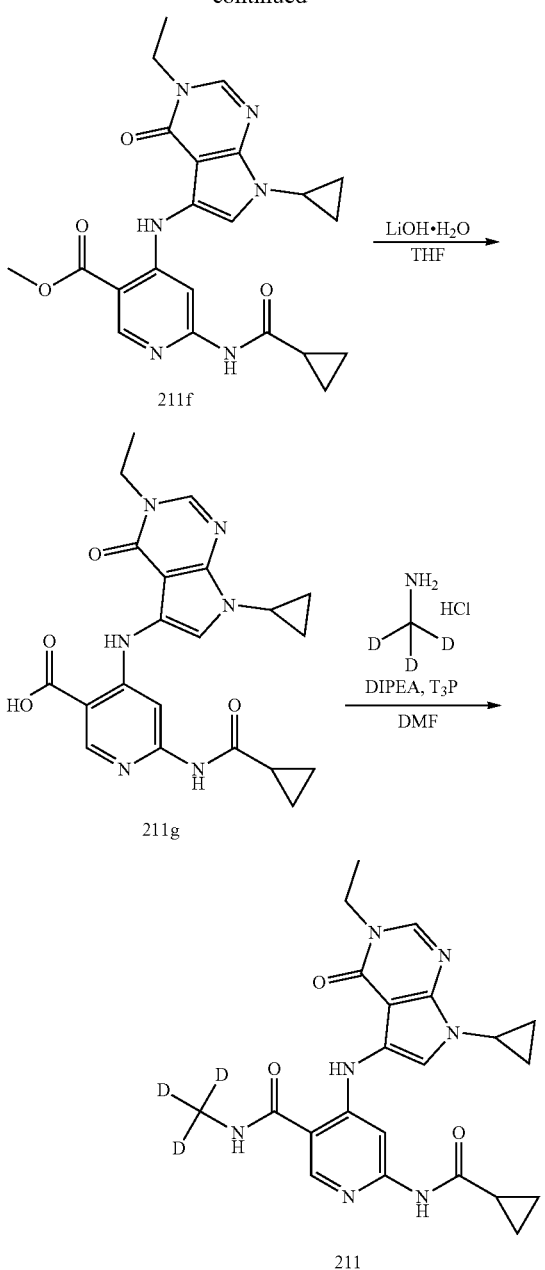

Step 1. 4-Chloro-7-cyclopropyl-7H-pyrrolo[2,3-d]pyrimidine (211b)

To a solution of 211a (3.0 g, 19.54 mmol), 2,2'-bipyridine (3.0 g, 19.21 mmol), Na$_2$CO$_3$ (4.14 g, 39.07 mmol) in DCE (40 mL) was added cyclopropylboronic acid (3.36 g, 39.07 mmol) at r.t. The mixture was stirred at 70° C. for 4 h. The resulting solution was added into DCM (40 mL) and filtered. The filtrate was washed by brine, dried over Na$_2$SO$_4$, filtered and concentrated. The crude was purified by flash chromatography on silica gel (PE/EA=10/1 to 1/1) to afford 211b (4.5 g, 95% yield, 80% purity) as an orange oil. LC-MS (Method 4) t$_R$=3.30 min, m/z (M+H)$^+$=194.1.

Step 2. 4-Chloro-7-cyclopropyl-5-iodo-7H-pyrrolo[2,3-d]pyrimidine (211c)

To a solution of 211b (4.5 g, 18.59 mmol) in DMF (30 mL) was added 1-iodopyrrolidine-2,5-dione (6.27 g, 27.89 mmol) at r.t. The mixture was stirred at 25° C. for 12 h. H$_2$O (30 mL) was added and the mixture was extracted by EA (50 mL). The combined organic layer was washed by brine, dried over Na$_2$SO$_4$, filtered and concentrated. The crude was purified by flash chromatography on silica gel (PE/EA=10/1 to 1/1) to afford 211c (3.6 g, 61% yield) as a brown solid. LC-MS (Method 4) t$_R$=4.18 min, m/z (M+H)$^+$=320.0.

Step 3. 7-Cyclopropyl-5-iodo-3,7-dihydro-4H-pyrrolo[2,3-d]pyrimidin-4-one (211d)

To a solution of 211c (1.5 g, 4.69 mmol) in dioxane (12 mL) was added NaOH (2 M, 23.5 mL) at r.t. The mixture was stirred at 100° C. for 16 h. The reaction mixture was concentrated. The aqueous residue was diluted with water (30 mL) and acidified to pH 4-6 using 1.5 N hydrochloric acid solution. The precipitated solid was filtered, washed with hexane and concentrated to afford 211d (1.3 g, 92% yield) as a white solid. LC-MS (Method 4) t$_R$=2.58 min, m/z (M+H)$^+$=302.0.

Step 4. 7-Cyclopropyl-3-ethyl-5-iodo-3,7-dihydro-4H-pyrrolo[2,3-d]pyrimidin-4-one (211e)

To a solution of 211d (1.3 g, 4.32 mmol) in acetone (8 mL) was added iodoethane (1.35 g, 8.64 mmol, 0.69 mL) and K$_2$CO$_3$ (1.79 g, 12.95 mmol) at room temperature and the reaction mixture was stirred at 55° C. for 16 h. The reaction mixture was cooled to room temperature and filtered. The solid was washed with ethyl acetate (40 mL) and the combined filtrate was evaporated to get the crude product, which was purified by flash chromatography on silica gel (PE/EA=10/1 to 1/1) to afford 211e (1.2 g, 84% yield) as a grey solid. LC-MS (Method 4) t$_R$=3.24 min, m/z (M+H)$^+$=330.1. $^1$H NMR (400 MHz, DMSO-d$_6$) δ 8.27 (s, 1H), 7.26 (s, 1H), 3.95 (q, J=7.1 Hz, 2H), 3.59-3.46 (m, 1H), 1.23 (t, J=7.1 Hz, 3H), 1.00-0.95 (m, 4H).

Step 5. Methyl 6-(cyclopropanecarboxamido)-4-((7-cyclopropyl-3-ethyl-4-oxo-4,7-dihydro-3H-pyrrolo[2,3-d]pyrimidin-5-yl)amino)nicotinate (211f)

To a solution of 211e (300 mg, 0.91 mmol), BrettPhos Pd G3 (40 mg, 0.044 mmol), Cs$_2$CO$_3$ (891 mg, 2.73 mmol) in dioxane (12 mL) was added 173c (257.3 mg, 1.09 mmol) at r.t. The mixture was stirred at 100° C. for 16 h under N$_2$ protection. H$_2$O (30 mL) was added and the mixture was extracted by EA (30 mL). The combined organic layer was washed by brine, dried over Na$_2$SO$_4$, filtered and concentrated. The crude was purified by flash chromatography on silica gel (DCM/MeOH=20/1 to 5/1) to afford 211f (80 mg, 20% yield) as a yellow solid. LC-MS (Method 4) t$_R$=4.47 min, m/z (M+H)$^+$=437.2.

Step 6. Methyl 6-(cyclopropanecarboxamido)-4-((7-cyclopropyl-3-ethyl-4-oxo-4,7-dihydro-3H-pyrrolo[2,3-d]pyrimidin-5-yl)amino)nicotinate (211g)

To a solution of 211f (80 mg, 0.18 mmol) in THF (6 mL) and water (2 mL) was added LiOH·H$_2$O (7.7 mg, 0.18 mmol) at r.t. The mixture was stirred at r.t. for 16 h. The resulting solution was diluted with water (10 mL) and acidified to pH 4-6 using 2 N hydrochloric acid solution. The solution was extracted by EA (30 mL). The combined organic layer was dried over Na$_2$SO$_4$, filtered and concentrated to afford 211g (70 mg, 90% yield) as a light-yellow solid. LC-MS (Method 4) t$_R$=2.56 min, m/z (M+H)$^+$=423.3.

Step 7. Methyl 6-(cyclopropanecarboxamido)-4-((7-cyclopropyl-3-ethyl-4-oxo-4,7-dihydro-3H-pyrrolo[2,3-d]pyrimidin-5-yl)amino)nicotinate (211)

To a solution of 211g (50 mg, 0.12 mmol). N-ethyl-N-isopropyl-propan-2-amine (38.2 mg, 0.30 mmol, 0.052 mL), T$_3$P (56.5 mg, 0.18 mmol) in DMF (3 mL) was added trideuteriomethanamine hydrochloride (25 mg, 0.36 mmol) at 25° C. The mixture was stirred at 25° C. for 1 h. H$_2$O (30 mL) was added and the mixture was extracted by EA (30 mL). The combined organic layer was washed by brine, dried over Na$_2$SO$_4$, filtered and concentrated. The crude was purified by Prep-HPLC (Method D) to afford 211 (2.5 mg, 4.8% yield) as a white solid. LC-MS (Method 4) t$_R$=1.76 min, m/z (M+H)$^+$=439.3. $^1$H NMR (400 MHz, DMSO-d$_6$) δ 10.75 (s, 1H), 10.74 (s, 1H), 8.46 (s, 1H), 8.44 (s, 1H), 8.24 (s, 1H), 7.99 (s, 1H), 7.01 (s, 1H), 3.96 (q, J=7.2 Hz, 2H), 3.59-3.50 (m, 1H), 2.04-1.94 (m, 1H), 1.26-1.20 (t, J=7.2 Hz, 3H), 1.08-0.96 (m, 4H), 0.83-0.76 (m, 4H).

Example 212

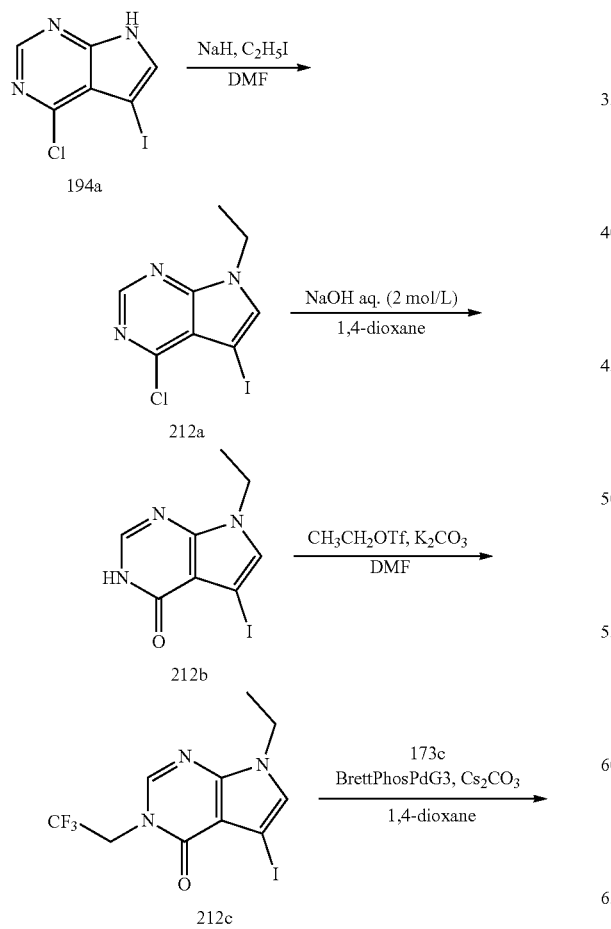

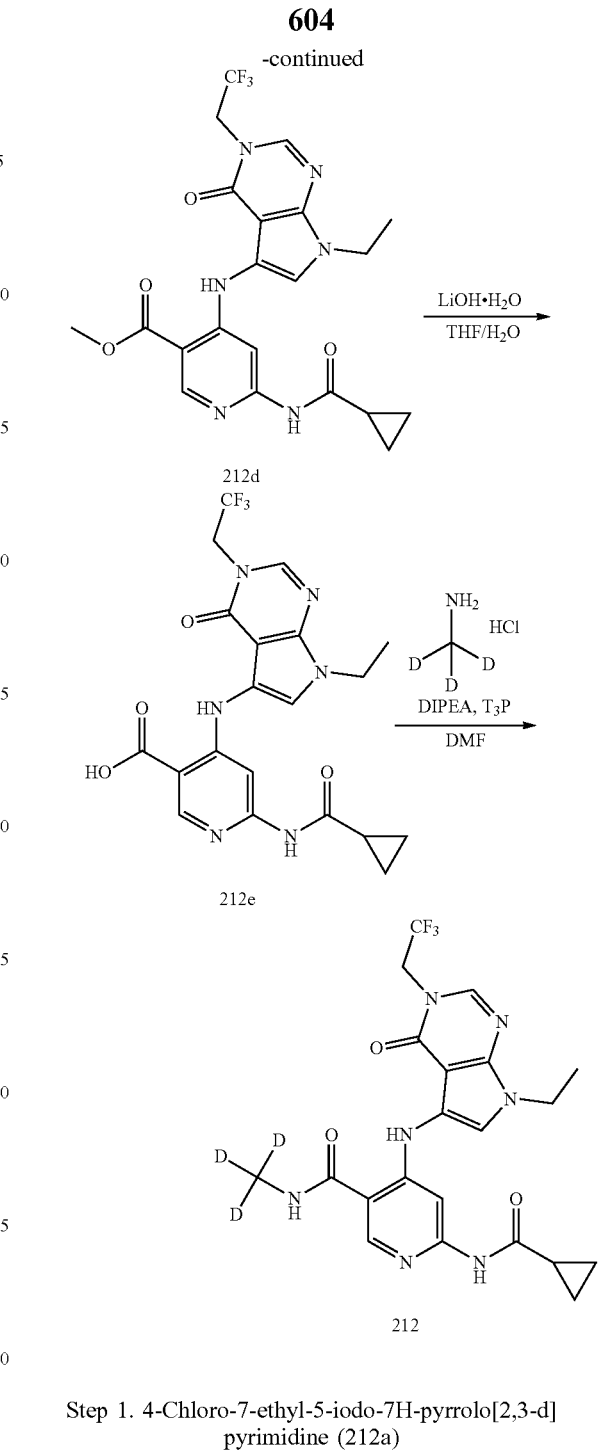

Step 1. 4-Chloro-7-ethyl-5-iodo-7H-pyrrolo[2,3-d]pyrimidine (212a)

To a solution of 194a (2 g, 7.16 mmol) in DMF (30 mL) was added sodium hydride (343.5 mg, 8.59 mmol, 60% purity in mineral oil) at 0° C. under nitrogen protection. 10 min later, iodoethane (1.34 g, 8.59 mmol, 0.69 mL) was added. The mixture was stirred from 0° C. to r.t. for 2 h. The resulting solution was added into H$_2$O (40 mL) and extracted by EA (40 mL*3). The combined organic layer was washed by brine, dried over Na$_2$SO$_4$ and filtered. The filtrate was concentrated to get the crude product. The crude was purified by flash chromatography on silica gel (PE/EA=10/1 to 1/1) to afford 212a (1.61 g, 73% yield) as a light-yellow solid. LC-MS (Method 4) t$_R$=4.19 min, m/z (M+H)$^+$=308.0.

Step 2. 7-Ethyl-5-iodo-3,7-dihydro-4H-pyrrolo[2,3-d]pyrimidin-4-one (212b)

Compound 212b (1.4 g, 92% yield), a grey solid, was synthesized by utilizing a similar preparative procedure of Step 3 in Example 211 with 212a (1.61 g, 5.24 mmol) as the starting material. LC-MS (Method 4) $t_R$=2.70 min, m/z (M+H)$^+$=290.0.

Step 3. 7-Ethyl-5-iodo-3-(2,2,2-trifluoroethyl)-3,7-dihydro-4H-pyrrolo[2,3-d]pyrimidin-4-one (212c)

To a solution of 212b (850 mg, 2.94 mmol), K$_2$CO$_3$ (1.15 g, 3.53 mmol) in DMF (12 mL) was added 2,2,2-trifluoroethyl trifluoromethanesulfonate (819 mg, 3.53 mmol, 0.51 mL) at r.t. The mixture was stirred at 100° C. for 3 h. The reaction mixture was cooled to room temperature. The resulting solution was added into H$_2$O (30 mL) and extracted by EA (30 mL*3). The combined organic layer was washed with brine (30 mL*3), dried over Na$_2$SO$_4$ and filtered. The filtrate was concentrated and the crude was purified by flash chromatography on silica gel (PE/EA=10/1 to 1/1) to afford 212c (900 mg, 82% yield) as a white solid. LC-MS (Method 4) $t_R$=3.01 min, m/z (M+H)$^+$=372.3.

Step 4. Methyl 6-(cyclopropanecarboxamido)-4-((7-ethyl-4-oxo-3-(2,2,2-trifluoroethyl)-4,7-dihydro-3H-pyrrolo[2,3-d]pyrimidin-5-yl)amino)nicotinate (212d)

Compound 212d (100 mg, 26% yield), a white solid, was synthesized by utilizing a similar preparative procedure of Step 5 in Example 211 with 212c (300 mg, 0.81 mmol) and 173c (190.2 mg, 0.81 mmol) as starting materials. LC-MS (Method 4) $t_R$=2.46 min, m/z (M+H)$^+$=479.3.

Step 5. 6-(Cyclopropanecarboxamido)-4-((7-ethyl-4-oxo-3-(2,2,2-trifluoroethyl)-4,7-dihydro-3H-pyrrolo[2,3-d]pyrimidin-5-yl)amino)nicotinic acid (212e)

Compound 212e (60 mg, 62% yield), a light yellow oil, was synthesized by utilizing a similar preparative procedure of Step 6 in Example 211 with 212d (100 mg, 0.21 mmol) as the starting material. LC-MS (Method 4) $t_R$=0.79 min, m/z (M+H)$^+$=465.3.

Step 6. 6-(Cyclopropanecarboxamido)-4-((7-ethyl-4-oxo-3-(2,2,2-trifluoroethyl)-4,7-dihydro-3H-pyrrolo[2,3-d]pyrimidin-5-yl)amino)-N-(methyl-d$_3$) nicotinamide (212)

Compound 212 (14.8 mg, 36% yield), a white solid, was synthesized by utilizing a similar preparative procedure of Step 7 in Example 211 with 212e (40 mg, 0.086 mmol) as the starting material. LC-MS (Method 4) $t_R$=1.99 min, m/z (M+H)$^+$=481.3. $^1$H NMR (400 MHz, DMSO-d$_6$) δ 10.78 (s, 1H), 10.75 (s, 1H), 8.48 (s, 1H), 8.47 (s, 1H), 8.25 (s, 1H), 7.98 (s, 1H), 7.18 (s, 1H), 4.90 (q, J=9.4 Hz, 2H), 4.15 (q, J=7.2 Hz, 2H), 2.04-1.95 (m, 1H), 1.37 (t, J=7.2 Hz, 3H), 0.83-0.76 (m, 4H).

Example 213

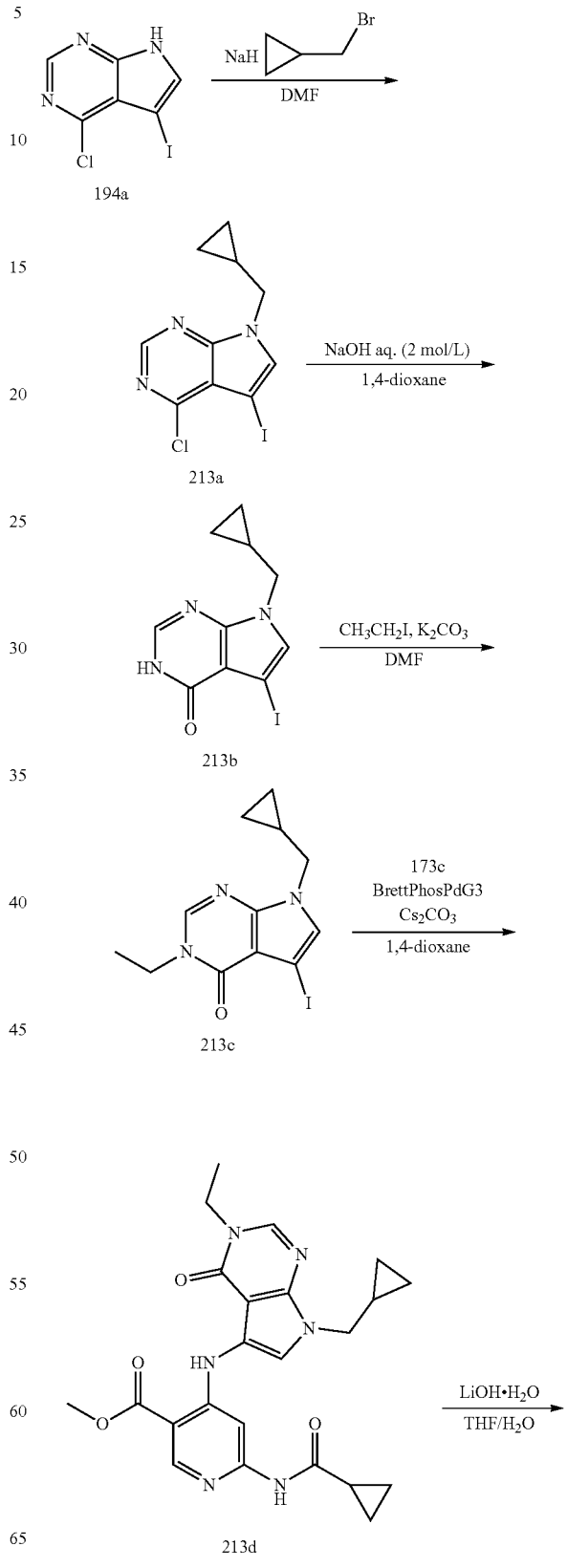

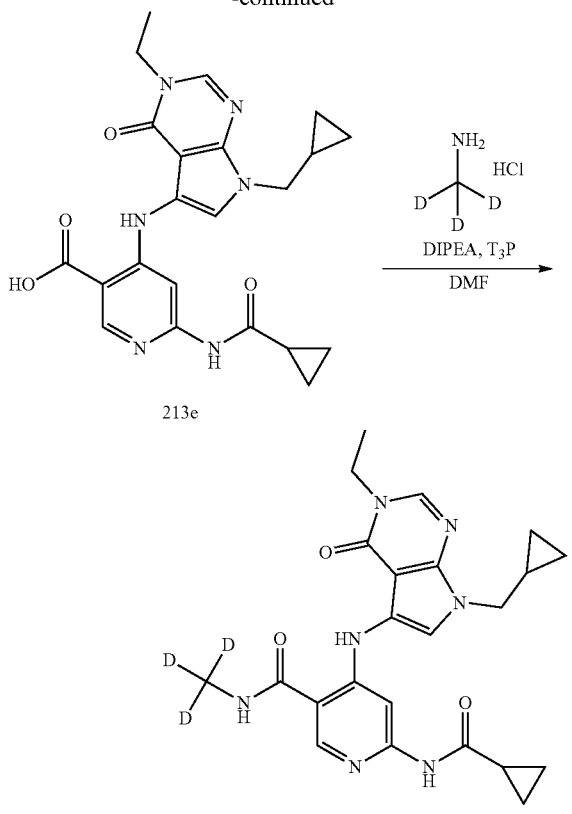

Step 1. 4-Chloro-7-(cyclopropylmethyl)-5-iodo-7H-pyrrolo[2,3-d]pyrimidine (213a)

Compound 213a (2 g, 84% yield), a white solid, was synthesized by utilizing a similar preparative procedure of Step 1 in Example 212 with 194a (2 g, 7.16 mmol) and (bromomethyl)cyclopropane (1.15 g, 8.59 mmol) as starting materials. LC-MS (Method 4) $t_R$=4.66 min, m/z (M+H)$^+$=334.0.

Step 2. 7-(Cyclopropylmethyl)-5-iodo-3,7-dihydro-4H-pyrrolo[2,3-d]pyrimidin-4-one (213b)

Compound 213b (1.6 g, 89% yield), a grey solid, was synthesized by utilizing a similar preparative procedure of Step 3 in Example 211 with 213a (1.9 g, 5.70 mmol) as the starting material. LC-MS (Method 4) $t_R$=3.12 min, m/z (M+H)$^+$=316.1.

Step 3. 7-(Cyclopropylmethyl)-3-ethyl-5-iodo-3,7-dihydro-4H-pyrrolo[2,3-d]pyrimidin-4-one (213c)

Compound 213c (0.85 g, 73% yield), a yellow oil, was synthesized by utilizing a similar preparative procedure of Step 4 in Example 211 with 213b (1 g, 3.17 mmol) as the starting material and DMF as the solvent. LC-MS (Method 4) $t_R$=5.39 min, m/z (M+H)$^+$=344.1. $^1$H NMR (400 MHz, DMSO-d$_6$) δ 8.26 (s, 1H), 7.42 (s, 1H), 3.99-3.90 (m, 4H), 1.29-1.13 (m, 4H), 0.53-0.44 (m, 2H), 0.42-0.34 (m, 2H).

Step 4. Methyl 6-(cyclopropanecarboxamido)-4-((7-(cyclopropylmethyl)-3-ethyl-4-oxo-4,7-dihydro-3H-pyrrolo[2,3-d]pyrimidin-5-yl)amino)nicotinate (213d)

Compound 213d (70 mg, 18% yield), a yellow solid, was synthesized by utilizing a similar preparative procedure of Step 5 in Example 211 with 213c (300 mg, 0.87 mmol) as the starting material. LC-MS (Method 4) $t_R$=5.11 min, m/z (M+H)$^+$=451.4.

Step 5. 6-(Cyclopropanecarboxamido)-4-((7-(cyclopropylmethyl)-3-ethyl-4-oxo-4,7-dihydro-3H-pyrrolo[2,3-d]pyrimidin-5-yl)amino)nicotinic acid (213e)

Compound 213e (50 mg, 74% yield), a yellow solid, was synthesized by utilizing a similar preparative procedure of Step 6 in Example 211 with 213d (70 mg, 0.16 mmol) as the starting material. LC-MS (Method 4) $t_R$=1.41 min, m/z (M+H)$^+$=437.2.

Step 6. 6-(Cyclopropanecarboxamido)-4-((7-(cyclopropylmethyl)-3-ethyl-4-oxo-4,7-dihydro-3H-pyrrolo[2,3-d]pyrimidin-5-yl)amino)-N-(methyl-d$_3$)nicotinamide (213)

Compound 213 (8.7 mg, 15% yield), a white solid, was synthesized by utilizing a similar preparative procedure of Step 7 in Example 211 with 213e (55 mg, 0.13 mmol) as the starting material. LC-MS (Method 4) $t_R$=3.23 min, m/z (M+H)$^+$=453.4. $^1$H NMR (400 MHz, DMSO-d$_6$) δ 10.78 (s, 1H), 10.74 (s, 1H), 8.47 (s, 1H), 8.45 (s, 1H), 8.22 (s, 1H), 8.03 (s, 1H), 7.21 (s, 1H), 4.01-3.91 (m, 4H), 2.03-1.96 (m, 1H), 1.28-1.20 (m, 4H), 0.81-0.77 (m, 4H), 0.59-0.50 (m, 2H), 0.47-0.39 (m, 2H).

Example 214

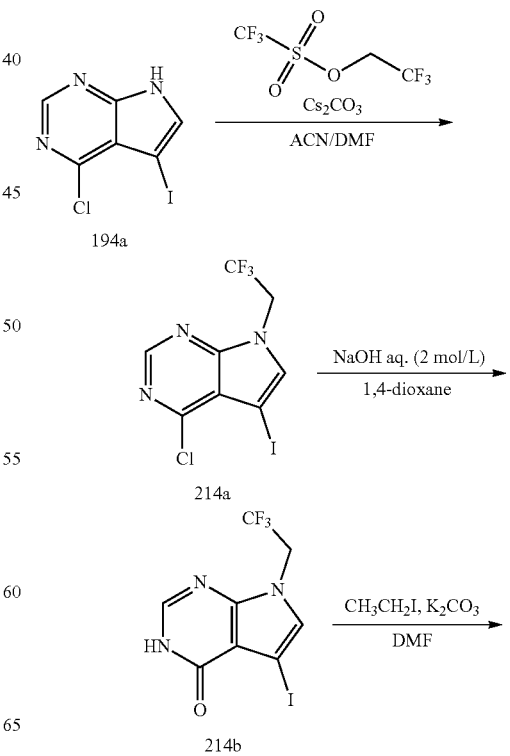

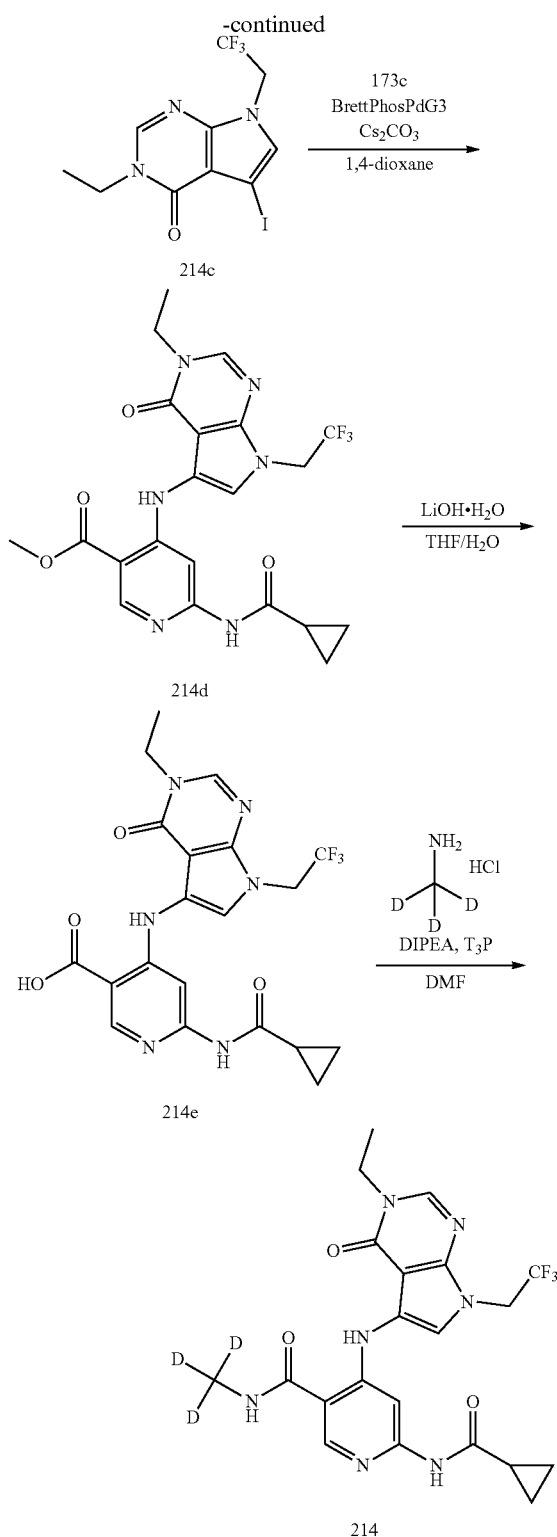

h under nitrogen protection. The solution was then added into H$_2$O (30 mL) and extracted by EA (50 mL). The combined organic layer was washed by brine, dried over Na$_2$SO$_4$ and filtered. The filtrate was concentrated to get the crude product. The crude was purified by flash chromatography (PE/EA=10/1 to 2/1) to afford 214a (1.58 g, 61% yield) as a yellow solid. LC-MS (Method 4) t$_R$=4.34 min, m/z (M+H)$^+$=362.0.

Step 2. 5-Iodo-7-(2,2,2-trifluoroethyl)-3,7-dihydro-4H-pyrrolo[2,3-d]pyrimidin-4-one (214b)

Compound 214b (1.4 g, 93% yield), a grey solid, was synthesized by utilizing a similar preparative procedure of Step 3 in Example 211 with 214a (1.58 g, 4.37 mmol) as the starting material. LC-MS (Method 4) t$_R$=4.62 min, m/z (M+H)$^+$=344.0.

Step 3. 3-Ethyl-5-iodo-7-(2,2,2-trifluoroethyl)-3,7-dihydro-4H-pyrrolo[2,3-d]pyrimidin-4-one (214c)

Compound 214c (1.1 g, 73% yield), a light yellow solid, was synthesized by utilizing a similar preparative procedure of Step 4 in Example 211 with 214b (1.4 g, 4.08 mmol) as the starting material and DMF as the solvent. LC-MS (Method 4) t$_R$=3.31 min, m/z (M+H)$^+$=372.0. $^1$H NMR (400 MHz, DMSO-d$_6$) δ 8.36 (s, 1H), 7.39 (s, 1H), 5.03 (q, J=9.2 Hz, 2H), 3.97 (q, J=7.2 Hz, 2H), 1.25 (t, J=7.2 Hz, 3H).

Step 4. Methyl 6-(cyclopropanecarboxamido)-4-((3-ethyl-4-oxo-7-(2,2,2-trifluoroethyl)-4,7-dihydro-3H-pyrrolo[2,3-d]pyrimidin-5-yl)amino)nicotinate (214d)

Compound 214d (80 mg, 21% yield), a yellow solid, was synthesized by utilizing a similar preparative procedure of Step 5 in Example 211 with 214c (300 mg, 0.81 mmol) as the starting material. LC-MS (Method 4) t$_R$=2.46 min, m/z (M+H)$^+$=479.3.

Step 5. 6-(Cyclopropanecarboxamido)-4-((3-ethyl-4-oxo-7-(2,2,2-trifluoroethyl)-4,7-dihydro-3H-pyrrolo[2,3-d]pyrimidin-5-yl)amino)nicotinic acid (214e)

Compound 214e (60 mg, 77% yield), a yellow solid, was synthesized by utilizing a similar preparative procedure of Step 6 in Example 211 with 214d (80 mg, 0.17 mmol) as the starting material. LC-MS (Method 4) t$_R$=0.77 min, m/z (M+H)$^+$=465.2.

Step 6. 6-(Cyclopropanecarboxamido)-4-((3-ethyl-4-oxo-7-(2,2,2-trifluoroethyl)-4,7-dihydro-3H-pyrrolo[2,3-d]pyrimidin-5-yl)amino)-N-(methyl-d$_3$)nicotinamide (214)

Compound 214 (4.1 mg, 6.6% yield), a white solid, was synthesized by utilizing a similar preparative procedure of Step 7 in Example 211 with 214e (60 mg, 0.13 mmol) as the starting material. LC-MS (Method 4) t$_R$=1.62 min, m/z (M+H)$^+$=481.3. $^1$H NMR (400 MHz, DMSO-d$_6$) δ 10.83 (s, 1H), 10.75 (s, 1H), 8.49 (s, 1H), 8.48 (s, 1H), 8.32 (s, 1H), 7.94 (s, 1H), 7.13 (s, 1H), 5.05 (q, J=9.2 Hz, 2H), 3.97 (q, J=7.2 Hz, 2H), 2.03-1.95 (m, 1H), 1.24 (t, J=7.2 Hz, 3H), 0.88-0.82 (m, 4H).

Step 1. 4-Chloro-5-iodo-7-(2,2,2-trifluoroethyl)-7H-pyrrolo[2,3-d]pyrimidine (214a)

To a solution of 194a (2 g, 7.16 mmol), Cs$_2$CO$_3$ (2.80 g, 8.59 mmol) in DMF (4 mL) and ACN (6 mL) was added 2,2,2-trifluoroethyl trifluoromethanesulfonate (1.99 g, 8.59 mmol, 1.24 mL) at r.t. The mixture was stirred at r.t. for 4

Example 215

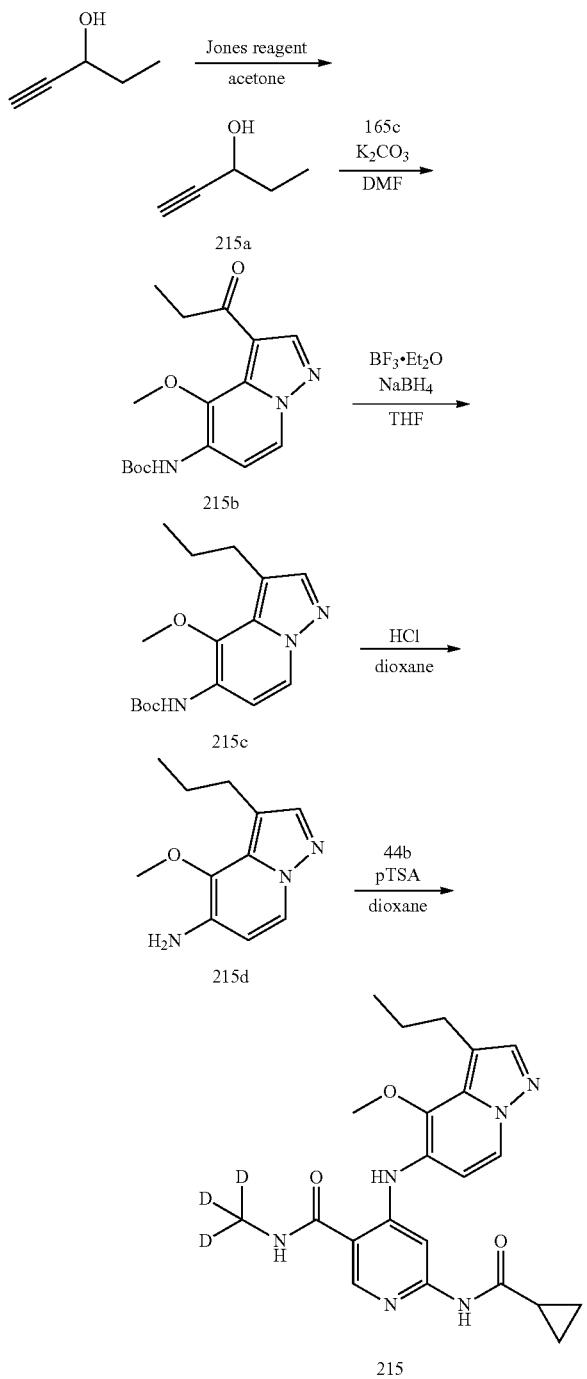

Step 1. Pent-1-yn-3-one (215a)

To a solution of pent-1-yn-3-ol (200 mg, 2.38 mmol) in acetone (2 mL) was added Jones reagent (4.76 mmol, 3 M, 1.6 mL) at an ice-bath, then the mixture was stirred at r.t. for 4 h. The mixture was quenched with i-PrOH (0.5 mL) at an ice-bath, and the mixture was stirred at r.t. for 30 min. Then the mixture was diluted with H₂O (15 mL), extracted with EtOAc (5 mL*3). The combined organic layer was washed with aq Na₂CO₃ (10 mL), and brine (10 mL), dried over Na₂SO₄ to get the crude compound 215a (15 mL, 2.38 mmol, 0.16 M in EtOAc) as a solution.

Step 2. Tert-butyl (4-methoxy-3-propionylpyrazolo[1,5-a]pyridin-5-yl)carbamate (215b)

To a solution of 165c (370 mg, 0.87 mmol) in DMF (10 mL) was added K₂CO₃ (302 mg, 2.18 mmol), then 215a (11 mL, 1.75 mmol, 0.16 M in EtOAc) was added into the mixture. Then the mixture was stirred at r.t. for 2 h. The mixture was diluted with H₂O (30 mL), extracted with EtOAc (20 mL*3), washed with brine (20 mL), dried over Na₂SO₄, concentrated and purified by flash chromatography (PE/EA=10/1 to 1/1) to get the compound 215b (120 mg, 43% yield) as a yellow solid. LC-MS (Method 4) $t_R$=2.83 min, m/z (M+H)⁺=320.2. ¹H NMR (400 MHz, CDCl₃) δ 8.33 (s, 1H), 8.29 (d, J=7.6 Hz, 1H), 8.06 (d, J=7.6 Hz, 1H), 7.37 (s, 1H), 3.85 (s, 3H), 2.95 (q, J=7.6 Hz, 2H), 1.55 (s, 9H), 1.25 (t, J=7.6 Hz, 3H).

Step 3. Tert-butyl (4-methoxy-3-propylpyrazolo[1,5-a]pyridin-5-yl)carbamate (215c)

To a solution of 215b (120 mg, 0.38 mmol) in THF (2 mL) was added BF₃·Et₂O (107 mg, 0.75 mmol) and NaBH₄ (28 mg, 0.75 mmol) at an ice-bath, then the mixture was stirred at r.t. for 24 h. The mixture was quenched with MeOH (0.5 mL) and concentrated to get the crude product 215c (110 mg, 96% yield) as a yellow oil. LC-MS (Method 4) $t_R$=3.42 min, m/z (M+H)⁺=306.2.

Step 4. 4-Methoxy-3-propylpyrazolo[1,5-a]pyridin-5-amine (215d)

To a solution of 215c (110 mg, 0.36 mmol) in dioxane (1.5 mL) was added a solution of HCl (g) in dioxane (4 M, 1.5 mL). The mixture was stirred at r.t. for 16 h. The mixture was concentrated to dryness. The residue was diluted with H₂O (20 mL), adjusted pH to 7-9 with aq Na₂CO₃, and extracted with EtOAc (20 mL*3). The organic layers were washed with aq Na₂CO₃ (20 mL) and brine (20 mL). The solution was dried over Na₂SO₄ and filtered. The filtrate was concentrated to give the title compound 215d (51 mg, 69% yield) as a brown solid. LC-MS (Method 4) $t_R$=2.27 min, m/z (M+H)⁺=206.1.

Step 5. 6-(Cyclopropanecarboxamido)-4-((4-methoxy-3-propylpyrazolo[1,5-a]pyridin-5-yl)amino)-N-(methyl-d₃)nicotinamide (215)

A mixture of 215d (50 mg, 0.24 mmol), 44b (63 mg, 0.24 mmol), pTSA (42 mg, 0.24 mmol) in dioxane (2 mL) was stirred at 100° C. for 15 h. The mixture was concentrated and purified by Prep-HPLC (Method E) to get the compound 215 (47 mg, 45% yield) as an off-white solid. LC-MS (Method 4) $t_R$=2.32 min, m/z (M+H)⁺=426.3. ¹H NMR (400 MHz, CDCl₃) δ 10.21 (s, 1H), 8.25 (s, 1H), 8.20 (d, J=7.6 Hz, 1H), 8.10 (s, 1H), 7.92 (s, 1H), 7.68 (s, 1H), 6.76 (d, J=7.6 Hz, 1H), 6.15 (s, 1H), 3.85 (s, 3H), 2.79 (q, J=7.6 Hz, 2H), 1.71-1.67 (m, 2H), 1.52-1.46 (m, 1H), 1.06-1.03 (m, 2H), 0.96 (t, J=7.6 Hz, 3H), 0.89-0.84 (m, 2H).

Example 216

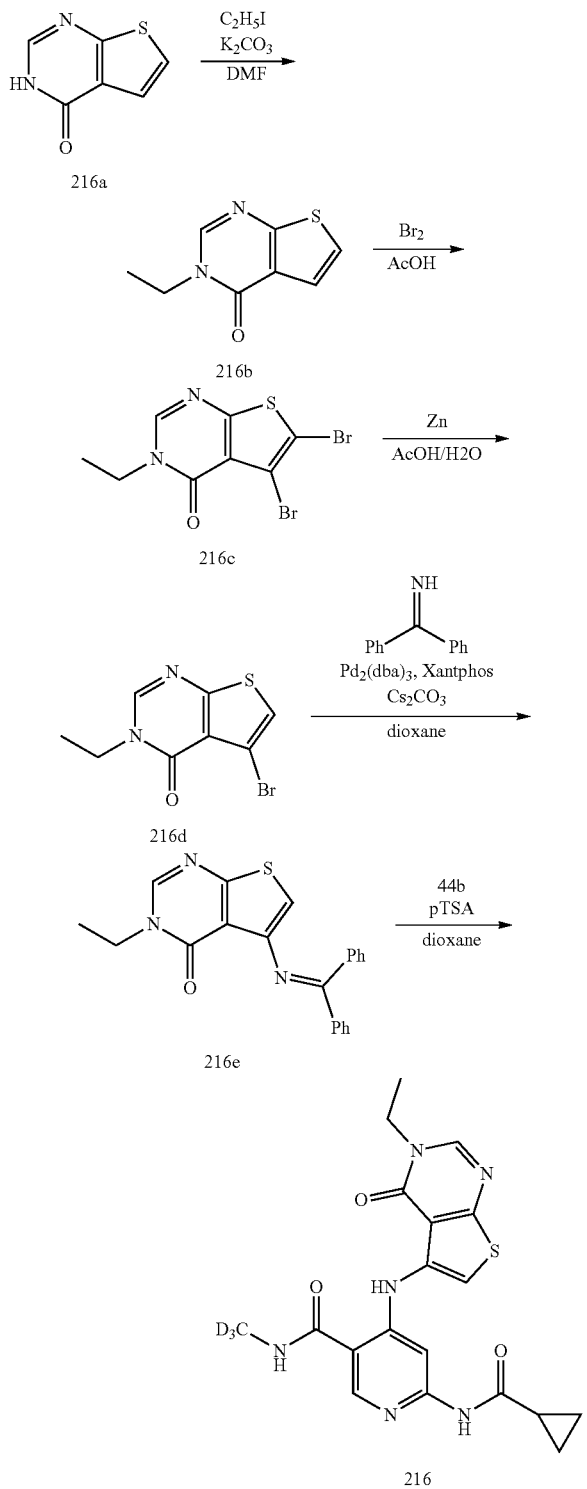

Step 1. 3-Ethylthieno[2,3-d]pyrimidin-4-(3-H)-one (216b)

A mixture of 216a (1.00 g, 6.57 mmol), K₂CO₃ (1.09 g, 7.89 mmol) and C₂H₅I (1.13 g, 7.23 mmol) in DMF (10 mL) was stirred at 50° C. overnight. After cooling to r.t., the mixture was diluted with water (20 mL) and extracted with EtOAc (30 mL*3). The organic layer was concentrated and the residue was purified by flash chromatography on silica gel (PE/EtOAc=3/1) to afford 216b (1.1 g, 93% yield) as a brown solid. ¹H NMR (400 MHz, CDCl₃) δ 8.01 (s, 1H), 7.49 (d, J=5.6 Hz, 1H), 7.25 (d, J=5.6 Hz, 1H), 4.09 (d, J=7.2 Hz, 2H), 1.27 (t, J=7.2 Hz, 3H).

Step 2. 5,6-Dibromo-3-ethylthieno[2,3-d]pyrimidin-4-(3H)-one (216c)

To a mixture of 216b (500 mg, 2.77 mmol) and KOAc (1.63 g, 16.65 mmol) in AcOH (10 mL) was added Br₂ (2.66 g, 16.65 mmol) dropwise at 0° C. After stirring at 120° C. for 16 h, the reaction mixture was concentrated. The residue was basified with sat. Na₂CO₃ solution to pH=8-9 and extracted with EtOAc (20 mL*3). The combined organic layer was dried over anhydrous sodium sulfate, filtered and evaporated under vacuum to afford 216c (650 mg, 69% yield) as a white solid. ¹H NMR (400 MHz, DMSO-d₆) δ 8.56 (s, 1H), 3.99 (d, J=7.2 Hz, 2H), 1.27 (t, J=7.2 Hz, 3H).

Step 3. 5-Bromo-3-ethylthieno[2,3-d]pyrimidin-4-(3H)-one (216d)

To a solution 216c (650 mg, 1.92 mmol) in AcOH/H₂O (6 mL, v/v=4/1) was added Zn dust (377 mg, 5.77 mmol) at room temperature. After stirring for 4 h at r.t., to the reaction was added another batch of Zn dust (377 mg, 5.77 mmol). The mixture was stirred at 60° C. for 30 min. After cooling to r.t., the reaction mixture was diluted with water (5 mL) and extracted with EtOAc (20 mL*3). The combined organic layer was dried over anhydrous sodium sulfate, filtered and concentrated under vacuum to afford 216d (350 mg, 70% yield) as a white solid. ¹H NMR (400 MHz, DMSO-d₆) δ 8.51 (s, 1H), 7.72 (s, 1H), 3.99 (d, J=7.2 Hz, 2H), 1.25 (t, J=7.2 Hz, 3H).

Step 4. 5-((Diphenylmethylene)amino)-3-ethylthieno[2,3-d]pyrimidin-4-(3H)-one (216e)

A mixture of 216d (340 mg, 1.31 mmol), diphenylmethanimine (285 mg, 1.57 mmol), Pd₂(dba)₃ (120 mg, 0.13 mmol), XantPhos (76 mg, 0.13 mmol) and Cs₂CO₃ (855 mg, 2.62 mmol) in 1,4-dioxane (3 mL) was stirred at 100° C. for 16 h. After cooling to r.t., the reaction mixture was diluted with water (5 mL) and extracted with EtOAc (10 mL*3). The combined organic layer was concentrated and the residue was purified by flash chromatography on silica gel (PE/EtOAc=2/1) to afford 216e (166 mg, 35% yield) as a yellow solid. ¹H NMR (400 MHz, DMSO-d₆) δ 8.32 (s, 1H), 7.68-7.65 (m, 2H), 7.60-7.40 (m, 3H), 7.29-7.28 (m, 3H), 7.14-7.12 (m, 2H), 6.50 (s, 1H), 3.91 (d, J=7.2 Hz, 2H), 1.19 (t, J=7.2 Hz, 3H).

Step 5. 6-(Cyclopropanecarboxamido)-4-((3-ethyl-4-oxo-3,4-dihydrothieno[2,3-d]pyrimidin-5-yl)amino)-N-(methyl-d₃)nicotinamide (216)

A mixture of 216e (136 mg, 0.38 mmol), 44b (97 mg, 0.38 mmol) and TsOH·H₂O (7 mg, 0.037 mmol) in dioxane (1 mL) was stirred at 60° C. for 12 h. The reaction mixture was concentrated and purified by flash chromatography on silica gel (DCM/MeOH=20/1) to afford compound 216 (44 mg, 28% yield) as a white solid. LC-MS (Method 2) t_R=3.62 min, m/z (M+H)⁺=416.0. ¹H NMR (400 MHz, DMSO-d₆) δ

11.27 (s, 1H), 10.85 (s, 1H), 8.50 (s, 1H), 8.48 (s, 1H), 8.47 (s, 1H), 8.36 (s, 1H), 7.04 (s, 1H), 4.02 (d, J=7.6 Hz, 2H), 2.02-1.99 (m, 1H), 1.28 (t, J=7.2 Hz, 3H), 0.84-0.80 (m, 4H).

Example 217

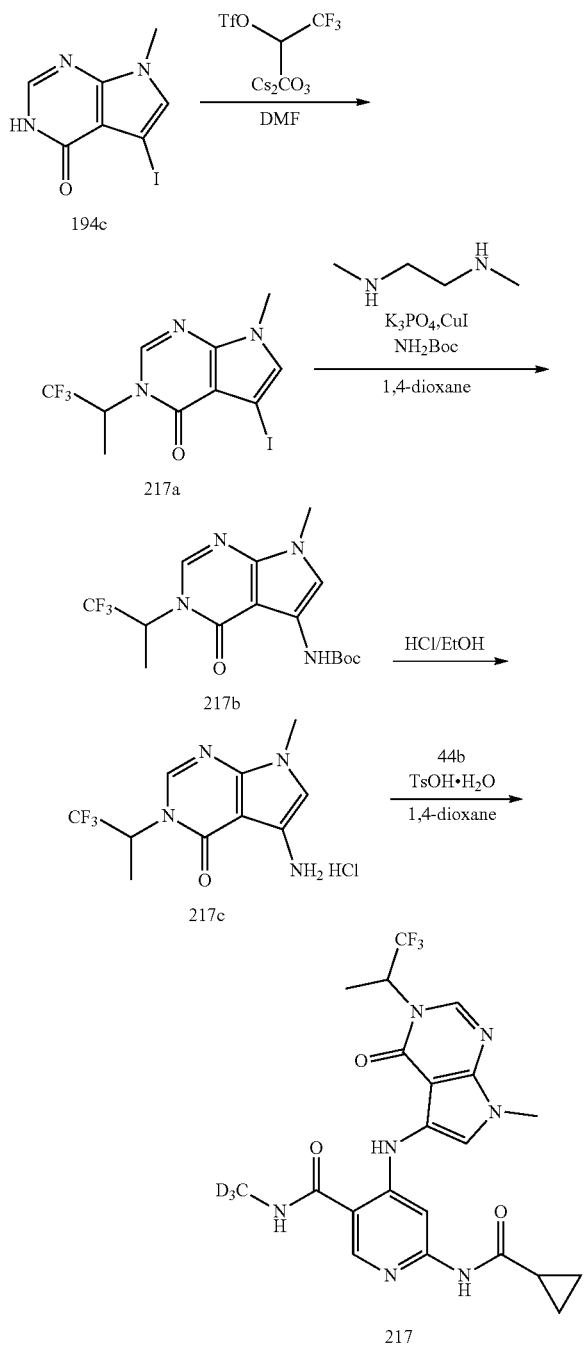

Step 1. 5-Iodo-7-methyl-3-(1,1,1-trifluoropropan-2-yl)-3,7-dihydro-4H-pyrrolo[2,3-d]pyrimidin-4-one (217a)

A mixture of 194c (2.0 g, 7.27 mmol), Cs$_2$CO$_3$ (7.11 g, 21.81 mmol) and 1,1,1-trifluoropropan-2-yl trifluoromethanesulfonate (3.58 g, 14.54 mmol) in DMF (50 mL) was stirred at 50° C. for 16 h. After cooling to r.t., the mixture was diluted with water (80 mL) and extracted with EtOAc (80 mL*3). The combined organic layer was concentrated and the residue was purified by flash chromatography on silica gel (PE/EtOAc=5/1) to afford 217a (1.52 g, 56% yield) as a yellow solid. $^1$H NMR (400 MHz, DMSO-d$_6$) δ 8.39 (s, 1H), 7.39 (s, 1H), 5.79-7.75 (m, 1H), 3.71 (s, 3H), 1.70 (d, J=7.2 Hz, 3H).

Step 2. Tert-butyl (7-methyl-4-oxo-3-(1,1,1-trifluoropropan-2-yl)-4,7-dihydro-3H-pyrrolo[2,3-d]pyrimidin-5-yl)carbamate (217b)

A mixture of 217a (1.51 g, 4.07 mmol), tert-butyl carbamate (715 mg, 6.10 mmol), CuI (387 mg, 2.03 mmol), K$_3$PO$_4$ (2.59 g, 12.21 mmol) and N,N-dimethylethane-1,2-diamine (179 mg, 2.03 mmol) in anhydrous dioxane (15 mL) was stirred at 90° C. for 18 h under N$_2$ atmosphere. After cooling to r.t., the mixture was concentrated and the residue was purified by flash chromatography on silica gel (PE/EtOAc=3/1) to afford 217b (1.39 g, 95% yield) as brown oil. LC-MS (Method 3) t$_R$=1.30 min, m/z (M+H)$^+$=361.3.

Step 3. 5-Amino-7-methyl-3-(1,1,1-trifluoropropan-2-yl)-3,7-dihydro-4H-pyrrolo[2,3-d]pyrimidin-4-one hydrochloride (217c)

A mixture of 217b (1.4 g, 3.89 mmol) and HCl (g) in EtOH (20 mL, 1 M) was stirred for 3 h at r.t. The formed solid was filtered and the filter cake was dried to afford 217c (977 mg, 85% yield) as a white solid. LC-MS (Method 3) t$_R$=0.88 min, m/z (M+H)$^+$=261.1.

Step 4. 6-(Cyclopropanecarboxamido)-N-(methyl-d$_3$)-4-((7-methyl-4-oxo-3-(1,1,1-trifluoropropan-2-yl)-4,7-dihydro-3H-pyrrolo[2,3-d]pyrimidin-5-yl)amino)nicotinamide (217)

A mixture of 217c (977 mg, 3.29 mmol), 44b (761 mg, 2.96 mmol) and TsOH·H$_2$O (125 mg, 0.66 mmol) in dioxane (10 mL) was stirred at 100° C. for 18 h. The reaction mixture was cooled and concentrated. The residue was purified by flash chromatography on silica gel (DCM/MeOH=95/5) to afford the crude 217 (830 mg, 54% yield). 15 mg of the crude compound was purified by Prep-HPLC (Method C) to afford 217 (7.3 mg, 54% yield) as a white solid. LC-MS (Method 2) t$_R$=2.57 min, m/z (M+H)$^+$=481.2. $^1$H NMR (400 MHz, DMSO-d$_6$) δ 10.81 (s, 1H), 10.73 (s, 1H), 8.47 (s, 1H), 8.45 (s, 1H), 8.35 (s, 1H), 7.93 (s, 1H), 7.10 (s, 1H), 5.80-5.75 (m, 1H), 3.70 (s, 3H), 2.22-1.97 (m, 1H), 1.70 (d, J=7.6 Hz, 3H), 0.81-0.76 (m, 4H).

Example 218

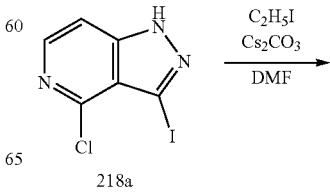

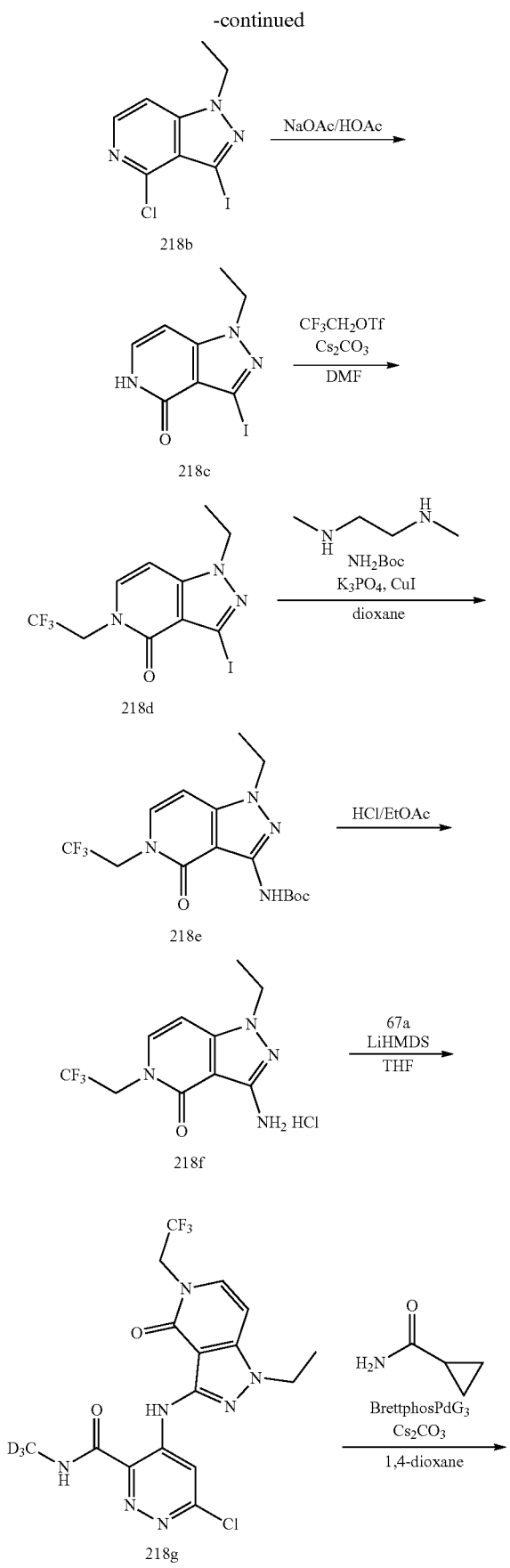

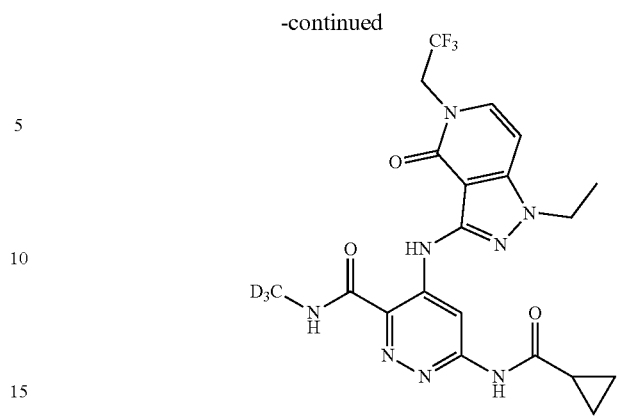

218

Step 1. 4-Chloro-1-ethyl-3-iodo-1H-pyrazolo[4,3-c]pyridine (218b)

A mixture of 218a (400 mg, 1.43 mmol), Cs$_2$CO$_3$ (932 mg, 2.87 mmol) and C$_2$H$_5$I (447 mg, 2.87 mmol) in DMF (5 mL) was stirred at 40° C. for 2 h. After cooling to r.t., the mixture was diluted with water (20 mL) and extracted with EtOAc (30 mL*3). The combined organic layer was concentrated and the residue was purified by flash chromatography on silica gel (PE/EtOAc=3/1) to afford 218b (380 mg, 86% yield) as a yellow solid. LC-MS (Method 3) t$_R$=1.26 min, m/z (M+H)$^+$=307.9.

Step 2. 1-Ethyl-3-iodo-1,5-dihydro-4H-pyrazolo[4,3-c]pyridin-4-one (218c)

A mixture of 218b (400 mg, 1.30 mmol) and NaOAc (213 mg, 2.60 mmol) in HOAc (10 mL) was stirred at 100° C. overnight. After cooling to r.t., the mixture was concentrated. And the residue was diluted with water (20 mL) and extracted with DCM (30 mL*3). The separated organic layer was concentrated to afford 218c (370 mg, 98% yield) as a white solid. LC-MS (Method 3) t$_R$=0.94 min, m/z (M+H)$^+$=290.1.

Step 3. 1-Ethyl-3-iodo-5-(2,2,2-trifluoroethyl)-1,5-dihydro-4H-pyrazolo[4,3-c]pyridin-4-one (218d)

A mixture of 218c (320 mg, 1.11 mmol), Cs$_2$CO$_3$ (721 mg, 2.21 mmol) and 2,2,2-trifluoroethyl methanesulfonate (217 mg, 1.22 mmol) in DMF (10 mL) was stirred at 40° C. for 2 h. After cooling to r.t., the mixture was diluted with water (20 mL) and extracted with EtOAc (30 mL*3). The combined organic layer was concentrated and the residue was purified by flash chromatography on silica gel (PE/EtOAc=3/1) to afford 218d (338 mg, 82% yield) as a white solid. $^1$H NMR (400 MHz, CDCl$_3$) δ 7.13 (d, J=7.6 Hz, 1H), 6.37 (d, J=7.6 Hz, 1H), 4.61 (q, J=8.4 Hz, 2H), 4.27 (q, J=7.2 Hz, 2H), 1.50 (t, J=7.2 Hz, 3H).

Step 4. Tert-butyl (1-ethyl-4-oxo-5-(2,2,2-trifluoroethyl)-4,5-dihydro-1H-pyrazolo[4,3-c]pyridin-3-yl)carbamate (218e)

A mixture of 218d (200 mg, 0.54 mmol), tert-butyl carbamate (126 mg, 1.08 mmol), CuI (51 mg, 0.27 mmol), K$_3$PO$_4$ (229 mg, 1.08 mmol) and N,N-dimethylethane-1,2- diamine (24 mg, 0.27 mmol) in anhydrous dioxane (5 mL) was stirred at 90° C. for 18 h under $N_2$ atmosphere. After cooling to r.t., the mixture was concentrated and the residue was purified by flash chromatography on silica gel (PE/EtOAc=1/1) to afford 218e (190 mg, 98% yield) as brown oil. LC-MS (Method 3) $t_R$=1.26 min, m/z $(M+H)^+$=361.2.

Step 5. 3-Amino-1-ethyl-5-(2,2,2-trifluoroethyl)-1,5-dihydro-4H-pyrazolo[4,3-c]pyridin-4-one hydrochloride (218f)

A mixture of 218e (190 mg, 0.53 mmol) in HCl/EtOAc (5 mL, 1 M) was stirred for 3 h at r.t. The formed solid was filtered. And the filter cake was dried to afford 218f (150 mg, 96% yield) as a brown solid. LC-MS (Method 3) $t_R$=1.05 min, m/z $(M+H)^+$=261.3.

Step 6. 6-Chloro-4-((1-ethyl-4-oxo-5-(2,2,2-trifluoroethyl)-4,5-dihydro-1H-pyrazolo[4,3-c]pyridin-3-yl)amino)-N-(methyl-$d_3$)pyridazine-3-carboxamide (218g)

To a solution of 218f (150 mg, 0.46 mmol) and 67a (96 mg, 0.46 mmol) in THF (5 mL) was added LiHMDS (1.84 mL, 1.84 mmol, 1.0 M in THF) at −78° C. The mixture was stirred at −78° C. for 10 min and stirred for 30 min at r.t. The reaction was quenched with ice-water (10 mL). And the formed solid was filtered and dried to afford 218g (173 mg, 72% yield) as a white solid. LC-MS (Method 3) $t_R$=1.32 min, m/z $(M+H)^+$=433.1.

Step 7. 6-(Cyclopropanecarboxamido)-4-((1-ethyl-4-oxo-5-(2,2,2-trifluoroethyl)-4,5-dihydro-1H-pyrazolo[4,3-c]pyridin-3-yl)amino)-N-(methyl-$d_3$) pyridazine-3-carboxamide (218)

A mixture of 218g (113 mg, 0.26 mmol), cyclopropanecarboxamide (111 mg, 1.31 mmol), BrettPhos Pd G3 (47 mg, 0.052 mmol) and $Cs_2CO_3$ (170 mg, 0.52 mmol) in 1,4-dioxane (1.5 mL) was stirred at 90° C. overnight under $N_2$ atmosphere. The reaction was cooled to r.t. and evaporated. The residue was purified by flash chromatography on silica gel (DCM/MeOH=20/1) to afford 218 (8 mg, 6% yield) as a yellow solid. LC-MS (Method 2) $t_R$=2.87 min, m/z $(M+H)^+$=482.2. $^1$H NMR (400 MHz, Trifluoroacetic acid-d) b 8.79 (s, 1H), 7.50 (d, J=7.6 Hz, 1H), 6.84 (d, J=7.6 Hz, 1H), 4.88-4.82 (m, 2H), 4.76 (q, J=7.2 Hz, 2H), 2.06-2.03 (m, 1H), 1.64 (t, J=7.2 Hz, 3H), 1.45-1.41 (m, 4H).

Example 219

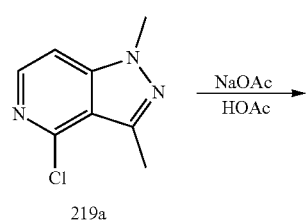

219a

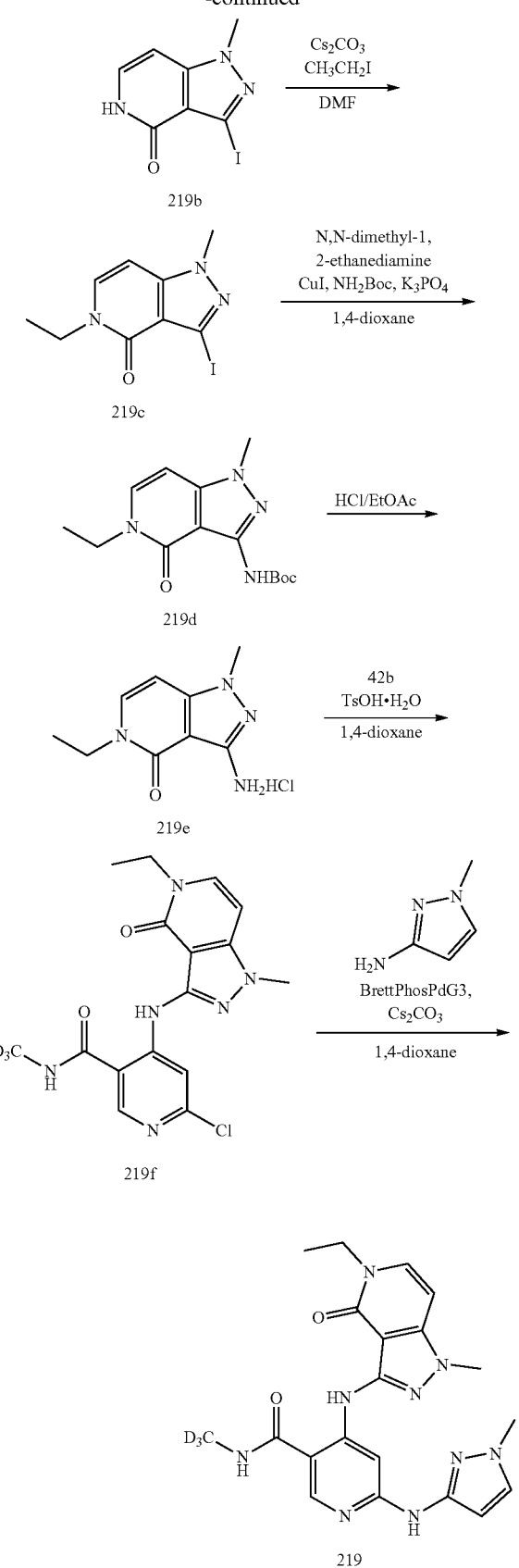

Step 1. 3-Iodo-1-methyl-1,5-dihydro-4H-pyrazolo[4,3-c]pyridin-4-one (219b)

A mixture of 219a (185 mg, 0.63 mmol) and sodium acetate (103 mg, 1.26 mmol) in HOAc (4 mL) was stirred at stirred at 100° C. for 16 h. After cooling to r.t., the mixture was diluted with water (20 mL) and adjusted pH to 9 with aq. $Na_2CO_3$. The formed solid was filtered and dried to afford 219b (129 mg, 74% yield) as a yellow solid. $^1H$ NMR (400 MHz, DMSO-$d_6$) 11.06 (s, 1H), 7.22-7.18 (m, 1H), 6.58 (d, J=7.2 Hz, 1H), 3.90 (s, 3H).

Step 2. 5-Ethyl-3-iodo-1-methyl-1,5-dihydro-4H-pyrazolo[4,3-c]pyridin-4-one (219c)

A mixture of 219b (329 mg, 1.20 mmol), $CH_3CH_2I$ (746 mg, 4.78 mmol) and $Cs_2CO_3$ (779 mg, 2.39 mmol) in DMF (3 mL) was stirred at stirred at 40° C. for 2 h. The mixture was poured into water (10 mL) and filtered. The filter cake was purified by flash chromatography on silica gel (PE/EtOAc=1/1) to afford 219c (247 mg, 68% yield) as a white solid. LC-MS (Method 3) $t_R$=1.00 min, m/z $(M+H)^+$=304.0.

Step 3. Tert-butyl (5-ethyl-1-methyl-4-oxo-4,5-dihydro-1H-pyrazolo[4,3-c]pyridin-3-yl)carbamate (219d)

A mixture of 219c (247 mg, 0.82 mmol), tert-butyl carbamate (143 mg, 1.22 mmol), CuI (78 mg, 0.41 mmol), $K_3PO_4$ (519 mg, 2.44 mmol) and N,N-dimethylethane-1,2-diamine (36 mg, 0.41 mmol) in anhydrous dioxane (3 mL) was stirred at 90° C. for 16 h under $N_2$ atmosphere. After cooling to r.t., the mixture was concentrated and the residue was purified by flash chromatography on silica gel (DCM/MeOH=10/1) to afford 219d (129 mg, 54% yield) as a gray solid. LC-MS (Method 3) $t_R$=1.13 min, m/z $(M+H)^+$=293.1.

Step 4. 3-Amino-5-ethyl-1-methyl-1,5-dihydro-4H-pyrazolo[4,3-c]pyridin-4-one hydrochloride (219e)

A mixture of 219d (129 mg, 0.44 mmol) in HCl/EtOAc (2 mL, 2 M) was stirred at 25° C. for 2 h. The mixture was concentrated to afford 219e (100 mg, 99% yield) as a yellow solid. LC-MS (Method 3) $t_R$=0.69 min, m/z $(M+H)^+$=193.1.

Step 5. 6-Chloro-4-((5-ethyl-1-methyl-4-oxo-4,5-dihydro-1H-pyrazolo[4,3-c]pyridin-3-yl)amino)-N-(methyl-$d_3$)nicotinamide (219f)

A mixture of 219e (50 mg, 0.22 mmol), 42b (54 mg, 0.26 mmol) and TsOH·$H_2O$ (8 mg, 0.042 mmol) in 1,4-dioxane (2 mL) was stirred at 100° C. for 16 h. The mixture was cooled, concentrated and the residue was purified by flash chromatography on silica gel (DCM/MeOH=20/1) to afford 219f (42 mg, 53% yield) as a yellow solid. LC-MS (Method 3) $t_R$=1.07 min, m/z $(M+H)^+$=364.3.

Step 6. 4-((1,5-Dimethyl-4-oxo-4,5-dihydro-1H-pyrazolo[4,3-c]pyridin-3-yl)amino)-N-(methyl-$d_3$)-6-((1-methyl-1H-pyrazol-3-yl)amino)nicotinamide (219)

A mixture of 219f (44 mg, 0.12 mmol), BrettPhos Pd G3 (21 mg, 0.023 mmol) and $Cs_2CO_3$ (188 mg, 0.58 mmol) in dioxane (0.5 mL) was stirred at stirred at 100° C. for 16 h under $N_2$. The mixture was cooled and concentrated under reduced pressure and purified by Prep-HPLC (Method A) to afford 219 (5.6 mg, 11% yield) as a white solid. LC-MS (Method 2) $t_R$=2.29 min, m/z $(M+H)^+$=425.2. $^1H$ NMR (400 MHz, DMSO-$d_6$) δ 11.64 (s, 1H), 9.30 (s, 1H), 8.44 (s, 1H), 8.40 (s, 1H), 8.27 (s, 1H), 7.55 (s, 1H), 7.52 (d, J=7.6 Hz, 1H), 6.57 (d, J=7.2 Hz, 1H), 6.24 (s, 1H), 3.93 (q, J=6.8 Hz, 2H), 3.78 (s, 3H), 3.31 (s, 3H), 1.22 (t, J=6.8 Hz, 3H).

Example 220

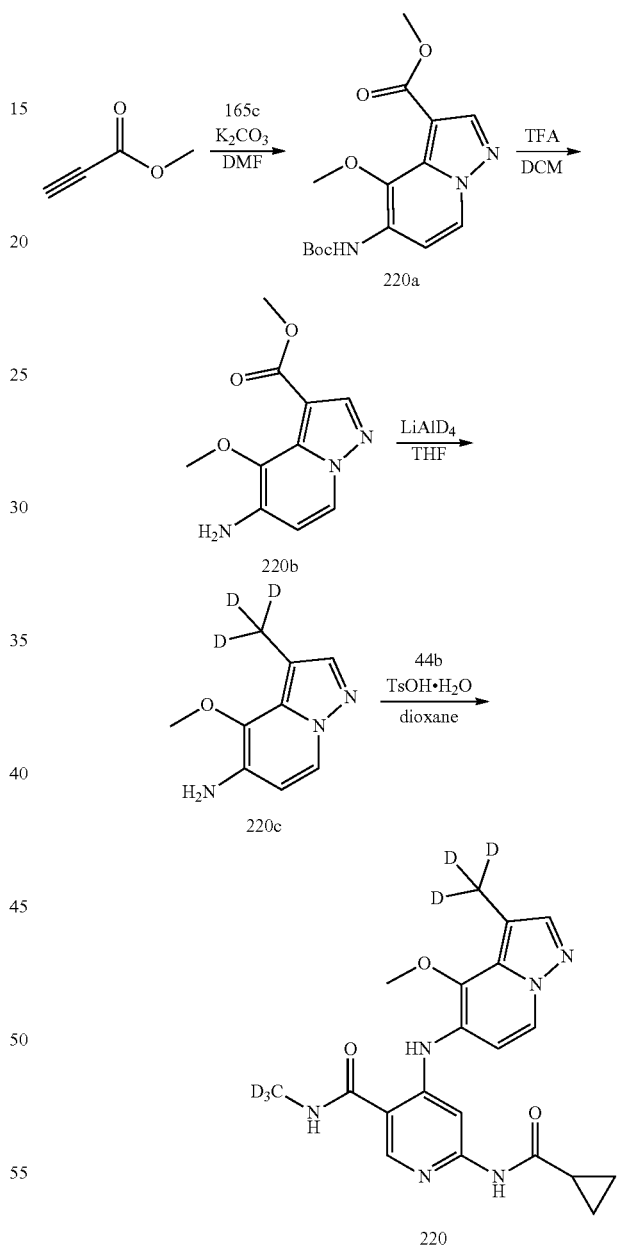

Step 1. Methyl 5-((tert-butoxycarbonyl)amino)-4-methoxypyrazolo[1,5-a]pyridine-3-carboxylate (220a)

A mixture of methyl propiolate (749 mg, 8.91 mmol, 7.93 mL), 165c (1.89 g, 4.45 mmol) and $K_2CO_3$ (1.23 g, 8.91 mmol) in DMF (5 mL) was stirred at 20° C. for 2 h. A black suspension was formed. The reaction mixture was concentrated and diluted with water (50 mL), then extracted with EtOAc (50 mL*2). The combined organic layer was washed with water (50 mL*2), brine (50 mL*2), dried over anhydrous $Na_2SO_4$, filtered and concentrated. The residue was purified by flash chromatography (EtOAc in PE is 10-30%) to give 220a (350 mg, 24% yield) as a yellow solid. LC-MS (Method 4) $t_R$=4.13 min, m/z (M+H)$^+$=322.1. $^1$H NMR (400 MHz, CDCl$_3$) δ 8.35 (s, 1H), 8.28 (d, J=7.6 Hz, 1H), 8.01 (d, J=7.6 Hz, 1H), 7.32 (brs, 1H), 3.89 (s, 3H), 3.88 (s, 3H), 1.55 (s, 9H).

Step 2. Methyl 5-amino-4-methoxypyrazolo[1,5-a]pyridine-3-carboxylate (220b)

To a solution of 220a (200 mg, 0.62 mmol) in DCM (3 mL) was added TFA (1 mL) at 0° C. After stirring for 2 h, the reaction mixture was concentrated to dryness and basified with sat. $Na_2CO_3$ to adjust pH to above 8. The mixture was then extracted with EtOAc (5 mL*3). The combined organic layer was washed with brine (5 mL), dried over $Na_2SO_4$ and filtered. The filtrate was concentrated to afford 220b (120 mg, 87% yield) as a brown oil. LC-MS (Method 3) $t_R$=0.88 min, m/z (M+H)$^+$=222.3.

Step 3. 4-Methoxy-3-(methyl-d$_3$)pyrazolo[1,5-a]pyridin-5-amine (220c)

To a solution of 220b (120 mg, 0.54 mmol) in THF (2 mL) was slowly added LiAlD$_4$ (137 mg, 3.25 mmol) at 0'C. After stirring at 0° C. for 0.5 h, the mixture was warmed to 60° C. and stirred for 2 h. After cooling to r.t., the mixture was quenched with H$_2$O (0.13 mL), 15% aq. NaOH (0.13 mL) and H$_2$O (0.26 mL) at 0° C. in turn. Then the mixture was stirred at r.t. for 15 min, dried over Na$_2$SO$_4$, filtered and concentrated. The residue was purified by Prep-HPLC (Method A) to afford 220c (60 mg, 61% yield) as a gray solid. LC-MS (Method 3) $t_R$=0.83 min, m/z (M+H)$^+$=181.3.

Step 4. 6-(Cyclopropanecarboxamido)-4-((4-methoxy-3-(methyl-d$_3$)pyrazolo[1,5-a]pyridin-5-yl)amino)-N-(methyl-d$_3$)nicotinamide (220)

A solution of 220c (60 mg, 0.33 mmol), 44b (77 mg, 0.30 mmol) and TsOH·H$_2$O (63 mg, 0.33 mmol) in dioxane/EtOH (0.5 mL/0.5 mL) was stirred at 100° C. for 12 h. The reaction mixture was cooled and concentrated. The residue was purified by flash chromatography (DCM/MeOH=20/1) to afford 220 (28 mg, 21% yield) as a white solid. LC-MS (Method 2) $t_R$=3.10 min, m/z (M+H)$^+$=401.1. $^1$H NMR (400 MHz, DMSO-d$_6$) δ 10.77 (s, 1H), 10.52 (s, 1H), 8.61 (s, 1H), 8.52 (s, 1H), 8.41 (d, J=7.6 Hz, 1H), 7.80 (s, 1H), 7.77 (s, 1H), 6.79 (d, J=7.6 Hz, 1H), 3.78 (s, 3H), 1.98-1.95 (m, 1H), 0.76-0.74 (m, 4H).

Example 221

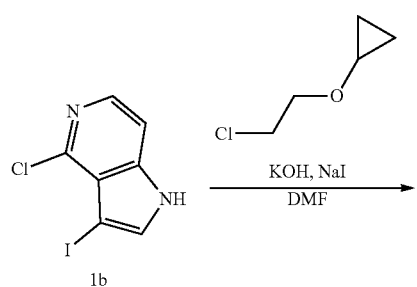

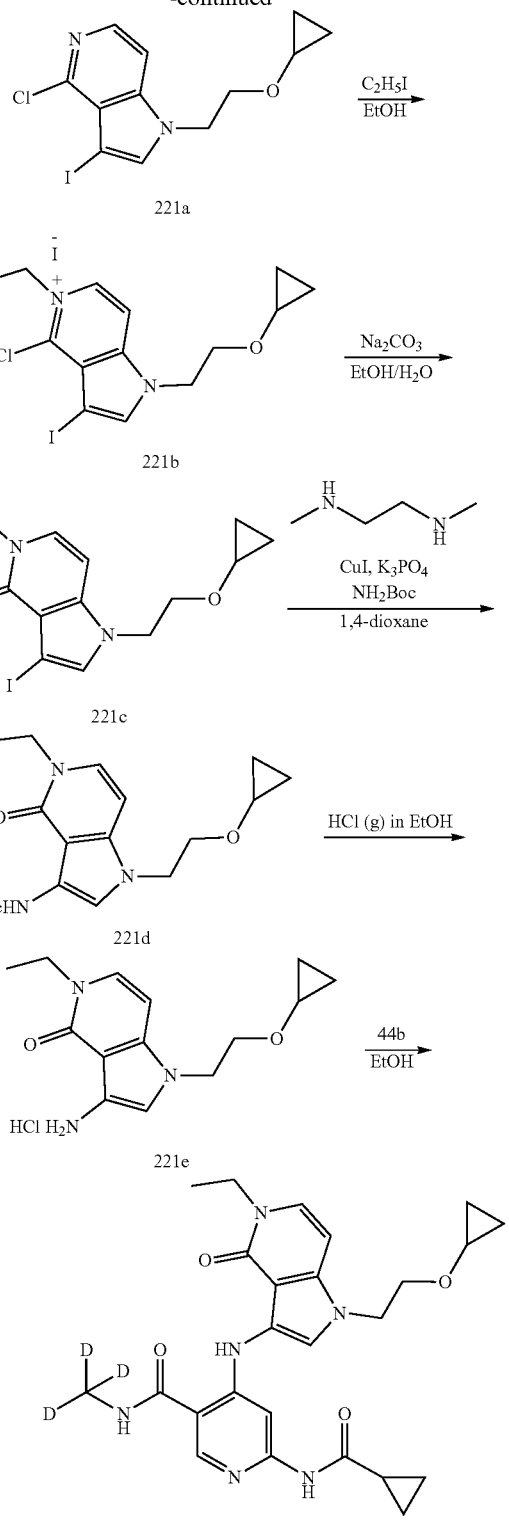

Step 1. 4-Chloro-1-(2-cyclopropoxyethyl)-3-iodo-1H-pyrrolo[3,2-c]pyridine (221a)

A solution of 1b (1.6 g, 5.75 mmol), 2-chloroethoxycyclopropane (554 mg, 4.60 mmol), NaI (86 mg, 0.57 mmol)

and KOH (644 mg, 11.49 mmol) in DMF (5 mL) was stirred at 70° C. for 16 h. After cooling to r.t., the reaction mixture was poured into water (15 mL), extracted with EtOAc (30 mL*2) and concentrated under reduced pressure. The residue was purified by flash chromatography on silica gel (PE/EtOAc=1/1) to afford 221a (260 mg, 12% yield) as a yellow solid. LC-MS (Method 3) $t_R$=1.32 min, m/z (M+H)$^+$=363.1.

Step 2. 4-Chloro-1-(2-cyclopropoxyethyl)-5-ethyl-3-iodo-1H-pyrrolo[3,2-c]pyridin-5-ium iodide (221b)

A mixture of 221a (180 mg, 0.49 mmol), $C_2H_5I$ (1 mL) and EtOH (1 mL) in a sealed tube was stirred at 70° C. for 4 h. After cooling to r.t., the reaction mixture was concentrated to afford 221b (194 mg, yield given) as a yellow solid. The crude product was used in the next step without purification. LC-MS (Method 3) $t_R$=1.34 min, m/z M$^+$=391.1.

Step 3. 1-(2-Cyclopropoxyethyl)-5-ethyl-3-iodo-1,5-dihydro-4H-pyrrolo[3,2-c]pyridin-4-one (221c)

A mixture of 221b (194 mg, 0.49 mmol), $Na_2CO_3$ (103 mg, 0.97 mmol) in EtOH (1 mL) and $H_2O$ (1 mL) was stirred for 15 min at 70° C. After cooling to r.t., the solvent was concentrated. The residue was purified by flash chromatography on silica gel (DCM/MeOH=1/10) to afford 221c (180 mg, 97% yield) as a yellow oil. LC-MS (Method 3) $t_R$=1.20 min, m/z (M+H)$^+$=373.1.

Step 4. Tert-butyl (1-(2-cyclopropoxyethyl)-5-ethyl-4-oxo-4,5-dihydro-1H-pyrrolo[3,2-c]pyridin-3-yl)carbamate (221d)

A mixture of 221c (160 mg, 0.43 mmol), tert-butyl carbamate (100 mg, 0.86 mmol), CuI (41 mg, 0.21 mmol), $K_3PO_4$ (182 mg, 0.86 mmol) and N,N-dimethylethane-1,2-diamine (19 mg, 0.21 mmol) in anhydrous dioxane (1 mL) was stirred at 90° C. for 16 h under $N_2$ atmosphere. After cooling to r.t., The mixture was concentrated and the residue was purified by flash chromatography on silica gel (PE/EtOAc=1/1) to afford 221d (90 mg, 58% yield) as a yellow oil. LC-MS (Method 3) $t_R$=1.37 min, m/z (M+H)$^+$=362.3.

Step 5. 3-Amino-1-(2-cyclopropoxyethyl)-5-ethyl-1,5-dihydro-4H-pyrrolo[3,2-c]pyridin-4-one hydrochloride (221e)

A mixture of 221d (279 mg, 1 mmol) in HCl/EtOAc (5 mL, 2 M) was stirred at r.t. for 2 h. The formed solid was filtered and the filter cake was dried to afford 221e (65 mg, 98% yield) as a white solid. LC-MS (Method 3) $t_R$=0.89 min, m/z (M+H)$^+$=262.1.

Step 6. 6-(Cyclopropanecarboxamido)-4-((1-(2-cyclopropoxyethyl)-5-ethyl-4-oxo-4,5-dihydro-1H-pyrrolo[3,2-c]pyridin-3-yl)amino)-N-(methyl-d$_3$)nicotinamide (221)

A solution of 221e (65 mg, 0.22 mmol) and 44b (56 mg, 0.22 mmol) in EtOH (0.5 mL) was stirred at 90° C. for 18 h. After cooling to r.t., the reaction mixture was concentrated and purified by Prep-HPLC (Method A) to afford the title compound 221 (10 mg, 10% yield) as a white solid. LC-MS (Method 2) $t_R$=3.04 min, m/z (M+H)$^+$=482.2. $^1$H NMR (400 MHz, DMSO-d$_6$) δ 10.88 (s, 1H), 10.71 (s, 1H), 8.42 (s, 1H), 8.38 (s, 1H), 8.04 (s, 1H), 7.33 (d, J=7.6 Hz, 1H), 7.09 (s, 1H), 6.56 (d, J=7.6 Hz, 1H), 4.16 (t, J=5.6 Hz, 2H), 3.74 (t, J=7.2 Hz, 2H), 3.74 (t, J=5.2 Hz, 2H), 3.26-3.23 (m, 1H), 2.01-2.00 (m, 1H), 1.22 (t, J=7.2 Hz, 3H), 0.80-1.25 (m, 4H), 0.37-0.34 (m, 4H).

Example 222

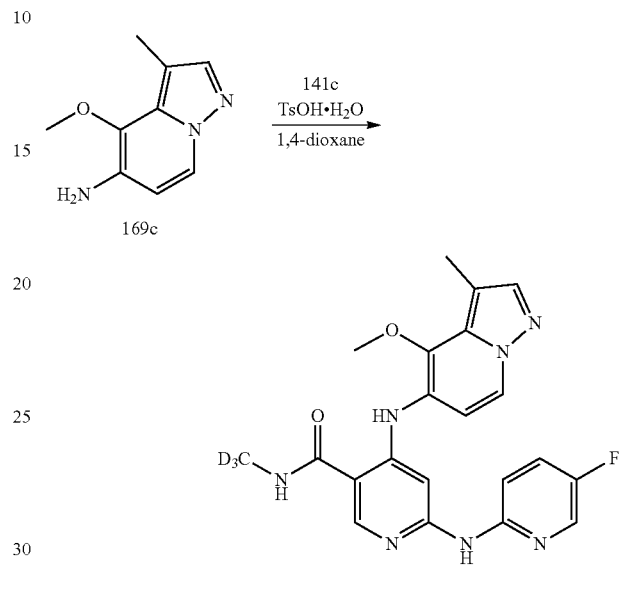

Step 1. 6-((5-Fluoropyridin-2-yl)amino)-4-((4-methoxy-3-methylpyrazolo[1,5-a]pyridin-5-yl)amino)-N-(methyl-d$_3$)nicotinamide (222)

A mixture of 169c (19 mg, 0.11 mmol), 141c (34 mg, 0.12 mmol) and TsOH·H$_2$O (9 mg, 0.05 mmol) in 1,4-dioxane (1 mL) was stirred at 100° C. for 16 h in a sealed tube. The reaction mixture was cooled, filtered and the filter cake was purified by Prep-HPLC (Method A) to afford 222 (10.5 mg, 21% yield) as a white solid. LC-MS (Method 2) $t_R$=3.08, m/z (M+H)$^+$=425.1. $^1$H NMR (400 MHz, DMSO-d$_6$) δ 10.61 (s, 1H), 9.79 (s, 1H), 8.52-8.49 (m, 3H), 8.17 (s, 1H), 7.76 (s, 1H), 7.67-7.60 (m, 2H), 7.54 (s, 1H), 6.97 (d, J=7.2 Hz, 1H), 3.80 (s, 3H), 2.39 (s, 3H).

Example 223

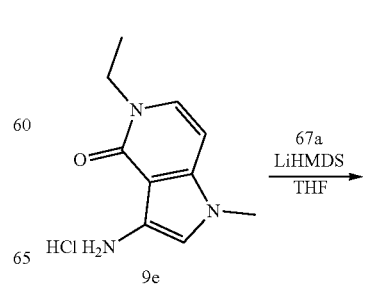

627

-continued

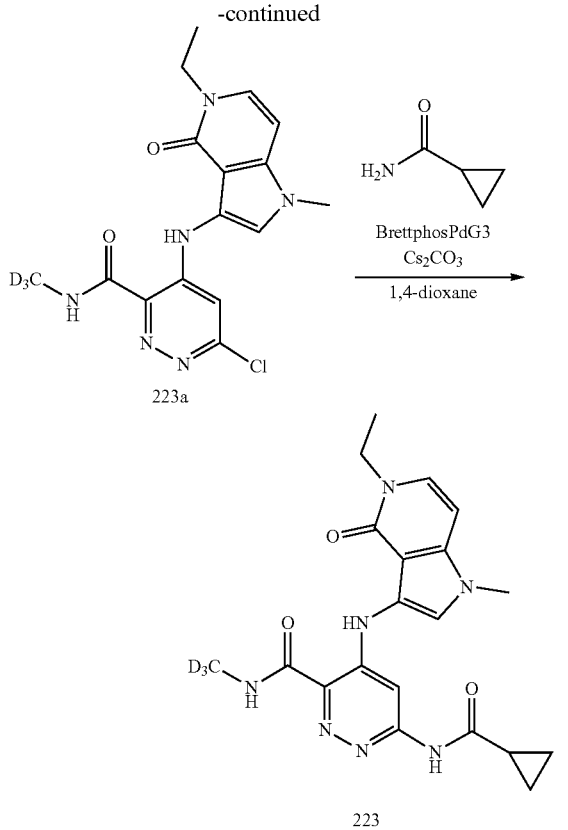

Example 224

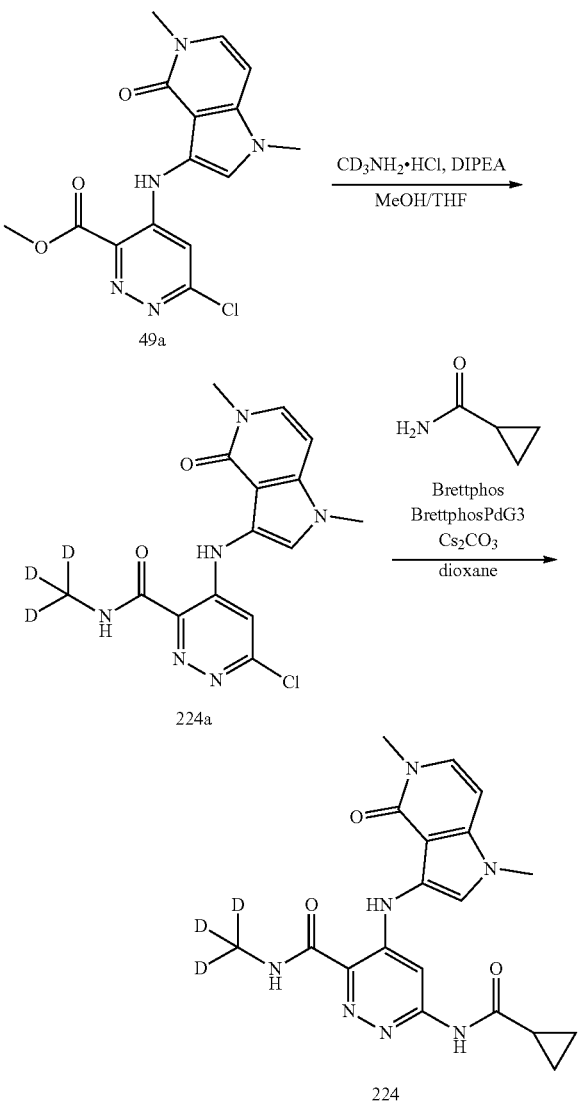

Step 1. 6-Chloro-4-((5-ethyl-1-methyl-4-oxo-4,5-dihydro-1H-pyrrolo[3,2-c]pyridin-3-yl)amino)-N-(methyl-$d_3$)pyridazine-3-carboxamide (223a)

To a solution of 9e (170 mg, 0.75 mmol) and 67a (156 mg, 0.75 mmol) in THF (2 mL) was added LiHMDS (3 mL, 3.0 mmol, 1 M in THF) at −40° C. The reaction was stirred at −40° C. to r.t. for 1 h. The reaction was quenched with $H_2O$ (2 mL) and extracted with ethyl acetate (10 mL*3). The combined organic layer was dried over anhydrous sodium sulfate, filtered and concentrated. The residue was purified by flash chromatography on silica gel (DCM/MeOH=20/1) to afford compound 223a (90 mg, 33% yield) as a yellow solid. LC-MS (Method 3) $t_R$=1.07 min, m/z (M+H)$^+$=364.3.

Step 2. 6-(Cyclopropanecarboxamido)-4-((5-ethyl-1-methyl-4-oxo-4,5-dihydro-1H-pyrrolo[3,2-c]pyridin-3-yl)amino)-N-(methyl-$d_3$)pyridazine-3-carboxamide (223)

A mixture of 223a (70 mg, 0.19 mmol), cyclopropanecarboxamide (82 mg, 0.96 mmol), BrettPhos Pd G3 (35 mg, 0.038 mmol) and $Cs_2CO_3$ (125 mg, 0.38 mmol) in 1,4-dioxane (1.5 mL) was stirred at 90° C. overnight under $N_2$ atmosphere. The reaction was cooled to r.t. and concentrated. The residue was purified by flash chromatography on silica gel (DCM/MeOH=20/1) to afford compound 223 (34 mg, 43% yield) as a white solid. LC-MS (Method 2) $t_R$=2.50 min, m/z (M+H)$^+$=413.1. $^1$H NMR (400 MHz, DMSO-$d_6$) δ 11.25 (s, 2H), 8.99 (s, 1H), 8.09 (s, 1H), 7.38 (d, J=7.6 Hz, 1H), 7.06 (s, 1H), 6.56 (d, J=7.6 Hz, 1H), 3.92 (q, J=7.2 Hz, 2H), 3.71 (s, 3H), 2.15-2.10 (m, 1H), 1.20 (t, J=6.8 Hz, 3H), 0.86-0.84 (m, 4H).

Step 1. 6-Chloro-4-((1,5-dimethyl-4-oxo-4,5-dihydro-1H-pyrrolo[3,2-c]pyridin-3-yl)amino)-N-(methyl-$d_3$)pyridazine-3-carboxamide (224a)

To a stirred solution of 49a (500 mg, 1.44 mmol) in MeOH (5 mL) and THF (5 mL) was added methan-$d_3$-amine hydrochloride (1.45 g, 20.5 mmol) and DIPEA (3.98 g, 30.8 mmol) at room temperature. The reaction mixture was stirred at 70° C. for 15 h. The reaction mixture was concentrated and purified by flash chromatography on silica gel (DCM/MeOH=100/1 to 10/1) to give 224a (350 mg, 69% yield) as a yellow solid. LC-MS (Method 4) $t_R$=2.06 min, m/z (M+H)$^+$=350.2.

Step 2. 6-(Cyclopropanecarboxamido)-4-((1,5-dimethyl-4-oxo-4,5-dihydro-1H-pyrrolo[3,2-c]pyridin-3-yl)amino)-N-(methyl-$d_3$)pyridazine-3-carboxamide (224)

To a solution of 224a (350 mg, 1.0 mmol) in dioxane (5 mL) was added BrettPhos Pd G3 (192 mg, 0.2 mmol), BrettPhos (107 mg, 0.2 mmol), Cs₂CO₃ (652 mg, 2 mmol) and cyclopropanecarboxamide (851 mg, 10 mmol). The mixture was stirred at 120° C. for 4 h under N₂ atmosphere. The mixture was diluted with H₂O (10 mL), extracted with EA (20 mL*3), washed with brine (20 mL), dried over Na₂SO₄, concentrated and purified by flash chromatography on silica gel (DCM/MeOH=100/1 to 10/1) to get the compound 224 (41 mg, 10% yield) as a yellow solid. LC-MS (Method 4) t_R=1.85 min, m/z (M+H)⁺=399.3. ¹H NMR (400 MHz, DMSO-d₆) δ 11.24 (s, 1H), 11.21 (s, 1H), 8.91 (s, 1H), 8.04 (s, 1H), 7.34 (d, J=7.6 Hz, 1H), 7.02 (s, 1H), 6.51 (d, J=7.6 Hz, 1H), 3.67 (s, 3H), 3.39 (s, 3H), 2.09-2.02 (m, 1H), 1.26-1.18 (m, 2H), 0.86-0.79 (m, 2H).

Example 225

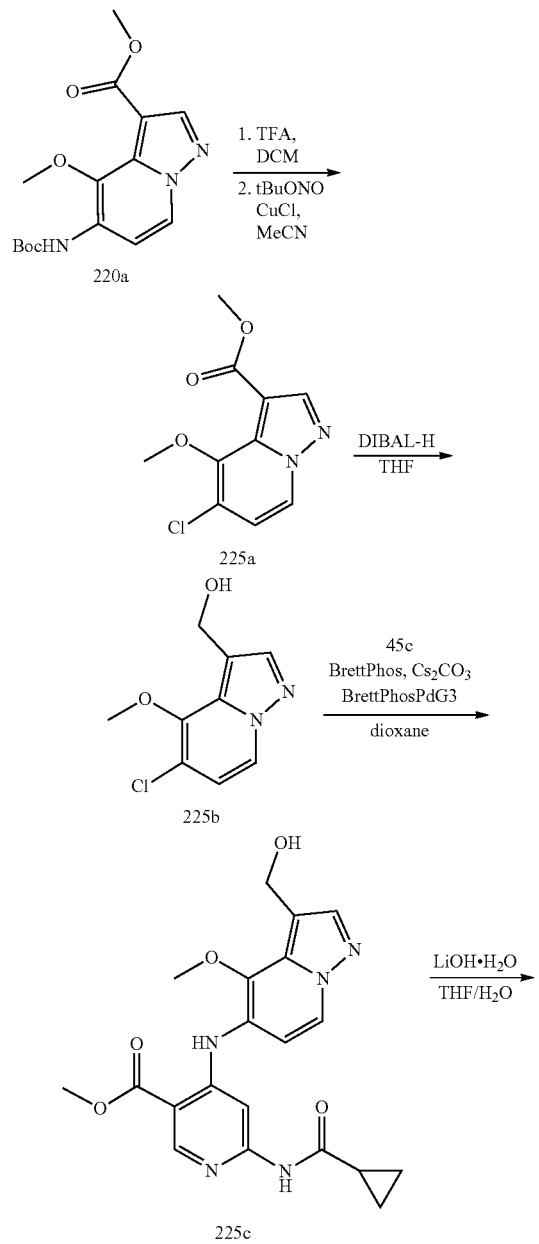

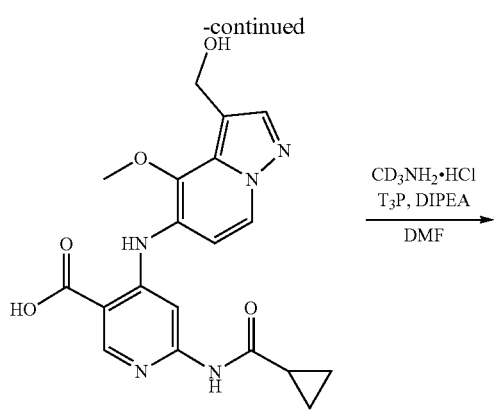

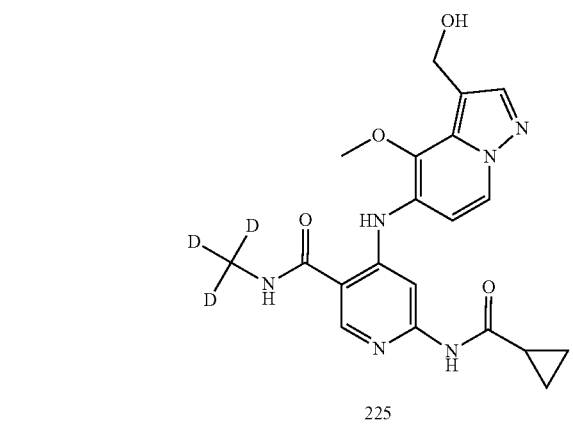 [SMILES: [2H]C([2H])([2H])NC(=O)c1cnc(NC(=O)C2CC2)cc1Nc1ccn2ncc(CO)c2c1OC]

Step 1. Methyl 5-chloro-4-methoxy-pyrazolo[1,5-a]pyridine-3-carboxylate (225a)

To a mixture of 225a (400 mg, 1.24 mmol) in DCM (3 mL) was added TFA (1 mL) at 20° C. The resulting mixture was stirred at 20° C. for 1 h. A yellow solution was formed. The reaction mixture was concentrated to give methyl 5-amino-4-methoxy-pyrazolo[1,5-a]pyridine-3-carboxylate hydrochloride (280 mg, crude) as a yellow solid.

LC-MS (Method 4) t_R=0.46 min, m/z (M+H)⁺=222.1.

To a mixture of methyl 5-amino-4-methoxy-pyrazolo[1,5-a]pyridine-3-carboxylate hydrochloride (280 mg, crude) in MeCN (5 mL) was added tert-butyl nitrite (196 mg, 1.90 mmol, 0.23 mL) at 0° C. After stirring for 10 min, CuCl (250 mg, 2.54 mmol) was added into the above mixture, and the resulting mixture was stirred at 80° C. for 12 h. A yellow solution was formed. The reaction mixture was concentrated and purified by column chromatograph (EA in PE is 10-30%) to give 225a (173 mg, 57% yield) as a yellow solid.

LC-MS (Method 4) t_R=2.31 min, m/z (M+H)⁺=241.2.

Step 2. (5-Chloro-4-methoxy-pyrazolo[1,5-a]pyridin-3-yl)methanol (225b)

To a mixture of 225a (173 mg, 0.719 mmol) in THF (5 mL), was added DIBAL-H (1.44 mL, 2.16 mmol, 1.5 M in toluene) at 0° C. The resulting mixture was stirred at 0° C. for 1 h. Then the reaction mixture was warmed to 20° C. and further stirred for 3 h. A yellow solution was formed. The reaction mixture was quenched with aq. Na₂CO₃ (50 mL) and extracted with EtOAc (50 mL*3). The combined organic layer was washed with brine (50 mL*2), dried over anhydrous Na₂SO₄, filtered and concentrated to give a yellow solid. The residue was purified by flash chromatography (EtOAc in PE is 10-60%) to give 225b (130 mg, 85% yield) as a white solid. LC-MS (Method 4) $t_R$=1.78 min, m/z (M+H)⁺=213.0. ¹H NMR (400 MHz, DMSO-$d_6$) 8.49 (d, J=7.6 Hz, 1H), 7.98 (s, 1H), 6.90 (d, J=7.2 Hz, 1H), 4.99 (t, J=5.2 Hz, 1H), 4.72 (d, J=5.2 Hz, 1H), 3.94 (s, 3H).

Step 3. Methyl 6-(cyclopropanecarboxamido)-4-((3-(hydroxymethyl)-4-methoxypyrazolo[1,5-a]pyridin-5-yl)amino)nicotinate (225c)

A mixture of 225b (50 mg, 0.235 mmol), 45c (90 mg, 0.258 mmol), BrettPhos (25.2 mg, 0.047 mmol), Cs₂CO₃ (383.1 mg, 1.18 mmol) and BrettPhos Pd G3 (21.3 mg, 0.024 mmol) in dioxane (3 mL) was degassed and purged with nitrogen. The resulting mixture was stirred at 100° C. under N₂ atmosphere for 24 h. A yellow suspension was formed. The reaction mixture was concentrated and purified by flash chromatography (MeOH in DCM is 0-8%) to give 225c (50 mg, 52% yield) as a yellow solid. LCMS (Method 4) $t_R$=1.72 min, m/z (M+H)⁺=412.2.

Step 4. 6-(Cyclopropanecarboxamido)-4-((3-(hydroxymethyl)-4-methoxypyrazolo[1,5-a]pyridin-5-yl)amino)nicotinic acid (225d)

A mixture of 225c (50 mg, 0.12 mmol) and LiOH·H₂O (15 mg, 0.36 mmol) in co-solvent of THF (3 mL) and water (1 mL) was stirred at 40° C. for 12 h. A yellow solution was formed. The reaction mixture was concentrated and dried in vacuo to give 225d (48 mg, yield given) as a yellow solid, which was used for the next step directly without further purification. LCMS (Method 4) $t_R$=0.86 min, m/z (M+H)⁺=398.2.

Step 5. 6-(Cyclopropanecarboxamido)-4-((3-(hydroxymethyl)-4-methoxypyrazolo[1,5-a]pyridin-5-yl)amino)-N-(methyl-$d_3$)nicotinamide (225)

A mixture of CD₃NH₂·HCl (26 mg, 0.36 mmol), 225d (48 mg, 0.12 mmol), DIPEA (78 mg, 0.60 mmol, 0.105 mL) and T₃P (115.3 mg, 0.36 mmol, 50% purity in EtOAc) in DMF (2 mL) was stirred at 20° C. for 12 h. A yellow solution was formed. The reaction mixture was filtered and purified by Prep-HPLC (Method E) to give 225 (3.0 mg, 6% yield) as a white solid. LCMS (Method 4) $t_R$=2.37 min, m/z (M+H)⁺=414.3. ¹H NMR (400 MHz, DMSO-$d_6$) δ 10.80 (s, 1H), 10.57 (s, 1H), 8.64 (s, 1H), 8.54 (s, 1H), 8.47 (d, J=7.2 Hz, 1H), 7.91 (s, 1H), 7.84 (s, 1H), 6.86 (d, J=7.2 Hz, 1H), 4.90 (brs, 1H), 4.75-4.69 (m, 2H), 3.81 (s, 2H), 1.98-1.90 (m, 1H), 0.76-0.71 (m, 4H).

Example 226

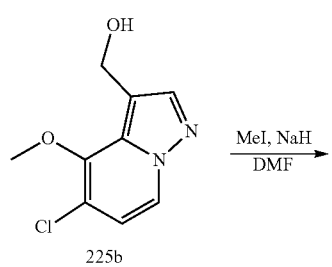

225b

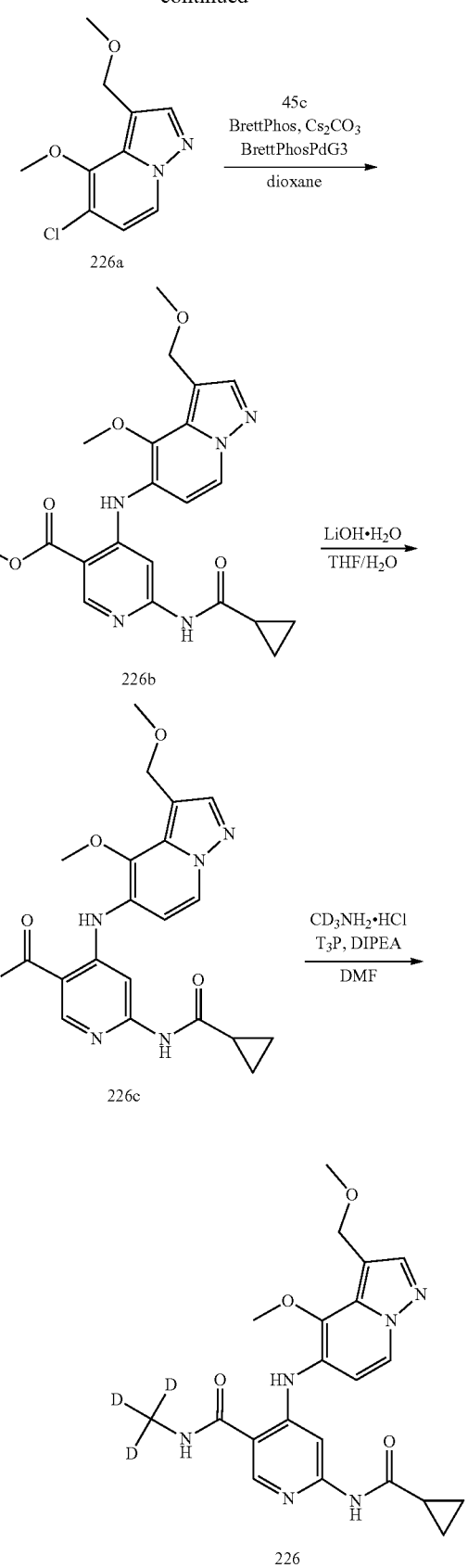

Step 1. 5-Chloro-4-methoxy-3-(methoxymethyl)pyrazolo[1,5-a]pyridine (226a)

To a mixture of 225b (140 mg, 0.658 mmol) in DMF (3 mL) was added NaH (53 mg, 1.32 mmol, 60% purity in mineral oil) and iodomethane (121.5 mg, 0.856 mmol, 0.053 mL) at 0° C. The resulting mixture was stirred at 20° C. for 1 h. A yellow solution was formed. The reaction mixture was quenched with water (50 mL) and extracted with EtOAc (50 mL*3). The combined organic layer was washed with brine (50 mL*2), dried over anhydrous Na$_2$SO$_4$, filtered and concentrated. The residue was purified by column chromatograph (EA in PE is 10-30%) to give 226a (90 mg, 60% yield) as a yellow oil. LC-MS (Method 4) $t_R$=2.46 min, m/z (M+H)$^+$=227.0. $^1$H NMR (400 MHz, CDCl$_3$) δ 8.18 (d, J=7.6 Hz, 1H), 7.92 (s, 1H), 6.71 (d, J=7.6 Hz, 1H), 4.70 (s, 2H), 4.04 (s, 3H), 3.42 (s, 3H).

Step 2. Methyl 6-(cyclopropanecarboxamido)-4-((4-methoxy-3-(methoxymethyl)pyrazolo[1,5-a]pyridin-5-yl)amino)nicotinate (226b)

A mixture of 226a (90 mg, 0.397 mmol), 45c (166 mg, 0.476 mmol), BrettPhos (42.6 mg, 0.079 mmol), Cs$_2$CO$_3$ (388.1 mg, 1.19 mmol) and BrettPhos Pd G3 (36 mg, 0.04 mmol) in dioxane (3 mL) was degassed and purged with nitrogen for 3 times. The resulting mixture was stirred at 100° C. under N$_2$ atmosphere for 24 h. A yellow suspension was formed. The reaction mixture was diluted with EtOAc (50 mL) and filtered through a pad of celite. The filtrate was concentrated and purified by flash chromatography (MeOH in DCM is 0-8%) to give 226b (168 mg, 99% yield) as a yellow solid. LCMS (Method 4) $t_R$=2.20 min, m/z (M+H)$^+$=426.2.

Step 3. 6-(Cyclopropanecarboxamido)-4-((4-methoxy-3-(methoxymethyl)pyrazolo[1,5-a]pyridin-5-yl)amino)nicotinic acid (226c)

A mixture of 226b (168 mg, 0.395 mmol) and LiOH·H$_2$O (50 mg, 1.18 mmol) in co-solvent of THF (6 mL) and water (2 mL) was stirred at 40° C. for 12 h. A yellow solution was formed. The reaction mixture was concentrated and dried in vacuo to give 226c (162 mg, 99% yield) as a yellow solid, which was used for the next step directly without further purification. LCMS (Method 4) $t_R$=1.73 min, m/z (M+H)$^+$=412.3.

Step 4. 6-(Cyclopropanecarboxamido)-4-((4-methoxy-3-(methoxymethyl)pyrazolo[1,5-a]pyridin-5-yl)amino)-N-(methyl-d$_3$)nicotinamide (226)

A mixture of CD$_3$NH$_2$·HCl (83 mg, 1.18 mmol), 226c (162 mg, 0.39 mmol), DIPEA (203.6 mg, 1.58 mmol, 0.27 mL) and T$_3$P (751.7 mg, 1.18 mmol, 50% purity in EtOAc) in DMF (5 mL) was stirred at 20° C. for 12 h. A yellow solution was formed. The reaction mixture was filtered and purified by Prep-HPLC (Method E) to give 226 (26.3 mg, 16% yield) as a white solid. LCMS (Method 4) $t_R$=1.76 min, m/z (M+H)$^+$=428.4. $^1$H NMR (400 MHz, DMSO-d$_6$) δ 10.78 (s, 1H), 10.58 (s, 1H), 8.62 (s, 1H), 8.51 (s, 1H), 8.48 (d, J=7.6 Hz, 1H), 7.93 (s, 1H), 7.83 (s, 1H), 6.89 (d, J=7.2 Hz, 1H), 4.58 (s, 2H), 3.78 (s, 3H), 3.25 (s, 3H), 1.98-1.90 (m, 1H), 0.76-0.71 (m, 4H).

Example 227

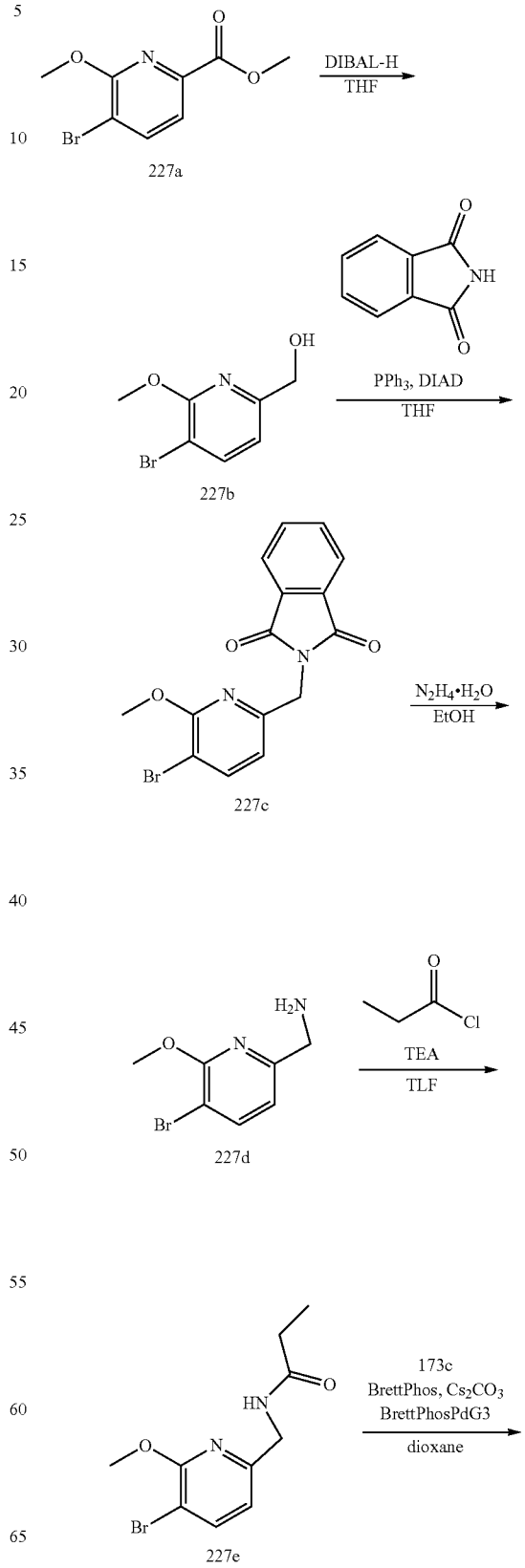

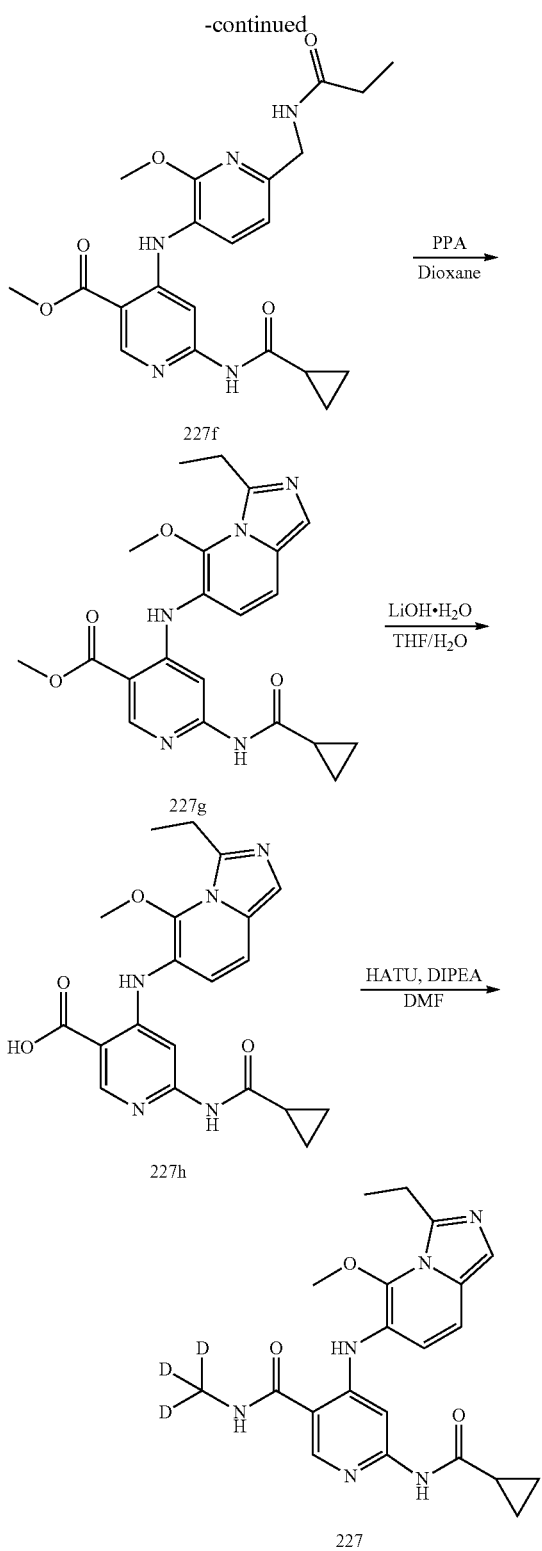

mixture was warmed to 20° C. and stirred for 12 h. A yellow solution was formed. The reaction mixture was quenched with aq. Na$_2$CO$_3$ (50 mL) and extracted with EtOAc (50 mL*3). The combined organic layer was washed with brine (50 mL*2), dried over anhydrous Na$_2$SO$_4$, filtered and concentrated to give 227b (886 mg, yield given) as a white solid, which was used for the next step directly without further purification. LC-MS (Method 4) $t_R$=2.99 min, m/z (M+H)$^+$=218.0.

Step 2. 2-((5-Bromo-6-methoxypyridin-2-yl)methyl)isoindoline-1,3-dione (227c)

To a mixture of 227b (886 mg, 4.06 mmol) and isoindoline-1,3-dione (658 mg, 4.47 mmol) in THF (15 mL) was added PPh$_3$ (1.28 g, 4.88 mmol) and DIAD (986 mg, 4.88 mmol) at 0° C. The resulting mixture was stirred at 20° C. for 12 h. A yellow solution was formed. The reaction mixture was quenched with water (50 mL) and extracted with EtOAc (50 mL*3). The combined organic layer was washed with brine (50 mL*2), dried over anhydrous Na$_2$SO$_4$, filtered and concentrated. The residue was purified by column chromatograph (EA in PE is 10-30%) to give 227c (2.50 g, yield given) as a yellow solid. LCMS (Method 4) $t_R$=3.46 min, m/z (M+H)$^+$=347.0.

Step 3. (5-Bromo-6-methoxypyridin-2-yl)methanamine (227d)

A mixture of 227c (2.50 g, 4.06 mmol) and N$_2$H$_4$·H$_2$O (1.35 g, 21.60 mmol, 80% purity) in ethanol (40 mL) was stirred at 80° C. for 2 h. A white suspension was formed. The reaction mixture was diluted with EtOAc (50 mL) and filtered through a pad of celite. The filtrate was concentrated and purified by flash chromatography (MeOH in DCM is 0-10%) to give 227d (1.56 g, yield given) as a yellow oil. LCMS (Method 4) $t_R$=1.01 min, m/z (M+H)$^+$=217.0.

Step 4. N-((5-bromo-6-methoxypyridin-2-yl)methyl)propionamide (227e)

To a mixture of 227d (1.89 g, 8.71 mmol) in DCM (30 mL) was added TEA (1.32 g, 13.06 mmol, 1.82 mL) and propionyl chloride (1.05 g, 11.32 mmol, 0.99 mL) at 0° C. The resulting mixture was stirred at 20° C. for 2 h. A yellow solution was formed. The reaction mixture was quenched with water (50 mL) and extracted with DCM (50 mL*3). The combined organic layer was washed with brine (50 mL*2), dried over anhydrous Na$_2$SO$_4$, filtered and concentrated. The residue was purified by column chromatograph (MeOH in DCM is 0-10%) to give 227e (1.79 g, 6.55 mmol, 75% yield) as a yellow oil. LCMS (Method 4) $t_R$=2.94 min, m/z (M+H)$^+$=273.1.

Step 5. Methyl 6-(cyclopropanecarboxamido)-4-((2-methoxy-6-(propionamidomethyl)pyridin-3-yl)amino)nicotinate (227f)

A solution of 227e (120 mg, 0.44 mmol), 173c (108 mg, 0.46 mmol), Cs$_2$CO$_3$ (429 mg, 1.32 mmol), BrettPhos (28.3 mg, 0.053 mmol) and BrettPhos Pd G3 (24 mg, 0.026 mmol) in dioxane (3 mL) was degassed and purged with nitrogen for 3 times. The resulting mixture was stirred at 100° C. under N$_2$ atmosphere for 12 h. A yellow suspension was formed. The reaction mixture was diluted with water (50 mL), then extracted with EtOAc (50 mL*2). The combined Step 1. (5-Bromo-6-methoxypyridin-2-yl)methanol (227b)

To a mixture of 227a (1.00 g, 4.06 mmol) in THF (30 mL), was added DIBAL-H (1.5 M, 6.2 mL) at −5° C. The resulting mixture was stirred at 0° C. for 1 h. The reaction organic layer was washed with water (50 mL*2), brine (50 mL*2), dried over anhydrous Na₂SO₄, filtered and concentrated. The residue was purified by flash chromatography (MeOH in DCM is 0-10%) to give 227f (120 mg, 64% yield) as a yellow oil. LCMS (Method 4) $t_R$=2.92 min, m/z (M+H)⁺=428.3. ¹H NMR (400 MHz, DMSO-d₆) δ 10.93 (s, 1H), 9.66 (s, 1H), 8.69 (s, 1H), 8.35 (t, J=6.0 Hz, 1H), 7.85 (s, 1H), 7.72 (d, J=8.0 Hz, 1H), 6.92 (d, J=8.0 Hz, 1H), 4.28 (d, J=6.0 Hz, 2H), 3.92 (s, 3H), 3.87 (s, 3H), 2.20 (q, J=7.6 Hz, 2H), 2.02-1.94 (m, 1H), 1.05 (t, J=7.6 Hz, 3H), 0.80-0.74 (m, 4H).

Step 6. Methyl 6-(cyclopropanecarboxamido)-4-((3-ethyl-5-methoxyimidazo[1,5-a]pyridin-6-yl)amino)nicotinate (227g)

To a mixture of 227f (90 mg, 0.21 mmol) in dioxane (10 mL) was added PPA (300 mg) at 20° C. The resulting mixture was stirred at 100° C. for 2 h. A black suspension was formed. The reaction mixture was concentrated in vacuo and diluted with water (50 mL), basified with 2 M aq. NaOH to pH=11 and extracted with EtOAc (50 mL*2). The combined organic layer was washed with water (50 mL*2), brine (50 mL*2), dried over anhydrous Na₂SO₄, filtered and concentrated. The residue was purified by flash chromatography (MeOH in DCM is 0-10%) to give 227g (50 mg, 58% yield) as a green solid. LCMS (Method 4) $t_R$=2.23 min, m/z (M+H)⁺=410.2.

Step 7. 6-(Cyclopropanecarboxamido)-4-((3-ethyl-5-methoxyimidazo[1,5-a]pyridin-6-yl)amino)nicotinic acid (227h)

A mixture of 227g (50 mg, 0.122 mmol) and LiOH·H₂O (15 mg, 0.366 mmol) in co-solvent of THF (3 mL) and water (1 mL) was stirred at 40° C. for 12 h. A yellow solution was formed. The reaction mixture was concentrated and dried in vacuo to give 227h (48 mg, 99% yield) as a yellow solid, which was used for the next step directly without further purification. LCMS (Method 4) $t_R$=0.85 min, m/z (M+H)⁺=396.2.

Step 8 6-(Cyclopropanecarboxamido)-4-((3-ethyl-5-methoxyimidazo[1,5-a]pyridin-6-yl)amino)-N-(methyl-d₃)nicotinamide (227)

A mixture of CD₃NH₂·HCl (13 mg, 0.18 mmol), 227g (48 mg, 0.121 mmol), DIPEA (47 mg, 0.364 mmol) and HATU (69 mg, 0.182 mmol) in DMF (2 mL) was stirred at 20° C. for 12 h. A yellow solution was formed. The reaction mixture was filtered and purified by Prep-HPLC (Method E) to give 227 (15 mg, 30% yield) as a white solid. LCMS (Method 4) $t_R$=1.79 min, m/z (M+H)⁺=412.2. ¹H NMR (400 MHz, DMSO-d₆) δ 10.69 (s, 1H), 10.04 (s, 1H), 8.58 (s, 1H), 8.50 (s, 1H), 7.48 (s, 1H), 7.30-7.26 (m, 2H), 6.59 (d, J=9.6 Hz, 1H), 3.87 (s, 3H), 3.14 (q, J=7.6 Hz, 2H), 1.96-1.89 (m, 1H), 1.05 (t, J=7.6 Hz, 3H), 0.75-0.68 (m, 4H).

Example 228

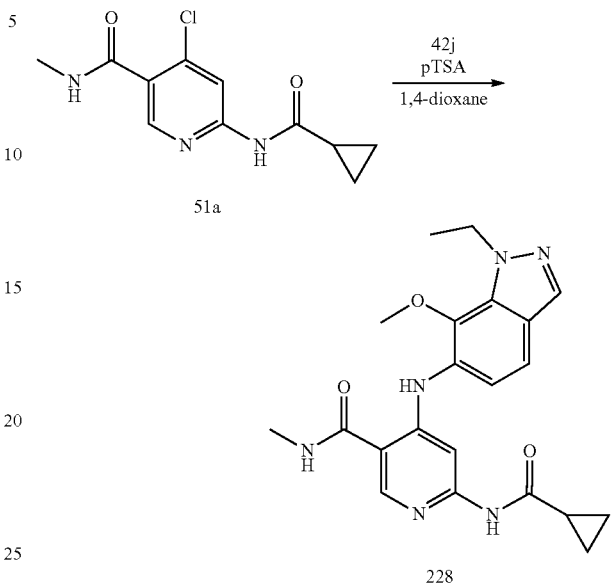

Step 1. 6-(Cyclopropanecarboxamido)-4-((1-ethyl-7-methoxy-1H-indazol-6-yl)amino)-N-methylnicotinamide (228)

To a solution of 51a (100 mg, 0.39 mmol), pTSA (67.9 mg, 0.39 mmol) in dioxane (7 mL) was added 42j (75 mg, 0.39 mmol) at r.t. The mixture was stirred at 100° C. for 16 h. The resulting solution was added H₂O (30 mL) and extracted by EA (30 mL*2). The combined organic layer was washed with brine (20 mL), dried over Na₂SO₄ and filtered. The filtrate was concentrated in vacuo. The residue was purified by Prep-HPLC (Method E) to afford 228 (26 mg, 16% yield) as a white solid. LC-MS (Method 4) $t_R$=1.99 min, m/z (M+H)⁺=409.3. ¹H NMR (400 MHz, DMSO-d₆) δ 10.72 (s, 1H), 10.54 (s, 1H), 8.66-8.60 (m, 1H), 8.52 (s, 1H), 8.04 (s, 1H), 7.83 (s, 1H), 7.51 (d, J=8.4 Hz, 1H), 7.10 (d, J=8.8 Hz, 1H), 4.55 (q, J=7.2 Hz, 2H), 3.79 (s, 3H), 2.80 (d, J=4.4 Hz, 3H), 2.00-1.89 (m, 1H), 1.40 (t, J=7.2 Hz, 3H), 0.78-0.66 (m, 4H).

Example 229

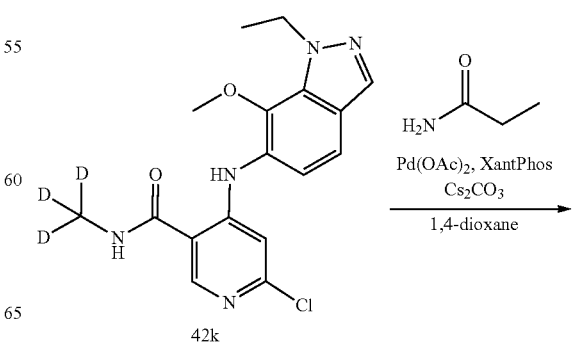

-continued

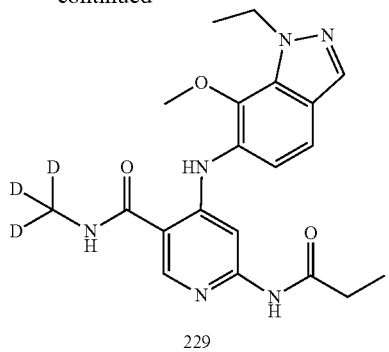

229

Step 1. 4-((1-Ethyl-7-methoxy-lii-indazol-6-yl)amino)-N-(methyl-d₃)-6-propionamidonicotinamide (229)

To a solution of 42k (19 mg, 0.05 mmol) and propionamide (8 mg, 0.11 mmol) in 1,4-dioxane (1 mL) was added Pd(OAc) 2 (1.3 mg, 0.006 mmol), XantPhos (3.5 mg, 0.006 mmol) and Cs₂CO₃ (33 mg, 0.10 mmol). The resulting mixture was stirred under nitrogen atmosphere at 100° C. for 8 h. After cooling to r.t., the reaction mixture was filtered. The filtrate was concentrated under reduced pressure. The residue was purified by Prep-HPLC (Method E) to afford compound 229 (6.2 mg, 29% yield) as a light-yellow solid. LC-MS (Method 4) $t_R$=1.94 min, m/z (M+H)⁺=400.3. ¹H NMR (400 MHz, CDCl₃) δ 10.24 (s, 1H), 8.24 (s, 1H), 7.96 (s, 1H), 7.91 (s, 1H), 7.84 (s, 1H), 7.47 (d, J=8.8 Hz, 1H), 7.17 (d, J=8.8 Hz, 1H), 6.18 (s, 1H), 4.62 (q, J. 7.2 Hz, 2H), 3.87 (s, 3H), 2.36 (q, J=7.6 Hz, 2H), 1.49 (t, J=7.2 Hz, 3H), 1.16 (t, J=7.6 Hz, 3H).

Example 230

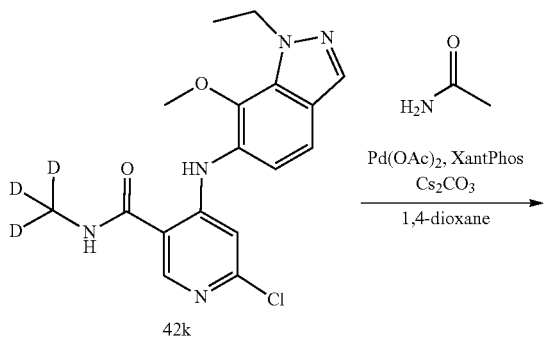

230

Step 1. 6-Acetamido-4-((1-ethyl-7-methoxy-1H-indazol-6-yl)amino)-N-(methyl-d₃)nicotinamide (230)

To a solution of 42k (29 mg, 0.08 mmol) and acetamide (15 mg, 0.25 mmol) in 1,4-dioxane (1 mL) was added Pd(OAc) 2 (1.8 mg, 0.008 mmol), XantPhos (4.7 mg, 0.008 mmol) and Cs₂CO₃ (52 mg, 0.16 mmol). The resulting mixture was stirred under nitrogen atmosphere at 100° C. for 8 h. After cooling to r.t., the reaction mixture was filtered. The filtrate was concentrated under reduced pressure. The residue was purified by Prep-HPLC (Method E) to afford compound 230 (11.7 mg, 38% yield) as a white solid. LC-MS (Method 4) $t_R$=1.75 min, m/z (M+H)⁺=386.3. ¹H NMR (400 MHz, CDCl₃) δ 10.28 (s, 1H), 8.26 (s, 1H), 7.96 (s, 1H), 7.94 (s, 1H), 7.91 (s, 1H), 7.46 (d, J=8.4 Hz, 1H), 7.16 (d, J=8.4 Hz, 1H), 6.23 (s, 1H), 4.62 (q, J=7.2 Hz, 2H), 3.88 (s, 3H), 2.12 (s, 3H), 1.49 (t, J=7.2 Hz, 3H).

Example 231

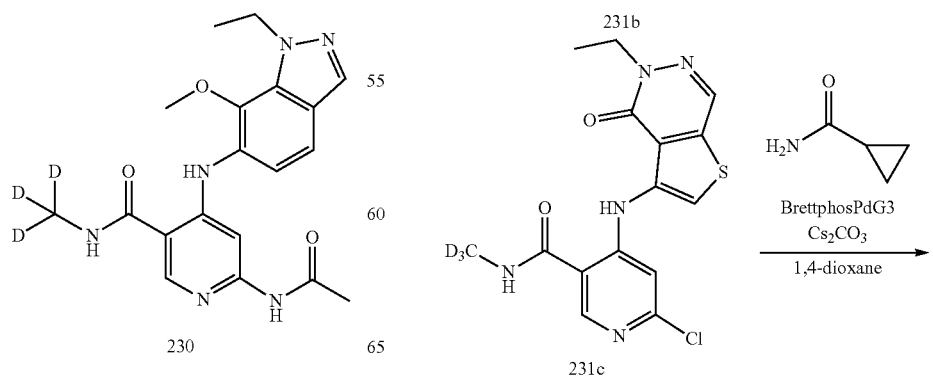

(s, 1H), 8.37 (s, 1H), 7.52 (s, 1H), 4.17 (q, J=7.2 Hz, 2H), 2.03-2.00 (m, 1H), 1.29 (t, J=7.2 Hz, 3H), 0.83-0.80 (m, 4H).

Example 232

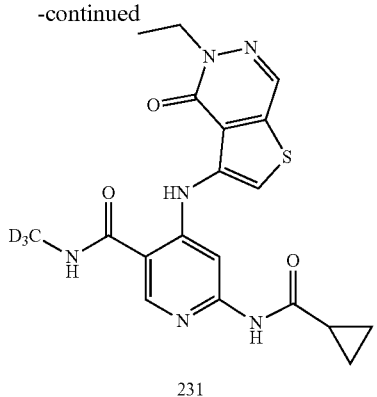

Step 1. 3-((Diphenylmethylene)amino)-5-ethylthieno[2,3-d]pyridazin-4-(5H)-one (231a)

A mixture of 178b (2 g, 7.72 mmol), diphenylmethanimine (2.24 g, 12.35 mmol), Pd₂(dba)₃ (707 mg, 0.77 mmol), XantPhos (446 mg, 0.77 mmol) and Cs₂CO₃ (4.01 g, 12.35 mmol) in 1,4-dioxane (15 mL) was stirred at 80° C. for 6 h under N₂ atmosphere. The reaction mixture was cooled and concentrated. The residue was purified by Prep-HPLC (Method A) to afford 231a (1.6 g, 58% yield) as a yellow solid. ¹H NMR (400 MHz, DMSO-d₆) δ 8.39 (s, 1H), 7.82-7.80 (m, 1H), 7.69-7.67 (m, 2H), 7.55-7.46 (m, 3H), 7.28-7.26 (m, 2H), 7.15-7.13 (m, 2H), 7.00 (s, 1H), 4.06 (q, J=7.2 Hz, 2H), 1.20 (t, J=7.6 Hz, 3H).

Step 2. 3-Amino-5-ethylthieno[2,3-d]pyridazin-4-(5H)-one hydrochloride (231b)

A mixture of 231a (1.6 g, 4.45 mmol) in HCl/EtOAc (16 mL, 2 M) was stirred for 2 h at r.t. The formed solid was filtered and the filter cake was dried to afford 231b (800 mg, 77% yield) as a yellow solid. LC-MS (Method 3) t$_R$=1.20 min, m/z (M+H)⁺=196.1.

Step 3. 6-Chloro-4-((5-ethyl-4-oxo-4,5-dihydrothieno[2,3-d]pyridazin-3-yl)amino)-N-(methyl-d₃)nicotinamide (231c)

To a mixture of 231b (600 mg, 2.59 mmol), 42b (592 mg, 2.85 mmol) in EtOH (40 mL) was added conc. HCl (0.022 mL, 0.26 mmol). The reaction mixture was stirred at 90° C. for 16 h. After cooling to r.t., the formed solid was filtered and the filter cake was dried to afford 231c (500 mg, 53% yield) as a yellow solid. LC-MS (Method 3) t$_R$=1.46 min, m/z (M+H)⁺=367.1.

Step 4. 6-(Cyclopropanecarboxamido)-4-((5-ethyl-4-oxo-4,5-dihydrothieno[2,3-d]pyridazin-3-yl)amino)-N-(methyl-d₃)nicotinamide (231)

A mixture of 231c (280 mg, 0.76 mmol), cyclopropanecarboxamide (324 mg, 3.82 mmol), BrettPhos Pd G3 (276 mg, 0.31 mmol) and Cs₂CO₃ (496 mg, 1.53 mmol) in 1,4-dioxane (5 mL) was stirred at 80° C. for 16 h. The reaction mixture was concentrated. The residue was purified by Prep-HPLC (Method A) to afford 231 (148 mg, 47% yield) as an off-white solid. LC-MS (Method 1) t$_R$=3.92 min, m/z (M+H)⁺=416.0. ¹H NMR (400 MHz, DMSO-d₆) δ 11.43 (s, 1H), 10.87 (s, 1H), 8.58 (s, 1H), 8.51 (s, 1H), 8.48

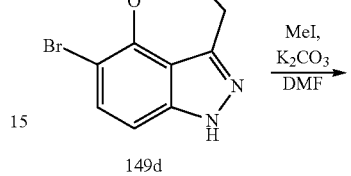

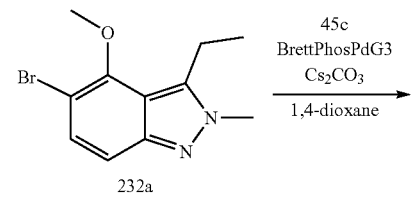

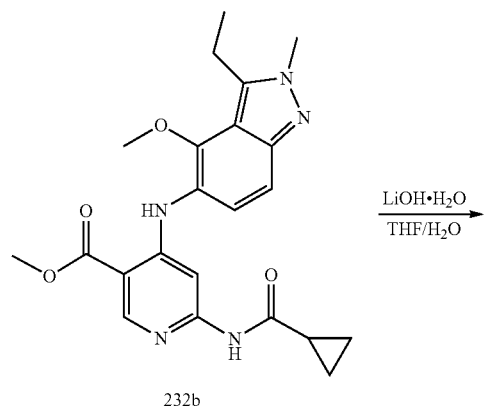

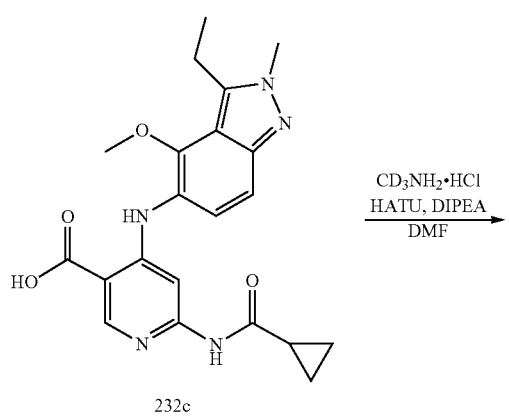

Step 4. 6-(Cyclopropanecarboxamido)-4-((3-ethyl-4-methoxy-2-methyl-2H-indazol-5-yl)amino)-N-(methyl-d₃)nicotinamide (232)

To a solution of 232c (5 mg, 0.012 mmol) and HATU (5 mg, 0.013 mmol) in DMF (1 mL) was added DIPEA (6.6 mg, 0.05 mmol). After stirred at r.t. for 10 min, methyl-d₃-amine hydrochloride (2 mg, 0.028 mmol) was added and the final mixture was stirred at r.t. for 1 h. Then the mixture was filtered and the filtrate was purified by Prep-HPLC (Method E) to afford 232 (1.6 mg, 31% yield) as a white solid. LC-MS (Method 4) $t_R$=2.71 min, m/z (M+H)⁺=426.3. ¹H NMR (400 MHz, CDCl₃) δ 9.87 (s, 1H), 8.19 (s, 1H), 8.05 (s, 1H), 7.61 (s, 1H), 7.36 (d, J=9.0 Hz, 1H), 7.12 (d, J=9.0 Hz, 1H), 6.11 (s, 1H), 4.07 (s, 3H), 3.84 (s, 3H), 3.12 (q, J=7.6 Hz, 2H), 1.48-1.41 (m, 1H), 1.29 (t, J=7.6 Hz, 3H), 1.01-0.95 (m, 2H), 0.82-0.76 (m, 2H).

Example 233

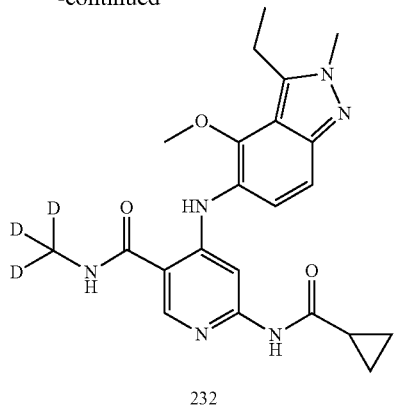

232

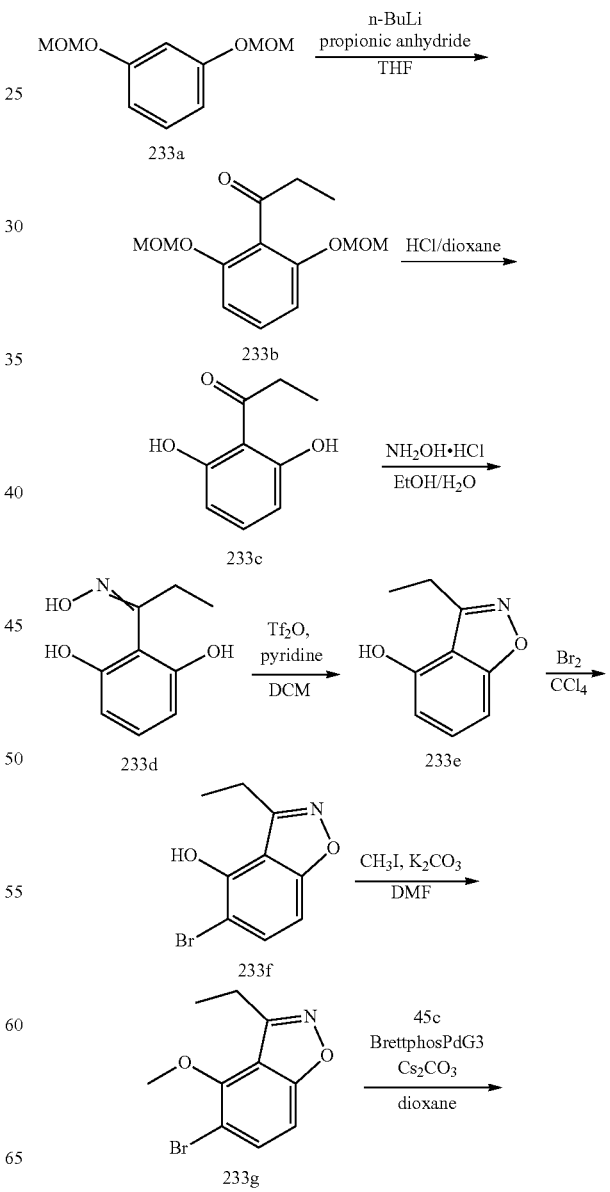

Step 1. 5-Bromo-3-ethyl-4-methoxy-2-methyl-2H-indazole (232a)

To a stirred mixture of 149d (215 mg, 0.84 mmol) and K₂CO₃ (242 mg, 1.75 mmol) in DMF (6 mL) was added CH₃I (135.6 mg, 0.95 mmol). After stirred at 70° C. for 2 h, the mixture was quenched with water, extracted with EA (12 mL*3). The combined organic layer was dried over anhydrous Na₂SO₄ and concentrated. The residue was purified by flash chromatography on silica gel (PE/EA=7/1) to give 232a (46 mg, 20% yield) as a yellow oil. LC-MS (Method 4) $t_R$=4.48 min, m/z (M+H)⁺=269.1.

Step 2. Methyl 6-(cyclopropanecarboxamido)-4-((3-ethyl-4-methoxy-2-methyl-2H-indazol-5-yl)amino)nicotinate (232b)

To a solution of 232a (46 mg, 0.17 mmol) and 45c (40 mg, 0.12 mmol) in anhydrous 1,4-dioxane (3.5 mL) was added BrettPhos Pd G3 (13 mg, 0.014 mmol) and Cs₂CO₃ (150 mg, 0.46 mmol). The resulting mixture was refluxed at 100° C. under nitrogen atmosphere for 16 h. Then the mixture was allowed to cooled down to r.t. The solvent was removed, and the residue was purified by flash chromatography on silica gel (DCM/MeOH=15/1) to provide a crude, which was further purified by Prep-HPLC (Method E) to afford compound 232b (8.6 mg, 12.0% yield) as a white solid. LC-MS (Method 4) $t_R$=3.21 min, m/z (M+H)⁺=424.3. ¹H-NMR (400 MHz, CDCl₃) δ 9.60 (s, 1H), 8.71 (s, 1H), 8.27 (s, 1H), 7.60 (s, 1H), 7.37 (d, J=9.0 Hz, 1H), 7.11 (d, J=9.0 Hz, 1H), 4.07 (s, 3H), 3.92 (s, 3H), 3.82 (s, 3H), 3.13 (q, J=7.6 Hz, 2H), 1.48-1.43 (m, 1H), 1.30 (t, J=7.6 Hz, 3H), 1.02-0.95 (m, 2H), 0.84-0.78 (m, 2H).

Step 3. 6-(Cyclopropanecarboxamido)-4-((3-ethyl-4-methoxy-2-methyl-2H-indazol-5-yl)amino)nicotinic acid (232c)

To a solution of 232b (7 mg, 0.016 mmol) in THF (0.4 mL) and H₂O (0.1 mL) was added LiOH·H₂O (14 mg, 0.036 mmol), and the mixture was stirred at 65° C. for 16 h. The reaction mixture was cooled down to r.t. and adjusted to pH=5 with 2 N HCl aqueous solution. The acidified solution was extracted with DCM/MeOH=6/1 (3 mL*7) and the combined organic layer was dried over anhydrous Na₂SO₄. Then it was concentrated to afford the crude compound 232c (5 mg, 76% yield) as a light yellow solid. LC-MS (Method 4) $t_R$=2.64 min, m/z (M+H)⁺=410.3.

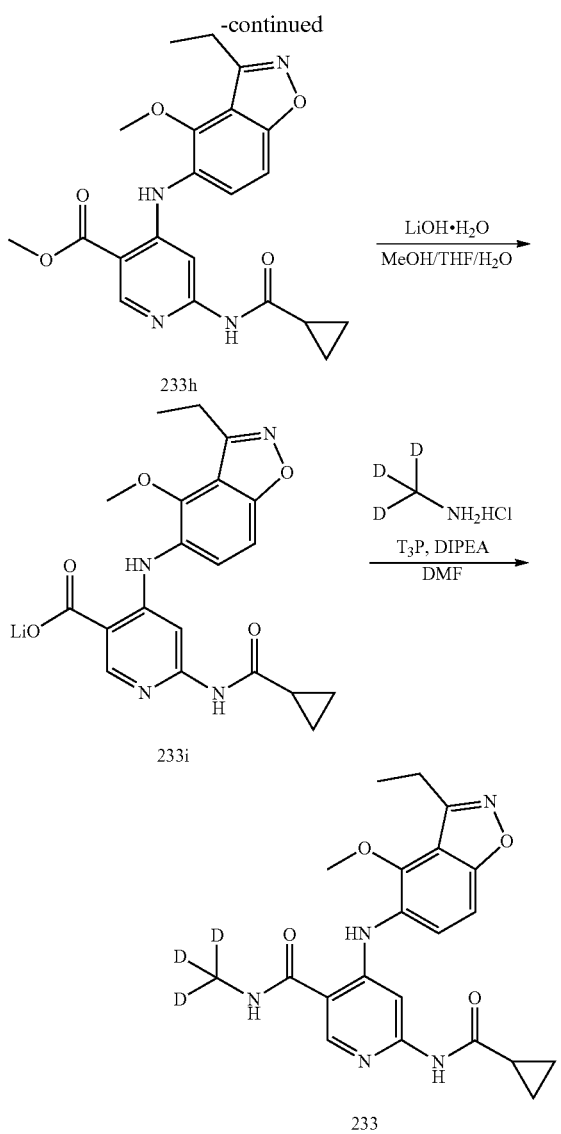

reaction mixture was stirred at 60° C. for 3 h. The reaction mixture was concentrated to give 233c (1.8 g, 92% yield) as a yellow oil. LC-MS (Method 4) $t_R$=1.57 min, m/z (M+H)$^+$=167.1.

Step 3. 1-(2,6-Dihydroxyphenyl)propan-1-one oxime (233d)

To a solution of 233c (1.4 g, 8.42 mmol) in EtOH (14 mL) and H$_2$O (6 mL) was added NH$_2$OH·HCl (705 mg, 10.22 mmol), CH$_3$COONa (528 mg, 6.44 mmol) at 25° C. The reaction mixture was stirred at 100° C. for 12 h under N$_2$ atmosphere, H$_2$O (10 mL) was added to the reaction mixture, and the mixture was diluted with EtOAc (50 mL), washed with brine (10 mL*3). The separated organic layer was concentrated and purified by flash chromatography on silica gel (PE/EtOAc=10/1 to 1/5) to give 233d (1.1 g, 72% yield) as a yellow solid. LC-MS (Method 4) $t_R$=1.62 min, m/z (M+H)$^+$=182.1.

Step 4. 3-Ethylbenzo[d]isoxazol-4-ol (233e)

To a solution of 233d (790 mg, 4.36 mmol) in DCM (8 mL) was added Tf$_2$O (1.23 g, 4.36 mmol) and pyridine (517 mg, 6.54 mmol) at 25° C. The reaction mixture was stirred at 25° C. for 3 h. The reaction mixture was concentrated and purified by flash chromatography on silica gel (PE/EtOAc=10/1 to 1/6) to give 233e (230 mg, 32% yield) as a yellow solid. LC-MS (Method 4) $t_R$=2.47 min, m/z (M+H)$^+$=164.1.

Step 5. 5-Bromo-3-ethylbenzo[d]isoxazol-4-ol (233f)

To a solution of 233e (210 mg, 1.29 mmol) in CCl$_4$ (5 mL) was added Br$_2$ (102.8 mg, 0.64 mmol) at −30° C. The reaction mixture was stirred at −30° C. for 1 h. The reaction mixture was concentrated and purified by flash chromatography on silica gel (PE/EtOAc=10/1 to 1/5) to give 233f (105 mg, 34% yield) as a yellow solid. LC-MS (Method 4) $t_R$=2.64 min, m/z (M+H)$^+$=242.0.

Step 6. 5-Bromo-3-ethyl-4-methoxybenzo[d]isoxazole (233g)

To a solution of 233f (95 mg, 0.39 mmol) in DMF (0.5 mL) was added CH$_3$I (277 mg, 1.96 mmol) and K$_2$CO$_3$ (108 mg, 0.78 mmol) at 25° C. The reaction mixture was stirred at 25° C. for 5 h. The reaction was concentrated and purified by flash chromatography on silica gel (PE/EtOAc=10/1 to 1/5) to give 233g (45 mg, 45% yield) as a yellow solid. LC-MS (Method 4) $t_R$=3.37 min, m/z (M+H)$^+$=256.0.

Step 7. Methyl 6-(cyclopropanecarboxamido)-4-((3-ethyl-4-methoxybenzo[d]isoxazol-5-yl)amino)nicotinate (233h)

To a solution of 45c (56 mg, 0.16 mmol) in dioxane (2 mL) was added 233g (40 mg, 0.16 mmol), BrettPhos Pd G3 (45 mg, 0.05 mmol), Cs$_2$CO$_3$ (104 mg, 0.32 mmol) at 25° C., the reaction mixture was stirred at 90° C. for 24 h under N$_2$ atmosphere. The mixture was diluted with H$_2$O (10 mL), extracted with EA (20 mL*3), washed with brine (10 mL), dried over Na$_2$SO$_4$, concentrated and purified by flash chromatography (DCM/MeOH=100/1 to 10/1) to give 233h Step 1. 1-(2,6-Bis(methoxymethoxy)phenyl)propan-1-one (233b)

To a solution of 233a (5 g, 25.23 mmol) in THF (50 mL) was added n-BuLi (12 mL, 30 mmol, 2.5 M) at 0° C. The reaction mixture was stirred at 0° C. for 1 h under N$_2$ atmosphere, then propionic anhydride (13.27 g, 102 mmol) was added to the reaction mixture at −78° C., the reaction mixture was stirred at −78° C. for 1 h. After quenching with water, the mixture was extracted with ethyl acetate. The collected organic layer was dried over sodium sulphate, filtered and evaporated. The crude product was purified by flash chromatography on silica gel (PE/EtOAc=10/1 to 1/3) to afford 233b (3 g, 47% yield) as a yellow oil. LC-MS (Method 4) $t_R$=3.46 min, m/z (M+H)$^+$=255.2.

Step 2. 1-(2,6-Dihydroxyphenyl)propan-1-one (233c)

To a solution of 233b (3 g, 11.80 mmol) in MeOH (20 mL) was added HCl (10 mL, 3 M in H$_2$O) at 25° C., the (50 mg, 39% yield) as a yellow solid. LC-MS (Method 4) $t_R$=2.65 min, m/z (M+H)$^+$=411.2.

Step 8. Lithium 6-(cyclopropanecarboxamido)-4-((3-ethyl-4-methoxybenzo[d]isoxazol-5-yl)amino)nicotinate (233i)

To a solution of 233h (45 mg, 0.054 mmol) in H$_2$O (0.5 mL), THF (0.5 mL), MeOH (0.5 mL) was added LiOH·H$_2$O (7 mg, 0.164 mmol) at 25° C. The reaction mixture was stirred at 25° C. for 5 h. The reaction mixture was concentrated to give 233i (60 mg, yield given) as a yellow solid. The crude product was used in next step directly without further purification. LC-MS (Method 4) $t_R$=1.85 min, m/z (M+H)$^+$=397.2.

Step 9. 6-(Cyclopropanecarboxamido)-4-((3-ethyl-4-methoxybenzo[d]isoxazol-5-yl)amino)-N-(methyl-d$_3$)nicotinamide (233)

To a solution of 233i (60 mg, 0.14 mmol) and methan-d$_3$-amine hydrochloride (11 mg, 0.162 mmol) in DMF (1 mL) was added T$_3$P (89 mg, 0.14 mmol, 50% wt in EtOA) and DIPEA (91 mg, 0.70 mmol) at 25° C. The reaction mixture was stirred at 25° C. for 5 h. The mixture was diluted with H$_2$O (5 mL), extracted with EA (10 mL*3), washed with brine (10 mL), dried over Na$_2$SO$_4$, concentrated and purified by flash chromatography (DCM/MeOH=100/1 to 10/1) to get the compound 233 (5.9 mg, 16% yield) as an off-white solid. LC-MS (Method 4) $t_R$=2.16 min, m/z (M+H)$^+$=413.3. $^1$H NMR (400 MHz, CDCl$_3$) δ 9.97 (s, 1H), 8.54 (s, 1H), 8.18 (s, 1H), 7.69 (s, 1H), 7.27 (d, J=8.4 Hz, 1H), 7.10 (d, J=8.4 Hz, 1H), 6.22 (s, 1H), 4.32 (s, 3H), 2.90 (q, J=7.6 Hz, 2H), 1.51-1.42 (m, 1H), 1.41 (t, J=7.6 Hz, 3H), 1.06-0.95 (m, 2H), 0.85-0.79 (m, 2H).

Example 234

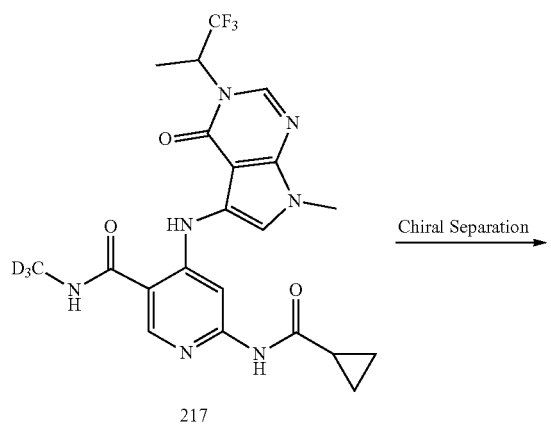

217

Chiral Separation →

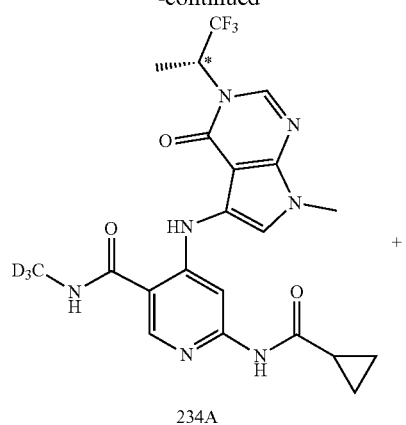

234A

+

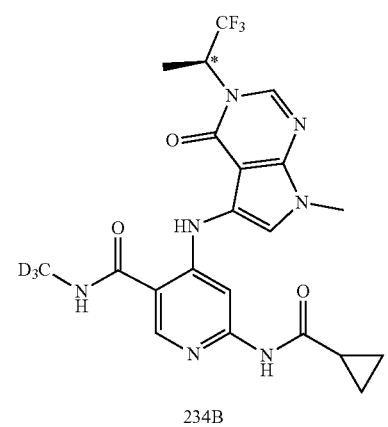

234B

Step 1. (R*)-6-(cyclopropanecarboxamido)-N-(methyl-d$_3$)-4-((7-methyl-4-oxo-3-(1,1,1-trifluoropropan-2-yl)-4,7-dihydro-3H-pyrrolo[2,3-d]pyrimidin-5-yl)amino)nicotinamide (234A) and (S*)-6-(cyclopropanecarboxamido)-N-(methyl-d$_3$)-4-((7-methyl-4-oxo-3-(1,1,1-trifluoropropan-2-yl)-4,7-dihydro-3H-pyrrolo[2,3-d]pyrimidin-5-yl)amino)nicotinamide (234B)

Compound 217 (250 mg, 0.52 mmol) was separated by Prep-Chiral HPLC to obtain compound 234A (66.6 mg, 26% yield) as a yellow solid and 234B (57.3 mg, 23% yield) as a white solid.

217A: LC-MS (Method 2) $t_R$=2.78 min, m/z (M+H)$^+$=481.0. $^1$H NMR (400 MHz, DMSO-d$_6$) δ 10.81 (s, 1H), 10.73 (s, 1H), 8.48 (s, 1H), 8.45 (s, 1H), 8.35 (s, 1H), 7.93 (s, 1H), 7.10 (s, 1H), 5.83-5.73 (m, 1H), 3.72 (s, 3H), 2.01-1.99 (m, 1H), 1.69 (d, J=7.2 Hz, 3H), 0.81-0.78 (m, 4H).

217B: LC-MS (Method 2) $t_R$=2.77 min, m/z (M+H)$^+$=481.1. $^1$H NMR (400 MHz, DMSO-d$_6$) δ 10.82 (s, 1H), 10.74 (s, 1H), 8.48 (s, 1H), 8.46 (s, 1H), 8.35 (s, 1H), 7.93 (s, 1H), 7.10 (s, 1H), 5.82-5.75 (m, 1H), 3.72 (s, 3H), 2.03-1.97 (m, 1H), 1.69 (d, J=7.2 Hz, 3H), 0.81-0.78 (m, 4H).

Example 235

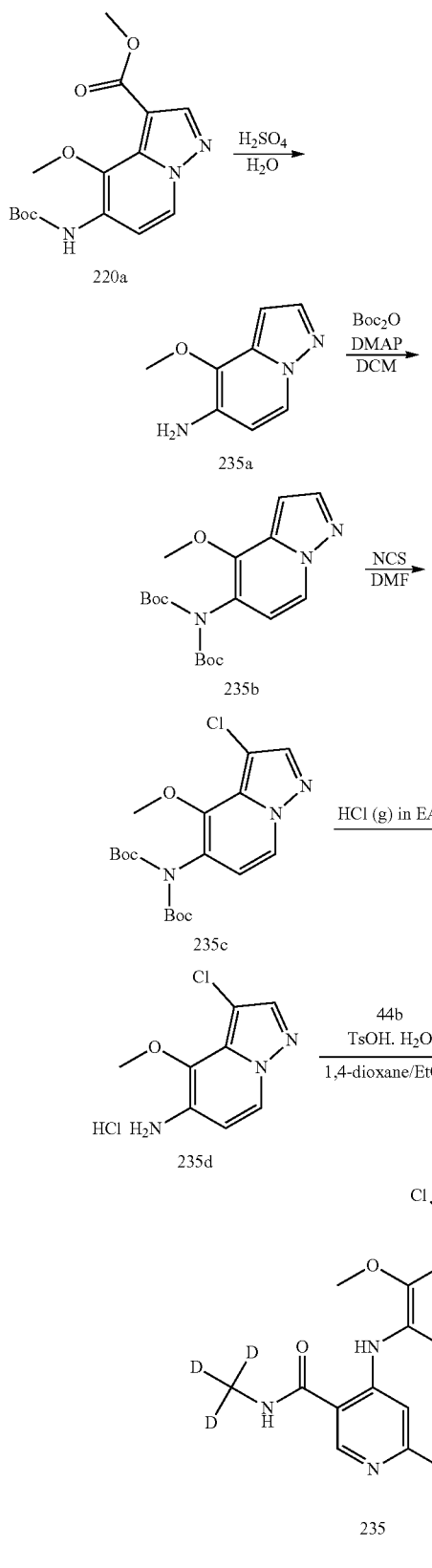

Step 1. 4-Methoxypyrazolo[1,5-a]pyridin-5-amine (235a)

A mixture of 220a (350 mg, 1.09 mmol) in conc. $H_2SO_4$/$H_2O$ (3 mL, v/v=1/1) was stirred at 60° C. for 2 h. After cooling to r.t., the mixture was basified with 10% NaOH to pH=9 and extracted with EtOAc (10 mL*3). The organic layer was dried over $Na_2SO_4$, filtered and concentrated to afford 235a (152 mg, 86% yield) as a black solid. LC-MS (Method 3) $t_R$=0.79 min, m/z (M+H)$^+$=164.0.

Step 2. Tert-butyl (tert-butoxycarbonyl)(4-methoxypyrazolo[1,5-a]pyridin-5-yl)carbamate (235b)

A mixture of 235a (177 mg, 1.08 mmol), $Boc_2O$ (474 mg, 2.17 mmol), DMAP (27 mg, 0.22 mmol) in DCM (1 mL) was stirred at 25° C. for 2 h. The mixture was concentrated and the residue was purified by flash chromatography on silica gel (PE/EtOAc=10/1) to afford 235b (86 mg, 22% yield) as a brown solid. LC-MS (Method 3) $t_R$=1.39 min, m/z (M+H)$^+$=364.3.

Step 3. Tert-butyl (tert-butoxycarbonyl)(3-chloro-4-methoxypyrazolo[1,5-a]pyridin-5-yl)carbamate (235c)

A mixture of 235b (80 mg, 0.22 mmol) and NCS (44 mg, 0.33 mmol) in DMF (0.4 mL) was stirred at 25° C. for 2 h. The mixture was diluted with water (5 mL) and extracted with EtOAc (10 mL*3). The combined organic layer was dried over $Na_2SO_4$ and filtered. The filtrate was concentrated to afford 235c (87 mg, 99% yield) as a red solid. LC-MS (Method 3) $t_R$=1.54 min, m/z (M+H)$^+$=398.2.

Step 4. 3-Chloro-4-methoxypyrazolo[1,5-a]pyridin-5-amine hydrochloride (235d)

A mixture of 235c (80 mg, 0.20 mmol) in HCl in EtOAc (0.5 mL, 2 M) was stirred at 25° C. for 2 h. The mixture was concentrated under reduced pressure and the residue was purified by Prep-HPLC (Method C) to afford 235d (30 mg, 64% yield) as a red solid. LC-MS (Method 3) $t_R$=0.99 min, m/z (M+H)$^+$=198.2.

Step 5. 4-((3-Chloro-4-methoxypyrazolo[1,5-a]pyridin-5-yl)amino)-6-(cyclopropanecarboxamido)-N-(methyl-d$_3$)nicotinamide (235)

A mixture of 44b (39 mg, 0.15 mmol), 235d (30 mg, 0.13 mmol) and TsOH·$H_2O$ (5 mg, 0.02 mmol) in 1,4-dioxane and EtOH (1 mL, v/v=1/1) was stirred at stirred at 100° C. for 16 h. The mixture was concentrated and the residue was purified by Prep-HPLC (Method A) to afford 235 (7 mg, 13% yield) as a white solid. LC-MS (Method 1) $t_R$=3.01 min, m/z (M+H)$^+$=418.1. $^1$H NMR (400 MHz, DMSO-d$_6$) δ 10.82 (s, 1H), 10.72 (s, 1H), 8.65 (s, 1H), 8.55-8.53 (m, 2H), 8.08 (s, 1H), 7.90 (s, 1H), 7.02 (d, J=7.2 Hz, 1H), 3.83 (s, 3H), 2.01-1.94 (m, 1H), 0.79-0.77 (m, 4H).

Example 236

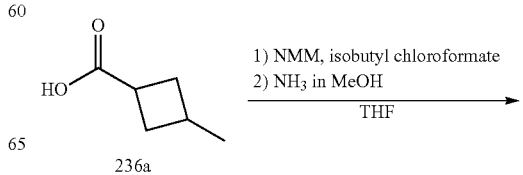

651

-continued

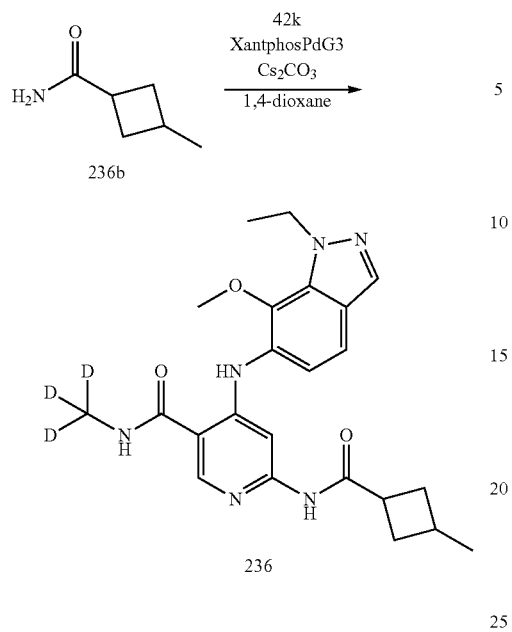

Step 1. 3-Methylcyclobutane-1-carboxamide (236b)

To a solution of 236a (1 g, 8.76 mmol) in THF (15 mL) was added 4-methylmorpholine (1.06 g, 10.51 mmol, 1.16 mL) at 0° C. under $N_2$ protection. Isobutyl chloroformate (1.29 g, 10.51 mmol) was added dropwise. The reaction was stirred for 30 min and ammonia (7 M, 12.52 mL) in $CH_3OH$ was added. Then the resulting mixture was stirred at 0° C. to r.t. overnight. The reaction mixture was diluted with HCl (1 M) and extracted with EA (20 mL*3). The organic layer was separated and dried over $MgSO_4$, filtered and concentrated. The residue was recrystallized from PE/EA to afford 236b (650 mg, 65% yield) as a white solid. $^1$H NMR (400 MHz, DMSO-$d_6$) δ 7.09 (s, 1H), 6.64 (s, 1H), 2.75-2.73 (m, 1H), 2.26-2.15 (m, 1H), 2.19-2.05 (m, 2H), 1.69-1.59 (m, 2H), 0.97 (d, J=6.4 Hz, 3H).

Step 2. 4-((1-Ethyl-7-methoxy-1H-indazol-6-yl)amino)-N-(methyl-$d_3$)-6-(3-methylcyclobutane-1-carboxamido)nicotinamide (236)

To a solution of 42k (100 mg, 0.28 mmol), $Cs_2CO_3$ (179.6 mg, 0.55 mmol), XantPhosPdG3 (26.1 mg, 0.028 mmol) in dioxane (12 mL) was added 236b (31.2 mg, 0.28 mmol) at r.t. The mixture was stirred at 100° C. for 16 h under nitrogen protection. The resulting solution was added into $H_2O$ (30 mL) and extracted with EA (30 mL). The combined organic layer was washed by brine (20 mL), dried over $Na_2SO_4$ and filtered. The filtrate was concentrated in vacuo. The residue was purified by Prep-HPLC (Method E) to afford 236 (25 mg, 20% yield) as a white solid. LC-MS (Method 4) $t_R$=2.32 min, m/z (M+H)$^+$=440.4. $^1$H NMR (400 MHz, DMSO-$d_6$) δ 10.58-10.54 (m, 1H), 10.26-10.18 (m, 1H), 8.60 (s, 1H), 8.50 (s, 1H), 8.07-8.05 (m, 1H), 7.90-7.86 (m, 1H), 7.55 (d, J=8.4 Hz, 1H), 7.14-7.12 (m, 1H), 4.56 (q, J=7.2 Hz, 2H), 3.77-3.75 (m, 3H), 3.10-3.08 (m, 1H), 2.31-2.06 (m, 3H), 1.72-1.61 (m, 2H), 1.41 (t, J=7.2 Hz, 3H), 1.07-1.05 (m, 1H), 0.97-0.95 (m, 2H).

652

Example 237

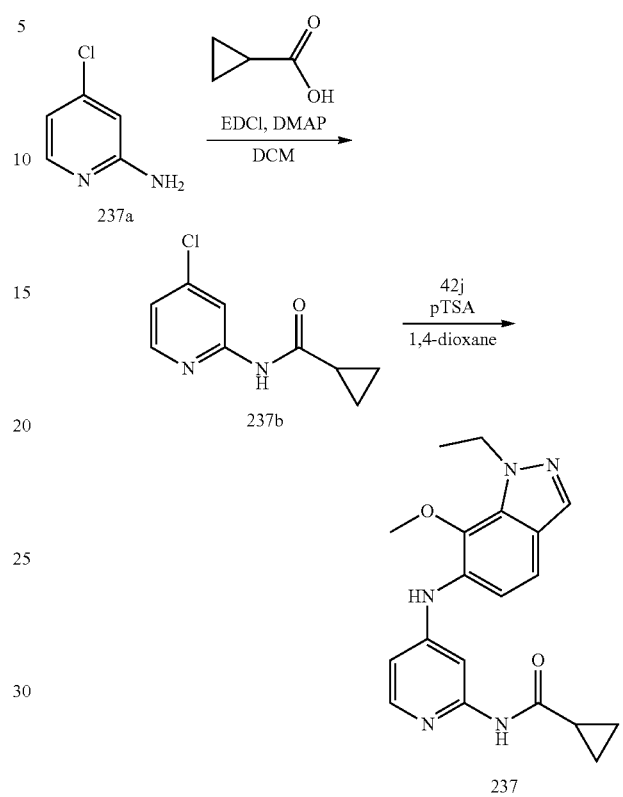

Step 1. N-(4-chloropyridin-2-yl)cyclopropanecarboxamide (237b)

To a solution of 237a (300 mg, 2.33 mmol) in 12 mL DCM was added DMAP (427.6 mg, 3.50 mmol). Cyclopropanecarboxylic acid (200.9 mg, 2.33 mmol) and EDCI (671 mg, 3.50 mmol) was added after a while. After stirring at room temperature for 12 h, the resulting solution was added into $H_2O$ (40 mL) and extracted by EA (40 mL). The organic layer was washed by brine (20 mL), dried over $Na_2SO_4$ and filtered. The filtrate was concentrated in vacuo. The residue was purified by flash chromatography on silica gel (PE/EA=10/1 to 1/1) to afford 237b (330 mg, 72% yield) as a white solid. LC-MS (Method 4) $t_R$=2.26 min, m/z (M+H)$^+$=197.1.

Step 2. N-(4-((1-ethyl-7-methoxy-1H-indazol-6-yl)amino)pyridin-2-yl)cyclopropanecarboxamide (237)

Compound 237 (10.5 mg, 6% yield), an off-white solid, was synthesized by utilizing a similar preparative procedure of Step 1 in Example 228 with 237b (100 mg, 0.51 mmol) and 42j (126.4 mg, 0.66 mmol) as starting materials. LC-MS (Method 4) $t_R$=1.80 min, m/z (M+H)$^+$=352.3. $^1$H NMR (400 MHz, DMSO-$d_6$) δ 10.46 (s, 1H), 8.61 (s, 1H), 8.01 (s, 1H), 7.89 (d, J=5.8 Hz, 1H), 7.60 (s, 1H), 7.45 (d, J=8.4 Hz, 1H), 6.98 (d, J=8.4 Hz, 1H), 6.47 (dd, J=5.8, 2.2 Hz, 1H), 4.55 (q, J=7.2 Hz, 2H), 3.73 (s, 3H), 1.97-1.91 (m, 1H), 1.39 (t, J=7.2 Hz, 3H), 0.76-0.70 (m, 4H).

Example 238

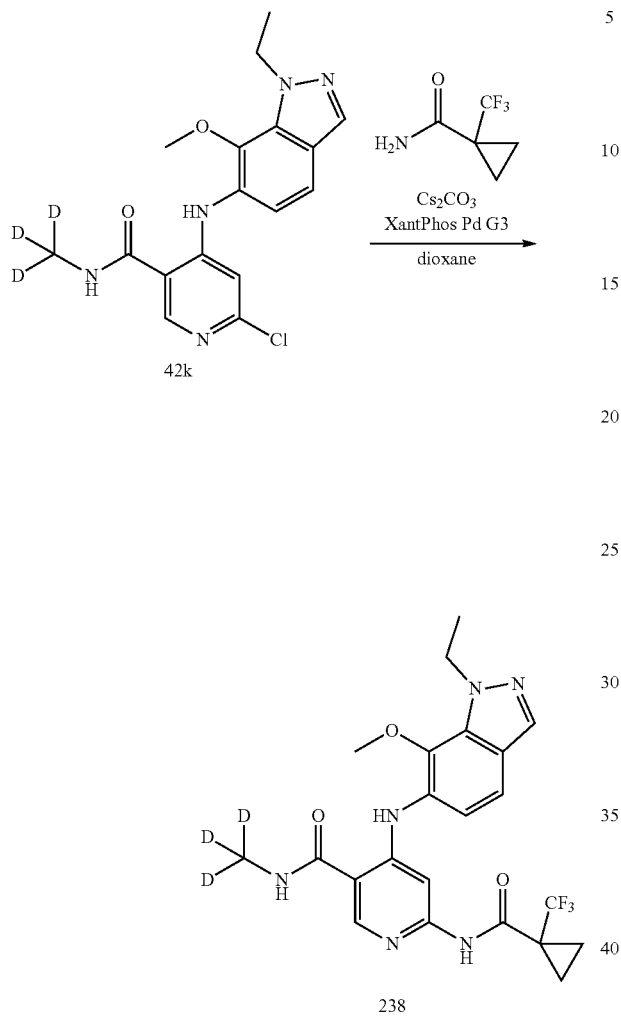

Step 1. 4-((1-Ethyl-7-methoxy-1H-indazol-6-yl)amino)-N-(methyl-d₃)-6-(1-(trifluoromethyl)cyclopropane-1-carboxamido)nicotinamide (238)

To a solution of 1-(trifluoromethyl)cyclopropane-1-carboxamide (38 mg, 0.25 mmol) and 42k (30 mg, 0.083 mmol) in dioxane (1 mL) was added Xantphos Pd G3 (7.6 mg, 0.008 mmol) and $Cs_2CO_3$ (53.9 mg, 0.166 mmol) at 25° C. The reaction mixture was stirred at 100° C. for 12 h under $N_2$ atmosphere, the mixture was diluted with $H_2O$ (2 mL), extracted with EA (10 mL*3), washed with brine (10 mL), dried over $Na_2SO_4$, concentrated and purified by flash chromatography on silica (DCM/MeOH=100/1 to 10/1) to get the compound 238 (14.5 mg, 37% yield) as a white solid. LC-MS (Method 4) $t_R$=2.64 min, m/z (M+H)⁺=480.4. ¹H NMR (400 MHz, CDCl₃) δ 10.39 (s, 1H), 8.47 (s, 1H), 8.34 (s, 1H), 7.93 (s, 1H), 7.88 (s, 1H), 7.47 (d, J=8.8 Hz, 1H), 7.13 (d, J=8.8 Hz, 1H), 6.35 (s, 1H), 4.63 (q, J=6.8 Hz, 2H), 3.87 (s, 3H), 1.49 (t, J=6.8 Hz, 3H), 1.32-1.27 (m, 4H).

Example 239

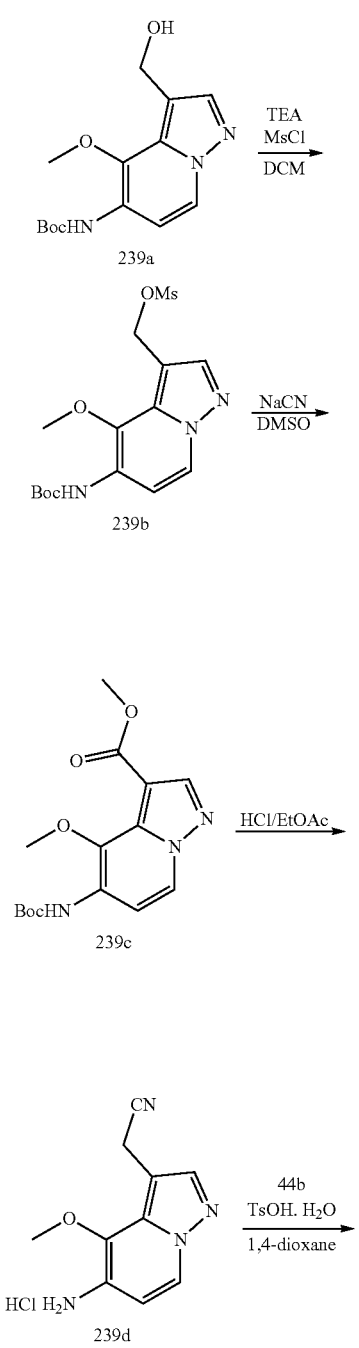

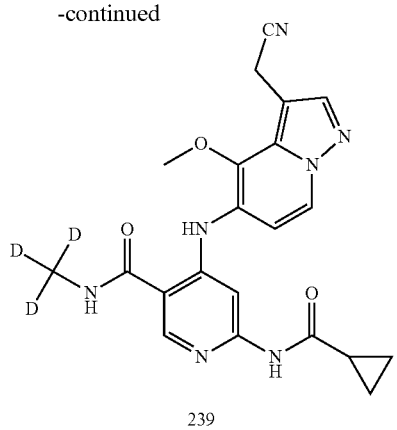

239

Step 1. Tert-butyl (3-(hydroxymethyl)-4-methoxy-pyrazolo[1,5-a]pyridin-5-yl)carbamate (239a)

To a mixture of 220a (300 mg, 0.93 mmol) in THF (2 mL) was added LiAlH$_4$ (71 mg, 1.87 mmol) at 0° C. After stirring at 20° C. for 1 h, the reaction was quenched with aqueous seignette salt (10 mL) and extracted with EtOAc (20 mL*2). The combined organic layer was concentrated and the residue was purified by flash chromatography on silica gel (PE/EtOAc=1/1) to afford 239a (180 mg, 66% yield) as a green oil. $^1$H NMR (400 MHz, CDCl$_3$) δ 8.21 (d, J=8.0 Hz, 1H), 7.84 (s, 1H), 7.72 (d, J=7.6 Hz, 1H), 6.95 (s, 1H), 4.87 (s, 2H), 3.95 (s, 3H), 1.55 (s, 9H).

Step 2. (5-((Tert-butoxycarbonyl)amino)-4-methoxypyrazolo[1,5-a]pyridin-3-yl)methyl methanesulfonate (239b)

To a mixture of 239a (160 mg, 0.55 mmol) and TEA (166 mg, 1.64 mmol) in DCM (2 mL) was added MSCl (94 mg, 0.82 mmol) at 0° C. After stirring at 0° C. for 0.5 h, the reaction mixture was diluted with ice-water (5 mL) and extracted with DCM (10 mL*2). The combined organic layer was concentrated to afford 239b (200 mg, 98% yield) as a yellow oil. $^1$H NMR (400 MHz, CDCl$_3$) δ 8.24 (d, J=7.6 Hz, 1H), 7.90 (s, 1H), 7.86 (d, J=7.6 Hz, 1H), 7.01 (s, 1H), 4.76 (s, 2H), 3.87 (s, 3H), 3.07 (s, 3H), 1.48 (s, 9H).

Step 3. Tert-butyl (3-(cyanomethyl)-4-methoxypyrazolo[1,5-a]pyridin-5-yl)carbamate (239c)

To a mixture of 239b (200 mg, 0.54 mmol) in DMSO (3 mL) was added NaCN (264 mg, 5.38 mmol) at r.t. After stirring at 60° C. for 2 h, the reaction mixture was poured into ice-water (20 mL) and extracted with EtOAc (30 mL*2). The combined organic layer was washed with brine (20 mL*2), and concentrated. The residue was purified by flash chromatography on silica gel (PE/EtOAc=3/1) to afford 239c (90 mg, 55% yield) as a yellow oil. $^1$H NMR (400 MHz, CDCl$_3$) δ 8.20 (d, J=8.0 Hz, 1H), 7.86 (s, 1H), 7.73 (d, J=7.2 Hz, 1H), 6.88 (s, 1H), 3.96 (s, 2H), 3.91 (s, 3H), 1.55 (s, 9H).

Step 4. 2-(5-Amino-4-methoxypyrazolo[1,5-a]pyridin-3-yl)acetonitrile hydrochloride (239d)

A mixture of 239c (80 mg, 0.26 mmol) in HCl/EtOAc (2 mL, 2 M) was stirred at r.t. for 1 h. The reaction mixture was concentrated to afford 239d (40 mg, 63% yield) as a yellow solid. LC-MS (Method 3) t$_R$=0.88 min, m/z (M+H)$^+$=203.1.

Step 5. 4-((3-(Cyanomethyl)-4-methoxypyrazolo[1,5-a]pyridin-5-yl)amino)-6-(cyclopropanecarboxamido)-N-(methyl-d$_3$)nicotinamide (239)

A mixture of 239d (40 mg, 0.168 mmol), 44b (65 mg, 0.25 mmol) and TsOH·H$_2$O (16 mg, 0.084 mmol) in 1,4-dioxane (2 mL) was stirred at 100° C. for 16 h. The reaction mixture was cooled, concentrated and the residue was purified by Prep-HPLC (Method A) to afford 239 (25 mg, 35% yield) as a white solid. LC-MS (Method 2) t$_R$=2.41 min, m/z (M+H)$^+$=423.1. $^1$H NMR (400 MHz, DMSO-d$_6$) δ 10.80 (s, 1H), 10.59 (s, 1H), 8.64 (s, 1H), 8.55 (s, 1H), 8.52 (d, J=7.2 Hz, 1H), 7.97 (s, 1H), 7.82 (s, 1H), 6.93 (d, J=7.2 Hz, 1H), 4.12 (s, 2H), 3.85 (s, 3H), 2.02-1.92 (m, 1H), 0.80-0.70 (m, 4H).

Example 240

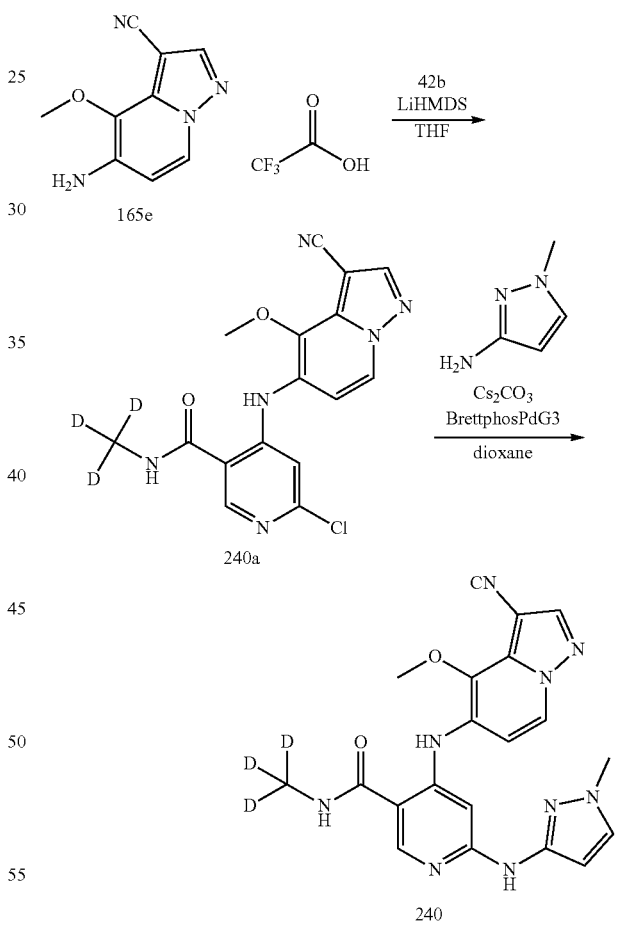

Step 1. 6-Chloro-4-((3-cyano-4-methoxypyrazolo[1,5-a]pyridin-5-yl)amino)-N-(methyl-d$_3$)nicotinamide (240a)

To a solution of 160e (94 mg, 0.31 mmol) and 42b (65 mg, 0.31 mmol) in THF (3 mL) was added LiHMDS (1.5 mL, 1.5 mmol, 1 M in THF) at −40° C. The reaction was stirred at −40° C. to r.t. for 1 h, quenched with H$_2$O (2 mL) and concentrated. The formed solid was collected by filtering and dried to afford 240a (62 mg, 55% yield) as a red solid. LC-MS (Method 3) $t_R$=1.09 min, m/z (M+H)$^+$=360.4.

Step 2. 4-((3-Cyano-4-methoxypyrazolo[1,5-a]pyridin-5-yl)amino)-N-(methyl-d$_3$)-6-((1-methyl-1H-pyrazol-3-yl)amino)nicotinamide (240)

A mixture of 240a (40 mg, 0.11 mmol), 1-methyl-1H-pyrazol-3-amine (32 mg, 0.33 mmol), BrettPhos Pd G3 (20 mg, 0.022 mmol) and Cs$_2$CO$_3$ (72 mg, 0.22 mmol) in 1,4-dioxane (1 mL) was stirred at 90° C. overnight under N$_2$ atmosphere. After cooling to r.t., the mixture was concentrated. The residue was purified by flash chromatography on silica gel (DCM/MeOH=10/1) to afford 240 (8 mg, 17% yield) as a white solid. LC-MS (Method 2) $t_R$=3.16 min, m/z (M+H)$^+$=421.1. $^1$H NMR (400 MHz, DMSO-d$_6$) δ 11.21 (s, 1H), 9.52 (s, 1H), 8.84 (d, J=7.2 Hz, 1H), 8.56 (s, 1H), 8.52 (s, 1H), 8.48 (s, 1H), 7.57-7.48 (m, 3H), 6.09 (s, 1H), 3.93 (s, 3H), 3.73 (s, 3H).

Example 241

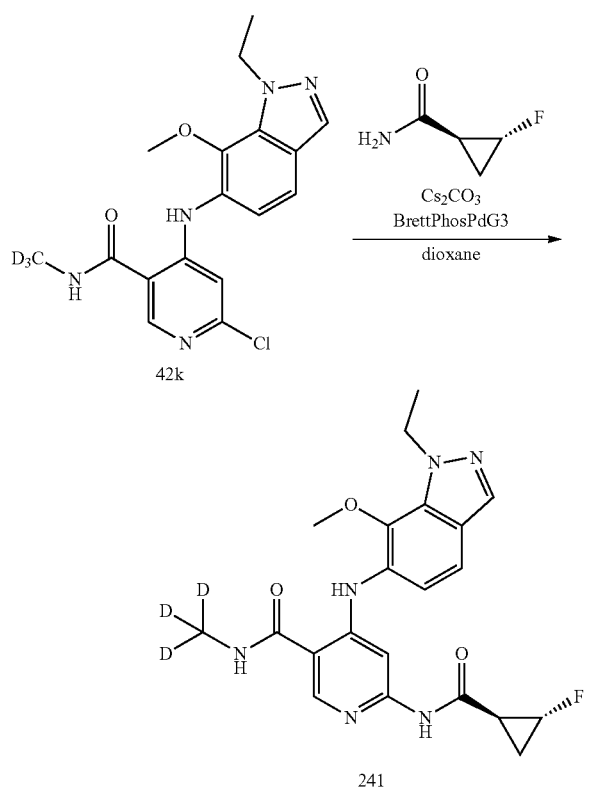

Step 1. 4-((1-Ethyl-7-methoxy-1H-indazol-6-yl)amino)-6-(trans-2-fluorocyclopropanecarboxamido)-N-(methyl-d$_3$)nicotinamide (241)

A mixture of 42k (50 mg, 0.138 mmol), trans-2-fluorocyclopropanecarboxamide (28 mg, 0.276 mmol), BrettPhos Pd G3 (25 mg, 0.028 mmol) and Cs$_2$CO$_3$ (135 mg, 0.413 mmol) in 1,4-dioxane (1 mL) was stirred at 90° C. for 16 h under N$_2$ atmosphere. The reaction mixture was cooled, concentrated and the residue was purified by Prep-HPLC (Method A) to afford 241 (14 mg, 23% yield) as a white solid. LC-MS (Method 2) $t_R$=2.57 min, m/z (M+H)$^+$=430.1. $^1$H NMR (400 MHz, DMSO-d$_6$) δ 10.87 (s, 1H), 10.54 (s, 1H), 8.62 (s, 1H), 8.52 (s, 1H), 8.03 (s, 1H), 7.76 (s, 1H), 7.50 (d, J=8.4 Hz, 1H), 7.08 (d, J=8.4 Hz, 1H), 4.87-4.70 (m, 1H), 4.54 (q, J=6.8 Hz, 2H), 3.78 (s, 3H), 2.45-2.42 (m, 1H), 1.50-1.42 (m, 1H), 1.39 (t, J=7.2 Hz, 3H), 1.17-1.09 (m, 1H).

Example 242

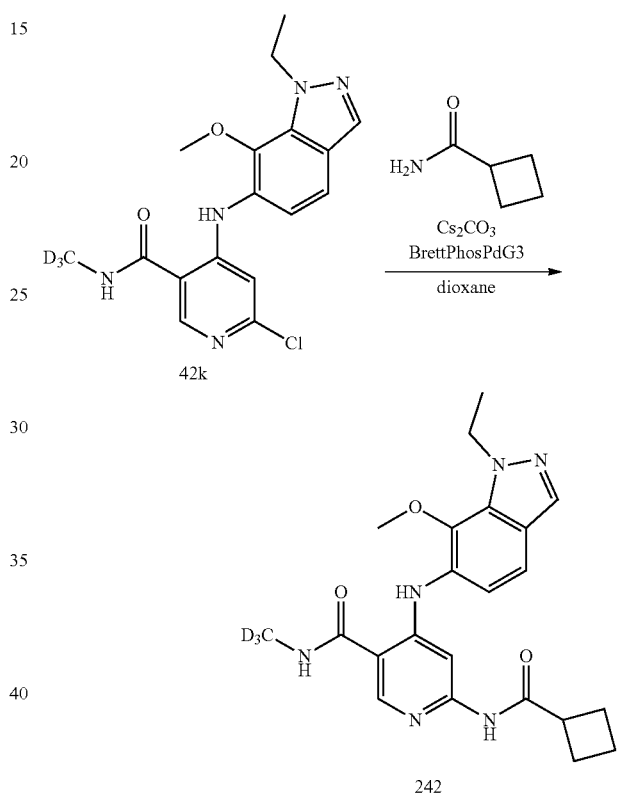

Step 1. 6-(Cyclobutanecarboxamido)-4-((1-ethyl-7-methoxy-1H-indazol-6-yl)amino)-N-(methyl-d$_3$)nicotinamide (242)

A mixture of 42k (50 mg, 0.14 mmol), cyclobutanecarboxamide (41 mg, 0.41 mmol), BrettPhos Pd G3 (25 mg, 0.028 mmol) and Cs$_2$CO$_3$ (90 mg, 0.28 mmol) in 1,4-dioxane (0.5 mL) was stirred at 90° C. for 16 h under N$_2$ atmosphere. After cooling to r.t., the mixture was concentrated. The residue was purified by flash chromatography on silica gel (DCM/MeOH=20/1) to afford 242 (15.5 mg, 26% yield) as a white solid. LC-MS (Method 1) $t_R$=3.13 min, m/z (M+H)$^+$=426.2. $^1$H NMR (400 MHz, DMSO-d$_6$) δ 10.56 (s, 1H), 10.20 (s, 1H), 8.59 (s, 1H), 8.51 (s, 1H), 8.06 (s, 1H), 7.89 (s, 1H), 7.55 (d, J=8.0 Hz, 1H), 7.14 (d, J=8.4 Hz, 1H), 4.57 (q, J=6.8 Hz, 2H), 3.81 (s, 3H), 2.45-2.43 (m, 1H), 2.13-2.09 (m, 2H), 2.06-2.02 (m, 2H), 1.90-1.86 (m, 1H), 1.74-1.72 (m, 1H), 1.39 (t, J=6.8 Hz, 3H).

Example 243

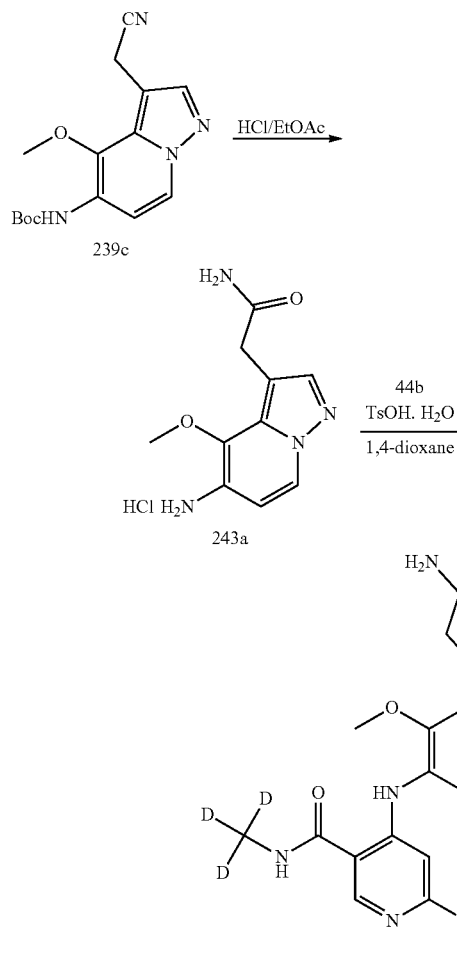

Step 1. 2-(5-Amino-4-methoxypyrazolo[1,5-a]pyridin-3-yl)acetamide hydrochloride (243a)

A mixture of 239c (80 mg, 0.26 mmol) in HCl/EtOAc (2 mL, 2 M) was stirred at r.t. for 1 h. The reaction mixture was concentrated to afford 243a (20 mg, 29% yield) as a yellow solid. LC-MS (Method 3) $t_R$=0.30 min, m/z (M+H)$^+$=221.1.

Step 2. 4-((3-(2-Amino-2-oxoethyl)-4-methoxypyrazolo[1,5-a]pyridin-5-yl)amino)-6-(cyclopropanecarboxamido)-N-(methyl-d$_3$)nicotinamide (243)

A mixture of 243a (20 mg, 0.078 mmol), 44b (65 mg, 0.25 mmol) and TsOH·H$_2$O (16 mg, 0.084 mmol) in 1,4-dioxane (2 mL) was stirred at 100° C. for 16 h. The reaction mixture was cooled, concentrated and residue was purified by Prep-HPLC (Method A) to afford 243 (9 mg, 26% yield) as a white solid. LC-MS (Method 2) $t_R$=2.10 min, m/z (M+H)$^+$=441.2. $^1$H NMR (400 MHz, DMSO-d$_6$) δ 10.77 (s, 1H), 10.51 (s, 1H), 8.82 (s, 1H), 8.53 (s, 1H), 8.44 (d, J=7.6 Hz, 1H), 7.82-7.81 (m, 2H), 7.29 (s, 1H), 6.86 (s, 1H), 6.82 (d, J=7.2 Hz, 1H), 3.76 (s, 3H), 3.62 (s, 2H), 1.99-1.93 (m, 1H), 0.76-0.74 (m, 4H).

Example 244

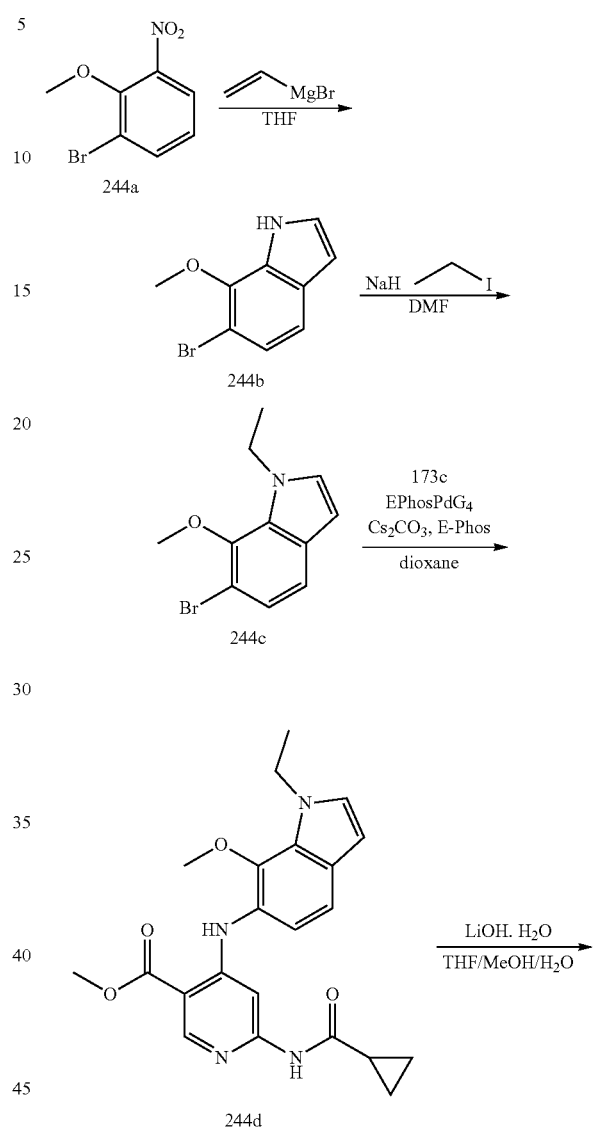

-continued

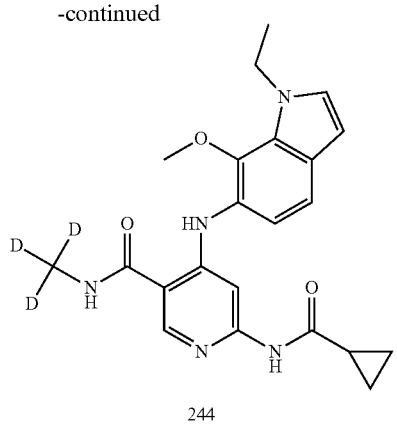

244

Step 1. 6-Bromo-7-methoxy-1H-indole (244b)

To a solution of 244a (5 g, 21.64 mmol) in THF (50 mL) at −40° C. under N₂ atmosphere was added vinylmagnesium bromide (64.93 mL, 64.93 mmol). The resulting mixture was stirred at −20° C. for 30 min. The reaction was then quenched with aq. NH₄Cl (150 mL) and extracted with EtOAc (200 mL*3). The combined organic layer was washed by brine (200 mL*2), dried over sodium sulphate and evaporated in vacuo. The residue was purified by flash chromatography on silica gel (PE/EA=30/1 to 8/1) to give 244b (1.5 g, 26% yield) as a white solid. LC-MS (Method 5) $t_R$=2.84 min, m/z (M+H)⁺=225.9.

Step 2. 6-Bromo-1-ethyl-7-methoxy-1H-indole (244c)

To a solution of 244b (1.5 g, 6.64 mmol) in DMF (15 mL) was added 60% NaH (292 mg, 7.30 mmol) at 0° C. and stirred for 0.5 h under N₂ atmosphere. Then C₂H₅I (1.55 g, 9.96 mmol) was added. The reaction mixture was stirred at 25° C. for 5 h. The reaction was quenched with aq. NH₄Cl (30 mL) and extracted with EtOAc (10 mL*3). The combined organic layer was washed by brine (30 mL*2), dried over sodium sulphate and evaporated in vacuo. The residue was purified by flash chromatography on silica gel (PE/EA=30/1 to 5/1) to give 244c (600 mg, 33% yield) as a yellow solid. LC-MS (Method 5) $t_R$=3.19 min, m/z (M+H)⁺=253.9.

Step 3. Methyl 6-(cyclopropanecarboxamido)-4-((1-ethyl-7-methoxy-1H-indol-6-yl)amino)nicotinate (244d)

To a solution of 244c (400 mg, 1.57 mmol) in dioxane (5 mL) was added Cs₂CO₃ (1.54 g, 4.72 mmol), E-PhosPd 4G (144.6 mg, 0.157 mmol), E-Phos (168.4 mg, 0.315 mmol) and 173c (370 mg, 1.57 mmol). The reaction mixture was stirred at 100° C. for 5 h under N₂ atmosphere. The mixture was cooled to room temperature and diluted with water (30 mL), extracted with EtOAc (5 mL*3). The combined organic layer was washed by brine (5 mL*2), dried over sodium sulphate and evaporated in vacuo. The residue was purified by Prep-TLC (DCM/MeOH=20/1) to give 244d (150 mg, 17% yield) as a yellow solid. LC-MS (Method 5) $t_R$=2.45 min, m/z (M+H)⁺=409.1.

Step 4. 6-(Cyclopropanecarboxamido)-4-((1-ethyl-7-methoxy-1H-indol-6-yl)amino)nicotinic acid (244e)

To a solution of 244d (150 mg, 0.367 mmol) in THF/MeOH/H₂O=3/2/1 (2 mL) was added LiOH·H₂O (30.9 mg, 0.735 mmol) and stirred at 40° C. for 16 h under N₂ atmosphere. The mixture was diluted with water (10 mL) and extracted with EtOAc (2 mL*3). The combined organic layer was washed by brine (2 mL*2), dried over sodium sulphate and evaporated in vacuo. The residue was purified by Prep-TLC (DCM/MeOH=10/1) to give 244e (100 mg, 59% yield) as a yellow solid. LC-MS (Method 5), $t_R$=1.55 min, m/z (M+H)⁺=395.0.

Step 5. 6-(Cyclopropanecarboxamido)-4-((1-ethyl-7-methoxy-1H-indol-6-yl)amino)-N-(methyl-d₃) nicotinamide (244)

To a solution of 244e (100 mg, 0.254 mmol) in DMF (2 mL) was added methan-d₃-amine hydrochloride (26.8 mg, 0.380 mmol), EDCI (58.5 mg, 0.304 mmol), HOBT (41.1 mg, 0.304 mmol) and TEA (153.8 mg, 1.52 mmol). The reaction mixture was stirred at 25° C. for 16 h under N₂ atmosphere. The mixture was diluted with water (10 mL) and extracted with EA (3 mL*3). The combined organic layer was washed by brine (2 mL*2), dried over sodium sulphate and evaporated in vacuo. The residue was purified by Prep-TLC (DCM/MeOH=10/1) to give the crude product (30 mg). Then the crude product was re-purified by Prep-HPLC (Method A) to give 244 (2.8 mg, 2.7% yield) as a yellow solid. LC-MS (Method 5) $t_R$=2.83 min, m/z (M+H)⁺=411.1. ¹H NMR (400 MHz, DMSO-d₆) δ 10.63 (s, 1H), 10.35 (s, 1H), 8.55 (s, 1H), 8.48 (s, 1H), 7.72 (s, 1H), 7.34 (d, J=3.2 Hz, 1H), 7.30 (d, J=8.4 Hz, 1H), 6.94 (d, J=8.4 Hz, 1H), 6.43 (d, J=2.8 Hz, 1H), 4.37 (q, J=7.2 Hz, 2H), 3.73 (s, 3H), 1.94-1.91 (m, 1H), 1.36 (t, J=7.2 Hz, 3H), 0.71-0.69 (m, 4H).

Example 245

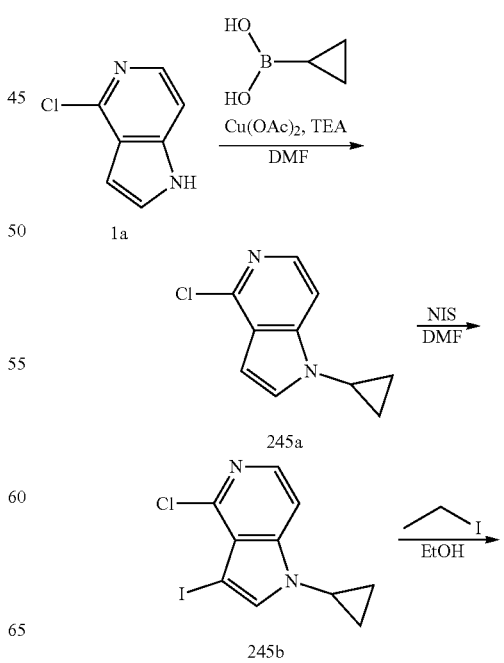

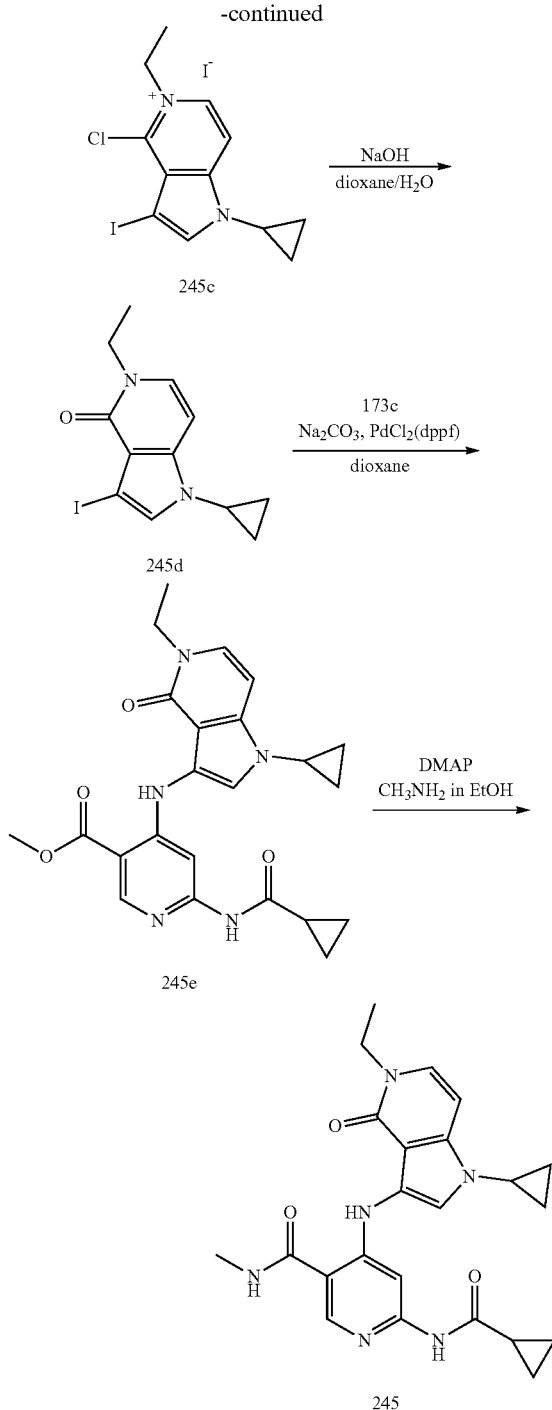

and evaporated in vacuo. The residue was purified by flash chromatography on silica gel (PE/EA=50/1 to 10/1) to give 245a (5.10 g, 81% yield) as a yellow solid. LC-MS (Method 5), $t_R$=1.28 min, m/z (M+H)$^+$=193.1.

Step 2. 4-Chloro-1-cyclopropyl-3-iodo-1H-pyrrolo[3,2-c]pyridine (245b)

To a solution of 245a (5.10 g, 28.6 mmol) in DMF (100 mL) was added NIS (9.65 g, 42.9 mmol). The reaction mixture was then stirred at 80° C. for 1 h. The mixture was cooled to room temperature and diluted with water (250 mL), extracted with EtOAc (200 mL*3). The combined organic layer was washed by brine (200 mL*2), dried over sodium sulphate and evaporated in vacuo. The residue was purified by flash chromatography on silica gel (PE/EA=20/1 to 5/1) to give 245b (2.09 g, 25% yield) as a yellow solid. LC-MS (Method 5) $t_R$=1.72 min, m/z (M+H)$^+$=318.9. $^1$H NMR (400 MHz, CDCl$_3$) δ 8.10 (d, J=6.0 Hz, 1H), 7.46 (d, J=5.6 Hz, 1H), 7.32 (s, 1H), 3.40-3.38 (m, 1H), 1.16-1.14 (m, 2H), 1.03-1.01 (m, 2H).

Step 3. 4-Chloro-1-cyclopropyl-5-ethyl-3-iodo-1H-pyrrolo[3,2-c]pyridin-5-ium iodide (245c)

A mixture of 245b (2.09 g, 6.57 mmol) and C$_2$H$_5$I (10 mL) in EtOH (10 mL) was stirred at 80° C. for 18 h. After cooling to room temperature, the reaction mixture was concentrated. The residue was purified by flash chromatography on silica gel (PE/EA=5/1) to give 245c (700 mg, 30% yield) as a yellow solid. LC-MS (Method 5) $t_R$=0.28 min, m/z M$^+$=346.9.

Step 4. 1-Cyclopropyl-5-ethyl-3-iodo-1,5-dihydro-pyrrolo[3,2-c]pyridin-4-one (245d)

To a solution of 245c (700 mg, 2.01 mmol) in H$_2$O/dioxane=1/1 (10 mL) was added NaOH (161 mg, 4.03 mmol) and stirred at 5° C. for 2 h. The mixture was diluted with water (20 mL) and extracted with EtOAc (20 mL*3). The combined organic layer was washed by brine (20 mL*2), dried over sodium sulphate and evaporated in vacuo. The residue was purified by flash chromatography on silica gel (PE/EA=10/1 to 3/1) to give 245d (260 mg, 94% yield) as a yellow solid. LC-MS (Method 5), $t_R$=0.91 min, m/z (M+H)$^+$=328.9. $^1$H NMR (400 MHz, CDCl$_3$) δ 7.04 (d, J=7.6 Hz, 1H), 6.97 (s, 1H), 6.50 (d, J=7.6 Hz, 1H), 4.03 (q, J=7.2 Hz, 2H), 3.28-3.25 (m, 1H), 1.35 (t, J=7.2 Hz, 3H), 1.03-1.01 (m, 2H), 0.98-0.97 (m, 2H).

Step 5. Methyl 6-(cyclopropanecarboxamido)-4-((1-cyclopropyl-5-ethyl-4-oxo-4,5-dihydro-1H-pyrrolo[3,2-c]pyridin-3-yl)amino)nicotinate (245e)

To a solution of 245d (260 mg, 0.792 mmol) in dioxane (5 mL) was added Na$_2$CO$_3$ (161 mg, 1.58 mmol), Pd(dppf)Cl$_2$ (23.0 mg, 0.031 mmol) and 173c (279 mg, 1.18 mmol). The reaction mixture was stirred at 100° C. for 5 h. The mixture was cooled to room temperature and diluted with water (10 mL), extracted with EtOAc (10 mL*3). The combined organic layer was washed by brine (20 mL*2), dried over sodium sulphate and evaporated in vacuo. The residue was purified by Prep-TLC (PE/EA=1/1) to give 245e (24.0 mg, 7% yield) as a yellow solid. LC-MS (Method 5) $t_R$=2.04 min, m/z (M+H)$^+$=436.3. $^1$H NMR (400 MHz, DMSO-d$_6$) δ 11.05 (s, 1H), 10.81 (s, 1H), 8.67 (s, 1H), 8.03 (s, 1H), 7.42 (d, J=7.2 Hz, 1H), 7.13 (s, 1H), 6.60 (d, J=7.6

Step 1. 4-Chloro-1-cyclopropyl-1H-pyrrolo[3,2-c]pyridine (245a)

To a solution of 1a (5.00 g, 32.8 mmol) in DMF (100 mL) was added cyclopropylboronic acid (8.46 g, 98.4 mmol), Cu(OAc)$_2$ (17.8 g, 98.4 mmol) and TEA (16.5 g, 164 mmol). The reaction mixture was stirred at 120° C. under O$_2$ atmosphere for 5 h. The mixture was cooled to room temperature and diluted with water (250 mL), extracted with EtOAc (200 mL*3). The combined organic layer was washed by brine (200 mL*2), dried over sodium sulphate Hz, 1H), 3.95 (q, J=7.2 Hz, 2H), 3.89 (s, 3H), 2.52-2.50 (m, 1H), 2.04-2.01 (m, 1H), 1.22 (t, J=7.2 Hz, 3H), 1.07-1.06 (m, 2H), 0.97-0.95 (m, 2H), 0.87-0.85 (m, 4H).

Step 6. 6-(Cyclopropanecarboxamido)-4-((1-cyclopropyl-5-ethyl-4-oxo-4,5-dihydro-1H-pyrrolo[3,2-c]pyridin-3-yl)amino)-N-methylnicotinamide (245)

DMAP (3.1 mg, 0.028 mmol) and 245e (12 mg, 0.028 mmol) was added to a solution of methylamine in ethanol (1.4 mL, 1 M). The reaction mixture was stirred at 80° C. for 16 h. The mixture was cooled to room temperature and evaporated in vacuo. The residue was purified by Prep-HPLC (Method A) to give 245 (0.4 mg, 3.6% yield) as a white solid. LC-MS (Method 5) $t_R$=2.13 min, m/z (M+H)$^+$=435.1. $^1$H NMR (400 MHz, DMSO-$d_6$) δ 10.91 (s, 1H), 10.75 (s, 1H), 8.43-8.38 (m, 2H), 8.07 (s, 1H), 7.39 (d, J=7.2 Hz, 1H), 7.04 (s, 1H), 6.57 (d, J=7.6 Hz, 1H), 3.95 (q, J=7.2 Hz, 2H), 3.31-3.32 (m, 1H), 2.78 (d, J=4.4 Hz, 3H), 2.04-2.00 (m, 1H), 1.23 (t, J=7.2 Hz, 3H), 1.04-1.02 (m, 2H), 0.96-0.92 (m, 2H), 0.84-0.78 (m, 4H).

Example 246

16 h. The mixture was cooled to room temperature and evaporated in vacuo. The residue was purified by Prep-HPLC (Method A) to give 246 (3.6 mg, 30% yield) as a white solid. LC-MS (Method 5) $t_R$=2.10 min, m/z (M 1-H)$^+$=435.1. $^1$H NMR (400 MHz, DMSO-$d_6$) δ 10.89 (s, 1H), 10.72 (s, 1H), 8.44-8.41 (m, 2H), 8.00 (s, 1H), 7.35 (d, J=7.6 Hz, 1H), 7.05 (s, 1H), 6.53 (d, J=7.6 Hz, 1H), 6.03-5.93 (m, 1H), 5.19-5.16 (m, 1H), 5.09-5.04 (m, 1H), 4.69-4.68 (m, 2H), 3.95 (q, J=7.2 Hz, 2H), 2.79 (d, J=4.4 Hz, 3H), 2.01-1.97 (m, 1H), 1.22 (t, J=6.8 Hz, 3H), 0.81-0.78 (m, 4H).

Example 247

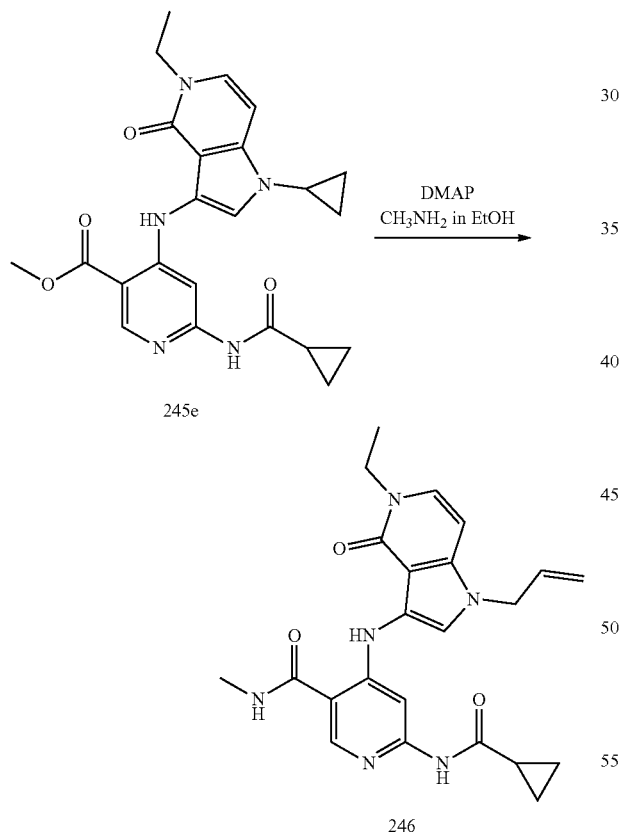

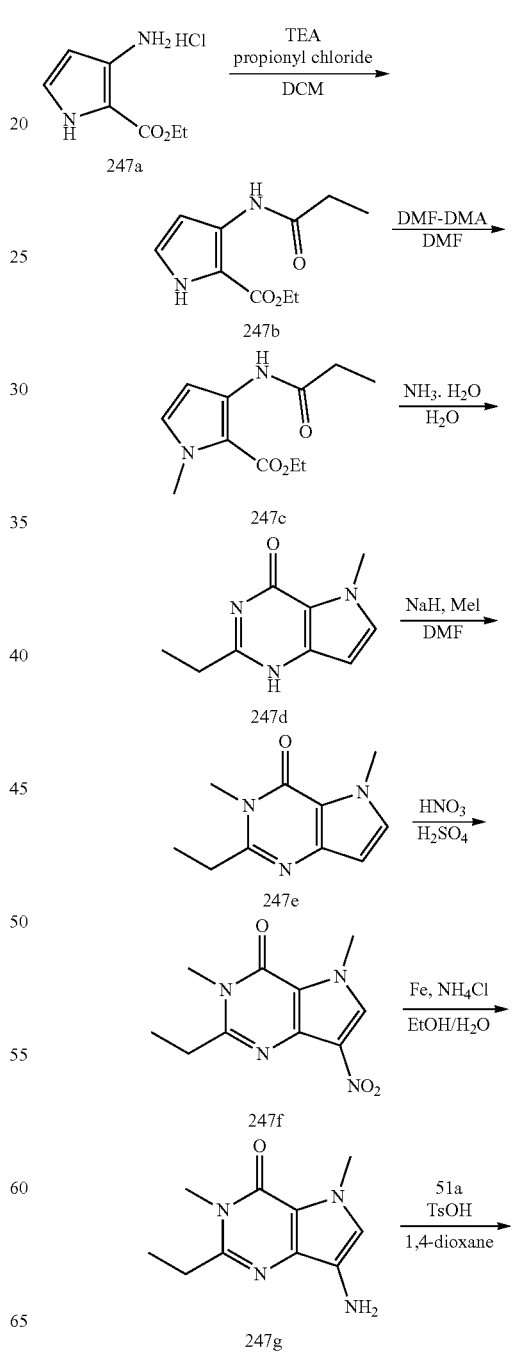

Step 1. 4-((1-Allyl-5-ethyl-4-oxo-4,5-dihydro-1H-pyrrolo[3,2-c]pyridin-3-yl)amino)-6-(cyclopropanecarboxamido)-N-methylnicotinamide (246)

DMAP (3.1 mg, 0.028 mmol) and 245e (12 mg, 0.028 mmol) was added to a solution of methylamine in ethanol (1.4 mL, 1 M). The reaction mixture was stirred at 80° C. for -continued

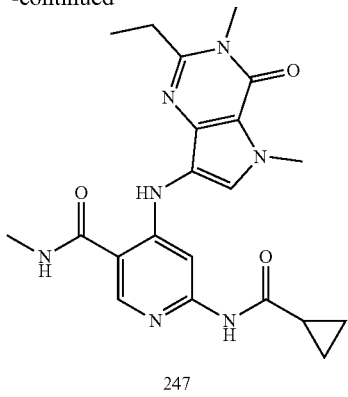

247

Step 1. Ethyl 3-propionamido-1H-pyrrole-2-carboxylate (247b)

To a stirred solution of 247a (10.0 g, 52.47 mmol) and TEA (21 mL, 151.08 mmol) in DCM (100 mL) was added propionyl chloride (5.7 mL, 65.24 mmol) dropwise at 0° C. After stirring at 0° C. for 5 min, the reaction solution was allowed to stirred at r.t. for 3 h. Then the reaction was quenched with 2 N HCl (30 mL) and neutralized with sat. NaHCO$_3$. The organic layer was separated and washed with brine (10 mL), dried over anhydrous Na$_2$SO$_4$ and filtered. The filtrate was concentrated and the residue was recrystallized from EA to give 247b (9.27 g, 84% yield) as a white solid. LC-MS (Method 4) $t_R$=2.14 min, m/z (M+H)$^+$=211.1.

Step 2. Ethyl 1-methyl-3-propionamido-1H-pyrrole-2-carboxylate (247c)

A solution of 247b (9.27 g, 44.10 mmol) in DMF-DMA (50 mL) and DMF (100 mL) was stirred at 90° C. for 16 h. After cooling down to r.t., the reaction solution was quenched with H$_2$O (150 mL) and extracted with DCM (80 mL*3). The combined organic layer was washed with brine (20 mL), dried over anhydrous Na$_2$SO$_4$ and filtered. The filtrate was concentrated under vacuum to give a residue which was purified by flash chromatography on silica gel (PE/EA=5/1) to afford the title compound 247c (7.13 g, 72% yield) as a white solid. LC-MS (Method 4) $t_R$=2.97 min, m/z (M+H)$^+$=225.2.

Step 3. 2-Ethyl-5-methyl-1,5-dihydro-4H-pyrrolo[3,2-d]pyrimidin-4-one (247d)

To a sealed tube was added 247c (7.13 g, 31.79 mmol) and NH$_3$·H$_2$O (100 mL, 28-30% w.t. in H$_2$O). The reaction mixture was stirred for 7 h under 115° C. After cooling down to r.t., the reaction solution was concentrated and the residue was purified by C-18 column (5-25% MeCN/H$_2$O (0.5% NH$_4$HCO$_3$), 30 min) to give the title compound 247d (632 mg, 11% yield) as a white solid. LC-MS (Method 4) $t_R$=0.71 min, m/z (M+H)$^+$=178.1.

Step 4. 2-Ethyl-3,5-dimethyl-3,5-dihydro-4H-pyrrolo[3,24]pyrimidin-4-one (247e)

To a solution of 247d (632 mg, 3.57 mmol) in DMF (10 mL) was added NaH (428 mg, 10.70 mmol, 60% purity in mineral oil) at 0° C. The mixture was stirred at 0° C. for 30 min. Then MeI was added and the resulting mixture was stirred at r.t. for 2 h. The mixture was diluted with H$_2$O (10 mL), extracted with DCM (10 mL*3). The combined organic layer was washed with brine (10 mL), dried over anhydrous Na$_2$SO$_4$ and filtered. The filtrate was concentrated to give a residue which was purified by flash chromatography on silica gel (DCM/MeOH=13/1) to afford the title compound 247e (330 mg, 49% yield) as a white solid. LC-MS (Method 4) $t_R$=0.85 min, m/z (M+H)$^+$=192.1. $^1$H NMR (400 MHz, CDCl$_3$) δ 6.98 (d, J=2.8 Hz, 1H), 6.33 (d, J=2.8 Hz, 1H), 4.07 (s, 3H), 3.58 (s, 3H), 2.80 (q, J=7.4 Hz, 2H), 1.35 (t, J=7.4 Hz, 3H).

Step 5. 2-Ethyl-3,5-dimethyl-7-nitro-3,5-dihydro-4H-pyrrolo[3,2-d]pyrimidin-4-one (247f)

To a solution of 247e (330 mg, 1.72 mmol) in conc. H$_2$SO$_4$ (4 mL) was added HNO$_3$ (0.5 mL) at 0° C. The resulting mixture was stirred at 0° C. for 1 h and quenched with H$_2$O (15 mL) at 0° C. After neutralized with sat. NaHCO$_3$ at 0° C., the mixture solution was extracted with DCM (10 mL*3). The combined organic layer was washed with brine (10 mL), dried over anhydrous Na$_2$SO$_4$ and filtered. The filtrate was concentrated to give the title compound 247f (298 mg, 73% yield) as a light yellow solid. LC-MS (Method 4) $t_R$=0.96 min, m/z (M+H)$^+$=237.1.

Step 6. 7-Amino-2-ethyl-3,5-dimethyl-3,5-dihydro-4H-pyrrolo[3,2-d]pyrimidin-4-one (247g)

To a solution of 247f (298 mg, 1.26 mmol) in EtOH (4 mL) and H$_2$O (1 mL) was added Fe powder (340 mg, 6.10 mmol) and NH$_4$Cl (675 mg, 12.62 mmol). The resulting mixture was stirred at 80° C. for 1 h. After cooling down to r.t., the reaction mixture was filtered. The filtrate was diluted with H$_2$O (8 mL) and extracted with DCM (10 mL*3). The combined organic layer was washed with brine (10 mL), dried over anhydrous Na$_2$SO$_4$ and filtered. The filtrate was concentrated to afford the title compound 247g (203 mg, 78% yield) as a brown solid. LC-MS (Method 4) $t_R$=0.69 min, m/z (M+H)$^+$=207.2.

Step 7. 6-(Cyclopropanecarboxamido)-4-((2-ethyl-3,5-dimethyl-4-oxo-4,5-dihydro-3H-pyrrolo[3,2-d]pyrimidin-7-yl)amino)-N-methylnicotinamide (247)

To a solution of 247g (39 mg, 0.19 mmol) and 51a (30 mg, 0.12 mmol) in anhydrous 1,4-dioxane (1 mL) was added TsOH (25 mg, 0.14 mmol). The resulting mixture was stirred at 90° C. for 5 h. After cooling down to r.t., the reaction mixture was concentrated and the residue was purified by Prep-HPLC (Method E) to afford compound 247 (8.0 mg, 10% yield). LC-MS (Method 4) $t_R$=1.25 min, m/z (M+H)$^+$=424.3. $^1$H NMR (400 MHz, DMSO-d$_6$) δ 10.61 (s, 1H), 10.21 (s, 1H), 8.49 (q, J=4.4 Hz, 1H), 8.43 (s, 1H), 7.64 (s, 1H), 7.34 (s, 1H), 3.95 (s, 3H), 3.46 (s, 3H), 2.77-2.70 (m, 5H), 1.96-1.88 (m, 1H), 1.14 (t, J=7.2 Hz, 3H), 0.73-0.68 (m, 4H).

Example 248

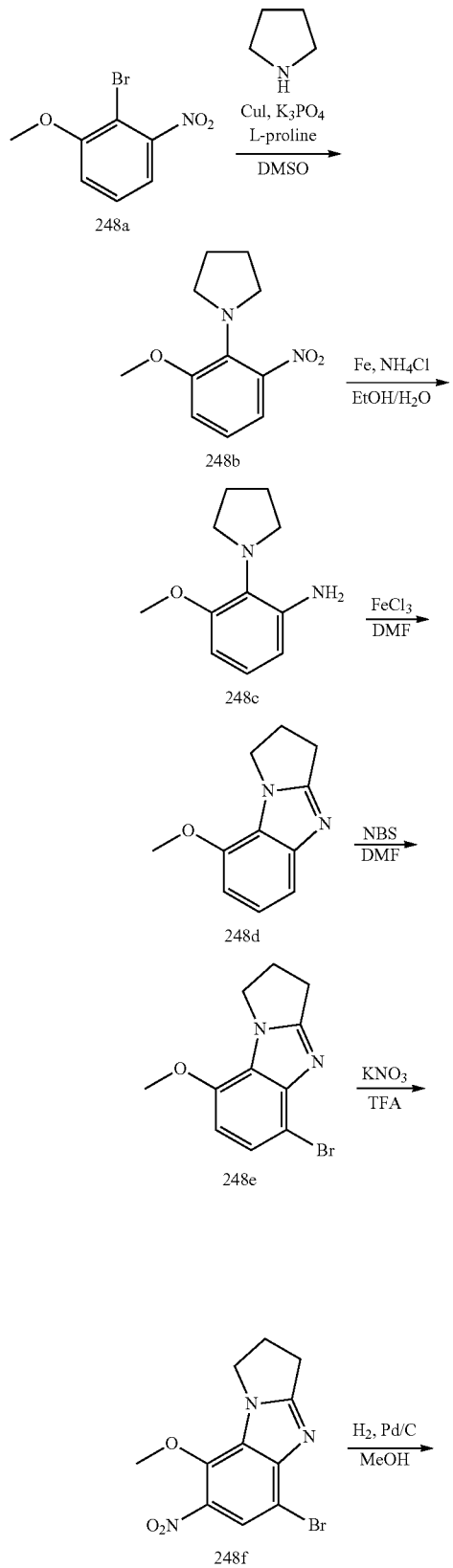

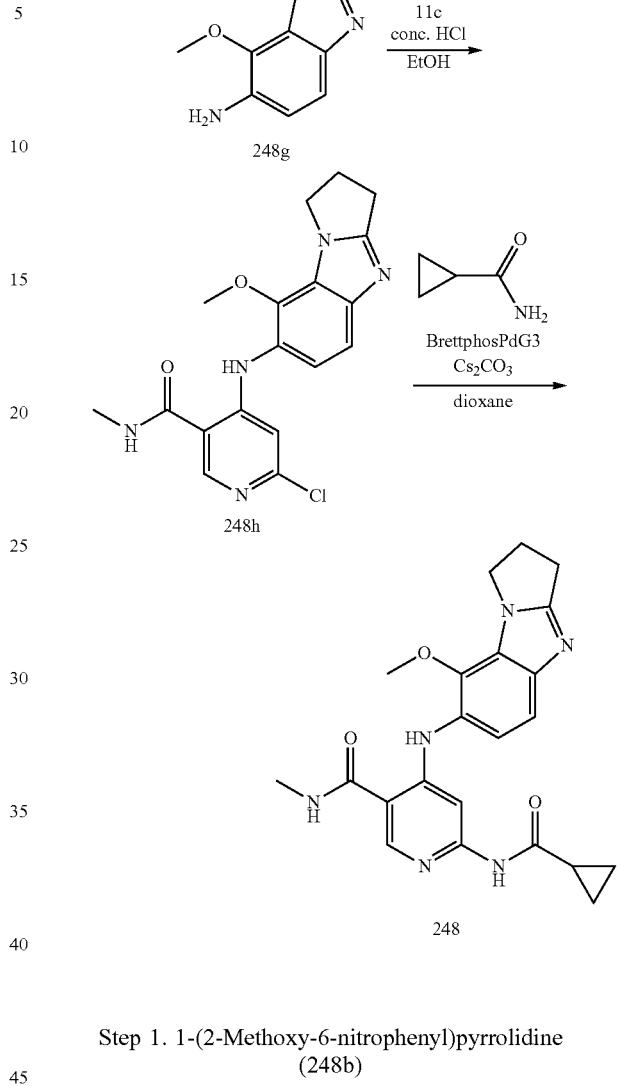

Step 1. 1-(2-Methoxy-6-nitrophenyl)pyrrolidine (248b)

A mixture of 248a (4.6 g, 19.82 mmol), pyrrolidine (2.82 g, 39.65 mmol), CuI (378 mg, 1.98 mmol), L-Proline (456 mg, 3.96 mmol) and $K_3PO_4$ (8.42 g, 39.65 mmol) in DMSO (20 mL) was stirred at 100° C. for 16 h under $N_2$ atmosphere. The reaction mixture was cooled, diluted with water (20 mL) and extracted with EtOAc (50 mL*3). The combined organic layer was dried over anhydrous $Na_2SO_4$, filtered and concentrated. The residue was purified by flash chromatography on silica gel (PE/EtOAc=10/1) to afford 248b (2.8 g, 64% yield) as a yellow solid. LC-MS (Method 3) $t_R$=1.47 min, m/z $(M+H)^+$=223.2.

Step 2. 3-Methoxy-2-(pyrrolidin-1-yl)aniline (248c)

A mixture of 248b (2.8 g, 12.60 mmol), Fe powder (3.52 g, 62.99 mmol) and $NH_4Cl$ (4.04 g, 75.59 mmol) in EtOH (10 mL) and water (10 mL) was stirred at 90° C. for 2 h. The reaction was cooled, filtered and the filtrate was concentrated to afford 248c (2.2 g, 91% yield) as a yellow solid. LC-MS (Method 3) $t_R$=1.28 min, m/z $(M+H)^+$=193.4.

Step 3. 8-Methoxy-2,3-dihydro-1H-benzo[d]pyrrolo[1,2-a]imidazole (248d)

A mixture of 248c (1.6 g, 8.32 mmol) and FeCl$_3$ (135 mg, 0.83 mmol) in DMF (16 mL) was stirred at 60° C. for 4 h. After cooling to r.t, the reaction mixture was diluted with water (20 mL) and extracted with EtOAc (20 mL*3). The combined organic layer was dried over anhydrous Na$_2$SO$_4$, filtered and concentrated. The residue was purified by flash chromatography on silica gel (PE/EtOAc=10/1) to afford 248d (600 mg, 38% yield) as a yellow solid. LC-MS (Method 3) $t_R$=1.14 min, m/z M+H)$^+$=189.2.

Step 4. 5-Bromo-8-methoxy-2,3-dihydro-1H-benzo[d]pyrrolo[1,2-a]imidazole (248e)

To a solution of 248d (200 mg, 0.85 mmol) in DMF (2 mL) was added NBS (121 mg, 0.68 mmol) at 0° C. After stirring at 0° C. for 1 h, the mixture was diluted with water (4 mL). The formed solid was collected by filtering and was dried to afford 248e (200 mg, 88% yield) as a yellow solid. LC-MS (Method 3) $t_R$=1.19 min, m/z (M+H)$^+$=267.1.

Step 5. 5-Bromo-8-methoxy-7-nitro-2,3-dihydro-1H-benzo[d]pyrrolo[1,2-a]imidazole (248f)

A mixture of 248e (200 mg, 0.75 mmol) and KNO$_3$ (151 mg, 1.50 mmol) in TFA (2 mL) was stirred at 70° C. for 16 h. After cooling to r.t., the solvent was removed by pumping through N$_2$. The residue was diluted with water (2 mL) and extracted with EtOAc (5 mL*3). The combined organic layer was dried over anhydrous Na$_2$SO$_4$, filtered and concentrated to to afford 248f (130 mg, 56% yield) as a yellow solid. LC-MS (Method 3) $t_R$=1.22 min, m/z (M+H)$^+$=312.2.

Step 6. 8-Methoxy-2,3-dihydro-1H-benzo[d]pyrrolo[1,2-a]imidazol-7-amine (248g)

A mixture of 248f (400 mg, 1.28 mmol) and Pd/C (40 mg, 10% wt wet in 50% water) in MeOH (4 mL) was stirred at r.t. overnight under H$_2$ (50 Psi) atmosphere. The mixture was filtered and the filter cake was washed with MeOH (4 mL). The combined filtrate was concentrated and the residue was purified by Prep-HPLC (Method A) to afford 248g (60 mg, 23% yield) as a white solid. LC-MS (Method 3) $t_R$=0.85 min, m/z (M+H)$^+$=204.0.

Step 7. 6-Chloro-4-((8-methoxy-2,3-dihydro-1H-benzo[d]pyrrolo[1,2-a]imidazol-7-yl)amino)-N-methylnicotinamide (248h)

A mixture of 248g (70 mg, 0.34 mmol), 11c (71 mg, 0.34 mmol) and conc. HCl (1 drop) in EtOH (1 mL) was stirred at 80° C. for 16 h. The reaction was cooled, concentrated and purified by Prep-HPLC (Method A) to afford 248h (24 mg, 19% yield) as a yellow solid. LC-MS (Method 3) $t_R$=0.85 min, m/z (MA-H)$^+$=372.3.

Step 8. 6-(Cyclopropanecarboxamido)-4-((8-methoxy-2,3-dihydro-1H-benzo[d]pyrrolo[1,2-a]imidazol-7-yl)amino)-N-methylnicotinamide (248)

A mixture of 248h (24 mg, 0.064 mmol), cyclopropanecarboxamide (27 mg, 0.32 mmol), BrettPhos Pd G3 (12 mg, 0.012 mmol) and Cs$_2$CO$_3$ (42 mg, 0.13 mmol) in dioxane (1 mL) was stirred at 100° C. for 16 h under N$_2$ atmosphere. After cooling to r.t., the mixture was filtered and the filtrate was concentrated. The residue was purified by Prep-HPLC (Method C) to afford 248 (6 mg, 22% yield) as a white solid. LC-MS (Method 1) $t_R$=2.52 min, m/z (M+H)$^+$=421.0. $^1$H NMR (400 MHz, DMSO-d$_6$) δ 10.61 (s, 1H), 10.32 (s, 1H), 8.58-8.54 (m, 1H), 8.48 (s, 1H), 7.63 (s, 1H), 7.31 (d, J=8.4 Hz, 1H), 7.04 (d, J=8.4 Hz, 1H), 4.24 (t, J=7.2 Hz, 2H), 3.77 (s, 3H), 2.93 (t, J=7.6 Hz, 2H), 2.68-2.62 (m, 3H), 2.73-2.50 (m, 2H), 1.95-1.90 (m, 1H), 0.73-0.68 (m, 4H).

Example 249

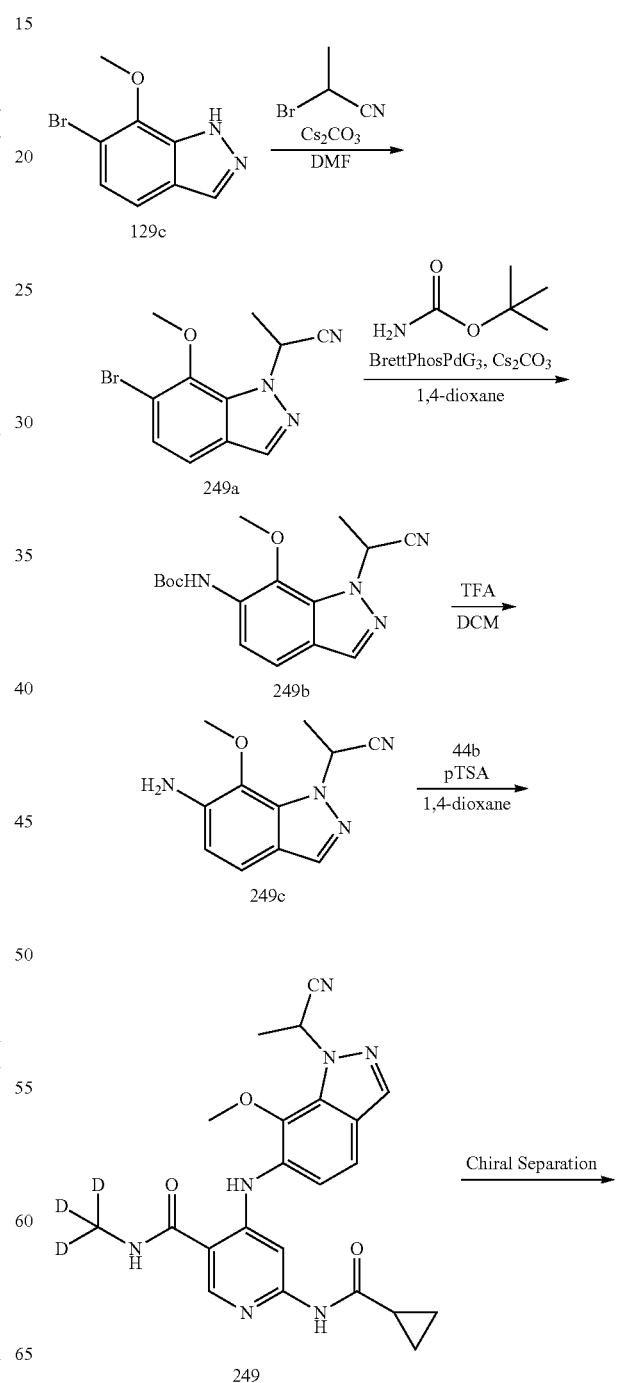

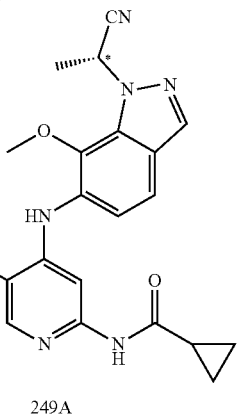

249A

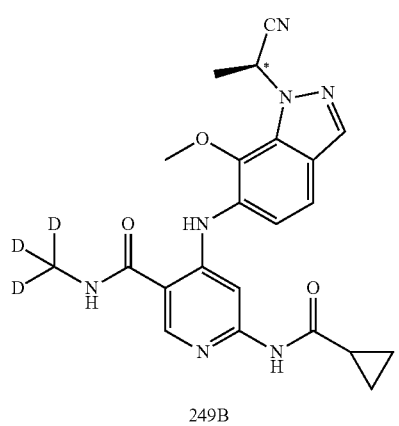 [SMILES: [2H]C([2H])([2H])NC(=O)c1cnc(NC(=O)C2CC2)cc1Nc1ccc2cnn([C@@H](C)C#N)c2c1OC]

249B

Step 1. 2-(6-Bromo-7-methoxy-1H-indazol-1-yl)propanenitrile (249a)

To a solution of 129c (300 mg, 1.32 mmol), Cs$_2$CO$_3$ (1.29 g, 3.96 mmol) in DMF (4 mL) was added 2-bromopropanenitrile (354 mg, 2.64 mmol) at r.t. The mixture was stirred at 25° C. for 2 h. The resulting solution was added H$_2$O (30 mL) and extracted with EA (30 mL). The combined organic layer was washed by brine (20 mL*3), dried over Na$_2$SO$_4$ and filtered. The filtrate was concentrated in vacuo. The residue was purified by flash chromatography on silica gel (PE/EA=10/1 to 1/1) to afford 249a (220 mg, 59% yield) as a white solid. LC-MS (Method 4) t$_R$=3.07 min, m/z (M+H)$^+$=280.1. $^1$H NMR (400 MHz, DMSO-d$_6$) δ 8.33 (s, 1H), 7.55 (d, J=8.4 Hz, 1H), 7.40 (d, J=8.8 Hz, 1H), 6.28 (q, J=6.8 Hz, 1H), 4.00 (s, 3H), 1.90 (d, J=7.2 Hz, 3H).

Step 2. Tert-butyl (1-(1-cyanoethyl)-7-methoxy-1H-indazol-6-yl)carbamate (249b)

To a solution of 249a (220 mg, 0.79 mmol), BrettPhos Pd G3 (71.2 mg, 0.079 mmol), Cs$_2$CO$_3$ (767.7 mg, 2.36 mmol) in dioxane (12 mL) was added tert-butyl carbamate (184 mg, 1.57 mmol) at r.t. The mixture was stirred at 100° C. for 16 h under nitrogen protection. The resulting solution was added H$_2$O (20 mL) and extracted by EA (30 mL). The combined organic layer was washed by brine (30 mL*3), dried over Na$_2$SO$_4$ and filtered. The filtrate was concentrated in vacuo. The residue was purified by flash chromatography on silica gel (PE/EA=10/1 to 1/1) to afford 249b (200 mg, 80% yield) as a white solid. LC-MS (Method 4) t$_R$=3.06 min, m/z (M+H)$^+$=317.2.

Step 3. 2-(6-Amino-7-methoxy-1H-indazol-1-yl)propanenitrile (249c)

To a solution of 249b (200 mg, 0.63 mmol) in DCM (10 mL) was added TFA (720.9 mg, 6.32 mmol, 0.48 mL) at r.t. The mixture was stirred at 25° C. for 2 h and concentrated to dryness. The residue was diluted with H$_2$O (10 mL), adjusted pH to 7-9 with 1 M Na$_2$CO$_3$ solution and extracted with EA (20 mL*3). The organic layer was washed with brine (10 mL), dried over Na$_2$SO$_4$ and filtered. The filtrate was concentrated and purified by flash chromatography on silica gel (PE/EA=10/1 to 1/2) to afford 249c (80 mg, 58% yield) as an off-white solid. LC-MS (Method 4) t$_R$=1.81 min, m/z (M+H)$^+$=217.1.

Step 4. 4-((1-(1-Cyanoethyl)-7-methoxy-1H-indazol-6-yl)amino)-6-(cyclopropanecarboxamido)-N-(methyl-d$_3$)nicotinamide (249)

To a solution of 249c (50 mg, 0.23 mmol), 4-methylbenzenesulfonic acid (39.9 mg, 0.23 mmol) in dioxane (10 mL) was added 44b (59.4 mg, 0.23 mmol) at r.t. The mixture was stirred at 100° C. for 16 h. The resulting solution was added H$_2$O (20 mL) and extracted with EA (30 mL). The combined organic layer was washed by brine (10 mL), dried over Na$_2$SO$_4$ and filtered. The filtrate was concentrated in vacuo. The residue was purified by Prep-HPLC (Method E) to afford 249 (30.5 mg, 30% yield) as a white solid. LC-MS (Method 4) t$_R$=2.01 min, m/z (M+H)$^+$=437.3. $^1$H NMR (400 MHz, DMSO-d$_6$) δ 10.75 (s, 1H), 10.61 (s, 1H), 8.64 (s, 1H), 8.54 (s, 1H), 8.25 (s, 1H), 7.85 (s, 1H), 7.58 (d, J=8.8 Hz, 1H), 7.22 (d, J=8.8 Hz, 1H), 6.30 (q, J=6.8 Hz, 1H), 3.83 (s, 3H), 1.99-1.91 (m, 1H), 1.88 (d, J=7.2 Hz, 3H), 0.77-0.69 (m, 4H).

Step 5. (R*)-4-((1-(1-cyanoethyl)-7-methoxy-1H-indazol-6-yl)amino)-6-(cyclopropanecarboxamido)-N-(methyl-d$_3$)nicotinamide (249A) and (S)-4-((1-(1-cyanoethyl)-7-methoxy-1H-indazol-6-yl)amino)-6-(cyclopropanecarboxamido)-N-(methyl-d$_3$)nicotinamide (249B)

249 (50 mg, 0.11 mmol) was separated by Chiral-HPLC to obtain 249A (11.6 mg, 13% yield) as a white solid and 249B (10.4 mg, 12% yield) as a white solid. 49A: LC-MS (Method 2) t$_R$=2.85 min, m/z (M+H)$^+$=437.1. $^1$H NMR (400 MHz, DMSO-d$_6$) δ 10.73 (s, 1H), 10.60 (s, 1H), 8.63 (s, 1H), 8.54 (s, 1H), 8.26 (s, 1H), 7.86 (s, 1H), 7.59 (d, J=8.4 Hz, 1H), 7.23 (d, J=8.4 Hz, 1H), 6.31 (q, J=7.2 Hz, 1H), 3.84 (s, 3H), 1.97-1.95 (m, 1H), 1.89 (d, J=7.2 Hz, 3H), 0.78-0.74 (m, 4H).

249B: LC-MS (Method 2) t$_R$=2.90 min, m/z (M+H)$^+$=437.1. $^1$H NMR (400 MHz, DMSO-d$_6$) δ 10.73 (s, 1H), 10.60 (s, 1H), 8.63 (s, 1H), 8.54 (s, 1H), 8.26 (s, 1H), 7.86 (s, 1H), 7.59 (d, J=8.4 Hz, 1H), 7.23 (d, J=8.4 Hz, 1H), 6.31 (q, J=7.2 Hz, 1H), 3.84 (s, 3H), 1.97-1.95 (m, 1H), 1.89 (d, J=7.2 Hz, 3H), 0.78-0.74 (m, 4H).

Example 250

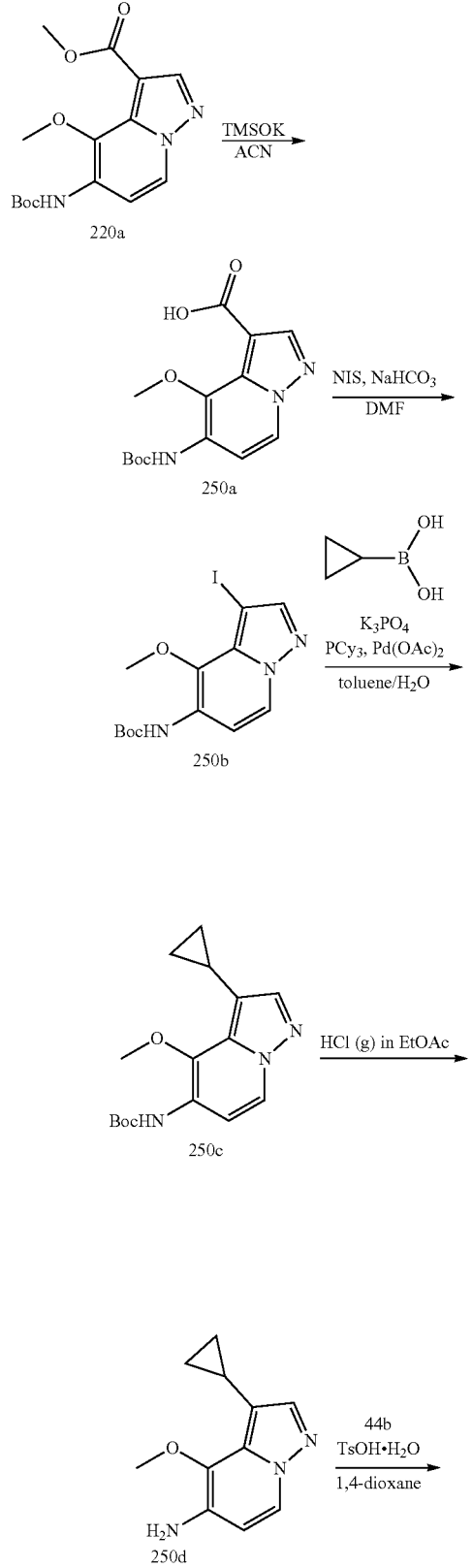

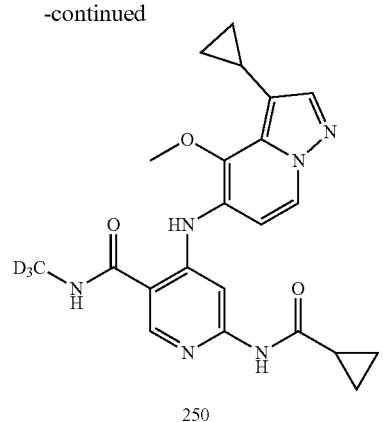

Step 1. 5-((Tert-butoxycarbonyl)amino)-4-methoxy-pyrazolo[1,5-a]pyridine-3-carboxylic acid (250a)

A mixture of 220a (1.79 g, 5.57 mmol) in ACN (20 mL) was added potassium trimethylsilanolate (2.86 g, 22.27 mmol) and stirred at 50° C. for 3 h. The mixture was concentrated and the residue was dissolved with water (10 mL). The aqueous layer was acidified with 2 M HCl to pH=2. The aqueous layer was extracted with EtOAc (30 mL*3), washed with brine (10 mL). The combined organic layer was concentrated. The residue was purified by flash chromatography on silica gel (DCM/MeOH=10/1) to afford compound 250a (1.32 g, 77% yield) as a yellow solid. LC-MS (Method 3) $t_R$=1.16 min, m/z (M+H)$^+$=308.2.

Step 2. Tert-butyl (3-iodo-4-methoxypyrazolo[1,5-a]pyridin-5-yl)carbamate (250b)

A mixture of 250a (1 g, 3.25 mmol) in DMF (10 mL) was added NaHCO$_3$(820 mg, 9.76 mmol) and NIS (952 mg, 4.23 mmol). The mixture was stirred at r.t. for 2 h and diluted with water (10 mL). The aqueous layer was extracted with EtOAc (30 mL*3). The combined organic layer was washed with brine (20 mL) and concentrated. The residue was purified by flash chromatography on silica gel (PE/EtOAc=5/1) to afford compound 250b (722 mg, 57% yield) as a blue solid. LC-MS (Method 3) $t_R$=1.32 min, m/z (M+H)$^+$=390.2.

Step 3. Tert-butyl (3-cyclopropyl-4-methoxypyra-zolo[1,5-a]pyridin-5-yl)carbamate (250c)

A mixture of 250b (200 mg, 0.51 mmol), cyclopropyl boronic acid (88 mg, 1.03 mmol), tricyclopentylphosphine (61 mg, 0.26 mmol), Pd(OAc)$_2$ (12 mg, 0.05 mmol) and K$_3$PO$_4$ (327 mg, 1.54 mmol) in toluene/H$_2$O (0.7 mL, v/v=6/1) was stirred at 90° C. under microwave for 4 h under N$_2$. After cooling to r.t., the mixture was concentrated. The residue was purified by flash chromatography on silica gel (PE/EtOAc=10/1) to afford 250c (30 mg, 19% yield) as a white solid. LC-MS (Method 3) $t_R$=1.75 min, m/z (M+H)$^+$=304.2.

Step 4. 3-Cyclopropyl-4-methoxypyrazolo[1,5-a] pyridin-5-amine hydrochloride (250d)

A mixture of 250c (30 mg, 0.10 mmol) in HCl/EtOAc (1 mL, 2 M) was stirred at 25° C. for 2 h. The formed solid was filtered. The filter cake was dried to afford compound 250d (20 mg, 84% yield) as a white solid. LC-MS (Method 3) $t_R$=1.08 min, m/z (M+H)$^+$=204.1.

Step 5. 6-(Cyclopropanecarboxamido)-4-((3-cyclopropyl-4-methoxypyrazolo[1,5-a]pyridin-5-yl)amino)-N-(methyl-d$_3$)nicotinamide (250)

A mixture of 44b (25 mg, 0.10 mmol), 250d (20 mg, 0.10 mmol) and TsOH·H$_2$O (2 mg, 0.01 mmol) in 1,4-dioxane (0.5 mL) was stirred at 100° C. for 16 h. The mixture was cooled, concentrated and the residue was purified by Prep-HPLC (Method A) to afford compound 250 (8 mg, 19% yield) as a white solid. LC-MS (Method 2) $t_R$=2.70 min, m/z (M+H)$^+$=424.1. $^1$H NMR (400 MHz, DMSO-d$_6$) δ 10.80 (s, 1H), 10.57 (s, 1H), 8.64 (s, 1H), 8.55 (s, 1H), 8.42 (d, J=7.6 Hz, 1H), 7.84 (s, 1H), 7.67 (s, 1H), 6.83 (d, J=7.6 Hz, 1H), 3.86 (s, 3H), 2.19-2.15 (m, 1H), 2.00-1.97 (m, 1H), 0.94-0.91 (m, 2H), 0.78-0.76 (m, 4H), 0.70-0.66 (m, 2H).

Example 251

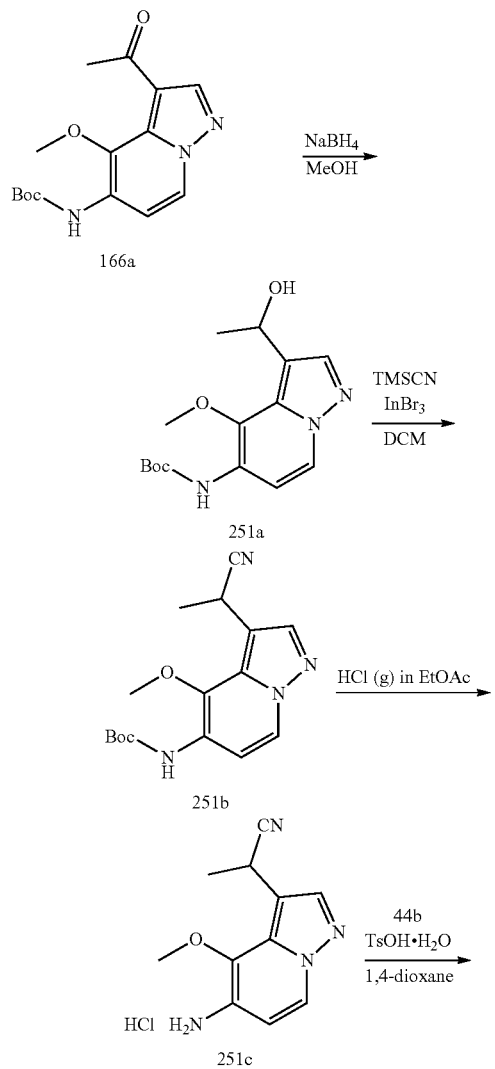

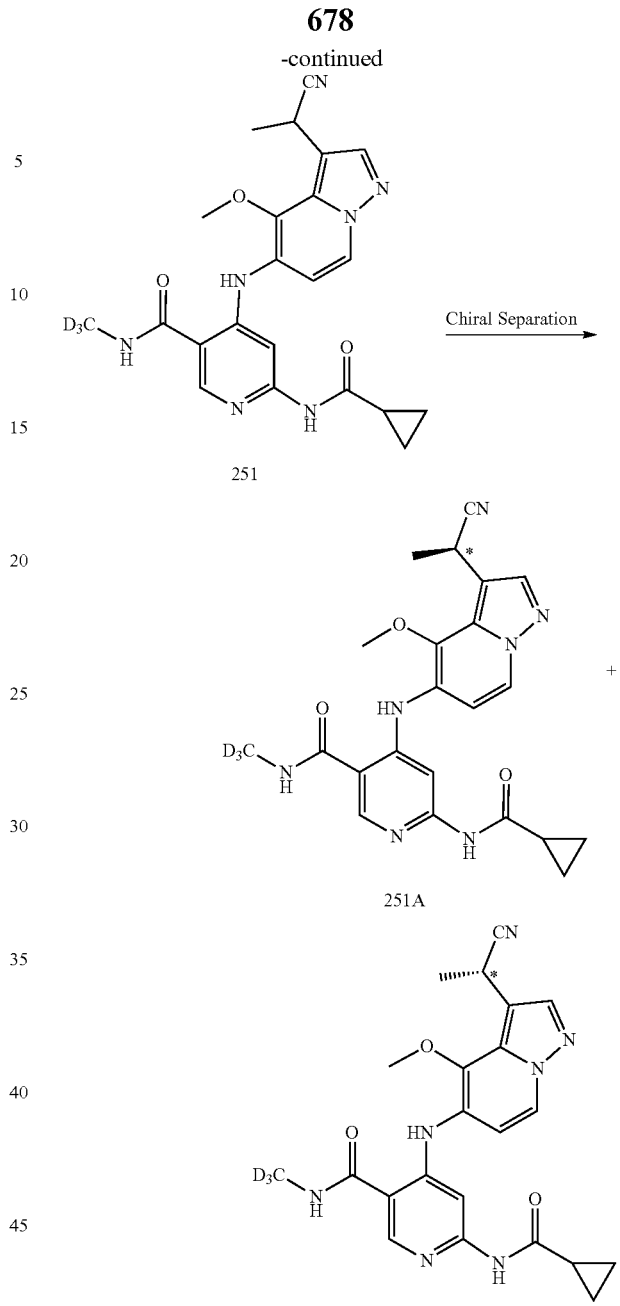

Step 1. Tert-butyl (3-(1-hydroxyethyl)-4-methoxypyrazolo[1,5-a]pyridin-5-yl)carbamate (251a)

To a mixture of 166a (300 mg, 0.98 mmol) in MeOH (3 mL) was added NaBH$_4$ (74 mg, 1.97 mmol) at 0° C. The reaction was stirred at r.t. for 2 h. The reaction mixture was diluted with ice-water (10 mL) and extracted with EtOAc (10 mL*2). The combined organic layer was dried over Na$_2$SO$_4$, filtered and concentrated to afford compound 251a (300 mg, 99% yield) as a yellow solid. $^1$H NMR (400 MHz, CDCl$_3$) δ 8.20 (d, J=7.6 Hz, 1H), 7.81 (s, 1H), 7.68 (d, J=8.0 Hz, 1H), 6.92 (s, 1H), 5.30 (q, J=6.4 Hz, 1H), 3.94 (s, 3H), 2.50 (s, 1H), 1.69 (d, J=6.4 Hz, 3H), 1.55 (s, 9H).

Step 2. Tert-butyl (3-(1-cyanoethyl)-4-methoxypyrazolo[1,5-a]pyridin-5-yl)carbamate (251b)

To a mixture of 251a (200 mg, 0.65 mmol) and InBr₃ (46 mg, 0.13 mmol) in DCM (4 mL) was added TMSCN (194 mg, 1.95 mmol) at r.t. The reaction was stirred at r.t. for 0.5 h and diluted with ice-water (5 mL). The mixture was extracted with DCM (10 mL). The separated organic layer was concentrated and the residue was purified by flash chromatography on silica gel (PE/EtOAc=4/1) to afford compound 251b (136 mg, 66% yield) as a yellow solid. ¹H NMR (400 MHz, CDCl₃) δ 8.21 (d, J=7.6 Hz, 1H), 7.90 (s, 1H), 7.71 (d, J=7.2 Hz, 1H), 6.87 (s, 1H), 4.36 (q, J=7.6 Hz, 1H), 3.92 (s, 3H), 1.74 (d, J=7.6 Hz, 3H), 1.55 (s, 9H).

Step 3. 2-(5-Amino-4-methoxypyrazolo[1,5-a]pyridin-3-yl)propanenitrile hydrochloride (251c)

A mixture of 251b (170 mg, 0.54 mmol) in HCl (g) EtOAc (3 mL, 2 M) was stirred at 30° C. for 1 h. The reaction mixture was concentrated to afford compound 251c (135 mg, 99% yield) as a yellow solid. LC-MS (Method 3) $t_R$=1.02 min, m/z (M+H)⁺=217.1.

Step 4. 4-((3-(1-Cyanoethyl)-4-methoxypyrazolo[1,5-a]pyridin-5-yl)amino)-6-(cyclopropanecarboxamido)-N-(methyl-d₃)nicotinamide (251)

A mixture of 251c (135 mg, 0.53 mmol), 44b (151 mg, 0.59 mmol) and TsOH·H₂O (51 mg, 0.27 mmol) in 1,4-dioxane (2 mL) was stirred at 100° C. for 16 h in a sealed tube. The reaction mixture was cooled, concentrated and the residue was purified by flash chromatography on silica gel (DCM/MeOH=20/1) to afford compound 251 (64 mg, 27% yield) as a white solid. LC-MS (Method 2) $t_R$=2.78 min, m/z (M+H)⁺=437.1. ¹H NMR (400 MHz, DMSO-d₆) δ 10.79 (s, 1H), 10.58 (s, 1H), 8.65 (s, 1H), 8.55 (s, 1H), 8.51 (d, J=7.6 Hz, 1H), 8.05 (s, 1H), 7.79 (s, 1H), 6.92 (d, J=7.2 Hz, 1H), 4.55 (q, J=7.2 Hz, 1H), 3.84 (s, 3H), 1.99-1.93 (m, 1H), 1.66 (d, J=7.2 Hz, 3H), 0.76-0.74 (m, 4H).

Step 5. (R*)-4-((3-(1-cyanoethyl)-4-methoxypyrazolo[1,5-a]pyridin-5-yl)amino)-6-(cyclopropanecarboxamido)-N-(methyl-d₃)nicotinamide (251A) and (S*)-4-((3-(1-cyanoethyl)-4-methoxypyrazolo[1,5-a]pyridin-5-yl)amino)-6-(cyclopropanecarboxamido)-N-(methyl-d₃)nicotinamide (251B)

251 (53 mg, 0.12 mmol) was separated by Chiral-HPLC to obtain 251A (19 mg, 36% yield) as a white solid and 251B (20 mg, 38% yield) as a white solid.

251A: LC-MS (Method 2) $t_R$=2.72 min, m/z (M+H)⁺=437.1. ¹H NMR (400 MHz, DMSO-d₆) δ 10.79 (s, 1H), 10.56 (s, 1H), 8.64 (s, 1H), 8.55 (s, 1H), 8.52 (d, J=7.2 Hz, 1H), 8.05 (s, 1H), 7.79 (s, 1H), 6.92 (d, J=7.2 Hz, 1H), 4.55 (q, J=6.8 Hz, 1H), 3.84 (s, 3H), 1.99-1.93 (m, 1H), 1.66 (d, J=7.2 Hz, 3H), 0.78-0.71 (m, 4H).

251-B: LC-MS (Method 2) $t_R$=2.72 min, m/z (M+H)⁺=437.1. ¹H NMR (400 MHz, DMSO-d₆) δ 10.79 (s, 1H), 10.56 (s, 1H), 8.64 (s, 1H), 8.55 (s, 1H), 8.52 (d, J=7.6 Hz, 1H), 8.05 (s, 1H), 7.79 (s, 1H), 6.92 (d, J=7.2 Hz, 1H), 4.55 (q, J=6.8 Hz, 1H), 3.84 (s, 3H), 1.99-1.93 (m, 1H), 1.66 (d, J=7.2 Hz, 3H), 0.78-0.71 (m, 4H).

Example 252

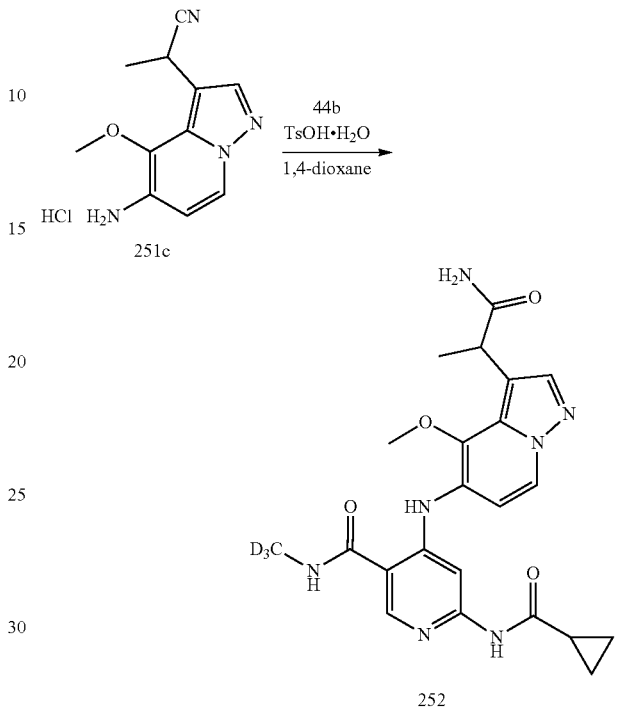

Step 1. 4-((3-(1-Amino-1-oxopropan-2-yl)-4-methoxypyrazolo[1,5-a]pyridin-5-yl)amino)-6-(cyclopropanecarboxamido)-N-(methyl-d₃)nicotinamide (252)

A mixture of 251c (135 mg, 0.53 mmol), 44b (151 mg, 0.59 mmol) and TsOH·H₂O (51 mg, 0.27 mmol) in 1,4-dioxane (2 mL) was stirred at 100° C. for 16 h in a sealed tube. The reaction mixture was cooled, concentrated and the residue was purified by flash chromatography on silica gel (DCM/MeOH=20/1) to afford the crude product (20 mg). The crude was further purified by Prep-HPLC (Method A) to afford compound 252 (7 mg, 3% yield) as a white solid. LC-MS (Method 2) $t_R$=2.20 min, m/z (M+H)⁺=455.1. ¹H NMR (400 MHz, DMSO-d₆) δ 10.77 (s, 1H), 10.50 (s, 1H), 8.62 (s, 1H), 8.53 (s, 1H), 8.43 (d, J=7.6 Hz, 1H), 7.88 (s, 1H), 7.80 (s, 1H), 7.18-7.14 (m, 1H), 6.80-6.82 (m, 2H), 4.01 (q, J=7.2 Hz, 1H), 3.78 (s, 3H), 1.98-1.93 (m, 1H), 1.44 (d, J=7.2 Hz, 3H), 0.75-0.74 (m, 4H).

Example 253

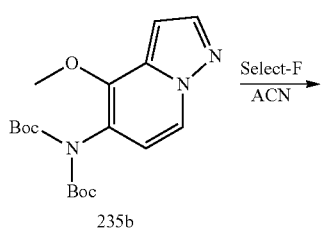

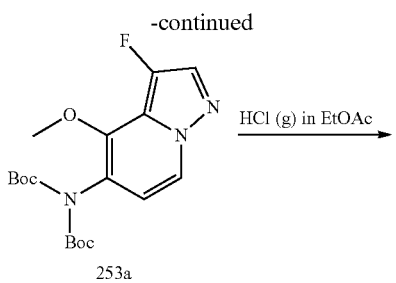

253a

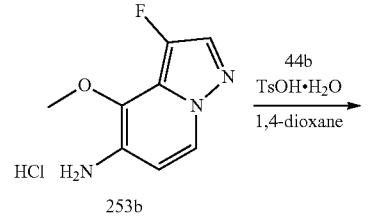

253b

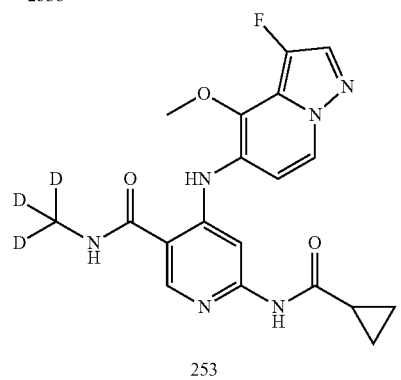

253

Step 1. Tert-butyl (tert-butoxycarbonyl)(3-fluoro-4-methoxypyrazolo[1,5-a]pyridin-5-yl)carbamate (253a)

A mixture of 235b (90 mg, 0.25 mmol) in ACN (5 mL) was cooled to 0° C. and to it was added selectfluor (88 mg, 0.25 mmol). After stirring for 3 h at r.t., the reaction mixture was concentrated under reduced pressure. The residue was purified by flash chromatography on silica gel (PE/EtOAc=3/1) to afford compound 253a (30 mg, 32% yield) as a purple solid. LC-MS (Method 3) $t_R$=1.34 min, m/z (M+H)$^+$=382.4.

Step 2. 3-Fluoro-4-methoxypyrazolo[1,5-a]pyridin-5-amine hydrochloride (253b)

A mixture of 253a (30 mg, 0.079 mmol) in HCl/EtOAc (5 mL, 2 M) was stirred for 3 h at r.t. The formed solid was filtered. The filter cake was dried to afford compound 253b (17 mg, 99% yield) as a white solid. LC-MS (Method 3) $t_R$=0.90 min, m/z (M+H)$^+$=182.3.

Step 3. 6-(Cyclopropanecarboxamido)-4-((3-fluoro-4-methoxypyrazolo[1,5-a]pyridin-5-yl)amino)-N-(methyl-d$_3$)nicotinamide (253)

To a solution of 253b (17 mg, 0.078 mmol) and 44b (20 mg, 0.078 mmol) in dioxane (1 mL) was added into TsOH·H$_2$O (3 mg, 0.016 mmol). The mixture was stirred at 100° C. for 18 h. After cooling to r.t., the reaction mixture was concentrated and the residue was purified by Prep-HPLC (Method A) to afford compound 253 (8 mg, 26% yield) as a white solid. LC-MS (Method 2) $t_R$=2.40 min, m/z (M+H)$^+$=402.1. $^1$H NMR (400 MHz, DMSO-d$_6$) δ 10.79 (s, 1H), 10.59 (s, 1H), 8.62 (s, 1H), 8.54 (s, 1H), 8.41 (d, J=7.6 Hz, 1H), 8.08 (d, J=3.2 Hz, 1H), 7.83 (s, 1H), 6.90 (d, J=7.6 Hz, 1H), 3.86 (s, 3H), 2.00-1.94 (m, 1H), 0.77-0.70 (m, 4H).

Example 254

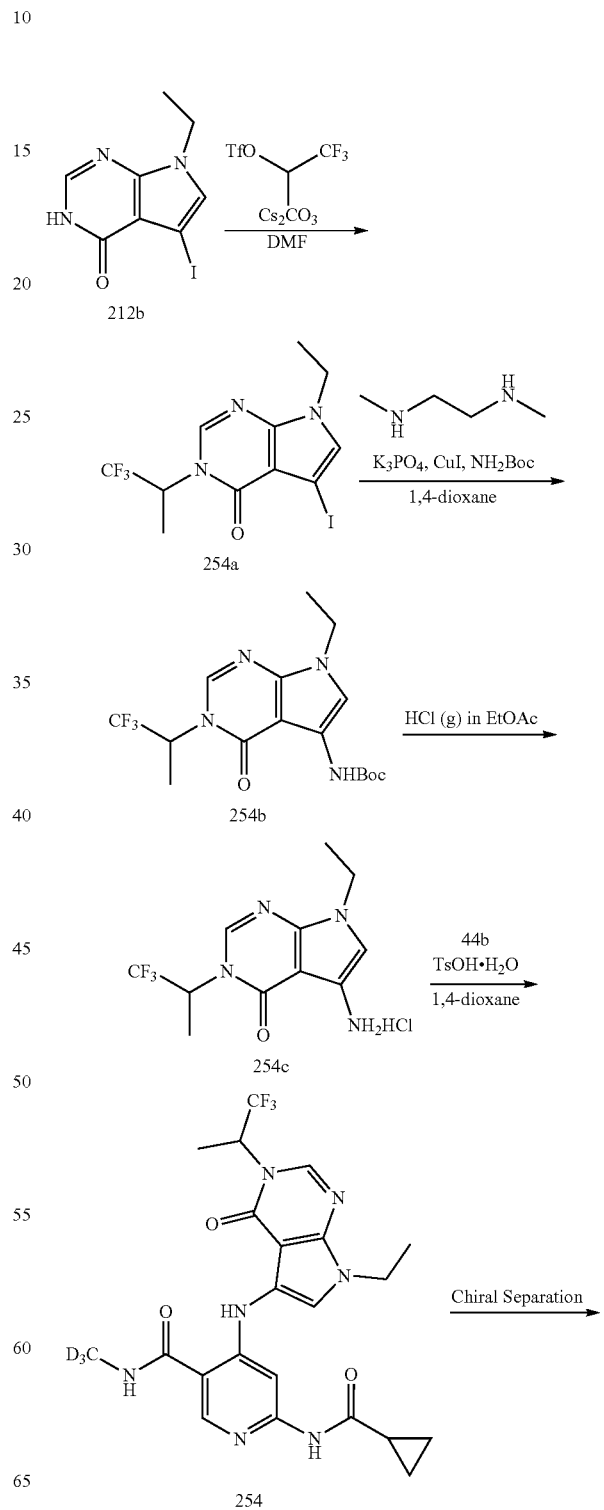

683

-continued

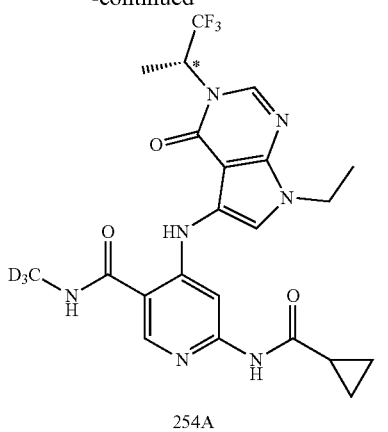

254A

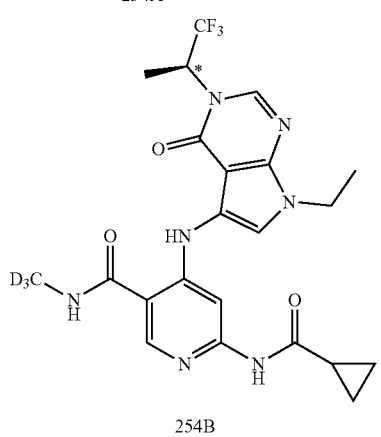

254B

Step 1. 7-Ethyl-5-iodo-3-(1,1,1-trifluoropropan-2-yl)-3H-pyrrolo[2,3-d]pyrimidin-4-(7H)-one (254a)

A mixture of 212b (1.5 g, 5.19 mmol), Cs$_2$CO$_3$ (5.07 g, 15.57 mmol) and 1,1,1-trifluoropropan-2-yl trifluoromethanesulfonate (3.83 g, 15.57 mmol) in DMF (15 mL) was stirred at 50° C. for 16 h. After cooling to r.t., the mixture was diluted with water (20 mL) and extracted with EtOAc (50 mL*3). The combined organic layer was concentrated and the residue was purified by flash chromatography on silica gel (PE/EtOAc=5/1) to afford compound 254a (415 mg, 21% yield) as a white solid. LC-MS (Method 3) t$_R$=1.32 min, m/z (M+H)$^+$=386.1.

Step 2. Tert-butyl (7-ethyl-4-oxo-3-(1,1,1-trifluoropropan-2-yl)-4,7-dihydro-3H-pyrrolo[2,3-d]pyrimidin-5-yl)carbamate (254b)

A mixture of 254a (200 mg, 0.52 mmol), tert-butyl carbamate (91 mg, 0.78 mmol), CuI (49 mg, 0.26 mmol), K$_3$PO$_4$ (331 mg, 1.56 mmol) and N,N-dimethylethane-1,2-diamine (23 mg, 0.26 mmol) in anhydrous dioxane (3 mL) was stirred at 90° C. for 18 h under N$_2$ atmosphere. After cooling to r.t., the mixture was concentrated and the residue was purified by flash chromatography on silica gel (PE/EtOAc=3/1) to afford compound 254b (140 mg, 72% yield) as a white solid. LC-MS (Method 3) t$_R$=1.45 min, m/z (M+H)$^+$=375.2.

684

Step 3. 5-Amino-7-ethyl-3-(1,1,1-trifluoropropan-2-yl)-3,7-dihydro-4H-pyrrolo[2,3-d]pyrimidin-4-one hydrochloride (254c)

A mixture of 254b (140 mg, 0.37 mmol) in HCl/EtOAc (2 mL, 2 M) was stirred at 40° C. for 2 h. The formed solid was filtered. The filter cake was dried to afford compound 254c (110 mg, 95% yield) as a yellow solid. LC-MS (Method 3) t$_R$=0.88 min, m/z (M+H)$^+$=275.3.

Step 4. 6-(Cyclopropanecarboxamido)-4-((7-ethyl-4-oxo-3-(1,1,1-trifluoropropan-2-yl)-4,7-dihydro-3H-pyrrolo[2,3-d]pyrimidin-5-yl)amino)-N-(methyl-d$_3$)nicotinamide (254)

A mixture of 254c (53 mg, 0.17 mmol), 44b (35 mg, 0.14 mmol) and TsOH·H$_2$O (6 mg, 0.034 mmol) in dioxane (0.5 mL) was stirred at 100° C. for 16 h. The reaction mixture was cooled and concentrated. The residue was purified by flash chromatography on silica gel (DCM/MeOH=95/5) to afford compound 254 (25 mg, 30% yield). LC-MS (Method 2) t$_R$=1.17 min, m/z (M+H)$^+$=495.3. $^1$H NMR (400 MHz, DMSO-d$_6$) δ 10.79 (s, 1H), 10.73 (s, 1H), 8.48 (s, 1H), 8.43 (s, 1H), 8.35 (s, 1H), 7.98 (s, 1H), 7.18 (s, 1H), 5.80-5.75 (m, 1H), 4.17 (d, J=7.2 Hz, 2H), 2.02-1.97 (m, 1H), 1.70 (d, J=7.2 Hz, 3H), 1.40 (t, J=7.2 Hz, 3H), 0.80-0.76 (m, 4H).

Step 5. (R*)-6-(cyclopropanecarboxamido)-4-((7-ethyl-4-oxo-3-(1,1,1-trifluoropropan-2-yl)-4,7-dihydro-3H-pyrrolo[2,3-d]pyrimidin-5-yl)amino)-N-(methyl-d$_3$)nicotinamide (254A) and (S*)-6-(cyclopropanecarboxamido)-4-((7-ethyl-4-oxo-3-(1,1,1-trifluoropropan-2-yl)-4,7-dihydro-3H-pyrrolo[2,3-d]pyrimidin-5-yl)amino)-N-(methyl-d$_3$) nicotinamide (254B)

254 (25 mg, 0.050 mmol) was separated by Prep-Chiral HPLC to obtain 254A (6.5 mg, 26% yield) as a white solid and 254B (6 mg, 24% yield) as a white solid.

254A: LC-MS (Method 2) t$_R$=3.21 min, m/z (M+H)$^+$=495.1. $^1$H NMR (300 MHz, DMSO-d$_6$) δ 10.84-10.76 (m, 2H), 8.53-8.49 (m, 2H), 8.39 (s, 1H), 8.00 (s, 1H), 7.23 (s, 1H), 5.84-5.80 (m, 1H), 4.23 (q, J=7.5 Hz, 2H), 2.03-1.97 (m, 1H), 1.72 (d, J=7.8 Hz, 3H), 1.41 (d, J=7.2 Hz, 3H), 0.81-0.78 (m, 4H).

254B: LC-MS (Method 2) t$_R$=3.21 min, m/z (M+H)$^+$=495.1. $^1$H NMR (300 MHz, DMSO-d$_6$) δ 10.82 (s, 1H), 10.76 (s, 1H), 8.53-8.49 (m, 2H), 8.38 (s, 1H), 8.00 (s, 1H), 7.22 (s, 1H), 5.84-5.80 (m, 1H), 4.22 (q, J=7.5 Hz, 2H), 2.06-2.01 (m, 1H), 1.72 (d, J=7.5 Hz, 3H), 1.40 (t, J=7.5 Hz, 3H), 0.88-0.75 (m, 4H).

Example 255

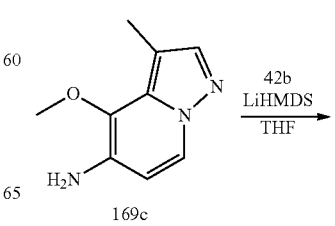

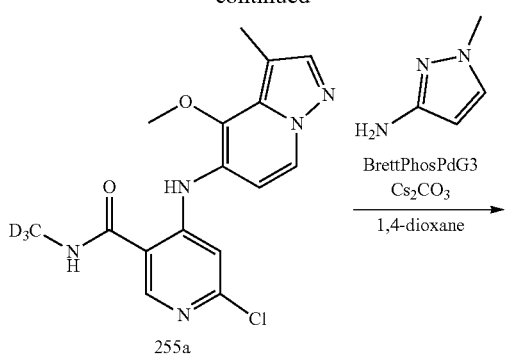

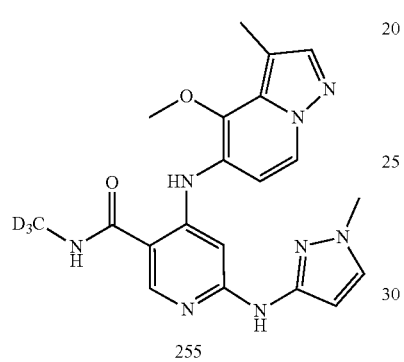

Step 1. 6-Chloro-4-((4-methoxy-3-methylpyrazolo[1,5-a]pyridin-5-yl)amino)-N-(methyl-d₃)nicotinamide (255a)

To a mixture of 169c (20 mg, 0.113 mmol) and 42b (25 mg, 0.119 mmol) in anhydrous THF (1 mL) was added LiHMDS (0.45 mL, 0.45 mmol, 1 M in THF) at 0° C. The reaction was stirred at 0° C. for 10 min and poured into ice-water (5 mL). The mixture was extracted with EtOAc (10 mL*2) and the combined organic layer was concentrated. The residue was purified by flash chromatography on silica gel (DCM/MeOH=20/1) to afford 255a (25 mg, 64% yield) as an off-white solid. ¹H NMR (400 MHz, CDCl₃) δ 10.13 (s, 1H), 8.34 (s, 1H), 8.20 (d, J=7.6 Hz, 1H), 7.71 (s, 1H), 6.81 (s, 1H), 6.58 (d, J=7.2 Hz, 1H), 6.37 (s, 1H), 3.85 (s, 3H), 2.45 (s, 3H).

Step 2. 4-((4-Methoxy-3-methylpyrazolo[1,5-a]pyridin-5-yl)amino)-N-(methyl-d₃)-6-((1-methyl-1H-pyrazol-3-yl)amino)nicotinamide (255)

A mixture of 255a (30 mg, 0.086 mmol), 1-methyl-1H-pyrazol-3-amine (42 mg, 0.43 mmol), BrettPhos Pd G3 (16 mg, 0.017 mmol) and Cs₂CO₃ (84 mg, 0.26 mmol) in 1,4-dioxane (1 mL) was stirred at 90° C. for 16 h under N₂ atmosphere. The reaction mixture was cooled, concentrated and the residue was purified by Prep-HPLC (Method A) to afford 255 (10 mg, 28% yield) as a white solid. LC-MS (Method 2) t_R=2.51 min, m/z (M+H)⁺=410.2. ¹H NMR (400 MHz, DMSO-d₆) δ 10.60 (s, 1H), 9.26 (s, 1H), 8.45 (d, J=7.6 Hz, 1H), 8.41-8.39 (m, 2H), 7.74 (s, 1H), 7.48 (d, J=2.0 Hz, 1H), 7.22 (s, 1H), 6.96 (d, J=7.6 Hz, 1H), 6.08 (s, 1H), 3.80 (s, 3H), 3.66 (s, 3H), 2.39 (s, 3H).

Example 256

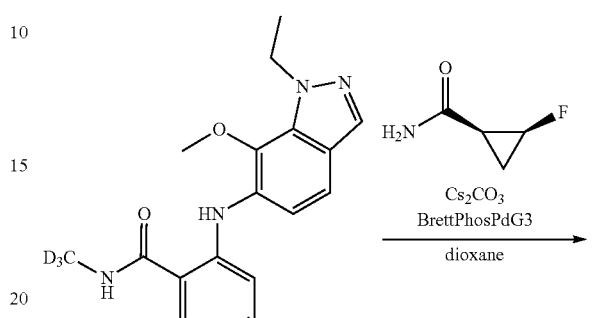

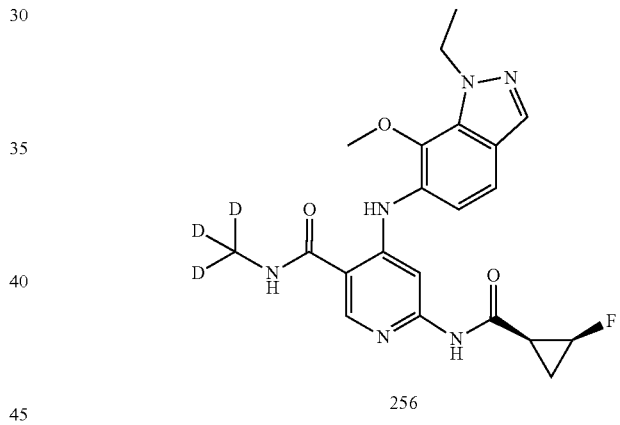

Step 1. 4-((1-Ethyl-7-methoxy-1H-indazol-6-yl)amino)-6-(cis-2-fluorocyclopropanecarboxamido)-N-(methyl-d₃)nicotinamide (256)

A mixture of 42k (50 mg, 0.14 mmol), cis-2-fluorocyclopropanecarboxamide (28 mg, 0.28 mmol), BrettPhos Pd G3 (25 mg, 0.028 mmol) and Cs₂CO₃ (224 mg, 0.69 mmol) in 1,4-dioxane (1 mL) was stirred at 90° C. for 16 h under N₂ atmosphere. The reaction mixture was cooled, concentrated and the residue was purified by Prep-HPLC (Method A) to afford 256 (4.8 mg, 8% yield) as a white solid. LC-MS (Method 2) t_R=2.49 min, m/z (M+H)⁺=430.1. ¹H NMR (400 MHz, DMSO-d₆) δ 10.73 (s, 1H), 10.56 (s, 1H), 8.60 (s, 1H), 8.52 (s, 1H), 8.03 (s, 1H), 7.82 (s, 1H), 7.52 (d, J=8.4 Hz, 1H), 7.11 (d, J=8.8 Hz, 1H), 4.96-4.75 (m, 1H), 4.55 (q, J=7.2 Hz, 2H), 3.89 (s, 3H), 2.18-2.11 (m, 1H), 1.57-1.47 (m, 1H), 1.40 (t, J=7.2 Hz, 3H), 1.35-1.06 (m, 1H).

Example 257

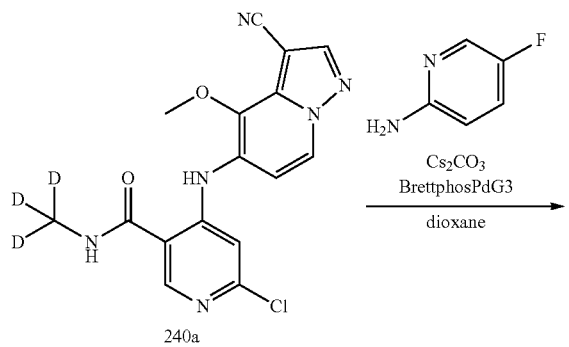

Step 1. 4-((3-Cyano-4-methoxypyrazolo[1,5-a]pyridin-5-yl)amino)-6-((5-fluoropyridin-2-yl)amino)-N-(methyl-d₃)nicotinamide (257)

A mixture of 240a (35 mg, 0.097 mmol), 5-fluoropyridin-2-amine (22 mg, 0.19 mmol), Cs₂CO₃ (63 mg, 0.19 mmol) and BrettPhos Pd G3 (18 mg, 0.019 mmol) in dioxane (0.5 mL) was stirred at 90° C. under N₂ atmosphere for 12 h. The reaction mixture was cooled, concentrated and purified by flash chromatography (DCM/MeOH=20/1) to afford compound 257 (13 mg, 31% yield) as a white solid. LC-MS (Method 2) $t_R$=2.66 min, m/z (M+H)⁺=436.1. ¹H NMR (400 MHz, DMSO-db) δ 11.16 (s, 1H), 10.02 (s, 1H), 8.90 (d, J=7.6 Hz, 1H), 8.63 (s, 1H), 8.60-8.53 (m, 2H), 8.29 (s, 1H), 7.84 (s, 1H), 7.70-7.65 (m, 1H), 7.58-7.56 (m, 1H), 7.49 (d, J=7.6 Hz, 1H), 3.92 (s, 3H).

Example 258

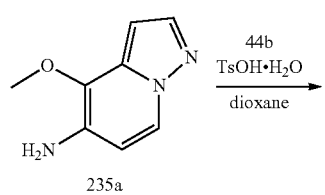

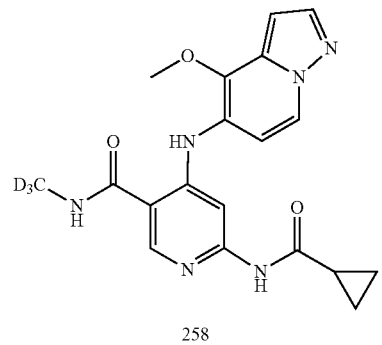

Step 1. 6-(Cyclopropanecarboxamido)-4-((4-methoxypyrazolo[1,5-a]pyridin-5-yl)amino)-N-(methyl-d₃)nicotinamide (258)

A solution of 235a (16.3 mg, 0.10 mmol), 44b (26 mg, 0.10 mmol) and TsOH·H₂O (4 mg, 0.02 mmol) in dioxane (0.5 mL) was stirred at 100° C. for 12 h. After cooling to r.t., the reaction mixture was concentrated and the residue was purified by flash chromatography on silica gel (DCM/MeOH=20/1) to afford compound 258 (4 mg, 10% yield) as a white solid. LC-MS (Method 2) $t_R$=2.21 min, m/z (M+H)⁺=384.1. ¹H NMR (400 MHz, DMSO-d₆) δ 10.76 (s, 1H), 10.51 (s, 1H), 8.60 (s, 1H), 8.52 (s, 1H), 8.51 (d, J=7.2 Hz, 1H), 7.98 (d, J=2.4 Hz, 1H), 7.82 (s, 1H), 6.90 (d, J=7.2 Hz, 1H), 6.70 (d, J=2.4 Hz, 1H), 3.92 (s, 3H), 1.98-1.95 (m, 1H), 0.76-0.74 (m, 4H).

Example 259

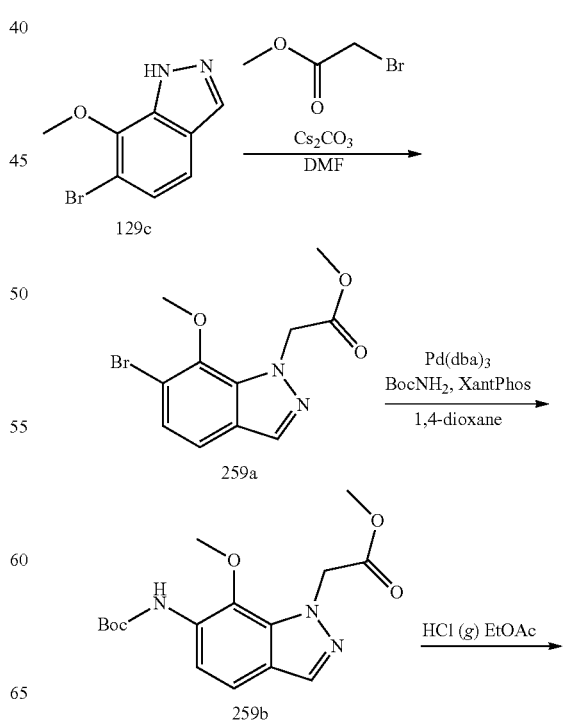

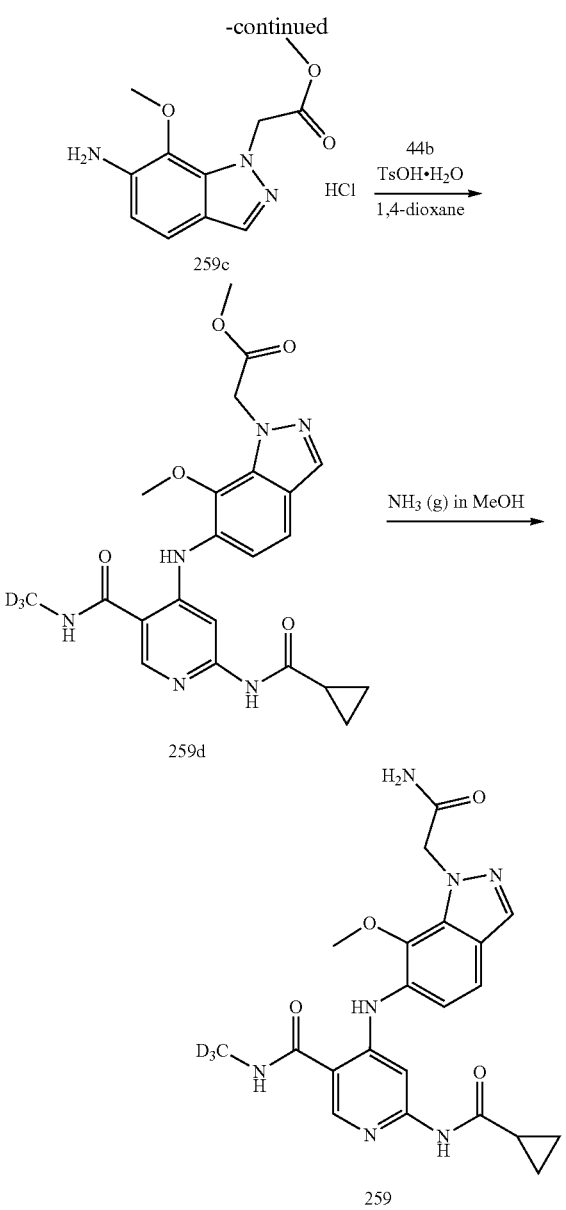

Step 1. Methyl 2-(6-bromo-7-methoxy-1H-indazol-1-yl)acetate (259a)

A mixture of 129c (1.1 g, 4.84 mmol), Cs$_2$CO$_3$ (3.16 g, 9.69 mmol) and methyl bromoacetate (1.11 g, 7.27 mmol) in DMF (10 mL) was stirred at 40° C. for 6 h. After cooling to r.t., the mixture was filtered and the filtrate was diluted with water (20 mL). The aqueous layer was extracted with EtOAc (30 mL*3) and the combined organic layer was washed with brine (30 mL*3), concentrated and purified by flash chromatography on silica gel (PE/EtOAc=2/1) to afford compound 259a (568 mg, 39% yield) as a yellow solid. LC-MS (Method 3) t$_R$=1.31 min, m/z (M+H)$^+$=299.0.

Step 2. Methyl 2-(6-((tert-butoxycarbonyl)amino)-7-methoxy-1H-indazol-1-yl)acetate (259b)

A mixture of 259a (324 mg, 1.08 mmol), BocNH$_2$ (254 mg, 2.17 mmol), Pd$_2$(dba)$_3$ (198 mg, 0.22 mmol), Xantphos (125 mg, 0.22 mmol) and Cs$_2$CO$_3$ (706 mg, 2.17 mmol) in 1,4-dioxane (10 mL) was stirred at 100° C. overnight under N$_2$ atmosphere. The mixture was cooled, concentrated and the residue was purified by flash chromatography on silica gel (PE/EtOAc=2/1) to afford compound 259b (350 mg, 96% yield) as a yellow solid. LC-MS (Method 3) t$_R$=1.27 min, m/z (M+H)$^+$=336.2.

Step 3. Methyl 2-(6-amino-7-methoxy-1H-indazol-1-yl)acetate hydrochloride (259c)

A mixture of 259b (350 mg, 1.04 mmol) in HCl/EtOAc (2 M, 10 mL) was stirred at r.t. for 4 h. The mixture was filtered and the filter cake was dried to afford compound 259c (251 mg, 88% yield) as a yellow solid. LC-MS (Method 3) t$_R$=0.90 min, m/z (M+H)$^+$=236.1.

Step 4. Methyl 2-(6-((2-(cyclopropanecarboxamido)-5-((methyl-d$_3$)carbamoyl)pyridin-4-yl)amino)-7-methoxy-1H-indazol-1-yl)acetate (259d)

A mixture of 259c (250 mg, 0.92 mmol), 44b (201 mg, 0.78 mmol) and TsOH·H$_2$O (35 mg, 0.18 mmol) in 1,4-dioxane (5 mL) was stirred at 90° C. overnight. The mixture was cooled, concentrated and the residue was purified by flash chromatography on silica gel (DCM/MeOH=94/6) to afford compound 259d (200 mg, 47% yield) as a brown solid. LC-MS (Method 3) t$_R$=0.98 min, m/z (M+H)$^+$=456.4.

Step 5. 4-((1-(2-Amino-2-oxoethyl)-7-methoxy-1H-indazol-6-yl)amino)-6-(cyclopropanecarboxamido)-N-(methyl-d$_3$)nicotinamide (259)

A mixture of 259d (230 mg, 0.50 mmol) and sat. NH$_3$ (g) in MeOH (20 mL) was stirred at 45° C. for 4 days. The mixture was concentrated to afford the crude product (200 mg, 90) as a yellow solid. 20 mg of the crude product was purified by Prep-HPLC (Method A) to afford compound 259 (9 mg, 41% yield) as a white solid. LC-MS (Method 2) t$_R$=2.17 min, m/z (M+H)$^+$=441.1. $^1$H NMR (400 MHz, DMSO-d$_6$) δ 10.69 (s, 1H), 10.52 (s, 1H), 8.59 (s, 1H), 8.52 (s, 1H), 8.03 (s, 1H), 7.87 (s, 1H), 7.52 (s, 1H), 7.51 (d, J=8.4 Hz, 1H), 7.20 (s, 1H), 7.12 (d, J=8.4 Hz, 1H), 5.11 (s, 2H), 3.73 (s, 3H), 1.96-1.93 (m, 1H), 0.75-0.73 (m, 4H).

Example 260

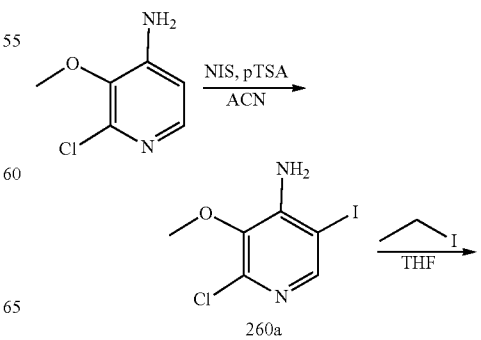

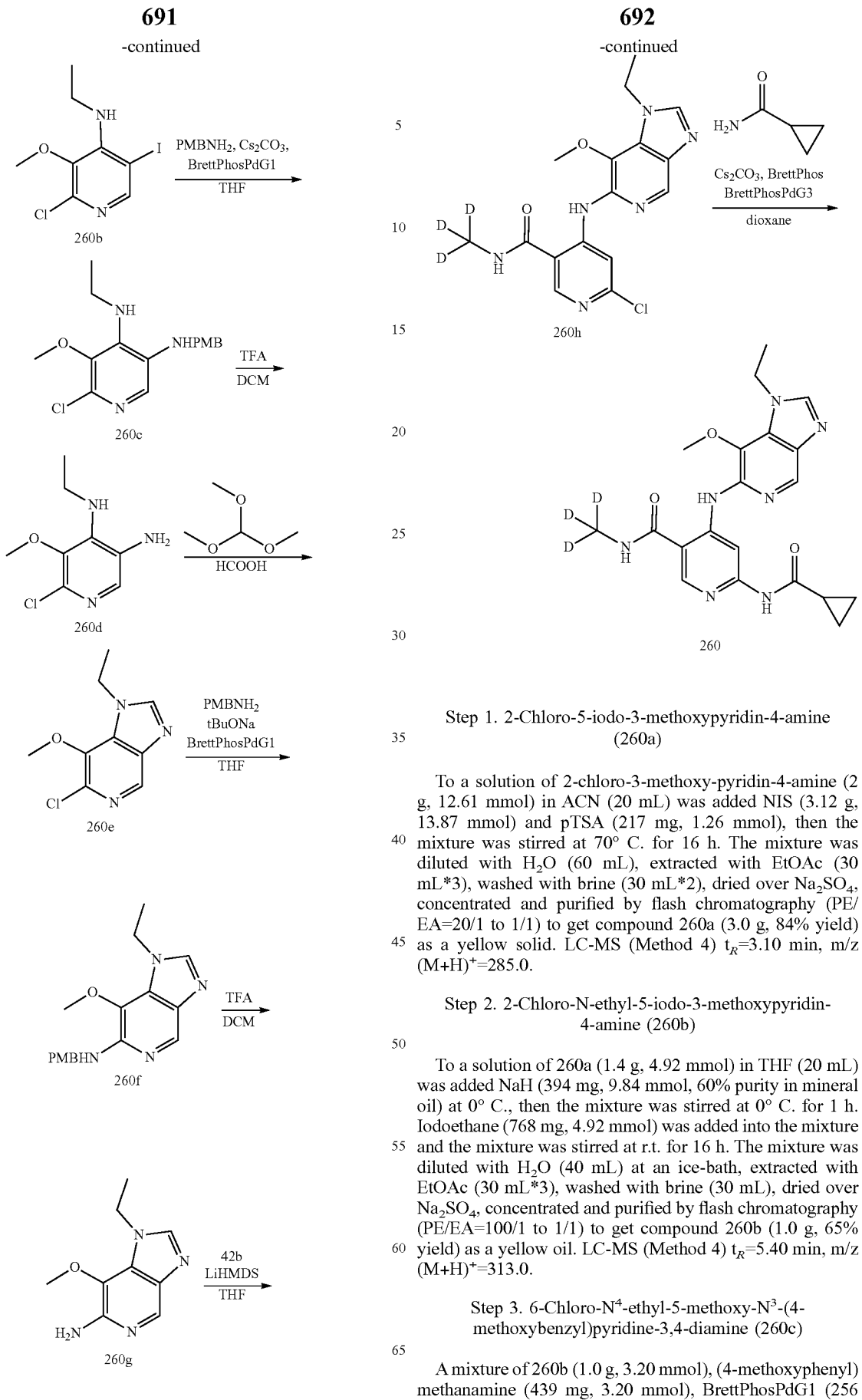

Step 1. 2-Chloro-5-iodo-3-methoxypyridin-4-amine (260a)

To a solution of 2-chloro-3-methoxy-pyridin-4-amine (2 g, 12.61 mmol) in ACN (20 mL) was added NIS (3.12 g, 13.87 mmol) and pTSA (217 mg, 1.26 mmol), then the mixture was stirred at 70° C. for 16 h. The mixture was diluted with H$_2$O (60 mL), extracted with EtOAc (30 mL*3), washed with brine (30 mL*2), dried over Na$_2$SO$_4$, concentrated and purified by flash chromatography (PE/EA=20/1 to 1/1) to get compound 260a (3.0 g, 84% yield) as a yellow solid. LC-MS (Method 4) t$_R$=3.10 min, m/z (M+H)$^+$=285.0.

Step 2. 2-Chloro-N-ethyl-5-iodo-3-methoxypyridin-4-amine (260b)

To a solution of 260a (1.4 g, 4.92 mmol) in THF (20 mL) was added NaH (394 mg, 9.84 mmol, 60% purity in mineral oil) at 0° C., then the mixture was stirred at 0° C. for 1 h. Iodoethane (768 mg, 4.92 mmol) was added into the mixture and the mixture was stirred at r.t. for 16 h. The mixture was diluted with H$_2$O (40 mL) at an ice-bath, extracted with EtOAc (30 mL*3), washed with brine (30 mL), dried over Na$_2$SO$_4$, concentrated and purified by flash chromatography (PE/EA=100/1 to 1/1) to get compound 260b (1.0 g, 65% yield) as a yellow oil. LC-MS (Method 4) t$_R$=5.40 min, m/z (M+H)$^+$=313.0.

Step 3. 6-Chloro-N$^4$-ethyl-5-methoxy-N$^3$-(4-methoxybenzyl)pyridine-3,4-diamine (260c)

A mixture of 260b (1.0 g, 3.20 mmol), (4-methoxyphenyl)methanamine (439 mg, 3.20 mmol), BrettPhosPdG1 (256 mg, 0.32 mmol), Cs₂CO₃ (2.61 g, 8.00 mmol) in THF (20 mL) was stirred at 50° C. for 48 h under N₂. The mixture was diluted H₂O (60 mL), extracted with EtOAc (50 mL*3), washed with brine (50 mL), dried over Na₂SO₄, concentrated and purified by flash chromatography (PE/EA=50/1 to 1/1) to get compound 260c (700 mg, 68% yield) as a yellow oil. LC-MS (Method 4) $t_R$=2.85 min, m/z (M+H)⁺=322.2.

Step 4. 6-Chloro-N⁴-ethyl-5-methoxypyridine-3,4-diamine (260d)

To a solution of 260c (700 mg, 2.18 mmol) in DCM (10 mL) was added TFA (3 mL), and the mixture was stirred at r.t. for 16 h. The mixture was concentrated and diluted with H₂O (30 mL), adjusted to pH>7 with aq Na₂CO₃ and extracted with EtOAc (30 mL*3). The combined organic layer was washed with brine (50 mL*2), dried over Na₂SO₄, concentrated and purified by flash chromatography (DCM/MeOH=100/1 to 10/1) to get compound 260d (300 mg, 68% yield) as a yellow solid. LC-MS (Method 4) $t_R$=1.22 min, m/z (M+H)⁺=202.1.

Step 5. 6-Chloro-1-ethyl-7-methoxy-1H-imidazo[4,5-c]pyridine (260e)

To a solution of 260d (300 mg, 1.49 mmol) in trimethoxymethane (1.58 g, 14.88 mmol, 1.63 mL) was added formic acid (71 mg, 1.49 mmol), then the mixture was stirred at 100° C. for 1 h. The mixture was concentrated and diluted with H₂O (20 mL), extracted with EtOAc (15 mL*3), washed with brine (15 mL), dried over Na₂SO₄, concentrated and purified by flash chromatography (PE/EA=20/1 to 1/2) to get compound 260e (200 mg, 64% yield) as a yellow solid. LC-MS (Method 4) $t_R$=1.95 min, m/z (M+H)⁺=212.1.

Step 6. 1-Ethyl-7-methoxy-N-(4-methoxybenzyl)-1H-imidazo[4,5-c]pyridin-6-amine (260f)

A mixture of 260e (140 mg, 0.66 mmol), (4-methoxyphenyl)methanamine (136 mg, 0.99 mmol), BrettPhosPdG1 (53 mg, 0.066 mmol), tBuONa (191 mg, 1.98 mmol) in THF (2 mL) was stirred at 70° C. for 24 h. The mixture was concentrated and purified by flash chromatography (DCM/MeOH=100/1 to 20/1) to get compound 260f (120 mg, 58% yield) as a yellow oil. LC-MS (Method 4) $t_R$=1.71 min, m/z (M+H)⁺=313.2.

Step 7. 1-Ethyl-7-methoxy-1H-imidazo[4,5-c]pyridin-6-amine (260g)

To a solution of 260f (120 mg, 0.38 mmol) in DCM (1 mL) was added TFA (2 mL), and the mixture was stirred at r.t. for 24 h. The mixture was concentrated and diluted with H₂O (20 mL), adjusted to pH>7 with aq Na₂CO₃ and extracted with EtOAc (20 mL*3). The combined organic layer was washed with brine (30 mL*2), dried over Na₂SO₄, concentrated and purified by flash chromography (DCM/MeOH=100/1 to 5/1) to get compound 260g (60 mg, 81% yield) as a yellow solid. LC-MS (Method 4) $t_R$=0.38 min, m/z (M+H)⁺=193.1.

Step 8. 6-Chloro-4-((1-ethyl-7-methoxy-1H-imidazo[4,5-c]pyridin-6-yl)amino)-N-(methyl-d₃)nicotinamide (260h)

To a solution of 260g (50 mg, 0.26 mmol), 42b (60 mg, 0.29 mmol) in THF (1 mL) was added LiHMDS (1 mL, 1.00 mmol, 1 M in THF) at 0° C., then the mixture was stirred at r.t. for 16 h. The mixture was diluted with H₂O (10 mL) and extracted with EtOAc (10 mL*3). The combined organic layer was washed with brine (20 mL), dried over Na₂SO₄, concentrated and purified by flash chromatography (DCM/MeOH=100/1 to 20/1) to get compound 260h (60 mg, 63% yield) as a yellow solid. LC-MS (Method 4) $t_R$=1.98 min, m/z (M+H)⁺=364.2.

Step 9. 6-(Cyclopropanecarboxamido)-4-((1-ethyl-7-methoxy-1H-imidazo[4,5-c]pyridin-6-yl)amino)-N-(methyl-d₃)nicotinamide (260)

A mixture of 260h (40 mg, 0.11 mmol), cyclopropanecarboxamide (94 mg, 1.10 mmol), BrettPhos (6 mg, 0.011 mmol), BrettPhos Pd G3 (10 mg, 0.011 mmol), Cs₂CO₃ (107 mg, 0.33 mmol) in DMA (1.5 mL) was stirred at 130° C. at M.W. for 1 h under N₂. The mixture was concentrated and purified by Prep-HPLC (Method E) to get compound 260 (15.8 mg, 35% yield) as a pale yellow solid. LC-MS (Method 4) $t_R$=1.64 min, m/z (M+H)⁺=413.3. ¹H NMR (400 MHz, DMSO-d₆) δ 11.46 (s, 1H), 10.64 (s, 1H), 9.09 (s, 1H), 8.59 (s, 1H), 8.51 (s, 1H), 8.46 (s, 1H), 8.26 (s, 1H), 4.33 (q, J=7.2 Hz, 2H), 3.85 (s, 3H), 1.97-1.95 (m, 1H), 1.41 (t, J=7.2 Hz, 3H), 0.77-0.73 (m, 4H).

Example 261

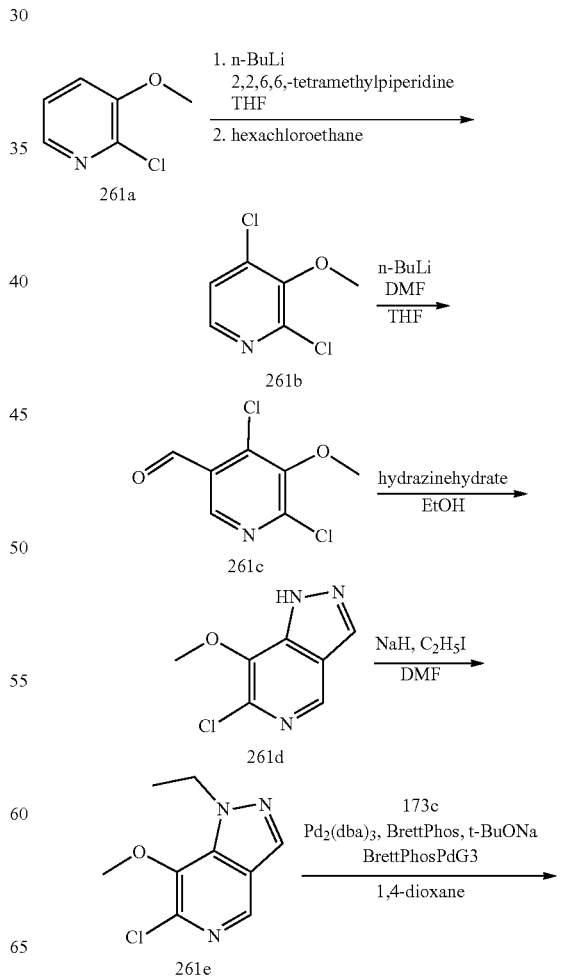

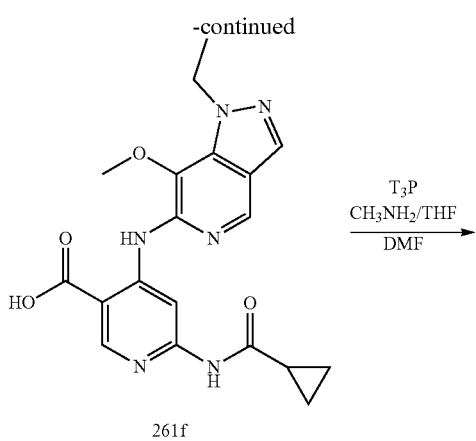

Step 1. 2,4-Dichloro-3-methoxypyridine (261b)

To a solution of n-BuLi (5.5 mL, 13.93 mmol, 2.5 M in THF) in THF (25 mL) was added 2,2,6,6-tetramethylpiperidine (2.3 g, 16.72 mmol) at −78° C. The reaction mixture was stirred at −78° C. for 15 min. Then to the reaction mixture was added a solution of 261a (2.0 g, 13.93 mmol) in THF (25 mL). The reaction mixture was stirred at −78° C. for 4 h. A solution of hexachloroethane (6.6 g, 27.86 mmol) in THF (50 mL) was added dropwise to the reaction and the temperature was kept below −60° C. After stirring for another 2 h at −78° C., the reaction mixture was quenched with sat. NH₄Cl (20 mL), diluted with water (40 mL) and extracted with EtOAc (30 mL*3). The organic layer was washed with brine (20 mL), dried over Na₂SO₄, filtered and concentrated. The residue was purified by flash chromatography on silica gel (PE/EtOAc=10/1) to afford compound 261b (700 mg, 28% yield) as a yellow oil. ¹H NMR (400 MHz, CDCl₃) δ 8.06 (d, J=5.2 Hz, 1H), 7.29 (d, J=5.6 Hz, 1H), 3.95 (s, 3H).

Step 2. 4,6-Dichloro-5-methoxynicotinaldehyde (261c)

To a solution of n-BuLi (9.4 mL, 23.59 mmol, 2.5 M in THF) in THF (30 mL) was added 261b (2.8 g, 15.73 mmol) at −78° C. After stirring at −78° C. for 30 min, to the reaction mixture was added anhydrous DMF (1.7 g, 23.59 mmol) at −78° C. After stirring for 2 h at −78° C., the reaction was quenched with sat. NH₄Cl (20 mL) and extracted with EtOAc (100 mL). The organic layer was washed with brine (20 mL), dried over Na₂SO₄, filtered and concentrated. The residue was purified by flash chromatography on silica gel (PE/EtOAc=5/1) to afford compound 261c (2.0 g, 61% yield) as a white solid. ¹H NMR (400 MHz, DMSO-d₆) δ 10.25 (s, 1H), 8.60 (s, 1H), 3.93 (s, 3H).

Step 3. 6-Chloro-7-methoxy-1H-pyrazolo[4,3-c]pyridine (261d)

A mixture of 261c (1.5 g, 7.28 mmol) and hydrazine hydrate (3.6 g, 21.84 mmol, 30% wt in water) in EtOH (20 mL) was stirred at 100° C. for 8 h. The reaction mixture was concentrated. The residue was purified by flash chromatography on silica gel (PE/EtOAc=3/1) to afford compound 261d (300 mg, 22% yield) as a white solid. ¹H NMR (400 MHz, DMSO-d₆) δ 13.95 (s, 1H), 8.67 (s, 1H), 8.37 (s, 1H), 4.04 (s, 3H).

Step 4. 6-Chloro-1-ethyl-7-methoxy-1H-pyrazolo[4,3-c]pyridine (261e)

To a mixture of 261d (740 mg, 4.03 mmol) in DMF (10 mL) was added NaH (322 mg, 8.06 mmol, 60% purity in mineral oil) at 0° C. The reaction mixture was stirred at 0° C. for 30 min. Iodoethane (2.5 g, 16.12 mmol) was added to the reaction at 0° C. After stirring at 30° C. for 1 h, the reaction was quenched with H₂O (10 mL) and extracted with EtOAc (20 mL*3). The combined organic layer was washed with brine (10 mL), dried over Na₂SO₄, filtered and concentrated. The residue was purified by flash chromatography on silica gel (PE/EtOAc=3/1) to afford compound 261e (410 mg, 48% yield) as a yellow oil. ¹H NMR (300 MHz, DMSO-d₆) δ 8.72 (s, 1H), 8.38 (s, 1H), 4.52 (q, J=7.2 Hz, 2H), 4.02 (s, 3H), 1.46 (t, J=7.2 Hz, 3H).

Step 5. 6-(Cyclopropanecarboxamido)-4-((1-ethyl-7-methoxy-1H-pyrazolo[4,3-c]pyridin-6-yl)amino)nicotinic acid (261f)

A mixture of 261e (70 mg, 0.33 mmol), 173c (86 mg, 0.36 mmol), Pd₂(dba)₃ (15 mg, 0.02 mmol), BrettPhos (27 mg, 0.05 mmol), t-BuONa (48 mg, 0.50 mmol) and BrettPhos Pd G3 (15 mg, 0.02 mmol) in 1,4-dioxane (1 mL) was stirred at 120° C. for 36 h under N₂ atmosphere. The reaction mixture was cooled and concentrated. The residue was purified by flash chromatography on silica gel (DCM/MeOH=15/1) to afford the crude compound. The crude compound was purified by Prep-HPLC (Method A) to afford compound 261f (15 mg, 11% yield) as a yellow solid. LC-MS (Method 3) $t_R$=1.06 min, m/z (M+H)⁺=397.4.

Step 6. 6-(Cyclopropanecarboxamido)-4-((1-ethyl-7-methoxy-1H-pyrazolo[4,3-c]pyridin-6-yl)amino)-N-methylnicotinamide (261)

A mixture of 261f (15 mg, 0.04 mmol) and T₃P (60 mg, 0.19 mmol, 50% wt in DMF) in DMF (0.5 mL) was stirred at r.t. for 2 h. Then CH₃NH₂ (0.49 mL, 0.49 mmol, 1 M in THF) was added to the reaction mixture. After stirring at 35° C. for 22 h, the reaction mixture was filtered. The filtrate was concentrated. The residue was purified by Prep-HPLC (Method A) to afford compound 261 (1.7 mg, 11% yield) as a yellow solid. LC-MS (Method 1) $t_R$=3.53 min, m/z (M+H)⁺=410.0. ¹H NMR (400 MHz, DMSO-d₆) δ 11.60 (s, 1H), 10.70 (s, 1H), 9.20 (s, 1H), 8.68-8.66 (m, 1H), 8.65 (s, 1H), 8.55 (s, 1H), 8.22 (s, 1H), 4.52 (q, J=6.8 Hz, 2H), 3.90

(s, 3H), 2.82 (d, J=4.4 Hz, 3H), 2.02-1.99 (m, 1H), 1.43 (t, J=7.2 Hz, 3H), 0.87-0.78 (m, 4H).

Example 262

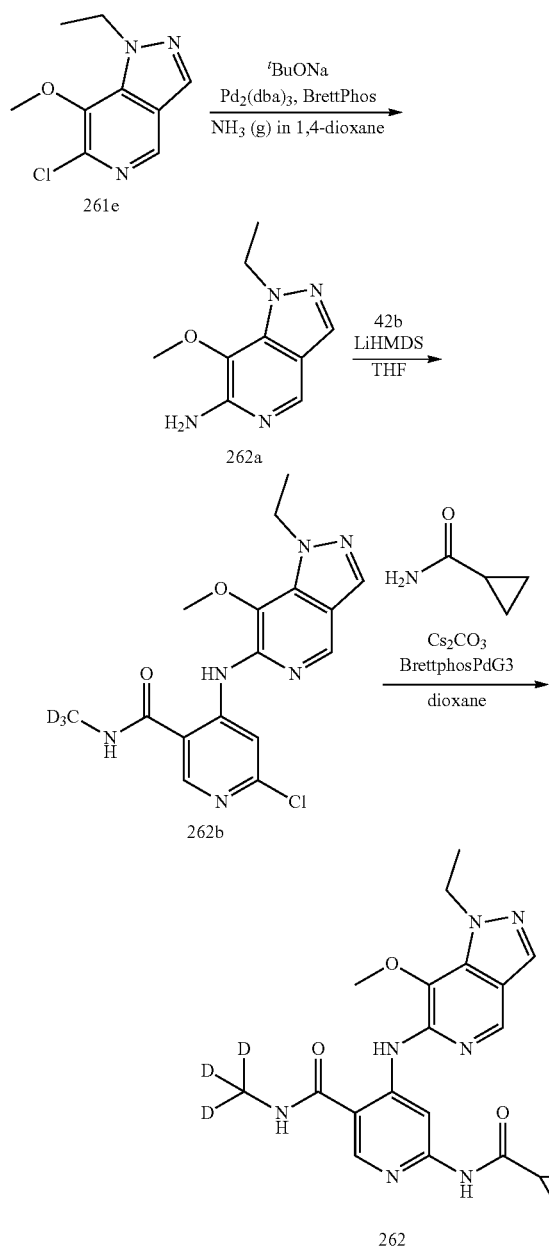

Step 1. 1-Ethyl-7-methoxy-1H-pyrazolo[4,3-c]pyridin-6-amine (262a)

A mixture of 261e (270 mg, 1.2 mmol), Pd$_2$(dba)$_3$ (11 mg, 0.0123 mmol), BrettPhos (34 mg, 0.064 mmol), tBuONa (183 mg, 1.9 mmol) in sat. NH$_3$/dioxane (3 mL) was stirred at 100° C. for 10 h. The mixture was concentrated. The residue was purified by Prep-HPLC (Method A) to get compound 262a (60 mg, 24% yield) as a white solid. LC-MS (Method 3) t$_R$=1.19 min, m/z (M+H)$^+$=193.2.

Step 2. 6-Chloro-4-((1-ethyl-7-methoxy-1H-pyrazolo[4,3-c]pyridin-6-yl)amino)-N-(methyl-d$_3$)nicotinamide (262b)

To a solution of 262a (150 mg, 0.78 mmol) and 42b (178 mg, 0.86 mmol) in THF (3 mL) was added LiHMDS (3.1 mL, 3.1 mmol, 1 M in THF) at −40° C. The reaction was stirred at −40° C. to r.t. for 1 h and quenched with H$_2$O (2 mL). The organic solvent was evaporated under reduced pressure. The formed solid was collected by filtering and was dried to afford compound 262b (90 mg, 32% yield) as a red solid. LC-MS (Method 3) t$_R$=1.25 min, m/z (M+H)$^+$=364.2.

Step 3. 6-(Cyclopropanecarboxamido)-4-((1-ethyl-7-methoxy-1H-pyrazolo[4,3-c]pyridin-6-yl)amino)-N-(methyl-d$_3$)nicotinamide (262)

A mixture of 262b (70 mg, 0.19 mmol), cyclopropanecarboxamide (82 mg, 0.96 mmol), BrettPhos Pd G3 (35 mg, 0.038 mmol) and Cs$_2$CO$_3$ (125 mg, 0.38 mmol) in 1,4-dioxane (1 mL) was stirred at 90° C. overnight under N$_2$ atmosphere. After cooling to r.t., the mixture was concentrated. The residue was purified by flash chromatography on silica gel (DCM/MeOH=20/1) to afford compound 262 (25 mg, 32% yield) as a white solid. LC-MS (Method 2) t$_R$=2.72 min, m/z (M+H)$^+$=413.1. $^1$H NMR (400 MHz, DMSO-d$_6$) δ 11.61 (s, 1H), 10.70 (s, 1H), 9.20 (s, 1H), 8.65 (s, 1H), 8.64 (s, 1H), 8.55 (s, 1H), 8.23 (s, 1H), 4.52 (q, J=7.2 Hz, 2H), 3.90 (s, 3H), 2.02-1.99 (m, 1H), 1.43 (t, J=7.2 Hz, 3H), 0.80-0.78 (m, 4H).

Example 263

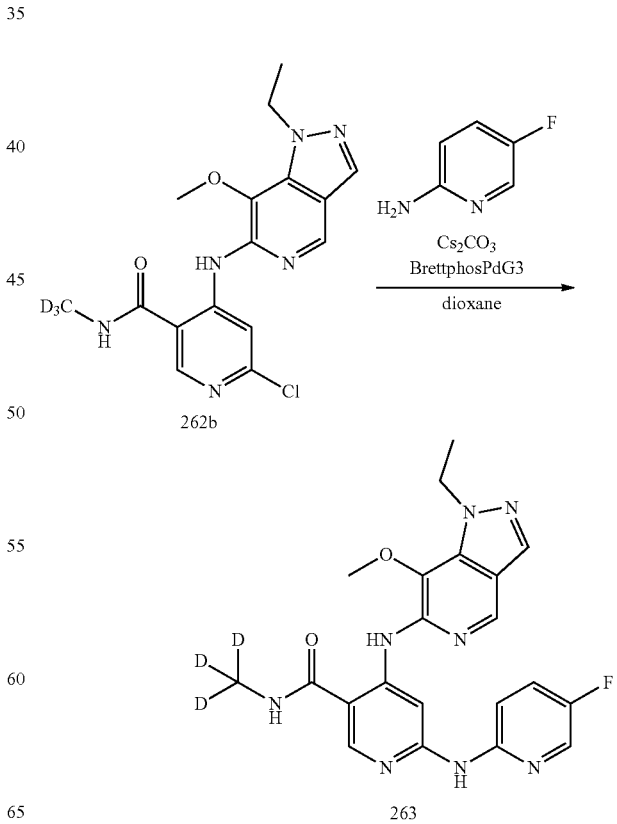

Step 1. 4-((1-Ethyl-7-methoxy-1/1-pyrazolo[4,3-c]
pyridin-6-yl)amino)-6-((5-fluoropyridin-2-yl)
amino)-N-(methyl-d₃)nicotinamide (263)

A mixture of 262b (50 mg, 0.14 mmol), 5-fluoropyridin-2-amine (46 mg, 0.41 mmol), BrettPhos Pd G3 (25 mg, 0.027 mmol) and Cs₂CO₃ (90 mg, 0.27 mmol) in 1,4-dioxane (1.0 mL) was stirred at 90° C. overnight under N₂ atmosphere. After cooling to r.t., the mixture was concentrated. The residue was purified by flash chromatography on silica gel (DCM/MeOH=20/1) to afford compound 263 (26.0 mg, 43% yield) as a white solid. LC-MS (Method 1) $t_R$=3.12 min, m/z (M+H)⁺=440.2. ¹H NMR (400 MHz, DMSO-d₆) δ 11.68 (s, 1H), 9.84 (s, 1H), 9.01 (s, 1H), 8.73 (s, 1H), 8.54 (s, 1H), 8.51 (s, 1H), 8.26-8.22 (m, 2H), 7.77-7.74 (m, 1H), 7.67-7.64 (m, 1H), 4.53 (q, J=7.2 Hz, 2H), 3.92 (s, 3H), 1.44 (t, J=7.2 Hz, 3H).

Example 264

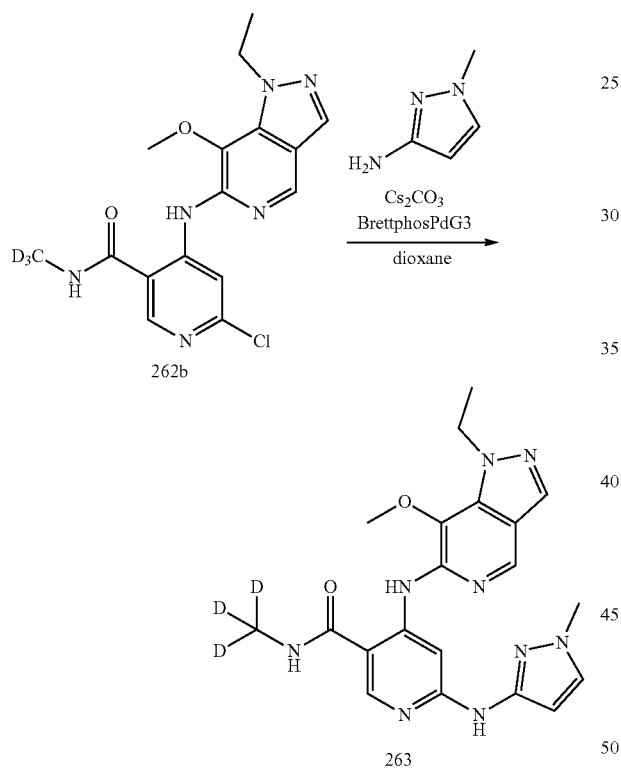

Step 1. 4-((1-Ethyl-7-methoxy-1H-pyrazolo[4,3-c]
pyridin-6-yl)amino)-N-(methyl-d₃)-6-((1-methyl-
1H-pyrazol-3-yl)amino)nicotinamide (264)

A mixture of 262b (50 mg, 0.14 mmol), 1-methyl-1H-pyrazol-3-amine (40 mg, 0.41 mmol), BrettPhos Pd G3 (25 mg, 0.027 mmol) and Cs₂CO₃ (90 mg, 0.27 mmol) in 1,4-dioxane (0.5 mL) was stirred at 90° C. overnight under N₂ atmosphere. After cooling to r.t., the mixture was concentrated. The residue was purified by flash chromatography on silica gel (DCM/MeOH=20/1) to afford compound 264 (20.5 mg, 35% yield) as a white solid. LC-MS (Method 2) $t_R$=2.77 min, m/z (M+H)⁺=425.1. ¹H NMR (400 MHz, DMSO-d₆) δ 11.75 (s, 1H), 9.33 (s, 1H), 8.74 (s, 1H), 8.67 (s, 1H), 8.50 (s, 1H), 8.49 (s, 1H), 8.29 (s, 1H), 7.58 (d, J=1.6 Hz, 1H), 6.29 (d, J=1.6 Hz, 1H), 4.58 (q, J=7.2 Hz, 2H), 3.98 (s, 3H), 3.81 (s, 3H), 1.50 (t, J=7.2 Hz, 3H).

Example 265

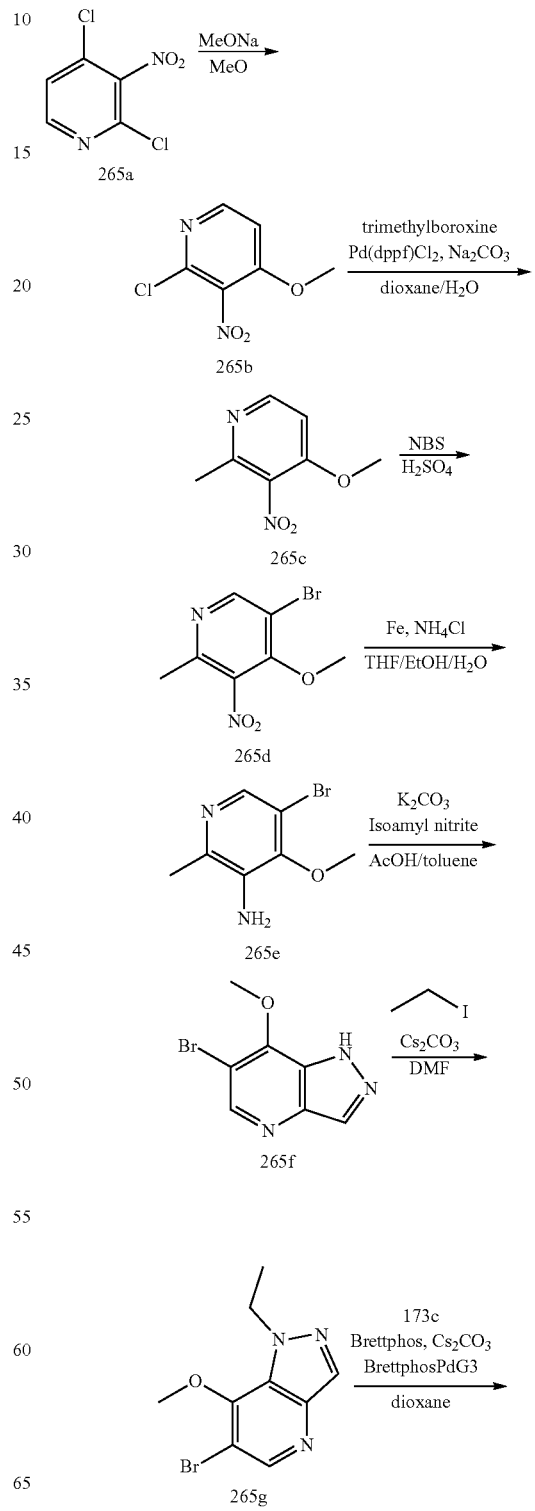

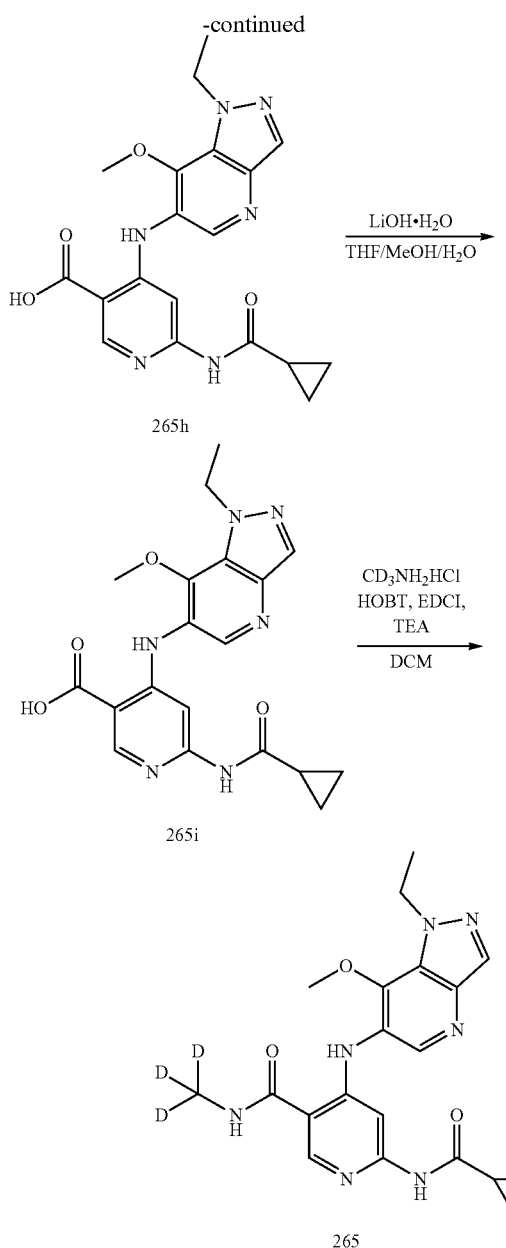

Step 1. 2-Chloro-4-methoxy-3-nitropyridine (265b)

To a solution of 265a (25 g, 130 mmol) in MeOH (500 mL) stirred at 0° C. was added MeONa (10.49 g, 190 mmol) at 0° C. Then the reaction mixture was stirred at 25° C. for 1 h. The resulting mixture was poured into water (100 mL) and extracted with EtOAc (250 mL*3). The combined organic layer was washed with brine (100 mL*2), dried over $Na_2SO_4$ and evaporated in vacuo to give the crude product. The residue was purified by flash chromatography on silica gel (PE/EtOAc=20/1 to 2/1) to give 265b (24 g, 94% yield) as a white solid. LC-MS (Method 5) $t_R$=1.27 min, m/z $(M+H)^+$=189.1. $^1$H NMR (400 MHz, DMSO-$d_6$) δ 7.84 (d, J=4.0 Hz, 1H), 7.55 (d, J=4.0 Hz, 1H), 4.04 (s, 3H).

Step 2. 4-Methoxy-2-methyl-3-nitropyridine (265c)

To a solution of 265b (23.1 g, 120 mmol), trimethylboroxine (36.9 g, 140 mmol) and $Na_2CO_3$ (38.9 g, 360 mmol) in dioxane/$H_2O$=5/1 (300 mL) was added Pd(dppf)Cl$_2$ (8.9 g, 120 mmol). Then the reaction mixture was allowed to 100° C. and stirred for 16 h under $N_2$. The mixture was cooled to room temperature and poured into water (200 mL) and extracted with EtOAc (200 mL*3). The combined organic layer was washed with brine (200 mL*2), dried over anhydrous $Na_2SO_4$ and evaporated in vacuo to give the crude product. The residue was purified by flash chromatography on silica gel (PE/EtOAc=20/1 to 2/1) to give 265c (14 g, 56% yield) as a yellow solid. LC-MS (Method 5) $t_R$=1.26 min, m/z $(M+H)^+$=169.1. $^1$H NMR (400 MHz, DMSO-$d_6$) δ 8.52 (d, J=4.0 Hz, 1H), 7.30 (d, J=4.0 Hz, 1H), 3.97 (s, 3H), 2.42 (s, 3H).

Step 3.
5-Bromo-4-methoxy-2-methyl-3-nitropyridine (265d)

To a solution of 265c (14 g, 83 mmol) in conc·$H_2SO_4$ (250 mL) at 0° C. was added NBS (29.65 g, 160 mmol) slowly at 0° C. Then the reaction mixture was allowed to warm to 60° C. and stirred for 16 h. The mixture was adjusted to pH=7 with saturated $Na_2CO_3$ (2000 mL). Then the resulting mixture was extracted with EtOAc (600 mL*3). The combined organic layer was washed with brine (100 mL*2), dried over anhydrous $Na_2SO_4$ and concentrated to give the crude product. The residue was purified by flash chromatography on silica gel (PE/EtOAc=20/1 to 10/1) to give 265d (8.3 g, 38% yield) as a yellow oil. LC-MS (Method 5) $t_R$=2.3 min, m/z $(M+H)^+$=247.0. $^1$H NMR (400 MHz, DMSO-$d_6$) δ 8.85 (s, 1H), 4.00 (s, 1H), 2.45 (s, 3H).

Step 4.
5-Bromo-4-methoxy-2-methylpyridin-3-amine (265e)

To a solution of 265d (8.3 g, 33 mmol) in THF (120 mL), EtOH (120 mL) and $H_2O$ (24 mL) was added Fe powder (9.3 g, 160 mmol) and $NH_4Cl$ (9.0 g, 160 mmol). The reaction mixture was stirred at 80° C. for 12 h. The reaction was cooled to 25° C. and quenched with water (100 mL) and extracted with EtOAc (20 mL*3). The combined organic layer was washed with brine (10 mL*2), dried over $Na_2SO_4$ and evaporated in vacuo to give the crude product. The residue was purified by flash chromatography on silica gel (PE/EtOAc=20/1 to 10/1) to give 265e (5.5 g, 72% yield) as a white solid. LC-MS (Method 5) $t_R$=0.44 min, m/z $(M+H)^+$=217.0. $^1$H NMR (400 MHz, DMSO-$d_6$) δ 7.75 (s, 1H), 5.19 (s, 1H), 3.78 (s, 3H), 2.43 (s, 3H).

Step 5. 6-Bromo-7-methoxy-1H-pyrazolo[4,3-b]pyridine (265f)

To a solution of 265e (5 g, 23 mmol) and $K_2CO_3$ (3.4 g, 34 mmol) in toluene (100 mL) and AcOH (100 mL) was cooled to 0° C. Isoamyl nitrite (4.31 g, 37 mmol) was added dropwise and stirred at 50° C. for 16 h. The mixture was adjusted to pH=7 with saturated $NaHCO_3$ (200 mL). Then the resulting mixture was extracted with EtOAc (100 mL*3). The combined organic layer was washed with brine (10 mL*2), dried over anhydrous $Na_2SO_4$ and concentrated to give the crude product. The residue was purified by flash chromatography on silica gel (PE/EtOAc=20/1 to 5/1) to give compound 265f (2.6 g, 46% yield) as a yellow solid. LC-MS (Method 5) $t_R$=1.32 min, m/z $(M+H)^+$=228.0. $^1$H NMR (400 MHz, DMSO-$d_6$) δ 8.46 (s, 1H), 8.41 (s, 1H), 4.21 (s, 3H).

Step 6. 6-Bromo-1-ethyl-7-methoxy-1H-pyrazolo[4,3-b]pyridine (265g)

A solution of 265f (1 g, 4.4 mmol) and Cs$_2$CO$_3$ (2.8 g, 8.8 mmol) in DMF (20 mL) was stirred and cooled to 0° C. Iodoethane (1.37 g, 8.8 mmol) was added dropwise and the reaction was stirred at 25° C. for 1 h. The resulting mixture was poured into water (20 mL) and extracted with EtOAc (10 mL*3). The combined organic layer was washed with brine (20 mL*2), dried over anhydrous Na$_2$SO$_4$ and concentrated to give the crude product. The residue was purified by flash chromatography on silica gel (PE/EtOAc=50/1 to 10/1) to give 265g (110 mg, 9% yield) as a yellow oil and 6-bromo-2-ethyl-7-methoxy-2H-pyrazolo[4,3-b]pyridine (1 g, 86% yield) as a yellow solid. LC-MS (Method 5) t$_R$=1.69 min, m/z (M+H)$^+$=256.0.

Step 7. Methyl 6-(cyclopropanecarboxamido)-4-((1-ethyl-7-methoxy-1H-pyrazolo[4,3-b]pyridin-6-yl)amino)nicotinate (265h)

To a solution of 173c (50 mg, 0.21 mmol), 265h (108 mg, 0.42 mmol) and Cs$_2$CO$_3$ (208 mg, 0.64 mmol) in dioxane (1 mL) was added BrettPhos Pd G3 (19 mg, 0.021 mmol) and BrettPhos (23 mg, 0.042 mmol). Then the reaction mixture was heated to 100° C. and stirred for 16 h under N$_2$. TLC (PE/EA=1/1) showed the reaction mixture was completed. The mixture was cooled to room temperature and poured into water (10 mL) and extracted with EtOAc (5 mL*3). The combined organic layer was washed with brine (5 mL*2), dried over anhydrous Na$_2$SO$_4$ and evaporated in vacuo to give the crude product. The residue was purified by Prep-TLC (PE/EtOAc=1/1) to give 265h (34 mg, 37% yield) as a yellow solid. LC-MS (Method 5) t$_R$=2.04 min, m/z (M+H)$^+$=411.1.

Step 8. 6-(Cyclopropanecarboxamido)-4-((1-ethyl-7-methoxy-1H-pyrazolo[4,3-b]pyridin-6-yl)amino)nicotinic acid (265i)

To a solution of 265h (34 mg, 0.083 mmol) in MeOH (5 mL), THF (5 mL) and H$_2$O (2 mL) was added LiOH·H$_2$O (10 mg, 0.25 mmol) at 0° C. Then the reaction mixture was allowed to 25° C. and stirred for 1 h. The mixture was added into H$_2$O (10 mL) and adjusted to pH=7 with 1 N HCl (10 mL). Then the resulting mixture was extracted with EtOAc (10 mL*3). The combined organic layer was washed with brine (10 mL*2), dried over anhydrous Na$_2$SO$_4$ and concentrated to give crude compound 265i (30 g, 88% yield) as a yellow solid. LC-MS (Method 5) t$_R$=1.53 min, m/z (M+H)$^+$=397.2.

Step 9. 6-(Cyclopropanecarboxamido)-4-((1-ethyl-7-methoxy-1H-pyrazolo[4,3-b]pyridin-6-yl)amino)-N-(methyl-d$_3$)nicotinamide (265)

To a solution of 265i (30 mg, 0.075 mmol), methan-d$_3$-amine hydrochloride (27 mg, 0.37 mmol), 1-hydroxybenzotriazole (10 mg, 0.075 mmol) and 3-(((ethylimino)methylene)amino)-N,N-dimethylpropan-1-amine hydrochloride (15 mg, 0.075 mmol) in DCM (5 mL) was added triethylamine (15 mg, 0.15 mmol). Then the reaction mixture was stirred for 16 h. The mixture was added into H$_2$O (5 mL) and extracted with EtOAc (5 mL*3). The combined organic layer was washed with brine (10 mL*2), dried over anhydrous Na$_2$SO$_4$ and concentrated to give the crude product. The residue was purified by Prep-HPLC (Method E) to give compound 265 (3.0 mg, 10% yield) as a white solid. LC-MS (Method 5) t$_R$=1.97 min, m/z (M+H)$^+$=413.3. $^1$H NMR (400 MHz, DMSO-d$_6$) δ 10.72 (s, 1H), 10.40 (s, 1H), 8.62 (s, 1H), 8.54 (s, 1H), 8.33 (s, 1H), 8.22 (s, 1H), 7.52 (s, 1H), 4.54 (q, J=7.2 Hz, 2H), 3.94 (s, 3H), 1.95-1.91 (m, 1H), 1.40 (t, J=7.2 Hz, 3H), 0.74-0.66 (m, 4H).

Example 266

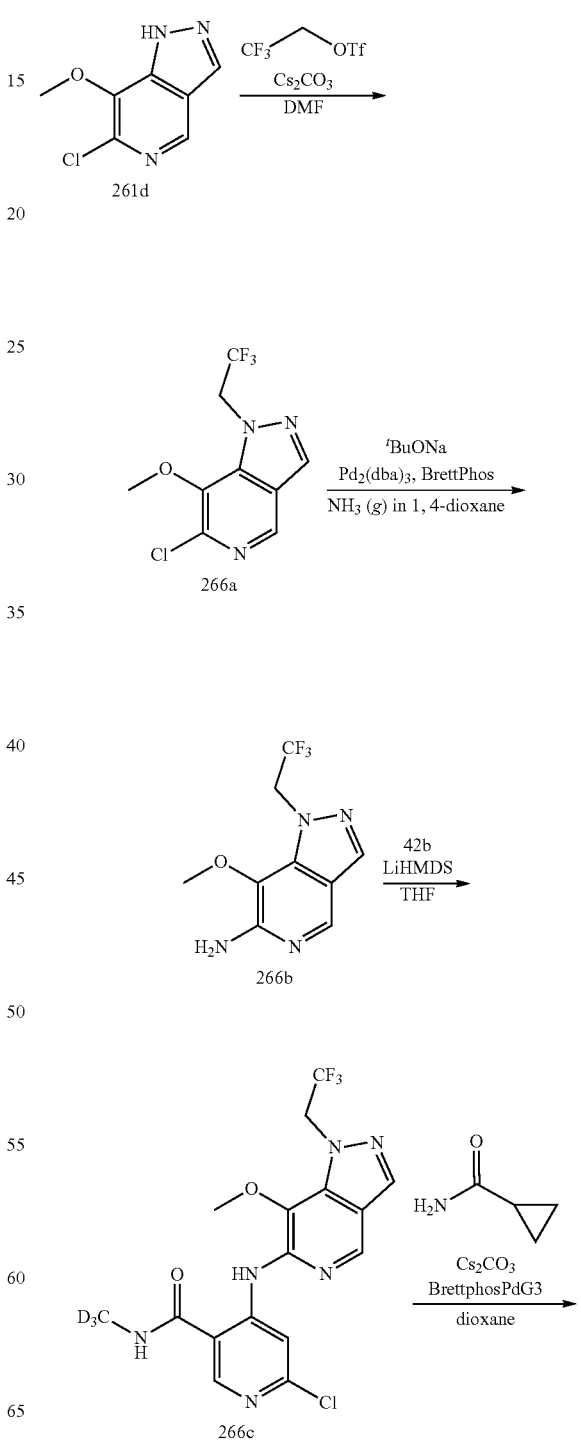

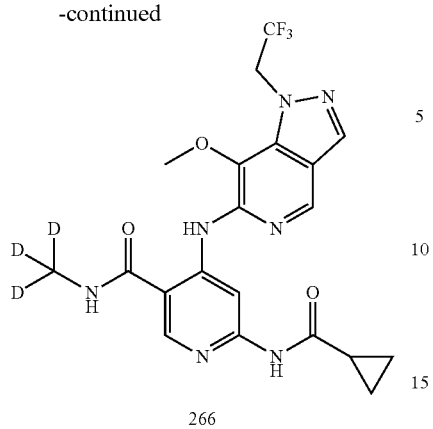

266

Step 1. 6-Chloro-7-methoxy-1-(2,2,2-trifluoroethyl)-1H-pyrazolo[4,3-c]pyridine (266a)

A mixture of 261d (1 g, 5.4 mmol), 2,2,2-trifluoroethyl trifluoromethanesulfonate (2.5 g, 11 mmol) and Cs$_2$CO$_3$ (3.5 g, 11 mmol) in DMF (10 mL) was stirred at 25° C. for 1 h. The reaction mixture was diluted with H$_2$O (20 mL) and extracted with EtOAc (20 mL). The organic layer was washed with brine (20 mL), dried over Na$_2$SO$_4$ and filtered. The filtrate was concentrated and the residue was purified by flash chromatography on silical gel (PE/EtOAc=3/1) to afford compound 266a (254 mg, 18% yield) as a yellow solid. LC-MS (Method 3) t$_R$=1.23 min, m/z (M+H)$^+$=266.0.

Step 2. 7-Methoxy-1-(2,2,2-trifluoroethyl)-1H-pyrazolo[4,3-c]pyridin-6-amine (266b)

A mixture of 266a (254 mg, 0.96 mmol), Pd$_2$(dba)$_3$ (17 mg, 0.019 mmol), BrettPhos (25 mg, 0.047 mmol), tBuONa (137 mg, 1.4 mmol) and sat. NH$_3$/dioxane (4 mL) was stirred at 100° C. for 12 h. The mixture was cooled, concentrated and the residue was purified by Prep-HPLC (Method A) to afford compound 266b (59 mg, 25% yield) as a white solid. LC-MS (Method 3) t$_R$=1.34 min, m/z (MA H)$^+$=247.2.

Step 3. 6-Chloro-4-((7-methoxy-1-(2,2,2-trifluoroethyl)-1H-pyrazolo[4,3-c]pyridin-6-yl)amino)-N-(methyl-d$_3$)nicotinamide (266c)

To a solution of 266b (45 mg, 0.18 mmol) and 42b (46 mg, 0.22 mmol) in THF (0.5 mL) was added LiHMDS (0.7 mL, 0.7 mmol, 1 M in THF) at −40° C. The reaction was stirred at −40° C. to r.t. for 1 h and quenched with H$_2$O (2 mL). The organic solvent was evaporated under reduced pressure. The formed solid was collected by filtering and was dried to afford compound 266c (12 mg, 16% yield) as a white solid. LC-MS (Method 3) t$_R$=1.63 min, m/z (M+H)$^+$=418.2.

Step 4. 6-(Cyclopropanecarboxamido)-4-((7-methoxy-1-(2,2,2-trifluoroethyl)-1H-pyrazolo[4,3-c]pyridin-6-yl)amino)-N-(methyl-d$_3$)nicotinamide (266)

A mixture of 266c (12 mg, 0.03 mmol), cyclopropanecarboxamide (12 mg, 0.14 mmol), BrettPhos Pd G3 (5 mg, 0.006 mmol) and Cs$_2$CO$_3$ (19 mg, 0.06 mmol) in 1,4-dioxane (0.3 mL) was stirred at 90° C. overnight under N$_2$ atmosphere. After cooling to r.t., the mixture was concentrated. The residue was purified by Prep-H PLC (Method A) to afford compound 266 (3.5 mg, 26% yield) as a white solid. LC-MS (Method 2) t$_R$=2.69 min, m/z (M+H)$^+$=467.1. $^1$H NMR (400 MHz, DMSO-d$_6$) δ 11.69 (s, 1H), 10.72 (s, 1H), 9.24 (s, 1H), 8.70 (s, 1H), 8.68 (s, 1H), 8.57 (s, 1H), 8.38 (s, 1H), 5.33 (q, J=8.4 Hz, 2H), 3.91 (s, 3H), 2.03-2.00 (m, 1H), 0.81-0.78 (m, 4H).

Example 267

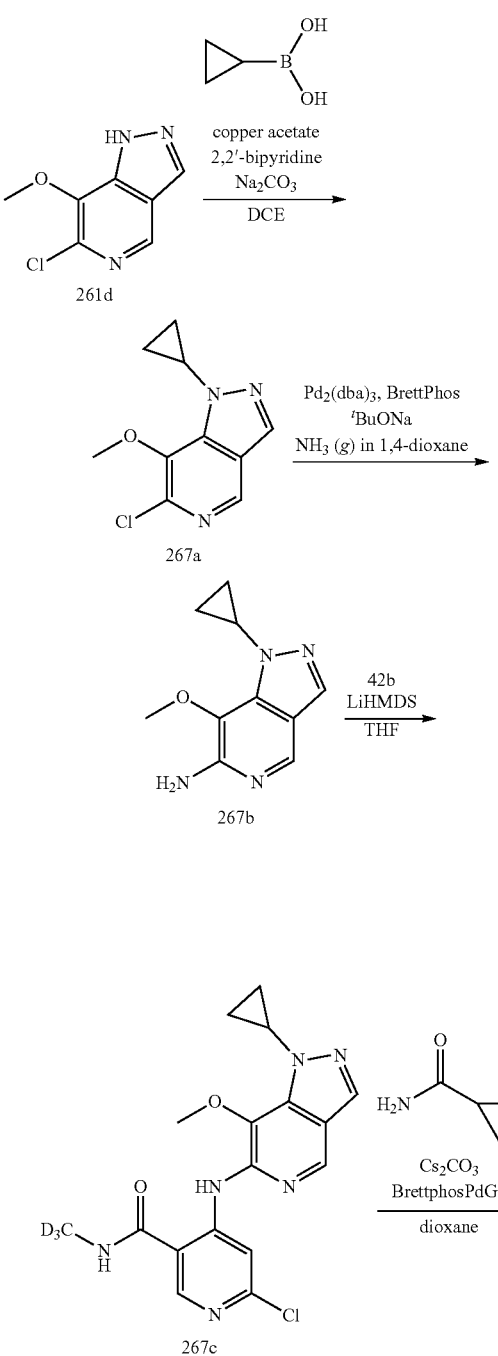

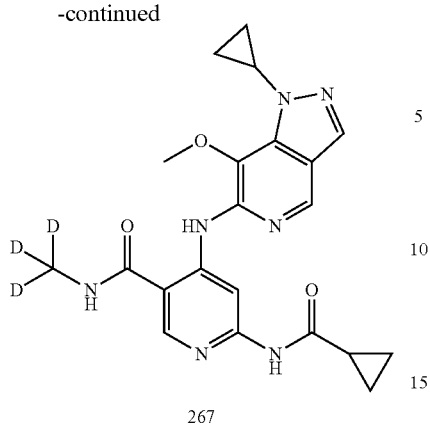

dioxane (0.5 mL) was stirred at 90° C. overnight under N₂ atmosphere. After cooling to r.t., the mixture was concentrated. And the residue was purified by flash chromatography on silica gel (DCM/MeOH=20/1) to afford compound 267 (10 mg, 30% yield) as a white solid. LC-MS (Method 2) $t_R$=2.56 min, m/z (M+H)⁺=425.1. ¹H NMR (400 MHz, DMSO-d₆) δ 11.72 (s, 1H), 10.71 (s, 1H), 9.30 (s, 1H), 8.66-8.64 (m, 2H), 8.57 (s, 1H), 8.16 (s, 1H), 4.04-4.02 (m, 1H), 3.98 (s, 3H), 2.04-2.02 (m, 1H), 1.23-1.14 (m, 4H), 0.82-0.81 (m, 4H).

Example 271

Step 1. 6-Chloro-1-cyclopropyl-7-methoxy-1H-pyrazolo[4,3-c]pyridine (267a)

A mixture of 261d (500 mg, 2.72 mmol), cyclopropyl boronic acid (514 mg, 5.99 mmol), copper acetate (494 mg, 2.72 mmol), 2,2'-bipyridine (425 mg, 2.72 mmol) and Na₂CO₃ (346 mg, 3.27 mmol) in DCE (6 mL) was stirred at 70° C. for 14 h under O₂ atmosphere. The mixture was cooled and filtered. The filtrate was diluted with EtOAc (20 mL), washed with NH₃·H₂O (10 mL) and 1 N HCl (10 mL). The separated organic layer was concentrated and the residue was purified by flash chromatography on silica gel (PE/EtOAc=3/1) to afford compound 267a (330 mg, 54% yield) as a yellow oil. LC-MS (Method 3) $t_R$=1.55 min, m/z (M+H)⁺=224.1.

Step 2. 1-Cyclopropyl-7-methoxy-1H-pyrazolo[4,3-c]pyridin-6-amine (267b)

A mixture of 267a (350 mg, 1.5 mmol), Pd₂(dba)₃ (281 mg, 0.313 mmol), BrettPhos (42 mg, 0.078 mmol), ᵗBuONa (225 mg, 2.3 mmol) in sat. NH₃/dioxane (5 mL) was stirred at 100° C. for 12 h under N₂. The mixture was cooled, concentrated and the residue was purified by Prep-HPLC (Method A) to 267b (67 mg, 20% yield) as a white solid. LC-MS (Method 3) $t_R$=1.19 min, m/z (M+H)⁺=205.2.

Step 3. 6-Chloro-4-((1-cyclopropyl-7-methoxy-1H-pyrazolo[4,3-c]pyridin-6-yl)amino)-N-(methyl-d₃)nicotinamide (267c)

To a solution of 267b (57 mg, 0.28 mmol) and 42b (64 mg, 0.31 mmol) in THF (1 mL) was added LiHMDS (1.1 mL, 1.1 mmol, 1 M in THF) at −40° C. The reaction was stirred at −40° C. to r.t. for 1 h and quenched with H₂O (2 mL). The organic solvent was evaporated under reduced pressure. The formed solid was collected by filtering and was dried to afford compound 267c (30 mg, 29% yield) as a brown solid. LC-MS (Method 3) $t_R$=1.37 min, m/z (M+H)⁺=376.2.

Step 4. 6-(Cyclopropanecarboxamido)-4-((1-cyclopropyl-7-methoxy-1H-pyrazolo[4,3-c]pyridin-6-yl)amino)-N-(methyl-d₃)nicotinamide (267)

A mixture of 267c (30 mg, 0.08 mmol), cyclopropanecarboxamide (34 mg, 0.40 mmol), BrettPhos Pd G3 (14 mg, 0.016 mmol) and Cs₂CO₃ (52 mg, 0.16 mmol) in 1,4-

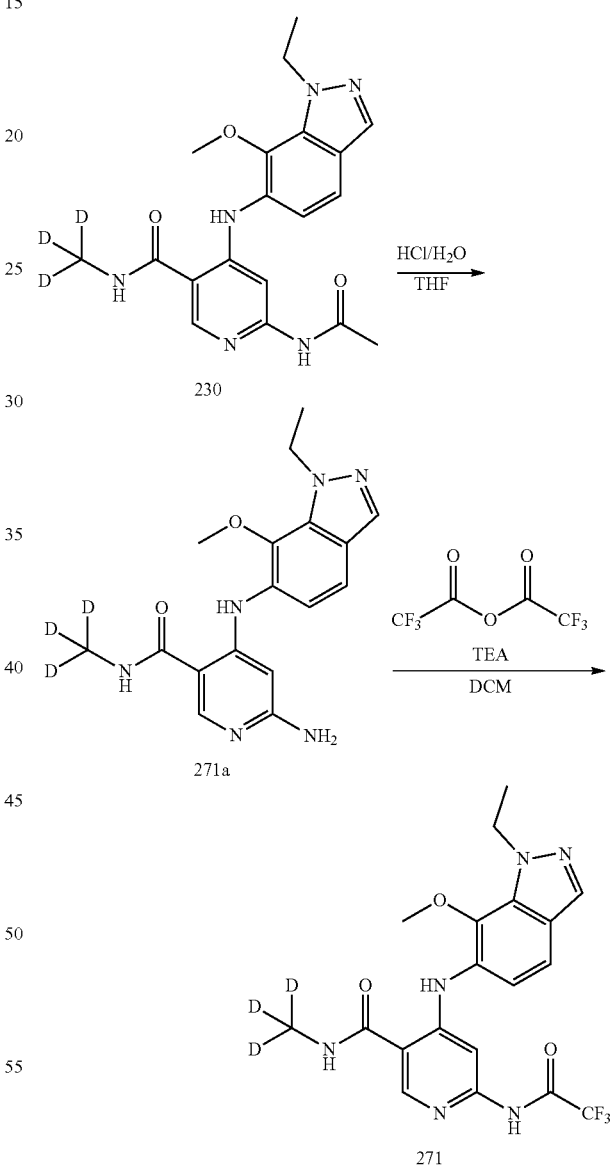

Step 1. 6-Amino-4-((1-ethyl-7-methoxy-1H-indazol-6-yl)amino)-N-(methyl-d₃)nicotinamide (271a)

To a solution of 230 (60 mg, 0.15 mmol) in THF (1 mL) was added HCl (1 mL, 2 M in H₂O) at 25° C. The reaction mixture was stirred at 60° C. for 5 h and was adjusted to pH>7 with aq Na$_2$CO$_3$ solution (5 mL). Then the mixture was extracted with EA (10 mL*3), washed with brine (10 mL), dried over Na$_2$SO$_4$, concentrated and purified by flash chromatography (DCM/MeOH=100/1 to 8/1) to get compound 271a (48 mg, 89% yield) as a white solid. LC-MS (Method 4) t$_R$=1.74 min, m/z (M+H)$^+$=344.2.

Step 2. 4-((1-Ethyl-7-methoxy-1H-indazol-6-yl) amino)-N-(methyl-d$_3$)-6-(2,2,2-trifluoroacetamido) nicotinamide (271)

To a solution of 271a (20 mg, 0.058 mmol) in DCM (1 mL) was added TEA (14.7 mg, 0.15 mmol) and Tf$_2$O (14.7 mg, 0.07 mmol) at 25° C. The reaction mixture was stirred at 25° C. for 0.5 h. The mixture was diluted with H$_2$O (2 mL), extracted with DCM (5 mL*3), washed with brine (5 mL), dried over Na$_2$SO$_4$, concentrated and purified by flash chromatography (DCM/MeOH=100/1 to 10/1) to get compound 271 (6.1 mg, 24% yield) as a white solid. LC-MS (Method 4) t$_R$=2.69 min, m/z (M+H)$^+$=440.3. $^1$H NMR (400 MHz, CDCl$_3$) δ 10.33 (s, 1H), 8.28 (s, 1H), 7.94 (s, 1H), 7.80 (s, 1H), 7.48 (d, J=8.8 Hz, 1H), 7.11 (d, J=8.4 Hz, 1H), 6.23 (s, 1H), 4.63 (q, J=6.8 Hz, 2H), 3.88 (s, 3H), 1.50 (t, J=6.8 Hz, 3H).

Example 272

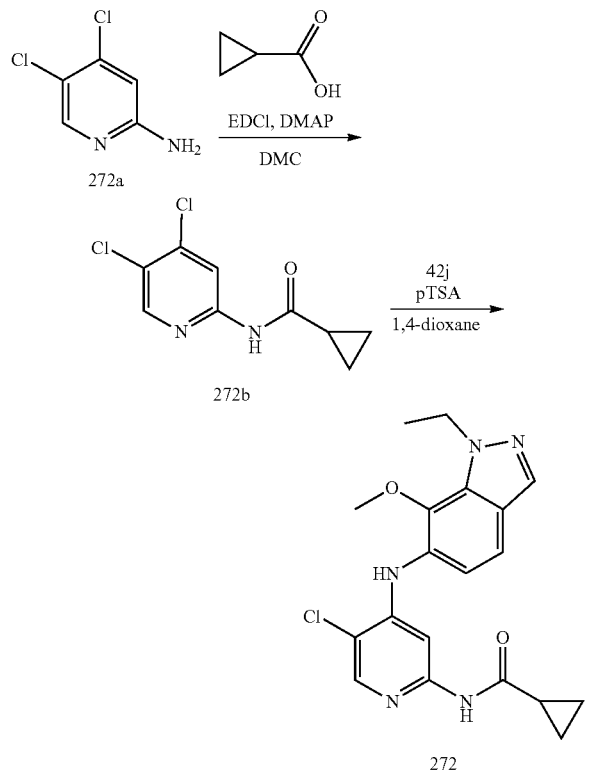

Step 1. N-(4,5-dichloropyridin-2-yl)cyclopropanecarboxamide (272b)

To a solution of 272a (300 mg, 1.84 mmol) in DCM (12 mL) was added DMAP (337.3 mg, 2.76 mmol) at r.t. Cyclopropanecarboxylic acid (158.4 mg, 1.84 mmol) and EDCI (423.4 mg, 2.21 mmol) was added after a while. The mixture was stirred at 25° C. for 3 h. The resulting solution was added H$_2$O (20 mL) and extracted by EA (30 mL). The combined organic layer was washed by brine (15 mL*3), dried over Na$_2$SO$_4$ and filtered. The filtrate was concentrated in vacuo and the residue was purified by flash chromatography (PE/EA=10/1 to 2/1) to afford 272b (160 mg, 37% yield) as a white solid. LC-MS (Method 4) t$_R$=2.83 min, m/z (M+H)$^+$=231.0.

Step 2. N-(5-chloro-4-((1-ethyl-7-methoxy-1H-indazol-6-yl)amino)pyridin-2-yl)cyclopropanecarboxamide (272)

To a solution of 272b (80 mg, 0.35 mmol), 4-methylbenzenesulfonic acid (59.6 mg, 0.35 mmol) in dioxane (7 mL) was added 42j (86.1 mg, 0.45 mmol) at r.t. The mixture was stirred at 100° C. for 16 h. The resulting solution was added H$_2$O (10 mL) and extracted with EA (20 mL) The combined organic layer was washed by brine (15 mL*3), dried over Na$_2$SO$_4$ and filtered. The filtrate was concentrated in vacuo and the residue was purified by Prep-HPLC (Method E) to afford 272 (2.6 mg, 2% yield) as a white solid. LC-MS (Method 4) t$_R$=2.26 min, m/z (M+H)$^+$=386.2. $^1$H NMR (400 MHz, DMSO-d$_6$) δ 10.53 (s, 1H), 8.15 (s, 1H), 8.07 (s, 1H), 8.06 (s, 1H), 7.50 (d, J=8.4 Hz, 1H), 7.43 (s, 1H), 6.98 (d, J=8.4 Hz, 1H), 4.54 (q, J=7.2 Hz, 2H), 3.72 (s, 3H), 1.93-1.84 (m, 1H), 1.36 (t, J=7.2 Hz, 3H), 0.71-0.65 (m, 2H), 0.65-0.59 (m, 2H).

Example 273

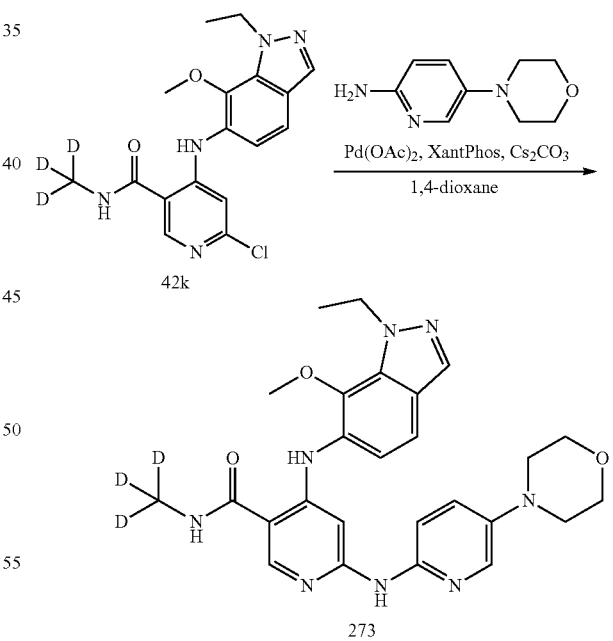

Step 1. 4-((1-Ethyl-7-methoxy-1H-indazol-6-yl) amino)-N-(methyl-d$_3$)-6-((5-morpholinopyridin-2-yl)amino)nicotinamide (273)

To a solution of 42k (22 mg, 0.06 mmol) and 5-morpholinopyridin-2-amine (12 mg, 0.07 mmol) in anhydrous 1,4-dioxane (1 mL) was added Pd(OAc)$_2$ (2.8 mg, 0.012 mmol), XantPhos (5.3 mg, 0.009 mmol) and Cs$_2$CO$_3$ (26 mg, 0.08 mmol). The resulting mixture was stirred under nitrogen atmosphere at 105° C. for 16 h. After cooled down to r.t., the reaction solution was filtered, and the filtrate was concentrated under reduced pressure to give a residue, which was purified by Prep-HPLC (Method E) to afford compound 273 (5.3 mg, 17% yield) as a white solid. LC-MS (Method 4) t$_R$=2.16 min, m/z (M+H)$^+$=506.4. $^1$H NMR (400 MHz, CDCl$_3$) δ 10.19 (s, 1H), 8.28 (s, 1H), 7.94 (s, 1H), 7.79 (s, 1H), 7.43 (d, J=8.4 Hz, 1H), 7.33 (d, J=8.8 Hz, 1H), 7.21-7.17 (m, 2H), 7.12 (s, 1H), 4.63 (q, J=7.2 Hz, 2H), 3.89 (s, 3H), 3.85-3.81 (m, 4H), 3.05-3.01 (m, 4H), 1.49 (t, J=7.2 Hz, 3H).

Example 274

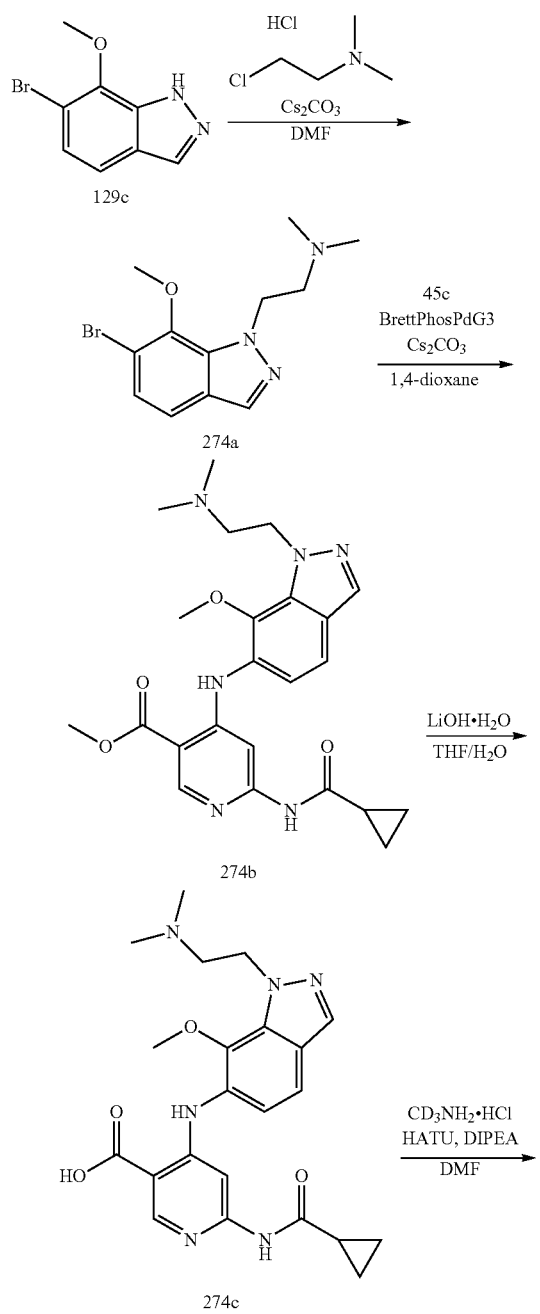

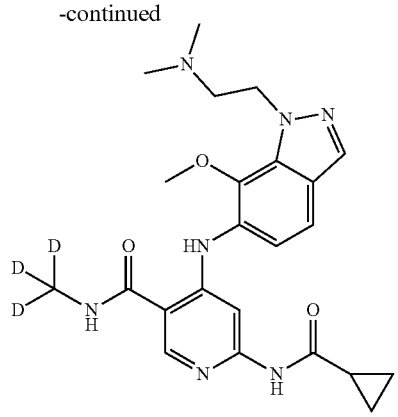

Step 1. 2-(6-Bromo-7-methoxy-1H-indazol-1-yl)-N,N-dimethylethan-1-amine (274a)

To a stirred solution of 129c (100.0 mg, 0.44 mmol) and 2-chloro-N,N-dimethylethan-1-amine hydrochloride (72 mg, 0.5 mmol) in DMF (4 mL) was added Cs$_2$CO$_3$ (275 mg, 0.85 mmol). The resulting reaction mixture was stirred at 85° C. for 1.5 h. Then it was allowed to cool down to r.t., and was quenched with water (10 mL), extracted with DCM (15 mL*3). The combined organic layer was washed with brine (10 mL), dried over anhydrous Na$_2$SO$_4$ and filtered. The filtrate was concentrated under vacuum to give a residue which was purified by flash chromatography on silica gel (DCM/MeOH=10/1) to afford compound 274a (86 mg, 65% yield) as a yellow oil. LC-MS (Method 4) t$_R$=1.42 min, m/z (M+H)$^+$=298.1.

Step 2. Methyl 6-(cyclopropanecarboxamido)-4-((1-(2-(dimethylamino)ethyl)-7-methoxy-1H-indazol-6-yl)amino)nicotinate (274b)

To a solution of 274a (75 mg, 0.25 mmol) and 129c (52 mg, 0.16 mmol) in anhydrous 1,4-dioxane (3.5 mL) was added BrettPhos Pd G3 (22 mg, 0.024 mmol) and Cs$_2$CO$_3$ (182 mg, 0.56 mmol). The resulting mixture was refluxed at 105° C. under nitrogen atmosphere for 16 h. Then the mixture was allowed to cool down to r.t. The solvent was removed, and the residue was purified by flash chromatography on silica gel (DCM/MeOH=15/1) to get a crude product, which was further purified by Prep-HPLC (Method E) to afford compound 274b (42.5 mg, 37% yield) as a white solid. LC-MS (Method 4) t$_R$=1.60 min, m/z (M+H)$^+$=453.3.

Step 3. 6-(Cyclopropanecarboxamido)-4-((1-(2-(dimethylamino)ethyl)-7-methoxy-1H-indazol-6-yl)amino)nicotinic acid (274c)

To a solution of 274b (42.5 mg, 0.094 mmol) in THF (1 mL) and H$_2$O (0.2 mL) was added LiOH·H$_2$O (58 mg, 1.38 mmol), and the mixture was stirred at 65° C. for 6 h. Then it was cooled down to r.t. and adjusted to pH=5 with 2 N aq. HCl. The acidified solution was concentrated to afford compound 274c (40 mg, 97% yield) as a light yellow solid. LC-MS (Method 4) t$_R$=0.56 min, m/z (M+H)$^+$=439.3.

Step 4. 6-(Cyclopropanecarboxamido)-4-((1-(2-(dimethylamino)ethyl)-7-methoxy-1H-indazol-6-yl)amino)-N-(methyl-d$_3$)nicotinamide (274)

To a solution of 274c (42.5 mg, 0.094 mmol) and HATU (42.3 mg, 0.11 mmol) in DMF (2 mL) was added DIPEA (78

μL, 0.45 mmol). After stirring at r.t. for 5 min, methyl-d₃-amine hydrochloride (11.4 mg, 0.16 mmol) was added and the resulting reaction mixture was stirred at r.t. for 1 h. Then the mixture was filtered and the filtrate was purified by Prep-HPLC (Method E) to afford compound 274 (6.5 mg, 15% yield) as a white solid. LC-MS (Method 4) $t_R$=0.69 min, m/z (M+H)⁺=455.4. ¹H NMR (400 MHz, CDCl₃) δ 10.18 (s, 1H), 8.22 (s, 1H), 8.17 (s, 1H), 7.90 (s, 1H), 7.90 (s, 1H), 7.44 (d, J=8.4 Hz, 1H), 7.15 (d, J=8.4 Hz, 1H), 6.19 (s, 1H), 4.69-4.65 (m, 2H), 3.87 (s, 3H), 2.84-2.80 (m, 2H), 2.31 (s, 6H), 1.50-1.44 (m, 1H), 1.03-0.99 (m, 2H), 0.85-0.80 (m, 2H).

Example 275

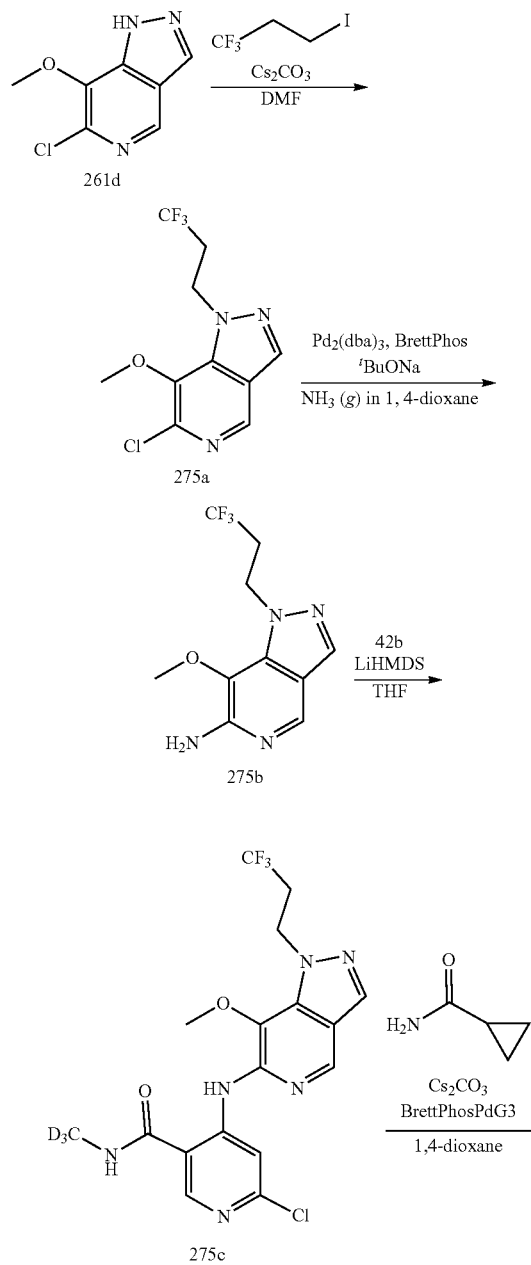

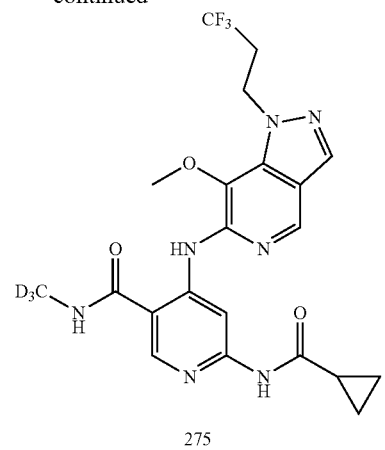

Step 1. 6-Chloro-7-methoxy-1-(3,3,3-trifluoropropyl)-1H-pyrazolo[4,3-c]pyridine (275a)

A mixture of 261d (470 mg, 2.56 mmol), 1,1,1-trifluoro-3-iodopropane (860 mg, 3.84 mmol) and Cs₂CO₃ (1.67 g, 5.12 mmol) in DMF (5 mL) was stirred at 40° C. for 2 h. The reaction mixture was diluted with H₂O (20 mL) and extracted with EtOAc (20 mL). The organic layer was washed with brine (20 mL), dried over Na₂SO₄ and filtered. The filtrate was concentrated and the residue was purified by flash chromatography on silical gel (PE/EtOAc=3/1) to afford compound 275a (180 mg, 25% yield) as a yellow oil. ¹H NMR (400 MHz, DMSO-d 6) δ 8.72 (s, 1H), 8.41 (s, 1H), 4.79 (t, J=6.8 Hz, 2H), 4.01 (s, 3H), 3.04-2.92 (m, 2H).

Step 2. 7-Methoxy-1-(3,3,3-trifluoropropyl)-1H-pyrazolo[4,3-c]pyridin-6-amine (275b)

A mixture of 275a (330 mg, 1.18 mmol), Pd₂(dba)₃ (54 mg, 59 umol), BrettPhos (32 mg, 0.059 mmol), ᵗBuONa (170 mg, 1.77 mmol) in sat. NH₃ in dioxane (4 mL) was stirred at 100° C. for 12 h. The mixture was cooled and concentrated. The residue was purified by Prep-HPLC (Method A) to afford compound 275b (100 mg, 32% yield) as a white solid. LC-MS (Method 3) $t_R$=1.44 min, m/z (M+H)⁺=261.2.

Step 3. 6-Chloro-4-((7-methoxy-1-(3,3,3-trifluoropropyl)-1H-pyrazolo[4,3-c]pyridin-6-yl)amino)-N-(methyl-d₃)nicotinamide (275c)

To a solution of 275b (80 mg, 0.31 mmol) and 42b (77 mg, 0.37 mmol) in THF (0.8 mL) was added LiHMDS (1.2 mL, 1.2 mmol, 1 M in THF) at −40° C. The reaction was stirred at −40° C. to r.t. for 1 h and quenched with H₂O (2 mL). The organic solvent was evaporated under reduced pressure. The formed solid was collected by filtering and was dried to afford compound 275c (50 mg, 38% yield) as a red solid. LC-MS (Method 3) $t_R$=1.31 min, m/z (M+H)⁺=432.1.

Step 4. 6-(Cyclopropanecarboxamido)-4-((7-methoxy-1-(3,3,3-trifluoropropyl)-1H-pyrazolo[4,3-c]pyridin-6-yl)amino)-N-(methyl-d₃)nicotinamide (275)

A solution of 275c (50 mg, 0.12 mmol), cyclopropanecarboxamide (49 mg, 0.58 mmol), BrettPhos Pd G3 (21 mg, 0.023 mmol) and Cs$_2$CO$_3$ (75 mg, 0.23 mmol) in 1,4-dioxane (0.5 mL) was stirred at 90° C. overnight under N$_2$ atmosphere. After cooling to r.t., the mixture was concentrated. The residue was purified by flash chromatography on silica gel (DCM/MeOH=20/1) to afford compound 275 (17 mg, 31% yield) as a white solid. LC-MS (Method 2) t$_R$=3.19 min, m/z (M+H)$^+$=481.1. $^1$H NMR (400 MHz, DMSO-d$_6$) δ 11.60 (s, 1H), 10.69 (s, 1H), 9.16 (s, 1H), 8.67 (s, 1H), 8.64 (s, 1H), 8.56 (s, 1H), 8.27 (s, 1H), 4.75 (t, J=6.8 Hz, 2H), 3.90 (s, 3H), 3.00-2.92 (m, 2H), 2.02-1.97 (m, 1H), 0.81-0.76 (m, 4H).

Example 276

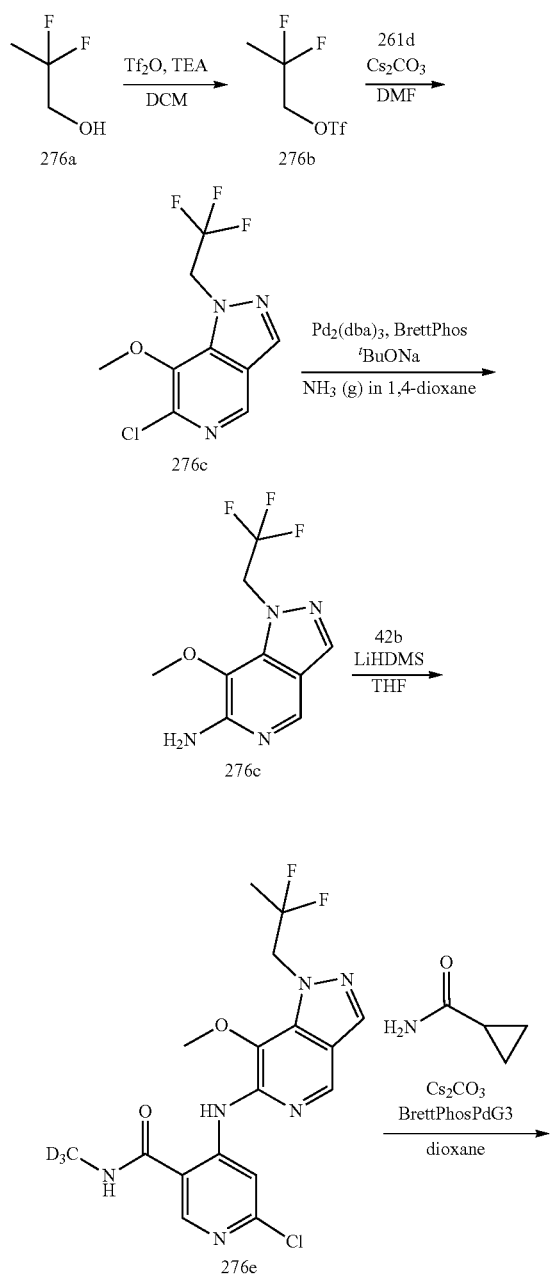

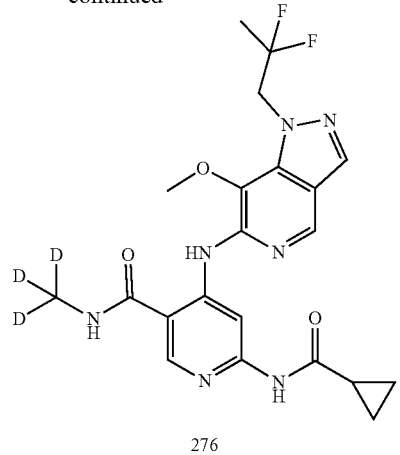

Step 1. 2,2-Difluoropropyl trifluoromethanesulfonate (276b)

To a solution of 276a (1 g, 10.4 mmol) and triethylamine (1.5 g, 15.6 mmol) in DCM (15 mL) was added trifluoromethanesulfonic anhydride (4.4 g, 15.6 mmol) dropwise at −20° C. The reaction was stirred at −20° C. for 16 h and diluted with DCM (10 mL). The mixture was washed with ice water (10 mL). The separated organic layer was washed with 20% Na$_2$CO$_3$ aqueous solution (10 mL) and brine (10 mL), dried over Na$_2$SO$_4$, filtered and concentrated in vacuo to afford 276b (2.3 g, 97% yield) as a black oil. $^1$H NMR (400 MHz, DMSO-d$_6$) δ 5.08 (t, J=13.6 Hz, 2H), 1.72 (t, J=19.2 Hz, 3H).

Step 2. 6-Chloro-1-(2,2-difluoropropyl)-7-methoxy-1H-pyrazolo[4,3-c]pyridine (276c)

A mixture of 261d (400 mg, 2.18 mmol), 276b (1.6 g, 7.01 mmol), Cs$_2$CO$_3$ (1.42 g, 4.36 mmol) in DMF (5 mL) was stirred at 30° C. for 1 h. The reaction mixture was diluted with H$_2$O (15 mL) and extracted with EtOAc (15 mL*3). The combined organic layer was washed with brine (20 mL), dried over Na$_2$SO$_4$ and filtered. The filtrate was concentrated and the residue was purified by flash chromatography on silical gel (PE/EtOAc=3/1) to afford 276c (120 mg, 21% yield) as a yellow oil. $^1$H NMR (400 MHz, DMSO-d$_6$) δ 8.73 (s, 1H), 8.45 (s, 1H), 4.98 (t, J=13.6 Hz, 2H), 4.02 (s, 3H), 1.71 (t, J=19.2 Hz, 3H).

Step 3. 1-(2,2-Difluoropropyl)-7-methoxy-1H-pyrazolo[4,3-c]pyridin-6-amine (276d)

A mixture of 276c (266 mg, 1 mmol), Pd$_2$(dba)$_3$ (46 mg, 0.05 mmol), BrettPhos (27 mg, 0.050 mmol) and tBuONa (147 mg, 1.52 mmol) in sat. NH$_3$/dioxane (4 mL) was stirred at 100° C. for 12 h under N$_2$. The mixture was cooled and concentrated. The residue was purified by Prep-HPLC (Method A) to afford 276d (100 mg, 41% yield) as a white solid. LC-MS (Method 3) t$_R$=1.27 min, m/z (M+H)$^+$=243.2.

Step 4. 6-Chloro-4-((1-(2,2-difluoropropyl)-7-methoxy-1H-pyrazolo[4,3-c]pyridin-6-yl)amino)-N-(methyl-d$_3$)nicotinamide (276e)

To a solution of 276d (90 mg, 0.37 mmol) and 42b (93 mg, 0.45 mmol) in THF (0.8 mL) was added LiHMDS (1.5 mL, 1.5 mmol, 1 M in THF) at −40° C. The reaction was stirred at −40° C. to r.t. for 1 h and quenched with H₂O (1 mL). The organic solvent was evaporated under reduce pressure. The formed solid was collected by filtering and was dried to afford 276e (50 mg, 38% yield) as a red solid. LC-MS (Method 3) t$_R$=1.60 min, m/z (M+H)⁺=414.2.

Step 5. 6-(Cyclopropanecarboxamido)-4-((1-(2,2-difluoropropyl)-7-methoxy-1H-pyrazolo[4,3-c]pyridin-6-yl)amino)-N-(methyl-d₃)nicotinamide (276)

A mixture of 276e (66 mg, 0.16 mmol), cyclopropanecarboxamide (67 mg, 0.8 mmol), BrettPhos Pd G3 (28 mg, 0.031 mmol) and Cs₂CO₃ (104 mg, 0.32 mmol) in 1,4-dioxane (1 mL) was stirred at 90° C. overnight under N₂ atmosphere. After cooling to r.t., the mixture was concentrated. The residue was purified by Prep-HPLC (Method A) to afford compound 276 (17 mg, 31% yield) as a white solid. LC-MS (Method 2) t$_R$=2.94 min, m/z (M+H)⁺=463.1. ¹H NMR (400 MHz, DMSO-d₆) δ 11.63 (s, 1H), 10.70 (s, 1H), 9.21 (s, 1H), 8.68 (s, 1H), 8.65 (s, 1H), 8.56 (s, 1H), 8.32 (s, 1H), 4.92 (t, J=12.4 Hz, 2H), 3.89 (s, 3H), 2.03-1.99 (m, 1H), 1.69 (t, J=19.2 Hz, 3H), 0.81-0.78 (m, 4H).

Example 277

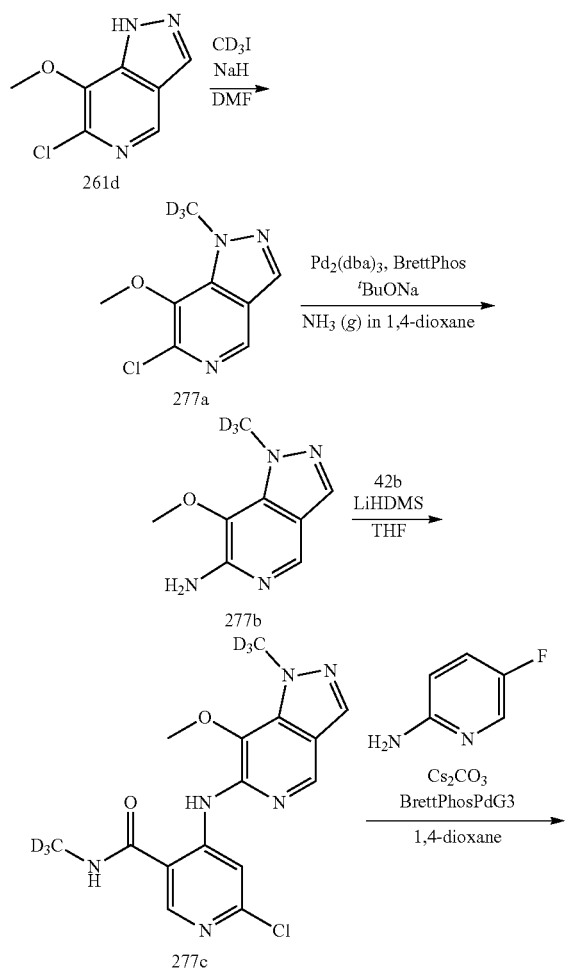

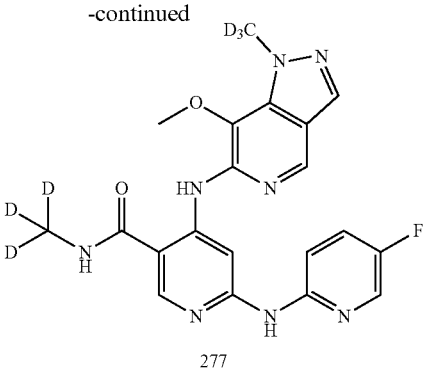

Step 1. 6-Chloro-7-methoxy-1-(methyl-d₃)-1H-pyrazolo[4,3-c]pyridine (277a)

To a mixture of 261d (600 mg, 3.27 mmol) in DMF (6 mL) was added NaH (261 mg, 6.54 mmol, 60% purity in mineral oil) at 0° C. After 30 min, CD₃I (948 mg, 6.54 mmol) was added at 0° C. The mixture was stirred at 30° C. for 1 h, diluted with H₂O (10 mL) and extracted with EtOAc (10 mL). The organic layer was washed with brine (10 mL), dried over Na₂SO₄ and filtered. The filtrate was concentrated and the residue was purified by flash chromatography on silical gel (PE/EtOAc=3/1) to afford compound 277a (200 mg, 31% yield) as a yellow solid. LC-MS (Method 3) t$_R$=1.37 min, m/z (M+H)⁺=201.1.

Step 2. 7-Methoxy-1-(methyl-d₃)-1H-pyrazolo[4,3-c]pyridin-6-amine (277b)

A mixture of 277a (180 mg, 0.90 mmol), Pd₂(dba)₃ (8 mg, 0.009 mmol), BrettPhos (24 mg, 0.045 mmol), ᵗBuONa (129 mg, 1.35 mmol) in sat. NH₃ in dioxane (2 mL) was stirred at 100° C. for 10 h under N₂. The mixture was cooled and concentrated. The residue was purified by Prep-HPLC (Method A) to afford compound 277b (37 mg, 23% yield) as a white solid. LC-MS (Method 3) t$_R$=0.89 min, m/z (M+H)⁺=182.2.

Step 3. 6-Chloro-4-((7-methoxy-1-(methyl-d₃)-1H-pyrazolo[4,3-c]pyridin-6-yl)amino)-N-(methyl-d₃)nicotinamide (277c)

To a solution of 277b (35 mg, 0.19 mmol) and 42b (48 mg, 0.23 mmol) in THF (0.4 mL) was added LiHMDS (0.8 mL, 0.8 mmol, 1 M in THF) at −40° C. The reaction was stirred at −40° C. to r.t. for 1 h and quenched with H₂O (2 mL). The organic solvent was evaporated under reduced pressure. The formed solid was collected by filtering and was purified by flash chromatography on silical gel (DCM/MtOH=20/1) to afford compound 277c (6 mg, 9% yield) as a red solid. LC-MS (Method 3) t$_R$=1.18 min, m/z (M+H)⁺=353.1.

Step 4. 6-((5-Fluoropyridin-2-yl)amino)-4-((7-methoxy-1-(methyl-d₃)-1H-pyrazolo[4,3-c]pyridin-6-yl)amino)-N-(methyl-d₃)nicotinamide (277)

A mixture of 277c (6 mg, 0.017 mmol), 5-fluoropyridin-2-amine (4 mg, 0.034 mmol), BrettPhos Pd G3 (3 mg, 0.003 mmol) and Cs₂CO₃ (11 mg, 0.034 mmol) in 1,4-dioxane (0.3 mL) was stirred at 90° C. overnight under N₂ atmosphere.

After cooling to r.t., the mixture was concentrated. The residue was purified by Prep-HPLC (Method A) to afford compound 277 (1.2 mg, 16% yield) as a white solid. LC-MS (Method 2) $t_R$=2.44 min, m/z (M+H)$^+$=429.1. $^1$H NMR (400 MHz, DMSO-$d_6$) δ 11.71 (s, 1H), 9.83 (s, 1H), 9.02 (s, 1H), 8.73 (s, 1H), 8.54-8.52 (m, 2H), 8.25 (d, J=2.8 Hz, 1H), 8.22 (s, 1H), 7.78-7.75 (m, 1H), 7.68-7.65 (m, 1H), 3.94 (s, 3H).

Example 278

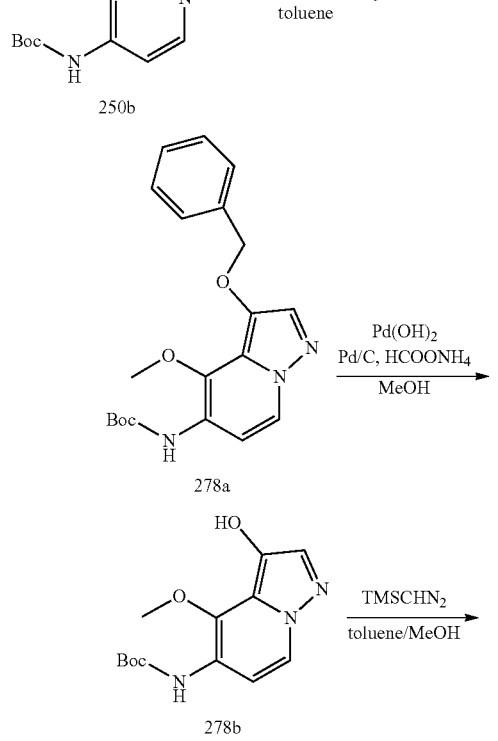

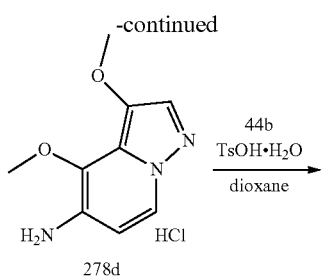

Step 1. Tert-butyl (3-(benzyloxy)-4-methoxypyrazolo[1,5-a]pyridin-5-yl)carbamate (278a)

A mixture of 250b (350 mg, 0.90 mmol), benzyl alcohol (486 mg, 4.50 mmol), trans-N,N-dimethylcyclohexane-1,2-diamine (26 mg, 0.18 mmol), K$_3$PO$_4$ (381 mg, 1.80 mmol) and CuI (34 mg, 0.18 mmol) in dioxane (5 mL) was stirred at 100° C. for 10 h under N$_2$ atmosphere under microwave. The mixture was cooled, concentrated under reduced pressure and purified by Prep-HPLC (Method A) to afford 278a (70 mg, 21% yield) as a yellow oil. LC-MS (Method 3) $t_R$=1.33 min, m/z (M+H)$^+$=370.4.

Step 2. Tert-butyl (3-hydroxy-4-methoxypyrazolo[1,5-a]pyridin-5-yl)carbamate (278b)

A mixture of 278a (70 mg, 0.19 mmol), Pd(OH)$_2$ (13 mg, 0.012 mmol), Pd/C (13 mg, 10% wt in 50% water), HCOONH$_4$ (95 mg, 1.52 mmol) and MeOH (3 mL) was stirred at 40° C. overnight under H$_2$ (50 Psi). The mixture was concentrated under reduced pressure and the residue was purified by flash chromatography on silica gel (PE/EtOAc=1/1) to afford 278b (40 mg, 75% yield) as a brown solid. LC-MS (Method 3) $t_R$=1.03 min, m/z (M+H)$^+$=280.3.

Step 3. Tert-butyl (3,4-dimethoxypyrazolo[1,5-a]pyridin-5-yl)carbamate (278c)

A solution of 278b (25 mg, 0.09 mmol) in toluene (1 mL) and MeOH (0.1 mL) was added into TMSCHN$_2$ (1 mL, 2 M in hexane). The mixture was stirred at r.t. for 12 h. The mixture was diluted with water (3 mL) and the aqueous layer was extracted with EtOAc (5 mL*3). The combined organic layer was concentrated under reduced pressure and purified by flash chromatography on silica gel (PE/EtOAc=3/1) to afford 278c (22 mg, 84% yield) as a white solid. LC-MS (Method 3) $t_R$=1.29 min, m/z (M+H)$^+$=294.2.

Step 4. 3,4-Dimethoxypyrazolo[1,5-a]pyridin-5-amine hydrochloride (278d)

A solution of 278c (22 mg, 0.07 mmol) in HCl/EtOAc (5 mL, 2 M) was stirred for 12 h at r.t. The formed solid was filtered. The filter cake was dried to afford 278d (13 mg, 99% yield) as a white solid. LC-MS (Method 3) $t_R$=0.70 min, m/z $(M+H)^+$=194.0.

Step 5. 6-(Cyclopropanecarboxamido)-4-((3,4-dimethoxypyrazolo[1,5-a]pyridin-5-yl)amino)-N-(methyl-$d_3$)nicotinamide (278)

A solution of 278d (13 mg, 0.05 mmol), 44b (14 mg, 0.05 mmol) and TsOH·H$_2$O (2 mg, 0.01 mmol) in dioxane (1 mL) was stirred at 100° C. for 12 h. After cooling to r.t., the reaction mixture was cooled, concentrated and purified by Prep-H PLC (Method A) to afford compound 278 (3 mg, 13% yield) as a white solid. LC-MS (Method 2) $t_R$=2.84 min, m/z $(M+H)^+$=414.1. $^1$H NMR (400 MHz, DMSO-$d_6$) δ 10.75 (s, 1H), 10.47 (s, 1H), 8.58 (s, 1H), 8.51 (s, 1H), 8.31 (d, J=8.0 Hz, 1H), 7.88 (s, 1H), 7.78 (s, 1H), 6.77 (d, J=7.2 Hz, 1H), 3.87 (s, 3H), 3.82 (s, 3H), 1.98-1.93 (m, 1H), 0.76-0.74 (m, 4H).

Example 279

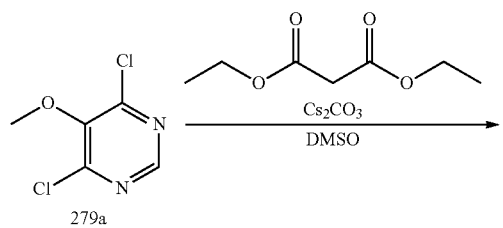

279a

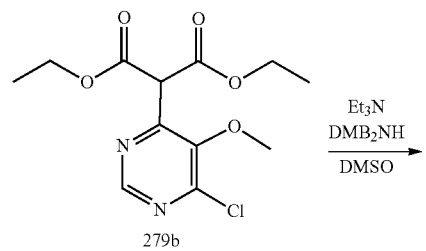

279b

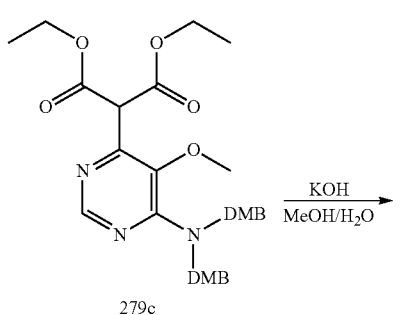

279c

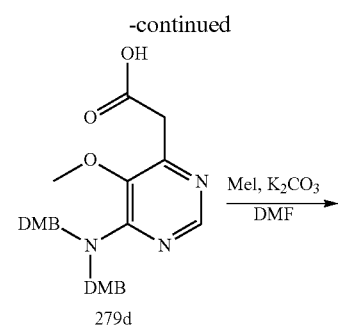

279d

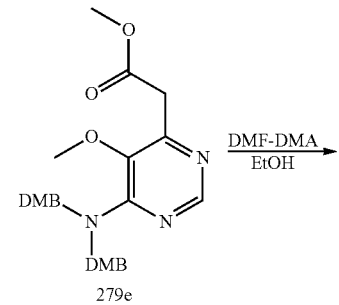

279e

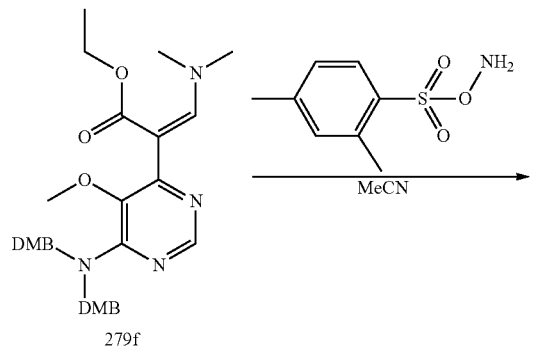

279f

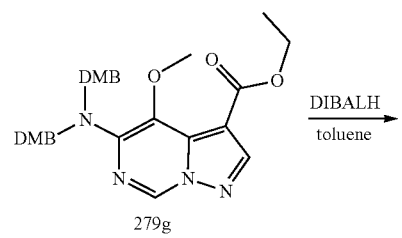

279g

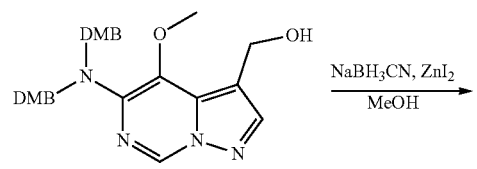

279h

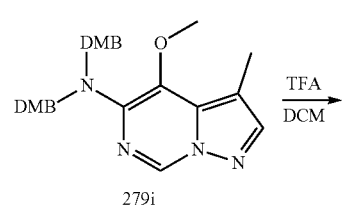

279i

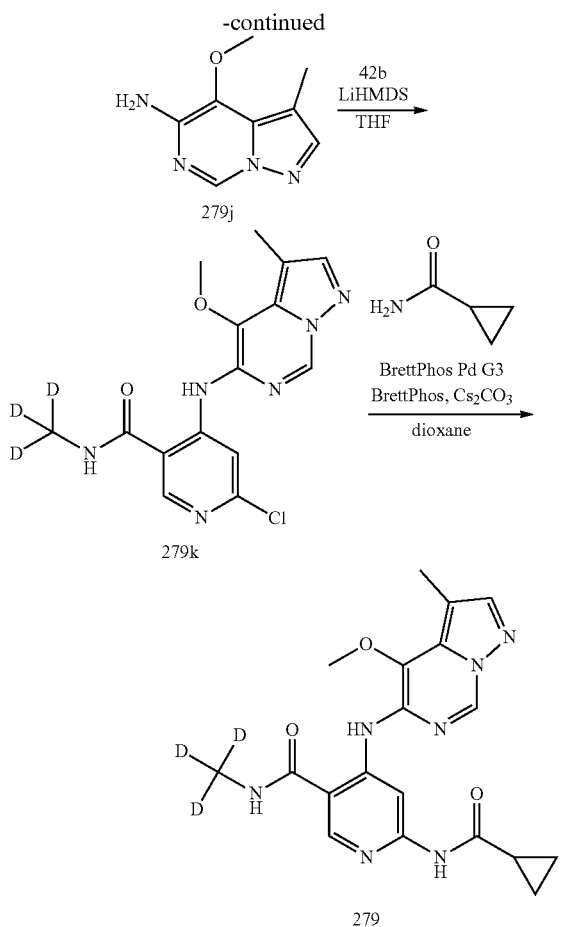

Step 1. Diethyl 2-(6-chloro-5-methoxypyrimidin-4-yl) malonate (279b)

To a stirred solution of 279a (50 g, 279 mmol) in DMSO (600 mL) was added 1,3-diethyl propanedioate (44.73 g, 279 mmol) and Cs$_2$CO$_3$ (182 g, 558 mmol) at 20° C. under nitrogen. The reaction mixture was stirred at 100° C. for 8 h. The reaction mixture was poured into water (600 mL) and extracted with EtOAc (800 mL*3). The combined organic layer was washed with brine (600 mL*2), dried over anhydrous Na$_2$SO$_4$ and concentrated to give crude 279b (50 g, 59% yield) as a yellow oil. LC-MS (Method 4) t$_R$=1.94 min, m/z (M+H)$^+$=303.0. $^1$H NMR (400 MHz, DMSO-d$_6$) δ 8.81 (s, 1H), 5.35 (s, 1H), 4.21 (q, J=7.2 Hz, 4H), 3.90 (s, 3H), 1.19 (t, J=7.2 Hz, 6H).

Step 2. Diethyl 2-(6-(bis(2,4-dimethoxybenzyl) amino)-5-methoxypyrimidin-4-yl) malonate (279c)

To a solution of 279b (50 g, 165 mmol) in DMSO (500 mL) was added bis((3,4-dimethylphenyl) methyl) amine (41.86 g, 165 mmol) and triethylamine (16.72 g, 165 mmol) at 20° C. under N$_2$. The reaction mixture was then warmed to 100° C. and stirred for 4 h. Then the mixture was cooled to room temperature and poured into water (600 mL). The aqueous layer was extracted with EtOAc (800 mL*3). The combined organic layer was washed with brine (600 mL*2), dried over anhydrous Na$_2$SO$_4$ and concentrated to give the crude product. The residue was purified by flash chromatography on silica gel (PE/EA=100/1 to 6/1) to give 279c (25 g, 29% yield) as a yellow oil. LC-MS (Method 4) t$_R$=2.29 min, m/z (M+H)$^+$=584.3. $^1$H NMR (400 MHz, DMSO-d$_6$) δ 8.23 (s, 1H), 6.99 (d, J=8.0 Hz, 2H), 6.51 (d, J=2.4 Hz, 2H), 6.45 (dd, J=8.0 Hz, 2.0 Hz, 2H), 5.01 (s, 1H), 4.59 (s, 4H), 4.16 (q, J=7.2 Hz, 4H), 3.73 (s, 6H), 3.62 (s, 6H), 3.52 (s, 3H), 1.16 (t, J=7.2 Hz, 6H).

Step 3. 2-(6-(Bis(2,4-dimethoxybenzyl) amino)-5-methoxypyrimidin-4-yl) acetic acid (279d)

To a solution of 279c (25 g, 42.8 mmol) in MeOH (195 mL) was added KOH (8.66 g, 85.6 mmol) in H$_2$O (65 mL). The reaction mixture was stirred at 60° C. for 16 h. The mixture was added into H$_2$O (30 mL) and adjusted to pH=6 with 1 N HCl. Then the resulting mixture was extracted with EtOAc (500 mL*3). The combined organic layer was washed with brine (200 mL*2), dried over anhydrous Na$_2$SO$_4$ and concentrated to give 279d (20 g, yield given). The crude product was used directly for the next step without further purification. LC-MS (Method 4) t$_R$=1.83 min, m/z (M+H)$^+$=484.2. $^1$H NMR (400 MHz, DMSO-d$_6$) δ 8.18 (s, 1H), 6.98 (d, J=8.4 Hz, 2H), 6.52 (d, J=2.4 Hz, 2H), 6.45 (dd, J=8.4 Hz, 2.0 Hz, 2H), 4.66-4.64 (m, 4H), 3.73 (s, 6H), 3.66 (s, 6H), 3.60 (s, 2H), 3.53 (s, 3H).

Step 4. Methyl 2-(6-(bis(2,4-dimethoxybenzyl) amino)-5-methoxypyrimidin-4-yl) acetate (279e)

To a stirred solution of 279d (20 g, 41.4 mmol) and MeI (7.64 g, 53.8 mmol) in DMF (200 mL) was added K$_2$CO$_3$ (11.44 g, 82.8 mmol). The reaction mixture was stirred at 20° C. for 8 h. The reaction mixture was poured into water (200 mL) and extracted with EtOAc (400 mL*3). The combined organic layer was washed with brine (200 mL*2), dried over anhydrous Na$_2$SO$_4$ and concentrated to give the crude product. The residue was purified by flash chromatography on silica gel (PE/EA=30/1 to 5/1) to give 279e (15 g, 73% yield) as a yellow solid. LC-MS (Method 4) t$_R$=1.84 min, m/z (M+H)$^+$=498.3. $^1$H NMR (400 MHz, DMSO-d$_6$) δ 8.19 (s, 1H), 6.97 (d, J=8.4 Hz, 2H), 6.52 (d, J=2.0 Hz, 2H), 6.45 (dd, J=8.4 Hz, 2.4 Hz, 2H), 4.64 (s, 4H), 3.76-3.71 (m, 8H), 3.66 (s, 6H), 3.62 (s, 3H), 3.52 (s, 3H).

Step 5. Ethyl (Z)-2-(6-(bis(2,4-dimethoxybenzyl) amino)-5-methoxypyrimidin-4-yl)-3-(dimethylamino)acrylate (279f)

To a solution of 279e (15 g, 30.1 mmol) in EtOH (150 ml) was added DMF-DMA (17.93 g, 150.5 mmol). The reaction mixture was stirred at 80° C. for 16 h. The mixture was concentrated in vacuum. The residue was purified by flash chromatography on silica gel (PE/EA=30/1 to 3/1) to give 279f (5.5 g, 32% yield) as a yellow solid. LC-MS (Method 4) t$_R$=1.75 min, m/z (M+H)$^+$=567.3.

Step 6. Ethyl 5-(bis(2,4-dimethoxybenzyl) amino)-4-methoxypyrazolo(1,5-c)pyrimidine-3-carboxylate (279g)

To a stirred solution of 279f (5.5 g, 10 mmol) in MeCN (60 mL) was added O-(2,4-dinitrophenyl) hydroxylamine (2.19 g, 11 mmol) at 20° C. under nitrogen. The reaction mixture was stirred at 50° C. for 16 h. The mixture was poured into water (30 mL) and extracted with EtOAc (100 mL*3). The combined organic layer was washed with brine (30 mL*2), dried over anhydrous Na₂SO₄ and concentrated to give the crude product. The crude product was purified by flash chromatography on silica gel (PE/EA=50/1 to 5/1) to give 279g (2.5 g, 47% yield) as a yellow solid. LC-MS (Method 4) $t_R$=2.15 min, m/z (M+H)⁺=537.3. ¹H NMR (400 MHz, CDCl₃) δ 8.78 (s, 1H), 8.31 (s, 1H), 7.08 (d, J=8.0 Hz, 2H), 6.42-6.38 (m, 4H), 4.79 (s, 4H), 4.31 (q, J=7.2 Hz, 2H), 3.78 (s, 6H), 3.69 (s, 6H), 3.58 (s, 3H), 1.36 (t, J=7.2 Hz, 3H).

Step 7. (5-(Bis(2,4-dimethoxybenzyl) amino)-4-methoxypyrazolo(1,5-c)pyrimidin-3-yl) methanol (279h)

To a stirred solution of 279g (2.5 g, 4.7 mmol) in toluene (30 mL) was added DIBAL-H (9.4 mL, 14.1 mmol, 1.5 M in toluene) at 0° C. under nitrogen. The reaction mixture was stirred at 20° C. for 2 h. The mixture was poured into water (10 mL) and filtered. The filtrate was extracted with EtOAc (50 mL*3). The combined organic layer was washed with brine (20 mL*2), dried over anhydrous Na₂SO₄ and concentrated to give the crude product. The crude product was purified by flash chromatography on silica gel (PE/EA=50/1 to 3/1) to give 279h (1.2 g, 51% yield) as a yellow solid. LC-MS (Method 4) $t_R$=2.37 min, m/z (M+H)⁺=495.2. ¹H NMR (400 MHz, DMSO-d₆) δ 9.04 (s, 1H), 7.93 (s, 1H), 7.04 (d, J=8.4 Hz, 2H), 6.51 (d, J=2.4 Hz, 2H), 6.43 (dd, J=8.4 Hz, 2.4 Hz, 2H), 4.83 (t, J=5.6 Hz, 1H), 4.63 (d, J=5.2 Hz, 2H), 4.54 (s, 4H), 3.72 (s, 6H), 3.67 (s, 6H), 3.65 (s, 3H).

Step 8. N,N-bis(2,4-dimethoxybenzyl)-4-methoxy-3-methylpyrazolo[1,5-c]pyrimidin-5-amine (279i)

To a stirred solution of 279h (100 mg, 0.20 mmol) and ZnI₂ (129 mg. 0.40 mmol) in MeOH (9 mL) was added NaBH₃CN (128 mg, 2.04 mmol) at 30° C. The solution was stirred at 30° C. for 16 h. The reaction mixture was poured into water (30 mL) and extracted with DCM (10 mL*3). The combined organic layer was washed with water (10 mL) and brine (10 mL), dried over Na₂SO₄ and concentrated to give the crude product. The crude product was purified by Prep-TLC (PE/EA=5/1) to give 279i (30 mg, 31% yield) as a yellow solid. LC-MS (Method 4) $t_R$=2.47 min, m/z (M+H)⁺=479.2. ¹H NMR (400 MHz, CDCl₃) δ 8.73 (s, 1H), 7.65 (s, 1H), 7.11 (d, J=8.0 Hz, 2H), 6.42-6.37 (m, 4H), 4.63 (s, 4H), 3.78 (s, 6H), 3.69 (s, 6H), 3.65 (s, 3H), 2.35 (s, 3H).

Step 9. 4-Methoxy-3-methylpyrazolo[1,5-c]pyrimidin-5-amine (279j)

To a stirred solution of 279i (30 mg, 0.062 mmol) in DCM (2 mL) was added TFA (0.1 mL) at 0° C. The solution was stirred at 25° C. for 1 h. The solution was concentrated in vacuum at 25° C. to give the crude product, which was purified by Prep-HPLC (Method E) to give 279j (9 mg, 80% yield) as a white solid. LC-MS (Method 4) $t_R$=2.04 min, m/z (M+H)⁺=179.1. ¹H NMR (400 MHz, CDCl₃) δ 8.72 (s, 1H), 7.89 (s, 1H), 4.33 (brs, 2H), 3.83 (s, 3H), 2.37 (s, 3H).

Step 10. 6-Chloro-4-((4-methoxy-3-methylpyrazolo[1,5-c]pyrimidin-5-yl)amino)-N-(methyl-d₃)nicotinamide (279k)

To a solution of 279j (9 mg, 1.24 mmol) and 42b in THF (2 mL) was added LiHMDS (0.40 mmol, 0.40 mL, 1 M in THF) at −40° C. The resulting mixture was stirred at 0° C. for 1 h. A yellow solution was formed. The reaction mixture was quenched with water (30 mL) and extracted with EtOAc (30 mL*3). The combined organic layer was washed with water (30 mL) and brine (30 mL), dried over anhydrous Na₂SO₄ and concentrated to give the crude product. The crude product was purified by Prep-TLC (PE/EA=1/1) to give 279k (15 mg, 85% yield) as a yellow solid. LC-MS (Method 3) $t_R$=1.21 min, m/z (M+H)⁺=350.2.

Step 11 6-(Cyclopropanecarboxamido)-4-((4-methoxy-3-methylpyrazolo[1,5-c]pyrimidin-5-yl)amino)-N-(methyl-d₃)nicotinamide (279)

A mixture of 279k (15 mg, 0.043 mmol), cyclopropanecarboxamide (6 mg, 0.064 mmol), BrettPhos (5 mg, 0.009 mmol), Cs₂CO₃ (42 mg, 0.129 mmol) and BrettPhos Pd G3 (4 mg, 0.005 mmol) in dioxane (1 mL) was degassed and purged with nitrogen for 3 times. The resulting mixture was stirred at 100° C. under N₂ atmosphere for 24 h. A yellow suspension was formed. The reaction mixture was concentrated and purified by Prep-HPLC (Method E) to give 279 (4.2 mg, 25% yield) as a white solid. LC-MS (Method 1) $t_R$=1.29 min, m/z (M+H)⁺=399.3. ¹H NMR (400 MHz, DMSO-d₆) δ 11.56 (s, 1H), 10.79 (s, 1H), 9.29 (s, 1H), 8.89 (s, 1H), 8.65 (s, 1H), 8.56 (s, 1H), 8.04 (s, 1H), 3.88 (s, 3H), 2.57 (s, 3H), 2.06-1.94 (m, 1H), 0.81-0.76 (m, 4H).

Example 280

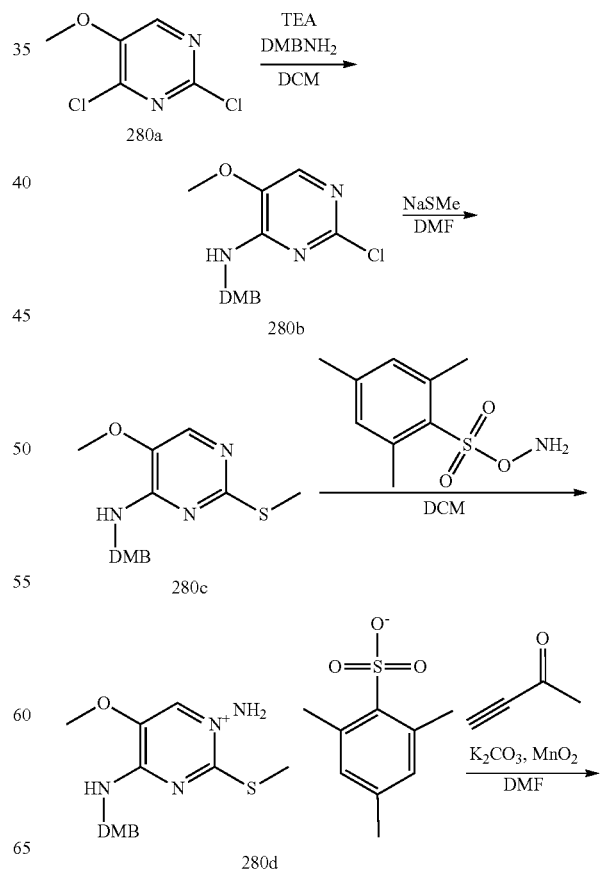

727
-continued

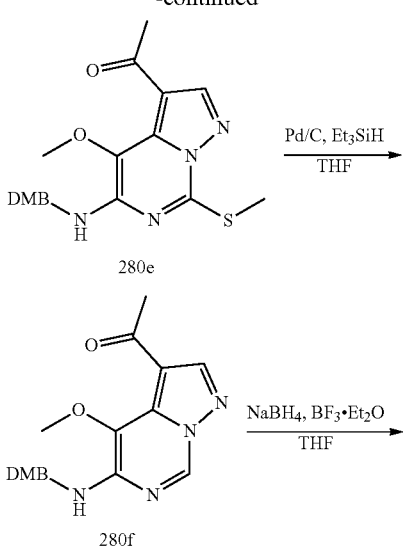
280e

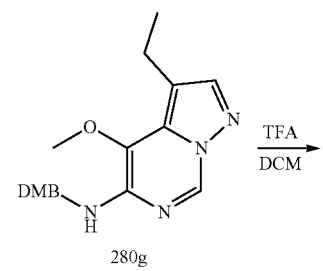
280f

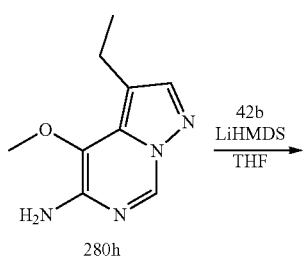
280g

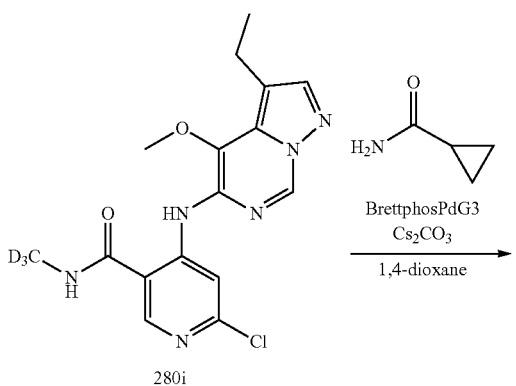
280i

728
-continued

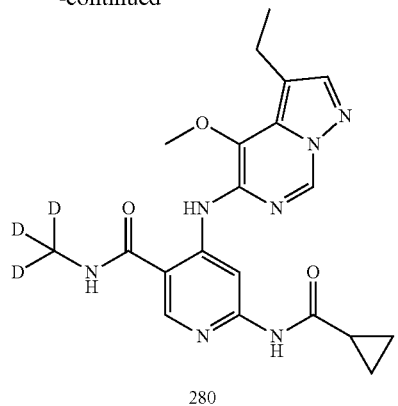
280

Step 1. 2-Chloro-N-(2,4-dimethoxybenzyl)-5-methoxypyrimidin-4-amine (280b)

To a solution of 280a (25.00 g, 139.66 mmol) in DCM (250 mL) was added TEA (28.26 g, 279.32 mmol) and (2,4-dimethoxyphenyl) methanamine (22.18 g, 132.68 mmol) at 0° C. Then the mixture was stirred at r.t. for 1 h, diluted with water (100 mL) and extracted with DCM (150 mL*2). The combined organic layer was concentrated and the residue was purified by flash chromatography on silica gel (PE/EA=2/1) to afford 280b (32.06 g, 74% yield) as a white solid. $^1$H NMR (400 MHz, DMSO-$d_6$) δ 7.69 (s, 1H), 7.65 (t, J=6.0 Hz, 1H), 6.99 (d, J=8.0 Hz, 1H), 6.55 (d, J=2.4 Hz, 1H), 6.47 (dd, J=8.4 Hz, 2.4 Hz, 1H), 4.42 (d, J=6.0 Hz, 2H), 3.86 (s, 3H), 3.80 (s, 3H), 3.73 (s, 3H).

Step 2. N-(2,4-dimethoxybenzyl)-5-methoxy-2-(methylthio)pyrimidin-4-amine (280c)

A mixture of 280b (12.00 g, 38.74 mmol) and MeSNa (4.07 g, 58.11 mmol) in DMF (50 mL) was stirred at 80° C. for 5 h. After cooling to r.t., the reaction mixture was diluted with water (80 mL) and extracted with EtOAc (100 mL*3). The combined organic layer was concentrated and the residue was purified by flash chromatography on silica gel (PE/EA=5/1) to afford 280c (4.3 g, 35% yield) as a yellow oil. LC-MS (Method 3) $t_R$=0.28 min, m/z (M+H)$^+$=322.3.

Step 3. 1-Amino-4-((2,4-dimethoxybenzyl)amino)-5-methoxy-2-(methylthio)pyrimidin-1-ium 2,4,6-trimethylbenzenesulfonate (280d)

To a solution of 280c (5.56 g, 17.30 mmol) in DCM (13 mL) was added 0-(mesitylsulfonyl)hydroxylamine (3.72 g, 17.30 mmol) at 0° C. Then the mixture was stirred at 0° C. for 3 h. The suspension was filtered and the filter cake was dried to afford 280d (2.2 g, 38% yield) as a white solid. LC-MS (Method 3) $t_R$=0.97 min, m/z M$^+$=337.3.

Step 4. 1-(5-((2,4-Dimethoxybenzyl)amino)-4-methoxy-7-(methylthio)pyrazolo[1,5-c]pyrimidin-3-yl)ethanone (280e)

To a solution of 280d (1.5 g, 4.45 mmol) and but-3-yn-2-one (363 mg, 5.33 mmol) in THF (15 mL) was added MnO$_2$ (580 mg, 6.67 mmol) and K$_2$CO$_3$ (922 mg, 6.67 mmol) at 0° C. After stirring at 35° C. for 4 h, the reaction mixture was filtered. The filtrate was diluted with water (25 mL) and extracted with EtOAc (50 mL*2). The combined organic layer was concentrated and the residue was purified by flash chromatography on silica gel (PE/EA=2/1) to afford 280e (330 mg, 18% yield) as a yellow solid. LC-MS (Method 3) $t_R$=1.24 min, m/z (M+H)$^+$=403.3.

Step 5. 1-(5-((2,4-Dimethoxybenzyl)amino)-4-methoxypyrazolo[1,5-c]pyrimidin-3-yl)ethanone (280f)

A mixture of 280e (320 mg, 0.79 mmol) and Pd/C (45 mg, 10% wt wetted in 50% water) in Et$_3$SiH (3 mL) and THF (3 mL) was stirred at 80° C. for 6 h. After cooling to r.t., the reaction mixture was diluted with water (5 mL) and extracted with EtOAc (8 mL*2). The combined organic layer was dried over Na$_2$SO$_4$, filtered and concentrated. The residue was purified by flash chromatography on silica gel (DCM/EtOAc=3/1) to afford 280f (97 mg, 34% yield) as a yellow solid. LC-MS (Method 3) $t_R$=1.16 min, m/z (M+H)$^+$=357.3.

Step 6. N-(2,4-dimethoxybenzyl)-3-ethyl-4-methoxypyrazolo[1,5-c]pyrimidin-5-amine (280g)

To a solution of 280f (95 mg, 0.27 mmol) in THF (1 mL) was added NaBH$_4$ (10 mg, 0.27 mmol) and BF$_3$·Et$_2$O (76 mg, 0.53 mmol) under ice-water bath. The mixture was stirred at r.t. for 1 h, poured into ice-water (2 mL) and extracted with EtOAc (5 mL*2). The combined organic layer was concentrated and the residue was purified by flash chromatography on silica gel (DCM/MeOH=20/1) to afford 280g (44 mg, 48% yield) as a yellow oil. LC-MS (Method 3) $t_R$=1.30 min, m/z (M+H)$^+$=343.4.

Step 7. 3-Ethyl-4-methoxypyrazolo[1,5-c]pyrimidin-5-amine (280h)

A mixture of 280g (42 mg, 0.12 mmol) in TFA/DCM (0.4 mL/1.2 mL) was stirred at 8° C. for 30 min. The solvent was removed. The residue was diluted with DCM (1 mL), adjusted to pH>7 with NH$_3$/1,4-dioxane (2 mL, 2 M). Then the mixture was concentrated and the residue was purified by flash chromatography on silica gel (DCM/MeOH=10/1) to afford 280h (14 mg, 59% yield) as a yellow oil. LC-MS (Method 3) $t_R$=1.09 min, m/z (M+H)$^+$=193.0.

Step 8. 6-Chloro-4-((3-ethyl-4-methoxypyrazolo[1,5-c]pyrimidin-5-yl)amino)-N-(methyl-d$_3$)nicotinamide (280i)

To a solution of 280h (14 mg, 0.073 mmol) and 42b (18 mg, 0.087 mmol) in THF (0.2 mL) was added LiHMDS (0.3 mL, 0.3 mmol, 1 M in THF) at −40° C. The reaction was stirred at −40° C. to r.t. for 1 h and quenched with H$_2$O (2 mL). The organic solvent was evaporated under reduced pressure. The formed solid was collected by filtering and was purified by flash chromatography on silical gel (DCM/MeOH=20/1) to afford 280i (6 mg, 9% yield) as a brown solid. LC-MS (Method 3) $t_R$=1.22 min, m/z (M+H)$^+$=364.2.

Step 9. 6-(Cyclopropanecarboxamido)-4-((3-ethyl-4-methoxypyrazolo[1,5-c]pyrimidin-5-yl)amino)-N-(methyl-d$_3$)nicotinamide (280)

A mixture of 280i (6 mg, 0.017 mmol), cyclopropanecarboxamide (4 mg, 0.034 mmol), BrettPhos Pd G3 (3 mg, 0.003 mmol) and Cs$_2$CO$_3$ (11 mg, 0.034 mmol) in 1,4-dioxane (0.3 mL) was stirred at 90° C. overnight under N$_2$ atmosphere. After cooling to r.t., the mixture was concentrated. And the residue was purified by Prep-HPLC (Method A) to afford 280 (1.2 mg, 16% yield) as a white solid. LC-MS (Method 1) $t_R$=1.30 min, m/z (M+H)$^+$=413.1. $^1$H NMR (400 MHz, DMSO-d$_6$) δ 11.44 (s, 1H), 10.73 (s, 1H), 9.23 (s, 1H), 8.81 (s, 1H), 8.65 (s, 1H), 8.56 (s, 1H), 8.04 (s, 1H), 3.88 (s, 3H), 2.81 (q, J=7.6 Hz, 2H), 2.06-1.94 (m, 1H), 1.27 (t, J=7.6 Hz, 3H), 0.80-0.76 (m, 4H).

Example 281

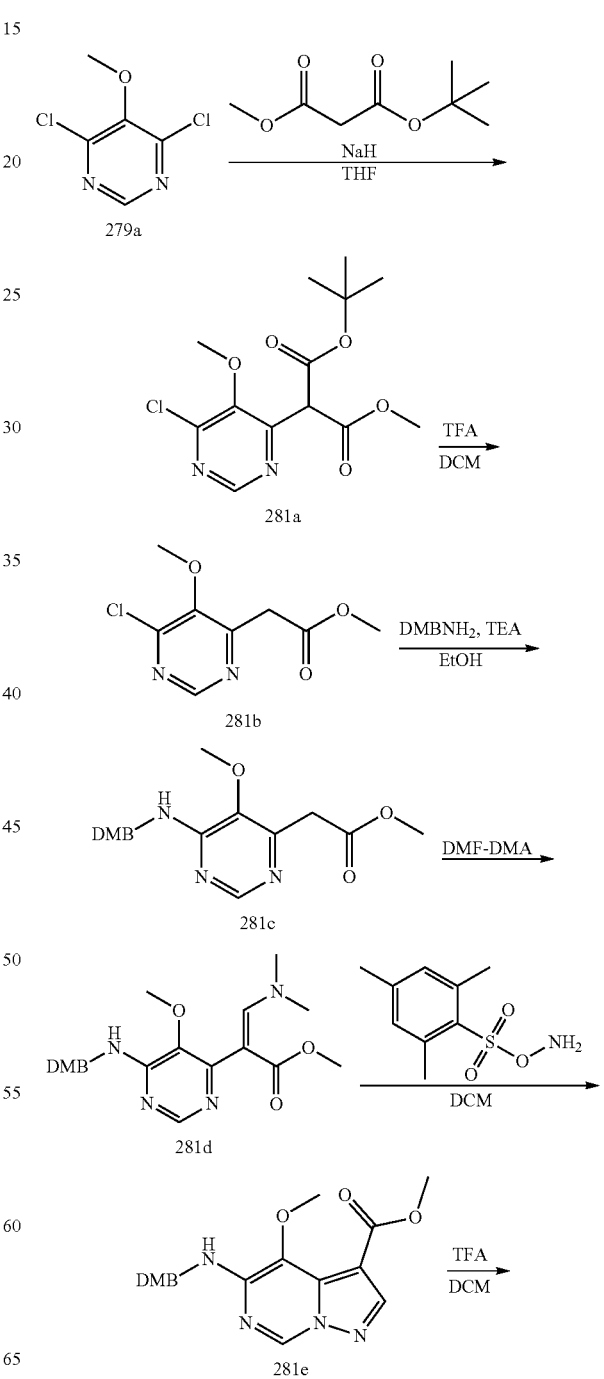

-continued

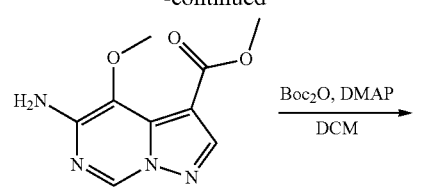
281f

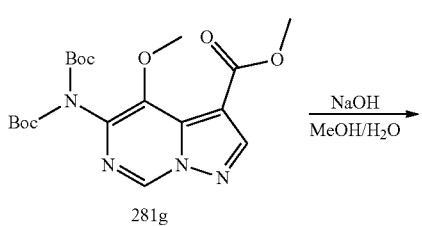
281g

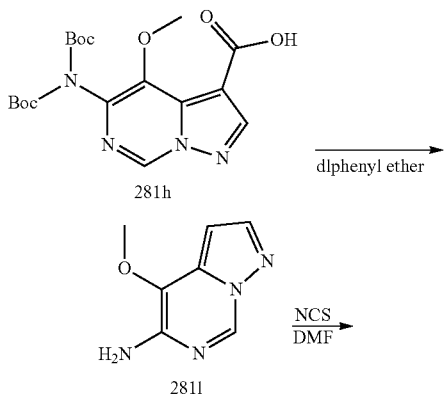
281h

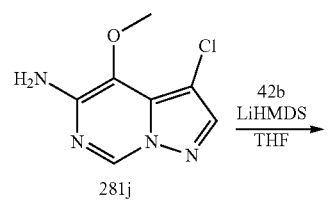
281i

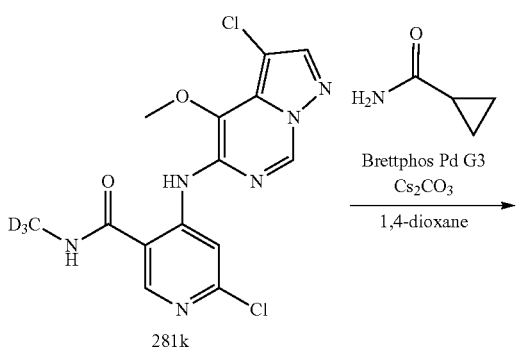
281j

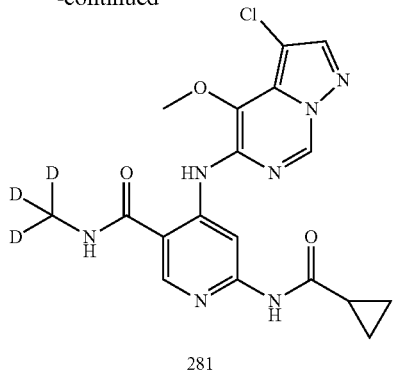
281k

-continued

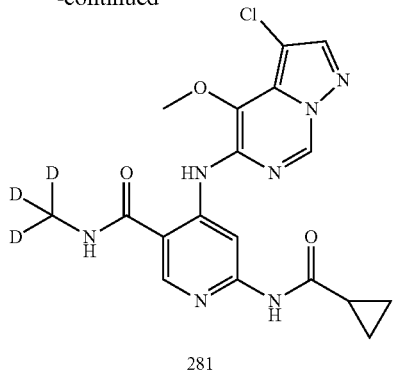
281

Step 1. 1-Tert-butyl 3-methyl 2-(6-chloro-5-methoxypyrimidin-4-yl)malonate (281a)

To a solution of tert-butyl methyl malonate (13.08 g, 75.08 mmol) in THF (200 mL) was added NaH (6.01 g, 150.16 mmol, 60% in mineral oil) at 0° C. The mixture was stirred at 0° C. for 30 min. Then a solution of 279a (11.2 g, 62.57 mmol) in THF (20 mL) was added to the mixture at 0° C. The mixture was stirred at 80° C. for 3 h and poured into ice-water (150 mL). The mixture was acidified with 2 N HCl to pH=2 and extracted with EtOAc (300 mL*2). The combined organic layer was washed with brine (100 mL), dried over $Na_2SO_4$, filtered and concentrated to afford 281a (19.8 g, yield given) as a yellow oil. LC-MS (Method 3) $t_R$=1.26 min, m/z (M+H−56)$^+$=261.2.

Step 2. Methyl 2-(6-chloro-5-methoxypyrimidin-4-yl)acetate (281b)

To a mixture of 281a (18.0 g, 56.83 mmol) in DCM (150 mL) was added TFA (75 mL) at 0° C. After stirring at r.t. for 4 h, the reaction mixture was concentrated. The residue was diluted with EtOAc (500 mL) and washed with sat. $NaHCO_3$ (150 mL) and brine (100 mL). The organic layer was concentrated. The residue was purified by flash chromatography on silica gel (PE/EA=10/1) to afford 281b (10.5 g, 85% yield) as yellow oil. $^1$H NMR (400 MHz, $CDCl_3$) δ 8.67 (s, 1H), 3.95 (s, 3H), 3.91 (s, 2H), 3.75 (s, 3H).

Step 3. Methyl 2-(6-((2,4-dimethoxybenzyl)amino)-5-methoxypyrimidin-4-yl)acetate (281c)

A mixture of 281b (1.0 g, 4.62 mmol), TEA (934 mg, 9.23 mmol) and $DMBNH_2$ (1.00 g, 6.00 mmol) in EtOH (10 mL) was stirred at 80° C. for 5 h. The mixture was diluted with $H_2O$ (20 mL), extracted with EtOAc (40 mL*2). The organic layer was concentrated and the residue was purified by flash chromatography on silica gel (PE/EA=1/1) to afford 281c (1.33 g, 83% yield) as a white solid. LC-MS (Method 3) $t_R$=1.07 min, m/z (M+H)$^+$=348.2.

Step 4. (Z)-Methyl 2-(6-((2,4-dimethoxybenzyl)amino)-5-methoxypyrimidin-4-yl)-3-(dimethylamino)acrylate (281d)

A mixture of 281c (1.33 g, 3.83 mmol) in DMF-DMA (10 mL) was stirred at 120° C. for 18 h. The mixture was concentrated to afford 281d (1.54 g, yield given) as a brown oil. LC-MS (Method 3) $t_R$=1.07 min, m/z (M+H)$^+$=403.3.

Step 5. Methyl 5-((2,4-dimethoxybenzyl)amino)-4-methoxypyrazolo[1,5-c]pyrimidine-3-carboxylate (281e)

To a mixture of 281d (1.61 g, 4.00 mmol) in DCM (30 mL) was added dropwise a solution of O-(mesitylsulfonyl)hydroxylamine (1.03 g, 4.80 mmol) in DCM (5 mL) at 0° C. The mixture was stirred at 0° C. for 2 h. Another batch of a solution of O-(mesitylsulfonyl)hydroxylamine (515 mg, 2.40 mmol) in DCM (5 mL) was added into the mixture at 0° C. The mixture was stirred at 0° C. for 1 h. The mixture was concentrated and purified by flash chromatography on silica gel (DCM/MeOH=50/1) to afford 281e (788 mg, 53% yield) as a yellow solid. $^1$H NMR (400 MHz, CDCl$_3$) δ 8.84 (s, 1H), 8.27 (s, 1H), 7.21 (d, J=8.4 Hz, 1H), 6.46 (d, 0.1=2.0 Hz, 1H), 6.41 (dd, J=8.0 Hz, 2.4 Hz, 1H), 5.64 (t, J=6.0 Hz, 1H), 4.64 (d, J=6.0 Hz, 2H), 3.86 (s, 3H), 3.85 (s, 3H), 3.80 (s, 3H), 3.79 (s, 3H).

Step 6. Methyl 5-amino-4-methoxypyrazolo[1,5-c]pyrimidine-3-carboxylate (281f)

To a mixture of 281e (4.26 g, 11.44 mmol) in DCM (15 mL) was added TFA (15 mL) dropwise at r.t. The reaction mixture was stirred at r.t. for 1 h and concentrated under vacuum at 30° C. The residue was dissolved in DCM (80 mL) and the solution was basified with 1 M NaOH to pH=12. The mixture was extracted with DCM (80 mL). The organic layer was concentrated and the residue was purified by flash chromatography on silica gel (DCM/MeOH=10/1) to afford 281f (1.94 g, 76% yield) as a yellow solid. $^1$H NMR (400 MHz, DMSO-d$_6$) δ 9.09 (s, 1H), 8.27 (s, 1H), 6.68 (brs, 2H), 3.77 (s, 3H), 3.71 (s, 3H).

Step 7. Methyl 5-[bis(tert-butoxycarbonyl)amino]-4-methoxy-pyrazolo[1,5-c]pyrimidine-3-carboxylate (281g)

A solution of 281f (1.94 g, 8.73 mmol), Boc$_2$O (2.29 g, 10.48 mmol) and DMAP (320 mg, 2.62 mmol) in DCM (50 mL) was stirred at 25° C. for 2 h. The solvent was removed in vacuo and the residue was purified by flash chromatography on silica gel (DCM/MeOH=20/1) to afford 281g (2.13 g, 58% yield) as a white solid. $^1$H NMR (400 MHz, DMSO-d$_6$) δ 9.56 (s, 1H), 8.68 (s, 1H), 3.85 (s, 3H), 3.82 (s, 3H), 1.41 (s, 18H).

Step 8. 5-[Bis(tert-butoxycarbonyl)amino]-4-methoxy-pyrazolo[1,5-c]pyrimidine-3-carboxylic acid (281h)

To a mixture of 281g (1.1 g, 2.60 mmol) in MeOH (14 mL) was added NaOH (208 mg, 5.21 mmol) in H$_2$O (7 mL) at r.t. The mixture was stirred at 35° C. for 10 h, concentrated and purified by Prep-HPLC (Method A) without working up. The product was dissolved in water (30 mL), acidified with 2 N HCl to pH=1 and extracted with EtOAc (50 mL*2). The combined organic layer was dried over Na$_2$SO$_4$, filtered and concentrated to afford 281h (240 mg, 45% yield) as a white solid. $^1$H NMR (400 MHz, DMSO-d$_6$) δ 12.72 (brs, 1H), 9.54 (s, 1H), 8.62 (s, 1H), 3.81 (s, 3H), 1.39 (s, 18H).

Step 9. 4-Methoxypyrazolo[1,5-c]pyrimidin-5-amine (281i)

A mixture of 281h (240 mg, 0.59 mmol) in diphenyl ether (3 mL) was stirred at 170° C. for 4 h. After cooling to r.t., the mixture was diluted with PE (5 mL) and filtered. The filtrate was concentrated and the residue was purified by flash chromatography on silica gel (DCM/MeOH=10/1) to afford the title compound 281i (40 mg, 42% yield) as a brown solid. LC-MS (Method 3) t$_R$=0.27 min, m/z (M+H)$^+$=165.1.

Step 10. 3-Chloro-4-methoxypyrazolo[1,5-c]pyrimidin-5-amine (281j)

A solution of 281i (13 mg, 0.079 mmol) and NCS (16 mg, 0.119 mmol) in DMF (0.2 mL) was stirred at 25° C. for 2 h. The mixture was diluted with water (5 mL) and extracted with EtOAc (10 mL*3). The organic layer was dried over Na$_2$SO$_4$, filtered and concentrated. The residue was purified by Prep-TLC (DCM/MeOH=20/1) to afford 281j (10 mg, 66% yield) as a white solid. LC-MS (Method 3) t$_R$=1.03 min, m/z (M+H)$^+$=199.0.

Step 11. 6-Chloro-4-((3-chloro-4-methoxypyrazolo[1,5-c]pyrimidin-5-yl)amino)-N-(methyl-d$_3$)nicotinamide (281k)

To a solution of 281j (50 mg, 0.25 mmol) and 42b (105 mg, 0.50 mmol) in THF (0.4 mL) was added LiHMDS (1.0 mL, 1.0 mmol, 1 M in THF) at -40° C. The reaction was stirred at -40° C. to r.t. for 1 h and quenched with H$_2$O (2 mL). The organic solvent was evaporated under reduced pressure. The formed solid was collected by filtering and was dried to afford 281k (20 mg, 22% yield) as a brown solid. LC-MS (Method 3) t$_R$=1.21 min, m/z (M+H)$^+$=370.2.

Step 12. 4-((3-Chloro-4-methoxypyrazolo[1,5-c]pyrimidin-5-yl)amino)-6-(cyclopropanecarboxamido)-N-(methyl-d$_3$)nicotinamide (281)

A mixture of 281k (20 mg, 0.054 mmol), cyclopropanecarboxamide (14 mg, 0.16 mmol), BrettPhos Pd G3 (10 mg, 0.010 mmol) and Cs$_2$CO$_3$ (35 mg, 0.11 mmol) in 1,4-dioxane (0.5 mL) was stirred at 90° C. overnight under N$_2$ atmosphere. After cooling to r.t., the mixture was concentrated. And the residue was purified by Prep-TLC (DCM/MeOH=20/1) to afford 281 (3 mg, 14% yield) as a white solid. LC-MS (Method 1) t$_R$=1.45 min, m/z (M+H)$^+$=419.1. $^1$H NMR (400 MHz, DMSO-d$_6$) δ 11.78 (s, 1H), 10.77 (s, 1H), 9.33 (s, 1H), 9.04 (s, 1H), 8.70 (s, 1H), 8.59 (s, 1H), 8.26 (s, 1H), 3.93 (s, 3H), 2.00-1.90 (m, 1H), 0.85-0.79 (m, 4H).

Example 282

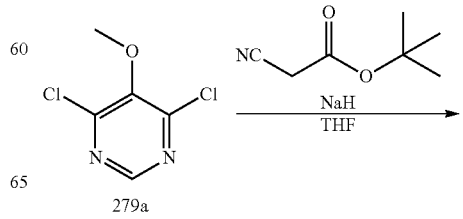

279a

735

-continued

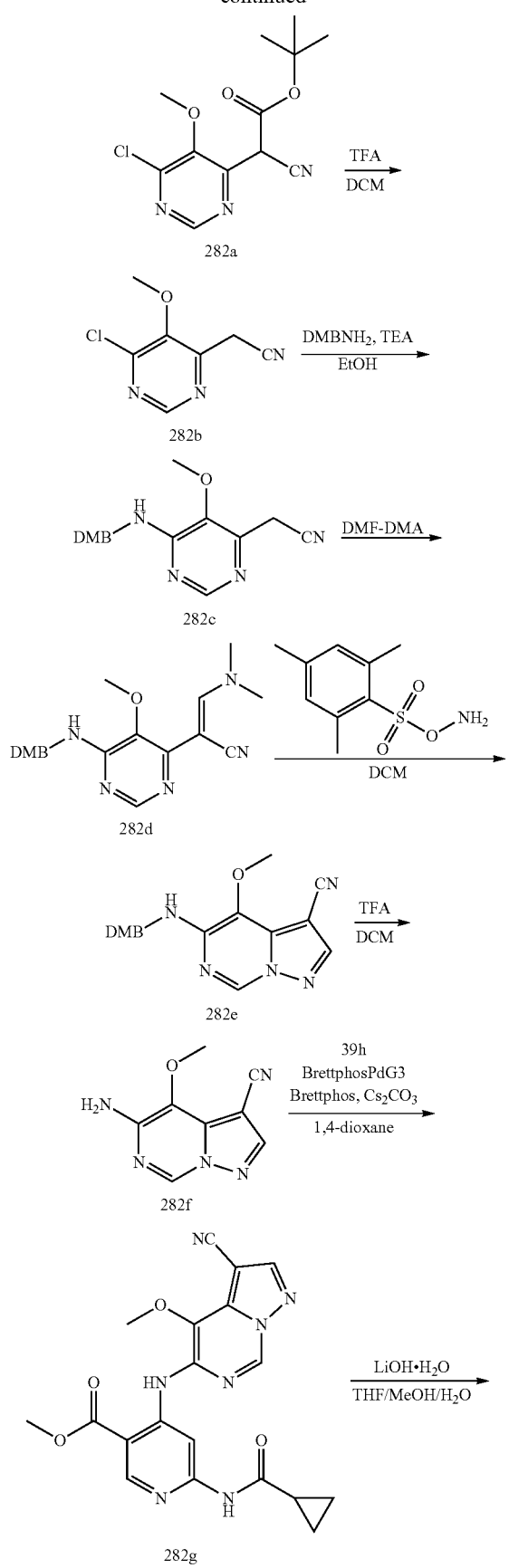

736

-continued

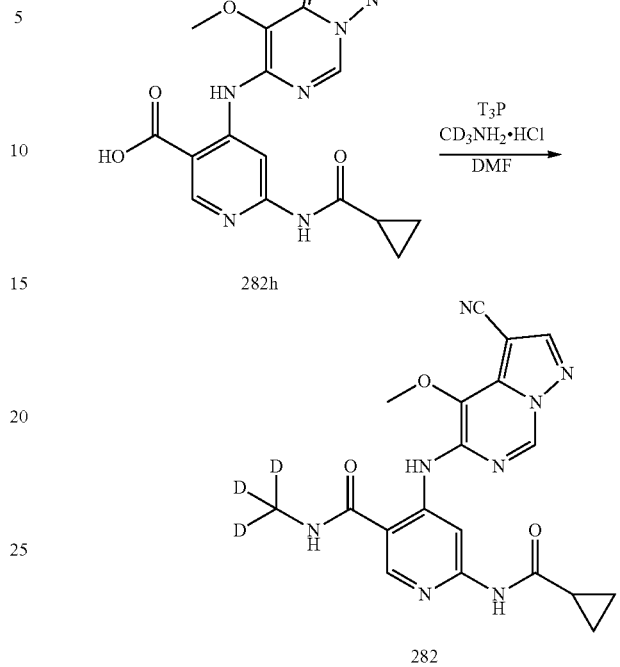

Step 1. Tert-butyl 2-(6-chloro-5-methoxypyrimidin-4-yl)-2-cyanoacetate (282a)

To a solution of tert-butyl 2-cyanoacetate (9.46 g, 67.04 mmol) in THF (200 mL) was added NaH (5.36 g, 134.08 mmol, 60% in mineral oil) at 0° C. After stirring at 0° C. for 30 min, to it was added a solution of 279a (10 g, 55.86 mmol) in THF (20 mL). The mixture was stirred at 80° C. for 2 h. After cooling to r.t., the reaction mixture was poured into ice-water (150 mL) and acidified with 2 N HCl to pH=2. The mixture was extracted with EtOAc (300 mL*2). The combined organic layer was washed with brine (100 mL), dried over $Na_2SO_4$, filtered. The filtrate was concentrated under reduced pressure to afford 282a (15 g, 95% yield) as a yellow solid. LC-MS (Method 3) $t_R$=1.13 min, m/z (M+H−56)$^+$=228.2.

Step 2.
2-(6-Chloro-5-methoxypyrimidin-4-yl)acetonitrile (282b)

To a mixture of 282a (7.5 g, 26.44 mmol) in DCM (100 mL) was added TFA (50 mL) at 0° C. The mixture was stirred at r.t. for 4 h. The solvent was concentrated. The residue was diluted with $H_2O$ (100 mL), adjusted to pH=9 with saturated $Na_2CO_3$ solution and extracted with EtOAc (100 mL*3). The combined organic layer was concentrated under reduced pressure to afford 282b (4.8 g, 99% yield) as a yellow oil. $^1$H NMR (400 MHz, CDCl$_3$) δ 8.72 (s, 1H), 4.05 (s, 3H), 3.97 (s, 2H).

Step 3. 2-(6-((2,4-Dimethoxybenzyl)amino)-5-methoxypyrimidin-4-yl)acetonitrile (282c)

A mixture of 282b (4.8 g, 26.14 mmol), TEA (7.3 mL, 52.3 mmol) and DMBNH$_2$ (5.68 g, 33.99 mmol) in EtOH (30 mL) was stirred at 80° C. for 2 h. After cooling to r.t., the mixture was diluted with H₂O (40 mL) and extracted with EtOAc (80 mL*2). The combined organic layer was concentrated under reduced pressure. The residue was purified by flash chromatography on silica gel (PE/EA=1/1) to afford 282c (5.35 g, 65% yield) as a yellow oil. LC-MS (Method 3) $t_R$=0.99 min, m/z (M+H)⁺=315.3.

Step 4. (Z)-2-(6-((2,4-dimethoxybenzyl)amino)-5-methoxypyrimidin-4-yl)-3-(dimethylamino)acrylonitrile (282d)

A mixture of 282c (5.35 g, 17.02 mmol) in DMF-DMA (35 mL) was stirred at 130° C. for 10 h. The mixture was cooled and concentrated under reduced pressure to afford 282d (6.29 g, yield given) as a yellow oil. LC-MS (Method 3) $t_R$=1.06 min, m/z (M+H)⁺=370.2.

Step 5. 5-((2,4-Dimethoxybenzyl)amino)-4-methoxypyrazolo[1,5-c]pyrimidine-3-carbonitrile (282e)

To a mixture 282d (3.0 g, 8.12 mmol) in DCM (50 mL) was added dropwise a solution of O-(mesitylsulfonyl)hydroxylamine (2.10 g, 9.75 mmol) in DCM (10 mL) at 0° C. The mixture was stirred at 0° C. for 2 h. Another batch of a solution of O-(mesitylsulfonyl)hydroxylamine (0.58 g, 2.69 mmol) in DCM (5 mL) was added to the reaction mixture at 0° C. The mixture was stirred at r.t. for 18 h and purified by flash chromatography on silica gel (DCM/EtOAc=20/1) to afford 282e (730 mg, 26% yield) as a yellow solid. ¹H NMR (400 MHz, CDCl₃) δ 8.80 (s, 1H), 8.03 (s, 1H), 7.21 (d, J=8.4 Hz, 1H), 6.47 (d, J=2.4 Hz, 1H), 6.41 (dd, J=8.4 Hz, 2.4 Hz, 1H), 5.56 (s, 1H), 4.64 (d, J=5.6 Hz, 2H), 3.90 (s, 3H), 3.89 (s, 3H), 3.76 (s, 3H).

Step 6. 5-Amino-4-methoxypyrazolo[1,5-c]pyrimidine-3-carbonitrile (282f)

To a solution of 282e (400 mg, 1.18 mmol) in DCM (2 mL) was added TFA (2 mL) dropwise at r.t. The reaction mixture was stirred at r.t. for 1 h and concentrated under vacuum at 30° C. The residue was dissolved in H₂O (80 mL) and the solution was adjusted to pH=12 with 1 M NaOH solution. The mixture was extracted with DCM (80 mL*3). The combined organic layer was concentrated and the residue was purified by flash chromatography on silica gel (DCM/MeOH=10/1) to afford 282f (100 mg, 44% yield) as a yellow solid. LC-MS (Method 2) $t_R$=0.60 min, m/z (M+H)⁺=190.2.

Step 7. Methyl 4-((3-cyano-4-methoxypyrazolo[1,5-c]pyrimidin-5-yl)amino)-6-(cyclopropanecarboxamido)nicotinate (282g)

A mixture of 282f (100 mg, 0.53 mmol), 39h (148 mg, 0.58 mmol), BrettPhos Pd G3 (48 mg, 0.053 mmol), BrettPhos (28 mg, 0.053 mmol) and Cs₂CO₃ (344 mg, 1.06 mmol) in 1,4-dioxane (1 mL) was stirred at 90° C. overnight under N₂ atmosphere. After cooling to r.t., the mixture was concentrated. And the residue was purified by flash chromatography on silica gel (DCM/EtOAc=20/1) to afford 282g (58 mg, 27%) as a brown solid. LC-MS (Method 2) $t_R$=1.60 min, m/z (M+H)⁺=408.2. ¹H NMR (400 MHz, DMSO-d₆) δ 9.59 (s, 1H), 9.36 (s, 1H), 8.81 (s, 1H), 8.71 (s, 1H), 4.03 (s, 3H), 3.92 (s, 3H), 2.07-2.04 (m, 1H), 0.85-0.81 (m, 4H).

Step 8. 4-((3-Cyano-4-methoxypyrazolo[1,5-c]pyrimidin-5-yl)amino)-6-(cyclopropanecarboxamido)nicotinic acid (282h)

A mixture of 282g (58 mg, 0.14 mmol) and LiOH·H₂O (18 mg, 0.43 mmol) in THF (3 mL), MeOH (0.6 mL) and water (0.6 mL) was stirred at 40° C. for 3 h. The reaction mixture was diluted with water (5 mL). The aqueous layer was acidified with 1 N HCl to pH=4 and was extracted with EtOAc (15 mL*3). The combined organic layer was washed with brine (15 mL), dried over Na₂SO₄, filtered, concentrated and purified by flash chromatography on silica gel (DCM/MeOH=50/1 to 10/1) to get compound 282h (20 mg, 35% yield) as a white solid.

Step 9. 4-((3-Cyano-4-methoxypyrazolo[1,5-c]pyrimidin-5-yl)amino)-6-(cyclopropanecarboxamido)-N-(methyl-d₃)nicotinamide (282)

A mixture of trideuteriomethanamine hydrochloride (25 mg, 0.184 mmol), 282h (20 mg, 0.051 mmol), DIPEA (36 mg, 0.275 mmol) and T₃P (117 mg, 0.184 mmol, 0.13 mL, 50% in EtOAc) in DMF (2 mL) was stirred at 25° C. for 12 h. A yellow solution was formed. The reaction mixture was filtered and purified by Prep-HPLC (Method E) to give 282 (2 mg, 9.5% yield) as a white solid. LC-MS (Method 2) $t_R$=1.23 min, m/z (M+H) 4=413.3. ¹H NMR (400 MHz, DMSO-d₆) δ 11.51 (s, 1H), 10.64 (s, 1H), 9.60 (s, 1H), 9.39 (s, 1H), 8.91 (s, 1H), 8.62 (s, 1H), 8.28 (s, 1H), 3.90 (s, 3H), 2.00-1.96 (m, 1H), 0.81-0.77 (m, 4H).

Summary of representative compounds are shown in Table 1.

Table 1. Exemplary Compounds

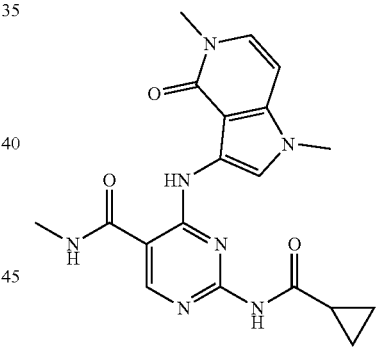

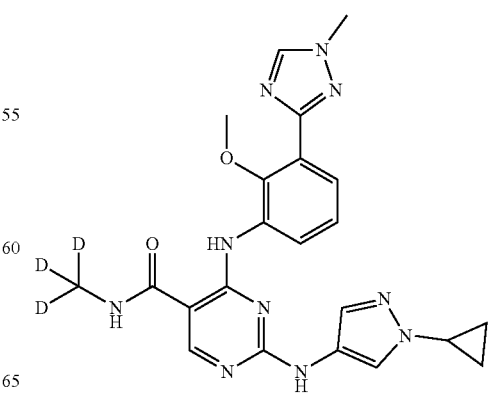

739
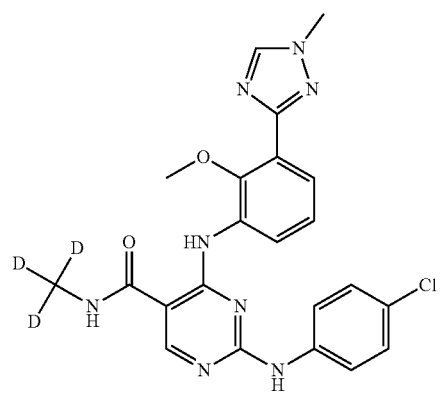 [SMILES: [2H]C([2H])([2H])NC(=O)c1cnc(Nc2ccc(Cl)cc2)nc1Nc1cccc(-c2ncn(C)n2)c1OC]
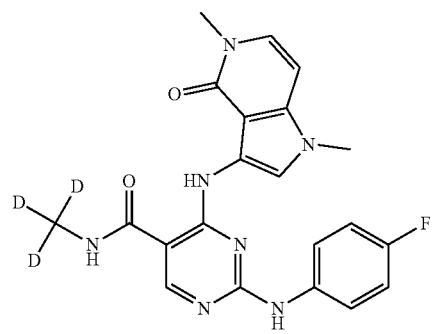 [SMILES: [2H]C([2H])([2H])NC(=O)c1cnc(Nc2ccc(F)cc2)nc1Nc1cn(C)c2ccn(C)c(=O)c12]
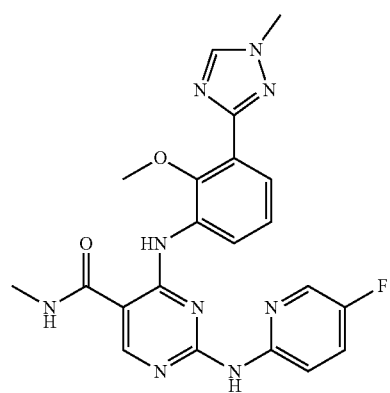 [SMILES: CNC(=O)c1cnc(Nc2ccc(F)cn2)nc1Nc1cccc(-c2ncn(C)n2)c1OC]
740
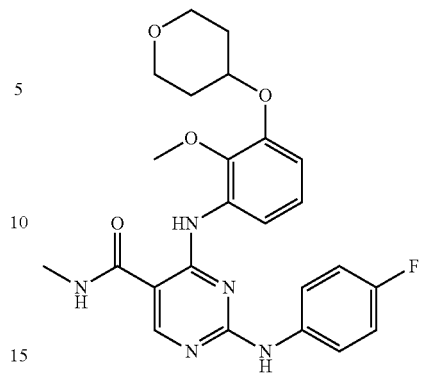
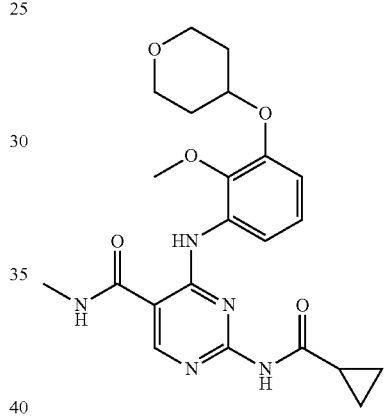
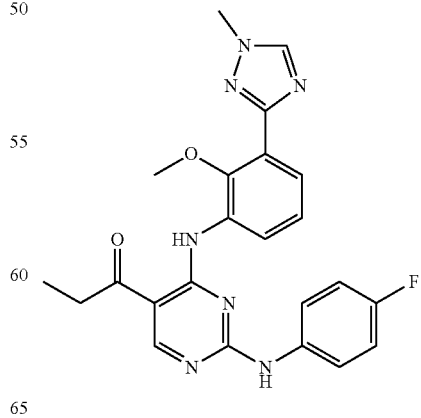

741
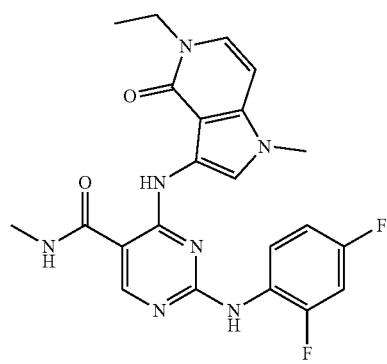 [SMILES: CCn1ccc2c(c(Nc3nc(Nc4ccc(F)cc4F)ncc3C(=O)NC)cn2C)c1=O]
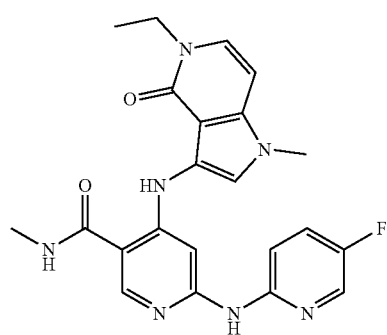 [SMILES: CCn1ccc2c(c(Nc3cc(Nc4ccc(F)cn4)ncc3C(=O)NC)cn2C)c1=O]
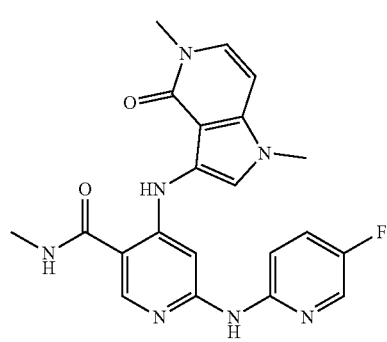 [SMILES: CNC(=O)c1cnc(Nc2ccc(F)cn2)cc1Nc1cn(C)c2ccn(C)c(=O)c12]
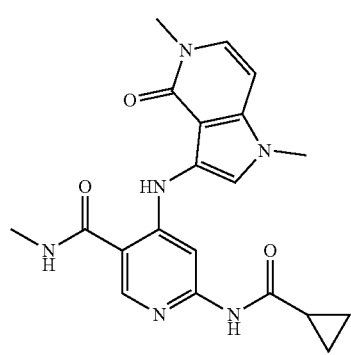
742
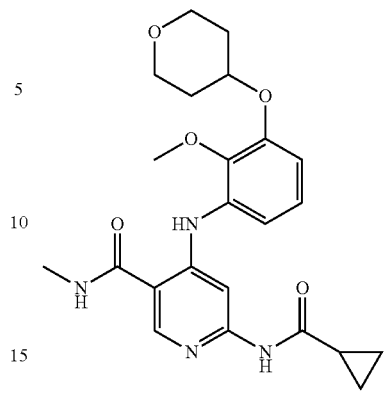
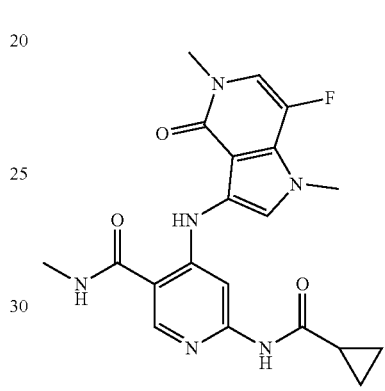
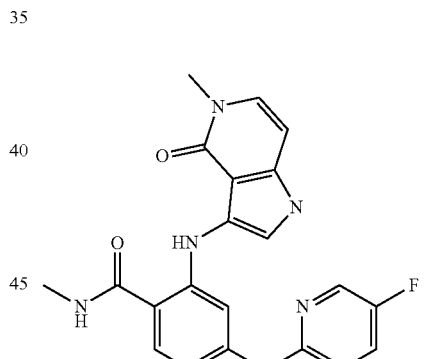
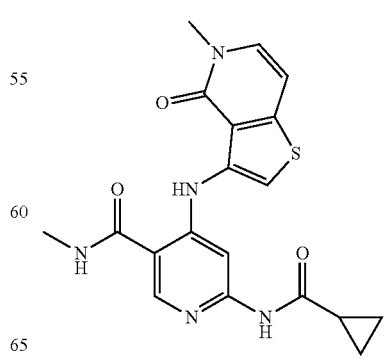

743
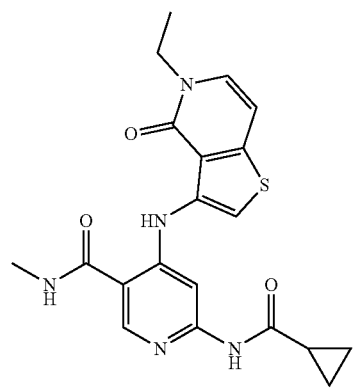 [SMILES: CCn1ccc2scc(Nc3cc(NC(=O)C4CC4)ncc3C(=O)NC)c2c1=O]
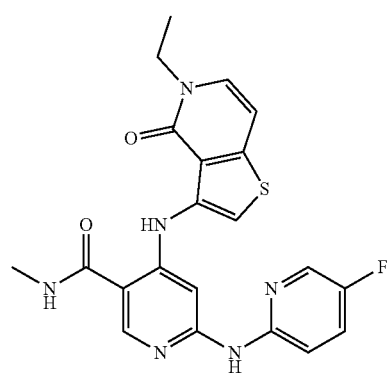 [SMILES: CCn1ccc2scc(Nc3cc(Nc4ccc(F)cn4)ncc3C(=O)NC)c2c1=O]
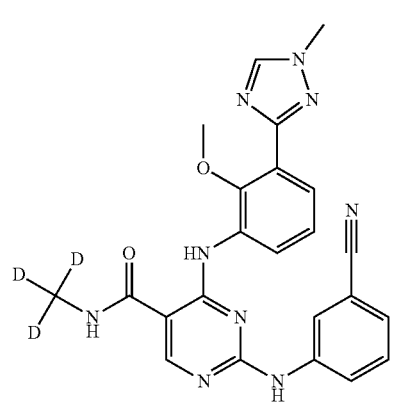
744
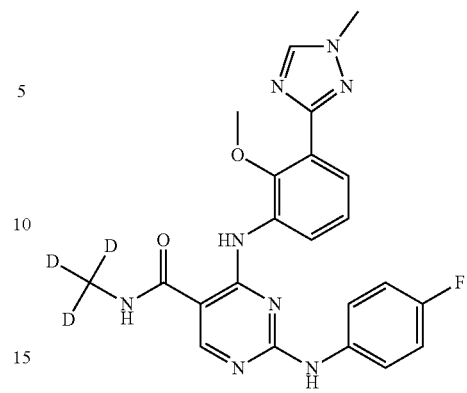
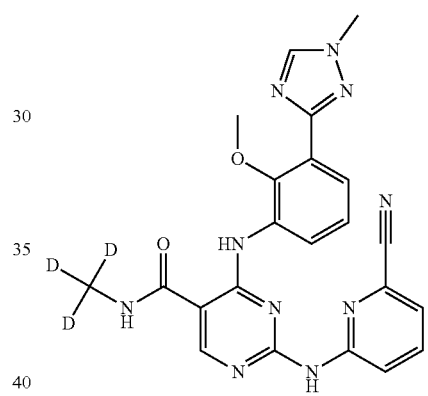
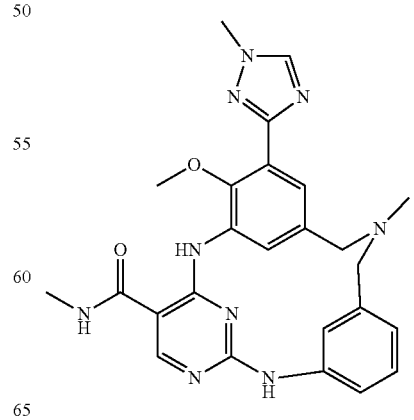

745
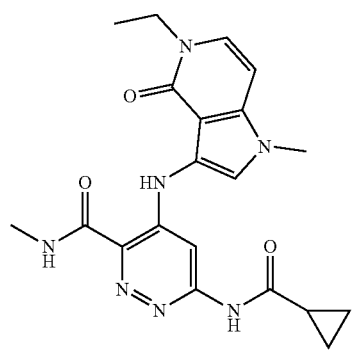 [SMILES: CCn1ccc2c(c(Nc3cc(NC(=O)C4CC4)nnc3C(=O)NC)cn2C)c1=O]
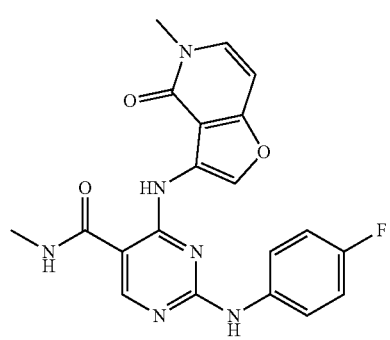 [SMILES: CNC(=O)c1cnc(Nc2ccc(F)cc2)nc1Nc1coc2ccn(C)c(=O)c12]
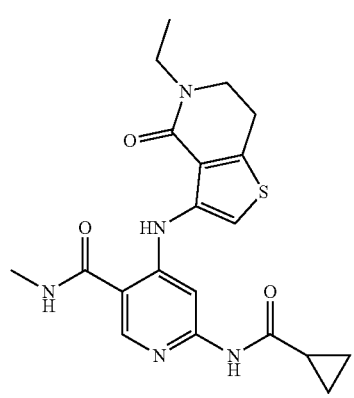
746
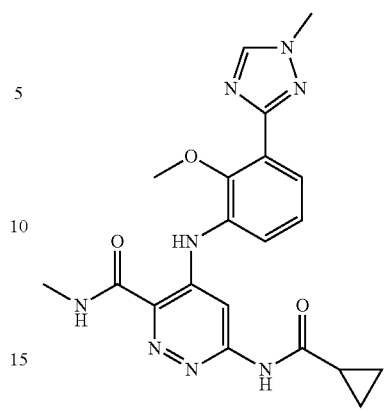
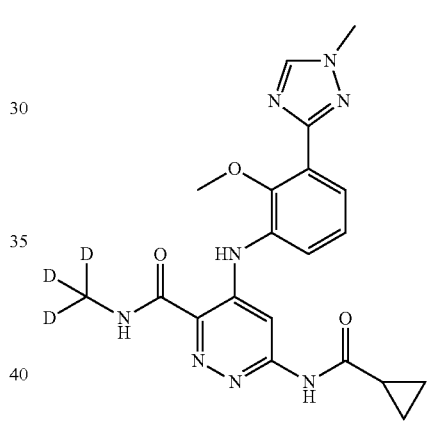
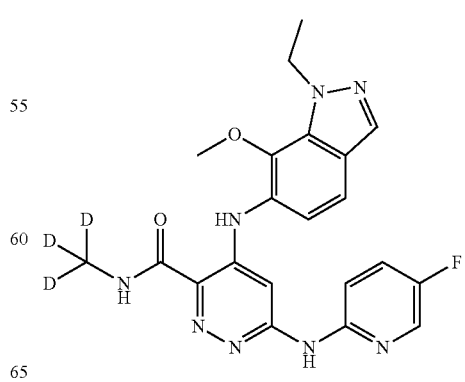

747
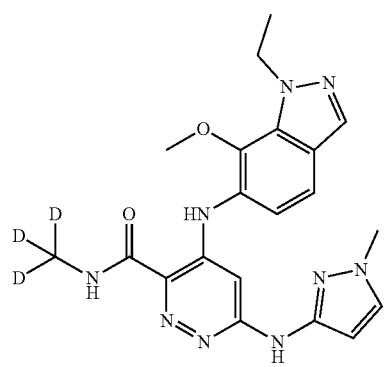
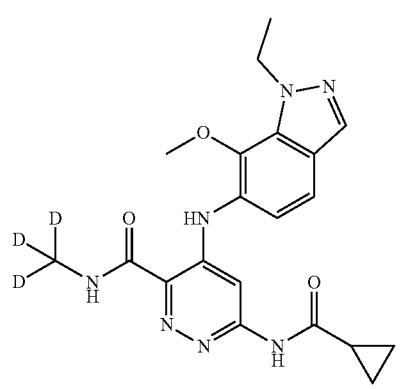 [SMILES: [2H]C([2H])([2H])NC(=O)c1nnc(NC(=O)C2CC2)cc1Nc1ccc2cnn(CC)c2c1OC]
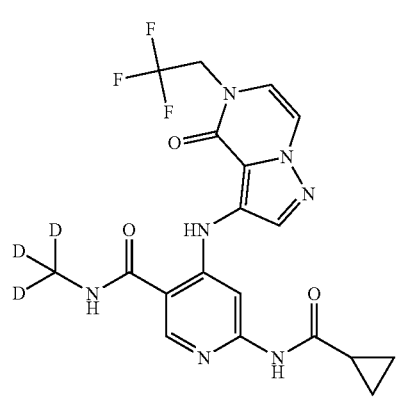 [SMILES: [2H]C([2H])([2H])NC(=O)c1cnc(NC(=O)C2CC2)cc1Nc1cnn2ccn(CC(F)(F)F)c(=O)c12]
748
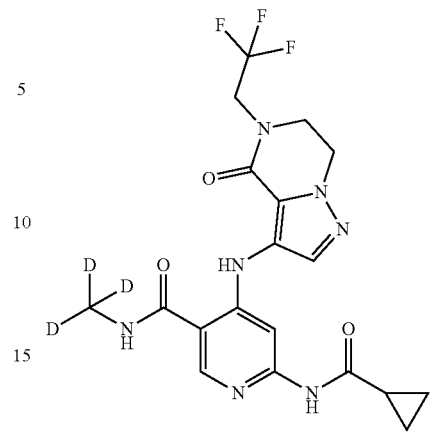
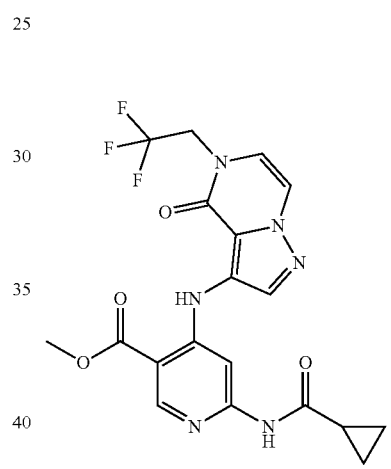
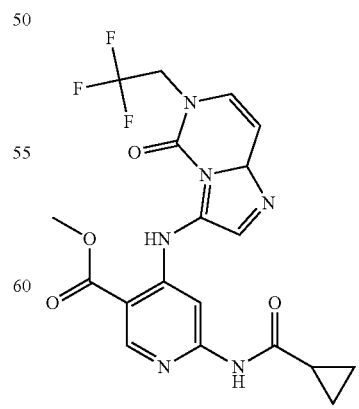

749
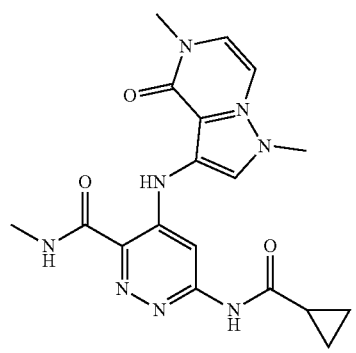
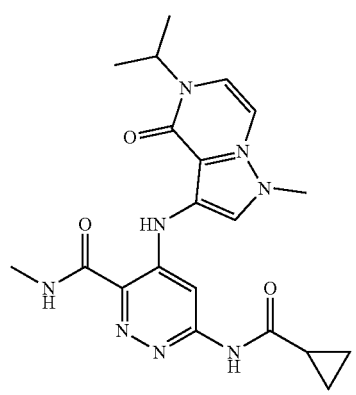
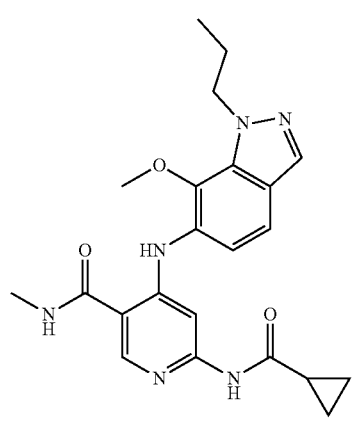 [SMILES: CCCn1ncc2ccc(Nc3cc(NC(=O)C4CC4)ncc3C(=O)NC)c(OC)c21]
750
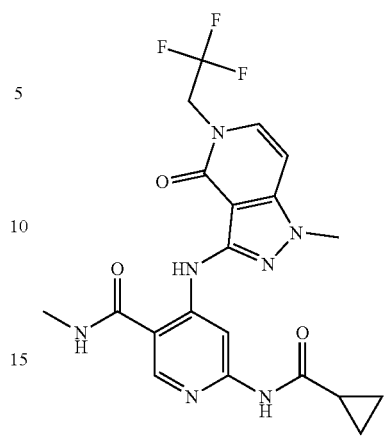
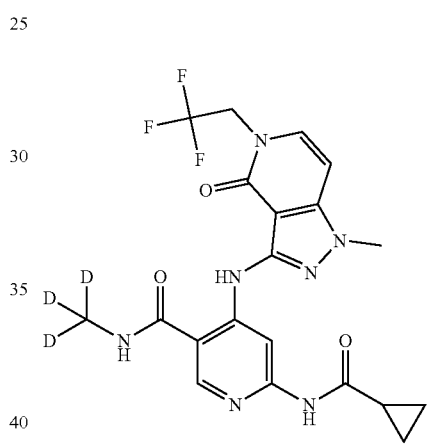
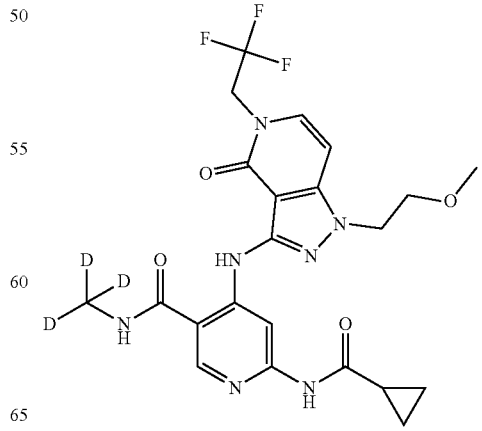

751
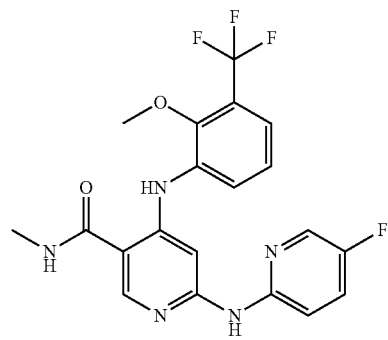 [SMILES: CNC(=O)c1cnc(Nc2ccc(F)cn2)cc1Nc1cccc(C(F)(F)F)c1OC]
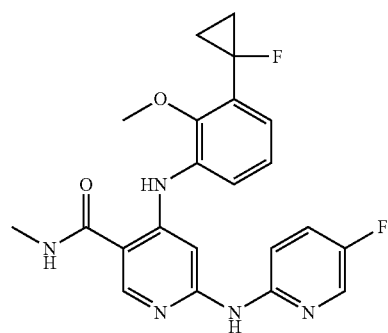 [SMILES: CNC(=O)c1cnc(Nc2ccc(F)cn2)cc1Nc1cccc(C2(F)CC2)c1OC]
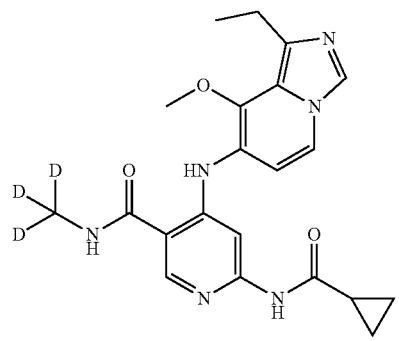 [SMILES: [2H]C([2H])([2H])NC(=O)c1cnc(NC(=O)C2CC2)cc1Nc1ccn2cnc(CC)c2c1OC]
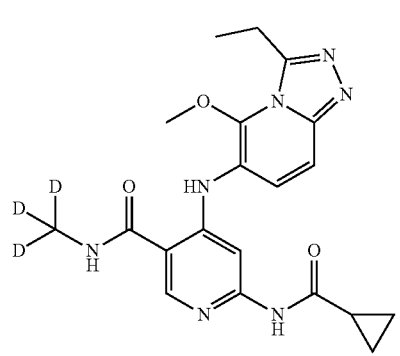
752
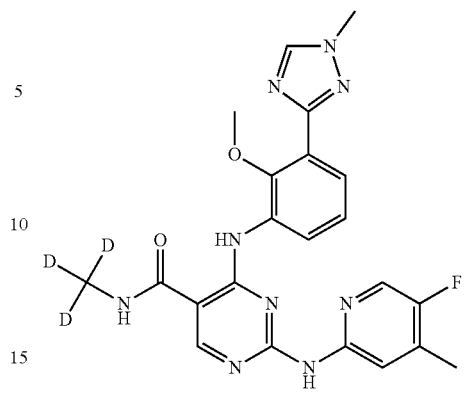
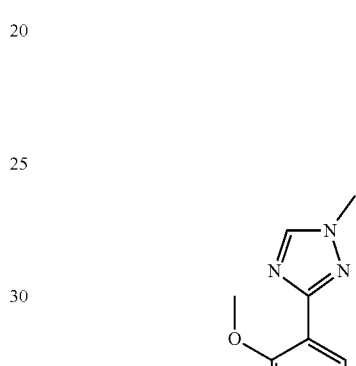
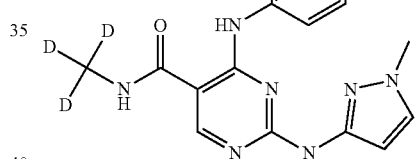
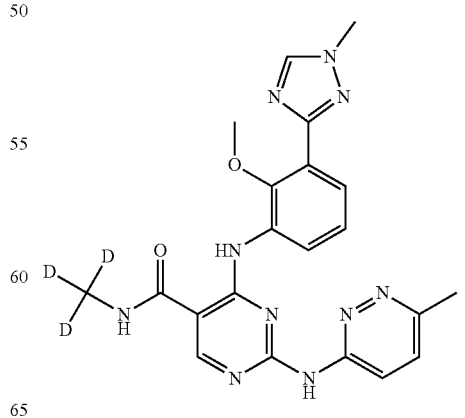

753
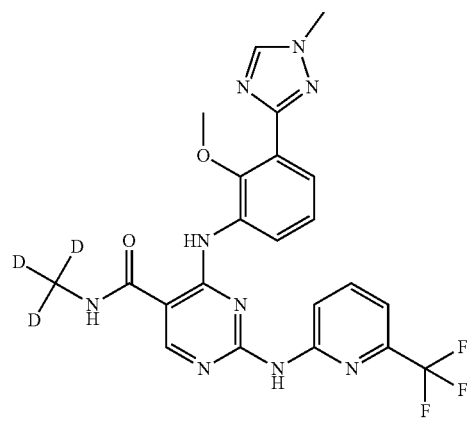 [SMILES: [2H]C([2H])([2H])NC(=O)c1cnc(Nc2cccc(C(F)(F)F)n2)nc1Nc1cccc(-c2ncn(C)n2)c1OC]
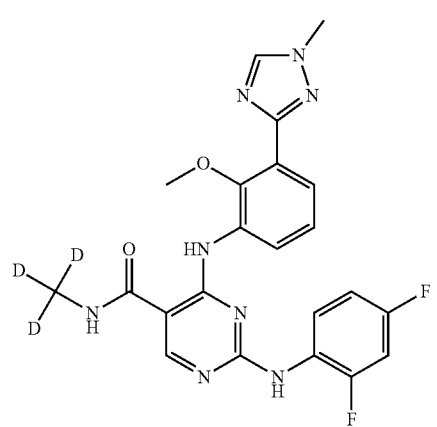 [SMILES: [2H]C([2H])([2H])NC(=O)c1cnc(Nc2ccc(F)cc2F)nc1Nc1cccc(-c2ncn(C)n2)c1OC]
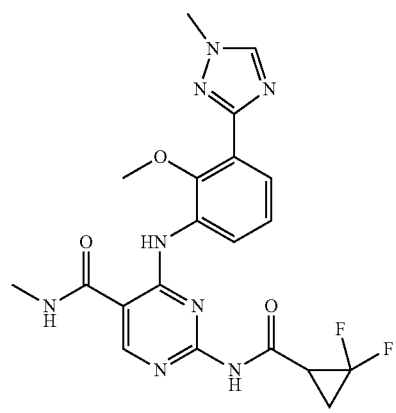 [SMILES: CNC(=O)c1cnc(NC(=O)C2CC2(F)F)nc1Nc1cccc(-c2ncn(C)n2)c1OC]
754
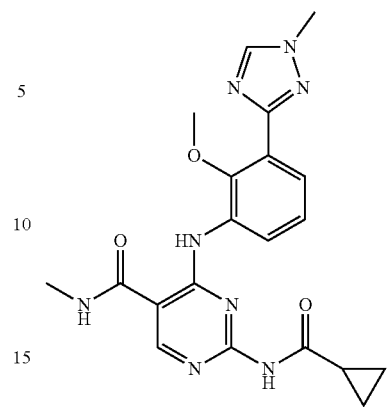
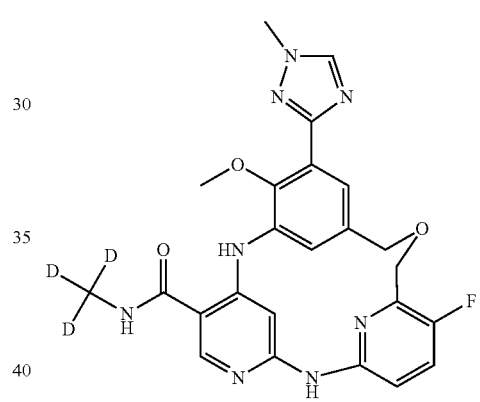
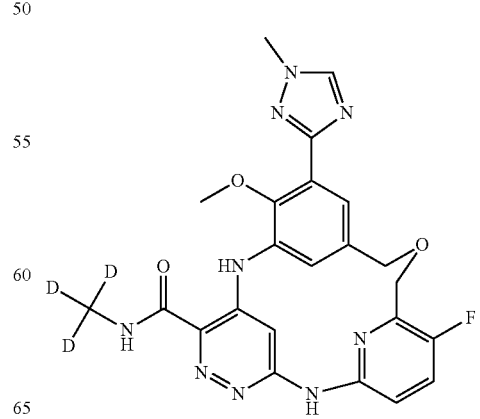

755
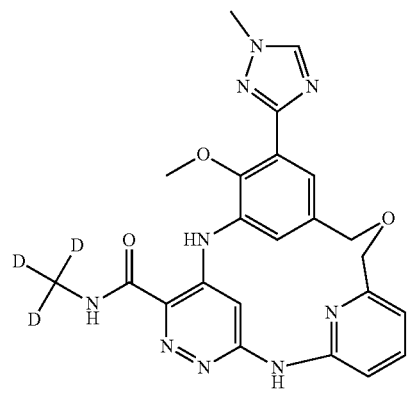 [SMILES: [2H]C([2H])([2H])NC(=O)c1nnc2cc1Nc1cc(cc(-c3ncn(C)n3)c1OC)COCc1cccc(n1)N2]
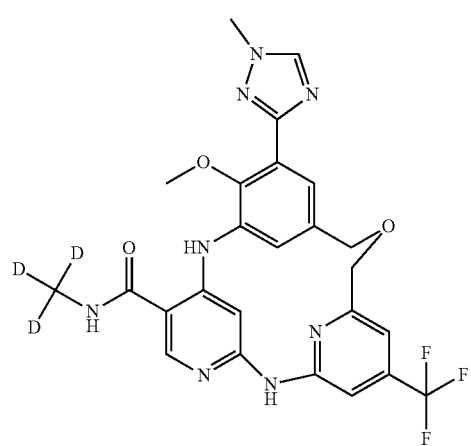 [SMILES: [2H]C([2H])([2H])NC(=O)c1cnc2cc1Nc1cc(cc(-c3ncn(C)n3)c1OC)COCc1cc(C(F)(F)F)cc(n1)N2]
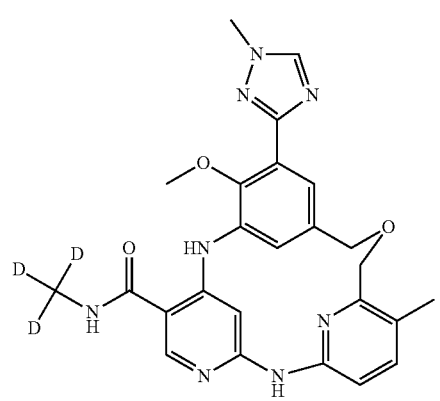 [SMILES: [2H]C([2H])([2H])NC(=O)c1cnc2cc1Nc1cc(cc(-c3ncn(C)n3)c1OC)COCc1nc(ccc1C)N2]
756
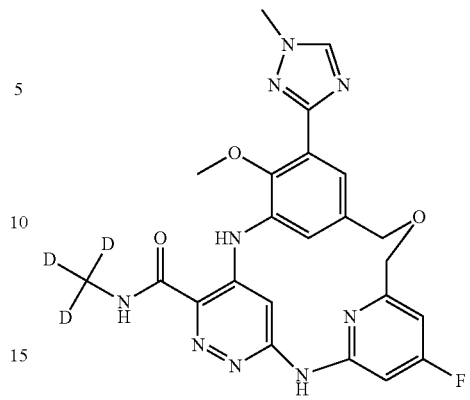
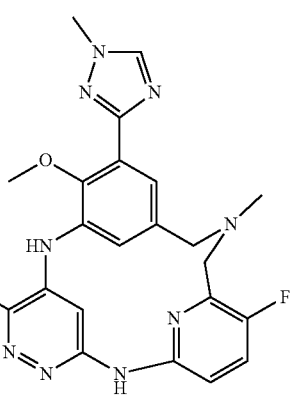
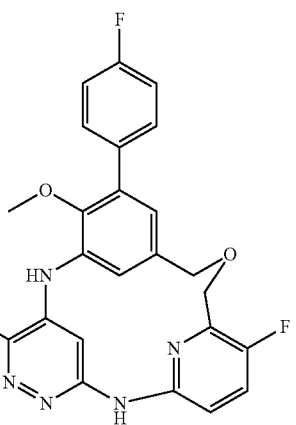

757
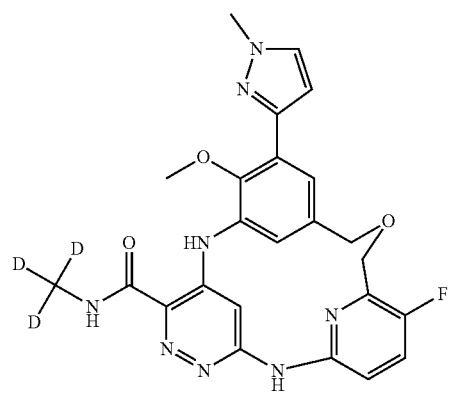 [SMILES: [2H]C([2H])([2H])NC(=O)c1nnc2cc1Nc1cc(cc(-c3ccn(C)n3)c1OC)COCc1nc(ccc1F)N2]
758
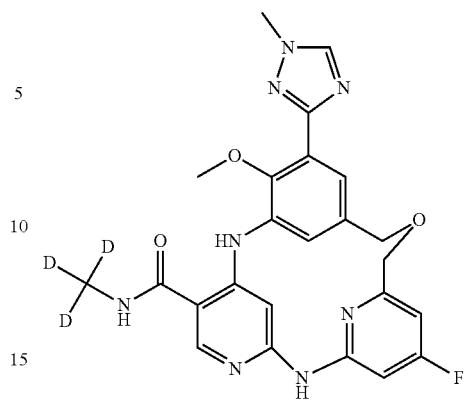
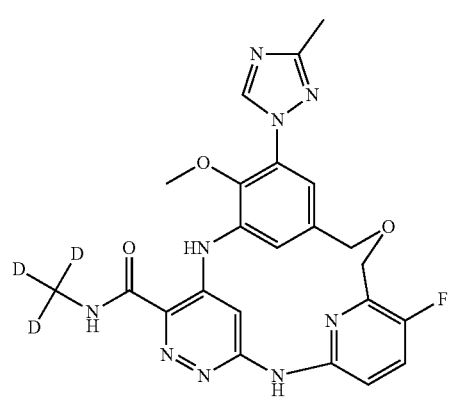 [SMILES: [2H]C([2H])([2H])NC(=O)c1nnc2cc1Nc1cc(cc(-n3cnc(C)n3)c1OC)COCc1nc(ccc1F)N2]
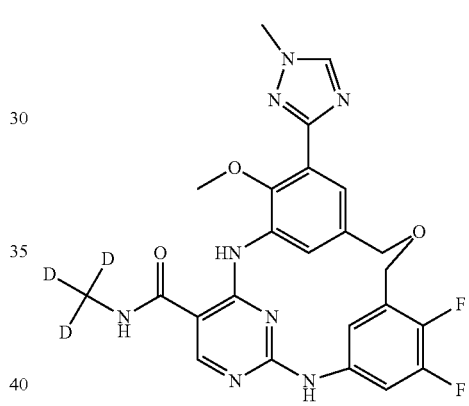
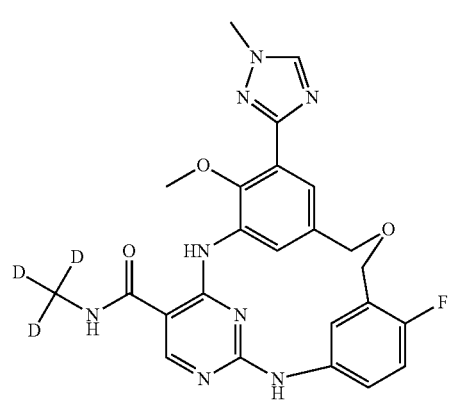 [SMILES: [2H]C([2H])([2H])NC(=O)c1cnc2nc1Nc1cc(cc(-c3ncn(C)n3)c1OC)COCc1cc(ccc1F)N2]
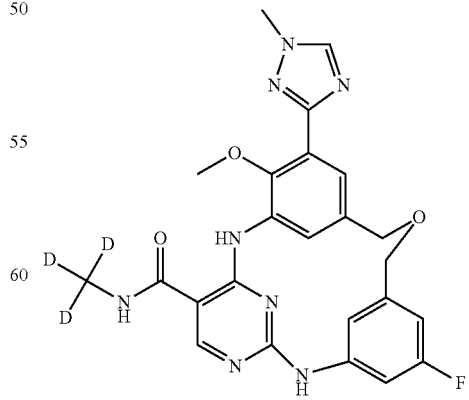

759 760
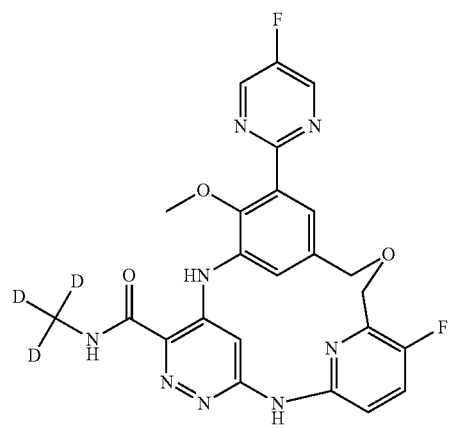 [SMILES: [2H]C([2H])([2H])NC(=O)c1nnc2cc1Nc1cc(cc(-c3ncc(F)cn3)c1OC)COCc1nc(ccc1F)N2]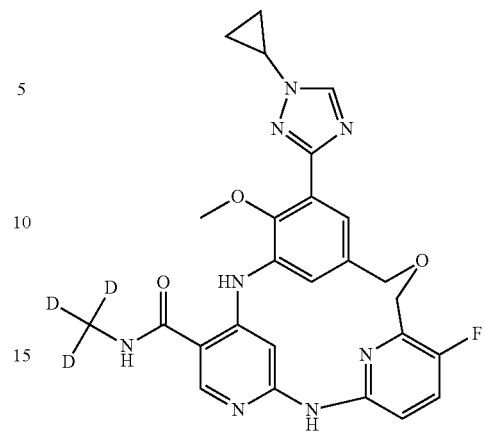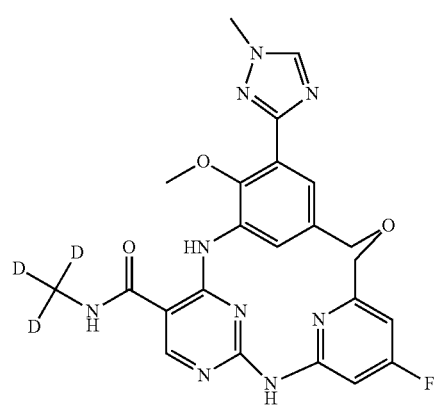 [SMILES: [2H]C([2H])([2H])NC(=O)c1cnc2nc1Nc1cc(cc(-c3ncn(C)n3)c1OC)COCc1cc(F)cc(n1)N2]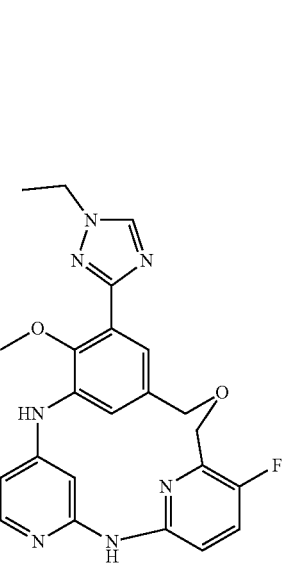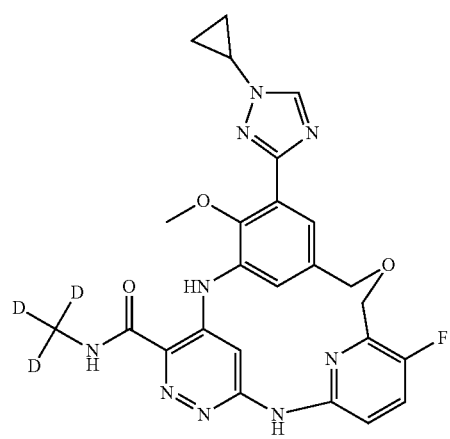

761                                          762
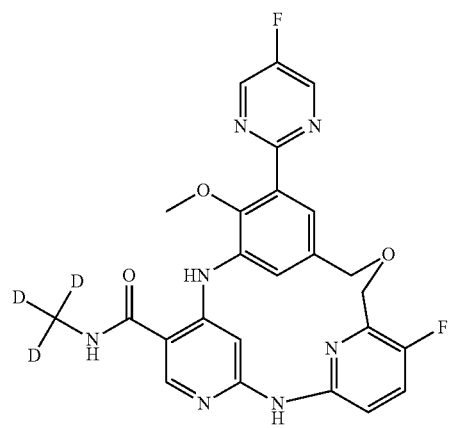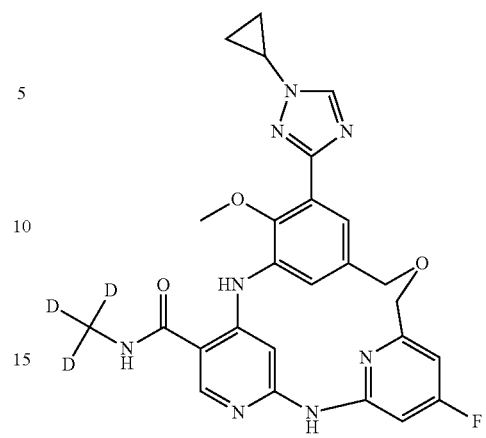
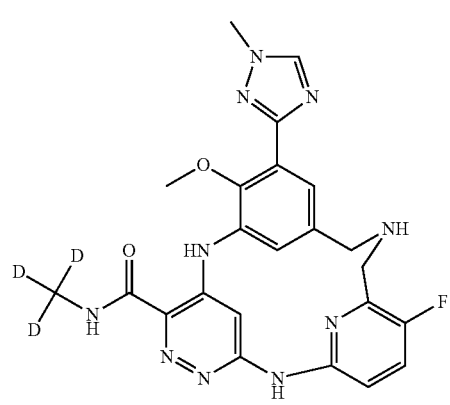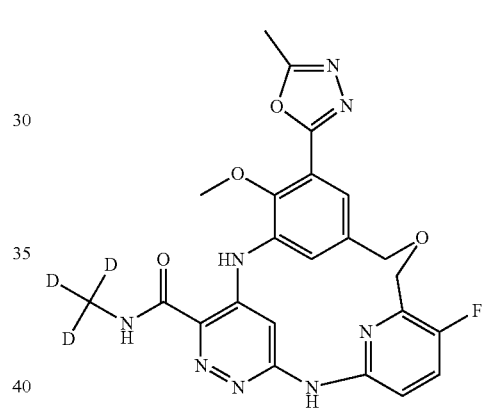
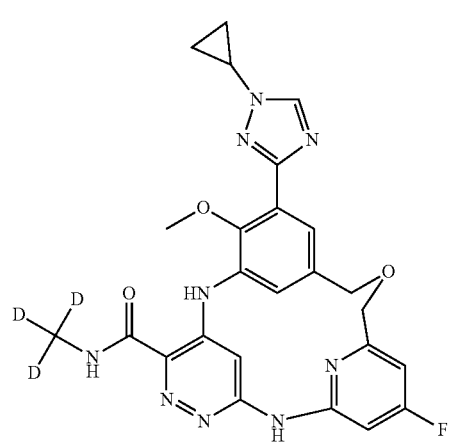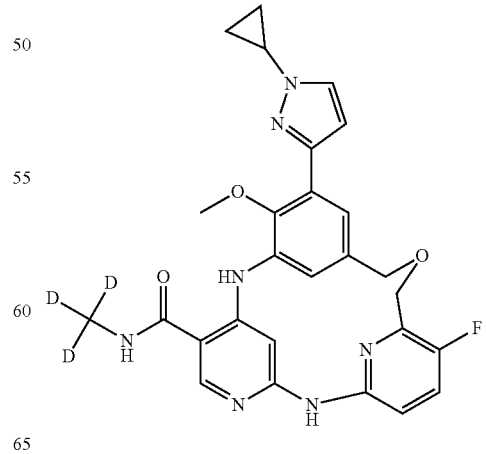

763
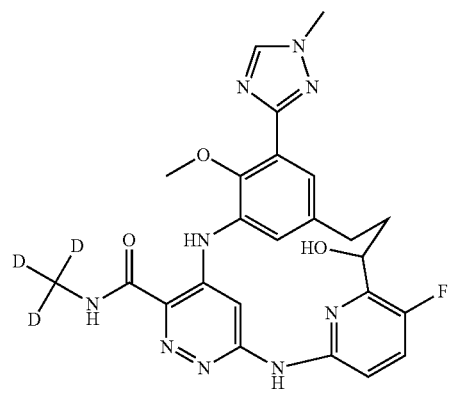 [SMILES: [2H]C([2H])([2H])NC(=O)c1nnc2cc1Nc1cc(cc(-c3ncn(C)n3)c1OC)CCC(O)c1nc(ccc1F)N2]
764
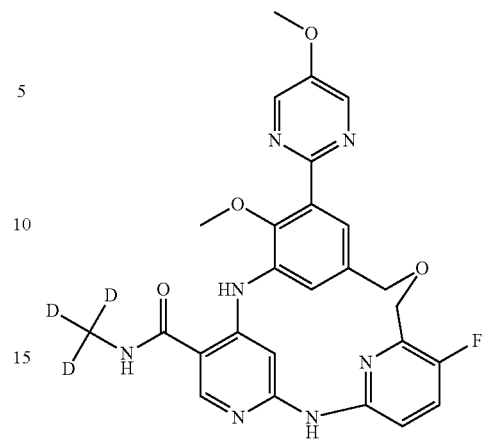
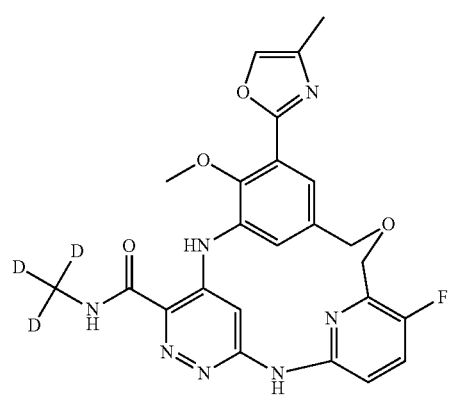 [SMILES: [2H]C([2H])([2H])NC(=O)c1nnc2cc1Nc1cc(cc(-c3nc(C)co3)c1OC)COCc1nc(ccc1F)N2]
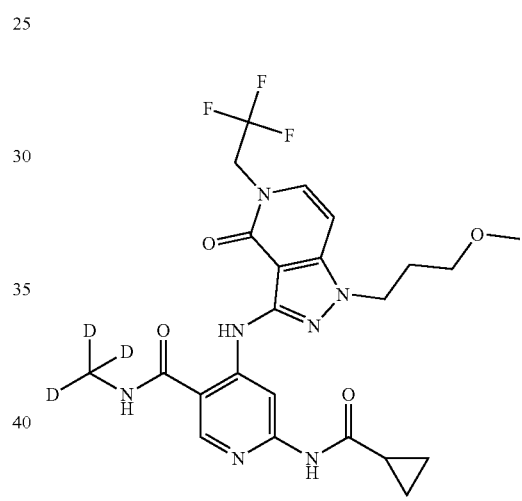
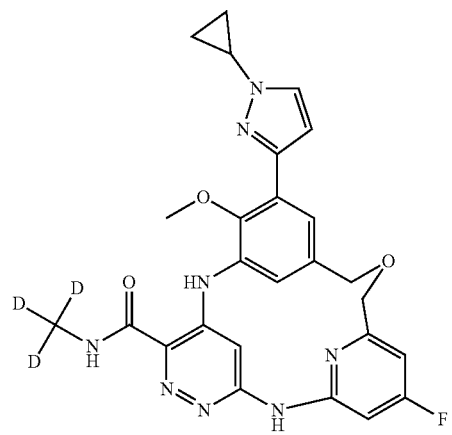 [SMILES: [2H]C([2H])([2H])NC(=O)c1nnc2cc1Nc1cc(cc(-c3ccn(C4CC4)n3)c1OC)COCc1cc(F)cc(n1)N2]
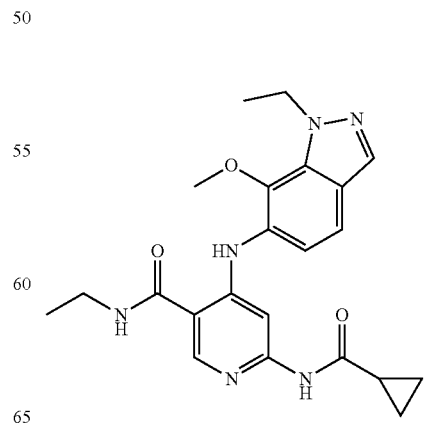

765
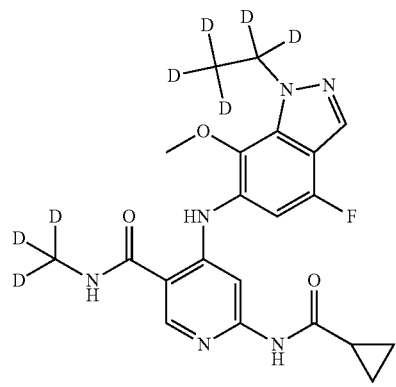 [SMILES: [2H]C([2H])([2H])NC(=O)c1cnc(NC(=O)C2CC2)cc1Nc1cc(F)c2cnn(C([2H])([2H])C([2H])([2H])[2H])c2c1OC]
766
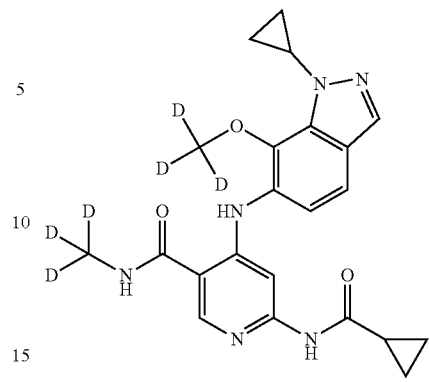
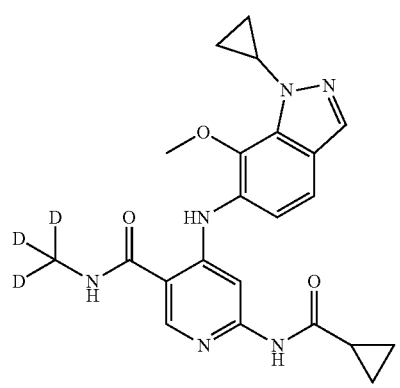
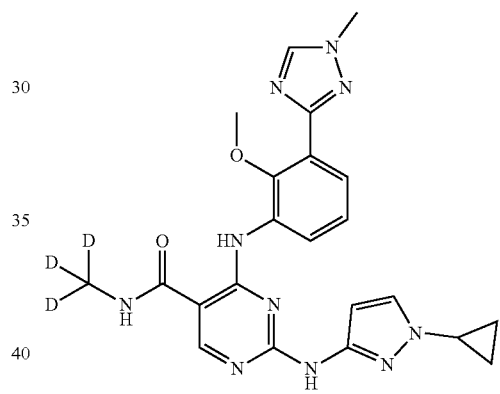
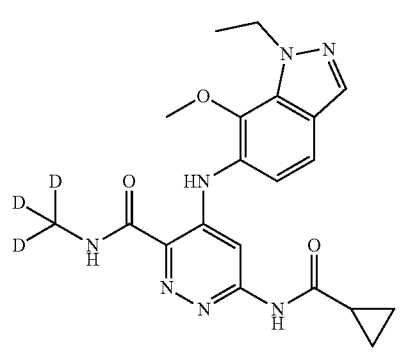
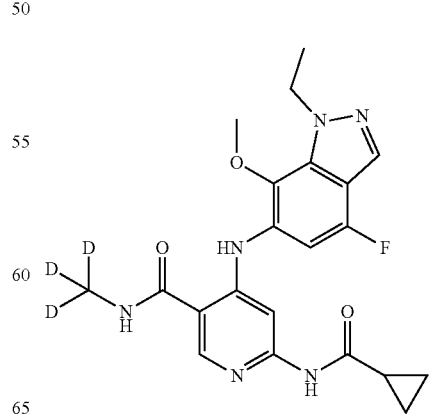

| 767 | 768 |
|---|---|
| 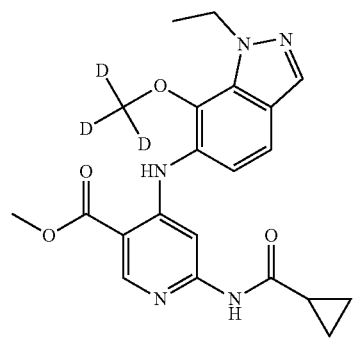 [SMILES: [2H]C([2H])([2H])Oc1c(Nc2cc(NC(=O)C3CC3)ncc2C(=O)OC)ccc2cnn(CC)c12] | 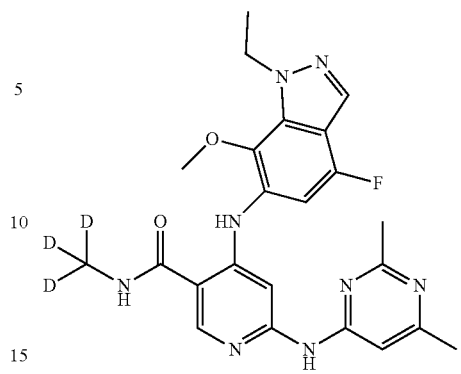 |
| 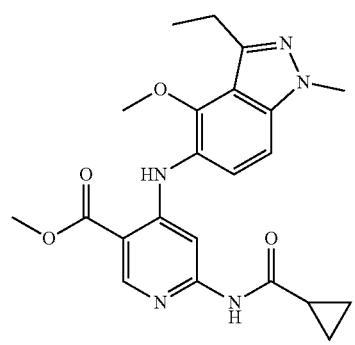 [SMILES: CCc1nn(C)c2ccc(Nc3cc(NC(=O)C4CC4)ncc3C(=O)OC)c(OC)c12] | |
| | 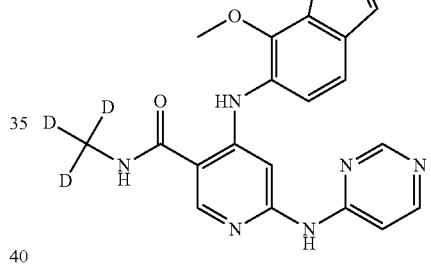 |
| 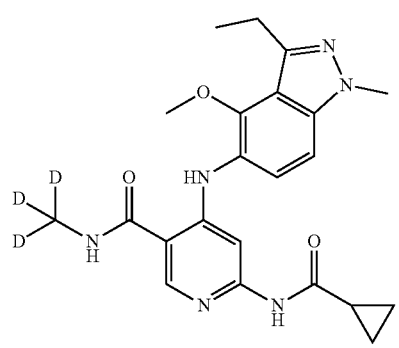 [SMILES: [2H]C([2H])([2H])NC(=O)c1cnc(NC(=O)C2CC2)cc1Nc1ccc2c(c(CC)nn2C)c1OC] | |
| 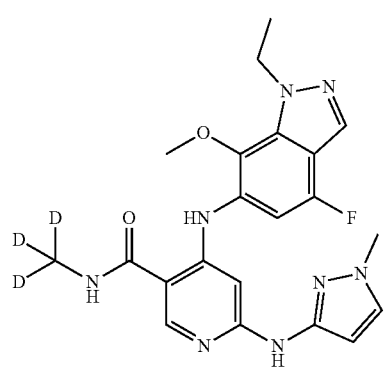 [SMILES: [2H]C([2H])([2H])NC(=O)c1cnc(Nc2ccn(C)n2)cc1Nc1cc(F)c2cnn(CC)c2c1OC] | 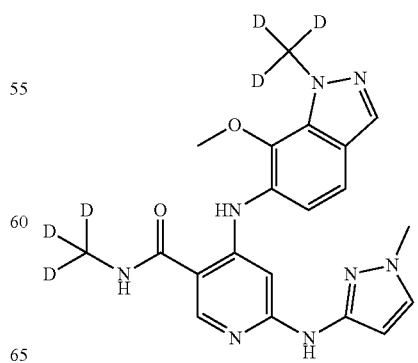 |

769 770
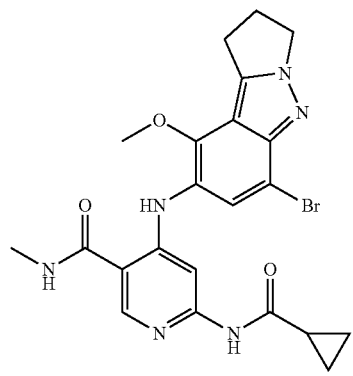 [SMILES: CNC(=O)c1cnc(NC(=O)C2CC2)cc1Nc1cc(Br)c2nn3c(c2c1OC)CCC3]
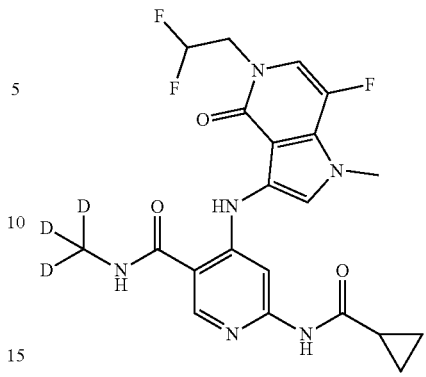
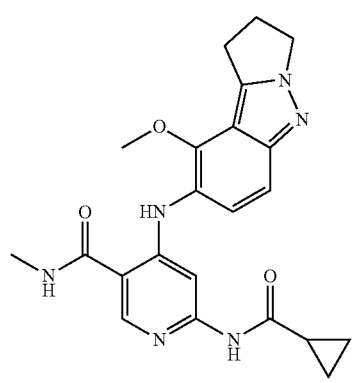 [SMILES: CNC(=O)c1cnc(NC(=O)C2CC2)cc1Nc1ccc2nn3c(c2c1OC)CCC3]
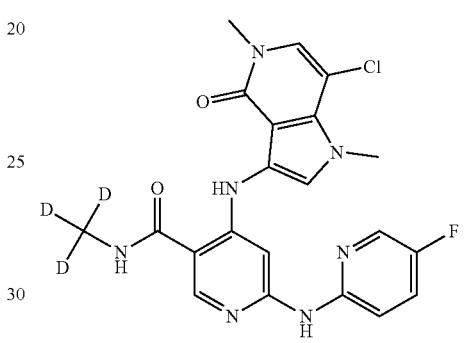
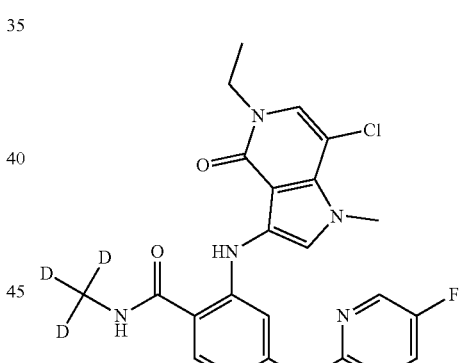
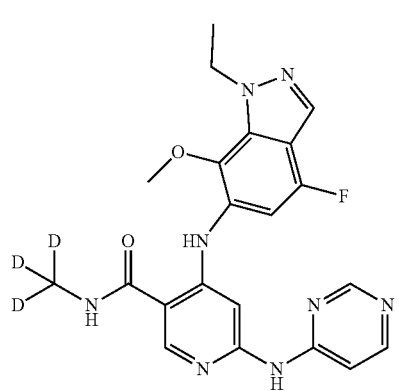 [SMILES: [2H]C([2H])([2H])NC(=O)c1cnc(Nc2ccncn2)cc1Nc1cc(F)c2cnn(CC)c2c1OC]
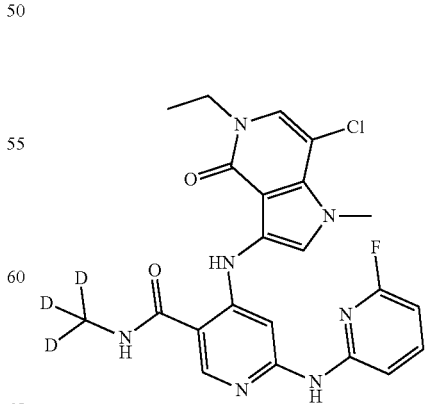

771
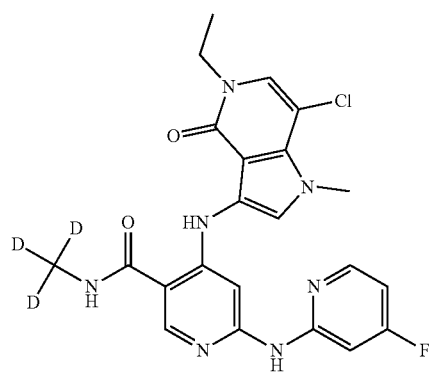 [SMILES: [2H]C([2H])([2H])NC(=O)c1cnc(Nc2cc(F)ccn2)cc1Nc1cn(C)c2c(Cl)cn(CC)c(=O)c12]
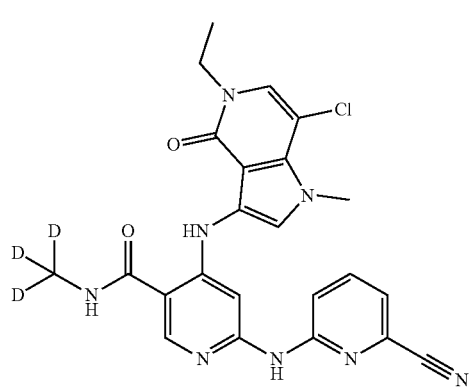 [SMILES: [2H]C([2H])([2H])NC(=O)c1cnc(Nc2cccc(C#N)n2)cc1Nc1cn(C)c2c(Cl)cn(CC)c(=O)c12]
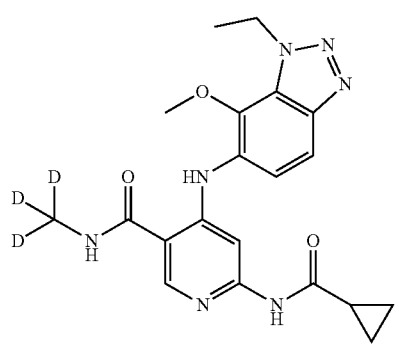 [SMILES: [2H]C([2H])([2H])NC(=O)c1cnc(NC(=O)C2CC2)cc1Nc1ccc2nnn(CC)c2c1OC]
772
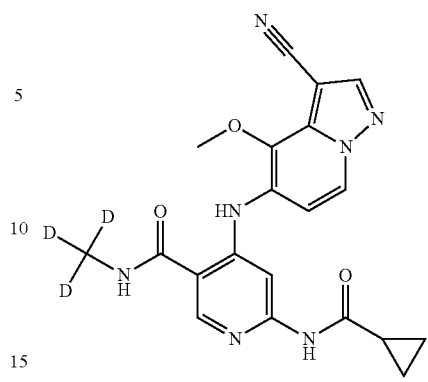
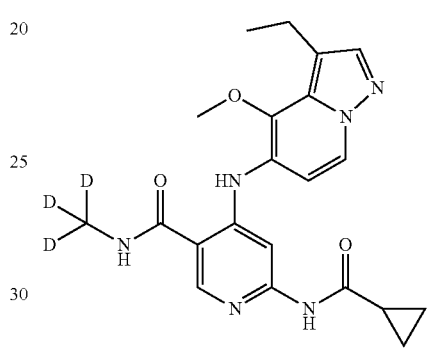
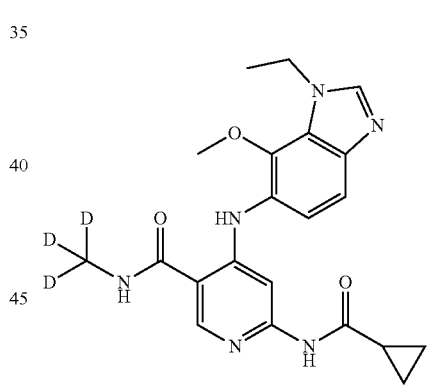
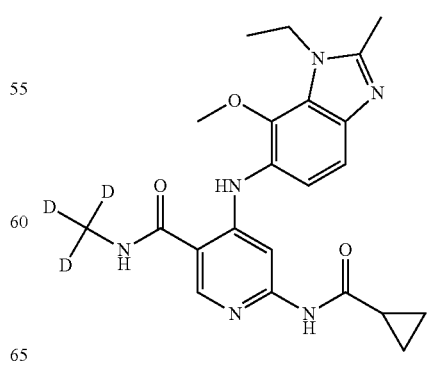

773
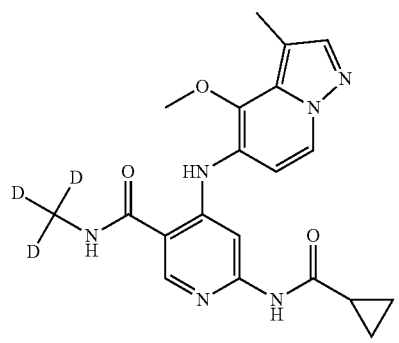 [SMILES: [2H]C([2H])([2H])NC(=O)c1cnc(NC(=O)C2CC2)cc1Nc1ccn2ncc(C)c2c1OC]
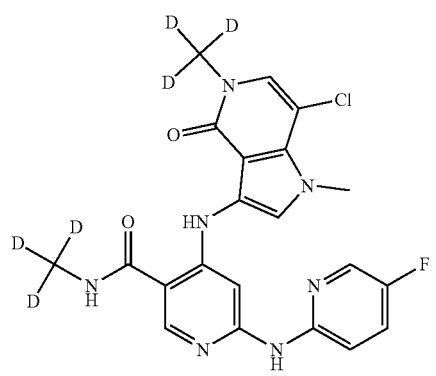 [SMILES: [2H]C([2H])([2H])NC(=O)c1cnc(Nc2ccc(F)cn2)cc1Nc1cn(C)c2c(Cl)cn(C([2H])([2H])[2H])c(=O)c12]
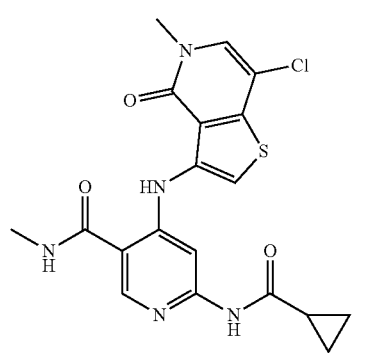 [SMILES: CNC(=O)c1cnc(NC(=O)C2CC2)cc1Nc1csc2c(Cl)cn(C)c(=O)c12]
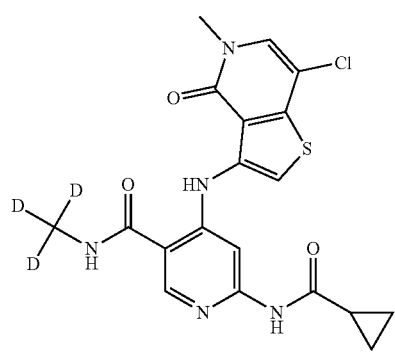
774
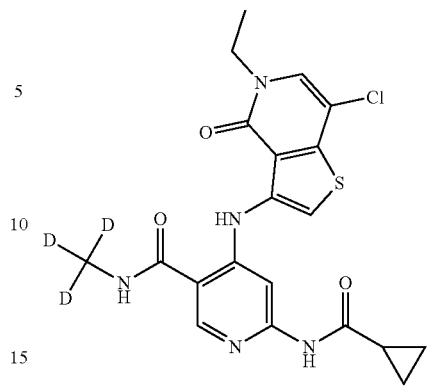
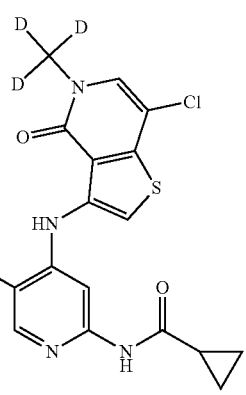
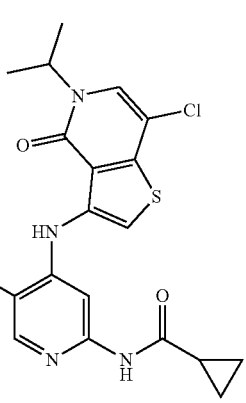

775
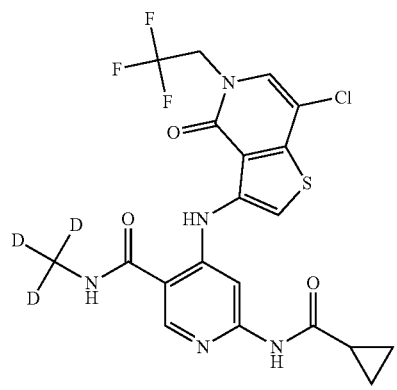 [SMILES: [2H]C([2H])([2H])NC(=O)c1cnc(NC(=O)C2CC2)cc1Nc1csc2c(Cl)cn(CC(F)(F)F)c(=O)c12]
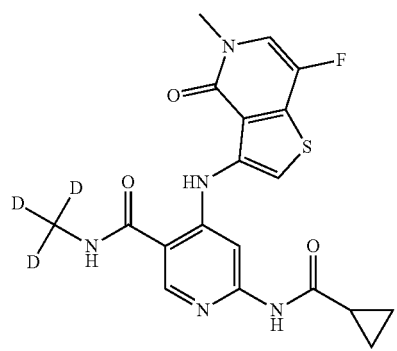 [SMILES: [2H]C([2H])([2H])NC(=O)c1cnc(NC(=O)C2CC2)cc1Nc1csc2c(F)cn(C)c(=O)c12]
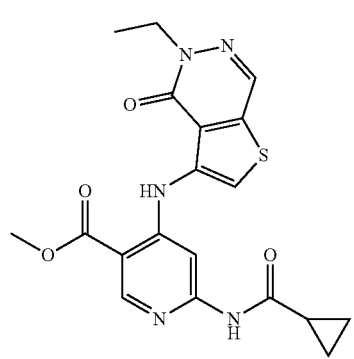 [SMILES: CCn1ncc2scc(Nc3cc(NC(=O)C4CC4)ncc3C(=O)OC)c2c1=O]
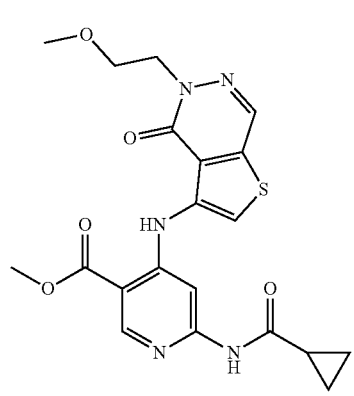 [SMILES: COCCn1ncc2scc(Nc3cc(NC(=O)C4CC4)ncc3C(=O)OC)c2c1=O]
776
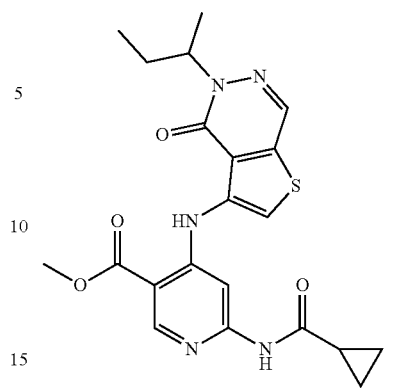
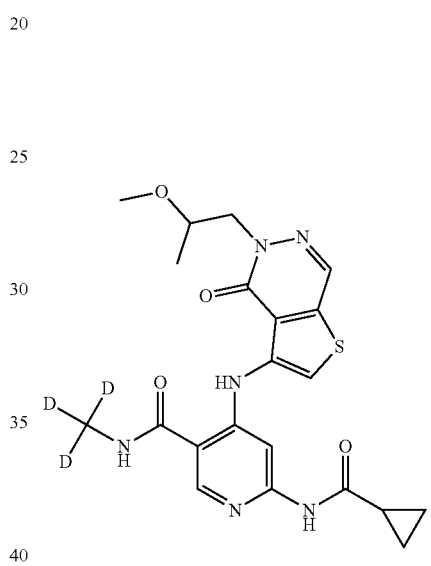
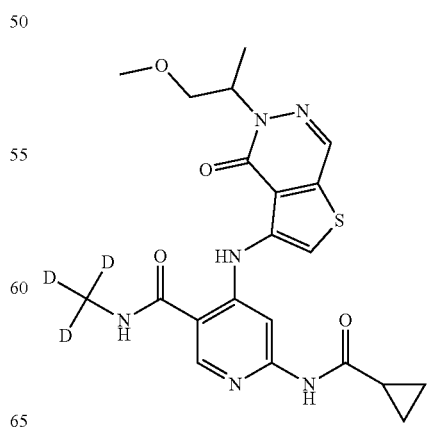

777
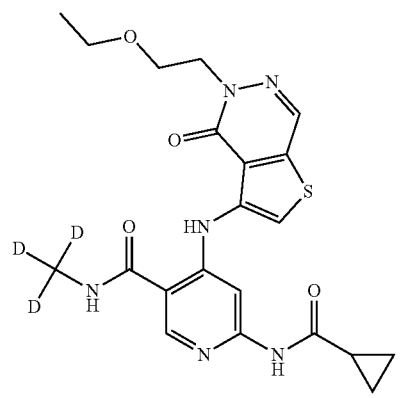 [SMILES: [2H]C([2H])([2H])NC(=O)c1cnc(NC(=O)C2CC2)cc1Nc1csc2cnn(CCOCC)c(=O)c12]
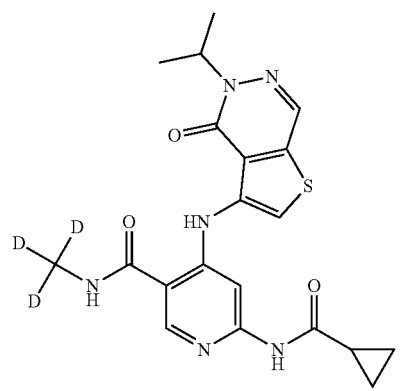 [SMILES: [2H]C([2H])([2H])NC(=O)c1cnc(NC(=O)C2CC2)cc1Nc1csc2cnn(C(C)C)c(=O)c12]
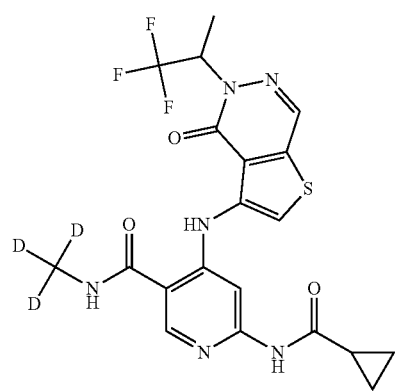 [SMILES: [2H]C([2H])([2H])NC(=O)c1cnc(NC(=O)C2CC2)cc1Nc1csc2cnn([C@@H](C)C(F)(F)F)c(=O)c12]
778
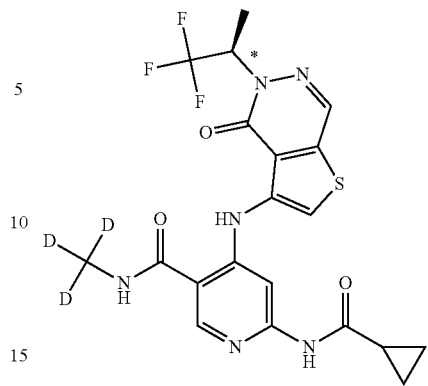
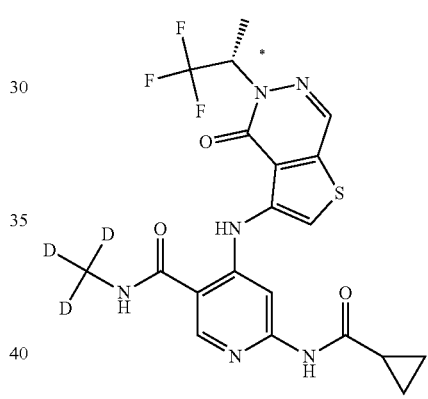
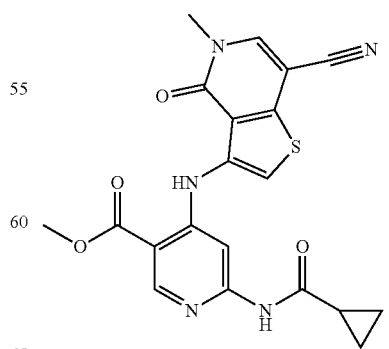

779
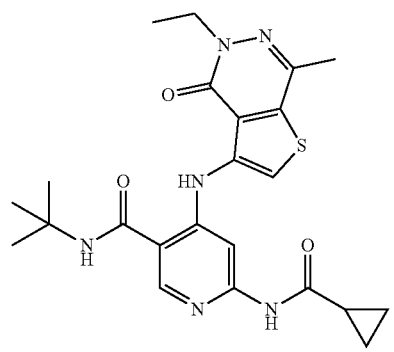 [SMILES: CCn1nc(C)c2scc(Nc3cc(NC(=O)C4CC4)ncc3C(=O)NC(C)(C)C)c2c1=O]
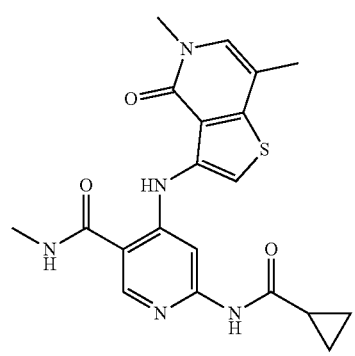 [SMILES: CNC(=O)c1cnc(NC(=O)C2CC2)cc1Nc1csc2c(C)cn(C)c(=O)c12]
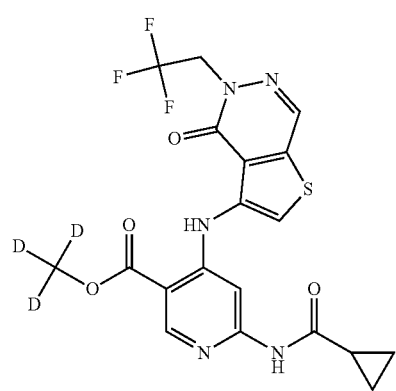 [SMILES: [2H]C([2H])([2H])OC(=O)c1cnc(NC(=O)C2CC2)cc1Nc1csc2cnn(CC(F)(F)F)c(=O)c12]
780
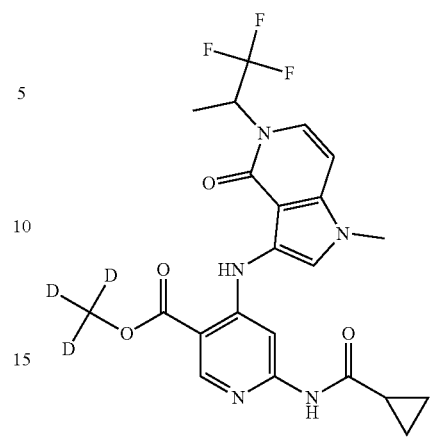
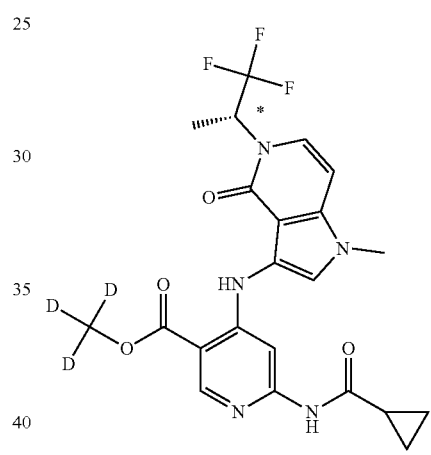
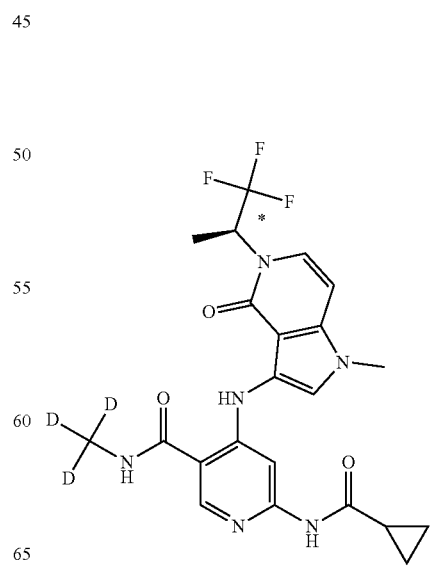

781
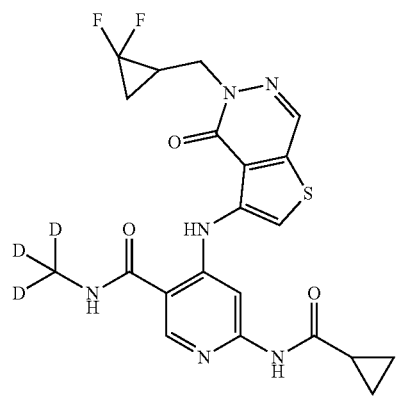 [SMILES: [2H]C([2H])([2H])NC(=O)c1cnc(NC(=O)C2CC2)cc1Nc1csc2cnn(CC3CC3(F)F)c(=O)c12]
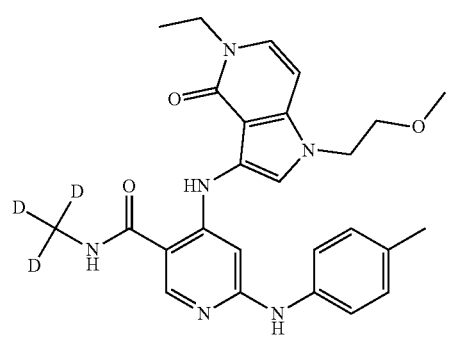 [SMILES: [2H]C([2H])([2H])NC(=O)c1cnc(Nc2ccc(C)cc2)cc1Nc1cn(CCOC)c2ccn(CC)c(=O)c12]
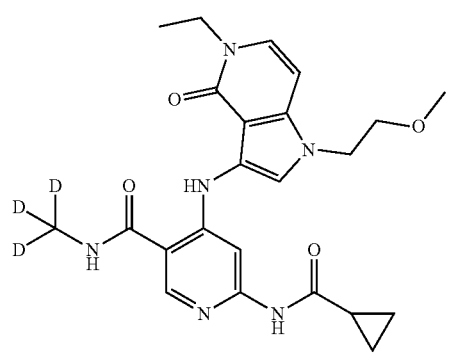 [SMILES: [2H]C([2H])([2H])NC(=O)c1cnc(NC(=O)C2CC2)cc1Nc1cn(CCOC)c2ccn(CC)c(=O)c12]
782
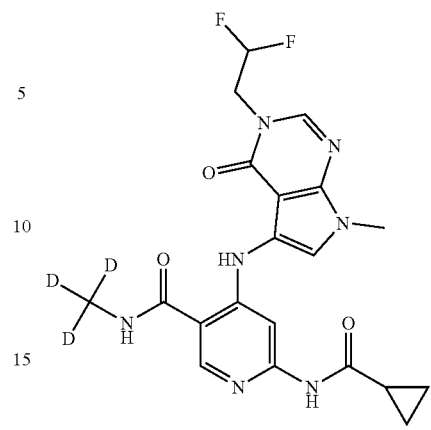
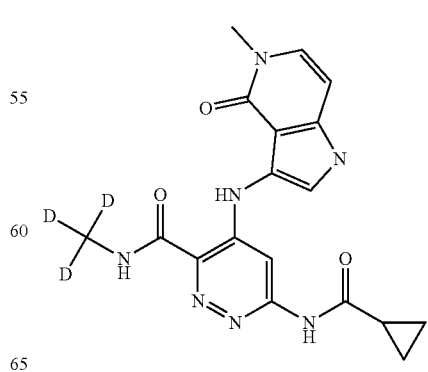

783
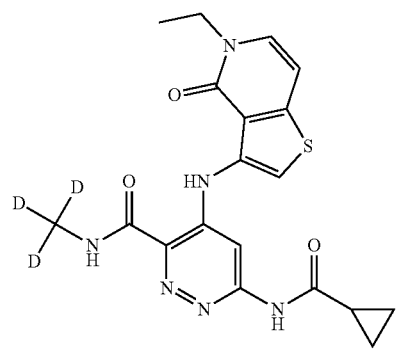 [SMILES: [2H]C([2H])([2H])NC(=O)c1nnc(NC(=O)C2CC2)cc1Nc1csc2ccn(CC)c(=O)c12]
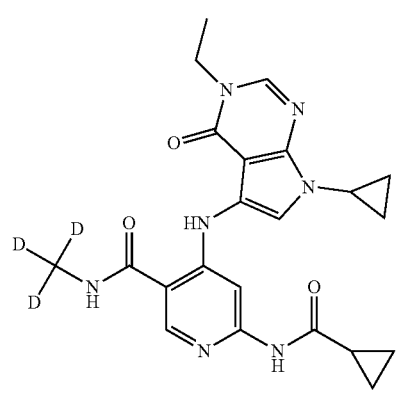 [SMILES: [2H]C([2H])([2H])NC(=O)c1cnc(NC(=O)C2CC2)cc1Nc1cn(C2CC2)c2ncn(CC)c(=O)c12]
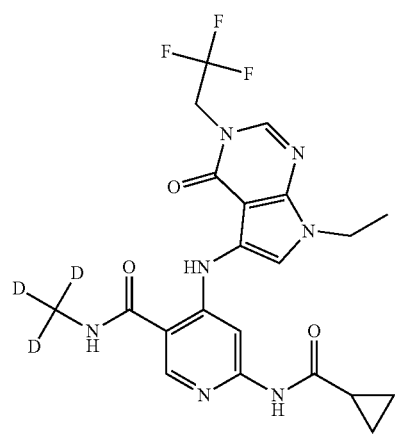 [SMILES: [2H]C([2H])([2H])NC(=O)c1cnc(NC(=O)C2CC2)cc1Nc1cn(CC)c2ncn(CC(F)(F)F)c(=O)c12]
784
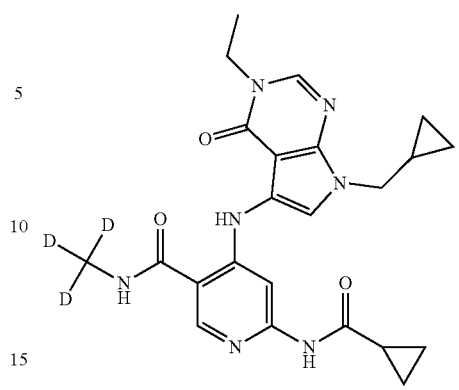
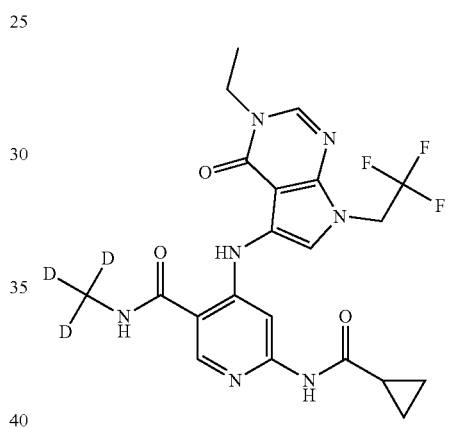
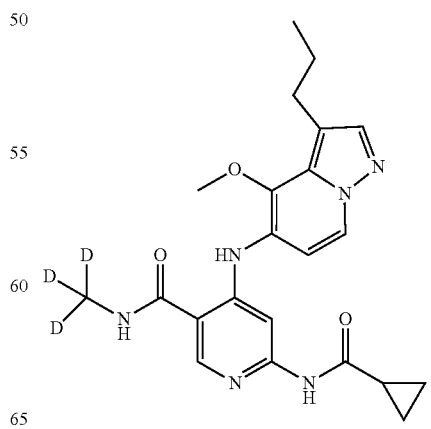

785
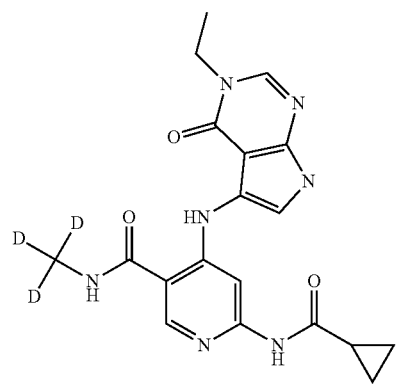 [SMILES: [2H]C([2H])([2H])NC(=O)c1cnc(NC(=O)C2CC2)cc1Nc1c[nH]c2ncn(CC)c(=O)c12]
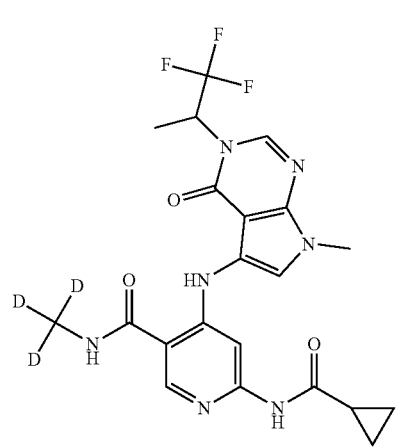 [SMILES: [2H]C([2H])([2H])NC(=O)c1cnc(NC(=O)C2CC2)cc1Nc1cn(C)c2ncn(C(C)C(F)(F)F)c(=O)c12]
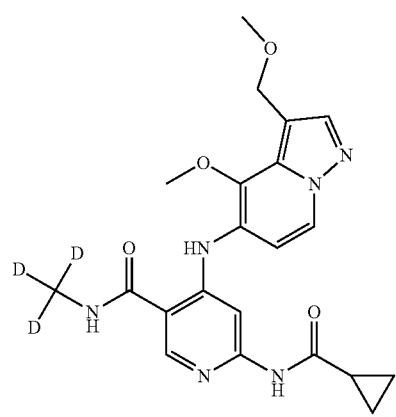 [SMILES: [2H]C([2H])([2H])NC(=O)c1cnc(NC(=O)C2CC2)cc1Nc1ccn2ncc(COC)c2c1OC]
786
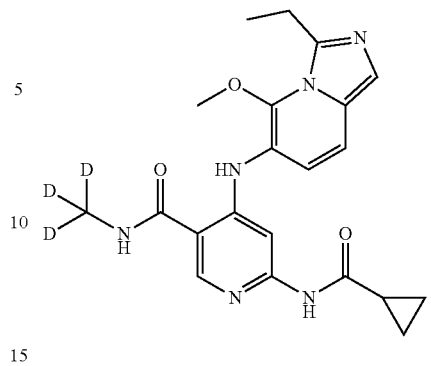
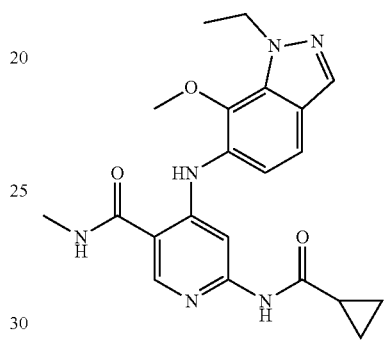
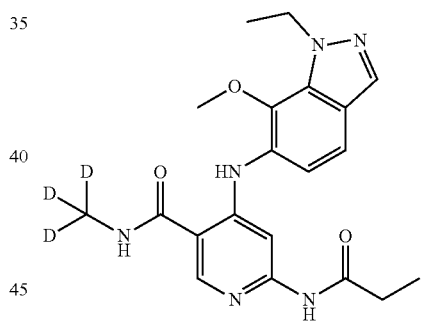
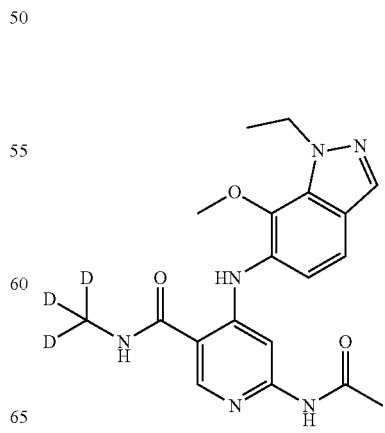

787
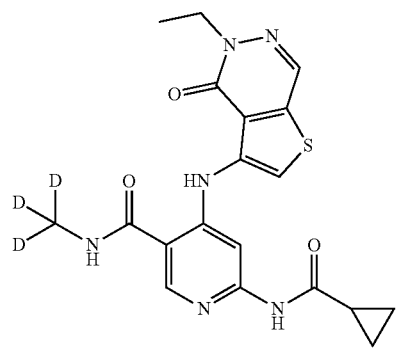 [SMILES: [2H]C([2H])([2H])NC(=O)c1cnc(NC(=O)C2CC2)cc1Nc1csc2cnn(CC)c(=O)c12]
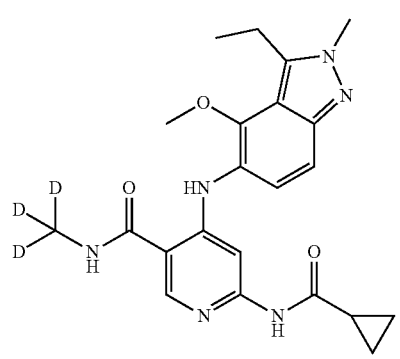 [SMILES: [2H]C([2H])([2H])NC(=O)c1cnc(NC(=O)C2CC2)cc1Nc1ccc2nn(C)c(CC)c2c1OC]
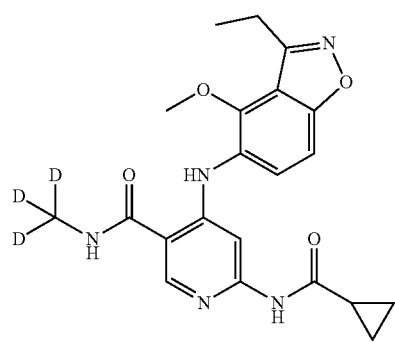 [SMILES: [2H]C([2H])([2H])NC(=O)c1cnc(NC(=O)C2CC2)cc1Nc1ccc2onc(CC)c2c1OC]
788
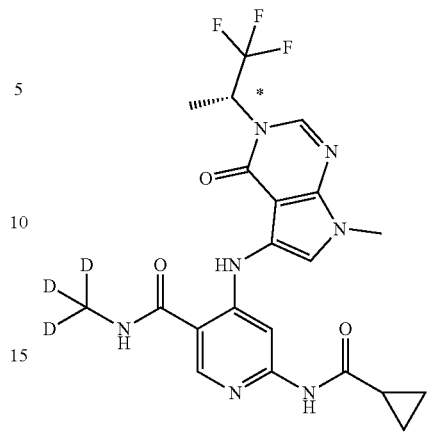
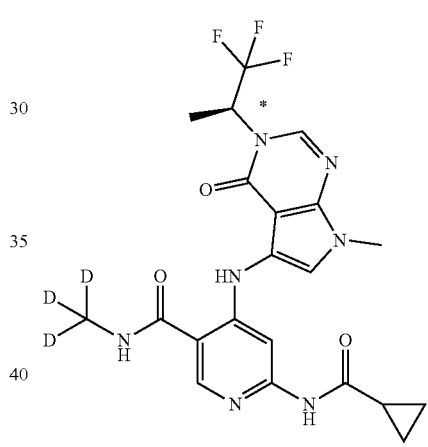
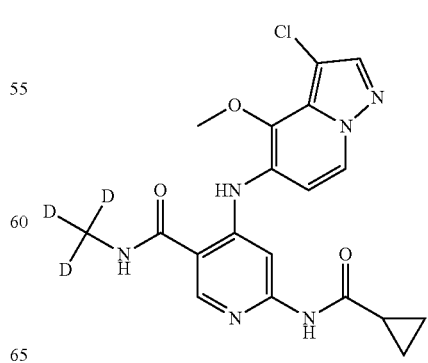

789                          790
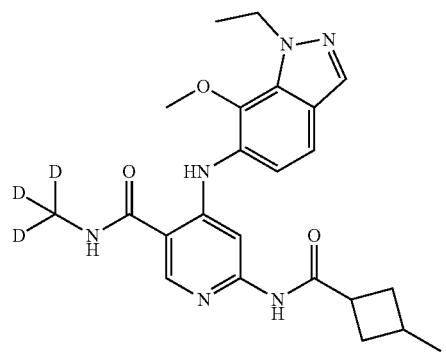 [SMILES: [2H]C([2H])([2H])NC(=O)c1cnc(NC(=O)C2CC(C)C2)cc1Nc1ccc2cnn(CC)c2c1OC] 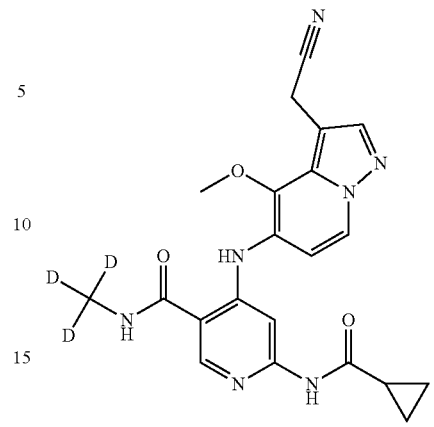
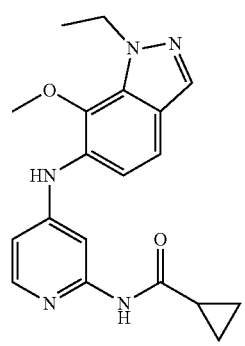 [SMILES: CCn1ncc2ccc(Nc3ccnc(NC(=O)C4CC4)c3)c(OC)c21] 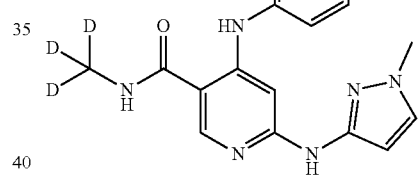
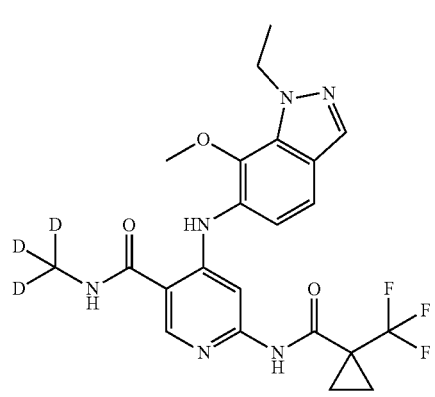 [SMILES: [2H]C([2H])([2H])NC(=O)c1cnc(NC(=O)C2(C(F)(F)F)CC2)cc1Nc1ccc2cnn(CC)c2c1OC] 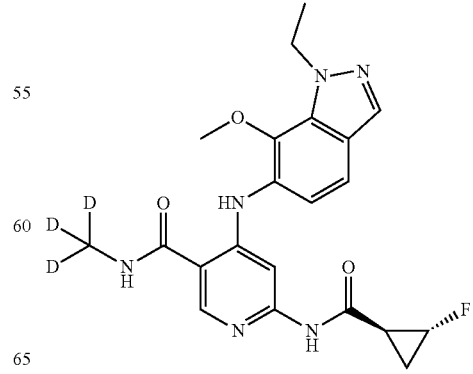

791 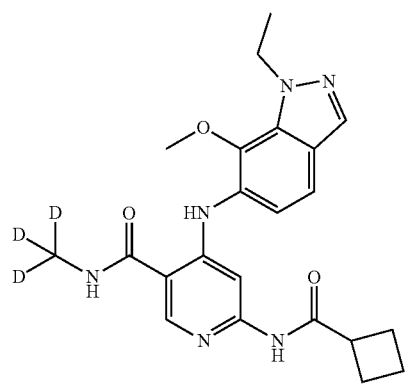 [SMILES: [2H]C([2H])([2H])NC(=O)c1cnc(NC(=O)C2CCC2)cc1Nc1ccc2cnn(CC)c2c1OC] 792 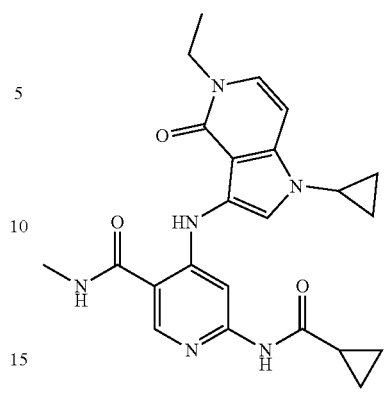
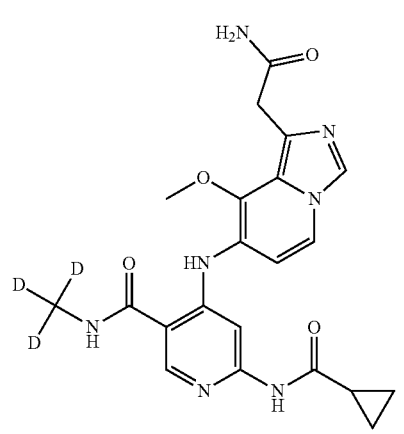 [SMILES: [2H]C([2H])([2H])NC(=O)c1cnc(NC(=O)C2CC2)cc1Nc1ccn2cnc(CC(N)=O)c2c1OC] 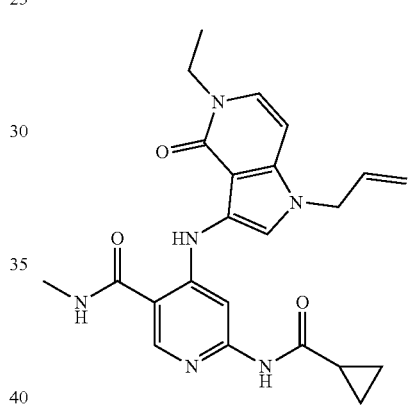
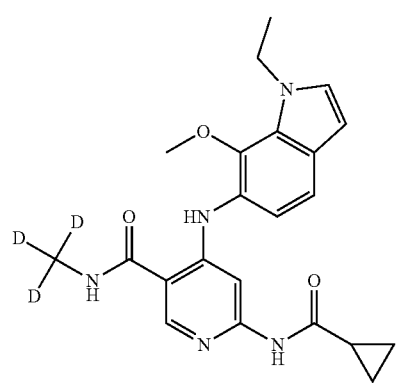 [SMILES: [2H]C([2H])([2H])NC(=O)c1cnc(NC(=O)C2CC2)cc1Nc1ccc2ccn(CC)c2c1OC] 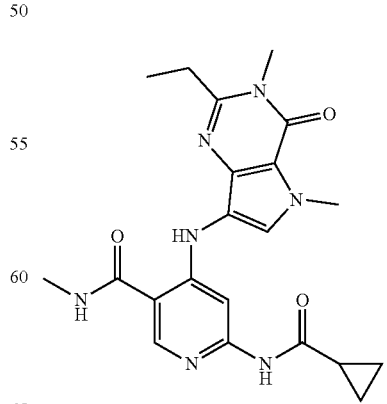

793
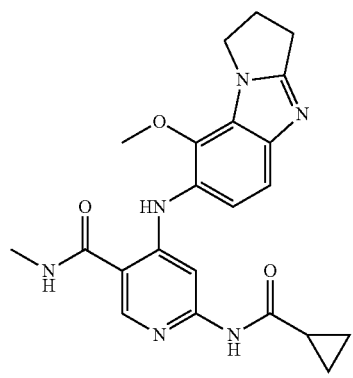 [SMILES: CNC(=O)c1cnc(NC(=O)C2CC2)cc1Nc1ccc2nc3n(c2c1OC)CCC3]
794
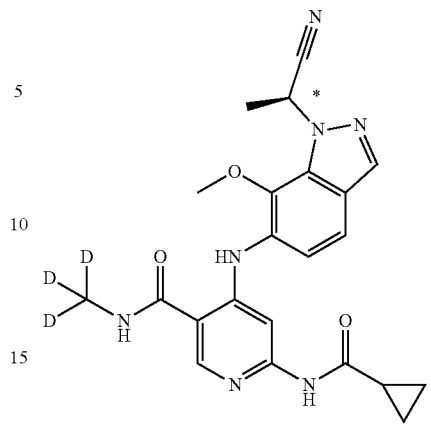
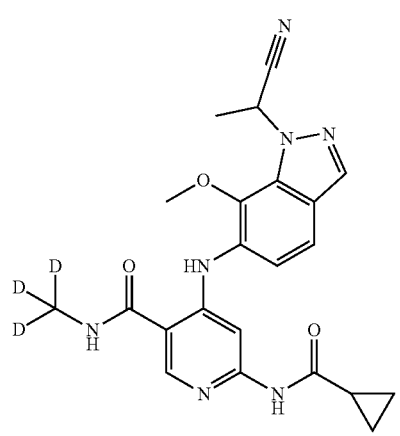 [SMILES: [2H]C([2H])([2H])NC(=O)c1cnc(NC(=O)C2CC2)cc1Nc1ccc2cnn(C(C)C#N)c2c1OC]
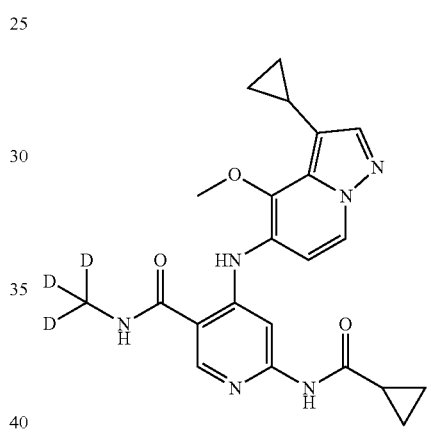
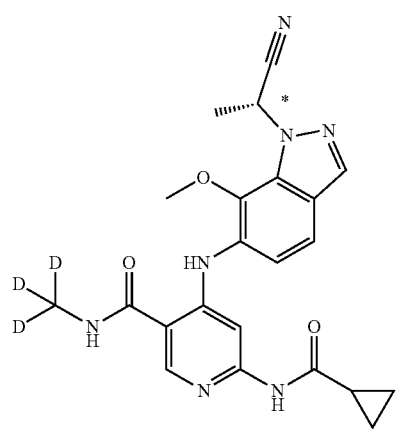
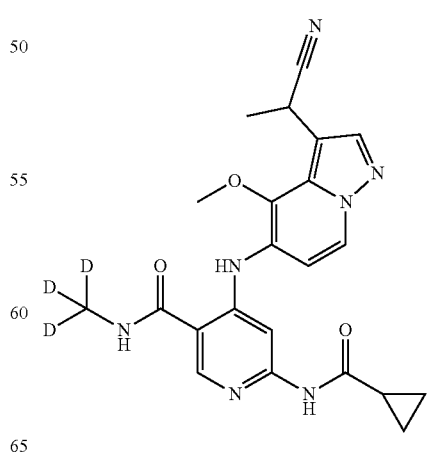

795
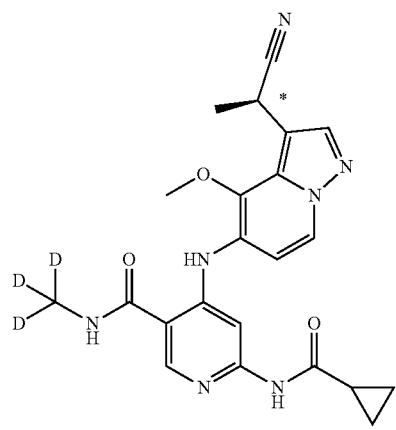 [SMILES: [2H]C([2H])([2H])NC(=O)c1cnc(NC(=O)C2CC2)cc1Nc1ccn2ncc([C@@H](C)C#N)c2c1OC]
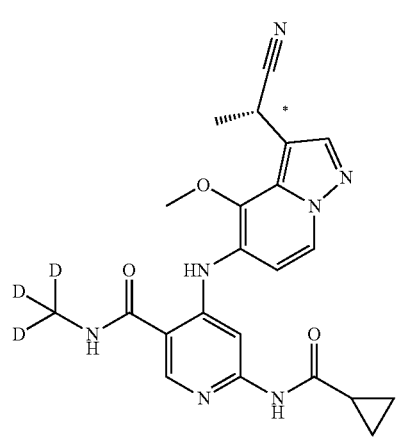 [SMILES: [2H]C([2H])([2H])NC(=O)c1cnc(NC(=O)C2CC2)cc1Nc1ccn2ncc([C@H](C)C#N)c2c1OC]
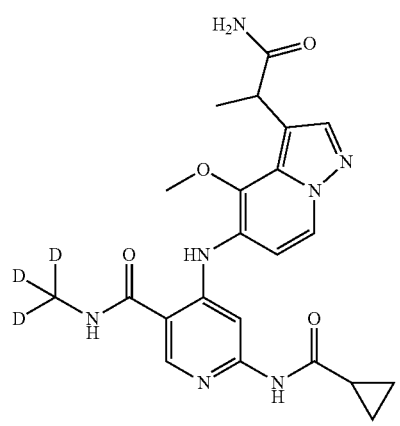 [SMILES: [2H]C([2H])([2H])NC(=O)c1cnc(NC(=O)C2CC2)cc1Nc1ccn2ncc(C(C)C(N)=O)c2c1OC]
796
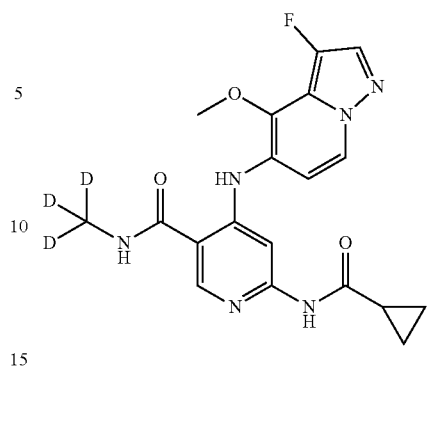
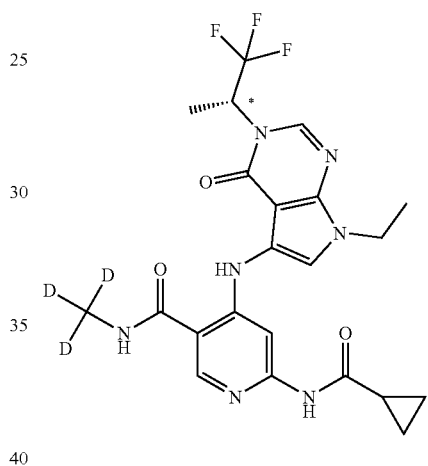
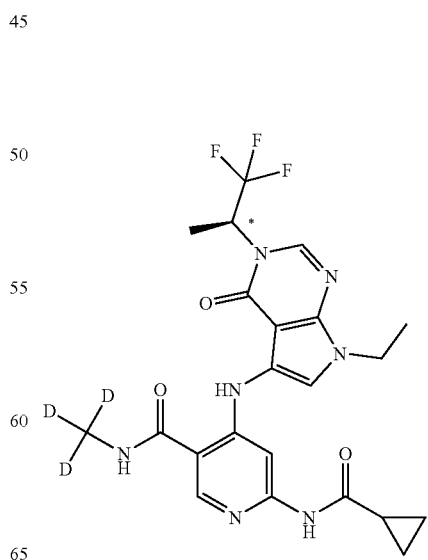

797
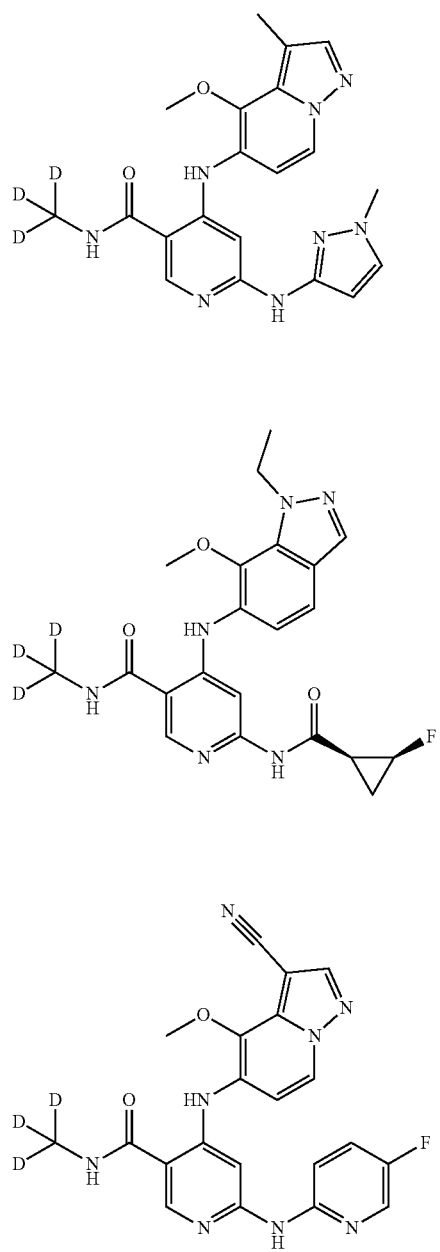
798
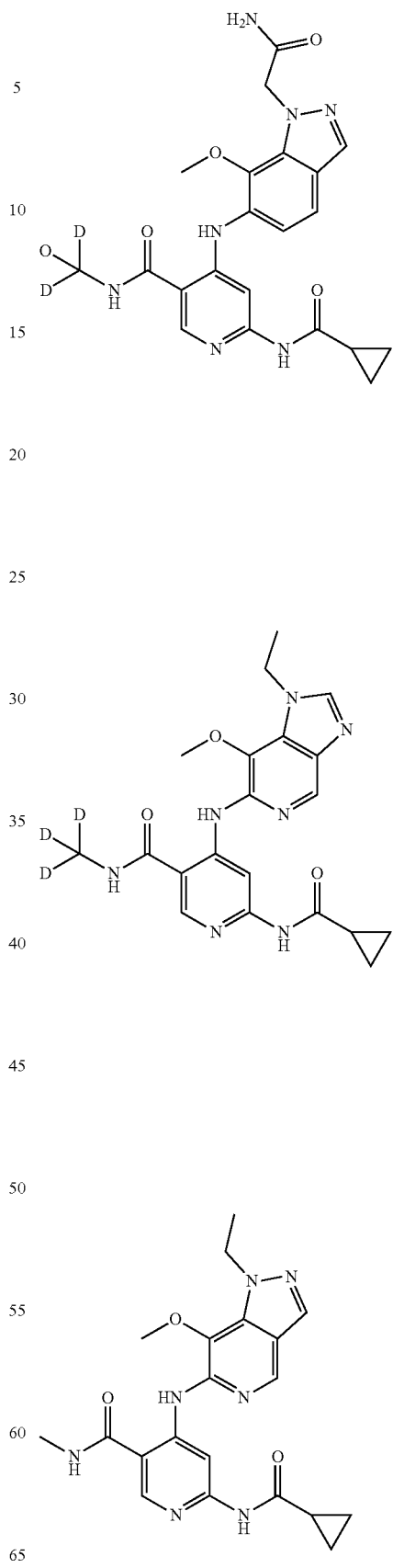

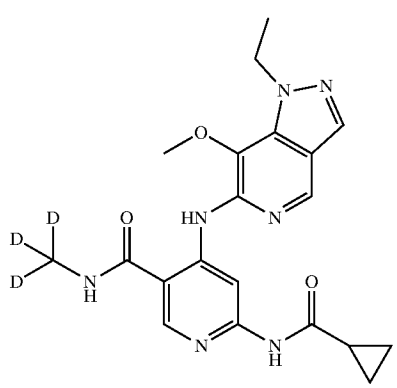

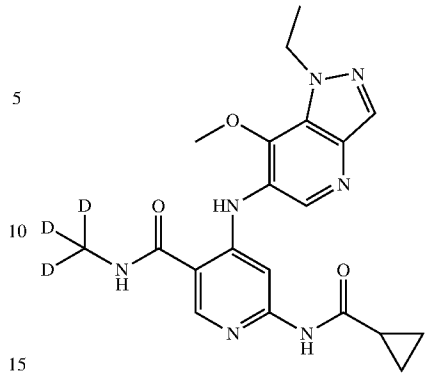

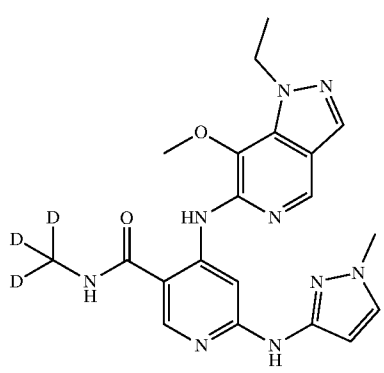 [SMILES: [2H]C([2H])([2H])NC(=O)c1cnc(Nc2ccn(C)n2)cc1Nc1ncc2cnn(CC)c2c1OC]

Binding Activity Test for JH2 Domain of JAK1 and TYK2

The compounds are prepared in DMSO for 200× top dose, then serial dilute it with 27-fold for 3 more points. Add 8 µL/well in echo source plate, echo will add 75 nL/well with 3-fold serial dilution for 11 points in assay plate. 75 nL DMSO for high control and low control.

Prepare 3× working solutions (1.5 nM) of JAK1-JH2 domain or TYK2-JH2 domain enzyme in assay buffer, add 5 µL of enzyme working solutions per well to the assay plate including high control. For low control, add 5 µL/well assay buffer. And then spin down at 1000 rpm and centrifuge for 30 seconds. After enzyme system prepared, add 5 µL of Tb-antibody solution into each wells of assay plate. Spin down at 1000 rpm and centrifuge for 30 sec. After Tb-antibody added, also add 5 µL of tracer into the assay plate. Spin down at 1000 rpm and centrifuge for 30 sec. Incubate for 60 mins at 25° C. firstly and then continue to incubate the plate at 4° C. overnight. Read by envision in FRET mode. The Luminescence value was recorded by a multi-label reader Envision (PerkinElmer). Inhibition Rate was calculated relative to vehicle (DMSO) treated control wells using following formula:

$$\% \text{ Inhibition} = 100 - \frac{RLU_{compound} - RLU \text{ lowcontrol}}{RLU \text{ high control} - RLU \text{ low control}} \times 100\%$$

wherein
RLU compound=the relative light unit of cells treated with test compounds
RLU_low control=the relative light unit of medium with DMSO only
RLU_high control=the relative light unit of cells treated with DMSO only The dose-response (percent inhibition) curve was plotted and IC50 values (the concentration that causes 50% growth inhibition) were determined by GraphPad software. The IC50 of tested compounds are shown in Table 2.

TABLE 2

| | IC50 on JH2 domain activity (nM) | | |
|---|---|---|---|
| Example | TYK2-JH2 (nM) | JAK1-JH2 (nM) | JAK1/TYK2 selectivity |
| 17 | 0.202 | — | — |
| 19 | 0.098 | — | — |
| 23 | 1.332 | — | — |
| 27 | 0.48 | — | — |

TABLE 2-continued

IC50 on JH2 domain activity (nM)

| Example | TYK2-JH2 (nM) | JAK1-JH2 (nM) | JAK1/TYK2 selectivity |
|---|---|---|---|
| 41(BMS986165) | 0.133 | 0.631 | 4.7 |
| 44 | 0.286 | 9.888 | 34.6 |
| 53 | 0.293 | — | — |
| 57 | 5.215 | — | — |
| 68 | 0.4 | — | — |
| 97 | 4.381 | >298.507 | — |
| 100 | 0.887 | — | — |
| 105 | 0.733 | — | — |
| 110 | 0.92 | — | — |
| 116 | 3.347 | — | — |
| 125 | 1.442 | — | — |
| 129 | 0.416 | 20.77 | 49.9 |
| 131 | 0.33 | 13.277 | 40.2 |
| 135 | 1.46 | — | — |
| 139 | 0.524 | 12.379 | 23.6 |
| 144 | 1.291 | — | — |
| 148 | >298.5 | — | — |
| 149 | 62.806 | — | — |
| 150 | 1.872 | — | — |
| 151 | 0.46 | 13.128 | 28.5 |
| 152 | 0.171 | 10.705 | 62.6 |
| 153 | 0.455 | 15.118 | 33.2 |
| 154 | 1.191 | — | — |
| 157 | 0.357 | 25.195 | 70.6 |
| 158 | 0.948 | — | — |
| 165 | 0.278 | 18.625 | 67.0 |
| 166 | 0.154 | 13.598 | 88.3 |
| 168 | 2.15 | — | — |
| 169 | 0.31 | 8.763 | 28.3 |
| 173 | 0.817 | — | — |
| 190 | 4.033 | — | — |
| 190A | 0.622 | — | — |
| 192 | 3.365 | — | — |
| 193 | 1.414 | — | — |
| 194 | 0.756 | — | — |
| 203 | 0.173 | 18.462 | 106.7 |
| 205 | 1.305 | — | — |
| 206 | 0.623 | 10.963 | 17.6 |
| 207 | 0.407 | — | — |
| 208 | 0.248 | 34.737 | 140.1 |
| 209 | 0.158 | 11.19 | 70.8 |
| 211 | 0.71 | — | — |
| 212 | 0.601 | — | — |
| 213 | 0.25 | — | — |
| 214 | 0.557 | — | — |
| 215 | 0.532 | — | — |
| 216 | 0.525 | — | — |
| 217 | 1.313 | — | — |
| 218 | 0.343 | — | — |
| 219 | 2.862 | — | — |
| 225 | 0.868 | 15.215 | 17.5 |
| 226 | 1.456 | 56.517 | 38.8 |
| 227 | 7.528 | — | — |
| 228 | 0.288 | 6.484 | 22.5 |
| 229 | 1.68 | 105.035 | 62.5 |
| 230 | 3.009 | 58.702 | 19.5 |
| 231 | 0.979 | — | — |
| 232 | 1.576 | — | — |
| 234A | 0.521 | 24.35 | 46.7 |
| 234B | 5.784 | 244.248 | 42.2 |
| 235 | 0.262 | 6.744 | 25.7 |
| 236 | 0.969 | 43.773 | 45.2 |
| 239 | 0.188 | 5.412 | 28.8 |
| 240 | 0.260 | 5.071 | 19.5 |
| 241 | 0.534 | 15.344 | 28.7 |
| 242 | 1.178 | 45.329 | 38.5 |
| 243 | 3.446 | 129.985 | 37.7 |
| 244 | 0.125 | 4.576 | 36.6 |
| 245 | 0.157 | 4.344 | 27.7 |
| 246 | 0.156 | 11.848 | 75.9 |
| 249 | 0.782 | 25.436 | 32.5 |
| 249A | 0.715 | 17.979 | 25.15 |
| 249B | 0.738 | 28.966 | 39.25 |
| 250 | 0.233 | 7.035 | 30.19 |
| 251 | 0.304 | 5.570 | 18.32 |
| 251A | 1.034 | 97.230 | 94.03 |
| 251B | 0.266 | 4.601 | 17.30 |
| 252 | 1.683 | 211.529 | 125.69 |
| 253 | 0.783 | 19.047 | 24.33 |
| 254A | 0.868 | 44.101 | 50.81 |
| 254B | 11.646 | 251.577 | 21.60 |
| 255 | 0.323 | 4.420 | 13.7 |
| 256 | 0.265 | 10.818 | 40.8 |
| 257 | 0.135 | 3.178 | 23.5 |
| 258 | 0.834 | 14.895 | 17.9 |
| 259 | 6.293 | 79.892 | 12.7 |
| 260 | 0.124 | 9.781 | 78.9 |
| 261 | 0.956 | 45.36 | 47.4 |
| 262 | 0.220 | 14.756 | 67.1 |
| 263 | 0.290 | 25.351 | 87.4 |
| 264 | 1.772 | 73.731 | 41.4 |
| 265 | 69.234 | — | — |
| 266 | 0.287 | 44.230 | 154 |
| 267 | 0.181 | 9.253 | 51.1 |
| 271 | 25.572 | — | — |
| 272 | 137.846 | — | — |
| 273 | 0.166 | 2.678 | 16.1 |
| 274 | 34.415 | — | — |
| 275 | 0.449 | 27.023 | 60.2 |
| 276 | 0.253 | 110.323 | 436.1 |
| 277 | 1.107 | 61.383 | 55.5 |
| 278 | 0.385 | 9.626 | 25.0 |
| 279 | 0.330 | — | — |
| 280 | 0.180 | — | — |
| 281 | 0.250 | — | — |
| 282 | 0.270 | — | — |

Conclusion: Most the exemplified compounds with different scaffolds have better JH2 TYK2 over JH2 JAK1 selectivity than BMS986165.

Biochemical Assay

Testing for JAK1, JAK2 and TYK2 Kinase Activities

JAK activity was determined in the reaction buffer 50 mM HEPES, 0.01% Brij35, 10 mM $MgCl_2$, 2 mM DTT by a microfluidic assay. The phosphorylation of a FAM labeled peptide substrate was monitored in the Caliper EZ Reader II (Perkin Elmer). The assay condition for each batch of enzyme (Carna Biosciences) was optimized to obtain 10% conversion rate of peptide substrate.

The test compounds were dissolved in DMSO to a stock concentration of 10 mM. Three-fold serially diluted compounds with top concentration of 5 μM were pre-incubated with JAK1, JAK2 or TYK2 for 10 min at ambient temperature. The final DMSO concentration of assay mixture was 1%. FAM labeled peptide substrate (final concentration 3 μM) and ATP (Km concentration or 1 mM) were sequentially added to initiate the kinase reaction at 28° C. for 90 min (JAK), 15 min (JAK2) and 30 min (TYK2), respectively. The reaction was stopped by adding 50 mM EDTA.

The well in the test plate without enzyme was defined as 100% inhibition. And the well without compound but with equivalent DMSO was defined as no inhibition. The percent inhibition was calculated by the following formula:

$$\% \text{ Inhibition} = \frac{\text{Conversion \%\_max} - \text{Conversion \%\_sample}}{\text{Conversion \%\_max} - \text{Conversion \%\_min}} \times 100$$

wherein

Conversion $\%_{\_max}$=the conversion rate in the positive well without addition of compound Conversion %_sample=the conversion rate of test compounds Conversion %_mm=the conversion rate in the well without addition of enzyme The dose-response (percent inhibition) curve was plotted and IC50 values were determined by GraphPad software. The IC50 values of tested compounds were list in Table 3.

TABLE 3

JAK1, JAK2 and TYK2 IC50 (nM) Values of Illustrative Compounds

| Example | JAK1 (5 nM) (1 mM ATP) | JAK2 (0.125 nM) (1 mM ATP) | TYK2 (1 nM) (1 mM ATP) |
|---|---|---|---|
| 10 | >5000 | >5000 | >5000 |
| 14 | >5000 | >5000 | >5000 |
| 17 | >5000 | >5000 | >5000 |
| 18 | >5000 | >5000 | >5000 |
| 19 | >5000 | >5000 | >5000 |
| 20 | >5000 | 173.25 | >5000 |
| 21 | — | — | >5000 |
| 22 | >5000 | >5000 | >5000 |
| 24 | — | — | >5000 |
| 27 | >5000 | >5000 | >5000 |
| 33 | >5000 | >5000 | >5000 |
| 35 | >5000 | >5000 | >5000 |
| 39 | >5000 | >5000 | >5000 |
| 41(BMS986165) | 731.7 | 2477.0 | 117.7 |
| 44 | >5000 | >5000 | >5000 |
| 165 | >5000 | >5000 | >5000 |
| 202 | >5000 | >5000 | >5000 |
| 261 | >5000 | >5000 | >5000 |
| 262 | >5000 | >5000 | >5000 |

Conclusion: Most the exemplified compounds with different scaffolds have better selectivity in JAK1, JAK2 and TYK2 kinases inhibition than BMS986165.

Anti-Proliferative Assay

Dimerization domain of Tel protein fused with JAK kinase domain was permanently transduced into Ba/F3 cells, whose proliferation is dependent on JAK activity in the absence of IL-3 induction. These engineered Ba/F3 cells (Ba/F3-FL-TYK2-P760L, Ba/F3-TEL-TYK2 and Ba/F3-TEL-JAK2) were used to monitor JAK inhibitory activities of the compounds in the cellular. Ba/F3 cells were cultured in RPMI-1640 (Corning) containing 10% fetal bovine serum. Cells were seeded at 2000/well of white flat bottom 96-well plates. The well containing medium only was used as background control. After 24h growth, cells were treated with compounds. The test compounds were dissolved in DMSO to a stock concentration of 20 mM. 3-fold serially diluted compounds for 9 concentrations with top concentration of 20 μM was added into the each well. The final DMSO concentration was 0.1%. The cells continued to grow at 37° C. in 5% $CO_2$ for 72 h after compound treatment. The viability was measured by cellular ATP determination using the Cell-Titer Glo luciferase reagent (Promega). The Luminescence value was recorded by a multi-label reader Envision (PerkinElmer). Inhibition Rate was calculated relative to vehicle (DMSO) treated control wells using following formula:

$$\% \text{ Inhibition} = 100 - \frac{\text{RLU\_compound} - \text{RLU\_blank}}{\text{RLU\_control} - \text{RLU\_blank}} \times 100\%$$

wherein

RLU compound=the relative light unit of cells treated with test compounds

RLU blank=the relative light unit of medium with DMSO only

RLU_control=the relative light unit of cells treated with DMSO only

The dose-response (percent inhibition) curve was plotted and IC50 values (the concentration that causes 50% growth inhibition) were determined by GraphPad software. The IC50 of tested compounds are shown in Table 4.

TABLE 4

Ba/F3 Cells IC50 Values of Exemplary Compounds

| Example | BaF3-FL-T2P760L (nM) | BaF3-TEL-JAK2 (nM) | BaF3-TEL-TYK2 (nM) |
|---|---|---|---|
| 1 | 483.5 | — | — |
| 2 | 198.5 | — | — |
| 3 | 70.69 | 2298 | 5443 |
| 4 | 547.8 | — | — |
| 5 | 1354 | — | — |
| 6 | 897.4 | — | — |
| 7 | 8022 | — | — |
| 8 | 156.8 | 7473 | >20000 |
| 9 | 740.3 | — | — |
| 10 | 54.45 | 3730 | 4028.5 |
| 11 | 123.6 | — | — |
| 12 | 416.2 | — | — |
| 13 | 6408 | — | — |
| 14 | 330.1 | >20000 | >20000 |
| 15 | 23.58 | >20000 | >20000 |
| 16 | 89.34 | — | — |
| 17 | 114.39 | — | >10000 |
| 18 | 48.43 | >20000 | >20000 |
| 19 | 34.91 | 4960 | >20000 |
| 20 | 78.04 | 1177 | 2530 |
| 21 | 77.48 | — | — |
| 22 | 861.2 | — | — |
| 23 | 62.92 | — | >20000 |
| 24 | 1387 | — | — |
| 25 | 7824 | — | — |
| 26 | >20000 | — | — |
| 27 | 50.91 | — | >20000 |
| 28 | 65 | >20000 | >20000 |
| 29 | >20000 | — | — |
| 30 | 198.90 | — | — |
| 31 | 302.80 | — | — |
| 32 | 856.4 | — | — |
| 33 | 499.15 | — | — |
| 34 | 125.24 | 4346 | 7178 |
| 35 | 48.2 | 789 | >20000 |
| 36 | 173.3 | 892.3 | 1964 |
| 37 | 988.3 | — | — |
| 38 | 830.5 | — | — |
| 39 | 88.11 | — | — |
| 40 | 18.17 | — | >10000.0 |
| 42 | 38.78 | — | — |
| 43 | 85.19 | — | — |
| 44 | 56.19 | — | — |
| 45 | 160.2 | — | — |
| 46 | 371.85 | — | — |
| 47 | 180.4 | — | — |
| 48 | 3808 | — | — |
| 49 | 110.61 | — | — |
| 50 | 370.5 | — | — |
| 51 | 80.17 | — | — |
| 52 | 126.97 | — | — |
| 53 | 144.1 | — | — |
| 54 | 1093.15 | — | — |
| 55 | 626.8 | — | — |
| 56 | 285.4 | — | — |
| 57 | >5000 | — | — |
| 58 | >5000 | — | — |
| 59 | 1928 | — | — |
| 60 | 1406 | — | — |
| 61 | 3510 | — | — |
| 62 | 1183 | — | — |
| 63 | 796.1 | — | — |
| 64 | 2039 | — | — |
| 65 | 171.7 | — | — |

TABLE 4-continued

Ba/F3 Cells IC50 Values of Exemplary Compounds

| Example | BaF3-FL-T2P760L (nM) | BaF3-TEL-JAK2 (nM) | BaF3-TEL-TYK2 (nM) |
|---|---|---|---|
| 66 | 42.12 | — | — |
| 67 | 44.44 | — | — |
| 68 | 42.1 | — | — |
| 69 | 79.89 | — | — |
| 70 | 30.01 | — | — |
| 71 | 48.71 | — | — |
| 72 | 248.8 | — | — |
| 73 | 7981 | — | — |
| 74 | 93.45 | — | — |
| 75 | 108.32 | — | — |
| 76 | 58.69 | — | — |
| 77 | 61.09 | — | — |
| 78 | 46.45 | — | — |
| 79 | 40.27 | — | — |
| 80 | 213.33 | — | — |
| 81 | 330.5 | — | — |
| 82 | 64.35 | — | — |
| 83 | 38.71 | — | — |
| 84 | 676.1 | — | — |
| 85 | 142.05 | — | — |
| 86 | 139.5 | — | — |
| 87 | 583.5 | — | — |
| 88 | 46.9 | — | — |
| 89 | 32.21 | — | — |
| 90 | 126.05 | — | — |
| 91 | 138 | — | — |
| 92 | 300.4 | — | — |
| 93 | 97.02 | — | — |
| 94 | 293 | — | — |
| 95 | 53.15 | — | — |
| 96 | 350.75 | — | — |
| 97 | 1269 | — | — |
| 98 | 487.6 | — | — |
| 99 | 56.73 | — | — |
| 100 | 374.4 | — | — |
| 101 | 808.7 | — | — |
| 102 | 807.5 | — | — |
| 103 | 761 | — | — |
| 104 | 2419 | — | — |
| 105 | 145.95 | — | — |
| 106 | 205.7 | — | — |
| 107 | 2096 | — | — |
| 108 | 523.3 | — | — |
| 109 | 146.6 | — | — |
| 110 | 101.54 | — | — |
| 111 | 153.5 | — | — |
| 112 | 477.4 | — | — |
| 113 | 2387 | — | — |
| 114 | 1100 | — | — |
| 115 | 1099 | — | — |
| 116 | 102.1 | — | — |
| 117 | 249.2 | — | — |
| 118 | 1057 | — | — |
| 119 | 1506 | — | — |
| 120 | 1119 | — | — |
| 121 | 42.16 | — | — |
| 122 | 34.66 | — | — |
| 123 | 100.4 | — | — |
| 124 | 34.82 | — | — |
| 125 | 31.86 | — | — |
| 126 | 521.65 | — | — |
| 127 | 377.9 | — | — |
| 128A | 736.1 | — | — |
| 128B | 1706 | — | — |
| 129 | 69.33 | — | — |
| 130 | 357.4 | — | — |
| 131 | 65.36 | — | — |
| 132 | 70.76 | — | — |
| 133 | 394.1 | — | — |
| 134 | 61.37 | — | — |
| 135 | 128.1 | — | — |
| 136 | 325.95 | — | — |
| 137 | 334.9 | — | — |
| 138 | 88.76 | — | — |
| 139 | 33.08 | — | — |
| 140 | 82.43 | — | — |
| 141 | 29.08 | — | — |
| 142 | 169.1 | — | — |
| 143 | 107.8 | — | — |
| 144 | 343.9 | — | — |
| 145 | 83.62 | — | — |
| 146 | 832.4 | — | — |
| 147 | 174.5 | — | — |
| 148 | 241.8 | — | — |
| 149 | 731.7 | — | — |
| 150 | 230.5 | — | — |
| 151 | 77.68 | — | — |
| 152 | 27.9 | — | — |
| 153 | 71.33 | — | — |
| 154 | 145.1 | — | — |
| 155 | 901.6 | — | — |
| 156 | 2900 | — | — |
| 157 | 53.89 | — | — |
| 158 | 68.36 | — | — |
| 159 | 28.34 | — | — |
| 160 | 29.7 | — | — |
| 161 | 21.57 | — | — |
| 162 | 25.89 | — | — |
| 163 | 36.71 | — | — |
| 164 | 349.1 | — | — |
| 165 | 98.2 | — | — |
| 166 | 51.58 | — | — |
| 167 | 100.22 | — | — |
| 168 | 727.7 | — | — |
| 169 | 64.91 | — | — |
| 170 | 27.62 | — | — |
| 171 | 105.39 | — | — |
| 172 | 109.4 | — | — |
| 173 | 86.48 | — | — |
| 174 | 147 | — | — |
| 175 | 123.72 | — | — |
| 176 | 182.6 | — | — |
| 177 | 91 | — | — |
| 178 | 287.2 | — | — |
| 179 | >5000.0 | — | — |
| 180 | 1353 | — | — |
| 181 | 1901 | — | — |
| 182 | 491.2 | — | — |
| 183 | 709.6 | — | — |
| 184 | 188.5 | — | — |
| 185 | 427.7 | — | — |
| 185A | 205.4 | — | — |
| 185B | 912 | — | — |
| 186 | 308.8 | — | — |
| 187 | 441.7 | — | — |
| 188 | 267.2 | — | — |
| 189 | 246.53 | — | — |
| 190 | 78.28 | — | — |
| 190A | 113.02 | — | — |
| 190B | 327.1 | — | — |
| 191 | 1267 | — | — |
| 192 | 123.6 | — | — |
| 193 | 368.5 | — | — |
| 194 | 562.4 | — | — |
| 195 | 560.2 | — | — |
| 196 | 45.67 | — | — |
| 197 | 54.26 | — | — |
| 198 | 585 | — | — |
| 199 | 174.7 | — | — |
| 200 | 647.8 | — | — |
| 201 | 162.1 | — | — |
| 201A | 240.7 | — | — |
| 201B | 764.2 | — | — |
| 202 | 45.69 | — | — |
| 203 | 46.56 | — | — |
| 204 | 327 | — | — |
| 205 | 252.1 | — | — |
| 206 | 68.51 | — | — |
| 207 | 148.75 | — | — |
| 208 | 64.61 | — | — |

TABLE 4-continued

Ba/F3 Cells IC50 Values of Exemplary Compounds

| Example | BaF3-FL-T2P760L (nM) | BaF3-TEL-JAK2 (nM) | BaF3-TEL-TYK2 (nM) |
|---|---|---|---|
| 209 | 52.57 | — | — |
| 210 | >5000 | — | — |
| 211 | 174 | — | — |
| 212 | 243.8 | — | — |
| 213 | 74.55 | — | — |
| 214 | 216.8 | — | — |
| 215 | 159 | — | — |
| 216 | 180.9 | — | — |
| 217 | 204.9 | — | — |
| 218 | 68.57 | — | — |
| 219 | 1262 | — | — |
| 220 | 540.9 | — | — |
| 221 | 294.3 | — | — |
| 222 | 155.4 | — | — |
| 223 | 82.72 | — | — |
| 224 | 213.7 | — | — |
| 225 | 564.9 | — | — |
| 226 | 221 | — | — |
| 227 | >5000 | — | — |
| 228 | 29.3 | — | — |
| 229 | 564.5 | — | — |
| 230 | 478.5 | — | — |
| 231 | 65.91 | — | — |
| 232 | 1698 | — | — |
| 233 | 3268 | — | — |
| 234A | 96.17 | — | — |
| 234B | 599 | — | — |
| 235 | 44.73 | — | — |
| 236 | 892.4 | — | — |
| 237 | 4071 | — | — |
| 238 | >5000.0 | — | — |
| 239 | 84.72 | — | — |
| 240 | 70.67 | — | — |
| 241 | 160.8 | — | — |
| 242 | 404.4 | — | — |
| 243 | >5000.0 | — | — |
| 244 | 18.11 | — | — |
| 245 | 56.44 | — | — |
| 246 | 75.68 | — | — |
| 247 | >5000 | — | — |
| 248 | 1424 | — | — |
| 249 | 357.3 | — | — |
| 249A | 495.5 | — | — |
| 249B | 342.4 | — | — |
| 250 | 159.6 | — | — |
| 251 | 117 | — | — |
| 251A | 540.5 | — | — |
| 251B | 102.9 | — | — |
| 252 | >5000 | — | — |
| 253 | 231.6 | — | — |
| 254A | 179.2 | — | — |
| 254B | 933.6 | — | — |
| 255 | 116.4 | — | — |
| 256 | 69.52 | — | — |
| 257 | 39.72 | — | — |
| 258 | 204.70 | — | — |
| 259 | >5000 | — | — |
| 260 | 142.7 | — | — |
| 261 | 113.2 | — | — |
| 262 | 41.56 | — | — |
| 263 | 41.69 | — | — |
| 264 | 278.1 | — | — |
| 265 | >5000.0 | — | — |
| 266 | 76.22 | — | — |
| 267 | 226.9 | — | — |
| 271 | 2607.0 | — | — |
| 272 | 4758.0 | — | — |
| 273 | 28.45 | — | — |
| 274 | >5000.0 | — | — |
| 275 | 117.6 | — | — |
| 276 | 88.2 | — | — |
| 277 | 60.2 | — | — |
| 278 | 130.2 | — | — |
| 279 | 70.1 | — | — |
| 280 | 40.2 | — | — |
| 281 | 48.2 | — | — |
| 282 | 75.2 | — | — |

Phosphorylation Inhibition of STAT in Human PBMC and Human Whole Blood Testing:

The inhibitory potential of test articles in human PBMC and human whole blood assay was evaluated by the method of flow cytometry.

IFN-alpha will activate JAK1 and TYK2 kinase in T cells by binding to IFN receptors, and then lead to phosphorylation of STAT1 and STAT2. The phosphorylated STAT1 enter nuclear and promote transcription and expression of IFN-gamma. To evaluate the efficacy of TYK2i in T cells, freshly prepared human PBMC or freshly collected human whole blood will be stimulated with certain unit of human IFN-alpha (Universal Type I IFN (1MU), R&D, 11200-2) for 20 mins in incubator. After stimulation, fix cells with Phosflow™ Fix Buffer I (BD, 557870), and then collect fixed cells by centrifugation (500 g, 8 mM). Wash cells once with pre-cooled PBS, and then permeabilize cells with cold Perm Buffer III buffer (BD, 558050) for 45 mins on ice. Collect cells by centrifugation (600 g, 8 min) and washed twice with cold PBS. Stain cells with anti-human CD3(FITC Mouse Anti-Human CD3, BD, 555332) and anti-pSTAT1_Y701(Alexa Fluor 647 Mouse Anti-Stat1 (pY701), BD, 612597) antibodies. Detect pSTAT1 by flow cytometry (CytoFlex S) and analyze data with FlowJo and GraphPad Prism 8 software. IC50 values of test articles were determined using 4-parameter logistic equation.

Exemplary results are summarized in Table 5.

TABLE 5

IC50 on pSTAT1 Inhibition(nM)

| Example | pSTAT1 inhibition in hWB | pSTAT1 inhibition in hPBMC |
|---|---|---|
| 44 | 218.94 | 14.89 |
| 71 | 823.4 | 79.46 |
| 83 | 1579 | 112.6 |
| 113 | 344.1 | / |
| 125 | 581 | 75.65 |
| 129 | 394.6 | / |
| 139 | 1181 | 23.31 |
| 151 | 1863 | / |
| 152 | 78.46 | / |
| 165 | 284.4 | / |
| 166 | 470.9 | 20.72 |
| 169 | 422.2 | 35.06 |
| 197 | 863.3 | 427.7 |
| 202 | 147.45 | 33.26 |
| 203 | 468.4 | / |
| 213 | 376.2 | 107.3 |
| 223 | 375.8 | 43.35 |
| 224 | 425.8 | / |
| 228 | 244.6 | / |
| 231 | 14445 | 3513 |

TABLE 5-continued

IC50 on pSTAT1 Inhibition(nM)

| Example | pSTAT1 inhibition in hWB | pSTAT1 inhibition in hPBMC |
|---|---|---|
| 234A | 495.1 | / |
| 235 | 440.4 | / |
| 239 | 156.6 | / |
| 244 | 189.6 | / |
| 246 | 286.9 | / |
| 256 | 255.5 | / |
| 262 | 101.5 | / |
| 266 | 94.3 | / |

Conclusion: Most the exemplified compounds have decent pSTAT1 inhibition in both hWB and hPBMC.

ADME

Microsomal Metabolic Stability Assay

Microsomes were pre-incubated with test compound or control compounds for 5 min at 37° C. in 100 mM potassium phosphate buffer, pH 7.4, 1.0 mM EDTA. The reaction was initiated by addition of 15 μL of the NADPH regenerating system to 30 μL of each incubation mixture per time point. The final incubation condition was composed of 0.5 mg/mL microsomal protein, 1 μM test article/positive control, 2 mM NADPH. The 0-minute samples were prepared by addition of a 30 μL aliquot of each incubation mixture to 135 μL quench reagent to precipitate proteins. And then a 15 μL aliquot of the NADPH regenerating system was added. At 5, 15, 30 and 45 minutes, the reaction will be stopped by the addition of cold acetonitrile solution containing internal standard. The samples taken at all time points were centrifuged at 5000×g for 15 minutes. 50 μL of supernatant are taken into 96-well assay plates pre-added with 50 μL ultrapure water, and then analyzed by LC/MS/MS.

Concentrations of test articles, control compounds in the samples were determined by using LC/MS/MS method. Plotting of the chromatograms and peak area integrations are carried out by Analyst (AB Sciex).

In the determination of the in vitro elimination constant (ke) of the control compounds, the analyte/internal standard peak area ratios will be converted to percentage remaining (% Remaining) with the following equation:

$$\% \text{ Remaining} = \frac{\text{Peak area ratio of analyte to } IS \text{ at each time point}}{\text{Peak area ratio of analyte to } IS \text{ at } t=0} \times 100\%$$

The $CL_{int}$ of microsomes was calculated using the formula: $CL_{int\ (mic)} = 0.693/T_{1/2}$/mg microsome protein per mL.

The slope was measured by the natural logarithm of the percentage of the residual compound and time, T1/2 was calculated according to the following formula.

$$T_{1/2} = \frac{0.693}{-\text{slope}}$$

Exemplary results are summarized in Table 6.

TABLE 6

| Example | Human LM T1/2 (min) | Human LM Clint (uL/min/mg) | Rat LM T1/2 (min) | Rat LM Clint (uL/min/mg) | Dog LM T1/2 (min) | Dog LM Clint (uL/min/mg) |
|---|---|---|---|---|---|---|
| 10 | 39.22 | 88.35 | 25.33 | 136.77 | 127.83 | 27.11 |
| 11 | 18.73 | 74 | 45.29 | 30.6 | / | / |
| 12 | 53.72 | 25.8 | 84.51 | 16.4 | / | / |
| 14 | 58.83 | 23.56 | 13.68 | 101.31 | 215.39 | 6.43 |
| 16 | 49.91 | 27.77 | 11.02 | 125.8 | 163.75 | 8.46 |
| 17 | 27.07 | 127.99 | 16.56 | 209.23 | 73.56 | 47.1 |
| 19 | 776.98 | 4.46 | 79.45 | 43.61 | 48.7 | 71.15 |
| 20 | 261.33 | 13.26 | 75.84 | 45.69 | 34.29 | 101.05 |
| 21 | 215.84 | 6.42 | 187.19 | 7.4 | 51.68 | 26.82 |
| 23 | 17.3 | 80 | 38.7 | 35.8 | 64.8 | 21.4 |
| 28 | 563.29 | 2.46 | 96.83 | 14.31 | 290.27 | 4.77 |
| 33 | 132.02 | 26.25 | 158.72 | 21.83 | 238.37 | 14.54 |
| 35 | 163.24 | 21.23 | 54.3 | 63.81 | > 186 | <18.6 |
| 42 | 116.77 | 11.87 | 31.58 | 43.9 | 11.89 | 116.56 |
| 43 | 144.7 | 9.58 | 28.6 | 48.46 | 45.05 | 30.77 |
| 44 | 71.54 | 19.38 | 12.54 | 110.54 | 20.74 | 66.85 |
| 45 | 26.69 | 51.92 | 12.59 | 110.07 | 158.27 | 8.76 |
| 47 | 30.7 | 45.2 | 17.3 | 80 | 55.4 | 25 |
| 49 | 96.25 | 14.4 | 42.78 | 32.4 | >120 | <11.5 |
| 52 | 172.16 | 8.05 | 44.99 | 30.8 | 124.67 | 11.12 |
| 58 | >120 | <11.5 | >120 | <11.5 | >120 | <11.5 |
| 66 | 213.74 | 6.48 | 202.6 | 6.84 | 59.88 | 23.15 |
| 67 | 183.9 | 7.54 | 29.26 | 47.36 | 43.49 | 31.87 |
| 68 | 214.94 | 6.45 | 29.42 | 47.12 | 121.14 | 11.44 |
| 69 | >120 | 0 | 417.99 | 3.32 | 721.52 | 1.92 |
| 70 | 109.57 | 12.65 | 186.64 | 7.43 | 45.56 | 30.42 |
| 71 | 50.57 | 27.41 | 63.16 | 21.95 | 245.98 | 5.63 |
| 72 | 82.22 | 16.86 | 15.93 | 87.02 | 85.56 | 16.2 |
| 74 | 79.37 | 17.46 | 8.61 | 161.05 | 12.89 | 107.51 |
| 75 | 63.6 | 21.79 | 61.19 | 22.65 | 36.75 | 37.71 |
| 76 | 67.48 | 20.54 | 70.74 | 19.59 | 112.68 | 12.3 |
| 77 | 302.03 | 4.59 | 113.97 | 12.16 | 90.18 | 15.37 |
| 78 | 63.05 | 21.98 | 64.7 | 21.42 | 163.13 | 8.5 |
| 79 | 49.95 | 27.75 | 52.88 | 26.21 | 154.57 | 8.97 |
| 82 | >120 | <11.5 | 68.98 | 20.09 | 78.03 | 17.76 |
| 83 | >120 | <11.5 | >120 | <11.5 | 51.95 | 26.68 |
| 86 | >120 | <11.5 | >120 | <11.5 | 69.4 | 19.97 |
| 95 | >120 | <11.5 | >120 | <11.5 | >120 | <11.5 |
| 96 | 82.95 | 16.71 | / | / | / | / |
| 98 | 42.52 | 32.59 | 12.11 | 114.44 | 37.2 | 37.26 |
| 99 | 38.55 | 89.89 | 19.15 | 180.96 | 104.69 | 33.1 |
| 100 | 91.58 | 28.55 | 47.67 | 49.49 | >186 | <18.6 |
| 105 | 248.51 | 5.58 | 30.18 | 45.92 | 133.25 | 10.4 |
| 110 | 28.39 | 48.82 | 18.98 | 73.03 | 86.9 | 15.95 |
| 121 | 10.24 | 135.33 | 12.08 | 114.73 | 69.6 | 19.91 |
| 123 | 26.21 | 52.98 | 25.02 | 55.62 | 84.76 | 18.73 |
| 129 | 34.65 | 40 | 15.86 | 87.4 | 28.52 | 48.6 |
| 131 | 14.59 | 95 | 12.76 | 108.6 | 21.06 | 65.8 |
| 132 | 57.8 | 24 | / | / | / | / |
| 139 | 59.75 | 23.28 | / | / | / | / |
| 141 | 18.24 | 76 | 29.62 | 46.8 | 14.78 | 93.8 |
| 147 | 23.5 | 59 | 11.1 | 124 | 25.5 | 54.4 |
| 151 | 21.84 | 63.46 | 20.89 | 66.34 | 29.62 | 46.79 |
| 152 | 32.66 | 42.44 | 25.6 | 54.15 | 2.9 | 477.8 |
| 153 | 27.48 | 50.44 | 15.31 | 90.5 | 26.7 | 51.91 |
| 154 | 43.92 | 31.56 | 35.68 | 38.85 | 82.53 | 16.79 |
| 157 | 17.35 | 79.91 | 13.23 | 105.66 | 32.89 | 42.15 |
| 158 | 91.21 | 15.2 | 52.48 | 26.42 | >186.4 | <7.4 |
| 161 | 18.59 | 74.56 | 21.84 | 63.45 | 50.98 | 27.19 |
| 163 | 16.89 | 82.08 | 13.71 | 101.1 | 114.36 | 12.12 |
| 165 | 37.99 | 36.87 | 31.96 | 43.64 | 99.71 | 14.3 |
| 167 | 24 | 57.8 | 9.29 | 149 | 30.8 | 45 |

TABLE 6-continued

| Example | Human LM T1/2 (min) | Human LM Clint (uL/min/mg) | Rat LM T1/2 (min) | Rat LM Clint (uL/min/mg) | Dog LM T1/2 (min) | Dog LM Clint (uL/min/mg) |
|---|---|---|---|---|---|---|
| 171 | 108.72 | 12.75 | 81.93 | 16.92 | 470.83 | 2.94 |
| 172 | 24.14 | 57.42 | 20.83 | 66.54 | 84.13 | 16.48 |
| 174 | 76.17 | 18.2 | 53.53 | 25.89 | >120 | <11.5 |
| 184 | >120 | <11.5 | 60.08 | 23.07 | >120 | <11.5 |
| 185 | >120 | <11.5 | >120 | <11.5 | >120 | <11.5 |
| 189 | 223.72 | 6.2 | 53.05 | 26.13 | 1207.19 | 1.15 |
| 190 | 20 | 69.28 | 29.88 | 46.39 | 94.03 | 14.74 |
| 191 | >120 | <11.5 | 106.14 | 13.06 | >120 | <11.5 |
| 192 | 51.65 | 26.84 | 19.1 | 72.58 | 63.43 | 21.85 |
| 193 | 128.7 | 10.8 | 25.79 | 53.75 | 123.45 | 11.23 |
| 195 | 34.65 | 40 | 157.5 | 8.8 | | |
| 197 | 17.85 | 77.66 | 4.79 | 289.6 | 66.53 | 20.83 |
| 198 | 52.48 | 26.41 | 25.76 | 53.8 | >120 | <11.5 |
| 200 | >120 | <11.5 | / | / | / | / |
| 201 | 21.52 | 64.4 | / | / | / | / |
| 234A | 56.99 | 24.32 | 39.27 | 35.30 | 126.70 | 10.94 |
| 254A | 60.16 | 23.04 | 35.15 | 39.43 | 297.21 | 4.66 |
| 257 | 145.71 | 9.51 | 68.51 | 20.23 | 153.85 | 9.01 |
| 259 | 315.7 | 4.39 | 295.11 | 4.70 | 150.03 | 9.24 |
| 263 | 47.47 | 29.19 | 33.93 | 40.85 | 14.26 | 97.19 |
| 264 | 114.63 | 12.09 | 90.04 | 15.39 | 82.01 | 16.90 |

Hepatocytes Metabolic Stability Assay

The vials of cryopreserved hepatocytes were removed from the liquid nitrogen container and immediately immersed in a 37° C. water bath for approximately 2 min. The melted ice pellets were transferred into tubes containing 50 mL of pre-warmed thawing medium and mixed well by gently inverting the tubes, and then centrifuged at 500 rpm for 3 minutes at room temperature. The supernatants were discarded, and cell pellets were re-suspended by adding appropriate volumes of pre-warmed incubation medium. The cells viability of each species was determined using Trypan Blue exclusion. Add 50 µL of pre-warmed 2× dosing solution to the wells designated for different time points. Then 50 µL of cells suspension (2×10⁶ cells/mL) were added into appropriate wells at corresponding time points of T15, T30, T60, T120. Start timing and put the plate in an incubator at 37° C. For T0 sample, add 300 µL of ACN containing internal standard to the wells, mix gently, then add 50 µL of pre-warmed hepatocytes solution (2×10⁶ cells/mL). The concentration of test compound was 1 µM and 1.0×10⁶ cells/mL in the final incubation. At each corresponding time point, test and control compounds reaction samples were stopped by adding 300 µL acetonitrile containing internal standard. All sample plates were thoroughly mixed and centrifuged at 5000×g for 15 minutes. The supernatants were diluted at ratio of 1:1 with ultra-pure water for test and positive controls. Then submitted for LC-MS/MS analysis.

The analyte/internal standard peak area ratios were converted to percentage remaining with the following equation:

% Remaining =

$$\frac{\text{Peak area ratio of analyte to } IS \text{ at each time point}}{\text{Peak area ratio of analyte to } IS \text{ at } t = 0} \times 100\%$$

The in vitro elimination constant, k of test compounds and control compounds were calculated from a log linear plot of % Remaining versus time, then the half-life ($T_{1/2}$), the estimation of the in vitro hepatic intrinsic clearance ($CL_{int}$) values were calculated from substrate disappearance rate in hepatocytes incubation:

$T_{1/2}=0.693/k$ $CL_{int\ (hep)}=k/\text{million cells per mL}$ $$T_{1/2} = \frac{0.693}{-\text{slope}}$$

Exemplary results are summarized in Table 7.

TABLE 7

| Example | Human hepatocyte stability T1/2 (min) | Human hepatocyte Clint(liver) (mL/min/kg) | Example | Human hepatocyte stability T1/2 (min) | Human hepatocyte Clint(liver) (mL/min/kg) |
|---|---|---|---|---|---|
| 41 | >216.8 | <17.8 | 151 | 193.69 | 9.1 |
| 44 | 89.4 | 43.1 | 152 | >240 | 0 |
| 67 | >240 | <7.35 | 157 | 127.11 | 13.87 |
| 105 | 202.93 | 8.69 | 165 | >240 | <7.35 |
| 132 | 93.07 | 18.94 | 166 | 156.68 | 11.25 |
| 134 | 98.16 | 17.96 | 169 | 206.14 | 8.60 |
| 137 | 122.59 | 14.38 | 197 | >240 | <7.35 |
| 139 | >240 | <7.35 | 262 | 95.22 | 18.52 |

Plasma Protein Binding by Equilibrium Dialysis

Aliquots of test compound stock solution and warfarin stock solution were spiked into plasma to give the matrix solutions with theoretical concentrations of test compound at 0.2 and 2 µM or warfarin at 2 µM. Immediately transfer 50 µL of the spiked plasma solution suspension to a 96-well plate to act as T=0 control sample. Assemble the dialysis set up following the manufacturer's instructions. Load cells with 150 µL of plasma sample and dialyzed against equal volume of dialysis buffer (PBS). The assay is performed in duplicate. Cover the unit with gas permeable lid and incubate for 5 hours at 37° C. at 100 rpm in a constant temperature shaking box. At the end of incubation, remove lid and pipette 50 µL of post-dialysis samples from both buffer and plasma solution chambers into separated 96-well plate for analysis, respectively. Add 50 µL of plasma solution to the buffer samples, and an equal volume of PBS to the collected plasma solution samples. Shake the plate at 1000 rpm for 2 minutes and add 600 µL of 50% ACN/MeOH containing an appropriate internal standard (IS) to precipitate protein and release compound. Vortex at 1000 rpm for 10 minutes. Centrifuge for 10 minutes at 4000 rpm. Then transfer 75 µL of the supernatant to new 96-well plates for analysis. Add 150 µL of distilled water to each sample and mix for analysis by LC-MS/MS.

The free rate (% Unbound), binding rate (% Bound), and recovery rate (% Recovery) of the compound are calculated as follows:

$$\% \text{ Unbound} = (\text{Area ratio}_{buffer\ chamber} / \text{Area ratio}_{plasma\ solution\ chamber}) \times 100$$

$$\% \text{ Bound} = 100 - \% \text{ Unbound}$$

$$\% \text{ Recovery} = (\text{Area ratio}_{buffer\ chamber} + \text{Area ratio}_{plasma\ solution\ chamber}) / (\text{Area ratio}_{Total\ sample}) \times 100$$

$$\% \text{ Remaining} = \text{Area ratio}_{5hr} / \text{Area ratio}_{0hr} \times 100$$

Exemplary results are summarized in Table 8

TABLE 8

| Example | % Bound (human) | Example | % Bound (human) | Example | % Bound (human) |
|---|---|---|---|---|---|
| 65 | 93.9 | 139 | 96.1 | 234A | 87.7 |
| 19 | 96.2 | 165 | 89.3 | 261 | 91.5 |
| 52 | 95.9 | 207 | 96.1 | 262 | 87.6 |
| 53 | 71.4 | 202 | 88.7 | — | — |
| 158 | 96.1 | 206 | 93 | — | — |
| 44 | 93.2 | 213 | 97.5 | — | — |
| 134 | 95.1 | 216 | 95.9 | — | — |
| 129 | 96.6 | 228 | 96 | — | — |
| 131 | 95.4 | 226 | 87.4 | — | — |
| 96 | 82.9 | 225 | 65.4 | — | — |

Kinetic Solubility

Aliquots of 8 µL of reference and test compound stock solutions (10 mM/5 mM) are added into 792 µL of 100 mM pH 7.4 phosphate buffer. The final DMSO concentration is 1%. Sample tubes are shaken for 2 hours at 1000 rpm at room temperature. Samples are centrifuged at 12000 rpm for 10 min to precipitate un-dissolved particles. And transfer the supernatants to a new tube or plate. Add 5 µL of samples (no diluted, 10 times diluted and 100 times diluted) and standard curve samples to 95 µL of ACN containing IS for LC-MS/MS analysis.

Exemplary results are summarized in Table 9

TABLE 9

| Test article | Test system | Solubility (µM) |
|---|---|---|
| 44 | PBS (pH 7.4) | 38.7 |
| 49 | PBS (pH 7.4) | 6.3 |
| 85 | PBS (pH 7.4) | 15.25 |
| 129 | PBS (pH 7.4) | 13.6 |
| 131 | PBS (pH 7.4) | 32.1 |
| 167 | PBS (pH 7.4) | 109 |
| 192 | PBS (pH 7.4) | 17.8 |
| 206 | PBS (pH 7.4) | 28.7 |
| 207 | PBS (pH 7.4) | 8.45 |
| 219 | PBS (pH 7.4) | 33.9 |
| 234A | PBS (pH 7.4) | 29.9 |
| 249 | PBS (pH 7.4) | 47.35 |
| 261 | PBS (pH 7.4) | 58.05 |
| 262 | PBS (pH 7.4) | 17.65 |

Applicant's disclosure is described herein in preferred embodiments with reference to the FIGURES, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the description, herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. A compound having the structural formula (III):

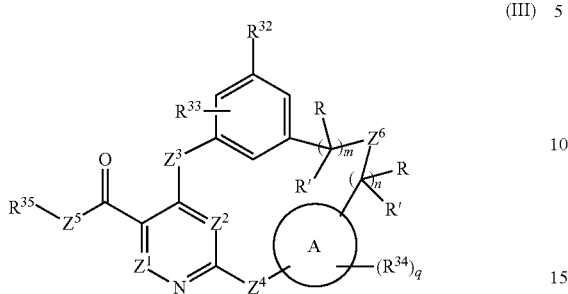

or a pharmaceutically acceptable form or an isotope derivative thereof,
wherein
Ring A is a 6-membered aryl or heteroaryl;
$X^1$ is NH;
$Z^1$ is CH or N,
$Z^2$ is CH, CF or N,
each of $Z^3$ and $Z^4$ is NH;
$Z^6$ is NH, NCH$_3$, CH$_2$ or O;
$R^{32}$ is a 5- or 6-membered heteroaryl group, each substituted with 0-3 $R^{32a}$;
$R^{32a}$ is independently at each occurrence, H, OCF$_3$, CN, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, (CH$_2$)$_r$NR$^g$R$^g$, —(CH$_2$)$_r$C(O)NR$^g$R$^g$, —(CH$_2$)$_r$NR$^b$C(O)R$^c$, —(CH$_2$)$_r$NR$^b$C(O)OR$^c$, —NR$^b$C(O)NR$^g$R$^g$, —S(O)$_v$NR$^g$R$^g$, —NR$^b$S(O)$_v$R$^c$, —S(O)$_v$R$^c$, C$_{1-6}$ alkyl substituted with 0-3 R$^a$, C$_{1-6}$ haloalkyl, C$_{2-6}$ alkenyl substituted with 0-3 R$^a$, 3- to 6-membered cycloalkyl substituted with 0-3 R$^a$, or 3- to 6-membered heterocycloalkyl comprising 1-3 heteroatoms selected from N, O and S substituted with 0-3 R$^a$;
each of $R^{33}$ and $R^{34}$ is independently selected from H, F, Cl, CN, OR$^g$, CH$_3$, CD$_3$, CF$_3$, OCD$_3$, OCF$_3$ and —(CH$_2$)$_p$-Q;
$R^{35}$ is H, F, a C$_1$-C$_3$ alkyl and CD$_3$, provided that $R^{35}$ is not F when $X^1$ is O or N;
$R^a$ at each occurrence is independently H, F, Cl, Br, OCF$_3$, CF$_3$, CHF$_2$, CN, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^g$R$^g$, —(CH$_2$)$_r$C(O)NR$^g$R$^g$, —(CH$_2$)$_r$NR$^b$C(O)R$^c$, —(CH$_2$)$_r$NR$^b$C(O)OR$^c$, —NR$^b$C(O)NR$^g$R$^g$, —S(O)$_v$NR$^g$R$^g$, —NR$^b$S(O)$_v$R$^c$, —S(O)R$^c$, —S(O)$_2$R$^c$, C$_{1-6}$ alkyl substituted with 0-3 R$^f$, C$_{1-6}$ haloalkyl, 3- to 6-membered cycloalkyl substituted with 0-3 R$^f$, or 3- to 6-membered heterocycloalkyl comprising 1-3 heteroatoms selected from N, O and S substituted with 0-3 R$^f$;
$R^b$ is H, C$_{1-6}$ alkyl substituted with 0-3 R$^d$, C$_{1-6}$ haloalkyl, C$_{3-6}$ cycloalkyl substituted with 0-2 R$^d$, or 5- to 7-membered heterocycloalkyl comprising 1-3 heteroatoms selected from N, O and S substituted with 0-3 R$^f$ or (CH$_2$)$_r$-phenyl substituted with 0-3 R$^d$;
$R^c$ is C$_{1-6}$ alkyl substituted with 0-3 R$^f$, (CH$_2$)$_r$—C$_{3-6}$ cycloalkyl substituted with 0-3 R$^f$ or (CH$_2$)$_r$-phenyl substituted with 0-3 R$^f$;
$R^d$ is independently at each occurrence, hydrogen, F, Cl, Br, OCF$_3$, CF$_3$, CN, NO$_2$, —OR$^e$, —(CH$_2$)$_r$C(O) R$^c$, —NR$^e$R$^e$, —NR$^e$C(O)OR$^c$, C$_{1-6}$ alkyl or (CH$_2$)$_r$-phenyl substituted with 0-3 R$^f$;
$R^e$ is independently at each occurrence, hydrogen, C$_{1-6}$ alkyl, C$_{3-6}$ cycloalkyl or (CH$_2$)$_r$-phenyl substituted with 0-3 R$^f$;
$R^f$ is independently at each occurrence, hydrogen, halo, CN, NH$_2$, OH, C$_{3-6}$ cycloalkyl, CF$_3$, O(C$_{1-6}$ alkyl) or a 5- to 7-membered heterocycloalkyl comprising 1-3 heteroatoms selected from N, O and S;
$R^g$ at each occurrence is independently H, C$_{1-4}$ alkyl substituted with 0-3 R$^f$, CF$_3$, C$_{3-10}$ cycloalkyl substituted with 0-1 R$^f$, (CH)$_r$-phenyl substituted with 0-3 R$^d$ or 5- to 7-membered heterocycloalkyl comprising 1-3 heteroatoms selected from N, O and S substituted with 0-3 R$^d$;
Q is a water solubilizing group, optionally selected from OH, OR, NRR', heterocyclic and heteroaryl groups, wherein R and R', together with the nitrogen atom to which they are bound, form a 4- to 7-membered ring comprising 0-2 heteroatoms selected from O, NR, S and SO$_2$;
R is H;
R' is H,
m is 1;
n is 1;
p is 0, 1, 2, 3 or 4;
q is 0, 1, 2, 3 or 4;
v is 0, 1, or 2; and
r is 0, 1, 2, 3, 4 or 5.

2. The compound of claim 1, having the structural formula:

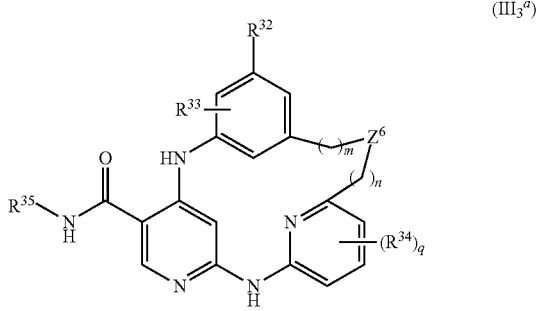

wherein $Z^6$ is O, m is 1, and n is 1.

3. The compound of claim 1, having the structural formula:

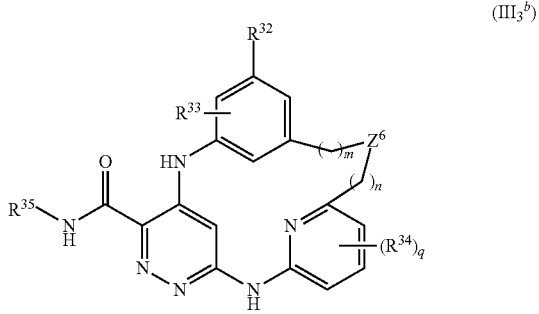

wherein $Z^6$ is O, m is 1, and n is 1.

4. The compound of claim 1, having the structural formula:

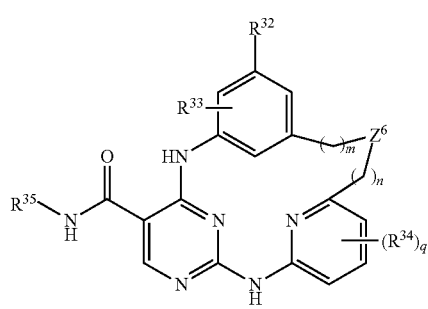

(III$_3{}^c$)

wherein Z$^6$ is O, m is 1, and n is 1.

5. The compound of claim 1, having the structural formula:

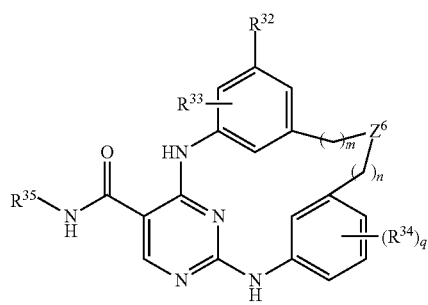

(III$_3{}^d$)

wherein Z$^6$ is O, m is 1, and n is 1.

6. The compound of claim 1, having the structural formula:

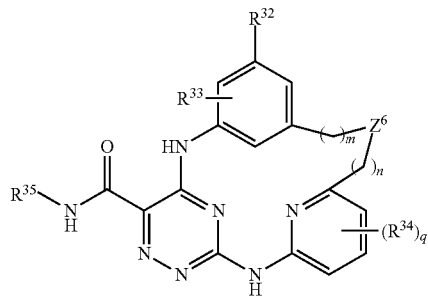

(III$_3{}^e$)

wherein Z$^6$ is O, m is 1, and n is 1.

7. The compound of claim 1, wherein R$^{32}$ is a 5-membered heteroaryl group comprising 1, 2 or 3 nitrogen atoms and 0 or 1 oxygen atom.

8. The compound of claim 1, having the structural formula:

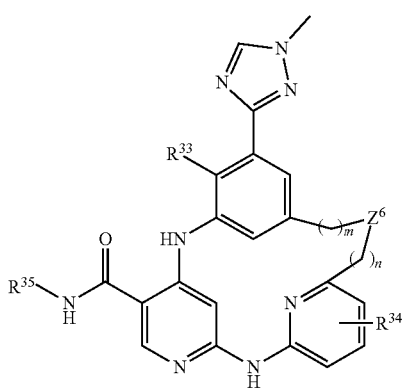

(III$_3{}^f$)

wherein Z$^6$ is O, m is 1, and n is 1.

9. The compound of claim 1, having the structural formula:

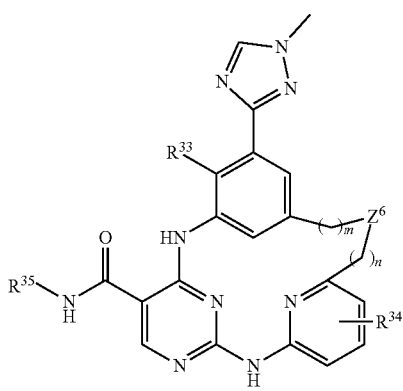

(III$_3{}^g$)

wherein Z$^6$ is O, m is 1, and n is 1.

10. The compound of claim 1, having the structural formula:

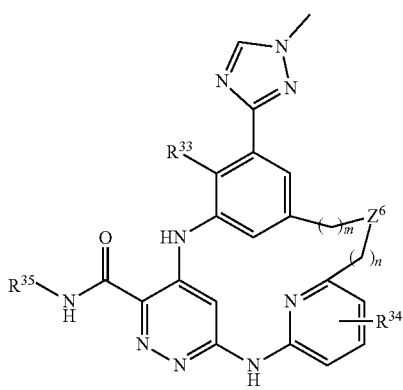

(III$_3{}^h$)

wherein Z$^6$ is O, m is 1, and n is 1.

11. The compound of claim 1, having the structural formula:

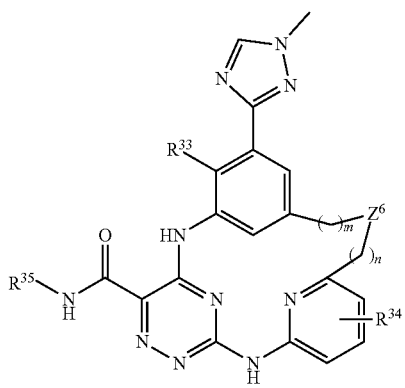

(III₃ⁱ)

wherein $Z^6$ is O, m is 1, and n is 1.

12. The compound of claim 1, wherein $Z^6$ is $NCH_3$.
13. The compound of claim 1, wherein $Z^6$ is $CH_2$.
14. The compound of claim 1, wherein $R^{33}$ is $OCH_3$.
15. The compound of claim 1, wherein $R^{34}$ is H.
16. The compound of claim 1, wherein $R^{34}$ is selected from F, Cl, CN, $CH_3$, $CF_3$ and $OCF_3$.
17. The compound of claim 1, wherein $R^{35}$ is $CH_3$.
18. The compound of claim 1, wherein $R^{35}$ is $CD_3$.
19. A compound of claim 1, selected from:

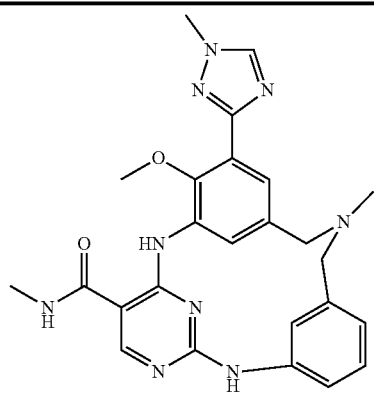

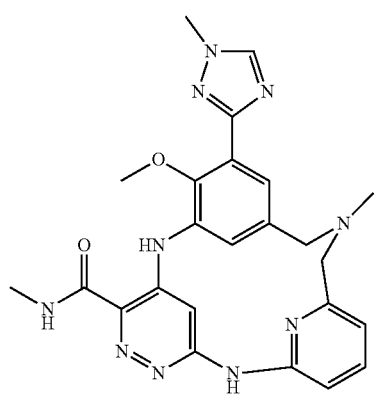

-continued

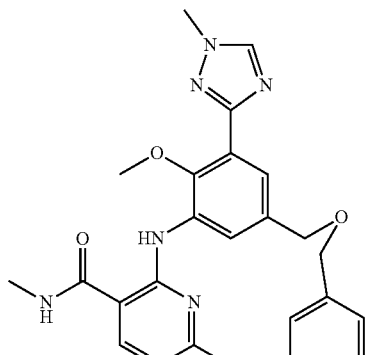

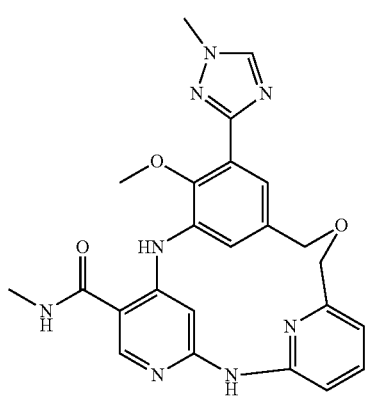 [SMILES: CNC(=O)c1cnc2cc1Nc1cc(cc(-c3ncn(C)n3)c1OC)COCc1cccc(n1)N2]

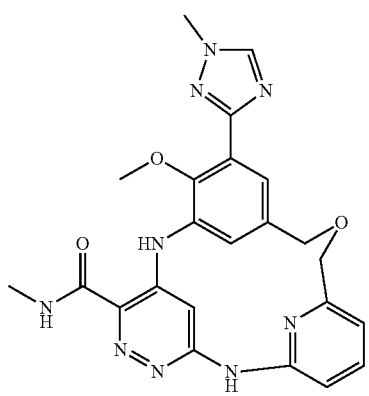 [SMILES: CNC(=O)c1nnc2cc1Nc1cc(cc(-c3ncn(C)n3)c1OC)COCc1cccc(n1)N2]

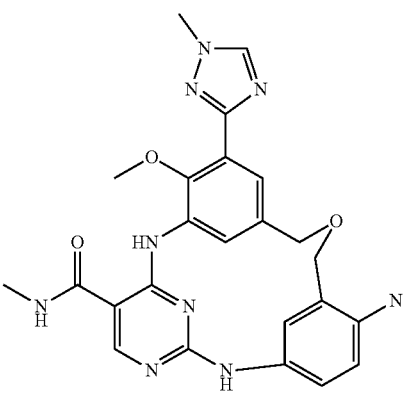 [SMILES: CNC(=O)c1cnc2nc1Nc1cc(cc(-c3ncn(C)n3)c1OC)COCc1cc(ccc1N)N2]

| 821 -continued | 822 -continued |
|---|---|
| 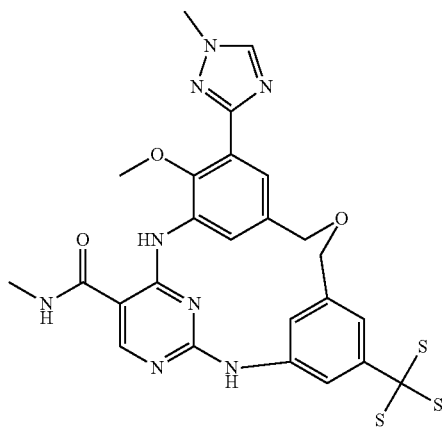 [SMILES: CNC(=O)c1cnc2nc1Nc1cc(cc(-c3ncn(C)n3)c1OC)COCc1cc(cc(C(S)(S)S)c1)N2] | 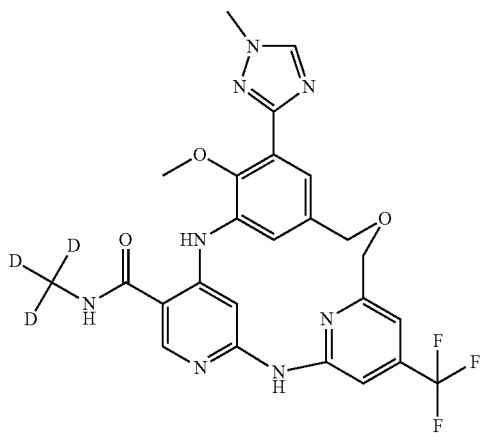 |
| 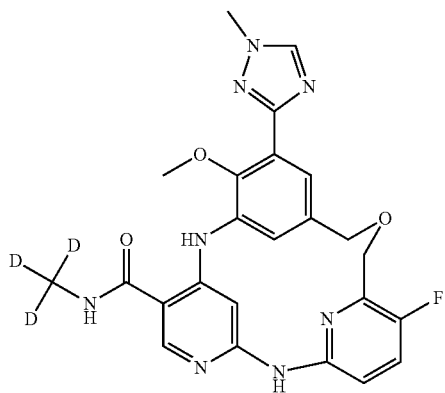 [SMILES: [2H]C([2H])([2H])NC(=O)c1cnc2cc1Nc1cc(cc(-c3ncn(C)n3)c1OC)COCc1nc(ccc1F)N2] | 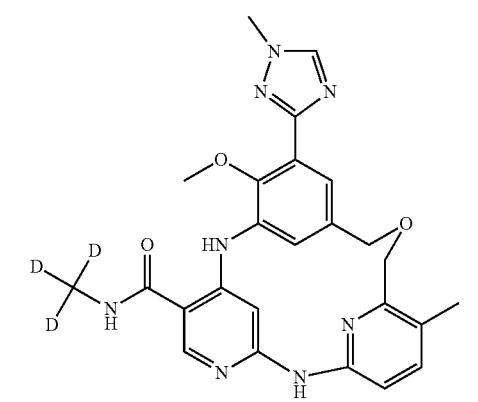 |
| 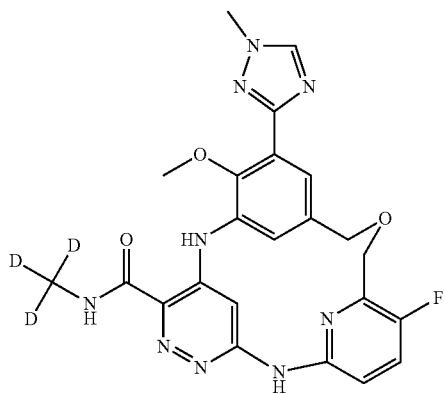 [SMILES: [2H]C([2H])([2H])NC(=O)c1nnc2cc1Nc1cc(cc(-c3ncn(C)n3)c1OC)COCc1nc(ccc1F)N2] | 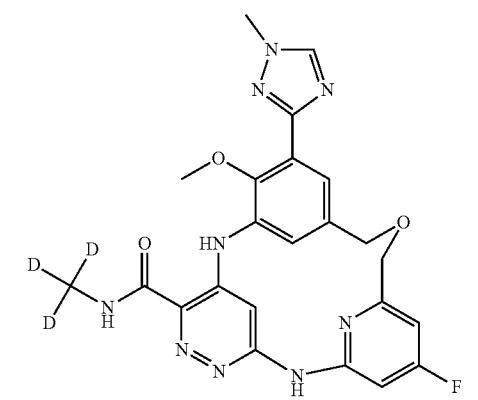 |
| 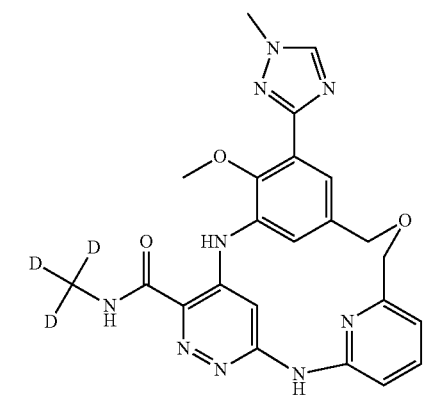 [SMILES: [2H]C([2H])([2H])NC(=O)c1nnc2cc1Nc1cc(cc(-c3ncn(C)n3)c1OC)COCc1cccc(n1)N2] | 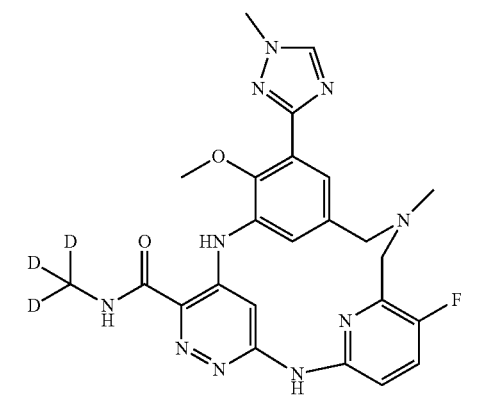 [SMILES: [2H]C([2H])([2H])NC(=O)c1nnc2cc1Nc1cc(cc(-c3ncn(C)n3)c1OC)CN(C)Cc1nc(ccc1F)N2] |

823
-continued
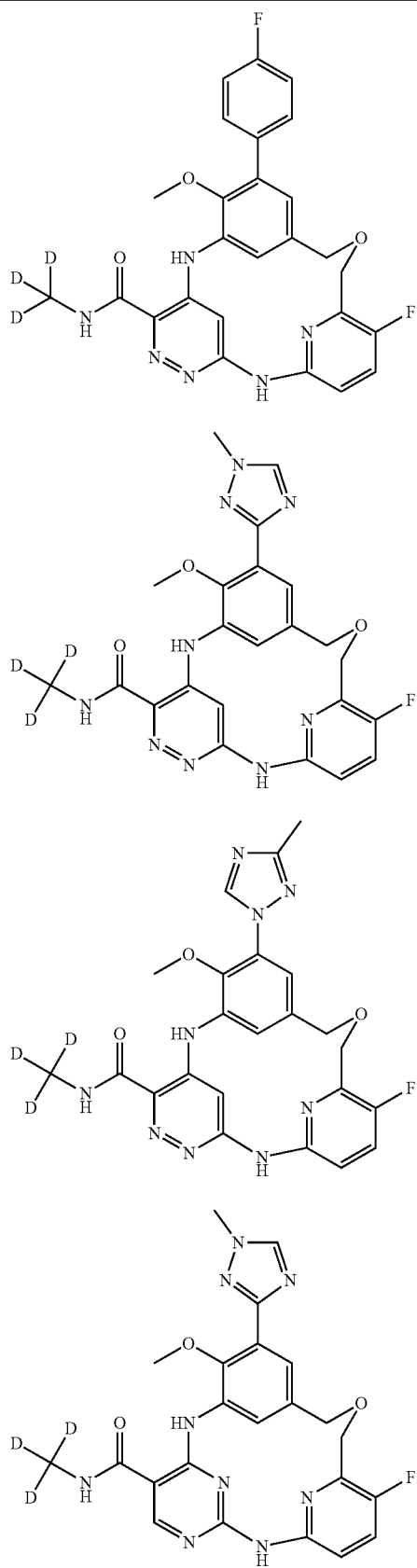
824
-continued
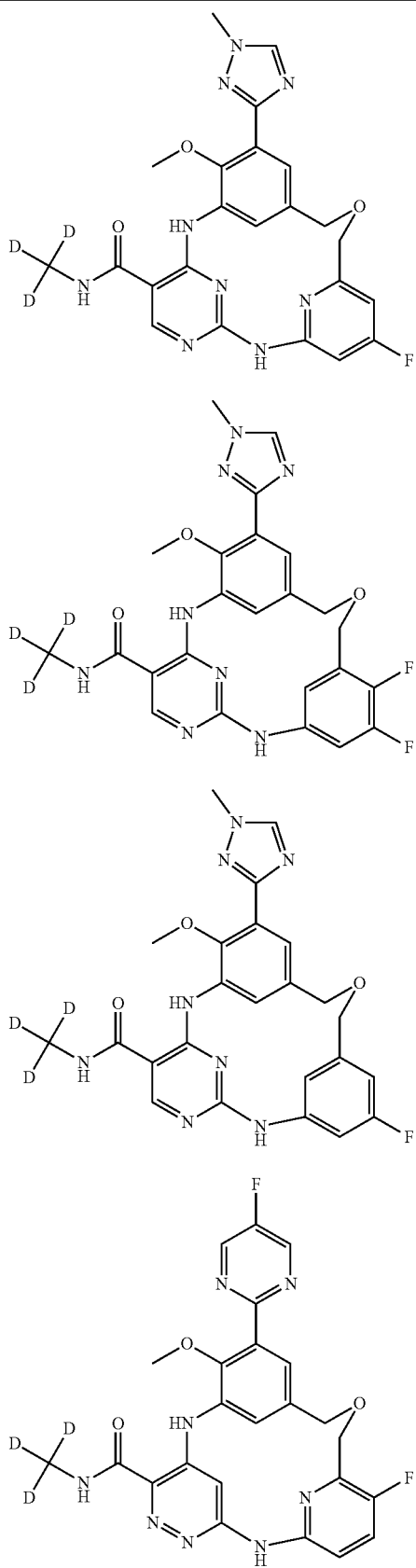

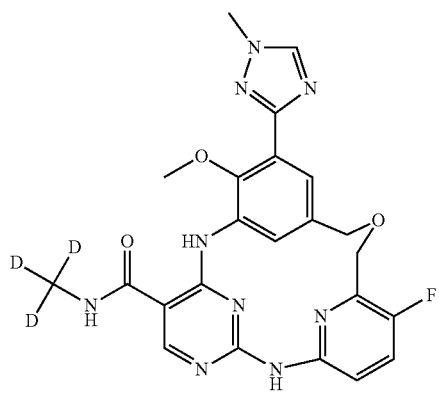 [SMILES: [2H]C([2H])([2H])NC(=O)c1cnc2nc1Nc1cc(cc(-c3ncn(C)n3)c1OC)COCc1nc(ccc1F)N2]
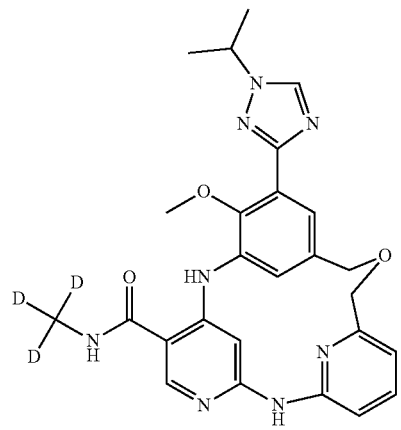
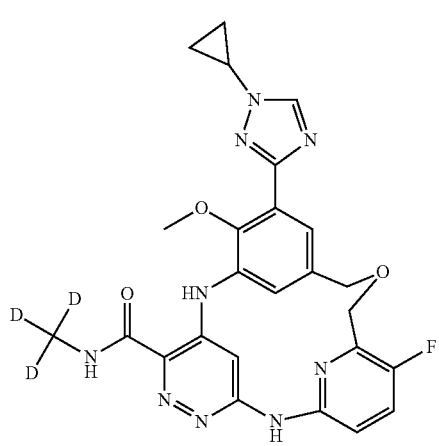 [SMILES: [2H]C([2H])([2H])NC(=O)c1nnc2cc1Nc1cc(cc(-c3ncn(C4CC4)n3)c1OC)COCc1nc(ccc1F)N2]
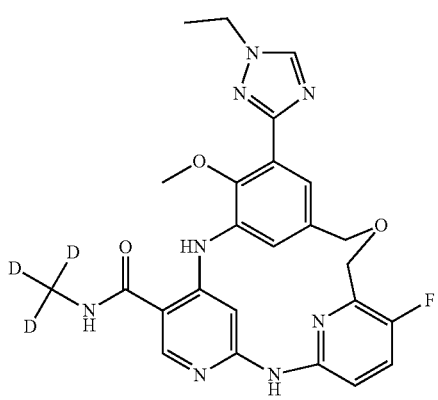
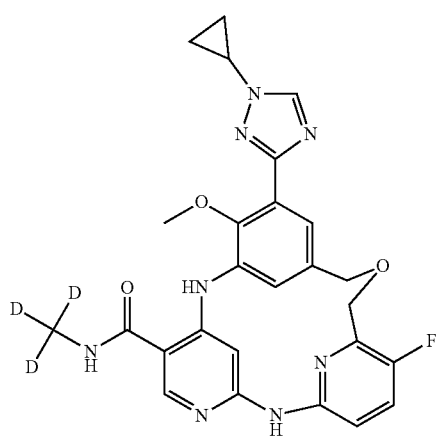 [SMILES: [2H]C([2H])([2H])NC(=O)c1cnc2cc1Nc1cc(cc(-c3ncn(C4CC4)n3)c1OC)COCc1nc(ccc1F)N2]
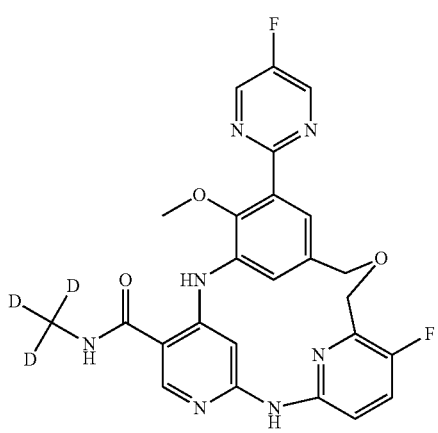 [SMILES: [2H]C([2H])([2H])NC(=O)c1cnc2cc1Nc1cc(cc(-c3ncc(F)cn3)c1OC)COCc1nc(ccc1F)N2]

827
-continued
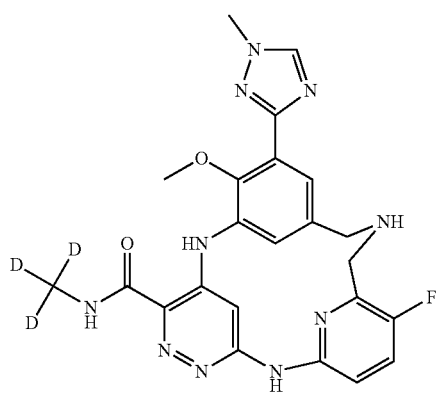 [SMILES: [2H]C([2H])([2H])NC(=O)c1nnc2cc1Nc1cc(cc(-c3ncn(C)n3)c1OC)CNCc1nc(ccc1F)N2]
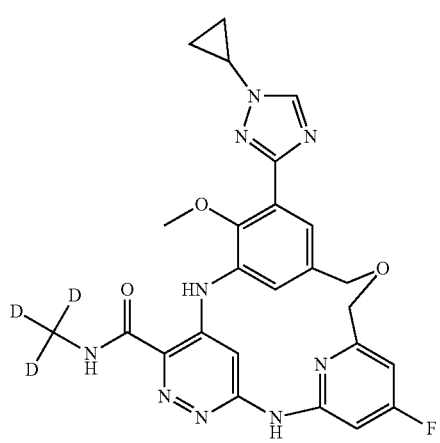 [SMILES: [2H]C([2H])([2H])NC(=O)c1nnc2cc1Nc1cc(cc(-c3ncn(C4CC4)n3)c1OC)COCc1cc(F)cc(n1)N2]
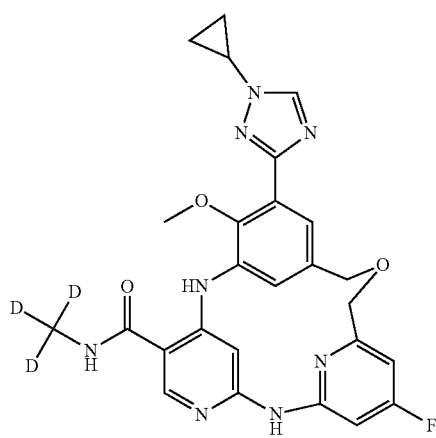 [SMILES: [2H]C([2H])([2H])NC(=O)c1cnc2cc1Nc1cc(cc(-c3ncn(C4CC4)n3)c1OC)COCc1cc(F)cc(n1)N2]
828
-continued
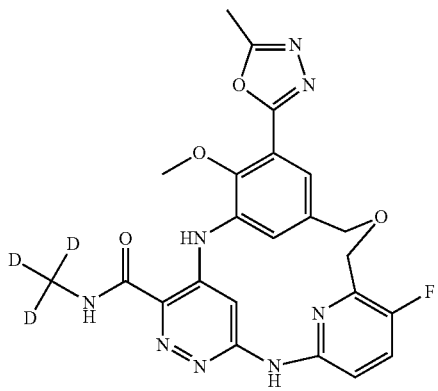 [SMILES: [2H]C([2H])([2H])NC(=O)c1nnc2cc1Nc1cc(cc(-c3nnc(C)o3)c1OC)COCc1nc(ccc1F)N2]
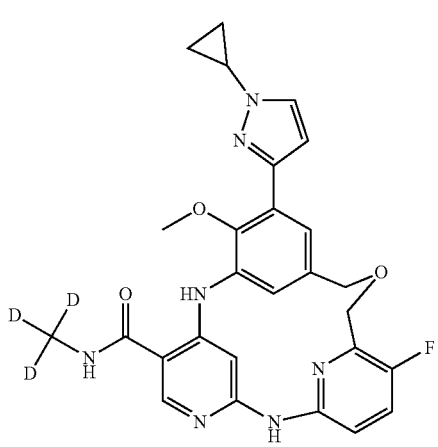 [SMILES: [2H]C([2H])([2H])NC(=O)c1cnc2cc1Nc1cc(cc(-c3ccn(C4CC4)n3)c1OC)COCc1nc(ccc1F)N2]
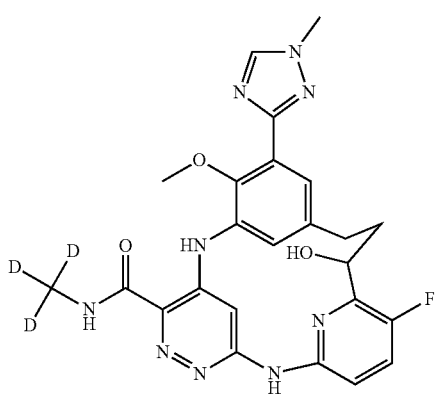 [SMILES: [2H]C([2H])([2H])NC(=O)c1nnc2cc1Nc1cc(cc(-c3ncn(C)n3)c1OC)CCC(O)c1nc(ccc1F)N2]

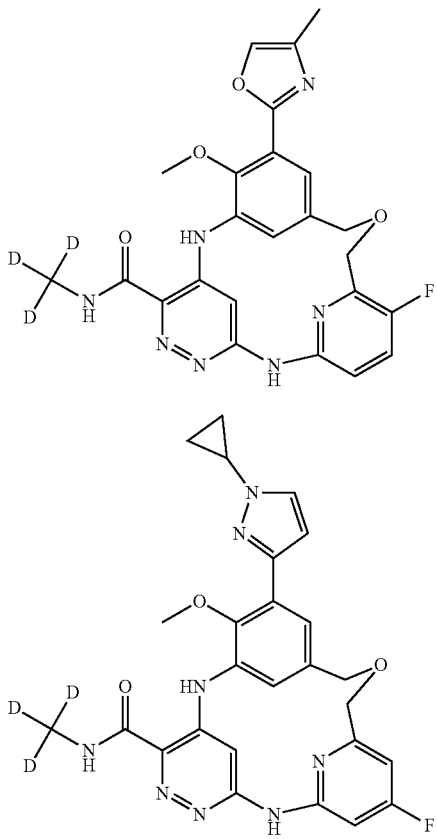

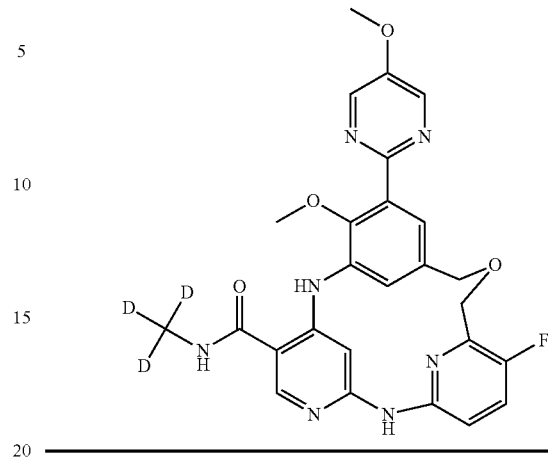

or a pharmaceutically acceptable excipient, carrier, or diluent.

20. A pharmaceutical composition comprising a compound according to claim 1, and a pharmaceutically acceptable excipient, carrier, or diluent.

21. A unit dosage form comprising a pharmaceutical composition according to claim 20.

22. A method for treating, reducing or preventing a disease or disorder, comprising administering to a subject in need thereof a therapeutically effective amount of a compound according to claim 1, wherein the disease or disorder is an inflammatory disease, an immune-mediated disease and cancer.

* * * * *